United States Patent
Lu et al.

(10) Patent No.: US 11,760,744 B2
(45) Date of Patent: Sep. 19, 2023

(54) FUSED RING COMPOUNDS

(71) Applicant: Genentech, Inc., South San Francisco, CA (US)

(72) Inventors: Aijun Lu, Beijing (CN); Sushant Malhotra, South San Francisco, CA (US); Alan G. Olivero, South San Francisco, CA (US); Cheng Shao, Beijing (CN); Yamin Zhang, Beijing (CN); Steven Do, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/642,824

(22) PCT Filed: Aug. 15, 2019

(86) PCT No.: PCT/CN2019/100814
§ 371 (c)(1),
(2) Date: Feb. 27, 2020

(87) PCT Pub. No.: WO2020/035031
PCT Pub. Date: Feb. 20, 2020

(65) Prior Publication Data
US 2023/0002345 A1 Jan. 5, 2023

(30) Foreign Application Priority Data
Aug. 16, 2018 (WO) ................ PCT/CN2018/100792

(51) Int. Cl.
| C07D 401/04 | (2006.01) |
| C07D 239/94 | (2006.01) |
| C07D 401/14 | (2006.01) |
| C07D 403/04 | (2006.01) |
| C07D 403/12 | (2006.01) |
| C07D 403/14 | (2006.01) |
| C07D 405/04 | (2006.01) |

(Continued)

(52) U.S. Cl.
CPC ......... *C07D 401/04* (2013.01); *C07D 239/94* (2013.01); *C07D 401/14* (2013.01); *C07D 403/04* (2013.01); *C07D 403/12* (2013.01); *C07D 403/14* (2013.01); *C07D 405/04* (2013.01); *C07D 413/12* (2013.01); *C07D 471/04* (2013.01)

(58) Field of Classification Search
CPC .. C07D 239/80; C07D 403/14; A61K 31/517; A61K 31/519
See application file for complete search history.

(56) References Cited

U.S. PATENT DOCUMENTS 10,590,115 B2 * 3/2020 Planken ............... C07D 403/04
2002/0025968 A1 2/2002 Pamukcu
(Continued)

FOREIGN PATENT DOCUMENTS

| CL | 201901762 | 6/2019 |
| EA | 026611 B1 | 4/2017 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*
(Continued)

*Primary Examiner* — Deepak R Rao
(74) *Attorney, Agent, or Firm* — Armstrong Teasdale LLP

(57) ABSTRACT

Provided are fused ring compounds of Formula (I), Formula (II), or Formula (III), as further detailed herein, which are used for the inhibition of Ras proteins, as well as compositions comprising these compounds and methods treatment by their administration.

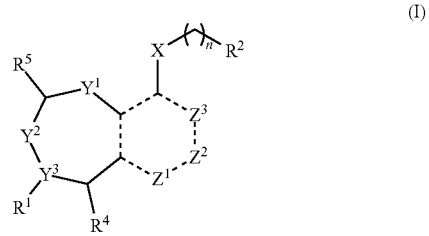

(I)

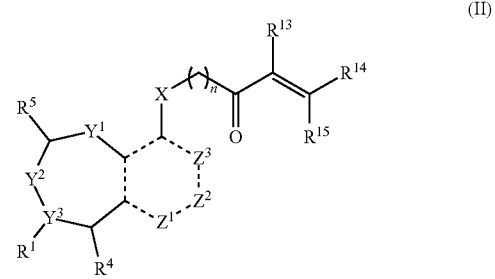

(II)

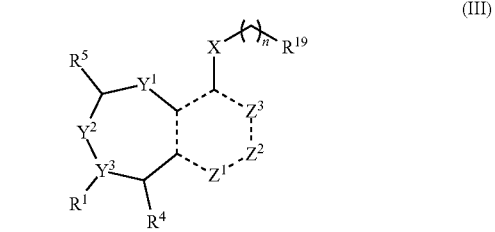

(III)

28 Claims, No Drawings

(51) Int. Cl.
*C07D 413/12* (2006.01)
*C07D 471/04* (2006.01)

(56) References Cited

U.S. PATENT DOCUMENTS

| 2010/0048557 A1 | 2/2010 | Zhu et al. |
| 2019/0248767 A1 | 8/2019 | Planken et al. |
| 2019/0270743 A1 | 9/2019 | Marx et al. |

FOREIGN PATENT DOCUMENTS

| WO | 9902558 A1 | 1/1999 |
| WO | 2013117288 A1 | 8/2013 |
| WO | 2015054572 A1 | 4/2015 |
| WO | 2016044772 A1 | 3/2016 |
| WO | 2017087528 A1 | 5/2017 |
| WO | 2017201161 A1 | 11/2017 |
| WO | 2018064510 A1 | 4/2018 |
| WO | 2018119183 A2 | 6/2018 |
| WO | 2019213516 A1 | 11/2019 |

OTHER PUBLICATIONS

Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Acute Leukemia, Merck Manual (Online Edition) 6 pages, pp. 1-6 (2013).*
Kummer, Klaus, "Pharmaceuticals in the Environment" Annual Review Environment and Resources, 35: 57-75 (2010).
Fall et al., "Selective Heck reaction of aryl bromides with cyclopent-2-en-1-one or cyclohex-2-en-l-one", Tetrahedron, 2009, vol. 65, pp. 489-495.
Fleisher et al., "Improved oral drug delivery: solubility limitations overcome by the use of prodrugs", Advanced Drug Delivery Reviews, 1996, vol. 19, No. 2, pp. 115-130.
Stella et al., "Prodrugs: A Chemical Approach to Targeted Drug Delivery", Directed Drug Delivery, Borchardt et al. (eds.), 1985, pp. 247-267.
Wilman, Derry E.V., "Prodrugs in Cancer Chemotherapy", Biochemical Society Transactions, 615th Meeting Belfast, 1986, vol. 14, pp. 375-382.
International Search Report and Written Opinion for PCT/CN2019/100814, dated Nov. 18, 2019, 12 pages.
CAS Reg No. 1376368-61-4, STN Entry Date Jun. 7, 2012; Ethanone, 1-[4-[2-(3-chlorophenyl)-5,6,7,8-tetrahydro-4-quinazolinyl]-1-piperazinyl]- [3].
CAS Reg No. 1512276-06-0, STN Entry Date Jan. 7, 2014; 1-Piperazineacetonitrile, 4-(5,6,7,8-tetrahydro-4-quinazolinyl- [3].
CAS Reg No. 1514723-35-3, STN Entry Date Jan. 9, 2014; Ethanone, 1-[1-(5,6,7,8-tetrahydro-4-quinazolinyl)-4-piperidinyl]- [3].

* cited by examiner

FUSED RING COMPOUNDS

CROSS REFERENCE TO RELATED APPLICATION

This application is a U.S. National Phase Application of PCT/CN2019/100814, filed on Aug. 15, 2019, which claims the benefit of priority to International Patent Application Ser. No. PCT/CN2018/100792, filed Aug. 16, 2018, the entire contents of which are incorporated by reference herein as if set forth in their entirety.

FIELD OF THE DISCLOSURE

This invention pertains to fused ring compounds of Formula (I), Formula (II), or Formula (III), as further detailed herein, which are used for the inhibition of Ras proteins, such as K-Ras, H-Ras, and N-Ras, as well as compositions comprising these compounds and methods of treatment by their administration.

BACKGROUND OF THE DISCLOSURE

Ras is a small GTP-binding protein that functions as a nucleotide-dependent switch for central growth signaling pathways. In response to extracellular signals, Ras is converted from a GDP-bound ($Ras^{GDP}$) to a GTP-bound ($Ras^{GTP}$) state, as catalyzed by guanine nucleotide exchange factors (GEFs), notably the SOS1 protein. Active $Ras^{GTP}$ mediates its diverse growth-stimulating functions through its direct interactions with effectors including Raf, PI3K, and Ral guanine nucleotide dissociation stimulator. The intrinsic GTPase activity of Ras then hydrolyzes GTP to GDP to terminate Ras signaling. The Ras GTPase activity can be further accelerated by its interactions with GTPase-activating proteins (GAPs), including the neurofibromin 1 tumor suppressor.

Mutant Ras has a reduced GTPase activity, which prolongs its activated conformation, thereby promoting Ras-dependent signaling and cancer cell survival or growth. Mutation in Ras which affects its ability to interact with GAP or to convert GTP back to GDP will result in a prolonged activation of the protein and consequently a prolonged signal to the cell telling it to continue to grow and divide. Because these signals result in cell growth and division, overactive RAS signaling may ultimately lead to cancer. Mutations in any one of the three main isoforms of RAS (H-Ras, N-Ras, or K-Ras) genes are common events in human tumorigenesis. Among the three Ras isoforms (K, N, and H), K-Ras is most frequently mutated.

The most common K-Ras mutations are found at residue G12 and G13 in the P-loop and at residue Q61. G12C is a frequent mutation of K-Ras gene (glycine-12 to cysteine). Mutations of Ras in cancer are associated with poor prognosis. Inactivation of oncogenic Ras in mice results in tumor shrinkage. Thus, Ras is widely considered an oncology target of exceptional importance.

SUMMARY OF THE DISCLOSURE

One aspect of the invention includes a compound of Formula (I):

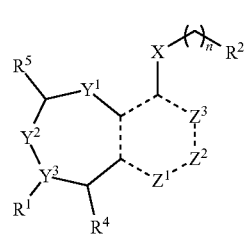

(I)

or a pharmaceutically acceptable salt thereof;
wherein,
$R^1$ is selected from the group consisting of H, $C_{6-10}$ aryl, 5- to 10-membered heteroaryl, and 5- to 10-membered heterocyclyl, wherein each aryl, heteroaryl, and heterocyclyl is optionally substituted with one to four substituents, wherein each substituent is independently selected from the group consisting of $C_{1-6}$ alkyl, $-NH_2$, $NH(CH_3)$, $-N(CH_3)_2$, halo, $C_{1-6}$ haloalkyl, oxo, $C_{1-6}$ hydroxyalkyl, $C_{3-6}$ cycloalkyl, $-OC(=O)CH=CH_2$, and hydroxy;

$R^2$ is an electrophilic moiety capable of forming a covalent bond with a cysteine residue at position 12 of a K-Ras G12C mutant protein;

$Y^1$ is $C(H)(R^6)$; or $Y^1$ is absent;

$Y^2$ is selected from the group consisting of $N(R^7)$ and $C(H)(R^8)$;

$Y^3$ is selected from the group consisting of $C(R^3)$ and N;

$Z^1$ is selected from the group consisting of N, $N(R^9)$, O, S, S(O), and $S(O)_2$;

$Z^2$ is $C(R^{10})$, $C(-L-R^{10a})$, or $Z^2$ is absent;

$Z^3$ is selected from the group consisting of N, $N(R^{11})$, and $C(R^{12})$;

$R^3$, $R^4$, $R^5$, $R^6$, $R^7$, $R^8$, $R^9$, $R^{10}$, $R^{11}$, and $R^{12}$ are each independently selected from the group consisting of H, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{2-6}$ alkynyl, $C_{1-6}$ alkylamino, amino, aryl, aryl substituted with a $C_{1-6}$ alkyl, $C_{1-6}$ aminoalkyl, carbamoyl, $C_{1-6}$ carbamoylalkyl, $C_{1-6}$ carboxyalkyl, cyano, $C_{1-6}$ cyanoalkyl, $C_{3-7}$ cycloalkyl, halo, $C_{1-6}$ haloalkoxy, $C_{1-6}$ haloalkyl, 5- to 10-membered heteroaryl, 4- to 10-membered heterocyclyl, hydroxy, and oxo;

or $R^1$ and $R^3$, together with the carbon to which they are bonded, may form an optionally substituted 3- to 6-membered cycloalkyl;

or $R^3$ and $R^4$, $R^3$ and $R^8$, $R^5$ and $R^6$, or $R^5$ and $R^8$, together with the atoms to which they are each bonded, may form a 3- to 6-membered cycloalkyl or a 3- to 6-membered heterocyclyl;

L is a bond, O, S, or $N(L^a)$;

$R^{10a}$ is selected from the group consisting of hydrogen, alkyl, hydroxyalkyl, dihydroxyalkyl, alkylaminylalkyl, dialkylaminylalkyl, $-L^b-NL^aL^c$, heterocyclyl, heterocyclylalkyl, aryl, heteroaryl, or heteroarylalkyl, wherein each of the $L^b$, heterocyclyl, heterocyclylalkyl, aryl, heteroaryl, and heteroarylalkyl may be optionally substituted with one or more $L^d$;

each $L^a$ is independently hydrogen or $C_{1-3}$ alkyl;

$L^b$ is $C_{1-4}$ alkylene;

each $L^c$ is independently hydrogen, acyl, $C_{1-3}$ alkyl, heteroalkyl, or hydroxyalkyl;

each $L^d$ is independently hydrogen, oxo, acyl, hydroxy, hydroxyalkyl, cyano, halogen, $C_{1-6}$ alkyl, aralkyl, haloalkyl, heteroalkyl, cycloalkyl, heterocyclylalkyl, alkoxy, dialkylaminyl, dialkylamidoalkyl, or dialkylaminylalkyl, wherein the $C_{1-6}$ alkyl may be optionally substituted with cycloalkyl;

X is selected from the group consisting of $C_{1-6}$ alkoxy, $C_{1-6}$ alkyl, amino, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of $C_{1-6}$ alkyl, amino, $C_{1-6}$ aminoalkyl, carbamoyl, $C_{1-6}$ carbamoylalkyl, carboxy, $C_{1-6}$ carboxyalkyl, cyano, $C_{1-6}$ cyanoalkyl, halo, $C_{1-6}$ haloalkyl, hydroxy, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

n is selected from 0, 1, and 2; and

------ represents a single bond or a double bond.

Another aspect of the invention includes a compound of Formula (II):

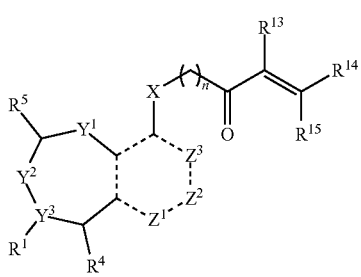

(II)

or a pharmaceutically acceptable salt thereof;
wherein, $R^1$ is selected from the group consisting of H, $C_{6-10}$ aryl, 5- to 10-membered heteroaryl, and 5- to 10-membered heterocyclyl, wherein each aryl, heteroaryl, and heterocyclyl is optionally substituted with one to four substituents, wherein each substituent is independently selected from the group consisting of $C_{1-6}$ alkyl, —NH$_2$, —NH(CH$_3$), —N(CH$_3$)$_2$, halo, $C_{1-6}$ haloalkyl, oxo, $C_{1-6}$ hydroxyalkyl, $C_{3-6}$ cycloalkyl, —OC(=O)CH=CH$_2$, and hydroxy;

$Y^1$ is C(H)(R$^6$); or $Y^1$ is absent;

$Y^2$ is selected from the group consisting of N(R$^7$) and C(H)(R$^8$);

$Y^3$ is selected from the group consisting of C(R$^3$) and N;

$Z^1$ is selected from the group consisting of N, N(R$^9$), O, S, S(O), and S(O)$_2$;

$Z^2$ is C(R$^{10}$), C(-L-R$^{10a}$), or $Z^2$ is absent;

$Z^3$ is selected from the group consisting of N, N(R''), and C(R$^{12}$);

$R^3$, $R^4$, $R^5$, $R^6$, $R^7$, $R^8$, $R^9$, $R^{10}$, $R^{11}$, and $R^{12}$ are each independently selected from the group consisting of H, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{2-6}$ alkynyl, $C_{1-6}$ alkylamino, amino, aryl, aryl substituted with a $C_{1-6}$ alkyl, $C_{1-6}$ aminoalkyl, carbamoyl, $C_{1-6}$ carbamoylalkyl, $C_{1-6}$ carboxyalkyl, cyano, $C_{1-6}$ cyanoalkyl, $C_{3-7}$ cycloalkyl, halo, $C_{1-6}$ haloalkoxy, $C_{1-6}$ haloalkyl, 5- to 10-membered heteroaryl, 4- to 10-membered heterocyclyl, hydroxy, and oxo;

or $R^1$ and $R^3$, together with the carbon to which they are bonded, may form an optionally substituted 3- to 6-membered cycloalkyl;

or $R^3$ and $R^4$, $R^3$ and $R^8$, $R^5$ and $R^6$, or $R^5$ and $R^8$, together with the atoms to which they are each bonded, may form a 3- to 6-membered cycloalkyl or a 3- to 6-membered heterocyclyl;

$R^{13}$ is selected from the group consisting of H, cyano, and halo; and $R^{14}$ and $R^{15}$ are each independently selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{3-6}$ cycloalkylamino, $C_{1-6}$ alkylsulfonylamino, $C_{6-12}$ dialkylamino, and $C_{1-6}$ haloalkoxy;

or $R^{13}$ and $R^{14}$ together form a triple bond between the carbons to which they are attached, or $R^{13}$ and $R^{14}$ together with the carbons to which they are each bonded form a $C_{3-7}$ cycloalkenyl optionally substituted with one or two halo substituents; and $R^{15}$ is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;

L is a bond, O, S, or N(L$^a$);

$R^{10a}$ is selected from the group consisting of hydrogen, alkyl, hydroxyalkyl, dihydroxyalkyl, alkylaminylalkyl, dialkylaminylalkyl, -L$^b$-NL$^a$L$^c$, heterocyclyl, heterocyclylalkyl, aryl, heteroaryl, or heteroarylalkyl, wherein each of the L$^b$, heterocyclyl, heterocyclylalkyl, aryl, heteroaryl, and heteroarylalkyl may be optionally substituted with one or more L$^d$;

each $L^a$ is independently hydrogen or $C_{1-3}$ alkyl;

$L^b$ is $C_{1-4}$ alkylene;

each $L^c$ is independently hydrogen, acyl, $C_{1-3}$ alkyl, heteroalkyl, or hydroxyalkyl;

each $L^d$ is independently hydrogen, oxo, acyl, hydroxy, hydroxyalkyl, cyano, halogen, $C_{1-6}$ alkyl, aralkyl, haloalkyl, heteroalkyl, cycloalkyl, heterocyclylalkyl, alkoxy, dialkylaminyl, dialkylamidoalkyl, or dialkylaminylalkyl, wherein the $C_{1-6}$alkyl may be optionally substituted with cycloalkyl;

X is selected from the group consisting of $C_{1-6}$ alkoxy, $C_{1-6}$ alkyl, amino, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of $C_{1-6}$ alkyl, amino, $C_{1-6}$ aminoalkyl, carbamoyl, $C_{1-6}$ carbamoylalkyl, carboxy, $C_{1-6}$ carboxyalkyl, cyano, $C_{1-6}$ cyanoalkyl, halo, $C_{1-6}$ haloalkyl, hydroxy, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

n is selected from 0, 1, and 2; and

------ represents a single bond or a double bond.

In another aspect, the invention includes a compound of Formula (III):

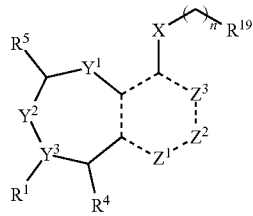

(III)

or a pharmaceutically acceptable salt thereof;
wherein, $R^1$ is selected from the group consisting of H, $C_{6-10}$ aryl, 5- to 10-membered heteroaryl, and 5- to 10-membered heterocyclyl, wherein each aryl, heteroaryl, and heterocyclyl is optionally substituted with one to four substituents, wherein each substituent is independently selected from the group consisting of $C_{1-6}$ alkyl, —$NH_2$, —$NH(CH_3)$, —$N(CH_3)_2$, halo, $C_{1-6}$ haloalkyl, oxo, $C_{1-6}$ hydroxyalkyl, $C_{3-6}$ cycloalkyl, —OC(=O)CH=$CH_2$, and hydroxy;

$Y^1$ is $C(H)(R^6)$; or $Y^1$ is absent;

$Y^2$ is selected from the group consisting of $N(R^7)$ and $C(H)(R^8)$;

$Y^3$ is selected from the group consisting of $C(R^3)$ and N;

$Z^1$ is selected from the group consisting of N, $N(R^9)$, O, S, S(O), and $S(O)_2$;

$Z^2$ is $C(R^{10})$, $C(-L-R^{10a})$, or $Z^2$ is absent;

$Z^3$ is selected from the group consisting of N, $N(R'')$, and $C(R^{12})$;

$R^3$, $R^4$, $R^5$, $R^6$, $R^7$, $R^8$, $R^9$, $R^{10}$, $R^{11}$, and $R^{12}$ are each independently selected from the group consisting of H, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{2-6}$ alkynyl, $C_{1-6}$ alkylamino, amino, aryl, aryl substituted with a $C_{1-6}$ alkyl, $C_{1-6}$ aminoalkyl, carbamoyl, $C_{1-6}$ carbamoylalkyl, $C_{1-6}$ carboxyalkyl, cyano, $C_{1-6}$ cyanoalkyl, $C_{3-7}$ cycloalkyl, halo, $C_{1-6}$ haloalkoxy, $C_{1-6}$ haloalkyl, 5- to 10-membered heteroaryl, 4- to 10-membered heterocyclyl, hydroxy, and oxo;

or $R^1$ and $R^3$, together with the carbon to which they are bonded, may form an optionally substituted 3- to 6-membered cycloalkyl;

or $R^3$ and $R^4$, $R^3$ and $R^8$, $R^5$ and $R^6$, or $R^5$ and $R^8$, together with the atoms to which they are each bonded, may form a 3- to 6-membered cycloalkyl or a 3- to 6-membered heterocyclyl;

$R^{19}$ is selected from the group consisting of oxiranyl, aziridinyl, and cyclopropyl, wherein the cyclopropyl is optionally substituted with at least one halogen;

L is a bond, O, S, or $N(L^a)$;

$R^{10a}$ is selected from the group consisting of hydrogen, alkyl, hydroxyalkyl, dihydroxyalkyl, alkylaminylalkyl, dialkylaminylalkyl, -$L^b$-$NL^aL^c$, heterocyclyl, heterocyclylalkyl, aryl, heteroaryl, or heteroarylalkyl, wherein each of the $L^b$, heterocyclyl, heterocyclylalkyl, aryl, heteroaryl, and heteroarylalkyl may be optionally substituted with one or more $L^d$;

each $L^a$ is independently hydrogen or $C_{1-3}$ alkyl;

$L^b$ is $C_{1-4}$ alkylene;

each $L^c$ is independently hydrogen, acyl, $C_{1-3}$ alkyl, heteroalkyl, or hydroxyalkyl;

each $L^d$ is independently hydrogen, oxo, acyl, hydroxy, hydroxyalkyl, cyano, halogen, $C_{1-6}$ alkyl, aralkyl, haloalkyl, heteroalkyl, cycloalkyl, heterocyclylalkyl, alkoxy, dialkylaminyl, dialkylamidoalkyl, or dialkylaminylalkyl, wherein the $C_{1-6}$alkyl may be optionally substituted with cycloalkyl;

X is selected from the group consisting of $C_{1-6}$ alkoxy, $C_{1-6}$ alkyl, amino, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of $C_{1-6}$ alkyl, amino, $C_{1-6}$ aminoalkyl, carbamoyl, $C_{1-6}$ carbamoylalkyl, carboxy, $C_{1-6}$ carboxyalkyl, cyano, $C_{1-6}$ cyanoalkyl, halo, $C_{1-6}$ haloalkyl, hydroxy, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

n is selected from 0, 1, and 2; and

------ represents a single bond or a double bond.

Another aspect of the invention includes a compound of Formula (IIa):

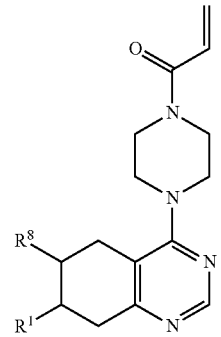

(IIa)

or a pharmaceutically acceptable salt thereof;

wherein $R^1$ and $R^8$ are each independently as defined above for Formula (I) or Formula (II).

Another aspect of the invention includes a compound of Formula (III):

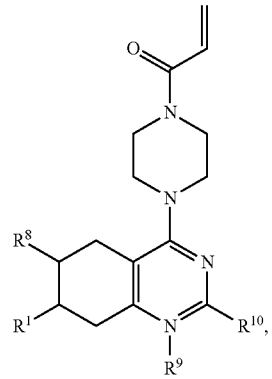

(III)

or a pharmaceutically acceptable salt thereof;

wherein $R^1$, $R^8$, $R^9$, and $R^{10}$ are each independently as defined above for Formula (I) or Formula (II).

Another aspect of the invention includes a compound of Formula (IIn):

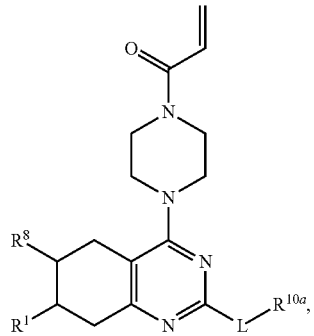

(IIn)

or a pharmaceutically acceptable salt thereof;
wherein $R^1$, $R^8$, L, and $R^{10a}$ are each independently as defined above for Formula (I) or Formula (II).

Another aspect of the invention includes a compound of Formula (IIm):

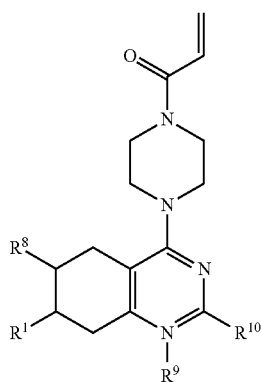

(IIm)

or a pharmaceutically acceptable salt thereof;
wherein $R^1$, $R^8$, $R^9$, and $R^{10}$ are each independently as defined above for Formula (I) or Formula (II).

Also provided is a pharmaceutical composition comprising a compound of the invention, or a pharmaceutically acceptable salt thereof, and a pharmaceutically acceptable excipient.

Another aspect includes a method of treating cancer comprising administering to an individual in need thereof a therapeutically effective amount of a compound of the invention, or a pharmaceutically acceptable salt thereof.

Another aspect includes a method of regulating activity of a mutant K-Ras G12C protein, the method comprising reacting the mutant protein with the compound of the invention, or a pharmaceutically acceptable salt thereof.

Another aspect includes a method of treating a disorder mediated by a K-Ras G12C mutation in an individual in need thereof, the method comprising: determining if the individual has the mutation; and if the individual is determined to have the mutation, then administering to the individual a therapeutically effective amount of the pharmaceutical composition of the invention.

Another aspect includes a method for preparing a labeled K-Ras G12C mutant protein, the method comprising reacting a K-Ras G12C mutant protein with a labeled compound of the invention, or a pharmaceutically acceptable salt thereof, to result in the labeled K-Ras G12C mutant protein.

Another aspect includes a method of inhibiting tumor metastasis, the method comprising administering a therapeutically effective amount of a compound of the invention, or a pharmaceutically acceptable salt thereof, or a pharmaceutical composition of the invention to an individual in need thereof.

Another aspect includes a method for tumor-agnostic treatment of cancer in an individual in need thereof, the method comprising determining if the individual has a tumor with a G12C mutation in a K-Ras, H-Ras, or N-Ras protein in the tumor; and, if the individual has a tumor with the mutation, administering a therapeutically effective amount of a compound of the invention, or a pharmaceutically acceptable salt thereof, or a pharmaceutical composition of the invention to the individual.

DETAILED DESCRIPTION OF THE DISCLOSURE

Definitions

The term "halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical. In one example, the alkyl radical is one to eighteen carbon atoms ($C_{1-18}$). In other examples, the alkyl radical is $C_{1-12}$, $C_{1-10}$, $C_{1-8}$, $C_{1-6}$, $C_{1-5}$, $C_{1-4}$, or $C_{1-3}$. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl and 1-octyl.

The term "amino" refers to —$NH_2$.
The term "alkylamino" refers to —NH-alkyl.
The term "cycloalkylamino" refers to —NH-cycloalkyl.
The term "dialkylamino" refers to —$N(alkyl)_2$.
The term "oxo" refers to =O.
The term "carboxy" refers to —C(=O)OH.
The term "carbamoyl" refers to —C(=O)$NH_2$.
The term "alkanoyl" refers to —C(=O)-alkyl.
The term "alkanoylamino" refers to —NH—C(=O)-alkyl.
The term "alkoxy" refers to —O-alkyl.
The term "alkylsulfanyl" refers to —S(=O)-alkyl.
The term "alkylsulfonyl" refers to —$S(=O)_2$-alkyl.
The term "alkylsulfonylamino" refers to —NH—$S(=O)_2$-alkyl.
The term "alkylthio" refers to —S-alkyl.

The term "aminoalkyl" refers to alkyl substituted with one amino substituent.

The term "carbamoylalkyl" refers to alkyl substituted with one carbamoyl substituent.

The term "carboxyalkyl" refers to alkyl substituted with one carboxy substituent.

The terms "cyano" or "nitrile" refers to —C≡N or —CN.

The term "cyanoalkyl" refers to alkyl substituted with one cyano substituent.

The term "haloalkoxy" refers to —O-haloalkyl.

The term "heterocyclylamino" refers to —NH-heterocyclyl.

The term "hydroxy" refers to —OH.

The term "hydroxyalkyl" refers to alkyl substituted with one hydroxy substituent.

The term "alkenyl" refers to linear or branched-chain monovalent hydrocarbon radical with at least one carbon-carbon double bond, and includes radicals having "cis" and "trans" orientations, or alternatively, "E" and "Z" orientations. In one example, the alkenyl radical is two to eighteen carbon atoms ($C_{2-18}$). In other examples, the alkenyl radical is $C_{2-12}$, $C_{2-10}$, $C_{2-8}$, $C_{2-6}$, or $C_{2-3}$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl.

The term "alkynyl" refers to a linear or branched monovalent hydrocarbon radical with at least one carbon-carbon, triple bond. In one example, the alkynyl radical is two to eighteen carbon atoms ($C_{2-18}$). In other examples, the alkynyl radical is $C_{2-12}$, $C_{2-10}$, $C_{2-8}$, $C_{2-6}$, or $C_{2-3}$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl, and but-3-ynyl.

The term "alkylene" refers to a saturated, branched, or straight chain hydrocarbon group having two monovalent radical centers derived by the removal of two hydrogen atoms from the same or two different carbon atoms of a parent alkane. In one example, the divalent alkylene group is one to eighteen carbon atoms ($C_{1-18}$). In other examples, the divalent alkylene group is $C_{1-12}$, $C_{1-10}$, $C_{1-8}$, $C_{1-6}$, $C_{1-5}$, $C_{1-4}$, or $C_{1-3}$. Example alkylene groups include methylene (—CH$_2$—), 1,1-ethyl (—CH(CH$_3$)—), (1,2-ethyl (—CH$_2$CH$_2$—), 1,1-propyl (—CH(CH$_2$CH$_3$)—), 2,2-propyl (—C(CH$_3$)$_2$—), 1,2-propyl (—CH(CH$_3$)CH$_2$—), 1,3-propyl (—CH$_2$CH$_2$CH$_2$—), 1,1-dimethyleth-1,2-yl (—C(CH$_3$)$_2$CH$_2$—), 1,4-butyl (—CH$_2$CH$_2$CH$_2$CH$_2$—), and the like.

The term "aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl.

The term "cycloalkyl" refers to a saturated hydrocarbon ring group. Cycloalkyl encompasses mono-, bi-, tricyclic, spiro and bridged, saturated ring systems. In one example, the cycloalkyl group is 3 to 12 carbon atoms ($C_{3-12}$). In other examples, cycloalkyl is $C_{3-7}$, $C_{3-8}$, $C_{3-10}$, or $C_{5-10}$. In other examples, the cycloalkyl group, as a monocycle, is $C_{3-8}$, $C_{3-6}$, or $C_{5-6}$. In another example, the cycloalkyl group, as a bicycle, is $C_7$-$C_{12}$. In another example, the cycloalkyl group, as a spiro system, is $C_{5-12}$. Examples of monocyclic cycloalkyl include cyclopropyl, cyclobutyl, cyclopentyl, cyclohexyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spirocycloalkyl include, spiro[2.2]pentane, spiro[2.3]hexane, spiro[2.4]heptane, spiro[2.5]octane and spiro[4.5]decane.

The term "cycloalkenyl" refers to a non-aromatic, hydrocarbon ring group with at least one carbon-carbon double bond. Cycloalkenyl encompasses mono-, bi-, bicyclic, spiro or bridged, saturated ring systems. Examples of monocyclic cycloalkenyl include 1-cyclopent-1-enyl, 1-cyclopent-2-enyl, 1-cyclopent-3-enyl, 1-cyclohex-1-enyl, 1-cyclohex-2-enyl, 1-cyclohex-3-enyl, and cyclohexadienyl. Exemplary arrangements of bicyclic cycloalkenyls having 7 to 12 ring atoms include, but are not limited to, [4,4], [4,5], [5,5], [5,6] or [6,6] ring systems. Exemplary bridged bicyclic cycloalkenyls include, but are not limited to, bicyclo[2.2.1]heptene, bicyclo[2.2.2]octene and bicyclo[3.2.2]nonene. Examples of spiro cycloalkyl include, spiro[2.2]pentene, spiro[2.3]hexene, spiro[2.4]heptene, spiro[2.5]octene and spiro[4.5]decene.

The terms "heterocyclic group", "heterocyclic", "heterocycle", "heterocyclyl", or "heterocyclo" are used interchangeably and refer to any mono-, bi-, tricyclic, spiro or bridged, saturated, partially saturated or unsaturated, non-aromatic ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles, spiro, and bridged ring systems, wherein the ring atoms are carbon, where at least one atom in the ring or ring system is a heteroatom selected from nitrogen, sulfur or oxygen. In other examples, heterocyclyl includes 4-10 or 5-10 ring atoms. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$OH$^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, 1,1-dioxoisothiazolyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-onyl, azaspiro[5.5]undecanyl, tetrahydroindolyl, octahydroindolyl, tetrahydroisoindolyl, tetrahydroindazolyl, 1,1-dioxohexahydrothiopyranyl.

The term "heteroaryl" refers to any mono-, bi-, or tricyclic aromatic ring system containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) 13$^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl, indazolyl and indolyl.

In particular embodiments, a heterocyclyl group or a heteroaryl group is attached at a carbon atom of the heterocyclyl group or the heteroaryl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group or heteroaryl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Fused" refers to any ring structure described herein that shares one or more atoms (e.g., carbon or nitrogen atoms) with an existing ring structure in the compounds of the invention.

The term "acyl" refers to a carbonyl containing substituent represented by the formula —C(=O)—R in which R is a substituent such as hydrogen, alkyl, cycloalkyl, aryl or heterocyclyl, wherein the alkyl, cycloalkyl, aryl and heterocyclyl are as defined herein. Acyl groups include alkanoyl (e.g., acetyl), aroyl (e.g., benzoyl), and heteroaroyl (e.g., pyridinoyl).

The term "alkylaminylalkyl" refers to -alkyl-NR$^x$-alky, wherein R$^x$ is hydrogen.

An "aralkyl" group comprises an aryl group covalently linked to an alkyl group, either of which may independently be optionally substituted or unsubstituted. An example of an aralkyl group is $(C_{1-6})$alkyl$(C_{6-10})$aryl, including, without limitation, benzyl, phenethyl, and naphthylmethyl. An example of a substituted aralkyl is where the alkyl group is substituted with hydroxyalkyl.

The term "dialkylaminyl" refers to —N(R$^y$)$_2$, wherein each R$^y$ is $C_{1-3}$ alkyl.

The term "dialkylaminylalkyl" refers to -alkyl-N(R$^y$)$_2$, wherein each R$^y$ is $C_{1-4}$ alkyl, wherein the alkyl of the -alkyl-N(R$^y$)$_2$ may be optionally substituted with hydroxy or hydroxyalkyl.

The term "dihydroxyalkyl" refers to a n alkyl group as defined herein wherein two carbon atoms are each substituted with a hydroxy group.

The term "haloalkyl" refers to an alkyl chain in which one or more hydrogen has been replaced by a halogen. Examples of haloalkyls are trifluoromethyl, difluoromethyl, and fluoromethyl.

The term "heteroalkyl" refers to an alkyl group, as defined herein, wherein one or more carbon atoms in the chain are replaced by a heteroatom selected from the group consisting of O, S, and N.

The term "heterocyclylalkyl" refers to a heterocyclyl group as defined herein linked to the remaining portion of the molecule via an alkyl linker, wherein the alkyl linker of the heterocyclylalkyl may be optionally substituted with hydroxy or hydroxyalkyl.

A "heteroarylalkyl" group comprises a heteroaryl group covalently linked to an alkyl group, wherein the radical is on the alkyl group, either of which is independently optionally substituted or unsubstituted. Examples of heteroarylalkyl groups include a heteroaryl group having 5, 6, 9, or 10 ring atoms bonded to a $C_{1-6}$ alkyl group. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl, quinazolinylmethyl, quinolinylmethyl, quinolinylethyl, benzofuranylmethyl, indolinylethyl, isoquinolinylmethyl, isoinodylmethyl, cinnolinylmethyl, and benzothiophenylethyl. Specifically excluded from the scope of this term are compounds having adjacent annular O and/or S atoms.

The terms "compound(s) of the invention," and "compound(s) of the present invention" and the like, unless otherwise indicated, include compounds of Formula (I), Formula (II), and Formula (III) and the compounds listed in the Tables herein, including stereoisomers (including atropisomers), geometric isomers, tautomers, isotopes, and salts (e.g., pharmaceutically acceptable salts) thereof.

The term "optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

As used herein a wavy line "〜〜" that intersects a bond in a chemical structure indicate the point of attachment of the atom to which the wavy bond is connected in the chemical structure to the remainder of a molecule, or to the remainder of a fragment of a molecule. Where the chemical structure contains two wavy lines intersecting a bond, the structure may be connected to the remainder of a molecule or to the remainder of a fragment of a molecule in either orientation.

In certain embodiments, divalent groups are described generically without specific bonding configurations. It is understood that the generic description is meant to include both bonding configurations, unless specified otherwise. For example, in the group $R^1$—$R^2$—$R^3$, if the group $R^2$ is described as —$CH_2C(O)$—, then it is understood that this group can be bonded both as $R^1$—$CH_2C(O)$—$R^3$, and as $R^1$—$C(O)CH_2$—$R^3$, unless specified otherwise.

The term "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

The term "pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulfate, phosphate, acetate, fumarate, maleate, tartrate, lactate, citrate, pyruvate, succinate, oxalate, methanesulfonate, p-toluenesulfonate, bisulfate, benzenesulfonate, ethanesulfonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulfonate, 2-naphthalenesulfonate, 2,5-dichlorobenzenesulfonate, D-mandelate, L-mandelate, cinnamate, benzoate, adipate, esylate, malonate, mesitylate (2-mesitylenesulfonate), napsylate (2-naphthalenesulfonate), camsylate (camphor-10-sulfonate, for example (1S)-(+)-10-camphorsulfonic acid salt), glutamate, glutarate, hippurate (2-(benzoylamino)acetate), orotate, xylate (p-xylene-2-sulfonate), and pamoic (2,2'-dihydroxy-1,1'-dinaphthylmethane-3,3'-dicarboxylate).

A "sterile" formulation is aseptic or free from all living microorganisms and their spores.

The term "stereoisomers" refer to compounds that have identical chemical constitution, but differ with regard to the arrangement of the atoms or groups in space. Stereoisomers include diastereomers, enantiomers, conformers and the like.

The term "chiral" refers to molecules which have the property of non-superimposability of the mirror image partner, while the term "achiral" refers to molecules which are superimposable on their mirror image partner.

The term "diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

The term "enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

"Atropisomers" are stereoisomers arising because of hindered rotation around a single bond, where energy differences due to steric strain or other contributors create a barrier to rotation that is high enough to allow for isolation of individual conformers.

Certain compounds of the invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

The invention described herein also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds of the present invention (e.g., those labeled with $^{3}H$ and $^{14}C$) are useful in compound and/or substrate tissue distribution assays. Tritiated (H) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

The term "amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-methoxybenzyl), Boc (tert-butyloxycarbonyl), Fmoc (9-fluorenylmethyloxycarbonyl) and Cbz (carbobenzyloxy). Further examples of these groups are found in T. W. Greene and P. G. M. Wuts, "Protecting Groups in Organic Synthesis, 3 ed., John Wiley & Sons, Inc., 1999. The term "protected amino" refers to an amino group substituted with one of the above amino-protecting groups.

The term "carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, 3 ed., John Wiley & Sons, Inc., 1999. The term "protected carboxy" refers to a carboxy group substituted with one of the above carboxy-protecting groups.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the invention including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, —CO—R, —CO—OR, or —CO—O—R—O—CO—R, where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of the invention. Prodrugs may be prepared by reacting a compound of the present invention with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at temperatures such as about −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention can be derivatized as an amide or alkyl ester. As another example, compounds of the invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

The term "leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of to a patient, the patient is typically in need thereof.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

A "therapeutically effective amount" means an amount of a compound of the present invention, such as a compound of Formula (I) and Formula (II), that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis ("prophylactic treatment") or during the course of clinical pathology ("therapeutic treatment"). Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function of a target protein, whether by inhibiting the activity or expression of the protein, such as K-Ras, H-Ras or N-Ras G12C. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, diffuse large B-Cell lymphoma (DLBCL), central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

When a substituent is depicted herein as attaching at the center of a ring, it should be understood that the substituent may attach at any position on the ring. If the ring is a bicyclic fused ring system, the substituent may attach at any position on either ring in the bicyclic ring system.

Unless otherwise stated, structures depicted herein are also meant to include compounds that differ only in the presence of one or more isotopically enriched atoms. Exemplary isotopes that can be incorporated into compounds of the invention, include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds of the invention, one or more carbon atoms are replaced by $^{13}C$- or $^{14}C$-enriched carbon. Positron emitting isotopes such as $^{15}$O, $^{13}$N, $^{11}$C, and $^{18}$F are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Ras Inhibitors

In an aspect, the invention provides compounds which are capable of selectively binding to and/or modulating a G12C mutant K-Ras, H-Ras or N-Ras protein. In one embodiment, the invention provides compounds capable of selectively binding to and/or modulating a G12C mutant K-Ras protein.

As noted, one aspect of the invention includes a compound of Formula (I):

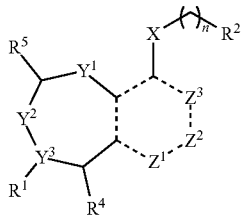

or a pharmaceutically acceptable salt thereof;
wherein,
$R^1$ is selected from the group consisting of H, $C_{6-10}$ aryl, 5- to 10-membered heteroaryl, and 5- to 10-membered heterocyclyl, wherein each aryl, heteroaryl, and heterocyclyl is optionally substituted with one to four substituents, wherein each substituent is independently selected from the group consisting of $C_{1-6}$ alkyl, $-NH_2$, $-NH(CH_3)$, $-N(CH_3)_2$, halo, $C_{1-6}$haloalkyl, oxo, $C_{1-6}$ hydroxyalkyl, $C_{3-6}$ cycloalkyl, $-OC(=O)CH=CH_2$, and hydroxy;
$R^2$ is an electrophilic moiety capable of forming a covalent bond with a cysteine residue at position 12 of a Ras G12C mutant protein;
$Y^1$ is $C(H)(R^6)$; or $Y^1$ is absent;
$Y^2$ is selected from the group consisting of $N(R^7)$ and $C(H)(R^8)$;

$Y^3$ is selected from the group consisting of $C(R^3)$ and N;
$Z^1$ is selected from the group consisting of N, $N(R^9)$, O, S, S(O), and $S(O)_2$;
$Z^2$ is $C(R^{10})$, $C(-L-R^{10a})$, or $Z^2$ is absent;
$Z^3$ is selected from the group consisting of N, $N(R^{11})$, and $C(R^{12})$;
$R^3$, $R^4$, $R^5$, $R^6$, $R^7$, $R^8$, $R^9$, $R^{10}$, $R^{11}$, and $R^{12}$ are each independently selected from the group consisting of H, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{2-6}$ alkynyl, $C_{1-6}$ alkylamino, amino, aryl, aryl substituted with a $C_{1-6}$ alkyl, $C_{1-6}$ aminoalkyl, carbamoyl, $C_{1-6}$ carbamoylalkyl, $C_{1-6}$ carboxyalkyl, cyano, $C_{1-6}$ cyanoalkyl, $C_{3-7}$ cycloalkyl, halo, $C_{1-6}$ haloalkoxy, $C_{1-6}$ haloalkyl, 5- to 10-membered heteroaryl, 4- to 10-membered heterocyclyl, hydroxy, and oxo;
or $R^1$ and $R^3$, together with the carbon to which they are bonded, may form an optionally substituted 3- to 6-membered cycloalkyl;
or $R^3$ and $R^4$, $R^3$ and $R^8$, $R^5$ and $R^6$, or $R^5$ and $R^8$, together with the atoms to which they are each bonded, may form a 3- to 6-membered cycloalkyl or a 3- to 6-membered heterocyclyl;
L is a bond, O, S, or $N(L^a)$;
$R^{10a}$ is selected from the group consisting of hydrogen, alkyl, hydroxyalkyl, dihydroxyalkyl, alkylaminylalkyl, dialkylaminylalkyl, $-L^b-NL^aL^c$, heterocyclyl, heterocyclylalkyl, aryl, heteroaryl, or heteroarylalkyl, wherein each of the $L^b$, heterocyclyl, heterocyclylalkyl, aryl, heteroaryl, and heteroarylalkyl may be optionally substituted with one or more $L^d$;
 each $L^a$ is independently hydrogen or $C_{1-3}$ alkyl;
 $L^b$ is $C_{1-4}$ alkylene;
 each $L^c$ is independently hydrogen, acyl, $C_{1-3}$ alkyl, heteroalkyl, or hydroxyalkyl;
 each $L^d$ is independently hydrogen, oxo, acyl, hydroxy, hydroxyalkyl, cyano, halogen, ($C_{1-6}$ alkyl, aralkyl, haloalkyl, heteroalkyl, cycloalkyl, heterocyclylalkyl, alkoxy, dialkylaminyl, dialkylamidoalkyl, or dialkylaminylalkyl, wherein the $C_{1-6}$alkyl may be optionally substituted with cycloalkyl;
X is selected from the group consisting of $C_{1-6}$ alkoxy, $C_{1-6}$ alkyl, amino, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of $C_{1-6}$ alkyl, amino, $C_{1-6}$ aminoalkyl, carbamoyl, $C_{1-6}$ carbamoylalkyl, carboxy, $C_{1-6}$ carboxyalkyl, cyano, $C_{1-6}$ cyanoalkyl, halo, $C_{1-6}$ haloalkyl, hydroxy, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;
n is selected from 0, 1, and 2; and
------ represents a single bond or a double bond.

According to some embodiments of the compound of Formula (I), or a pharmaceutically acceptable salt thereof $R^2$ is an electrophilic moiety capable of forming a covalent bond with a cysteine residue at position 12 of a K-Ras G12C mutant protein.

According to some embodiments of the compound of Formula (I), or a pharmaceutically acceptable salt thereof $R^2$ is an electrophilic moiety capable of forming a covalent bond with a cysteine residue at position 12 of a H-Ras G12C mutant protein According to some embodiments of the compound of Formula (I), or a pharmaceutically acceptable salt thereof $R^2$ is an electrophilic moiety capable of forming a covalent bond with a cysteine residue at position 12 of a N-Ras G12C mutant protein In the above definition of $R^2$, the electrophilic moiety that is capable of forming a covalent bond with a cysteine residue is determined via K-Ras G12C-alkylation studies and Homogeneous Time Resolved Fluorescence (HTRF) assays. The G12C mutation of the K-Ras gene is a change in amino acid from glycine to cysteine at the 12th amino acid. The compounds according to the present disclosure were discovered using the HTRF assay and the K-Ras G12C-alkylation assay, as further detailed elsewhere herein below, and then NMR spectroscopy was later used to validate the specificity with which the molecule was attaching to G12C.

In another aspect, the invention includes a compound of Formula (II):

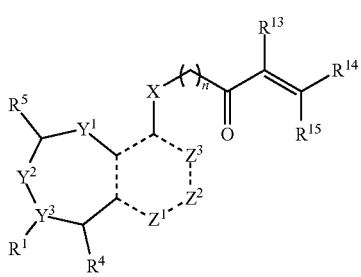

(II)

or a pharmaceutically acceptable salt thereof;
wherein, $R^1$ is selected from the group consisting of H, $C_{6-10}$ aryl, 5- to 10-membered heteroaryl, and 5- to 10-membered heterocyclyl, wherein each aryl, heteroaryl, and heterocyclyl is optionally substituted with one to four substituents, wherein each substituent is independently selected from the group consisting of $C_{1-6}$ alkyl, $-NH_2$, $-NH(CH_3)$, $-N(CH_3)_2$, halo, $C_{1-6}$ haloalkyl, oxo, $C_{1-6}$ hydroxyalkyl, $C_{3-6}$ cycloalkyl, $-OC(=O)CH=CH_2$, and hydroxy;

$Y^1$ is $C(H)(R^6)$; or $Y^1$ is absent;

$Y^2$ is selected from the group consisting of $N(R^7)$ and $C(H)(R^8)$;

$Y^3$ is selected from the group consisting of $C(R^3)$ and N;

$Z^1$ is selected from the group consisting of N, $N(R^9)$, O, S, S(O), and $S(O)_2$;

$Z^2$ is $C(R^{10})$, $C(-L-R^{10a})$, or $Z^2$ is absent;

$Z^3$ is selected from the group consisting of N, $N(R'')$, and $C(R^{12})$;

$R^3$, $R^4$, $R^5$, $R^6$, $R^7$, $R^8$, $R^9$, $R^{10}$, $R^{11}$, and $R^{12}$ are each independently selected from the group consisting of H, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{2-6}$ alkynyl, $C_{1-6}$ alkylamino, amino, aryl, aryl substituted with a $C_{1-6}$ alkyl, $C_{1-6}$ aminoalkyl, carbamoyl, $C_{1-6}$ carbamoylalkyl, $C_{1-6}$ carboxyalkyl, cyano, $C_{1-6}$ cyanoalkyl, $C_{3-7}$ cycloalkyl, halo, $C_{1-6}$ haloalkoxy, $C_{1-6}$ haloalkyl, 5- to 10-membered heteroaryl, 4- to 10-membered heterocyclyl, hydroxy, and oxo;

or $R^1$ and $R^3$, together with the carbon to which they are bonded, may form an optionally substituted 3- to 6-membered cycloalkyl;

or $R^3$ and $R^4$, $R^3$ and $R^8$, $R^5$ and $R^6$, or $R^5$ and $R^8$, together with the atoms to which they are each bonded, may form a 3- to 6-membered cycloalkyl or a 3- to 6-membered heterocyclyl;

$R^{13}$ is selected from the group consisting of H, cyano, and halo; and $R^{14}$ and $R^{15}$ are each independently selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{3-6}$ cycloalkylamino, $C_{1-6}$ alkylsulfonylamino, $C_{6-12}$ dialkylamino, and $C_{1-6}$ haloalkoxy;

or $R^{13}$ and $R^{14}$ together form a triple bond between the carbons to which they are attached, or $R^{13}$ and $R^{14}$ together with the carbons to which they are each bonded form a $C_{3-7}$ cycloalkenyl optionally substituted with one or two halo substituents; and $R^{15}$ is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;

L is a bond, O, S, or $N(L^a)$;

$R^{10a}$ is selected from the group consisting of hydrogen, alkyl, hydroxyalkyl, dihydroxyalkyl, alkylaminylalkyl, dialkylaminylalkyl, $-L^b-NL^aL^c$, heterocyclyl, heterocyclylalkyl, aryl, heteroaryl, or heteroarylalkyl, wherein each of the $L^b$, heterocyclyl, heterocyclylalkyl, aryl, heteroaryl, and heteroarylalkyl may be optionally substituted with one or more $L^d$;

each $L^a$ is independently hydrogen or $C_{1-3}$ alkyl;

$L^b$ is $C_{1-4}$ alkylene;

each $L^c$ is independently hydrogen, acyl, $C_{1-3}$ alkyl, heteroalkyl, or hydroxyalkyl;

each $L^d$ is independently hydrogen, oxo, acyl, hydroxy, hydroxyalkyl, cyano, halogen, $C_{1-6}$ alkyl, aralkyl, haloalkyl, heteroalkyl, cycloalkyl, heterocyclylalkyl, alkoxy, dialkylaminyl, dialkylamidoalkyl, or dialkylaminylalkyl, wherein the $C_{1-6}$alkyl may be optionally substituted with cycloalkyl;

X is selected from the group consisting of $C_{1-6}$ alkoxy, $C_{1-6}$ alkyl, amino, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of $C_{1-6}$ alkyl, amino, $C_{1-6}$ aminoalkyl, carbamoyl, $C_{1-6}$ carbamoylalkyl, carboxy, $C_{1-6}$ carboxyalkyl, cyano, $C_{1-6}$ cyanoalkyl, halo, $C_{1-6}$ haloalkyl, hydroxy, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

n is selected from 0, 1, and 2; and

------ represents a single bond or a double bond.

In another aspect, the invention includes a compound of Formula (III):

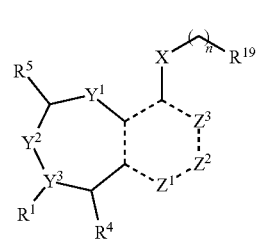

(III)

or a pharmaceutically acceptable salt thereof;
wherein,
$R^1$ is selected from the group consisting of H, $C_{6-10}$ aryl, 5- to 10-membered heteroaryl, and 5- to 10-membered heterocyclyl, wherein each aryl, heteroaryl, and heterocyclyl is optionally substituted with one to four substituents, wherein each substituent is independently selected from the group consisting of $C_{1-6}$ alkyl, —$NH_2$, —$NH(CH_3)$, —$N(CH_3)_2$, halo, $C_{1-6}$ haloalkyl, oxo, $C_{1-6}$ hydroxyalkyl, $C_{3-6}$ cycloalkyl, —OC(=O)CH=$CH_2$, and hydroxy;

$Y^1$ is C(H)($R^6$); or $Y^1$ is absent;

$Y^2$ is selected from the group consisting of N($R^7$) and C(H)($R^8$);

$Y^3$ is selected from the group consisting of C($R^3$) and N;

$Z^1$ is selected from the group consisting of N, N($R^9$), O, S, S(O), and S(O)$_2$;

$Z^2$ is C($R^{10}$), C(-L-$R^{10a}$), or $Z^2$ is absent;

$Z^3$ is selected from the group consisting of N, N(R″), and C($R^{12}$);

$R^3$, $R^4$, $R^5$, $R^6$, $R^7$, $R^8$, $R^9$, $R^{10}$, $R^{11}$, and $R^{12}$ are each independently selected from the group consisting of H, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{2-6}$ alkynyl, $C_{1-6}$ alkylamino, amino, aryl, aryl substituted with a $C_{1-6}$ alkyl, $C_{1-6}$ aminoalkyl, carbamoyl, $C_{1-6}$ carbamoylalkyl, $C_{1-6}$ carboxyalkyl, cyano, $C_{1-6}$ cyanoalkyl, $C_{3-7}$ cycloalkyl, halo, $C_{1-6}$ haloalkoxy, $C_{1-6}$ haloalkyl, 5- to 10-membered heteroaryl, 4- to 10-membered heterocyclyl, hydroxy, and oxo;

or $R^1$ and $R^3$, together with the carbon to which they are bonded, may form an optionally substituted 3- to 6-membered cycloalkyl;

or $R^3$ and $R^4$, $R^3$ and $R^8$, $R^5$ and $R^6$, or $R^5$ and $R^8$, together with the atoms to which they are each bonded, may form a 3- to 6-membered cycloalkyl or a 3- to 6-membered heterocyclyl;

$R^{19}$ is selected from the group consisting of oxiranyl, aziridinyl, and cyclopropyl, wherein the cyclopropyl is optionally substituted with at least one halogen;

L is a bond, O, S, or N($L^a$);

$R^{10a}$ is selected from the group consisting of hydrogen, alkyl, hydroxyalkyl, dihydroxyalkyl, alkylaminylalkyl, dialkylaminylalkyl, -$L^b$-N$L^aL^c$, heterocyclyl, heterocyclylalkyl, aryl, heteroaryl, or heteroarylalkyl, wherein each of the $L^b$, heterocyclyl, heterocyclylalkyl, aryl, heteroaryl, and heteroarylalkyl may be optionally substituted with one or more $L^d$;

each $L^a$ is independently hydrogen or $C_{1-3}$ alkyl;

$L^b$ is $C_{1-4}$ alkylene;

each $L^c$ is independently hydrogen, acyl, $C_{1-3}$ alkyl, heteroalkyl, or hydroxyalkyl;

each $L^d$ is independently hydrogen, oxo, acyl, hydroxy, hydroxyalkyl, cyano, halogen, $C_{1-6}$ alkyl, aralkyl, haloalkyl, heteroalkyl, cycloalkyl, heterocyclylalkyl, alkoxy, dialkylaminyl, dialkylamidoalkyl, or dialkylaminylalkyl, wherein the $C_{1-6}$alkyl may be optionally substituted with cycloalkyl;

X is selected from the group consisting of $C_{1-6}$ alkoxy, $C_{1-6}$ alkyl, amino, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of $C_{1-6}$ alkyl, amino, $C_{1-6}$ aminoalkyl, carbamoyl, $C_{1-6}$ carbamoylalkyl, carboxy, $C_{1-6}$ carboxyalkyl, cyano, $C_{1-6}$ cyanoalkyl, halo, $C_{1-6}$ haloalkyl, hydroxy, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

n is selected from 0, 1, and 2; and

------ represents a single bond or a double bond.

According to some embodiments of the compound of Formula (I), Formula (II), or Formula (III), or a pharmaceutically acceptable salt thereof, three of the ------ bonds are single bonds and two or three of the ------ bonds are double bonds. More particularly, according to some embodiments of the compound of Formula (I), Formula (II), or Formula (III), or a pharmaceutically acceptable salt thereof, the ------ bonds are defined such that the ring containing these bonds is heteroaromatic. According to another embodiment of the compound of Formula (I), Formula (II), or Formula (III), or a pharmaceutically acceptable salt thereof, four of the ------ bonds are single bonds and two of the ------ bonds are double bonds.

According to some embodiments of the compound of Formula (I), Formula (II), or Formula (III), or a pharmaceutically acceptable salt thereof, $R^1$ is $C_{6-10}$ aryl optionally substituted with one to four substituents, wherein each substituent is independently selected from the group consisting of $C_{1-6}$ alkyl, —$NH_2$, halo, $C_{1-6}$ haloalkyl, oxo, $C_{1-6}$ hydroxyalkyl, —OC(=O)CH=$CH_2$, and hydroxy.

According to some embodiments of the compound of Formula (I), Formula (II), or Formula (III), or a pharmaceutically acceptable salt thereof, $R^1$ is selected from the group consisting of

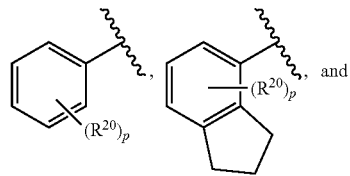, and

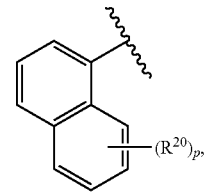, wherein each $R^{20}$ is independently selected from the group consisting of $C_{1-6}$ alkyl, —$NH_2$, halo, $C_{1-6}$ haloalkyl, hydroxy, $C_{1-6}$ hydroxyalkyl, $C_{3-6}$ cycloalkyl, and —OC(=O)CH=$CH_2$, and p is 0, 1, 2, 3, or 4. In one embodiment, each $R^{20}$ is independently selected from the group consisting of $C_{1-6}$ alkyl, —$NH_2$, —$NH(CH_3)$, —$N(CH_3)_2$, halo, $C_{1-6}$ haloalkyl, $C_{1-6}$ hydroxyalkyl, —OC(=O)CH=$CH_2$, and hydroxy, and p is 0, 1, 2, 3, or 4.

According to some embodiments of the compound of Formula (I), Formula (II), or Formula (III), or a pharmaceutically acceptable salt thereof, $R^1$ is selected from the group consisting of

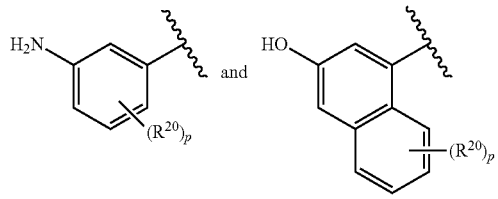

wherein each $R^{20}$ is independently selected from the group consisting of $C_{1-6}$ alkyl, —$NH_2$, halo, $C_{1-6}$ haloalkyl, hydroxy, $C_{1-6}$ hydroxyalkyl, $C_{3-6}$ cycloalkyl, and —OC(=O)CH=CH$_2$, and p is 0, 1, 2, 3, or 4. In one embodiment, each $R^{20}$ is independently selected from the group consisting of $C_{1-6}$ alkyl, —$NH_2$, —NH($CH_3$), —N($CH_3$)$_2$, halo, $C_{1-6}$ haloalkyl, $C_{1-6}$ hydroxyalkyl, —OC(=O)CH=CH$_2$, and hydroxy, and p is 0, 1, 2, 3, or 4.

According to some embodiments of the compound of Formula (I), Formula (II), or Formula (III), or a pharmaceutically acceptable salt thereof, $R^1$ is selected from the group consisting of

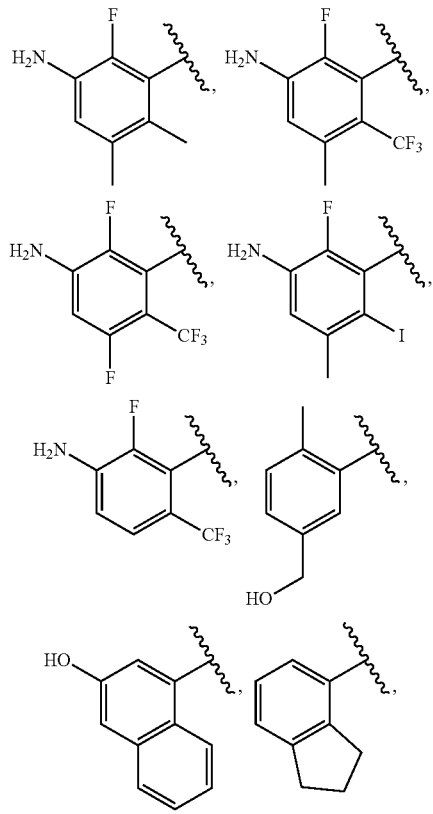

According to some embodiments of the compound of Formula (I), Formula (II), or Formula (III), or a pharmaceutically acceptable salt thereof, $R^1$ is selected from the group consisting of

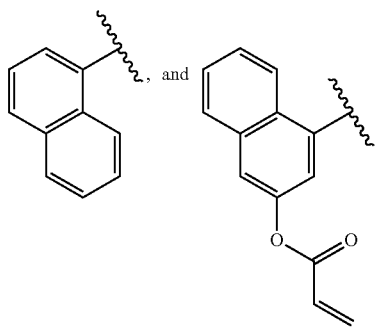

According to some embodiments of the compound of Formula (I), Formula (II), or Formula (III), or a pharmaceutically acceptable salt thereof, $R^1$ is selected from the group consisting of

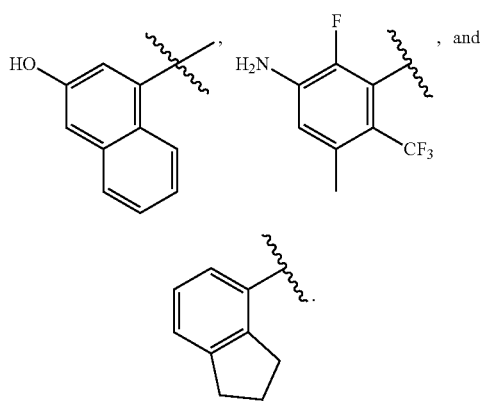

According to some embodiments of the compound of Formula (I), Formula (II), or Formula (III), or a pharmaceutically acceptable salt thereof, $R^1$ is:

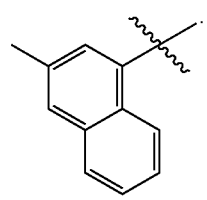 [SMILES: *c1cc(C)cc2ccccc12]

According to some embodiments of the compound of Formula (I), Formula (II), or Formula (III), or a pharmaceutically acceptable salt thereof, $R^1$ is 5- to 10-membered heteroaryl optionally substituted with one to four substituents, wherein each substituent is independently selected from the group consisting of $C_{1-6}$ alkyl, —$NH_2$, —NH($CH_3$), —N($CH_3$)$_2$, $C_{1-6}$ haloalkyl, $C_{3-6}$ cycloalkyl, and halo. In one embodiment, the $C_{3-6}$ cycloalkyl is cyclopropyl.

According to some embodiments of the compound of Formula (I), Formula (II), or Formula (III), or a pharmaceutically acceptable salt thereof, $R^1$ is selected from the group consisting of

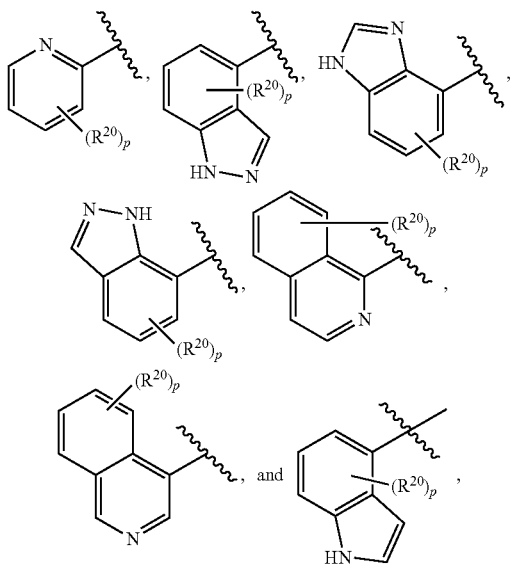

wherein each $R^{20}$ is independently selected from the group consisting of $C_{1-6}$ alkyl, —$NH_2$, —$NH(CH_3)$, —$N(CH_3)_2$, halo, $C_{1-6}$ haloalkyl, hydroxy, $C_{1-6}$ hydroxyalkyl, $C_{3-6}$ cycloalkyl, and —OC(=O)CH=$CH_2$, and p is 0, 1, 2, 3, or 4. In one embodiment, each $R^{20}$ is independently selected from the group consisting of $C_{1-6}$ alkyl, —$NH_2$, —NH($CH_3$), —$N(CH_3)_2$, halo, $C_{1-6}$ haloalkyl, and $C_{3-6}$ cycloalkyl, and each p is independently 0, 1, 2, 3, or 4. In one embodiment, the $C_{3-6}$ cycloalkyl is cyclopropyl.

According to some embodiments of the compound of Formula (I), Formula (II), or Formula (III), or a pharmaceutically acceptable salt thereof, $R^1$ is selected from the group consisting of

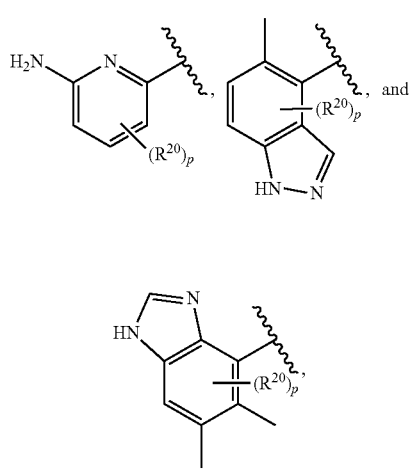

wherein each $R^{20}$ is independently selected from the group consisting of $C_{1-6}$ alkyl, —$NH_2$, —$NH(CH_3)$, —$N(CH_3)_2$, halo, $C_{1-6}$ haloalkyl, hydroxy, $C_{1-6}$ hydroxyalkyl, $C_{3-6}$ cycloalkyl, and —OC(=O)CH=$CH_2$, and p is 0, 1, 2, 3, or 4. In one embodiment, each $R^{20}$ is independently selected from the group consisting of $C_{1-6}$ alkyl, —$NH_2$, —NH($CH_3$), —$N(CH_3)_2$, halo, $C_{1-6}$ haloalkyl, and $C_{3-6}$ cycloalkyl, and each p is independently 0, 1, 2, 3, or 4.

According to some embodiments of the compound of Formula (I), Formula (II), or Formula (III), or a pharmaceutically acceptable salt thereof, $R^1$ is selected from the group consisting of:

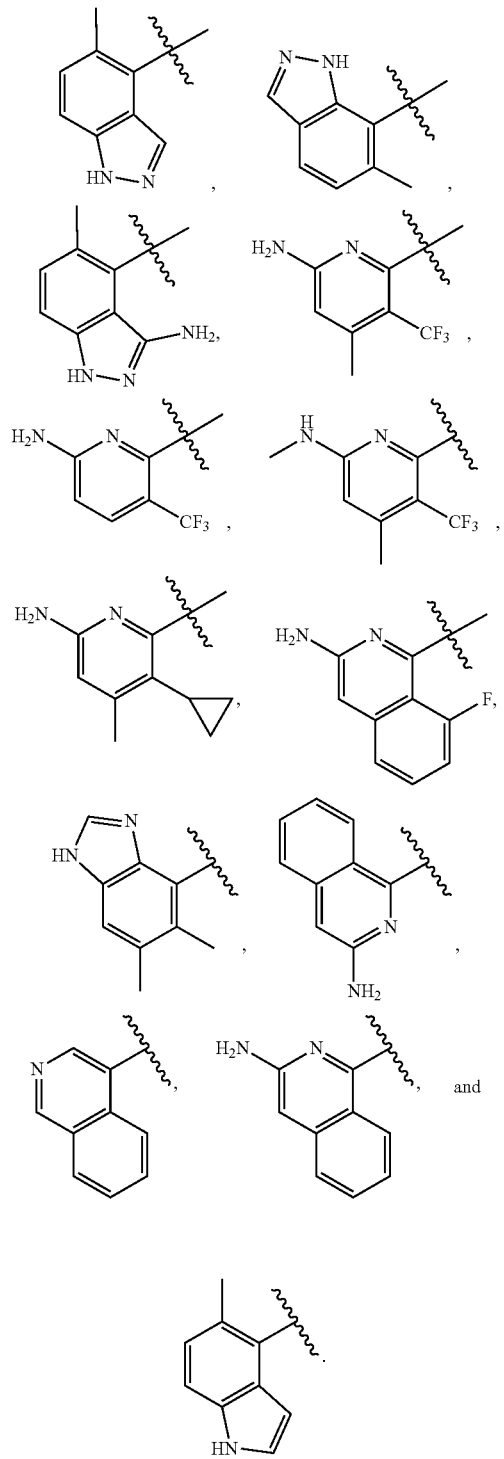

According to some embodiments of the compound of Formula (I), Formula (II), or Formula (III), or a pharmaceutically acceptable salt thereof, $R^1$ is selected from the group consisting of:

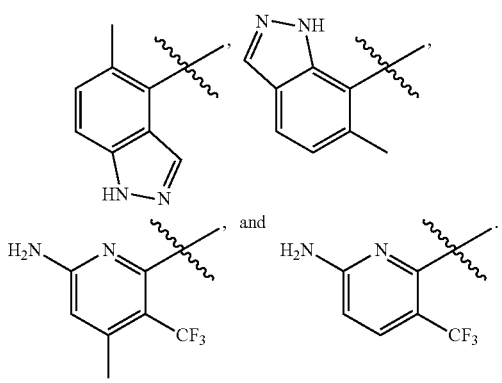

According to some embodiments of the compound of Formula (I), Formula (II), or Formula (III), or a pharmaceutically acceptable salt thereof, $R^1$ is H.

According to some embodiments of the compound of Formula (I), Formula (II), or Formula (III), or a pharmaceutically acceptable salt thereof, $R^1$ is 5- to 10-membered heterocyclyl optionally substituted with one to four substituents, wherein each substituent is independently selected from the group consisting of $C_{1-6}$ alkyl and oxo.

According to some embodiments of the compound of Formula (I), Formula (II), or Formula (III), or a pharmaceutically acceptable salt thereof, $R^1$ is selected from the group consisting of:

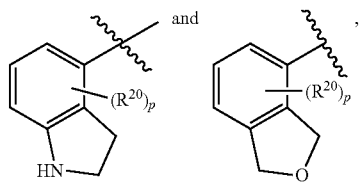

wherein each $R^{20}$ is independently selected from the group consisting of $C_{1-6}$ alkyl, —$NH_2$, —$NH(CH_3)$, —$N(CH_3)_2$, halo, $C_{1-6}$ haloalkyl, hydroxy, $C_{1-6}$ hydroxyalkyl, $C_{3-6}$ cycloalkyl, and —$OC(=O)CH=CH_2$, and p is 0, 1, 2, 3, or 4. In one embodiment, each $R^{20}$ is independently $C_{1-6}$ alkyl; and each p is independently 0, 1, 2, 3, or 4.

According to some embodiments of the compound of Formula (I), Formula (II), or Formula (III), or a pharmaceutically acceptable salt thereof, $R^1$ has the following structure:

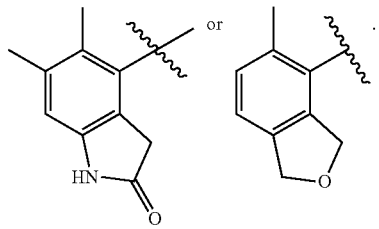 [SMILES: *c1c(C)c(C)cc2c1CC(=O)N2 ; *c1c(C)ccc2c1COC2]

According to some embodiments of the compound of Formula (I), Formula (II), or Formula (III), or a pharmaceutically acceptable salt thereof, $R^1$ is $C_{6-10}$ aryl or 5- to 10-membered heteroaryl optionally substituted with one to four substituents, wherein at least one substitution is amino.

In one embodiment of the compound of Formula (I), Formula (II), or Formula (III), or a pharmaceutically acceptable salt thereof, $R^1$ is 5- to 10-membered heteroaryl comprising at least one ring nitrogen atom. In still another embodiment of the compound of Formula (I), Formula (II), or Formula (III), or a pharmaceutically acceptable salt thereof, $R^1$ is 5- to 10-membered heterocyclyl. In one embodiment, where $R^1$ is 5- to 10-membered heterocyclyl, the heterocyclyl moiety comprises at least one nitrogen or oxygen atom.

In a further embodiment of the compound of Formula (I), Formula (II), or Formula (III), or a pharmaceutically acceptable salt thereof, $R^1$ is substituted or unsubstituted phenyl, pyridinyl, indazolyl, isoquinolinyl, dihydro-1H-indenyl, naphthalenyl, dihydroisobenzofuranyl, or benzoimidazolyl. In yet another embodiment of the compound of Formula (I), Formula (II), or Formula (III), or a pharmaceutically acceptable salt thereof, $R^1$ is substituted phenyl, pyridinyl, indazolyl, isoquinolinyl, naphthalenyl, dihydroisobenzofuranyl, or benzoimidazolyl.

In still another embodiment of the compound of Formula (I), Formula (II), or Formula (III), or a pharmaceutically acceptable salt thereof, $R^1$ is substituted phenyl, or pyridinyl. In another embodiment of the compound of Formula (I), Formula (II), or Formula (III), or a pharmaceutically acceptable salt thereof, $R^1$ is substituted indazolyl, isoquinolinyl, naphthalenyl, or benzoimidazolyl.

In one embodiment of the compound of Formula (I), Formula (II), or Formula (III), or a pharmaceutically acceptable salt thereof $R^1$ has a formula selected from the group consisting of:

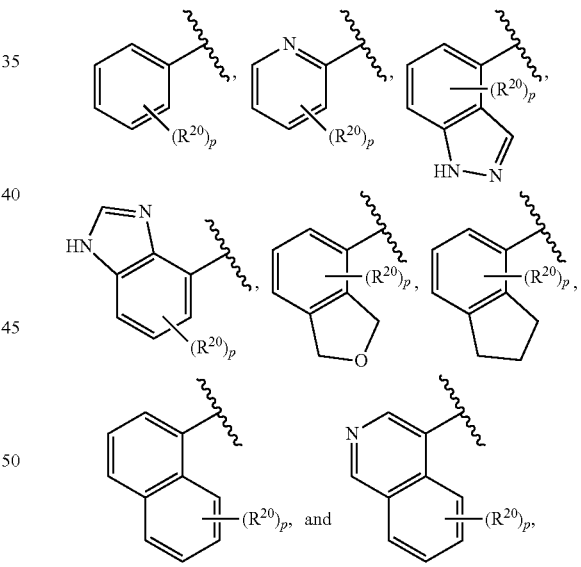

wherein each $R^{20}$ is independently selected from the group consisting of $C_{1-6}$ alkyl, —$NH_2$, —$NH(CH_3)$, —$N(CH_3)_2$, halo, $C_{1-6}$ haloalkyl, hydroxy, $C_{1-6}$ hydroxyalkyl, $C_{3-6}$ cycloalkyl, and —$OC(=O)CH=CH_2$, and p is 0, 1, 2, 3, or 4. In one embodiment, the $C_{3-6}$ cycloalkyl is cyclopropyl. In one embodiment, p is 1. In another embodiment, p is 2. In still another embodiment, p is 3. In one preferred embodiment, p is 3 where at least one $R^{20}$ is amino.

In still another embodiment of the compound of Formula (I), Formula (II), or Formula (III), or a pharmaceutically acceptable salt thereof, $R^1$ has formula selected from the group consisting of:

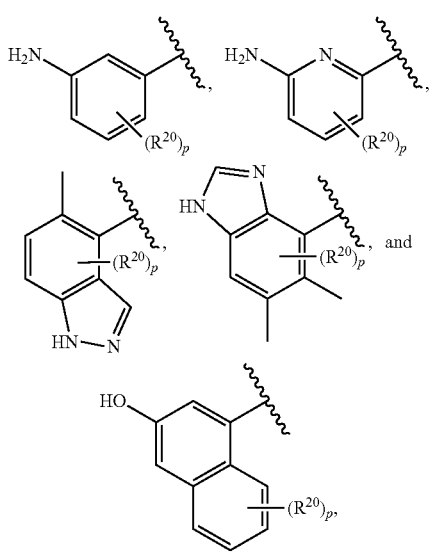

wherein $R^{20}$ and p are as defined above.

According to some embodiments of the compound of Formula (I), Formula (II), or Formula (III), or a pharmaceutically acceptable salt thereof, $R^1$ is selected from the group consisting of:

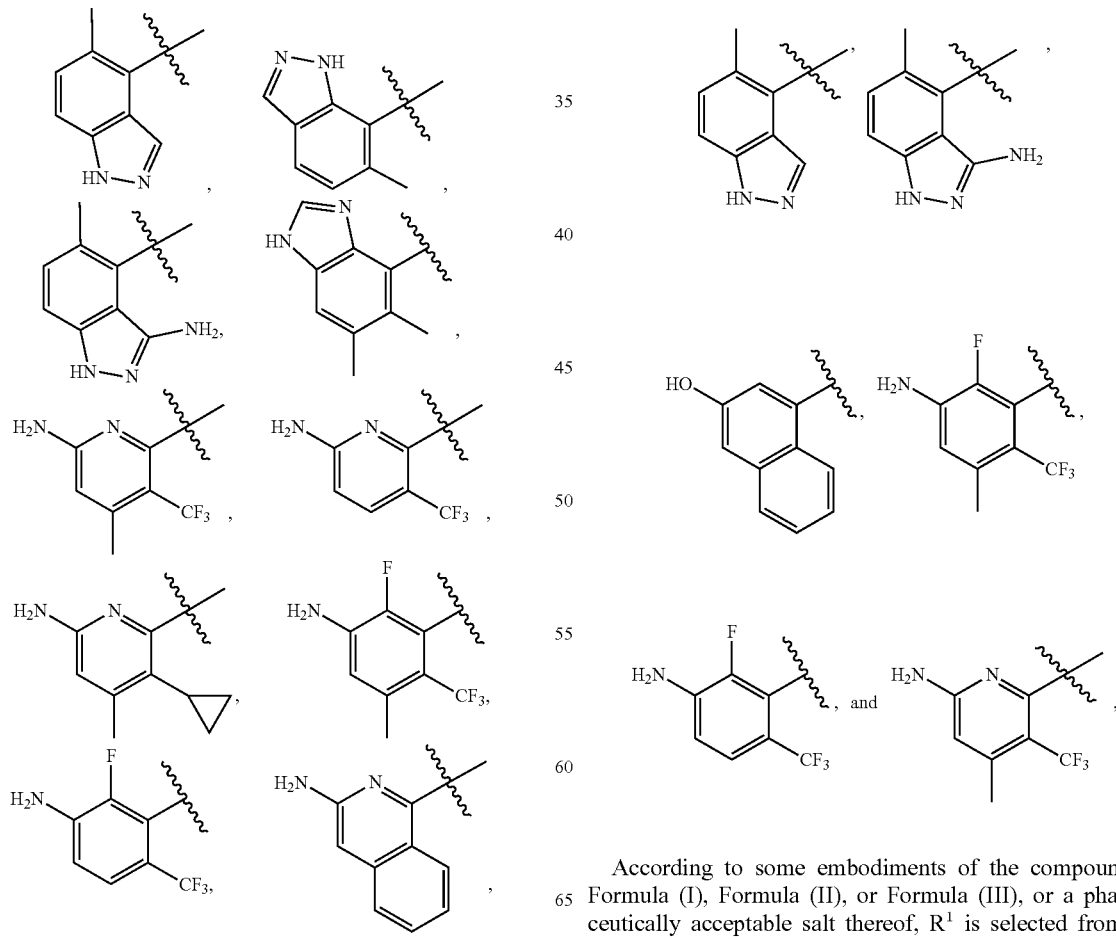

According to some embodiments of the compound of Formula (I), Formula (II), or Formula (III), or a pharmaceutically acceptable salt thereof, $R^1$ is selected from the group consisting of:

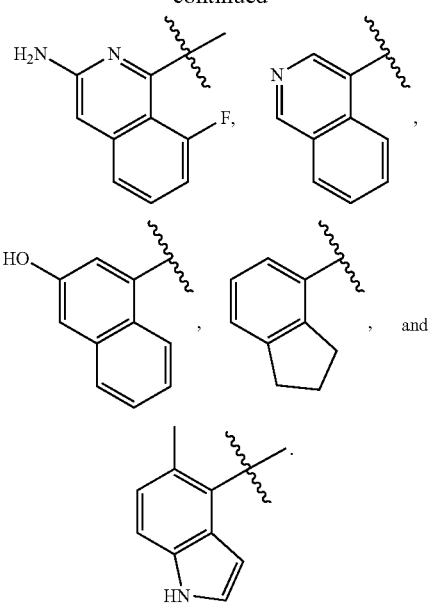

According to some embodiments of the compound of Formula (I), Formula (II), or Formula (III), or a pharmaceutically acceptable salt thereof, $R^1$ is selected from the group consisting of:

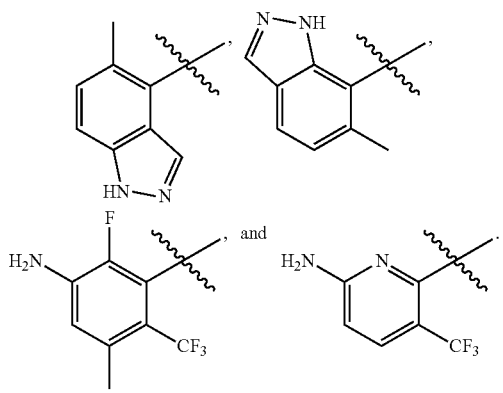

In still another embodiment of the compound of Formula (I), Formula (II), or Formula (III), or a pharmaceutically acceptable salt thereof, R$^1$ is:

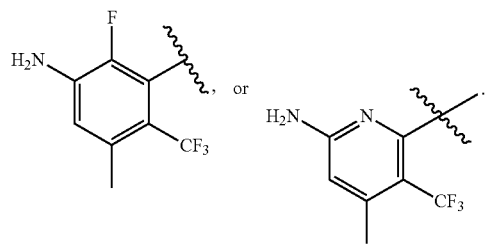 [SMILES: *c1c(F)c(N)cc(C)c1C(F)(F)F ; *c1nc(N)cc(C)c1C(F)(F)F]

According to some embodiments of the compound of Formula (I), Formula (II), or Formula (III), or a pharmaceutically acceptable salt thereof, R$^1$ and R$^3$, together with the carbon to which they are bonded, may form an optionally substituted 3- to 6-membered cycloalkyl. In one embodiment, the 3- to 6-membered cycloalkyl is a cyclohexyl.

According to some embodiments of the compound of Formula (I), Formula (II), or Formula (III), or a pharmaceutically acceptable salt thereof, Z$^1$ is N; Z$^2$ is C(R$^{10}$) or C(-L-R$^{10a}$); Z$^3$ is N; and R$^{10}$, -L, and R$^{10a}$ are as defined above for Formula (I), Formula (II), or Formula (III).

According to some embodiments of the compound of Formula (I), Formula (II), or Formula (III), or a pharmaceutically acceptable salt thereof, Z$^1$ is N; Z$^2$ is C(R$^{10}$); Z$^3$ is N; and R$^{10}$ is H.

According to some embodiments of the compound of Formula (I), Formula (II), or Formula (III), or a pharmaceutically acceptable salt thereof, Z$^1$ is N; Z$^2$ is C(-L-R$^{10a}$); Z$^3$ is N; and -L and R$^{10a}$ are as defined above for Formula (I), Formula (II), or Formula (III). In one particular embodiment, L is O. In another embodiment, L is O, and R$^{10a}$ is selected from the group consisting of heterocyclylalkyl and heteroarylalkyl, wherein each heterocyclylalkyl and heteroarylalkyl are optionally substituted with one or more L$^d$, wherein L$^d$ is as defined above for Formula (I), Formula (II), or Formula (III). In one particular embodiment, each L$^d$ is independently selected from the group consisting of hydrogen, oxo, halogen, and C$_{1-6}$ alkyl.

According to some embodiments of the compound of Formula (I), Formula (II), or Formula (III), or a pharmaceutically acceptable salt thereof, Z$^2$ is C(-L-R$^{10a}$); and -L-R$^{10a}$ is selected from the group consisting of

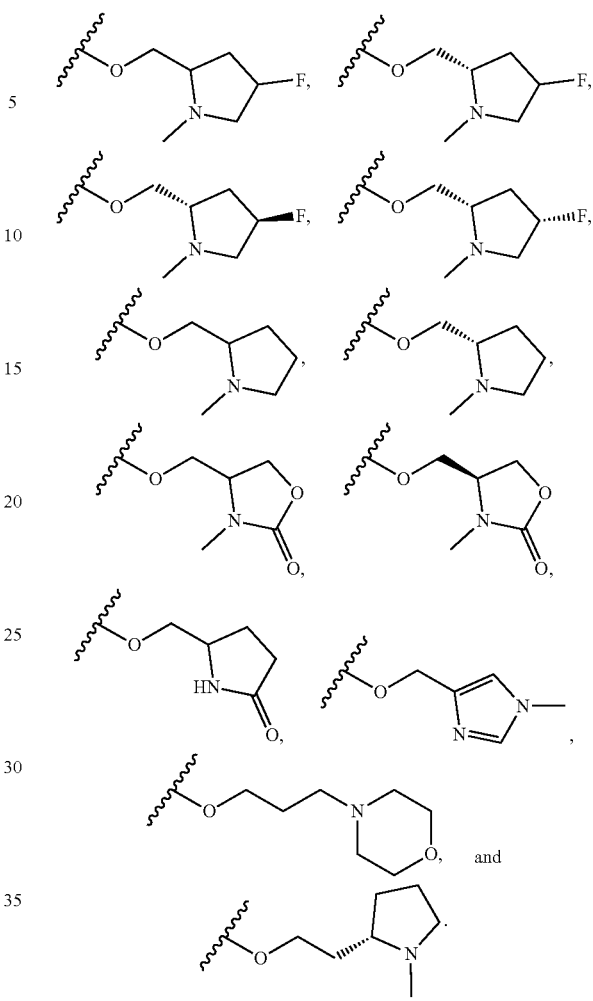

In one such embodiment, Z$^1$ is N and Z$^3$ is N.

According to some embodiments of the compound of Formula (I), Formula (II), or Formula (III), or a pharmaceutically acceptable salt thereof, Z$^1$ is N; Z$^2$ is C(R$^{10}$); Z$^3$ is C(R$^{12}$); and R$^{10}$ and R$^{12}$ are each independently as defined above for Formula (I), Formula (II), or Formula (III).

According to some embodiments of the compound of Formula (I), Formula (II), or Formula (III), or a pharmaceutically acceptable salt thereof, Z$^1$ is N; Z$^2$ is C(R$^{10}$); Z$^3$ is C(R$^{12}$); R$^{10}$ is hydrogen; and R$^{12}$ is as defined above for Formula (I), Formula (II), or Formula (III).

According to some embodiments of the compound of Formula (I), Formula (II), or Formula (III), or a pharmaceutically acceptable salt thereof, Z$^1$ is S(O)$_2$; Z$^2$ is absent; and Z$^3$ is N.

According to some embodiments of the compound of Formula (I), Formula (II), or Formula (III), or a pharmaceutically acceptable salt thereof, Z$^1$ is O; Z$^2$ is absent; and Z$^3$ is N.

According to some embodiments of the compound of Formula (I), Formula (II), or Formula (III), or a pharmaceutically acceptable salt thereof, Z$^1$ is N(R$^9$); Z$^2$ is absent; Z$^3$ is N; and R$^9$ is as defined above for Formula (I), Formula (II), or Formula (III).

According to some embodiments of the compound of Formula (I), Formula (II), or Formula (III), or a pharmaceutically acceptable salt thereof, $Z^1$ is N; $Z^2$ is absent; $Z^3$ is N(R''); and $R^{11}$ is as defined above for Formula (I), Formula (II), or Formula (III).

According to some embodiments of the compound of Formula (I), Formula (II), or Formula (III), or a pharmaceutically acceptable salt thereof, $Z^1$ is S(O); $Z^2$ is absent; and $Z^3$ is N.

According to some embodiments of the compound of Formula (I), Formula (II), or Formula (III), or a pharmaceutically acceptable salt thereof, $Z^1$ is S; $Z^2$ is absent; and $Z^3$ is N.

According to some embodiments of the compound of Formula (I), Formula (II), or Formula (III), or a pharmaceutically acceptable salt thereof, $Z^1$ is N($R^9$); $Z^2$ is C($R^{10}$); and $Z^3$ is N.

According to some embodiments of the compound of Formula (I), Formula (II), or Formula (III), or a pharmaceutically acceptable salt thereof, $Z^1$ is N($R^9$); $Z^2$ is C($R^{10}$); $Z^3$ is N; and $R^9$ is aryl substituted with a $C_{1-6}$ alkyl.

According to some embodiments of the compound of Formula (I), Formula (II), or Formula (III), or a pharmaceutically acceptable salt thereof, $R^9$ is an aryl substituted with a $C_3$ alkyl. In one embodiment of the compound of Formula (I), Formula (II), or Formula (III), or a pharmaceutically acceptable salt thereof, $R^9$ is phenyl substituted with isopropyl.

In one embodiment of the compound of Formula (I), Formula (II), or Formula (III), or a pharmaceutically acceptable salt thereof, $R^9$ is

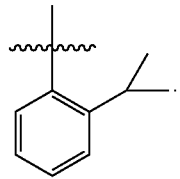 [SMILES: *c1ccccc1C(C)C]

In one embodiment of the compound of Formula (I), Formula (II), or Formula (III), or a pharmaceutically acceptable salt thereof, $R^{10}$ is oxo.

According to some embodiments of the compound of Formula (I), Formula (II), or Formula (III), or a pharmaceutically acceptable salt thereof, $Y^1$ is absent; $Y^2$ is C(H)($R^8$); $Y^3$ is C($R^3$); and $R^3$ and $R^8$ are as defined above for Formula (I), Formula (II), or Formula (III).

According to some embodiments of the compound of Formula (I), Formula (II), or Formula (III), or a pharmaceutically acceptable salt thereof, $Y^1$ is absent; $Y^2$ is C(H)($R^8$); $Y^3$ is C($R^3$); $R^3$ is as defined above for Formula (I), Formula (II), or Formula (III); and $R^8$ is selected from the group consisting of H and $C_{1-6}$ alkyl.

According to some embodiments of the compound of Formula (I), Formula (II), or Formula (III), or a pharmaceutically acceptable salt thereof, $Y^1$ is absent; $Y^2$ is C(H)($R^8$); $Y^3$ is C($R^3$); $R^3$ is as defined above for Formula (I), Formula (II), or Formula (III); and $R^8$ is selected from the group consisting of H, methyl, ethyl, and isopropyl.

According to some embodiments of the compound of Formula (I), Formula (II), or Formula (III), or a pharmaceutically acceptable salt thereof, $Y^1$ is absent; $Y^2$ is C(H)($R^8$); $Y^3$ is C($R^3$); and $R^3$, $R^4$, $R^5$, and $R^8$ are each independently as defined above for Formula (I), Formula (II), or Formula (III).

According to some embodiments of the compound of Formula (I), Formula (II), or Formula (III), or a pharmaceutically acceptable salt thereof, $Y^1$ is absent; $Y^2$ is C(H)($R^8$); $Y^3$ is C($R^3$); and $R^3$, $R^4$, and $R^5$ are hydrogen; and $R^8$ is as defined above for Formula (I), Formula (II), or Formula (III).

According to some embodiments of the compound of Formula (I), Formula (II), or Formula (III), or a pharmaceutically acceptable salt thereof, $Y^1$ is absent; $Y^2$ is C(H)($R^8$); $Y^3$ is C($R^3$); $R^3$, $R^4$, and $R^5$ are hydrogen; and $R^8$ is selected from the group consisting of H and $C_{1-6}$ alkyl. According to one such embodiment, $R^8$ is selected from the group consisting of H and methyl.

According to some embodiments of the compound of Formula (I), Formula (II), or Formula (III), or a pharmaceutically acceptable salt thereof, $Y^1$ is C(H)($R^6$); $Y^2$ is C(H)($R^8$); $Y^3$ is C($R^3$); and $R^3$, $R^4$, $R^5$, $R^6$, and $R^8$ are each independently as defined above for Formula (I), Formula (II), or Formula (III).

According to some embodiments of the compound of Formula (I), Formula (II), or Formula (III), or a pharmaceutically acceptable salt thereof, $Y^1$ is C(H)($R^6$); $Y^2$ is C(H)($R^8$); $Y^3$ is C($R^3$); $R^3$, $R^4$, $R^5$, $R^6$, and $R^8$ are each hydrogen.

According to some embodiments of the compound of Formula (I), Formula (II), or Formula (III), or a pharmaceutically acceptable salt thereof, $Y^1$ is C(H)($R^6$); $Y^2$ is N($R^7$); $Y^3$ is C($R^3$); and $R^3$, $R^4$, $R^5$, $R^6$, and $R^7$ are each independently as defined above for Formula (I), Formula (II), or Formula (III).

According to some embodiments of the compound of Formula (I), Formula (II), or Formula (III), or a pharmaceutically acceptable salt thereof, $Y^1$ is C(H)($R^6$); $Y^2$ is N($R^7$); $Y^3$ is C($R^3$); $R^3$, $R^4$, $R^5$, and $R^6$ are each hydrogen; and $R^7$ is as defined above for Formula (I), Formula (II), or Formula (III).

According to some embodiments of the compound of Formula (I), Formula (II), or Formula (III), or a pharmaceutically acceptable salt thereof, $Y^1$ is absent; $Y^2$ is N($R^7$); $Y^3$ is C($R^3$); and $R^3$, $R^4$, $R^5$, and $R^7$ are each independently as defined above for Formula (I), Formula (II), or Formula (III).

According to some embodiments of the compound of Formula (I), Formula (II), or Formula (III), or a pharmaceutically acceptable salt thereof, $Y^1$ is absent; $Y^2$ is N($R^7$); $Y^3$ is C($R^3$); $R^3$, $R^4$, and $R^5$ are each hydrogen; and $R^8$ is as defined above for Formula (I), Formula (II), or Formula (III).

According to some embodiments of the compound of Formula (I), Formula (II), or Formula (III), or a pharmaceutically acceptable salt thereof, $Y^1$ is absent; $Y^2$ is C(H)($R^8$); $Y^3$ is N; and $R^8$ is as defined above for Formula (I), Formula (II), or Formula (III).

According to some embodiments of the compound of Formula (I), Formula (II), or Formula (III), or a pharmaceutically acceptable salt thereof, wherein $Y^1$ is absent; $Y^2$ is C(H)($R^8$); $Y^3$ is N; and $R^8$ is hydrogen.

According to some embodiments of the compound of Formula (I), Formula (II), or Formula (III), or a pharmaceutically acceptable salt thereof, X is a 4- to 7-membered heterocyclyl.

According to some embodiments of the compound of Formula (I), Formula (II), or Formula (III), or a pharmaceutically acceptable salt thereof, $R^3$, $R^4$, $R^5$, $R^6$, $R^7$, $R^8$, $R^9$, $R^{10}$, $R^{11}$, and $R^{12}$ are each independently selected from the group consisting of H, halo, $C_{3-7}$ cycloalkyl, $C_{1-6}$ alkyl, aryl substituted with $C_{1-6}$ alkyl, and oxo.

According to some embodiments of the compound of Formula (I), Formula (II), or Formula (III), or a pharmaceutically acceptable salt thereof, $R^3$, $R^4$, $R^5$, $R^6$, $R^7$, $R^8$, $R^9$, $R^{10}$, $R^{11}$, and $R^{12}$ are each independently selected from the group consisting of H, $C_{1-6}$ alkyl, aryl substituted with $C_3$ alkyl, and oxo According to some embodiments of the compound of Formula (I), Formula (II), or Formula (III), or a pharmaceutically acceptable salt thereof, $R^3$, $R^4$, $R^5$, $R^6$, $R^7$, $R^8$, $R^9$, $R^{10}$, $R^{11}$, and $R^{12}$ are each independently selected from the group consisting of H, methyl, ethyl, isopropyl, phenyl substituted with isopropyl, and oxo.

According to some embodiments of the compound of Formula (I), Formula (II), or Formula (III), or a pharmaceutically acceptable salt thereof, X is a 4- to 7-membered heterocyclyl, which is optionally substituted with 1 to 4 substituents, wherein each substituent is independently selected from the group consisting of $C_{1-6}$ alkyl, cyano, $C_{1-6}$ cyanoalkyl, and $C_{1-6}$ hydroxy alkyl; wherein two geminal substituents may be taken together to form a 4- to 7-membered spiroheterocyclyl.

According to some embodiments of the compound of Formula (I), Formula (II), or Formula (III), or a pharmaceutically acceptable salt thereof, X is selected from the group consisting of:

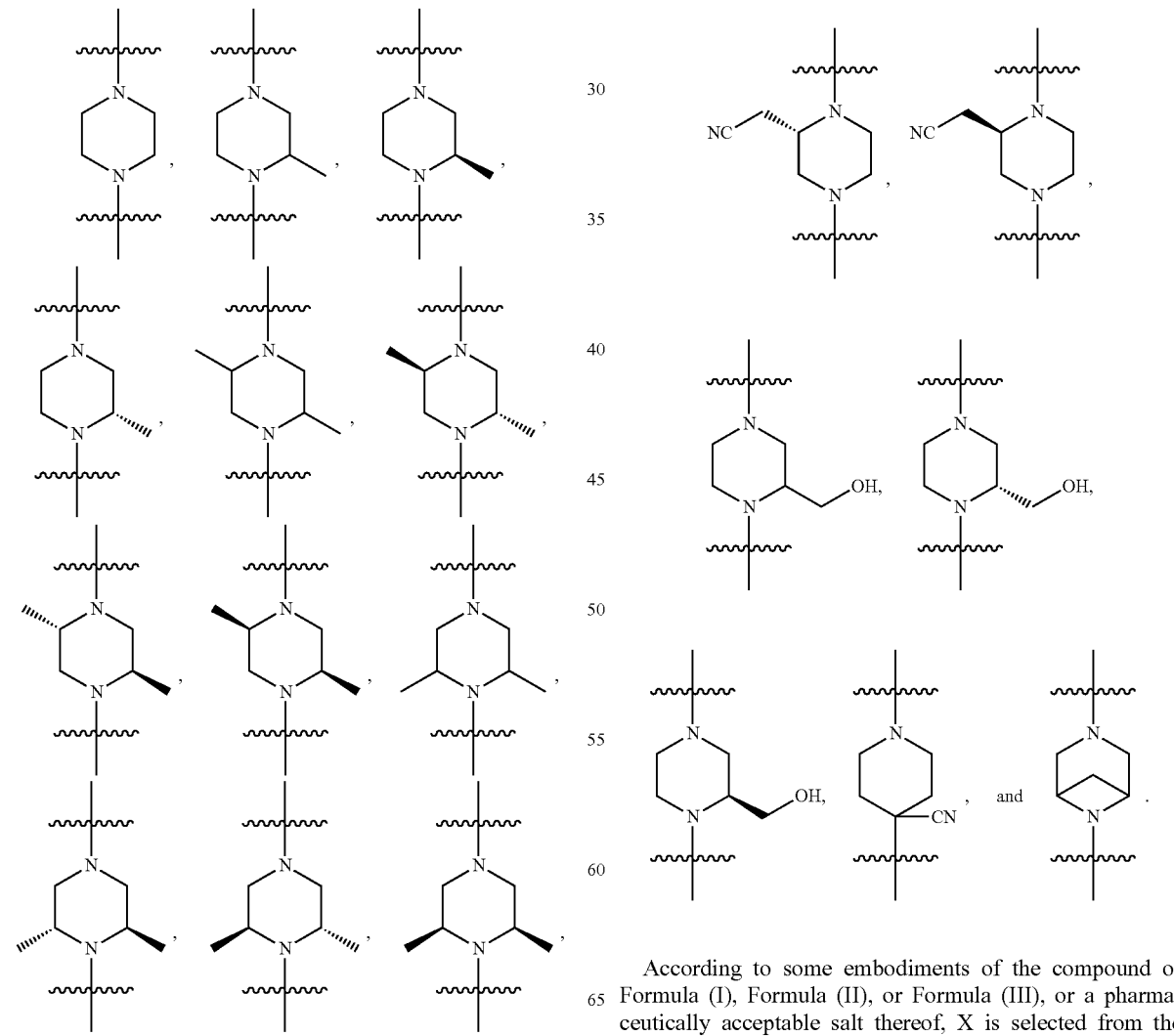

According to some embodiments of the compound of Formula (I), Formula (II), or Formula (III), or a pharmaceutically acceptable salt thereof, X is selected from the group consisting of:

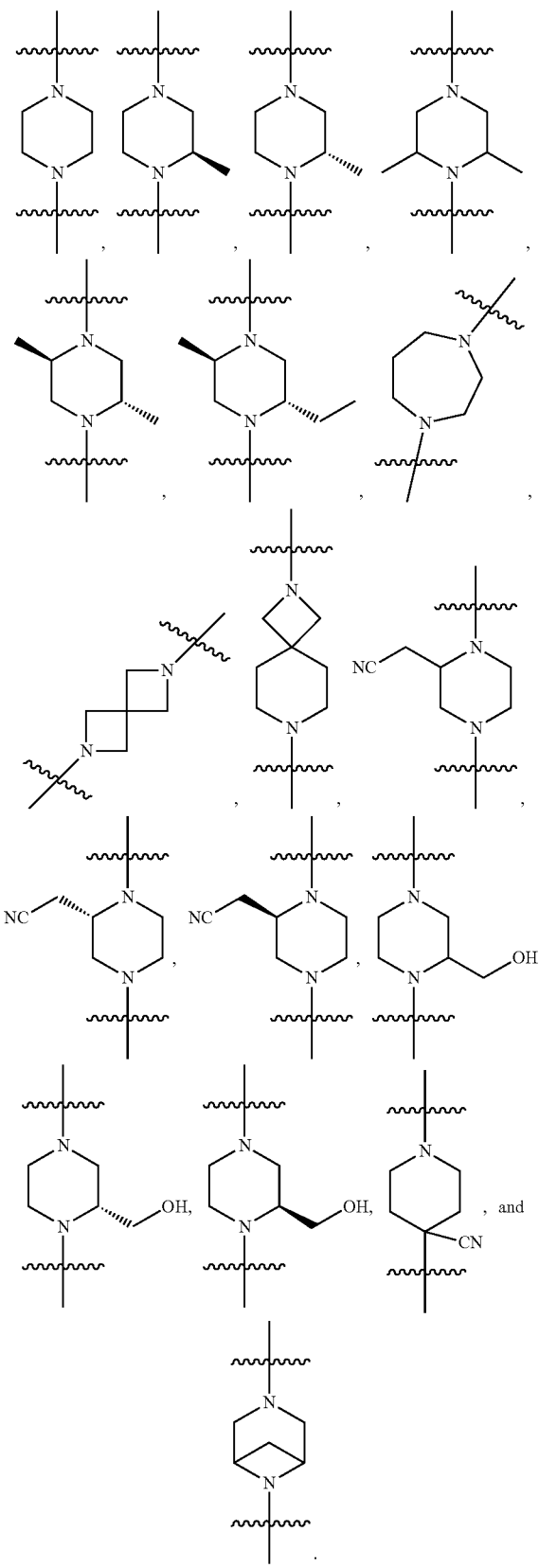

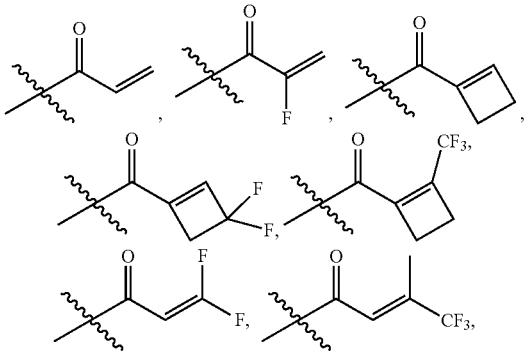

ceutically acceptable salt thereof, X is a piperazine, which may be unsubstituted or substituted. In some embodiments, the piperazine is substituted with one or more groups selected from among CH$_3$, CH$_2$CN, CH$_2$OH, CN, CF$_3$, CH$_2$CF$_3$, and CHF$_2$.

According to some embodiments of the compound of Formula (I), Formula (II), or Formula (III), or a pharmaceutically acceptable salt thereof, X is a homopiperazine, which may be unsubstituted or substituted. In some embodiments, the homopiperazine is substituted with one or more groups selected from among CH$_3$, CH$_2$CN, CH$_2$OH, CN, CF$_3$, CH$_2$CF$_3$, and CHF$_2$.

According to some embodiments of the compound of Formula (I), Formula (II), or Formula (III), or a pharmaceutically acceptable salt thereof, X is 4- to 7-membered heterocyclylamino.

According to some embodiments of the compound of Formula (I), Formula (II), or Formula (III), or a pharmaceutically acceptable salt thereof, X is

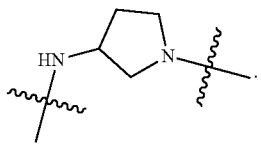 [SMILES: *NC1CCN(*)C1]

According to some embodiments of the compound of Formula (I), Formula (II), or Formula (III), or a pharmaceutically acceptable salt thereof, X is

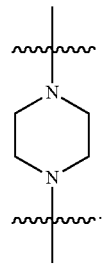 [SMILES: *N1CCN(*)CC1]

According to some embodiments of the compound of Formula (I), Formula (II), or Formula (III), or a pharmaceutically acceptable salt thereof, n is 0.

According to some embodiments of the compound of Formula (I), or a pharmaceutically acceptable salt thereof, R$^2$ is selected from the group consisting of:

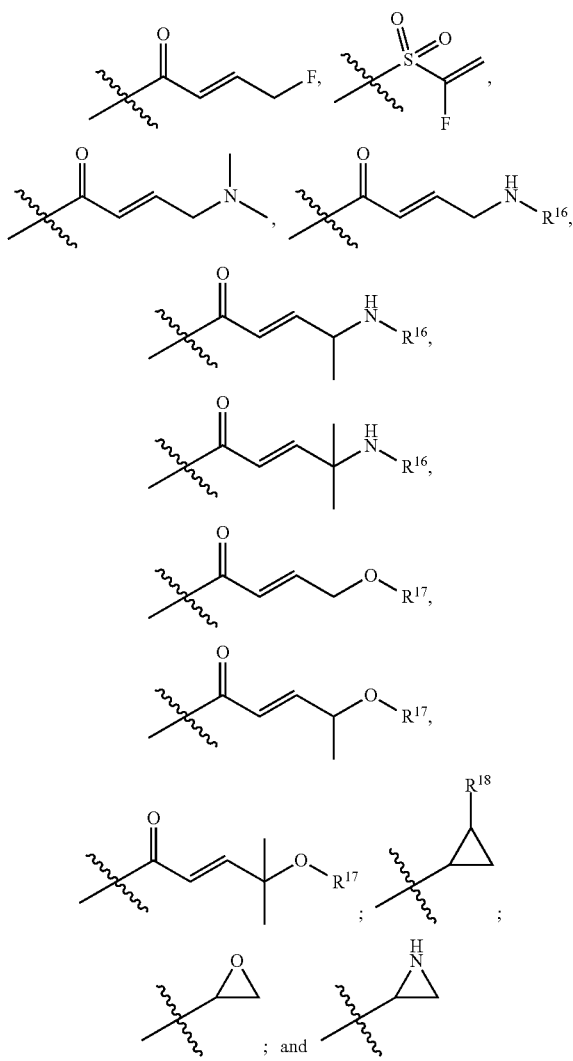

wherein:

R¹⁶ is selected from the group consisting of $C_{1-6}$ alkanoyl, $C_{1-6}$ alkyl, $C_{1-6}$ alkylsulfonyl, and $C_{3-6}$ cycloalkyl;

R¹⁷ is selected from the group consisting of $C_{1-6}$ alkyl and $C_{1-6}$ haloalkyl; and R¹⁸ is halo.

According to some embodiments of the compound of Formula (I), or a pharmaceutically acceptable salt thereof, R² is selected from the group consisting of:

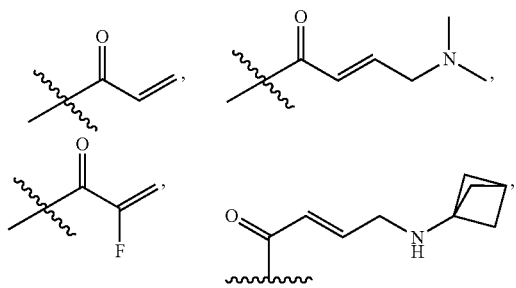

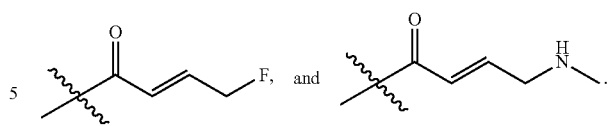

According to some embodiments of the compound of Formula (I), or a pharmaceutically acceptable salt thereof, R² is

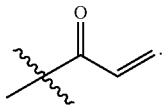

According to some embodiments of the compound of Formula (I), or a pharmaceutically acceptable salt thereof, X and R² together may together be selected from the group consisting of:

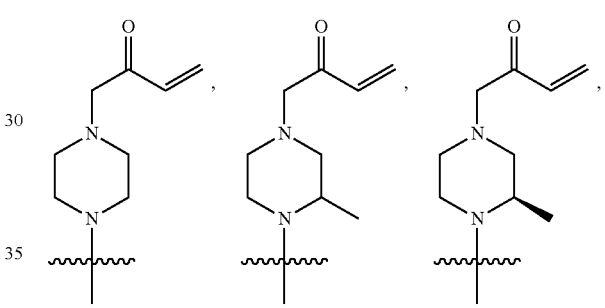

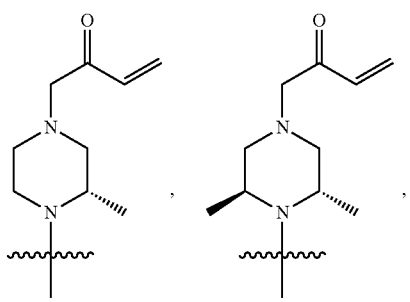

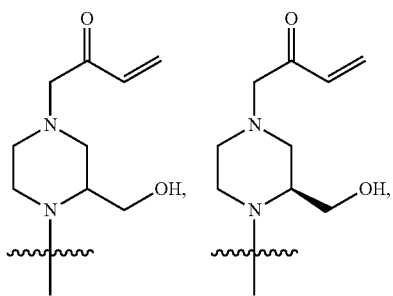

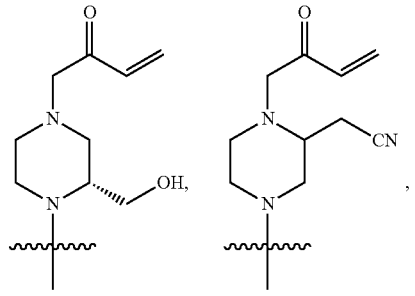
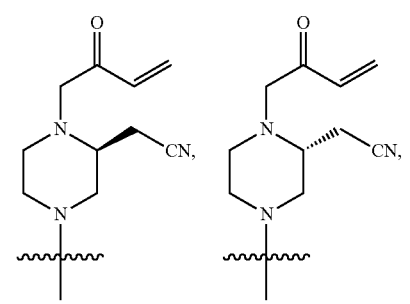
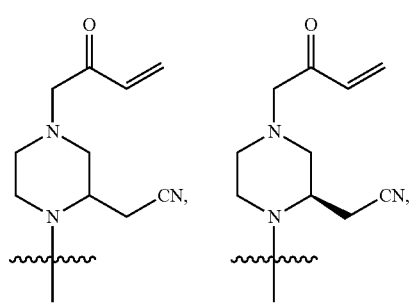
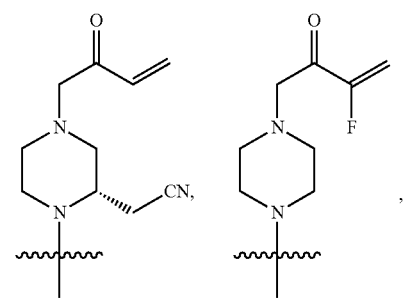
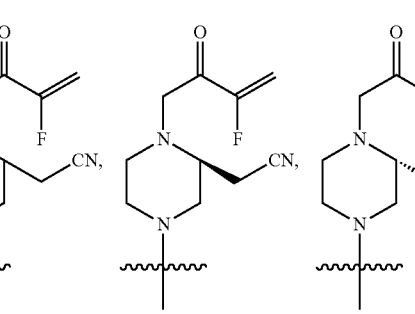
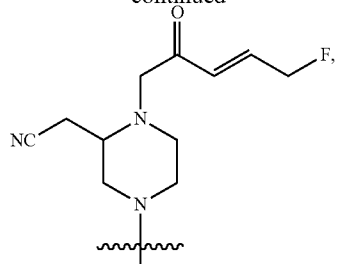
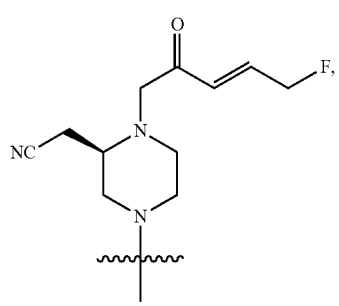
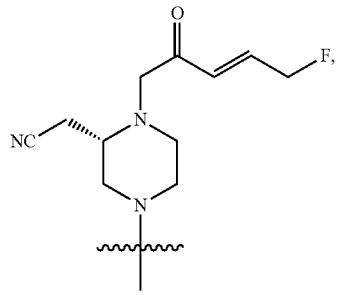
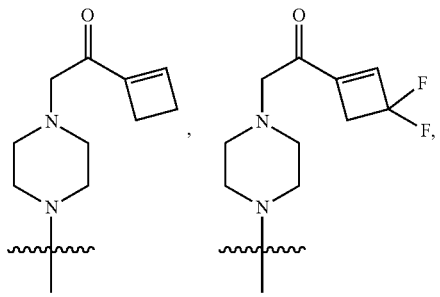
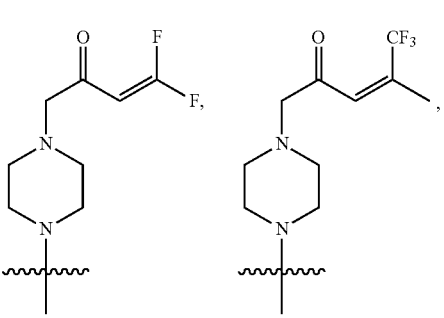

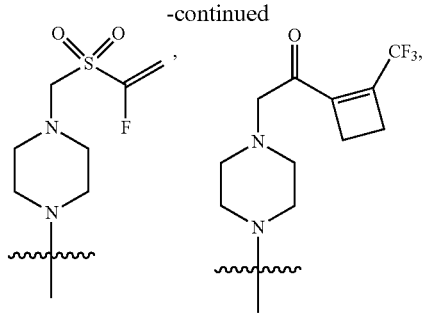 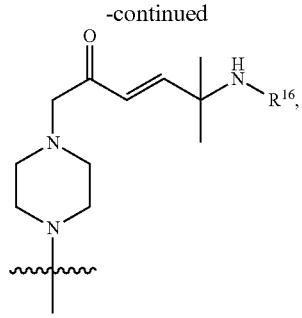
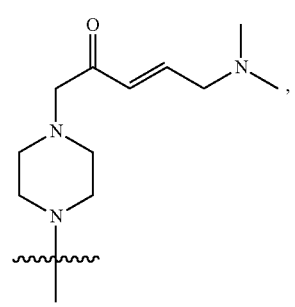 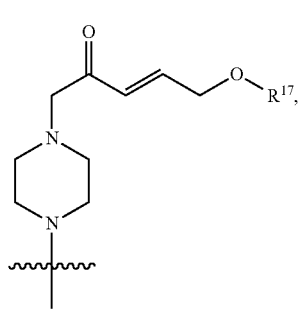
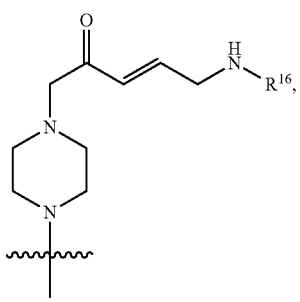 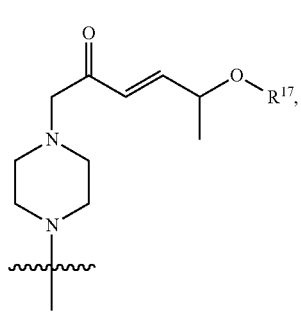
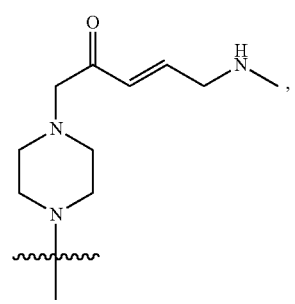 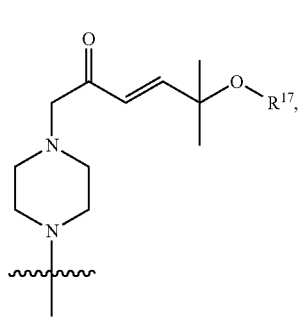
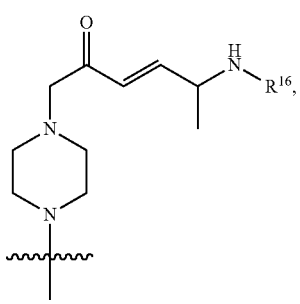 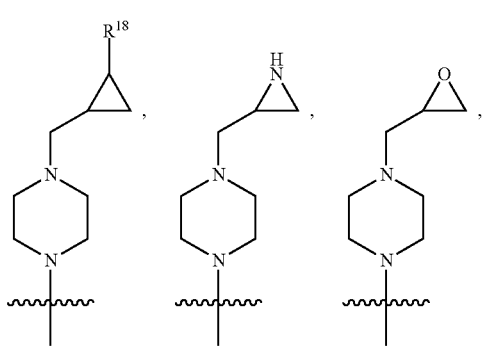

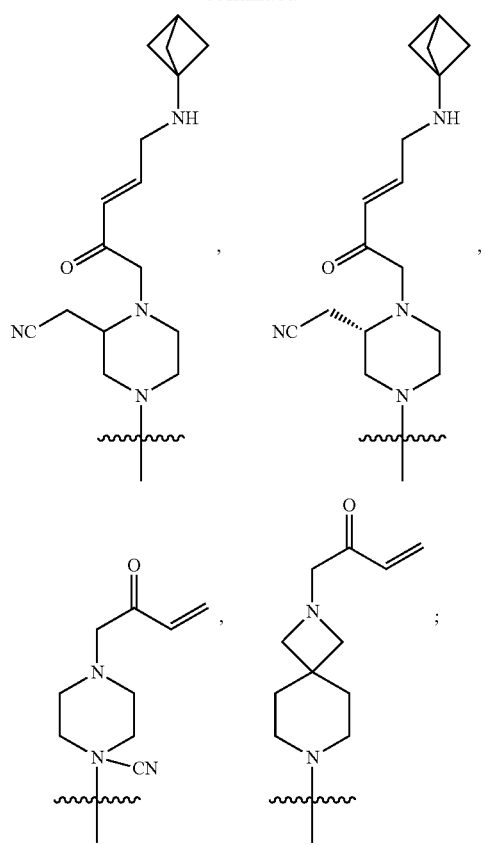
wherein $R^{16}$, $R^{17}$, and $R^{18}$ are as defined above.
According to some embodiments of the compound of Formula (I), or a pharmaceutically acceptable salt thereof, X and $R^2$ together may together be selected from the group consisting of:

-continued
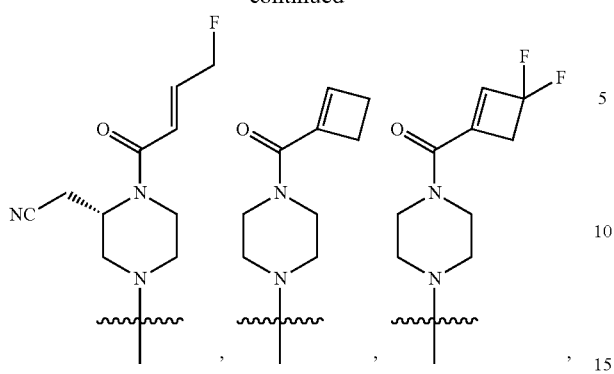
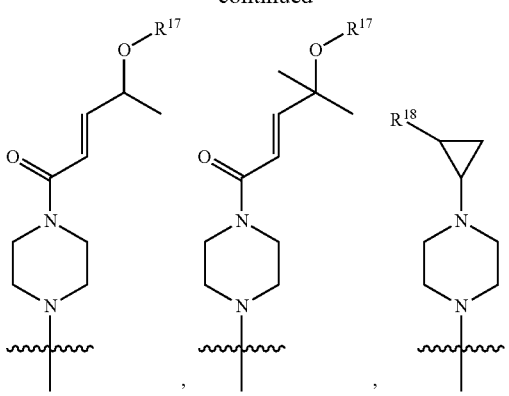
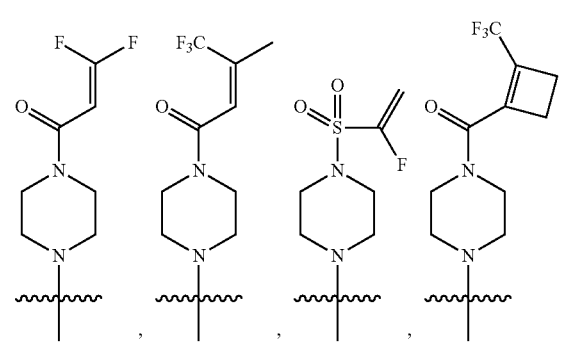
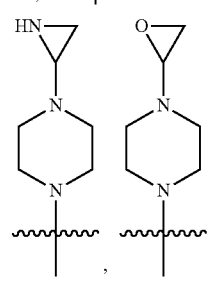
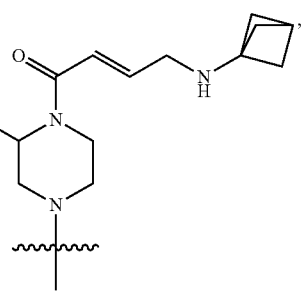
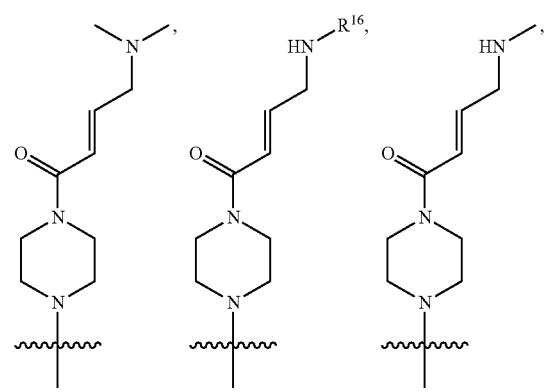
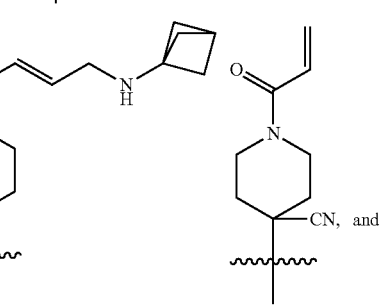
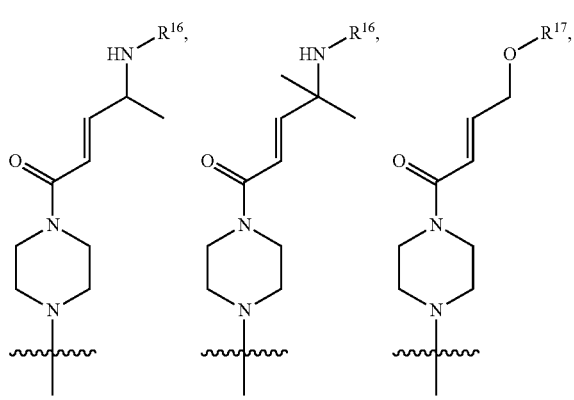
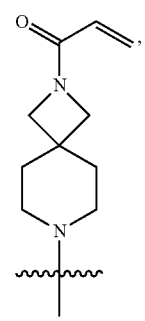
wherein $R^{16}$, $R^{17}$, and $R^{18}$ are as defined above.
According to some embodiments of the compound of Formula (I), or a pharmaceutically acceptable salt thereof, X and $R^2$ together may be:

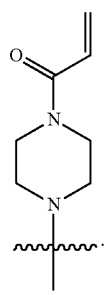

According to some embodiments, R$^{16}$ is selected from the group consisting of C$_{1-6}$ alkanoyl, C$_{1-6}$ alkyl, C$_{1-6}$ alkylsulfonyl, and C$_{3-6}$ cycloalkyl. In one particular embodiment, R$^{16}$ is methyl.

According to some embodiments, R$^{17}$ is selected from the group consisting of C$_{1-6}$ alkyl and C$_{1-6}$ haloalkyl.

According to some embodiments of the compound of Formula (II), or a pharmaceutically acceptable salt thereof, R$^{13}$ is selected from the group consisting of H, cyano, and halo; and R$^{14}$ and R$^{15}$ are each independently selected from the group consisting of H, C$_{1-6}$ alkyl, C$_{1-6}$ haloalkyl, cyano, and halo; wherein C$_{1-6}$ alkyl is optionally substituted with one substituent selected from the group consisting of: methanesulfonyl (mesyl), p-toluenesulfonyl (tosyl), an alkyl or aryl sulfonate leaving group, C$_{1-6}$ alkanoylamino, C$_{1-6}$ alkoxy, C$_{1-6}$ alkylamino, C$_{1-6}$ alkylsulfonylamino, C$_{6-12}$ dialkylamino, C$_{3-6}$ cycloalkylamino, and C$_{1-6}$ haloalkoxy.

According to some embodiments of the compound of Formula (II), or a pharmaceutically acceptable salt thereof, R$^{13}$ and R$^{14}$ together form a triple bond between the carbons to which they are attached, or R$^{13}$ and R$^{14}$ together with the carbons to which they are each bonded form a C$_{3-7}$ cycloalkenyl optionally substituted with one or two halo substituents; and R$^{15}$ is selected from the group consisting of H, C$_{1-6}$ alkyl, C$_{1-6}$ haloalkyl, cyano, and halo; wherein C$_{1-6}$ alkyl is optionally substituted with one substituent selected from the group consisting of: C$_{1-6}$ alkanoylamino, C$_{1-6}$ alkoxy, C$_{1-6}$ alkylamino, C$_{1-6}$ alkylsulfonylamino, C$_{6-12}$ dialkylamino, and C$_{1-6}$ haloalkoxy.

According to some embodiments of the compound of Formula (II), or a pharmaceutically acceptable salt thereof, R$^{13}$, R$^{14}$, and R$^{15}$ are each H.

According to some embodiments of the compound of Formula (II), or a pharmaceutically acceptable salt thereof, R$^{13}$ is H, and one of R$^{14}$ and R$^{15}$ is H and the other of R$^{14}$ and R$^{15}$ is Q substituted with dialkylamino, and more particularly is C$_1$ substituted with a dimethylamino group.

According to some embodiments of the compound of Formula (II), or a pharmaceutically acceptable salt thereof, R$^{13}$ is halo, and in particular may be F, and R$^{14}$ and R$^{15}$ are each H.

According to some embodiments of the compound of Formula (II), or a pharmaceutically acceptable salt thereof, R$^{13}$ is H, and one of R$^{14}$ and R$^{15}$ is Fl and the other of R$^{14}$ and R$^{15}$ is selected from the group consisting of C$_{1-6}$ alkyl and C$_{1-6}$ haloalkyl, wherein the C$_{1-6}$ alkyl is optionally substituted with one substituent selected from the group consisting of C$_{1-6}$ alkylamino and C$_{3-6}$ cycloalkylamino. In one embodiment, R$^{13}$ is H, and one of R$^{14}$ and R$^{15}$ is Fl and the other of R$^{14}$ and R$^{15}$ is C$_1$ alkyl substituted with one substituent selected from the group consisting of C$_{1-6}$ alkylamino and C$_{3-6}$ cycloalkylamino.

According to some embodiments of the compound of Formula (III), or a pharmaceutically acceptable salt thereof, R$^{19}$ is oxiranyl.

According to some embodiments of the compound of Formula (III), or a pharmaceutically acceptable salt thereof, R$^{19}$ is aziridinyl.

According to some embodiments of the compound of Formula (III), or a pharmaceutically acceptable salt thereof, R$^{19}$ is cyclopropyl, optionally substituted with at least one halogen.

According to some embodiments of the compound of Formula (I), Formula (II), or Formula (III), or a pharmaceutically acceptable salt thereof, Z$^1$ is N; Z$^2$ is C(R$^{10}$) or C(-L-R$^{10a}$); Z$^3$ is N; Y$^1$ is absent; Y$^2$ is C(H)(R$^8$); Y$^3$ is C(R$^3$); X is an optionally substituted 4- to 7-membered heterocyclyl; n is 0; and R$^3$, R$^8$, R$^{10}$, R$^{10a}$, and L are each independently as defined above for Formula (I), Formula (II), or Formula (III). In one such embodiment, Z$^2$ is C(R$^{10}$), and R$^{10}$ is H. In another such embodiment, Z$^2$ is C(-L-R$^{10a}$), L is O, and R$^{10a}$ is heterocyclylalkyl or heteroarylalkyl, wherein the heterocyclylalkyl and heteroarylalkyl are optionally substituted with one or more L$^d$, and each L$^d$ is independently as defined above for Formula (I), Formula (II), or Formula (III). In one embodiment, each L$^d$ is independently 1 selected from the group consisting of hydrogen, oxo, halogen, and C$_{1-6}$ alkyl.

According to some embodiments of the compound of Formula (I), Formula (II), or Formula (III), or a pharmaceutically acceptable salt thereof, Z$^1$ is N; Z$^2$ is C(R$^{10}$) or C(-L-R$^{10a}$); Z$^3$ is N; Y$^1$ is absent; Y$^2$ is C(H)(R$^8$); Y$^3$ is C(R$^3$); X is an optionally substituted 4- to 7-membered heterocyclyl; n is 0; and R$^3$, R$^4$, R$^5$, R$^8$, R$^{10}$, R$^{10a}$, and L are each independently selected from the group consisting of hydrogen, halo, C$_{3-7}$ cycloalkyl, and C$_{1-6}$ alkyl. In one such embodiment, Z$^2$ is C(R$^{10}$), and R$^{10}$ is H. In another such embodiment, Z$^2$ is C(-L-R$^{10a}$), L is O, and R$^{10a}$ is heterocyclylalkyl or heteroarylalkyl, wherein the heterocyclylalkyl and heteroarylalkyl are optionally independently substituted with one or more L$^d$, and each L$^d$ is as defined above for Formula (I), Formula (II), or Formula (III). In one embodiment, each L$^d$ is independently selected from the group consisting of hydrogen, oxo, halogen, and C$_{1-6}$ alkyl.

According to some embodiments of the compound of Formula (I), Formula (II), or Formula (III), or a pharmaceutically acceptable salt thereof, Z$^1$ is N(R$^9$); Z$^2$ is C(R$^{10}$); Z$^3$ is N; Y$^1$ is absent; Y$^2$ is C(H)(R$^8$); Y$^3$ is C(R$^3$); X is a 4- to 7-membered heterocyclyl; n is 0; and R$^3$, R$^8$, R$^9$, and R$^{10}$ are each independently as defined above for Formula (I), Formula (II), or Formula (III).

According to some embodiments of the compound of Formula (I), Formula (II), or Formula (III), or a pharmaceutically acceptable salt thereof, Z$^1$ is N(R$^9$); Z$^2$ is C(R$^{10}$); Z$^3$ is N; Y$^1$ is absent; Y$^2$ is C(H)(R$^8$); Y$^3$ is C(R$^3$); X is a 4- to 7-membered heterocyclyl; n is 0; and R$^3$, R$^4$, R$^5$, R$^8$, R$^9$, and R$^{10}$ are each independently selected from the group consisting of hydrogen, halo, C$_{3-7}$ cycloalkyl, C$_{1-6}$ alkyl, aryl substituted with C$_{1-6}$ alkyl, and oxo.

According to some embodiments of the compound of Formula (I), Formula (II), or Formula (III), or a pharmaceutically acceptable salt thereof, wherein Z$^1$ is N(R$^9$); Z$^2$ is C(R$^{10}$); Z$^3$ is N; Y$^1$ is absent; Y$^2$ is C(H)(R$^8$); Y$^3$ is N; X is a 4- to 7-membered heterocyclyl; n is 0; and R$^8$, R$^9$, and R$^{10}$ are each independently as defined above for Formula (I), Formula (II), or Formula (III).

According to some embodiments of the compound of Formula (I), Formula (II), or Formula (III), or a pharmaceutically acceptable salt thereof Z$^1$ is N(R$^9$); Z$^2$ is C(R$^{10}$);

$Z^3$ is N; $Y^1$ is absent; $Y^2$ is C(H)($R^8$); $Y^3$ is N; X is a 4- to 7-membered heterocyclyl; n is 0; and $R^4$, $R^5$, $R^8$, $R^9$, and $R^{10}$ are each independently selected from the group consisting of hydrogen, halo, $C_{3-7}$ cycloalkyl, $C_{1-6}$ alkyl, aryl substituted with $C_{1-6}$ alkyl, and oxo.

According to some embodiments of the compound of Formula (I), Formula (II), or Formula (III), or a pharmaceutically acceptable salt thereof, particular combinations of $R^1$, $R^2$ (when present), $R^3$, $R^4$, $R^5$, $R^6$, $R^7$, $R^8$, $R^9$, $R^{10}$, $R^{11}$, $R^{12}$, X, $Z^1$, $Z^2$, $Z^3$, $Y^1$, $Y^2$, and n include:

(i) an embodiment where $Z^1$ is N; $Z^2$ is C($R^{10}$); $Z^3$ is N; $Y^1$ is absent; $Y^2$ is C(H)($R^8$); $Y^3$ is C($R^3$); $R^3$, $R^4$, $R^5$, and $R^{10}$ are each hydrogen; $R^1$ and $R^8$ are each independently as defined above for Formula (I), Formula (II), or Formula (III); X is an optionally substituted 4- to 7-membered heterocyclyl; n is 0; and $R^2$ is

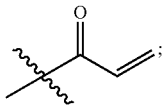 [SMILES: *C(=O)C=C]

(ii) an embodiment where $Z^1$ is N; $Z^2$ is C($R^{10}$); $Z^3$ is N; $Y^1$ is C(H)($R^6$); $Y^2$ is C(H)($R^8$); $Y^3$ is C($R^3$); $R^3$, $R^4$, $R^5$, $R^6$, $R^8$, and $R^{10}$ are each hydrogen; $R^1$ is as defined above for Formula (I), Formula (II), or Formula (III); X is a 4- to 7-membered heterocyclyl; n is 0; and $R^2$ is

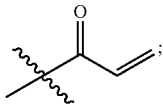 [SMILES: *C(=O)C=C]

(iii) an embodiment where $Z^1$ is N; $Z^2$ is C($R^{10}$); $Z^3$ is N; $Y^1$ is C(H)($R^6$); $Y^2$ is N($R^7$); $Y^3$ is C($R^3$); $R^3$, $R^4$, $R^5$, $R^6$, and $R^{10}$ are each hydrogen; $R^1$ and $R^7$ are each independently as defined above for Formula (I), Formula (II), or Formula (III); X is a 4- to 7-membered heterocyclyl; n is 0; and $R^2$ is

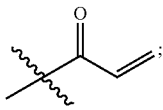

(iv) an embodiment where $Z^1$ is N; $Z^2$ is C($R^{10}$); $Z^3$ is N; $Y^1$ is absent; $Y^2$ is N($R^7$); $Y^3$ is C($R^3$); $R^3$, $R^4$, $R^5$, and $R^{10}$ are each hydrogen; $R^1$ and $R^7$ are each independently as defined above for Formula (I), Formula (II), or Formula (III); X is a 4- to 7-membered heterocyclyl; n is 0; and $R^2$ is

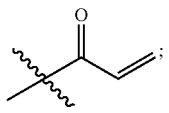 [SMILES: *C(=O)C=C]

(v) an embodiment where $Z^1$ is N; $Z^2$ is C($R^{10}$); $Z^3$ is C($R^{12}$); $Y^1$ is absent; $Y^2$ is C(H)($R^8$); $Y^3$ is C($R^3$); $R^3$, $R^4$, $R^5$, and $R^{10}$ are each hydrogen; $R^1$, $R^8$, and $R^{12}$ are each independently as defined above for Formula (I), Formula (II), or Formula (III); X is a 4- to 7-membered heterocyclyl; n is 0; and $R^2$ is

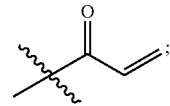

(vi) an embodiment where $Z^1$ is S(O)$_2$; $Z^2$ is absent; $Z^3$ is N; $Y^1$ is absent; $Y^2$ is C(H)($R^8$); $Y^3$ is C($R^3$); $R^3$, $R^4$, and $R^5$ are each hydrogen; $R^1$ and $R^8$ are each independently defined above for Formula (I), Formula (II), or Formula (III); X is a 4- to 7-membered heterocyclyl; n is 0; and $R^2$ is

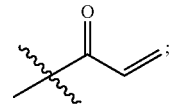 [SMILES: *C(=O)C=C]

(vii) an embodiment where $Z^1$ is O; $Z^2$ is absent; $Z^3$ is N; $Y^1$ is absent; $Y^2$ is C(H)($R^8$); $Y^3$ is C($R^3$); $R^3$, $R^4$, and $R^5$ are each hydrogen; $R^1$ and $R^8$ are each independently as defined above for Formula (I), Formula (II), or Formula (III); X is a 4- to 7-membered heterocyclyl; n is 0; and $R^2$ is

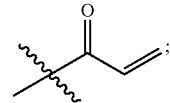 [SMILES: *C(=O)C=C]

(viii) an embodiment where $Z^1$ is N($R^9$); $Z^2$ is absent; $Z^3$ is N; $Y^1$ is absent; $Y^2$ is C(H)($R^8$); $Y^3$ is C($R^3$); $R^3$, $R^4$, and $R^5$ are each hydrogen; $R^1$, $R^8$, and $R^9$ are each independently as defined above for Formula (I), Formula (II), or Formula (III); X is a 4- to 7-membered heterocyclyl; n is 0; and $R^2$ is

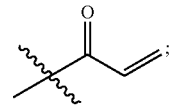 [SMILES: *C(=O)C=C]

(ix) an embodiment where $Z^1$ is N; $Z^2$ is absent; $Z^3$ is N(R″); $Y^1$ is absent; $Y^2$ is C(H)($R^8$); $Y^3$ is C($R^3$); $R^3$, $R^4$, and $R^5$ are each hydrogen; $R^1$, $R^8$, and $R^{11}$ are each independently as defined above for Formula (I), Formula (II), or Formula (III); X is a 4- to 7-membered heterocyclyl; n is 0; and $R^2$ is

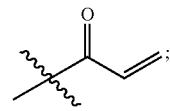 [SMILES: *C(=O)C=C]

(x) an embodiment where $Z^1$ is S(O); $Z^2$ is absent; $Z^3$ is N; $Y^1$ is absent; $Y^2$ is C(H)($R^8$); $Y^3$ is C($R^3$); $R^3$, $R^4$, and $R^5$ are each hydrogen; $R^1$ and $R^8$ are each independently as defined above for Formula (I), Formula (II), or Formula (III); X is a 4- to 7-membered heterocyclyl; n is 0; and R² is

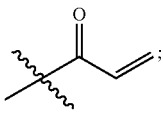 [SMILES: *C(=O)C=C]

(xi) an embodiment where Z¹ is S; Z² is absent; Z³ is N; Y¹ is absent; Y² is C(H)(R⁸); Y³ is C(R³); R³, R⁴, and R⁵ are each hydrogen; R¹ and R⁸ are each independently as defined above for Formula (I), Formula (II), or Formula (III); X is a 4- to 7-membered heterocyclyl; n is 0; and R² is

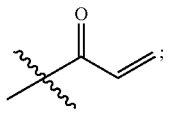 [SMILES: *C(=O)C=C]

(xii) an embodiment where Z¹ is N(R⁹); Z² is C(R¹⁰); Z³ is N; Y¹ is absent; Y² is C(H)(R⁸); Y³ is C(R³); R³, R⁴, R⁵, and R⁸ are each hydrogen; R¹ is as defined above for Formula (I), Formula (II), or Formula (III); R⁹ is an aryl substituted with a C₁₋₆ alkyl; R¹⁰ is oxo; X is a 4- to 7-membered heterocyclyl; n is 0; and R² is

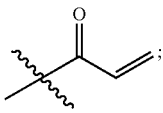 [SMILES: *C(=O)C=C]

(xiii) an embodiment where Z¹ is N(R⁹); Z² is C(R¹⁰); Z³ is N; Y¹ is absent; Y² is C(H)(R⁸); Y³ is N; R⁴, R⁵, and R⁸ are each hydrogen; R¹ is as defined above for Formula (I), Formula (II), or Formula (III); R⁹ is an aryl substituted with a C₁₋₆ alkyl; R¹⁰ is oxo; X is a 4- to 7-membered heterocyclyl; n is 0; and R² is

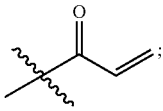 [SMILES: *C(=O)C=C]

and (ix) an embodiment where Z¹ is N; Z² is C(-L-R¹⁰ᵃ); Z³ is N; Y¹ is absent; Y² is C(H)(R⁸); Y³ is C(R³); R³, R⁴, R⁵, and R⁸ are each independently selected from the group consisting of H and C₁₋₆ alkyl; R¹ is as defined above for Formula (I), Formula (II), or Formula (III); L is O; R¹⁰ᵃ is heterocyclylalkyl or heteroarylalkyl, wherein the heterocyclylalkyl and heteroarylalkyl are optionally independently substituted with one or more Lᵈ; Lᵈ is as defined above for Formula (I), Formula (II), or Formula (III); X is an optionally substituted 4- to 7-membered heterocyclyl; n is 0; and R² is

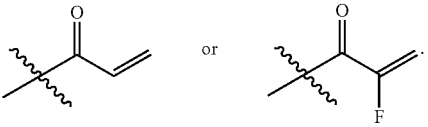

According to some embodiments of the compound of Formula (I), Formula (II), or Formula (III), or a pharmaceutically acceptable salt thereof, particular combinations of R¹, R² (when present), R³, R⁴, R⁵, R⁶, R⁷, R⁸, R⁹, R¹⁰, R¹¹, R¹², X, Z¹, Z², Z³, Y¹, Y², and n include any one of embodiments (i)-(ix), wherein X is

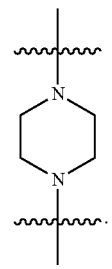 [SMILES: *N1CCN(*)CC1]

According to some embodiments of the compound of Formula (I), Formula (II), or Formula (III), or a pharmaceutically acceptable salt thereof, particular combinations of R¹, R² (when present), R³, R⁴, R⁵, R⁶, R⁷, R⁸, R⁹, R¹⁰, R¹¹, R¹², X, Z¹, Z², Z³, Y¹, Y², and n include any one of embodiments (i)-(ix), wherein R¹ is selected from the group consisting of:

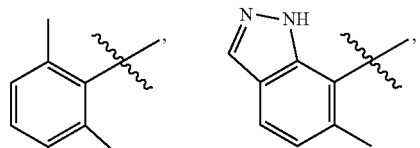

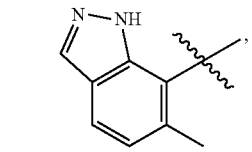

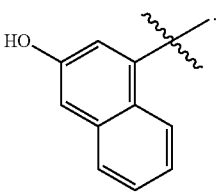

In still another embodiment of the compound of Formula (I), Formula (II), or Formula (III), or a pharmaceutically acceptable salt thereof, $R^1$ is:
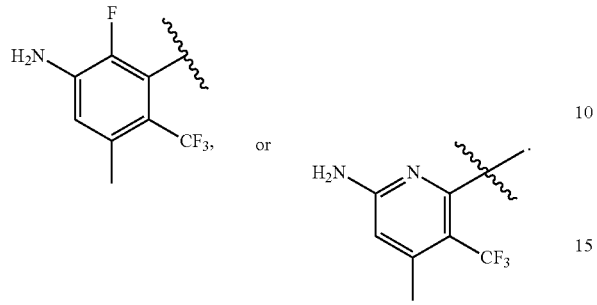
According to some embodiments of Formula (I) or of Formula (II), the compound has a formula selected from the group consisting of:
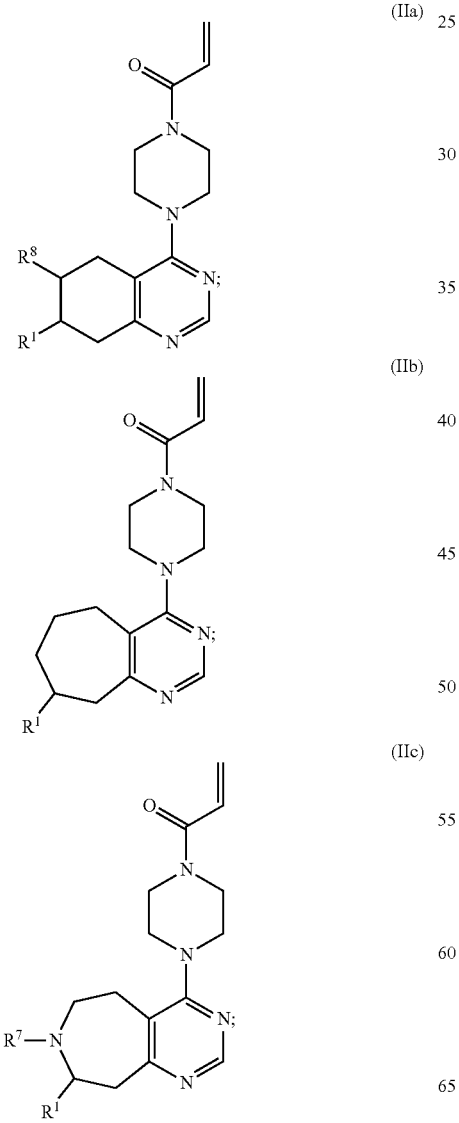
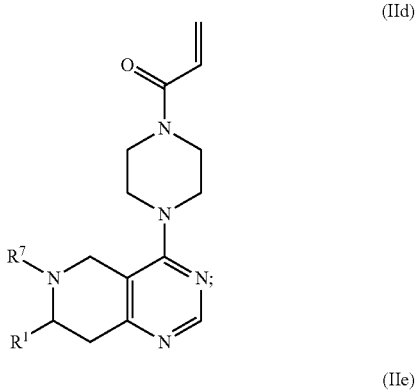
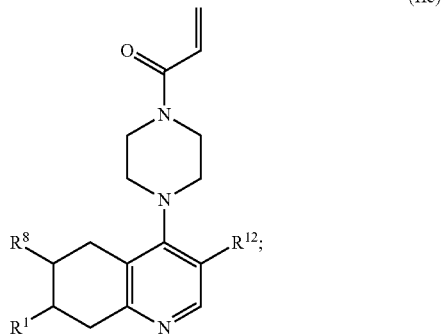
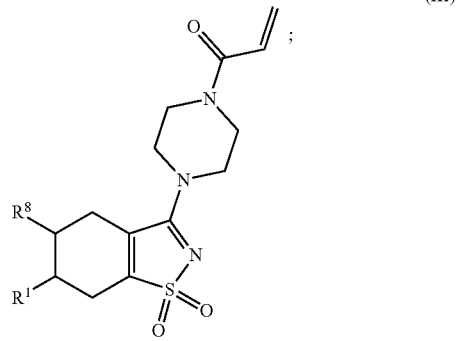
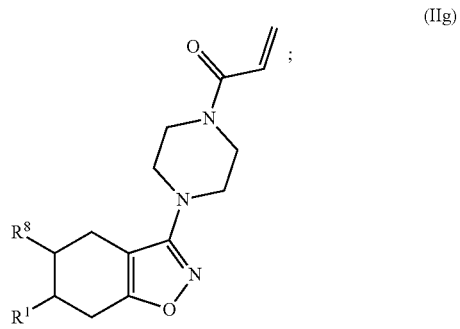

or a pharmaceutically acceptable salt thereof, wherein $R^1$, $R^7$, $R^8$, $R^9$, $R^{10}$, $R^{10a}$, $R^{11}$, $R^{12}$, and L are each independently defined as above for Formula (I).

According to some embodiments of Formula (I) or of Formula (II), the compound has formula (IIa):

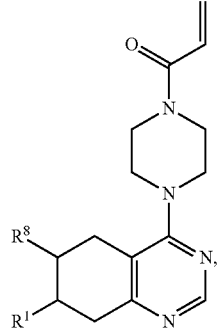
(IIa)

or a pharmaceutically acceptable salt thereof, wherein $R^1$ and $R^8$ are independently as defined above for Formula (I) or Formula (II).

According to some embodiments of Formula (I) or of Formula (II), the compound of Formula (IIa) has a formula selected from the group consisting of:

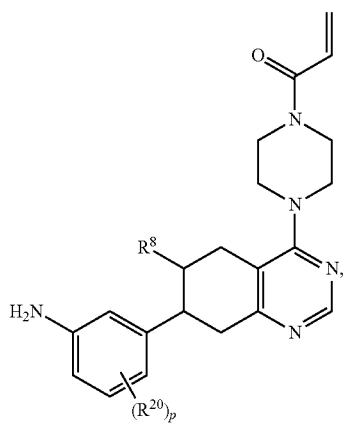
(IIa-1)

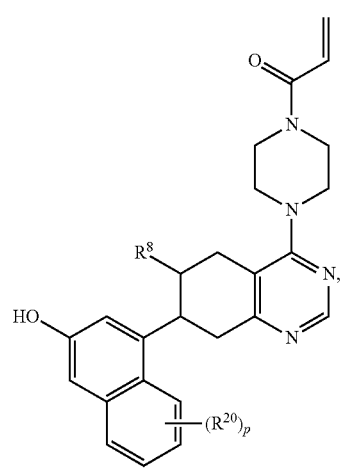
(IIa-2)

-continued

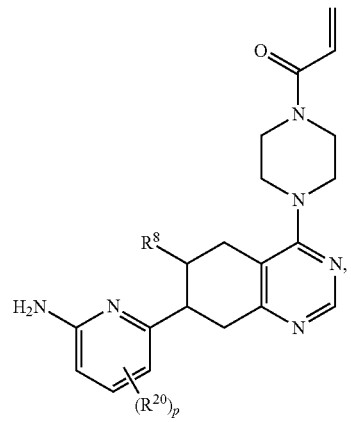
(IIa-3)

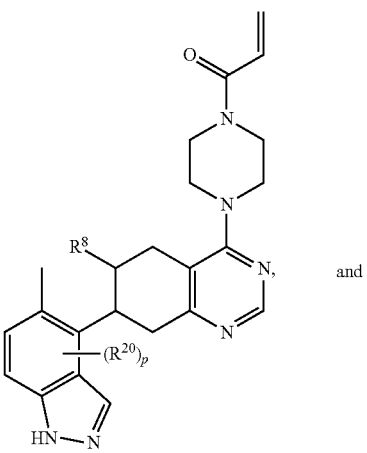
(IIa-4)

and

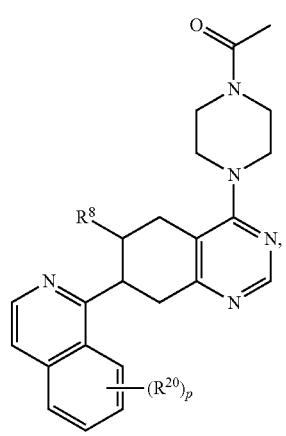
(IIa-5)

or a pharmaceutically acceptable salt thereof, wherein each $R^J$ is independently selected from the group consisting of $C_{1-6}$ alkyl, $NH_2$, $NH(CH_3)$, $N(CH_3)_2$, halo, $C_{1-6}$ haloalkyl, hydroxy, $C_{3-6}$ cycloalkyl, $C_{1-6}$ hydroxyalkyl, and —OC(=O)CH=CH$_2$; each p is independently 0, 1, 2, 3, or 4; and $R^8$ is as defined above for Formula (I) or Formula (II).

According to some embodiments of Formula (I) or of Formula (II), the compound of Formula (IIa) has a formula selected from the group consisting of:
(IIa-6)
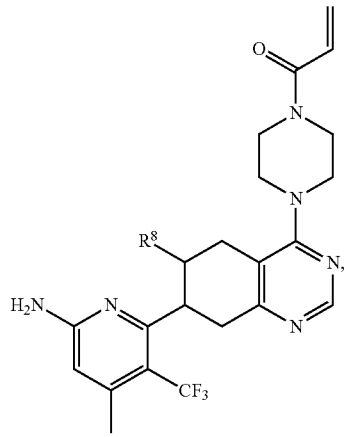
(IIa-7)
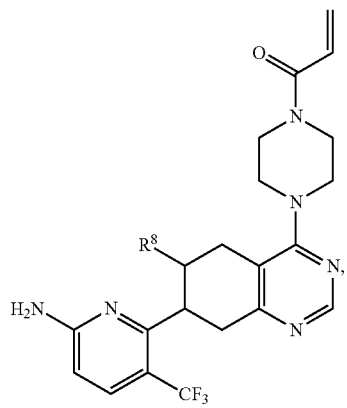
(IIa-8)
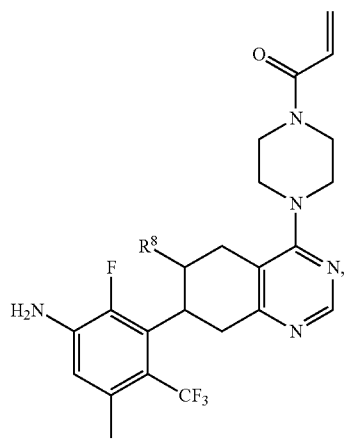
(IIa-9)
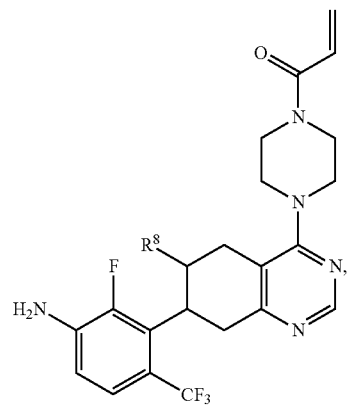
(IIa-10)
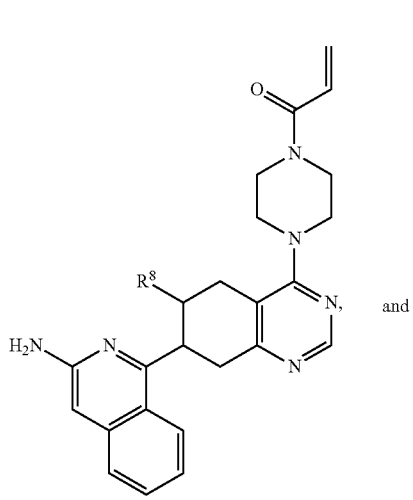
and
(IIa-11)
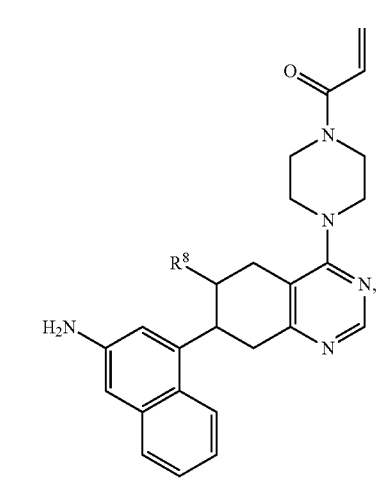
or a pharmaceutically acceptable salt thereof, wherein $R^8$ is as defined above for Formula (I) or Formula (II).

According to some embodiments of Formula (I) or of Formula (II), the compound has Formula (III):

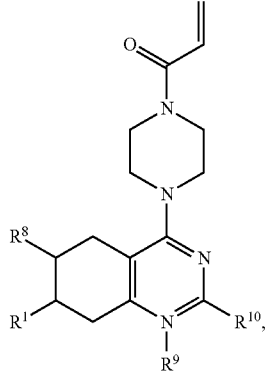
(III)

or a pharmaceutically acceptable salt thereof, wherein $R^1$, $R^8$, $R^9$, and $R^{10}$ are independently as defined above for Formula (I) or Formula (II).

According to some embodiments of Formula (I) or of Formula (II), the compound of Formula (III) has a formula selected from the group consisting of:

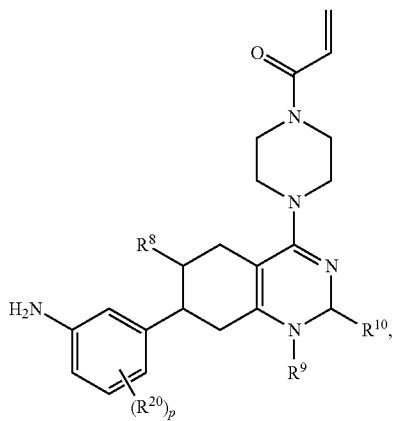
(III-1)

(III-2)

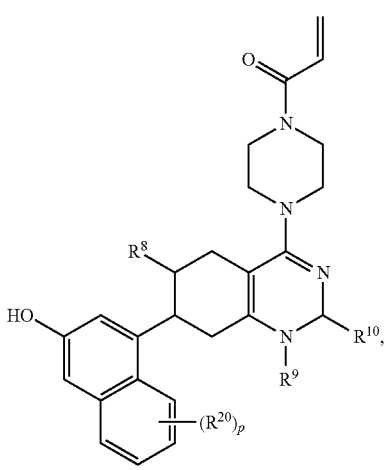

-continued

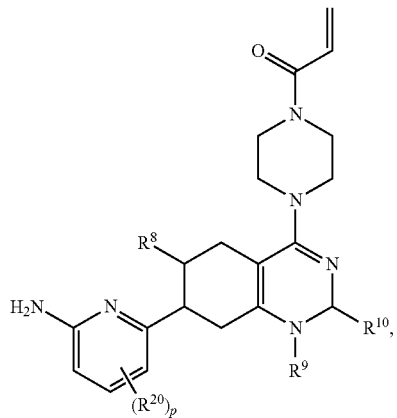
(III-3)

(III-4)

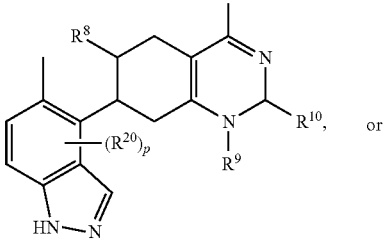
(III-5)

or a pharmaceutically acceptable salt thereof, wherein $R^{20}$ is selected from the group consisting of ($C_{1-6}$ alkyl, $NH_2$, $NH(CH_3)$, $N(CH_3)_2$, halo, $C_{1-6}$ haloalkyl, hydroxy, $C_{3-6}$ cycloalkyl, $C_{1-6}$ hydroxyalkyl, and —OC(=O)CH=CH$_2$; p is 0, 1, 2, 3, or 4; and $R^8$, $R^9$, and $R^{10}$ are independently as defined above for Formula (I) or Formula (II).

According to some embodiments of Formula (I) or of Formula (II), the compound of Formula (III) has a formula selected from the group consisting of:

(III-6)
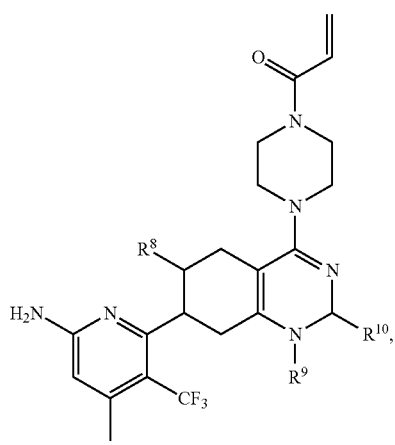
(III-9)
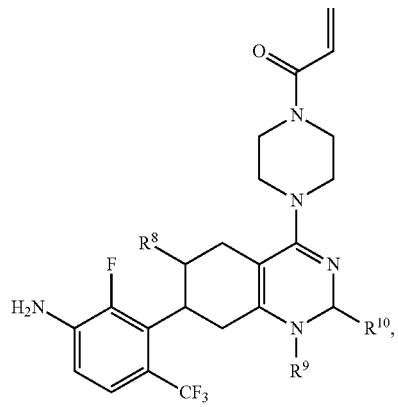
(III-7)
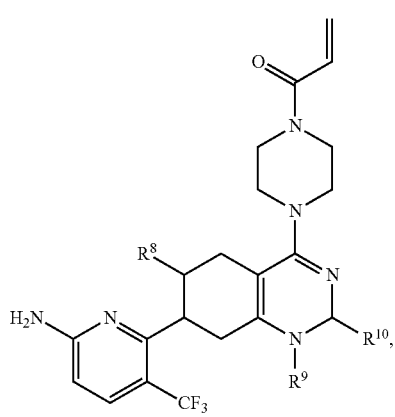
(III-10)
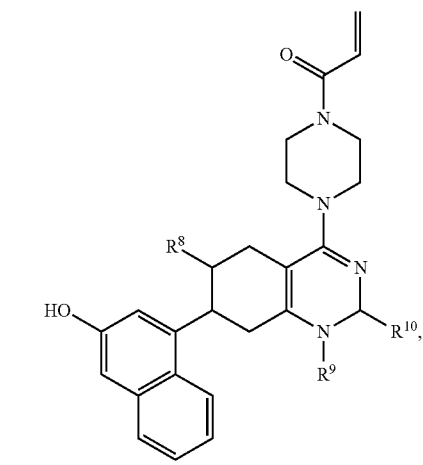
(III-8)
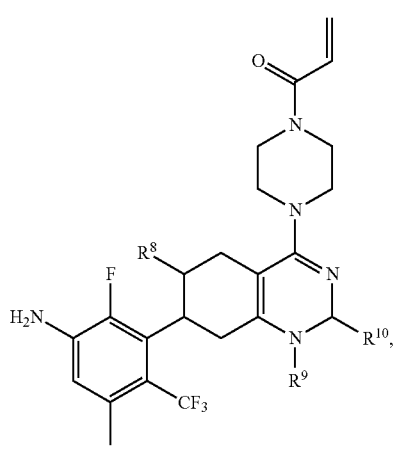
(III-11)
or a pharmaceutically acceptable salt thereof; wherein $R^8$, $R^9$, and $R^{10}$ are independently as defined above for Formula (I) or Formula (II).
According to some embodiments of Formula (I) or of Formula (II), the compound has Formula (IIm):

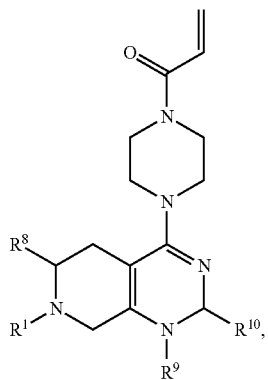

(IIm)

or a pharmaceutically acceptable salt thereof, wherein $R^1$, $R^8$, $R^9$, and $R^{10}$ are independently as defined above for Formula (I) or Formula (II).

According to some embodiments of Formula (I) or of Formula (II), the compound has Formula (IIn):

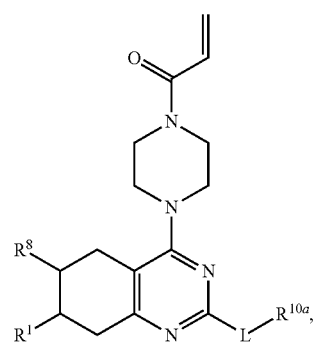

(IIn)

or a pharmaceutically acceptable salt thereof, wherein $R^1$, $R^8$, L, and $R^{10a}$ are independently as defined above for Formula (I) or Formula (II).

According to some embodiments of Formula (I) or of Formula (II), the compound of Formula (IIn) has a formula selected from the group consisting of:

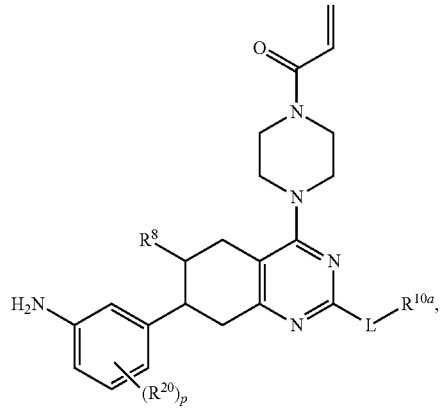

(IIn-1)

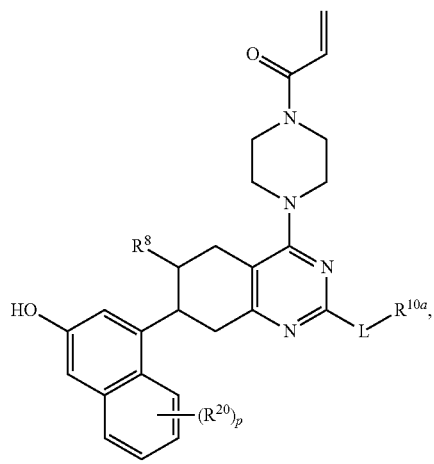

(IIn-2)

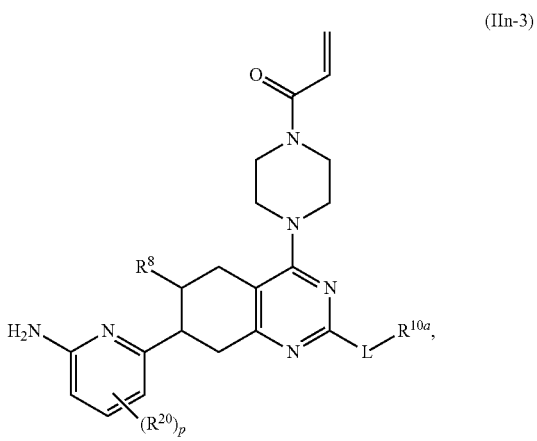

(IIn-3)

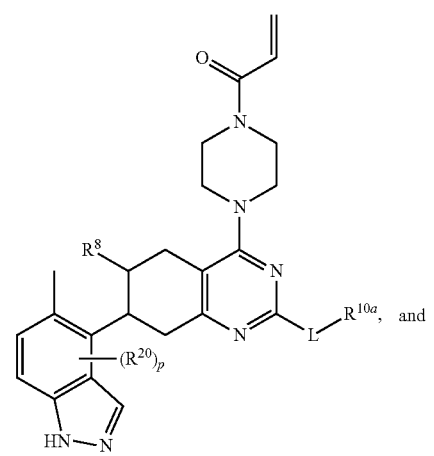

(IIn-4)

(IIn-5)

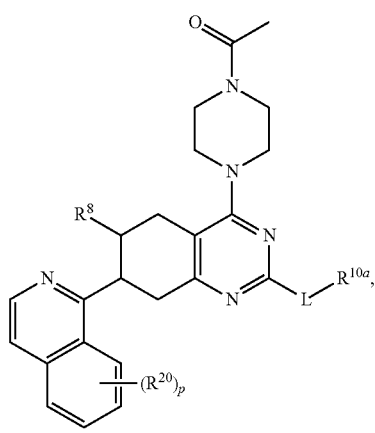

or a pharmaceutically acceptable salt thereof, wherein each $R^{20}$ is independently selected from the group consisting of $C_{1-6}$ alkyl, $NH_2$, $NH(CH_3)$, $N(CH_3)_2$, halo, $C_{1-6}$ haloalkyl, hydroxy, $C_{3-6}$ cycloalkyl, $C_{1-6}$ hydroxyalkyl, and —OC(=O)CH=CH$_2$; each p is independently 0, 1, 2, 3, or 4; and $R^8$, L, and $R^{10a}$ are independently as defined above for Formula (I) or Formula (II).

According to some embodiments of Formula (I) or of Formula (II), the compound of Formula (IIn) has a formula selected from the group consisting of:

(IIn-6)

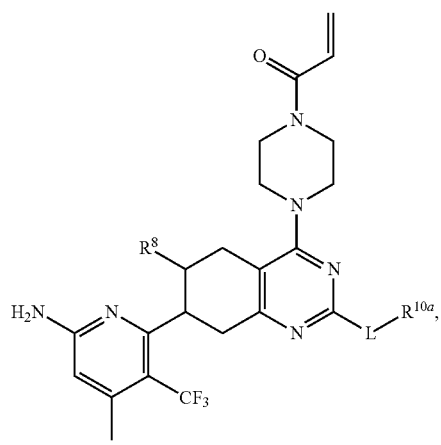

(IIn-7)

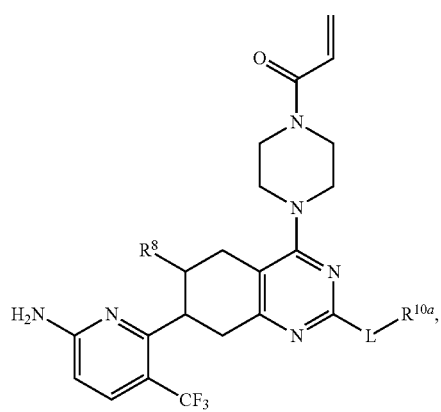

(IIn-8)

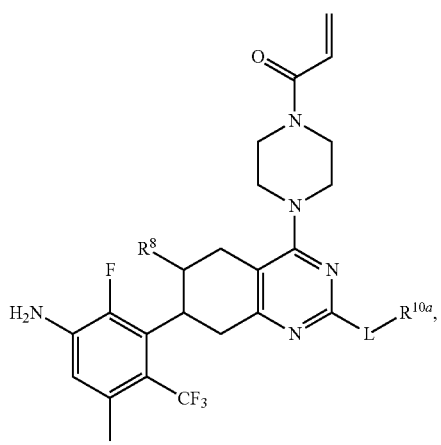

(IIn-9)

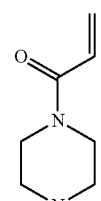

(IIn-10)

-continued (IIn-11)

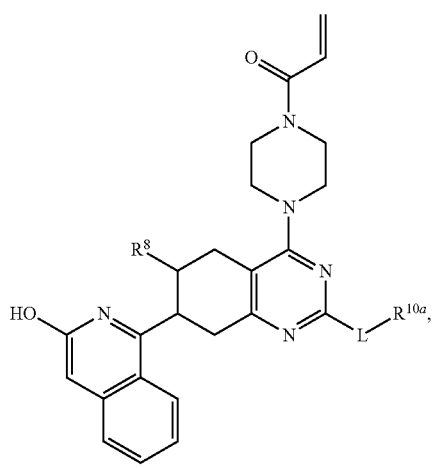

or a pharmaceutically acceptable salt thereof; wherein $R^8$, L, and $R^{10a}$ are independently as defined above for Formula (I) or Formula (II).

According to some embodiments of Formula (I) or of Formula (II), or a pharmaceutically acceptable salt thereof, the compound has Formula (IIa), wherein $R^8$ is selected from the group consisting of H and $C_{1-6}$ alkyl.

According to some embodiments of Formula (I) or of Formula (II), or a pharmaceutically acceptable salt thereof, the compound has Formula (IIa), wherein $R^8$ is selected from the group consisting of H, methyl, and isopropyl.

According to some embodiments of Formula (I) or of Formula (II), or a pharmaceutically acceptable salt thereof, the compound has Formula (III), wherein $R^8$ is selected from the group consisting of H and methyl; $R^9$ is aryl substituted with $C_{1-6}$ alkyl; and $R^{10}$ is oxo.

According to some embodiments of Formula (I) or of Formula (II), or a pharmaceutically acceptable salt thereof, the compound has Formula (III), wherein $R^8$ is hydrogen; $R^9$ is aryl substituted with $C_{1-6}$ alkyl; and $R^{10}$ is oxo.

According to some embodiments of Formula (I) or of Formula (II), or a pharmaceutically acceptable salt thereof, the compound has Formula (IIm), wherein $R^8$ is selected from the group consisting of H and methyl; $R^9$ is aryl substituted with $C_{1-6}$ alkyl; and $R^{10}$ is oxo.

According to some embodiments of Formula (I) or of Formula (II), or a pharmaceutically acceptable salt thereof, the compound has Formula (IIm), wherein $R^8$ is hydrogen; $R^9$ is aryl substituted with $C_{1-6}$ alkyl; and $R^{10}$ is oxo.

According to some embodiments of Formula (I) or of Formula (II), or a pharmaceutically acceptable salt thereof, the compound has Formula (IIn), wherein $R^8$ is selected from the group consisting of hydrogen and $C_{1-6}$ alkyl; L is O; $R^{10a}$ is selected from the group consisting of heterocyclylalkyl and heteroarylalkyl, wherein each heterocyclyolalkyl and heteroarylalkyl are optionally substituted with one or more $L^d$; and each $L^d$ is independently selected from the group consisting of hydrogen, oxo, halogen, and $C_{1-6}$ alkyl.

According to some embodiments of Formula (I) or of Formula (II), the compound has Formula (IIa), (III), (IIm), or (IIn) wherein $R^1$ is selected from the group consisting of

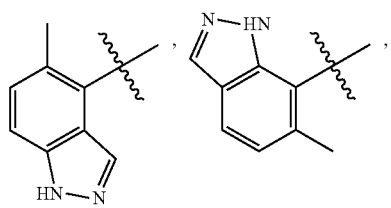

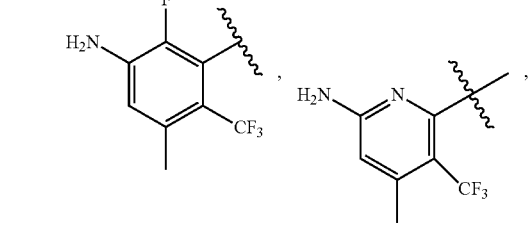

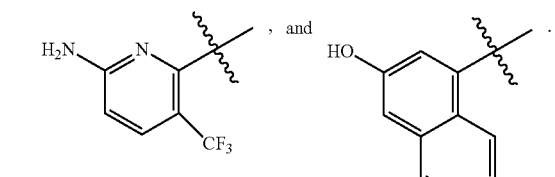

According to some embodiments of Formula (I) or of Formula (II), or a pharmaceutically acceptable salt thereof, the compound is selected from the group consisting of the compounds of Table 1, shown below, or a pharmaceutically acceptable salt thereof.

TABLE 1

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 1 | 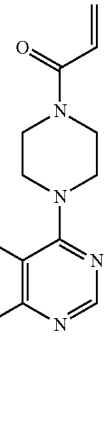 | 1-(4-(7-(6-amino-4-methyl-3-(trifluoromethyl)pyridin-2-yl)-6-methyl-5,6,7,8-tetrahydroquinazolin-4-yl)piperazin-1-yl)prop-2-en-1-one | >50<br>>50 | 461.2 |
| 1a | 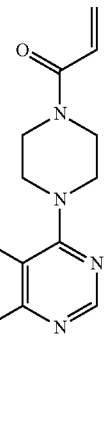 | 1-(4-((6R,7S)-7-(6-amino-4-methyl-3-(trifluoromethyl)pyridin-2-yl)-6-methyl-5,6,7,8-tetrahydroquinazolin-4-yl)piperazin-1-yl)prop-2-en-1-one | | |
| 1b | 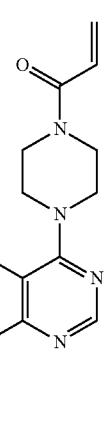 | 1-(4-((6S,7R)-7-(6-amino-4-methyl-3-(trifluoromethyl)pyridin-2-yl)-6-methyl-5,6,7,8-tetrahydroquinazolin-4-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 2 | 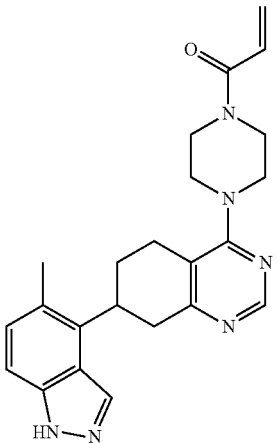 racemic | 1-(4-(7-(5-methyl-1H-indazol-4-yl)-5,6,7,8-tetrahydroquinazolin-4-yl)piperazin-1-yl)prop-2-en-1-one | 0.84 | 403.2 |
| 3 | 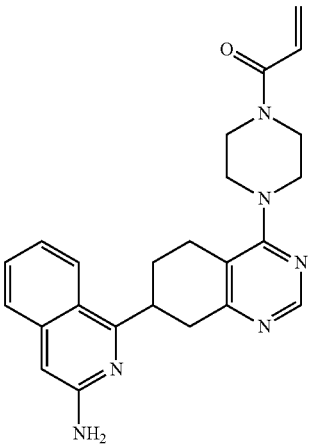 [SMILES: C=CC(=O)N1CCN(c2ncnc3c2CCC(c2nc(N)cc4ccccc24)C3)CC1] | 1-(4-(7-(3-aminoisoquinolin-1-yl)-5,6,7,8-tetrahydroquinazolin-4-yl)piperazin-1-yl)prop-2-en-1-one | >50 0.71 | 415.0 |
| 3a | 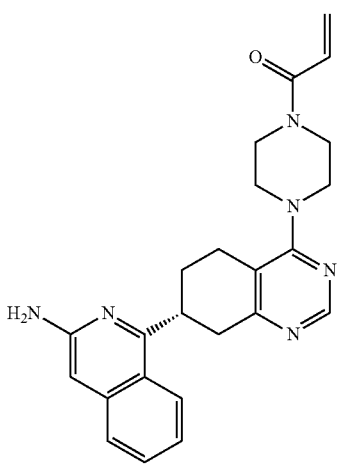 assumed | (R)-1-(4-(7-(3-aminoisoquinolin-1-yl)-5,6,7,8-tetrahydroquinazolin-4-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 3b | 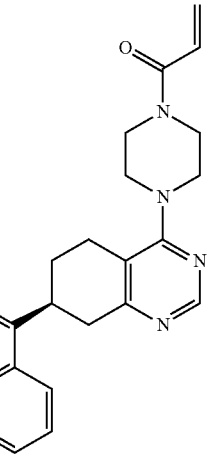 assumed | (S)-1-(4-(7-(3-aminoisoquinolin-1-yl)-5,6,7,8-tetrahydroquinazolin-4-yl)piperazin-1-yl)prop-2-en-1-one | | |
| 4 | 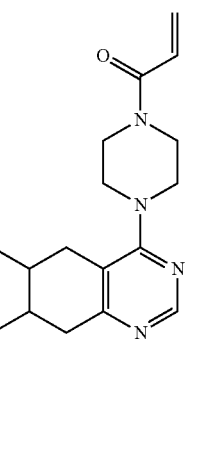 | 1-(4-(7-(5-(hydroxymethyl)-2-methylphenyl)-6-methyl-5,6,7,8-tetrahydroquinazolin-4-yl)piperazin-1-yl)prop-2-en-1-one | >50 0.39 | 407.2 |
| 4a | 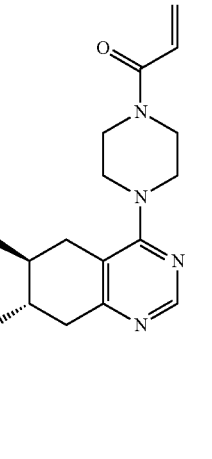 assumed | 1-(4-((6S,7S)-7-(5-(hydroxymethyl)-2-methylphenyl)-6-methyl-5,6,7,8-tetrahydroquinazolin-4-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 4b | 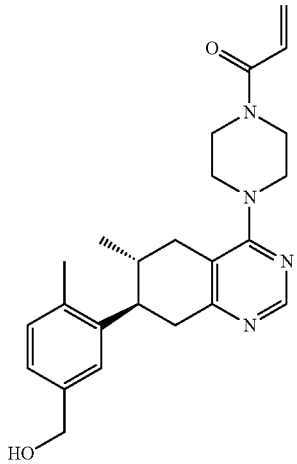 [SMILES: C=CC(=O)N1CCN(c2ncnc3c2CC(C)C(c2cc(CO)ccc2C)C3)CC1] assumed | 1-[4-[(6R,7R)-7-[5-(hydroxymethyl)-2-methyl-phenyl]-6-methyl-5,6,7,8-tetrahydroquinazolin-4-yl]piperazin-1-yl]prop-2-en-1-one | | |
| 5 | 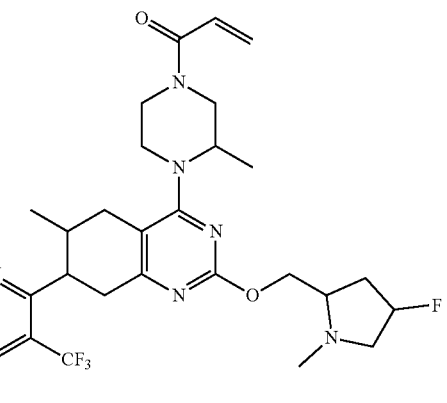 | 1-(4-(2-((4-fluoro-1-methylpyrrolidin-2-yl)methoxy)-6-methyl-7-(4-methyl-6-(methylamino)-3-(trifluoromethyl)pyridin-2-yl)-5,6,7,8-tetrahydroquinazolin-4-yl)-3-methylpiperazin-1-yl)prop-2-en-1-one | >20 0.045 | 620.3 |
| 5a | 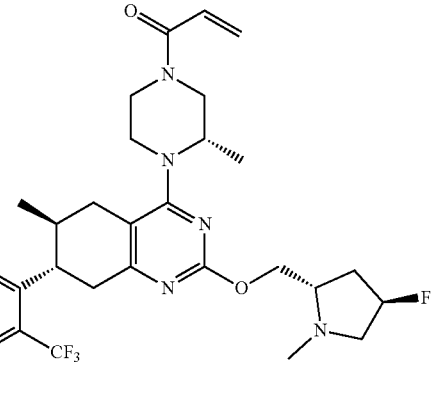 assumed | 1-[(3S)-4-[(6S,7S)-2-[[(2S,4R)-4-fluoro-1-methyl-pyrrolidin-2-yl]methoxy]-6-methyl-7-[4-methyl-6-(methylamino)-3-(trifluoromethyl)-2-pyridyl]-5,6,7,8-tetrahydroquinazolin-4-yl]-3-methyl-piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 5b | 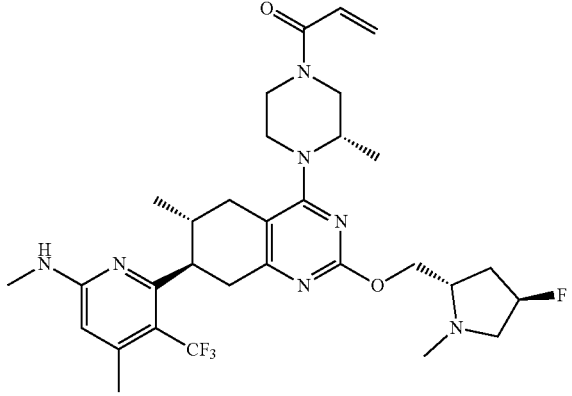 [SMILES: C=CC(=O)N1CCN(c2nc(OCC3CC(F)CN3C)nc3c2CC(C)C(c2nc(NC)cc(C)c2C(F)(F)F)C3)C(C)C1] assumed | 1-[(3S)-4-[(6R,7R)-2-[[(2S,4R)-4-fluoro-1-methyl-pyrrolidin-2-yl]methoxy]-6-methyl-7-[4-methyl-6-(methylamino)-3-(trifluoromethyl)-2-pyridyl]-5,6,7,8-tetrahydroquinazolin-4-yl]-3-methyl-piperazin-1-yl]prop-2-en-1-one | | |
| 6 | 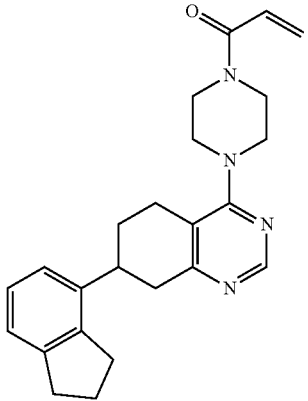 [SMILES: C=CC(=O)N1CCN(c2ncnc3c2CCC(c2cccc4c2CCC4)C3)CC1] | 1-(4-(7-(2,3-dihydro-1H-inden-4-yl)-5,6,7,8-tetrahydroquinazolin-4-yl)piperazin-1-yl)prop-2-en-1-one | 2.3 >50 | 389.2 |
| 6a | 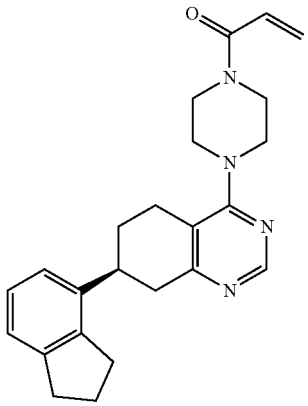 assumed | 1-[4-[(7S)-7-indan-4-yl-5,6,7,8-tetrahydroquinazolin-4-yl]piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 6b | 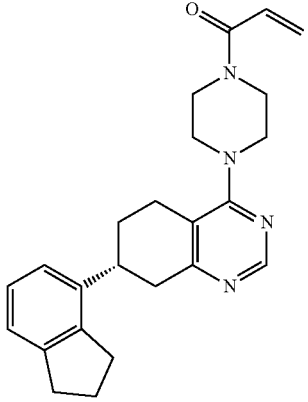 assumed | 1-[4-[(7R)-7-indan-4-yl-5,6,7,8-tetrahydroquinazolin-4-yl]piperazin-1-yl]prop-2-en-1-one | | |
| 7 | 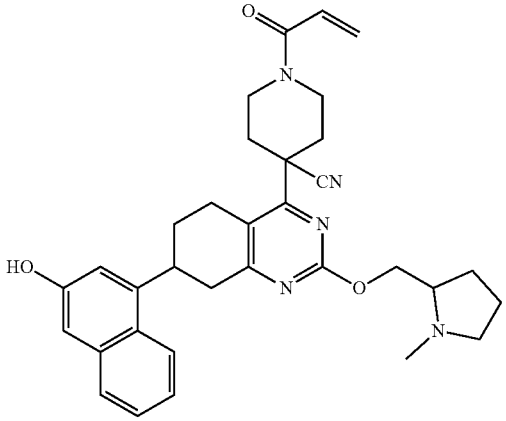 [SMILES: C=CC(=O)N1CCC(C#N)(c2nc(OCC3CCCN3C)nc3c2CCC(c2cc(O)cc4ccccc24)C3)CC1] | 1-acryloyl-4-(7-(3-hydroxynaphthalen-1-yl)-2-((1-methylpyrrolidin-2-yl)methoxy)-5,6,7,8-tetrahydroquinazolin-4-yl)piperidine-4-carbonitrile | 0.087 | 552.3 |
| 7a | 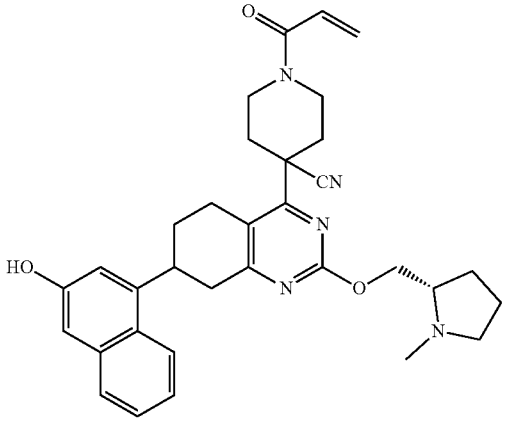 [SMILES: C=CC(=O)N1CCC(C#N)(c2nc(OC[C@@H]3CCCN3C)nc3c2CCC(c2cc(O)cc4ccccc24)C3)CC1] | 4-[7-(3-hydroxy-1-naphthyl)-2-[[(2S)-1-methylpyrrolidin-2-yl]methoxy]-5,6,7,8-tetrahydroquinazolin-4-yl]-1-prop-2-enoyl-piperidine-4-carbonitrile | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 8 | 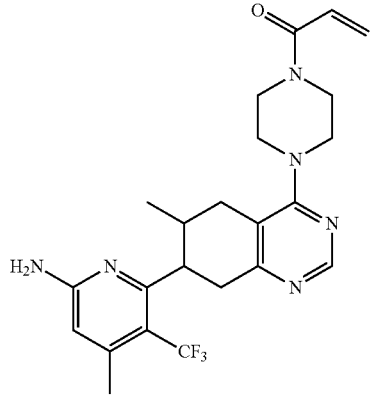 [SMILES: C=CC(=O)N1CCN(c2ncnc3c2CC(C)C(c2nc(N)cc(C)c2C(F)(F)F)C3)CC1] | 1-(4-(7-(6-amino-4-methyl-3-(trifluoromethyl)pyridin-2-yl)-6-methyl-5,6,7,8-tetrahydroquinazolin-4-yl]piperazin-1-yl)prop-2-en-1-one | 3.5 0.045 | 461.2 |
| 8a | 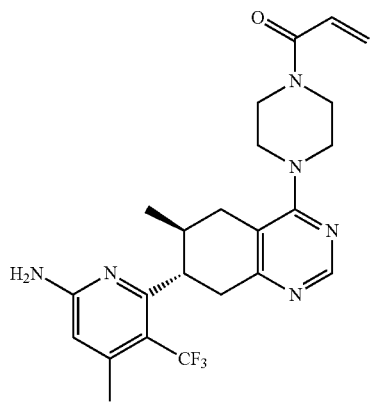<br>assumed | 1-[4-[(6S,7S)-7-[6-amino-4-methyl-3-(trifluoromethyl)-2-pyridyl]-6-methyl-5,6,7,8-tetrahydroquinazolin-4-yl]piperazin-1-yl]prop-2-en-1-one | | |
| 8b | 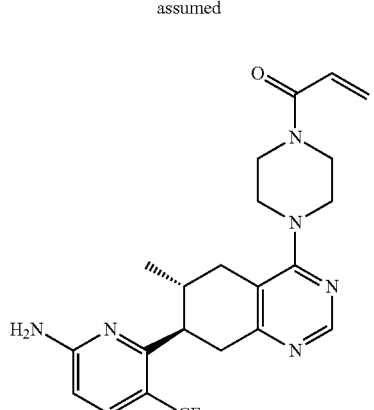<br>assumed | 1-[4-[(6R,7R)-7-[6-amino-4-methyl-3-(trifluoromethyl)-2-pyridyl]-6-methyl-5,6,7,8-tetrahydroquinazolin-4-yl]piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 9 | 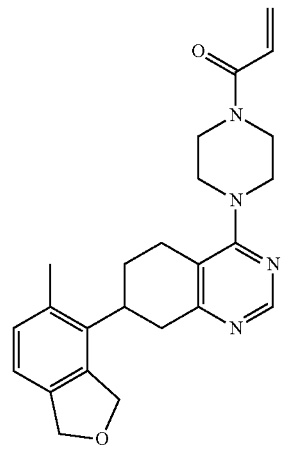 [SMILES: C=CC(=O)N1CCN(c2ncnc3c2CCC(c2c(C)ccc4c2COC4)C3)CC1] | 1-(4-(7-(5-methyl-1,3-dihydroisobenzofuran-4-yl)-5,6,7,8-tetrahydroquinazolin-4-yl)piperazin-1-yl)prop-2-en-1-one | 4.2 >50 | 405.2 |
| 9a | assumed | (S)-1-(4-(7-(5-methyl-1,3-dihydroisobenzofuran-4-yl)-5,6,7,8-tetrahydroquinazolin-4-yl)piperazin-1-yl)prop-2-en-1-one | | |
| 9b | assumed | (R)-1-(4-(7-(5-methyl-1,3-dihydroisobenzofuran-4-yl)-5,6,7,8-tetrahydroquinazolin-4-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 10 | 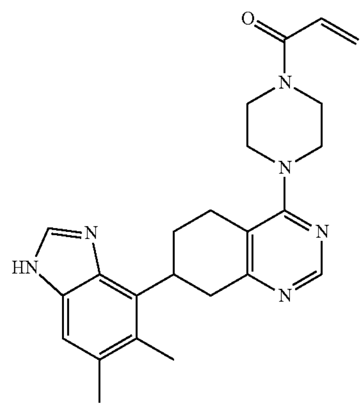 [SMILES: C=CC(=O)N1CCN(c2ncnc3c2CCC(c2c(C)c(C)cc4[nH]cnc24)C3)CC1] | 1-(4-(7-(5,6-dimethyl-1H-benzo[d]imidazol-4-yl)-5,6,7,8-tetrahydroquinazolin-4-yl)piperazin-1-yl)prop-2-en-1-one | 19 0.27 | 417.3 |
| 10a | assumed | 1-[4-[(7R)-7-(5,6-dimethyl-1H-benzimidazol-4-yl)-5,6,7,8-tetrahydroquinazolin-4-yl]piperazin-1-yl]prop-2-en-1-one | | |
| 10b | assumed | 1-[4-[(7S)-7-(5,6-dimethyl-1H-benzimidazol-4-yl)-5,6,7,8-tetrahydroquinazolin-4-yl]piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 11 | 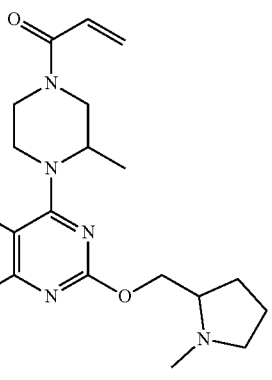 | 1-(4-(7-(3-amino-2-fluoro-5,6-dimethylphenyl)-6-methyl-2-((1-methylpyrrolidin-2-yl)methoxy)-5,6,7,8-tetrahydroquinazolin-4-yl)-3-methylpiperazin-1-yl)prop-2-en-1-one | 1.3<br><0.01 | 551.4 |
| 11a | 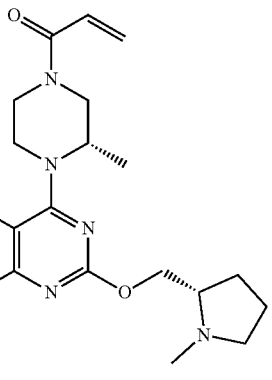<br>assumed | 1-[(3S)-4-[(6S,7S)-7-(3-amino-2-fluoro-5,6-dimethyl-phenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one | | |
| 11b | 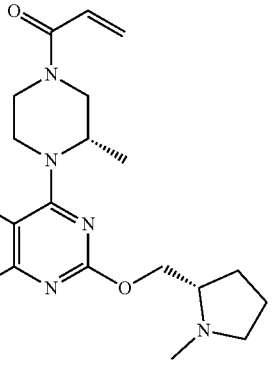<br>assumed | 1-[(3S)-4-[(6R,7R)-7-(3-amino-2-fluoro-5,6-dimethyl-phenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 12 | 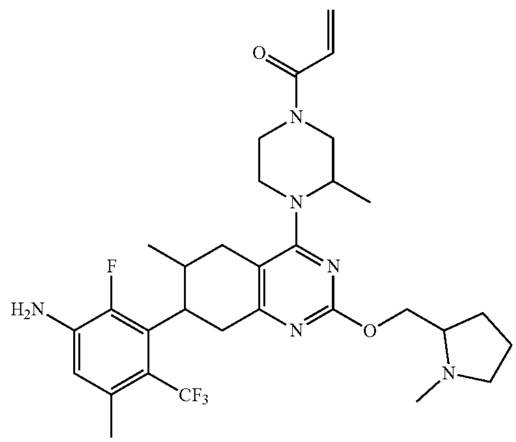 [SMILES: C=CC(=O)N1CCN(c2nc(OCC3CCCN3C)nc3c2CC(C)C(c2c(F)c(N)cc(C)c2C(F)(F)F)C3)C(C)C1] | 1-(4-(7-(3-amino-2-fluoro-5-methyl-6-(trifluoromethyl)phenyl)-6-methyl-2-((1-methylpyrrolidin-2-yl)methoxy)-5,6,7,8-tetrahydroquinazolin-4-yl)-3-methylpiperazin-1-yl)prop-2-en-1-one | 0.61<br><0.01 | 605.4 |
| 12a | assumed | 1-((S)-4-((6S,7S)-7-(3-amino-2-fluoro-5-methyl-6-(trifluoromethyl)phenyl)-6-methyl-2-(((S)-1-methylpyrrolidin-2-yl]methoxy)-5,6,7,8-tetrahydroquinazolin-4-yl)-3-methylpiperazin-1-yl)prop-2-en-1-one | | |
| 12b | assumed | 1-((S)-4-((6R,7R)-7-(3-amino-2-fluoro-5-methyl-6-(trifluoromethyl)phenyl)-6-methyl-2-(((S)-1-methylpyrrolidin-2-yl]methoxy)-5,6,7,8-tetrahydroquinazolin-4-yl)-3-methylpiperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 13 | 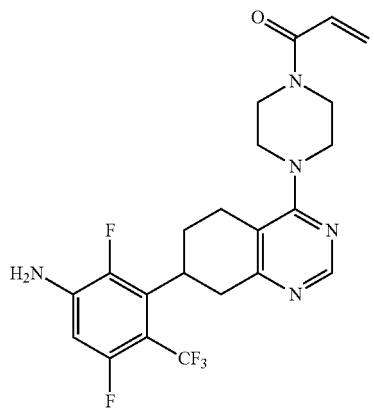 [SMILES: C=CC(=O)N1CCN(c2ncnc3c2CCC(c2c(F)c(N)cc(F)c2C(F)(F)F)C3)CC1] | 1-(4-(7-(3-amino-2,5-difluoro-6-(trifluoromethyl)phenyl)-5,6,7,8-tetrahydroquinazolin-4-yl)piperazin-1-yl)prop-2-en-1-one | 2 0.084 | 468.2 |
| 13a | 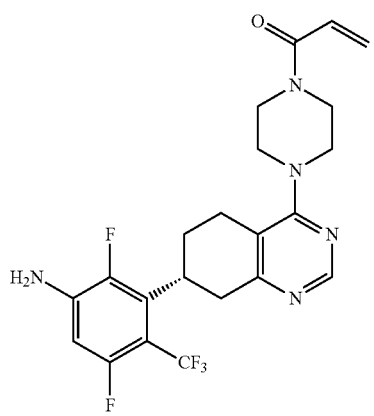<br>assumed | (R)-1-(4-(7-(3-amino-2,5-difluoro-6-(trifluoromethyl)phenyl)-5,6,7,8-tetrahydroquinazolin-4-yl)piperazin-1-yl)prop-2-en-1-one | | |
| 13b | 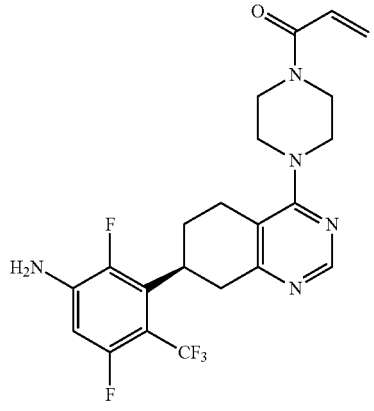<br>assumed | (S)-1-(4-(7-(3-amino-2,5-difluoro-6-(trifluoromethyl)phenyl)-5,6,7,8-tetrahydroquinazolin-4-yl)piperazin-1-yl)prop-2-en-1-one | | |

TABLE 1-continued

*Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.*

| Compound # | Structure | Name | IC50 | LCMS (M + H)+ |
|---|---|---|---|---|
| 14 | 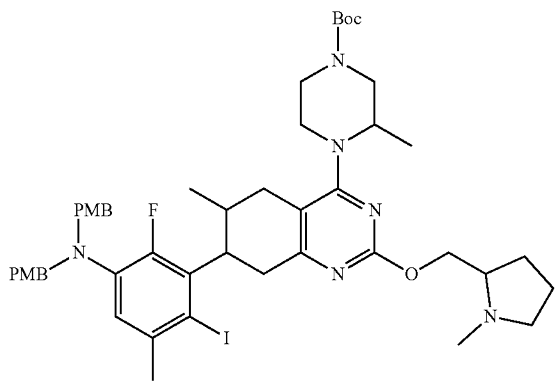 | tert-butyl 4-(7-(3-(bis(4-methoxybenzyl)amino)-2-fluoro-6-iodo-5-methylphenyl)-6-methyl-2-((1-methylpyrrolidin-2-yl)methoxy)-5,6,7,8-tetrahydroquinazolin-4-yl)-3-methylpiperazine-1-carboxylate | >50<br>>50 | 949.4 |
| 14a | assumed | tert-butyl(S)-4-((6R,7R)-7-(3-(bis(4-methoxybenzyl)amino)-2-fluoro-6-iodo-5-methylphenyl)-6-methyl-2-(((S)-1-methylpyrrolidin-2-yl)methoxy)-5,6,7,8-tetrahydroquinazolin-4-yl)-3-methylpiperazine-1-carboxylate | | |
| 14b | assumed | tert-butyl(S)-4-((6S,7S)-7-(3-(bis(4-methoxybenzyl)amino)-2-fluoro-6-iodo-5-methylphenyl)-6-methyl-2-(((S)-1-methylpyrrolidin-2-yl)methoxy)-5,6,7,8-tetrahydroquinazolin-4-yl)-3-methylpiperazine-1-carboxylate | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 15 | 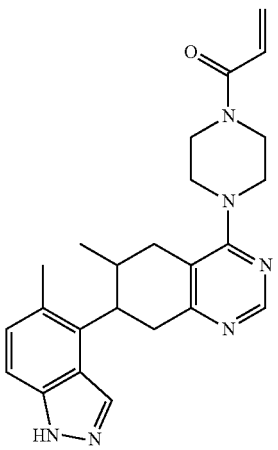 [SMILES: C=CC(=O)N1CCN(c2ncnc3c2CC(C)C(c2c(C)ccc4[nH]ncc24)C3)CC1] | 1-(4-(6-methyl-7-(5-methyl-1H-indazol-4-yl)-5,6,7,8-tetrahydroquinazolin-4-yl)piperazin-1-yl)prop-2-en-1-one | 0.0688.6 | 417.2 |
| 15a | 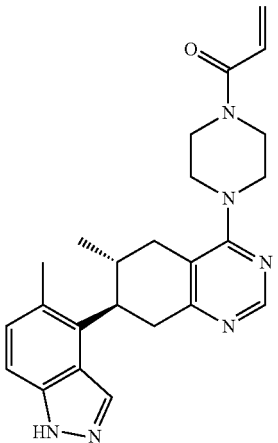 assumed | 1-[4-[(6R,7R)-6-methyl-7-(5-methyl-1H-indazol-4-yl)-5,6,7,8-tetrahydroquinazolin-4-yl]piperazin-1-yl]prop-2-en-1-one | | |
| 15b | 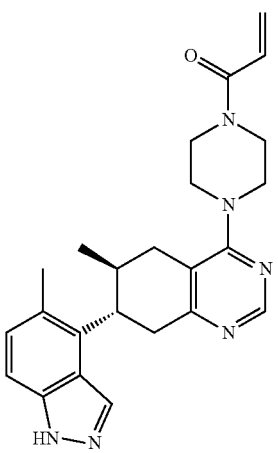 assumed | 1-[4-[(6S,7S)-6-methyl-7-(5-methyl-1H-indazol-4-yl)-5,6,7,8-tetrahydroquinazolin-4-yl]piperazin-1-yl]prop-2-en-1-one | | |

TABLE 1-continued

*Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.*

| Compound # | Structure | Name | IC50 | LCMS (M + H)+ |
|---|---|---|---|---|
| 16 | 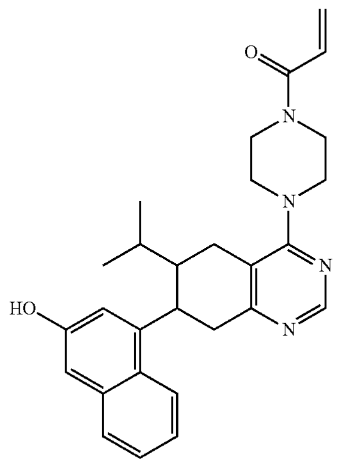 [SMILES: C=CC(=O)N1CCN(c2ncnc3c2CC(C(C)C)C(c2cc(O)cc4ccccc24)C3)CC1] | 1-(4-(7-(3-hydroxynaphthalen-1-yl)-6-isopropyl-5,6,7,8-tetrahydroquinazolin-4-yl)piperazin-1-yl)prop-2-en-1-one | 0.12 | 457.3 |
| 17 | 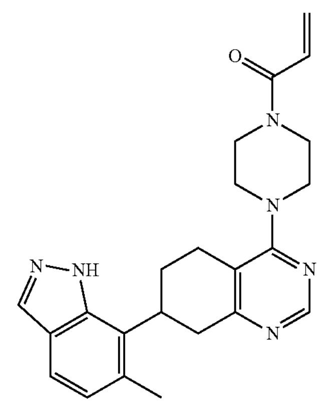 [SMILES: C=CC(=O)N1CCN(c2ncnc3c2CCC(c2c(C)ccc4cn[nH]c24)C3)CC1] | 1-[4-[7-(6-methyl-1H-indazol-7-yl)-5,6,7,8-tetrahydroquinazolin-4-yl]piperazin-1-yl]prop-2-en-1-one | 0.7 | 403.3 |
| 18 | 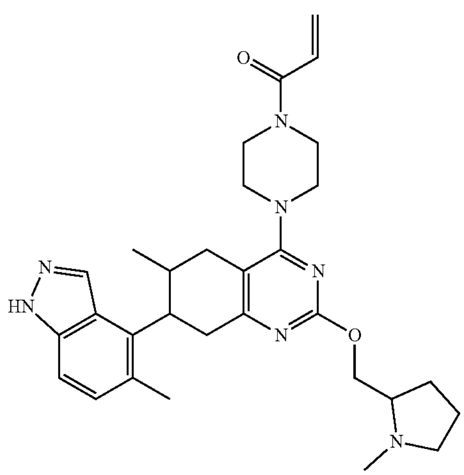 | 1-(4-(6-methyl-7-(5-methyl-1H-indazol-4-yl)-2-((1-methylpyrrolidin-2-yl)methoxy)-5,6,7,8-tetrahydroquinazolin-4-yl)piperazin-1-yl)prop-2-en-1-one | 0.024 | 530.5 |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 18a | 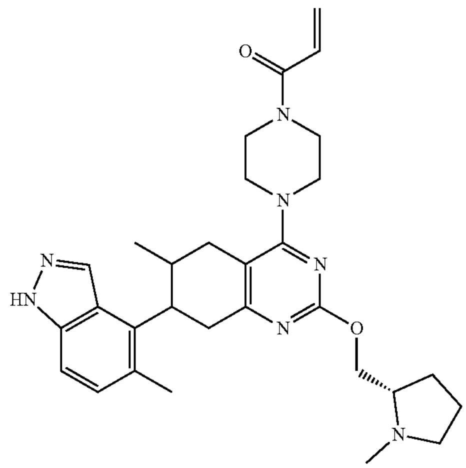 | 1-(4-(6-methyl-7-(5-methyl-1H-indazol-4-yl)-2-(((S)-1-methylpyrrolidin-2-yl)methoxy)-5,6,7,8-tetrahydroquinazolin-4-yl)piperazin-1-yl)prop-2-en-1-one | | |
| 19 | 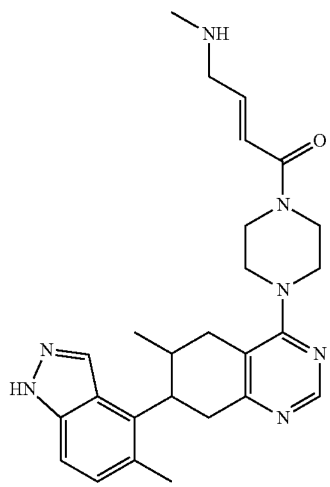 [SMILES: CNC/C=C/C(=O)N1CCN(c2ncnc3c2CC(C)C(c2c(C)ccc4[nH]ncc24)C3)CC1] | (E)-1-(4-(6-methyl-7-(5-methyl-1H-indazol-4-yl)-5,6,7,8-tetrahydroquinazolin-4-yl)piperazin-1-yl)-4-(methylamino)but-2-en-1-one | 0.93 >30 | 460.2 |
| 19a | assumed | (E)-1-(4-((6R,7R)-6-methyl-7-(5-methyl-1H-indazol-4-yl)-5,6,7,8-tetrahydroquinazolin-4-yl)piperazin-1-yl)-4-(methylamino)but-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 19b | 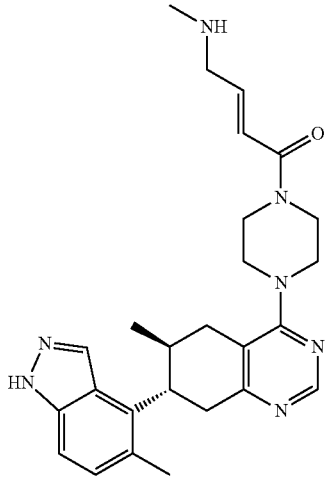 assumed | (E)-1-(4-((6S,7S)-6-methyl-7-(5-methyl-1H-indazol-4-yl)-5,6,7,8-tetrahydroquinazolin-4-yl)piperazin-1-yl)-4-(methylamino)but-2-en-1-one | | |
| 20 | 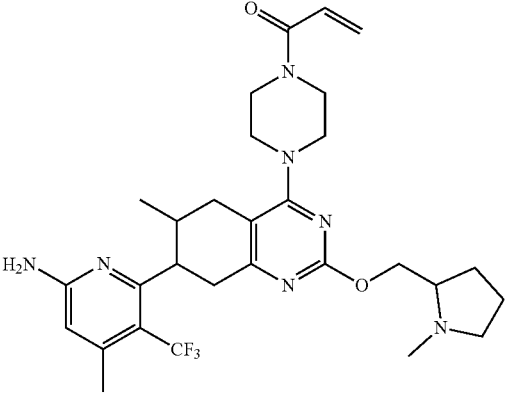 [SMILES: C=CC(=O)N1CCN(c2nc(OCC3CCCN3C)nc3c2CC(C)C(c2nc(N)cc(C)c2C(F)(F)F)C3)CC1] | 1-(4-(7-(6-amino-4-methyl-3-(trifluoromethyl)pyridin-2-yl)-6-methyl-2-((1-methylpyrrolidin-2-yl)methoxy)-5,6,7,8-tetrahydroquinazolin-4-yl)piperazin-1-yl)prop-2-en-1-one | <0.01 1.4 | 574.3 |
| 20a | 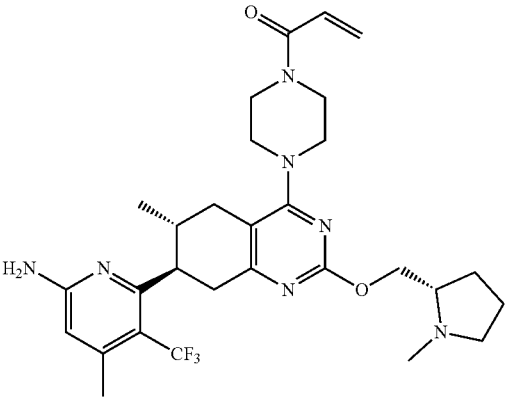 assumed | 1-(4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 20b | 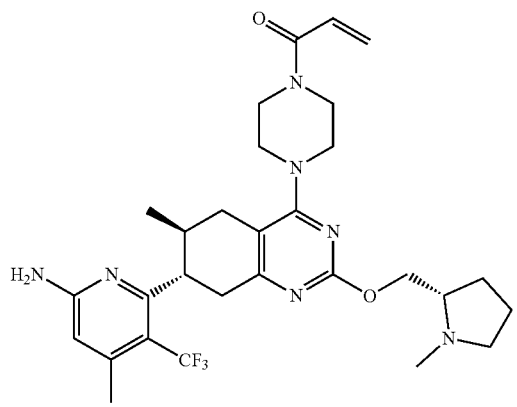 assumed | 1-(4-((6S,7S)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one | | |
| 21 | 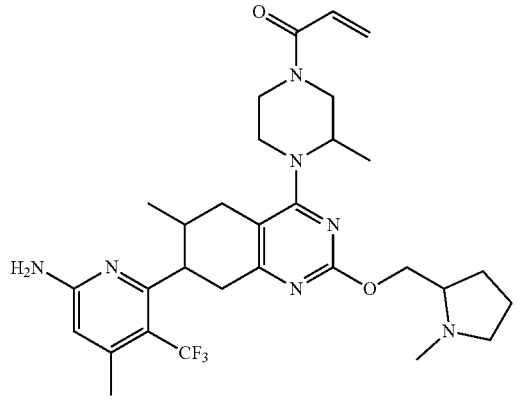 [SMILES: C=CC(=O)N1CCN(c2nc(OCC3CCCN3C)nc3c2CC(C)C(c2nc(N)cc(C)c2C(F)(F)F)C3)C(C)C1] | 1-(4-(7-(6-amino-4-methyl-3-(trifluoromethyl)pyridin-2-yl)-6-methyl-2-((1-methylpyrrolidin-2-yl)methoxy)-5,6,7,8-tetrahydroquinazolin-4-yl)-3-methylpiperazin-1-yl)prop-2-en-1-one | 1.1 <0.01 | 588.4 |
| 21a | 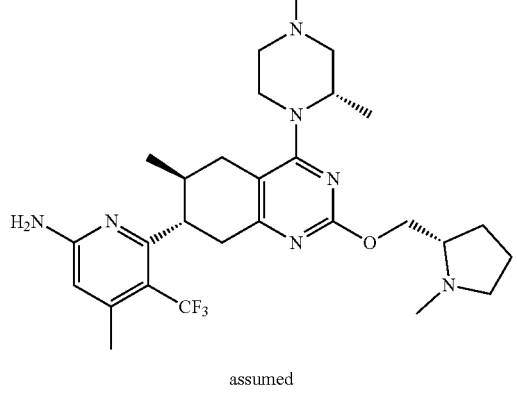 assumed | 1-((S)-4-((6S,7S)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one | | |

TABLE 1-continued

*Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.*

| Compound # | Structure | Name | IC50 | LCMS (M + H)+ |
|---|---|---|---|---|
| 21b | 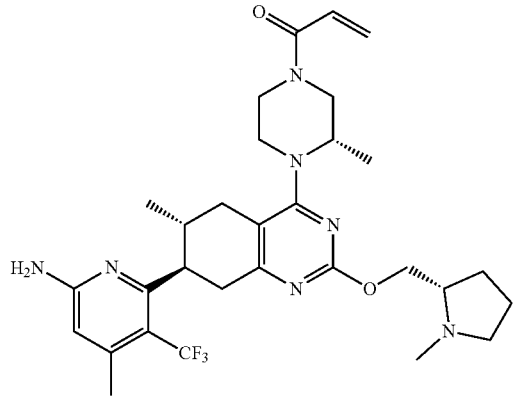 assumed | 1-((S)-4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one | | |
| 22 | 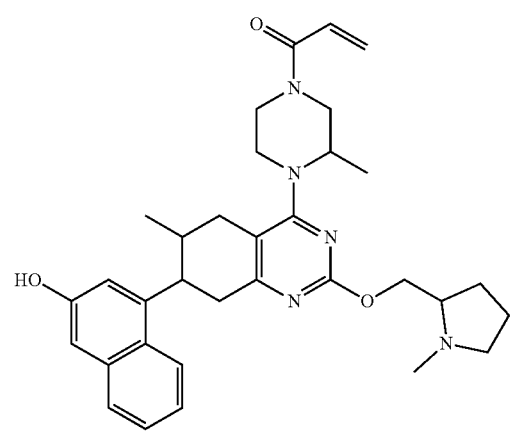 [SMILES: C=CC(=O)N1CCN(c2nc(OCC3CCCN3C)nc3c2CC(C)C(c2cc(O)cc4ccccc24)C3)C(C)C1] | 1-(4-(7-(3-hydroxynaphthalen-1-yl)-6-methyl-2-((1-methylpyrrolidin-2-yl)methoxy)-5,6,7,8-tetrahydroquinazolin-4-yl)-3-methylpiperazin-1-yl)prop-2-en-1-one | 0.02 <0.01 | 556.3 |
| 22a | 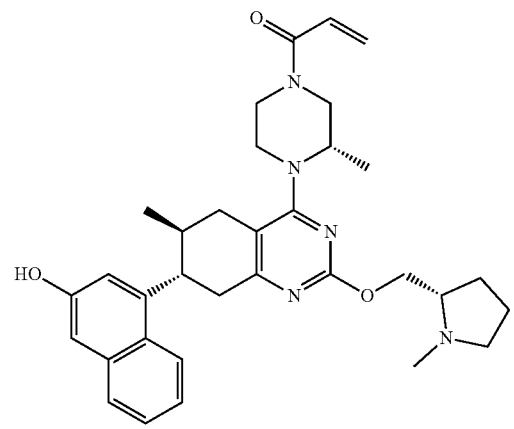 assumed | 1-((S)-4-((6S,7S)-7-(3-hydroxynaphthalen-1-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 22b | 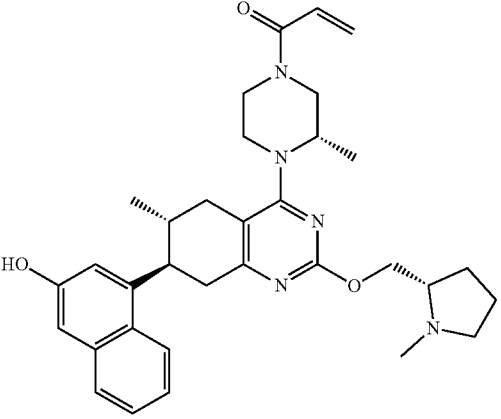 assumed | 1-((S)-4-((6R,7R)-7-(3-hydroxynaphthalen-1-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one | | |
| 23 | 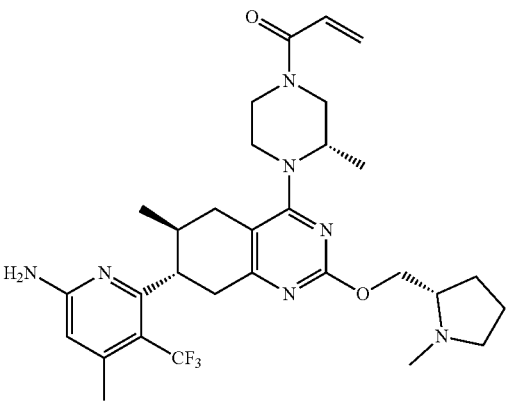 assumed | 1-(4-(7-(3-amino-2-fluoro-6-(trifluoromethyl)phenyl)-6-methyl-2-((1-methylpyrrolidin-2-yl)methoxy)-5,6,7,8-tetrahydroquinazolin-4-yl)-3-methylpiperazin-1-yl)prop-2-en-1-one | 0.72 <0.01 | 591.2 |
| 23a | 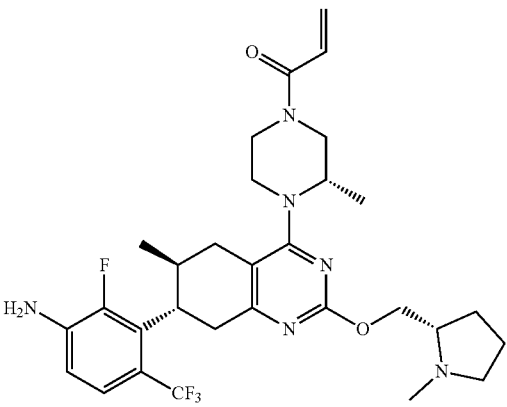 assumed | 1-((S)-4-((6S,7S)-7-(3-amino-2-fluoro-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 23b | 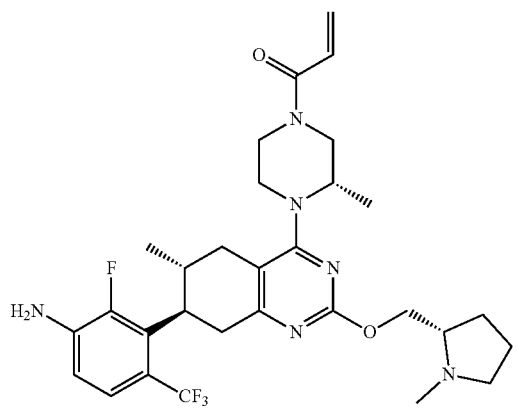 assumed | 1-((S)-4-((6R,7R)-7-(3-amino-2-fluoro-6-(trifluoromethyl)phenyl)-6-methyl-2-(((S)-1-methylpyrrolidin-2-yl]methoxy)-5,6,7,8-tetrahydroquinazolin-4-yl)-3-methylpiperazin-1-yl)prop-2-en-1-one | | |
| 24 | 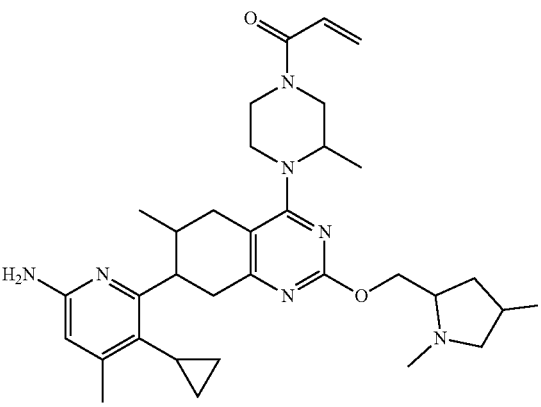 | 1-(4-(7-(6-amino-3-cyclopropyl-4-methylpyridin-2-yl)-2-((4-fluoro-1-methylpyrrolidin-2-yl]methoxy)-6-meth-5,6,7,8-tetrahydroquinazolin-4-yl)-3-methylpiperazin-1-yl)prop-2-en-1-one | >50 0.021 | 578.4 |
| 24a | 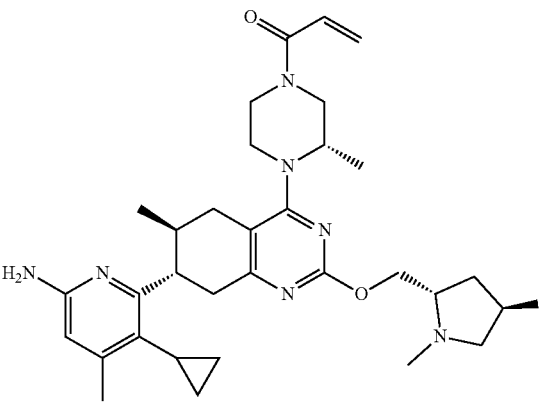 assumed | 1-((S)-4-((6S,7S)-7-(6-amino-3-cyclopropyl-4-methylpyridin-2-yl)-2-(((2S,4R)-4-fluoro-1-methylpyrrolidin-2-yl)methoxy)-6-methyl-5,6,7,8-tetrahydroquinazolin-4-yl)-3-methylpiperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 24b | 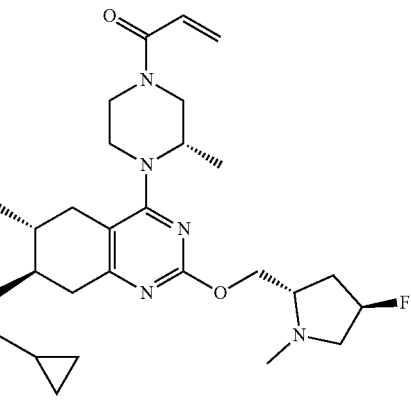 assumed | 1-((S)-4-((6R,7R)-7-(6-amino-3-cyclopropyl-4-methylpyridin-2-yl)-2-(((2S,4R)-4-fluoro-1-methylpyrrolidin-2-yl]methoxy)-6-methyl-5,6,7,8-tetrahydroquinazolin-4-yl)-3-methylpiperazin-1-yl)prop-2-en-1-one | | |
| 25 | 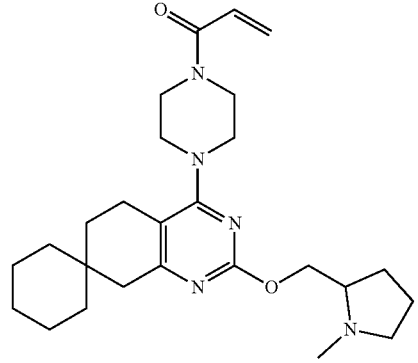 | 1-(4-(2'-((1-methylpyrrolidin-2-yl)methoxy)-5',8'-dihydro-6'H-spiro[cyclohexane-1,7'-quinazolin]-4'-yl)piperazin-1-yl)prop-2-en-1-one | 5.4 | 454.6 |
| 25a | 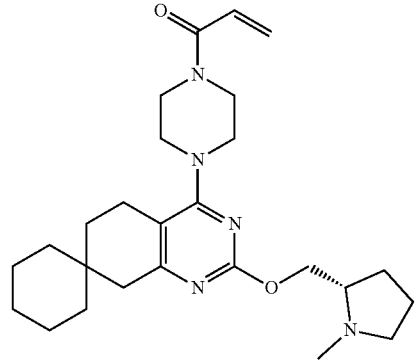 | (S)-1-(4-(2'-((1-methylpyrrolidin-2-yl)methoxy)-5',8'-dihydro-6'H-spiro[cyclohexane-1,7'-quinazolin]-4'-yl)piperazin-1-yl)prop-2-en-1-one | | |

TABLE 1-continued

*Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.*

| Compound # | Structure | Name | IC50 | LCMS (M + H)+ |
|---|---|---|---|---|
| 26 | 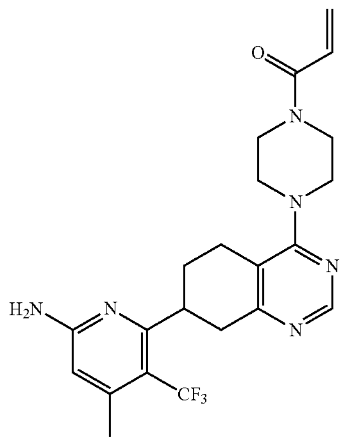 [SMILES: C=CC(=O)N1CCN(c2ncnc3c2CCC(c2nc(N)cc(C)c2C(F)(F)F)C3)CC1] | 1-[4-[7-[6-amino-4-methyl-3-(trifluoromethyl)-2-pyridyl]-5,6,7,8-tetrahydroquinazolin-4-yl]piperazin-1-yl]prop-2-en-1-one | 0.27 0.18 4.8 | 447.2 |
| 26a | 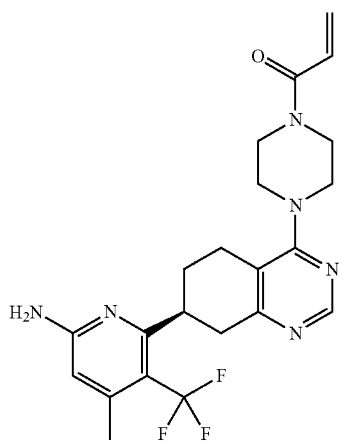 [SMILES: C=CC(=O)N1CCN(c2ncnc3c2CC[C@H](c2nc(N)cc(C)c2C(F)(F)F)C3)CC1] | (S)-1-(4-(7-(6-amino-4-methyl-3-(trifluoromethyl)pyridin-2-yl)-5,6,7,8-tetrahydroquinazolin-4-yl)piperazin-1-yl)prop-2-en-1-one | | |
| 26b | 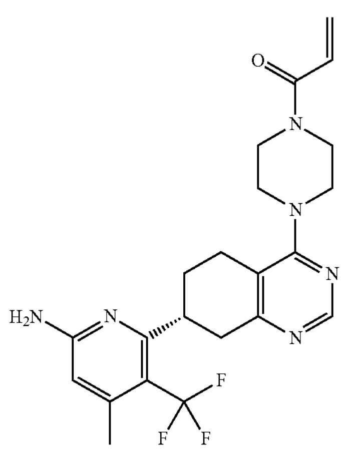 [SMILES: C=CC(=O)N1CCN(c2ncnc3c2CC[C@@H](c2nc(N)cc(C)c2C(F)(F)F)C3)CC1] | (R)-1-(4-(7-(6-amino-4-methyl-3-(trifluoromethyl)pyridin-2-yl)-5,6,7,8-tetrahydroquinazolin-4-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 27 | 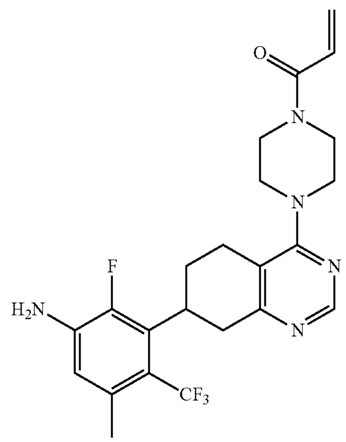 [SMILES: C=CC(=O)N1CCN(c2ncnc3c2CCC(c2c(F)c(N)cc(C)c2C(F)(F)F)C3)CC1] | 1-(4-(7-(3-amino-2-fluoro-5-methyl-6-(trifluoromethyl)phenyl)-5,6,7,8-tetrahydroquinazolin-4-yl)piperazin-1-yl)prop-2-en-1-one | 0.0893 | 464.2 |
| 27a | assumed | 1-[4-[(7S)-7-[3-amino-2-fluoro-5-methyl-6-(trifluoromethyl)phenyl]-5,6,7,8-tetrahydroquinazolin-4-yl]piperazin-1-yl]prop-2-en-1-one | | |
| 27b | assumed | 1-[4-[(7R)-7-[3-amino-2-fluoro-5-methyl-6-(trifluoromethyl)phenyl]-5,6,7,8-tetrahydroquinazolin-4-yl]piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 28 | 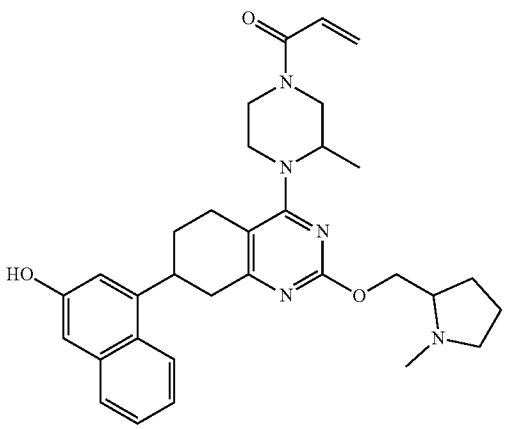 [SMILES: C=CC(=O)N1CCN(c2nc(OCC3CCCN3C)nc3c2CCC(c2cc(O)cc4ccccc24)C3)C(C)C1] | 1-(4-(7-(3-hydroxynaphthalen-1-yl)-2-((1-methylpyrrolidin-2-yl)methoxy)-5,6,7,8-tetrahydroquinazolin-4-yl)-3-methylpiperazin-1-yl)prop-2-en-1-one | 0.13<br><0.01 | 542.3 |
| 28a | 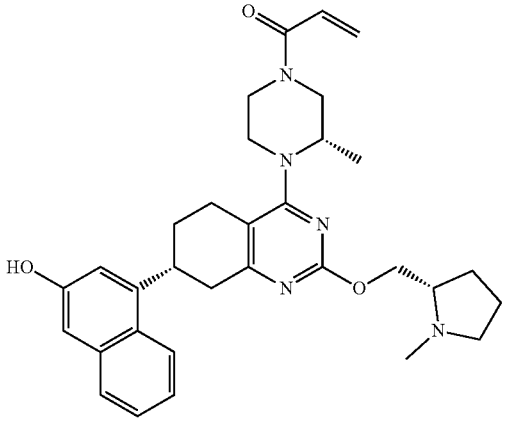assumed | 1-[(3S)-4-[(7R)-7-(3-hydroxy-1-naphthyl)-2-[[(2S)-1-methylpyrrolidin-2-yl]methoxy]-5,6,7,8-tetrahydroquinazolin-4-yl]-3-methyl-piperazin-1-yl]prop-2-en-1-one | | |
| 28b | 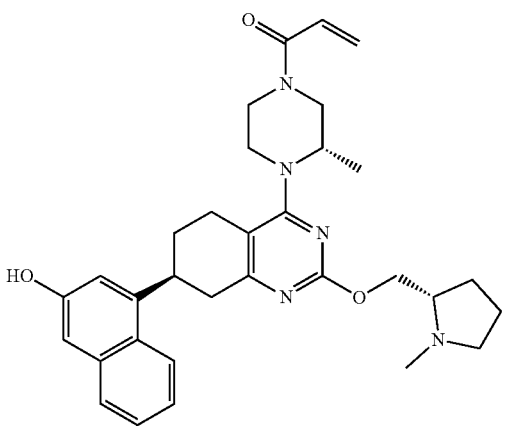assumed | 1-[(3S)-4-[(7S)-7-(3-hydroxy-1-naphthyl)-2-[[(2S)-1-methylpyrrolidin-2-[[(2S)-1-5,6,7,8-tetrahydroquinazolin-4-yl]-3-methyl-piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 29 | 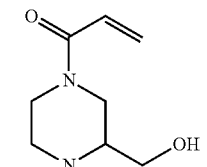 | 1-(3-(hydroxymethyl)-4-(7-(3-hydroxynaphthalen-1-yl)-2-((1-methylpyrrolidin-2-yl)methoxy)-5,6,7,8-tetrahydroquinazolin-4-yl)piperazin-1-yl)prop-2-en-1-one | 0.53<br><0.01 | 558.3 |
| 29a | 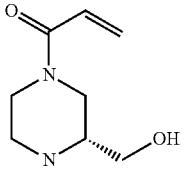<br>assumed | 1-[(3R)-3-(hydroxymethyl)-4-[(7R)-7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one | | |
| 29b | 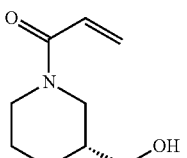<br>assumed | 1-[(3R)-3-(hydroxymethyl)-4-[(7S)-7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
| --- | --- | --- | --- | --- |
| 30 | 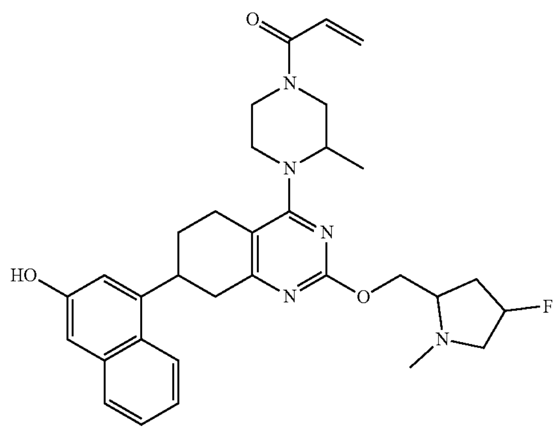 [SMILES: C=CC(=O)N1CCN(c2nc(OCC3CC(F)CN3C)nc3c2CCC(c2cc(O)cc4ccccc24)C3)C(C)C1] | 1-(4-(2-((4-fluoro-1-methylpyrrolidin-2-yl)ethoxy)-7-(3-hydroxynaphthalen-1-yl)-5,6,7,8-tetrahydroquinazolin-4-yl)-3-methylpiperazin-1-yl)prop-2-en-1-one | 0.011 1.2 | 560.3 |
| 30a | assumed | 1-[(3S)-4-[(7S)-2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one | | |
| 30b | assumed | 1-[(3S)-4-[(7R)-2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 31 | 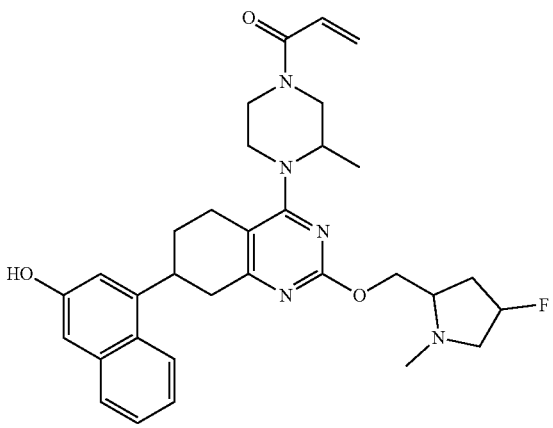 [SMILES: C=CC(=O)N1CCN(c2nc(OCC3CC(F)CN3C)nc3c2CCC(c2cc(O)cc4ccccc24)C3)C(C)C1] | 1-(4-(2-((4-fluoro-1-methylpyrrolidin-2-yl)methoxy)-7-(3-hydroxynaphthalen-1-yl)-5,6,7,8-tetrahydroquinazolin-4-yl)-3-methylpiperazin-1-yl)prop-2-en-1-one | <0.01 0.25 | 560.3 |
| 31a | 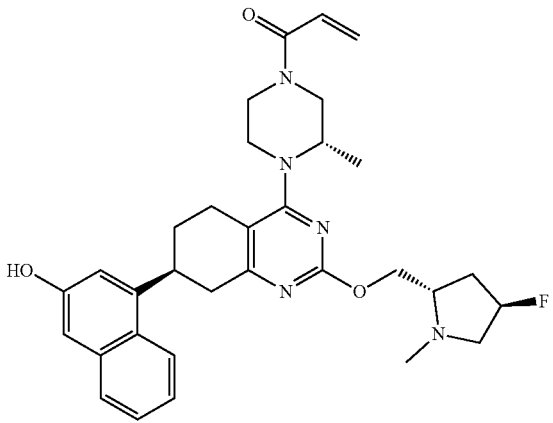 [SMILES: C=CC(=O)N1CCN(c2nc(OC[C@@H]3C[C@@H](F)CN3C)nc3c2CC[C@H](c2cc(O)cc4ccccc24)C3)[C@@H](C)C1] | 1-[(3S)-4-[(7S)-2-[[(2S,4R)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one | | |
| 31b | 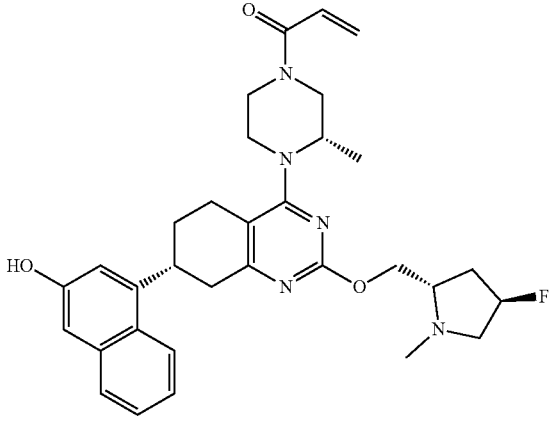 [SMILES: C=CC(=O)N1CCN(c2nc(OC[C@@H]3C[C@@H](F)CN3C)nc3c2CC[C@@H](c2cc(O)cc4ccccc24)C3)[C@@H](C)C1] | 1-[(3S)-4-[(7R)-2-[[(2S,4R)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 32 | 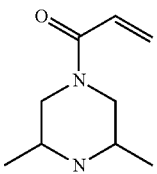 | 1-(4-(7-(3-hydroxynaphthalen-1-yl)-6-methyl-2-((1-methylpyrrolidin-2-yl)methoxy)-5,6,7,8-tetrahydroquinazolin-4-yl)-3,5-dimethylpiperazin-1-yl)prop-2-en-1-one | <0.01 0.056 | 570.3 |
| 32a | 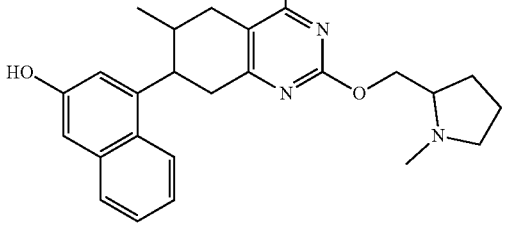 assumed | 1-[(3S,5S)-4-[(6R,7R)-7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one | | |
| 32b | 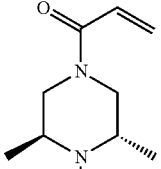 assumed | 1-[(3S,5S)-4-[(6S,7S)-7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 33 | 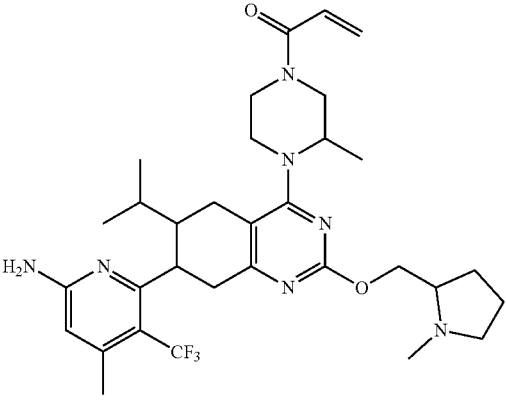 [SMILES: C=CC(=O)N1CCN(c2nc(OCC3CCCN3C)nc3c2CC(C(C)C)C(c2nc(N)cc(C)c2C(F)(F)F)C3)C(C)C1] | 1-(4-(7-(6-amino-4-methyl-3-(trifluoromethyl)pyridin-2-yl)-6-isopropyl-2-((1-methylpyrrolidin-2-yl)methoxy)-5,6,7,8-tetrahydroquinazolin-4-yl)-3-methylpiperazin-1-yl)prop-2-en-1-one | <0.01 0.3 | 616.4 |
| 33a | 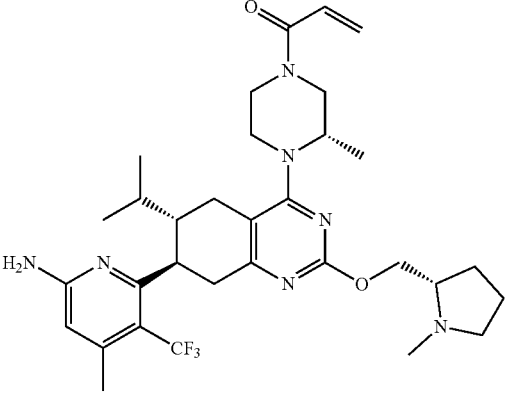<br>assumed | 1-((S)-4-((6S,7R)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one | | |
| 33b | 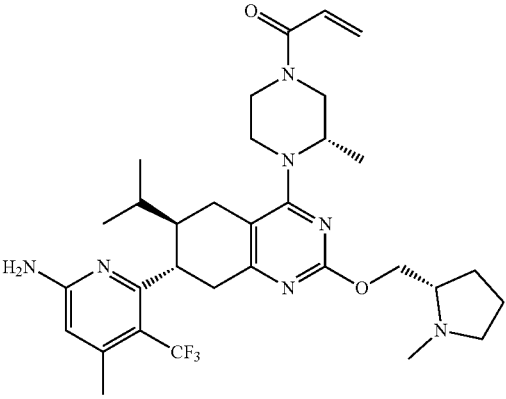<br>assumed | 1-((S)-4-((6R,7S)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 34 | 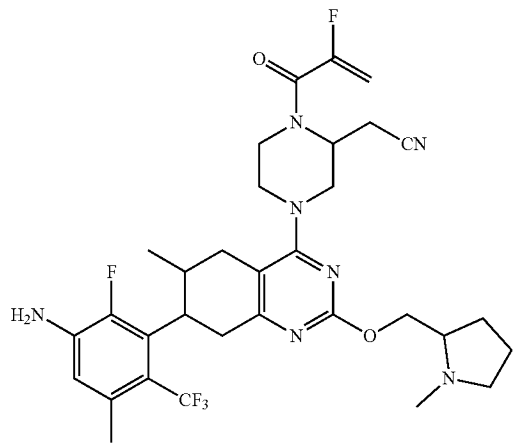 [SMILES: C=C(F)C(=O)N1CCN(c2nc(OCC3CCCN3C)nc3c2CC(C)C(c2c(F)c(N)cc(C)c2C(F)(F)F)C3)CC1CC#N] | 2-(4-(7-(3-amino-2-fluoro-5-methyl-6-(trifluoromethyl)phenyl)-6-methyl-2-((1-methylpyrrolidin-2-yl)methoxy)-5,6,7,8-tetrahydroquinazolin-4-yl)-1-(2-fluoroacryloyl)piperazin-2-yl)acetonitrile | 8.9<br>0.68<br><0.01<br><0.01 | 648.3 |
| 34a | assumed | 2-((R)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile | | |
| 34b | assumed | 2-((R)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 34c | 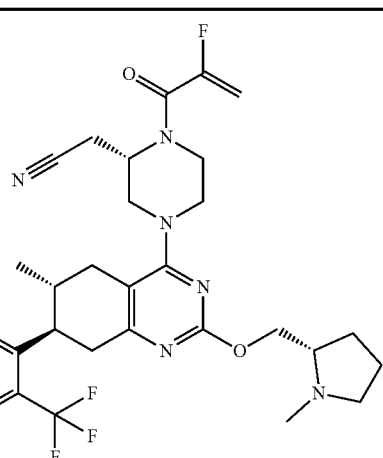 assumed | 2-((S)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile | | |
| 34d | 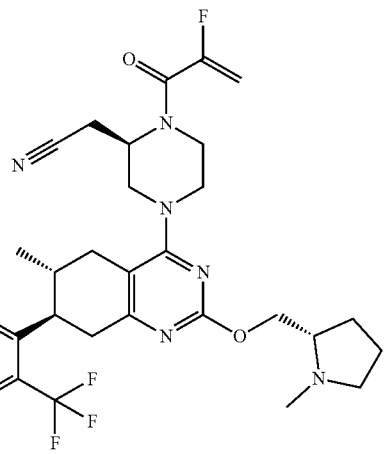 assumed | 2-((S)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile | | |
| 35 | 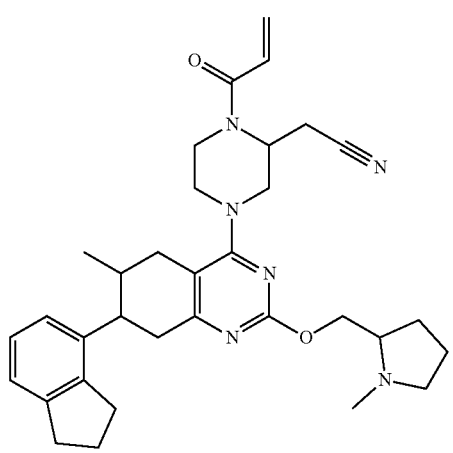 [SMILES: C=CC(=O)N1CCN(c2nc(OCC3CCCN3C)nc3c2CC(C)C(c2cccc4c2CCC4)C3)CC1CC#N] | 2-(1-acryloyl-4-(7-(2,3-dihydro-1H-inden-4-yl)-6-methyl-2-((1-methylpyrrolidin-2-yl)methoxy)-5,6,7,8-tetrahydroquinazolin-4-yl)piperazin-2-yl)acetonitrile | 0.19<br>0.011<br>0.022<br><0.01 | 555.3 |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 35a | 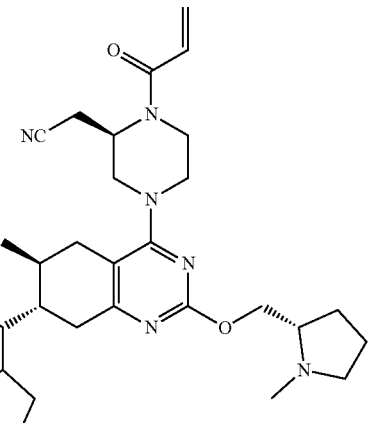 assumed | 2-((R)-1-acryloyl-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile | | |
| 35b | 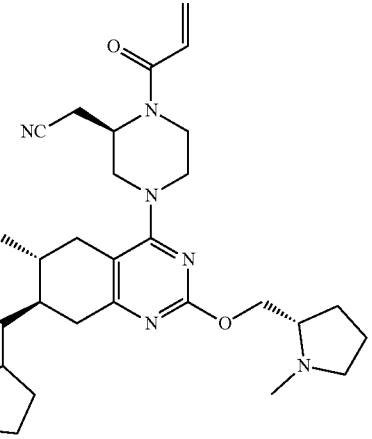 assumed | 2-((R)-1-acryloyl-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile | | |
| 35c | 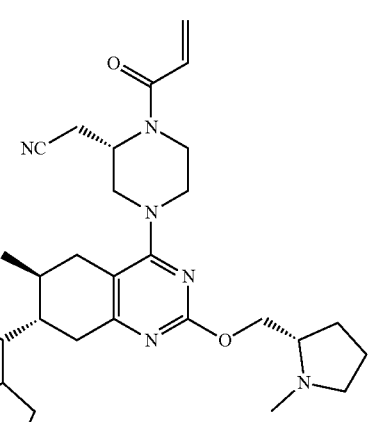 assumed | 2-((S)-1-acryloyl-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 35d | 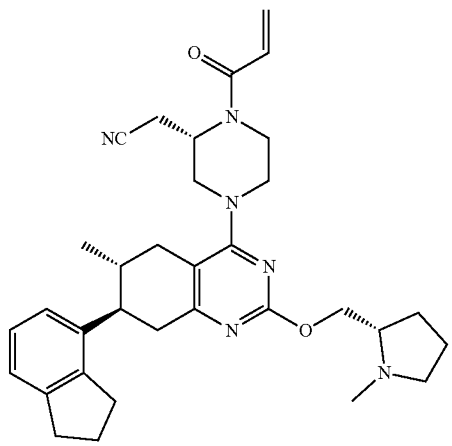 | 2-((S)-1-acryloyl-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile assumed | | |
| 36 | 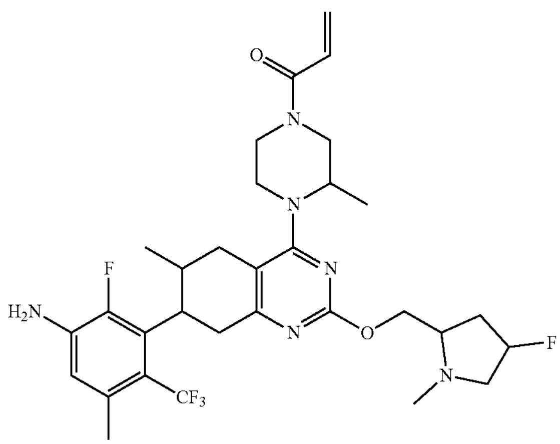 [SMILES: C=CC(=O)N1CCN(c2nc(OCC3CC(F)CN3C)nc3c2CC(C)C(c2c(F)c(N)cc(C)c2C(F)(F)F)C3)C(C)C1] | 1-(4-(7-(3-amino-2-fluoro-5-methyl-6-(trifluoromethyl)phenyl)-2-((4-fluoro-1-methylpyrrolidin-2-yl)methoxy)-6-methyl-5,6,7,8-tetrahydroquinazolin-4-yl)-3-methylpiperazin-1-yl)prop-2-en-1-one | 0.36 <0.01 | 623.4 |
| 36a | 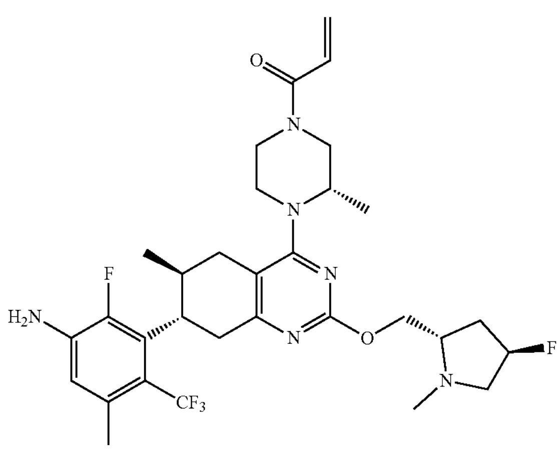 | 1-[(3S)-4-[(6S,7S)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one assumed | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 36b | 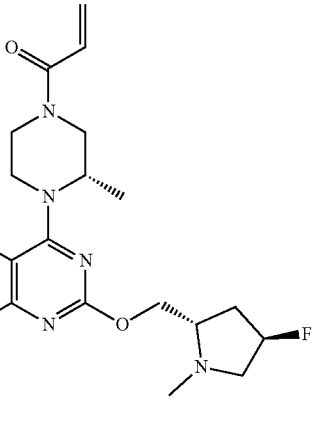 assumed | 1-[(3S)-4-[(6R,7R)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one | | |
| 37 | 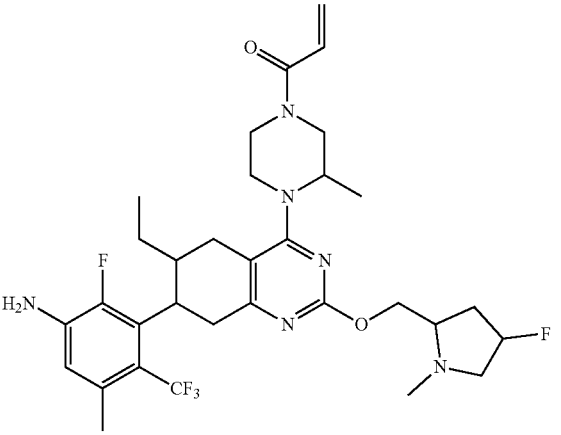 [SMILES: C=CC(=O)N1CCN(c2nc(OCC3CC(F)CN3C)nc3c2CC(CC)C(c2c(F)c(N)cc(C)c2C(F)(F)F)C3)C(C)C1] | 1-(4-(7-(3-amino-2-fluoro-5-methyl-6-(trifluoromethyl)phenyl)-6-ethyl-2-((4-fluoro-1-methylpyrrolidin-2-yl)methoxy)-5,6,7,8-tetrahydroquinazolin-4-yl)-3-methylpiperazin-1-yl)prop-2-en-1-one | <0.01 2.2 | 637.3 |
| 37a | 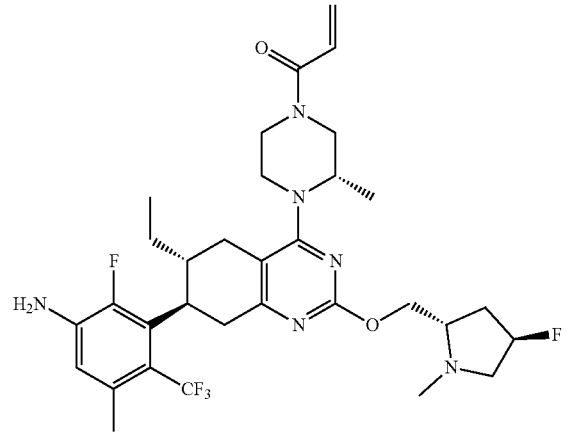 assumed | 1-[(3S)-4-[(6R,7R)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 37b | 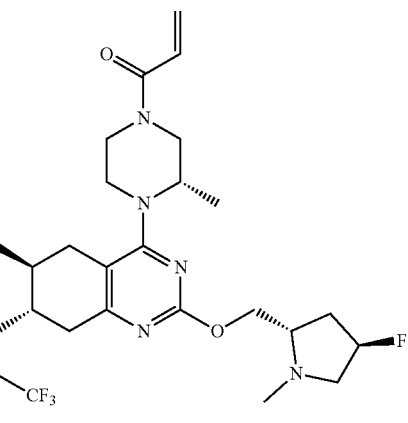 assumed | 1-[(3S)-4-[(6S,7S)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one | | |
| 38 | 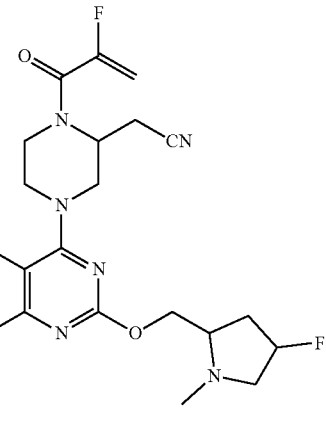 | 2-(4-(7-(3-amino-2-fluoro-5-methyl-6-(trifluoromethyl)phenyl)-2-((4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile | 3.6 <0.01 0.015 1.7 | 666.3 |
| 38a | 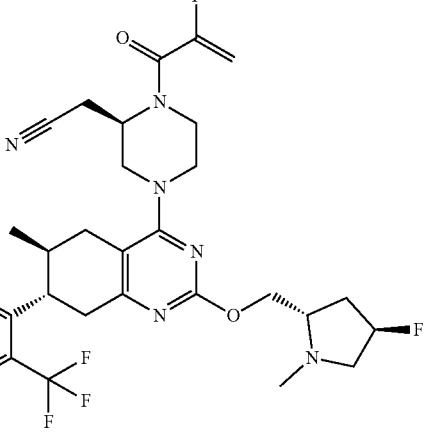 configuration assumed from potency | 2-((R)-4-((6S,7S)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 38b | 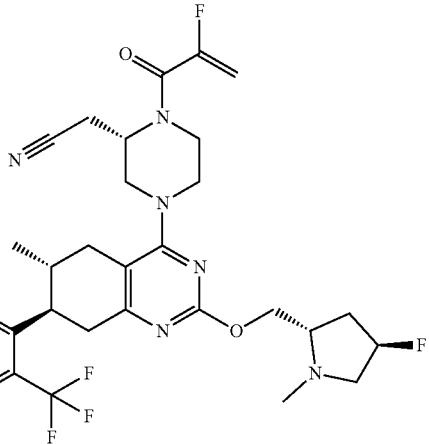 configuration assumed from potency | 2-((S)-4-((6R,7R)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile | | |
| 38c | 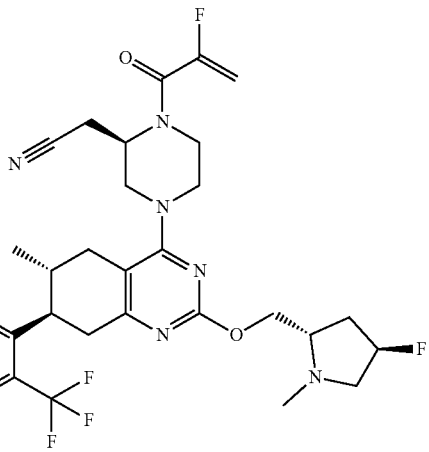 configuration assumed from potency | 2-((R)-4-((6R,7R)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile | | |
| 38d | 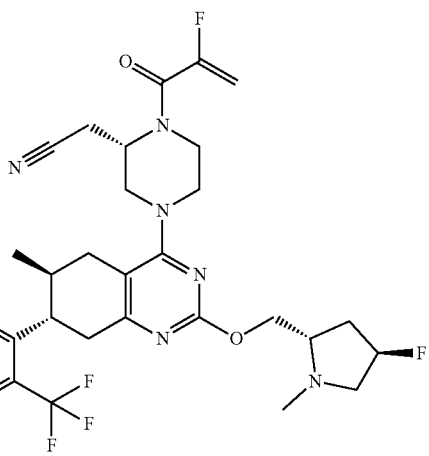 configuration assumed from potency | 2-((S)-4-((6S,7S)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 39 | 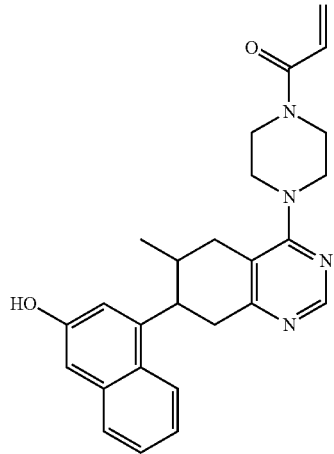 [SMILES: C=CC(=O)N1CCN(c2ncnc3c2CC(C)C(c2cc(O)cc4ccccc24)C3)CC1] | 1-(4-(7-(3-hydroxynaphthalen-1-yl)-6-methyl-5,6,7,8-tetrahydroquinazolin-4-yl)piperazin-1-yl)prop-2-en-1-one | 0.18 | 429.2 |
| 40 | 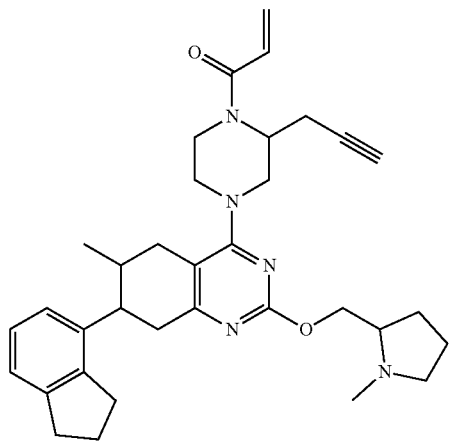 [SMILES: C#CCC1CN(c2nc(OCC3CCCN3C)nc3c2CC(C)C(c2cccc4c2CCC4)C3)CCN1C(=O)C=C] | 1-(4-(7-(2,3-dihydro-1H-inden-4-yl)-6-methyl-2-((1-methylpyrrolidin-2-yl)methoxy)-5,6,7,8-tetrahydroquinazolin-4-yl)-2-(prop-2-yn-1-yl)piperazin-1-yl)prop-2-en-1-one | <0.01<br>0.56<br>1.2<br>0.029 | 554.4 |
| 40a | 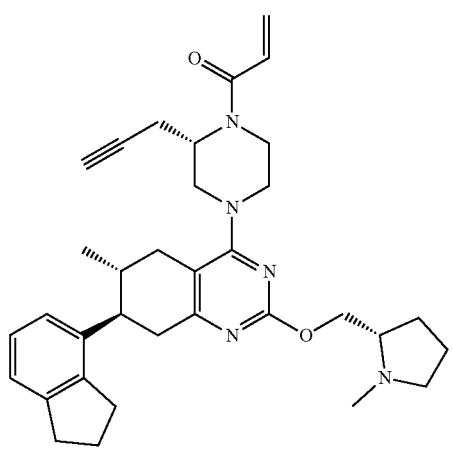 [SMILES: C#CC[C@H]1CN(c2nc(OC[C@@H]3CCCN3C)nc3c2C[C@@H](C)[C@H](c2cccc4c2CCC4)C3)CCN1C(=O)C=C] | 1-((S)-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
| --- | --- | --- | --- | --- |
| 40b | 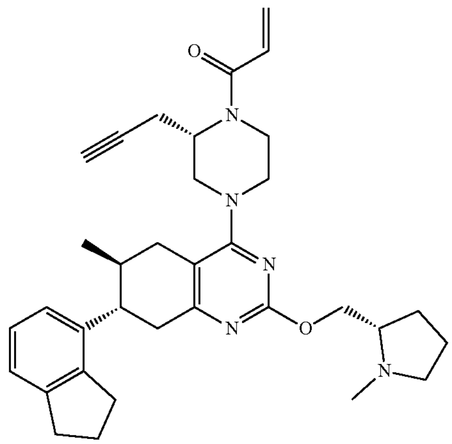 [SMILES: C#CC[C@H]1CN(c2nc(OC[C@@H]3CCCN3C)nc3c2C[C@H](C)[C@@H](c2cccc4c2CCC4)C3)CCN1C(=O)C=C] | 1-((S)-4-((6S,7S)-7-(2,3-dihydro-1H-inden-4-yl)-6-methyl-2-(((S)-1-methylpyrrolidin-2-yl]methoxy)-5,6,7,8-tetrahydroquinazolin-4-yl)-2-(prop-2-yn-1-yl)piperazin-1-yl)prop-2-en-1-one | | |
| 40c | 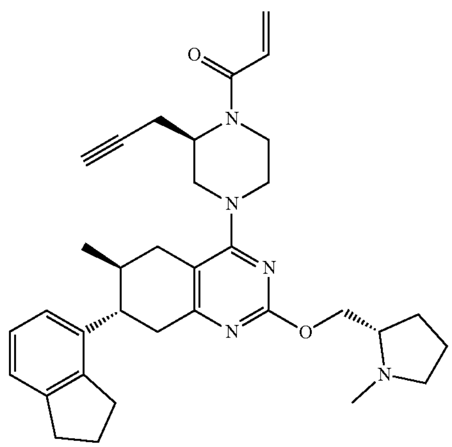 [SMILES: C#CC[C@@H]1CN(c2nc(OC[C@@H]3CCCN3C)nc3c2C[C@H](C)[C@@H](c2cccc4c2CCC4)C3)CCN1C(=O)C=C] | 1-((R)-4-((6S,7S)-7-(2,3-dihydro-1H-inden-4-yl)-6-methyl-2-(((S)-1-methylpyrrolidin-2-yl]methoxy)-5,6,7,8-tetrahydroquinazolin-4-yl)-2-(prop-2-yn-1-yl)piperazin-1-yl)prop-2-en-1-one | | |
| 40d | 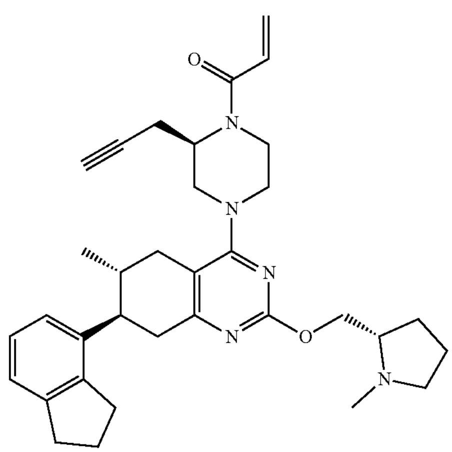 [SMILES: C#CC[C@@H]1CN(c2nc(OC[C@@H]3CCCN3C)nc3c2C[C@@H](C)[C@H](c2cccc4c2CCC4)C3)CCN1C(=O)C=C] | 1-((R)-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 41 | 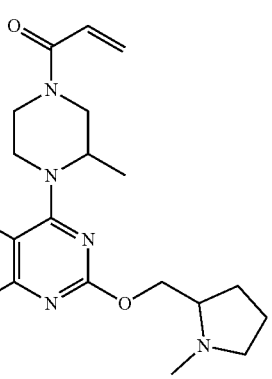 | 1-(4-(7-(6-amino-3-(trifluoromethyl)pyridin-2-yl)-6-methyl-2-((1-methylpyrrolidin-2-yl)methoxy)-5,6,7,8-tetrahydroquinazolin-4-yl)-3-methylpiperazin-1-yl)prop-2-en-1-one | 0.5<br><0.01 | 574.3 |
| 41a | 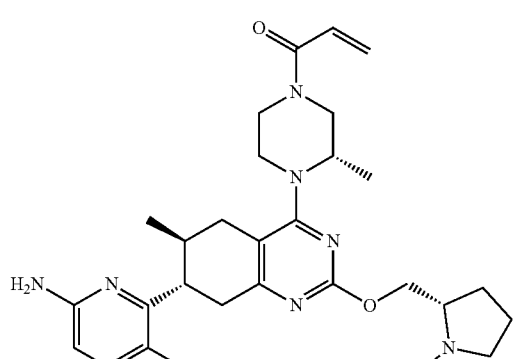 | 1-((S)-4-((6S,7S)-7-(6-amino-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one | | |
| 41b | 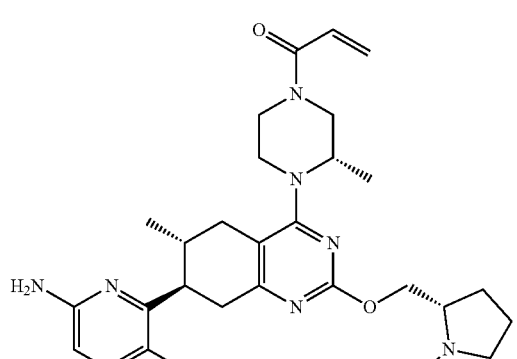 | 1-((S)-4-((6R,7R)-7-(6-amino-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 42 | 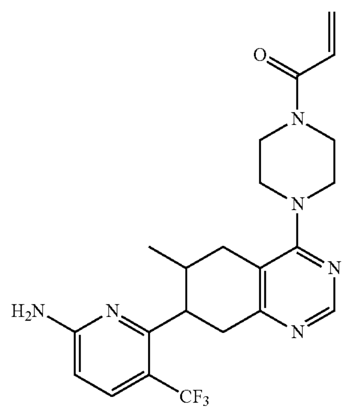 [SMILES: C=CC(=O)N1CCN(c2ncnc3c2CC(C)C(c2nc(N)ccc2C(F)(F)F)C3)CC1] | 1-(4-(7-(6-amino-3-(trifluoromethyl)pyridin-2-yl)-6-methyl-5,6,7,8-tetrahydroquinazolin-4-yl)piperazin-1-yl)prop-2-en-1-one | 2.7 0.067 | 447.2 |
| 42a | 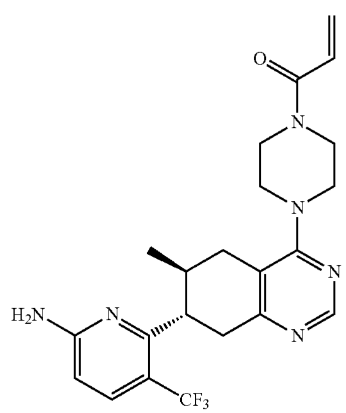 [SMILES: C=CC(=O)N1CCN(c2ncnc3c2C[C@H](C)[C@@H](c2nc(N)ccc2C(F)(F)F)C3)CC1] | 1-(4-((6S,7S)-7-(6-amino-3-(trifluoromethyl)pyridin-2-yl)-6-methyl-5,6,7,8-tetrahydroquinazolin-4-yl)piperazin-1-yl)prop-2-en-1-one | | |
| 42b | 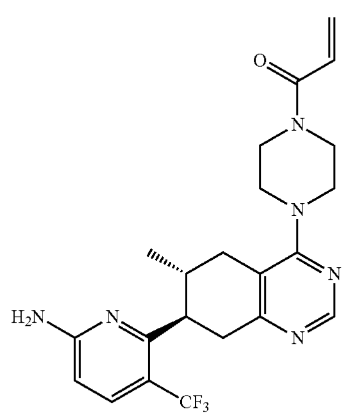 [SMILES: C=CC(=O)N1CCN(c2ncnc3c2C[C@@H](C)[C@H](c2nc(N)ccc2C(F)(F)F)C3)CC1] | 1-(4-((6R,7R)-7-(6-amino-3-(trifluoromethyl)pyridin-2-yl)-6-methyl-5,6,7,8-tetrahydroquinazolin-4-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 43 | 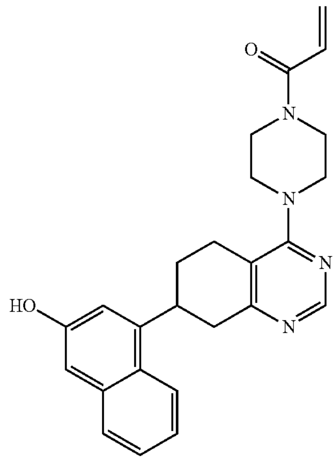 [SMILES: C=CC(=O)N1CCN(c2ncnc3c2CCC(c2cc(O)cc4ccccc24)C3)CC1] | 1-[4-[7-(3-hydroxy-1-naphthyl)-5,6,7,8-tetrahydroquinazolin-4-yl]piperazin-1-yl]prop-2-en-1-one | 0.2 | 415.2 |
| 44 | 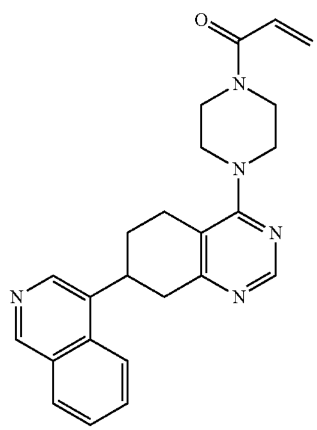 [SMILES: C=CC(=O)N1CCN(c2ncnc3c2CCC(c2cncc4ccccc24)C3)CC1] | 1-(4-(7-(isoquinolin-4-yl)-5,6,7,8-tetrahydroquinazolin-4-yl)piperazin-1-yl)prop-2-en-1-one | >50 8.7 | 400.3 |
| 44a | | 1-[4-[(7R)-7-(4-isoquinolyl)-5,6,7,8-tetrahydroquinazolin-4-yl]piperazin-1-yl]prop-2-en-1-one | | | assumed

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 44b | 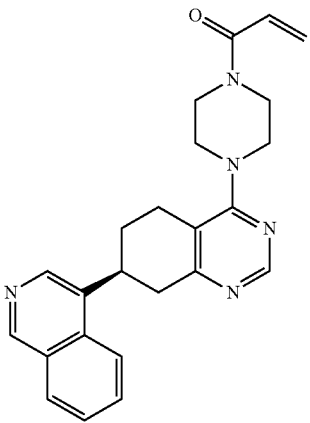 assumed | 1-[4-[(7S)-7-(4-isoquinolyl)-5,6,7,8-tetrahydroquinazolin-4-yl]piperazin-1-yl]prop-2-en-1-one | | |
| 45 | 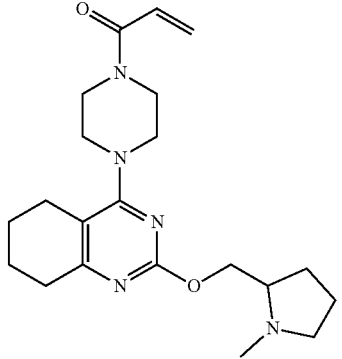 [SMILES: C=CC(=O)N1CCN(c2nc(OCC3CCCN3C)nc3c2CCCC3)CC1] | 1-(4-(2-((1-methylpyrrolidin-2-yl)methoxy)-5,6,7,8-tetrahydroquinazolin-4-yl)piperazin-1-yl)prop-2-en-1-one | >50 | 386.3 |
| 45a | 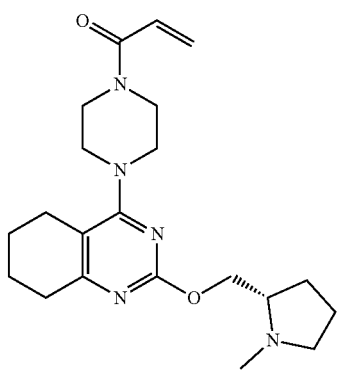 [SMILES: C=CC(=O)N1CCN(c2nc(OC[C@@H]3CCCN3C)nc3c2CCCC3)CC1] | 1-[4-[2-[[(2S)-1-methylpyrrolidin-2-yl]methoxy]-5,6,7,8-tetrahydroquinazolin-4-yl]piperazin-1-yl]prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 46 | 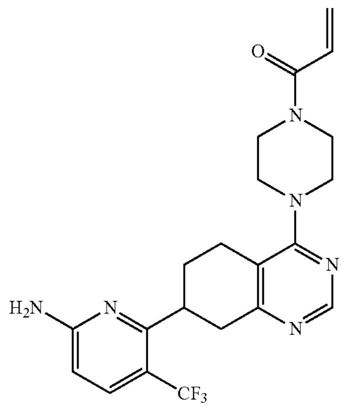 [SMILES: C=CC(=O)N1CCN(c2ncnc3c2CCC(c2nc(N)ccc2C(F)(F)F)C3)CC1] | 1-(4-(7-(6-amino-3-(trifluoromethyl)pyridin-2-yl)-5,6,7,8-tetrahydroquinazolin-4-yl)piperazin-1-yl)prop-2-en-1-one | 2 0.23 | 433.2 |
| 46a | 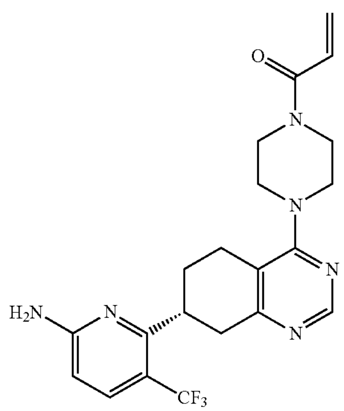 [SMILES: C=CC(=O)N1CCN(c2ncnc3c2CC[C@@H](c2nc(N)ccc2C(F)(F)F)C3)CC1] | (R)-1-(4-(7-(6-amino-3-(trifluoromethyl)pyridin-2-yl)-5,6,7,8-tetrahydroquinazolin-4-yl)piperazin-1-yl)prop-2-en-1-one | | |
| 46b | 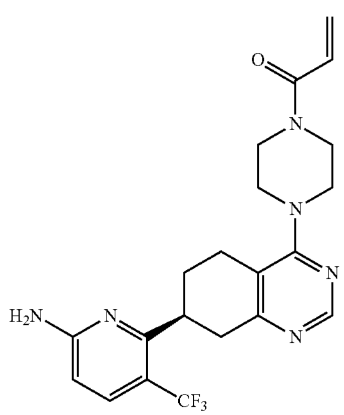 [SMILES: C=CC(=O)N1CCN(c2ncnc3c2CC[C@H](c2nc(N)ccc2C(F)(F)F)C3)CC1] | (S)-1-(4-(7-(6-amino-3-(trifluoromethyl)pyridin-2-yl)-5,6,7,8-tetrahydroquinazolin-4-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 47 | 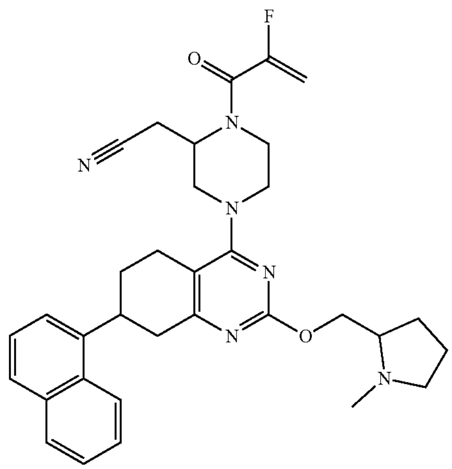 [SMILES: C=C(F)C(=O)N1CCN(c2nc(OCC3CCCN3C)nc3c2CCC(c2cccc4ccccc24)C3)CC1CC#N] | 2-(1-(2-fluoroacryloyl)-4-(2-((1-methylpyrrolidin-2-yl)methoxy)-7-(naphthalen-1-yl)-5,6,7,8-tetrahydroquinazolin-4-yl)piperazin-2-yl)acetonitrile | 0.15<br>1.5<br>0.13<br><0.01 | 569.2 |
| 47a | Peak 1 | 2-[1-(2-fluoroprop-2-enoyl)-4-[2-[[(2S)-1-methylpyrrolidin-2-yl]methoxy]-7-(1-naphthyl)-5,6,7,8-tetrahydroquinazolin-4-yl]piperazin-2-yl]acetonitrile | | |
| 47b | Peak 2 | 2-[1-(2-fluoroprop-2-enoyl)-4-[2-[[(2S)-1-methylpyrrolidin-2-yl]methoxy]-7-(1-naphthyl)-5,6,7,8-tetrahydroquinazolin-4-yl]piperazin-2-yl]acetonitrile | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 47c | Peak 3 | 2-[1-(2-fluoroprop-2-enoyl)-4-[2-[[(2S)-1-methylpyrrolidin-2-yl]methoxy]-7-(1-naphthyl)-5,6,7,8-tetrahydroquinazolin-4-yl]piperazin-2-yl]acetonitrile | | |
| 47d | Peak 4 | 2-((2S)-1-(2-fluoroacryloyl)-4-(2-(((S)-1-methylpyrrolidin-2-yl)methoxy)-7-(naphthalen-1-yl)-5,6,7,8-tetrahydroquinazolin-4-yl)piperazin-2-yl)acetonitrile | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 48 | 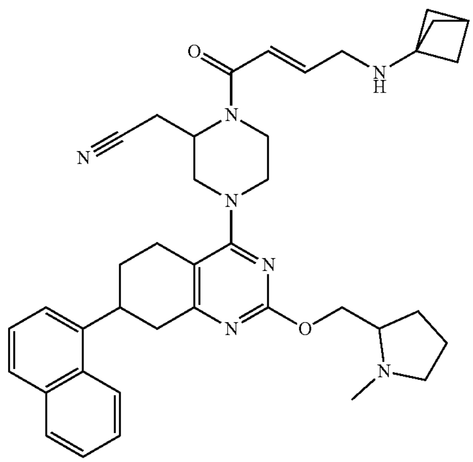 [SMILES: CN1CCCC1COc1nc2c(c(N3CCN(C(=O)/C=C/CNC45CC(C4)C5)C(CC#N)C3)n1)CCC(c1cccc3ccccc13)C2] | (E)-2-(1-(4-(bicyclo[1.1.1]pentan-1-ylamino)but-2-enoyl)-4-(2-((1-methylpyrrolidin-2-yl)methoxy)-7-(naphthalen-1-yl)-5,6,7,8-tetrahydroquinazolin-4-yl)piperazin-2-yl)acetonitrile | 0.011 | 646.4 |
| 48a | 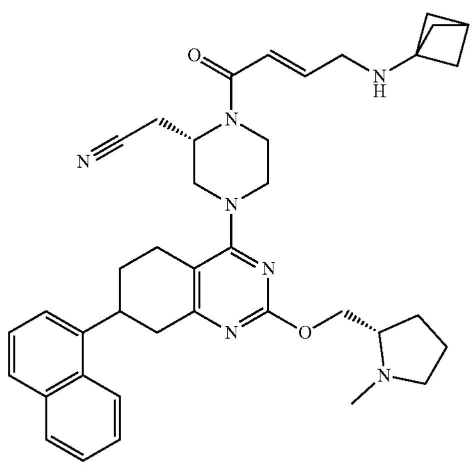 [SMILES: CN1CCC[C@H]1COc1nc2c(c(N3CCN(C(=O)/C=C/CNC45CC(C4)C5)[C@@H](CC#N)C3)n1)CCC(c1cccc3ccccc13)C2] | 2-((2S)-1-((E)-4-(bicyclo[1.1.1]pentan-1-ylamino)but-2-enoyl)-4-(2-(((S)-1-methylpyrrolidin-2-yl)methoxy)-7-(naphthalen-1-yl)-5,6,7,8-tetrahydroquinazolin-4-yl)piperazin-2-yl)acetonitrile | | |
| 49 | 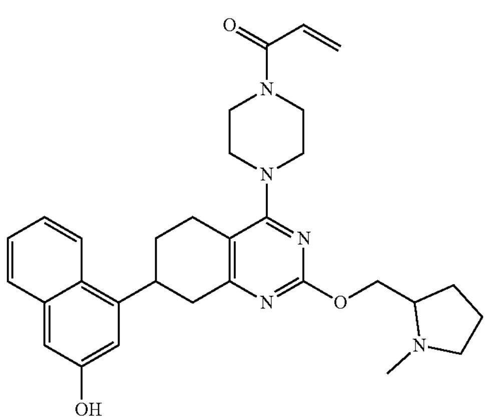 [SMILES: C=CC(=O)N1CCN(c2nc(OCC3CCCN3C)nc3c2CCC(c2cc(O)cc4ccccc24)C3)CC1] | 1-(4-(7-(3-hydroxynaphthalen-1-yl)-2-((1-methylpyrrolidin-2-yl)methoxy)-5,6,7,8-tetrahydroquinazolin-4-yl)piperazin-1-yl)prop-2-en-1-one | 0.023 | 528.3 |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 49a | 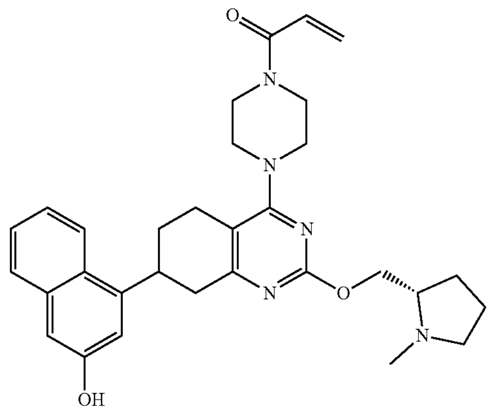 [SMILES: C=CC(=O)N1CCN(c2nc(OC[C@@H]3CCCN3C)nc3c2CCC(c2cc(O)cc4ccccc24)C3)CC1] | 1-[4-[7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one | | |
| 50 | 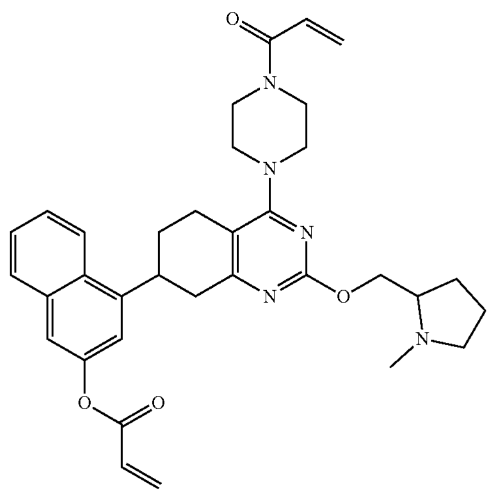 [SMILES: C=CC(=O)Oc1cc(C2CCc3c(nc(OCC4CCCN4C)nc3N3CCN(C(=O)C=C)CC3)C2)c2ccccc2c1] | 4-(4-(4-acryloylpiperazin-1-yl)-2-((1-methylpyrrolidin-2-yl)methoxy)-5,6,7,8-tetrahydroquinazolin-7-yl)naphthalen-2-yl acrylate | 0.16 | 582.3 |
| 50a | 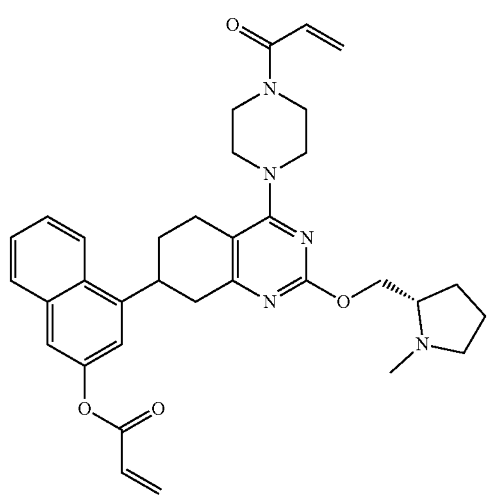 [SMILES: C=CC(=O)Oc1cc(C2CCc3c(nc(OC[C@@H]4CCCN4C)nc3N3CCN(C(=O)C=C)CC3)C2)c2ccccc2c1] | 4-(4-(4-acryloylpiperazin-1-yl)-2-(((S)-1-methylpyrrolidin-2-yl)methoxy)-5,6,7,8-tetrahydroquinazolin-7-yl)naphthalen-2-yl acrylate | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 51 | 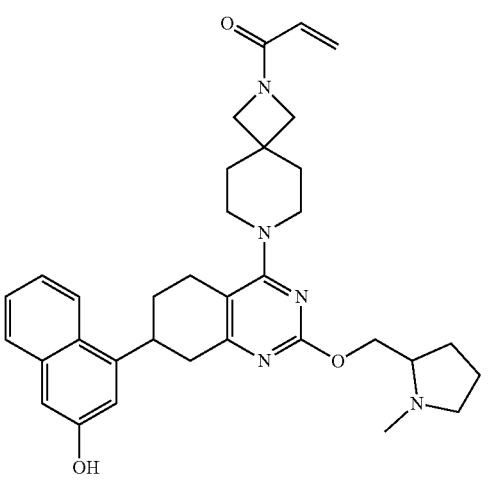 [SMILES: C=CC(=O)N1CC2(CCN(c3nc(OCC4CCCN4C)nc4c3CCC(c3cc(O)cc5ccccc35)C4)CC2)C1] | 1-[7-[7-(3-hydroxy-1-naphthyl)-2-[(1-methylpyrrolidin-2-yl)methoxy]-5,6,7,8-tetrahydroquinazolin-4-yl]-2,7-diazaspiro[3.5]nonan-2-yl]prop-2-en-1-one | 0.046 | 568.3 |
| 52 | 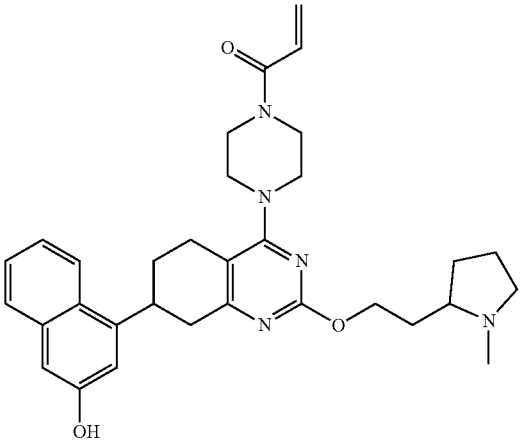 [SMILES: C=CC(=O)N1CCN(c2nc(OCCC3CCCN3C)nc3c2CCC(c2cc(O)cc4ccccc24)C3)CC1] | 1-(4-(7-(3-hydroxynaphthalen-1-yl)-2-(2-(1-methylpyrrolidin-2-yl)ethoxy)-5,6,7,8-tetrahydroquinazolin-4-yl)piperazin-1-yl)prop-2-en-1-one | 0.051 | 542.3 |
| 52a | 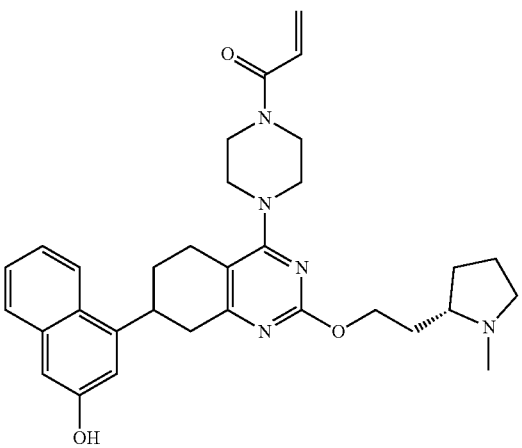 [SMILES: C=CC(=O)N1CCN(c2nc(OCC[C@@H]3CCCN3C)nc3c2CCC(c2cc(O)cc4ccccc24)C3)CC1] | 1-(4-(7-(3-hydroxynaphthalen-1-yl)-2-(2-((S)-1-methylpyrrolidin-2-yl)ethoxy)-5,6,7,8-tetrahydroquinazolin-4-yl)piperazin-1-yl)prop-2-en-1-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 53 | 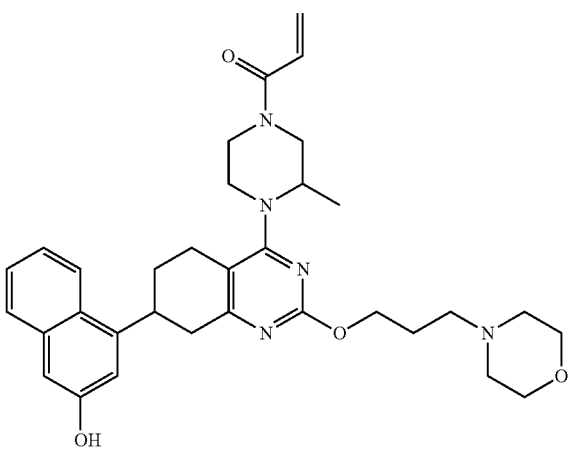 | 1-(4-(7-(3-hydroxynaphthalen-1-yl)-2-(3-morpholinopropoxy)-5,6,7,8-tetrahydroquinazolin-4-yl)-3-methylpiperazin-1-yl)prop-2-en-1-one | 0.022 | 572.3 |
| 53a | 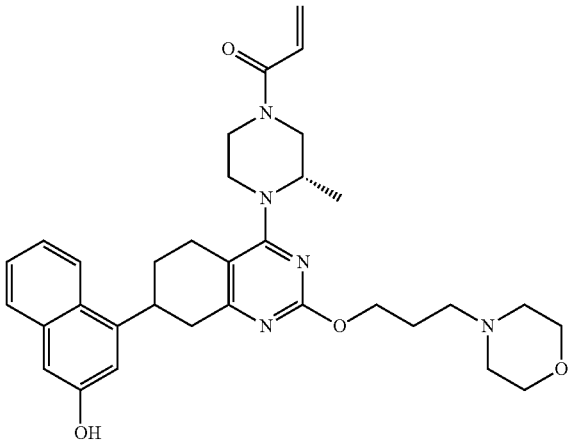 [SMILES: C=CC(=O)N1CCN(c2nc(OCCCN3CCOCC3)nc3c2CCC(c2cc(O)cc4ccccc24)C3)[C@@H](C)C1] | 1-((3S)-4-(7-(3-hydroxynaphthalen-1-yl)-2-(3-morpholinopropoxy)-5,6,7,8-tetrahydroquinazolin-4-yl)-3-methylpiperazin-1-yl)prop-2-en-1-one | | |
| 54 | 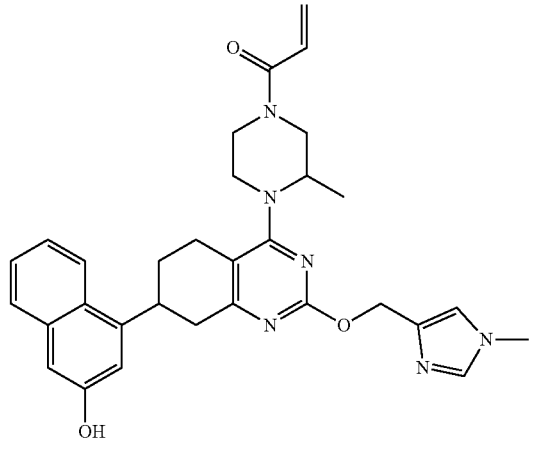 | 1-(4-(7-(3-hydroxynaphthalen-1-yl)-2-((1-methyl-1H-imidazol-4-yl)methoxy)-5,6,7,8-tetrahydroquinazolin-4-yl)-3-methylpiperazin-1-yl)prop-2-en-1-one | 0.47 | 539.3 |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 54a | 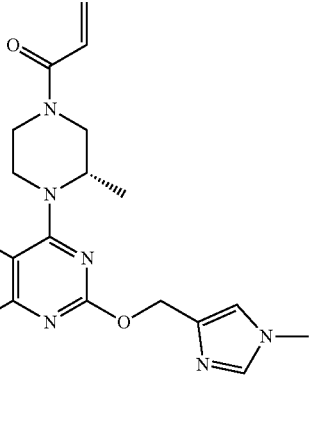 | 1-((3S)-4-(7-(3-hydroxynaphthalen-1-yl)-2-((1-methyl-1H-imidazol-4-yl)methoxy)-5,6,7,8-tetrahydroquinazolin-4-yl)-3-methylpiperazin-1-yl)prop-2-en-1-one | | |
| 55 | 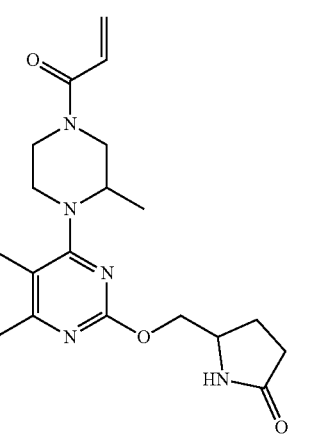 | 5-(((4-(4-acryloyl-2-methylpiperazin-1-yl)-7-(3-hydroxynaphthalen-1-yl)-5,6,7,8-tetrahydroquinazolin-2-yl)oxy)methyl)pyrrolidin-2-one | 1.4 | 542.3 |
| 55a | 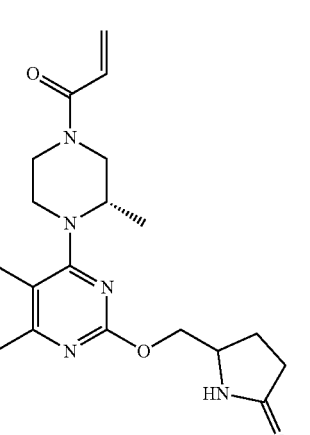 | 5-(((4-((S)-4-acryloyl-2-methylpiperazin-1-yl)-7-(3-hydroxynaphthalen-1-yl)-5,6,7,8-tetrahydroquinazolin-2-yl)oxy)methyl)pyrrolidin-2-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 56 | 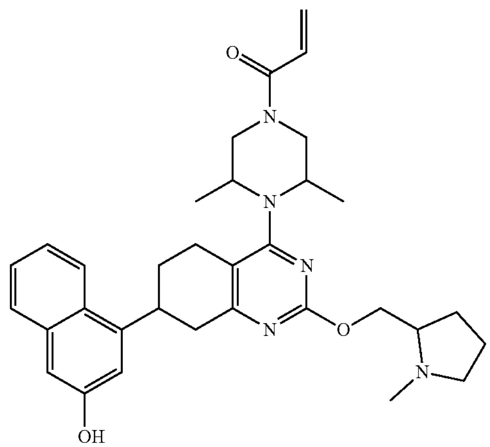 [SMILES: C=CC(=O)N1CC(C)N(c2nc(OCC3CCCN3C)nc3c2CCC(c2cc(O)cc4ccccc24)C3)C(C)C1] | 1-(4-(7-(3-hydroxynaphthalen-1-yl)-2-((1-methylpyrrolidin-2-yl)methoxy)-5,6,7,8-tetrahydroquinazolin-4-yl)-3,5-dimethylpiperazin-1-yl)prop-2-en-1-one | 0.073 | 556.4 |
| 56a | 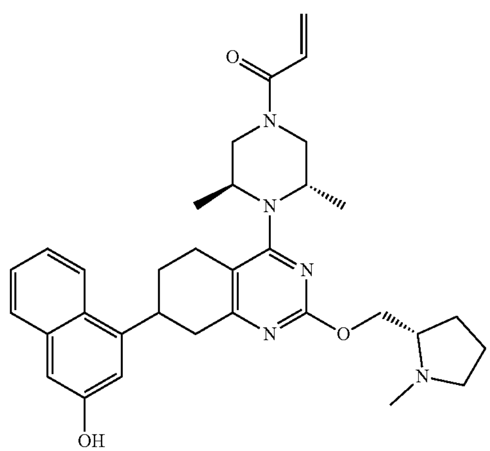 [SMILES: C=CC(=O)N1C[C@H](C)N(c2nc(OC[C@@H]3CCCN3C)nc3c2CCC(c2cc(O)cc4ccccc24)C3)[C@@H](C)C1] | 1-((3S,5S)-4-(7-(3-hydroxynaphthalen-1-yl)-2-(((S)-1-methylpyrrolidin-2-yl)methoxy)-5,6,7,8-tetrahydroquinazolin-4-yl)-3,5-dimethylpiperazin-1-yl)prop-2-en-1-one | | |
| 57 | 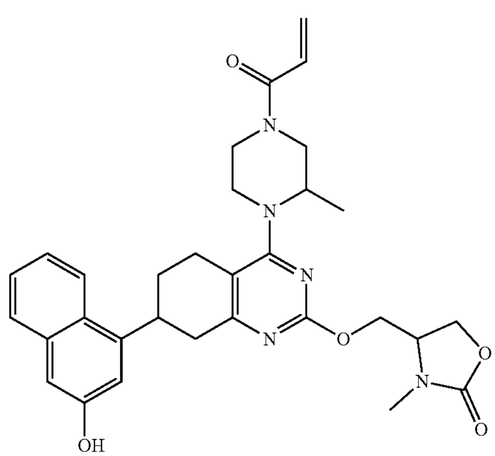 | 4-(((4-(4-acryloyl-2-methylpiperazin-1-yl)-7-(3-hydroxynaphthalen-1-yl)-5,6,7,8-tetrahydroquinazolin-2-yl)oxy)methyl)-3-methyloxazolidin-2-one | 20<br>14<br>0.053<br>0.045 | 558.3 |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 57a | 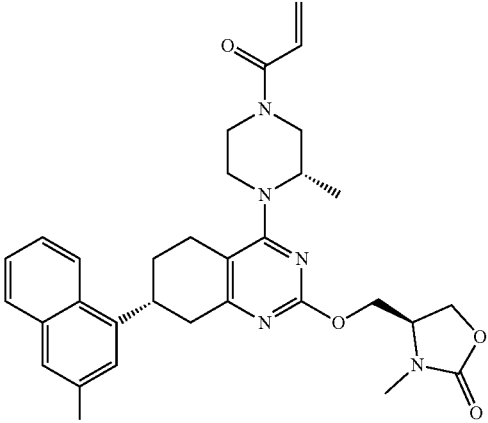 configuration assumed from potency | (S)-4-((((R)-4-((S)-4-acryloyl-2-methylpiperazin-1-yl)-7-(3-hydroxynaphthalen-1-yl)-5,6,7,8-tetrahydroquinazolin-2-yl)oxy)methyl)-3-methyloxazolidin-2-one | | |
| 57b | 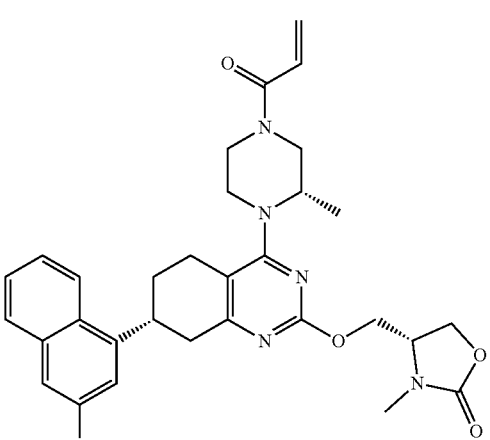 configuration assumed from potency | (R)-4-((((R)-2-((S)-4-acryloyl-2-methylpiperazin-1-yl)-7-(3-hydroxynaphthalen-1-yl)-5,6,7,8-tetrahydroquinazolin-2-yl)oxy)methyl)-3-methyloxazolidin-2-one | | |
| 57c | 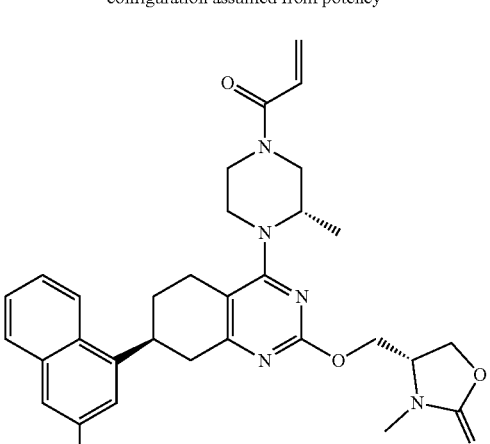 configuration assumed from potency | (R)-4-((((S)-4-((S)-4-acryloyl-2-methylpiperazin-1-yl)-7-(3-hydroxynaphthalen-1-yl)-5,6,7,8-tetrahydroquinazolin-2-yl)oxy)methyl)-3-methyloxazolidin-2-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 57d | 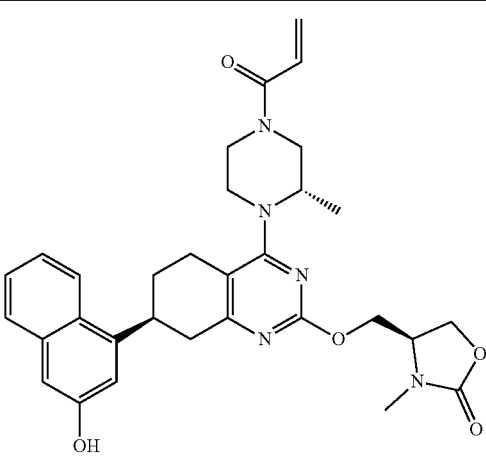 configuration assumed from potency | (S)-4-((((S)-4-((S)-4-acryloyl-2-methylpiperazin-1-yl)-7-(3-hydroxynaphthalen-1-yl)-5,6,7,8-tetrahydroquinazolin-2-yl)oxy)methyl)-3-methyloxazolidin-2-one | | |
| 58 | 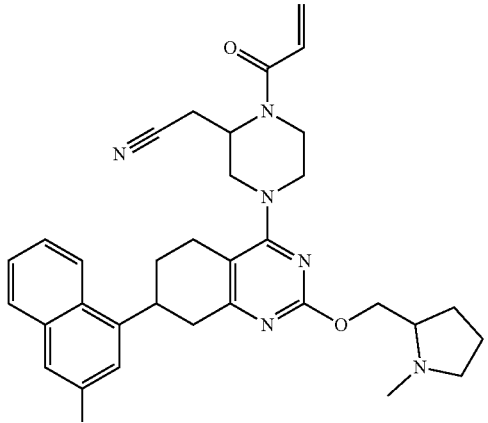 | 2-(1-acryloyl-4-(7-(3-hydroxynaphthalen-1-yl)-2-((1-methylpyrrolidin-2-yl)methoxy)-5,6,7,8-tetrahydroquinazolin-4-yl)piperazin-2-yl)acetonitrile | 0.028 0.13 0.029 0.024 0.029 | 567.3 |
| 58a | 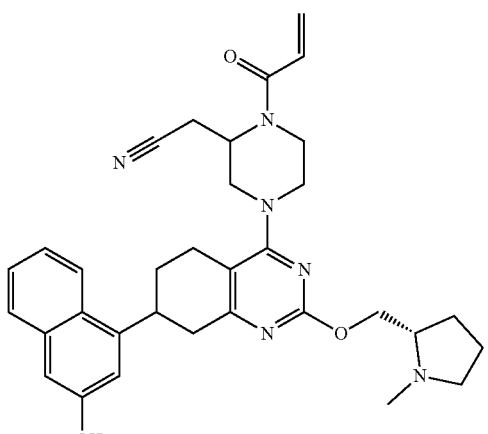 | 2-(1-acryloyl-4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 58b | 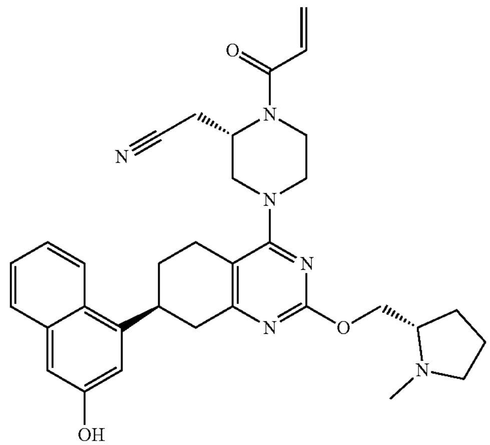 [SMILES: C=CC(=O)N1CCN(c2nc(OC[C@@H]3CCCN3C)nc3c2CC[C@H](c2cc(O)cc4ccccc24)C3)C[C@@H]1CC#N] | 2-((S)-1-acryloyl-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 58c | 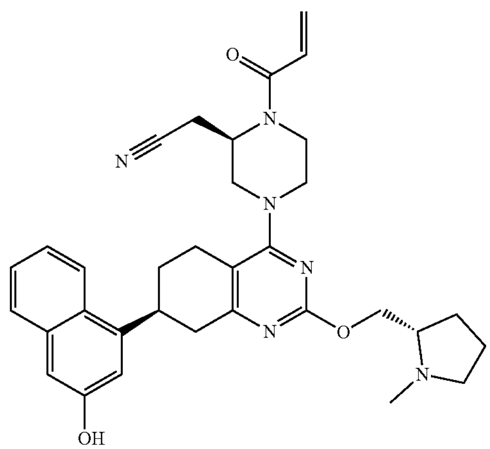 [SMILES: C=CC(=O)N1CCN(c2nc(OC[C@@H]3CCCN3C)nc3c2CC[C@H](c2cc(O)cc4ccccc24)C3)C[C@H]1CC#N] | 2-((R)-1-acryloyl-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 58d | 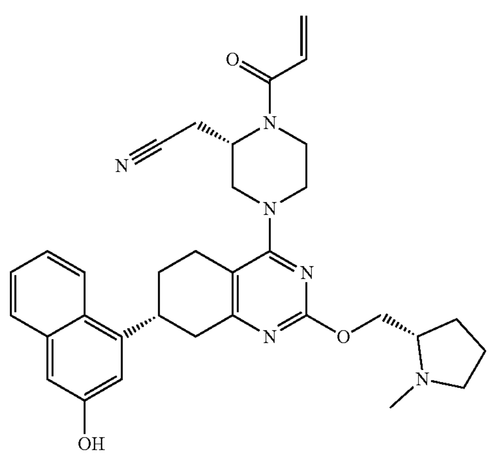 [SMILES: C=CC(=O)N1CCN(c2nc(OC[C@@H]3CCCN3C)nc3c2CC[C@@H](c2cc(O)cc4ccccc24)C3)C[C@@H]1CC#N] | 2-((S)-1-acryloyl-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 58e | 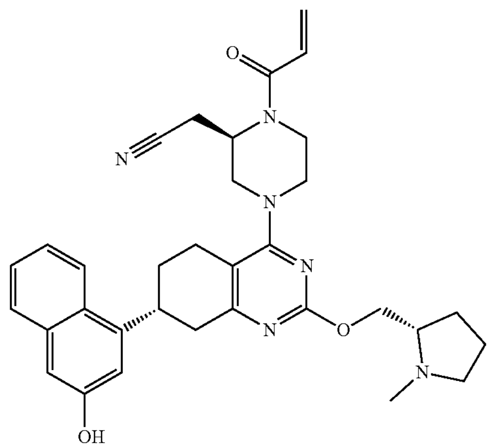 [SMILES: C=CC(=O)N1CCN(c2nc(OC[C@@H]3CCCN3C)nc3c2CC[C@@H](c2cc(O)cc4ccccc24)C3)C[C@H]1CC#N] | 2-((R)-1-acryloyl-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 59 | 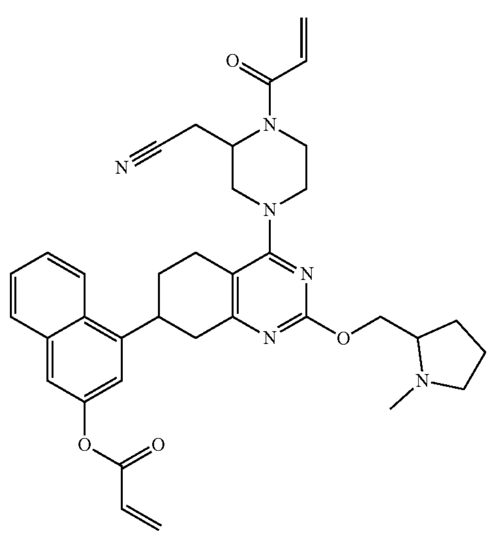 | 4-(4-(4-acryloyl-3-(cyanomethyl)piperazin-1-yl)-2-((1-methylpyrrolidin-2-yl)methoxy)-5,6,7,8-tetrahydroquinazolin-7-yl)naphthalen-2-yl acrylate | 0.25 | 621.3 |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 59a | 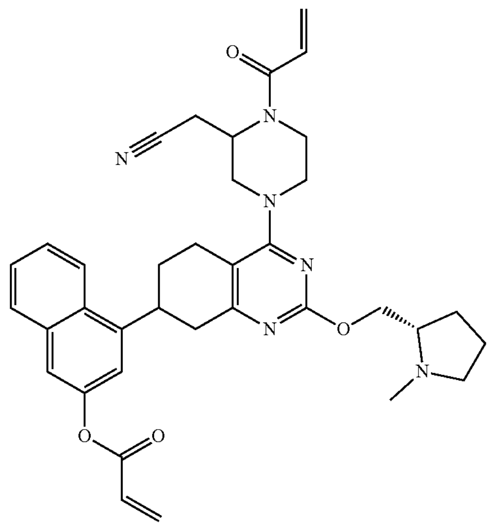 [SMILES: C=CC(=O)Oc1cc(C2CCc3c(nc(OC[C@@H]4CCCN4C)nc3N3CCN(C(=O)C=C)C(CC#N)C3)C2)c2ccccc2c1] | 4-(4-(4-acryloyl-3-(cyanomethyl)piperazin-1-yl)-2-(((S)-1-methylpyrrolidin-2-yl)methoxy)-5,6,7,8-tetrahydroquinazolin-7-yl)naphthalen-2-yl acrylate | | |
| 60 | 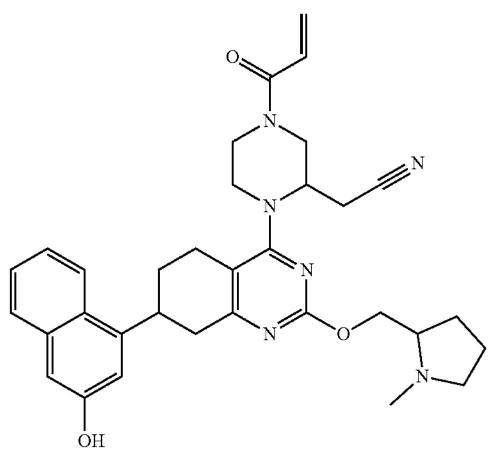 [SMILES: C=CC(=O)N1CCN(c2nc(OCC3CCCN3C)nc3c2CCC(c2cc(O)cc4ccccc24)C3)C(CC#N)C1] | 2-(4-acryloyl-1-(7-(3-hydroxynaphthalen-1-yl)-2-((1-methylpyrrolidin-2-yl)methoxy)-5,6,7,8-tetrahydroquinazolin-4-yl)piperazin-2-yl)acetonitrile | 0.026 | 567.3 |
| 61 | 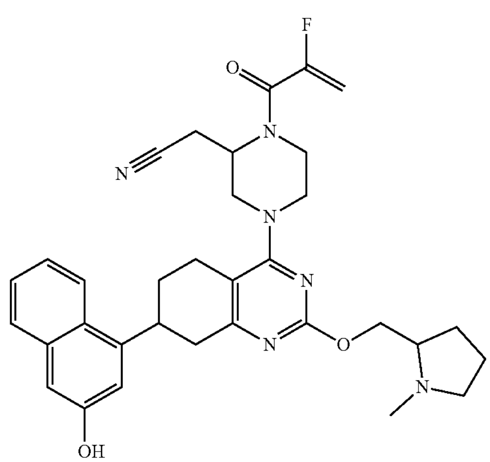 | 2-(1-(2-fluoroacryloyl)-4-(7-(3-hydroxynaphthalen-1-yl)-2-((1-methylpyrrolidin-2-yl)methoxy)-5,6,7,8-tetrahydroquinazolin-4-yl)piperazin-2-yl)acetonitrile | 0.038<br>0.64<br>0.083<br>0.028<br>0.09 | 585.3 |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 61a | 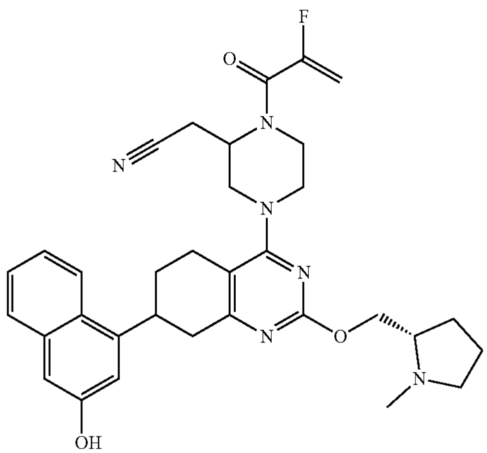 [SMILES: C=C(F)C(=O)N1CCN(c2nc(OC[C@@H]3CCCN3C)nc3c2CCC(c2cc(O)cc4ccccc24)C3)CC1CC#N] | 2-(1-(2-fluoroacryloyl)-4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 61b | 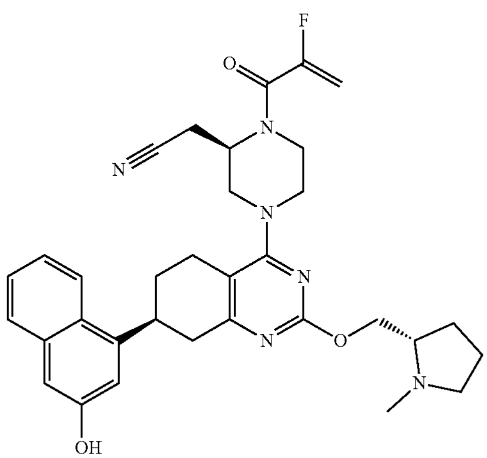 [SMILES: C=C(F)C(=O)N1CCN(c2nc(OC[C@@H]3CCCN3C)nc3c2CC[C@H](c2cc(O)cc4ccccc24)C3)C[C@H]1CC#N] | 2-((R)-1-(2-fluoroacryloyl)-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 61c | 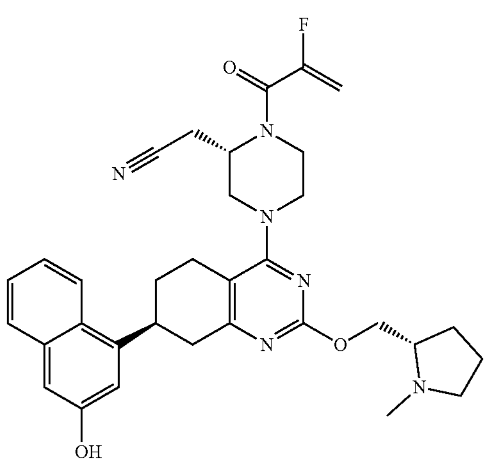 [SMILES: C=C(F)C(=O)N1CCN(c2nc(OC[C@@H]3CCCN3C)nc3c2CC[C@H](c2cc(O)cc4ccccc24)C3)C[C@@H]1CC#N] | 2-((S)-1-(2-fluoroacryloyl)-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 61d | 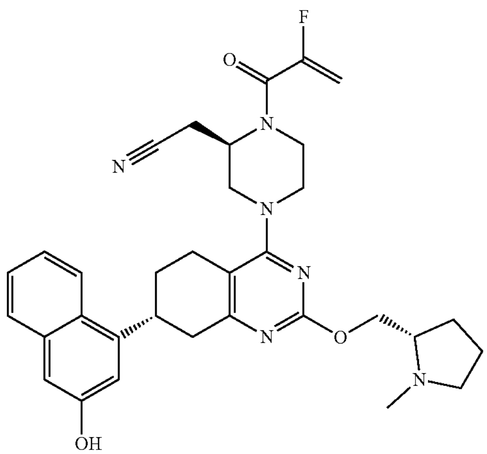 [SMILES: C=C(F)C(=O)N1CCN(c2nc(OC[C@@H]3CCCN3C)nc3c2CC[C@@H](c2cc(O)cc4ccccc24)C3)C[C@H]1CC#N] | 2-((R)-1-(2-fluoroacryloyl)-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 61e | 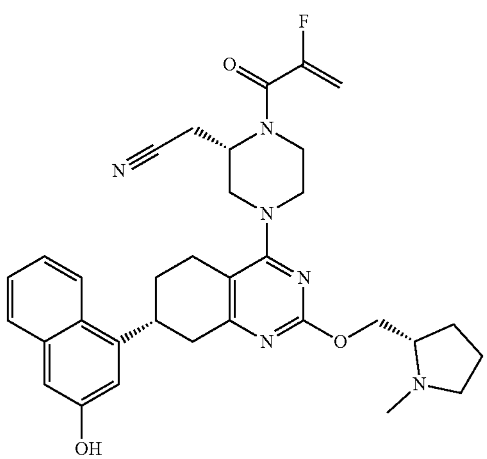 | 2-((S)-1-(2-fluoroacryloyl)-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 62 | 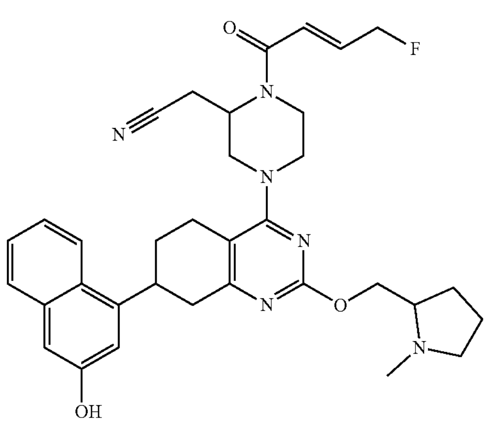 | (E)-2-(1-(4-fluorobut-2-enoyl)-4-(7-(3-hydroxynaphthalen-1-yl)-2-(((1-methylpyrrolidin-2-yl)methoxy)-5,6,7,8-tetrahydroquinazolin-4-yl)piperazin-2-yl)acetonitrile | 0.018 0.18 0.073 <0.01 0.66 | 599.3 |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
|---|---|---|---|---|
| 62a | 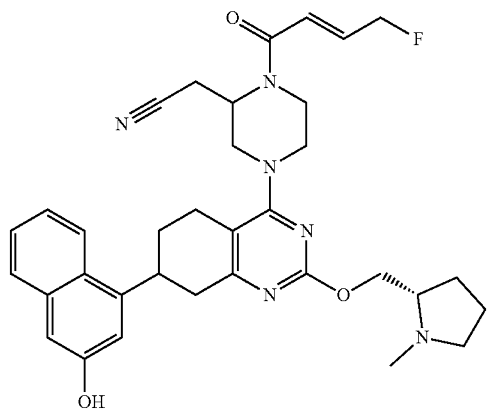 [SMILES: CN1CCC[C@H]1COc1nc2c(c(N3CCN(C(=O)/C=C/CF)C(CC#N)C3)n1)CCC(c1cc(O)cc3ccccc13)C2] | 2-(1-((E)-4-fluorobut-2-enoyl)-4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 62b | 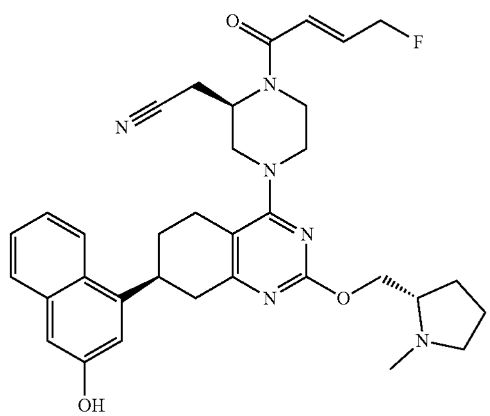 [SMILES: CN1CCC[C@H]1COc1nc2c(c(N3CCN(C(=O)/C=C/CF)[C@H](CC#N)C3)n1)CC[C@H](c1cc(O)cc3ccccc13)C2] | 2-((R)-1-((E)-4-fluorobut-2-enoyl)-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 62c | 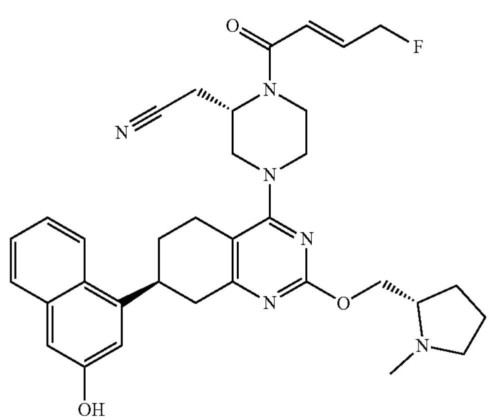 [SMILES: CN1CCC[C@H]1COc1nc2c(c(N3CCN(C(=O)/C=C/CF)[C@@H](CC#N)C3)n1)CC[C@H](c1cc(O)cc3ccccc13)C2] | 2-((S)-1-((E)-4-fluorobut-2-enoyl)-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |

TABLE 1-continued

*Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.*

| Compound # | Structure | Name | IC50 | LCMS (M + H)+ |
|---|---|---|---|---|
| 62d | 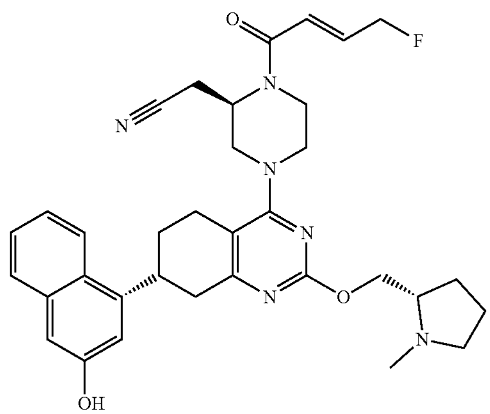 | 2-((R)-1-((E)-4-fluorobut-2-enoyl)-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 62e | 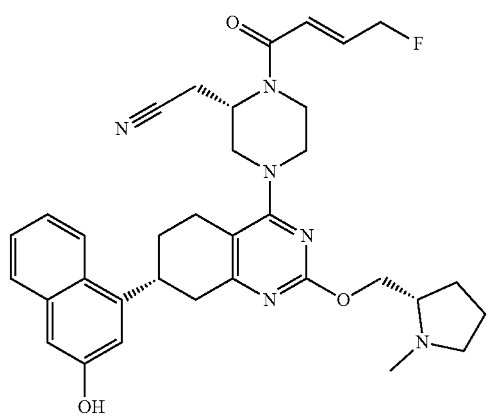 [SMILES: CN1CCC[C@H]1COc1nc2c(c(N3CCN(C(=O)/C=C/CF)[C@@H](CC#N)C3)n1)CC[C@@H](c1cc(O)cc3ccccc13)C2] | 2-((S)-1-((E)-4-fluorobut-2-enoyl)-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile | | |
| 63 | 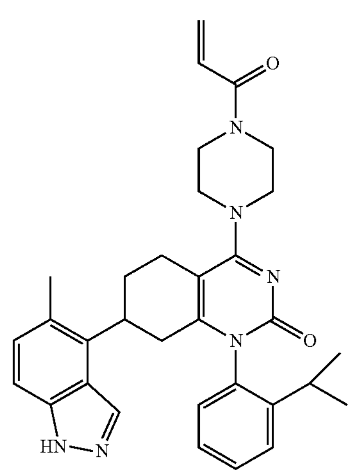 [SMILES: C=CC(=O)N1CCN(c2nc(=O)n(-c3ccccc3C(C)C)c3c2CCC(c2c(C)ccc4[nH]ncc24)C3)CC1] | 4-(4-acryloylpiperazin-1-yl)-1-(2-isopropylphenyl)-7-(5-methyl-1H-indazol-4-yl)-5,6,7,8-tetrahydroquinazolin-2(1H)-one | | |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Name | IC50 | LCMS (M + H)+ |
| --- | --- | --- | --- | --- |
| 64 | 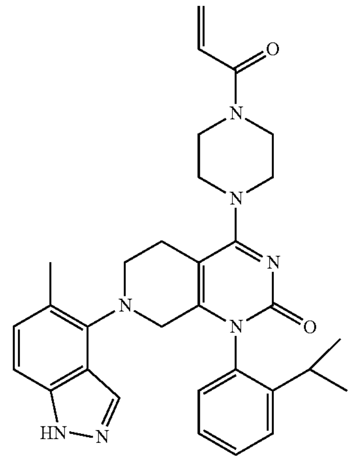 [SMILES: C=CC(=O)N1CCN(c2nc(=O)n(-c3ccccc3C(C)C)c3c2CCN(c2c(C)ccc4[nH]ncc24)C3)CC1] | 4-(4-acryloylpiperazin-1-yl)-1-(2-isopropylphenyl)-7-(5-methyl-1H-indazol-4-yl)-5,6,7,8-tetrahydropyrido[3,4-d]pyrimidin-2(1H)-one | | |

Synthesis of Ras Inhibitors

Compounds of the present disclosure can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, vol. 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds.) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, vol. 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained herein.

For illustrative purposes, reaction Schemes below provide routes for synthesizing the compounds of the invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, or, about 20° C.

Some compounds in following schemes are depicted with generalized substituents; however, one skilled in the art will immediately appreciate that the nature of the substituents can varied to afford the various compounds contemplated in this invention. Moreover, the reaction conditions are exemplary and alternative conditions are well known. The reaction sequences in the following examples are not meant to limit the scope of the invention as set forth in the claims.

Methods of Treatment with and Uses of Ras Inhibitors

Compounds of the present disclosure are useful as Ras inhibitors. In one aspect, the compounds of the present disclosure are useful as K-Ras inhibitors. In another aspect, the compounds of the present disclosure are useful as N-Ras inhibitors. In another aspect, the compounds of the present disclosure are useful as H-Ras inhibitors. Accordingly, in one embodiment is provided a method of contacting a cell, such as an ex vivo cell, with a compound of the present invention, or a pharmaceutically acceptable salt thereof, to inhibit Ras activity (e.g., K-Ras, H-Ras, and/or N-Ras activity) in the cell.

Further provided is a method of preventing, treating, or lessening the severity of a disease or condition responsive to the inhibition of Ras (e.g., K-Ras, H-Ras, and/or N-Ras) in a patient, comprising administering to the patient a therapeutically effective amount of a compound of the present invention, or a pharmaceutically acceptable salt thereof.

In one aspect, the present disclosure is directed to a method of preventing, treating, or lessening the severity of a disease or condition responsive to the inhibition of K-Ras in a patient, comprising administering to the patient a therapeutically effective amount of a compound of the present invention, or a pharmaceutically acceptable salt thereof.

In one aspect, the present disclosure is directed to a method of preventing, treating, or lessening the severity of a disease or condition responsive to the inhibition of H-Ras in a patient, comprising administering to the patient a therapeutically effective amount of a compound of the present invention, or a pharmaceutically acceptable salt thereof.

In one aspect, the present disclosure is directed to a method of preventing, treating, or lessening the severity of a disease or condition responsive to the inhibition of N-Ras in a patient, comprising administering to the patient a therapeutically effective amount of a compound of the present invention, or a pharmaceutically acceptable salt thereof.

Also provided is a method for treating cancer in a patient, comprising administering to the patient a therapeutically effective amount of a compound of the present invention, or a pharmaceutically acceptable salt thereof.

Also provided is a method of inhibiting Ras (e.g., K-Ras, H-Ras, and/or N-Ras) in a patient in need of therapy, comprising administering to the patient a therapeutically effective amount of a compound of the present invention, or a pharmaceutically acceptable salt thereof.

In one aspect, the present disclosure is directed to a method of inhibiting K-Ras in a patient in need of therapy, comprising administering to the patient a therapeutically effective amount of a compound of the present invention, or a pharmaceutically acceptable salt thereof.

In one aspect, the present disclosure is directed to a method of inhibiting H-Ras in a patient in need of therapy, comprising administering to the patient a therapeutically effective amount of a compound of the present invention, or a pharmaceutically acceptable salt thereof.

In one aspect, the present disclosure is directed to a method of inhibiting N-Ras in a patient in need of therapy, comprising administering to the patient a therapeutically effective amount of a compound of the present invention, or a pharmaceutically acceptable salt thereof.

Also provided is a pharmaceutical composition comprising a therapeutically effective amount of a compound of the present invention, or a pharmaceutically acceptable salt thereof, and a pharmaceutically acceptable excipient. Compounds of the invention, including pharmaceutical compositions comprising such compounds, may be used in the methods described herein.

Embodiments of the present disclosure provide a method of inhibiting Ras-mediated cell signaling comprising contacting a cell with a therapeutically effective amount of one or more compounds disclosed herein, or a pharmaceutically acceptable salt thereof. Inhibition of Ras-mediated signal transduction can be assessed and demonstrated by a wide variety of ways known in the art. Non-limiting examples include a showing of (a) a decrease in GTPase activity of Ras; (b) a decrease in GTP binding affinity or an increase in GDP binding affinity; (c) an increase in K off of GTP or a decrease in K off of GDP; (d) a decrease in the levels of signaling transduction molecules downstream in the Ras pathway, such as a decrease in pMEK level; and/or (e) a decrease in binding of Ras complex to downstream signaling molecules including but not limited to Raf. Kits and commercially available assays can be utilized for determining one or more of the above.

Embodiments also provide methods of using the compounds or pharmaceutical compositions of the present invention to treat disease conditions, including but not limited to conditions implicated by G12C K-Ras mutation, G12C H-Ras mutation and/or G12C N-Ras mutation (e.g., cancer).

In some embodiments the invention provides a method of treating a disorder in a subject in need thereof, wherein the said method comprises determining if the subject has a K-Ras, H-Ras or N-Ras G12C mutation and if the subject is determined to have a K-Ras, H-Ras or N-Ras G12C mutation, then administering to the subject a therapeutically effective amount of at least one compound of the present invention, or a pharmaceutically acceptable salt thereof.

K-Ras, H-Ras or N-Ras G12C mutations have also been identified in hematological malignancies (e.g., cancers that affect blood, bone marrow, and/or lymph nodes). Accordingly, certain embodiments are directed to administration of a disclosed compound of the present invention, or a pharmaceutically acceptable salt thereof (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMoL) and/or other leukemias. In other embodiments, the compounds of the present invention, or a pharmaceutically acceptable salt thereof are useful for treatment of lymphomas such as all subtypes of Hodgkin's lymphoma or non-Hodgkin's lymphoma.

Determining whether a tumor or cancer comprises a G12C K-Ras, H-Ras or N-Ras mutation can be undertaken by assessing the nucleotide sequence encoding the K-Ras, H-Ras or N-Ras protein, by assessing the amino acid sequence of the K-Ras, H-Ras or N-Ras protein, or by assessing the characteristics of a putative K-Ras, H-Ras or N-Ras mutant protein. The sequences of wild-type human K-Ras (e.g. Accession No. NP203524), H-Ras (e.g. Accession No. NP001123914) and N-Ras (e.g. Accession No. NP002515) are known in the art.

Methods for detecting a mutation in a K-Ras, H-Ras or N-Ras nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C K-Ras, H-Ras or N-Ras mutations by real-time PCR. In real-time PCR, fluorescent probes specific for the K-Ras, H-Ras or N-Ras G12C mutation are used. When a mutation is present, the probe binds and fluorescence is detected. In some embodiments, the K-Ras, H-Ras or N-Ras G12C mutation is identified using a direct sequencing method of specific regions (e.g., exon 2 and/or exon 3) in the K-Ras, H-Ras or N-Ras gene. This technique will identify all possible mutations in the region sequenced.

Methods for detecting a mutation in a K-Ras, H-Ras or N-Ras protein are known by those of skill in the art. These methods include, but are not limited to, detection of a K-Ras, H-Ras or N-Ras mutant using a binding agent (e.g., an antibody) specific for the mutant protein, protein electrophoresis and Western blotting, and direct peptide sequencing. Methods for determining whether a tumor or cancer comprises a G12C K-Ras, H-Ras or N-Ras mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

Embodiments also relate to a method of treating a hyperproliferative disorder in a mammal that comprises administering to said mammal a therapeutically effective amount of a compound of the present invention, or a pharmaceutically acceptable salt thereof. In some embodiments, said method relates to the treatment of cancer such as acute myeloid leukemia, cancer in adolescents, childhood adrenocortical carcinoma, AIDS-related cancers (e.g. lymphoma and Kaposi's sarcoma), anal cancer, appendix cancer, astrocytomas, atypical teratoid rhabdoid tumor, basal cell carcinoma, bile duct cancer, bladder cancer, bone cancer, brain stem glioma, brain tumor, breast cancer, bronchial tumors, Burkitt lymphoma, carcinoid tumor, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, Merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, oropharyngeal cancer, ovarian cancer, pancreatic cancer, papillomatosis, paraganglioma, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e. g., psoriasis), restenosis, or benign prostatic hyperplasia (BPH).

In certain particular embodiments, the invention relates to methods for treatment of lung cancers, the methods comprise administering a therapeutically effective amount of a compound of the present invention, or a pharmaceutically acceptable salt thereof (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

In one embodiment, the invention provides a method of tumor-agnostic treatment of cancer in an individual in need thereof, the method comprising determining if the individual has a tumor with a G12C mutation in a K-Ras, H-Ras, or N-Ras protein in the tumor, and, if the individual has a tumor with the mutation, administering a therapeutically effective amount of a compound of the present invention, or a pharmaceutically acceptable salt thereof, as described herein. "Tumor-agnostic" as used herein refers to cancers (tumors) having a specific genetic mutation or common biomarker that can be treated with a compound or pharmaceutically acceptable salt thereof as described herein, regardless of the tumor type. Thus, in one embodiment, a compound or a pharmaceutically acceptable salt thereof as described herein can be administered to an individual described herein having any cancer comprising a G12C mutation.

In some embodiments, the invention provides methods of inhibiting K-Ras, H-Ras, or N-Ras G12C activity in a cell by contacting said cell with an amount of a compound of the present invention, or a pharmaceutically acceptable salt thereof sufficient to inhibit the activity of K-Ras, H-Ras or N-Ras G12C in said cell. In some embodiments, the invention provides methods of inhibiting K-Ras, H-Ras or N-Ras G12C activity in a tissue by contacting said tissue with an amount of a compound of the present invention, or a pharmaceutically acceptable salt thereof sufficient to inhibit the activity of K-Ras, H-Ras or N-Ras G12C in said tissue. In some embodiments, the invention provides methods of inhibiting K-Ras, H-Ras or N-Ras G12C activity in an organism by contacting said organism with an amount of a compound of the present invention, or a pharmaceutically acceptable salt thereof sufficient to inhibit the activity of K-Ras, H-Ras or N-Ras G12C in said organism. In some embodiments, the invention provides methods of inhibiting K-Ras, H-Ras or N-Ras G12C activity in an animal by contacting said animal with an amount of a compound of the present invention, or a pharmaceutically acceptable salt thereof sufficient to inhibit the activity of K-Ras, H-Ras or N-Ras G12C in said animal. In some embodiments, the invention provides methods of inhibiting K-Ras, H-Ras or N-Ras G12C activity in a mammal by contacting said mammal with an amount of a compound of the present invention, or a pharmaceutically acceptable salt thereof sufficient to inhibit the activity of K-Ras, H-Ras or N-Ras G12C in said mammal. In some embodiments, the invention provides methods of inhibiting K-Ras, H-Ras or N-Ras G12C activity in a human by contacting said human with an amount of a compound of the present invention, or a pharmaceutically acceptable salt thereof sufficient to inhibit the activity of K-Ras, H-Ras or N-Ras G12C in said human. In other embodiments, the present invention provides methods of treating a disease mediated by K-Ras, H-Ras or N-Ras G12C activity in a subject in need of such treatment.

In some embodiments, the invention provides methods of treating cancer comprising administering to an individual in need thereof a therapeutically effective amount of the compound of the present invention, or a pharmaceutically acceptable salt thereof, or the pharmaceutical composition of the present invention. In some embodiments, the individual is a human. In some embodiments, the administering is via the oral route. In some embodiments, the administering is via injection. In some embodiments, the cancer is mediated by a K-Ras G12C, H-Ras G12C or N-Ras G12C mutation. In some embodiments, the cancer is mediated by a K-Ras G12C mutation. In some embodiments, the cancer is a hematological cancer, pancreatic cancer, MYH associated polyposis, colorectal cancer or lung cancer. In some embodiments, the cancer is lung adenocarcinoma.

In some embodiments, the invention provides methods for regulating activity of a mutant protein selected from the group consisting of K-Ras G12C, H-Ras G12C and N-Ras G12C, the method comprising reacting the mutant protein with the compound of the present invention, or a pharmaceutically acceptable salt thereof.

In some embodiments, the invention provides methods for inhibiting proliferation of a cell population, the method comprising contacting the cell population with the compound of the present invention, or a pharmaceutically acceptable salt thereof. In some embodiments, the inhibition of proliferation is measured as a decrease in cell viability of the cell population.

In some embodiments, the invention provides methods for treating a disorder mediated by a mutation selected from the group consisting of K-Ras G12C, H-Ras G12C and N-Ras G12C in an individual in need thereof, the method comprising: determining if the individual has the mutation; and if the individual is determined to have the mutation, then administering to the individual a therapeutically effective amount of the compound of the present invention, or a pharmaceutically acceptable salt thereof, or the pharmaceutical composition of the present invention. In some embodiments, the disorder is mediated by a K-Ras G12C mutation. In some embodiments, the disorder is a cancer. In some embodiments, the cancer is agnostic. In another embodiment, the cancer is a hematological cancer, pancreatic cancer, MYH associated polyposis, colorectal cancer or lung cancer. In some embodiments, the cancer is lung adenocarcinoma. In another embodiment, the cancer is colorectal cancer.

In some embodiments, the invention provides methods for preparing a labeled K-Ras G12C, H-Ras G12C or N-Ras G12C mutant protein, the method comprising reacting a K-Ras G12C, H-Ras G12C or N-Ras G12C mutant protein with a compound of the present invention, or a pharmaceutically acceptable salt thereof, to result in the labeled K-Ras G12C, H-Ras G12C or N-Ras G12C mutant protein.

In some embodiments, the invention provides methods for inhibiting tumor metastasis comprising administering to an individual in need thereof a therapeutically effective amount of the compound of the present invention, or a pharmaceutically acceptable salt thereof, or the pharmaceutical composition of the present invention to a subject in need thereof.

In some embodiments, the invention provides uses of a compound of the present invention, or a pharmaceutically acceptable salt thereof, in the manufacture of a medicament for treating cancer. In some embodiments, the medicament is formulated for oral administration. In some embodiments, the medicament is formulated for injection. In some embodiments, the cancer is mediated by a K-Ras G12C, H-Ras G12C or N-Ras G12C mutation. In some embodiments, the cancer is mediated by a K-Ras G12C mutation. In some embodiments, the cancer is mediated by a H-Ras G12C mutation. In some embodiments, the cancer is mediated by a N-Ras G12C mutation. In some embodiments, the cancer is a hematological cancer, pancreatic cancer, MYH associated polyposis, colorectal cancer or lung cancer. In some embodiments, the cancer is lung adenocarcinoma. In some embodiments, the invention provides uses of a compound of the present invention, or a pharmaceutically acceptable salt thereof, in the manufacture of a medicament for inhibiting tumor metastasis.

In some embodiments, the invention provides a compound of the present invention, or a pharmaceutically acceptable salt thereof, or a pharmaceutical composition of the present invention, for use in a method of treatment of the human or animal body by therapy. In some embodiments, the invention provides a compound of the present invention, or a pharmaceutically acceptable salt thereof, or a pharmaceutical composition of the present invention, for use in a method of treating cancer. In some embodiments, the cancer is mediated by a K-Ras G12C, H-Ras G12C or N-Ras G12C mutation. In some embodiments, the cancer is mediated by a K-Ras G12C mutation. In some embodiments, the cancer is mediated by a H-Ras G12C mutation. In some embodiments, the cancer is mediated by a N-Ras G12C mutation. In some embodiments, the cancer is agnostic. In another embodiment, the cancer is a hematological cancer, pancreatic cancer, MYH associated polyposis, colorectal cancer or lung cancer. In some embodiments, the cancer is lung adenocarcinoma. In some embodiments, the invention provides a compound of the present invention, or a pharmaceutically acceptable salt thereof, or a pharmaceutical composition of the present invention, for use in a method of inhibiting tumor metastasis.

Dosage & Administration

The present invention provides pharmaceutical compositions or medicaments containing a therapeutically effective amount of a compound of the present invention, or a pharmaceutically acceptable salt thereof and at least one therapeutically inert excipient, as well as methods of using the compounds of the invention to prepare such compositions and medicaments.

An embodiment, therefore, includes a pharmaceutical composition comprising a therapeutically effective amount of a compound of the present invention, or a pharmaceutically acceptable salt thereof. A further embodiment includes a pharmaceutical composition comprising a therapeutically effective amount of a compound of the present invention, or a pharmaceutically acceptable salt thereof, together with a pharmaceutically acceptable excipient.

In one example, a therapeutically effective amount of a compound of the present invention, or a pharmaceutically acceptable salt thereof, with the desired degree of purity may be formulated by mixing with physiologically acceptable excipients, i.e., excipients that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of the present invention, or a pharmaceutically acceptable salt thereof is formulated in an acetate buffer, at pH 5. In another embodiment, compound of the present invention, or a pharmaceutically acceptable salt thereof is sterile. The compound of the present invention, or a pharmaceutically acceptable salt thereof may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "therapeutically effective amount" of the compound of the present invention, or a pharmaceutically acceptable salt thereof to be administered will be governed by such considerations, and is the minimum amount necessary to inhibit K-Ras, H-Ras, and/or N-Ras activity. Typically such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container may have deposited thereon a label that describes the contents of the container. The label may also include appropriate warnings.

Sustained-release preparations may be prepared. Suitable examples of sustained-release preparations include semipermeable matrices of solid hydrophobic polymers containing a therapeutically effective amount of a compound of the present invention, or a pharmaceutically acceptable salt thereof, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

A dose to treat human patients may range from about 0.01 mg to about 1000 mg of a compound of the present invention, or a pharmaceutically acceptable salt thereof. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

A therapeutically effective amount of a compound of the present invention, or a pharmaceutically acceptable salt thereof may be administered by any suitable means, including oral, topical (including buccal and sublingual), rectal, vaginal, transdermal, parenteral, subcutaneous, intraperitoneal, intrapulmonary, intradermal, intrathecal, epidural and intranasal, and, if desired for local treatment, intralesional administration. Parenteral infusions include intramuscular, intravenous, intraarterial, intraperitoneal, or subcutaneous administration.

A therapeutically effective amount of a compound of the present invention, or a pharmaceutically acceptable salt thereof may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a therapeutically effective amount of a compound of the present invention, or a pharmaceutically acceptable salt thereof and an excipient. Suitable excipients include carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and taste and/or odour correctants, and are well known to those skilled in the art and are described in detail in, e.g., Ansel, H. C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, R. C., *Handbook of Pharmaceutical Excipients*, Chicago, Pharmaceutical Press, 2005. The formulations may also include one or more buffers, surfactants, lubricating agents, suspending agents, preservatives, opaquing agents, glidants, processing aids, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the compound of the present invention, or a pharmaceutically acceptable salt thereof are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In certain embodiments, pharmaceutical compositions are formulated in any conventional manner using one or more physiologically acceptable excipients and auxiliaries which facilitate processing of the active compounds into preparations which can be used pharmaceutically. Proper formulation is dependent upon the route of administration chosen. Any pharmaceutically acceptable techniques and excipients are optionally used as suitable. Pharmaceutical compositions comprising a therapeutically effective amount of a compound of the present invention, or a pharmaceutically acceptable salt thereof are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable excipient and a therapeutically effective amount of a compound of the present invention, or a pharmaceutically acceptable salt thereof, described herein as an active ingredient. The active ingredient is in free-acid or freebase form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, excipients, such as preserving, stabilizing, wetting or emulsifying agents, solution promoters, salts for regulating the osmotic pressure, buffers, and/or other therapeutically valuable substances.

Methods for the preparation of compositions comprising a therapeutically effective amount of a compound of the present invention, or a pharmaceutically acceptable salt thereof described herein include formulating the compound of the present invention, or a pharmaceutically acceptable salt thereof with one or more inert, pharmaceutically acceptable excipients to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising a therapeutically effective amount of a compound of the present invention, or a pharmaceutically acceptable salt thereof illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly (methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of the present invention, or a pharmaceutically acceptable salt thereof. The term "solubilizing agent" generally includes agents that result in formation of a micellar solution or a true solution of the agent. Certain acceptable nonionic surfactants, for example polysorbate 80, are useful as solubilizing agents, as are ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or excipients useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days.

The invention further provides veterinary compositions comprising at least one active ingredient as above defined together with a veterinary excipient therefore. Veterinary excipients are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of the present invention, or a pharmaceutically acceptable salt thereof may be employed alone or in combination with other therapeutic agents for the treatment of a disease or disorder described herein. The second compound of the pharmaceutical combination formulation or dosing regimen preferably has complementary activities to the compound of the present invention, or a pharmaceutically acceptable salt thereof such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Combination therapies according to the present invention thus comprise the administration of a compound of the present invention, or a pharmaceutically acceptable salt thereof, and the use of at least one other treatment method. The amounts of the compound of the present invention, or a pharmaceutically acceptable salt thereof and the other pharmaceutically active agent(s) and the relative timings of administration will be selected in order to achieve the desired combined therapeutic effect.

In various embodiments of the method, the additional therapeutic agent is an epidermal growth factor receptor (EGFR) inhibitor, phosphatidylinositol kinase (PI3K) inhibitor, insulin-like growth factor receptor (IGF1R) inhibitor, a Janus kinase (JAK) inhibitor, a Met kinase inhibitor, a SRC family kinase inhibitor, a mitogen-activated protein kinase (MEK) inhibitor, an extracellular-signal-regulated kinase (ERK) inhibitor, a topoisomerase inhibitor (such as irinotecan, or such as etoposide, or such as doxorubicin), a taxane (such as anti-microtubule agents including paclitaxel and docetaxel), an anti-metabolite agent (such as 5-FU or such as gemcitabine), or an alkylating agent (such as cisplatin or such as cyclophosphamide), or a taxane.

In some embodiments, the additional therapeutic agent is an epidermal growth factor receptor (EGFR) inhibitor, such as Erlotinib or such as Afatinib. In some embodiments the additional therapeutic agent is Iressa. In some embodiments the additional therapeutic agent is a monoclonal antibody such as cetuximab (Erbitux) or panitumumab (Vectibix). In some embodiments the GFR inhibitor is a dual or pan-HER inhibitor. In other embodiments, the additional therapeutic agent is a phosphatidylinositol-3-kinase (PI3K) inhibitor, such as GDC-0941, MLN1117, BYL719 (Alpelisib) or BKM120 (Buparlisib). GDC-0941 refers to 2-(1H-indazol-4-yl)-6-(4-methanesulfonyl-piperazin-1-ylmethyl)-4-morpholin-4-yl-thieno[3,2-d]pyrimidine or a salt thereof (e.g., bismesylate salt).

In still different embodiments, the additional therapeutic agent is an insulin-like growth factor receptor (IGF1R) inhibitor. For example, in some embodiments the insulin-like growth factor receptor (IGF1R) inhibitor is NVP-AEW541. In other embodiments, the additional therapeutic agent is IGOSI-906 (Linsitinib), BMS-754807, or in other embodiments the additional therapeutic agent is a neutralizing monoclonal antibody specific to IGF1R such as AMG-479 (ganitumab), CP-751,871 (figitumumab), IMC-A12 (cixutumumab), MK-0646 (dalotuzumab), or R-1507 (robatumumab).

In some other embodiments, the additional therapeutic agent is a Janus kinase (JAK) inhibitor. In some embodiments, the additional therapeutic agent is CYT387, GLPG0634, Baricitinib, Lestaurtinib, momelotinib, Pacritinib, Ruxolitinib, or TG101348.

In some other embodiments, the additional therapeutic agent is an anti-glypican 3 antibody. In some embodiments, the anti-glypican 3 antibody is codrituzumab.

In some other embodiments, the additional therapeutic agent is an antibody drug conjugate (ADC). In some embodiments, the ADC is polatuzumab vedotin, RG7986, RG7882, RG6109, or RO7172369.

In some other embodiments, the additional therapeutic agent is an MDM2 antagonist. In some embodiments, the MDM2 antagonist is idasanutlin.

In some other embodiments, the additional therapeutic agent is an agonistic antibody against CD40. In some embodiments, the agonistic antibody against CD40 is selicrelumab (RG7876).

In some other embodiments, the additional therapeutic agent is a bispecific antibody. In some embodiments, the bispecific antibody is RG7828 (BTCT4465A), RG7802, RG7386 (FAP-DR5), RG6160, RG6026, ERY974, or anti-HER2/CD3.

In some other embodiments, the additional therapeutic agent is a targeted immunocytokine. In some embodiments, the targeted immunocytokine is RG7813 or RG7461.

In some other embodiments, the additional therapeutic agent is an antibody targeting colony stimulating factor-1 receptor (CSF-1R). In some embodiments, the CSF-1R antibody is emactuzumab.

In some other embodiments, the additional therapeutic agent is a personalised cancer vaccine. In some embodiments, the personalised cancer vaccine is RG6180.

In some other embodiments, the additional therapeutic agent is an inhibitor of BET (bromodomain and extraterminal family) proteins (BRD2/3/4/T). In some embodiments, the BET inhibitor is RG6146.

In some other embodiments, the additional therapeutic agent is an antibody designed to bind to TIGIT. In some embodiments, the anti-TIGIT antibody is RG6058 (MTIG7192A).

In some other embodiments, the additional therapeutic agent is a selective estrogen receptor degrader (SERD). In some other embodiments, the SERD is RG6047 (GDC-0927) or RG6171 (GDC-9545).

In some other embodiments the additional therapeutic agent is an MET kinase inhibitor, such as Crizotinib, tivantinib, AMG337, cabozantinib, or foretinib. In other embodiments the additional therapeutic agent is a neutralizing monoclonal antibody to MET such as onartuzumab.

In more embodiments, the additional therapeutic agent is a SRC family non-receptor tyrosine kinase inhibitor. For example in some embodiments the additional therapeutic agent is an inhibitor of the subfamily of SRC family non-receptor tyrosine kinases. Exemplary inhibitors in this respect include Dasatinib. Other examples in this regard include Ponatinib, saracatinib, and bosutinib.

In yet different embodiments, the additional therapeutic agent is a mitogen-activated protein kinase (MEK) inhibitor. In some of these embodiments, the mitogen-activated protein kinase (MEK) inhibitor is trametinib, selumetinib, COTELLIC® (cobimetinib), PD0325901, or RO5126766. In other embodiments the MEK inhibitor is GSK-1120212, also known as trametinib.

In yet different embodiments, the additional therapeutic agent is an extracellular-signal-regulated kinase (ERK) inhibitor. In some of these embodiments, the mitogen-activated protein kinase (MEK) inhibitor is SCH722984 or GDC-0994.

In other embodiments the protein kinase inhibitor is taselisib, ipatasertib, GDC-0575, GDC-5573 (HM95573), RG6114 (GDC-0077), CKI27, Afatinib, Axitinib, Bevacizumab, Bostutinib, Cetuximab, Crizotinib, Dasatinib, Erlotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, or Vemurafenib. In still more embodiments, the additional therapeutic agent is a topoisomerase inhibitor. In some of these embodiments, the topoisomerase inhibitor is Irinotecan. In some more embodiments, the additional therapeutic agent is a taxane. Exemplary taxanes include Taxol and Docetaxel.

In addition to the above additional therapeutic agent, other chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methyl melamines including altretamine, triethylenemelamine, triethylenephosphoramide, triethylenethiophosphaoramide and trimethylol melamine; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard;

nitrosoureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; Xeloda®; ibandronate; camptothecin-11 (CPT-11); topoisomerase inhibitor RFS 2000; and difluoromethylornithine (DMFO). Where desired, the compounds or pharmaceutical composition of the present invention can be used in combination with commonly prescribed anti-cancer drugs such as Herceptin®, Avastin®, Gazyva®, Tecentriq®, Alecensa®, Perjeta®, Venclexta™, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chIoroethyI)amine, Troxacitabine, Uramustine, Vadimezan, Vinflunine, ZD6126 or Zosuquidar.

The exact method for administering the compound and the additional therapeutic agent will be apparent to one of ordinary skill in the art. In some exemplary embodiments the compound and the additional therapeutic agent are co-administered. In other embodiments, the compound and the additional therapeutic agent are separately administered.

In some embodiments, the compound and the additional therapeutic agent are administered with the second agent simultaneously or separately. This administration in combination can include simultaneous administration of the two agents in the same dosage form, simultaneous administration in separate dosage forms, and separate administration. That is, the compound and any of the additional therapeutic agents described herein can be formulated together in the same dosage form and administered simultaneously. Alternatively, the compound and any of the additional therapeutic agents described herein can be simultaneously administered, wherein both the agents are present in separate formulations. In another alternative, the compound can be administered just followed by and any of the additional therapeutic agents described herein, or vice versa. In some embodiments of the separate administration protocol, the compound and any of the additional therapeutic agents described herein are administered a few minutes apart, or a few hours apart, or a few days apart.

Articles of Manufacture

In another embodiment of the invention, an article of manufacture, or "kit", containing materials useful for the treatment of the diseases and disorders described above is provided. In one embodiment, the kit comprises a container comprising compound of the present invention, or a pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of the present invention, or a pharmaceutically acceptable salt thereof or a formulation thereof which is effective for treating the condition and may have a sterile access port (for example, the container may be an intravenous solution bag or a vial having a stopper pierceable by a hypodermic injection needle). At least one active agent in the composition is a compound of the present invention, or a pharmaceutically acceptable salt thereof. Alternatively, or additionally, the article of manufacture may further comprise a second container comprising a pharmaceutical diluent, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In another embodiment, the kits are suitable for the delivery of solid oral forms of a compound of the present invention, or a pharmaceutically acceptable salt thereof, such as tablets or capsules. Such a kit can include a number of unit dosages. An example of such a kit is a "blister pack". Blister packs are well known in the packaging industry and are widely used for packaging pharmaceutical unit dosage forms.

ADDITIONAL EMBODIMENTS

Additional embodiments are provided herein below.

Embodiment 1: A compound having Formula (I):

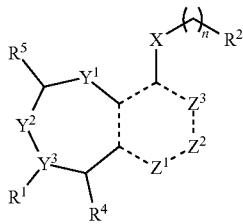

(I)

or a pharmaceutically acceptable salt thereof; wherein:

$R^1$ is selected from the group consisting of H, $C_{6-10}$ aryl, 5- to 10-membered heteroaryl, and 5- to 10-membered heterocyclyl, wherein each aryl, heteroaryl, and heterocyclyl is optionally substituted with one to four substituents, wherein each substituent is independently selected from the group consisting of $C_{1-6}$ alkyl, —$NH_2$, —$NH(CH_3)$, —$N(CH_3)_2$, halo, $C_{1-6}$haloalkyl, oxo, $C_{1-6}$ hydroxyalkyl, $C_{3-6}$ cycloalkyl, —OC(=O)CH=$CH_2$, and hydroxy;

$R^2$ is an electrophilic moiety capable of forming a covalent bond with a cysteine residue at position 12 of a K-Ras G12C mutant protein;

$Y^1$ is $C(H)(R^6)$; or $Y^1$ is absent;

$Y^2$ is selected from the group consisting of $N(R^7)$ and $C(H)(R^8)$;

$Y^3$ is selected from the group consisting of $C(R^3)$ and N;

$Z^1$ is selected from the group consisting of N, $N(R^9)$, O, S, S(O), and $S(O)_2$;

$Z^2$ is $C(R^{10})$, $C(-L-R^{10a})$, or $Z^2$ is absent;

$Z^3$ is selected from the group consisting of N, $N(R^{11})$, and $C(R^{12})$;

$R^3$, $R^4$, $R^5$, $R^6$, $R^7$, $R^8$, $R^9$, $R^{10}$, $R^{11}$, and $R^{12}$ are each independently selected from the group consisting of H, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{2-6}$ alkynyl, $C_{1-6}$ alkylamino, amino, aryl, aryl substituted with a $C_{1-6}$ alkyl, $C_{1-6}$ aminoalkyl, carbamoyl, $C_{1-6}$ carbamoylalkyl, $C_{1-6}$ carboxyalkyl, cyano, $C_{1-6}$ cyanoalkyl, $C_{3-7}$ cycloalkyl, halo, $C_{1-6}$ haloalkoxy, $C_{1-6}$ haloalkyl, 5- to 10-membered heteroaryl, 4- to 10-membered heterocyclyl, hydroxy, and oxo;

or $R^1$ and $R^3$, together with the carbon to which they are bonded, may form an optionally substituted 3- to 6-membered cycloalkyl;

or $R^3$ and $R^4$, $R^3$ and $R^8$, $R^5$ and $R^6$, or $R^5$ and $R^8$, together with the atoms to which they are each bonded, may form a 3- to 6-membered cycloalkyl or a 3- to 6-membered heterocyclyl;

L is a bond, O, S, or $N(L^a)$;

$R^{10a}$ is selected from the group consisting of hydrogen, alkyl, hydroxyalkyl, dihydroxyalkyl, alkylaminylalkyl, dialkylaminylalkyl, $-L^b-NL^aL^c$, heterocyclyl, heterocyclylalkyl, aryl, heteroaryl, or heteroarylalkyl, wherein each of the $L^b$, heterocyclyl, heterocyclylalkyl, aryl, heteroaryl, and heteroarylalkyl may be optionally substituted with one or more $L^d$;

each $L^a$ is independently hydrogen or $C_{1-3}$ alkyl;

$L^b$ is $C_{1-4}$ alkylene;

each $L^c$ is independently hydrogen, acyl, $C_{1-3}$ alkyl, heteroalkyl, or hydroxyalkyl;

each $L^d$ is independently hydrogen, oxo, acyl, hydroxy, hydroxyalkyl, cyano, halogen, $C_{3-6}$ alkyl, aralkyl, haloalkyl, heteroalkyl, cycloalkyl, heterocyclylalkyl, alkoxy, dialkylaminyl, dialkylamidoalkyl, or dialkylaminylalkyl, wherein the $C_{1-6}$alkyl may be optionally substituted with cycloalkyl;

X is selected from the group consisting of $C_{1-6}$ alkoxy, $C_{1-6}$ alkyl, amino, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of $C_{1-6}$ alkyl, amino, $C_{1-6}$ aminoalkyl, carbamoyl, $C_{1-6}$ carbamoylalkyl, carboxy, $C_{1-6}$ carboxyalkyl, cyano, $C_{1-6}$ cyanoalkyl, halo, $C_{1-6}$ haloalkyl, hydroxy, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

n is selected from 0, 1, and 2; and

------ represents a single bond or a double bond.

Embodiment 2: The compound of Embodiment 1 having a Formula (II):

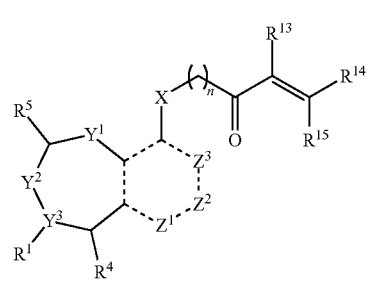

(II)

or a pharmaceutically acceptable salt thereof; wherein:

$R^1$ is selected from the group consisting of H, $C_{6-10}$ aryl, 5- to 10-membered heteroaryl, and 5- to 10-membered heterocyclyl, wherein each aryl, heteroaryl, and heterocyclyl is optionally substituted with one to four substituents, wherein each substituent is independently selected from the group consisting of $C_{1-6}$ alkyl, —$NH_2$, —$NH(CH_3)$, —$N(CH_3)_2$, halo, $C_{1-6}$ haloalkyl, oxo, $C_{1-6}$ hydroxyalkyl, $C_{3-6}$ cycloalkyl, —OC(=O)CH=$CH_2$, and hydroxy;

$Y^1$ is $C(H)(R^6)$; or $Y^1$ is absent;

$Y^2$ is selected from the group consisting of $N(R^7)$ and $C(H)(R^8)$;

$Y^3$ is selected from the group consisting of $C(R^3)$ and N;

$Z^1$ is selected from the group consisting of N, $N(R^9)$, O, S, S(O), and $S(O)_2$;

$Z^2$ is $C(R^{10})$, $C(-L-R^{10a})$, or $Z^2$ is absent;

$Z^3$ is selected from the group consisting of N, $N(R'')$, and $C(R^{12})$;

$R^3$, $R^4$, $R^5$, $R^6$, $R^7$, $R^8$, $R^9$, $R^{10}$, $R^{11}$, and $R^{12}$ are each independently selected from the group consisting of H, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{2-6}$ alkynyl, $C_{1-6}$ alkylamino, amino, aryl, aryl substituted with a $C_{1-6}$ alkyl, $C_{1-6}$ aminoalkyl, carbamoyl, $C_{1-6}$ carbamoylalkyl, $C_{1-6}$ carboxyalkyl, cyano, $C_{1-6}$ cyanoalkyl, $C_{3-7}$ cycloalkyl, halo, $C_{1-6}$ haloalkoxy, $C_{1-6}$ haloalkyl, 5- to 10-membered heteroaryl, 4- to 10-membered heterocyclyl, hydroxy, and oxo;

or $R^1$ and $R^3$, together with the carbon to which they are bonded, may form an optionally substituted 3- to 6-membered cycloalkyl;

or $R^3$ and $R^4$, $R^3$ and $R^8$, $R^5$ and $R^6$, or $R^5$ and $R^8$, together with the atoms to which they are each bonded, may form a 3- to 6-membered cycloalkyl or a 3- to 6-membered heterocyclyl;

$R^{13}$ is selected from the group consisting of H, cyano, and halo; and $R^{14}$ and $R^{15}$ are each independently selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{3-6}$ cycloalkylamino, $C_{1-6}$ alkylsulfonylamino, $C_{6-12}$ dialkylamino, and $C_{1-6}$ haloalkoxy;

or $R^{13}$ and $R^{14}$ together form a triple bond between the carbons to which they are attached, or $R^{13}$ and $R^{14}$ together with the carbons to which they are each bonded form a $C_{3-7}$ cycloalkenyl optionally substituted with one or two halo substituents; and $R^{15}$ is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;

L is a bond, O, S, or $N(L^a)$;

$R^{10a}$ is selected from the group consisting of hydrogen, alkyl, hydroxyalkyl, dihydroxyalkyl, alkylaminylalkyl, dialkylaminylalkyl, $-L^b-NL^aL^c$, heterocyclyl, heterocyclylalkyl, aryl, heteroaryl, or heteroarylalkyl, wherein each of the $L^b$, heterocyclyl, heterocyclylalkyl, aryl, heteroaryl, and heteroarylalkyl may be optionally substituted with one or more $L^d$;

each $L^a$ is independently hydrogen or $C_{1-3}$ alkyl;

$L^b$ is $C_{1-4}$ alkylene;

each $L^c$ is independently hydrogen, acyl, $C_{1-3}$ alkyl, heteroalkyl, or hydroxyalkyl;

each $L^d$ is independently hydrogen, oxo, acyl, hydroxy, hydroxyalkyl, cyano, halogen, $C_{1-6}$ alkyl, aralkyl, haloalkyl, heteroalkyl, cycloalkyl, heterocyclylalkyl, alkoxy, dialkylaminyl, dialkylamidoalkyl, or dialkylaminylalkyl, wherein the $C_{1-6}$alkyl may be optionally substituted with cycloalkyl;

X is selected from the group consisting of $C_{1-6}$ alkoxy, $C_{1-6}$ alkyl, amino, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of $C_{1-6}$ alkyl, amino, $C_{1-6}$ aminoalkyl, carbamoyl, $C_{1-6}$ carbamoylalkyl, carboxy, $C_{1-6}$ carboxyalkyl, cyano, $C_{1-6}$ cyanoalkyl, halo, $C_{1-6}$ haloalkyl, hydroxy, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

n is selected from 0, 1, and 2; and

------ represents a single bond or a double bond.

Embodiment 3: The compound of Embodiment 1 having a Formula (III):

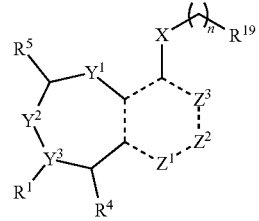

(III)

or a pharmaceutically acceptable salt thereof; wherein;

$R^1$ is selected from the group consisting of H, $C_{6-10}$ aryl, 5- to 10-membered heteroaryl, and 5- to 10-membered heterocyclyl, wherein each aryl, heteroaryl, and heterocyclyl is optionally substituted with one to four substituents, wherein each substituent is independently selected from the group consisting of $C_{1-6}$ alkyl, $-NH_2$, $-NH(CH_3)$, $-N(CH_3)_2$, halo, $C_{1-6}$ haloalkyl, oxo, $C_{1-6}$ hydroxyalkyl, $C_{3-6}$ cycloalkyl, $-OC(=O)CH=CH_2$, and hydroxy;

$Y^1$ is $C(H)(R^6)$; or $Y^1$ is absent;

$Y^2$ is selected from the group consisting of $N(R^7)$ and $C(H)(R^8)$;

$Y^3$ is selected from the group consisting of $C(R^3)$ and N;

$Z^1$ is selected from the group consisting of N, $N(R^9)$, O, S, S(O), and $S(O)_2$;

$Z^2$ is $C(R^{10})$, $C(-L-R^{10a})$, or $Z^2$ is absent;

$Z^3$ is selected from the group consisting of N, $N(R'')$, and $C(R^{12})$;

$R^3$, $R^4$, $R^5$, $R^6$, $R^7$, $R^8$, $R^9$, $R^{10}$, $R^{11}$, and $R^{12}$ are each independently selected from the group consisting of H, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{2-6}$ alkynyl, $C_{1-6}$ alkylamino, amino, aryl, aryl substituted with a $C_{1-6}$ alkyl, $C_{1-6}$ aminoalkyl, carbamoyl, $C_{1-6}$ carbamoylalkyl, $C_{1-6}$ carboxyalkyl, cyano, $C_{1-6}$ cyanoalkyl, $C_{3-7}$ cycloalkyl, halo, $C_{1-6}$ haloalkoxy, $C_{1-6}$ haloalkyl, 5- to 10-membered heteroaryl, 4- to 10-membered heterocyclyl, hydroxy, and oxo;

or $R^1$ and $R^3$, together with the carbon to which they are bonded, may form an optionally substituted 3- to 6-membered cycloalkyl;

or $R^3$ and $R^4$, $R^3$ and $R^8$, $R^5$ and $R^6$, or $R^5$ and $R^8$, together with the atoms to which they are each bonded, may form a 3- to 6-membered cycloalkyl or a 3- to 6-membered heterocyclyl;

$R^{19}$ is selected from the group consisting of oxiranyl, aziridinyl, and cyclopropyl, wherein the cyclopropyl is optionally substituted with at least one halogen;

L is a bond, O, S, or $N(L^a)$;

$R^{10a}$ is selected from the group consisting of hydrogen, alkyl, hydroxyalkyl, dihydroxyalkyl, alkylaminylalkyl, dialkylaminylalkyl, $-L^b-NL^aL^c$, heterocyclyl, heterocyclylalkyl, aryl, heteroaryl, or heteroarylalkyl, wherein each of the $L^b$, heterocyclyl, heterocyclylalkyl, aryl, heteroaryl, and heteroarylalkyl may be optionally substituted with one or more $L^d$;

each $L^a$ is independently hydrogen or $C_{1-3}$ alkyl;

$L^b$ is $C_{1-4}$ alkylene;

each $L^c$ is independently hydrogen, acyl, $C_{1-3}$ alkyl, heteroalkyl, or hydroxyalkyl;

each $L^d$ is independently hydrogen, oxo, acyl, hydroxy, hydroxyalkyl, cyano, halogen, $C_{1-6}$ alkyl, aralkyl, haloalkyl, heteroalkyl, cycloalkyl, heterocyclylalkyl, alkoxy, dialkylaminyl, dialkylamidoalkyl, or dialkylaminylalkyl, wherein the $C_{1-6}$alkyl may be optionally substituted with cycloalkyl;

X is selected from the group consisting of $C_{1-6}$ alkoxy, $C_{1-6}$ alkyl, amino, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of $C_{1-6}$ alkyl, amino, $C_{1-6}$ aminoalkyl, carbamoyl, $C_{1-6}$ carbamoylalkyl, carboxy, $C_{1-6}$ carboxyalkyl, cyano, $C_{1-6}$ cyanoalkyl, halo, $C_{1-6}$ haloalkyl, hydroxy, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

n is selected from 0, 1, and 2; and

------ represents a single bond or a double bond.

Embodiment 4: The compound of any one of Embodiments 1-3, or a pharmaceutically acceptable salt thereof, wherein $R^1$ is $C_{6-10}$ aryl optionally substituted with one to four substituents, wherein each substituent is independently selected from the group consisting of $C_{1-6}$ alkyl, —$NH_2$, halo, $C_{1-6}$ haloalkyl, oxo, $C_{1-6}$ hydroxyalkyl, —OC(=O)CH=$CH_2$, and hydroxy.

Embodiment 5: The compound of Embodiment 4, or a pharmaceutically acceptable salt thereof, wherein $R^1$ is selected from the group consisting of

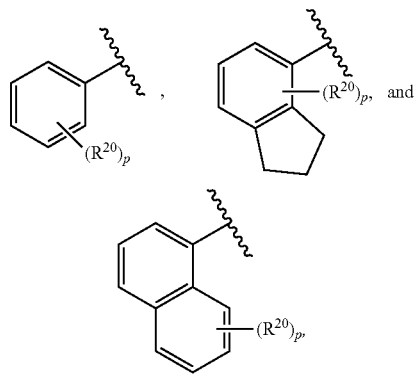

wherein each $R^{20}$ is independently selected from the group consisting of $C_{1-6}$ alkyl, —$NH_2$, —$NH(CH_3)$, —$N(CH_3)_2$, halo, $C_{1-6}$ haloalkyl, $C_{1-6}$ hydroxyalkyl, —OC(=O)CH=$CH_2$, and hydroxy, and p is 0, 1, 2, 3, or 4.

Embodiment 6: The compound of Embodiment 5, or a pharmaceutically acceptable salt thereof, wherein $R^1$ is selected from the group consisting of

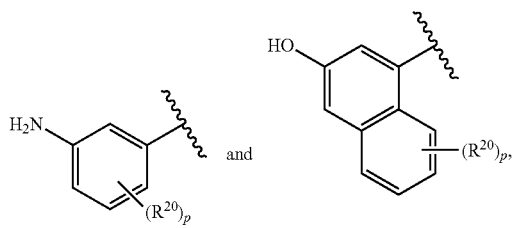

wherein each $R^{20}$ is independently selected from the group consisting of $C_{1-6}$ alkyl, —$NH_2$, —$NH(CH_3)$, —$N(CH_3)_2$, halo, $C_{1-6}$ haloalkyl, $C_{1-6}$ hydroxyalkyl, —OC(=O)CH=$CH_2$, and hydroxy, and p is 0, 1, 2, 3, or 4.

Embodiment 7: The compound of Embodiment 5, or a pharmaceutically acceptable salt thereof, wherein $R^1$ is selected from the group consisting of

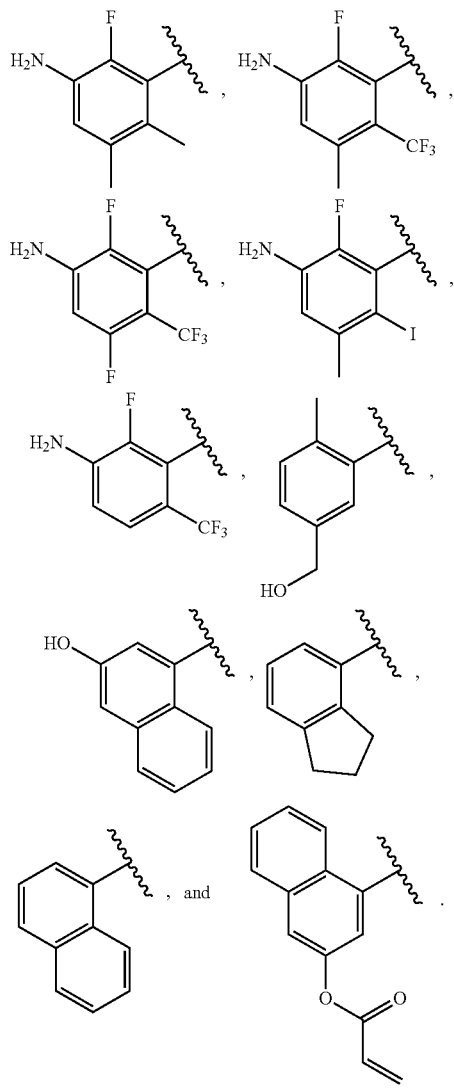

Embodiment 8: The compound of Embodiment 7, or a pharmaceutically acceptable salt thereof, wherein $R^1$ is selected from the group consisting of

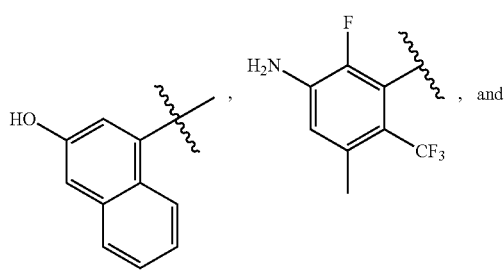

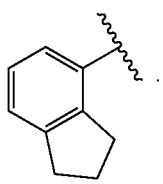

Embodiment 9: The compound of Embodiment 8, or a pharmaceutically acceptable salt thereof, wherein $R^1$ is:

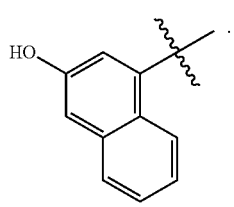

Embodiment 10: The compound of any one of Embodiments 1-3, or a pharmaceutically acceptable salt thereof, wherein $R^1$ is 5- to 10-membered heteroaryl optionally substituted with one to four substituents, wherein each substituent is independently selected from the group consisting of $C_{1-6}$ alkyl, —$NH_2$, —$NH(CH_3)$, —$N(CH_3)_2$, $C_{1-6}$ haloalkyl, $C_{3-6}$ cycloalkyl, and halo.

Embodiment 11: The compound of Embodiment 10, or a pharmaceutically acceptable salt thereof, wherein $R^1$ is selected from the group consisting of

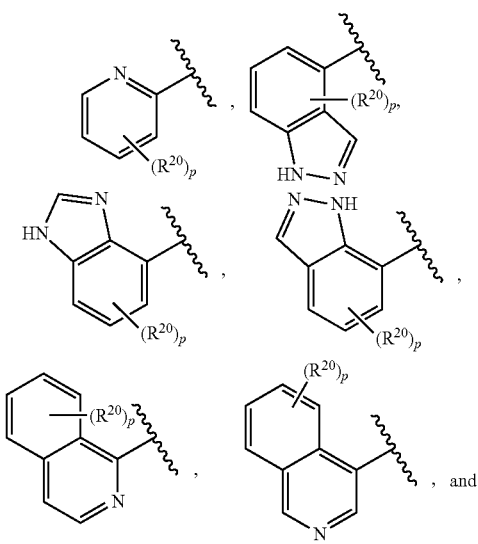

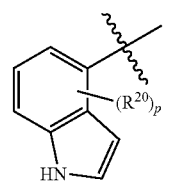

wherein each $R^{20}$ is independently selected from the group consisting of $C_{1-6}$ alkyl, —$NH_2$, —$NH(CH_3)$, —$N(CH_3)_2$, halo, $C_{1-6}$ haloalkyl, and $C_{3-6}$ cycloalkyl, and each p is independently 0, 1, 2, 3, or 4.

Embodiment 12: The compound of Embodiment 11, or a pharmaceutically acceptable salt thereof, wherein $R^1$ is selected from the group consisting of

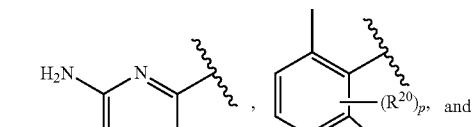

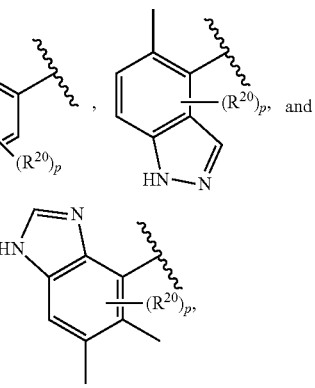

wherein each $R^{20}$ is independently selected from the group consisting of $C_{1-6}$ alkyl, —$NH_2$, —$NH(CH_3)$, —$N(CH_3)_2$, halo, $C_{1-6}$ haloalkyl, and $C_{3-6}$ cycloalkyl, and each p is independently 0, 1, 2, 3, or 4.

Embodiment 13: The compound of Embodiment 11, or a pharmaceutically acceptable salt thereof, wherein $R^1$ is selected from the group consisting of:

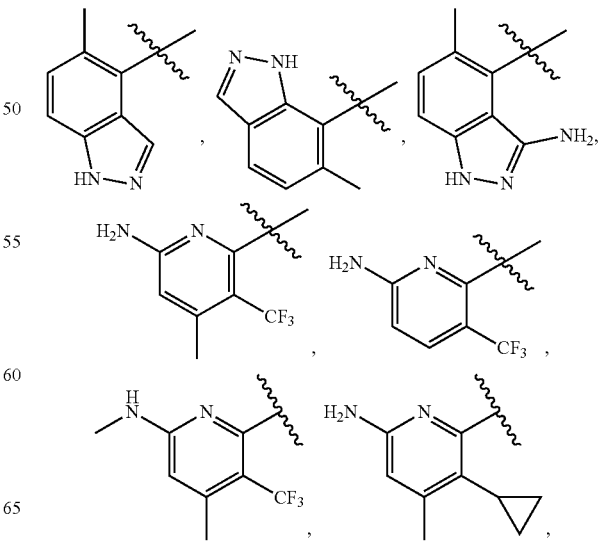

-continued

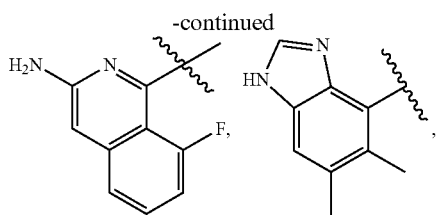

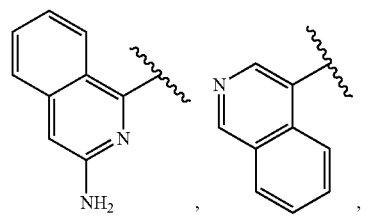

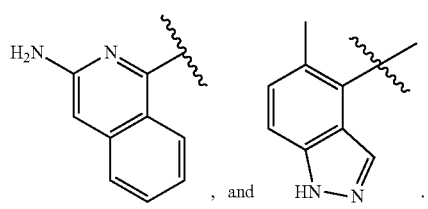

Embodiment 14: The compound of Embodiment 13, or a pharmaceutically acceptable salt thereof, wherein $R^1$ is selected from the group consisting of:

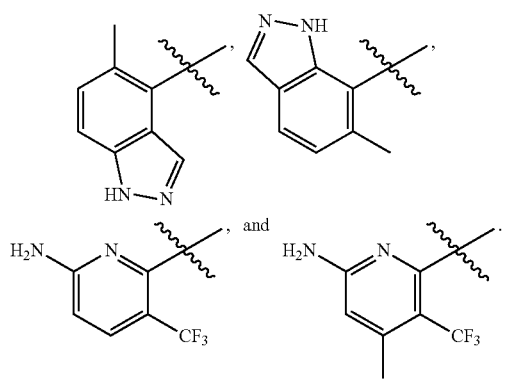

Embodiment 15: The compound of any one of Embodiments 1-3, or a pharmaceutically acceptable salt thereof, wherein $R^1$ is hydrogen.

Embodiment 16: The compound of any one of Embodiments 1-3, or a pharmaceutically acceptable salt thereof, wherein $R^1$ is 5- to 10-membered heterocyclyl optionally substituted with one to four substituents, wherein each substituent is independently selected from the group consisting of $C_{1-6}$ alkyl and oxo.

Embodiment 17: The compound of Embodiment 16, or a pharmaceutically acceptable salt thereof, wherein $R^1$ is selected from the group consisting of:

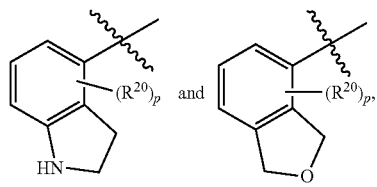

wherein each $R^{20}$ is independently $C_{1-6}$ alkyl; and each p is independently 0, 1, 2, 3, or 4.

Embodiment 18: The compound of Embodiment 17, or a pharmaceutically acceptable salt thereof, wherein $R^1$ has the following structure:

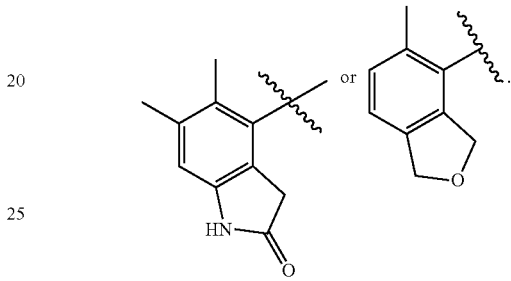

Embodiment 19: The compound of any one of Embodiments 1-3, or a pharmaceutically acceptable salt thereof, wherein $R^1$ and $R^3$, together with the carbon to which they are bonded, may form an optionally substituted 3- to 6-membered cycloalkyl.

Embodiment 20: The compound of any one of Embodiments 1-3, or a pharmaceutically acceptable salt thereof, wherein $Z^1$ is N; $Z^2$ is $C(R^{10})$ or $C(-L-R^{10a})$; and $Z^3$ is N.

Embodiment 21: The compound of Embodiment 20, or a pharmaceutically acceptable salt thereof, wherein $Z^2$ is $C(R^{10})$, and $R^{10}$ is H.

Embodiment 22: The compound of Embodiment 20, or a pharmaceutically acceptable salt thereof, wherein $Z^2$ is $C(-L-R^{10a})$.

Embodiment 23: The compound of Embodiment 22, or a pharmaceutically acceptable salt thereof, wherein L is O.

Embodiment 24: The compound of Embodiment 22 or Embodiment 23, or a pharmaceutically acceptable salt thereof, wherein $R^{10a}$ is selected from the group consisting of heterocyclylalkyl and heteroarylalkyl, wherein each heterocyclylalkyl and heteroarylalkyl are optionally substituted with one or more $L^d$.

Embodiment 24: The compound of Embodiment 24, or a pharmaceutically acceptable salt thereof, wherein each $L^d$ is independently selected from the group consisting of hydrogen, oxo, halogen, and $C_{1-6}$ alkyl.

Embodiment 25: The compound of Embodiment 22, or a pharmaceutically acceptable salt thereof, wherein $-L-R^{10a}$ is selected from the group consisting of

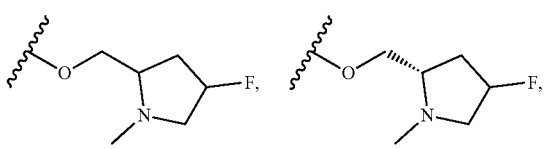

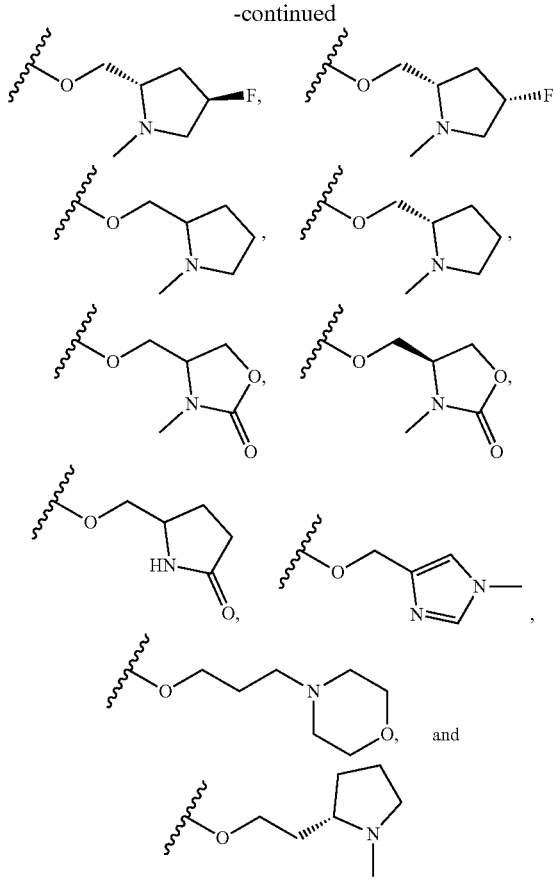

Embodiment 27: The compound of any one of Embodiments 1-3, or a pharmaceutically acceptable salt thereof, wherein $Z^1$ is $N(R^9)$; $Z^2$ is $C(R^{10})$; and $Z^3$ is N.

Embodiment 28: The compound of Embodiment 27, or a pharmaceutically acceptable salt thereof, wherein $R^9$ is aryl substituted with a $C_{1-6}$ alkyl.

Embodiment 29: The compound of Embodiment 28, or a pharmaceutically acceptable salt thereof, wherein $R^9$ is phenyl substituted with isopropyl.

Embodiment 30: The compound of Embodiment 29, or a pharmaceutically acceptable salt thereof, wherein $R^9$ is

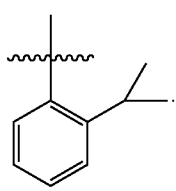 [SMILES: *c1ccccc1C(C)C]

Embodiment 31: The compound of any one of Embodiments 27-30, wherein $R^{10}$ is oxo.

Embodiment 32: The compound of any one of Embodiments 1-3, or a pharmaceutically acceptable salt thereof, where $Y^1$ is absent; $Y^3$ is $C(H)(R^8)$; and $Y^3$ is $C(R^3)$.

Embodiment 33: The compound of Embodiment 32, or a pharmaceutically acceptable salt thereof, wherein $R^8$ is selected from the group consisting of H and $C_1$-$C_6$ alkyl.

Embodiment 34: The compound of Embodiment 33, or a pharmaceutically acceptable salt thereof, wherein $R^8$ is selected from the group consisting of H, methyl, ethyl, and isopropyl.

Embodiment 35: The compound of any one of Embodiments 1-3, or a pharmaceutically acceptable salt thereof, where $Y^1$ is absent; $Y^2$ is $C(H)(R^8)$; and $Y^3$ is N.

Embodiment 36: The compound of Embodiment 35, or a pharmaceutically acceptable salt thereof, wherein $R^8$ is H.

Embodiment 37: The compound of any one of Embodiments 1-3, or a pharmaceutically acceptable salt thereof, wherein $R^3$, $R^4$, $R^5$, $R^6$, $R^7$, $R^8$, $R^9$, $R^{10}$, $R^{11}$, and $R^{12}$ are each independently selected from the group consisting of H, halo, $C_{3-7}$ cycloalkyl, $C_{1-6}$ alkyl, aryl substituted with $C_{1-6}$ alkyl, and oxo.

Embodiment 38: The compound of Embodiment 37, or a pharmaceutically acceptable salt thereof, wherein $R^3$, $R^4$, $R^5$, $R^6$, $R^7$, $R^8$, $R^9$, $R^{10}$, $R^{11}$, and $R^{12}$ are each independently selected from the group consisting of H, $C_{1-6}$ alkyl, aryl substituted with $C_3$ alkyl, and oxo.

Embodiment 39: The compound of Embodiment 37, or a pharmaceutically acceptable salt thereof, wherein $R^3$, $R^4$, $R^5$, $R^6$, $R^7$, $R^8$, $R^9$, $R^{10}$, $R^{11}$, and $R^{12}$ are each independently selected from the group consisting of H, methyl, ethyl, isopropyl, phenyl substituted with isopropyl, and oxo.

Embodiment 40: The compound of any one of Embodiments 1-3, or a pharmaceutically acceptable salt thereof, wherein X is a 4- to 7-membered heterocyclyl, which is optionally substituted with 1 to 4 substituents, wherein each substituent is independently selected from the group consisting of $C_{1-6}$ alkyl, cyano, $C_{1-6}$ cyanoalkyl, and $C_{1-6}$ hydroxyalkyl; wherein two geminal substituents may be taken together to form a 4- to 7-membered spiroheterocyclyl.

Embodiment 41: The compound of Embodiment 40, or a pharmaceutically acceptable salt thereof, wherein X is selected from the group consisting of:

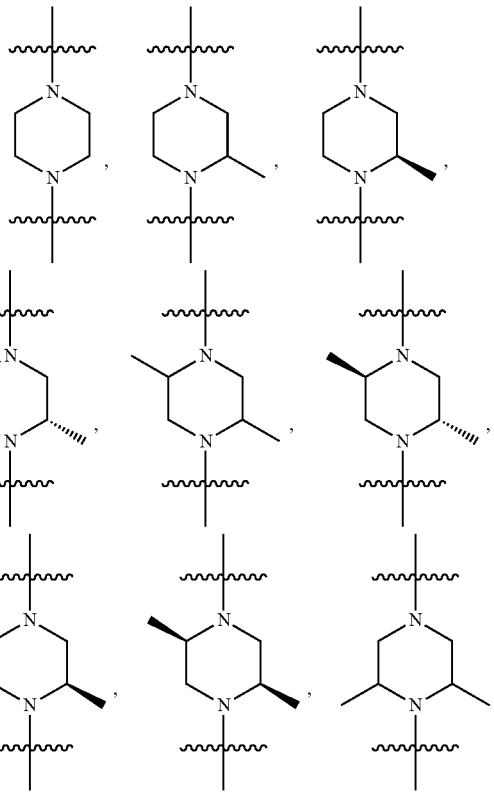

-continued

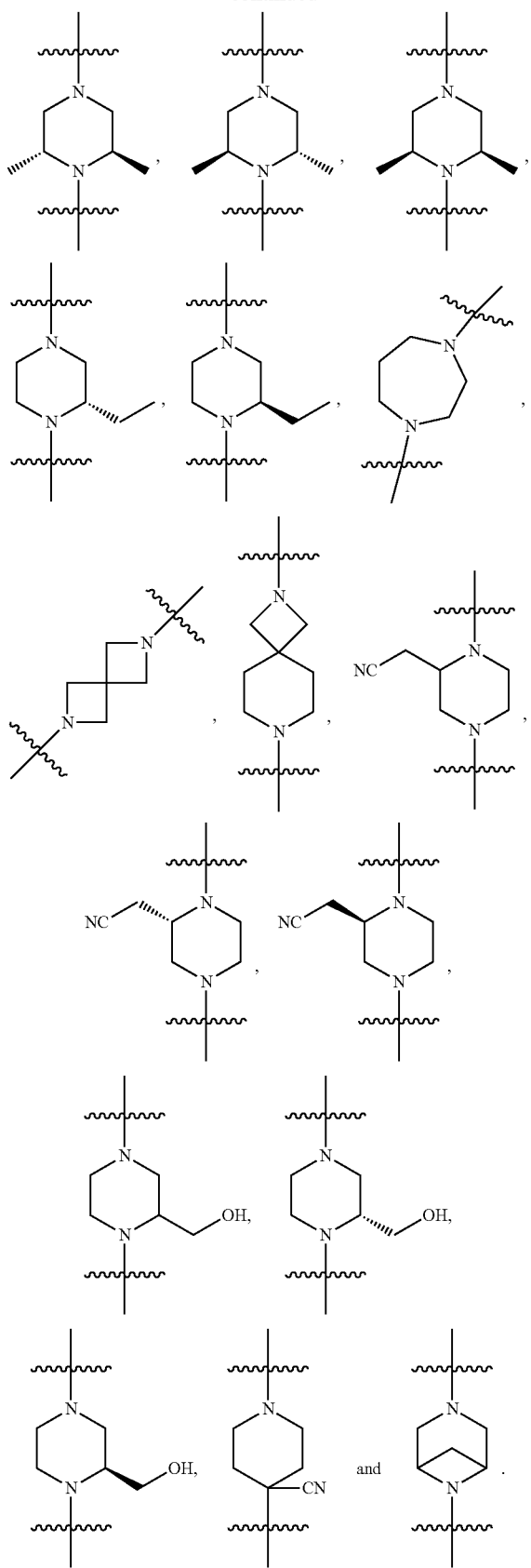

Embodiment 42: The compound of Embodiment 41, or a pharmaceutically acceptable salt thereof, wherein X is

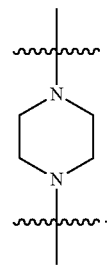

Embodiment 43: The compound of any one of Embodiments 1-3, or a pharmaceutically acceptable salt thereof, wherein n is 0.

Embodiment 44: The compound of Embodiment 1, or a pharmaceutically acceptable salt thereof, wherein $R^2$ is selected from the group consisting of:

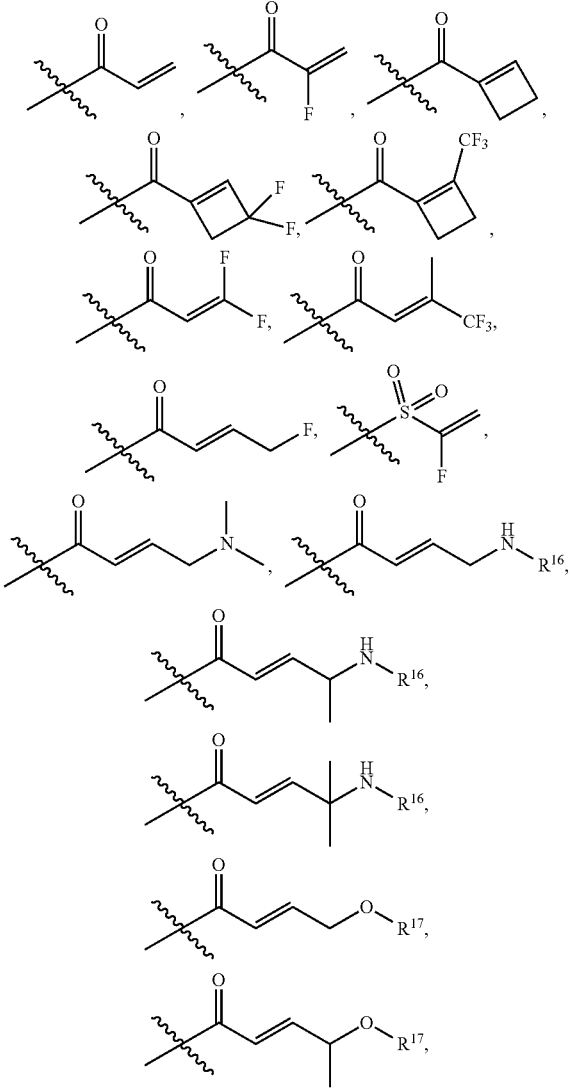

-continued

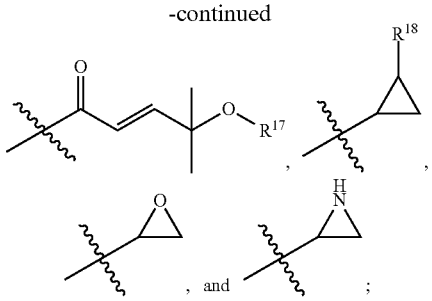

wherein:

$R^{16}$ is selected from the group consisting of $C_{1-6}$ alkanoyl, $C_{1-6}$ alkyl, $C_{1-6}$ alkylsulfonyl, and $C_{3-6}$ cycloalkyl;

$R^{17}$ is selected from the group consisting of $C_{1-6}$ alkyl and $C_{1-6}$ haloalkyl; and $R^{18}$ is halo.

Embodiment 45: The compound of Embodiment 1, or a pharmaceutically acceptable salt thereof, wherein $R^2$ is selected from the group consisting of:

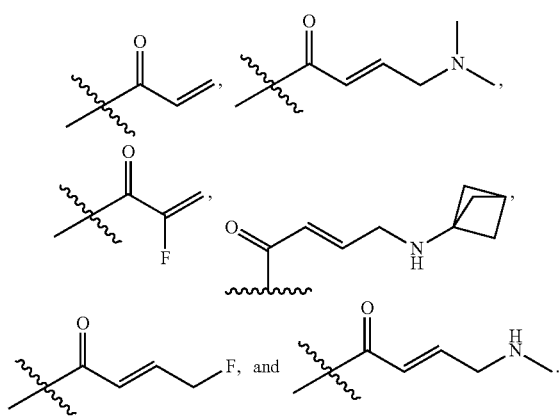

Embodiment 46: The compound of Embodiment 1, or a pharmaceutically acceptable salt thereof, wherein $R^2$ is

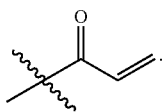

Embodiment 47: The compound of Embodiment 2, or a pharmaceutically acceptable salt thereof, wherein $R^{13}$ is selected from the group consisting of H, cyano, and halo; and $R^{14}$ and $R^{15}$ are each independently selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{1-6}$ alkylsulfonylamino, $C_{6-12}$ dialkylamino, $C_{3-6}$ cycloalkylamino, and $C_{1-6}$ haloalkoxy.

Embodiment 48: The compound of Embodiment 2, or a pharmaceutically acceptable salt thereof, wherein $R^{13}$ and $R^{14}$ together form a triple bond between the carbons to which they are attached, or $R^{13}$ and $R^{14}$ together with the carbons to which they are each bonded form a $C_{3-7}$ cycloalkenyl optionally substituted with one or two halo substituents;

and $R^{15}$ is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy.

Embodiment 49: The compound of Embodiment 2, or a pharmaceutically acceptable salt thereof, wherein $R^{13}$, $R^{14}$, and $R^{15}$ are each H.

Embodiment 50: The compound of Embodiment 2, or a pharmaceutically acceptable salt thereof, wherein $R^{13}$ is F, and $R^{14}$ and $R^{15}$ are each H.

Embodiment 51: The compound of Embodiment 2, or a pharmaceutically acceptable salt thereof, wherein $R^{13}$ is H; one of $R^{14}$ and $R^{15}$ is H; and the other of $R^{14}$ and $R^{15}$ is selected from the group consisting of $C_{1-6}$ alkyl and $C_{1-6}$ haloalkyl, wherein the $C_{1-6}$ alkyl is optionally substituted with one substituent selected from the group consisting of: $C_{1-6}$ alkylamino and $C_{3-6}$ cycloalkylamino.

Embodiment 52: The compound of any one of Embodiments 1-3, or a pharmaceutically acceptable salt thereof, wherein $Z^1$ is N; $Z^2$ is $C(R^{10})$ or $C(\text{-L-}R^{10a})$; $Z^3$ is N; $Y^1$ is absent; $Y^2$ is $C(H)(R^8)$; $Y^3$ is $C(R^3)$; X is an optionally substituted 4- to 7-membered heterocyclyl; and n is 0.

Embodiment 53: The compound of Embodiment 52, or a pharmaceutically acceptable salt thereof, wherein $R^3$, $R^4$, $R^5$, $R^8$, and $R^{10}$ are independently selected from the group consisting of hydrogen, halo, $C_{3-7}$ cycloalkyl, and $C_{1-6}$ alkyl.

Embodiment 54: The compound of any one of Embodiments 1-3, or a pharmaceutically acceptable salt thereof, wherein $Z^1$ is $N(R^9)$; $Z^2$ is $C(R^{10})$; $Z^3$ is N; $Y^1$ is absent; $Y^2$ is $C(H)(R^8)$; $Y^3$ is $C(R^3)$; X is a 4- to 7-membered heterocyclyl; and n is 0.

Embodiment 55: The compound of Embodiment 54, or a pharmaceutically acceptable salt thereof, wherein $R^3$, $R^4$, $R^5$, $R^8$, $R^9$, and $R^{10}$ are independently selected from the group consisting of hydrogen, halo, $C_{3-7}$ cycloalkyl, $C_{1-6}$ alkyl, aryl substituted with $C_{1-6}$ alkyl, and oxo.

Embodiment 56: The compound of any one of Embodiments 1-3, or a pharmaceutically acceptable salt thereof, wherein $Z^1$ is $N(R^9)$; $Z^2$ is $C(R^{10})$; $Z^3$ is N; $Y^1$ is absent; $Y^2$ is $C(H)(R^8)$; $Y^3$ is N; X is a 4- to 7-membered heterocyclyl; and n is 0.

Embodiment 57: The compound of Embodiment 56, or a pharmaceutically acceptable salt thereof, wherein $R^4$, $R^5$, $R^8$, $R^9$, and $R^{10}$ are independently selected from the group consisting of hydrogen, halo, $C_{3-7}$ cycloalkyl, $C_{1-6}$ alkyl, aryl substituted with $C_{1-6}$ alkyl, and oxo.

Embodiment 58: The compound of Embodiment 1 or Embodiment 2, or a pharmaceutically acceptable salt thereof, having a Formula (IIa):

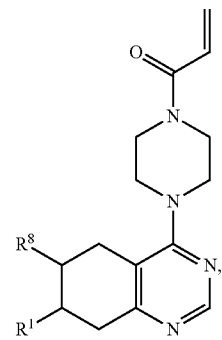

or a pharmaceutically acceptable salt thereof.

Embodiment 59: The compound of Embodiment 58, or a pharmaceutically acceptable salt thereof, wherein $R^8$ is selected from the group consisting of H and $C_{1-6}$ alkyl.

Embodiment 60: The compound of Embodiment 59, or a pharmaceutically acceptable salt thereof, wherein $R^8$ is selected from the group consisting of H, methyl, and isopropyl.

Embodiment 61: The compound of Embodiment 58, or a pharmaceutically acceptable salt thereof, having a formula selected from the group consisting of:

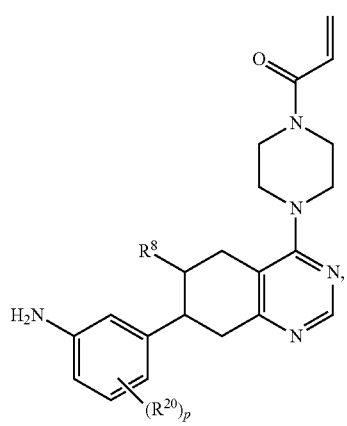
(IIa-1)

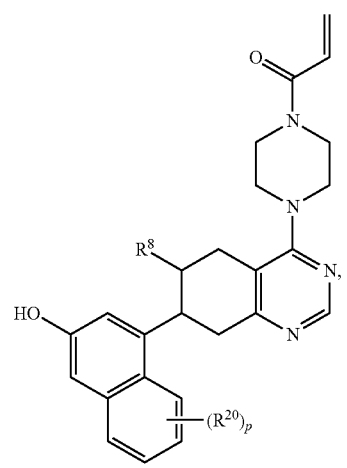
(IIa-2)

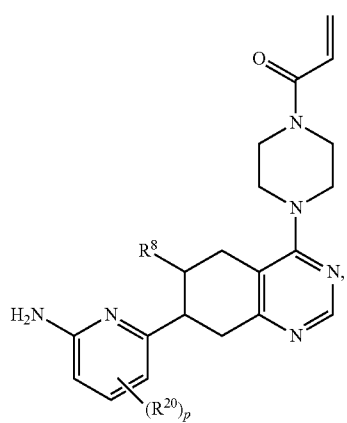
(IIa-3)

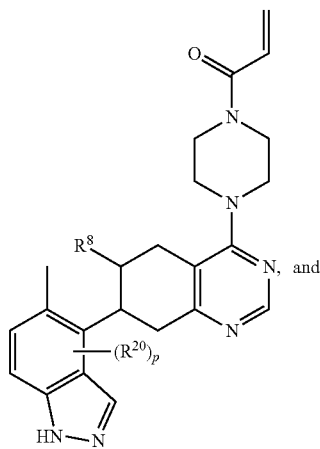
(IIa-4)

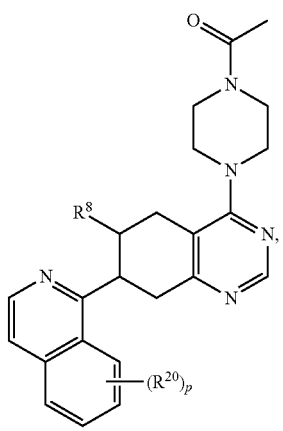
(IIa-5)

or a pharmaceutically acceptable salt thereof, wherein each $R^{20}$ is independently selected from the group consisting of $C_{1-6}$ alkyl, $NH_2$, $NH(CH_3)$, $N(CH_3)_2$, halo, $C_{1-6}$ haloalkyl, hydroxy, $C_{3-6}$ cycloalkyl, $C_{1-6}$ hydroxyalkyl, and —OC(=O)CH=$CH_2$; and each p is independently 0, 1, 2, 3, or 4.

Embodiment 62: The compound of Embodiment 58, or a pharmaceutically acceptable salt thereof, having a formula selected from the group consisting of:

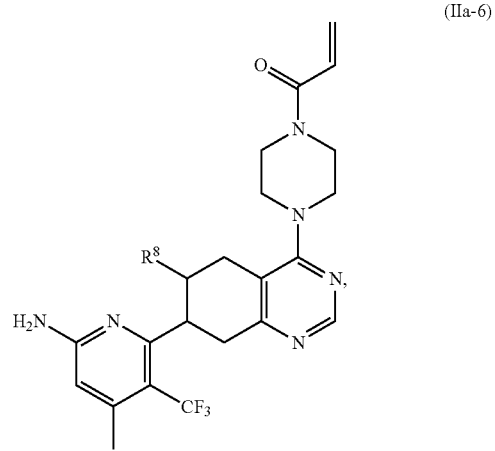
(IIa-6)

(IIa-7)
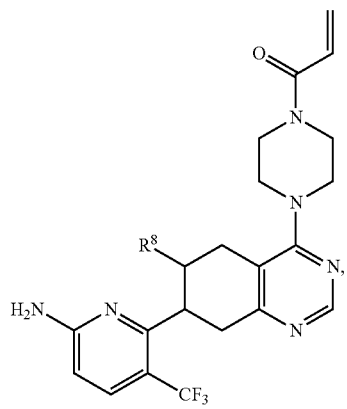

(IIa-8)
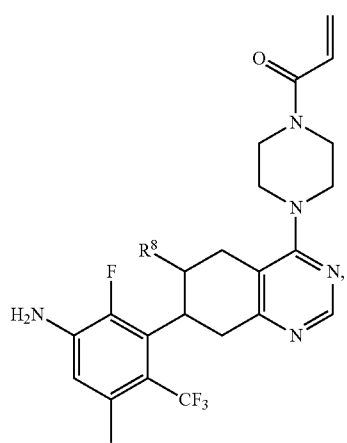

(IIa-9)
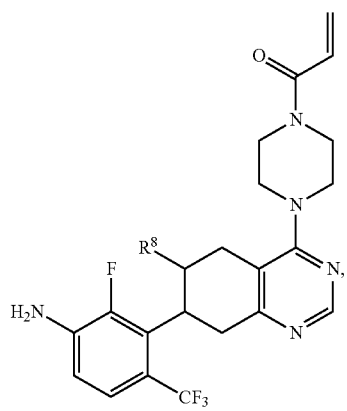

(IIa-10)
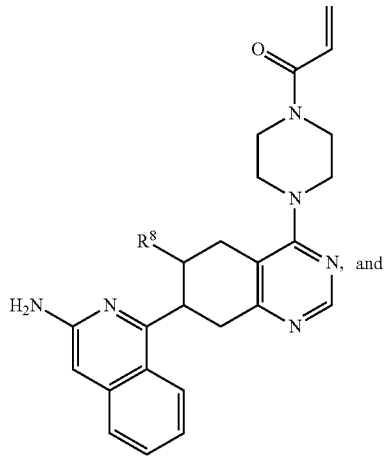
and (IIa-11)
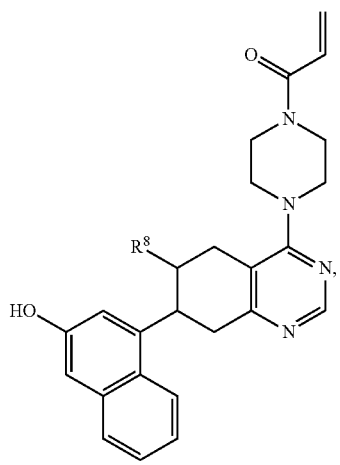

or a pharmaceutically acceptable salt thereof.

Embodiment 63: The compound of Embodiment 1 or Embodiment 2, or a pharmaceutically acceptable salt thereof, having a Formula (III):

(III)
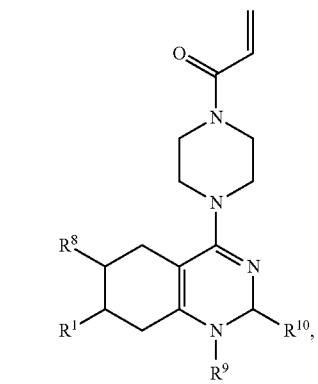

or a pharmaceutically acceptable salt thereof.

Embodiment 64: The compound of Embodiment 63, or a pharmaceutically acceptable salt thereof, wherein $R^8$ is hydrogen; $R^9$ is aryl substituted with $C_{1-6}$ alkyl; and $R^{10}$ is oxo.

Embodiment 65: The compound of Embodiment 63, or a pharmaceutically acceptable salt thereof, having a formula selected from the group consisting of:

(III-1)
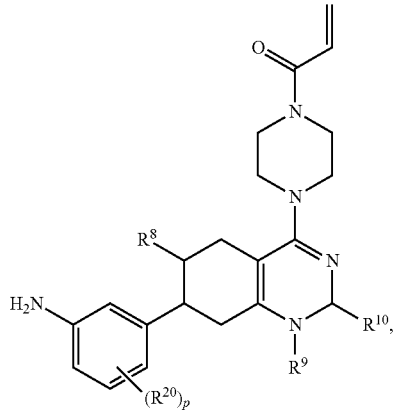

(III-2)
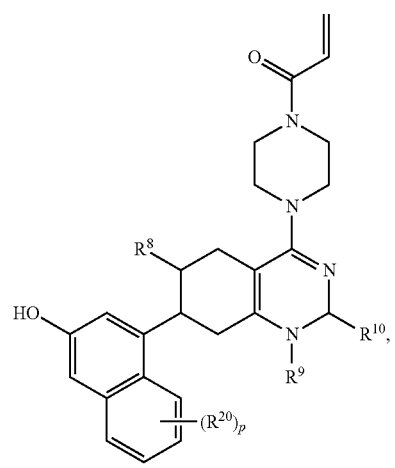

(III-3)
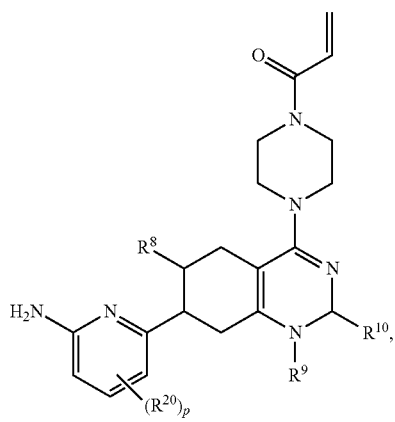

(III-4)
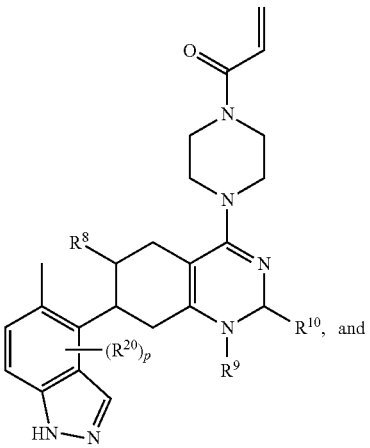

(III-5)
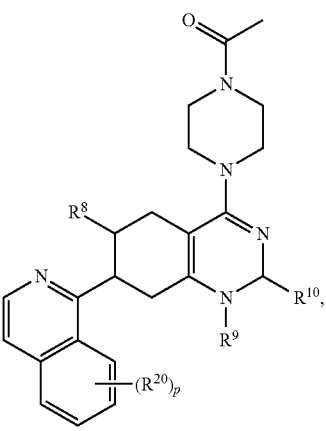

a pharmaceutically acceptable salt thereof, wherein $R^{20}$ is selected from the group consisting of $C_{1-6}$ alkyl, $NH_2$, $NH(CH_3)$, $N(CH_3)_2$, halo, $C_{1-6}$ haloalkyl, hydroxy, $C_{3-6}$ cycloalkyl, $C_{1-6}$ hydroxyalkyl, and $-OC(=O)CH=CH_2$; and p is 0, 1, 2, 3, or 4.

Embodiment 66: The compound of Embodiment 63, or a pharmaceutically acceptable salt thereof, having a formula selected from the group consisting of:

(III-6)
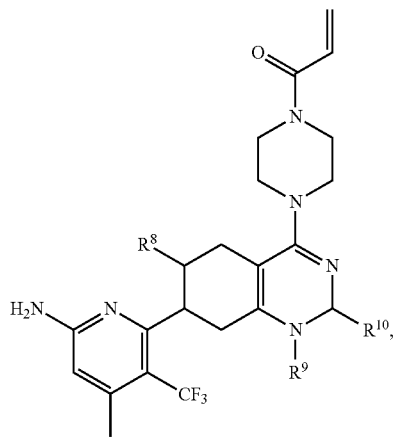

(III-7)
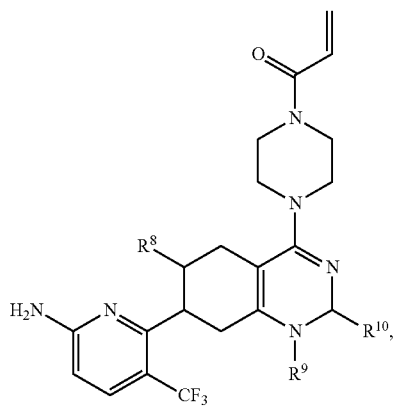

(III-8)
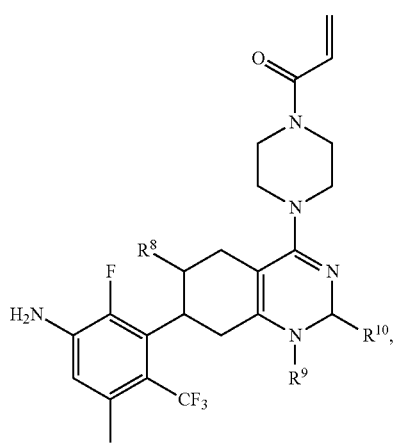

(III-9)
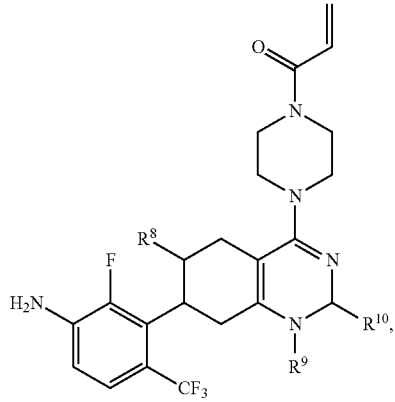

(III-10)
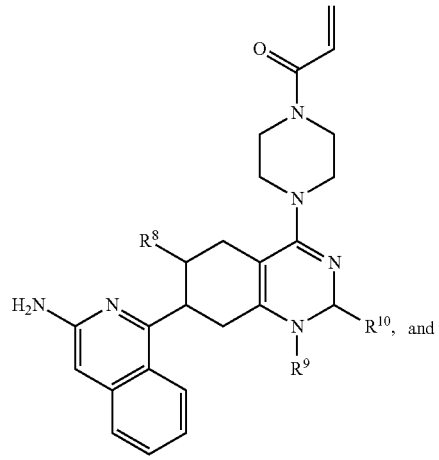

(III-11)
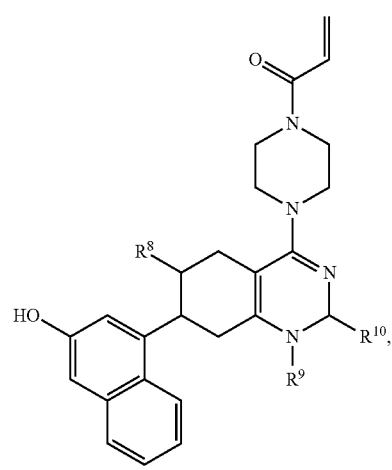

or a pharmaceutically acceptable salt thereof.

Embodiment 67: The compound of Embodiment 1 or Embodiment 2, or a pharmaceutically acceptable salt thereof, having a Formula (IIn):

(IIn)
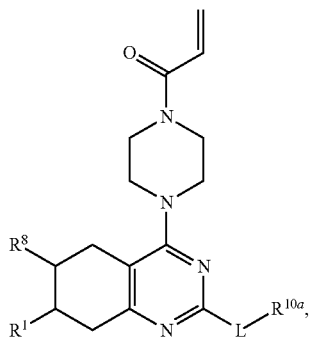

or a pharmaceutically acceptable salt thereof.

Embodiment 68: The compound of Embodiment 67, or a pharmaceutically acceptable salt thereof, having a formula selected from the group consisting of:

(IIn-1)
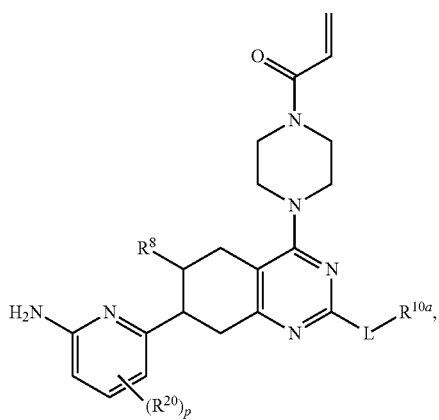

(IIn-2)
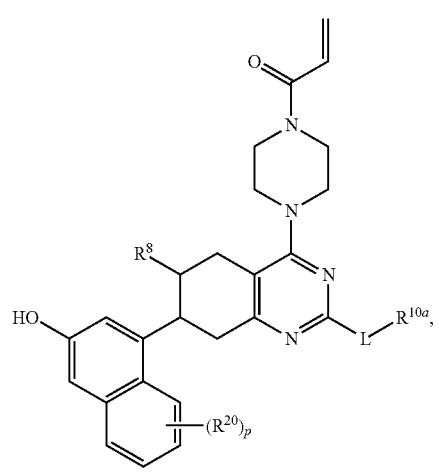

(IIn-3)
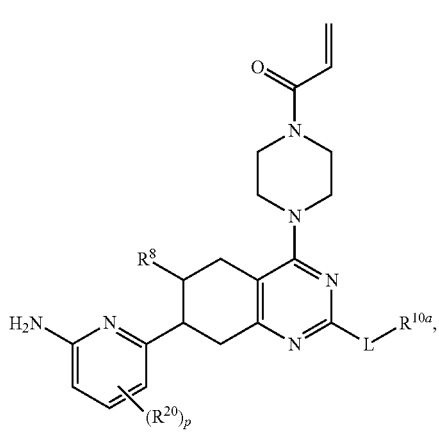

(IIn-4)
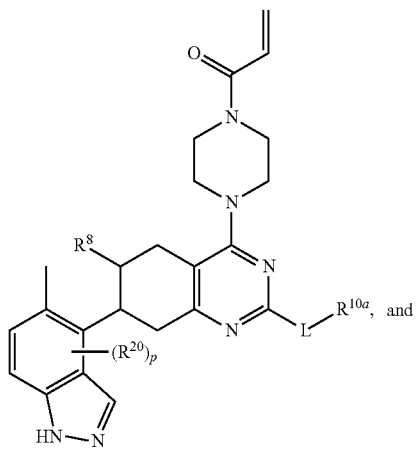

(IIn-5)
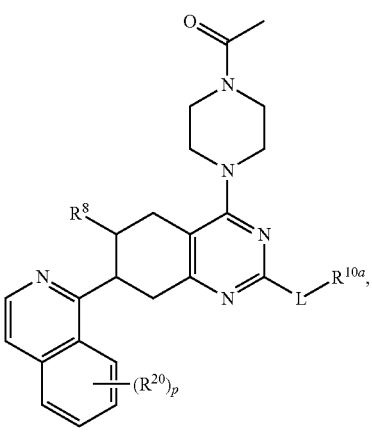

or a pharmaceutically acceptable salt thereof, wherein each $R^{20}$ is independently selected from the group consisting of $C_{1-6}$ alkyl, $NH_2$, $NH(CH_3)$, $N(CH_3)_2$, halo, $C_{1-6}$ haloalkyl, hydroxy, $C_{3-6}$ cycloalkyl, $C_{1-6}$ hydroxyalkyl, and —OC(=O)CH=CH$_2$; and each p is independently 0, 1, 2, 3, or 4.

Embodiment 69: The compound of Embodiment 67, or a pharmaceutically acceptable salt thereof, having a formula selected from the group consisting of:

(IIn-6)
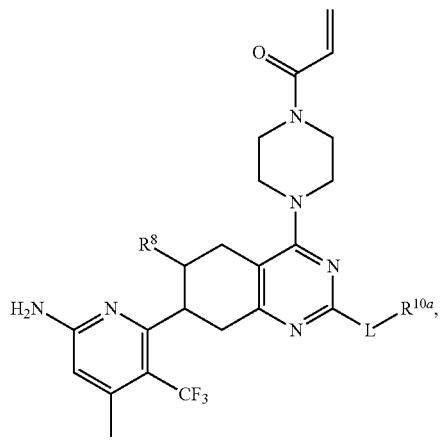

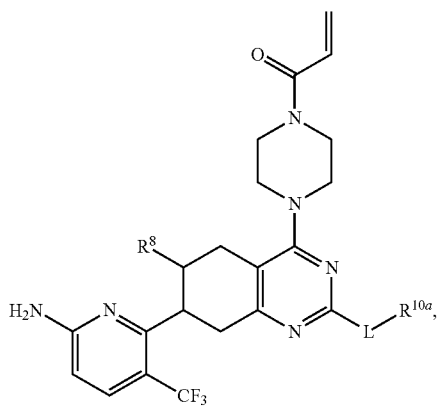

(IIn-7)

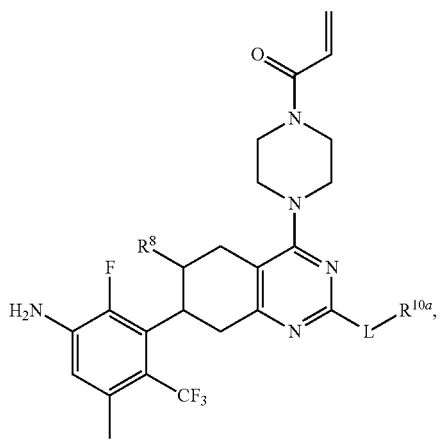

(IIn-8)

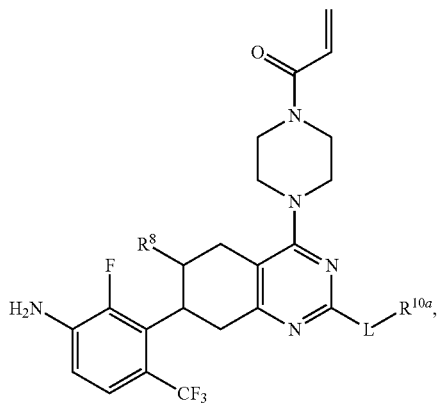

(IIn-9)

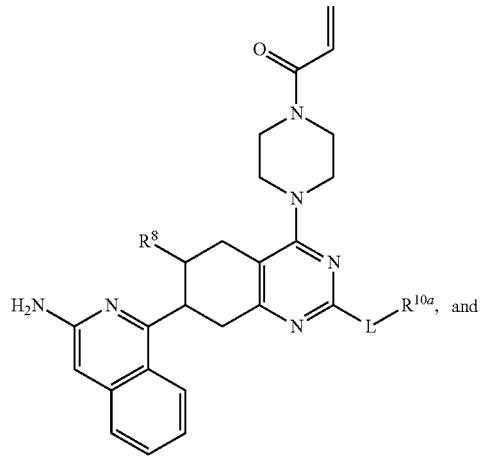

(IIn-10)

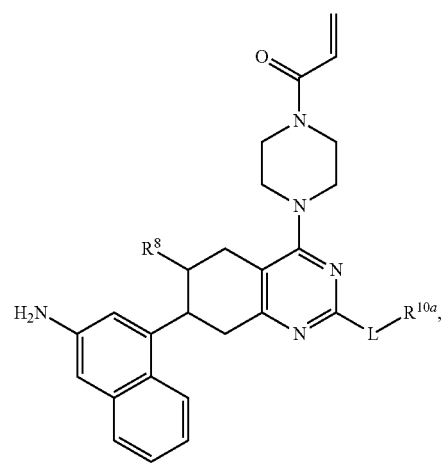

(IIn-11)

or a pharmaceutically acceptable salt thereof.

Embodiment 70: The compound of Embodiment 1 or Embodiment 2, or a pharmaceutically acceptable salt thereof, having a Formula (IIm):

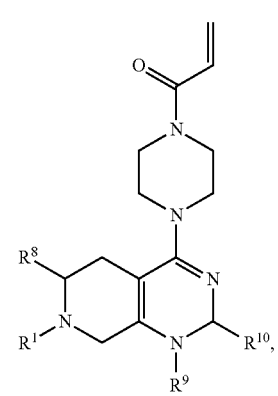

(IIm)

or a pharmaceutically acceptable salt thereof.

Embodiment 71: The compound of Embodiment 70, or a pharmaceutically acceptable salt thereof, wherein $R^8$ is hydrogen; $R^9$ is aryl substituted with $C_{1-6}$ alkyl; and $R^{10}$ is oxo.

Embodiment 72: The compound of any one of Embodiment 58, 63, 67, or 70, or a pharmaceutically acceptable salt thereof, wherein R¹ is selected from the group consisting of

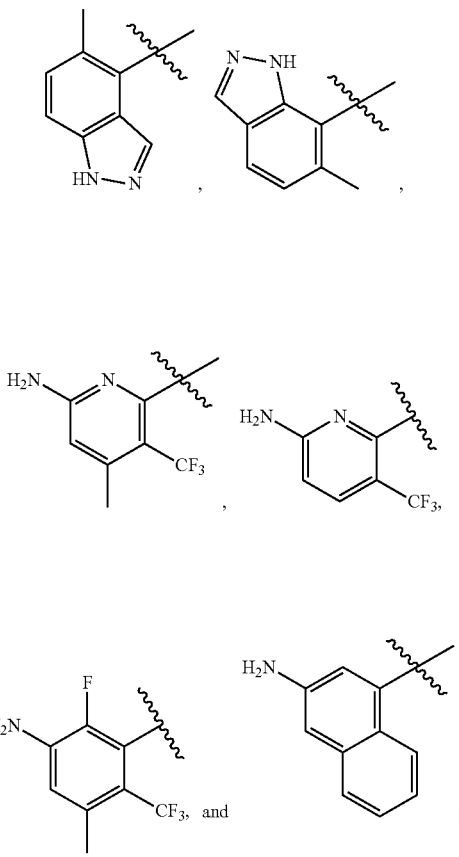

Embodiment 73: The compound of Embodiment 1 or Embodiment 2, selected from the group consisting of the compounds of Table 1, or a pharmaceutically acceptable salt thereof.

Embodiment 74: The compound of Embodiment 1 or Embodiment 2, or a pharmaceutically acceptable salt thereof having the following structure:

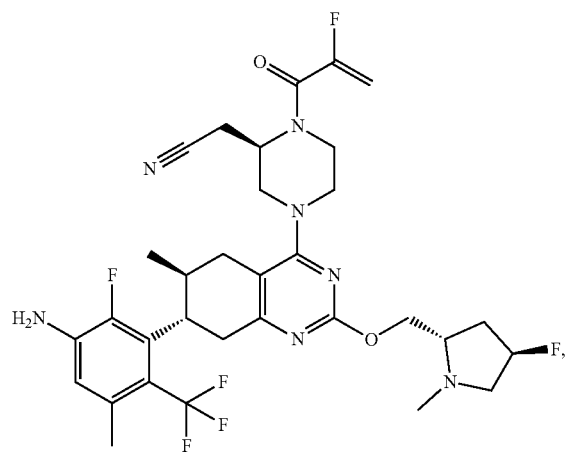 [SMILES: C=C(F)C(=O)N1CCN(c2nc(OC[C@@H]3C[C@@H](F)CN3C)nc3c2C[C@H](C)[C@@H](c2c(F)c(N)cc(C)c2C(F)(F)F)C3)C[C@H]1CC#N]

or a pharmaceutically acceptable salt thereof.

Embodiment 75: The compound of Embodiment 1 or Embodiment 2, or a pharmaceutically acceptable salt thereof having the following structure:

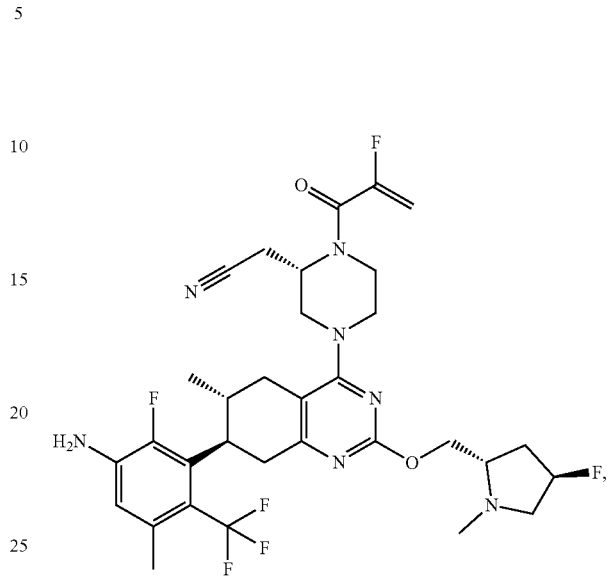

or a pharmaceutically acceptable salt thereof.

Embodiment 76: The compound of Embodiment 1 or Embodiment 2, or a pharmaceutically acceptable salt thereof having the following structure:

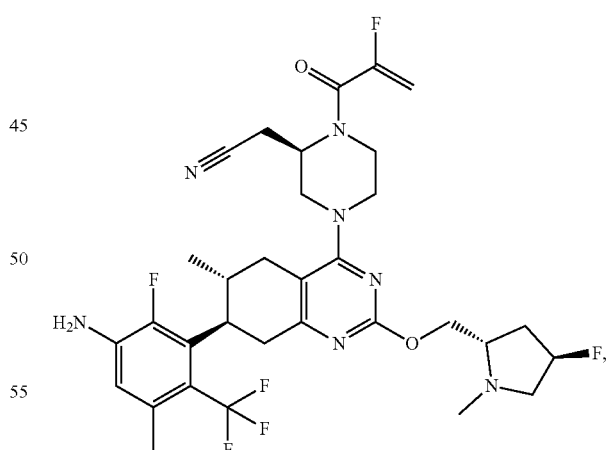

or a pharmaceutically acceptable salt thereof.

Embodiment 77: The compound of Embodiment 1 or Embodiment 2, or a pharmaceutically acceptable salt thereof having the following structure:

247
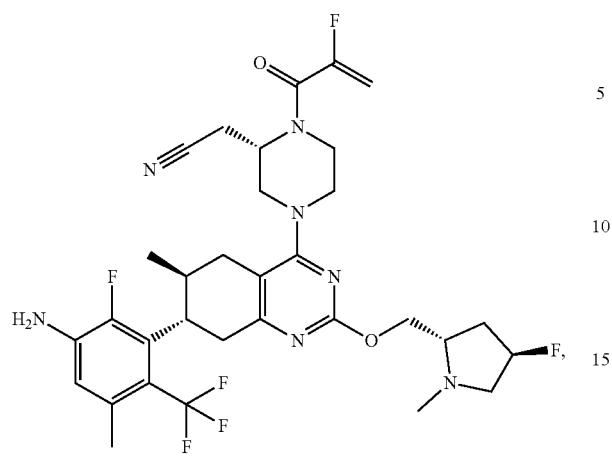
or a pharmaceutically acceptable salt thereof.
Embodiment 78: The compound of Embodiment 1 or Embodiment 2, or a pharmaceutically acceptable salt thereof have a structure selected from the group consisting of:
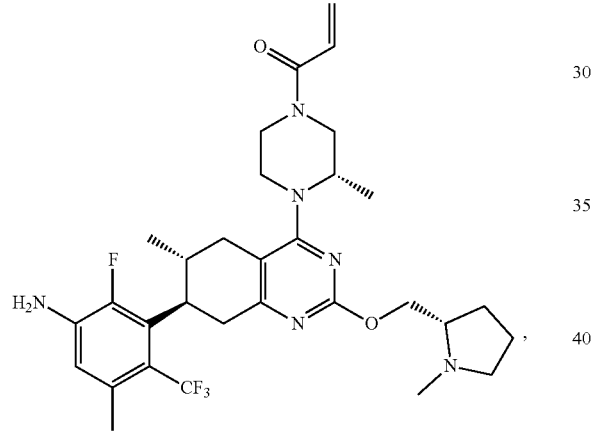
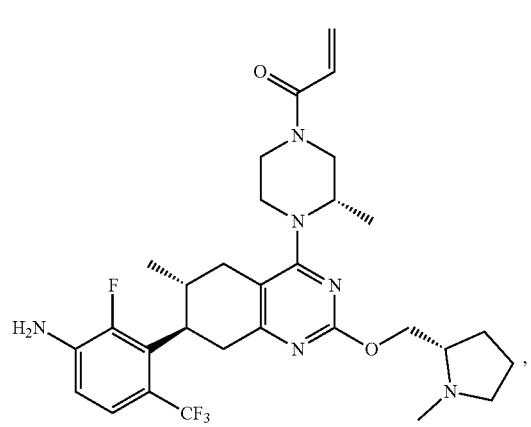
248
-continued
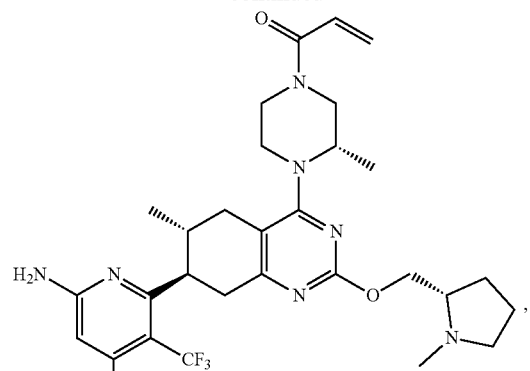
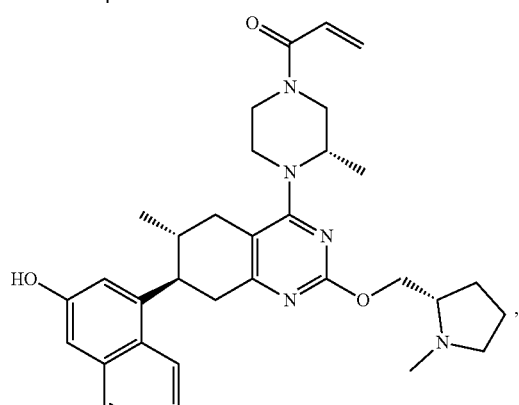
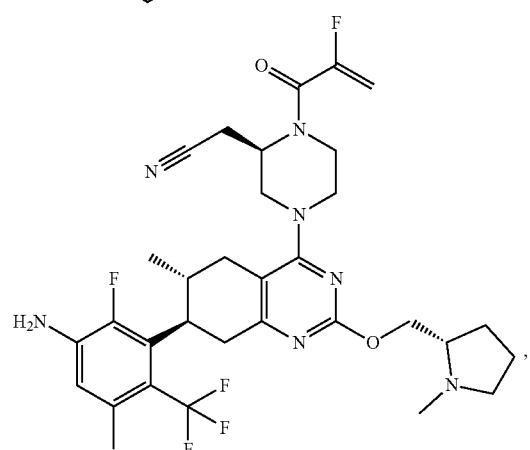
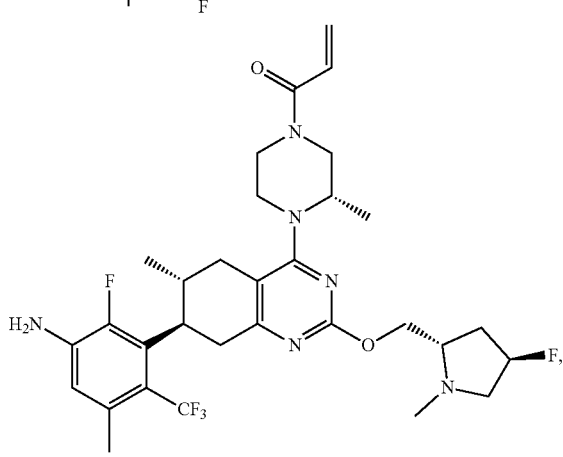

-continued

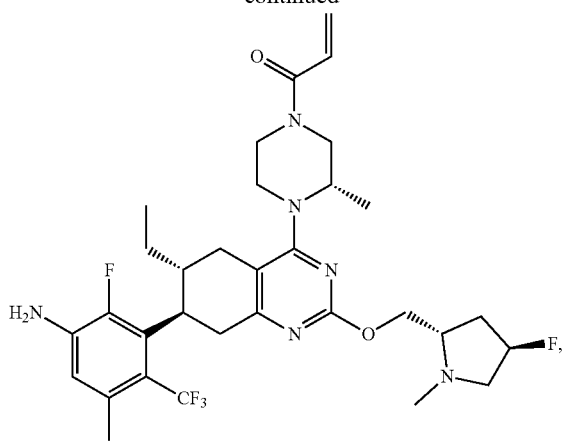

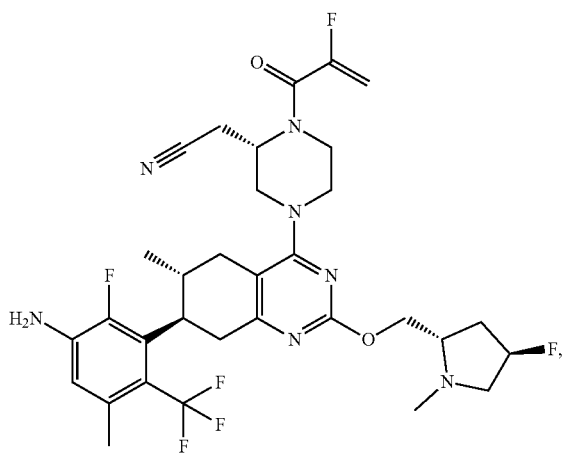 [SMILES: C=C(F)C(=O)N1CCN(c2nc(OC[C@@H]3C[C@@H](F)CN3C)nc3c2C[C@@H](C)[C@H](c2c(F)c(N)cc(C)c2C(F)(F)F)C3)C[C@@H]1CC#N]

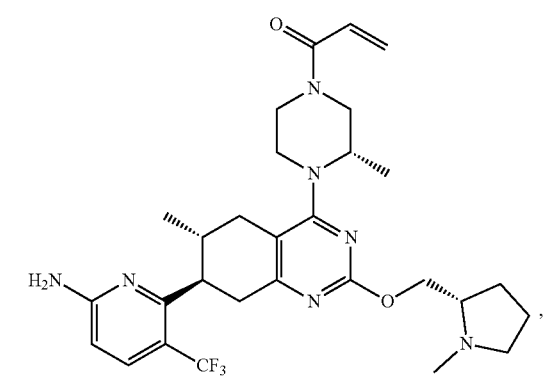

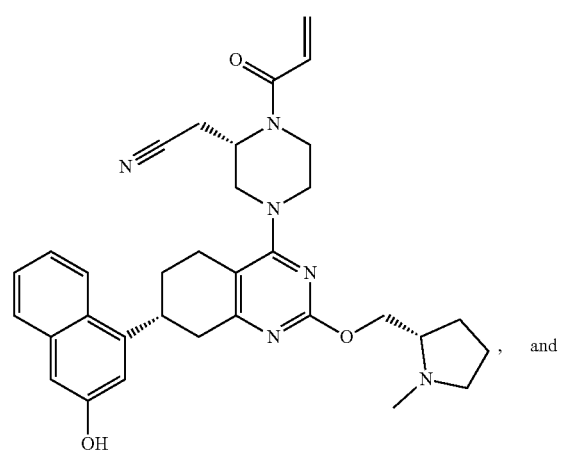

-continued

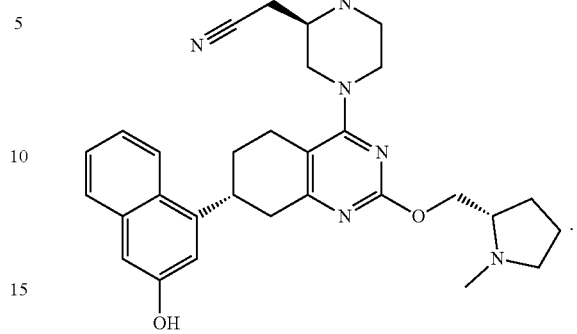

Embodiment 79: A compound or pharmaceutically acceptable salt thereof of Table 1.

Embodiment 80: A pharmaceutical composition comprising the compound of any one of Embodiments 1-79, or a pharmaceutically acceptable salt thereof, and a pharmaceutically acceptable excipient.

Embodiment 81: The pharmaceutical composition of Embodiment 80, wherein the pharmaceutical composition is formulated for oral administration.

Embodiment 82: The pharmaceutical composition of Embodiment 80, wherein the pharmaceutical composition is formulated for injection.

Embodiment 83: A method of treating cancer comprising administering to an individual in need thereof a therapeutically effective amount of the compound of any one of Embodiments 1-79, or a pharmaceutically acceptable salt thereof, or the pharmaceutical composition of any one of Embodiments 80-82.

Embodiment 84: The method of Embodiment 83, wherein the individual is a human.

Embodiment 85: The method of Embodiment 83, wherein the administering is via the oral route.

Embodiment 86: The method of Embodiment 83, wherein the administering is via injection.

Embodiment 87: The method of Embodiment 83, wherein the cancer is mediated by a K-Ras G12C mutation.

Embodiment 88: The method of Embodiment 83, wherein the cancer is a hematological cancer, pancreatic cancer, MYH associated polyposis, colorectal cancer, lung cancer, or is agnostic.

Embodiment 89: The method of Embodiment 83, wherein the cancer is lung adenocarcinoma.

Embodiment 90: A method for regulating activity of a K-Ras G12C mutant protein, the method comprising reacting the mutant protein with the compound of any one of Embodiments 1-79, or a pharmaceutically acceptable salt thereof.

Embodiment 91: A method for inhibiting proliferation of a cell population, the method comprising contacting the cell population with the compound of any one of Embodiments 1-79, or a pharmaceutically acceptable salt thereof.

Embodiment 92: The method of Embodiment 91, wherein the inhibition of proliferation is measured as a decrease in cell viability of the cell population.

Embodiment 93: A method for treating a disorder mediated by a K-Ras G12C mutation in an individual in need thereof, the method comprising: determining if the individual has the mutation; and if the individual is determined to have the mutation, then administering to the individual a therapeutically effective amount of the compound of any one of Embodiments 1-79, or a pharmaceutically acceptable salt thereof, or the pharmaceutical composition of any one of Embodiments 80-82.

Embodiment 94: The method of Embodiment 93, wherein the disorder is a cancer.

Embodiment 95: The method of Embodiment 94, wherein the cancer is a hematological cancer, pancreatic cancer, MYH associated polyposis, colorectal cancer, lung cancer, or is agnostic.

Embodiment 96: The method of Embodiment 94, wherein the cancer is lung adenocarcinoma.

Embodiment 97: A method for preparing a labeled K-Ras G12C mutant protein, the method comprising reacting a K-Ras G12C mutant protein with a labeled compound of any one of Embodiments 1-79, or a pharmaceutically acceptable salt thereof, to result in the labeled K-Ras G12C mutant protein.

Embodiment 98: A method for inhibiting tumor metastasis comprising administering to an individual in need thereof a therapeutically effective amount of the compound of any one of Embodiments 1-79, or a pharmaceutically acceptable salt thereof, or the pharmaceutical composition of any one of Embodiments 80-82 to an individual in need thereof.

Embodiment 99: A method for tumor-agnostic treatment of cancer in an individual in need thereof, the method comprising determining if the individual has a tumor with a G12C mutation in a K-Ras, H-Ras, or N-Ras protein in the tumor, and if the individual has a tumor with the mutation, administering a therapeutically effective amount of the compound of any one of Embodiments 1-79, or a pharmaceutically acceptable salt thereof, or the pharmaceutical composition of any one of Embodiments 80-82 to the individual.

Embodiment 100: Use of a compound of any one of Embodiments 1-79, or a pharmaceutically acceptable salt thereof, in the manufacture of a medicament for treating cancer.

Embodiment 101: The use of Embodiment 100, wherein the medicament is formulated for oral administration.

Embodiment 102: The use of Embodiment 100, wherein the medicament is formulated for injection.

Embodiment 103: The use of Embodiment 100, wherein the cancer is mediated by a K-Ras G12C mutation.

Embodiment 104: The use of Embodiment 100, wherein the cancer is a hematological cancer, pancreatic cancer, MYH associated polyposis, colorectal cancer, lung cancer, or is agnostic.

Embodiment 105: The use of Embodiment 100, wherein the cancer is lung adenocarcinoma.

Embodiment 106: Use of a compound of any one of Embodiments 1-79, or a pharmaceutically acceptable salt thereof, in the manufacture of a medicament for inhibiting tumor metastasis.

Embodiment 107: The compound of any one of Embodiments 1-79, or a pharmaceutically acceptable salt thereof, or the pharmaceutical composition of any one of Embodiments 80-82, for use in a method of treatment of the human or animal body by therapy.

Embodiment 108: The compound of any one of Embodiment 1-79, or a pharmaceutically acceptable salt thereof, or the pharmaceutical composition of any one of Embodiments 80-82, for use in a method of treating cancer.

Embodiment 109: The compound, pharmaceutically acceptable salt thereof, or pharmaceutical composition of Embodiment 108, wherein the cancer is mediated by a K-Ras G12C mutation.

Embodiment 110: The compound, pharmaceutically acceptable salt thereof, or pharmaceutical composition of Embodiment 108, wherein the cancer is a hematological cancer, pancreatic cancer, MYH associated polyposis, colorectal cancer, lung cancer, or is agnostic.

Embodiment 111: The compound, pharmaceutically acceptable salt thereof, or pharmaceutical composition of Embodiment 108, wherein the cancer is lung adenocarcinoma.

Embodiment 112: The compound of any one of Embodiments 1-79, or a pharmaceutically acceptable salt thereof, or the pharmaceutical composition of any one of Embodiments 80-82, for use in a method of inhibiting tumor metastasis.

EXAMPLES

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Some of the compound structures provided herein contain the designation "assumed". Unless otherwise indicated, the term "assumed" is intended to indicate that stereochemistry for the compound was assigned based on potency, and thus could be different from that depicted for the compound.

The following abbreviations are used in the Examples:
ACN—acetonitrile
$B_2pin_2$—bis(pinacolato)diboron
BINAP—(+/−)-2,2'-bis(diphenylphosphino)-1,1'-binaphthyl
BOC—tert-butyloxycarbonyl
$BOC_2O$—di-tert-butyl dicarbonate
$B(O-iPr)_3$—triisopropyl borate
BOP—(benzotriazol-1-yloxy)tris(dimethylamino)phosphonium hexafluorophosphate
DBU—1,8-diazabicyclo[5.4.0]undec-7-ene
DCE—diethyl carbonate
DCM—dichloromethane
DDQ—2,3-dichloro-5,6-dicyano-1,4-benzoquinone
DHP—3,4-dihydro-2h-pyran
DIEA—N,N-diisopropylethylamine
DIPEA—N,N-diisopropylethylamine
DMA—N,N-dimethylacetamide
DMAP—4-dimethylaminopyridine
DMF—N,N-dimethylformamide
DMSO—dimethyl sulfoxide
EA—ethyl acetate
EtOAc—ethyl acetate
EtOH—ethanol or ethyl alcohol
HATU—1-(bis(dimethylamino)methylene)-1H-1$\lambda^4$-[1,2,3]triazolo[4,5-b]pyridine-4-ium 3-oxide hexafluorophosphate(V)
$HC(OMe)_3$—trimethoxymethane
IPAC—iso-propylacetate
$(i-PrO)_3B$—triisopropyl borate
KF—potassium fluoride
KHMDS—potassium bis(trimethylsilyl)amide
KOAc—potassium acetate
LDA—lithium diisopropylamide
LiHMDS—lithium bis(trimethylsilyl)amide or lithium hexamethyldisilazide
m-CBPA or m-CPBA—3-chloroperoxybenzoic acid
MeCN—acetonitrile MeOH—methanol or methyl alcohol
MeONa—sodium methoxide or sodium methanolate
NBS—1-bromo-2,5-pyrrolidinedione
n-BuLi—n-butyllithium
NIS—N-iodosuccinimide
NMP—1-methyl-2-pyrrolidinone
Oxone—potassium peroxymonosulfate
P(t-Bu)$_3$HBF$_4$—tri-tert-butylphosphonium tetrafluoroborate
PCy$_3$—tricyclohexyl phosphine
Pd/C—palladium on carbon
Pd$_2$(dba)$_3$—bis(dibenzylideneacetone)palladium
Pd$_2$(dba)$_3$CHCl$_3$—tris(dibenzylidenacetone)dipalladium (O) chloroform
Pd(PPh$_3$)$_2$Cl$_2$—bis(triphenylphosphine)palladium(II) chloride
Pd(dppf)Cl$_2$—1,1'-bis(diphenylphosphino)ferrocene-palladium(II)dichloride
Pd(dppf)Cl$_2$CH$_2$Cl$_2$—[1,1'-bis(diphenylphosphino)ferrocene]dichloropalladium(II), complexed with dichloromethane
Pd(OAc)$_2$—palladium (II) acetate
Pd(pph$_3$)Cl$_2$—bis(triphenylphosphine)palladium(II) chloride
PE—petroleum ether
PMBCl—4-methoxybenzylchloride
PMB—p-methoxybenzyl
P(t-Bu)$_3$HBF$_4$—tri-tert-butylphosphine tetrafluoroborate
RBF—rubidium fluoride
[Rh(COD)Cl]$_2$—chloro(1,5-cyclooctadiene)rhodium(I) dimer
r.t.—room temperature
SEMCl—2-(trimethylsilyl)ethoxymethyl chloride
SEM—2-(trimethylsilyl)ethoxymethyl
SFC—supercritical fluid chromatography
Sn$_2$(n-Bu)$_6$—hexabutylditin
TBSCl—tert-butyldimethylsilyl chloride
t-BuOK—potassium tert-butoxide
Tf$_2$O—trifluoromethanesulfonic anhydride
TFA—trifluoroacetic acid
THF—tetrahydrofuran
THP—tetrahydropyran
TMG—tetramethylguanidine
Tol—toluene
TsOH—p-toluenesulfonic acid
Zn(Me)$_2$—dimethylzinc Examples 1a and 1b Example 1a

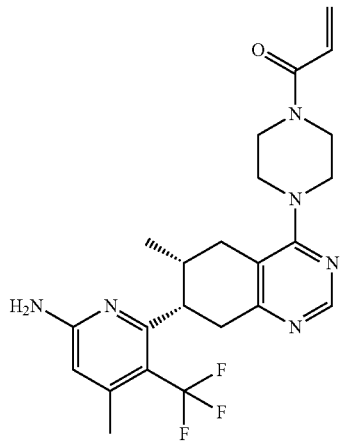

Example 1b

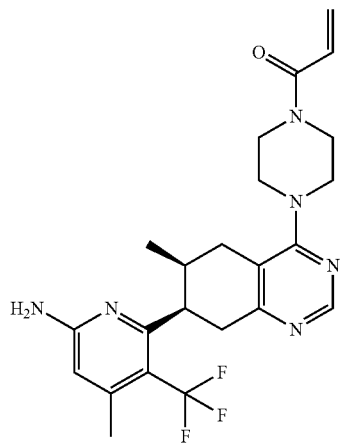

1-(4-((6R,7S)-7-(6-amino-4-methyl-3-(trifluoromethyl)pyridin-2-yl)-6-methyl-5,6,7,8-tetrahydroquinazolin-4-yl)piperazin-1-yl)prop-2-en-1-one (Example 1a)

1-(4-((6S,7R)-7-(6-amino-4-methyl-3-(trifluoromethyl)pyridin-2-yl)-6-methyl-5,6,7,8-tetrahydroquinazolin-4-yl)piperazin-1-yl)prop-2-en-1-one (Example 1b)

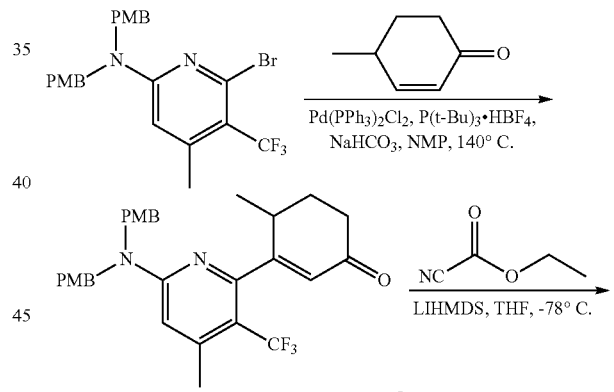

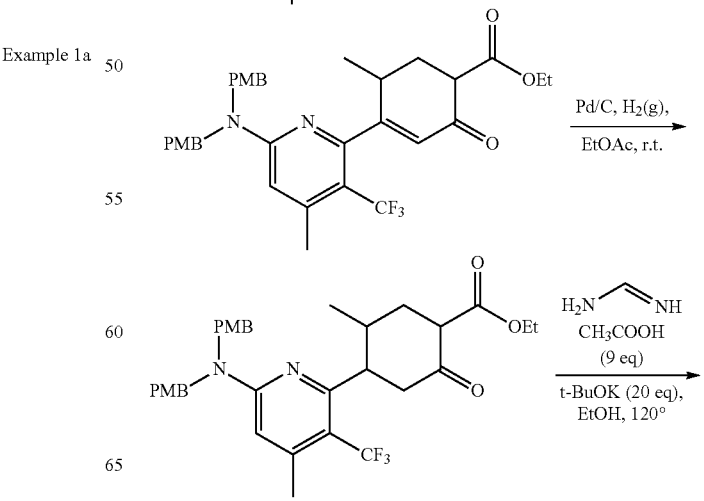

255
-continued

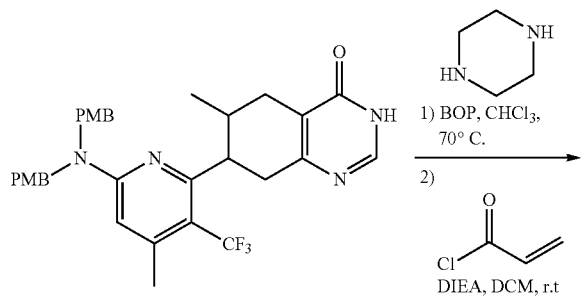

1) BOP, CHCl₃, 70° C.
2)

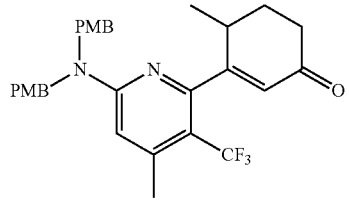
DIEA, DCM, r.t

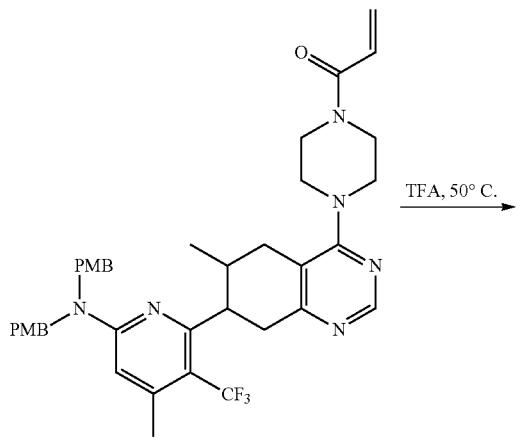

TFA, 50° C.

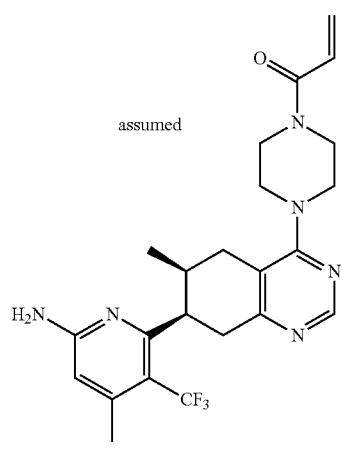

1a assumed

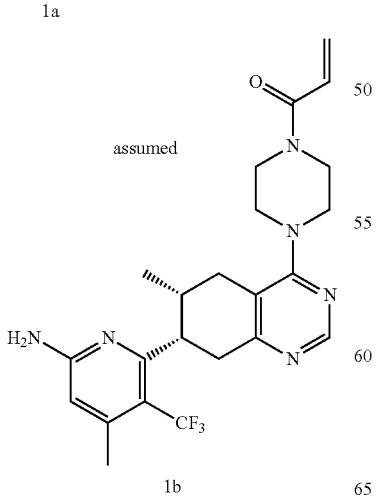

1b assumed

256

Step 1: 3-[6-[bis[(4-methoxyphenyl)methyl]amino]-4-methyl-3-(trifluoromethyl)-2-pyridyl]-4-methyl-cyclohex-2-en-1-one

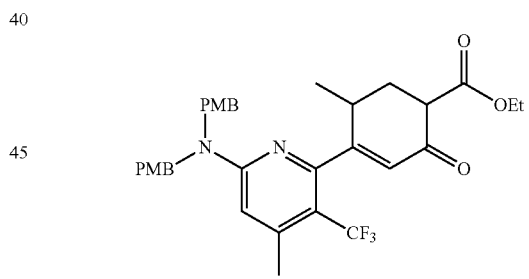

Under nitrogen, a solution of 6-bromo-N,N-bis[(4-methoxyphenyl)methyl]-4-methyl-5-(trifluoromethyl)pyridin-2-amine (9.00 g, 18.18 mmol), 4-methylcyclohex-2-en-1-one (3.96 g, 36.36 mmol), bis(triphenylphosphine)palladium(II) chloride (1.30 g, 1.80 mmol), tri-tert-butylphosphine tetrafluoroborate (1.10 g, 3.60 mmol) and sodium bicarbonate (4.60 g, 54.54 mmol) in 1-methyl-2-pyrrolidinone (30 mL) was stirred for 10 hours at 140° C. After completion, the reaction mixture was diluted with dichloromethane, washed with water. The organic layer was dried over anhydrous sodium sulfate and concentrated under vacuum. The residue was purified by flash chromatography on silica gel eluting with petroleum ether/ethyl acetate (4/1) to afford 3-[6-[bis[(4-methoxyphenyl)methyl]amino]-4-methyl-3-(trifluoromethyl)-2-pyridyl]-4-methyl-cyclohex-2-en-1-one (2.20 g, 4.20 mmol, 23% yield) as a yellow solid. LCMS (ESI, m/z): 525.2 [M+H]+.

Step 2: ethyl-4-[6-[bis[(4-methoxyphenyl)methyl]amino]-4-methyl-3-(trifluoromethyl)-2-pyridyl]-5-methyl-2-oxo-cyclohex-3-ene-1-carboxylate Under nitrogen, a solution of 3-[6-[bis[(4-methoxyphenyl)methyl]amino]-4-methyl-3-(trifluoromethyl)-2-pyridyl]-4-methyl-cyclohex-2-en-1-one (2.20 g, 4.20 mmol) in tetrahydrofuran (100 mL) was dropwise added lithium bis(trimethylsilyl)amide (5.5 mL, 5.46 mmol, 1.0 M in THF) and stirred for 1 hour at −78° C. Then ethyl cyanoformate (0.60 g, 6.29 mmol) was dropwise added and stirred at −78° C. for 0.5 hours. After completion, the reaction was quenched with aqueous saturated ammonium chloride, diluted with dichloromethane, washed with water. The organic layer was dried over anhydrous sodium sulfate and concentrated under vacuum to afford crude product ethyl 4-[6-[bis[(4-methoxyphenyl)methyl]amino]-4-methyl-3-(trifluoromethyl)-2-pyridyl]-5-methyl-2-oxo-cyclohex-3-ene-1-carboxylate (1.40 g, crude) as a yellow solid. LCMS (ESI, m/z): 597.2 [M+H]+.

Step 3: ethyl 4-[6-[bis[(4-methoxyphenyl)methyl]amino]-4-methyl-3-(trifluoromethyl)-2-pyridyl]-5-methyl-2-oxo-cyclohexanecarboxylate

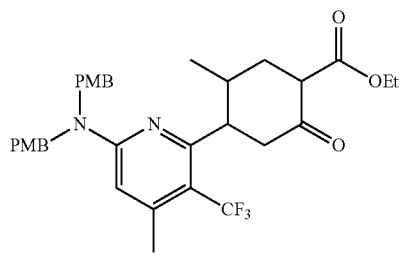

Under hydrogen, a solution of ethyl 4-[6-[bis[(4-methoxyphenyl)methyl]amino]-4-methyl-3-(trifluoromethyl)-2-pyridyl]-5-methyl-2-oxo-cyclohex-3-ene-1-carboxylate (1.40 g, 2.34 mmol) in ethyl acetate (100 mL) was added Pd/C (10%) (1.40 g) and stirred at 0° C. for 20 minutes. After filtration, the filtrate was concentrated under reduced pressure to afford crude product ethyl 4-[6-[bis[(4-methoxyphenyl)methyl]amino]-4-methyl-3-(trifluoromethyl)-2-pyridyl]-5-methyl-2-oxo-cyclohexanecarboxylate (1.00 g, crude) as a yellow solid. LCMS (ESI, m/z): 599.3 [M+H]+.

Step 4: 7-(6-(bis(4-methoxybenzyl)amino)-4-methyl-3-(trifluoromethyl)pyridin-2-yl)-6-methyl-5,6,7,8-tetrahydroquinazolin-4(3H)-one

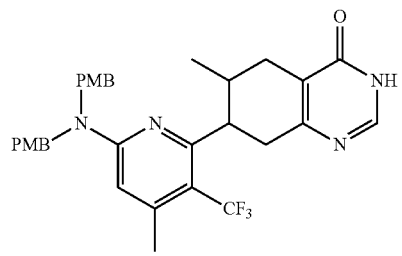

A solution of ethyl 4-[6-[bis[(4-methoxyphenyl)methyl]amino]-4-methyl-3-(trifluoromethyl)-2-pyridyl]-5-methyl-2-oxo-cyclohexanecarboxylate (1.00 g, crude), formamidine acetate (1.70 g, 16.70 mmol) and potassium tert-butoxide (3.80 g, 33.41 mmol) in ethyl alcohol (50 mL) was stirred at 120° C. for 5 hours. After completion, the reaction mixture was concentrated under vacuum. The reaction mixture was diluted with dichloromethane, adjusted to pH=7 with HCl/1,4-dioxane, washed with water. The organic layer was dried over anhydrous sodium sulfate and concentrated under vacuum. The residue was purified by flash chromatography on silica gel eluting with dichloromethane/methyl alcohol (20/1) to afford 7-[6-[bis[(4-methoxyphenyl)methyl]amino]-4-methyl-3-(trifluoromethyl)-2-pyridyl]-6-methyl-5,6,7,8-tetrahydro-3H-quinazolin-4-one (0.40 g, 0.64 mmol, 38.3% yield) as a solid. LCMS (ESI, m/z): 579.3 [M+H]+.

Step 5: 1-[4-[7-[6-[bis[(4-methoxyphenyl)methyl]amino]-4-methyl-3-(trifluoromethyl)-2-pyridyl]-6-methyl-5,6,7,8-tetrahydroquinazolin-4-yl]piperazin-1-yl]prop-2-en-1-one

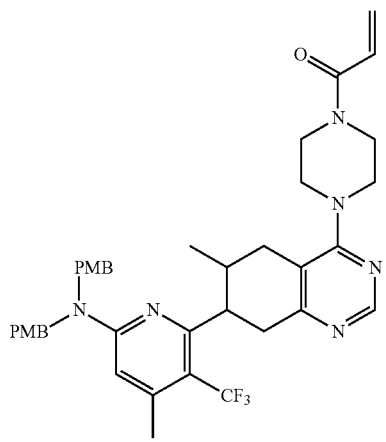

A solution of 7-[6-[bis[(4-methoxyphenyl)methyl]amino]-4-methyl-3-(trifluoromethyl)-2-pyridyl]-6-methyl-5,6,7,8-tetrahydro-3H-quinazolin-4-one (370.0 mg, 0.64 mmol), piperazine (550.8 mg, 6.39 mmol) and BOP (565.6 mg, 1.28 mmol) in chloroform (6 mL) was stirred at 70° C. for 5 hours. After completion, the resulting solution was diluted with dichloromethane, washed with water. The organic layer was dried over anhydrous sodium sulfate and concentrated under vacuum. The residue was dissolved in dichloromethane (10 mL), and acryloyl chloride (0.15 mL, 12.79 mmol) was dropwise added and stirred at 25° C. for 10 minutes. After completion, the resulting solution was quenched with water, diluted with dichloromethane, washed with water. The organic layer was dried over anhydrous sodium sulfate and concentrated under vacuum. The resulting residue was purified by reverse phase chromatography (acetonitrile 0-80% in water) to afford 1-[4-[7-[6-[bis[(4-methoxyphenyl)methyl]amino]-4-methyl-3-(trifluoromethyl)-2-pyridyl]-6-methyl-5,6,7,8-tetrahydroquinazolin-4-yl]piperazin-1-yl]prop-2-en-1-one (70.0 mg, 0.10 mmol, 15.6% yield) as white solid. LCMS (ESI, m/z): 701.3 [M+H]+.

Step 6: 1-(4-((6R,7S)-7-(6-amino-4-methyl-3-(trifluoromethyl)pyridin-2-yl)-6-methyl-5,6,7,8-tetrahydroquinazolin-4-yl)piperazin-1-yl)prop-2-en-1-one (Example 1a); 1-(4-((6S,7R)-7-(6-amino-4-methyl-3-(trifluoromethyl)pyridin-2-yl)-6-methyl-5,6,7,8-tetrahydroquinazolin-4-yl)piperazin-1-yl)prop-2-en-1-one (Example 1b)

Example 1a

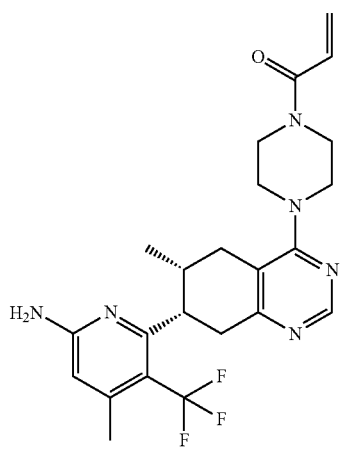

Example 1b

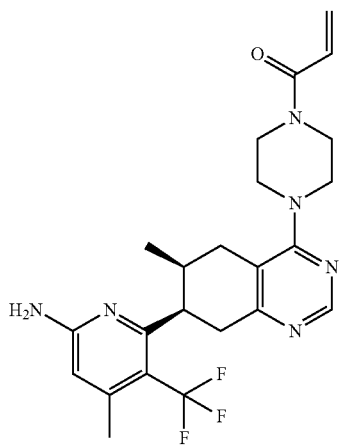

A solution of 1-[4-[7-[6-[bis[(4-methoxyphenyl)methyl]amino]-4-methyl-3-(trifluoromethyl)-2-pyridyl]-6-methyl-5,6,7,8-tetrahydroquinazolin-4-yl]piperazin-1-yl]prop-2-en-1-one (70.0 mg, 0.10 mmol) in trifluoroacetic acid (5 mL) was stirred at 50° C. for 12 hours. After completion, the resulting solution was concentrated under vacuum. The crude product was purified by Prep-HPLC with the following conditions: Column: XBridge Prep C18 OBD Column 19×150 mm 5 um; Mobile Phase A: Water (10 MMOL/L NH$_4$HCO$_3$), Mobile Phase B: ACN; Flow rate: 25 mL/min; Gradient: 31% B to 54% B in 7 min; 254/210 nm; Rt: 5.88 min to afford 20 mg product as a white solid. The product was further purified by Chiral-Prep-HPLC with following condition (Column, CHIRALPAK IF2*25 cm, 5 um; mobile phase: MTBE (10 mM NH$_3$-MEOH): EtOH; Detector, UV 254 nm) to afford the title compounds. The stereochemistry or relative configurations of the title compounds was assigned based on NMR and potency differences from trans-isomers (Examples 8a and 8b). The absolute configurations of the title compounds was not determined.

Example 1a: 1-(4-((6R,7S)-7-(6-amino-4-methyl-3-(trifluoromethyl)pyridin-2-yl)-6-methyl-5,6,7,8-tetrahydroquinazolin-4-yl)piperazin-1-yl)prop-2-en-1-one (5.3 mg, 0.012 mmol, 11.5% yield, white solid) $^1$H NMR (300 MHz, Methanol-d$_4$, ppm) δ 8.27 (s, 1H), 6.82 (dd, J=16.8, 10.6 Hz, 1H), 6.25 (dd, J=16.8, 2.0 Hz, 1H), 6.15 (s, 1H), 5.79 (dd, J=10.6, 2.0 Hz, 1H), 3.95-3.72 (m, 4H), 3.68-3.53 (m, 3H), 3.45 (brs, 2H), 2.85-2.53 (m, 4H), 2.26 (d, J=2.9 Hz, 3H), 2.03 (brs, 1H), 1.48 (d, J=1.2 Hz, 3H). LCMS (ESI, m/z): 461.2 [M+H]$^+$. Chiral HPLC: Chiralpak IF-3 (0.46*5 cm, 3 um); detected at 254 nm; MtBE (0.1% DEA): EtOH=90:10, 1.0 ml/min; Retention time: 1.259 min (faster peak).

Example 1b: 1-(4-((6S,7R)-7-(6-amino-4-methyl-3-(trifluoromethyl)pyridin-2-yl)-6-methyl-5,6,7,8-tetrahydroquinazolin-4-yl)piperazin-1-yl)prop-2-en-1-one (5.0 mg, 0.011 mmol, 10.9% yield, white solid) $^1$H NMR (300 MHz, Methanol-d$_4$, ppm) δ 8.27 (s, 1H), 6.82 (dd, J=16.8, 10.6 Hz, 1H), 6.25 (dd, J=16.8, 2.0 Hz, 1H), 6.15 (s, 1H), 5.79 (dd, J=10.6, 2.0 Hz, 1H), 3.95-3.72 (m, 4H), 3.68-3.53 (m, 3H), 3.45 (brs, 2H), 2.85-2.53 (m, 4H), 2.26 (d, J=2.9 Hz, 3H), 2.03 (brs, 1H), 1.48 (d, J=1.2 Hz, 3H). LCMS (ESI, m/z): 461.2 [M+H]$^+$. Chiral HPLC: Chiralpak IF-3 (0.46*5 cm, 3 um); detected at 254 nm; MtBE (0.1% DEA): EtOH=90:10, 1.0 ml/min; Retention time: 1.932 min (slower peak).

Example 2

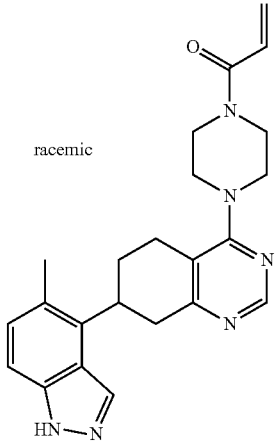 [SMILES: C=CC(=O)N1CCN(c2ncnc3c2CCC(c2c(C)ccc4[nH]ncc24)C3)CC1]

1-(4-(7-(5-methyl-1H-indazol-4-yl)-5,6,7,8-tetrahydroquinazolin-4-yl)piperazin-1-yl)prop-2-en-1-one (racemate)

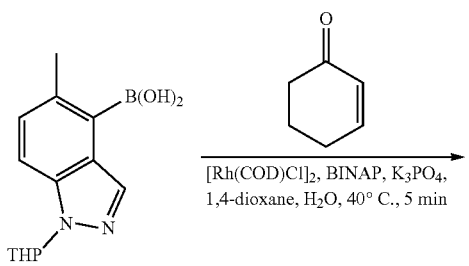

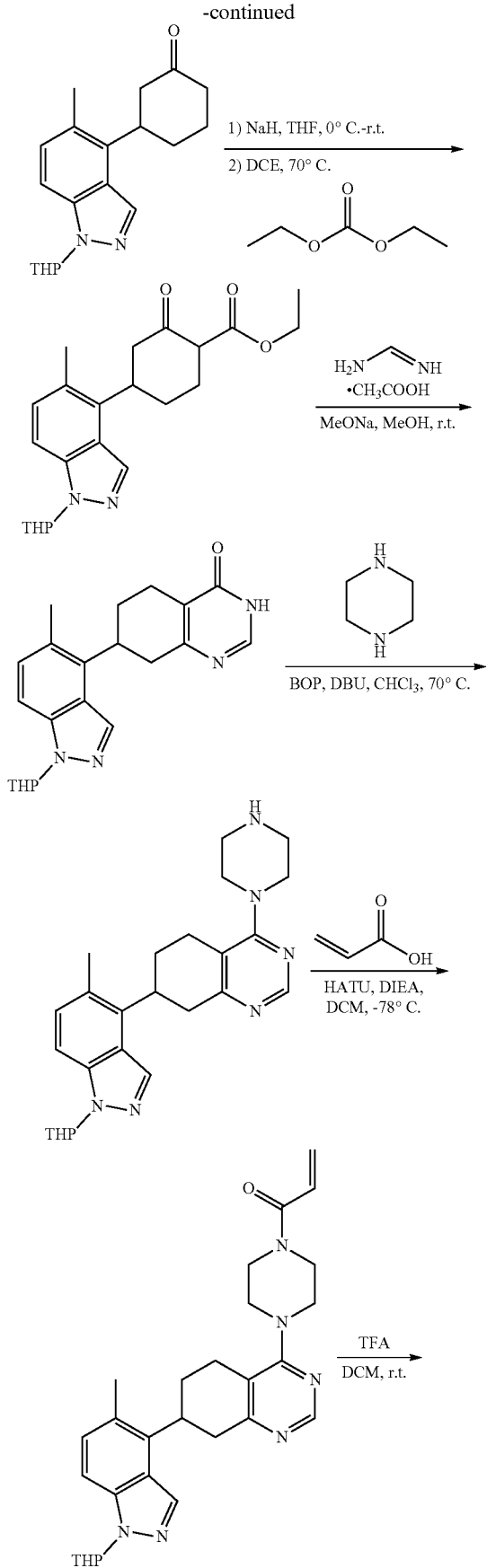

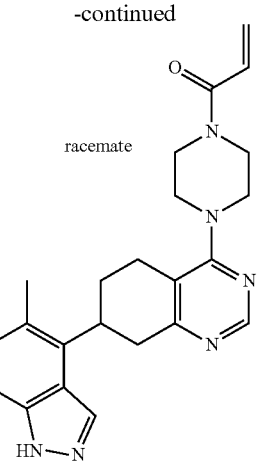

racemate

Step 1: 3-(5-methyl-1-tetrahydropyran-2-yl-indazol-4-yl)cyclohexanone

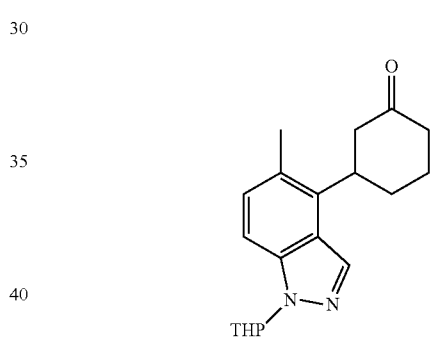

Under nitrogen, a solution of (5-methyl-1-tetrahydropyran-2-yl-indazol-4-yl)boronic acid (1.07 g, 4.13 mmol), 2-cyclohexen-1-one (0.5 mL, 5.16 mmol), BINAP (482.6 mg, 0.77 mmol), dichloro(cycloocta-1,5-diene)ruthenium (II) (108.5 mg, 0.39 mmol) and aqueous saturated potassium phosphate (1.28 mL) in 1,4-dioxane (10 mL) and water (2 mL) was stirred at 40° C. for 5 minutes. After completion, the resulting solution was diluted with ethyl acetate and washed with water. The organic layer was dried over anhydrous sodium sulfate and concentrated under vacuum. The residue was purified by flash chromatography on silica gel eluting with petrol ether/ethyl acetate (3/11) to afford 3-(5-methyl-1-tetrahydropyran-2-yl-indazol-4-yl)cyclohexanone (0.55 g, 1.76 mmol, 34.1% yield) as a light yellow oil. LCMS (ESI, m/z): 313.2 [M+H]$^+$.

Step 2: ethyl 4-(5-methyl-1-tetrahydropyran-2-yl-indazol-4-yl)-2-oxo-cyclohexanecarboxylate

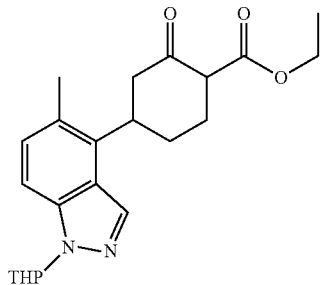

A solution of 3-(5-methyl-1-tetrahydropyran-2-yl-indazol-4-yl)cyclohexanone (1.00 g, 3.20 mmol) in tetrahydrofuran (2 mL) was added NaH (384.1 mg, 9.60 mmol) and stirred at 0° C. for 10 minutes. Then diethyl carbonate (0.78 mL, 6.40 mmol) was dropwise added and stirred at 70° C. for 30 minutes. After completion, the reaction was quenched with aqueous saturated ammonium chloride, diluted with ethyl acetate and washed by water. The organic layer was dried over anhydrous sodium sulfate and concentrated under vacuum. The residue was purified by flash chromatography on silica gel eluting with petrol ether/ethyl acetate (3/1) to afford ethyl 4-(5-methyl-1-tetrahydropyran-2-yl-indazol-4-yl)-2-oxo-cyclohexanecarboxylate (150.0 mg, 1.17 mmol, 12.2% yield) as a light yellow oil. LCMS (ESI, m/z): 385.2 [M+H]$^+$.

Step 3: 7-(5-methyl-1-tetrahydropyran-2-yl-indazol-4-yl)-5,6,7,8-tetrahydro-3H-quinazolin-4-one

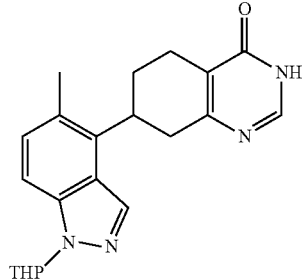

A solution of ethyl 4-(5-methyl-1-tetrahydropyran-2-yl-indazol-4-yl)-2-oxo-cyclohexanecarboxylate (80.0 mg, 0.21 mmol), formamidine acetate (75.7 mg, 0.73 mmol) and sodium methoxide (56.2 mg, 1.04 mmol) in methyl alcohol (1 mL) was stirred at 50° C. for 2 hours. After completion, the reaction mixture was adjusted to pH=6.0 with HCl in 1,4-dioxane. The resulting solution was purified by reverse phase chromatography (acetonitrile/water=10%-40%)) to afford 7-(5-methyl-1-tetrahydropyran-2-yl-indazol-4-yl)-5,6,7,8-tetrahydro-3H-quinazolin-4-one (57.0 mg, 0.16 mmol, 76% yield) as a white yellow solid. LCMS (ESI, m/z): 365.2 [M+H]$^+$.

Step 4: 7-(5-methyl-1-tetrahydropyran-2-yl-indazol-4-yl)-4-piperazin-1-yl-5,6,7,8-tetrahydroquinazoline

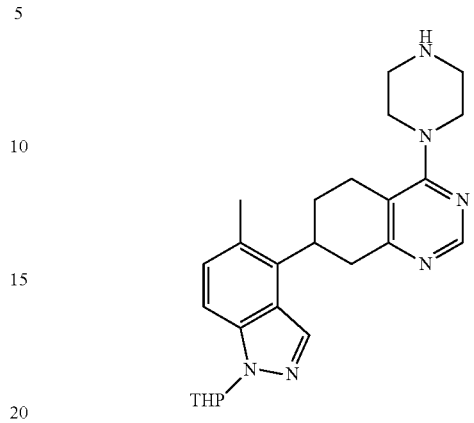

A solution of 7-(5-methyl-1-tetrahydropyran-2-yl-indazol-4-yl)-5,6,7,8-tetrahydro-3H-quinazolin-4-one (120.0 mg, 0.33 mmol), piperazine (283.6 mg, 3.29 mmol), BOP (291.3 mg, 0.66 mmol) and 1,8-diazabicyclo[5.4.0]undec-7-ene (0.15 mL, 0.99 mmol) in chloroform (3 mL) was stirred at 70° C. for 1 hour. After completion, the solution was concentrated under vacuum. The residue was purified by flash chromatography on silica gel eluting with dichloromethane/methanol (5:1) to afford 7-(5-methyl-1-tetrahydropyran-2-yl-indazol-4-yl)-4-piperazin-1-yl-5,6,7,8-tetrahydroquinazoline (120.0 mg, 0.28 mmol, 84.3% yield) as a white solid. LCMS (ESI, m/z): 433.2 [M+H]$^+$.

Step 5: 1-[4-[7-(5-methyl-1-tetrahydropyran-2-yl-indazol-4-yl)-5,6,7,8-tetrahydroquinazolin-4-yl]piperazin-1-yl]prop-2-en-1-one

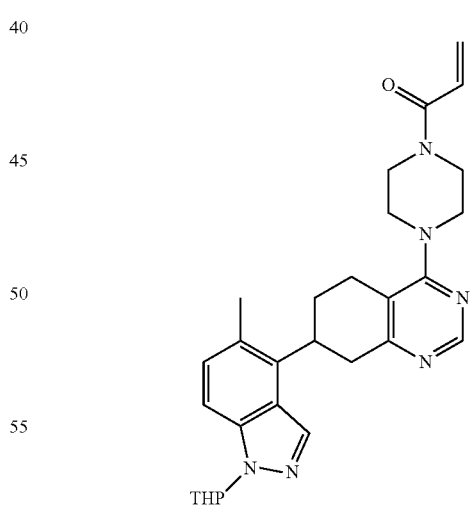

A solution of 7-(5-methyl-1-tetrahydropyran-2-yl-indazol-4-yl)-4-piperazin-1-yl-5,6,7,8-tetrahydroquinazoline (120.0 mg, 0.28 mmol), acrylic acid (99.9 mg, 1.39 mmol), HATU (158.2 mg, 0.42 mmol) and N,N-diisopropylethylamine (0.14 mL, 0.83 mmol) in dichloromethane (6 mL) was stirred at 25° C. for 10 minutes. After completion, the reaction was quenched by aqueous saturated ammonium chloride, diluted with dichloromethane and washed by water. The organic layer was dried over anhydrous sodium sulfate and concentrated under vacuum. The residue was purified by flash chromatography on silica gel eluting with dichloromethane/methanol (10:1) to afford 1-[4-[7-(5-methyl-1-tetrahydropyran-2-yl-indazol-4-yl)-5,6,7,8-tetrahydroquinazolin-4-yl]piperazin-1-yl]prop-2-en-1-one (60.0 mg, 0.12 mmol, 44.4% yield) as a white solid. LCMS (ESI, m/z): 487.3 [M+H]+.

Step 6: 1-(4-(7-(5-methyl-1H-indazol-4-yl)-5,6,7,8-tetrahydroquinazolin-4-yl)piperazin-1-yl)prop-2-en-1-one

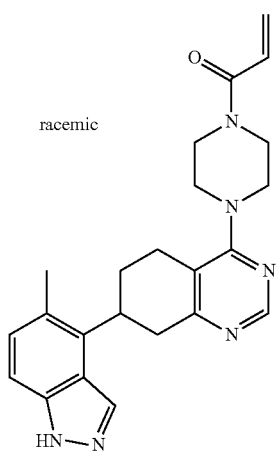 [SMILES: C=CC(=O)N1CCN(c2ncnc3c2CCC(c2c(C)ccc4[nH]ncc24)C3)CC1]

A solution of 1-[4-[7-(5-methyl-1-tetrahydropyran-2-yl-indazol-4-yl)-5,6,7,8-tetrahydroquinazolin-4-yl]piperazin-1-yl]prop-2-en-1-one (60.0 mg, 0.12 mmol) in trifluoroacetic acid (2 mL) and dichloromethane (5 mL) was stirred at 25° C. for 2 hours. After completion, the solvent was concentrated under vacuum. The crude product was purified by Prep-HPLC with the following conditions: Column: X Bridge C18, 19*150 mm, 5 um; Mobile Phase A: Water/0.05% TFA, Mobile Phase B: ACN; Flow rate: 20 mL/min; Gradient: 30% B to 70% B in 10 min; 254 nm. RT:[7 min]. This resulted in 1-[4-[7-(5-methyl-1H-indazol-4-yl)-5,6,7,8-tetrahydroquinazolin-4-yl]piperazin-1-yl]prop-2-en-1-one (12.9 mg, 0.03 mmol, 26% yield) as white solid. LCMS (ESI, m/z): 403.2 [M+H]+.

Example 2: $^1$H NMR (300 MHz, Methanol-$d_4$, ppm) δ 8.51 (s, 1H), 8.07 (s, 1H), 7.34 (d, J=8.4 Hz, 1H), 7.25 (d, J=8.4 Hz, 1H), 6.82 (dd, J=16.8, 10.8 Hz, 1H), 6.26 (dd, J=16.8, 1.8 Hz, 1H), 5.79 (dd, J=10.8, 1.9 Hz, 1H), 3.93-3.84 (m, 2H), 3.80-3.70 (m, 5H), 3.57-3.42 (m, 2H), 3.38-3.35 (m, 1H), 3.28-3.22 (m, 1H), 3.14-2.92 (m, 2H), 2.90-2.81 (m, 1H), 2.50 (s, 3H), 2.40-2.24 (m, 1H), 2.20-2.09 (m, 1H).

Examples 3a and 3b

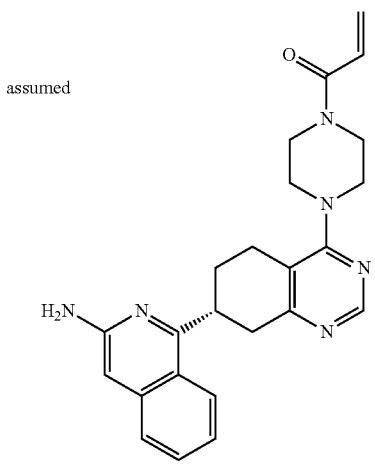

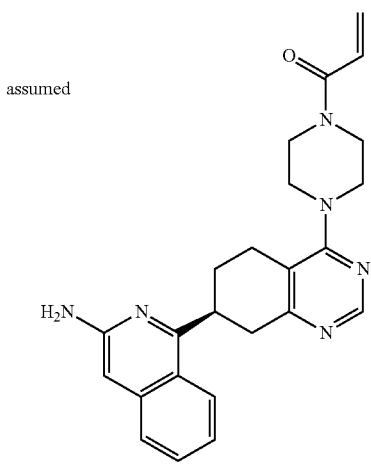

(R)-1-(4-(7-(3-aminoisoquinolin-1-yl)-5,6,7,8-tetrahydroquinazolin-4-yl)piperazin-1-yl)prop-2-en-1-one (Example 3a)

(S)-1-(4-(7-(3-aminoisoquinolin-1-yl)-5,6,7,8-tetrahydroquinazolin-4-yl)piperazin-1-yl)prop-2-en-1-one (Example 3b)

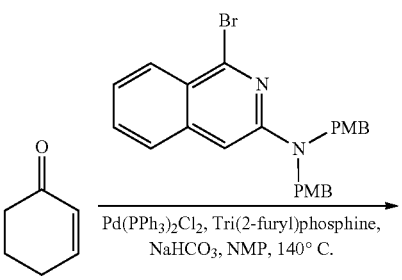

267

-continued

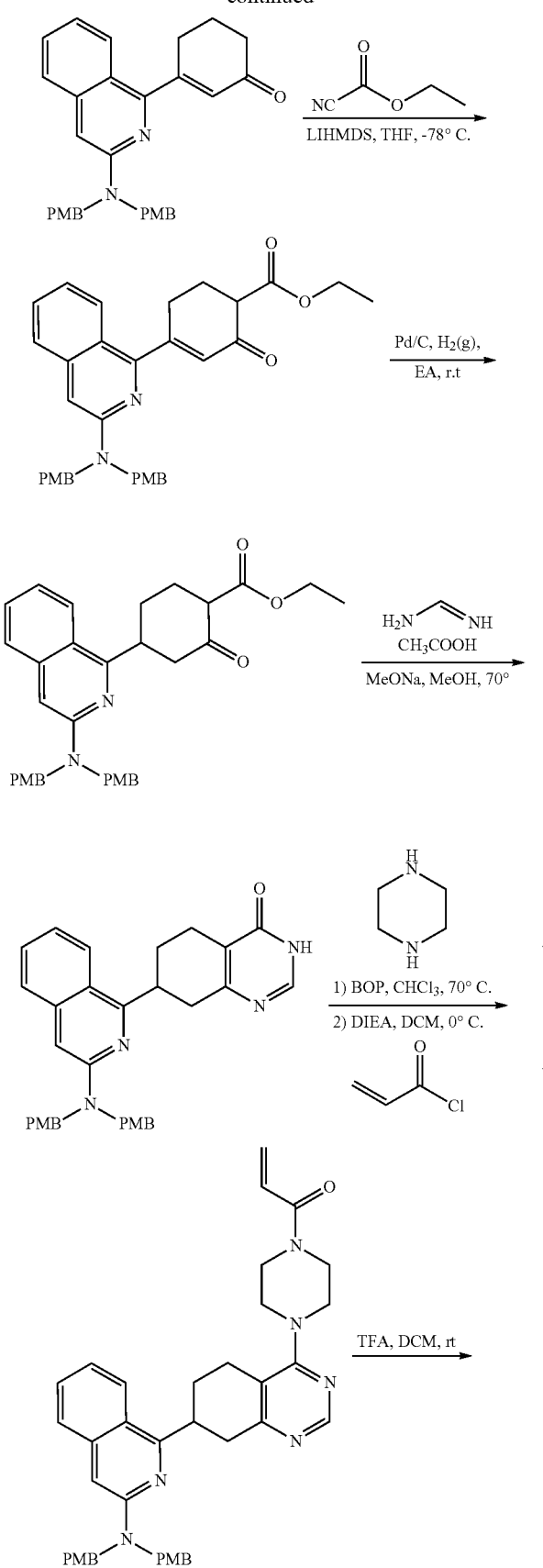

268

-continued

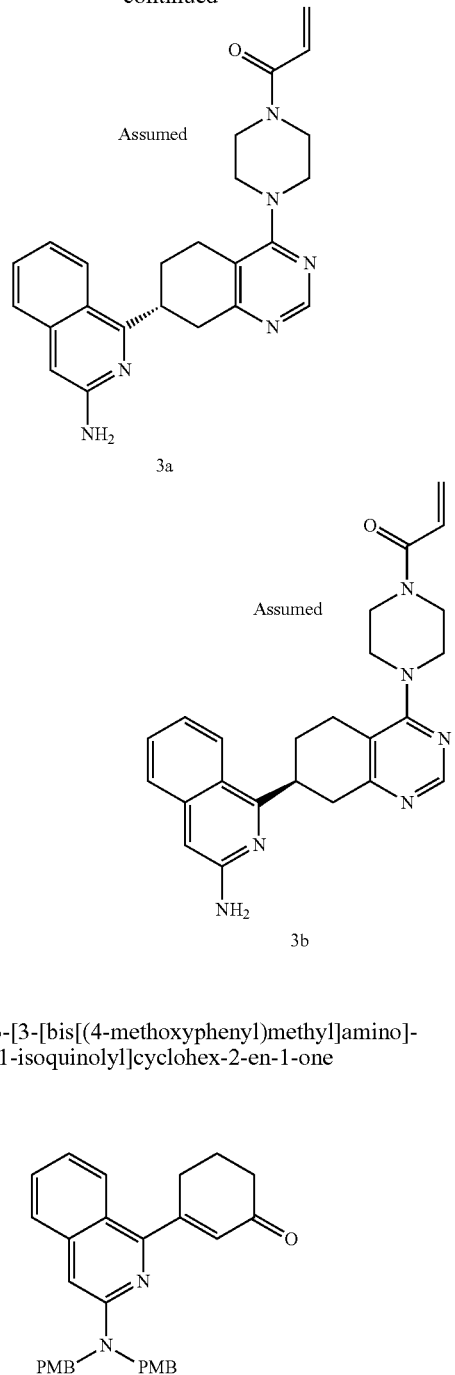

Step 1: 3-[3-[bis[(4-methoxyphenyl)methyl]amino]-1-isoquinolyl]cyclohex-2-en-1-one Under nitrogen, a solution of 1-bromo-N,N-bis[(4-methoxyphenyl)methyl]isoquinolin-3-amine (11.00 g, 23.74 mmol), 2-cyclohexen-1-one (4.56 g, 47.48 mmol), bis(triphenylphosphine)palladium(II) dichloride (1.67 g, 2.37 mmol), tri(2-furyl)phosphine (1.10 g, 4.75 mmol) and sodium bicarbonate (5.98 g, 71.22 mmol) in 1-methyl-2-pyrrolidinone (50 mL) was stirred for 5 hours at 140° C. After completion, the reaction mixture was diluted with dichloromethane and washed by water. The organic layer was dried over anhydrous sodium sulfate and concentrated under vacuum. The residue was purified by flash chromatography on silica gel eluting with petroleumeum ether/ethyl acetate (10/1) to afford 3-[3-[bis[(4-methoxyphenyl)methyl]

amino]-1-isoquinolyl]cyclohex-2-en-1-one (7.00 g, 14.63 mmol, 50.5% yield) as a red oil. LCMS (ESI, m/z): 479.2 [M+H]+.

Step 2: ethyl 4-[3-[bis[(4-methoxyphenyl)methyl]amino]-1-isoquinolyl]-2-oxo-cyclohex-3-ene-1-carboxylate

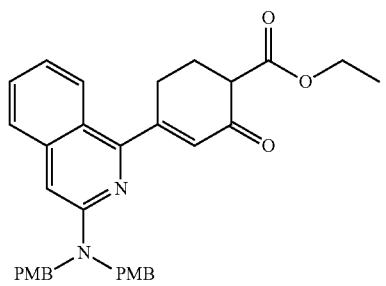

Under nitrogen, a solution of 3-[3-[bis[(4-methoxyphenyl)methyl]amino]-1-isoquinolyl]cyclohex-2-en-1-one (7.00 g, 14.63 mmol) in tetrahydrofuran (60 mL) was dropwise added lithium bis(trimethyslilyl)amide (58.5 mL, 58.51 mmol, 1.0 M in THF) and stirred for 1 hour at −78° C. Then ethyl cyanoformate (4.35 g, 43.88 mmol) was dropwise added and stirred at −78° C. for 1 hour. After completion, the reaction was quenched with aqueous saturated ammonium chloride. The reaction mixture was diluted with dichloromethane. The organic layer was washed with water, dried over anhydrous sodium sulfate and concentrated under vacuum. The residue was purified by flash chromatography on silica gel eluting with petroleum ether/ethyl acetate (8/1) to afford ethyl 4-[3-[bis[(4-methoxyphenyl)methyl]amino]-1-isoquinolyl]-2-oxo-cyclohex-3-ene-1-carboxylate (3.80 g, 6.35 mmol, 43.4% yield) as a red oil. LCMS (ESI, m/z): 551.2 [M+H]+.

Step 3: ethyl 4-[3-[bis[(4-methoxyphenyl)methyl]amino]-1-isoquinolyl]-2-oxo-cyclohexanecarboxylate

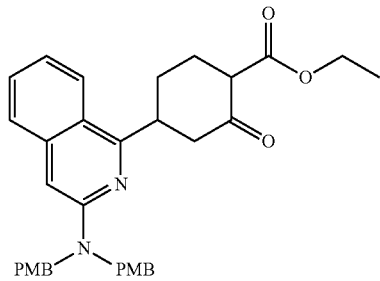

Under hydrogen, a solution of ethyl 4-[3-[bis[(4-methoxyphenyl)methyl]amino]-1-isoquinolyl]-2-oxo-cyclohex-3-ene-1-carboxylate (3.40 g, 6.17 mmol) in ethyl acetate (20 mL) was added Pd/C (1.00 g, 6.17 mmol) and stirred for 2 hours at 25° C. After filtration, the filtrate was concentrated under reduced pressure. The residue was purified by flash chromatography on silica gel eluting with petroleum ether/ethyl acetate (7:1) to afford ethyl 4-[3-[bis[(4-methoxyphenyl)methyl]amino]-1-isoquinolyl]-2-oxo-cyclohexanecarboxylate (1.80 g, 3.26 mmol, 47.5% yield) as a yellow oil. LCMS (ESI, m/z): 553.3 [M+H]+.

Step 4: 7-[3-[bis[(4-methoxyphenyl)methyl]amino]-1-isoquinolyl]-5,6,7,8-tetrahydro-3H-quinazolin-4-one

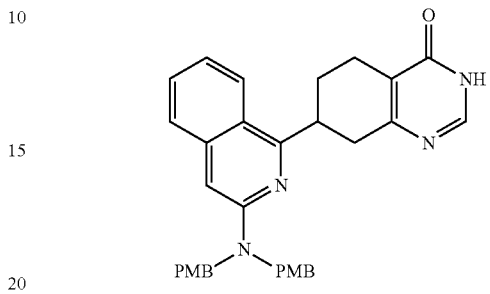

A solution of ethyl 4-[3-[bis[(4-methoxyphenyl)methyl]amino]-1-isoquinolyl]-2-oxo-cyclohexanecarboxylate (1.80 g, 3.26 mmol), sodium methoxide (1.76 g, 32.57 mmol) and formamidine acetate (2.03 g, 19.54 mmol) in methyl alcohol (10 mL) was stirred at 70° C. for 2 hours. After completion, the reaction was concentrated under vacuum. The residue was purified by flash chromatography on silica gel eluting with dichloromethane/methyl alcohol (10/1) to afford 7-[3-[bis[(4-methoxyphenyl)methyl]amino]-1-isoquinolyl]-5,6,7,8-tetrahydro-3H-quinazolin-4-one (0.70 g, 1.31 mmol, 37.1% yield) as a yellow oil. LCMS (ESI, m/z): 533.2 [M+H]+.

Step 5: 1-[4-[7-[3-[bis[(4-methoxyphenyl)methyl]amino]-1-isoquinolyl]-5,6,7,8-tetrahydroquinazolin-4-yl]piperazin-1-yl]prop-2-en-1-one

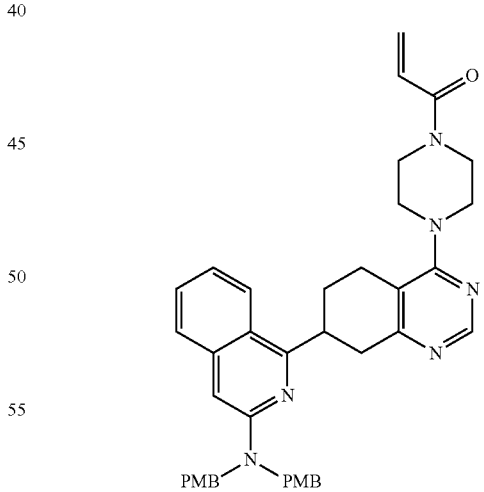

A solution of piperazine (0.57 g, 6.57 mmol), 7-[3-[bis[(4-methoxyphenyl)methyl]amino]-1-isoquinolyl]-5,6,7,8-tetrahydro-3H-quinazolin-4-one (0.70 g, 1.31 mmol), 1H-benzotriazol-1-yloxytris(dimethylamino)phosphonium hexafluorophosphate (0.87 g, 1.97 mmol) and 1,8-diazabicyclo[5.4.0]undec-7-ene (0.39 mL, 2.63 mmol) in chloroform (8 mL) was stirred at 70° C. for 2 hours. Then acryloyl chloride (0.36 g, 3.94 mmol) was dropwise added and stirred at room temperature for 30 minutes. After completion, the solution was concentrated under vacuum. The residue was purified by flash chromatography on silica gel eluting with dichloromethane/methyl alcohol (10/1) to afford 1-[4-[7-[3-[bis[(4-methoxyphenyl)methyl]amino]-1-isoquinolyl]-5,6,7,8-tetrahydroquinazolin-4-yl]piperazin-1-yl]prop-2-en-1-one (0.40 g, 0.42 mmol, 31.6% yield) as a yellow solid. LCMS (ESI, m/z): 655.3 [M+H]+.

Step 6: (R)-1-(4-(7-(3-aminoisoquinolin-1-yl)-5,6,7,8-tetrahydroquinazolin-4-yl)piperazin-1-yl)prop-2-en-1-one (Example 3a) and (S)-1-(4-(7-(3-aminoisoquinolin-1-yl)-5,6,7,8-tetrahydroquinazolin-4-yl)piperazin-1-yl)prop-2-en-1-one (Example 3b)

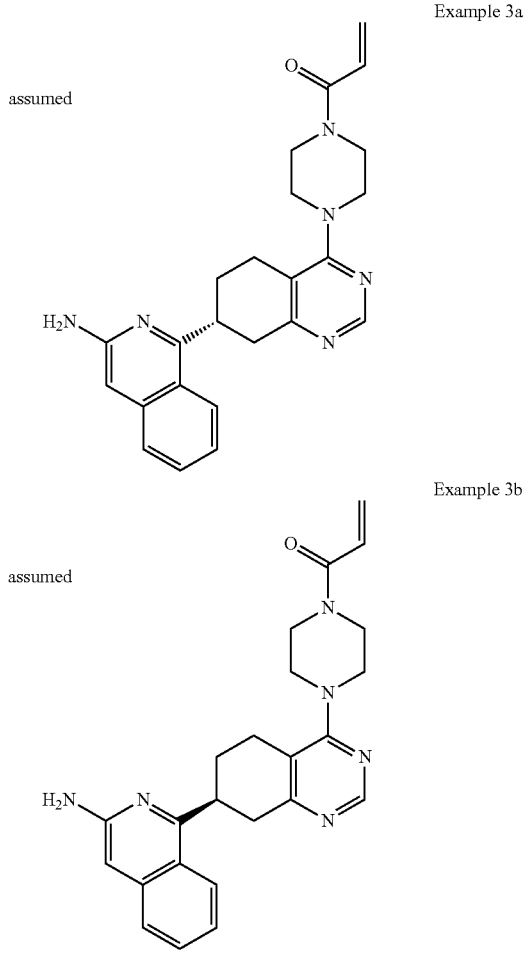

Example 3a

Example 3b

A solution of 1-[4-[7-[3-[bis[(4-methoxyphenyl)methyl]amino]-1-isoquinolyl]-5,6,7,8-tetrahydroquinazolin-4-yl]piperazin-1-yl]prop-2-en-1-one (0.40 g, 0.42 mmol) in trifluoroacetic acid (2 mL) and dichloromethane (4 mL) was stirred at 25° C. for 30 minutes. After completion, the solution was concentrated under vacuum. Then the crude was purified by Prep-HPLC with the following condition YMC-Actus Triart C18 Column 30×250 mm 5 um; Mobile Phase A: Water (10 mmol/1 ammonium bicarbonate), Mobile Phase B: acetonitrile; Flow rate: 60 mL/min; Gradient: 33% B to 52% B in 7 min; 254/220 nm; Rt: 5.77 min to afford the product. The mixture of enantiomer was separated by Prep-Chiral-HPLC with the following condition: Column: CHIRALPAK ID-03, 2.0 cm I.D*25 cm L (5 um); Mobile Phase A: hexane:dichloromethane=3:1 (10 mM NH3-MEOH)—HPLC, Mobile Phase B: IPA—HPLC; Flow rate: 18 mL/min; Gradient: 50 B to 50 B in 22 min; 220/254 nm; RT1:12.518; RT2:16.645 to afford the title compounds. The stereochemistry of the title compounds was assigned based on potency data.

Example 3a: (R)-1-(4-(7-(3-aminoisoquinolin-1-yl)-5,6,7,8-tetrahydroquinazolin-4-yl)piperazin-1-yl)prop-2-en-1-one (11.3 mg, 0.026 mmol, 6.4% yield, white solid). $^1$H NMR (300 MHz, Methanol-d$_4$, ppm) a 8.50 (s, 1H), 8.14 (d, J=8.5 Hz, 1H), 7.64-7.54 (m, 1H), 7.52-7.45 (m, 1H), 7.31-7.20 (m, 1H), 6.84 (dd, J=16.8, 10.6 Hz, 1H), 6.69 (d, J=0.9 Hz, 1H), 6.27 (dd, J=16.8, 2.0 Hz, 1H), 5.81 (dd, J=10.6, 2.0 Hz, 1H), 4.27-4.11 (m, 1H), 3.96-3.71 (m, 4H), 3.70-3.58 (m, 2H), 3.52-3.35 (m, 3H), 3.20-2.92 (m, 2H), 2.81-2.66 (m, 1H), 2.23 (d, J=13.0 Hz, 1H), 2.07-1.88 (m, 1H). LCMS (ESI, m/z): 415.2 [M+H]$^+$. Chiral HPLC: CHIRALPAK ID-3 (4.6*50 mm, 3 um); detected at 254 nm; n-hexane/IPA=50/50; flow: 1 mL/min; Retention time: 12.518 min (faster peak).

Example 3b: (S)-1-(4-(7-(3-aminoisoquinolin-1-yl)-5,6,7,8-tetrahydroquinazolin-4-yl)piperazin-1-yl)prop-2-en-1-one (11.5 mg, 0.028 mmol, 6.6% yield, white solid). $^1$H NMR (300 MHz, Methanol-d$_4$, ppm) a 8.50 (s, 1H), 8.14 (d, J=8.5 Hz, 1H), 7.64-7.54 (m, 1H), 7.52-7.45 (m, 1H), 7.31-7.20 (m, 1H), 6.84 (dd, J=16.8, 10.6 Hz, 1H), 6.69 (d, J=0.9 Hz, 1H), 6.27 (dd, J=16.8, 2.0 Hz, 1H), 5.81 (dd, J=10.6, 2.0 Hz, 1H), 4.27-4.11 (m, 1H), 3.96-3.71 (m, 4H), 3.70-3.58 (m, 2H), 3.52-3.35 (m, 3H), 3.20-2.92 (m, 2H), 2.81-2.66 (m, 1H), 2.23 (d, J=13.0 Hz, 1H), 2.07-1.88 (m, 1H). LCMS (ESI, m/z): 415.2 [M+H]$^+$. Chiral HPLC: CHIRALPAK ID-3 (4.6*50 mm, 3 um); detected at 254 nm; n-hexane/IPA=50/50; flow: 1 mL/min; Retention time: 16.645 min (slower peak).

Examples 4a and 4b

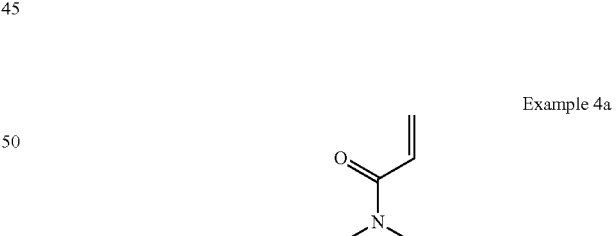
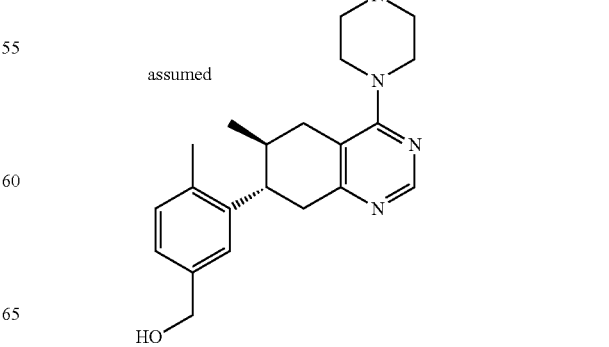

Example 4a

Example 4b
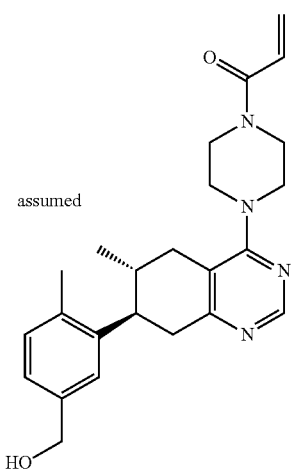
1-(4-((6S,7S)-7-(5-(hydroxymethyl)-2-methylphenyl)-6-methyl-5,6,7,8-tetrahydroquinazolin-4-yl)piperazin-1-yl)prop-2-en-1-one (Example 4a)
1-[4-[(6R,7R)-7-[5-(hydroxymethyl)-2-methyl-phenyl]-6-methyl-5,6,7,8-tetrahydroquinazolin-4-yl]piperazin-1-yl]prop-2-en-1-one (Example 4b)
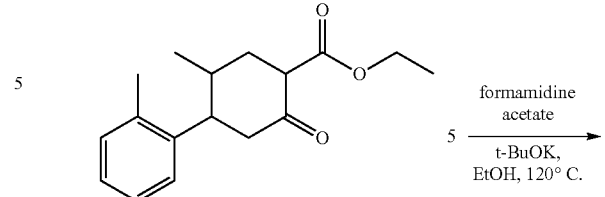
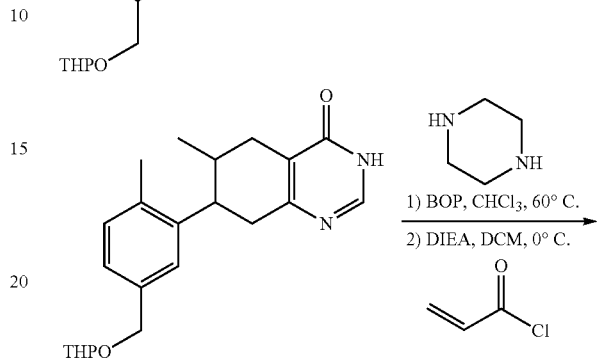
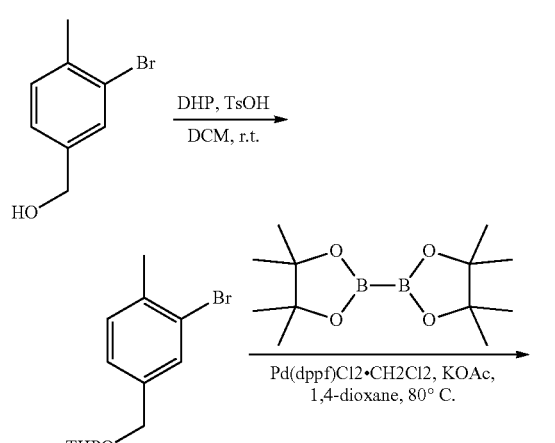
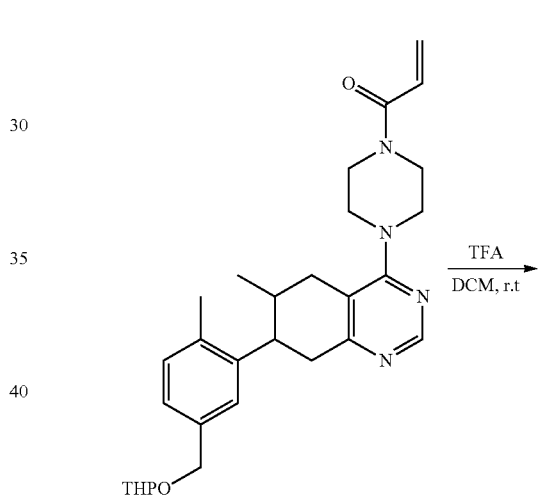
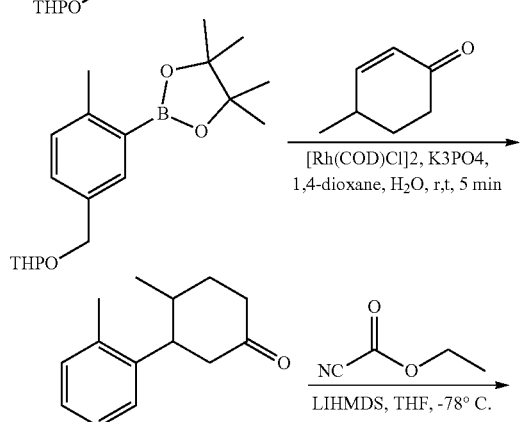
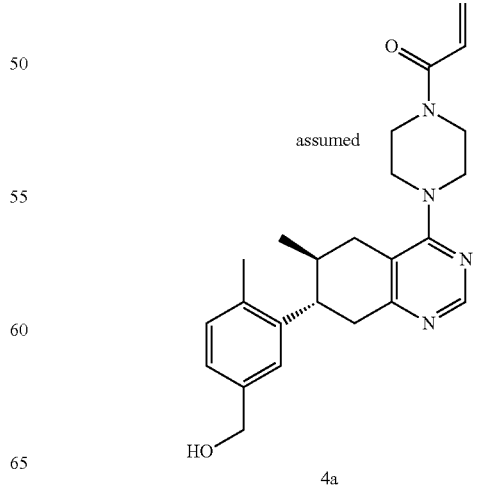

-continued

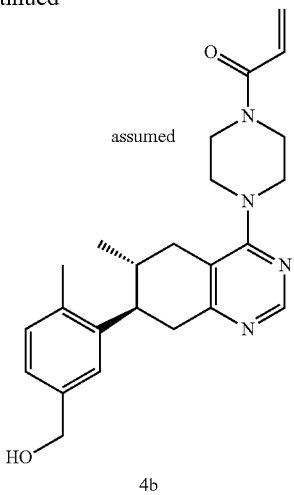

assumed

4b

Step 1: 2-[(3-bromo-4-methyl-phenyl)methoxy]tetrahydropyran

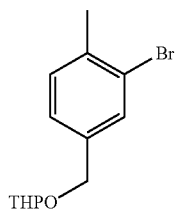

A solution of (3-bromo-4-methyl-phenyl)methanol (9.00 g, 44.76 mmol) and p-toluenesulfonic acid (3.85 g, 22.38 mmol) in dichloromethane (40 mL) was stirred at 25° C. for 10 minutes. Then 3,4-dihydro-2h-pyran (7.53 g, 89.53 mmol) was added and stirred at 25° C. for 30 minutes. After completion, the reaction was quenched with aqueous saturated sodium hydrogen carbonate and diluted with dichloromethane. The organic layer was washed with water, dried over anhydrous sodium sulfate and concentrated under vacuum. The residue was purified by flash chromatography on silica gel eluting with petroleumeum ether/ethyl acetate (10/1) to afford 2-[(3-bromo-4-methyl-phenyl)methoxy]tetrahydropyran (9.20 g, 30.64 mmol, 68.5% yield) as a colorless oil.

Step 2: 4,4,5,5-tetramethyl-2-[2-methyl-5-(tetrahydropyran-2-yloxymethyl)phenyl]-1,3,2-dioxaborolane

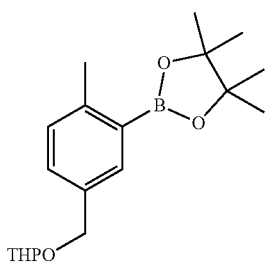

Under nitrogen, a solution of 2-[(3-bromo-4-methyl-phenyl)methoxy]tetrahydropyran (9.20 g, 30.64 mmol), bis(pinacolato)diboronm (16.4 g, 64.52 mmol), 1,1'-bis(diphenylphosphino)ferrocene-palladium(II)dichloride dichloromethane complex (2.63 g, 3.23 mmol) and potassium acetate (6.32 g, 64.52 mmol) in 1,4-dioxane (60 mL) was stirred for 40 minutes at 80° C. After completion, the reaction mixture was diluted with dichloromethane. The organic layer was washed with water, dried over anhydrous sodium sulfate and concentrated under vacuum. The residue was purified by flash chromatography on silica gel eluting with petroleumeum ether/ethyl acetate (10/1) to afford 4,4,5,5-tetramethyl-2-[2-methyl-5-(tetrahydropyran-2-yloxymethyl)phenyl]-1,3,2-dioxaborolane (9.00 g, 27.09 mmol, 79.8% yield) as a colorless oil.

Step 3: 4-methyl-3-[2-methyl-5-(tetrahydropyran-2-yloxymethyl)phenyl]cyclohexanone

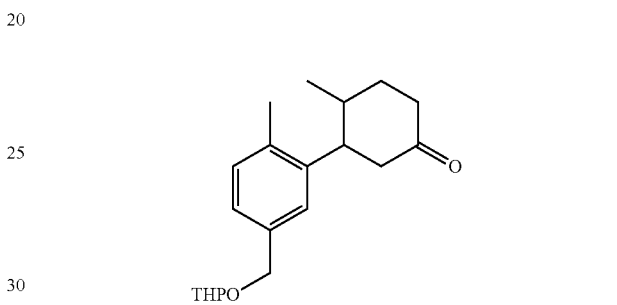

Under nitrogen, a solution of 4,4,5,5-tetramethyl-2-[2-methyl-5-(tetrahydropyran-2-yloxymethyl)phenyl]-1,3,2-dioxaborolane (9.00 g, 27.09 mmol), 4-methylcyclohex-2-en-1-one (3.28 g, 29.80 mmol) and chloro(1,5-cyclooctadiene)rhodium(I) dimer (1.34 g, 2.71 mmol) in 1,4-dioxane (50 mL) was added aqueous saturated potassium phosphate (10 mL) and stirred for 5 minutes at 25° C. After completion, the reaction mixture was concentrated under vacuum, diluted with dichloromethane and washed by water. The organic layer was dried over anhydrous sodium sulfate and concentrated under vacuum. The residue was purified by flash chromatography on silica gel eluting with petroleumeum ether/ethyl acetate (10/1) to afford 4-methyl-3-[2-methyl-5-(tetrahydropyran-2-yloxymethyl)phenyl]cyclohexanone (4.50 g, 14.22 mmol, 47.2% yield) as a light yellow oil. LCMS: (ESI, m/z): 317.2 [M+H]$^+$

Step 4: ethyl 5-methyl-4-[2-methyl-5-(tetrahydropyran-2-yloxymethyl)phenyl]-2-oxo-cyclohexanecarboxylate

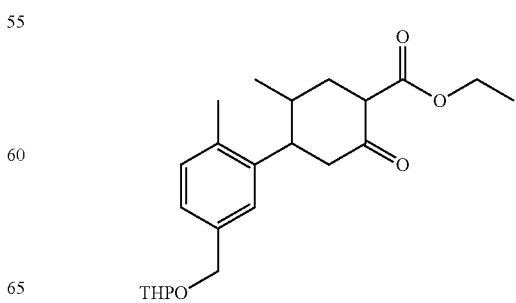

Under nitrogen, a solution of 4-methyl-3-[2-methyl-5-(tetrahydropyran-2-yloxymethyl)phenyl]cyclohexanone (4.50 g, 14.22 mmol) in tetrahydrofuran (70 mL) was dropwise added lithium bis(trimethylsilyl)amide (14.22 mL, 14.22 mmol, 1.0 M in tetrahydrofuran) and stirred for 10 minutes at −78° C. Then ethyl cyanoformate (1.69 g, 17.07 mmol) was dropwise added and stirred at −78° C. for 30 minutes. After completion, the reaction was quenched with water, concentrated under vacuum, diluted with dichloromethane and washed by water. The organic layer was dried over anhydrous sodium sulfate and concentrated under vacuum to afford the crude ethyl 5-methyl-4-[2-methyl-5-(tetrahydropyran-2-yloxymethyl)phenyl]-2-oxo-cyclohexanecarboxylate (5.00 g, crude) as a yellow oil. The crude product would be directly used in the next step without purification. LCMS: (ESI, m/z): 389.2 [M+H]$^+$ Step 5: 6-methyl-7-[2-methyl-5-(tetrahydropyran-2-yloxymethyl)phenyl]-5,6,7,8-tetrahydro-3H-quinazolin-4-one

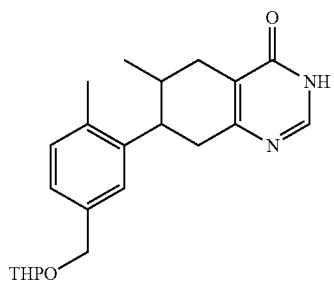

A solution of ethyl 5-methyl-4-[2-methyl-5-(tetrahydropyran-2-yloxymethyl)phenyl]-2-oxo-cyclohexanecarboxylate (3.00 g, 7.72 mmol), formamidine acetate (4.02 g, 38.61 mmol) and potassium tert-butoxide (6.07 g, 54.05 mmol) in ethanol (40 mL) was stirred at 120° C. for 1 hour. After completion, the reaction mixture was diluted with water, adjusted PH=7.0 with HCl/dioxane, concentrated under vacuum, extracted with ethyl acetate and the organic layers were combined. The organic layer was dried over anhydrous sodium sulfate and concentrated under vacuum. The residue was purified by flash chromatography on silica gel eluting with dichloromethane/ethyl acetate (3/1) to afford 6-methyl-7-[2-methyl-5-(tetrahydropyran-2-yloxymethyl)phenyl]-5,6,7,8-tetrahydro-3H-quinazolin-4-one (1.50 g, 3.74 mmol, 48.5% yield) as a white solid. LCMS: (ESI, m/z): 369.2 [M+H]$^+$ Step 6: 1-[4-[6-methyl-7-[2-methyl-5-(tetrahydropyran-2-yloxymethyl)phenyl]-5,6,7,8-tetrahydroquinazolin-4-yl]piperazin-1-yl]prop-2-en-1-one

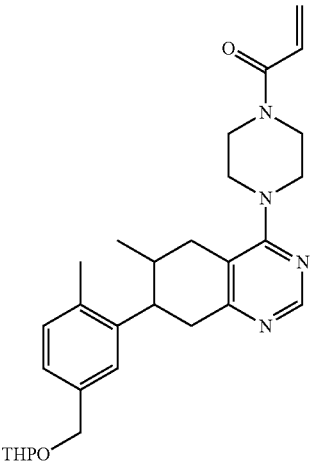

A solution of 6-methyl-7-[2-methyl-5-(tetrahydropyran-2-yloxymethyl)phenyl]-5,6,7,8-tetrahydro-3H-quinazolin-4-one (1.00 g, 2.71 mmol), piperazine (1.17 g, 13.57 mmol), benzotriazol-1-yloxy)tris(dimethylamino)phosphonium hexafluorophosphate (2.40 g, 5.430 mmol) and 1,8-diazabicyclo[5.4.0]undec-7-ene (1.24 g, 8.14 mmol) in chloroform (10 mL) was stirred at 60° C. for 1 hour. After completion, the reaction mixture was diluted with dichloromethane and washed by water. The organic layer was dried over anhydrous sodium sulfate and concentrated under vacuum to afford the crude product. Then a solution of the crude product and ethyldiisopropylamine (0.70 g, 5.43 mmol) in dichloromethane (10 mL) was stirred at room temperature. Then acryloyl chloride (0.25 g, 2.71 mmol) was dropwise added and stirred at room temperature for 20 minutes. After completion, the reaction was quenched with water, diluted with dichloromethane, washed with brine, dried over anhydrous sodium sulfate and concentrated under vacuum to afford the crude 1-[4-[6-methyl-7-[2-methyl-5-(tetrahydropyran-2-yloxymethyl)phenyl]-5,6,7,8-tetrahydroquinazolin-4-yl]piperazin-1-yl]prop-2-en-1-one (1.30 g, crude). The crude product would be directly used in the next step without purification. LCMS: (ESI, m/z): 491.3 [M+H]$^+$ Step 7: 1-(4-((6S,7S)-7-(5-(hydroxymethyl)-2-methylphenyl)-6-methyl-5,6,7,8-tetrahydroquinazolin-4-yl)piperazin-1-yl)prop-2-en-1-one (Example 4a) and 1-[4-[(6R,7R)-7-[5-(hydroxymethyl)-2-methyl-phenyl]-6-methyl-5,6,7,8-tetrahydroquinazolin-4-yl]piperazin-1-yl]prop-2-en-1-one (Example 4b)

4a

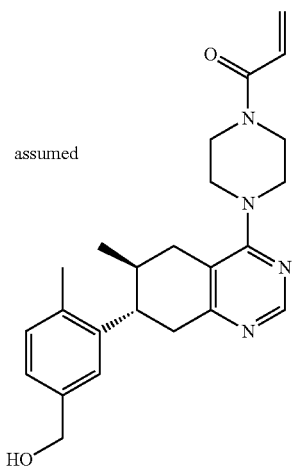

4b

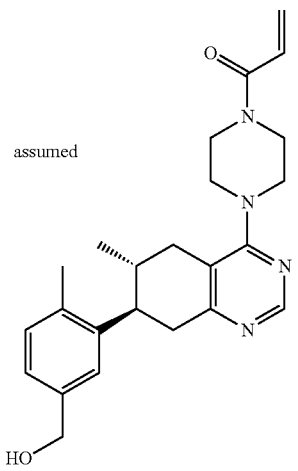

A solution of 1-[4-[6-methyl-7-[2-methyl-5-(tetrahydropyran-2-yloxymethyl)phenyl]-5,6,7,8-tetrahydroquinazolin-4-yl]piperazin-1-yl]prop-2-en-1-one (1.30 g, 2.65 mmol) in trifluoroacetic acid (2 mL) and 1,2-dichloroethane (5 mL) was stirred at 25° C. for 30 minutes. After completion, the reaction mixture was concentrated under vacuum, diluted with dichloromethane, washed with brine, dried over anhydrous sodium sulfate and concentrated under vacuum. The residue was purified by flash chromatography on silica gel eluting with dichloromethane/methanol (10/1) to afford the crude. Then the crude product was purified by Prep-HPLC with the following conditions: column: xbridge shield APP8 OBD column, 30*150 mm, 5 um; mobile phase A: water (10 mmol/L ammonium bicarbonate), mobile phase B: acetonitrile (0.1% diethylamine); flow rate: 60 mL/min; gradient: 23 B to 43 B in 7 min; 254 nm; RT: 6.18 min to afford the product. The mixture of enantiomer was separated by Chiral-Prep-HPLC with the following conditions: column: chiralpak ic, 2*25 cm, 5 um; mobile phase A: n-hexane/dichloromethane=3/1 (10 mM ammonia—methanol), mobile phase B: ethanol; flow rate: 40 mL/min; gradient: 30 B to 30 B in 19 min; 220/254 nm) to afford the title compounds. The absolute configuration of the title compounds was inferred from potency data and a protein X-ray structure of compound 21b.

Example 4a: 1-(4-((6S,7S)-7-(5-(hydroxymethyl)-2-methylphenyl)-6-methyl-5,6,7,8-tetrahydroquinazolin-4-yl)piperazin-1-yl)prop-2-en-1-one (57.5 mg, 0.14 mmol, 5.3% yield, white solid). $^1$H NMR (300 MHz, DMSO-d$_6$, ppm) 8.48 (s, 1H), 7.17 (s, 1H), 7.12 (d, J=7.8 Hz, 1H), 7.05 (dd, J=8.0, 1.6 Hz, 1H), 6.84 (dd, J=16.6, 10.4 Hz, 1H), 6.15 (dd, J=16.7, 2.4 Hz, 1H), 5.72 (dd, J=10.4, 2.5 Hz, 1H), 5.05 (t, J=5.7 Hz, 1H), 4.44 (d, J=5.7 Hz, 2H), 3.84-3.43 (m, 6H), 3.31-3.22 (m, 2H), 3.13-2.91 (m, 2H), 2.81-2.55 (m, 3H), 2.31 (s, 3H), 2.07-1.88 (m, 1H), 0.80 (d, J=6.4 Hz, 3H). LCMS: (ESI, m/z): 407.2 [M+H]$^+$. Chiral HPLC: CHIRALPAK IC-3 (4.6*50 mm, 3 um); detected at 254 nm; n-hexane/ethanol=70/30; flow: 1 mL/min; Retention time: 12.524 min(faster peak).

Example 4b: 1-[4-[(6R,7R)-7-[5-(hydroxymethyl)-2-methyl-phenyl]-6-methyl-5,6,7,8-tetrahydroquinazolin-4-yl]piperazin-1-yl]prop-2-en-1-one (52.7 mg, 0.13 mmol, 4.9% yield, white solid). $^1$H NMR (300 MHz, DMSO-d$_6$, ppm) 8.48 (s, 1H), 7.17 (s, 1H), 7.12 (d, J=7.8 Hz, 1H), 7.05 (dd, J=8.0, 1.6 Hz, 1H), 6.84 (dd, J=16.6, 10.4 Hz, 1H), 6.15 (dd, J=16.7, 2.4 Hz, 1H), 5.72 (dd, J=10.4, 2.5 Hz, 1H), 5.05 (t, J=5.7 Hz, 1H), 4.44 (d, J=5.7 Hz, 2H), 3.84-3.43 (m, 6H), 3.31-3.22 (m, 2H), 3.13-2.91 (m, 2H), 2.81-2.55 (m, 3H), 2.31 (s, 3H), 2.07-1.88 (m, 1H), 0.80 (d, J=6.4 Hz, 3H). LCMS: (ESI, m/z): 407.2 [M+H]$^+$. Chiral HPLC: CHIRALPAK IC-3 (4.6*50 mm, 3 um); detected at 254 nm; n-hexane/ethanol=70/30; flow: 1 mL/min; Retention time: 14.975 min (slower peak).

Examples 5a and 5b

Example 5a

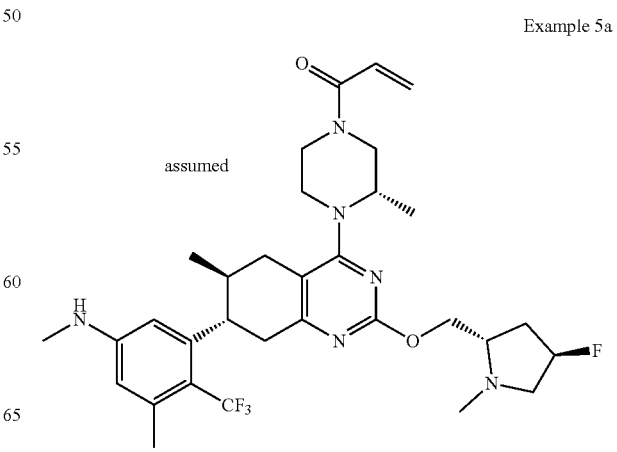

Example 5b
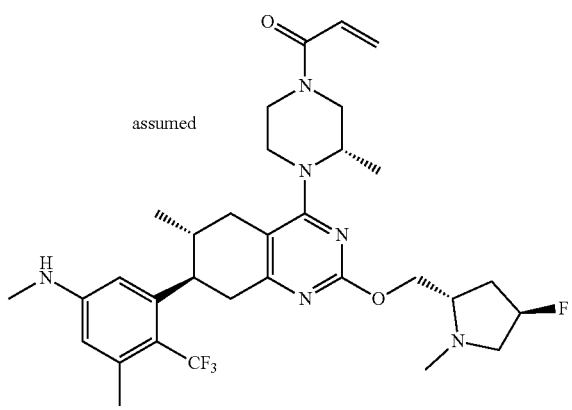
1-[(3S)-4-[(6S,7S)-2-[[(2S,4R)-4-fluoro-1-methyl-pyrrolidin-2-yl]methoxy]-6-methyl-7-[4-methyl-6-(methylamino)-3-(trifluoromethyl)-2-pyridyl]-5,6,7,8-tetrahydroquinazolin-4-yl]-3-methyl-piperazin-1-yl]prop-2-en-1-one (Example 5a)
1-[(3S)-4-[(6R,7R)-2-[[(2S,4R)-4-fluoro-1-methyl-pyrrolidin-2-yl]methoxy]-6-methyl-7-[4-methyl-6-(methylamino)-3-(trifluoromethyl)-2-pyridyl]-5,6,7,8-tetrahydroquinazolin-4-yl]-3-methyl-piperazin-1-yl]prop-2-en-1-one (Example 5b)
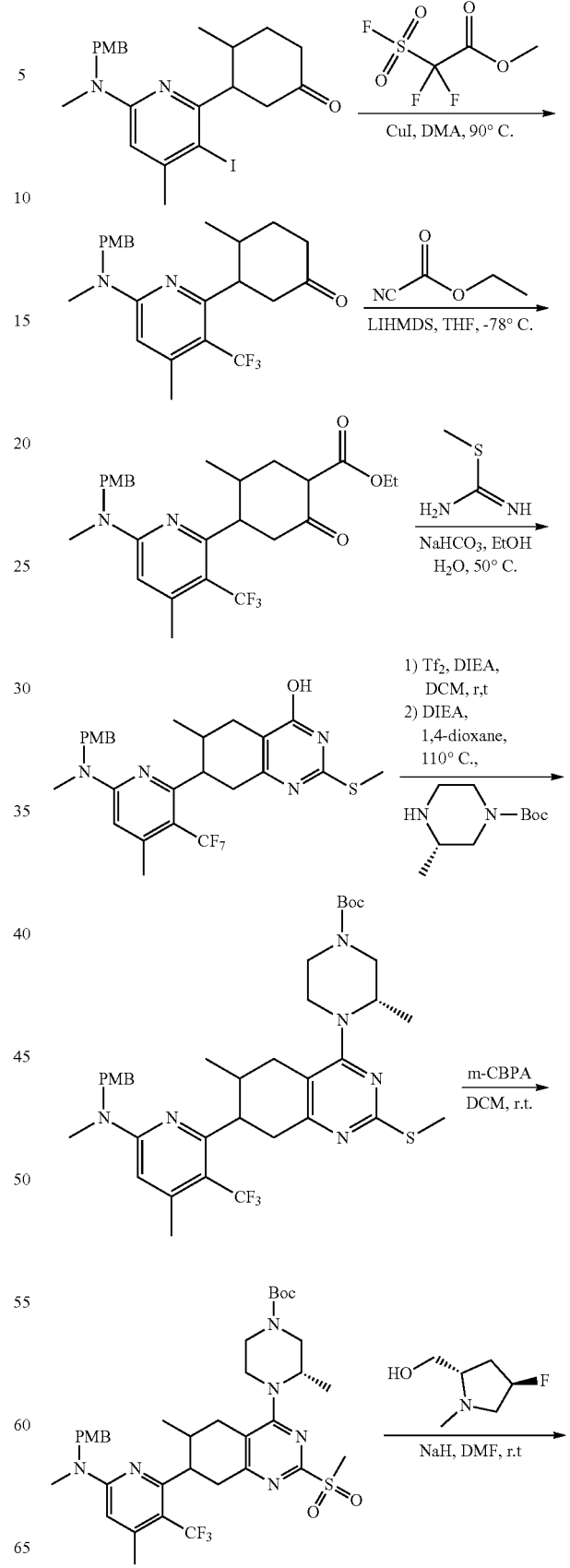

-continued

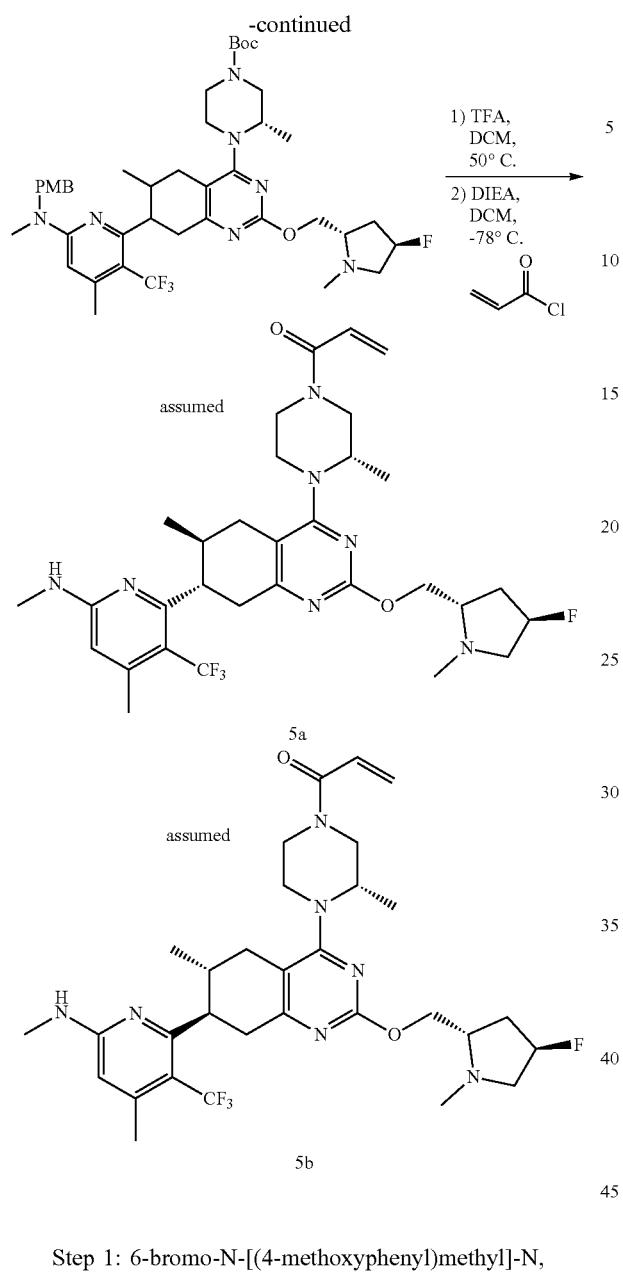

Step 1: 6-bromo-N-[(4-methoxyphenyl)methyl]-N,4-dimethyl-pyridin-2-amine

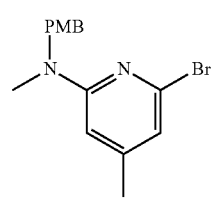

A solution of N-(4-methoxybenzyl)-N-methylamine (74.00 g, 489.90 mmol) and 2,6-dibromo-4-methylpyridine (41.00 g, 163.30 mmol) in dimethyl sulfoxide (100 mL) was stirred at 100° C. for 4 hours. After completion, the reaction mixture was diluted with water, extracted with ethyl acetate and the organic layers were combined. The organic layer was washed with brine, dried over anhydrous sodium sulfate and concentrated under vacuum. The residue was purified by flash chromatography on silica gel eluting with petroleumeum ether/ethyl acetate (8/1) to afford 6-bromo-N-[(4-methoxyphenyl)methyl]-N,4-dimethyl-pyridin-2-amine (44.00 g, 137.00 mmol, 80.8% yield) as a yellow oil. LC-MS: (ESI, m/z): 321.1 [M+H]⁺

Step 2: [6-[(4-methoxyphenyl)methyl-methyl-amino]-4-methyl-2-pyridyl]boronic acid

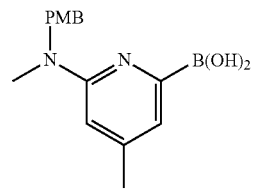

Under nitrogen, a solution of 6-bromo-N-[(4-methoxyphenyl)methyl]-N,4-dimethyl-pyridin-2-amine (44.00 g, 137.00 mmol) in tetrahydrofuran (150 mL) was dropwise added n-BuLi (98.69 mL, 246.70 mmol, 2.5 M in n-hexane) and stirred for 30 minutes at −78° C. Then triisopropyl borate (77.3 g, 411.2 mmol) was added and stirred at −78° C. for 60 minutes. After completion, the reaction mixture was concentrated under vacuum to afford the crude product. The crude product [6-[(4-methoxyphenyl)methyl-methyl-amino]-4-methyl-2-pyridyl]boronic acid (35.00 g, crude) would be directly used in the next step without purification. LC-MS: (ESI, m/z): 287.1 [M+H]⁺

Step 3: 3-[6-[(4-methoxyphenyl)methyl-methyl-amino]-4-methyl-2-pyridyl]-4-methyl-cyclohexanone

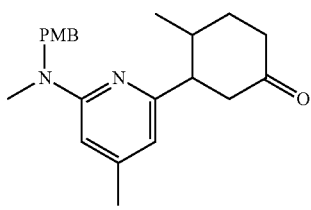

Under nitrogen, a solution of [6-[(4-methoxyphenyl)methyl-methyl-amino]-4-methyl-2-pyridyl]boronic acid (35.00 g, crude), 4-methylcyclohex-2-en-1-one (21.60 g, 182.9 mmol) and chloro(1,5-cyclooctadiene)rhodium(I) dimer (5.60 g, 12.19 mmol) in 1,4-dioxane (100 mL) was added aqueous saturated potassium phosphate (20 mL) and stirred for 4 hours at 25° C. After completion, the reaction mixture was concentrated under vacuum, diluted with dichloromethane, washed with brine, dried over anhydrous sodium sulfate and concentrated under vacuum. The residue was purified by flash chromatography on silica gel eluting with petroleumeum ether/ethyl acetate (5/1) to afford 3-[6-[(4-methoxyphenyl)methyl-methyl-amino]-4-methyl-2-pyridyl]-4-methyl-cyclohexanone (24.00 g, 68.18 mmol, 57.2% yield) as a yellow oil. LC-MS: (ESI, m/z): 353.2 [M+H]⁺

Step 4: 3-[3-iodo-6-[(4-methoxyphenyl)methyl-methyl-amino]-4-methyl-2-pyridyl]-4-methyl-cyclohexanone

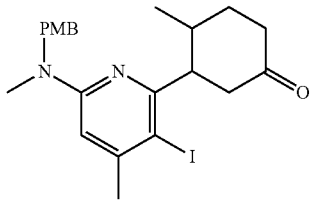

A solution of 3-[6-[(4-methoxyphenyl)methyl-methyl-amino]-4-methyl-2-pyridyl]-4-methyl-cyclohexanone (24.00 g, 68.18 mmol) and N-iodosuccinimide (22.90 g, 102.30 mmol) in acetonitrile (80 mL) was stirred at 25° C. for 60 minutes. After completion, the reaction mixture was concentrated under vacuum. The residue was purified by flash chromatography on silica gel eluting with petroleumeum ether/ethyl acetate (3/1) to afford 3-[3-iodo-6-[(4-methoxyphenyl)methyl-methyl-amino]-4-methyl-2-pyridyl]-4-methyl-cyclohexanone (14.00 g, 29.28 mmol, 43.07% yield) as a yellow oil. LC-MS: (ESI, m/z): 479.1 $[M+H]^+$

Step 5: 3-[6-[(4-methoxyphenyl)methyl-methyl-amino]-4-methyl-3-(trifluoromethyl)-2-pyridyl]-4-methyl-cyclohexanone

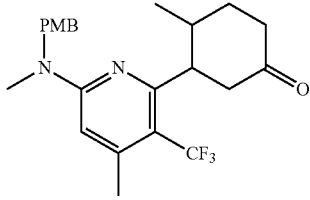

Under nitrogen, a solution of 3-[3-iodo-6-[(4-methoxyphenyl)methyl-methyl-amino]-4-methyl-2-pyridyl]-4-methyl-cyclohexanone (14.00 g, 29.28 mmol), methyl-2,2-difluoro-2-(fluorosulfonyl)acetate (28.10 g, 146.30 mmol) and copper (I) iodide (16.70 g, 87.80 mmol) in N,N-dimethylacetamide (50 mL) was stirred for 5 hours at 90° C. After filtration, the filtrate was collected, diluted with water, extracted with ethyl acetate and the organic layers were combined. The organic layer was washed with brine, dried over anhydrous sodium sulfate and concentrated under vacuum. The residue was purified by flash chromatography on silica gel eluting with petroleumeum ether/ethyl acetate (3/1) to afford 3-[6-[(4-methoxyphenyl)methyl-methyl-amino]-4-methyl-3-(trifluoromethyl)-2-pyridyl]-4-methyl-cyclohexanone (9.00 g, 20.33 mmol, 69.5% yield) as a yellow oil. LC-MS: (ESI, m/z): 421.2 $[M+H]^+$

Step 6: ethyl 4-[6-[(4-methoxyphenyl)methyl-methyl-amino]-4-methyl-3-(trifluoromethyl)-2-pyridyl]-5-methyl-2-oxo-cyclohexanecarboxylate

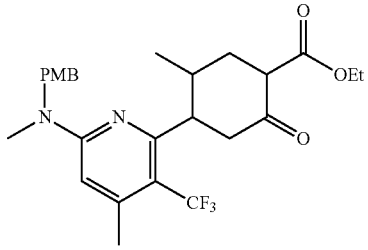

Under nitrogen, a solution of 3-[6-[(4-methoxyphenyl)methyl-methyl-amino]-4-methyl-3-(trifluoromethyl)-2-pyridyl]-4-methyl-cyclohexanone (9.00 g, 21.40 mmol) in tetrahydrofuran (50 mL) was dropwise added lithium bis(trimethylsilyl)amide (32.1 mL, 32.11 mmol, 1.0 M in tetrahydrofuran) and stirred for 20 minutes at −78° C. Then ethyl cyanoformate (2.55 g, 25.69 mmol) was added and stirred at −78° C. for 50 minutes. After completion, the reaction was quenched with water, concentrated under vacuum, diluted with dichloromethane, washed with brine, dried over anhydrous sodium sulfate and concentrated under vacuum to afford the crude product ethyl 4-[6-[(4-methoxyphenyl)methyl-methyl-amino]-4-methyl-3-(trifluoromethyl)-2-pyridyl]-5-methyl-2-oxo-cyclohexanecarboxylate (12.00 g, crude) that would be directly used in the next step without purification. LC-MS: (ESI, m/z): 493.2 $[M+H]^+$

Step 7: 7-[6-[(4-methoxyphenyl)methyl-methyl-amino]-4-methyl-3-(trifluoromethyl)-2-pyridyl]-6-methyl-2-methylsulfanyl-5,6,7,8-tetrahydroquinazolin-4-ol

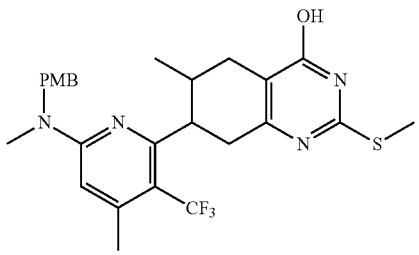

A solution of ethyl 4-[6-[(4-methoxyphenyl)methyl-methyl-amino]-4-methyl-3-(trifluoromethyl)-2-pyridyl]-5-methyl-2-oxo-cyclohexanecarboxylate (12.00 g, 15.84 mmol), 2-methylisothiourea (14.30 g, 158.4 mmol) and sodium bicarbonate (33.30 g, 395.90 mmol) in ethanol (60 mL) and water (12 mL) was stirred at 50° C. for 5 hours. After completion, the reaction mixture was concentrated under vacuum, diluted with dichloromethane, washed with brine, dried over anhydrous sodium sulfate and concentrated under vacuum. The residue was purified by flash chromatography on silica gel eluting with dichloromethane/ethyl acetate (1/1) to afford 7-[6-[(4-methoxyphenyl)methyl-methyl-amino]-4-methyl-3-(trifluoromethyl)-2-pyridyl]-6-methyl-2-methylsulfanyl-5,6,7,8-tetrahydroquinazolin-4-ol (3.80 g, 7.33 mmol, 44% yield) as a white solid. LC-MS: (ESI, m/z): 519.2 $[M+H]^+$ Step 8: tert-butyl (3S)-4-[7-[6-[(4-methoxyphenyl)methyl-methyl-amino]-4-methyl-3-(trifluoromethyl)-2-pyridyl]-6-methyl-2-methylsulfanyl-5,6,7,8-tetrahydroquinazolin-4-yl]-3-methyl-piperazine-1-carboxylate

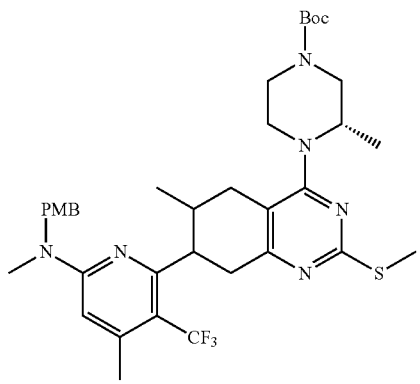

A solution of 7-[6-[(4-methoxyphenyl)methyl-methyl-amino]-4-methyl-3-(trifluoromethyl)-2-pyridyl]-6-methyl-2-methylsulfanyl-5,6,7,8-tetrahydroquinazolin-4-ol (3.80 g, 7.33 mmol), N,N-diisopropylethylamine (4.73 g, 36.64 mmol) in dichloromethane (15 mL) was added trifluoromethanesulfonic anhydride (3.72 g, 13.19 mmol) and stirred at room temperature for 30 minutes. After completion, the reaction mixture was concentrated under vacuum to afford the crude. Then a solution of the crude product and tert-butyl (3S)-3-methyl-1-piperazinecarboxylate (14.68 g, 73.28 mmol) in 1,4-dioxane (10 mL) was stirred at 110° C. for 5 hours. After completion, the reaction mixture was concentrated under vacuum. The residue was purified by flash chromatography on silica gel eluting with dichloromethane/ethyl acetate (5/1) to afford tert-butyl (3S)-4-[7-[6-[(4-methoxyphenyl)methyl-methyl-amino]-4-methyl-3-(trifluoromethyl)-2-pyridyl]-6-methyl-2-methylsulfanyl-5,6,7,8-tetrahydroquinazolin-4-yl]-3-methyl-piperazine-1-carboxylate (4.00 g, 5.71 mmol, 71.7% yield) as a white solid. LC-MS: (ESI, m/z): 701.3 [M+H]$^+$ Step 9: tert-butyl (3S)-4-[7-[6-[(4-methoxyphenyl)methyl-methyl-amino]-4-methyl-3-(trifluoromethyl)-2-pyridyl]-6-methyl-2-methylsulfonyl-5,6,7,8-tetrahydroquinazolin-4-yl]-3-methyl-piperazine-1-carboxylate

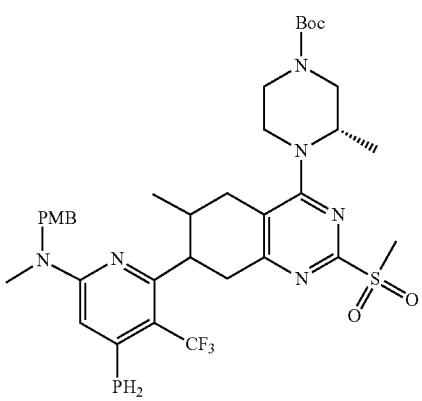

A solution of tert-butyl (3S)-4-[7-[6-[(4-methoxyphenyl)methyl-methyl-amino]-4-methyl-3-(trifluoromethyl)-2-pyridyl]-6-methyl-2-methylsulfanyl-5,6,7,8-tetrahydroquinazolin-4-yl]-3-methyl-piperazine-1-carboxylate (4.00 g, 5.71 mmol) and 3-chloroperoxybenzoic acid (1.97 g, 11.41 mmol) in dichloromethane (20 mL) was stirred at 25° C. for 30 minutes. After completion, the reaction mixture was quenched by aqueous saturated sodium bisulfite, diluted with dichloromethane, washed with brine, dried over anhydrous sodium sulfate and concentrated under vacuum to afford tert-butyl (3S)-4-[7-[6-[(4-methoxyphenyl)methyl-methyl-amino]-4-methyl-3-(trifluoromethyl)-2-pyridyl]-6-methyl-2-methylsulfonyl-5,6,7,8-tetrahydroquinazolin-4-yl]-3-methyl-piperazine-1-carboxylate (5.00 g, crude) as a yellow oil. LC-MS: (ESI, m/z): 733.3 [M+H]$^+$ Step 10: tert-butyl (3S)-4-[2-[[(2S,4R)-4-fluoro-1-methyl-pyrrolidin-2-yl]methoxy]-7-[6-[(4-methoxyphenyl)methyl-methyl-amino]-4-methyl-3-(trifluoromethyl)-2-pyridyl]-6-methyl-5,6,7,8-tetrahydroquinazolin-4-yl]-3-methyl-piperazine-1-carboxylate

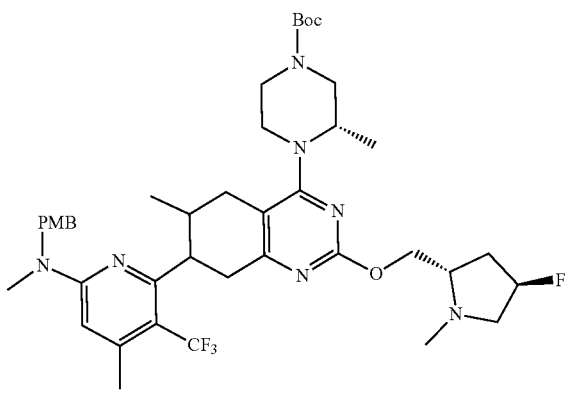

A solution of [(2S,4R)-4-fluoro-1-methyl-pyrrolidin-2-yl]methanol (1.83 g, 13.71 mmol) in N,N-dimethylformamide (20 mL) was added sodium hydride (0.44 g, 14.67 mmol, 60% dispersion in mineral oil) and stirred at 0° C. for 10 minutes. Then tert-butyl (3S)-4-[7-[6-[(4-methoxyphenyl)methyl-methyl-amino]-4-methyl-3-(trifluoromethyl)-2-pyridyl]-6-methyl-2-methylsulfonyl-5,6,7,8-tetrahydroquinazolin-4-yl]-3-methyl-piperazine-1-carboxylate (5.00 g, 4.57 mmol) was added and stirred at 0° C. for 30 minutes. After completion, the reaction mixture was quenched by water, extracted with ethyl acetate, dried over anhydrous sodium sulfate and concentrated under vacuum. The residue was purified by flash chromatography on silica gel eluting with dichloromethane/methanol (10/1) to afford tert-butyl (3S)-4-[2-[[(2S,4R)-4-fluoro-1-methyl-pyrrolidin-2-yl]methoxy]-7-[6-[(4-methoxyphenyl)methyl-methyl-amino]-4-methyl-3-(trifluoromethyl)-2-pyridyl]-6-methyl-5,6,7,8-tetrahydroquinazolin-4-yl]-3-methyl-piperazine-1-carboxylate (1.80 g, 2.06 mmol, 45.1% yield) as a white solid. LC-MS: (ESI, m/z): 786.4 [M+H]$^+$ Step 11: 1-[(3S)-4-[(6S,7S)-2-[[(2S,4R)-4-fluoro-1-methyl-pyrrolidin-2-yl]methoxy]-6-methyl-7-[4-methyl-6-(methylamino)-3-(trifluoromethyl)-2-pyridyl]-5,6,7,8-tetrahydroquinazolin-4-yl]-3-methyl-piperazin-1-yl]prop-2-en-1-one (Example 5a); 1-[(3S)-4-[(6R,7R)-2-[[(2S,4R)-4-fluoro-1-methyl-pyrrolidin-2-yl]methoxy]-6-methyl-7-[4-methyl-6-(methylamino)-3-(trifluoromethyl)-2-pyridyl]-5,6,7,8-tetrahydroquinazolin-4-yl]-3-methyl-piperazin-1-yl]prop-2-en-1-one (Example 5b)

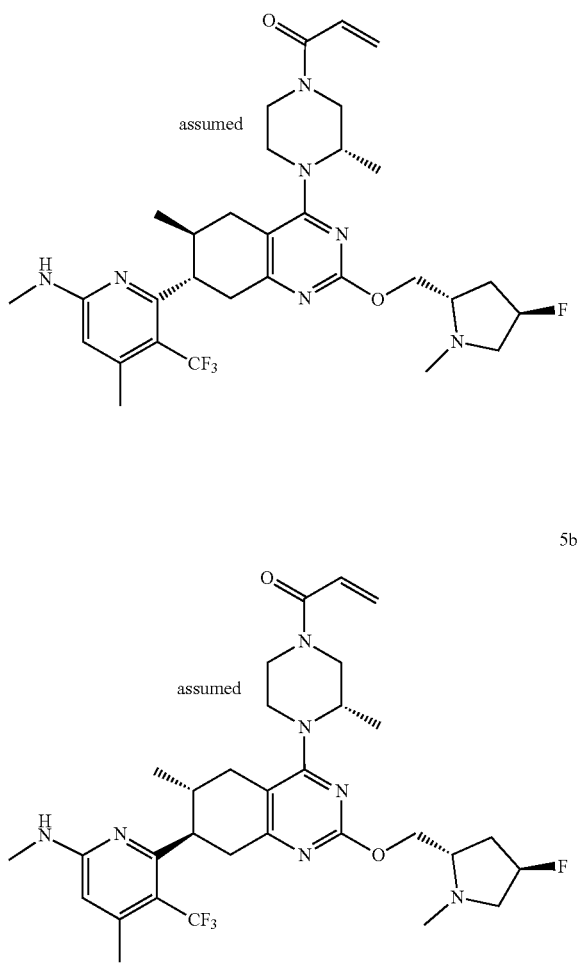

A solution of tert-butyl (3S)-4-[2-[[(2S,4R)-4-fluoro-1-methyl-pyrrolidin-2-yl]methoxy]-7-[6-[(4-methoxyphenyl)methyl-methyl-amino]-4-methyl-3-(trifluoromethyl)-2-pyridyl]-6-methyl-5,6,7,8-tetrahydroquinazolin-4-yl]-3-methyl-piperazine-1-carboxylate (1.00 g, 1.270 mmol) in trifluoroacetic acid (8 mL) was stirred at 50° C. for 20 minutes. After completion, the reaction mixture was concentrated under vacuum. The crude product 6-[2-[[(2S,4R)-4-fluoro-1-methyl-pyrrolidin-2-yl]methoxy]-6-methyl-4-[(2S)-2-methylpiperazin-1-yl]-5,6,7,8-tetrahydroquinazolin-7-yl]-N,4-dimethyl-5-(trifluoromethyl)pyridin-2-amine (1.50 g, crude) would be directly used in the next step without purification. Then a solution of 6-[2-[[(2S,4R)-4-fluoro-1-methyl-pyrrolidin-2-yl]methoxy]-6-methyl-4-[(2S)-2-methylpiperazin-1-yl]-5,6,7,8-tetrahydroquinazolin-7-yl]-N,4-dimethyl-5-(trifluoromethyl)pyridin-2-amine (1.50 g, crude) and N,N-diisopropylethylamine (0.77 g, 5.97 mmol) in dichloromethane (10 mL) was stirred at −78° C. Then acryloyl chloride (0.110 g, 1.190 mmol) was added and stirred at −78° C. for 30 minutes. After completion, the reaction mixture was quenched with water, diluted with dichloromethane, washed with brine, dried over anhydrous sodium sulfate and concentrated under vacuum. The residue was purified by flash chromatography on silica gel eluting with dichloromethane/methanol (10/1) to afford the product. The crude product was purified by Prep-HPLC with the following conditions: Column: XBridge Prep OBD C18 Column, 30×150 mm 5 um; Mobile Phase A: water (10 mmol/L ammonium bicarbonate), Mobile Phase B: acetonitrile; Flow rate: 60 mL/min; Gradient: 45 B to 75 B in 7 min; 254 nm; RT: 5.67 min to afford the desired product. The mixture of diasteroisomer was separated by Prep-Chiral-HPLC with the following condition: Column: CHIRALPAK IF, 2*25 cm, 5 um; Mobile Phase A: hexane (8 mmol/L ammonia. methanol)—HPLC, Mobile Phase B: ethanol—HPLC; Flow rate: 20 mL/min; Gradient: 15 B to 15 B in 33 min; 254/220 nm; Injection Volumn: 0.5 ml; Number Of Runs: 14 to afford the title compounds. The absolute configuration of the title compounds was inferred from potency data and a protein X-ray structure of compound 21b.

Example 5a: 1-[(3S)-4-[(6S,7S)-2-[[(2S,4R)-4-fluoro-1-methyl-pyrrolidin-2-yl]methoxy]-6-methyl-7-[4-methyl-6-(methylamino)-3-(trifluoromethyl)-2-pyridyl]-5,6,7,8-tetrahydroquinazolin-4-yl]-3-methyl-piperazin-1-yl]prop-2-en-1-one (96.2 mg, 0.15 mmol, 13% yield, white solid). $^1$H NMR (300 MHz, DMSO-$d_6$, ppm) δ 6.97 (q, J=4.6 Hz, 1H), 6.92-6.72 (m, 1H), 6.25-6.10 (m, 2H), 5.72 (dd, J=10.3, 2.4 Hz, 1H), 5.19 (d, J=27.0, 1H), 4.47-3.76 (m, 6H), 3.55-3.37 (m, 3H), 3.23-3.04 (m, 3H), 3.03-2.84 (m, 2H), 2.82-2.62 (m, 4H), 2.50-2.36 (m, 5H), 2.30 (s, 3H), 2.22-2.01 (m, 2H), 1.99-1.74 (m, 1H), 1.24 (brs, 3H), 0.74 (d, J=6.3 Hz, 3H). LC-MS: (ESI, m/z): 620.3 [M+H]$^+$. Chiral HPLC: CHIRALPAK IG-3 (4.6*50 mm, 3 um); detected at 254 nm; n-hexane/ethanol=90/10; flow: 1 mL/min; Retention time: 15.5 min (slower peak).

Example 5b: 1-[(3S)-4-[(6R,7R)-2-[[(2S,4R)-4-fluoro-1-methyl-pyrrolidin-2-yl]methoxy]-6-methyl-7-[4-methyl-6-(methylamino)-3-(trifluoromethyl)-2-pyridyl]-5,6,7,8-tetrahydroquinazolin-4-yl]-3-methyl-piperazin-1-yl]prop-2-en-1-one (101.8 mg, 0.16 mmol, 13.6% yield, white solid). $^1$H NMR (300 MHz, DMSO-$d_6$, ppm) δ 6.96 (q, J=4.5 Hz, 1H), 6.91-6.73 (m, 1H), 6.25-6.11 (m, 2H), 5.72 (dd, J=10.4, 2.4 Hz, 1H), 5.21 (d, J=25.5 Hz, 1H), 4.39-3.54 (m, 6H), 3.53-3.35 (m, 3H), 3.21-2.97 (m, 3H), 2.95-2.68 (m, 6H), 2.62-2.52 (m, 1H), 2.48-2.42 (m, 1H), 2.38 (s, 3H), 2.31 (s, 3H), 2.21-1.71 (m, 3H), 0.98 (d, J=7.1 Hz, 3H), 0.74 (d, J=6.3 Hz, 3H). LC-MS: (ESI, m/z): 620.3 [M+H]$^+$. Chiral HPLC: CHIRALPAK IG-3 (4.6*50 mm, 3 um); detected at 254 nm; n-hexane/ethanol=90/10; flow: 1 mL/min; Retention time: 12.0 min (faster peak).

Examples 6a and 6b
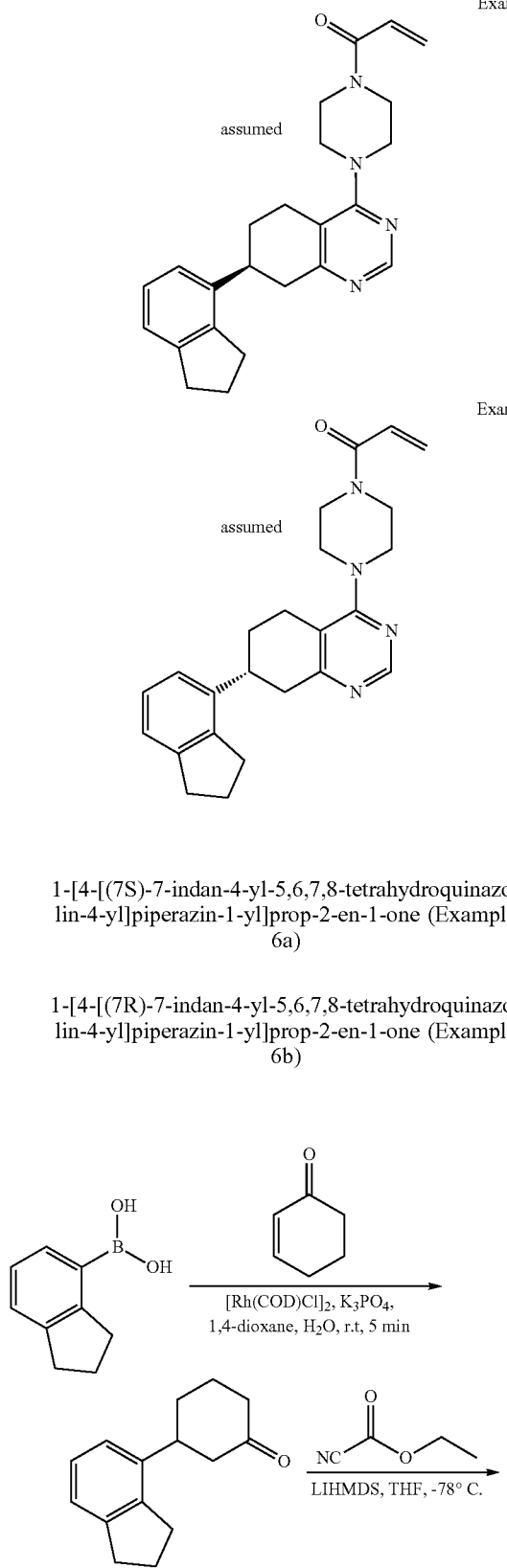
1-[4-[(7S)-7-indan-4-yl-5,6,7,8-tetrahydroquinazolin-4-yl]piperazin-1-yl]prop-2-en-1-one (Example 6a)
1-[4-[(7R)-7-indan-4-yl-5,6,7,8-tetrahydroquinazolin-4-yl]piperazin-1-yl]prop-2-en-1-one (Example 6b)
-continued
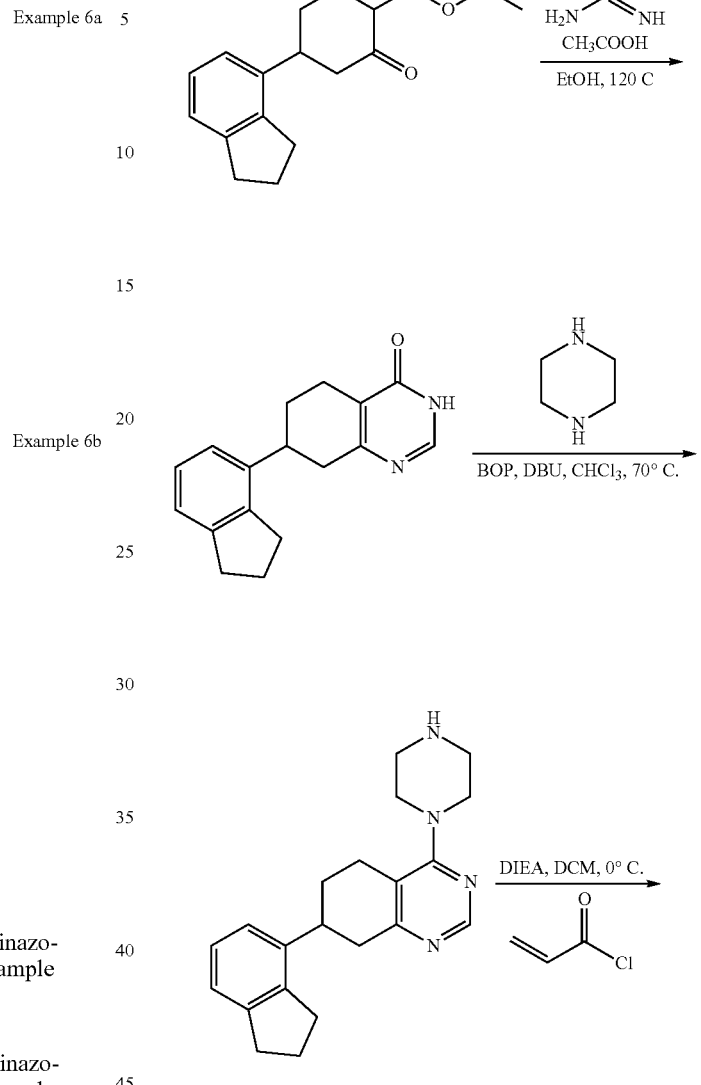
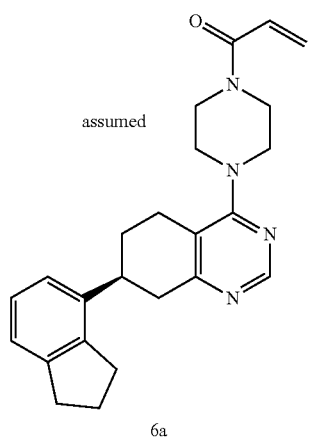
6a assumed

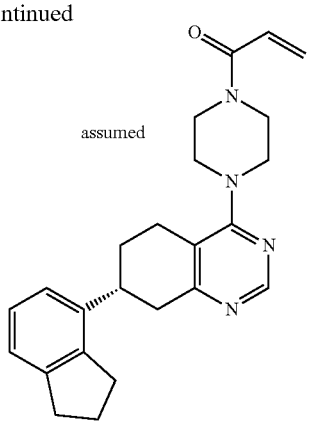

6b

Step 1: 3-indan-4-ylcyclohexanone

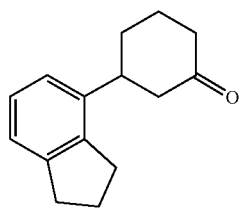 [SMILES: O=C1CCCC(c2cccc3c2CCC3)C1]

Under nitrogen, a solution of indan-4-ylboronic acid (10.0 g, 40.13 mmol), 2-cyclohexen-1-one (19.30 g, 200.60 mmol) and chloro(1,5-cyclooctadiene)rhodium(I) dimer (1.98 g, 4.01 mmol) in 1,4-dioxane (30 mL) was added aqueous saturated potassium phosphate (6 mL) and stirred for 30 minutes at 25° C. After completion, the reaction mixture was diluted with dichloromethane, washed with brine, dried over anhydrous sodium sulfate and concentrated under vacuum. The residue was purified by flash chromatography on silica gel eluting with petroleumeum ether/ethyl acetate (5/1) to afford 3-indan-4-ylcyclohexanone (4.50 g, 19.73 mmol, 49.2% yield) as yellow oil. LC-MS: (ESI, m/z): 215.1 [M+H]$^+$ Step 2: ethyl 4-indan-4-yl-2-oxo-cyclohexanecarboxylate

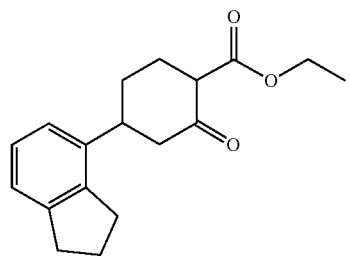 [SMILES: CCOC(=O)C1CCC(c2cccc3c2CCC3)CC1=O]

Under nitrogen, a solution of 3-indan-4-ylcyclohexanone (2.00 g, 9.33 mmol) in tetrahydrofuran (15 mL) was dropwise added lithium bis(trimethylsilyl)amide (12.1 mL, 12.13 mmol, 1.0 M in tetrahydrofuran) and stirred for 20 minutes at −78° C. Then ethyl cyanoformate (1.11 g, 11.20 mmol) was dropwise added and stirred at −78° C. for 30 minutes. After completion, the reaction mixture was quenched with water, diluted with dichloromethane, washed with brine, dried over anhydrous sodium sulfate and concentrated under vacuum to afford the crude ethyl 4-indan-4-yl-2-oxo-cyclohexanecarboxylate (2.00 g, 5.59 mmol, 59.9% yield) as a yellow oil. LC-MS: (ESI, m/z): 287.2 [M+H]$^+$ Step 3: 7-indan-4-yl-5,6,7,8-tetrahydro-3H-quinazolin-4-one

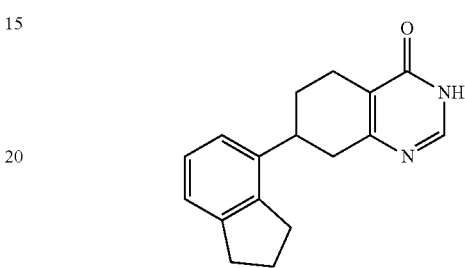

A solution of ethyl 4-indan-4-yl-2-oxo-cyclohexanecarboxylate (2.00 g, 5.59 mmol), formamidine acetate (2.91 g, 27.94 mmol) and sodium tert-butoxide (3.76 g, 39.11 mmol) in ethanol (20 mL) was stirred at 120° C. for 3 hours. After completion, the reaction mixture was concentrated under vacuum. The residue was purified by flash chromatography on silica gel eluting with dichloromethane/ethyl acetate (5/1) to afford 7-indan-4-yl-5,6,7,8-tetrahydro-3H-quinazolin-4-one (0.80 g, 3.01 mmol, 51.1% yield) as a white solid. LC-MS: (ESI, m/z): 267.1 [M+H]$^+$ Step 4: 7-indan-4-yl-4-piperazin-1-yl-5,6,7,8-tetrahydroquinazoline

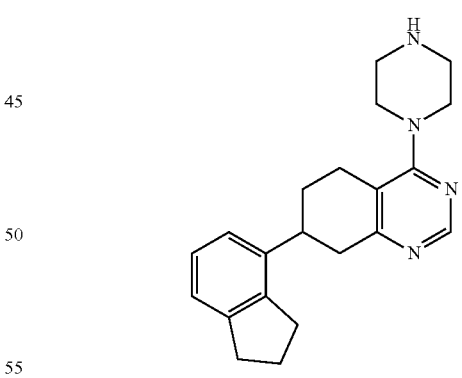

A solution of 7-indan-4-yl-5,6,7,8-tetrahydro-3H-quinazolin-4-one (0.78 g, 2.93 mmol), piperazine (1.26 g, 14.64 mmol), 1,8-diazabicyclo[5.4.0]undec-7-ene (1.34 g, 8.79 mmol) and benzotriazol-1-yloxy)tris(dimethylamino)phosphonium hexafluorophosphate (2.59 g, 5.86 mmol) in chloroform (10 mL) was stirred at 70° C. for 2 hours. After completion, the reaction mixture was concentrated under vacuum. The crude product was purified by reverse-phase to afford the desired product 7-indan-4-yl-4-piperazin-1-yl-5,6,7,8-tetrahydroquinazoline (0.64 g, 1.91 mmol, 53.6% yield) as a white solid. LC-MS: (ESI, m/z): 335.2 [M+H]$^+$ Step 5: 1-[4-[(7S)-7-indan-4-yl-5,6,7,8-tetrahydro-quinazolin-4-yl]piperazin-1-yl]prop-2-en-1-one (Example 6a); 1-[4-[(7R)-7-indan-4-yl-5,6,7,8-tetrahydroquinazolin-4-yl]piperazin-1-yl]prop-2-en-1-one (Example 6b)

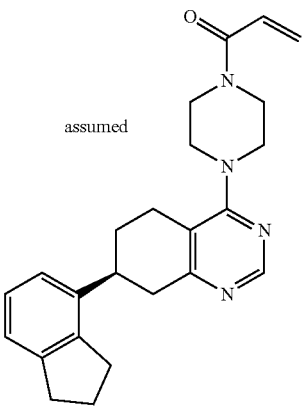

6a assumed

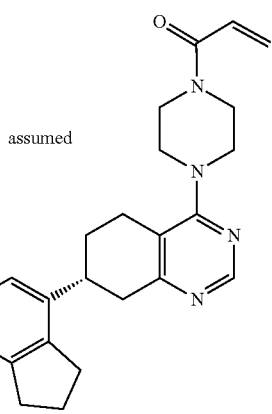

6b assumed

A solution of 7-indan-4-yl-4-piperazin-1-yl-5,6,7,8-tetrahydroquinazoline (0.64 g, 1.91 mmol) and N,N-diisopropylethylamine (0.49 g, 3.83 mmol) in dichloromethane (8 mL) was stirred at 25° C. Then acryloyl chloride (0.17 g, 1.91 mmol) was added and stirred at 25° C. for 20 minutes. After completion, the reaction mixture was quenched by water, diluted with dichloromethane, washed with water, dried over anhydrous sodium sulfate and concentrated under vacuum. The residue was purified by flash chromatography on silica gel eluting with dichloromethane/methanol (10/1) to afford the product. The mixture of enantiomer was separated by Chiral-Prep-HPLC with the following conditions: Column: CHIRALPAK IG, 3*25 cm, 5 um; Mobile Phase A: hexane:dichloromethane=3:1 (10 mM ammonia-methanol)—HPLC, Mobile Phase B: ethanol—HPLC; Flow rate: 45 mL/min; Gradient: 10 B to 10 B in 20 min; 254 nm; Injection Volumn: 1.5 ml; Number Of Runs: 8 to afford the title compounds. The absolute configuration of the title compounds was inferred from potency data and a protein X-ray structure of compound 21b.

Example 6a: 1-[4-[(7S)-7-indan-4-yl-5,6,7,8-tetrahydro-quinazolin-4-yl]piperazin-1-yl]prop-2-en-1-one (17.9 mg, 0.45 mmol, 23.6% yield, white solid). $^1$H NMR (300 MHz, Chloroform-d, ppm) 8.60 (s, 1H), 7.15 (d, J=5.7 Hz, 2H), 7.00 (dd, J=5.7, 3.1 Hz, 1H), 6.60 (dd, J=16.8, 10.5 Hz, 1H), 6.33 (dd, J=16.8, 1.9 Hz, 1H), 5.74 (dd, J=10.5, 1.9 Hz, 1H), 3.79 (brs, 3H), 3.72-3.57 (m, 1H), 3.51 (dt, J=13.0, 5.0 Hz, 2H), 3.43-3.12 (m, 4H), 3.18-2.82 (m, 5H), 2.77-2.65 (m, 2H), 2.20-2.02 (m, 3H), 1.92-1.74 (m, 1H). LC-MS: (ESI, m/z): 389.2 [M+H]$^+$. Chiral HPLC: CHIRALPAK IF-3 (4.6*50 mm, 3 um); detected at 254 nm; n-hexane/ethanol=85/15; flow: 1 mL/min; Retention time: 12.417 min (faster peak).

Example 6b: 1-[4-[(7R)-7-indan-4-yl-5,6,7,8-tetrahydro-quinazolin-4-yl]piperazin-1-yl]prop-2-en-1-one (17.7 mg, 0.45 mmol, 23.3% yield, white solid). $^1$H NMR (300 MHz, Chloroform-d, ppm) 8.60 (s, 1H), 7.15 (d, J=5.7 Hz, 2H), 7.00 (dd, J=5.7, 3.1 Hz, 1H), 6.60 (dd, J=16.8, 10.5 Hz, 1H), 6.33 (dd, J=16.8, 1.9 Hz, 1H), 5.74 (dd, J=10.5, 1.9 Hz, 1H), 3.79 (brs, 3H), 3.72-3.57 (m, 1H), 3.51 (dt, J=13.0, 5.0 Hz, 2H), 3.43-3.12 (m, 4H), 3.18-2.82 (m, 5H), 2.77-2.65 (m, 2H), 2.20-2.02 (m, 3H), 1.92-1.74 (m, 1H). LC-MS: (ESI, m/z): 389.2 [M+H]$^+$. Chiral HPLC: CHIRALPAK IF-3 (4.6*50 mm, 3 um); detected at 254 nm; n-hexane/ethanol=85/15; flow: 1 mL/min; Retention time: 14.642 min (slower peak).

Example 7a

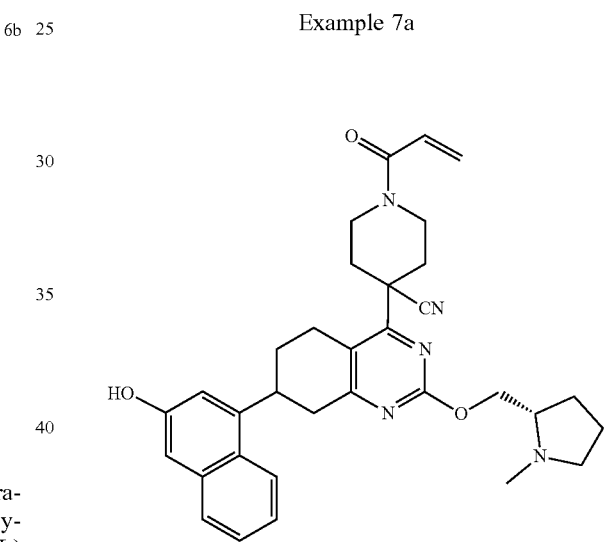

4-[7-(3-hydroxy-1-naphthyl)-2-[[(2S)-1-methylpyrrolidin-2-yl]methoxy]-5,6,7,8-tetrahydroquinazolin-4-yl]-1-prop-2-enoyl-piperidine-4-carbonitrile

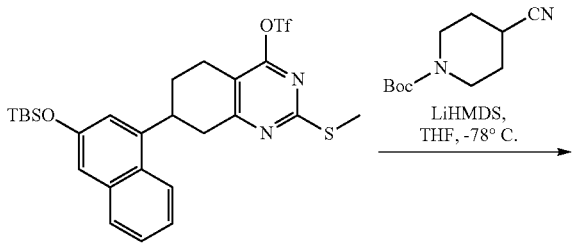

297
-continued

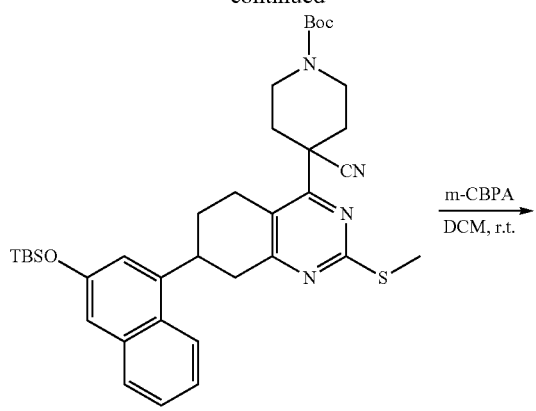

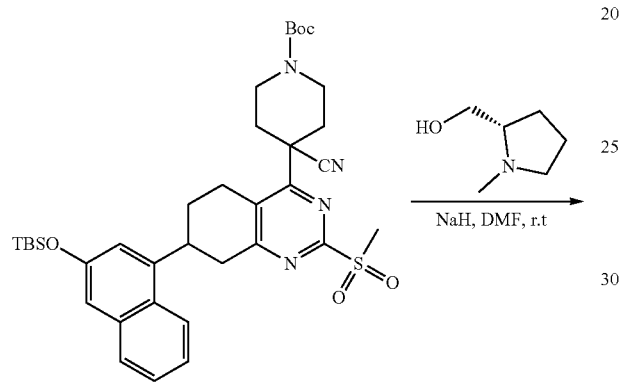

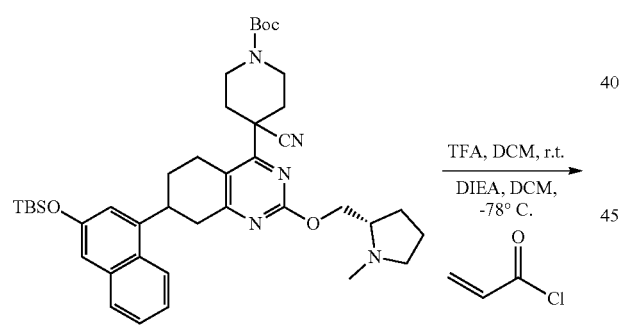

298
-continued

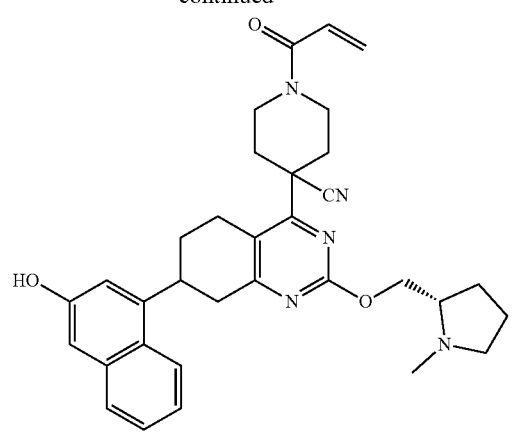

Step 1: tert-butyl 4-[7-[3-[tert-butyl(dimethyl)silyl]oxy-1-naphthyl]-2-methylsulfanyl-5,6,7,8-tetrahydroquinazolin-4-yl]-4-cyano-piperidine-1-carboxylate

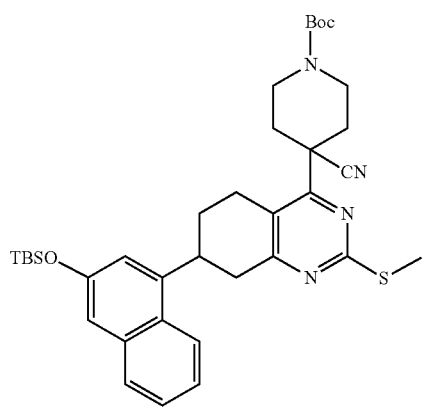 [SMILES: CSc1nc2c(c(C3(C#N)CCN(C(=O)OC(C)(C)C)CC3)n1)CCC(c1cc(O[Si](C)(C)C(C)(C)C)cc3ccccc13)C2]

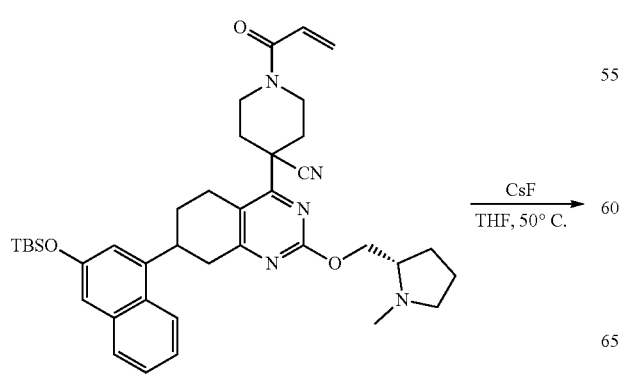

Under nitrogen, a solution of 1-Boc-4-cyanopiperidine (2.16 g, 10.26 mmol) in tetrahydrofuran (20 mL) was added lithium bis(trimethylsilyl)amide (12.83 mL, 12.83 mmol, 1.0 M in tetrahydrofuran) and stirred for 10 minutes at −78° C. Then [7-[3-[tert-butyl(dimethyl)silyl]oxy-1-naphthyl]-2-methylsulfanyl-5,6,7,8-tetrahydroquinazolin-4-yl]trifluoromethanesulfonate (3.00 g, 5.13 mmol) was added and stirred at −78° C. for 30 minutes. After completion, the reaction was quenched with water, diluted with dichloromethane, washed with brine, dried over anhydrous sodium sulfate and concentrated under vacuum. The residue was purified by flash chromatography on silica gel eluting with petroleumeum ether/ethyl acetate (5/1) to afford tert-butyl 4-[7-[3-[tert-butyl(dimethyl)silyl]oxy-1-naphthyl]-2-methylsulfanyl-5,6,7,8-tetrahydroquinazolin-4-yl]-4-cyano-piperidine-1-carboxylate (2.30 g, 3.35 mmol, 65.3% yield) as a yellow oil. LC-MS: (ESI, m/z): 645.3 [M+H]⁺

Step 2: tert-butyl 4-[7-[3-[tert-butyl(dimethyl)silyl]oxy-1-naphthyl]-2-methylsulfonyl-5,6,7,8-tetrahydroquinazolin-4-yl]-4-cyano-piperidine-1-carboxylate

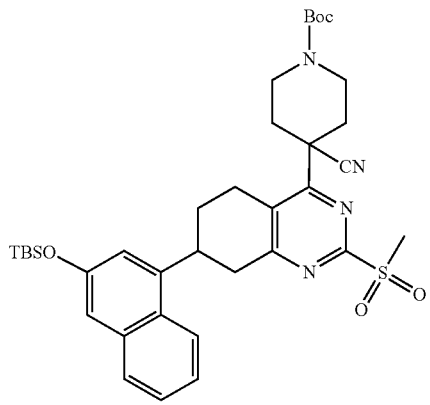 [SMILES: CC(C)(C)OC(=O)N1CCC(C#N)(c2nc(S(C)(=O)=O)nc3c2CCC(c2cc(O[Si](C)(C)C(C)(C)C)cc4ccccc24)C3)CC1]

A solution of 3-chloroperoxybenzoicacid (0.80 g, 4.65 mmol) and tert-butyl 4-[7-[3-[tert-butyl(dimethyl)silyl]oxy-1-naphthyl]-2-methylsulfanyl-5,6,7,8-tetrahydroquinazolin-4-yl]-4-cyano-piperidine-1-carboxylate (1.00 g, 1.55 mmol) in dichloromethane (15 mL) was stirred at 25° C. for 30 minutes. After completion, the reaction was quenched by aqueous saturated sodium sulfite solution, diluted with dichloromethane and washed by water. The organic layer was dried over anhydrous sodium sulfate and concentrated under vacuum to afford the crude tert-butyl 4-[7-[3-[tert-butyl(dimethyl)silyl]oxy-1-naphthyl]-2-methylsulfonyl-5,6,7,8-tetrahydroquinazolin-4-yl]-4-cyano-piperidine-1-carboxylate (1.00 g, crude). LC-MS: (ESI, m/z): 677.3 [M+H]$^+$ Step 3: tert-butyl 4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]-4-cyano-piperidine-1-carboxylate

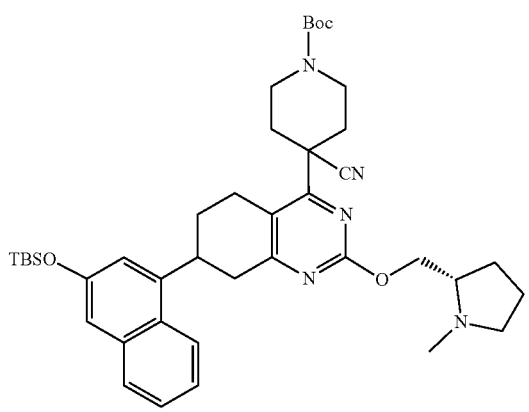 [SMILES: CN1CCC[C@H]1COc1nc2c(c(C3(C#N)CCN(C(=O)OC(C)(C)C)CC3)n1)CCC(c1cc(O[Si](C)(C)C(C)(C)C)cc3ccccc13)C2]

A solution of N-methyl-L-prolinol (0.38 g, 3.32 mmol) in DMF (30 mL) was added sodium hydride (0.22 g, 5.54 mmol, 60% dispersion in mineral oil) and stirred at 25° C. for 20 minutes. Then the crude tert-butyl 4-[7-[3-[tert-butyl(dimethyl)silyl]oxy-1-naphthyl]-2-methylsulfonyl-5,6,7,8-tetrahydroquinazolin-4-yl]-4-cyano-piperidine-1-carboxylate (1.00 g, 1.11 mmol) was added and stirred at 25° C. for 30 minutes. After completion, the reaction was quenched by water, diluted with dichloromethane, washed with brine, dried over anhydrous sodium sulfate and concentrated under vacuum. The residue was purified by flash chromatography on silica gel eluting with dichloromethane/methanol (8/1) to afford tert-butyl 4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]-4-cyano-piperidine-1-carboxylate (0.40 g, 0.56 mmol, 45.6% yield) as a yellow solid. LC-MS: (ESI, m/z): 712.4 [M+H]$^+$ Step 4: 4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]-1-prop-2-enoyl-piperidine-4-carbonitrile

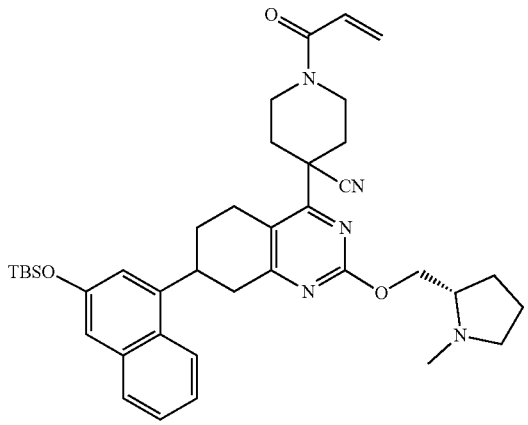 [SMILES: C=CC(=O)N1CCC(C#N)(c2nc(OC[C@@H]3CCCN3C)nc3c2CCC(c2cc(O[Si](C)(C)C(C)(C)C)cc4ccccc24)C3)CC1]

A solution of tert-butyl 4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]-4-cyano-piperidine-1-carboxylate (0.40 g, 0.56 mmol) and trifluoroacetic acid (1 mL) in dichloromethane (6 mL) was stirred at 25° C. for 20 minutes. After completion, the reaction mixture was concentrated under vacuum to afford the crude product. Then a solution of the crude product and N,N-diisopropylethylamine (0.22 g, 1.69 mmol) in dichloromethane (6 mL) was stirred for 10 minutes at 25° C. Then acryloyl chloride (0.05 g, 0.56 mmol) was added and stirred at 25° C. for 30 minutes. After completion, the reaction was quenched with water, diluted with dichloromethane, washed with brine, dried over anhydrous sodium sulfate and concentrated under vacuum to the crude product 4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]-1-prop-2-enoyl-piperidine-4-carbonitrile (0.20 g, crude). LC-MS:(ESI, m/z): 666.4 [M+H]$^+$

Step 5: 4-[7-(3-hydroxy-1-naphthyl)-2-[[(2S)-1-methylpyrrolidin-2-yl]methoxy]-5,6,7,8-tetrahydroquinazolin-4-yl]-1-prop-2-enoyl-piperidine-4-carbonitrile

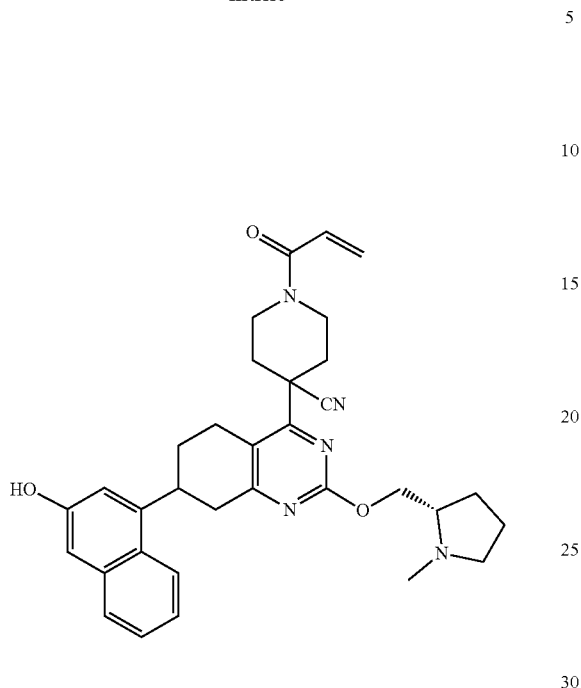

A solution of 4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]-1-prop-2-enoyl-piperidine-4-carbonitrile (0.20 g, 0.20 mmol) and cesium fluoride (0.09 g, 0.60 mmol) in tetrahydrofuran (2 mL) was stirred at 25° C. for 30 minutes. After completion, the reaction mixture was concentrated under vacuum. The residue was purified by flash chromatography on silica gel eluting with dichloromethane/methanol (10/1) as a mixture of four compounds. The crude product was purified by Prep-HPLC with the following conditions: Column: XBridge Shield RP18 OBD Column, 30*150 mm, 5 um; Mobile Phase A:Water (10 mmol/L ammonium bicarbonate), Mobile Phase B: acetonitrile; Flow rate: 60 mL/min; Gradient: 38 B to 57 B in 7 min; 254 nm; RT: 6.52 min to afford the product 4-[7-(3-hydroxy-1-naphthyl)-2-[[(2S)-1-methylpyrrolidin-2-yl]methoxy]-5,6,7,8-tetrahydroquinazolin-4-yl]-1-prop-2-enoyl-piperidine-4-carbonitrile (55.7 mg, 0.10 mmol, 18.8% yield) as a yellow solid. LC-MS: (ESI, m/z): 552.3 [M+H]$^+$.

Example 7a: $^1$H NMR (300 MHz, DMSO-d$_6$, ppm) δ 9.68 (s, 1H), 8.08 (d, J=8.5 Hz, 1H), 7.70 (dd, J=8.2, 1.4 Hz, 1H), 7.44-7.34 (m, 1H), 7.33-7.25 (m, 1H), 7.05-6.94 (m, 2H), 6.85 (dd, J=16.7, 10.5 Hz, 1H), 6.12 (dd, J=16.7, 2.4 Hz, 1H), 5.70 (dd, J=10.5, 2.4 Hz, 1H), 4.68-4.45 (m, 1H), 4.38-4.20 (m, 2H), 4.18-4.05 (m, 1H), 4.01-3.85 (m, 1H), 3.51-3.35 (m, 1H), 3.25-3.11 (m, 3H), 3.08-2.86 (m, 3H), 2.72-2.53 (m, 1H), 2.45-2.10 (m, 8H), 2.08-1.83 (m, 3H), 1.73-1.51 (m, 3H).

Examples 8a and 8b

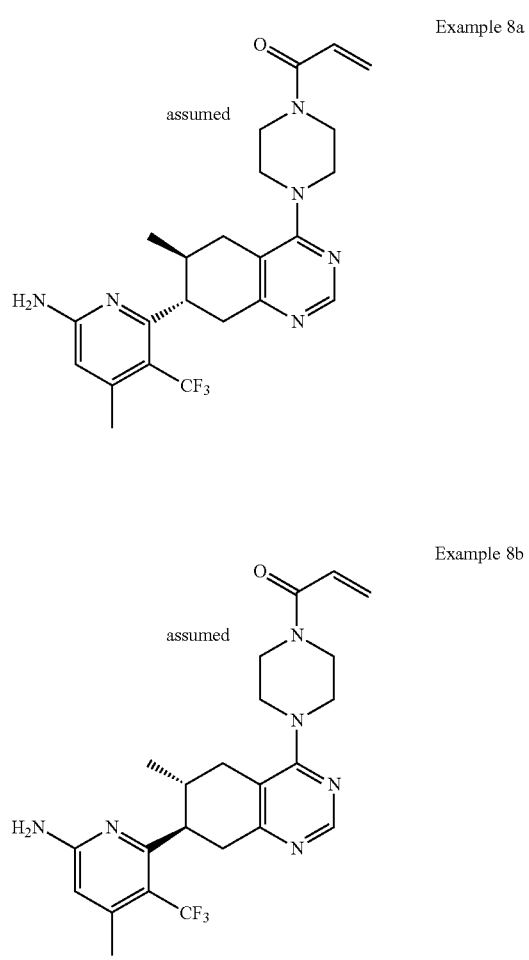

Example 8a 1-(4-((6S,7S)-7-(6-amino-4-methyl-3-(trifluoromethyl)pyridin-2-yl)-6-methyl-5,6,7,8-tetrahydroquinazolin-4-yl)piperazin-1-yl)prop-2-en-1-one (Example 8a)

Example 8b 1-(4-((6R,7R)-7-(6-amino-4-methyl-3-(trifluoromethyl)pyridin-2-yl)-6-methyl-5,6,7,8-tetrahydroquinazolin-4-yl)piperazin-1-yl)prop-2-en-1-one (Example 8b)

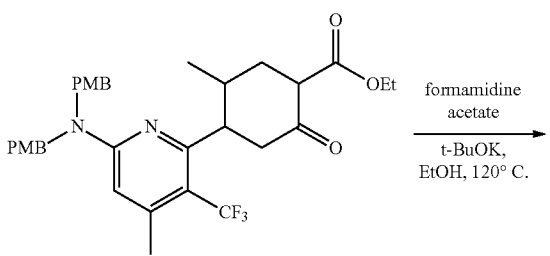

303
-continued

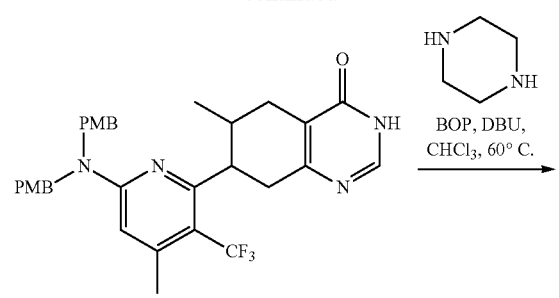

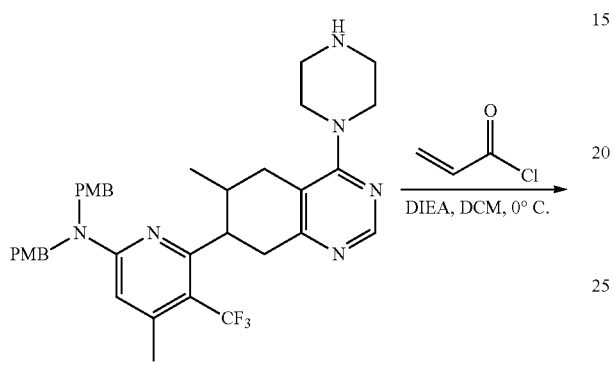

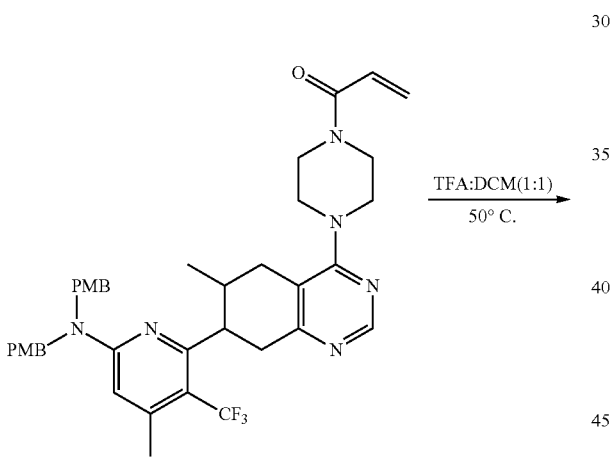

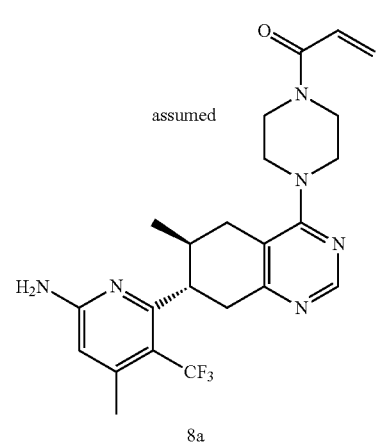

304
-continued

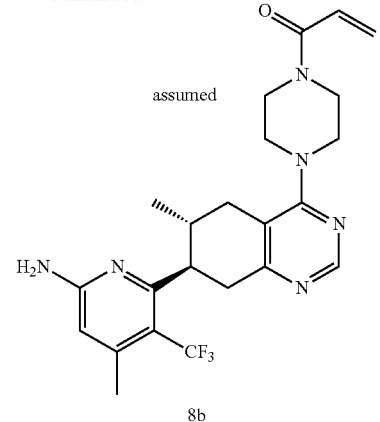

Step 1: 7-(6-(bis(4-methoxybenzyl)amino)-4-methyl-3-(trifluoromethyl)pyridin-2-yl)-6-methyl-5,6,7,8-tetrahydroquinazolin-4(3H)-one

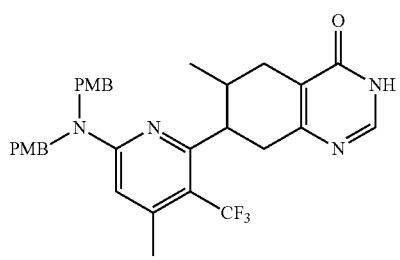

A solution of ethyl 4-[6-[bis[(4-methoxyphenyl)methyl]amino]-4-methyl-3-(trifluoromethyl)-2-pyridyl]-5-methyl-2-oxo-cyclohexanecarboxylate (1.00 g, 1.67 mmol), formamidine acetate (1.74 g, 16.7 mmol) and potassium tert-butoxide (3.75 g, 33.41 mmol) in ethanol (50 mL) was stirred at 120° C. for 5 hours. After completion, the reaction mixture was concentrated under vacuum. The reaction mixture was diluted with dichloromethane, adjusted to pH=7 with HCl/1,4-dioxane and washed by water. The organic layer was dried over anhydrous sodium sulfate and concentrated under vacuum. The residue was purified by flash chromatography on silica gel eluting with dichloromethane/methanol (20/1) to afford 7-[6-[bis[(4-methoxyphenyl)methyl]amino]-4-methyl-3-(trifluoromethyl)-2-pyridyl]-6-methyl-5,6,7,8-tetrahydro-3H-quinazolin-4-one (0.37 g, 0.64 mmol, 38.3% yield) as a yellow solid. LC-MS: (ESI, m/z): 579.3 [M+H]$^+$ Step 2: N,N-bis[(4-methoxyphenyl)methyl]-4-methyl-6-(6-methyl-4-piperazin-1-yl-5,6,7,8-tetrahydroquinazolin-7-yl)-5-(trifluoromethyl)pyridin-2-amine

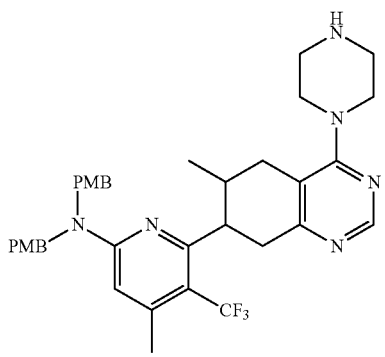

A solution of 7-[6-[bis[(4-methoxyphenyl)methyl]amino]-4-methyl-3-(trifluoromethyl)-2-pyridyl]-6-methyl-5,6,7,8-tetrahydro-3H-quinazolin-4-one (1.60 g, 2.77 mmol), piperazine (1.19 g, 13.83 mmol), benzotriazol-1-yloxytris(dimethylamino)-phosphonium hexafluorophosphate (2.45 g, 5.53 mmol) and 1,8-diazabicyclo[5.4.0]undec-7-ene (1.26 g, 8.3 mmol) in chloroform (15 mL) was stirred at 60° C. for 2 hours. After completion, the reaction was quenched with water. The resulting solution was extracted with dichloromethane and the organic layers were combined. The organic layer was dried over anhydrous sodium sulfate and concentrated under vacuum. The residue was purified by flash chromatography on silica gel eluting with dichloromethane/methanol (10/1) to afford N,N-bis[(4-methoxyphenyl)methyl]-4-methyl-6-(6-methyl-4-piperazin-1-yl-5,6,7,8-tetrahydroquinazolin-7-yl)-5-(trifluoromethyl)pyridin-2-amine (1.40 g, 2.16 mmol, 78.3% yield) as a yellow solid. LC-MS: (ESI, m/z): 647.3 [M+H]$^+$ Step 3: 1-[4-[7-[6-[bis[(4-methoxyphenyl)methyl]amino]-4-methyl-3-(trifluoromethyl)-2-pyridyl]-6-methyl-5,6,7,8-tetrahydroquinazolin-4-yl]piperazin-1-yl]prop-2-en-1-one

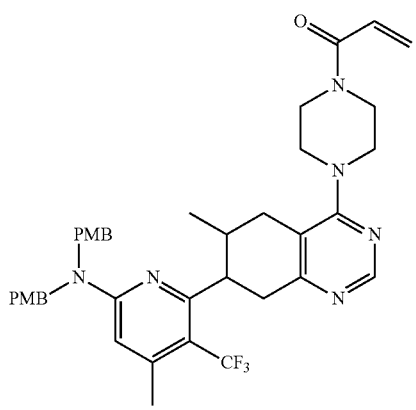

A solution of N,N-bis[(4-methoxyphenyl)methyl]-4-methyl-6-(6-methyl-4-piperazin-1-yl-5,6,7,8-tetrahydroquinazolin-7-yl)-5-(trifluoromethyl)pyridin-2-amine (2.00 g, 3.09 mmol) and N,N-diisopropylethylamine (3.99 g, 30.92 mmol) in dichloromethane (20 mL) was stirred at 0° C. for 5 minutes. Then acrylyl chloride (0.48 g, 5.26 mmol) was added and stirred at 0° C. for 10 minutes. After completion, the reaction mixture was concentrated under vacuum. The reaction mixture was diluted with water. The resulting solution was extracted with dichloromethane and the organic layers were combined. The organic layer was dried over anhydrous sodium sulfate and concentrated under vacuum. The residue was purified by flash chromatography on silica gel eluting with dichloromethane/methanol (10/1) to afford 1-[4-[7-[6-[bis[(4-methoxyphenyl)methyl]amino]-4-methyl-3-(trifluoromethyl)-2-pyridyl]-6-methyl-5,6,7,8-tetrahydroquinazolin-4-yl]piperazin-1-yl]prop-2-en-1-one (1.50 g, 2.14 mmol, 69.2% yield) as a yellow solid. LC-MS: (ESI, m/z): 701.3 [M+H]$^+$ Step 4: 1-[4-[(6S,7S)-7-[6-amino-4-methyl-3-(trifluoromethyl)-2-pyridyl]-6-methyl-5,6,7,8-tetrahydroquinazolin-4-yl]piperazin-1-yl]prop-2-en-1-one (Example 8a) and 1-[4-[(6R,7R)-7-[6-amino-4-methyl-3-(trifluoromethyl)-2-pyridyl]-6-methyl-5,6,7,8-tetrahydroquinazolin-4-yl]piperazin-1-yl]prop-2-en-1-one (Example 8b)

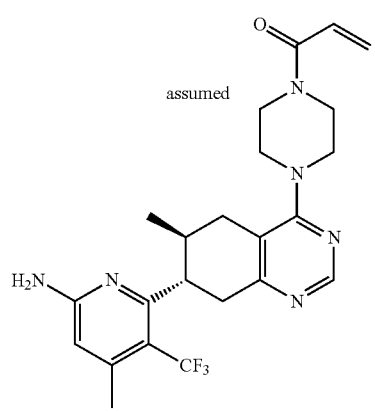

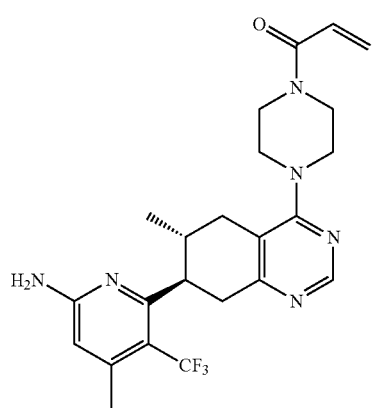

A solution of 1-[4-[7-[6-[bis[(4-methoxyphenyl)methyl]amino]-4-methyl-3-(trifluoromethyl)-2-pyridyl]-6-methyl-5,6,7,8-tetrahydroquinazolin-4-yl]piperazin-1-yl]prop-2-en-1-one (1.50 g, 2.14 mmol) and trifluoroacetic acid (6.36 mL, 85.62 mmol) in dichloromethane (6 mL) was stirred at 50° C. for 12 hours. After completion, the reaction mixture was concentrated under vacuum, diluted with dichloromethane, adjusted to pH=7 with saturated aqueous saturated sodium bicarbonate and washed by water. The organic layer was dried over anhydrous sodium sulfate and concentrated under vacuum to afford the desired product. The mixture of enantiomer was separated by Prep-Chiral-HPLC with the following condition: Column: CHIRALPAK IG-3, 4.6*50 mm, 3 um; Mobile Phase A: Hex (0.1% DEA): EtOH=70:30, Mobile Phase B; Flow rate: 1 mL/min; Gradient: 0 B to 0 B in min; nm; RT1: 2.246; RT2: 2.814 to afford as a white solid.

Example 8a: 1-[4-[(6S,7S)-7-[6-amino-4-methyl-3-(trifluoromethyl)-2-pyridyl]-6-methyl-5,6,7,8-tetrahydroquinazolin-4-yl]piperazin-1-yl]prop-2-en-1-one (47.3 mg, 0.10 mmol, 4.8% yield, white solid). $^1$H NMR (400 MHz, DMSO-$d_6$, ppm) δ 8.46 (s, 1H), 6.84 (dd, J=16.4, 10.4 Hz, 1H), 6.48 (s, 2H), 6.21-6.13 (m, 2H), 5.72 (dd, J=10.4, 2.4 Hz, 1H), 3.75 (brs, 2H), 3.64-3.52 (m, 4H), 3.30-3.27 (m, 2H), 3.16-3.02 (m, 2H), 2.87 (dd, J=17.2, 4.8 Hz, 1H), 2.65-2.54 (m, 2H), 2.30 (q, J=3.6 Hz, 3H), 2.08 (brs, 1H), 0.75 (d, J=6.4 Hz, 3H). LC-MS: (ESI, m/z): 461.2 [M+H]$^+$. Chiral HPLC: CHIRALPAK IG-3 (4.6*50 mm); detected at 254 nm; Hex (0.1% DEA)/EtOH=70/30; flow=1.0 mL/min; Retention time: 2.236 min (faster peak).

Example 8b: 1-[4-[(6R,7R)-7-[6-amino-4-methyl-3-(trifluoromethyl)-2-pyridyl]-6-methyl-5,6,7,8-tetrahydroquinazolin-4-yl]piperazin-1-yl]prop-2-en-1-one (46.2 mg, 0.10 mmol, 4.7% yield, white solid). $^1$H NMR (400 MHz, DMSO-$d_6$, ppm) δ 8.46 (s, 1H), 6.84 (dd, J=16.4, 10.4 Hz, 1H), 6.48 (s, 2H), 6.21-6.13 (m, 2H), 5.72 (dd, J=10.4, 2.4 Hz, 1H), 3.75 (brs, 2H), 3.64-3.52 (m, 4H), 3.30-3.27 (m, 2H), 3.16-3.02 (m, 2H), 2.87 (dd, J=17.2, 4.8 Hz, 1H), 2.65-2.54 (m, 2H), 2.30 (q, J=3.6 Hz, 3H), 2.08 (brs, 1H), 0.75 (d, J=6.4 Hz, 3H). LC-MS: (ESI, m/z): 461.2 [M+H]$^+$. Chiral HPLC: CHIRALPAK IG-3 (4.6*50 mm); detected at 254 nm; Hex (0.1% DEA)/EtOH=70/30; flow=1.0 mL/min; Retention time: 2.795 min (slower peak).

Examples 9a and 9b

Example 9a

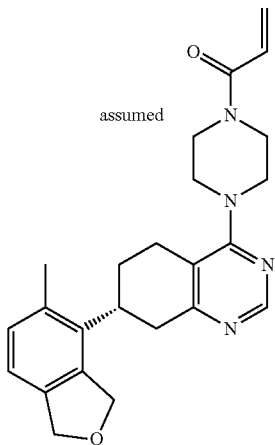

Example 9b (S)-1-(4-(7-(5-methyl-1,3-dihydroisobenzofuran-4-yl)-5,6,7,8-tetrahydroquinazolin-4-yl)piperazin-1-yl)prop-2-en-1-one (Example 9a)

(R)-1-(4-(7-(5-methyl-1,3-dihydroisobenzofuran-4-yl)-5,6,7,8-tetrahydroquinazolin-4-yl)piperazin-1-yl)prop-2-en-1-one (Example 9b)

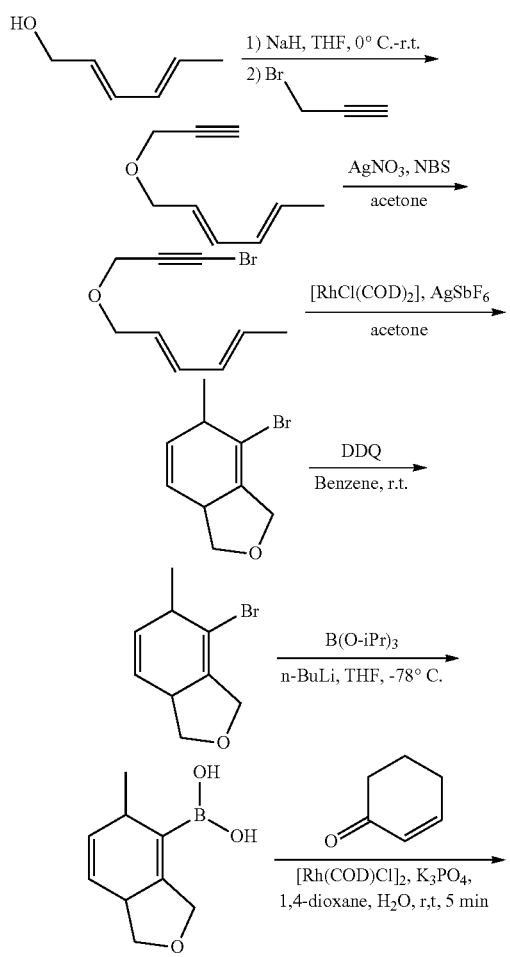

309
-continued

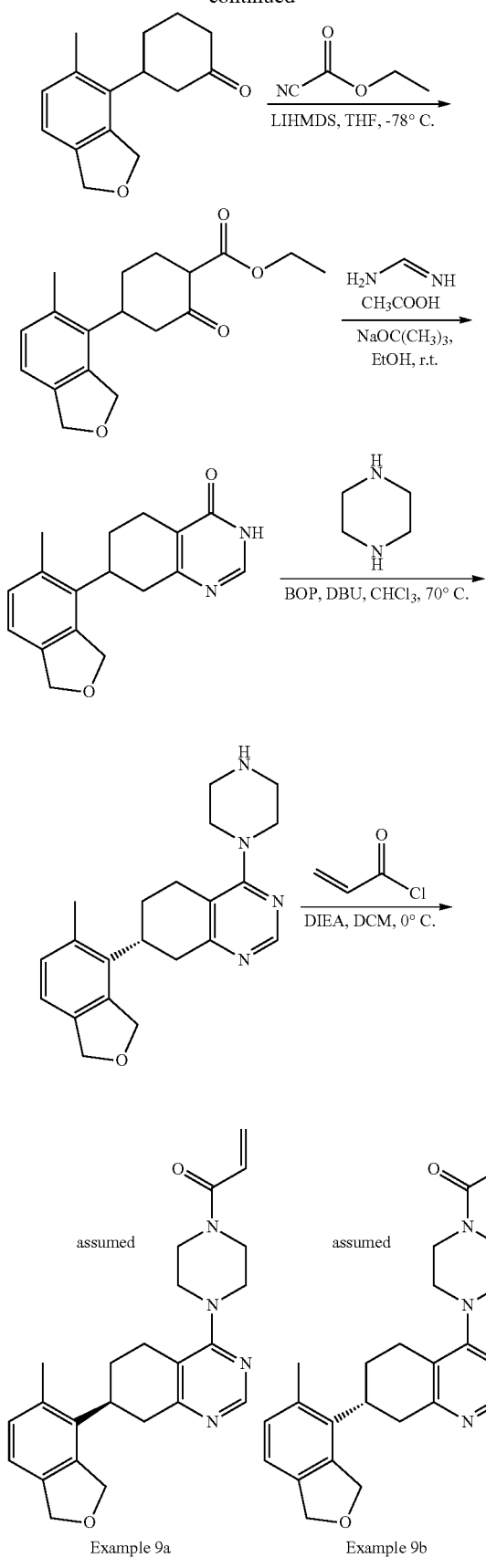

Example 9a

Example 9b

310

Step 1: (2E,4E)-1-(prop-2-yn-1-yloxy)hexa-2,4-diene

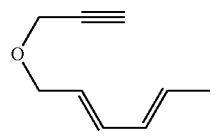

A solution of sodium hydride (15.7 g, 392.3 mmol, 60% dispersion in mineral oil) in tetrahydrofuran (50 mL) was added (E,E)-2,4-Hexadien-1-ol (35.0 g, 356.63 mmol) in tetrahydrofuran (50 mL) at 0° C. and stirred for 45 min at room temperature. Then the reaction mixture was added 3-bromopropyne (50.91 g, 427.96 mmol) at 0° C. and stirred for 12 hours at room temperature. After completion, the reaction was quenched with saturated ammonium chloride solution. The reaction mixture was extracted with dichloromethane and the organic layers were combined. The organic layer was dried over anhydrous sodium sulfate and concentrated under vacuum. The residue was purified by flash chromatography on silica gel eluting with petroleumeum ether/ethyl acetate (20/1) to afford (2E,4E)-1-prop-2-ynoxyhexa-2,4-diene (30.0 g, 220.3 mmol, 61.8% yield) as a yellow oil.

Step 2: (2E,4E)-1-(3-bromoprop-2-ynoxy)hexa-2,4-diene

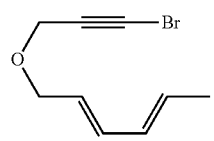

A solution of (2E,4E)-1-prop-2-ynoxyhexa-2,4-diene (5.00 g, 36.71 mmol), 1-bromo-2,5-pyrrolidinedione (7.19 g, 40.38 mmol) and silver nitrate (6.24 g, 36.71 mmol) in acetone (10 mL) was stirred for 1 hour. After completion, the reaction mixture was diluted with diethyl ether and washed by water. The organic layer was dried over anhydrous sodium sulfate and concentrated under vacuum. The residue was purified by flash chromatography on silica gel eluting with petroleumeum ether/ethyl acetate (20/1) to afford (2E,4E)-1-(3-bromoprop-2-ynoxy)hexa-2,4-diene (2.50 g, 11.62 mmol, 31.7% yield) as a yellow oil.

Step 3: 7-bromo-6-methyl-1,3,3a,6-tetrahydroisobenzofuran

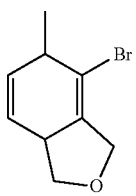

A solution of chloro(1,5-cyclooctadiene)rhodium(I) dimer (1.15 g, 2.32 mmol) and silver hexafluoroantimonate (1.63 g, 4.65 mmol) in acetone (200 mL) was stirred at room temperature for 0.5 hours. Then (2E,4E)-1-(3-bromoprop-2-ynoxy)hexa-2,4-diene (20.00 g, 92.98 mmol) was added and stirred at room temperature for 0.5 hours. After completion, the reaction mixture was diluted with diethyl ether and washed by water. The organic layer was dried over anhydrous sodium sulfate and concentrated under vacuum. The residue was purified by flash chromatography on silica gel eluting with petroleumeum ether/dichloromethane (1/2) to afford 7-bromo-6-methyl-1,3,3a,6-tetrahydroisobenzofuran (16.00 g, 74.38 mmol, 80% yield) as a yellow oil.

Step 4: 4-bromo-5-methyl-1,3-dihydroisobenzofuran

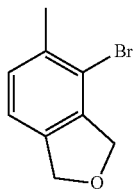

A solution of 7-bromo-6-methyl-1,3,3a,6-tetrahydroisobenzofuran (16.00 g, 74.39 mmol) in benzene (123 mL) was added 2,3-dichloro-5,6-dicyano-1,4-benzoquinone (25.33 g, 111.58 mmol) and stirred at room temperature for 18 hours. After completion, the reaction mixture was passed through a plug of silica and the solvent was removed by rotary evaporation. The crude reaction mixture was purified by column chromatography petroleumeum ether/ethyl acetate (1/2) to provide 4-bromo-5-methyl-1,3-dihydroisobenzofuran (7.00 g, 32.85 mmol, 44.2% yield) as a white solid.

Step 5: (5-methyl-1,3-dihydroisobenzofuran-4-yl)boronic acid

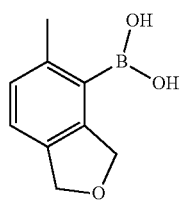

Under nitrogen, a solution of 4-bromo-5-methyl-1,3-dihydroisobenzofuran (5.00 g, 23.47 mmol) and n-butyllithium (14.08 mL, 35.21 mmol) in tetrahydrofuran (40 mL) was stirred at −78° C. for 10 minutes. Then triisopropyl borate (2.65 g, 140.82 mmol) was added and stirred at −78° C. for 0.5 hours. After completion, the solvent was concentrated under vacuum to afford the crude product. The crude was used for next step directly without purification. LC-MS: (ESI, m/z): 179.2 [M+H]$^+$.

Step 6: 3-(5-methyl-1,3-dihydroisobenzofuran-4-yl)cyclohexan-1-one

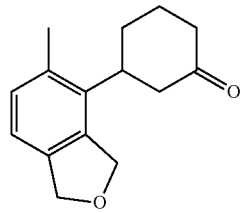 [SMILES: Cc1ccc2c(c1C1CCCC(=O)C1)COC2]

Under nitrogen, a solution of (5-methyl-1,3-dihydroisobenzofuran-4-yl)boronic acid (5.0 g, crude), cyclohex-2-en-1-one (4.02 g, 41.85 mmol) and chloro(1,5-cyclooctadiene)rhodium(I) dimer (1.38 g, 2.79 mmol) in 1,4-dioxane (50 mL) was added aqueous saturated potassium phosphate (10 mL) and stirred at room temperature for 5 minutes. After completion, the solvent was concentrated under vacuum. The residue was diluted with dichloromethane and washed by water. The organic layer was dried over anhydrous sodium sulfate and concentrated under vacuum. The residue was purified by flash chromatography on silica gel eluting with petroleumeum ether/ethyl acetate (3/1) to afford 3-(5-methyl-1,3-dihydroisobenzofuran-4-yl)cyclohexan-1-one (4.40 g, 19.13 mmol, 31.7% yield) as a colorless oil. LC-MS: (ESI, m/z): 231.1 [M+H]$^+$.

Step 7: ethyl 4-(5-methyl-1,3-dihydroisobenzofuran-4-yl)-2-oxocyclohexane-1-carboxylate

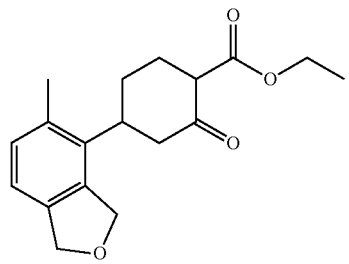 [SMILES: CCOC(=O)C1CCC(c2c(C)ccc3c2COC3)CC1=O]

Under nitrogen, a solution of 3-(5-methyl-1,3-dihydroisobenzofuran-4-yl)cyclohexan-1-one (4.40 g, 19.13 mmol) in tetrahydrofuran (40 mL) was stirred at −78° C. for 30 minutes. Then ethyl cyanoformate (4.36 g, 43.99 mmol) was dropwise added lithium bis(trimethylsilyl)amide (38 mL, 38.26 mmol, 1.0 M in THF) and stirred at −78° C. for 2 hours. After completion, the reaction was quenched with water, concentrated under vacuum, diluted with dichloromethane and washed with water dried over anhydrous sodium sulfate and concentrated under vacuum. The residue was purified by flash chromatography on silica gel eluting with petroleumeum ether/ethyl acetate (3/1) to afford ethyl 4-(5-methyl-1,3-dihydroisobenzofuran-4-yl)-2-oxocyclohexane-1-carboxylate (3.00 g, 9.92 mmol, 46.2% yield) as a colorless oil. LC-MS: (ESI, m/z): 303.2 [M+H]$^+$

Step 8: 7-(5-methyl-1,3-dihydroisobenzofuran-4-yl)-5,6,7,8-tetrahydroquinazolin-4(3H)-one

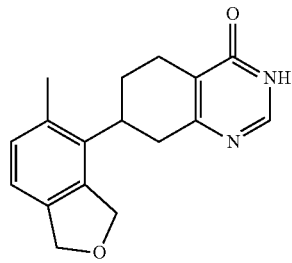

A solution of ethyl 4-(5-methyl-1,3-dihydroisobenzofuran-4-yl)-2-oxo-cyclohexanecarboxylate (3.00 g, 9.92 mmol), formamidine acetate (5.16 g, 49.61 mmol) and sodium tert-butoxide (6.67 g, 69.45 mmol) in ethanol (40 mL) was stirred at 120° C. for 2 hours. After completion, the solvent was concentrated under vacuum. The residue was diluted with dichloromethane and washed with water, dried over anhydrous sodium sulfate and concentrated under vacuum. The residue was purified by flash chromatography on silica gel eluting with dichloromethane/methanol (10/1) to afford 7-(5-methyl-1,3-dihydroisobenzofuran-4-yl)-5,6,7,8-tetrahydro-3H-quinazolin-4-one (550.0 mg, 1.95 mmol, 19.6% yield) as a yellow solid. LC-MS: (ESI, m/z): 283.1 [M+H]$^+$

Step 9: 7-(5-methyl-1,3-dihydroisobenzofuran-4-yl)-4-(piperazin-1-yl)-5,6,7,8-tetrahydroquinazoline

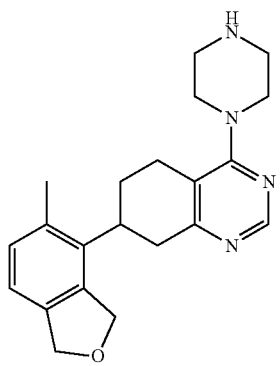 [SMILES: Cc1ccc2c(c1C1CCc3c(ncnc3N3CCNCC3)C1)COC2]

A solution of 7-(5-methyl-1,3-dihydroisobenzofuran-4-yl)-5,6,7,8-tetrahydro-3H-quinazolin-4-one (0.75 g, 2.66 mmol), benzotriazol-1-yloxytris(dimethylamino)-phosphonium hexafluorophosphate (2.35 g, 5.31 mmol), piperazine (2.29 g, 26.56 mmol) and 1,8-diazabicyclo[5.4.0]undec-7-ene (1.2 g, 7.97 mmol) in chloroform (10 mL) was stirred at 70° C. for 12 hours. After completion, the solvent was concentrated under vacuum. The residue was purified by flash chromatography on reversed phase column eluting with acetonitrile/water (6/4) to afford 7-(5-methyl-1,3-dihydroisobenzofuran-4-yl)-4-piperazin-1-yl-5,6,7,8-tetrahydroquinazoline (0.60 g, 1.71 mmol, 64.5% yield) as a yellow solid. LC-MS: (ESI, m/z): 351.2 [M+H]$^+$.

Step 10: (S)-1-(4-(7-(5-methyl-1,3-dihydroisobenzofuran-4-yl)-5,6,7,8-tetrahydroquinazolin-4-yl)piperazin-1-yl)prop-2-en-1-one (Example 9a) and (R)-1-(4-(7-(5-methyl-1,3-dihydroisobenzofuran-4-yl)-5,6,7,8-tetrahydroquinazolin-4-yl)piperazin-1-yl)prop-2-en-1-one (Example 9b)

9a

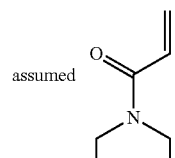

9b

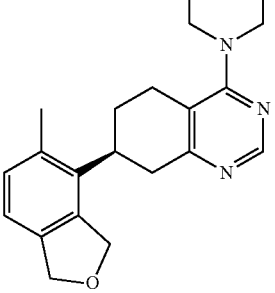

A solution of 7-(5-methyl-1,3-dihydroisobenzofuran-4-yl)-4-piperazin-1-yl-5,6,7,8-tetrahydroquinazoline (600.0 mg, 1.71 mmol) and N,N-diisopropylethylamine (441.71 mg, 3.42 mmol) in dichloromethane (60 mL) was dropwise added acryloyl chloride (232.4 mg, 2.57 mmol) and stirred at 0° C. for 0.5 hours. After completion, the reaction was quenched with water. The resulting solution was diluted with dichloromethane and washed by water. The organic layer was dried over anhydrous sodium sulfate and concentrated under vacuum. The residue was purified by flash chromatography on silica gel eluting with petroleumeum dichloromethane/methanol (3/1) to afford the diastereoisomers as a white solid. Then the diastereoisomers was isolated by Prep-Chiral-HPLC (Column: CHIRAL ART Cellulose-SB, 4.6*100 mm, 3.0 um; Mobile Phase A: MtBE (0.1% DEA): MeOH=50:50, Mobile Phase B; Flow rate: 1 m/min to afford the title compounds. The absolute configuration of the title compounds was inferred from potency data and a protein X-ray structure of compound 21b.

Example 9a: (S)-1-(4-(7-(5-methyl-1,3-dihydroisobenzofuran-4-yl)-5,6,7,8-tetrahydroquinazolin-4-yl)piperazin-1- yl)prop-2-en-1-one (78.9 mg, 0.19 mmol, 11.4% yield, light yellow solid). $^1$H NMR (300 MHz, DMSO-d$_6$, ppm) δ 8.49 (s, 1H), 7.13-7.05 (m, 2H), 6.84 (dd, J=16.5, 10.5 Hz, 1H), 6.14 (dd, J=16.5, 2.4 Hz, 1H), 5.72 (dd, J=10.5, 2.4 Hz, 1H), 5.12-5.02 (m, 2H), 4.91 (s, 2H), 3.75-3.60 (m, 4H), 3.52-3.39 (m, 3H), 3.29-3.26 (m, 2H), 2.96-2.83 (m, 2H), 2.79-2.73 (m, 1H), 2.71-2.60 (m, 1H), 2.37 (s, 3H), 1.98-1.95 (m, 1H), 1.82-1.71 (m, 1H). LC-MS: (ESI, m/z): 405.2 [M+H]$^+$. Chiral HPLC: CHIRAL Cellulose-SB (0.46*10 cm); detected at 254 nm; MtBE (0.1% DEA)/MeOH=50/50; flow=1.0 mL/min; Retention time: 2.444 min (faster peak).

Example 9b: (R)-1-(4-(7-(5-methyl-1,3-dihydroisobenzofuran-4-yl)-5,6,7,8-tetrahydroquinazolin-4-yl)piperazin-1-yl)prop-2-en-1-one (138.5 mg, 0.34 mmol, 20% yield, light yellow solid). $^1$H NMR (300 MHz, DMSO-d$_6$, ppm) a 8.49 (s, 1H), 7.13-7.05 (m, 2H), 6.84 (dd, J=16.5, 10.5 Hz, 1H), 6.14 (dd, J=16.5, 2.4 Hz, 1H), 5.72 (dd, J=10.5, 2.4 Hz, 1H), 5.12-5.02 (m, 2H), 4.91 (s, 2H), 3.75-3.60 (m, 4H), 3.52-3.39 (m, 3H), 3.29-3.26 (m, 2H), 2.96-2.83 (m, 2H), 2.79-2.73 (m, 1H), 2.71-2.60 (m, 1H), 2.37 (s, 3H), 1.98-1.95 (m, 1H), 1.82-1.71 (m, 1H). LC-MS: (ESI, m/z): 405.2 [M+H]$^+$. Chiral HPLC: CHIRAL Cellulose-SB (0.46*10 cm); detected at 254 nm; MtBE (0.1% DEA)/MeOH=50/50; flow=1.0 mL/min; Retention time: 4.071 min (slower peak).

Examples 10a and 10b

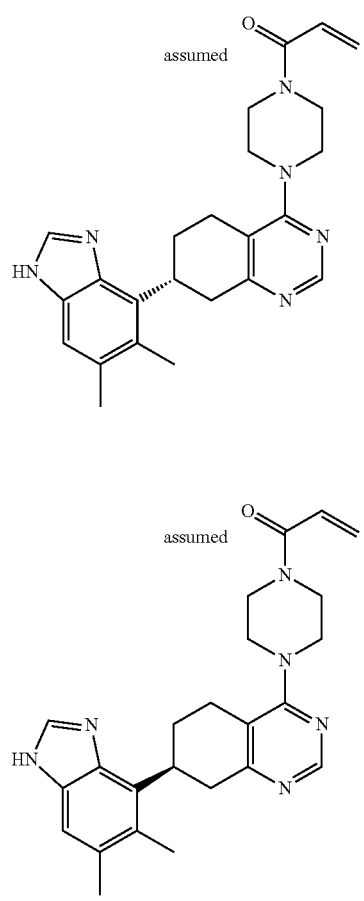

1-[4-[(7R)-7-(5,6-dimethyl-1H-benzimidazol-4-yl)-5,6,7,8-tetrahydroquinazolin-4-yl]piperazin-1-yl]prop-2-en-1-one (Example 10a)

1-[4-[(7S)-7-(5,6-dimethyl-1H-benzimidazol-4-yl)-5,6,7,8-tetrahydroquinazolin-4-yl]piperazin-1-yl]prop-2-en-1-one (Example 10b)

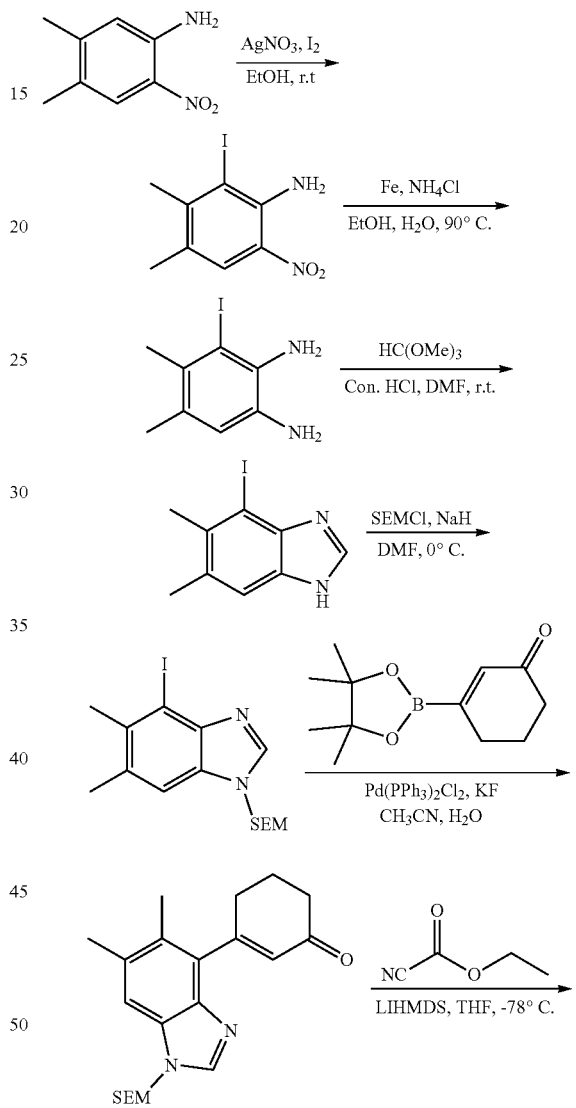

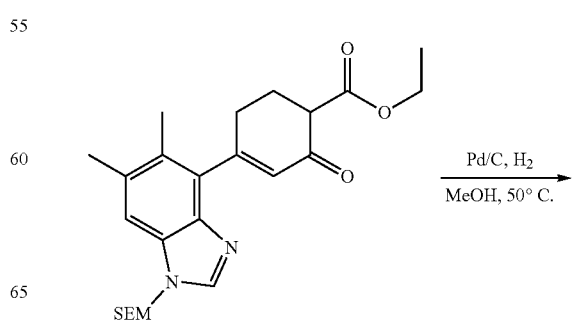

317

-continued

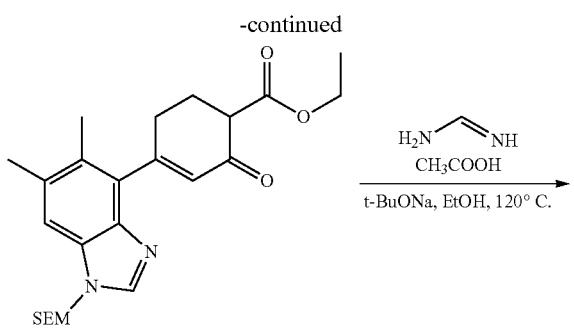

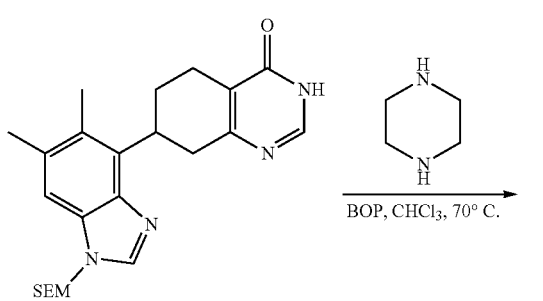

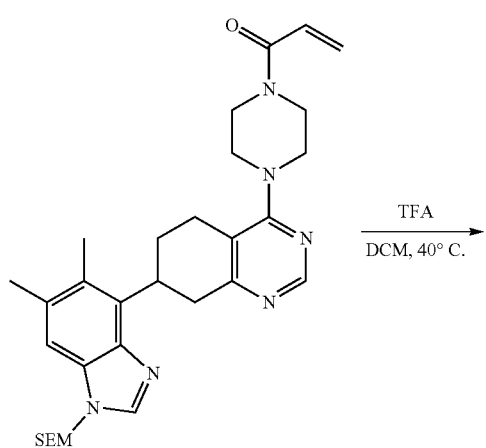

318

-continued

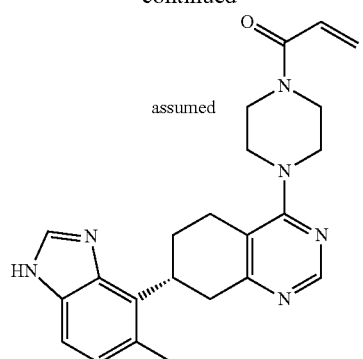

Example 10a

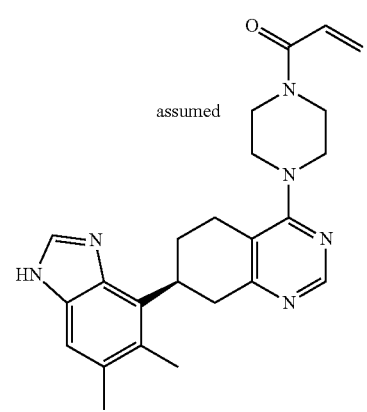

Example 10b

Step 1: 2-iodo-3,4-dimethyl-6-nitroaniline

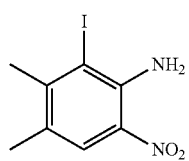

A solution of 4,5-dimethyl-2-nitroaniline (25.00 g, 150.44 mmol), silver sulfate (51.60 g, 165.48 mmol) and iodine (42.00 g, 165.48 mmol) in ethanol (500 mL) was stirred at room temperature for 2 hours. After completion, the reaction mixture was filtrated, and the filtrate was concentrated under reduced pressure. The residue was diluted with dichloromethane and washed with saturated sodium sulfite solution, dried over anhydrous sodium sulfate and concentrated under vacuum to afford crude 2-iodo-3,4-dimethyl-6-nitroaniline (31.00 g, crude) as a yellow solid. LC-MS: (ESI, m/z): 293.0 [M+H]$^+$

Step 2: 3-iodo-4,5-dimethylbenzene-1,2-diamine

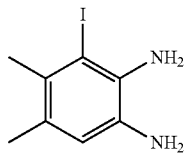

A solution of 2-iodo-3,4-dimethyl-6-nitro-aniline (25.00 g, 85.60 mmol), iron (14.34 g, 256.79 mmol) and ammonium chloride (22.68 g, 427.98 mmol) in ethanol (400 mL) and water (40 mL) was stirred at 90° C. for 12 hours. After completion, the reaction mixture was filtrated, and the filtrate was concentrated under reduced pressure. The residue was diluted with dichloromethane and washed with saturated sodium chloride solution dried over anhydrous sodium sulfate and concentrated under vacuum to afford 3-iodo-4,5-dimethyl-benzene-1,2-diamine (22.00 g, crude) as a crude product. LC-MS: (ESI, m/z): 263.0 [M+H]$^+$.

Step 3: 4-iodo-5,6-dimethyl-1H-benzo[d]imidazole

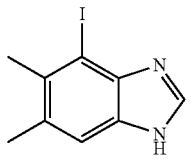

A solution of 3-iodo-4,5-dimethylbenzene-1,2-diamine (22.00 g, 83.94 mmol) and trimethoxymethane (93.0 mL, 839.69 mmol) in N,N-dimethylformamide (150 mL) was added concentrated hydrochloric acid (10 mL) and stirred at room temperature for 2 hours. After completion, the reaction mixture was diluted with water. The reaction mixture was adjusted to pH=7 with saturated sodium bicarbonate solution. The resulting solution was extracted with dichloromethane and the organic layers were combined. The organic layer was dried over anhydrous sodium sulfate and concentrated under vacuum. The residue was purified by flash chromatography on silica gel eluting with dichloromethane/methanol (10/1) to afford 4-iodo-5,6-dimethyl-1H-benzo[d]imidazole (20.0 g, 73.53 mmol, 91.9% yield) as a yellow solid. LC-MS: (ESI, m/z): 273.0 [M+H]$^+$.

Step 4: 2-[(4-iodo-5,6-dimethyl-benzimidazol-1-yl)methoxy]ethyl-trimethyl-silane

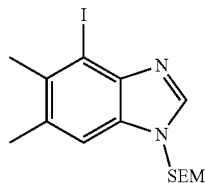 [SMILES: Cc1cc2c(ncn2COCC[Si](C)(C)C)c(I)c1C]

A solution of 4-iodo-5,6-dimethyl-1H-benzimidazole (10.00 g, 36.75 mmol) in N,N-dimethylformamide (130 mL) was added and sodium hydride (1.43 g, 47.78 mmol, 80% dispersion in mineral oil) and stirred at 0° C. for 30 minutes. Then 2-(trimethylsilyl)ethoxymethyl chloride (7.98 g, 47.78 mmol) was added and stirred at 0° C. for 0.5 hours. After completion, the reaction was quenched with saturated ammonium chloride. The resulting solution was extracted with ethyl acetate and the organic layers were combined. The organic layer was washed with water, dried over anhydrous sodium sulfate and concentrated under vacuum. The residue was purified by flash chromatography on silica gel eluting with dichloromethane/methanol (10/1) to afford 2-[(4-iodo-5,6-dimethyl-benzimidazol-1-yl)methoxy]ethyl-trimethyl-silane (8.00 g, 19.88 mmol, 54.1% yield) as a yellow oil. LC-MS: (ESI, m/z): 403.1 [M+H]$^+$.

Step 5: 3-[5,6-dimethyl-1-(2-trimethylsilylethoxymethyl)benzimidazol-4-yl]cyclohex-2-en-1-one

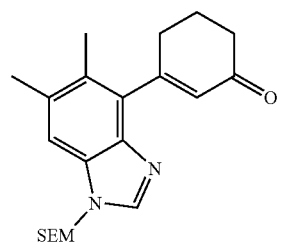 [SMILES: Cc1cc2c(ncn2COCC[Si](C)(C)C)c(C2=CC(=O)CCC2)c1C]

Under nitrogen, a solution of 2-[(4-iodo-5,6-dimethyl-benzimidazol-1-yl)methoxy]ethyl-trimethyl-silane (2.00 g, 4.97 mmol), 3-(4,4,5,5-tetramethyl-1,3,2-dioxaborolan-2-yl)cyclohex-2-en-1-one (1.66 g, 7.46 mmol), bis(triphenylphosphine)palladium(II) chloride (0.35 g, 0.50 mmol) and potassium fluoride (0.58 g, 9.94 mmol) in acetonitrile (10 mL) and water (2 mL) was stirred at 80° C. for 3 hours. After completion, the solvent was concentrated under vacuum. The reaction mixture was diluted with water. The resulting solution was extracted with dichloromethane and the organic layers were combined. The organic layer was dried over anhydrous sodium sulfate and concentrated under vacuum. The residue was purified by flash chromatography on silica gel eluting with petroleumeum ether/ethyl acetate (5/1) to afford 3-[5,6-dimethyl-1-(2-trimethylsilylethoxymethyl)benzimidazol-4-yl]cyclohex-2-en-1-one (1.80 g, 4.86 mmol, 97.7% yield) as a yellow oil. LC-MS: (ESI, m/z): 371.2 [M+H]$^+$

Step 6: ethyl 4-[5,6-dimethyl-1-(2-trimethylsilylethoxymethyl)benzimidazol-4-yl]-2-oxo-cyclohex-3-ene-1-carboxylate

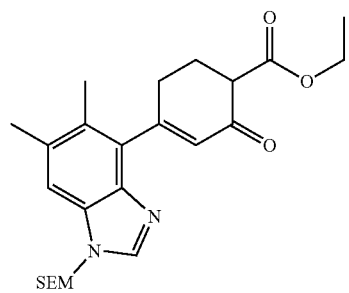 [SMILES: CCOC(=O)C1CCC(c2c(C)c(C)cc3c2ncn3COCC[Si](C)(C)C)=CC1=O]

Under nitrogen, a solution of 3-[5,6-dimethyl-1-(2-trimethylsilylethoxymethyl)benzimidazol-4-yl]cyclohex-2-en-1-one (1.00 g, 2.7 mmol) in tetrahydrofuran (10 mL) was added lithium bis(trimethylsilyl)amide (8.1 mL, 8.1 mmol, 1.0 M in THF) and stirred at −78° C. for 30 minutes. Then ethyl cyanoformate (0.8 g, 8.1 mmol) was added and stirred at −78° C. for 2 hours. After completion, the reaction was quenched with water. The resulting solution was extracted with dichloromethane and the organic layers were combined. The organic layer was dried over anhydrous sodium sulfate and concentrated under vacuum. The residue was purified by flash chromatography on silica gel eluting with petroleumeum ether/ethyl acetate (1/1) to afford ethyl 4-[5,6-dimethyl-1-(2-trimethylsilylethoxymethyl)benzimidazol-4-yl]-2-oxo-cyclohex-3-ene-1-carboxylate (0.40 g, 0.90 mmol, 33.5% yield) as a yellow oil. LC-MS: (ESI, m/z): 443.2 [M+H]$^+$ Step 7: ethyl 4-[5,6-dimethyl-1-(2-trimethylsilylethoxymethyl)benzimidazol-4-yl]-2-oxo-cyclohexanecarboxylate

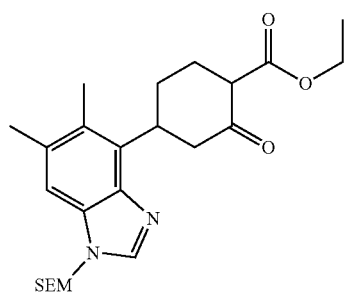 [SMILES: CCOC(=O)C1CCC(c2c(C)c(C)cc3c2ncn3COCC[Si](C)(C)C)CC1=O]

Under hydrogen, a solution of ethyl 4-[5,6-dimethyl-1-(2-trimethylsilylethoxymethyl)benzimidazol-4-yl]-2-oxo-cyclohex-3-ene-1-carboxylate (3.00 g, 6.78 mmol) and Pd/C (10%) (3.00 g, 6.78 mmol) in methyl alcohol (75 mL) was stirred at 50° C. for 12 hours. After completion, the reaction mixture was filtrated and the filtrate was concentrated under reduced pressure. The crude product was used for next step directly without purification. LC-MS: (ESI, m/z): 445.2 [M+H]$^+$ Step 8: 7-[5,6-dimethyl-1-(2-trimethylsilylethoxymethyl)benzimidazol-4-yl]-5,6,7,8-tetrahydro-3H-quinazolin-4-one

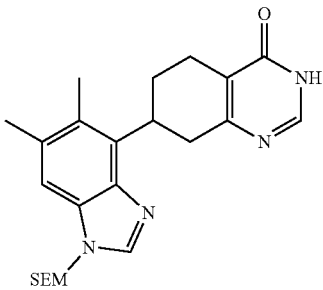 [SMILES: Cc1cc2c(ncn2COCC[Si](C)(C)C)c(C2CCc3c(nc[nH]c3=O)C2)c1C]

A solution of ethyl 4-[5,6-dimethyl-1-(2-trimethylsilylethoxymethyl)benzimidazol-4-yl]-2-oxo-cyclohexanecarboxylate (3.00 g, 6.75 mmol), formamidine acetate (3.51 g, 33.74 mmol) and sodium tert-butoxide (4.54 g, 47.23 mmol) in ethanol (60 mL) was stirred at 120° C. for 1 hour. After completion, the solvent was concentrated under vacuum. The reaction mixture was diluted with water. The resulting solution was extracted with dichloromethane and the organic layers were combined. The organic layer was dried over anhydrous sodium sulfate and concentrated under vacuum. The residue was purified by flash chromatography on silica gel eluting with dichloromethane/methanol (10/1) to afford 7-[5,6-dimethyl-1-(2-trimethylsilylethoxymethyl)benzimidazol-4-yl]-5,6,7,8-tetrahydro-3H-quinazolin-4-one (0.90 g, 2.12 mmol, 31.4% yield) as a yellow solid. LC-MS: (ESI, m/z): 425.2 [M+H]$^+$ Step 9: 2-[[5,6-dimethyl-4-(4-piperazin-1-yl-5,6,7,8-tetrahydroquinazolin-7-yl)benzimidazol-1-yl]methoxy]ethyl-trimethyl-silane

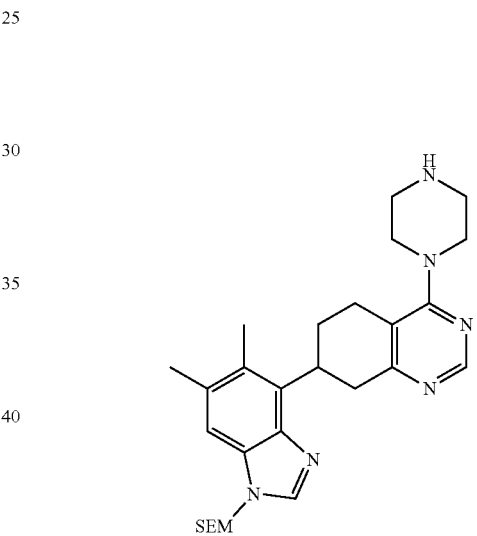

A solution of 7-[5,6-dimethyl-1-(2-trimethylsilylethoxymethyl)benzimidazol-4-yl]-5,6,7,8-tetrahydro-3H-quinazolin-4-one (900.0 mg, 2.12 mmol), benzotriazol-1-yloxytris(dimethylamino)-phosphonium hexafluorophosphate (1.87 g, 4.24 mmol), piperazine (1.83 g, 21.2 mmol) and 1,8-diazabicyclo[5.4.0]undec-7-ene (968.06 mg, 6.36 mmol) in chloroform (10 mL) was stirred at 70° C. for 4 hours. After completion, the resulting solution was diluted with dichloromethane and washed by water. The organic layer was dried over anhydrous sodium sulfate and concentrated under vacuum. The residue was purified by flash chromatography on silica gel eluting with dichloromethane/methanol (1/1) to afford 2-[[5,6-dimethyl-4-(4-piperazin-1-yl-5,6,7,8-tetrahydroquinazolin-7-yl)benzimidazol-1-yl]methoxy]ethyl-trimethyl-silane (600.0 mg, 1.22 mmol, 57.4% yield) as a color solid. LC-MS: (ESI, m/z): 493.3 [M+H]$^+$ Step 10: 1-[4-[7-[5,6-dimethyl-1-(2-trimethylsilylethoxymethyl)benzimidazol-4-yl]-5,6,7,8-tetrahydroquinazolin-4-yl]piperazin-1-yl]prop-2-en-1-one

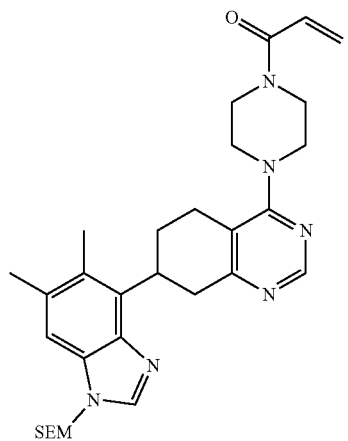 [SMILES: C=CC(=O)N1CCN(c2ncnc3c2CCC(c2c(C)c(C)cc4c2ncn4COCC[Si](C)(C)C)C3)CC1]

A solution of 2-[[5,6-dimethyl-4-(4-piperazin-1-yl-5,6,7,8-tetrahydroquinazolin-7-yl)benzimidazol-1-yl]methoxy]ethyl-trimethyl-silane (600.0 mg, 1.22 mmol) and N,N-diisopropylethylamine (314.75 mg, 2.44 mmol) in dichloromethane (10 mL) was dropwise added acryloyl chloride (132.26 mg, 1.46 mmol) and stirred at 0° C. for 1 hour. After completion, the reaction was quenched with water. The resulting solution was diluted with dichloromethane and washed by water. The organic layer was dried over anhydrous sodium sulfate and concentrated under vacuum to afford 1-[4-[7-[5,6-dimethyl-1-(2-trimethylsilylethoxymethyl)benzimidazol-4-yl]-5,6,7,8-tetrahydroquinazolin-4-yl]piperazin-1-yl]prop-2-en-1-one (600 mg, crude) as a yellow solid. LC-MS: (ESI, m/z): 547.3 [M+H]$^+$ Step 11: 1-[4-[(7R)-7-(5,6-dimethyl-1H-benzimidazol-4-yl)-5,6,7,8-tetrahydroquinazolin-4-yl]piperazin-1-yl]prop-2-en-1-one (Example 10a) and 1-[4-[(7S)-7-(5,6-dimethyl-1H-benzimidazol-4-yl)-5,6,7,8-tetrahydroquinazolin-4-yl]piperazin-1-yl]prop-2-en-1-one (Example 10b)

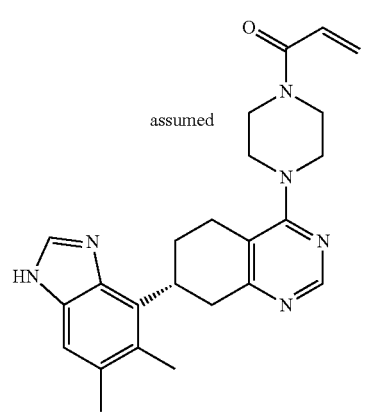

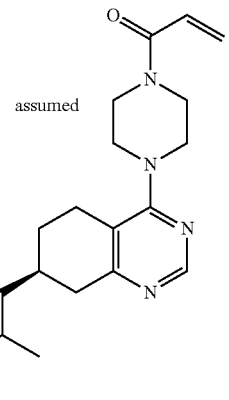

A solution of 1-[4-[7-[5-methyl-1-(2-trimethylsilylethoxymethyl)benzimidazol-4-yl]-5,6,7,8-tetrahydroquinazolin-4-yl]piperazin-1-yl]prop-2-en-1-one (584.6 mg, crude) in trifluoroacetic acid (4 mL) and dichloromethane (4 mL) was stirred at 40° C. for 0.5 hours. After completion, the solvent was concentrated under vacuum. The reaction mixture was diluted with dichloromethane. The resulting solution was adjusted to pH=7 with saturated sodium bicarbonate solution. The resulting solution was extracted with dichloromethane and the organic layers were combined. The organic layer was dried over anhydrous sodium sulfate and concentrated under vacuum. The residue was purified by flash chromatography on silica gel eluting with dichloromethane/methanol (5/1) to afford the diastereoisomers as a white solid. Then the diastereoisomers was isolated by Prep-Chiral-HPLC (Column: CHIRAL ART Cellulose-SB, 4.6*100 mm, 3.0 um; Mobile Phase A: Hex (0.1% DEA): EtOH=50:50, Mobile Phase B; Flow rate: 1 mL/min to afford the title compounds. The absolute configuration of the title compounds was inferred from potency data and a protein X-ray structure of compound 21b.

Example 10a: 1-[4-[(7R)-7-(5,6-dimethyl-1H-benzimidazol-4-yl)-5,6,7,8-tetrahydroquinazolin-4-yl]piperazin-1-yl]prop-2-en-1-one (63.7 mg, 0.15 mmol, 13.9% yield, white solid). $^1$H NMR (300 MHz, DMSO-d$_6$, ppm) δ 12.15 (brs, 1H), 8.49 (s, 1H), 7.98 (s, 1H), 7.21 (brs, 1H), 6.85 (dd, J=16.5, 10.2 Hz, 1H), 6.15 (dd, J=16.5, 2.4 Hz, 1H), 5.72 (dd, J=10.5, 2.4 Hz, 1H), 3.99-3.48 (m, 8H), 3.30-3.20 (m, 2H), 2.95-2.81 (m, 2H), 2.69-2.64 (m, 2H), 2.34 (d, J=12.5 Hz, 6H), 1.87 (d, J=12.2 Hz, 1H). LC-MS: (ESI, m/z): 417.3 [M+H]$^+$. Chiral HPLC: CHIRAL Cellulose-SB (4.6*100 mm); detected at 254 nm; Hex (0.1% DEA)/EtOH=50/50; flow=1.0 mL/min; Retention time: 2.621 min (faster peak).

Example 10b: 1-[4-[(7S)-7-(5,6-dimethyl-1H-benzimidazol-4-yl)-5,6,7,8-tetrahydroquinazolin-4-yl]piperazin-1-yl]prop-2-en-1-one (81.5 mg, 0.19 mmol, 17.8% yield, white solid). $^1$H NMR (300 MHz, DMSO-d$_6$, ppm) δ 12.15 (brs, 1H), 8.49 (s, 1H), 7.98 (s, 1H), 7.21 (brs, 1H), 6.85 (dd, J=16.5, 10.2 Hz, 1H), 6.15 (dd, J=16.5, 2.4 Hz, 1H), 5.72 (dd, J=10.5, 2.4 Hz, 1H), 3.99-3.48 (m, 8H), 3.30-3.20 (m, 2H), 2.95-2.81 (m, 2H), 2.69-2.64 (m, 2H), 2.34 (d, J=12.5 Hz, 6H), 1.87 (d, J=12.2 Hz, 1H). LC-MS: (ESI, m/z): 417.3 [M+H]$^+$. Chiral HPLC: CHIRAL Cellulose-SB (4.6*100 mm); detected at 254 nm; Hex (0.1% DEA)/EtOH=50/50; flow=1.0 mL/min; Retention time: 3.244 min (slower peak).

Examples 11a and 11b
Example 11a
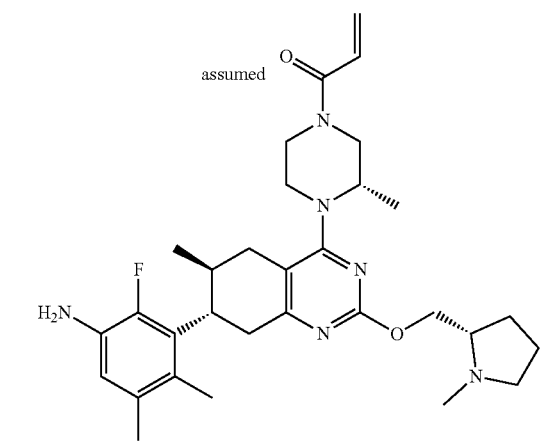
1-[(3S)-4-[(6S,7S)-7-(3-amino-2-fluoro-5,6-dimethyl-phenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one (Example 11a)
Example 11b
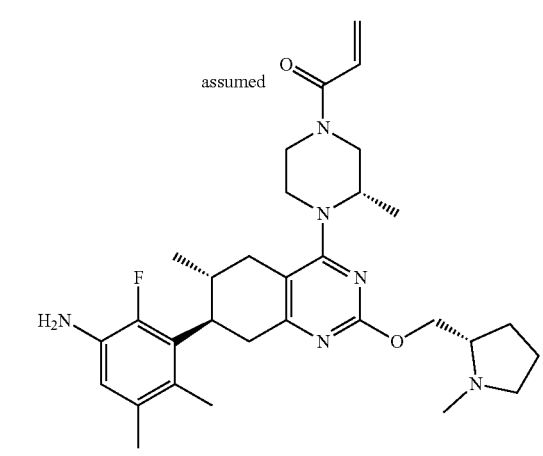
1-[(3S)-4-[(6R,7R)-7-(3-amino-2-fluoro-5,6-dimethyl-phenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one (Example 11b)
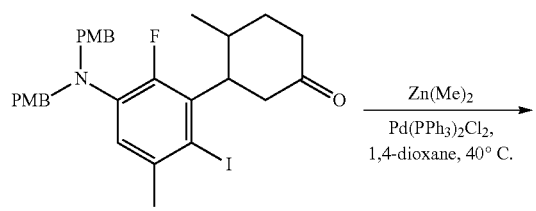
-continued
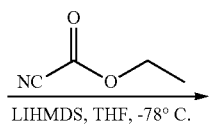
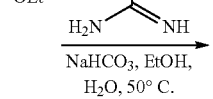
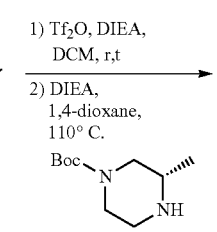
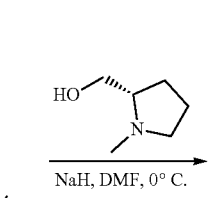

-continued

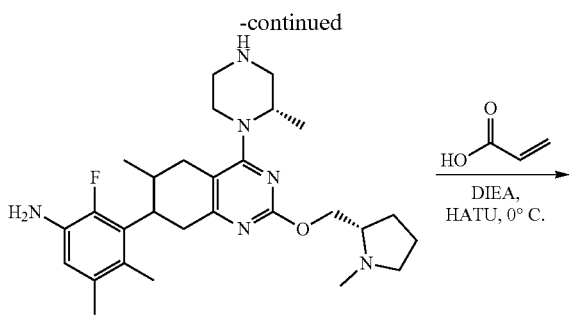

assumed

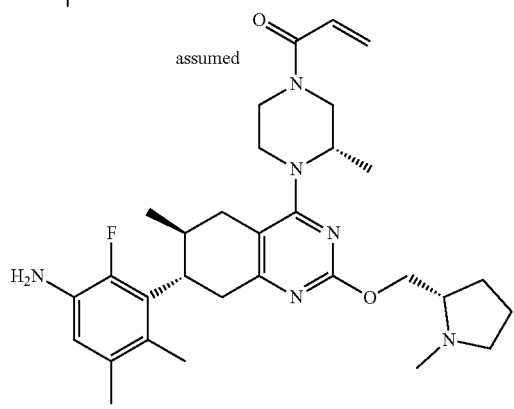

Example 11a assumed

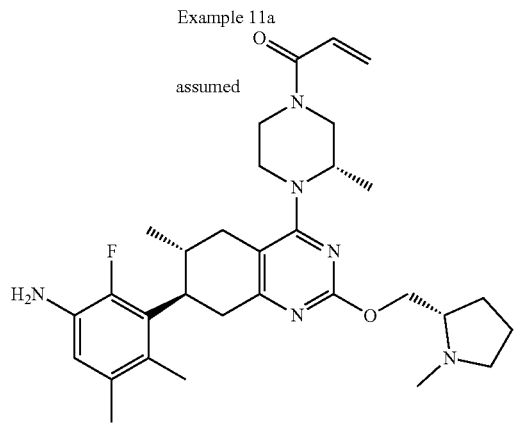

Example 11b

Step 1: 3-(3-(bis(4-methoxybenzyl)amino)-2-fluoro-5,6-dimethylphenyl)-4-methylcyclohexan-1-one

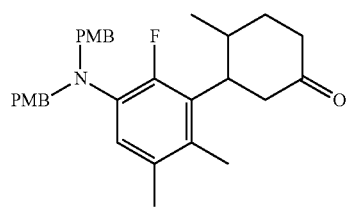

Under nitrogen, a solution of 3-[3-[bis[(4-methoxyphenyl)methyl]amino]-2-fluoro-6-iodo-5-methyl-phenyl]-4-methyl-cyclohexanone (15.00 g, 24.94 mmol) and bis(triphenylphosphine)palladium(II) chloride (1.75 g, 2.49 mmol) in 1,4-dioxane (100 mL) was stirred for time at 40° C. for 5 minutes. Then dimethylzinc (74.81 mL, 74.81 mmol) was added and stirred at 40° C. for 2 hours. After completion, the reaction was quenched with water. The solvent was concentrated under vacuum. The residue was diluted with dichloromethane and washed by water. The organic layer was dried over anhydrous sodium sulfate and concentrated under vacuum. The residue was purified by flash chromatography on silica gel eluting with petroleumeum ether/ethyl acetate (5/1) to afford 3-(3-(bis(4-methoxybenzyl)amino)-2-fluoro-5,6-dimethylphenyl)-4-methylcyclohexan-1-one (5.90 g, 12.04 mmol, 48.4% yield) as a colorless oil. LC-MS: (ESI, m/z): 490.3 [M+H]$^+$.

Step 2: ethyl 4-[3-[bis[(4-methoxyphenyl)methyl]amino]-2-fluoro-5,6-dimethyl-phenyl]-5-methyl-2-oxo-cyclohexanecarboxylate

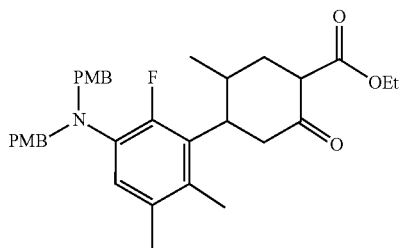

Under nitrogen, a solution of 3-(3-(bis(4-methoxybenzyl)amino)-2-fluoro-5,6-dimethylphenyl)-4-methylcyclohexan-1-one (5.00 g, 10.21 mmol) in tetrahydrofuran (60 mL) was dropwise added and lithium bis(trimethylsilyl)amide (20.42 mL, 20.42 mmol, 1.0 M in THF) and stirred at −78° C. for 30 minutes. Then ethyl cyanoformate (2.33 g, 23.49 mmol) was added and stirred at −78° C. for 2 hours. After completion, the reaction was quenched with water. The solvent was concentrated under vacuum. The residue was diluted with dichloromethane and washed by water. The organic layer was dried over anhydrous sodium sulfate and concentrated under vacuum. The residue was purified by flash chromatography on silica gel eluting with petroleumeum ether/ethyl acetate (3/1) to afford ethyl 4-[3-[bis[(4-methoxyphenyl)methyl]amino]-2-fluoro-5,6-dimethyl-phenyl]-5-methyl-2-oxo-cyclohexanecarboxylate (3.00 g, 5.34 mmol, 52.3% yield) as a colorless oil. LC-MS: (ESI, m/z): 562.3 [M+H]$^+$ Step 3: 7-[3-[bis[(4-methoxyphenyl)methyl]amino]-2-fluoro-5,6-dimethyl-phenyl]-6-methyl-2-methylsulfanyl-5,6,7,8-tetrahydroquinazolin-4-ol

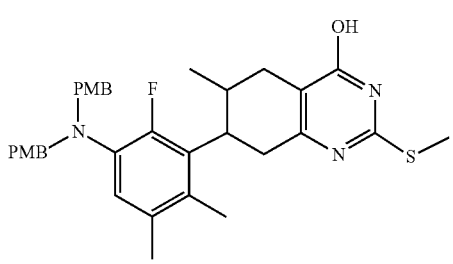

A solution of ethyl 4-[3-[bis[(4-methoxyphenyl)methyl]amino]-2-fluoro-5,6-dimethyl-phenyl]-5-methyl-2-oxo-cyclohexanecarboxylate (3.00 g, 5.34 mmol), 2-methylisothiourea (14.85 g, 53.41 mmol) and sodium bicarbonate (11.22 g, 133.53 mmol) in ethanol (187 mL) and water (37 mL) was stirred at 50° C. for 6 hours. After completion, the reaction was concentrated under vacuum, diluted with water, extracted with dichloromethane. The organic layers were combined and concentrated under vacuum. The residue was purified by flash chromatography on silica gel eluting with dichloromethane/ethyl acetate (1/1) to afford 7-[3-[bis[(4-methoxyphenyl)methyl]amino]-2-fluoro-5,6-dimethyl-phenyl]-6-methyl-2-methylsulfanyl-5,6,7,8-tetrahydroquinazolin-4-ol (1.30 g, 2.21 mmol, 41.4% yield) as a colorless solid. LC-MS: (ESI, m/z): 588.3 [M+H]⁺.

Step 4: tert-butyl (3S)-4-[7-[3-[bis[(4-methoxyphenyl)methyl]amino]-2-fluoro-5,6-dimethyl-phenyl]-6-methyl-2-methylsulfanyl-5,6,7,8-tetrahydroquinazolin-4-yl]-3-methyl-piperazine-1-carboxylate

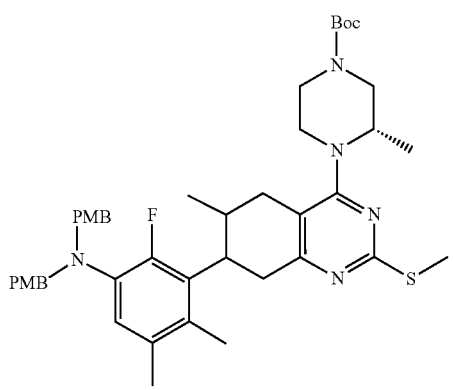

A solution of 7-[3-[bis[(4-methoxyphenyl)methyl]amino]-2-fluoro-5,6-dimethyl-phenyl]-6-methyl-2-methylsulfanyl-5,6,7,8-tetrahydroquinazolin-4-ol (1.50 g, 2.55 mmol) and N,N-diisopropylethylamine (3.29 g, 25.52 mmol) in dichloromethane (5 mL) was stirred at 0° C. for 0.5 hour. Then trifluoromethanesulfonic anhydride (1.44 g, 5.1 mmol) was added and stirred at 0° C. for 5 minutes. The solvent was concentrated under vacuum to afford the crude product. Then the crude product, N,N-diisopropylethylamine (3.29 g, 25.52 mmol) and tert-butyl (3S)-3-methyl-1-piperazinecarboxylate (1.02 g, 5.1 mmol) was added and stirred in 1,4-doxane (15 mL) at 110° C. for 5 hour. After completion, the solvent was concentrated under vacuum. The residue was purified by flash chromatography on silica gel eluting with eluting with dichloromethane/methanol (4/1) to afford tert-butyl (3S)-4-[7-[3-[bis[(4-methoxyphenyl)methyl]amino]-2-fluoro-5,6-dimethyl-phenyl]-6-methyl-2-methylsulfanyl-5,6,7,8-tetrahydroquinazolin-4-yl]-3-methyl-piperazine-1-carboxylate (1.40 g, 1.82 mmol, 71.2% yield) as a yellow solid. LC-MS: (ESI, m/z): 770.4 [M+H]⁺.

Step 5: tert-butyl (3S)-4-[7-[3-[bis[(4-methoxyphenyl)methyl]amino]-2-fluoro-5,6-dimethyl-phenyl]-6-methyl-2-methylsulfonyl-5,6,7,8-tetrahydroquinazolin-4-yl]-3-methyl-piperazine-1-carboxylate

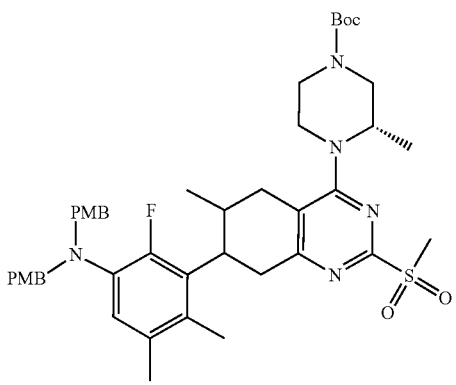

A solution of tert-butyl (3S)-4-[7-[3-[bis[(4-methoxyphenyl)methyl]amino]-2-fluoro-5,6-dimethyl-phenyl]-6-methyl-2-methylsulfanyl-5,6,7,8-tetrahydroquinazolin-4-yl]-3-methyl-piperazine-1-carboxylate (1.30 g, 1.69 mmol) and oxone (3.11 g, 5.06 mmol) in tetrahydrofuran (10 mL) and water (5 mL) was stirred at room temperature for 6 hours. After completion, the reaction was quenched with saturated sodium sulfite. The resulting solution was extracted with dichloromethane and the organic layers were combined. The organic layer was dried over anhydrous sodium sulfate and concentrated under vacuum. The residue was purified by flash chromatography on silica gel eluting with petroleumeum ether/ethyl acetate (3/1) to afford tert-butyl (3S)-4-[7-[3-[bis[(4-methoxyphenyl)methyl]amino]-2-fluoro-5,6-dimethyl-phenyl]-6-methyl-2-methylsulfonyl-5,6,7,8-tetrahydroquinazolin-4-yl]-3-methyl-piperazine-1-carboxylate (1.20 g, 1.49 mmol, 88.6% yield) as a colorless solid. LC-MS: (ESI, m/z): 802.4 [M+H]⁺

Steps 6 and 7: tert-butyl (3S)-4-[7-[3-[bis[(4-methoxyphenyl)methyl]amino]-2-fluoro-5,6-dimethyl-phenyl]-6-methyl-2-[[(2S)-1-methylpyrrolidin-2-yl]methoxy]-5,6,7,8-tetrahydroquinazolin-4-yl]-3-methyl-piperazine-1-carboxylate

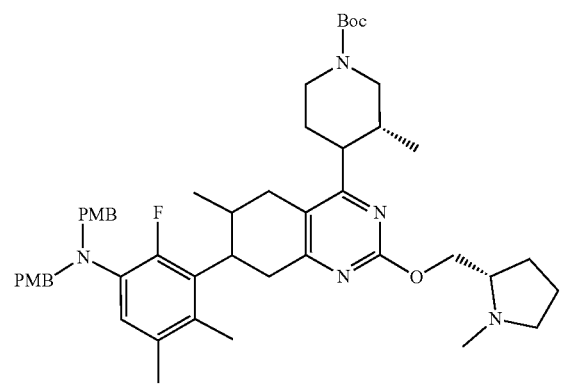

A solution of N-methyl-L-prolinol (0.69 g, 5.98 mmol) and sodium hydride (0.18 g, 7.48 mmol, 60% dispersion in mineral oil) in N,N-dimethylformamide (10 mL) was stirred at 0° C. for 0.5 hour. Then tert-butyl (3S)-4-[7-[3-[bis[(4-methoxyphenyl)methyl]amino]-2-fluoro-5,6-dimethyl-phenyl]-6-methyl-2-methylsulfonyl-5,6,7,8-tetrahydroquinazolin-4-yl]-3-methyl-piperazine-1-carboxylate (1.2 g, 1.5 mmol) was added and stirred at room temperature for 1 hour. After completion, the reaction was quenched with saturated ammonium chloride. The resulting solution was extracted with ethyl acetate and the organic layers were combined. The organic layer was dried over anhydrous sodium sulfate and concentrated under vacuum. The residue was purified by flash chromatography on silica gel eluting with dichloromethane/methanol (10/1) to afford tert-butyl (3S)-4-[7-[3-[bis[(4-methoxyphenyl)methyl]amino]-2-fluoro-5,6-dimethyl-phenyl]-6-methyl-2-[[(2S)-1-methylpyrrolidin-2-yl]methoxy]-5,6,7,8-tetrahydroquinazolin-4-yl]-3-methyl-piperazine-1-carboxylate (0.80 g, 0.96 mmol, 63.9% yield) as a colorless oil. LC-MS: (ESI, m/z): 836.5 [M+H]+

Step 8: 2-fluoro-4,5-dimethyl-3-[6-methyl-4-[(2S)-2-methylpiperazin-1-yl]-2-[[(2S)-1-methylpyrrolidin-2-yl]methoxy]-5,6,7,8-tetrahydroquinazolin-7-yl]aniline

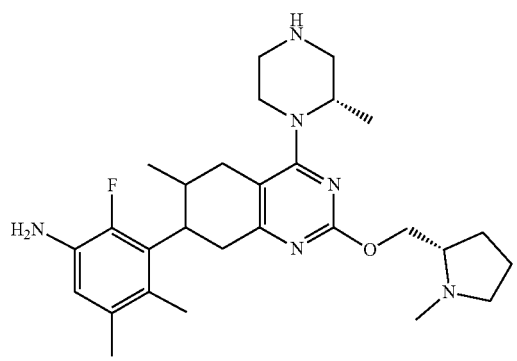 [SMILES: Cc1cc(N)c(F)c(C2Cc3nc(OC[C@@H]4CCCN4C)nc(N4CCNC[C@@H]4C)c3CC2C)c1C]

A solution of tert-butyl (3S)-4-[7-[3-[bis[(4-methoxyphenyl)methyl]amino]-2-fluoro-5,6-dimethyl-phenyl]-6-methyl-2-[[(2S)-1-methylpyrrolidin-2-yl]methoxy]-5,6,7,8-tetrahydroquinazolin-4-yl]-3-methyl-piperazine-1-carboxylate (1.10 g, 1.31 mmol) in trifluoroacetic acid (4.0 mL) was stirred at 70° C. for 12 hours. After completion, the solvent was concentrated under vacuum. The residue was purified by flash chromatography on reverse-phase column eluting with water/acetonitrile (1/2) to afford 2-fluoro-4,5-dimethyl-3-[6-methyl-4-[(2S)-2-methylpiperazin-1-yl]-2-[[(2S)-1-methylpyrrolidin-2-yl]methoxy]-5,6,7,8-tetrahydroquinazolin-7-yl]aniline (0.50 g, 1.00 mmol, 76.6% yield) as a light yellow solid. LC-MS: (ESI, m/z): 497.3 [M+H]+.

Step 9: 1-[(3S)-4-[(6S,7S)-7-(3-amino-2-fluoro-5,6-dimethyl-phenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one (Example 11a) and 1-[(3S)-4-[(6R,7R)-7-(3-amino-2-fluoro-5,6-dimethyl-phenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one (Example 11b)

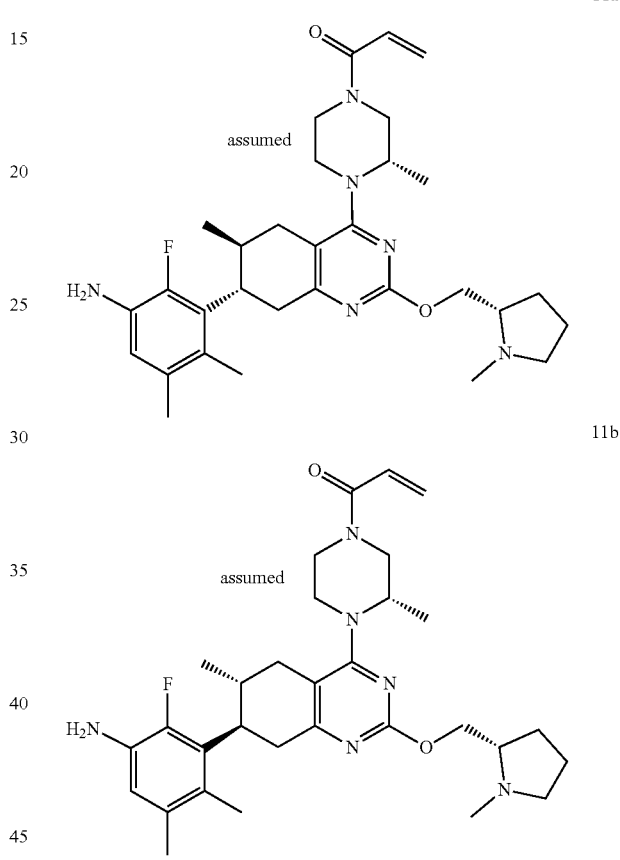

A solution of 2-fluoro-4,5-dimethyl-3-[6-methyl-4-[(2S)-2-methylpiperazin-1-yl]-2-[[(2S)-1-methylpyrrolidin-2-yl]methoxy]-5,6,7,8-tetrahydroquinazolin-7-yl]aniline (500.0 mg, 1.01 mmol), acrylic acid (91.12 mg, 1.01 mmol), N,N-diisopropylethylamine (194.8 mg, 1.51 mmol) and O-(7-2-(7-Azabenzotriazol-1-yl)-N,N,N,N-tetramethyluronium hexafluorophosphate (421.07 mg, 1.11 mmol) in dichloromethane (100 mL) was stirred at 0° C. for 15 minutes. After completion, the reaction was quenched with water. The resulting solution was extracted with dichloromethane and the organic layers were combined. The organic layer was dried over anhydrous sodium sulfate and concentrated under vacuum. The residue was purified by flash chromatography on silica gel eluting with petroleumeum dichloromethane/methanol (3/1) to afford the diastereoisomers as a white solid. Then the diastereoisomers was isolated by Prep-Chiral-HPLC (Column: CHIRALPAK IG-3, 4.6*50 mm, 3 um; Mobile Phase A: (Hex:DCM=3:1) (0.1% DEA): EtOH=50:50, Mobile Phase B; Flow rate: 1 m/min to afford the title compounds. The absolute configuration of the title compounds was inferred from potency data and a protein X-ray structure of compound 21b.

Example 11a: 1-[(3S)-4-[(6S,7S)-7-(3-amino-2-fluoro-5,6-dimethyl-phenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one (32.8 mg, 0.05 mmol, 5.9% yield, white solid). ¹H NMR (300 MHz, DMSO-d₆, ppm) δ 6.90-6.77 (m, 1H), 6.49 (d, J=9.0 Hz, 1H), 6.15 (d, J=16.8 Hz, 1H), 5.72 (d, J=10.5 Hz, 1H), 4.70 (s, 2H), 4.33-4.00 (m, 5H), 3.90-3.85 (m, 1H), 3.66-3.62 (m, 1H), 3.50-3.39 (m, 2H), 3.16-3.05 (m, 1H), 2.93-2.84 (m, 4H), 2.65-2.61 (m, 1H), 2.43-2.38 (m, 1H), 2.32 (s, 3H), 2.16-2.10 (m, 8H), 1.94-1.85 (m, 1H), 1.70-1.55 (m, 3H), 0.97 (brs, 3H), 0.81 (d, J=6.3 Hz, 3H). LC-MS: (ESI, m/z): 551.3 [M+H]⁺. Chiral HPLC: CHIRALPAK IG-3 (0.46*5 cm); detected at 254 nm; (Hex:DCM=3:1)(0.1% DEA)/EtOH=50/50; flow=1.0 mL/min; Retention time: 2.374 min (slower peak).

Example 11b: 1-[(3S)-4-[(6R,7R)-7-(3-amino-2-fluoro-5,6-dimethyl-phenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one (33.4 mg, 0.06 mmol, 6% yield, white solid). ¹H NMR (300 MHz, DMSO-d₆, ppm) δ 6.90-6.78 (m, 1H), 6.49 (d, J=9.0 Hz, 1H), 6.15 (d, J=16.8 Hz, 1H), 5.73-5.69 (m, 1H), 4.70 (s, 2H), 4.38-3.88 (m, 6H), 3.48-3.31 (m, 1H), 3.15-3.03 (m, 3H), 2.95-2.82 (m, 4H), 2.45-2.40 (m, 1H), 2.32 (s, 4H), 2.17-2.09 (m, 8H), 1.94-1.88 (m, 1H), 1.66-1.56 (m, 3H), 1.27 (d, J=6.3 Hz, 3H), 0.81 (d, J=6.3 Hz, 3H). LC-MS: (ESI, m/z): 551.3 [M+H]⁺. Chiral HPLC: CHIRALPAK IG-3 (0.46*5 cm); detected at 254 nm; (Hex:DCM=3:1)(0.1% DEA)/EtOH=50/50; flow=1.0 mL/min; Retention time: 1.261 min (faster peak).

Example 12a and 12b

Example 12a

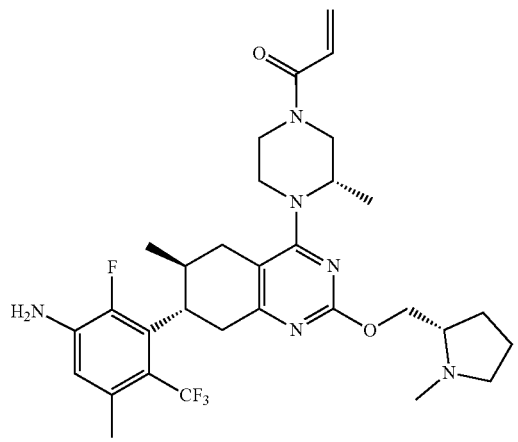

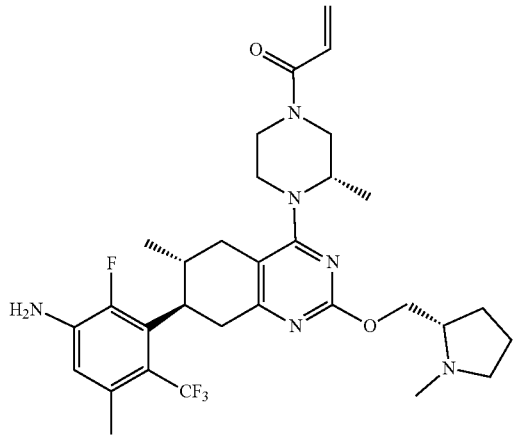

Example 12b 1-((S)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 12a)

1-((S)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 12b)

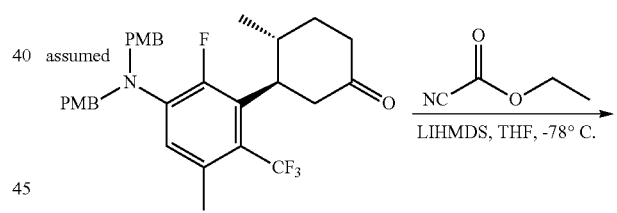

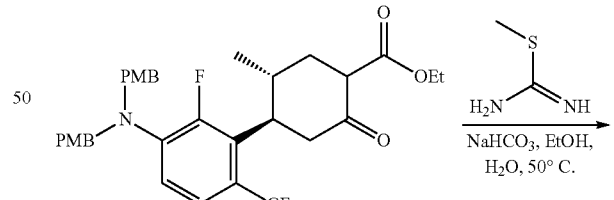

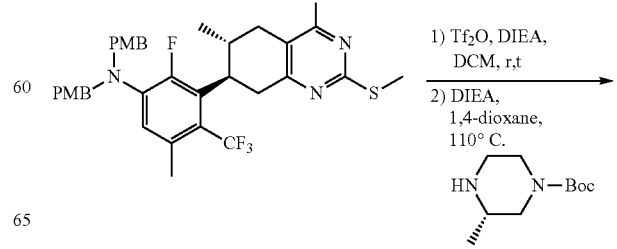

-continued

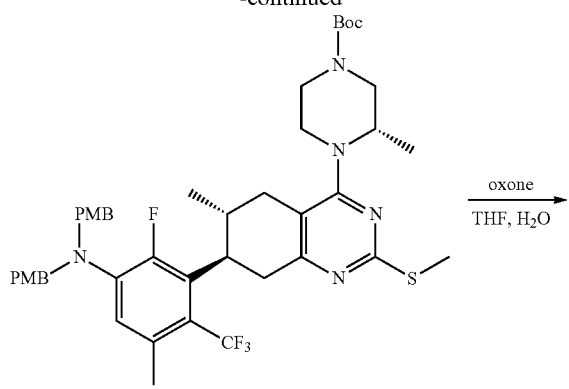

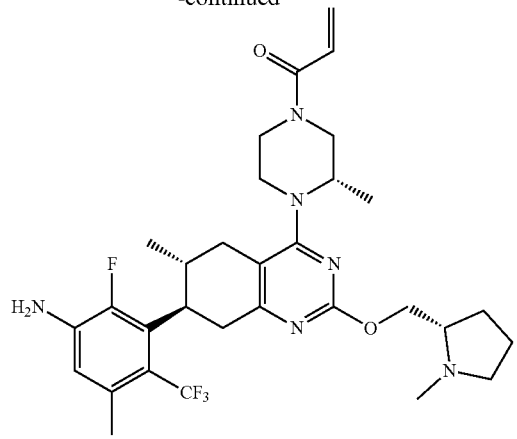

Example 12b

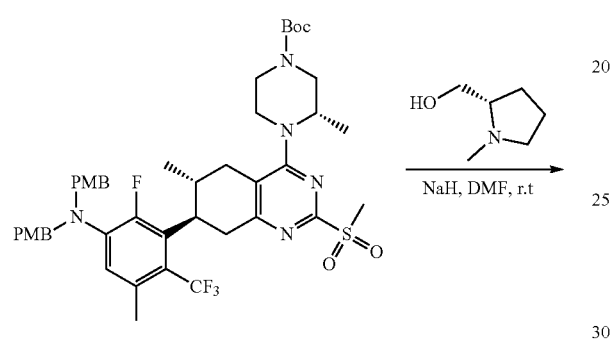

Step 1: ethyl (4R,5R)-4-(3-(bis(4-methoxybenzyl)amino)-2-fluoro-5-methyl-6-(trifluoromethyl)phenyl)-5-methyl-2-oxocyclohexane-1-carboxylate

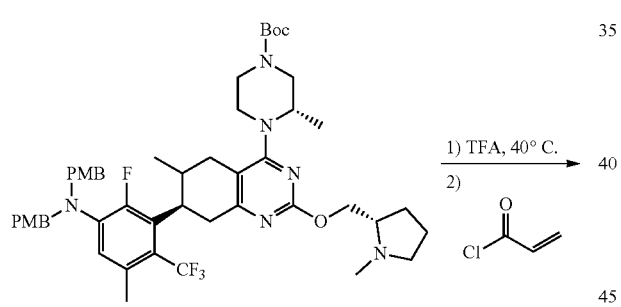

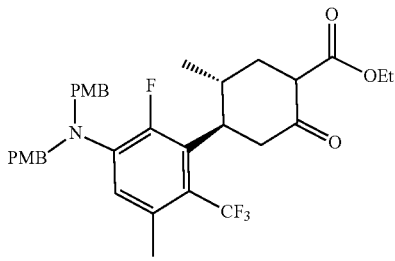

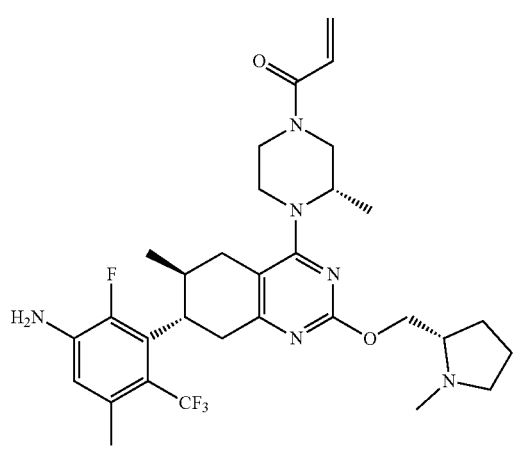

Example 12a

Under nitrogen, a solution of (3R,4R)-3-(3-(bis(4-methoxybenzyl)amino)-2-fluoro-5-methyl-6-(trifluoromethyl)phenyl)-4-methylcyclohexan-1-one (2.70 g, 4.97 mmol) in tetrahydrofuran (30 mL) was dropwise added lithium bis(trimethylsilyl)amide (9.93 mL, 9.93 mmol) and stirred at −78° C. for 0.5 hours. Then ethyl cyanoformate (1.13 g, 11.42 mmol) was added and stirred at −78° C. for 2 hours. After completion, the reaction was quenched with water. After completion, the reaction was quenched with water. The solvent was concentrated under vacuum. The residue was diluted with dichloromethane and washed by water. The organic layer was dried over anhydrous sodium sulfate and concentrated under vacuum. The residue was purified by flash chromatography on silica gel eluting with petroleumeum ether/ethyl acetate (4/1) to afford ethyl (4R, 5R)-4-(3-(bis(4-methoxybenzyl)amino)-2-fluoro-5-methyl-6-(trifluoromethyl)phenyl)-5-methyl-2-oxocyclohexane-1-carboxylate (1.70 g, 2.76 mmol, 55.6% yield) as a colorless oil. LC-MS: (ESI, m/z): 616.3 [M+H]$^+$

Step 2: (6R,7R)-7-(3-(bis(4-methoxybenzyl)amino)-2-fluoro-5-methyl-6-(trifluoromethyl)phenyl)-6-methyl-2-(methylthio)-5,6,7,8-tetrahydroquinazolin-4-ol

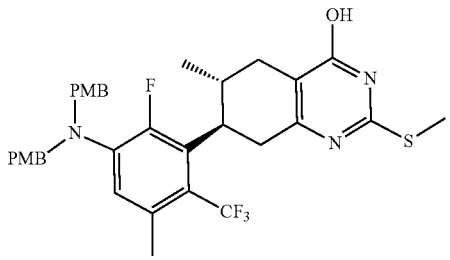

A solution of ethyl (4R,5R)-4-(3-(bis(4-methoxybenzyl)amino)-2-fluoro-5-methyl-6-(trifluoromethyl)phenyl)-5-methyl-2-oxocyclohexane-1-carboxylate (1.70 g, 2.76 mmol), 2-methyl-2-thiopseudourea sulfate (7.68 g, 27.61 mmol) and sodium bicarbonate (5.80 g, 69.03 mmol) in ethanol (12 mL) and water (2.5 mL) was stirred at 50° C. for 4 hours. After completion, the solvent was concentrated under vacuum. The reaction mixture was diluted with water. The resulting solution was extracted with dichloromethane and the organic layers were combined. The organic layer was dried over anhydrous sodium sulfate and concentrated under vacuum. The residue was purified by flash chromatography on silica gel eluting with dichloromethane/ethyl acetate (4/1) to afford (6R,7R)-7-(3-(bis(4-methoxybenzyl)amino)-2-fluoro-5-methyl-6-(trifluoromethyl)phenyl)-6-methyl-2-(methylthio)-5,6,7,8-tetrahydroquinazolin-4-ol (0.65 g, 1.01 mmol, 36.7% yield) as a yellow solid. LC-MS: (ESI, m/z): 642.2 [M+H]$^+$.

Step 3: tert-butyl (S)-4-((6R,7R)-7-(3-(bis(4-methoxybenzyl)amino)-2-fluoro-5-methyl-6-(trifluoromethyl)phenyl)-6-methyl-2-(methylthio)-5,6,7,8-tetrahydroquinazolin-4-yl)-3-methylpiperazine-1-carboxylate

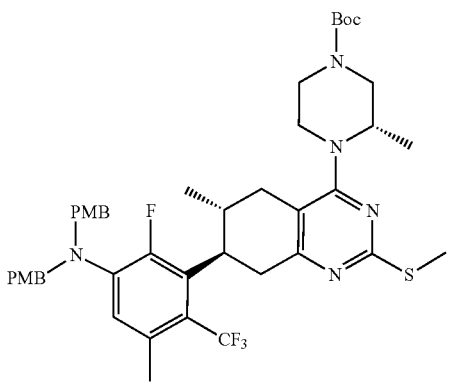

A solution of (6R,7R)-7-(3-(bis(4-methoxybenzyl)amino)-2-fluoro-5-methyl-6-(trifluoromethyl)phenyl)-6-methyl-2-(methylthio)-5,6,7,8-tetrahydroquinazolin-4-ol (650.0 mg, 1.01 mmol) and N,N-diisopropylethylamine (653.32 mg, 5.06 mmol) in dichloromethane (5 mL) was stirred at 0° C. for 0.5 hour. Then trifluoromethanesulfonic anhydride (571.3 mg, 2.03 mmol) was added and stirred at 0° C. for 5 minutes. The solvent was concentrated under vacuum to afford the crude product. Then The crude product, N,N-diisopropylethylamine (653.3 mg, 5.06 mmol) and tert-butyl (3S)-3-methyl-1-piperazinecarboxylate (202.9 mg, 1.01 mmol) was added and stirred in 1,4-dioxane (5 mL) at 110° C. for 5 hours. After completion, the solvent was concentrated under vacuum. The residue was purified by flash chromatography on silica gel eluting with eluting with dichloromethane/methanol (4/1) to afford tert-butyl (S)-4-((6R,7R)-7-(3-(bis(4-methoxybenzyl)amino)-2-fluoro-5-methyl-6-(trifluoromethyl)phenyl)-6-methyl-2-(methylthio)-5,6,7,8-tetrahydroquinazolin-4-yl)-3-methylpiperazine-1-carboxylate (660.0 mg, 0.80 mmol, 79.1% yield) as a yellow solid. LC-MS: (ESI, m/z): 824.4 [M+H]$^+$

Step 4: tert-butyl (S)-4-((6R,7R)-7-(3-(bis(4-methoxybenzyl)amino)-2-fluoro-5-methyl-6-(trifluoromethyl)phenyl)-6-methyl-2-(methylsulfonyl)-5,6,7,8-tetrahydroquinazolin-4-yl)-3-methylpiperazine-1-carboxylate

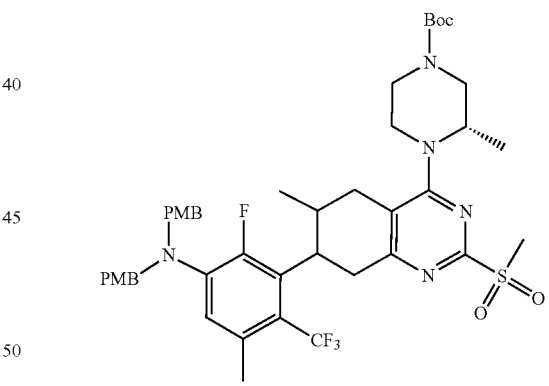

A solution of tert-butyl (S)-4-((6R,7R)-7-(3-(bis(4-methoxybenzyl)amino)-2-fluoro-5-methyl-6-(trifluoromethyl)phenyl)-6-methyl-2-(methylthio)-5,6,7,8-tetrahydroquinazolin-4-yl)-3-methylpiperazine-1-carboxylate (660.0 mg, 0.80 mmol) and potassium peroxymonosulfate (1.48 g, 2.4 mmol) in tetrahydrofuran (6 mL) and water (3 mL) was stirred at room temperature for 3 hours. After completion, the solvent was concentrated under vacuum to afford the crude product. The crude product was used for next step directly without purification. LC-MS: (ESI, m/z): 856.4 [M+H]$^+$

Step 5: tert-butyl (S)-4-((6R,7R)-7-(3-(bis(4-methoxybenzyl)amino)-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-3-methylpiperazine-1-carboxylate

Step 6: 1-((S)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 12a); 1-((S)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 12b)

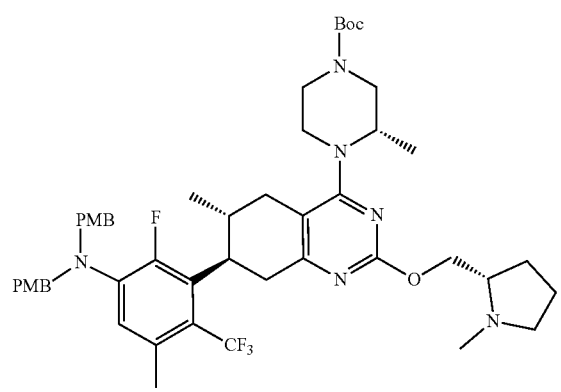

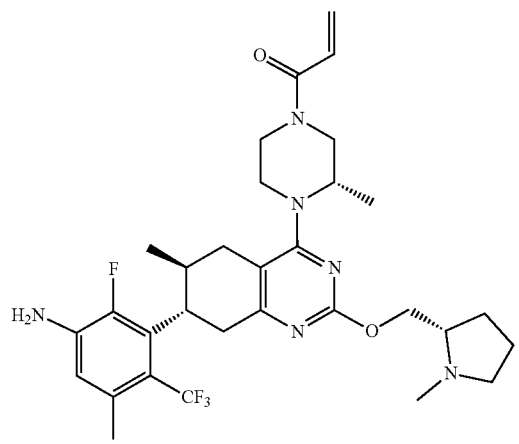

Example 12a

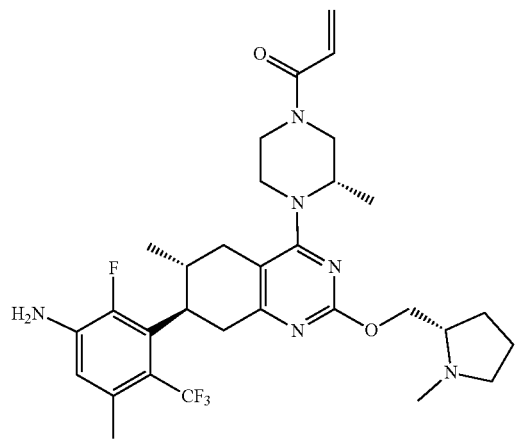

Example 12b

A solution of sodium hydride (163.56 mg, 4.09 mmol, 60% dispersion in mineral oil) and N-methyl-L-prolinol (470.92 mg, 4.09 mmol) in N,N-dimethylformamide (18 mL) was stirred at 0° C. for 0.5 hour. Then tert-butyl (S)-4-((6R,7R)-7-(3-(bis(4-methoxybenzyl)amino)-2-fluoro-5-methyl-6-(trifluoromethyl)phenyl)-6-methyl-2-(methylsulfonyl)-5,6,7,8-tetrahydroquinazolin-4-yl)-3-methylpiperazine-1-carboxylate (777.8 mg, 0.82 mmol) was added and stirred at room temperature for 6 hours. After completion, the reaction was quenched with saturated ammonium chloride solution. The resulting solution was extracted with dichloromethane and the organic layers were combined. The organic layer was dried over anhydrous sodium sulfate and concentrated under vacuum. The residue was purified by flash chromatography on silica gel eluting with dichloromethane/methanol (7/1) to afford tert-butyl (S)-4-((6R,7R)-7-(3-(bis(4-methoxybenzyl)amino)-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-3-methylpiperazine-1-carboxylate (550.0 mg, 0.62 mmol, 75.5% yield) as a yellow solid. LC-MS: (ESI, m/z): 891.5 [M+H]$^+$.

A solution of tert-butyl (S)-4-((6R,7S)-7-(3-(bis(4-methoxybenzyl)amino)-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-3-methylpiperazine-1-carboxylate (660.0 mg, 0.74 mmol) in trifluoroacetic acid (1.5 mL) and dichloromethane (7 mL) was stirred at 40° C. for 12 hours. After completion, the solvent was concentrated under vacuum to afford the crude product. The crude product was used for next step directly without purification. Then to the crude product and N,N-diisopropylethylamine (477.75 mg, 3.7 mmol) in dichloromethane (7 mL) was dropwise added acrylyl chloride (67.04 mg, 0.74 mmol) and stirred at −78° C. for 10 min. After completion, the solvent was concentrated under vacuum. The residue was purified by flash chromatography on silica gel eluting with dichloromethane/methanol (10/1)

to afford to afford the crude product. The mixture was purified by cSFC. The stereochemistry of the title compounds was assigned based on potency.

Example 12a: (Peak 1): CHIRALPAK IF-3 4.6*50 mm 3 um, Hex(0.1% DEA):EtOH=75:25, 1.0 ml/min, RT=1.61 min (faster). $^1$H NMR (300 MHz, DMSO-$d_6$, ppm) δ 6.95-6.70 (m, 1H), 6.58 (d, J=8.8 Hz, 1H), 6.16 (d, J=16.7 Hz, 1H), 5.84-5.62 (m, 3H), 4.37-4.15 (m, 3H), 4.09-3.98 (m, 1H), 3.92-3.57 (m, 1H), 3.50-3.04 (m, 5H), 3.02-2.77 (m, 4H), 2.70-2.55 (m, 1H), 2.43-2.09 (m, 9H), 2.01-1.80 (m, 1H), 1.73-1.47 (m, 3H), 1.07-0.91 (m, 3H), 0.82 (d, J=6.2 Hz, 3H). LC-MS: (ESI, m/z): 605.4 [M+H]$^+$ Example 12b: (Peak 2): CHIRALPAK IF-3 4.6*50 mm 3 um, Hex(0.1% DEA):EtOH=75:25, 1.0 ml/min, RT=2.22 min (slower). $^1$H NMR (300 MHz, DMSO-$d_6$, ppm) δ 6.95-6.70 (m, 1H), 6.58 (d, J=8.8 Hz, 1H), 6.16 (d, J=17.7 Hz, 1H), 5.87-5.60 (m, 3H), 4.46-3.77 (m, 6H), 3.58-3.40 (m, 1H), 3.24-3.01 (m, 3H), 3.00-2.68 (m, 4H), 2.44-2.04 (m, 10H), 2.01-1.79 (m, 1H), 1.73-1.46 (m, 3H), 1.27 (d, J=6.3 Hz, 3H), 0.81 (d, J=6.3 Hz, 3H).

Examples 13a and 13b (R)-1-(4-(7-(3-amino-2,5-difluoro-6-(trifluoromethyl)phenyl)-5,6,7,8-tetrahydroquinazolin-4-yl)piperazin-1-yl)prop-2-en-1-one (Example 13a)

(S)-1-(4-(7-(3-amino-2,5-difluoro-6-(trifluoromethyl)phenyl)-5,6,7,8-tetrahydroquinazolin-4-yl)piperazin-1-yl)prop-2-en-1-one (Example 13b)

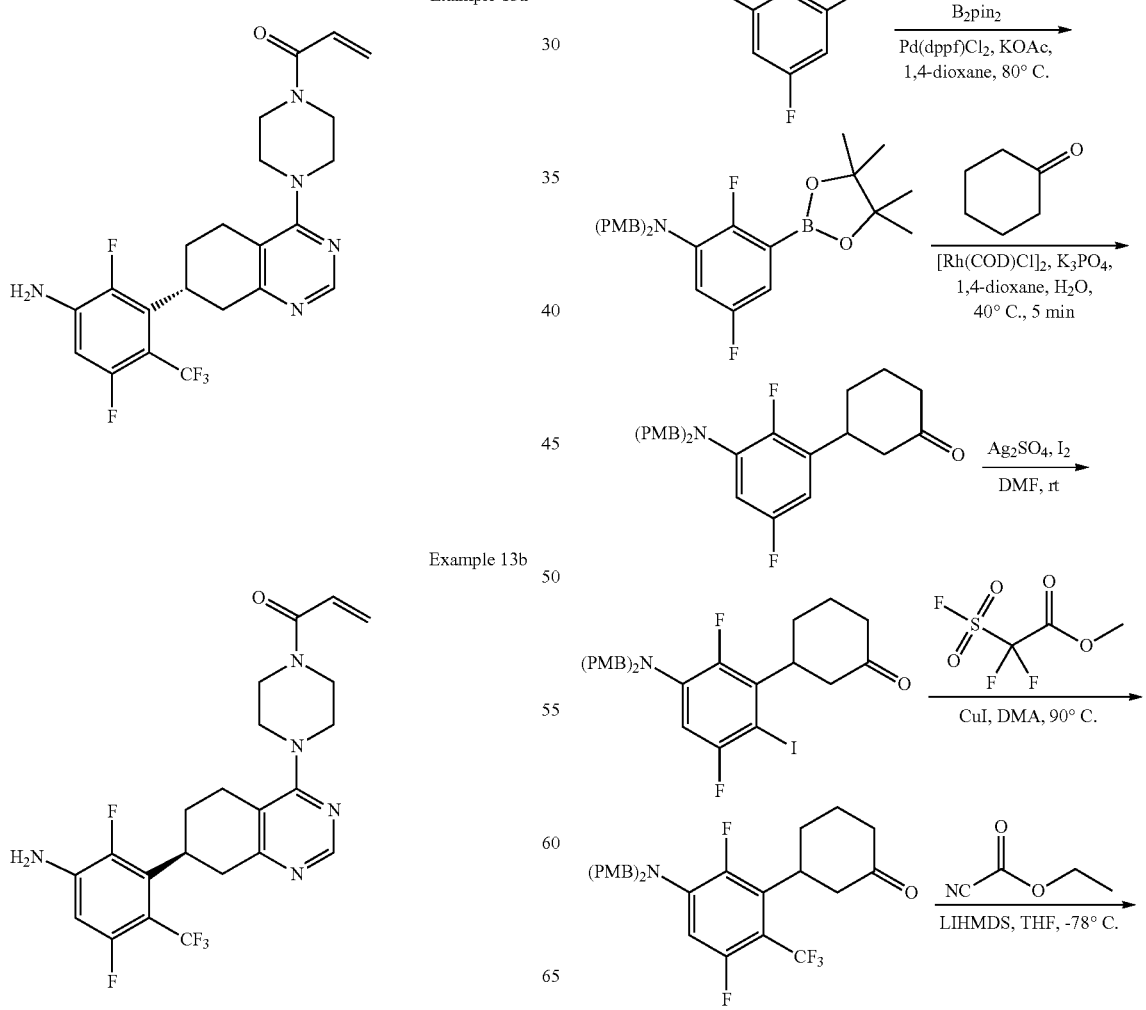

343

-continued

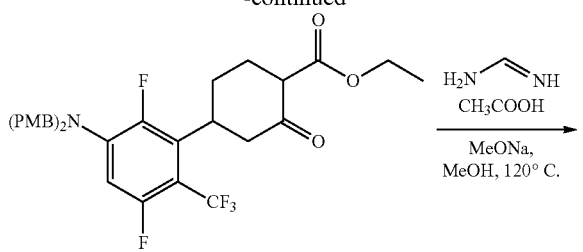

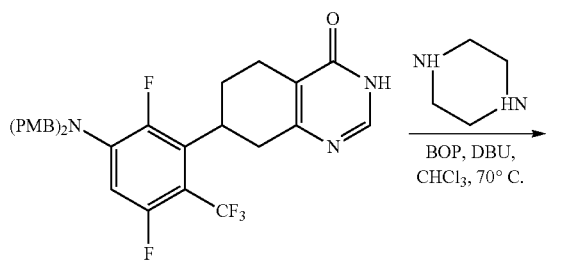

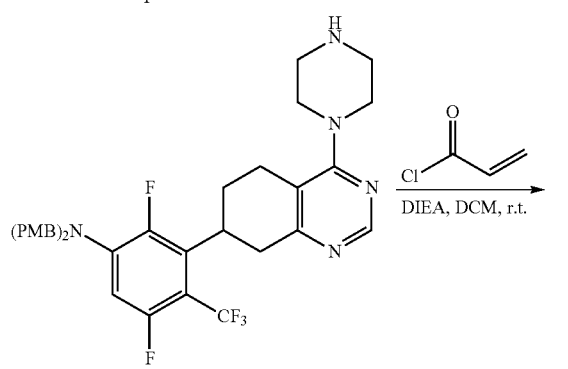

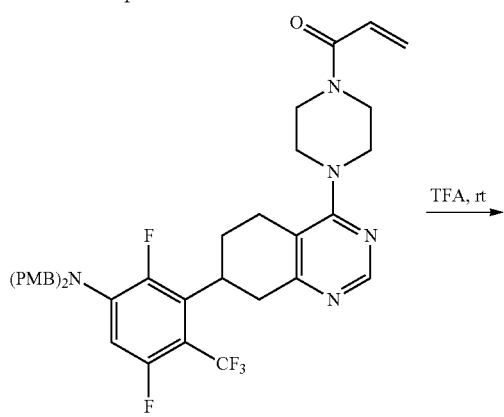

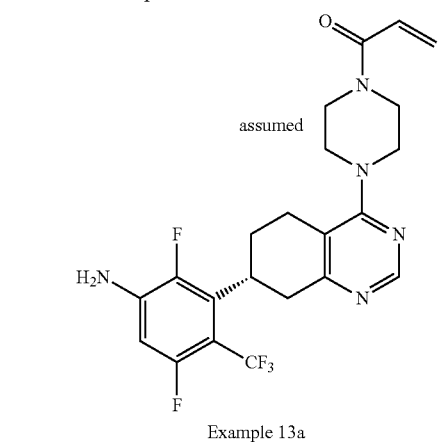

Example 13a

344

-continued

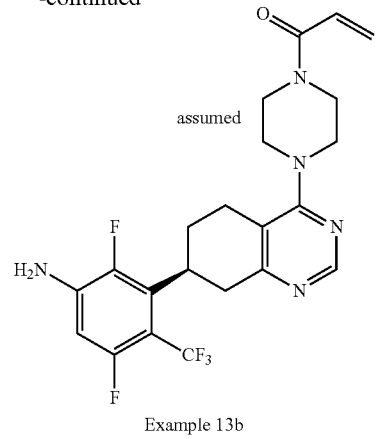

Example 13b

Step 1: 3-bromo-2,5-difluoroaniline

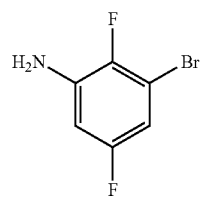

A solution of 1-bromo-2,5-difluoro-3-nitro-benzene (20.00 g, 84.04 mmol), iron powder (14.08 g, 252.11 mmol) and ammonium chloride (22.27 g, 420.19 mmol) in ethanol (400 mL) and water (80 mL) was stirred at 80° C. for 2 hours. After completion, the reaction mixture was filtrated, and the filtrate was concentrated under reduced pressure. The residue was diluted with dichloromethane and washed with saturated sodium chloride solution, dried over anhydrous sodium sulfate and concentrated under vacuum to afford 3-bromo-2,5-difluoroaniline (12.00 g, 57.69 mmol, 68.7% yield) as a red oil. LC-MS: (ESI, m/z): 207.9 [M+H]$^+$.

Step 2: 3-bromo-2,5-difluoro-N,N-bis(4-methoxybenzyl)aniline

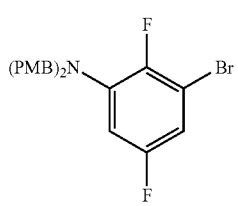

A solution of 3-bromo-2,5-difluoro-aniline (12.00 g, 57.69 mmol) and sodium hydride (11.54 g, 288.46 mmol, 60% dispersion in mineral oil) in N,N-dimethylformamide (150 mL) was stirred at 0° C. for 0.5 hours. Then 4-methoxybenzylchloride (38.8 mL, 288.46 mmol) was added and stirred at room temperature for 0.5 hours. After completion, the reaction was quenched with saturated ammonium chloride. The resulting solution was extracted with ethyl acetate and the organic layers were combined. The organic layer was washed with water, dried over anhydrous sodium sulfate and concentrated under vacuum. The residue was purified by flash chromatography on silica gel eluting with petroleumeum ether/ethyl acetate (10/1) to afford 3-bromo-2,5-difluoro-N,N-bis(4-methoxybenzyl)aniline (20.00 g, 44.61 mmol, 77.3% yield) as a yellow oil. LC-MS: (ESI, m/z): 448.1 [M+H]$^+$.

Step 3: 2,5-difluoro-N,N-bis(4-methoxybenzyl)-3-(4,4,5,5-tetramethyl-1,3,2-dioxaborolan-2-yl)aniline

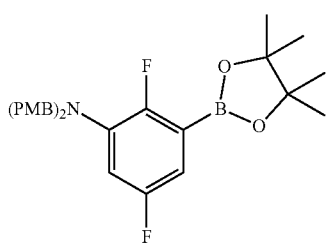

Under nitrogen, a solution of 3-bromo-2,5-difluoro-N,N-bis[(4-methoxyphenyl)methyl]aniline (20.00 g, 44.61 mmol), bis(pinacolato)diboron (33.99 g, 133.84 mmol), 1,1'-bis(diphenylphosphino)ferrocene-palladium(II)dichloride (3.27 g, 4.46 mmol) and potassium acetate (8.74 g, 89.23 mmol) in 1,4-dioxane (200 mL) was stirred at 80° C. for 3 hours. After completion, the resulting solution was concentrated under vacuum, diluted with dichloromethane and washed by water. The organic layer was dried over anhydrous sodium sulfate and concentrated under vacuum. The residue was purified by flash chromatography on silica gel eluting with petroleumeum ether/ethyl acetate (10/1) to afford 2,5-difluoro-N,N-bis(4-methoxybenzyl)-3-(4,4,5,5-tetramethyl-1,3,2-dioxaborolan-2-yl)aniline (14.00 g, 28.26 mmol, 63.3% yield) as a yellow solid. LC-MS: (ESI, m/z): 496.2 [M+H]$^+$.

Step 4: 3-(3-(bis(4-methoxybenzyl)amino)-2,5-difluorophenyl)cyclohexan-1-one

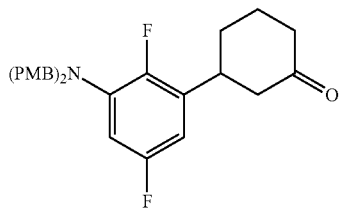

Under nitrogen, a solution of 2-cyclohexen-1-one (8.15 g, 84.79 mmol), 2,5-difluoro-N,N-bis(4-methoxybenzyl)-3-(4,4,5,5-tetramethyl-1,3,2-dioxaborolan-2-yl)aniline (14.00 g, 28.26 mmol), chloro(1,5-cyclooctadiene)rhodium(I) dimer (0.70 g, 1.41 mmol) in 1,4-dioxane (100 mL) was added aqueous saturated potassium phosphate (10 mL) and stirred at 40° C. for 5 minutes. After completion, the resulting solution was concentrated under vacuum, diluted with dichloromethane and washed by water. The organic layer was dried over anhydrous sodium sulfate and concentrated under vacuum. The residue was purified by flash chromatography on silica gel eluting with petroleumeum ether/ethyl acetate (5/1) to afford 3-(3-(bis(4-methoxybenzyl)amino)-2,5-difluorophenyl)cyclohexan-1-one (8.00 g, 17.19 mmol, 60.8% yield) as a yellow liquid. LC-MS: (ESI, m/z): 466.2 [M+H]$^+$.

Step 5: 3-(3-(bis(4-methoxybenzyl)amino)-2,5-difluoro-6-iodophenyl)cyclohexan-1-one

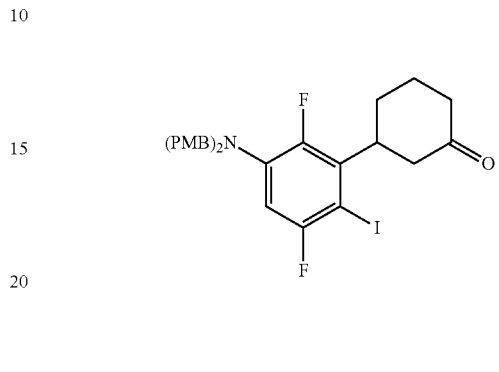

A solution of 3-(3-(bis(4-methoxybenzyl)amino)-2,5-difluorophenyl)cyclohexan-1-one (6.00 g, 12.89 mmol), silver sulfate (4.42 g, 14.18 mmol) and iodine (3.60 g, 14.18 mmol) in DMF (60 mL) was stirred at room temperature for 1 hour. After completion, the reaction mixture was filtrated, and the filtrate was concentrated under reduced pressure. The residue was purified by flash chromatography on silica gel eluting with petroleumeum ether/ethyl acetate (5/1) to afford 3-(3-(bis(4-methoxybenzyl)amino)-2,5-difluoro-6-iodophenyl)cyclohexan-1-one (3.50 g, 5.92 mmol, 45.9% yield) as a colorless oil. LC-MS: (ESI, m/z): 592.1 [M+H]$^+$.

Step 6: 3-(3-(bis(4-methoxybenzyl)amino)-2,5-difluoro-6-(trifluoromethyl)phenyl)cyclohexan-1-one

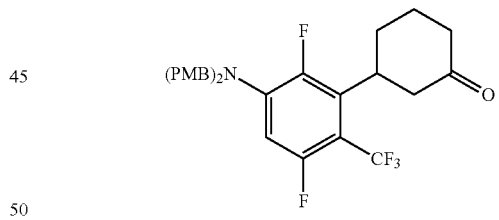

Under nitrogen, a solution of 3-(3-(bis(4-methoxybenzyl)amino)-2,5-difluoro-6-iodophenyl)cyclohexan-1-one (4.00 g, 6.76 mmol), methyl 2,2-difluoro-2-(fluorosulfonyl)acetate (6.50 g, 33.82 mmol) and cuprous iodide (1.29 g, 6.76 mmol) in N,N-dimethylacetamide (40 mL) was stirred at 90° C. for 2 hours. After completion, the reaction was diluted with water, extracted with ethyl acetate and the organic layers were combined. The organic layer was washed with water, dried over anhydrous sodium sulfate and concentrated under vacuum. The residue was purified by flash chromatography on silica gel eluting with petroleumeum ether/ethyl acetate (3/1) to afford 3-(3-(bis(4-methoxybenzyl)amino)-2,5-difluoro-6-(trifluoromethyl)phenyl)cyclohexan-1-one (2.00 g, 3.75 mmol, 55.4% yield) as a light yellow solid. LC-MS: (ESI, m/z): 534.2 [M+H]$^+$.

Step 7: ethyl 4-(3-(bis(4-methoxybenzyl)amino)-2,5-difluoro-6-(trifluoromethyl)phenyl)-2-oxocyclohexane-1-carboxylate

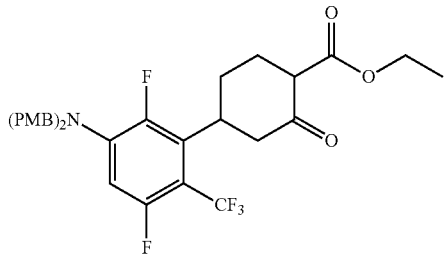

Under nitrogen, a solution of 3-(3-(bis(4-methoxybenzyl)amino)-2,5-difluoro-6-(trifluoromethyl)phenyl)cyclohexan-1-one (1.80 g, 3.37 mmol) in tetrahydrofuran (20 mL) was added lithium bis(trimethylsilyl)amide (6.75 mL, 6.75 mmol, 1.0 M in THF) and stirred at −78° C. for 0.5 hours. Then ethyl cyanoformate (0.77 g, 7.76 mmol) was added and stirred at −78° C. for 2 hours. After completion, the reaction was quenched with water. The resulting solution was extracted with ethyl acetate and the organic layers were combined. The organic layer was dried over anhydrous sodium sulfate and concentrated under vacuum. The residue was purified by flash chromatography on silica gel eluting with petroleumeum ether/ethyl acetate (4/1) to afford ethyl 4-(3-(bis(4-methoxybenzyl)amino)-2,5-difluoro-6-(trifluoromethyl)phenyl)-2-oxocyclohexane-1-carboxylate (0.70 g, 1.16 mmol, 34.3% yield) as a colorless oil. LC-MS: (ESI, m/z): 606.2 [M+H]$^+$.

Step 8: 7-(3-(bis(4-methoxybenzyl)amino)-2,5-difluoro-6-(trifluoromethyl)phenyl)-5,6,7,8-tetrahydroquinazolin-4(3H)-one

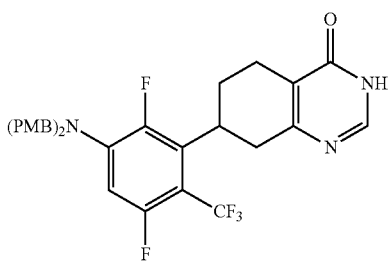

A solution of ethyl 4-(3-(bis(4-methoxybenzyl)amino)-2,5-difluoro-6-(trifluoromethyl)phenyl)-2-oxocyclohexane-1-carboxylate (800.0 mg, 1.32 mmol), formamidine acetate (687.7 mg, 6.61 mmol) and MeONa (888.7 mg, 9.25 mmol) in methanol (10 mL) was stirred at 120° C. for 2 hours. After completion, the solvent was concentrated under vacuum. The residue was diluted with dichloromethane and washed by water. The organic layer was dried over anhydrous sodium sulfate and concentrated under vacuum. The residue was purified by flash chromatography on silica gel eluting with dichloromethane/methanol (10/1) to afford 7-(3-(bis(4-methoxybenzyl)amino)-2,5-difluoro-6-(trifluoromethyl)phenyl)-5,6,7,8-tetrahydroquinazolin-4(3H)-one (400.0 mg, 0.68 mmol, 51.7% yield) as a yellow solid. LC-MS: (ESI, m/z): 586.2 [M+H]$^+$.

Step 9: 2,5-difluoro-N,N-bis(4-methoxybenzyl)-3-(4-(piperazin-1-yl)-5,6,7,8-tetrahydroquinazolin-7-yl)-4-(trifluoromethyl)aniline

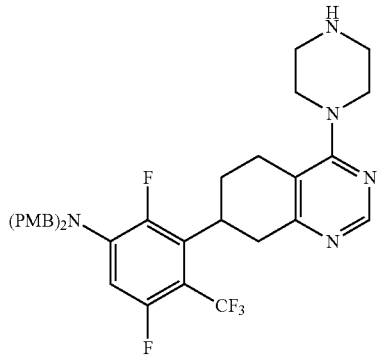

A solution of 7-(3-(bis(4-methoxybenzyl)amino)-2,5-difluoro-6-(trifluoromethyl)phenyl)-5,6,7,8-tetrahydroquinazolin-4(3H)-one (400.0 mg, 0.68 mmol), benzotriazol-1-yloxytris(dimethylamino)-phosphonium hexafluorophosphate (604.3 mg, 1.37 mmol), piperazine (588.4 mg, 6.83 mmol) and 1,8-diazabicyclo[5.4.0]undec-7-ene (312.0 mg, 2.05 mmol) in chloroform (6 mL) was stirred at 70° C. for 4 hours. After completion, the reaction was quenched with water. The resulting solution was extracted with dichloromethane and the organic layers were combined. The organic layer was dried over anhydrous sodium sulfate and concentrated under vacuum. The residue was purified by flash chromatography on silica gel eluting with dichloromethane/methanol (1/1) to afford 2,5-difluoro-N,N-bis(4-methoxybenzyl)-3-(4-(piperazin-1-yl)-5,6,7,8-tetrahydroquinazolin-7-yl)-4-(trifluoromethyl)aniline (300.0 mg, 0.46 mmol, 67.2% yield) as a color solid. LC-MS: (ESI, m/z): 654.3 [M+H]$^+$.

Step 10: 1-(4-(7-(3-(bis(4-methoxybenzyl)amino)-2,5-difluoro-6-(trifluoromethyl)phenyl)-5,6,7,8-tetrahydroquinazolin-4-yl)piperazin-1-yl)prop-2-en-1-one

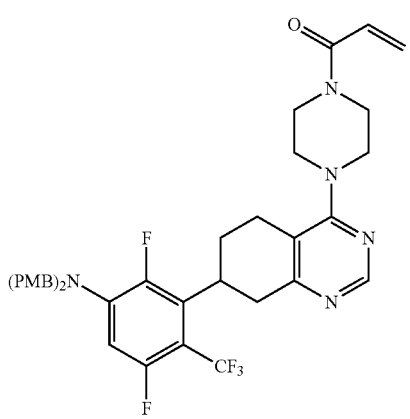

A solution of 2,5-difluoro-N,N-bis(4-methoxybenzyl)-3-(4-(piperazin-1-yl)-5,6,7,8-tetrahydroquinazolin-7-yl)-4-(trifluoromethyl)aniline (250.0 mg, 0.38 mmol) and N,N- diisopropylethylamine (98.7 mg, 0.76 mmol) in dichloromethane (4 mL) was dropwise added acryloyl chloride (51.9 mg, 0.57 mmol) and stirred at 0° C. for 0.5 hours. After completion, the reaction was quenched with water. The resulting solution was extracted with dichloromethane and the organic layers were combined. The organic layer was dried over anhydrous sodium sulfate and concentrated under vacuum. The residue was purified by flash chromatography on silica gel eluting with dichloromethane/methanol (10/1) to afford 1-(4-(7-(3-(bis(4-methoxybenzyl)amino)-2,5-difluoro-6-(trifluoromethyl)phenyl)-5,6,7,8-tetrahydroquinazolin-4-yl)piperazin-1-yl)prop-2-en-1-one (270.0 mg, 0.38 mmol, 99.8% yield) as a yellow oil. LC-MS: (ESI, m/z): 708.3 [M+H]⁺.

Step 11: (R)-1-(4-(7-(3-amino-2,5-difluoro-6-(trifluoromethyl)phenyl)-5,6,7,8-tetrahydroquinazolin-4-yl)piperazin-1-yl)prop-2-en-1-one (Example 13a) and (S)-1-(4-(7-(3-amino-2,5-difluoro-6-(trifluoromethyl)phenyl)-5,6,7,8-tetrahydroquinazolin-4-yl)piperazin-1-yl)prop-2-en-1-one (Example 13b)

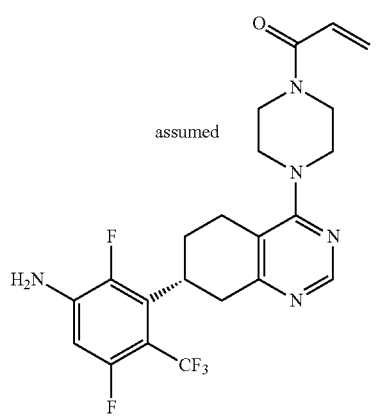

13a


13b

A solution of 1-(4-(7-(3-(bis(4-methoxybenzyl)amino)-2,5-difluoro-6-(trifluoromethyl)phenyl)-5,6,7,8-tetrahydroquinazolin-4-yl)piperazin-1-yl)prop-2-en-1-one (200.0 mg, 0.28 mmol) in trifluoroacetic acid (3 mL) and dichloromethane (3 mL) was stirred at room temperature for 3 hours. After completion, the solvent was concentrated under vacuum. The residue was diluted with dichloromethane. The reaction mixture was adjusted to pH=7 with N,N-diisopropylethylamine. The residue was purified by flash chromatography on reverse-phase column eluting with water/acetonitrile (4/6) to afford the diastereoisomers as a white solid. Then the diastereoisomers was isolated by Prep-Chiral-HPLC (Column: CHIRALPAK IC-3, 4.6*50 mm 3 um; Mobile Phase A: Hex (0.1% DEA): EtOH=50:50, Mobile Phase B; Flow rate: 1 m/min to afford the title compounds. The absolute configuration of the title compounds was inferred from potency data and a protein X-ray structure of compound 21b.

Example 13a: (R)-1-(4-(7-(3-amino-2,5-difluoro-6-(trifluoromethyl)phenyl)-5,6,7,8-tetrahydroquinazolin-4-yl)piperazin-1-yl)prop-2-en-1-one (34.2 mg, 0.07 mmol, 25.9% yield, white solid). ¹H NMR (300 MHz, DMSO-$d_6$) δ 8.52 (s, 1H), 6.83 (dd, J=16.8, 10.5 Hz, 1H), 6.54 (dd, J=14.4, 7.2 Hz, 1H), 6.29 (s, 2H), 6.14 (dd, J=16.8, 2.4 Hz, 1H), 5.72 (dd, J=10.5, 2.4 Hz, 1H), 3.75-3.69 (m, 2H), 3.65-3.52 (m, 5H), 3.22-3.20 (m, 1H), 3.04-2.97 (m, 3H), 2.85-2.74 (m, 1H), 2.68-2.62 (m, 1H), 1.99 (brs, 2H). LC-MS: (ESI, m/z): 468.2 [M+H]⁺. Chiral HPLC: CHIRALPAK IC-3 (4.6*50 mm); detected at 254 nm; Hex (0.1% DEA)/EtOH=50/50; flow=1.0 mL/min; Retention time: 1.444 min (faster peak).

Example 13b: (S)-1-(4-(7-(3-amino-2,5-difluoro-6-(trifluoromethyl)phenyl)-5,6,7,8-tetrahydroquinazolin-4-yl)piperazin-1-yl)prop-2-en-1-one (34.0 mg, 0.07 mmol, 25.7% yield, white solid). ¹H NMR (300 MHz, DMSO-$d_6$) δ 8.52 (s, 1H), 6.83 (dd, J=16.8, 10.5 Hz, 1H), 6.54 (dd, J=14.4, 7.2 Hz, 1H), 6.29 (s, 2H), 6.14 (dd, J=16.8, 2.4 Hz, 1H), 5.72 (dd, J=10.5, 2.4 Hz, 1H), 3.75-3.69 (m, 2H), 3.65-3.52 (m, 5H), 3.22-3.20 (m, 1H), 3.04-2.97 (m, 3H), 2.85-2.74 (m, 1H), 2.68-2.62 (m, 1H), 1.99 (brs, 2H). LC-MS: (ESI, m/z): 468.2 [M+H]⁺. Chiral HPLC: CHIRALPAK IC-3 (4.6*50 mm); detected at 254 nm; Hex (0.1% DEA)/EtOH=50/50; flow=1.0 mL/min; Retention time: 1.920 min (slower peak).

Examples 14a and 14b

Example 14a

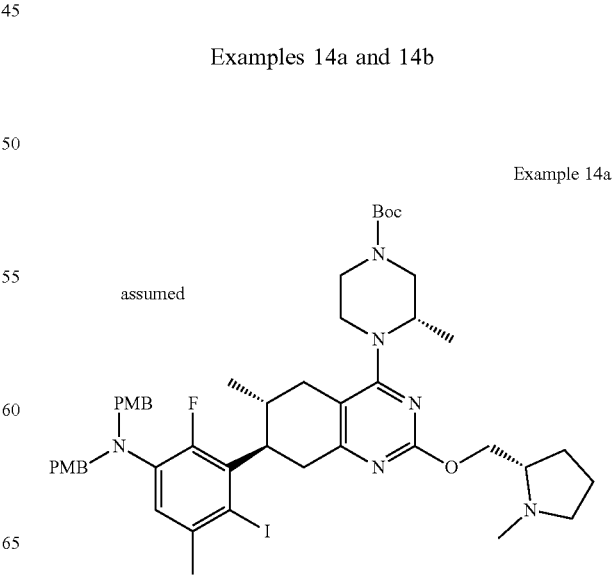

Example 14b

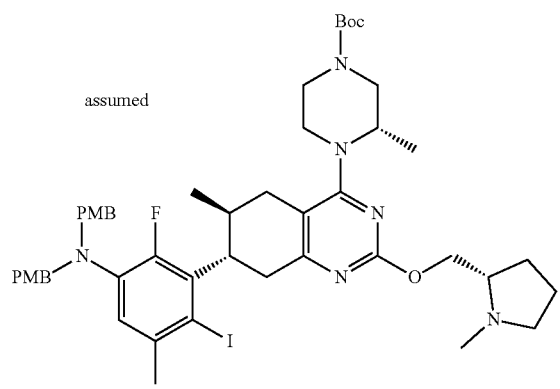

tert-butyl (S)-4-((6R,7R)-7-(3-(bis(4-methoxybenzyl)amino)-2-fluoro-6-iodo-5-methylphenyl)-6-methyl-2-(((S)-1-methylpyrrolidin-2-yl)methoxy)-5,6,7,8-tetrahydroquinazolin-4-yl)-3-methylpiperazine-1-carboxylate (Example 14a)

tert-butyl (S)-4-((6S,7S)-7-(3-(bis(4-methoxybenzyl)amino)-2-fluoro-6-iodo-5-methylphenyl)-6-methyl-2-(((S)-1-methylpyrrolidin-2-yl)methoxy)-5,6,7,8-tetrahydroquinazolin-4-yl)-3-methylpiperazine-1-carboxylate (Example 14b)

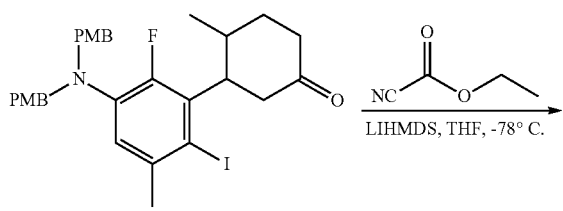

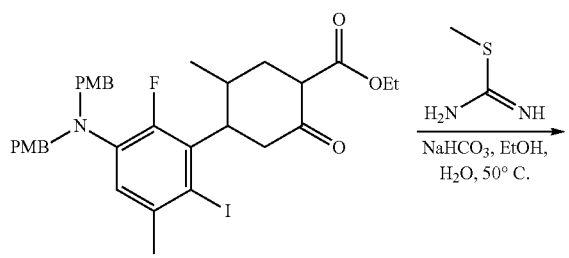

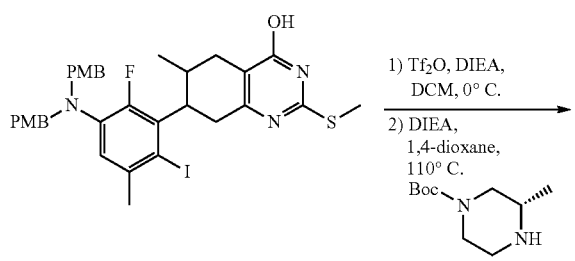

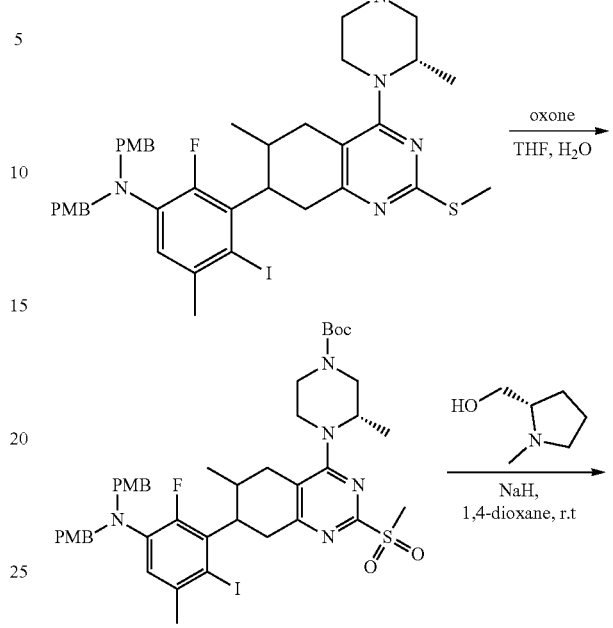

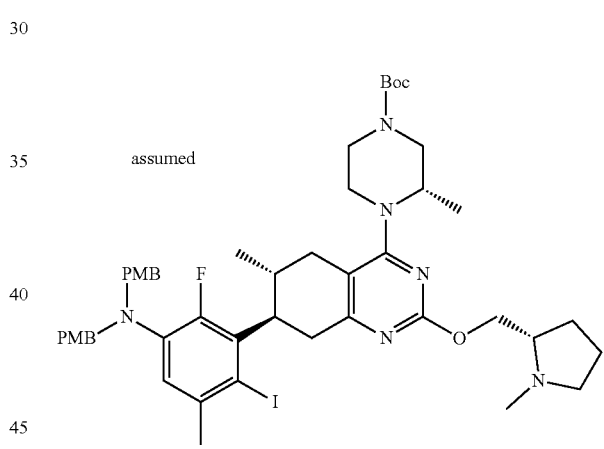

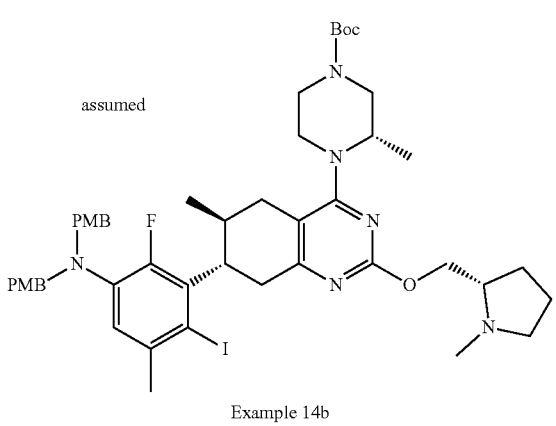

Example 14b

Step 1: ethyl 4-(3-(bis(4-methoxybenzyl)amino)-2-fluoro-6-iodo-5-methylphenyl)-5-methyl-2-oxocyclohexane-1-carboxylate

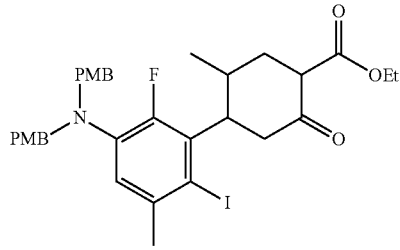

Under nitrogen, a solution of 3-(3-(bis(4-methoxybenzyl)amino)-2-fluoro-6-iodo-5-methylphenyl)-4-methylcyclohexan-1-one (6.00 g, 9.98 mmol) in tetrahydrofuran (50 mL) was dropwise added lithium bis(trimethylsilyl)amide (19.95 mL, 19.95 mmol, 1.0 M in THF) and stirred at −78° C. for 0.5 hours. Then ethyl cyanoformate (2.27 g, 22.94 mmol) was dropwise added and stirred at −78° C. for 2 hours. After completion, the reaction was quenched with water. The resulting solution was extracted with ethyl acetate and the organic layers were combined. The organic layer was dried over anhydrous sodium sulfate and concentrated under vacuum. The residue was purified by flash chromatography on silica gel eluting with petroleumeum ether/ethyl acetate (4/1) to afford ethyl 4-(3-(bis(4-methoxybenzyl)amino)-2-fluoro-6-iodo-5-methylphenyl)-5-methyl-2-oxocyclohexane-1-carboxylate (2.50 g, 3.71 mmol, 37.2% yield) as a colorless oil. LC-MS: (ESI, m/z): 674.2 [M+H]⁺.

Step 2: 7-(3-(bis(4-methoxybenzyl)amino)-2-fluoro-6-iodo-5-methylphenyl)-6-methyl-2-(methylthio)-5,6,7,8-tetrahydroquinazolin-4-ol

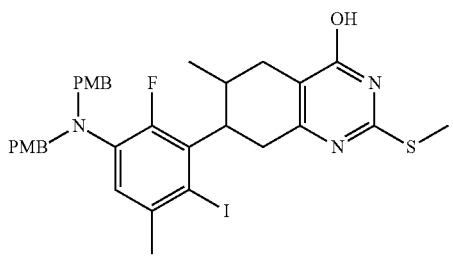

A solution of ethyl 4-(3-(bis(4-methoxybenzyl)amino)-2-fluoro-6-iodo-5-methylphenyl)-5-methyl-2-oxocyclohexane-1-carboxylate (3.00 g, 4.45 mmol), 2-methylisothiourea (12.38 g, 44.54 mmol) and sodium bicarbonate (9.35 g, 111.35 mmol) in ethanol (50 mL) and water (10 mL) was stirred at 50° C. for 1 hour. After completion, the reaction mixture was filtrated, and the filtrate was concentrated under reduced pressure. The residue was purified by flash chromatography on silica gel eluting with dichloromethane/ethyl acetate (3/1) to afford 7-(3-(bis(4-methoxybenzyl)amino)-2-fluoro-6-iodo-5-methylphenyl)-6-methyl-2-(methylthio)-5,6,7,8-tetrahydroquinazolin-4-ol (0.70 g, 1.00 mmol, 22.5% yield) as a yellow solid. LC-MS: (ESI, m/z): 700.1 [M+H]⁺.

Step 3: tert-butyl (3S)-4-(7-(3-(bis(4-methoxybenzyl)amino)-2-fluoro-6-iodo-5-methylphenyl)-6-methyl-2-(methylthio)-5,6,7,8-tetrahydroquinazolin-4-yl)-3-methylpiperazine-1-carboxylate

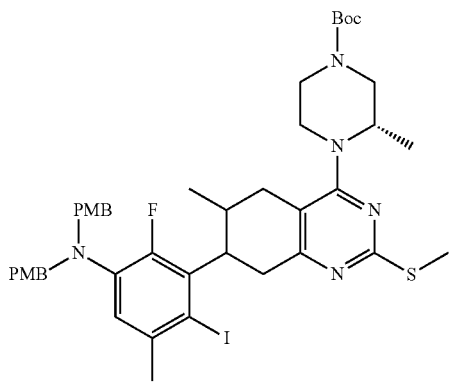

A solution of 7-(3-(bis(4-methoxybenzyl)amino)-2-fluoro-6-iodo-5-methylphenyl)-6-methyl-2-(methylthio)-5,6,7,8-tetrahydroquinazolin-4-ol (700.0 mg, 1.00 mmol) and N,N-diisopropylethylamine (0.45 g, 3.00 mmol) in dichloromethane (5 mL) was stirred at 0° C. for 5 minutes. Then trifluoromethanesulfonic anhydride (564.6 mg, 2.00 mmol) was added and stirred at 0° C. for 30 minutes. The solvent was concentrated under vacuum to afford the crude product. Then the crude product, N,N-diisopropylethylamine (1.29 g, 10.01 mmol) and tert-butyl (3S)-3-methyl-1-piperazinecarboxylate (1.20 g, 6.00 mmol) in 1,4-dioxane (6 mL) was stirred at 110° C. for 5 hours. After completion, the solvent was concentrated under vacuum. The residue was diluted with dichloromethane and washed with water, dried over anhydrous sodium sulfate and concentrated under vacuum. The residue was purified by flash chromatography on silica gel eluting with petroleumeum ether/ethyl acetate (3/1) to afford tert-butyl (3S)-4-(7-(3-(bis(4-methoxybenzyl)amino)-2-fluoro-6-iodo-5-methylphenyl)-6-methyl-2-(methylthio)-5,6,7,8-tetrahydroquinazolin-4-yl)-3-methylpiperazine-1-carboxylate (400.0 mg, 0.45 mmol, 45.3% yield) as a yellow solid. LC-MS: (ESI, m/z): 882.3 [M+H]⁺.

Step 4: tert-butyl (3S)-4-(7-(3-(bis(4-methoxybenzyl)amino)-2-fluoro-6-iodo-5-methylphenyl)-6-methyl-2-(methylsulfonyl)-5,6,7,8-tetrahydroquinazolin-4-yl)-3-methylpiperazine-1-carboxylate

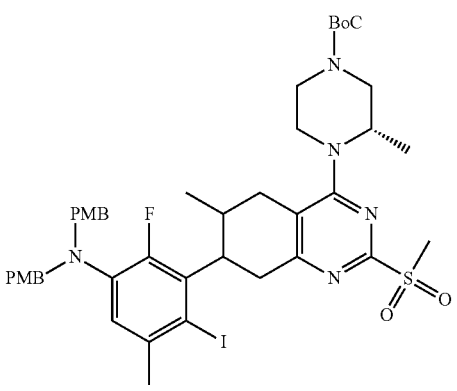

A solution of tert-butyl (3S)-4-(7-(3-(bis(4-methoxybenzyl)amino)-2-fluoro-6-iodo-5-methylphenyl)-6-methyl-2-(methylthio)-5,6,7,8-tetrahydroquinazolin-4-yl)-3-methylpiperazine-1-carboxylate (660.0 mg, 0.80 mmol) and potassium peroxymonosulfate (1.48 g, 2.4 mmol) in tetrahydrofuran (6 mL) and water (3 mL) was stirred at room temperature for 3 hours. After completion, the resulting solution was diluted with dichloromethane, washed with aqueous saturated sodium thiosulfate solution, dried over anhydrous sodium sulfate and concentrated under vacuum to afford the crude product. The crude product was used for next step directly without purification. LC-MS: (ESI, m/z): 914.3[M+H]$^+$.

Step 5: tert-butyl (S)-4-((6R,7R)-7-(3-(bis(4-methoxybenzyl)amino)-2-fluoro-6-iodo-5-methylphenyl)-6-methyl-2-(((S)-1-methylpyrrolidin-2-yl)methoxy)-5,6,7,8-tetrahydroquinazolin-4-yl)-3-methylpiperazine-1-carboxylate (Example 14a) and tert-butyl (S)-4-((6S,7S)-7-(3-(bis(4-methoxybenzyl)amino)-2-fluoro-6-iodo-5-methylphenyl)-6-methyl-2-(((S)-1-methylpyrrolidin-2-yl)methoxy)-5,6,7,8-tetrahydroquinazolin-4-yl)-3-methylpiperazine-1-carboxylate (Example 14b)

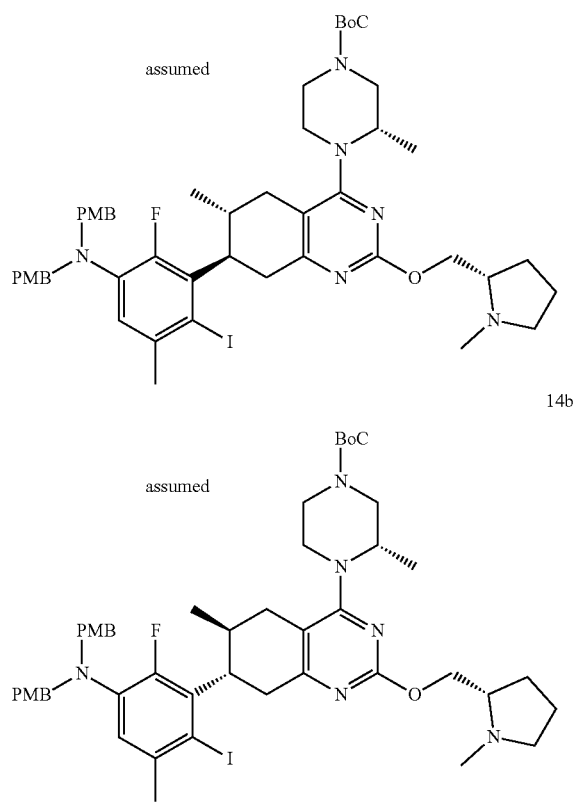

A solution of N-methyl-L-prolinol (75.6 mg, 0.66 mmol) and sodium hydride (65.7 mg, 1.64 mmol, 60% dispersion in mineral oil) in 1,4-dioxane (4 mL) was stirred at room temperature for 5 minutes. Then tert-butyl (3S)-4-(7-(3-(bis(4-methoxybenzyl)amino)-2-fluoro-6-iodo-5-methylphenyl)-6-methyl-2-(methylsulfonyl)-5,6,7,8-tetrahydroquinazolin-4-yl)-3-methylpiperazine-1-carboxylate (300.0 mg, 0.33 mmol) was added and stirred at room temperature for 1 hour. After completion, the reaction was quenched with water. The resulting solution was extracted with dichloromethane and the organic layers were combined. The organic layer was dried over anhydrous sodium sulfate and concentrated under vacuum. The residue was purified by flash chromatography on silica gel eluting with dichloromethane/methanol (10/1) to afford the diastereoisomers as a white solid. Then the diastereoisomers was isolated by Prep-Chiral-HPLC (Column: CHIRALPAK IE-3, 4.6*50 mm 3 um; Mobile Phase A: MtBE(0.1% DEA): EtOH=80:20, Mobile Phase B; Flow rate: 1 m/min to afford the title compounds. The stereo chemistry of title compounds was arbitrarily assigned.

Example 14a: tert-butyl(S)-4-((6R,7R)-7-(3-(bis(4-methoxybenzyl)amino)-2-fluoro-6-iodo-5-methylphenyl)-6-methyl-2-(((S)-1-methylpyrrolidin-2-yl)methoxy)-5,6,7,8-tetrahydroquinazolin-4-yl)-3-methylpiperazine-1-carboxylate (54.4 mg, 0.06 mmol, 17.5% yield, white solid). $^1$H NMR (300 MHz, DMSO-d$_6$) δ 7.17 (d, J=8.4 Hz, 4H), 6.94 (d, J=8.7 Hz, 1H), 6.84 (d, J=8.7 Hz, 4H), 4.24-4.12 (m, 6H), 4.00 (dd, J=10.8, 6.6 Hz, 1H), 3.95-3.85 (m, 1H), 3.70-3.67 (m, 7H), 3.48-3.42 (m, 2H), 2.95-2.90 (m, 2H), 2.84 (d, J=9.3 Hz, 2H), 2.60-2.56 (m, 2H), 2.47-2.40 (m, 1H), 2.34-2.28 (m, 7H), 2.19-2.09 (m, 1H), 1.93-1.84 (m, 1H), 1.67-1.53 (m, 3H), 1.42 (s, 9H), 1.23 (s, 1H), 1.00-0.93 (m, 4H), 0.80 (d, J=6.0 Hz, 3H). LCMS (ESI, m/z): 949.4 [M+H]$^+$. Chiral HPLC: CHIRALPAK IE-3 (4.6*50 mm); detected at 254 nm; MtBE(0.1% DEA)/EtOH=70/30; flow=1.0 mL/min; Retention time: 0.992 min (faster peak).

Example 14b: tert-butyl(S)-4-((6S,7S)-7-(3-(bis(4-methoxybenzyl)amino)-2-fluoro-6-iodo-5-methylphenyl)-6-methyl-2-(((S)-1-methylpyrrolidin-2-yl)methoxy)-5,6,7,8-tetrahydroquinazolin-4-yl)-3-methylpiperazine-1-carboxylate (44.3 mg, 0.05 mmol, 14.2% yield white solid). $^1$H NMR (300 MHz, DMSO-d$_6$) δ 7.17 (d, J=8.4 Hz, 4H), 6.94 (d, J=8.7 Hz, 1H), 6.84 (d, J=8.7 Hz, 4H), 4.25-4.12 (m, 5H), 4.08-3.97 (m, 2H), 3.94-3.82 (m, 2H), 3.73-3.70 (m, 7H), 3.44-3.40 (m, 2H), 3.10 (brs, 2H), 2.96-2.90 (m, 2H), 2.83-2.80 (m, 2H), 2.45-2.39 (m, 1H), 2.32-2.28 (m, 7H), 2.19-2.11 (m, 1H), 1.94-1.85 (m, 1H), 1.69-1.53 (m, 3H), 1.42 (s, 9H), 1.30-1.23 (m, 4H), 0.80 (d, J=6.0 Hz, 3H). LCMS (ESI, m/z): 949.4 [M+H]$^+$. Chiral HPLC: CHIRALPAK IE-3 (4.6*50 mm); detected at 254 nm; MtBE(0.1% DEA)/EtOH=70/30; flow=1.0 mL/min; Retention time: 1.553 min (slower peak).

Examples 15a and 15b

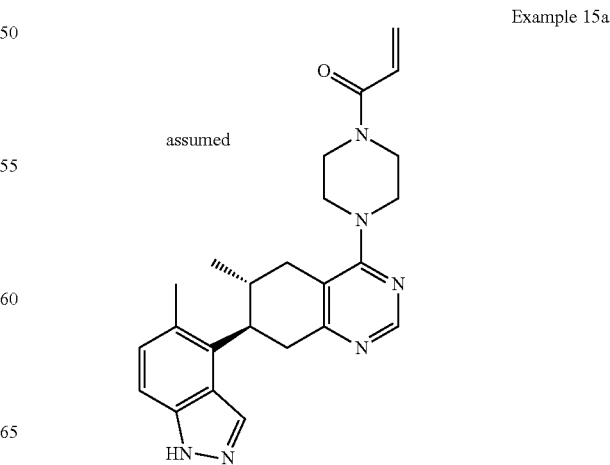

Example 15a

-continued

Example 15b

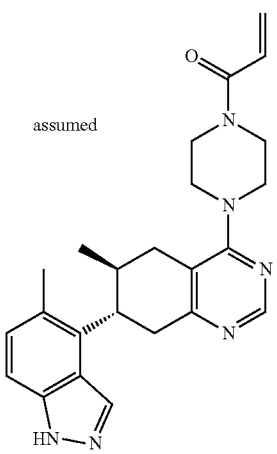

assumed 1-(4-((6R,7R)-6-methyl-7-(5-methyl-1H-indazol-4-yl)-5,6,7,8-tetrahydroquinazolin-4-yl)piperazin-1-yl)prop-2-en-1-one (Example 15a)

1-(4-((6S,7S)-6-methyl-7-(5-methyl-1H-indazol-4-yl)-5,6,7,8-tetrahydroquinazolin-4-yl)piperazin-1-yl)prop-2-en-1-one (Example 15b)

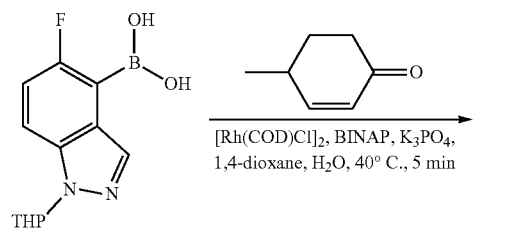

[Rh(COD)Cl]$_2$, BINAP, K$_3$PO$_4$, 1,4-dioxane, H$_2$O, 40° C., 5 min

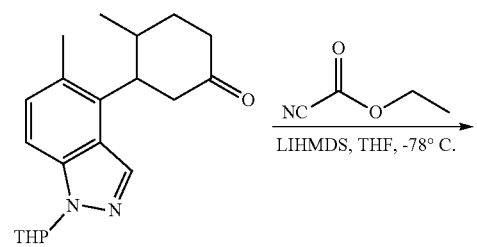

LIHMDS, THF, -78° C.

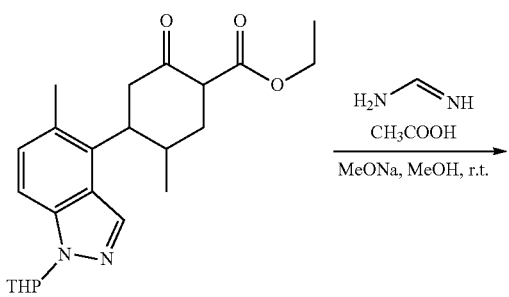

MeONa, MeOH, r.t.

-continued

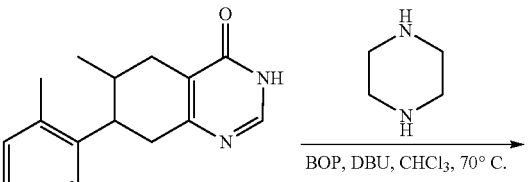

BOP, DBU, CHCl$_3$, 70° C.

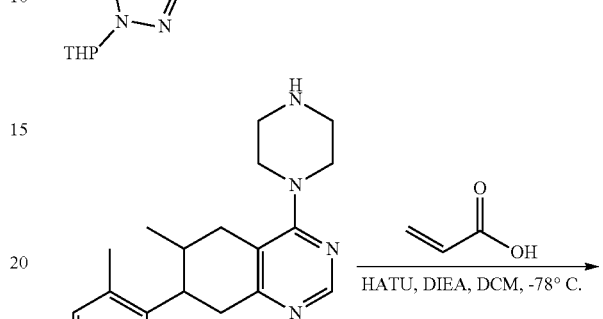

HATU, DIEA, DCM, -78° C.

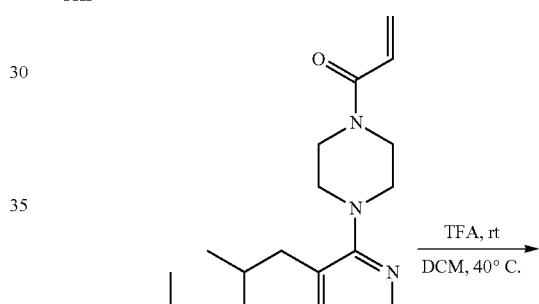

TFA, rt
DCM, 40° C.

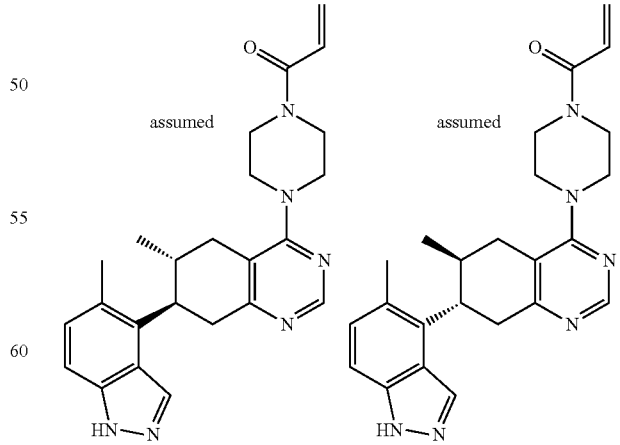

assumed    assumed

Example 15a    Example 15b

Step 1: 4-methyl-3-(5-methyl-1-tetrahydropyran-2-yl-indazol-4-yl)cyclohexanone

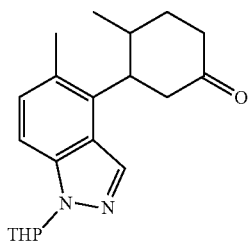

Under nitrogen, a solution of (5-methyl-1-tetrahydropyran-2-yl-indazol-4-yl)boronic acid (3.00 g, 11.76 mmol), 4-methylcyclohex-2-en-1-one (2.58 g, 23.58 mmol), (+/−)-2,2'-bis(diphenylphosphino)-1,1'-binaphthyl (1.44 g, 2.34 mmol) and chloro(1,5-cyclooctadiene)rhodium(I)dimer (0.60 g, 1.20 mmol) in 1,4-dioxane (15 mL) was added aqueous saturated potassium phosphate (3 mL) and stirred for 5 min at 40° C. After completion, the reaction mixture was concentrated under vacuum. The reaction mixture was diluted with dichloromethane and washed by water. The organic layer was dried over anhydrous sodium sulfate and concentrated under vacuum. The residue was purified by flash chromatography on silica gel eluting with petroleum ether/ethyl acetate (2/1) to afford 4-methyl-3-(5-methyl-1-tetrahydropyran-2-yl-indazol-4-yl)cyclohexanone (1.50 g, 4.60 mmol, 39% yield) as a yellow solid. LCMS (ESI, m/z): 327.2 [M+H]$^+$.

Step 2: ethyl 5-methyl-4-(5-methyl-1-tetrahydropyran-2-yl-indazol-4-yl)-2-oxo-cyclohexanecarboxylate

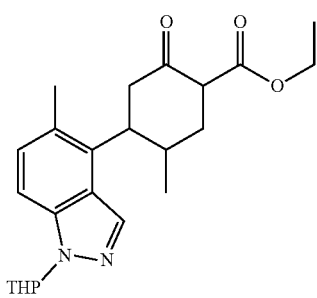

Under nitrogen, a solution of 4-methyl-3-(5-methyl-1-tetrahydropyran-2-yl-indazol-4-yl)cyclohexanone (1.50 g, 4.62 mmol) in tetrahydrofuran (50 mL) was dropwise added lithiumbis(trimethylsilyl)amide (6.0 mL, 6.00 mmol) (1M in THF) and stirred for 1 hour at −78° C. Then ethyl cyanoformate (0.69 g, 6.93 mmol) was added and stirred at −78° C. for 0.5 hours. After completion, the resulting solution was quenched with aqueous saturated ammonium chloride. The reaction mixture was diluted with dichloromethane and washed by water. The organic layer was dried over anhydrous sodium sulfate and concentrated under vacuum. The residue was purified by flash chromatography on silica gel eluting with petroleum ether/ethyl acetate (2/1) to afford ethyl 5-methyl-4-(5-methyl-1-tetrahydropyran-2-yl-indazol-4-yl)-2-oxo-cyclohexanecarboxylate (0.78 g, 1.96 mmol, 42.3% yield) as a yellow solid. LCMS (ESI, m/z): 399.2 [M+H]$^+$.

Step 3: 6-methyl-7-(5-methyl-1-tetrahydropyran-2-yl-indazol-4-yl)-5,6,7,8-tetrahydro-3H-quinazolin-4-one

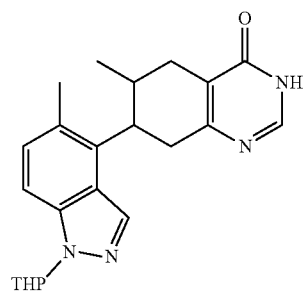

A solution of ethyl 5-methyl-4-(5-methyl-1-tetrahydropyran-2-yl-indazol-4-yl)-2-oxo-cyclohexanecarboxylate (0.72 g, 1.806 mmol), formamidine acetate (0.57 g, 5.43 mmol) and sodium methoxide (0.39 g, 7.24 mmol) in methyl alcohol (20 mL) was stirred at 25° C. for 3 hours. After completion, the reaction mixture was concentrated under vacuum. The reaction mixture was diluted with dichloromethane, adjusted to pH=7 with HCl in 1,4-dioxane and washed by water. The organic layer was dried over anhydrous sodium sulfate and concentrated under vacuum. The residue was purified by flash chromatography on silica gel eluting with petroleum ether/ethyl acetate (1/1) to afford 6-methyl-7-(5-methyl-1-tetrahydropyran-2-yl-indazol-4-yl)-5,6,7,8-tetrahydro-3H-quinazolin-4-one (450.0 mg, 1.20 mmol, 66.4% yield) as a yellow solid. LCMS (ESI, m/z): 379.2 [M+H]$^+$.

Step 4: 6-methyl-7-(5-methyl-1-tetrahydropyran-2-yl-indazol-4-yl)-4-piperazin-1-yl-5,6,7,8-tetrahydroquinazoline

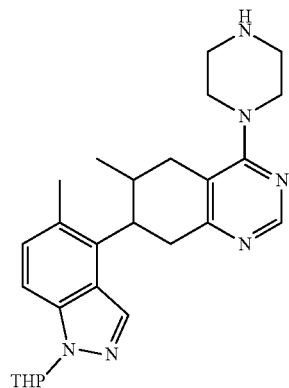

A solution of 6-methyl-7-(5-methyl-1-tetrahydropyran-2-yl-indazol-4-yl)-5,6,7,8-tetrahydro-3H-quinazolin-4-one (0.45 g, 1.13 mmol), piperazine (0.25 g, 2.97 mmol), BOP (0.68 g, 1.55 mmol) and 1,8-diazabicyclo[5.4.0]undec-7-ene (0.53 mL, 3.57 mmol) in chloroform (10 mL) was stirred at 70° C. for 1 hour. After completion, the reaction mixture was diluted with dichloromethane and washed by water. The organic layer was dried over anhydrous sodium sulfate and concentrated under vacuum. The residue was purified by flash chromatography on silica gel eluting with dichloromethane/methanol (20/1) to afford 6-methyl-7-(5-methyl-1-tetrahydropyran-2-yl-indazol-4-yl)-4-piperazin-1-yl-5,6,7,8-tetrahydroquinazoline (460.0 mg, 1.03 mmol, 86.6% yield) as a yellow solid. LCMS (ESI, m/z): 447.3 [M+H]$^+$.

Step 5: 1-[4-[6-methyl-7-(5-methyl-1-tetrahydropyran-2-yl-indazol-4-yl)-5,6,7,8-tetrahydroquinazolin-4-yl]piperazin-1-yl]prop-2-en-1-one

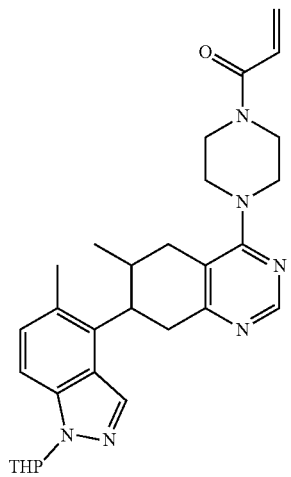

A solution of acrylic acid (142.0 mg, 1.97 mmol), 6-methyl-7-(5-methyl-1-tetrahydropyran-2-yl-indazol-4-yl)-4-piperazin-1-yl-5,6,7,8-tetrahydroquinazoline (440.0 mg, 0.99 mmol), HATU (487.0 mg, 1.28 mmol) and N,N-diisopropylethylamine (0.34 mL, 1.97 mmol) in dichloromethane (3 mL) was stirred at −78° C. for 0.5 hours. After completion, the reaction mixture was diluted with water and extracted with dichloromethane. Then the organic layers were combined and washed with brine. The organic layers was dried over anhydrous sodium sulfate and concentrated under vacuum. The residue was purified by flash chromatography on silica gel eluting with petroleum ether/ethyl acetate (1/1) to afford 1-[4-[6-methyl-7-(5-methyl-1-tetrahydropyran-2-yl-indazol-4-yl)-5,6,7,8-tetrahydroquinazolin-4-yl]piperazin-1-yl]prop-2-en-1-one (200.0 mg, 0.40 mmol, 40.5% yield) as a solid. LCMS (ESI, m/z): 501.3 [M+H]$^+$.

Step 5: 1-(4-((6R,7R)-6-methyl-7-(5-methyl-1H-indazol-4-yl)-5,6,7,8-tetrahydroquinazolin-4-yl)piperazin-1-yl)prop-2-en-1-one (Example 15a); 1-(4-((6S,7S)-6-methyl-7-(5-methyl-1H-indazol-4-yl)-5,6,7,8-tetrahydroquinazolin-4-yl)piperazin-1-yl)prop-2-en-1-one (Example 15b)

A solution of 1-[4-[6-methyl-7-(5-methyl-1-tetrahydropyran-2-yl-indazol-4-yl)-5,6,7,8-tetrahydroquinazolin-4-yl]piperazin-1-yl]prop-2-en-1-one (180.0 mg, 0.36 mmol) in trifluoroacetic acid (1 mL) and dichloromethane (5 mL) was stirred at 40° C. for 1 hour. After completion, the solvent was concentrated under vacuum. The residue was purified by Prep-HPLC with the condition with Column: XBridge Prep C18 OBD Column 19×150 mm 5 um; Mobile Phase A: Water (10 MMOL/L NH4HCO3), Mobile Phase B: ACN; Flow rate: 25 mL/min; Gradient: 25% B to 50% B in 7 min; 254220 nm; Rt: 7.23 min. The mixture of enantiomer was separated by Chiral-Prep-HPLC with the following conditions: Column: CHIRALPAK IA, 2*25 cm, 5 um; Mobile Phase A: Hex (8 mmol/L NH3·MeOH)—HPLC, Mobile Phase B: IPA—HPLC; Flow rate: 12 mL/min; Gradient: 50 B to 50 B in 23 min; 220/254 nm; RT1:10.5; RT2:16.5 to afford the title compounds. The absolute configuration of the title compounds was inferred from potency data and a protein X-ray structure of compound 21b.

Example 15a: 1-[4-[(6R,7R)-6-methyl-7-(5-methyl-1H-indazol-4-yl)-5,6,7,8-tetrahydroquinazolin-4-yl]piperazin- 1-yl]prop-2-en-1-one (4.3 mg, 0.01 mmol, 2.9% yield, white solid). $^1$H NMR (300 MHz, DMSO-d$_6$, ppm) δ 12.97 (s, 1H), 8.52 (s, 1H), 8.09 (s, 1H), 7.32 (d, J=8.1 Hz, 1H), 7.19 (d, J=8.4 Hz, 1H), 6.86 (dd, J=16.8, 10.5 Hz, 1H), 6.17 (dd, J=16.8, 2.4 Hz, 1H), 5.77 (dd, J=10.2, 2.1 Hz, 1H), 3.82-3.74 (m, 2H), 3.68-3.52 (m, 4H), 3.43-3.40 (m, 1H), 3.28 (brs, 2H), 3.20-3.12 (m, 1H), 3.01-2.97 (m, 1H), 2.77-2.62 (m, 2H), 2.44 (s, 4H), 0.73 (d, J=6.0 Hz, 3H). LCMS (ESI, m/z): 417.2 [M+H]$^+$. Chiral HPLC: CHIRALPAK IA-3 (0.46*5 cm; 3 um); detected at 254 nm; Hex (0.1% DEA): IPA=50:50; flow=1.0 ml/min; Retention time: 1.281 min (faster peak).

Example 15b: 1-[4-[(6S,7S)-6-methyl-7-(5-methyl-1H-indazol-4-yl)-5,6,7,8-tetrahydroquinazolin-4-yl]piperazin-1-yl]prop-2-en-1-one (5.2 mg, 0.01 mmol, 3.5% yield, white solid). $^1$H NMR (300 MHz, DMSO-d$_6$, ppm) δ 12.97 (s, 1H), 8.52 (s, 1H), 8.09 (s, 1H), 7.32 (d, J=8.1 Hz, 1H), 7.19 (d, J=8.4 Hz, 1H), 6.86 (dd, J=16.8, 10.5 Hz, 1H), 6.17 (dd, J=16.8, 2.4 Hz, 1H), 5.77 (dd, J=10.2, 2.1 Hz, 1H), 3.82-3.74 (m, 2H), 3.68-3.52 (m, 4H), 3.43-3.40 (m, 1H), 3.28 (brs, 2H), 3.20-3.12 (m, 1H), 3.01-2.97 (m, 1H), 2.77-2.62 (m, 2H), 2.44 (s, 4H), 0.73 (d, J=6.0 Hz, 3H). LCMS (ESI, m/z): 417.2 [M+H]$^+$. Chiral HPLC: CHIRALPAK IA-3; detected at 254 nm; Hex (0.1% DEA):IPA=50:50; flow=1.0 ml/min; Retention time: 1.872 min (slower peak).

Example 16

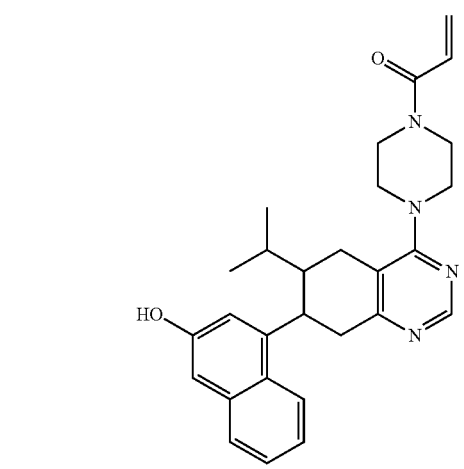

1-(4-(7-(3-hydroxynaphthalen-1-yl)-6-isopropyl-5,6,7,8-tetrahydroquinazolin-4-yl)piperazin-1-yl)prop-2-en-1-one

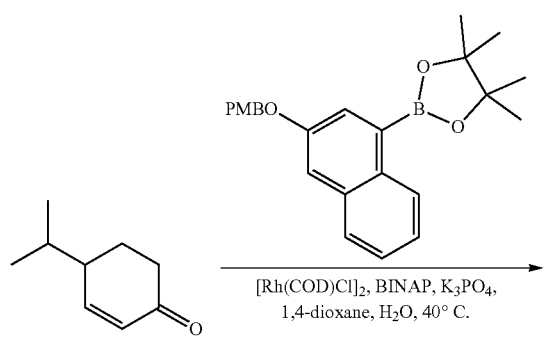

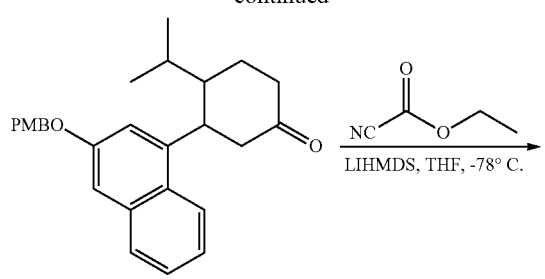

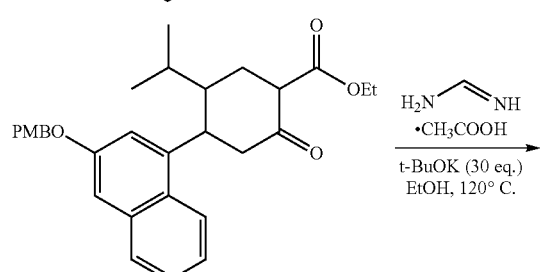

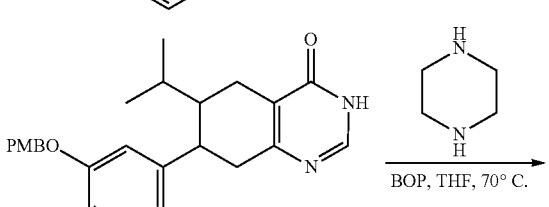

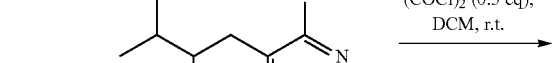

365
-continued

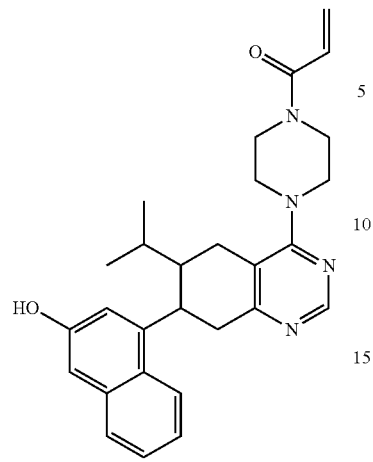

Step 1: 4-isopropyl-3-(3-(4-methoxybenzyloxy)naphthalen-1-yl)cyclohexanone

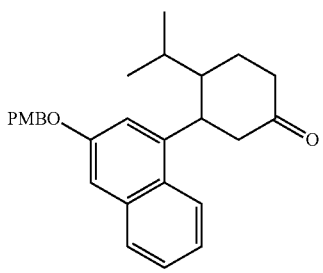

Under nitrogen, a solution of 4-isopropylcyclohex-2-en-1-one (0.27 g, 1.92 mmol), 2-[3-[(4-methoxyphenyl)methoxy]-1-naphthyl]-4,4,5,5-tetramethyl-1,3,2-dioxaborolane (0.50 g, 1.28 mmol), chloro(1,5-cyclooctadiene)rhodium(I) dimer (0.06 g, 0.13 mmol), (+/−)-2,2'-Bis(diphenylphosphino)-1,1'-binaphthyl (0.16 g, 0.26 mmol) in 1,4-dioxane (3 mL) was added aqueous saturated potassium phosphate (0.6 mL) and stirred for 5 minutes at 40° C. After completion, the reaction mixture was concentrated under vacuum. The reaction mixture was diluted with dichloromethane and washed by water. The organic layer was dried over anhydrous sodium sulfate and concentrated under vacuum. The residue was purified by flash chromatography on silica gel eluting with petroleum ether/ethyl acetate (1/1) to afford 4-isopropyl-3-[3-[(4-methoxyphenyl)methoxy]-1-naphthyl]cyclohexanone (0.14 g, 0.35 mmol, 27.1% yield) as a yellow solid. LCMS (ESI, m/z): 403.2 [M+H]$^+$.

366
Step 2: ethyl 5-isopropyl-4-[3-[(4-methoxyphenyl)methoxy]-1-naphthyl]-2-oxo-cyclohexanecarboxylate

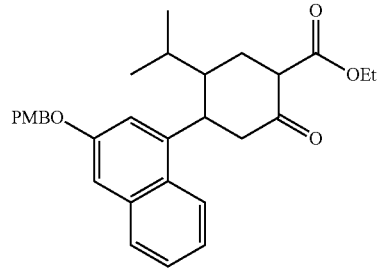

Under nitrogen, a solution of 4-isopropyl-3-[3-[(4-methoxyphenyl)methoxy]-1-naphthyl]cyclohexanone (0.67 g, 1.66 mmol) in tetrahydrofuran (30 mL) was dropwise added lithium bis(trimethylsilyl)amide (3.3 ml, 3.33 mmol, 1.0 M in THF) and stirred for 1 hour at −78° C. Then ethyl cyanoformate (0.38 g, 3.83 mmol) was added and stirred at −78° C. for 0.5 hours. After completion, the reaction was quenched with aqueous saturated ammonium chloride and concentrated under vacuum. The reaction mixture was diluted with dichloromethane, washed with water. The organic layer was dried over anhydrous sodium sulfate and concentrated under vacuum to afford crude product ethyl 5-isopropyl-4-[3-[(4-methoxyphenyl)methoxy]-1-naphthyl]-2-oxo-cyclohexanecarboxylate (600.0 mg, crude) as a yellow solid. LCMS (ESI, m/z): 475.2 [M+H]$^+$.

Step 3: 6-isopropyl-7-[3-[(4-methoxyphenyl)methoxy]-1-naphthyl]-5,6,7,8-tetrahydro-3H-quinazolin-4-one

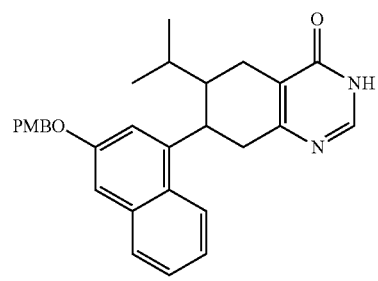

A solution of ethyl 5-isopropyl-4-[3-[(4-methoxyphenyl)methoxy]-1-naphthyl]-2-oxo-cyclohexanecarboxylate (0.60 g, crude), formamidine acetate (1.97 g, 18.96 mmol) and potassium tert-butoxide (4.26 g, 37.93 mmol) in ethanol (50 mL) was stirred at 120° C. for 3 hours. After completion, the reaction mixture was concentrated under vacuum. The reaction mixture was diluted with dichloromethane, adjusted to pH=7 with HCl/1,4-dioxane and washed by water. The organic layer was dried over anhydrous sodium sulfate and concentrated under vacuum. The residue was purified by flash chromatography on silica gel eluting with dichloromethane/methyl alcohol (20/1) to afford 6-isopropyl-7-[3-[(4-methoxyphenyl)methoxy]-1-naphthyl]-5,6,7,8-tetrahydro-3H-quinazolin-4-one (150.0 mg, 0.33 mmol, 26.1% yield) as a solid. LCMS (ESI, m/z): 455.2 [M+H]$^+$.

Step 4: 6-isopropyl-7-[3-[(4-methoxyphenyl)methoxy]-1-naphthyl]-4-piperazin-1-yl-5,6,7,8-tetrahydroquinazoline

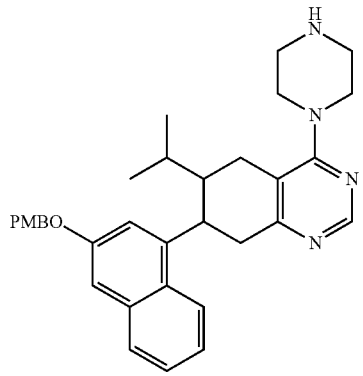

A solution of 6-isopropyl-7-[3-[(4-methoxyphenyl)methoxy]-1-naphthyl]-5,6,7,8-tetrahydro-3H-quinazolin-4-one (0.19 g, 0.42 mmol), piperazine (0.36 g, 4.18 mmol), benzotriazol-1-yloxytris(dimethylamino)-phosphonium hexafluorophosphate (0.24 g, 0.54 mmol) and 1,8-diazabicyclo[5.4.0]undec-7-ene (0.13 mL, 0.84 mmol) in tetrahydrofuran (4 mL) was stirred at 70° C. for 2 hours. After completion, the reaction mixture was concentrated under vacuum. The reaction mixture was diluted with dichloromethane and washed by water. The organic layer was dried over anhydrous sodium sulfate and concentrated under vacuum to afford 6-isopropyl-7-[3-[(4-methoxyphenyl)methoxy]-1-naphthyl]-4-piperazin-1-yl-5,6,7,8-tetrahydroquinazoline (160.0 mg, crude) as a yellow oil. The crude was used for next step without purification. LCMS (ESI, m/z): 523.3 [M+H]$^+$.

Step 5: 1-[4-[6-isopropyl-7-[3-[(4-methoxyphenyl)methoxy]-1-naphthyl]-5,6,7,8-tetrahydroquina-zolin-4-yl]piperazin-1-yl]prop-2-en-1-one

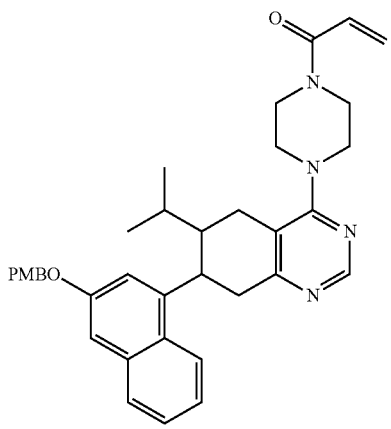

A solution of the crude 6-isopropyl-7-[3-[(4-methoxyphenyl)methoxy]-1-naphthyl]-4-piperazin-1-yl-5,6,7,8-tetrahydroquinazoline (0.16 g, crude) and N,N-diisopropylethylamine (98.7 mg, 0.76 mmol) in dichloromethane (10 mL) was dropwise added acrylyl chloride (0.03 g, 0.31 mmol) and stirred at 25° C. for 1 hour. After completion, the reaction mixture was diluted with dichloromethane and washed by water. The organic layer was dried over anhydrous sodium sulfate and concentrated under vacuum. The residue was purified by flash chromatography on silica gel eluting with dichloromethane/methyl alcohol (20/1) to afford 1-[4-[6-isopropyl-7-[3-[(4-methoxyphenyl)methoxy]-1-naphthyl]-5,6,7,8-tetrahydroquina-zolin-4-yl]piperazin-1-yl]prop-2-en-1-one (80.0 mg, 0.14 mmol, 45.3% yield) as a yellow solid. LCMS (ESI, m/z): 577.3 [M+H]$^+$

Step 6: 1-(4-(7-(3-hydroxynaphthalen-1-yl)-6-isopropyl-5,6,7,8-tetrahydroquinazolin-4-yl)piperazin-1-yl)prop-2-en-1-one

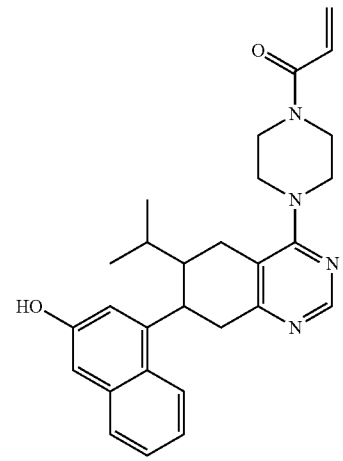 [SMILES: C=CC(=O)N1CCN(c2ncnc3c2CC(C(C)C)C(c2cc(O)cc4ccccc24)C3)CC1]

A solution of 1-[4-[6-isopropyl-7-[3-[(4-methoxyphenyl)methoxy]-1-naphthyl]-5,6,7,8-tetrahydroquinazolin-4-yl]piperazin-1-yl]prop-2-en-1-one (0.06 g, 0.10 mmol), ethanedioyl dichloride (0.02 mL, 0.21 mmol) in dichloromethane (2 mL) was stirred at 25° C. for 48 hours. After completion, the reaction mixture was diluted with dichloromethane and washed by water. The organic layer was dried over anhydrous sodium sulfate and concentrated under vacuum. The crude product was purified by Prep-HPLC with the following conditions: Column: Column: XBridge Shield RP18 OBD Column 30*150 mm, 5 um; Mobile Phase A:Water (10 MMOL/L NH4HCO3), Mobile Phase B: ACN; Flow rate: 60 m/min; Gradient: 36% B to 56% B in 7 min; 220/254 nm; Rt: 6.22 min. to afford 1-(4-(7-(3-hydroxynaphthalen-1-yl)-6-isopropyl-5,6,7,8-tetrahydroquinazolin-4-yl)piperazin-1-yl)prop-2-en-1-one (11.3 mg, 0.025 mmol, 23.8% yield) as a white solid. LCMS (ESI, m/z): 457.3 [M+H]$^+$ Example 16: $^1$H NMR (300 MHz, DMSO-d$_6$, ppm) δ 9.68 (s, 1H), 8.50 (s, 1H), 8.13 (d, J=8.5 Hz, 1H), 7.70 (d, J=8.1 Hz, 1H), 7.38 (t, J=7.4 Hz, 1H), 7.31-7.28 (m, 1H), 7.03-6.97 (m, 2H), 6.84 (dd, J=16.7, 10.4 Hz, 1H), 6.15 (dd, J=16.7, 2.4 Hz, 1H), 5.72 (dd, J=10.4, 2.4 Hz, 1H), 3.97 (brs, 1H), 3.76-3.62 (m, 4H), 3.52-3.47 (m, 3H), 3.32-3.29 (m, 1H), 3.18-3.09 (m, 1H), 2.85-2.65 (m, 2H), 2.56-2.54 (m, 1H), 2.04 (brs, 1H), 1.70 (brs, 1H), 0.96 (d, J=6.8 Hz, 3H), 0.65 (d, J=6.7 Hz, 3H).

Example 17

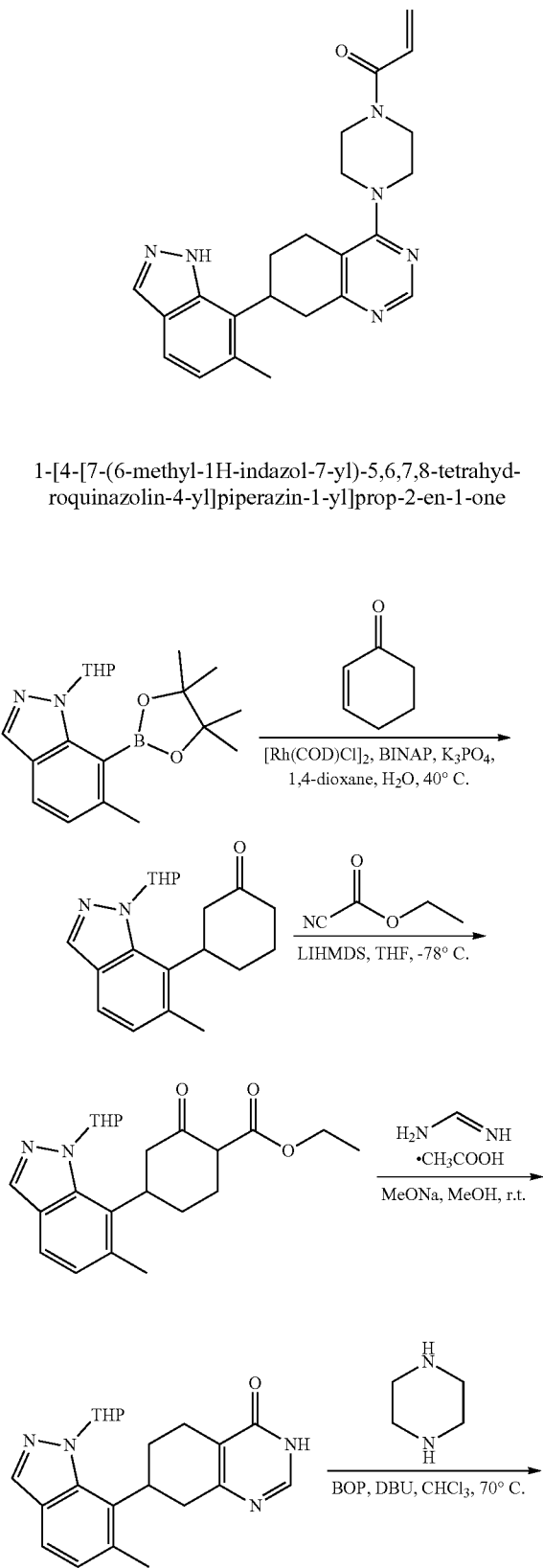

1-[4-[7-(6-methyl-1H-indazol-7-yl)-5,6,7,8-tetrahydroquinazolin-4-yl]piperazin-1-yl]prop-2-en-1-one

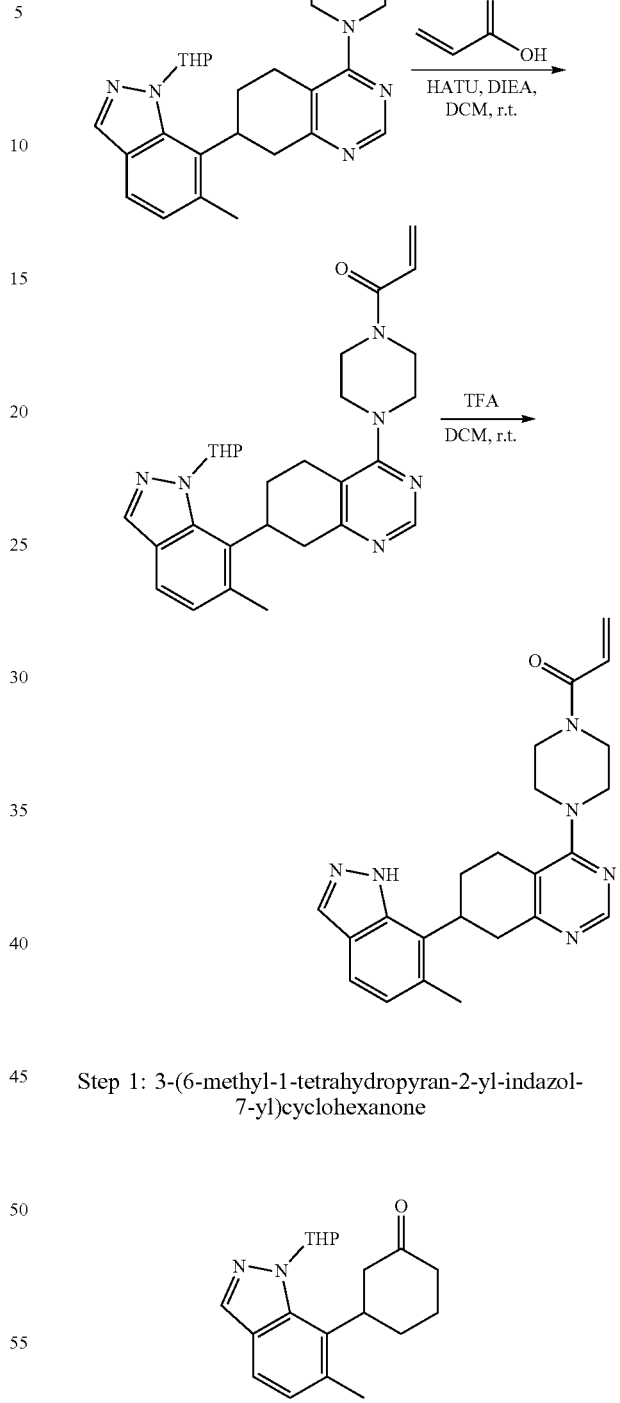

Step 1: 3-(6-methyl-1-tetrahydropyran-2-yl-indazol-7-yl)cyclohexanone

Under nitrogen, a solution of 6-methyl-1-tetrahydropyran-2-yl-7-(4,4,5,5-tetramethyl-1,3,2-dioxaborolan-2-yl)indazole (1.51 g, 2.65 mmol), 2-cyclohexen-1-one (0.76 g, 7.94 mmol), (+/−)-2,2'-bis(diphenylphosphino)-1,1'-binaphthyl (0.33 g, 0.53 mmol) and chloro(1,5-cyclooctadiene)rhodium(I) dimer (0.13 g, 0.26 mmol) in 1,4-dioxane (10 mL) was was added aqueous saturated potassium phosphate (2 mL) and stirred for 5 minutes at 40° C. After completion, the reaction mixture was concentrated under vacuum. The reaction mixture was diluted with dichloromethane and washed by water. The organic layer was dried over anhydrous sodium sulfate and concentrated under vacuum. The residue was purified by flash chromatography on silica gel eluting with petroleum ether/ethyl acetate (3/1) to afford 3-(6-methyl-1-tetrahydropyran-2-yl-indazol-7-yl)cyclohexanone (1.00 g, 2.43 mmol, 91.9% yield) as a yellow solid. LCMS (ESI, m/z): 313.2 [M+H]$^+$.

Step 2: ethyl 4-(6-methyl-1-tetrahydropyran-2-yl-indazol-7-yl)-2-oxo-cyclohexanecarboxylate

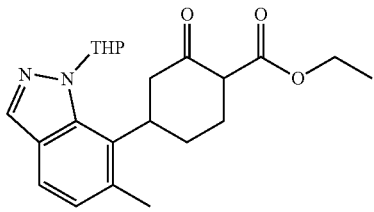

Under nitrogen, a solution of 3-(6-methyl-1-tetrahydropyran-2-yl-indazol-7-yl)cyclohexanone (1.00 g, 2.55 mmol) in tetrahydrofuran (20 mL) was dropwise added lithiumbis(trimethylsilyl)amide (0.56 g, 3.32 mmol) and stirred for 1 hour at −78° C. Then ethyl cyanoformate (0.38 g, 3.80 mmol) was added and stirred at −78° C. for 0.5 hours. After completed, the reaction was quenched with aqueous saturated ammonium chloride, diluted with dichloromethane and washed by water. The organic layer was dried over anhydrous sodium sulfate and concentrated under vacuum. The residue was purified by flash chromatography on silica gel eluting with petroleum ether/ethyl acetate (1/1) to afford ethyl 4-(6-methyl-1-tetrahydropyran-2-yl-indazol-7-yl)-2-oxo-cyclohexanecarboxylate (0.68 g, 1.78 mmol, 69.6% yield) as a yellow solid. LCMS (ESI, m/z): 385.2 [M+H]$^+$.

Step 3: 7-(6-methyl-1-tetrahydropyran-2-yl-indazol-7-yl)-5,6,7,8-tetrahydro-3H-quinazolin-4-one

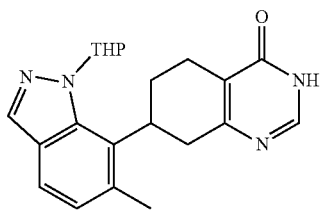

A solution of ethyl 4-(6-methyl-1-tetrahydropyran-2-yl-indazol-7-yl)-2-oxo-cyclohexanecarboxylate (0.60 g, 1.56 mmol), formamidine acetate (0.49 g, 4.69 mmol) and sodium methoxide (0.42 g, 7.82 mmol) in methyl alcohol (5 mL) was stirred at 25° C. for 1 hour. After completion, the reaction mixture was concentrated under vacuum. The reaction mixture was diluted with dichloromethane, adjusted to pH=7 with HCl/1,4-dioxane and washed by water. The organic layer was dried over anhydrous sodium sulfate and concentrated under vacuum. The residue was purified by flash chromatography on silica gel eluting with petroleum ether/ethyl acetate (1/1) to afford 7-(6-methyl-1-tetrahydropyran-2-yl-indazol-7-yl)-5,6,7,8-tetrahydro-3H-quinazolin-4-one (0.52 g, 1.44 mmol, 92.1% yield) as a solid. LCMS (ESI, m/z): 365.2 [M+H]$^+$.

Step 4: 7-(6-methyl-1-tetrahydropyran-2-yl-indazol-7-yl)-4-piperazin-1-yl-5,6,7,8-tetrahydroquinazoline

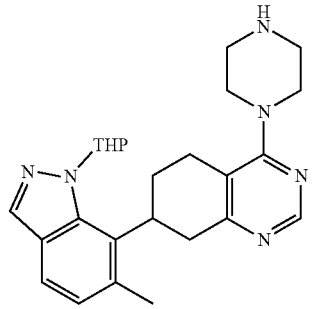

A solution of 7-(6-methyl-1-tetrahydropyran-2-yl-indazol-7-yl)-5,6,7,8-tetrahydro-3H-quinazolin-4-one (0.50 g, 1.33 mmol), piperazine (1.72 g, 19.99 mmol), benzotriazol-1-yloxytris(dimethylamino)-phosphonium hexafluorophosphate (0.88 g, 2.0 mmol) and 1,8-diazabicyclo[5.4.0]undec-7-ene (0.53 mL, 3.57 mmol) in chloroform (10 mL) was stirred at 70° C. for 1 hour. After completion, the reaction mixture was concentrated under vacuum. The reaction mixture was diluted with dichloromethane and washed by water. The organic layer was dried over anhydrous sodium sulfate and concentrated under vacuum. The residue was purified by flash chromatography on silica gel eluting with dichloromethane/methanol (20/1) to afford 7-(6-methyl-1-tetrahydropyran-2-yl-indazol-7-yl)-4-piperazin-1-yl-5,6,7,8-tetrahydroquinazoline (0.43 g, 0.99 mmol, 74.3% yield) as a yellow solid. LCMS (ESI, m/z): 433.3 [M+H]$^+$.

Step 5: 1-[4-[7-(6-methyl-1-tetrahydropyran-2-yl-indazol-7-yl)-5,6,7,8-tetrahydroquinazolin-4-yl]piperazin-1-yl]prop-2-en-1-one

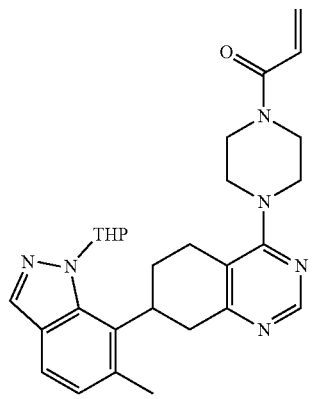

A solution of 7-(6-methyl-1-tetrahydropyran-2-yl-indazol-7-yl)-4-piperazin-1-yl-5,6,7,8-tetrahydroquinazoline (0.30 g, 0.70 mmol), acrylic acid (0.25 g, 3.51 mmol), N,N-diisopropylethylamine (0.24 mL, 1.41 mmol) and HATU (0.35 g, 0.91 mmol) in dichloromethane (10 mL) was stirred at 25° C. for 5 hours. After completion, the reaction was quenched by water. The reaction mixture was diluted with dichloromethane and washed by water. The organic layer was dried over anhydrous sodium sulfate and concentrated under vacuum. The residue was purified by flash chromatography on silica gel eluting with dichloromethane/methanol (20/1) to afford 1-[4-[7-(6-methyl-1-tetrahydropyran-2-yl-indazol-7-yl)-5,6,7,8-tetrahydroquinazolin-4-yl]piperazin-1-yl]prop-2-en-1-one (100.0 mg, 0.21 mmol, 29.2% yield) as a light yellow solid. LCMS (ESI, m/z): 487.3 [M+H]+.

Step 6: 1-[4-[7-(6-methyl-1H-indazol-7-yl)-5,6,7,8-tetrahydroquinazolin-4-yl]piperazin-1-yl]prop-2-en-1-one

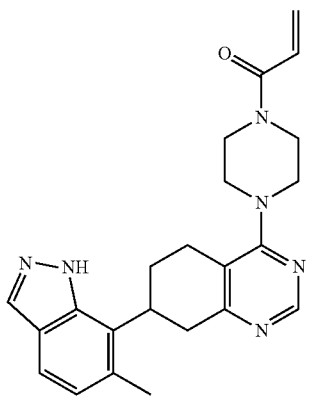

A solution of 1-[4-[7-(6-methyl-1-tetrahydropyran-2-yl-indazol-7-yl)-5,6,7,8-tetrahydroquinazolin-4-yl]piperazin-1-yl]prop-2-en-1-one (0.10 g, 0.14 mmol) in trifluoroacetic acid (1 mL) and dichloromethane (1 mL) was stirred at 25° C. for 1 hour. After completion, the solvent was concentrated under vacuum. The crude product was further isolated by Prep-HPLC with the condition: XBridge Prep C18 OBD Column 19×150 mm 5 um; Mobile Phase A:Water (10 MMOL/L NH4HCO3), Mobile Phase B: ACN; Flow rate: 25 mL/min; Gradient: 22% B to 43% B in 10 min; 254220 nm; Rt: 8.48 min to afford 1-[4-[7-(6-methyl-1H-indazol-7-yl)-5,6,7,8-tetrahydroquinazolin-4-yl]piperazin-1-yl]prop-2-en-1-one (37.9 mg, 0.094 mmol, 65.5% yield) as a white solid. LCMS (ESI, m/z): 403.3 [M+H]+.

Example 17: 1H NMR (300 MHz, DMSO-d6, ppm) δ 12.75 (s, 1H), 8.51 (s, 1H), 7.99 (s, 1H), 7.50 (d, J=8.1 Hz, 1H), 6.95 (d, J=8.2 Hz, 1H), 6.84 (dd, J=16.7, 10.5 Hz, 1H), 6.14 (dd, J=16.7, 2.4 Hz, 1H), 5.71 (dd, J=10.4, 2.4 Hz, 1H), 3.79-3.61 (m, 6H), 3.52-3.46 (m, 2H), 3.29-3.19 (m, 2H), 2.99-2.88 (m, 2H), 2.72-2.68 (m, 1H), 2.46 (s, 3H), 2.45-2.34 (m, 1H), 1.90-1.85 (m, 1H).

Example 18a

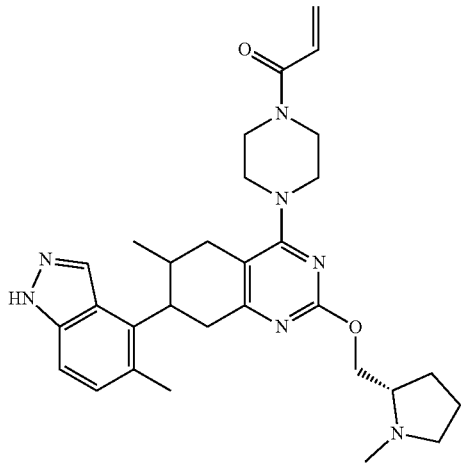 [SMILES: C=CC(=O)N1CCN(c2nc(OC[C@@H]3CCCN3C)nc3c2CC(C)C(c2c(C)ccc4[nH]ncc24)C3)CC1]

1-(4-(6-methyl-7-(5-methyl-11H-indazol-4-yl)-2-(((S)-1-methylpyrrolidin-2-yl)methoxy)-5,6,7,8-tetrahydroquinazolin-4-yl)piperazin-1-yl)prop-2-en-11-one

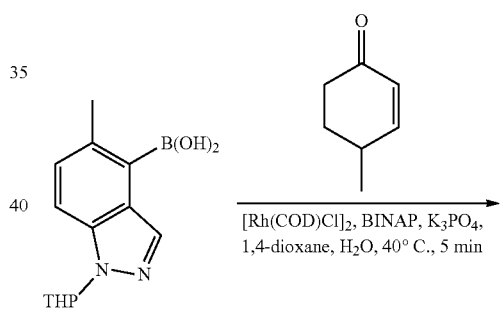

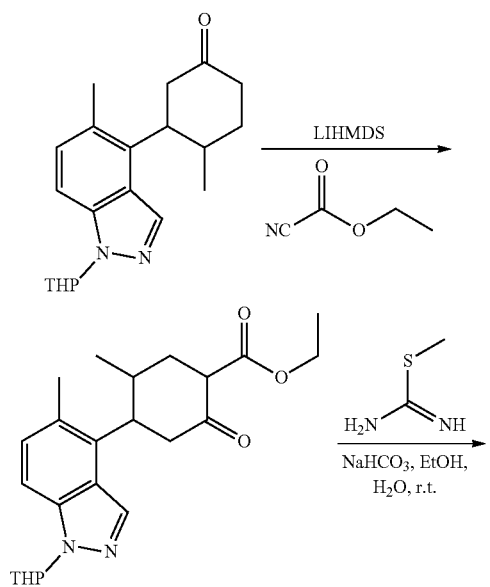

375
-continued

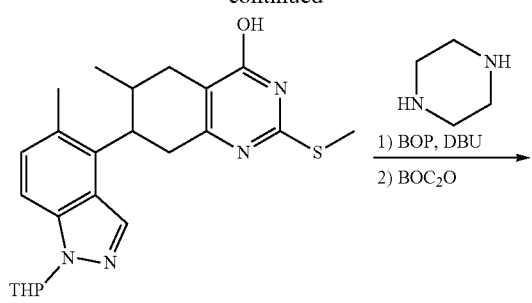

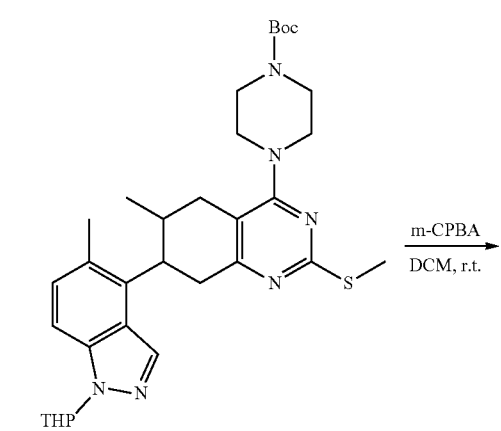

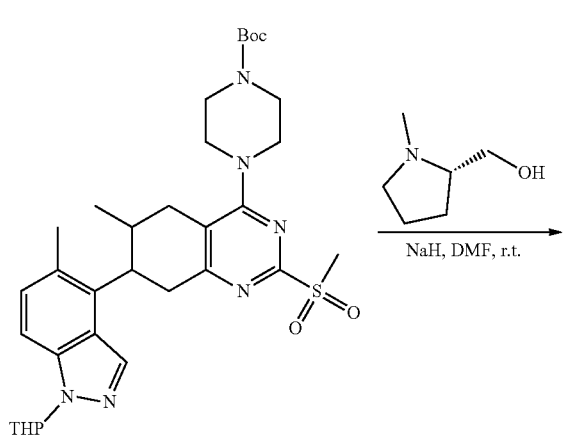

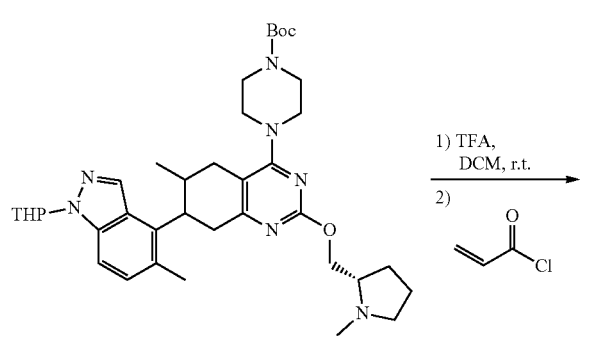

376
-continued

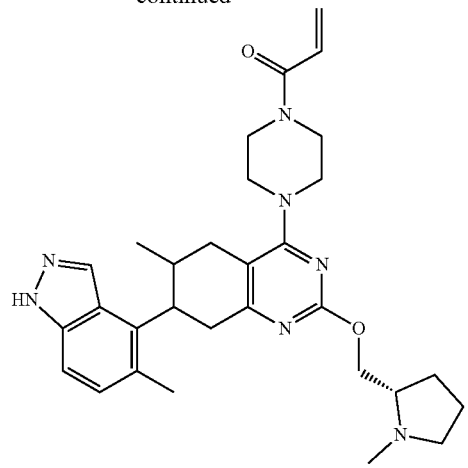

Step 1: 4-methyl-3-(5-methyl-1-tetrahydropyran-2-yl-indazol-4-yl)cyclohexanone

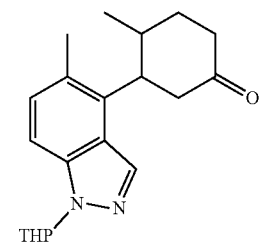

Under nitrogen, a solution of (5-methyl-1-tetrahydropyran-2-yl-indazol-4-yl)boronic acid (3.00 g, 11.76 mmol), 4-methylcyclohex-2-en-1-one (2.58 g, 23.58 mmol), (+/−)-2,2'-bis(diphenylphosphino)-1,1'-binaphthyl (1.44 g, 2.34 mmol), chloro(1,5-cyclooctadiene)rhodium(I) dimer (0.60 g, 1.20 mmol) in 1,4-dioxane (30 mL) was added aqueous saturated potassium phosphate (6 mL) and stirred at 40° C. for 5 minutes. After completion, the reaction mixture was concentrated under vacuum. The reaction mixture was diluted with dichloromethane and washed by water. The organic layer was dried over anhydrous sodium sulfate and concentrated under vacuum. The residue was purified by flash chromatography on silica gel eluting with petrol ether/ethyl acetate (2/1) to afford 4-methyl-3-(5-methyl-1-tetrahydropyran-2-yl-indazol-4-yl)cyclohexanone (1.50 g, 4.60 mmol, 39% yield) as a yellow solid. LCMS (ESI, m/z): 327.2 [M+H]$^+$.

Step 2: ethyl 5-methyl-4-(5-methyl-1-(tetrahydro-2H-pyran-2-yl)-1H-indazol-4-yl)-2-oxocyclohexane-1-carboxylate

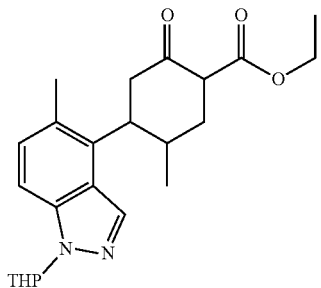

Under nitrogen, a solution of 4-methyl-3-(5-methyl-1-tetrahydropyran-2-yl-indazol-4-yl)-cyclohexanone (1.50 g, 4.62 mmol) in tetrahydrofuran (50 mL) was dropwise added lithiumbis(trimethylsilyl)amide (6.0 ml, 6 mmol, 1.0 M in THF) and stirred for 1 hour at −78° C. Then ethyl cyanoformate (0.69 g, 6.93 mmol) was added and stirred at −78° C. for 0.5 hours. After completion, the reaction was quenched with aqueous saturated ammonium chloride. The reaction mixture was diluted with dichloromethane and washed by water. The organic layer was dried over anhydrous sodium sulfate and concentrated under vacuum. The residue was purified by flash chromatography on silica gel eluting with petrol ether/ethyl acetate (2/1) to afford ethyl 5-methyl-4-(5-methyl-1-(tetrahydro-2H-pyran-2-yl)-1H-indazol-4-yl)-2-oxocyclohexane-1-carboxylate (0.78 g, 1.96 mmol, 42.3% yield) as a yellow solid. LCMS (ESI, m/z): 399.2 [M+H]$^+$.

Step 3: 6-methyl-2-methylsulfanyl-7-(5-methyl-1-tetrahydropyran-2-yl-indazol-4-yl)-5,6,7,8-tetrahydroquinazolin-4-ol

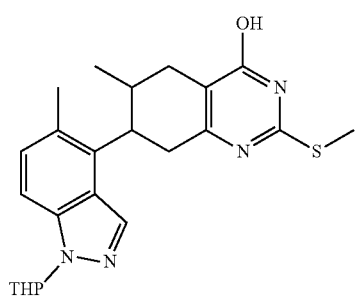

A solution of ethyl 5-methyl-4-(5-methyl-1-(tetrahydro-2H-pyran-2-yl)-1H-indazol-4-yl)-2-oxocyclohexane-1-carboxylate (0.20 g, 0.5 mmol), 2-methylisothiourea (0.27 g, 3.01 mmol) and sodium bicarbonate (0.43 g, 5.02 mmol) in ethanol (5 mL) and water (1 mL) was stirred at 25° C. for 12 hours. After completion, the reaction mixture was diluted with dichloromethane and washed by water. The organic layer was dried over anhydrous sodium sulfate and concentrated under vacuum. The residue was purified by flash chromatography on silica gel eluting with petrol ether/ethyl acetate (3/1) to afford 6-methyl-2-methylsulfanyl-7-(5-methyl-1-tetrahydropyran-2-yl-indazol-4-yl)-5,6,7,8-tetrahydroquinazolin-4-ol (100.0 mg, 0.24 mmol, 46.9% yield) as a yellow solid. LCMS (ESI, m/z): 425.2 [M+H]$^+$.

Step 4: tert-butyl 4-[6-methyl-2-methylsulfanyl-7-(5-methyl-1-tetrahydropyran-2-yl-indazol-4-yl)-5,6,7,8-tetrahydroquinazolin-4-yl]piperazine-1-carboxylate

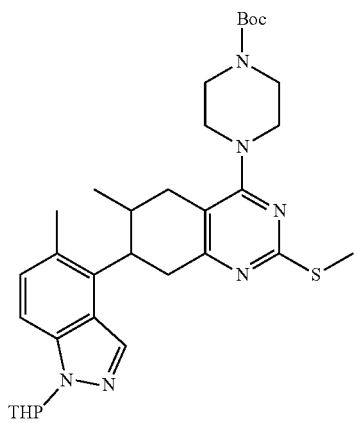

A solution of piperazine (0.28 g, 3.30 mmol), 6-methyl-2-methylsulfanyl-7-(5-methyl-1-tetrahydropyran-2-yl-indazol-4-yl)-5,6,7,8-tetrahydroquinazolin-4-ol (0.14 g, 0.33 mmol), benzotriazol-1-yloxytris(dimethylamino)-phosphonium hexafluorophosphate (0.19 g, 0.43 mmol) and 1,8-diazabicyclo[5.4.0]undec-7-ene (0.15 mL, 0.99 mmol) in chloroform (3 mL) was stirred at 70° C. for 3 hours. Then di-tert-butyl dicarbonate (1.44 g, 6.60 mmol) was added and stirred at 25° C. for 2 hours. After completion, the reaction mixture was concentrated under vacuum. The reaction mixture was diluted with dichloromethane and washed by water. The organic layer was dried over anhydrous sodium sulfate and concentrated under vacuum. The residue was purified by flash chromatography on silica gel eluting with petrol ether/ethyl acetate (3/1) to afford tert-butyl 4-[6-methyl-2-methylsulfanyl-7-(5-methyl-1-tetrahydropyran-2-yl-indazol-4-yl)-5,6,7,8-tetrahydroquinazolin-4-yl]piperazine-1-carboxylate (130.0 mg, 0.22 mmol, 66.5% yield) as a yellow solid. LCMS (ESI, m/z): 593.3 [M+H]$^+$.

Step 5: tert-butyl-4-[6-methyl-2-methylsulfonyl-7-(5-methyl-1-tetrahydropyran-2-yl-indazol-4-yl)-5,6,7,8-tetrahydroquinazolin-4-yl]piperazine-1-carboxylate

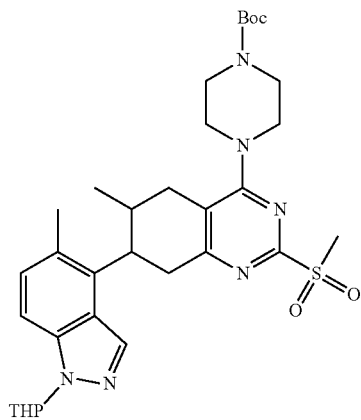

A solution of tert-butyl 4-[6-methyl-2-methylsulfanyl-7-(5-methyl-1-tetrahydropyran-2-yl-indazol-4-yl)-5,6,7,8-tetrahydroquinazolin-4-yl]piperazine-1-carboxylate (0.20 g, 0.34 mmol) and 3-chloroperoxybenzoic acid (0.17 g, 1.01 mmol) in dichloromethane (3 mL) was stirred at 25° C. for 1 hour. After completion, the reaction was quenched by aqueous saturated NaHSO₃. The reaction mixture was diluted with dichloromethane, washed with water, dried over anhydrous sodium sulfate and concentrated under vacuum to afford the crude tert-butyl-4-[6-methyl-2-methylsulfonyl-7-(5-methyl-1-tetrahydropyran-2-yl-indazol-4-yl)-5,6,7,8-tetrahydroquinazolin-4-yl]piperazine-1-carboxylate (200.0 mg, crude) which would be directly used in the next step without purification. LCMS (ESI, m/z): 625.3 [M+H]⁺.

Step 6: tert-butyl 4-[6-methyl-2-[[(2S)-1-methylpyrrolidin-2-yl]methoxy]-7-(5-methyl-1-tetrahydropyran-2-yl-indazol-4-yl)-5,6,7,8-tetrahydroquinazolin-4-yl]piperazine-1-carboxylate

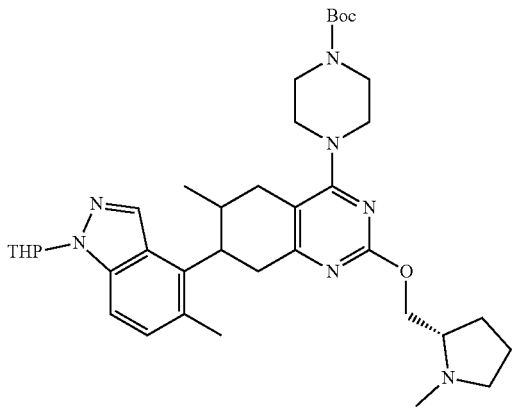

A solution of N-methyl-L-prolinol (66.7 mg, 0.58 mmol) and sodium hydride (0.09 g, 2.88 mmol, 60% dispersion in mineral oil) in N,N-dimethylformamide (2 mL) was stirred at 25° C. for 10 minutes. Then crude product tert-butyl 4-[6-methyl-2-methylsulfonyl-7-(5-methyl-1-tetrahydropyran-2-yl-indazol-4-yl)-5,6,7,8-tetrahydroquinazolin-4-yl]piperazine-1-carboxylate (0.18 g, 0.29 mmol) was added and stirred at 25° C. for 20 hours. After completion, the resulting solution was quenched by and extracted with dichloromethane. Then the organic layers were combined, washed with water, dried over anhydrous sodium sulfate and concentrated under vacuum. The residue was purified by flash chromatography on silica gel eluting with dichloromethane/methanol (20/1) to afford tert-butyl 4-[6-methyl-2-[[(2S)-1-methylpyrrolidin-2-yl]methoxy]-7-(5-methyl-1-tetrahydropyran-2-yl-indazol-4-yl)-5,6,7,8-tetrahydroquinazolin-4-yl]piperazine-1-carboxylate (150.0 mg, 0.23 mmol, 78.9% yield) as a yellow solid. LCMS (ESI, m/z): 660.4 [M+H]⁺.

Step 7a: 6-methyl-7-(5-methyl-1H-indazol-4-yl)-2-(((S)-1-methylpyrrolidin-2-yl)methoxy)-4-(piperazin-1-yl)-5,6,7,8-tetrahydroquinazoline

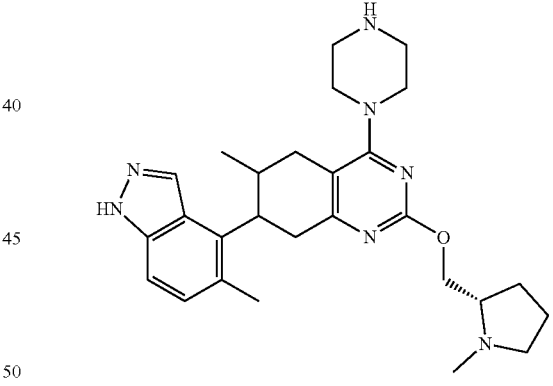

A solution of tert-butyl 4-[6-methyl-2-[[(2S)-1-methylpyrrolidin-2-yl]methoxy]-7-(5-methyl-1-tetrahydropyran-2-yl-indazol-4-yl)-5,6,7,8-tetrahydroquinazolin-4-yl]piperazine-1-carboxylate (0.14 g, 0.21 mmol) in dichloromethane (4 mL) and trifluoroacetic acid (0.2 mL) and was stirred at 25° C. for 3 hours. After completion, the solution was concentrated under vacuum to afford 6-methyl-7-(5-methyl-1H-indazol-4-yl)-2-[[(2S)-1-methylpyrrolidin-2-yl]methoxy]-4-piperazin-1-yl-5,6,7,8-tetrahydroquinazoline (150.0 mg, crude) which would be directly used in the next step without purification. LCMS (ESI, m/z): 476.3 [M+H]⁺.

Step 7b: 1-(4-(6-methyl-7-(5-methyl-1H-indazol-4-yl)-2-(((S)-1-methylpyrrolidin-2-yl)methoxy)-5,6,7,8-tetrahydroquinazolin-4-yl)piperazin-1-yl)prop-2-en-1-one

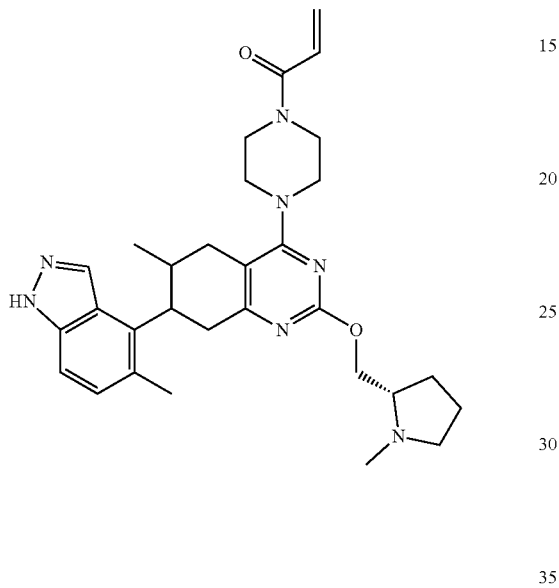

A solution of 6-methyl-7-(5-methyl-1H-indazol-4-yl)-2-[[(2S)-1-methylpyrrolidin-2-yl]methoxy]-4-piperazin-1-yl-5,6,7,8-tetrahydroquinazoline (0.15 g, 0.27 mmol) and N,N-diisopropyl-ethylamine (0.09 mL, 0.54 mmol) in dichloromethane (2 mL) was stirred at −78° C. for 10 minutes. Then acrylyl chloride (0.02 mL, 0.24 mmol) was added and stirred at −78° C. for 0.5 hours. After completion, the reaction was quenched by water, diluted with dichloromethane, washed with water. The organic layer was dried over anhydrous sodium sulfate and concentrated under vacuum. The crude product was further isolated by Prep-HPLC with the condition: Column: XBridge Prep OBD C18 Column 30×150 mm 5 um; Mobile Phase A:Water (10 MMOL/L NH4HCO3), Mobile Phase B: ACN; Flow rate: 60 mL/min; Gradient: 22% B to 42% B in 10 min; 254/220 nm; Rt: 9.02 min to afford 1-[4-[6-methyl-7-(5-methyl-1H-indazol-4-yl)-2-[[(2S)-1-methylpyrrolidin-2-yl]methoxy]-5,6,7,8-tetrahydroquinazolin-4-yl]piperazin-1-yl]prop-2-en-1-one (7.6 mg, 0.014 mmol, 5.4% yield) as a white solid. LCMS (ESI, m/z): 530.5 [M+H]$^+$.

Example 18a: $^1$H NMR (300 MHz, DMSO-$d_6$, ppm) δ 12.96 (s, 1H), 8.08 (s, 1H), 7.29 (d, J=8.5 Hz, 1H), 7.17 (d, J=8.6 Hz, 1H), 6.85 (dd, J=16.7, 10.5 Hz, 1H), 6.15 (dd, J=16.7, 2.4 Hz, 1H), 5.72 (dd, J=10.4, 2.4 Hz, 1H), 4.30-4.19 (m, 1H), 4.07-3.93 (m, 1H), 3.87-3.71 (m, 2H), 3.71-3.48 (m, 4H), 3.32-3.20 (m, 3H), 3.17-3.00 (m, 1H), 3.00-2.82 (m, 2H), 2.73-2.52 (m, 3H), 2.41 (s, 4H), 2.33 (s, 3H), 2.20-2.11 (m, 1H), 1.97-1.85 (m, 1H), 1.73-1.48 (m, 3H), 0.70 (d, J=6.1 Hz, 3H).

Examples 19a and 19b

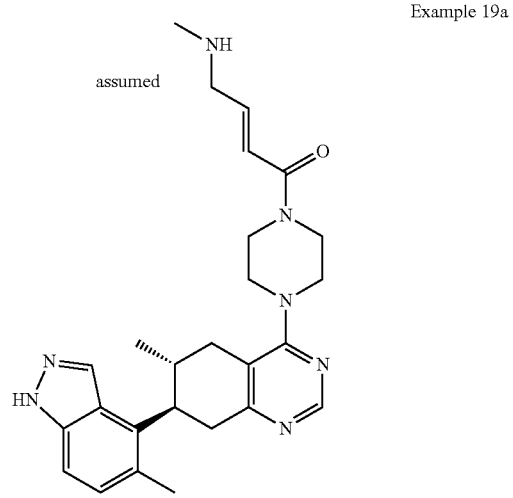

Example 19a

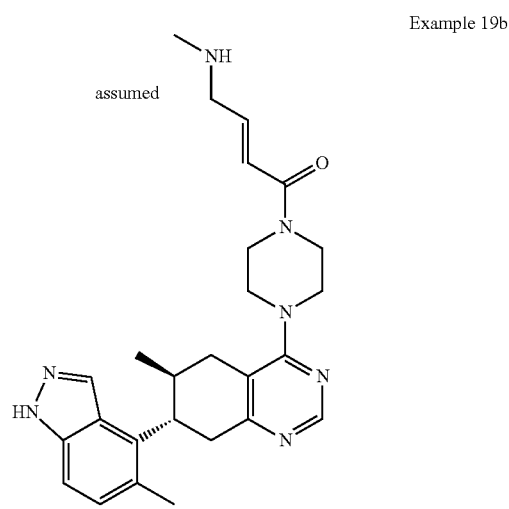

Example 19b

383

(E)-1-(4-(((6R,7R)-6-methyl-7-(5-methyl-1H-indazol-4-yl)-5,6,7,8-tetrahydroquinazolin-4-yl)piperazin-1-yl)-4-(methylamino)but-2-en-1-one (Example 19a)

(E)-1-(4-(((6S,7S)-6-methyl-7-(5-methyl-1H-indazol-4-yl)-5,6,7,8-tetrahydroquinazolin-4-yl)piperazin-1-yl)-4-(methylamino)but-2-en-1-one (Example 19b)

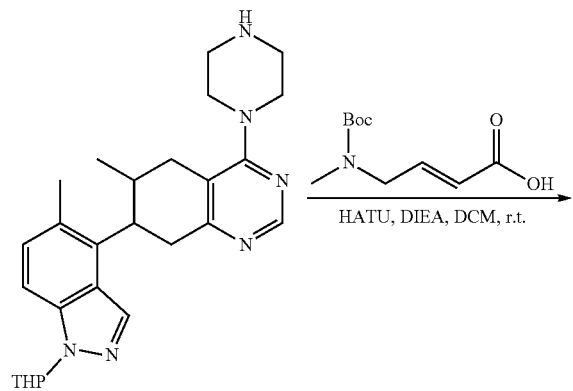

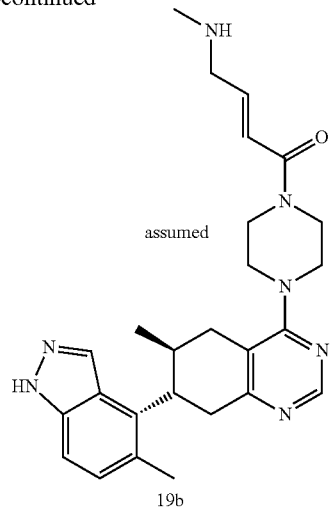

384

-continued

Step 1: tert-butyl N-methyl-N-[(E)-4-[4-[6-methyl-7-(5-methyl-1-tetrahydropyran-2-yl-indazol-4-yl)-5,6,7,8-tetrahydroquinazolin-4-yl]piperazin-1-yl]-4-oxo-but-2-enyl]carbamate A solution of 6-methyl-7-(5-methyl-1-tetrahydropyran-2-yl-indazol-4-yl)-4-piperazin-1-yl-5,6,7,8-tetrahydroquinazoline (0.59 g, 0.79 mmol), (E)-4-[tert-butoxy-carbonyl(methyl)amino]but-2-enoic acid (0.51 g, 2.38 mmol), HATU (0.39 g, 1.03 mmol) and N,N-diisopropylethylamine (0.28 mL, 1.59 mmol) in dichloromethane (3 mL) and N,N-dimethylformamide (3 mL) was stirred at 25° C. for 0.5 hours. After completion, the reaction mixture was diluted with water and extracted with dichloromethane. Then the organic layers were combined and washed with brine. The organic layers was dried over anhydrous sodium sulfate and concentrated under vacuum. The residue was purified by flash chromatography on silica gel eluting with dichloromethane/methanol (20/1) to afford tert-butyl N-methyl-N-[(E)-4-[4-[6-methyl-7-(5-methyl-1-tetrahydropyran-2-yl-indazol-4-yl)-5,6,7,8-tetrahydroquinazolin-4-yl]piperazin-1- yl]-4-oxo-but-2-enyl]carbamate (0.15 g, 0.17 mmol, 22% yield) as a solid. LCMS (ESI, m/z): 644.4 [M+H]⁺.

Step 2: (E)-1-(4-((6R,7R)-6-methyl-7-(5-methyl-1H-indazol-4-yl)-5,6,7,8-tetrahydroquinazolin-4-yl)piperazin-1-yl)-4-(methylamino)but-2-en-1-one (Example 19a) and (E)-1-(4-((6S,7S)-6-methyl-7-(5-methyl-1H-indazol-4-yl)-5,6,7,8-tetrahydroquinazolin-4-yl)piperazin-1-yl)-4-(methylamino)but-2-en-1-one (Example 19b)

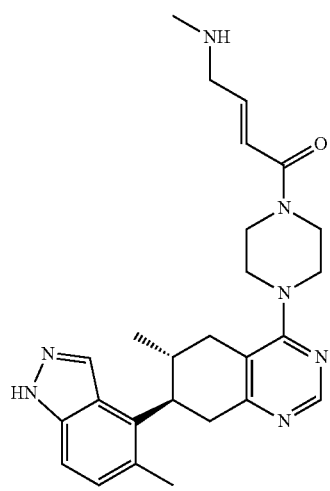

19a

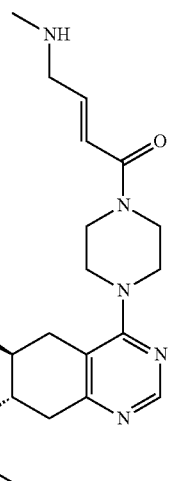

19b

A solution of tert-butyl N-methyl-N-[(E)-4-[4-[6-methyl-7-(5-methyl-1-tetrahydropyran-2-yl-indazol-4-yl)-5,6,7,8-tetrahydroquinazolin-4-yl]piperazin-1-yl]-4-oxo-but-2-enyl]carbamate (0.13 g, 0.20 mmol) in trifluoroacetic acid (1.5 mL) and dichloromethane (1.5 mL) was stirred at 25° C. for 1 hour. After completion, the solvent was concentrated under vacuum. Then the crude product was purified by Prep-HPLC with the following conditions: Column: XBridge Shield RP18 OBD Column 30*150 mm, 5 um; Mobile Phase A:Water (10 MMOL/L NH4HCO3), Mobile Phase B: ACN; Flow rate: 60 mL/min; Gradient: 13% B to 36% B in 10 min; 220/254 nm; Rt: 9.53 min to afford the desired product. The mixture of enantiomers was separated by Chiral-Prep-HPLC with the following conditions: Column: CHIRALPAK IC, 2*25 cm, 5 um; Mobile Phase A:Hex:DCM=1:1 (10 mM NH3-MEOH)—HPLC, Mobile Phase B: Hex—HPLC; Flow rate: 20 mL/min; Gradient: 50 B to 50 B in 16 min; 254/220 nm) to afford the title compounds. The absolute configuration of the title compounds was inferred from potency data and a protein X-ray structure of compound 21b.

Example 19a: (E)-1-(4-((6R,7R)-6-methyl-7-(5-methyl-1H-indazol-4-yl)-5,6,7,8-tetrahydroquinazolin-4-yl)piperazin-1-yl)-4-(methylamino)but-2-en-1-one (3.5 mg, 0.0076 mmol, 3.8% yield, white solid). ¹H NMR (300 MHz, DMSO-d₆, ppm) a 12.95 (s, 1H), 8.48 (s, 1H), 8.05 (s, 1H), 7.27 (d, J=9.0 Hz, 1H), 7.16 (d, J=8.5 Hz, 1H), 6.82-6.55 (m, 2H), 3.86-3.45 (m, 8H), 3.30-3.05 (m, 5H), 3.05-2.90 (m, 1H), 2.75-2.58 (m, 2H), 2.41 (s, 4H), 2.28 (s, 3H), 0.70 (d, J=6.3 Hz, 3H). LCMS (ESI, m/z): 460.2 [M+H]⁺. Chiral HPLC: CHIRALPAK IC-3 (0.46*5 cm; 3 um); detected at 254 nm; (Hex:DCM=1:1)(0.1% DEA): EtOH=50:50; flow=1.0 ml/min; Retention time: 2.159 min (faster peak).

Example 19b: (E)-1-(4-((6S,7S)-6-methyl-7-(5-methyl-1H-indazol-4-yl)-5,6,7,8-tetrahydroquinazolin-4-yl)piperazin-1-yl)-4-(methylamino)but-2-en-1-one (2.3 mg, 0.005 mmol, 2.5% yield, white solid). ¹H NMR (300 MHz, DMSO-d₆, ppm) a 12.95 (s, 1H), 8.48 (s, 1H), 8.05 (s, 1H), 7.27 (d, J=9.0 Hz, 1H), 7.16 (d, J=8.5 Hz, 1H), 6.82-6.55 (m, 2H), 3.86-3.45 (m, 8H), 3.30-3.05 (m, 5H), 3.05-2.90 (m, 1H), 2.75-2.58 (m, 2H), 2.41 (s, 4H), 2.28 (s, 3H), 0.70 (d, J=6.3 Hz, 3H). LCMS (ESI, m/z): 460.2 [M+H]⁺. Chiral HPLC: CHIRALPAK IC-3 (0.46*5 cm; 3 um); detected at 254 nm; (Hex:DCM=1:1)(0.1% DEA): EtOH=50:50; flow=1.0 ml/min; Retention time: 3.065 min (slower peak).

Examples 20a and 20b

Example 20a

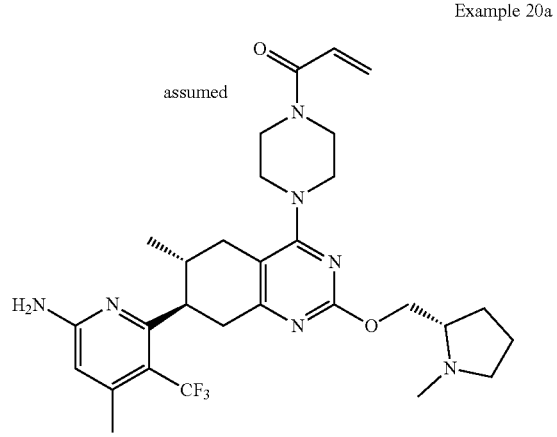

assumed

Example 20b
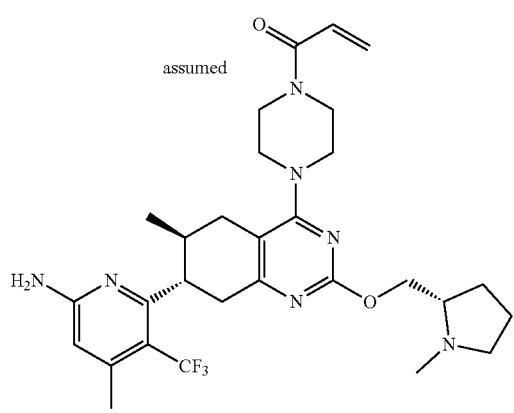
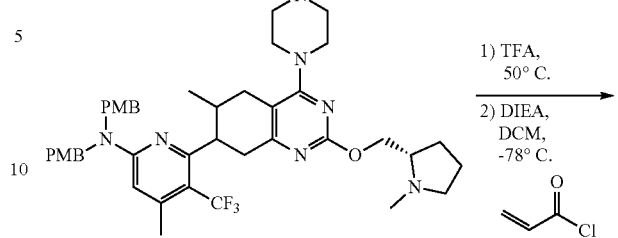
1-(4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one (Example 20a)
1-(4-((6S,7S)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one (Example 20b)
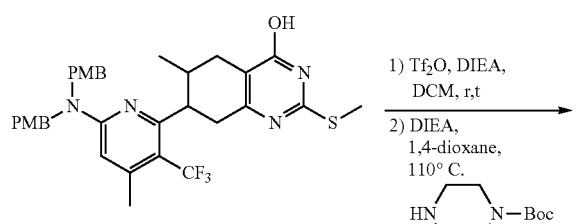
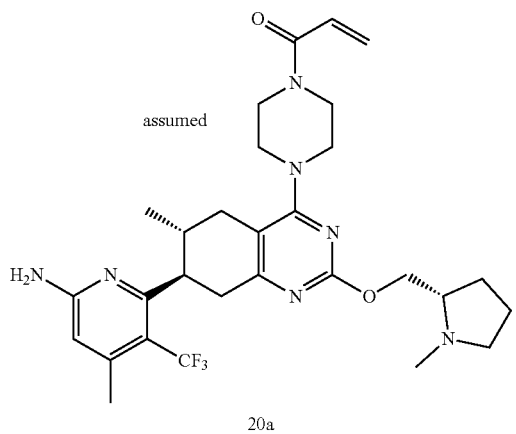
20a
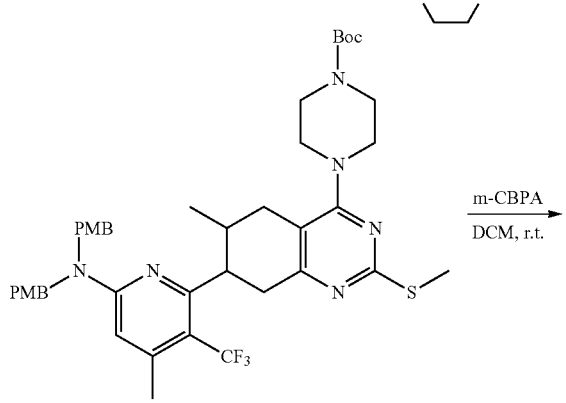
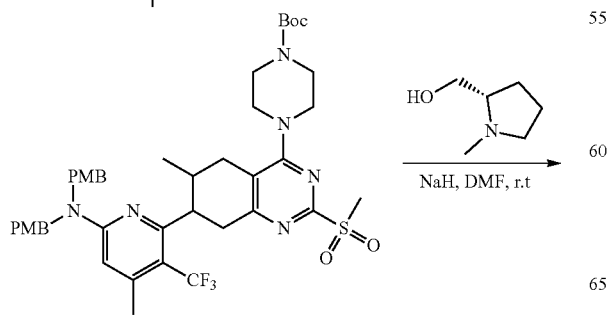
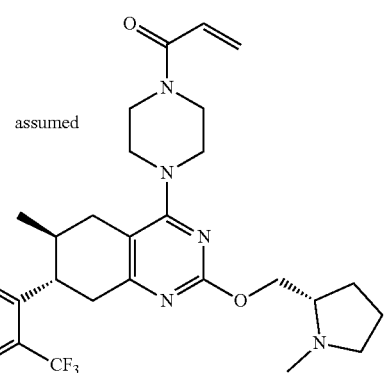
20b

Step 1: tert-butyl 4-(7-(6-(bis(4-methoxybenzyl)amino)-4-methyl-3-(trifluoromethyl)pyridin-2-yl)-6-methyl-2-(methylthio)-5,6,7,8-tetrahydroquinazolin-4-yl)piperazine-1-carboxylate

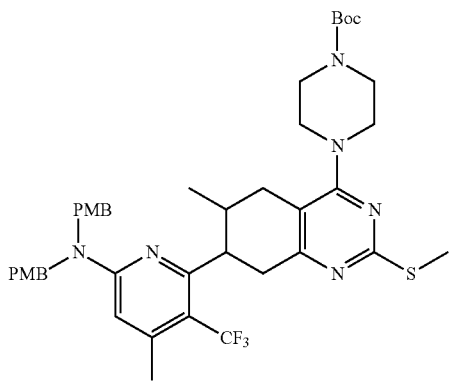

A solution of 7-[6-[bis[(4-methoxyphenyl)methyl]amino]-4-methyl-3-(trifluoromethyl)-2-pyridyl]-6-methyl-2-methylsulfanyl-5,6,7,8-tetrahydroquinazolin-4-ol (1.30 g, 2.08 mmol) and N,N-diisopropylethylamine (1.81 mL, 10.4 mmol) in dichloromethane (10 mL) was added trifluoromethanesulfonic anhydride (0.63 mL, 3.75 mmol) and stirred at 25° C. for 1 hour. After completion, the solvent was concentrated under vacuum. The residue was diluted with 1,4-dioxane, and adjusted to pH>7 with N,N-diisopropylethylamine. Then tert-butyl 1-piperazinecarboxylate (1.16 g, 6.24 mmol) was added and stirred at 110° C. for 12 hours. After completion, the solvent was concentrated under vacuum. The residue was purified by flash chromatography on silica gel eluting with petrol ether/ethyl acetate (3/1) to afford tert-butyl 4-(7-(6-(bis(4-methoxybenzyl)amino)-4-methyl-3-(trifluoromethyl)pyridin-2-yl)-6-methyl-2-(methylthio)-5,6,7,8-tetrahydroquinazolin-4-yl)piperazine-1-carboxylate (1.30 g, 2.08 mmol) as a yellow solid. LCMS (ESI, m/z): 793.4 [M+H]$^+$.

Step 2: tert-butyl 4-[7-[6-[bis[(4-methoxyphenyl)methyl]amino]-4-methyl-3-(trifluoromethyl)-2-pyridyl]-6-methyl-2-methylsulfonyl-5,6,7,8-tetrahydroquinazolin-4-yl]piperazine-1-carboxylate

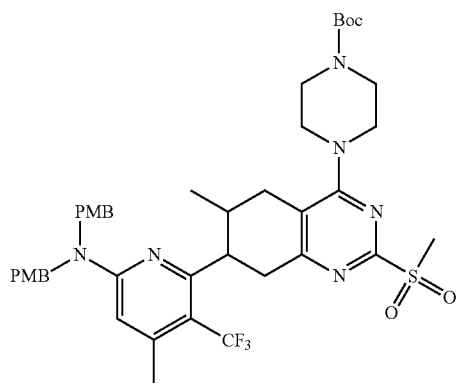

A solution of tert-butyl 4-(7-(6-(bis(4-methoxybenzyl)amino)-4-methyl-3-(trifluoromethyl)pyridin-2-yl)-6-methyl-2-(methylthio)-5,6,7,8-tetrahydroquinazolin-4-yl)piperazine-1-carboxylate (1.00 g, 1.26 mmol) and 3-chloroperoxybenzoic acid (0.65 g, 3.78 mmol) in dichloromethane (10 mL) was stirred at 25° C. for 1 hour. After completion, the reaction was quenched by aqueous saturated Na$_2$SO$_3$. The reaction mixture was diluted with dichloromethane, washed with water, dried over anhydrous sodium sulfate and concentrated under vacuum to afford the crude tert-butyl 4-[7-[6-[bis[(4-methoxyphenyl)methyl]amino]-4-methyl-3-(trifluoromethyl)-2-pyridyl]-6-methyl-2-methylsulfonyl-5,6,7,8-tetrahydroquinazolin-4-yl]piperazine-1-carboxylate (1.20 g, crude) which would be directly used in the next step without purification.

Step 3: tert-butyl 4-[7-[6-[bis[(4-methoxyphenyl)methyl]amino]-4-methyl-3-(trifluoromethyl)-2-pyridyl]-6-methyl-2-[[(2S)-1-methylpyrrolidin-2-yl]methoxy]-5,6,7,8-tetrahydroquinazolin-4-yl]piperazine-1-carboxylate

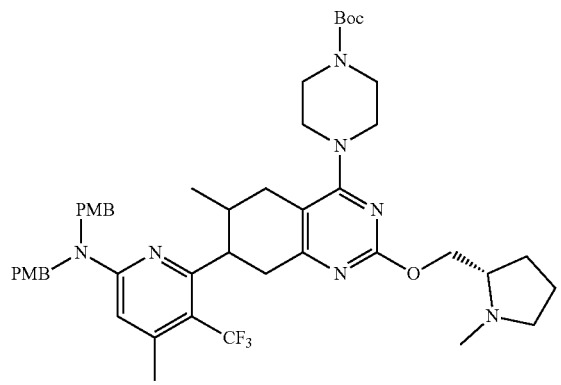

A solution of N-methyl-L-prolinol (635.9 mg, 5.53 mmol) and sodium hydride (0.22 g, 5.53 mmol, 60% dispersion in mineral oil) in N,N-dimethylformamide (5 mL) was stirred at 25° C. for 10 minutes. Then the last step crude product tert-butyl 4-[7-[6-[bis[(4-methoxyphenyl)methyl]amino]-4-methyl-3-(trifluoromethyl)-2-pyridyl]-6-methyl-2-methylsulfonyl-5,6,7,8-tetrahydroquinazolin-4-yl]piperazine-1-carboxylate (1.20 g, crude) was added and stirred at 25° C. for 20 hours. After completion, the reaction was quenched by water. The resulting solution was extracted with dichloromethane and the organic layers were combined. The organic layer was washed with water, dried over anhydrous sodium sulfate and concentrated under vacuum. The residue was purified by flash chromatography on silica gel eluting with dichloromethane/methanol (20/1) to afford tert-butyl 4-[7-[6-[bis[(4-methoxyphenyl)methyl]amino]-4-methyl-3-(trifluoromethyl)-2-pyridyl]-6-methyl-2-[[(2S)-1-methylpyrrolidin-2-yl]methoxy]-5,6,7,8-tetrahydroquinazolin-4-yl]piperazine-1-carboxylate (700.0 mg, 0.81 mmol, 73.6% yield) as a yellow solid. LCMS (ESI, m/z): 860.5 [M+H]$^+$.

Step 4: 1-(4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one (Example 20a) 1-(4-((6S,7S)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one (Example 20b)

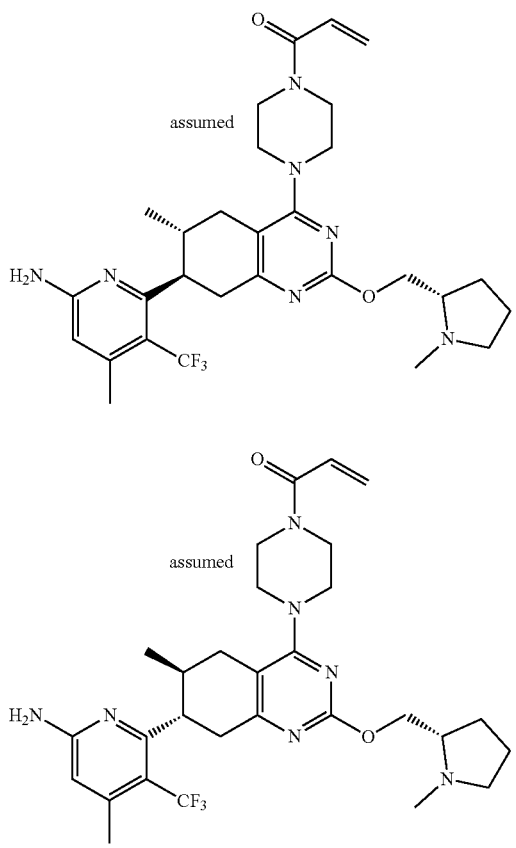

20a

20b

A solution of tert-butyl 4-[7-[6-[bis[(4-methoxyphenyl)methyl]amino]-4-methyl-3-(trifluoromethyl)-2-pyridyl]-6-methyl-2-[[(2S)-1-methylpyrrolidin-2-yl]methoxy]-5,6,7,8-tetrahydroquinazolin-4-yl]piperazine-1-carboxylate (0.70 g, 0.81 mmol) in trifluoroacetic acid (5 mL) was stirred at 50° C. for 12 hours. After completion, the solvent was concentrated under vacuum to afford the crude 4-methyl-6-[6-methyl-2-[[(2S)-1-methylpyrrolidin-2-yl]methoxy]-4-piperazin-1-yl-5,6,7,8-tetrahydroquinazolin-7-yl]-5-(trifluoromethyl)pyridin-2-amine (500 mg, crude). A solution of the crude 4-methyl-6-[6-methyl-2-[[(2S)-1-methylpyrrolidin-2-yl]methoxy]-4-piperazin-1-yl-5,6,7,8-tetrahydroquinazolin-7-yl]-5-(trifluoromethyl)pyridin-2-amine (0.50 g, crude) in dichloromethane (10 mL) was adjusted to pH>7 with N,N-diisopropylethylamine. Then acrylyl chloride (0.07 g, 0.78 mmol) was added and stirred at −78° C. for 20 minutes. After completion, the resulting solution was concentrated under vacuum. The crude product was purified by Prep-HPLC with the following conditions: Column: XBridge Prep OBD C18 Column, 30×150 mm 5 um; Mobile Phase A: Water (10 MMOL/L NH4HCO3), Mobile Phase B: ACN; Flow rate: 60 mL/min; Gradient: 35 B to 53 B in 7 min; 254/220 nm; RT1:6.57; RT2; Injection Volumn: ml; Number Of Runs. The mixture of diasteroisomer was separated by Prep-Chiral-HPLC with the following condition: Column: CHIRALPAK IE, 2*25 cm, 5 um; Mobile Phase A: MTBE (10 mM NH3-MEOH)—HPLC, Mobile Phase B: MeOH—HPLC; Flow rate: 20 mL/min; Gradient: 5 B to 5 B in 21 min; 220/254 nm; RT1:11.022; RT2:13.553; Injection Volumn: 0.3 ml to afford the title compounds. The stereo chemistry of title compounds was arbitrarily assigned.

Example 20a: 1-(4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one (51.4 mg, 0.09 mmol, 10.3% yield, white solid). $^1$H NMR (300 MHz, DMSO-d$_6$) δ 6.80 (dd, J=16.7, 10.4 Hz, 1H), 6.44 (s, 2H), 6.27-6.03 (m, 2H), 5.69 (dd, J=10.4, 2.5 Hz, 1H), 4.21 (dd, J=10.7, 4.8 Hz, 1H), 3.97 (dd, J=10.7, 6.5 Hz, 1H), 3.81-3.43 (m, 6H), 3.32-3.18 (m, 2H), 3.14-2.84 (m, 3H), 2.79-2.65 (m, 1H), 2.60-2.51 (m, 1H), 2.48-2.38 (m, 2H), 2.38-2.21 (m, 6H), 2.20-2.0 (m, 2H), 1.97-1.81 (m, 1H), 1.73-1.41 (m, 3H), 0.71 (d, J=6.3 Hz, 3H). LCMS (ESI, m/z): 574.3 [M+H]$^+$. Chiral HPLC: CHIRALPAK IE-3 (0.46*5 cm; 3 um); detected at 254 nm; MtBE(0.1% DEA): MeOH=95:5; flow=1.0 ml/min; Retention time: 2.928 min (faster peak).

Example 20b: 1-(4-((6S,7S)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one (48.5 mg, 0.08 mmol, 9.8% yield, white solid). $^1$H NMR (300 MHz, DMSO-d$_6$) δ 6.80 (dd, J=16.7, 10.4 Hz, 1H), 6.44 (s, 2H), 6.22-6.06 (m, 2H), 5.69 (dd, J=10.4, 2.4 Hz, 1H), 4.20 (dd, J=10.8, 4.8 Hz, 1H), 3.99 (dd, J=10.7, 6.5 Hz, 1H), 3.71 (brs, 2H), 3.62-3.45 (m, 4H), 3.31-3.20 (m, 2H), 3.15-2.86 (m, 3H), 2.86-2.66 (m, 1H), 2.61-2.52 (m, 1H), 2.49-2.32 (m, 2H), 2.28 (d, J=11.7 Hz, 6H), 2.20-2.11 (m, 1H), 2.10-1.98 (m, 1H), 1.97-1.81 (m, 1H), 1.79-1.41 (m, 3H), 0.71 (d, J=6.3 Hz, 3H). LCMS (ESI, m/z): 574.3 [M+H]$^+$. Chiral HPLC: CHIRALPAK IE-3 (0.46*5 cm; 3 um); detected at 254 nm; MtBE(0.1% DEA): MeOH=95:5; flow=1.0 ml/min; Retention time: 3.483 min (slower peak).

Examples 21a and 21b

Example 21a

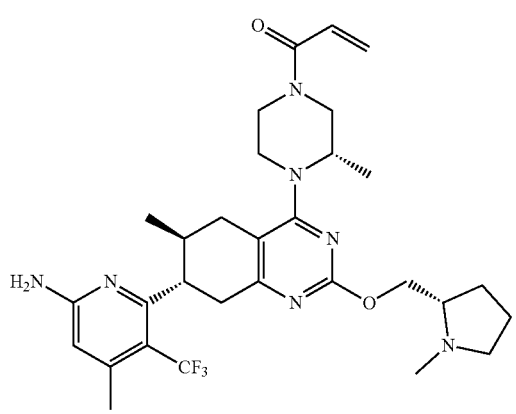

393
Example 21b
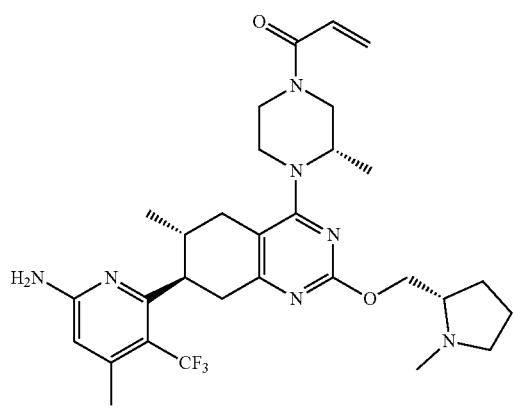
1-((S)-4-(((6S,7S)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 21a)
1-((S)-4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 21b)
394
-continued
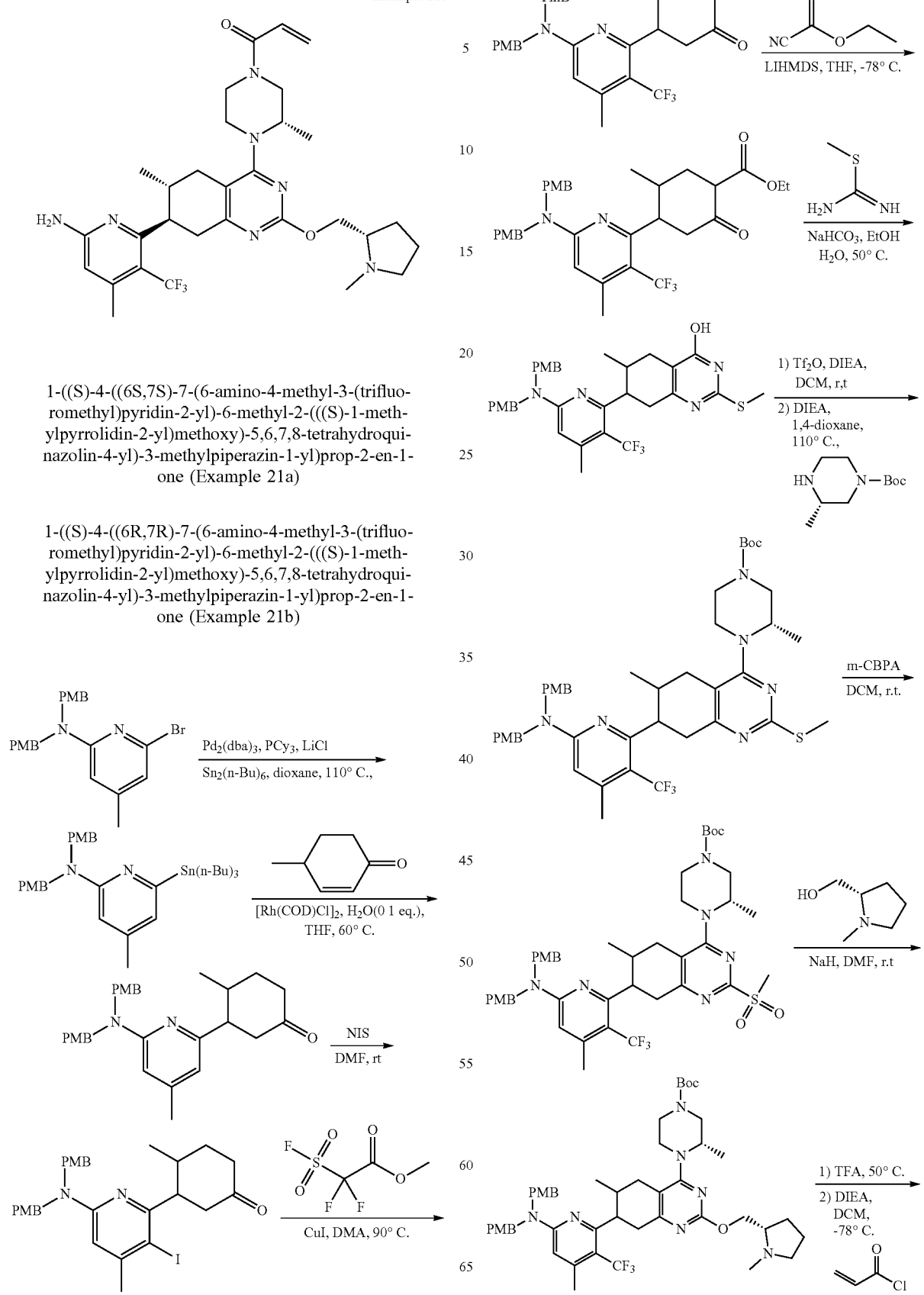

395
-continued

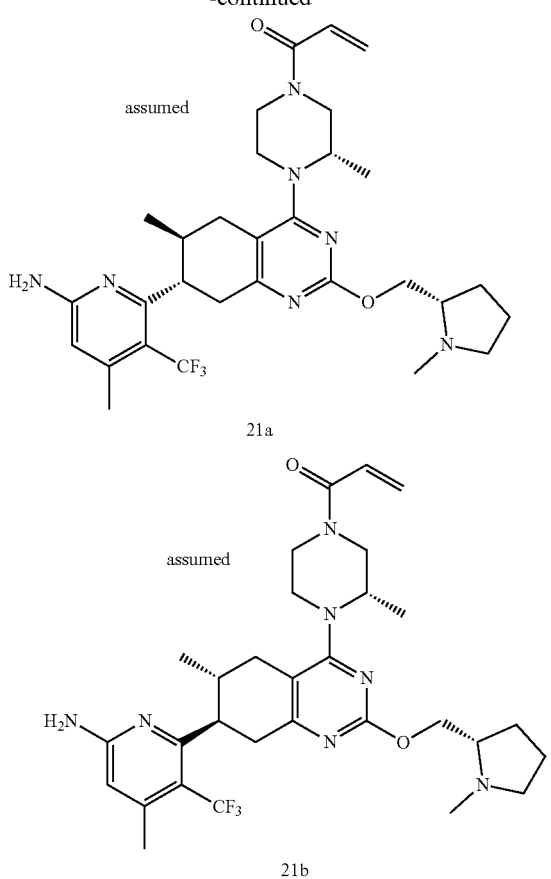

assumed

21a assumed

21b

Step 1: N,N-bis(4-methoxybenzyl)-4-methyl-6-(tributylstannyl)pyridin-2-amine

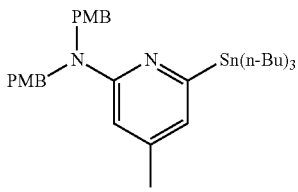

Under nitrogen, a solution of 6-bromo-N,N-bis[(4-methoxyphenyl)methyl]-4-methyl-pyridin-2-amine (42.00 g, 98.28 mmol), hexabutylditin (74.5 mL, 147.43 mmol), bis(dibenzylideneacetone)palladium (5.65 g, 9.83 mmol), lithium chloride (21.33 g, 491.42 mmol) and tricyclohexyl phosphine (5.51, 19.66 mol) in dioxane (300 L) was stirred for 4 hours at 110° C. After completion, the reaction was concentrated under reduced pressure. The residue was purified by flash chromatography on silica gel eluting with petroleum ether/ethyl acetate (1/1) to afford N,N-bis[(4-methoxyphenyl)methyl]-4-methyl-6-tributylstannyl-pyridin-2-amine (60.0 g, 79.1 mmol, 84.0% yield) as a yellow oil. LCMS (ESI, m/z): 639.3 [M+H]$^+$.

396

Step 2: 3-[6-[bis[(4-methoxyphenyl)methyl]amino]-4-methyl-2-pyridyl]-4-methyl-cyclohexanone

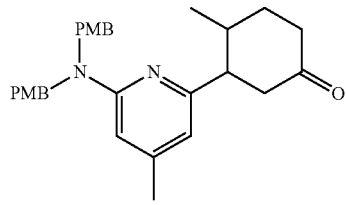

Under nitrogen, a solution of 4-methylcyclohex-2-en-1-one (2.18, 19.77 mol) and chloro(1,5-cyclooctadiene)rhodium(I) dimer (0.65 g, 1.32 mmol) in tetrahydrofuran (100 mL) was added N,N-bis[(4-methoxyphenyl)methyl]-4-methyl-6-tributylstannyl-pyridin-2-amine (10.00 g, 13.18 mmol) and stirred at 60° C. for 3 hours. After completion, the reaction mixture was concentrated under vacuum. The reaction mixture was diluted with dichloromethane and washed by water. The organic layer was dried over anhydrous sodium sulfate and concentrated under vacuum. The residue was purified by flash chromatography on silica gel eluting with petroleum ether/ethyl acetate (3:1) to afford 3-[6-[bis[(4-methoxyphenyl)methyl]amino]-4-methyl-2-pyridyl]-4-methyl-cyclohexanone (3.40 g, 7.41 mmol, 56.3% yield) as a yellow oil. LCMS (ESI, m/z): 459.3 [M+H]$^+$.

Step 3: 3-[6-[bis[(4-methoxyphenyl)methyl]amino]-3-iodo-4-methyl-2-pyridyl]-4-methyl-cyclohexanoe

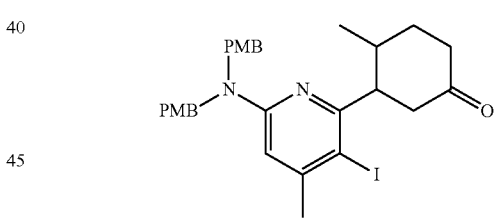

A solution of 3-[6-[bis[(4-methoxyphenyl)methyl]amino]-4-methyl-2-pyridyl]-4-methyl-cyclohexanone (10.00 g, 21.81 mmol) and N-iodosuccinimide (6.38 g, 28.35 mmol) in N,N-dimethylformamide (125 mL) was stirred at r.t. for 3 hours. After completion, the reaction mixture was diluted with water, extracted with dichloromethane and the organic layers were combined. The organic layers was washed with water, dried over anhydrous sodium sulfate and concentrated under vacuum. The residue was purified by flash chromatography on silica gel eluting with petroleum ether/ethyl acetate (3/1) to afford 3-[6-[bis[(4-methoxyphenyl)methyl]amino]-3-iodo-4-methyl-2-pyridyl]-4-methyl-cyclohexanoe (11.00 g, 18.82 mmol, 86.3% yield) as a yellow solid. LCMS (ESI, m/z): 585.2 [M+H]$^+$.

Step 4: 3-[6-[bis[(4-methoxyphenyl)-methyl]amino]-4-methyl-3-(trifluoromethyl)-2-pyridyl]-4-methyl-cyclohexanone

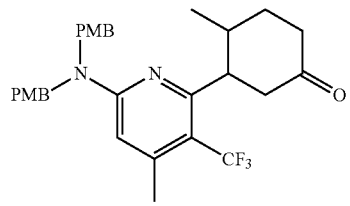

Under nitrogen, a solution of methyl 2,2-difluoro-2-(fluorosulfonyl)acetate (16.43 g, 85.54 mmol) and cuprous iodide (9.76 g, 51.33 mmol) in DMF (60 mL) was added 3-[6-[bis[(4-methoxyphenyl)methyl]amino]-3-iodo-4-methyl-2-pyridyl]-4-methyl-cyclohexanone (10.00 g, 17.11 mmol) and stirred at 90° C. for 2 hours. After completion, the reaction mixture was added water, extracted with dichloromethane and the organic layers were combined. The organic layers was washed with water, dried over anhydrous sodium sulfate and concentrated under vacuum. The residue was purified by flash chromatography on silica gel eluting with petroleum ether/ethyl acetate (3/1) to afford 3-[6-[bis[(4-methoxyphenyl)-methyl]amino]-4-methyl-3-(trifluoromethyl)-2-pyridyl]-4-methyl-cyclohexanone (8.50 g, 16.14 mmol, 94.3% yield) as a yellow solid. LCMS (ESI, m/z): 527.2 [M+H]$^+$.

Step 5: ethyl 4-[6-[bis[(4-methoxyphenyl)methyl]amino]-4-methyl-3-(trifluoromethyl)-2-pyridyl]-5-methyl-2-oxo-cyclohexanecarboxylate

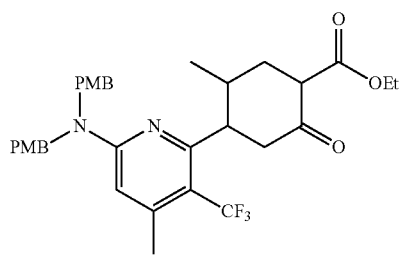

Under nitrogen, a solution of 3-[6-[bis[(4-methoxyphenyl)methyl]amino]-4-methyl-3-(trifluoromethyl)-2-pyridyl]-4-methyl-cyclohexanone (12.0 g, 22.79 mmol) in tetrahydrofuran (400 mL) was dropwise added lithium bis(trimethylsilyl)amide (45.6 mL, 45.58 mmol, 1M in THF) and stirred for 1 hour at −78° C. Then ethyl cyanoformate (5.19 g, 52.41 mmol) was dropwise added and stirred at −78° C. for 0.5 hours. After completion, the reaction was quenched with aqueous saturated ammonium chloride. The reaction mixture was diluted with dichloromethane, washed with water. The organic layer was dried over anhydrous sodium sulfate and concentrated under vacuum to afford the crude product ethyl 4-[6-[bis[(4-methoxyphenyl)methyl]amino]-4-methyl-3-(trifluoromethyl)-2-pyridyl]-5-methyl-2-oxo-cyclohexanecarboxylate (10.70 g, crude) as a yellow solid. LCMS (ESI, m/z): 599.3 [M+H]$^+$.

Step 6: 7-[6-[bis[(4-methoxyphenyl)methyl]amino]-4-methyl-3-(trifluoromethyl)-2-pyridyl]-6-methyl-2-methylsulfanyl-5,6,7,8-tetrahydro-3H-quinazolin-4-one

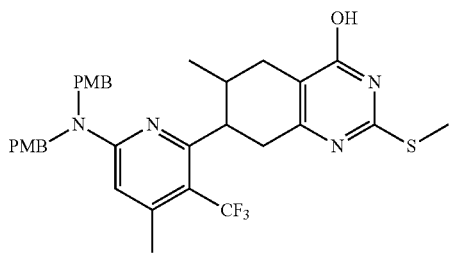

A solution of ethyl 4-[6-[bis[(4-methoxyphenyl)methyl]amino]-4-methyl-3-(trifluoromethyl)-2-pyridyl]-5-methyl-2-oxo-cyclohexanecarboxylate (9.00 g, 15.03 mmol), 2-methylisothiourea (27.11 g, 300.68 mmol) and sodium bicarbonate (31.95 g, 375.85 mmol) in ethanol (50 mL) and water (10 mL) was stirred at 50° C. for 12 hours. After completion, the reaction mixture was concentrated under vacuum and diluted with dichloromethane, washed with water. The organic layer was dried over anhydrous sodium sulfate and concentrated under vacuum. The residue was purified by flash chromatography on silica gel eluting with dichloromethane/ethyl acetate (1/1) to afford to 7-[6-[bis[(4-methoxyphenyl)methyl]amino]-4-methyl-3-(trifluoromethyl)-2-pyridyl]-6-methyl-2-methylsulfanyl-5,6,7,8-tetrahydro-3H-quinazolin-4-one (2.30 g, 3.68 mmol, 24.5% yield) as a white solid. LCMS (ESI, m/z): 625.2 [M+H]$^+$.

Step 7: tert-butyl (3S)-4-[7-[6-[bis[(4-methoxyphenyl)methyl]amino]-4-methyl-3-(trifluoromethyl)-2-pyridyl]-6-methyl-2-methylsulfanyl-5,6,7,8-tetrahydroquinazolin-4-yl]-3-methyl-piperazine-1-carboxylate

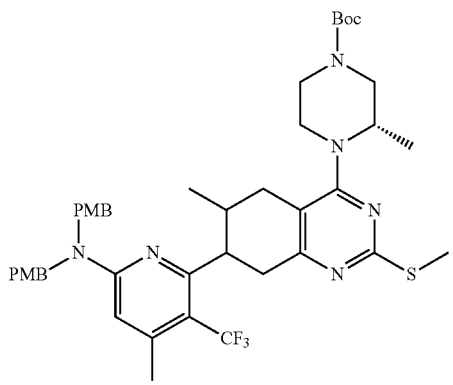

A solution of 7-[6-[bis[(4-methoxyphenyl)methyl]amino]-4-methyl-3-(trifluoromethyl)-2-pyridyl]-6-methyl-2-methylsulfanyl-5,6,7,8-tetrahydroquinazolin-4-ol (1.00 g, 1.60 mmol), and N,N-diisopropylethylamine (1.39 mL, 8.00 mmol) in dichloromethane (5 mL) was added trifluoromethanesulfonic anhydride (0.48 mL, 2.88 mmol) and stirred at r.t. for 1 hour. After completion, the solvent was concentrated under vacuum. The residue was diluted with 1,4-dioxane (10 mL) and adjusted to pH>7 with DIEA. Then tert-butyl (3S)-3-methyl-1-piperazinecarboxylate (1.60 g, 8.00 mmol) was added and stirred at 110° C. for 12 hours. After completion, the solvent was concentrated under vacuum. The residue was purified by flash chromatography on silica gel eluting with petroleum ether/ethyl acetate (3/1) to afford tert-butyl (3S)-4-[7-[6-[bis[(4-methoxyphenyl)methyl]amino]-4-methyl-3-(trifluoromethyl)-2-pyridyl]-6-methyl-2-methylsulfanyl-5,6,7,8-tetrahydroquinazolin-4-yl]-3-methyl-piperazine-1-carboxylate (850.0 mg, 1.05 mmol, 65.8% yield) as a yellow solid. LCMS (ESI, m/z): 807.4 [M+H]$^+$.

Step 8: tert-butyl(3S)-4-[7-[6-[bis[(4-methoxyphenyl)methyl]amino]-4-methyl-3-(trifluoromethyl)-2-pyridyl]-6-methyl-2-methylsulfonyl-5,6,7,8-tetrahydroquinazolin-4-yl]-3-methyl-piperazine-1-carboxylate

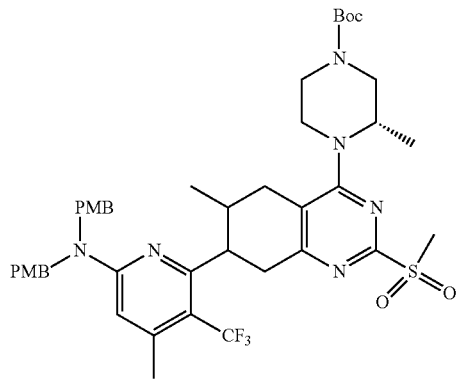

A solution of tert-butyl (3S)-4-[7-[6-[bis[(4-methoxyphenyl)methyl]amino]-4-methyl-3-(trifluoromethyl)-2-pyridyl]-6-methyl-2-methylsulfanyl-5,6,7,8-tetrahydroquinazolin-4-yl]-3-methyl-piperazine-1-carboxylate (0.20 g, 0.25 mmol) and 3-chloroperoxybenzoic acid (0.13 g, 0.74 mmol) in dichloromethane (3 mL) was stirred at r.t. for 1 hour. After completion, the reaction was quenched by aqueous saturated Na$_2$SO$_3$. The reaction mixture was diluted with dichloromethane, washed with water, dried over anhydrous sodium sulfate and concentrated under vacuum to afford the crude tert-butyl(3S)-4-[7-[6-[bis[(4-methoxyphenyl)methyl]amino]-4-methyl-3-(trifluoromethyl)-2-pyridyl]-6-methyl-2-methylsulfonyl-5,6,7,8-tetrahydroquinazolin-4-yl]-3-methyl-piperazine-1-carboxylate (300 mg, crude) which would be directly used in the next step without purification. LCMS (ESI, m/z): 839.4 [M+H]$^+$.

Step 9: tert-butyl(3S)-4-[7-[6-[bis[(4-methoxyphenyl)methyl]amino]-4-methyl-3-(trifluoromethyl)-2-pyridyl]-6-methyl-2-[[(2S)-1-methylpyrrolidin-2-yl]methoxy]-5,6,7,8-tetrahydroquinazolin-4-yl]-3-methyl-piperazine-1-carboxylate A solution of N-methyl-L-prolinol (141.4 mg, 1.23 mmol) and sodium hydride (0.05 g, 1.23 mmol, 60% dispersion in mineral oil) in N,N-dimethylformamide (3 mL) was stirred at r.t. for 10 min. Then tert-butyl(3S)-4-[7-[6-[bis[(4-methoxyphenyl)methyl]amino]-4-methyl-3-(trifluoromethyl)-2-pyridyl]-6-methyl-2-methylsulfonyl-5,6,7,8-tetrahydroquinazolin-4-yl]-3-methyl-piperazine-1-carboxylate (0.30 g, crude) was added and stirred at r.t. for 5 hours. After completion, the reaction was quenched by aqueous saturated ammonium chloride. The resulting solution was extracted with dichloromethane and the organic layers were combined. The organic layer was washed with water, dried over anhydrous sodium sulfate and concentrated under vacuum. The residue was purified by flash chromatography on silica gel eluting with dichloromethane/methanol (20/1) to afford tert-butyl(3S)-4-[7-[6-[bis[(4-methoxyphenyl)methyl]amino]-4-methyl-3-(trifluoromethyl)-2-pyridyl]-6-methyl-2-[[(2S)-1-methylpyrrolidin-2-yl]methoxy]-5,6,7,8-tetrahydroquinazolin-4-yl]-3-methyl-piperazine-1-carboxylate (100.0 mg, 0.11 mmol, 46.4% yield) as a yellow solid. LCMS (ESI, m/z): 874.5 [M+H]$^+$.

Step 10: 1-((S)-4-((6S,7S)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 21a); 1-((S)-4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 21b)

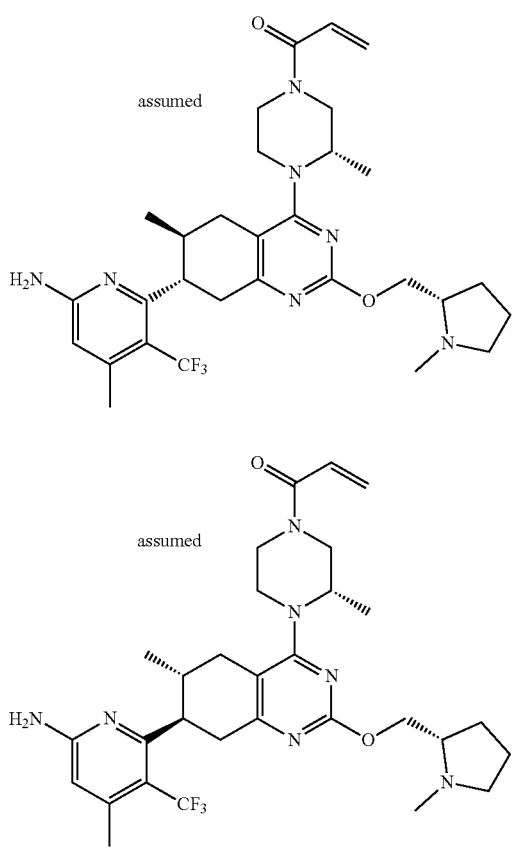

A solution of tert-butyl (3S)-4-[7-[6-[bis[(4-methoxyphenyl)methyl]amino]-4-methyl-3-(trifluoromethyl)-2-pyridyl]-6-methyl-2-[[(2S)-1-methylpyrrolidin-2-yl]methoxy]-5,6,7,8-tetrahydroquinazolin-4-yl]-3-methylpiperazine-1-carboxylate (0.70 g, 0.80 mmol) in trifluoroacetic acid (5 mL) was stirred at 50° C. for 12 hours. After completion, the solvent was concentrated under vacuum to afford crude 4-methyl-6-[6-methyl-4-[(2S)-2-methylpiperazin-1-yl]-2-[[(2S)-1-methylpyrrolidin-2-yl]methoxy]-5,6,7,8-tetrahydroquinazolin-7-yl]-5-(trifluoromethyl)pyridin-2-amine (900 mg, crude). A solution of the crude 4-methyl-6-[6-methyl-4-[(2S)-2-methylpiperazin-1-yl]-2-[[(2S)-1-methylpyrrolidin-2-yl]methoxy]-5,6,7,8-tetrahydroquinazolin-7-yl]-5-(trifluoromethyl)pyridin-2-amine (0.90 g, crude) in dichloromethane (10 mL) was adjusted to pH>7 with DIEA. Then acrylyl chloride (0.14 g, 1.52 mmol) was added and stirred at −78° C. for 20 minutes. After completion, the resulting solution was quenched with aqueous saturated ammonium chloride and concentrated under vacuum. Then the crude product was purified by Prep-HPLC with the following conditions: Column, CHIRALPAK IE2*25 cm, 5 um S90IE0SCJ-VA001S90IE0SCJ-VA001; mobile phase: Hex (8 mmol/L NH3·MeOH); Detector, UV 254 nm. The mixture of diastereoisomer was separated by Prep-Chiral-HPLC with the following condition: Column: CHIRALPAK IE-3, 4.6*50 mm, 3 um; Mobile Phase A: Hex (0.1% DEA): EtOH=50:50, Mobile Phase B; Flow rate: 1 ml/min to afford the title compounds. The absolute configuration of the title compounds was inferred from potency data and a protein X-ray structure of compound 21b.

Example 21a: 1-((S)-4-((6S,7S)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (84.1 mg, 0.14 mmol, 8.5% yield, white solid). $^1$H NMR (300 MHz, DMSO-$d_6$, ppm) δ 6.97-6.71 (m, 1H), 6.44 (s, 2H), 6.27-6.10 (m, 2H), 5.72 (dd, J=10.4, 2.5 Hz, 1H), 4.39-3.94 (m, 5H), 3.92-3.52 (m, 1H), 3.50-3.41 (m, 1H), 3.28-3.17 (m, 2H), 3.13-2.67 (m, 5H), 2.65-2.57 (m, 1H), 2.48-2.40 (m, 1H), 2.38-2.22 (m, 6H), 2.21-1.78 (m, 3H), 1.72-1.51 (m, 3H), 1.02-0.88 (m, 3H), 0.71 (d, J=6.4 Hz, 3H). LCMS (ESI, m/z): 588.4 [M+H]$^+$. Chiral HPLC: CHIRALPAK IE-3 (4.6*50 mm 3 um); detected at 254 nm; Hex (0.1% DEA): EtOH=50:50; flow=1.0 ml/min; Retention time: 2.100 min (slower peak).

Example 21b: 1-((S)-4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (74.9 mg, 0.13 mmol, 7.6% yield, white solid). $^1$H NMR (300 MHz, DMSO-$d_6$, ppm) δ 6.95-6.70 (m, 1H), 6.45 (s, 2H), 6.26-6.10 (m, 2H), 5.75 (dd, J=10.4, 2.4 Hz, 1H), 4.43-3.67 (m, 6H), 3.38-3.25 (m, 2H), 3.16-2.68 (m, 6H), 2.48-2.41 (m, 2H), 2.36-2.23 (m, 6H), 2.14 (q, J=8.6 Hz, 1H), 2.08-1.85 (m, 2H), 1.71-1.45 (m, 3H), 1.22 (brs, 3H), 0.70 (d, J=6.4 Hz, 3H). LCMS (ESI, m/z): 588.4 [M+H]$^+$. Chiral HPLC: CHIRALPAK IE-3 (4.6*50 mm 3 um); detected at 254 nm; Hex (0.1% DEA): EtOH=50:50; flow=1.0 ml/min; Retention time: 1.780 min (faster peak).

Examples 22a and 22b

Example 22a

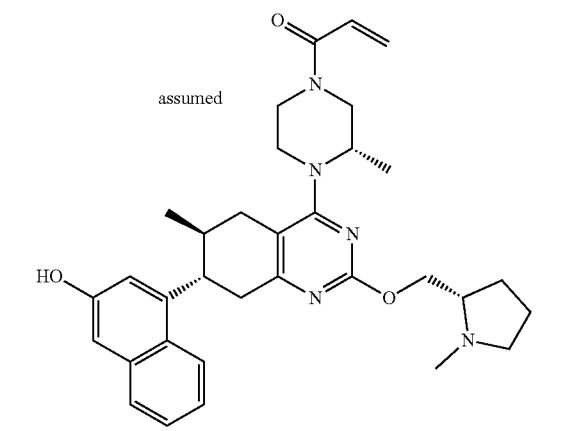

Example 22b
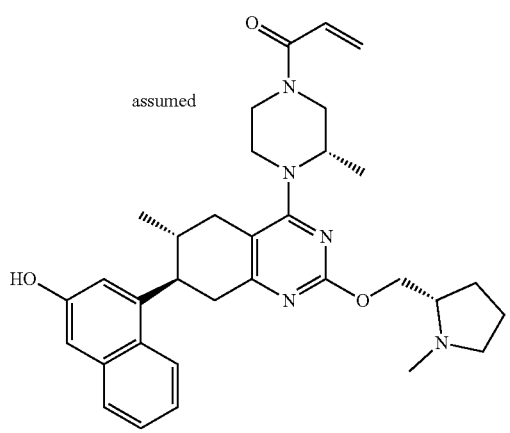
assumed
1-((S)-4-((6S,7S)-7-(3-hydroxynaphthalen-1-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 22a)
1-((S)-4-((6R,7R)-7-(3-hydroxynaphthalen-1-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 22b)
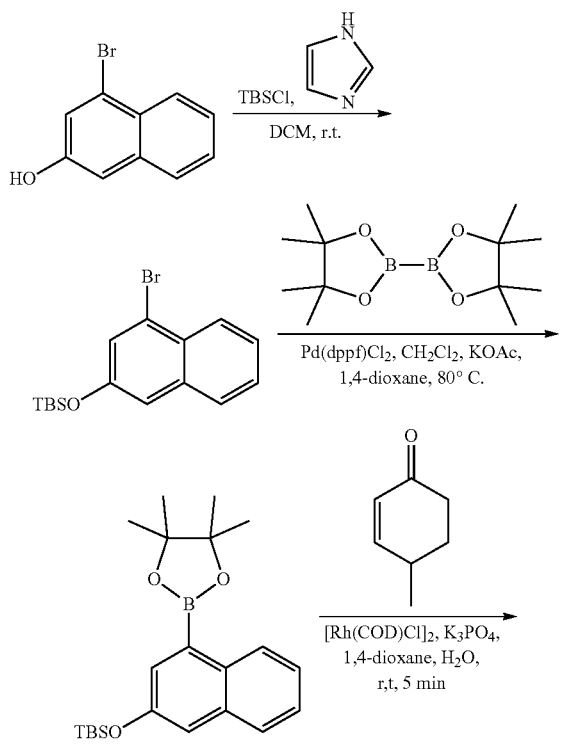
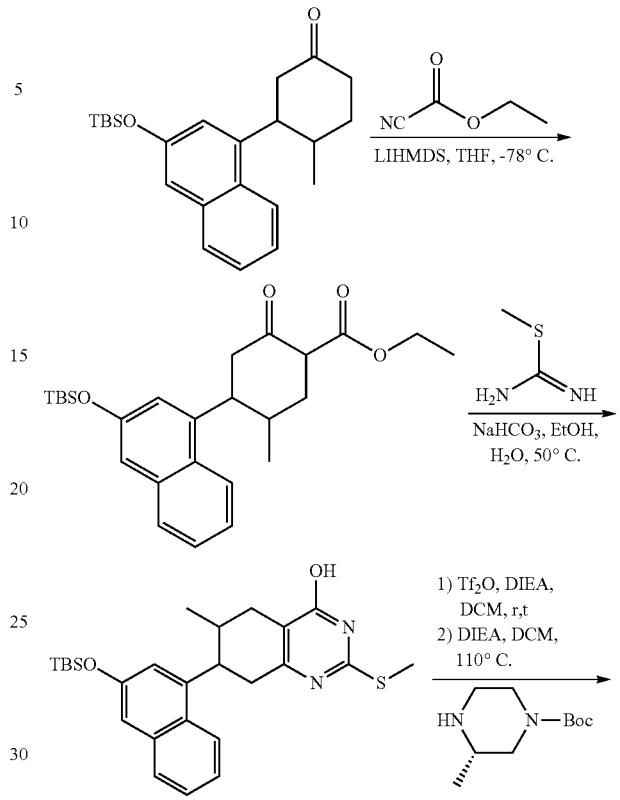
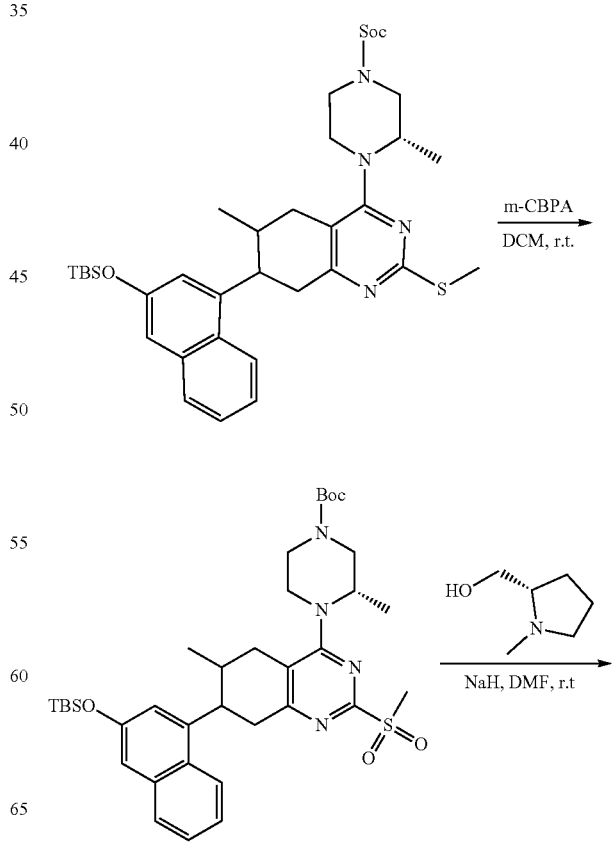

405

-continued

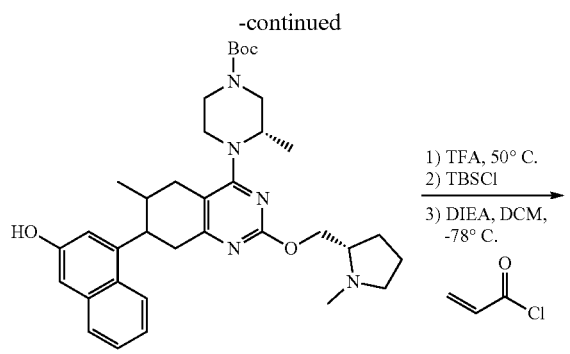

1) TFA, 50° C.
2) TBSCl
3) DIEA, DCM, -78° C.

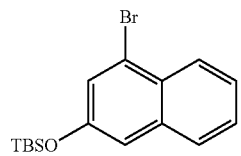 [SMILES: CC(C)(C)[Si](C)(C)Oc1cc(Br)c2ccccc2c1]

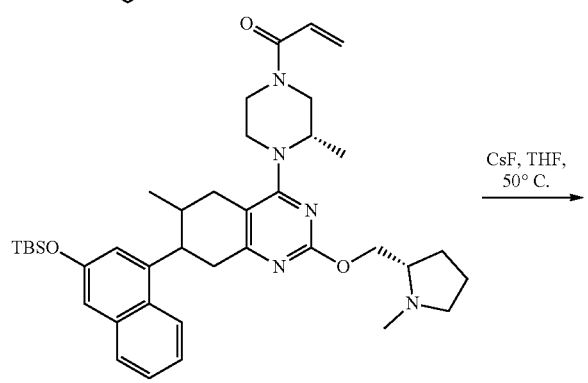

CsF, THF, 50° C.

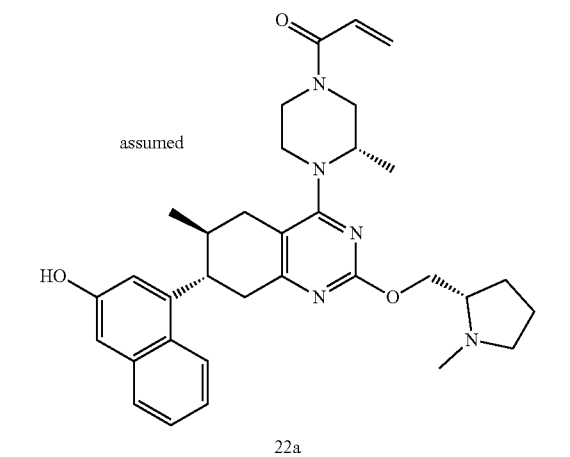

22a

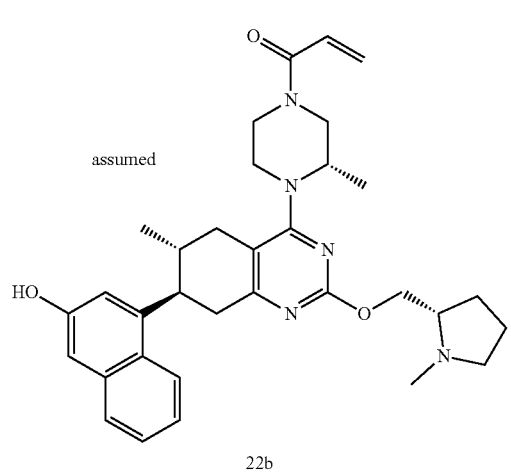

22b

406

Step 1:
(4-bromo-2-naphthyl)oxy-tert-butyl-dimethyl-silane

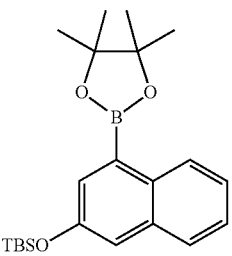 [SMILES: CC1(C)OB(c2cc(O[Si](C)(C)C(C)(C)C)cc3ccccc23)OC1(C)C]

A solution of 4-bromonaphthalen-2-ol (35.00 g, 156.90 mmol), tert-Butyldimethylsilyl chloride (35.47 g, 235.35 mmol) and imidazole (32.04 g, 470.7 mmol) in dichloromethane (200 mL) was stirred at 25° C. for 1 hour. After completion, the solvent was diluted with dichloromethane and washed with water, dried over anhydrous sodium sulfate and concentrated under vacuum. The residue was purified by flash chromatography on silica gel eluting with petroleum ether/ethyl acetate (20/1) to afford (4-bromo-2-naphthyl)oxy-tert-butyl-dimethyl-silane (48.00 g, 142.29 mmol, 90.7% yield) as a yellow oil.

Step 2: tert-butyl-dimethyl-[[4-(4,4,5,5-tetramethyl-1,3,2-dioxaborolan-2-yl)-2-naphthyl]oxy]silane Under nitrogen, a solution of (4-bromo-2-naphthyl)oxy-tert-butyl-dimethyl-silane (48.00 g, 142.29 mmol), bis(pinacolato)diboron (108.40 g, 426.88 mmol), Pd(dppf)Cl$_2$·CH$_2$Cl$_2$ (11.76 g, 14.23 mmol) and potassium acetate (41.80 g, 426.88 mmol) in 1,4-dioxane (200 mL) was stirred for 3 hours at 80° C. After completion, the reaction mixture was concentrated under vacuum. The reaction mixture was diluted with dichloromethane and washed by water. The organic layer was dried over anhydrous sodium sulfate and concentrated under vacuum. The residue was purified by flash chromatography on silica gel eluting with petrol ether/ethyl acetate (3/1) to afford tert-butyl-dimethyl-[[4-(4,4,5,5-tetramethyl-1,3,2-dioxaborolan-2-yl)-2-naphthyl]oxy]silane (50.00 g, 130.08 mmol, 91.4% yield) as a white solid. LCMS (ESI, m/z): 385.2 [M+H]$^+$.

Step 3: 3-[3-[tert-butyl(dimethyl)silyl]oxy-1-naphthyl]-4-methyl-cyclohexanone

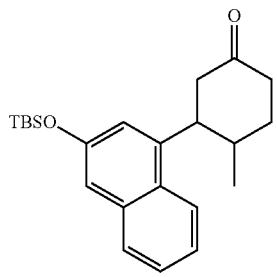

Under nitrogen, a solution of 4-methylcyclohex-2-en-1-one (12.90 g, 117.07 mmol), tert-butyl-dimethyl-[[4-(4,4,5,5-tetramethyl-1,3,2-dioxaborolan-2-yl)-2-naphthyl]oxy]silane (30.00 g, 78.05 mmol), chloro(1,5-cyclooctadiene)rhodium(I) dimer (3.86 g, 7.80 mmol), (+/−)-2,2'-bis(diphenylphosphino)-1,1'-binaphthyl (9.72 g, 15.61 mmol) in 1,4-dioxane (50 mL) was added aqueous saturated potassium phosphate (10 mL) and stirred at room temperature for 5 minutes. After completion, the reaction mixture was concentrated under vacuum. The reaction mixture was diluted with dichloromethane and washed by water. The organic layer was dried over anhydrous sodium sulfate and concentrated under vacuum. The residue was purified by flash chromatography on silica gel eluting with petrol ether/ethyl acetate (3/1) to afford 3-[3-[tert-butyl(dimethyl)silyl]oxy-1-naphthyl]-4-methyl-cyclohexanone (16.00 g, 43.41 mmol, 55.6% yield) as a yellow solid. LCMS (ESI, m/z): 369.2 [M+H]$^+$.

Step 4: ethyl 4-[3-[tert-butyl(dimethyl)silyl]oxy-1-naphthyl]-5-methyl-2-oxo-cyclohexanecarboxylate

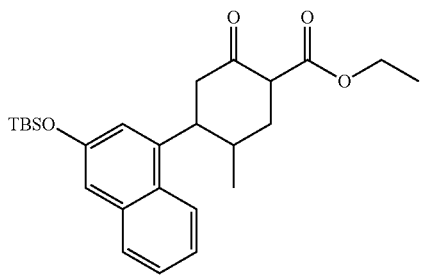

Under nitrogen, a solution of 3-[3-[tert-butyl(dimethyl)silyl]oxy-1-naphthyl]-4-methyl-cyclohexanone (17.00 g, 46.12 mmol) in tetrahydrofuran (200 mL) was dropwise added lithium bis(trimethylsilyl)amide (92.2 mL, 92.25 mmol, 1.0 M in THF) and stirred for 1 hour at −78° C. Then ethyl cyanoformate (10.51 g, 106.08 mmol) was added and stirred at −78° C. for 0.5 hours. After completion, the reaction was quenched with aqueous saturated ammonium chloride. The reaction mixture was diluted with dichloromethane, washed with water. The organic layer was dried over anhydrous sodium sulfate and concentrated under vacuum to afford crude product ethyl 4-[3-[tert-butyl(dimethyl)silyl]oxy-1-naphthyl]-5-methyl-2-oxo-cyclohexanecarboxylate (20.00 g, crude) as a yellow solid. LCMS (ESI, m/z): 441.2 [M+H]$^+$.

Step 5: 7-[3-[tert-butyl(dimethyl)silyl]oxy-1-naphthyl]-6-methyl-2-methylsulfanyl-5,6,7,8-tetrahydroquinazolin-4-ol

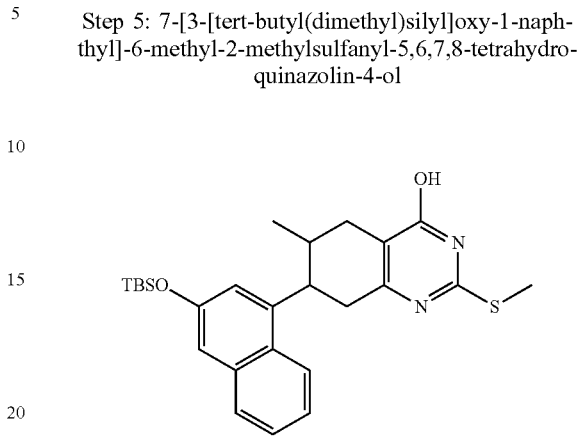

A solution of ethyl 4-[3-[tert-butyl(dimethyl)silyl]oxy-1-naphthyl]-5-methyl-2-oxo-cyclohexanecarboxylate (20.00 crude), 2-methylisothiourea (122.75 g, 1361.6 mmol) and sodium bicarbonate (144.70 g, 1702 mmol) in ethanol (200 mL) and water (40 mL) was stirred at 50° C. for 12 hours. After completion, the reaction mixture was concentrated under vacuum and diluted with dichloromethane, washed with water. The organic layer was dried over anhydrous sodium sulfate and concentrated under vacuum. The residue was purified by flash chromatography on silica gel eluting with dichloromethane/ethyl acetate (1/1) to afford to 7-[3-[tert-butyl(dimethyl)silyl]oxy-1-naphthyl]-6-methyl-2-methylsulfanyl-5,6,7,8-tetrahydroquinazolin-4-ol (10.30 g, 22.07 mmol) as a white solid. LCMS (ESI, m/z): 467.2 [M+H]$^+$.

Step 6: tert-butyl (3S)-4-[7-[3-[tert-butyl(dimethyl)silyl]oxy-1-naphthyl]-6-methyl-2-methylsulfanyl-5,6,7,8-tetrahydroquinazolin-4-yl]-3-methyl-piperazine-1-carboxylate

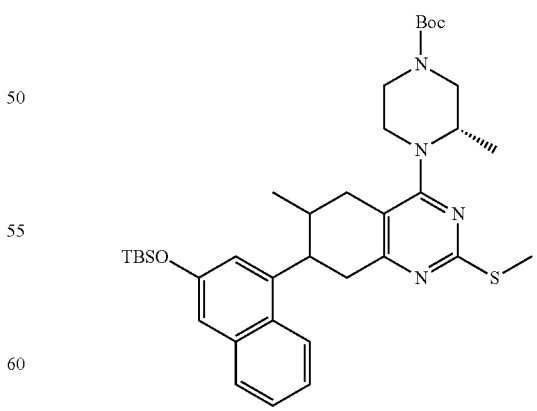

A solution of 7-[3-[tert-butyl(dimethyl)silyl]oxy-1-naphthyl]-6-methyl-2-methylsulfanyl-5,6,7,8-tetrahydroquinazolin-4-ol (2.00 g, 4.29 mmol) and N,N-diisopropylethylamine (3.73 mL, 21.43 mmol) in DCM (10 mL) was added trifluoromethanesulfonic anhydride (1.3 mL, 7.71 mmol) and stirred at r.t. for 1 hour. After completion, the solvent was concentrated under vacuum. The residue was diluted with dichloromethane (10 mL), and adjusted to pH>7 with DIEA. Then tert-butyl (3S)-3-methyl-1-piperazinecarboxylate (2.57 g, 12.86 mmol) was added and stirred at 110° C. for 12 hours. After completion, the solvent was concentrated under vacuum. The residue was purified by flash chromatography on silica gel eluting with petrol ether/ethyl acetate (3/1) to afford tert-butyl (3S)-4-[7-[3-[tert-butyl(dimethyl)silyl]oxy-1-naphthyl]-6-methyl-2-methylsulfanyl-5,6,7,8-tetrahydroquinazolin-4-yl]-3-methyl-piperazine-1-carboxylate (1.80 g, 2.77 mmol, 64.7% yield) as a yellow solid. LCMS (ESI, m/z): 649.4 [M+H]$^+$.

Step 7: tert-butyl(3S)-4-[7-[3-[tert-butyl(dimethyl)silyl]oxy-1-naphthyl]-6-methyl-2-methylsulfonyl-5,6,7,8-tetrahydroquinazolin-4-yl]-3-methyl-piperazine-1-carboxylate Step 8: tert-butyl (3S)-4-[7-(3-hydroxy-1-naphthyl)-6-methyl-2-[[(2S)-1-methylpyrrolidin-2-yl]methoxy]-5,6,7,8-tetrahydroquinazolin-4-yl]-3-methyl-piperazine-1-carboxylate

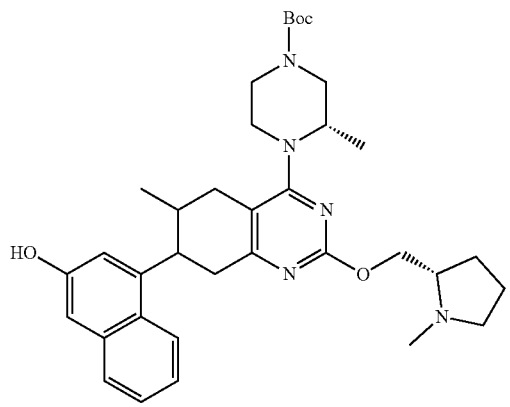

A solution of N-methyl-L-prolinol (1.83 g, 15.93 mmol) and sodium hydride (0.64 g, 15.93 mmol, 60% dispersion in mineral oil) in N,N-dimethylformamide (10 mL) was stirred at 25° C. for 10 minutes. Then the crude product tert-butyl (3S)-4-[7-[3-[tert-butyl(dimethyl)silyl]oxy-1-naphthyl]-6-methyl-2-methylsul-fonyl-5,6,7,8-tetrahydroquinazolin-4-yl]-3-methyl-piperazine-1-carboxylate (3.5 g, crude) was added and stirred at 25° C. for 6 hours. After completion, the reaction was quenched by aqueous saturated ammonium chloride. The resulting solution was extracted with dichloromethane and the organic layers were combined. The organic layer was washed with water, dried over anhydrous sodium sulfate and concentrated under vacuum. The residue was purified by flash chromatography on silica gel eluting with dichloromethane/methanol (20/1) to afford tert-butyl (3S)-4-[7-(3-hydroxy-1-naphthyl)-6-methyl-2-[[(2S)-1-methylpyrrolidin-2-yl]methoxy]-5,6,7,8-tetrahydroquinazolin-4-yl]-3-methyl-piperazine-1-carboxylate (1.20 g, 1.99 mmol, 62.6% yield) as a yellow solid. LCMS (ESI, m/z): 602.3 [M+H]$^+$.

Step 9: 1-((S)-4-(7-(3-(tert-butyldimethylsilyloxy)naphthalen-1-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one

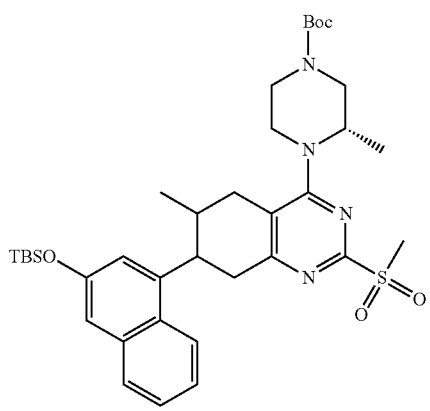 [SMILES: CC1Cc2c(nc(S(C)(=O)=O)nc2N2CCN(C(=O)OC(C)(C)C)C[C@@H]2C)CC1c1cc(O[Si](C)(C)C(C)(C)C)cc2ccccc12]

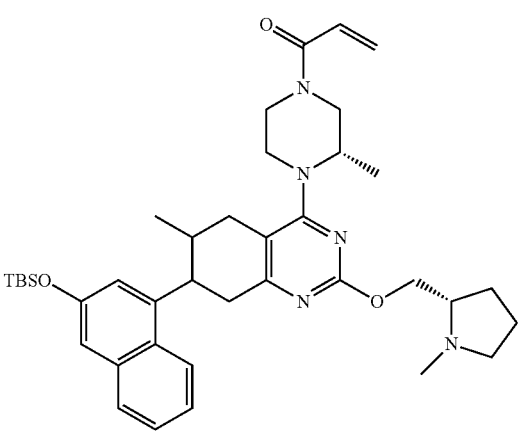 [SMILES: C=CC(=O)N1CCN(c2nc(OC[C@@H]3CCCN3C)nc3c2CC(C)C(c2cc(O[Si](C)(C)C(C)(C)C)cc4ccccc24)C3)[C@@H](C)C1]

A solution of tert-butyl (3S)-4-[7-[3-[tert-butyl(dimethyl)silyl]oxy-1-naphthyl]-6-methyl-2-methylsulfanyl-5,6,7,8-tetrahydroquinazolin-4-yl]-3-methyl-piperazine-1-carboxylate (2.70 g, 4.16 mmol) and 3-chloroperoxybenzoic acid (2.15 g, 12.48 mmol) in dichloromethane (10 mL) was stirred at 25° C. for 1 hour. After completion, the reaction was quenched by aqueous saturated Na$_2$SO$_3$. The reaction mixture was diluted with dichloromethane and washed by water. The organic layer was dried over anhydrous sodium sulfate and concentrated under vacuum to afford the crude tert-butyl(3S)-4-[7-[3-[tert-butyl(dimethyl)silyl]oxy-1-naphthyl]-6-methyl-2-methylsulfonyl-5,6,7,8-tetrahydroquinazolin-4-yl]-3-methyl-piperazine-1-carboxylate (3.50 g, crude) which would be directly used in the next step without purification.

A solution of tert-butyl (3S)-4-[7-(3-hydroxy-1-naphthyl)-6-methyl-2-[[(2S)-1-methyl-pyrrolidin-2-yl]methoxy]-5,6,7,8-tetrahydroquinazolin-4-yl]-3-methyl-piperazine-1-carboxylate (0.7 g, 1.16 mmol) in dichloromethane (5 mL) and trifluoroacetic acid (1 mL) was stirred at 50° C. for 0.5 hour. After completion, the solvent was concentrated under vacuum. A solution of the crude in dichloromethane (5 mL) was adjusted to pH>7 with N,N-diisopropylethylamine. Then imidazole (0.24 g, 3.49 mmol) and tert-Butyldimethylsilyl chloride (0.88 g, 5.82 mmol) was added and stirred at 25° C. for 1 hour. After completion, the solvent was concentrated under vacuum. The residue was purified by flash chromatography on reverse-phase eluting with methanol/H₂O (100/0) to afford the crude tert-butyl-dimethyl-[[4-[6-methyl-4-[(2S)-2-methylpiperazin-1-yl]-2-[[(2S)-1-methylpyrrolidin-2-yl]methoxy]-5,6,7,8-tetrahydroquinazolin-7-yl]-2-naphthyl]oxy]silane (790 mg, crude). A solution of the crude tert-butyl-[[4-[6-methyl-4-[(2S)-2-methylpiperazin-1-yl]-2-[[(2S)-1-methylpyrrolidin-2-yl]methoxy]-5,6,7,8-tetrahydroquinazolin-7-yl]-2-naphthyl]oxy]silane (790 mg, crude) in dichloromethane (5 mL) was adjusted to pH>7 with N,N-diisopropylethylamine. Then acrylyl chloride (0.10 g, 1.15 mmol) was added and stirred at −78° C. for 20 min. After completion, the reaction was quenched by water. The reaction mixture was diluted with dichloromethane and washed by water. The organic layer was dried over anhydrous sodium sulfate and concentrated under vacuum. The residue was purified by flash chromatography on silica gel eluting with dichloromethane/methanol (5/1) to afford 1-((S)-4-(7-(3-(tert-butyldimethylsilyloxy)naphthalen-1-yl)-6-methyl-2-(((S)-1-methylpyr-rolidin-2-yl)methoxy)-5,6,7,8-tetrahydroquinazolin-4-yl)-3-methylpiperazin-1-yl)prop-2-en-1-one (560.0 mg, 0.84 mmol, 65.2% yield) as a yellow solid. LCMS (ESI, m/z): 670.4 [M+H]⁺.

Step 10: 1-((S)-4-((6S,7S)-7-(3-hydroxynaphthalen-1-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 22a); 1-((S)-4-((6R,7R)-7-(3-hydroxynaphthalen-1-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 22b)

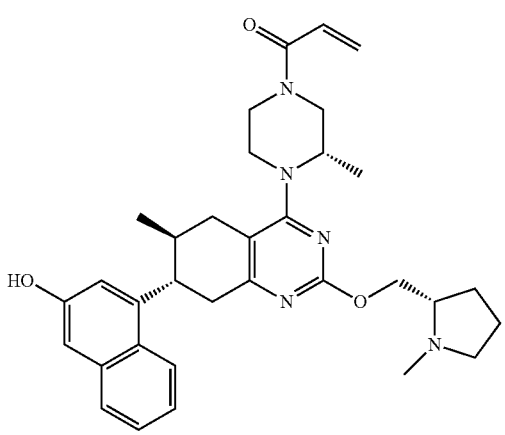

22a

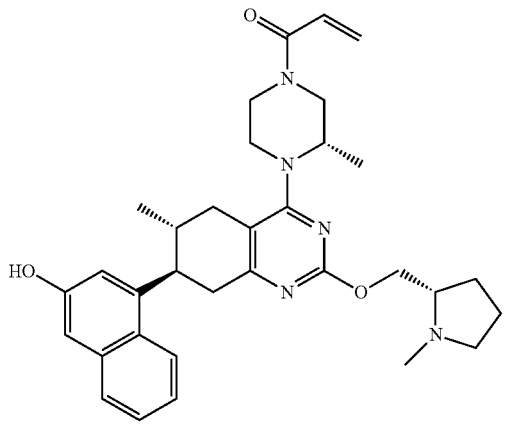

22b

A solution of 1-((S)-4-(7-(3-(tert-butyldimethylsilyloxy)naphthalen-1-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (0.50 g, 0.75 mmol) and CsF (0.34 g, 2.24 mmol) in tetrahydrofuran (5 mL) was stirred at 50° C. for 1 hour. After completion, the solvent was concentrated under vacuum. Then the crude product was purified by Prep-HPLC with the following conditions: XBridge Prep OBD C18 Column, 30×150 mm 5 um; Mobile Phase A:Water (10 MMOL/L NH4HCO3), Mobile Phase B: ACN; Flow rate: 60 ml/min; Gradient: 30 B to 60 B in 7 min; 254 nm; RT1:6.45; RT2; Injection Volumn: ml; Number Of Runs; The mixture of diasteroisomer was separated by Prep-Chiral-HPLC with the following condition: Column: CHIRALPAK ID-03, 2.0 cm I.D*25 cm L (5 um); Mobile Phase A: MTBE (10 mM NH3-MEOH)—HPLC, Mobile Phase B: EtOH—HPLC; Flow rate: 38 mL/min; Gradient: 10 B to 10 B in 28 min; 220/254 nm; RT1:9.157; RT2: 20.703; Injection Volumn: 3 ml; Number Of Runs: 3 to afford the title compounds. The absolute configuration of the title compounds was inferred from potency data and a protein X-ray structure of compound 21b.

Example 22a: 1-((S)-4-((6S,7S)-7-(3-hydroxynaphthalen-1-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (89.9 mg, 0.16 mmol, 21.7% yield, white solid). ¹H NMR (400 MHz, DMSO-$d_6$) δ 9.63 (s, 1H), 8.14 (d, J=8.7 Hz, 1H), 7.70 (d, J=8.2 Hz, 1H), 7.39 (t, J=7.5 Hz, 1H), 7.28 (t, J=7.7 Hz, 1H), 7.14 (s, 2H), 6.93-6.78 (m, 1H), 6.18 (d, J=15.8 Hz, 1H), 5.73 (dd, J=10.6, 2.2 Hz, 1H), 4.40-4.02 (m, 5H), 3.98-3.61 (m, 2H), 3.56-3.45 (m, 1H), 3.40-3.33 (m, 1H), 3.28-3.20 (m, 1H), 3.11-2.90 (m, 3H), 2.89-2.74 (m, 1H), 2.69-2.60 (m, 2H), 2.33 (s, 3H), 2.23-2.00 (m, 2H), 1.99-1.84 (m, 1H), 1.78-1.51 (m, 3H), 1.05 (d, J=8.4 Hz, 3H), 0.78 (d, J=6.4 Hz, 3H). LCMS (ESI, m/z): 556.3 [M+H]⁺. Chiral HPLC: CHIRALPAK ID-3 (0.46*5 cm; 3 um); detected at 254 nm; MtBE(0.1% DEA): EtOH=90:10; flow=1.0 ml/min; Retention time: 2.793 min (slower peak).

Example 22b: 1-((S)-4-((6R,7R)-7-(3-hydroxynaphthalen-1-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (83.0 mg, 0.15 mmol, 20% yield, white solid). ¹H NMR (400 MHz, DMSO-$d_6$) δ 9.64 (s, 1H), 8.10 (d, J=8.6 Hz, 1H), 7.70 (d, J=8.2 Hz, 1H), 7.38 (t, J=7.5 Hz, 1H), 7.28 (t, J=7.7 Hz, 1H), 7.09-6.98 (m, 2H), 6.97-6.72 (m, 1H), 6.22-6.11 (m, 1H), 5.72 (dd, J=10.4, 2.4

Hz, 1H), 4.45-3.99 (m, 5H), 3.92-3.81 (m, 1H), 3.78-3.63 (m, 1H), 3.52-3.36 (m, 1H), 3.25-2.92 (m, 4H), 2.88-2.70 (m, 1H), 2.65-2.57 (m, 1H), 2.33 (s, 3H), 2.24-2.01 (m, 2H), 2.00-1.85 (m, 1H), 1.77-1.51 (m, 3H), 1.41 (s, 1H), 1.30-1.14 (m, 3H), 1.13-1.08 (m, 1H), 0.82 (d, J=6.4 Hz, 3H). LCMS (ESI, m/z): 556.3 [M+H]$^+$. Chiral HPLC: CHIRAL-PAK ID-3 (0.46*5 cm; 3 um); detected at 254 nm; MtBE (0.1% DEA): EtOH=90:10; flow=1.0 ml/min; Retention time: 1.387 min (faster peak).

Examples 23a and 23b 1-((S)-4-((6S,7S)-7-(3-amino-2-fluoro-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 23a)

1-((S)-4-((6R,7R)-7-(3-amino-2-fluoro-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 23b)

Example 23a

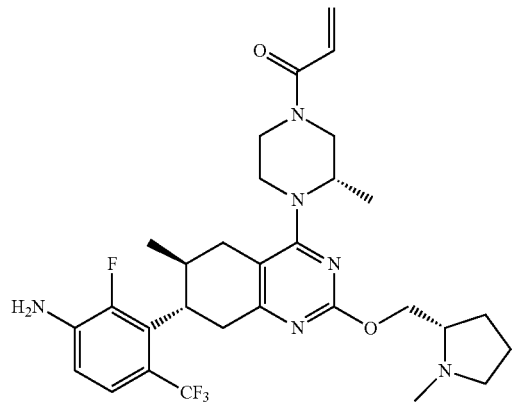

Example 23b

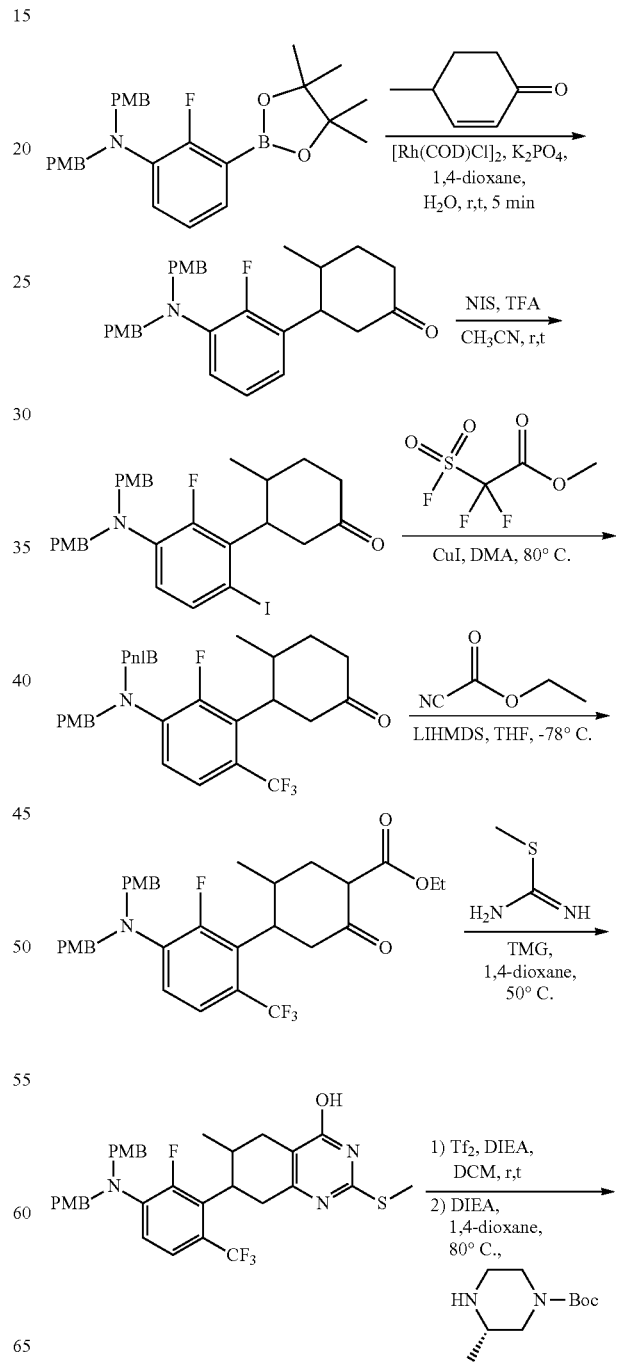

415
-continued

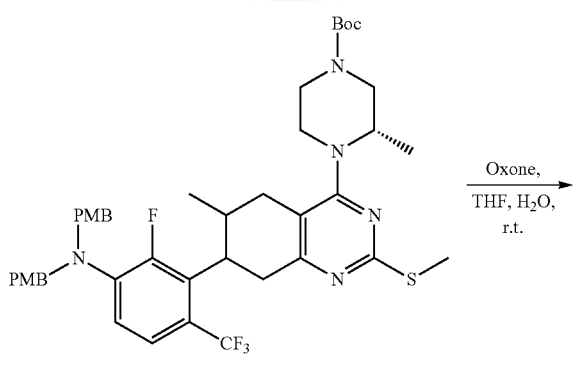

Oxone,
THF, H₂O,
r.t.

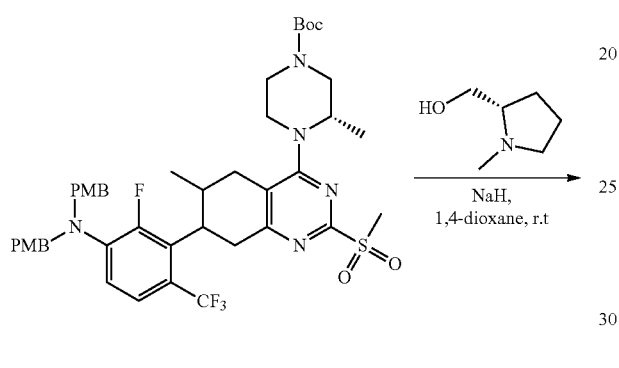

NaH,
1,4-dioxane, r.t

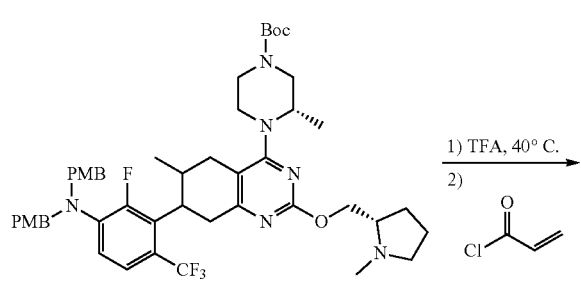

1) TFA, 40° C.
2)

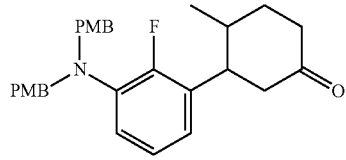

23a

416
-continued

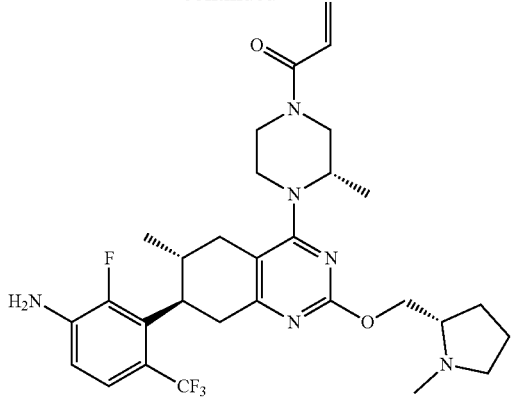

23b

Step 1: 3-[3-[bis[(4-methoxyphenyl)methyl]amino]-
2-fluoro-phenyl]-4-methyl-cyclohexanone

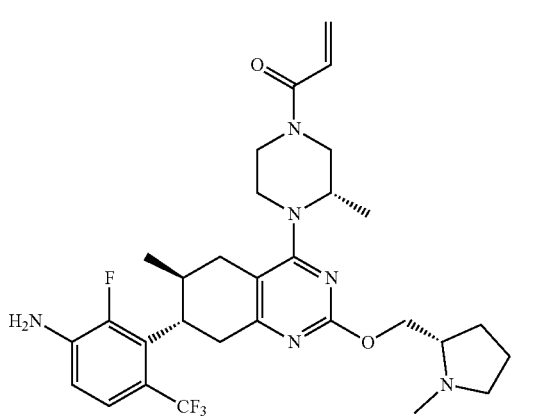

Under nitrogen, a solution of 2-fluoro-N,N-bis[(4-methoxyphenyl)methyl]-3-(4,4,5,5-tetramethyl-1,3,2-dioxaborolan-2-yl)aniline (13.00 g, 27.23 mmol), 4-methyl-cyclohex-2-en-1-one (4.50 g, 40.85 mmol) and chloro(1,5-cyclooctadiene)rhodium(I) dimer (1.35 g, 2.72 mmol) in 1,4-dioxane (50 mL) was added aqueous saturated potassium phosphate (10 mL) and stirred for 5 minutes at 50° C. After completion, the reaction mixture was concentrated under vacuum. The reaction mixture was diluted with dichloromethane and washed with water. The organic layer was dried over anhydrous sodium sulfate and concentrated under vacuum. The residue was purified by flash chromatography on silica gel eluting with petrol ether/ethyl acetate (3/1) to afford 3-[3-[bis[(4-methoxyphenyl)methyl]amino]-2-fluoro-phenyl]-4-methyl-cyclohexanone (5.20 g, 11.27 mmol, 41.4% yield) as a yellow solid. LCMS (ESI, m/z): 462.2 [M+H]⁺.

Step 2: 3-[3-[bis[(4-methoxyphenyl)methyl]amino]-
2-fluoro-6-iodo-phenyl]-4-methyl-cyclohexanone

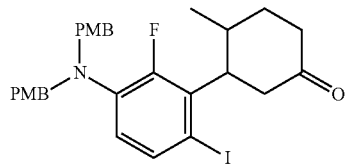

A solution of 3-[3-[bis[(4-methoxyphenyl)methyl] amino]-2-fluoro-phenyl]-4-methyl-cyclohexanone (9.00 g, 19.5 mmol) and N-iodosuccinimide (5.70 g, 25.35 mmol) in acetonitrile (10 mL) was added trifluoroacetic acid (0.15 mL, 1.95 mmol) and stirred at 25° C. for 15 minutes. After completion, the solvent was concentrated under vacuum. The residue was purified by flash chromatography on silica gel eluting with petrol ether/ethyl acetate (3/1) to afford 3-[3-[bis[(4-methoxyphenyl)methyl]amino]-2-fluoro-6-iodo-phenyl]-4-methyl-cyclohexanone (6.20 g, 5.80 mmol, 29.8% yield) as a yellow solid. LCMS (ESI, m/z): 588.1 [M+H]$^+$.

Step 3: 3-[3-[bis[(4-methoxy-phenyl)methyl]amino]-2-fluoro-6-(trifluoromethyl)phenyl]-4-methyl-cyclohexanone

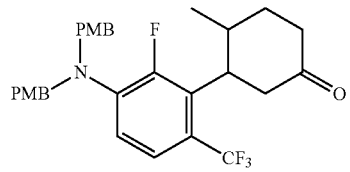

Under nitrogen, a solution of methyl 2,2-difluoro-2-(fluorosulfonyl)acetate (5.63 g, 29.32 mmol) and cuprous iodide (3.35 g, 17.59 mmol) in DMF (10 mL) was added 3-[3-[bis[(4-methoxyphenyl)methyl]amino]-2-fluoro-6-iodo-phenyl]-4-methyl-cyclohexanone (6.50 g, 5.86 mmol) at 80° C. for 2 hours. After completion, the reaction mixture was added water, extracted with dichloromethane and the organic layers were combined. The organic layers was washed with water, dried over anhydrous sodium sulfate and concentrated under vacuum. The residue was purified by flash chromatography on silica gel eluting with petroleum ether/ethyl acetate (3/1) to afford 3-[3-[bis[(4-methoxy-phenyl)methyl]amino]-2-fluoro-6-(trifluoromethyl)phenyl]-4-methyl-cyclohexanone (3.00 g, 5.67 mmol, 96.6% yield) as a yellow solid. LCMS (ESI, m/z): 530.2 [M+H]$^+$.

Step 4: ethyl 4-[3-[bis[(4-methoxyphenyl)methyl]-amino]-2-fluoro-6-(trifluoromethyl)phenyl]-5-methyl-2-oxo-cyclohexanecarboxylate

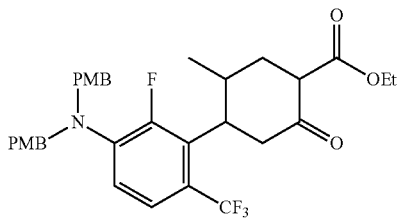

Under nitrogen, a solution of 3-[3-[bis[(4-methoxyphenyl)methyl]amino]-2-fluoro-6-(trifluoromethyl)phenyl]-4-methyl-cyclohexanone (3.30 g, 6.23 mmol) in tetrahydrofuran (100 mL) was dropwise added lithium bis(trimethylsilyl)amide (12.46 ml, 12.46 mmol, 1M in THF) was dropwised and stirred for 1 hour at −78° C. Then ethyl cyanoformate (1.42 g, 14.33 mmol) was dropwise added and stirred at −78° C. for 0.5 hours. After completion, the reaction was quenched with aqueous saturated ammonium chloride. The reaction mixture was diluted with dichloromethane, washed with water. The organic layer was dried over anhydrous sodium sulfate and concentrated under vacuum to afford the crude product ethyl 4-[3-[bis[(4-methoxyphenyl)methyl]-amino]-2-fluoro-6-(trifluoromethyl)phenyl]-5-methyl-2-oxo-cyclohexanecarboxylate (3.9 g, crude) as a yellow solid.

Step 5: 7-[3-[bis[(4-methoxyphenyl)methyl]amino]-2-fluoro-6-(trifluoromethyl)phenyl]-6-methyl-2-methylsulfanyl-5,6,7,8-tetrahydroquinazolin-4-ol

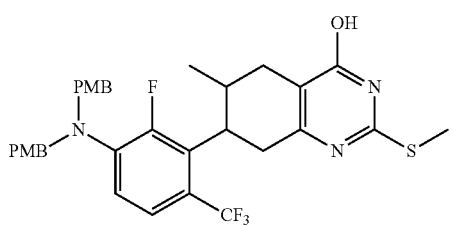

A solution of ethyl 4-[3-[bis[(4-methoxyphenyl)methyl]amino]-2-fluoro-6-(trifluoromethyl)phenyl]-5-methyl-2-oxo-cyclohexanecarboxylate (3.9 g, crude), 2-methylisothiourea (7.67 g, 85.2 mmol) and tetramethylguanidine (13.35 mL, 106.38 mmol) in 1,4-dioxane was stirred at 50° C. for 12 hours. After completion, the reaction mixture was concentrated under vacuum and diluted with dichloromethane, washed with water. The organic layer was dried over anhydrous sodium sulfate and concentrated under vacuum. The residue was purified by flash chromatography on silica gel eluting with dichloromethane/ethyl acetate (1/1) to afford to 7-[3-[bis[(4-methoxyphenyl)methyl]amino]-2-fluoro-6-(trifluoromethyl)phenyl]-6-methyl-2-methylsulfanyl-5,6,7,8-tetrahydroquinazolin-4-ol (0.90 g, 1.43 mmol, 33.7% yield) as a white solid. LCMS (ESI, m/z): 628.2 [M+H]$^+$.

Step 6: tert-butyl(3S)-4-[7-[3-[bis[(4-methoxyphenyl)methyl]-amino]-2-fluoro-6-(trifluoromethyl)phenyl]-6-methyl-2-methylsulfanyl-5,6,7,8-tetrahydroquinazolin-4-yl]-3-methyl-piperazine-1-carboxylate

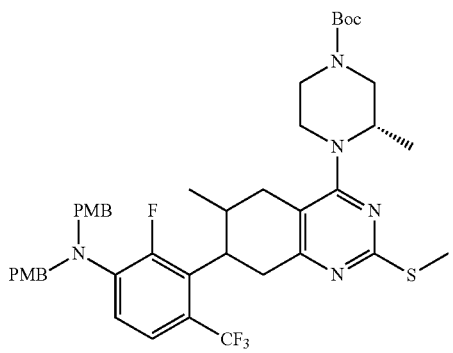

A solution of 7-[3-[bis[(4-methoxyphenyl)methyl]amino]-2-fluoro-6-(trifluoromethyl)-phenyl]-6-methyl-2-methylsulfanyl-5,6,7,8-tetrahydroquinazolin-4-ol (0.90 g, 1.43 mmol), trifluoromethanesulfonic anhydride (0.43 mL, 2.58 mmol) and N,N-diisopropylethylamine (1.25 mL, 7.17 mmol) in DCM (5 mL) was stirred at r.t. for 1 hour. After completion, the solvent was concentrated under vacuum. The reaction mixture was diluted with 1,4-dioxane, and adjusted to pH>7 with DIEA. Then tert-butyl (3S)-3-methyl-1-piperazinecarboxylate (0.86 g, 4.3 mmol) was added and stirred at 80° C. for 12 hours. After completion, the solvent was concentrated under vacuum. The residue was purified by flash chromatography on silica gel eluting with petroleum ether/ethyl acetate (3/1) to afford tert-butyl(3S)-4-[7-[3-[bis[(4-methoxyphenyl)methyl]-amino]-2-fluoro-6-(trifluoromethyl)phenyl]-6-methyl-2-methylsulfanyl-5,6,7,8-tetrahydroquinazolin-4-yl]-3-methyl-piperazine-1-carboxylate (0.86 g, 1.06 mmol, 74.1% yield) as a yellow solid. LCMS (ESI, m/z): 810.4 [M+H]$^+$.

Step 7: tert-butyl (3S)-4-[7-[3-[bis[(4-methoxyphenyl)methyl]amino]-2-fluoro-6-(trifluoromethyl)phenyl]-6-methyl-2-methylsulfonyl-5,6,7,8-tetrahydroquinazolin-4-yl]-3-methyl-piperazine-1-carboxylate Step 8: tert-butyl (3S)-4-[7-[3-[bis[(4-methoxyphenyl)methyl]amino]-2-fluoro-6-(trifluoromethyl)-phenyl]-6-methyl-2-[[(2S)-1-methylpyrrolidin-2-yl]methoxy]-5,6,7,8-tetrahydroquinazolin-4-yl]-3-methyl-piperazine-1-carboxylate

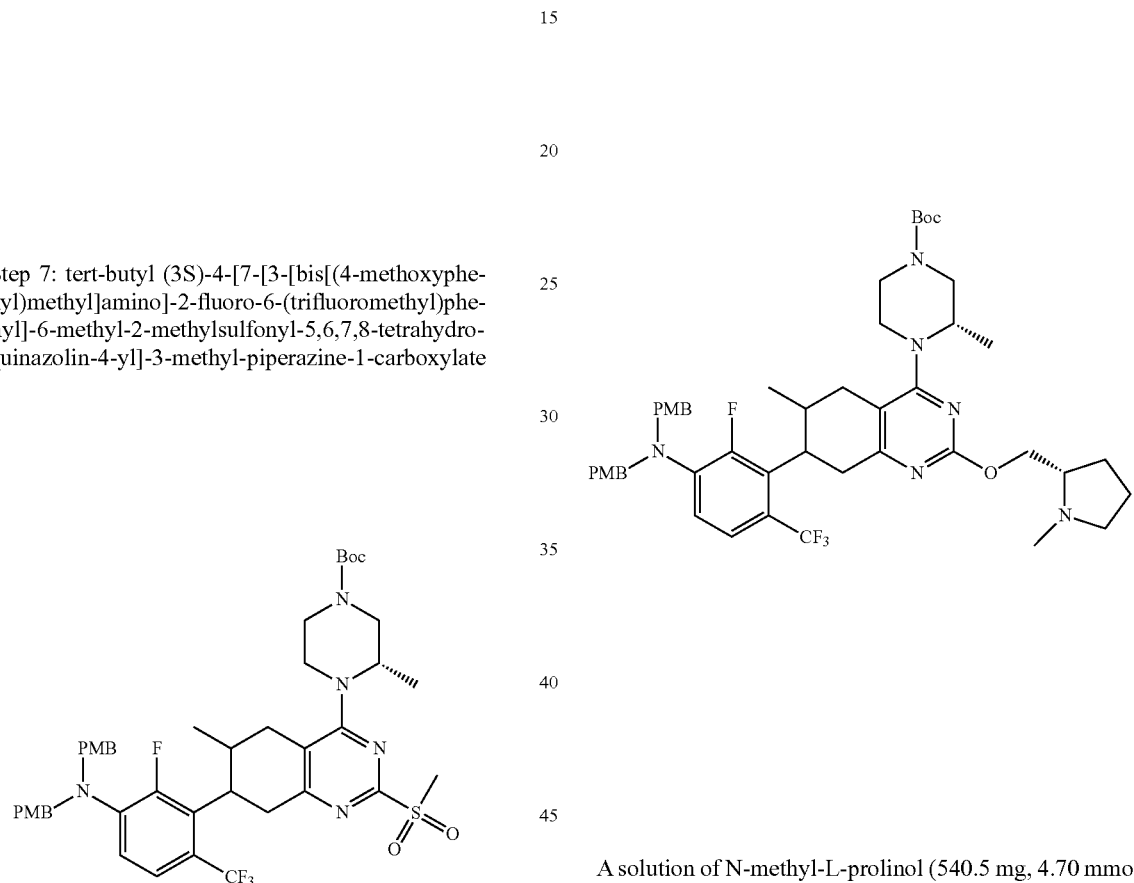

A solution of tert-butyl(3S)-4-[7-[3-[bis[(4-methoxyphenyl)methyl]amino]-2-fluoro-6-(trifluoro-methyl)phenyl]-6-methyl-2-methylsulfanyl-5,6,7,8-tetrahydroquinazolin-4-yl]-3-methyl-piperazine-1-carboxylate (0.80 g, 0.99 mmol) and oxone (0.5 g, 2.96 mmol) in THF (5 mL) was stirred at 25° C. for 1 hour. After completion, the reaction was quenched by aqueous saturated Na$_2$SO$_3$. The reaction mixture was diluted with dichloromethane, washed with water. The organic layer was dried over anhydrous sodium sulfate and concentrated under vacuum to afford the crude tert-butyl (3S)-4-[7-[3-[bis[(4-methoxyphenyl)methyl]amino]-2-fluoro-6-(trifluoromethyl)phenyl]-6-methyl-2-methylsulfonyl-5,6,7,8-tetrahydroquinazolin-4-yl]-3-methyl-piperazine-1-carboxylate (0.90 g, crude) which would be directly used in the next step without purification.

A solution of N-methyl-L-prolinol (540.5 mg, 4.70 mmol) and sodium hydride (0.19 g, 4.7 mmol, 60% dispersion in mineral oil) in 1,4-dioxane (4.5 mL) was stirred at 25° C. for 10 minutes. Then the crude product tert-butyl (3S)-4-[7-[3-[bis[(4-methoxyphenyl)methyl]amino]-2-fluoro-6-(trifluoromethy-1)phenyl]-6-methyl-2-methylsulfonyl-5,6,7,8-tetrahydroquinazolin-4-yl]-3-methyl-piperazine-1-carboxylate (0.90 g, crude) was added and stirred at 25° C. for 6 hours. After completion, the resulting solution was quenched by and extracted with dichloromethane. Then the organic layers were combined, washed with water, dried over anhydrous sodium sulfate and concentrated under vacuum. The residue was purified by flash chromatography on silica gel eluting with dichloromethane/methanol (20/1) to afford tert-butyl (3S)-4-[7-[3-[bis[(4-methoxyphenyl)methyl]amino]-2-fluoro-6-(trifluoromethyl)-phenyl]-6-methyl-2-[[(2S)-1-methylpyrrolidin-2-yl]methoxy]-5,6,7,8-tetrahydroquinazolin-4-yl]-3-methyl-piperazine-1-carboxylate (0.46 g, 0.52 mmol, 55.8% yield) as a yellow solid. LCMS (ESI, m/z): 877.5 [M+H]$^+$.

Step 9: 1-((S)-4-((6S,7S)-7-(3-amino-2-fluoro-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 23a); 1-((S)-4-((6R,7R)-7-(3-amino-2-fluoro-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 23b)

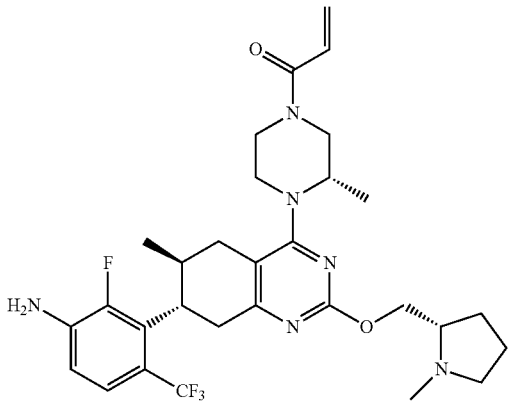

23a

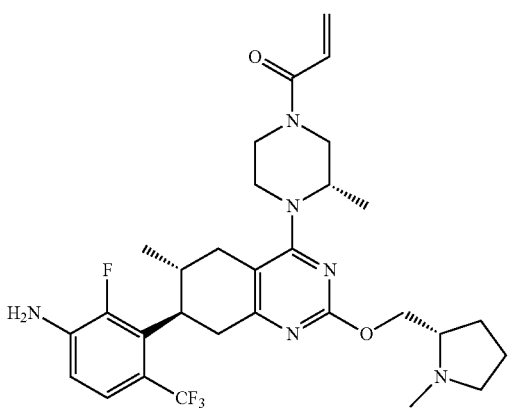

23b

A solution of tert-butyl (3S)-4-[7-[3-[bis[(4-methoxyphenyl)methyl]amino]-2-fluoro-6-(trifluoromethyl)phenyl]-6-methyl-2-[[(2S)-1-methylpyrrolidin-2-yl]methoxy]-5,6,7,8-tetrahydroquinazolin-4-yl]-3-methyl-piperazine-1-carboxylate (1.40 g, 1.60 mmol) in dichloromethane (5 mL) and trifluoroacetic acid (1.37 mL) was stirred at 40° C. for 0.5 hour. After completion, the solvent was concentrated under vacuum to afford 2-fluoro-3-[6-methyl-4-[(2S)-2-methylpiperazin-1-yl]-2-[[(2S)-1-methylpyrroli-din-2-yl]methoxy]-5,6,7,8-tetrahydroquinazolin-7-yl]-4-(trifluoromethyl)aniline (1.5 g, crude) as a yellow solid. A solution of the crude 2-fluoro-3-[6-methyl-4-[(2S)-2-methylpiperazin-1-yl]-2-[[(2S)-1-methylpyrrolidin-2-yl]methoxy]-5,6,7,8-tetrahydroquinazolin-7-yl]-4-(trifluoromethyl)aniline (1.50 g, crude) in dichloromethane (20 mL) was adjusted to pH>7 with DIEA. Then acrylyl chloride (0.21 g, 2.35 mmol) was dropwise added and stirred at 25° C. for 20 minutes. After completion, the solvent was concentrated under vacuum. Then the crude product was purified by Prep-HPLC with the following conditions: Column: XBridge Prep OBD C18 Column, 30×150 mm 5 um; Mobile Phase A:Water (10 MMOL/L NH4HCO3), Mobile Phase B: ACN; Flow rate: 60 mL/min; Gradient: 30 B to 48 B in 7 min; 254 nm; RT1:9.40; RT2; Injection Volumn: ml; Number Of Runs; The mixture of enantiomer was separated by Chiral-Prep-HPLC with the following conditions: Column: CHIRAL-PAK IE, 2*25 cm, 5 um; Mobile Phase A: Hex (8 mmol/L NH3·MeOH)—HPLC, Mobile Phase B: EtOH—HPLC; Flow rate: 17 m/min; Gradient: 50 B to 50 B in 16.5 min; 220/254 nm; RT1:10.132; RT2:12.679; Injection Volumn: 0.6 mL; Number Of Runs: 11 to afford the title compounds. The absolute configuration of the title compounds was inferred from potency data and a protein X-ray structure of compound 21b.

Example 23a: 1-((S)-4-((6S,7S)-7-(3-amino-2-fluoro-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (40.3 mg, 0.068 mmol, 2.6% yield, white solid). $^1$H NMR (300 MHz, DMSO-$d_6$, ppm) δ 7.22 (d, J=8.6 Hz, 1H), 6.90-6.72 (m, 2H), 6.14 (d, J=16.7 Hz, 1H), 5.87 (s, 2H), 5.72 (dd, J=10.4, 2.4 Hz, 1H), 4.38-3.98 (m, 5H), 3.94-3.55 (m, 1H), 3.52-3.41 (m, 2H), 3.29-3.18 (m, 1H), 3.10-2.80 (m, 5H), 2.67-2.58 (m, 1H), 2.45-2.07 (m, 6H), 1.98-1.82 (m, 1H), 1.72-1.49 (m, 3H), 0.97 (d, J=7.9 Hz, 3H), 0.82 (d, J=6.3 Hz, 3H). LCMS (ESI, m/z): 591.2 [M+H]$^+$. Chiral HPLC: CHIRAL-PAK IE-3 (4.6*50 mm 3 um); detected at 254 nm; Hex (0.1% DEA): EtOH=50:50; flow=1.0 ml/min; Retention time: 2.031 min (slower peak).

Example 23b: 1-((S)-4-((6R,7R)-7-(3-amino-2-fluoro-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (56.6 mg, 0.096 mmol, 3.7% yield, white solid). $^1$H NMR (300 MHz, DMSO-$d_6$) δ 7.23 (d, J=8.6 Hz, 1H), 6.93-6.70 (m, 2H), 6.14 (d, J=16.5 Hz, 1H), 5.88 (s, 2H), 5.73 (dd, J=10.4, 2.5 Hz, 1H), 4.44-3.79 (m, 6H), 3.55-3.40 (m, 1H), 3.31-3.23 (m, 1H), 3.22-2.78 (m, 6H), 2.60-2.56 (m, 1H), 2.45-2.05 (m, 6H), 2.00-1.82 (m, 1H), 1.72-1.48 (m, 3H), 1.25 (brs, 3H), 0.82 (d, J=6.4 Hz, 3H). LCMS (ESI, m/z): 591.2 [M+H]$^+$. Chiral HPLC: CHIRALPAK IE-3 (4.6*50 mm 3 um); detected at 254 nm; Hex (0.1% DEA): EtOH=50:50; flow=1.0 ml/min; Retention time: 1.564 min (faster peak).

Examples 24a and 24b

Example 24a

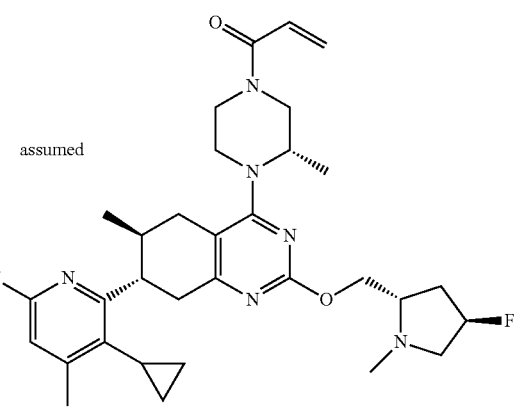

assumed

-continued
Example 24b
assumed
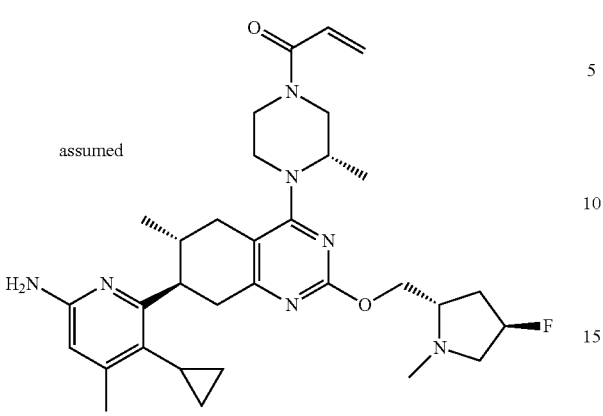
1-((S)-4-((6S,7S)-7-(6-amino-3-cyclopropyl-4-methylpyridin-2-yl)-2-(((2S,4R)-4-fluoro-1-methylpyrrolidin-2-yl)methoxy)-6-methyl-5,6,7,8-tetrahydroquinazolin-4-yl)-3-methylpiperazin-1-yl)prop-2-en-1-one (Example 24a)
1-((S)-4-((6R,7R)-7-(6-amino-3-cyclopropyl-4-methylpyridin-2-yl)-2-(((2S,4R)-4-fluoro-1-methylpyrrolidin-2-yl)methoxy)-6-methyl-5,6,7,8-tetrahydroquinazolin-4-yl)-3-methylpiperazin-1-yl)prop-2-en-1-one (Example 24b)
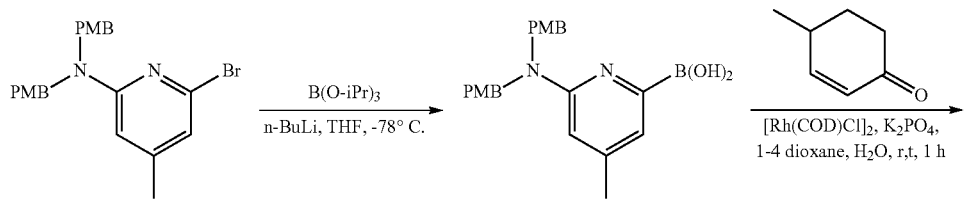
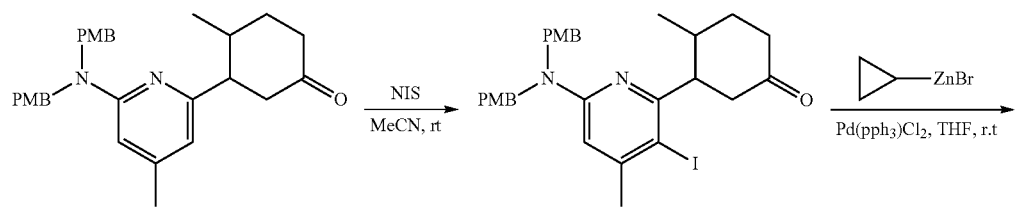
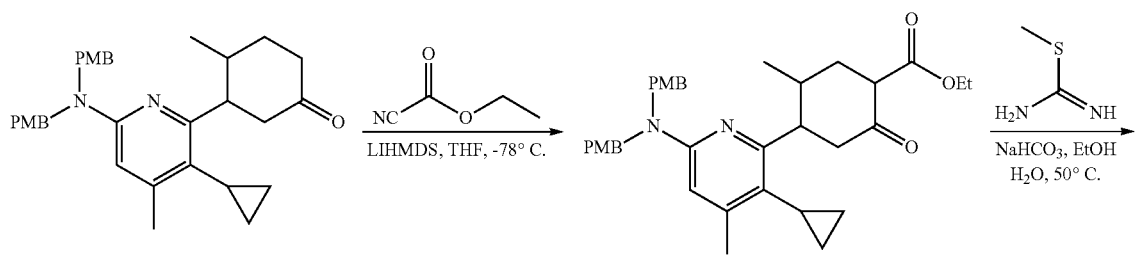
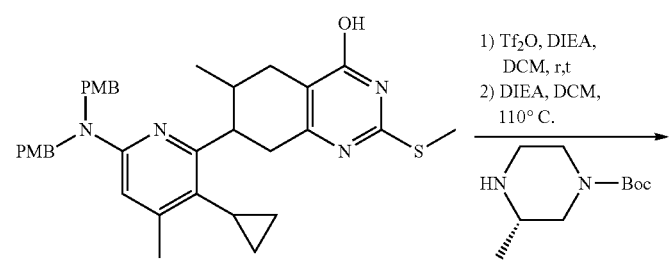

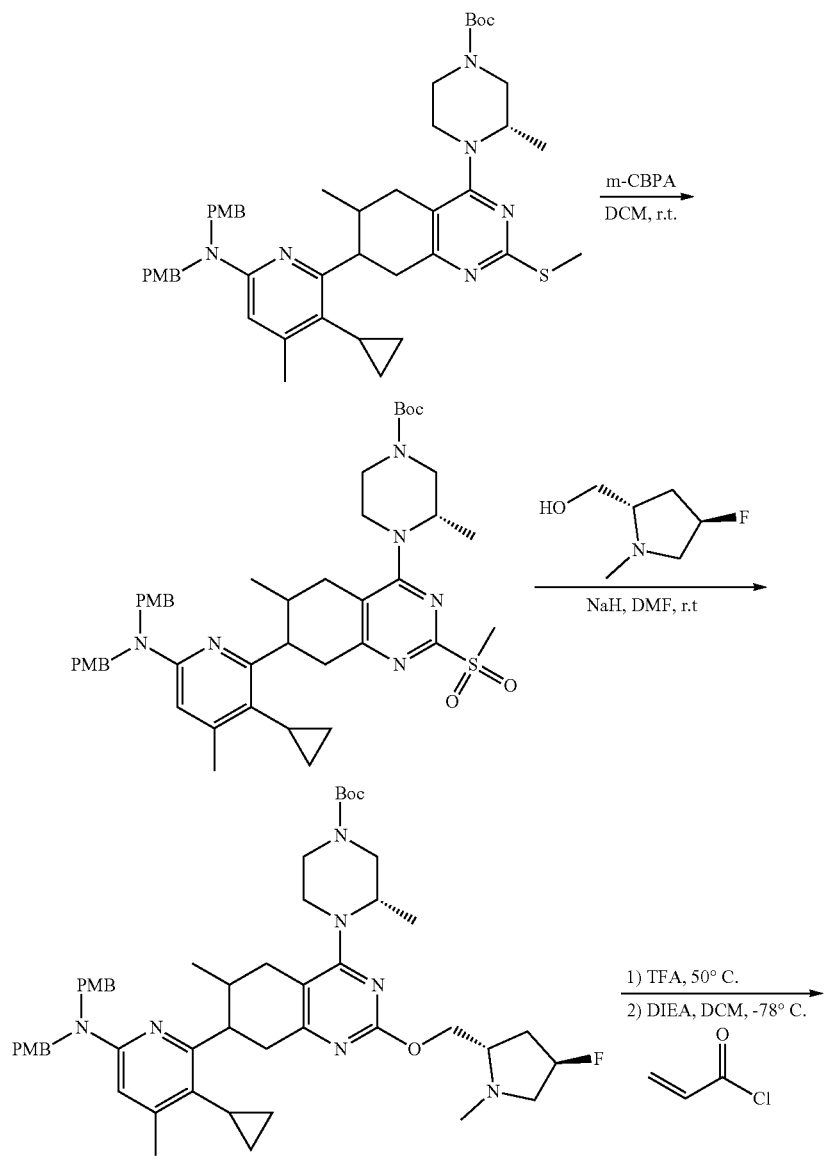
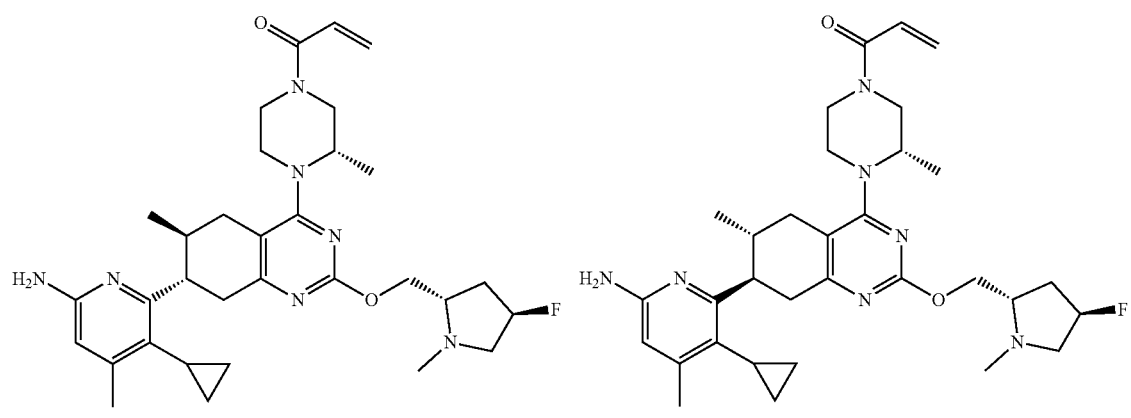
24a  24b

Step 1: (6-(bis(4-methoxybenzyl)amino)-4-methylpyridin-2-yl)boronic acid

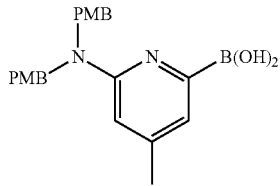

Under nitrogen, a solution of triisopropyl borate (44.01 g, 234.01 mmol) in tetrahydrofuran (200 mL) was stirred at −78° C. for 5 minutes. Then 6-bromo-N,N-bis[(4-methoxyphenyl)-methyl]-4-methyl-pyridin-2-amine (20.00 g, 46.8 mmol) was dropwise added and stirred at −78° C. for 30 minutes. Then n-butyllithium (2.5 M in Hexane) (28 mL, 70.2 mmol) was added and stirred at −78° C. for 20 minutes. After completion, the solvent was concentrated under vacuum to afford the crude (6-(bis(4-methoxybenzyl)amino)-4-methylpyridin-2-yl)boronic acid (60.0 g, crude) as yellow oil. LCMS (ESI, m/z): 393.2 [M+H]⁺.

Step 2: 3-(6-(bis(4-methoxybenzyl)amino)-4-methylpyridin-2-yl)-4-methylcyclohexan-1-one

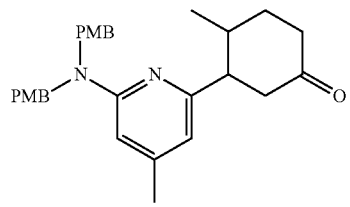

Under nitrogen, The crude (6-(bis(4-methoxybenzyl)amino)-4-methylpyridin-2-yl)boronic acid (60.0 g, crude), 4-methylcyclohex-2-en-1-one (5.16 g, 46.8 mmol) and chloro(1,5-cyclooctadiene)rhodium(I) dimer (2.31 g, 4.68 mmol) in 1,4-dioxane (200 mL) was added saturated potassium phosphate solution (40 mL) and stirred at 25° C. for 1 hour. After completion, the reaction was diluted with water, extracted with ethyl acetate, dried over anhydrous sodium sulfate and concentrated under vacuum. The residue was purified by flash chromatography on silica gel eluting with petroleum ether/ethyl acetate (10/1) to afford 3-(6-(bis(4-methoxybenzyl)amino)-4-methylpyridin-2-yl)-4-methylcyclohexan-1-one (11.00 g, 23.9 mmol, 51.3% yield) as a yellow solid. LCMS (ESI, m/z): 459.3 [M+H]⁺.

Step 3: 3-(6-(bis(4-methoxybenzyl)amino)-3-iodo-4-methylpyridin-2-yl)-4-methylcyclohexan-1-one

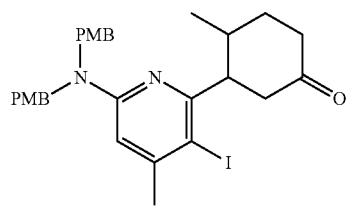

A solution of 3-(6-(bis(4-methoxybenzyl)amino)-4-methylpyridin-2-yl)-4-methylcyclohexan-1-one (25.0 g, 54.50 mmol) and N-iodosuccinimide (14.19 g, 63.0 mmol) in acetonitrile (250 mL) was stirred at room temperature for 2 minutes. Then trifluoroacetic acid (0.60 g, 5.20 mmol) was added and stirred at 25° C. for 20 minutes. After completion, the solvent was concentrated under vacuum. The solution was diluted with water. The resulting solution was extracted with ethyl acetate and the organic layers were combined. The organic layer was dried over anhydrous sodium sulfate and concentrated under vacuum. The residue was purified by flash chromatography on silica gel eluting with petroleum ether/ethyl acetate (3/1) to afford 3-(6-(bis(4-methoxybenzyl)amino)-3-iodo-4-methylpyridin-2-yl)-4-methylcyclohexan-1-one (30.00 g, 51.3 mmol, 94.1% yield) as a yellow oil. LCMS (ESI, m/z): 585.2 [M+H]⁺.

Step 4: 3-[6-[bis[(4-methoxyphenyl)methyl]amino]-3-cyclopropyl-4-methyl-2-pyridyl]-4-methyl-cyclohexanone

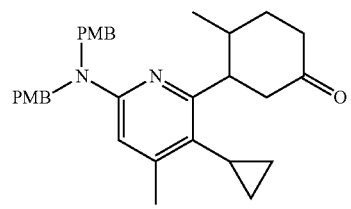

Under nitrogen, a solution of bis(triphenylphosphine)palladium(II) chloride (2.64 g, 3.70 mmol) and bromo(cyclopropyl)zinc (0.5 M in THF) (60 mL, 28.2 mmol) in tetrahydrofuran (110 mL) was stirred at 25° C. for 3 minutes. The reaction mixture was diluted with water, extracted with dichloromethane. The organic layers were combined, dried over anhydrous sodium sulfate and concentrated under vacuum. The residue was purified by flash chromatography on silica gel eluting with petroleum ether/ethyl acetate (10/1) to afford 3-[6-[bis[(4-methoxyphenyl)methyl]amino]-3-cyclopropyl-4-methyl-2-pyridyl]-4-methyl-cyclohexanone (8.00 g, 16.0 mmol, 85.2% yield) as a yellow solid. LCMS (ESI, m/z): 499.3 [M+H]⁺

Step 5: ethyl 4-(6-(bis(4-methoxybenzyl)amino)-3-cyclopropyl-4-methylpyridin-2-yl)-5-methyl-2-oxo-cyclohexane-1-carboxylate

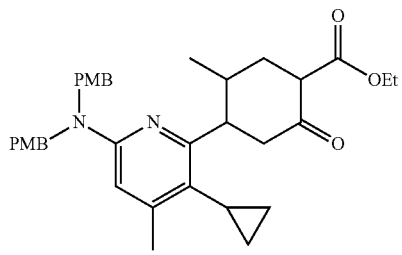

Under nitrogen, a solution of 3-[6-[bis[(4-methoxyphenyl)methyl]amino]-3-cyclopropyl-4-methyl-2-pyridyl]-4-methyl-cyclohexanone (8.40 g, 16.85 mmol) in tetrahydrofuran (20 mL) was dropwise added lithium bis (trimethylsilyl)amide (25.27 mL, 25.27 mmol, 1.0 M in THF) at −78° C. and stirred for 20 minutes at −78° C. Then ethyl cyanoformate (2.00 g, 20.21 mmol) was added and stirred at −78° C. for 30 minutes. After completion, the reaction was quenched with water. The reaction mixture was diluted with dichloromethane. The organic layer was washed with brine, dried over anhydrous sodium sulfate and concentrated under vacuum to afford the crude ethyl 4-(6-(bis (4-methoxybenzyl)amino)-3-cyclopropyl-4-methylpyridin-2-yl)-5-methyl-2-oxocyclohexane-1-carboxylate (12.00 g, crude) as a yellow oil. LCMS (ESI, m/z): 571.3 [M+H]$^+$.

Step 6: 7-[6-[bis[(4-methoxyphenyl)methyl]amino]-3-cyclopropyl-4-methyl-2-pyridyl]-6-methyl-2-methylsulfanyl-5,6,7,8-tetrahydroquinazolin-4-ol

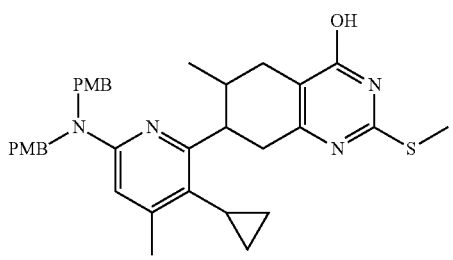

Then a solution of the crude ethyl 4-(6-(bis(4-methoxybenzyl)amino)-3-cyclopropyl-4-methylpyridin-2-yl)-5-methyl-2-oxocyclohexane-1-carboxylate (12.00 g, crude), sodium bicarbonate (35.37 g, 421.13 mmol) and 2-methylisothiourea (15.19 g, 168.45 mmol) in ethanol (25 mL) and water (5 mL) was stirred at 50° C. for 12 hours. After completion, the reaction mixture was concentrated under vacuum, diluted with dichloromethane. The organic layer was washed with brine. The organic layer was dried over anhydrous sodium sulfate and concentrated under vacuum. The residue was purified by flash chromatography on silica gel eluting with dichloromethane/ethyl acetate (6/1) to afford 7-[6-[bis[(4-methoxyphenyl)methyl]amino]-3-cyclopropyl-4-methyl-2-pyridyl]-6-methyl-2-methylsulfanyl-5,6,7,8-tetrahydroquinazolin-4-ol (1.90 g, 2.93 mmol, 17.4% yield) as a white solid. LCMS (ESI, m/z): 597.3 [M+H]$^+$.

Step 7: tert-butyl(3S)-4-[7-[6-[bis[(4-methoxyphenyl)methyl]-amino]-3-cyclopropyl-4-methyl-2-pyridyl]-6-methyl-2-methylsulfanyl-5,6,7,8-tetrahydroquinazolin-4-yl]-3-methyl-piperazine-1-carboxylate

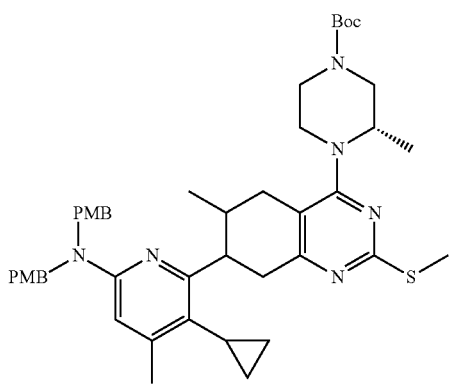

A solution of 7-[6-[bis[(4-methoxyphenyl)methyl]amino]-3-cyclopropyl-4-methyl-2-pyridyl]-6-methyl-2-methylsulfanyl-5,6,7,8-tetrahydroquinazolin-4-ol (1.9 g, 3.18 mmol), trifluoro-methanesulfonic anhydride (0.96 mL, 5.73 mmol) and N,N-diisopropylethylamine (2.77 mL, 15.92 mmol) in DCM (10 mL) was stirred at r.t. for 1 hour. After completion, the solvent was concentrated under vacuum. The reaction mixture was diluted with dichloromethane (10 mL), and adjusted to pH>7 with N,N-diisopropylethylamine. Then tert-butyl (3S)-3-methyl-1-piperazinecarboxylate (1.91 g, 9.55 mmol) was added and stirred at 110° C. for 12 hours. After completion, the solvent was concentrated under vacuum. The residue was purified by flash chromatography on silica gel eluting with petroleum ether/ethyl acetate (3/1) to afford tert-butyl(3S)-4-[7-[6-[bis [(4-methoxyphenyl)methyl]-amino]-3-cyclopropyl-4-methyl-2-pyridyl]-6-methyl-2-methylsulfanyl-5,6,7,8-tetrahydroquinazolin-4-yl]-3-methyl-piperazine-1-carboxylate (1.90 g, 2.44 mmol, 76.6% yield) as a yellow solid. LCMS (ESI, m/z): 779.4 [M+H]$^+$.

Step 8: tert-butyl(3S)-4-[7-[6-[bis[(4-methoxyphenyl)methyl]amino]-3-cyclopropyl-4-methyl-2-pyridyl]-6-methyl-2-methylsulfonyl-5,6,7,8-tetrahydroquinazolin-4-yl]-3-methyl-piperazine-1-carboxylate

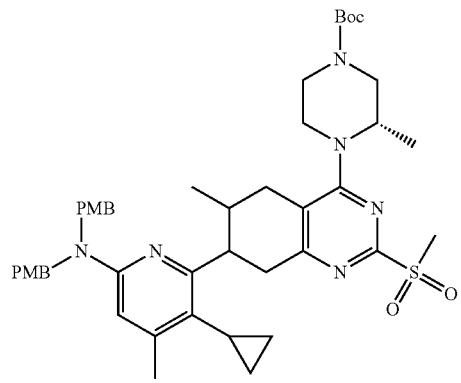

A solution of tert-butyl-4-[7-[6-[bis[(-methoxyphenyl) methyl]amino]-3-cyclopropyl-4-methyl-2-pyridyl]-6-methyl-2-methylsulfanyl-5,6,7,8-tetrahydroquinazolin-4-yl]-3-methyl-piperazine-1-carboxylate (1.90 g, 2.44 mmol) and m-CBPA (1.24 g, 7.32 mmol) in DCM (10 mL) and water (5 mL) was stirred at 25° C. for 1 hour. After completion, the reaction was quenched by aqueous saturated Na$_2$SO$_3$. The reaction mixture was diluted with dichloromethane and washed with water. The organic layer was dried over anhydrous sodium sulfate and concentrated under vacuum to afford the crude tert-butyl(3S)-4-[7-[6-[bis[(4-methoxyphenyl)methyl]amino]-3-cyclopropyl-4-methyl-2-pyridyl]-6-methyl-2-methylsulfonyl-5,6,7,8-tetrahydroquinazolin-4-yl]-3-methyl-piperazine-1-carboxylate (2.00 g, crude) which would be directly used in the next step without purification.

Step 9: tert-butyl (3S)-4-[7-[6-[bis[(4-methoxyphenyl)methyl]amino]-3-cyclopropyl-4-methyl-2-pyridyl]-2-1[[(2S,4R)-4-fluoro-1-methyl-pyrrolidin-2-yl]methoxy]-6-methyl-5,6,7,8-tetrahydroquinazolin-4-yl]-3-methyl-piperazine-1-carboxylate Step 10: 1-((S)-4-((6S,7S)-7-(6-amino-3-cyclopropyl-4-methylpyridin-2-yl)-2-(((2S,4R)-4-fluoro-1-methylpyrrolidin-2-yl)methoxy)-6-methyl-5,6,7,8-tetrahydroquinazolin-4-yl)-3-methylpiperazin-1-yl)prop-2-en-1-one (Example 24a) 1-((S)-4-((6R,7R)-7-(6-amino-3-cyclopropyl-4-methylpyridin-2-yl)-2-(((2S,4R)-4-fluoro-1-methylpyrrolidin-2-yl)methoxy)-6-methyl-5,6,7,8-tetrahydroquinazolin-4-yl)-3-methylpiperazin-1-yl)prop-2-en-1-one (Example 24b)

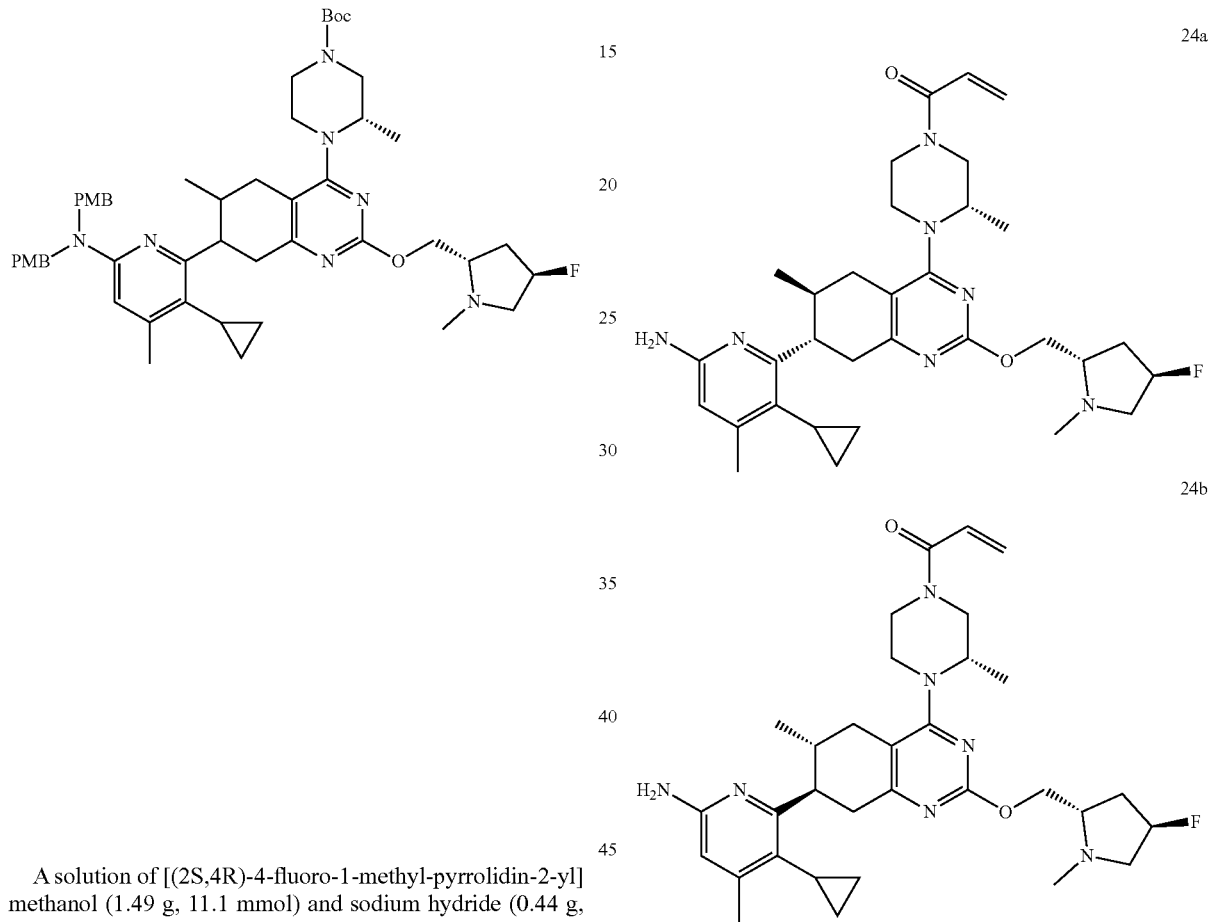

A solution of [(2S,4R)-4-fluoro-1-methyl-pyrrolidin-2-yl]methanol (1.49 g, 11.1 mmol) and sodium hydride (0.44 g, 11.1 mmol, 60% dispersion in mineral oil) in DMF (10 mL) was stirred at 25° C. for 10 minutes. Then the last step crude product tert-butyl (3S)-4-[7-[6-[bis[(4-methoxyphenyl)methyl]amino]-3-cyclopropyl-4-methyl-2-pyridyl]-6-methyl-2-methylsulfonyl-5,6,7,8-tetrahydroquinazolin-4-yl]-3-methyl-piperazine-1-carboxylate (2.00 g, crude) was added and stirred at 25° C. for 6 hours. After completion, the reaction was quenched by aqueous saturated ammonium chloride. The reaction mixture was diluted with dichloromethane, washed with water. The organic layer was dried over anhydrous sodium sulfate and concentrated under vacuum. The residue was purified by flash chromatography on silica gel eluting with dichloromethane/methanol (5/1) to afford tert-butyl (3S)-4-[7-[6-[bis[(4-methoxyphenyl)methyl]amino]-3-cyclopropyl-4-methyl-2-pyridyl]-2-[[(2S,4R)-4-fluoro-1-methyl-pyrrolidin-2-yl]methoxy]-6-methyl-5,6,7,8-tetrahydroquinazolin-4-yl]-3-methyl-piperazine-1-carboxylate (1.10 g, 1.27 mmol, 57.4% yield) as a yellow solid. LCMS (ESI, m/z): 864.5 [M+H]$^+$.

A solution of tert-butyl (3S)-4-[7-[6-[bis[(4-methoxyphenyl)methyl]amino]-3-cyclopropyl-4-methyl-2-pyridyl]-2-[[(2S,4R)-4-fluoro-1-methyl-pyrrolidin-2-yl]methoxy]-6-methyl-5,6,7,8-tetrahydroquinazolin-4-yl]-3-methyl-piperazine-1-carboxylate (1.10 g, 1.27 mmol) in trifluoroacetic acid (10 mL) was stirred at 25° C. for 0.5 hour. After completion, the solvent was concentrated under vacuum. A solution of the crude 5-cyclopropyl-6-((6R,7R)-2-(((2S,4R)-4-fluoro-1-methylpyrrolidin-2-yl)methoxy)-6-methyl-4-((S)-2-methylpiperazin-1-yl)-5,6,7,8-tetrahydroquinazolin-7-yl)-4-methylpyridin-2-amine in dichloromethane (10 mL) was adjusted to pH>9 with DIEA. Then acrylyl chloride (0.08 g, 0.86 mmol) was added and stirred at 25° C. for 20 minutes. After completion, the reaction was quenched with water. After completion, the reaction mixture was diluted with dichloromethane and washed with water. The organic layer was dried over anhydrous sodium sulfate and concentrated under vacuum. The residue was purified by flash chromatography on reverse-phase eluting with Acetonitrile/water (45/55) to afford the product. The product was further purified by Prep-HPLC with the following condition: Column: XBridge Shield RP18 OBD Column, 30*150 mm, 5 um; Mobile Phase A:Water (10 MMOL/L NH4HCO3), Mobile Phase B: ACN; Flow rate: 60 mL/min; Gradient: 34 B to 64 B in 7 min; 254 nm; The mixture of diasteroisomer was separated by Prep-Chiral-HPLC with the following condition: Column: CHIRALPAK IE, 3*25 cm, 5 um; Mobile Phase A:Hex: DCM=3:1 (10 mM NH3-MEOH)—HPLC, Mobile Phase B: EtOH—HPLC; Flow rate: 30 mL/min; Gradient: 50 B to 50 B in 30 min; 220/254 nm; RT1:16.281; RT2:25.907; Injection Volumn: 3 ml to afford the title compounds. The absolute configuration of the title compounds was inferred from potency data and a protein X-ray structure of compound 21b.

Example 24a: 1-((S)-4-((6S,7S)-7-(6-amino-3-cyclopropyl-4-methylpyridin-2-yl)-2-(((2S,4R)-4-fluoro-1-methylpyrrolidin-2-yl)methoxy)-6-methyl-5,6,7,8-tetrahydroquinazolin-4-yl)-3-methylpiperazin-1-yl)prop-2-en-1-one (16.4 mg, 0.028 mmol, 3% yield) as a white solid. $^1$H NMR (300 MHz, DMSO-d$_6$, ppm) δ 6.91-6.76 (m, 1H), 6.21-5.95 (m, 2H), 5.70 (dd, J=10.3, 2.4 Hz, 1H), 5.48 (s, 2H), 5.15 (d, J=56.4 Hz, 1H), 4.46-3.83 (m, 5H), 3.65-3.34 (m, 4H), 3.29-3.19 (m, 1H), 3.15-2.65 (m, 4H), 2.59 (s, 1H), 2.44-2.37 (m, 5H), 2.25 (s, 3H), 2.17-2.02 (m, 1H), 1.97-1.75 (m, 2H), 1.60-1.49 (m, 1H), 1.08-0.89 (m, 5H), 0.69 (d, J=6.4 Hz, 3H), 0.50-0.30 (m, 2H). LCMS (ESI, m/z): 578.4 [M+H]$^+$. Chiral HPLC: CHIRALPAK IE-3 (4.6*50 mm 3 um); detected at 254 nm; (Hex:DCM=3:1)(0.1% DEA): EtOH; flow=1.5 ml/min; Retention time: 2.342 min (slower peak).

Example 24b: 1-((S)-4-((6R,7R)-7-(6-amino-3-cyclopropyl-4-methylpyridin-2-yl)-2-(((2S,4R)-4-fluoro-1-methylpyrrolidin-2-yl)methoxy)-6-methyl-5,6,7,8-tetrahydroquinazolin-4-yl)-3-methylpiperazin-1-yl)prop-2-en-1-one (22.7 mg, 0.039 mmol, 4.1% yield). $^1$H NMR (300 MHz, DMSO-d$_6$, ppm) δ 6.91-6.75 (m, 1H), 6.30-5.95 (m, 2H), 5.72 (dd, J=10.3, 2.4 Hz, 1H), 5.49 (s, 2H), 5.15 (d, J=56.4 Hz, 1H), 4.47-3.78 (m, 6H), 3.62-3.36 (m, 3H), 3.21-2.65 (m, 5H), 2.49-2.41 (m, 3H), 2.37 (s, 3H), 2.25 (s, 3H), 2.17-2.02 (m, 1H), 1.99-1.74 (m, 2H), 1.60-1.48 (m, 1H), 1.26 (d, J=6.6 Hz, 3H), 0.95 (d, J=8.4 Hz, 2H), 0.69 (d, J=6.4 Hz, 3H), 0.44-0.29 (m, 2H). LCMS (ESI, m/z): 578.4 [M+H]$^+$. Chiral HPLC: CHIRALPAK IE-3 (4.6*50 mm 3 um); detected at 254 nm; (Hex:DCM=3:1)(0.1% DEA): EtOH; flow=1.5 ml/min; Retention time: 1.470 min (faster peak).

Example 25a

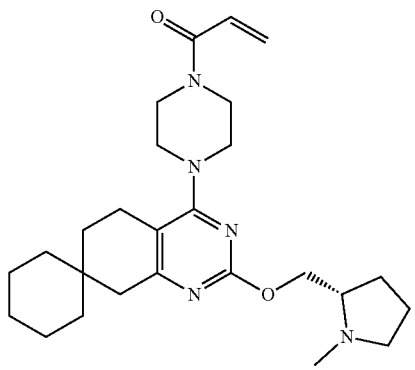 [SMILES: C=CC(=O)N1CCN(c2nc(OC[C@@H]3CCCN3C)nc3c2CCC2(CCCCC2)C3)CC1]

(S)-1-(4-(2'-((1-methylpyrrolidin-2-yl)methoxy)-5',8'-dihydro-6'H-spiro[cyclohexane-1,7'-quinazolin]-4'-yl)piperazin-1-yl)prop-2-en-1-one

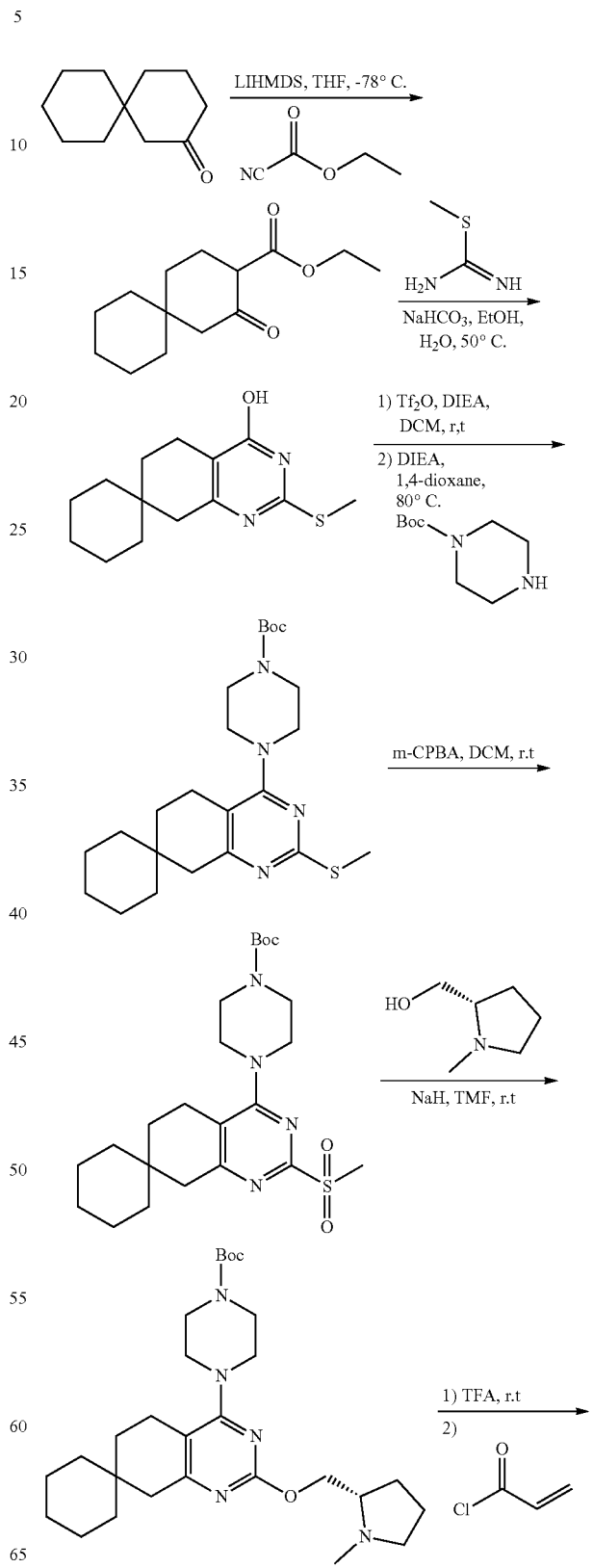

-continued

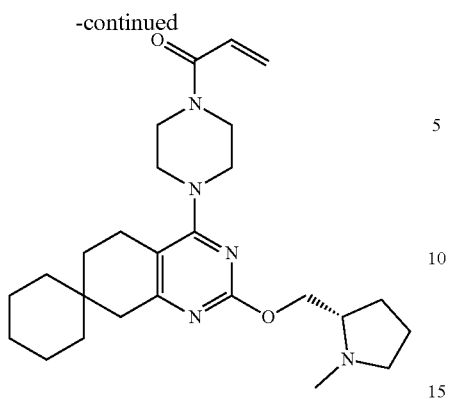

Step 1: ethyl 2-oxospiro [5.5] undecane-3-carboxylate

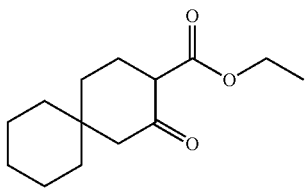 [SMILES: CCOC(=O)C1CCC2(CCCCC2)CC1=O]

Under nitrogen, a solution of spiro [5.5] undecan-4-one (3.0 g, 18.04 mmol) in tetrahydrofuran (30 mL) was added Lithium bis(trimethylsilyl)amide (27.0 mL, 1 mol/L in hexane) and stirred 0.5 hours at −78° C. Then ethyl cyanoformate (3.6 g, 36.09 mmol) was added and stirred at −78° C. for 2 hours. After completion, the solution was quenched with water and extracted with ethyl acetate. Then the organic layers were combined, dried over anhydrous sodium sulfate and concentrated under vacuum. The residue was purified by flash chromatography on silica gel column eluting with ethyl acetate/petroleum ether (1/4) to afford ethyl 4-oxospiro [5.5] undecane-3-carboxylate (2.0 g, 8.39 mmol, 46.5% yield) as yellow oil. LCMS (ESI, m/z): 239.3 [M+H]⁺.

Step 2: 2'-(methylthio)-5',8'-dihydro-3'H-spiro[cyclohexane-1,7'-quinazolin]-4'(6'H)-one

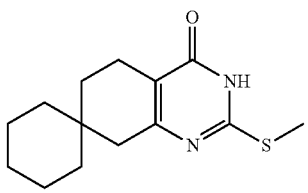 [SMILES: CSc1nc2c(c(=O)[nH]1)CCC1(CCCCC1)C2]

A solution of ethyl 4-oxospiro [5.5] undecane-3-carboxylate (2.20 g, 9.23 mmol) and 2-methylisothiourea (8.32 g, 92.31 mmol) in ethanol (20 mL) was stirred at 50° C. for 0.5 hours. Then sodium bicarbonate (15.51 g, 184.63 mmol) was added and stirred at 50° C. for 10 hours. After completion, the solution was diluted with water and extracted with ethyl acetate. Then the organic layers were combined, dried over anhydrous sodium sulfate and concentrated under vacuum. The residue was purified by flash chromatography on silica gel column eluting with methanol/dichloromethane (1/10) to afford 2'-(methylthio)-5',8'-dihydro-3'H-spiro[cyclohexane-1,7'-quinazolin]-4'(6'H)-one (600 mg, 2.27 mmol, 24.6% yield) as a yellow solid. LCMS (ESI, m/z): 265.4 [M+H]⁺.

Step 3: tert-butyl 4-(2'-(methylthio)-5', 8'-dihydro-6'H-spiro [cyclohexane-1, 7'-quinazolin]-4'-yl) piperazine-1-carboxylate

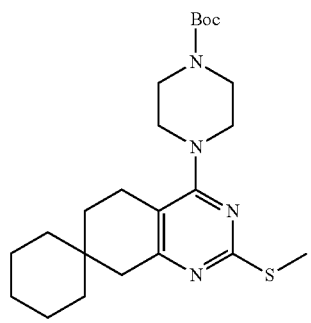 [SMILES: CSc1nc2c(c(N3CCN(C(=O)OC(C)(C)C)CC3)n1)CCC1(CCCCC1)C2]

A solution of 2'-(methylthio)-5',8'-dihydro-3'H-spiro[cyclohexane-1,7'-quinazolin]-4'(6'H)-one (600.0 mg, 2.27 mmol) and N,N-diisopropylethylamine (585.5 mg, 4.54 mmol) in dichloromethane (6 mL) was stirred at 25° C. for 0.5 hours. Then trifluoromethanesulfonic anhydride (960.4 mg, 3.4 mmol) was added and stirred at 25° C. for 2 hours. The resulting solution was concentrated under vacuum and diluted with 1,4-dioxane (6 mL). Then the solution of tert-butyl 1-piperazinecarboxylate (845.34 mg, 4.54 mmol) and N,N-diisopropylethylamine (585.5 mg, 4.54 mmol) was added and stirred at 80° C. for 3 hours. After completion, the solution was diluted with water and extracted with ethyl acetate. Then the organic layers were combined, dried over anhydrous sodium sulfate and concentrated under vacuum. The residue was purified by flash chromatography on silica gel column eluting with ethyl acetate/petroleum ether (1/6) to afford tert-butyl 4-(2'-(methylthio)-5', 8'-dihydro-6'H-spiro[cyclohexane-1,7'-quinazolin]-4'-yl)piperazine-1-carboxylate (500 mg, 1.16 mmol, 50.9% yield)] as a yellow solid. LCMS (ESI, m/z): 433.3 [M+H]⁺.

Step 4: tert-butyl 4-(2'-(methylsulfonyl)-5',8'-dihydro-6'H-spiro [cyclohexane-1,7'-quinazolin]-4'-yl) piperazine-1-carboxylate

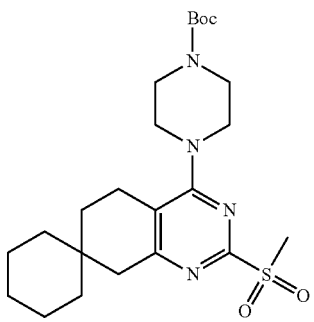 [SMILES: CC(C)(C)OC(=O)N1CCN(c2nc(S(C)(=O)=O)nc3c2CCC2(CCCCC2)C3)CC1]

A solution of tert-butyl 4-(2'-(methylthio)-5',8'-dihydro-6'H-spiro[cyclohexane-1,7'-quinazolin]-4'-yl)piperazine-1-carboxylate (300.0 mg, 0.69 mmol) and 3-chloroperoxybenzoic acid (239.3 mg, 1.39 mmol) in dichloromethane (10 mL) was stirred at 25° C. for 3 hours. After completion, the solution was diluted with water and extracted with ethyl acetate. Then the organic layers were combined, dried over anhydrous sodium sulfate and concentrated under vacuum. The residue was purified by flash chromatography on silica gel column eluting with ethyl acetate/petroleum ether (1/5) to afford tert-butyl 4-(2'-(methylsulfonyl)-5',8'-dihydro-6'H-spiro[cyclohexane-1,7'-quinazolin]-4'-yl)piperazine-1-carboxylate (260 mg, 0.56 mmol, 80.7% yield) as a yellow solid. LCMS (ESI, m/z): 465.2 [M+H]+.

Step 5: tert-butyl 4-[2-[[(2S)-1-methylpyrrolidin-2-yl]methoxy]spiro[6,8-dihydro-5H-quinazoline-7,1'-cyclohexane]-4-yl]piperazine-1-carboxylate

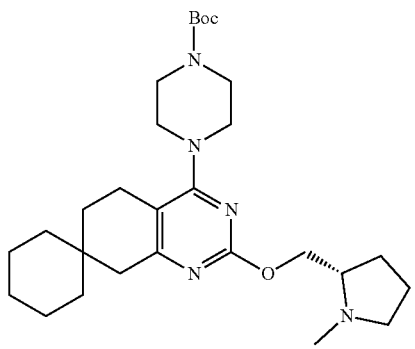 [SMILES: CN1CCC[C@H]1COc1nc2c(c(N3CCN(C(=O)OC(C)(C)C)CC3)n1)CCC1(CCCCC1)C2]

Under nitrogen, a solution of n-methyl-1-prolinol (99.15 mg, 0.86 mmol) in tetrahydrofuran (6 mL) was added sodium hydride (30.99 mg, 1.29 mmol, 60% dispersion in mineral oil). The resulting solution was stirred 0.5 hours at 25° C. Then tert-butyl 4-(2'-(methylsulfonyl)-5',8'-dihydro-6'H-spiro[cyclohexane-1,7'-quinazolin]-4'-yl)piperazine-1-carboxylate (200.0 mg, 0.43 mmol) was added and stirred at 25° C. for 2 hours. After completion, the solution was diluted with water and extracted with ethyl acetate. Then the organic layers were combined, dried over anhydrous sodium sulfate and concentrated under vacuum. The residue was purified by flash chromatography on silica gel column eluting with methanol/dichloromethane (1/10) to afford tert-butyl 4-[2-[[(2S)-1-methylpyrrolidin-2-yl]methoxy]spiro[6,8-dihydro-5H-quinazoline-7,1'-cyclohexane]-4-yl]piperazine-1-carboxylate (150 mg, 0.30 mmol, 69.7% yield) as a yellow solid. LCMS (ESI, m/z): 500.7 [M+H]+.

Step 6a: (S)-2'-((1-methylpyrrolidin-2-yl)methoxy)-4'-(piperazin-1-yl)-5',8'-dihydro-6'H-spiro[cyclohexane-1,7'-quinazoline]

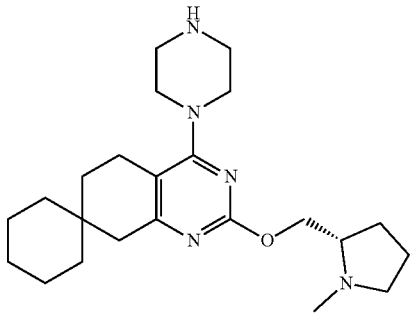 [SMILES: CN1CCC[C@H]1COc1nc2c(c(N3CCNCC3)n1)CCC1(CCCCC1)C2]

A solution of tert-butyl 4-[2-[[(2S)-1-methylpyrrolidin-2-yl]methoxy]spiro[6,8-dihydro-5H-quinazoline-7,1'-cyclohexane]-4-yl]piperazine-1-carboxylate (150.0 mg, 0.30 mmol) and trifluoroacetic acid (1.00 mL) in dichloromethane (2.00 mL) was stirred at 25° C. for 2 hours. After completion, the solution was diluted with water and extracted with dichloromethane. Then the organic layers were combined, dried over anhydrous sodium sulfate and concentrated under vacuum. The residue was purified by flash chromatography on silica gel column eluting with methanol/dichloromethane (1/5) to afford 2-[[(2S)-1-methylpyrrolidin-2-yl]methoxy]-4-piperazin-1-yl-spiro[6,8-dihydro-5H-quinazoline-7,1'-cyclohexane] (100 mg, 0.25 mmol, 83.4% yield) as a yellow solid. LCMS (ESI, m/z): 400.6 [M+H]+.

Step 6b: (S)-1-(4-(2'-((1-methylpyrrolidin-2-yl)methoxy)-5',8'-dihydro-6'H-spiro[cyclohexane-1,7'-quinazolin]-4'-yl)piperazin-1-yl)prop-2-en-1-one

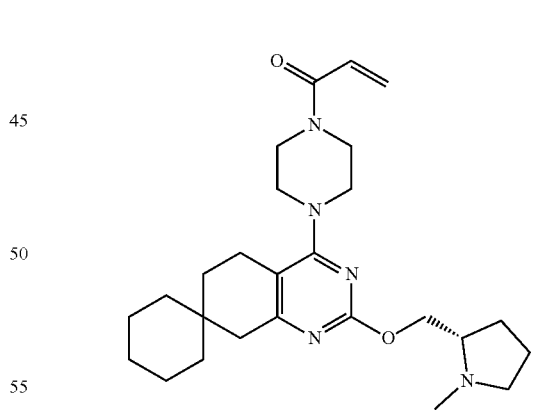

A solution of 2-[[(2S)-1-methylpyrrolidin-2-yl]methoxy]-4-piperazin-1-yl-spiro[6,8-dihydro-5H-quinazoline-7,1'-cyclohexane] (200.0 mg, 0.50 mmol) and N,N-diisopropylethylamine (0.09 mL, 0.50 mmol) in dichloromethane (10 mL) was stirred at −78° C. for 5 minutes. Then acryloyl chloride (46.0 mg, 0.51 mmol) was added and stirred at −78° C. for 0.5 hours. The resulting solution was concentrated under vacuum. The crude product was purified by Prep-HPLC with the following conditions: Column: XBridge Shield RP18 OBD Column, 30*150 mm, 5 um; Mobile Phase A: Water (10 MMOL/L NH4HCO3), Mobile Phase B: ACN; Flow rate: 60 mL/min; Gradient: 29 B to 70 B in 7 min; 220 nm; RT1:6.5; RT2; Injection Volumn: mL; Number of Runs, to afford (S)-1-(4-(2'-((1-methylpyrrolidin-2-yl)methoxy)-5',8'-dihydro-6'H-spiro[cyclohexane-1,7'-quinazolin]-4'-yl)piperazin-1-yl)prop-2-en-1-one (20.3 mg, 0.04 mmol, 8.9% yield) as a white solid. LCMS (ESI, m/z): 454.6 [M+H]$^+$ Example 25a: $^1$H NMR (400 MHz, Methanol-d$_4$, ppm) 6.84-6.78 (m, 1H), 6.28 (d, J=2.0 Hz, 1H), 5.81 (d, J=2.0 Hz, 1H), 4.40-4.39 (m, 2H), 3.80-3.78 (m, 4H), 3.54-3.79 (m, 4H), 3.26 (s, 1H), 3.06 (s, 1H), 2.66 (s, 3H), 2.63-2.54 (m, 3H), 2.55 (s, 2H), 2.20-2.13 (m, 1H), 1.93-1.83 (m, 2H), 1.79-1.76 (m, 1H), 1.60 (m, 2H), 1.58-1.45 (m, 6H), 1.44-1.40 (m, 4H).

Example 26

(S)-1-(4-(7-(6-amino-4-methyl-3-(trifluoromethyl)pyridin-2-yl)-5,6,7,8-tetrahydroquinazolin-4-yl)piperazin-1-yl)prop-2-en-1-one (Example 26a)

(R)-1-(4-(7-(6-amino-4-methyl-3-(trifluoromethyl)pyridin-2-yl)-5,6,7,8-tetrahydroquinazolin-4-yl)piperazin-1-yl)prop-2-en-1-one (Example 26b)

Example 26a

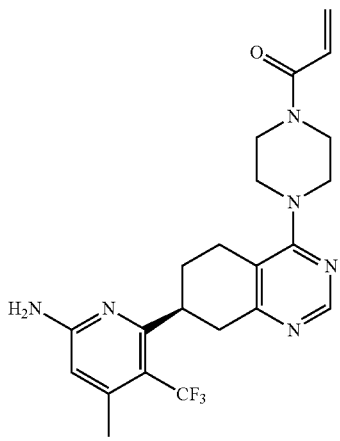

Example 26b

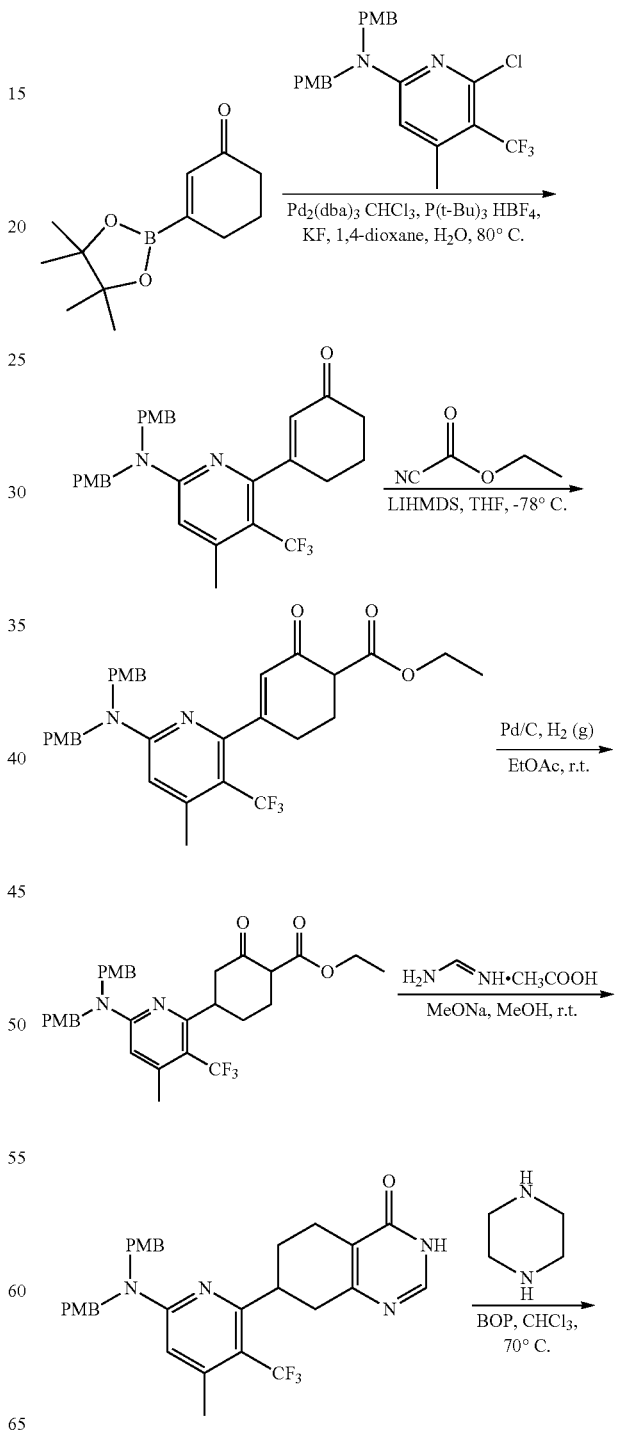

-continued

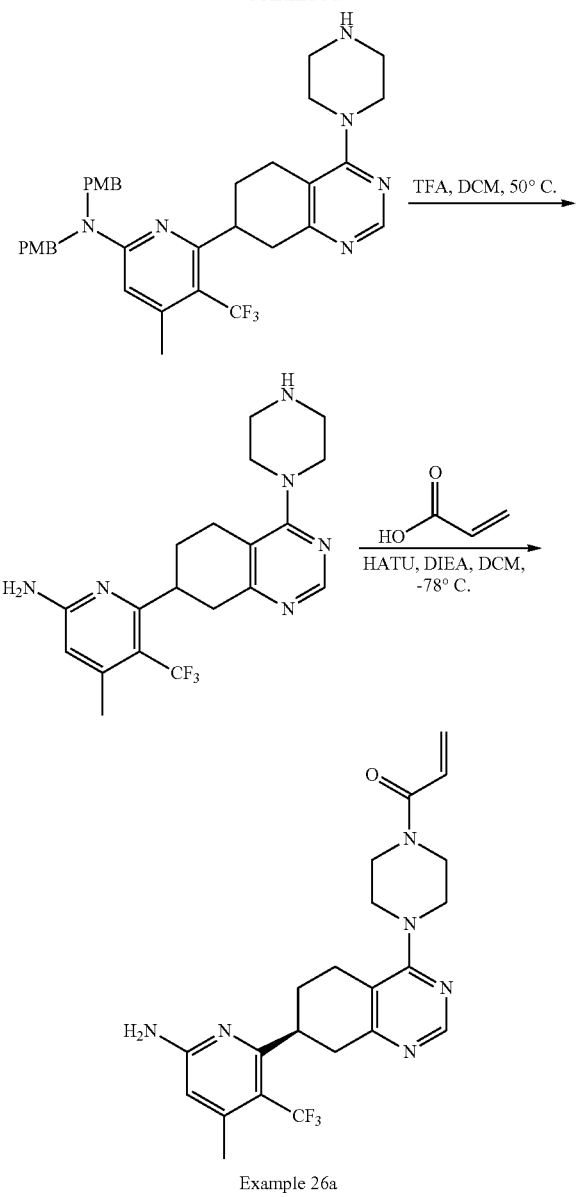

Example 26a

Example 26b

Step 1: 3-[6-[bis[(4-methoxyphenyl)methyl]amino]-4-methyl-3-(trifluoromethyl)-2-pyridyl]cyclohex-2-en-1-one

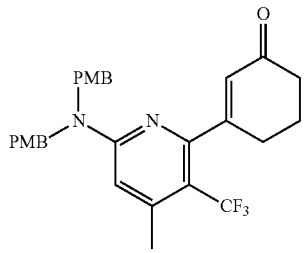

Under nitrogen, a solution of 6-chloro-N,N-bis[(4-methoxyphenyl)methyl]-4-methyl-5-(trifluoromethyl)pyridin-2-amine (20.24 g, 44.89 mmol), 3-(4,4,5,5-tetramethyl-1,3,2-dioxaborolan-2-yl)cyclohex-2-en-1-one (4.99 g, 22.45 mmol), tris(dibenzylideneacetone)dipalladium-chloroform adduct (3.48 g, 3.37 mmol), tri-tert-butylphosphine tetrafluoroborate (1.3 g, 4.49 mmol) and potassium fluoride (2.6 g, 44.89 mmol) in 1,4-dioxane (100 mL) and water (10 mL) was stirred at 80° C. for 2 hours. After completion, the resulting solution was diluted with ethyl acetate and washed with water. The organic layer was dried over anhydrous sodium sulfate and concentrated under vacuum. The residue was purified by flash chromatography on silica gel column eluting with dichloromethane/methanol (97/3) to afford 3-[6-[bis[(4-methoxyphenyl)methyl]amino]-4-methyl-3-(trifluoromethyl)-2-pyridyl]cyclohex-2-en-1-one (5.96 g, 11.32 mmol, 50.4% yield) as a yellow solid. LCMS (ESI, m/z): 511.2 [M+H]$^+$.

Step 2: ethyl 4-[6-[bis[(4-methoxyphenyl)methyl]amino]-4-methyl-3-(trifluoromethyl)-2-pyridyl]-2-oxo-cyclohex-3-ene-1-carboxylate

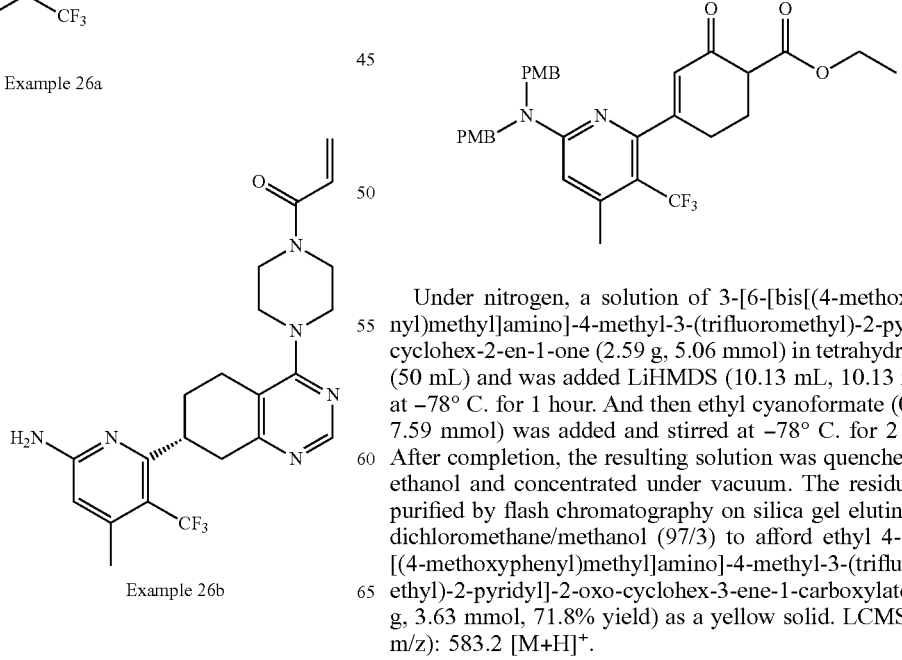

Under nitrogen, a solution of 3-[6-[bis[(4-methoxyphenyl)methyl]amino]-4-methyl-3-(trifluoromethyl)-2-pyridyl]cyclohex-2-en-1-one (2.59 g, 5.06 mmol) in tetrahydrofuran (50 mL) and was added LiHMDS (10.13 mL, 10.13 mmol) at −78° C. for 1 hour. And then ethyl cyanoformate (0.75 g, 7.59 mmol) was added and stirred at −78° C. for 2 hours. After completion, the resulting solution was quenched with ethanol and concentrated under vacuum. The residue was purified by flash chromatography on silica gel eluting with dichloromethane/methanol (97/3) to afford ethyl 4-[6-[bis[(4-methoxyphenyl)methyl]amino]-4-methyl-3-(trifluoromethyl)-2-pyridyl]-2-oxo-cyclohex-3-ene-1-carboxylate (2.21 g, 3.63 mmol, 71.8% yield) as a yellow solid. LCMS (ESI, m/z): 583.2 [M+H]$^+$.

Step 3: ethyl 4-[6-[bis[(4-methoxyphenyl)methyl] amino]-4-methyl-3-(trifluoromethyl)-2-pyridyl]-2-oxo-cyclohexanecarboxylate

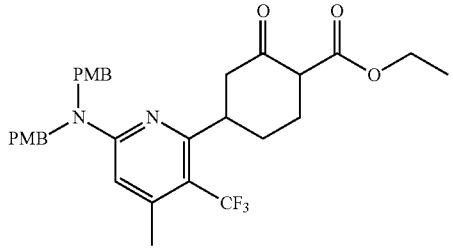

Under hydrogen, a solution of ethyl 4-[6-[bis[(4-methoxyphenyl)methyl]amino]-4-methyl-3-(trifluoromethyl)-2-pyridyl]-2-oxo-cyclohex-3-ene-1-carboxylate (2.95 g, 5.06 mmol) and Pd/C (0.30 g, 2.84 mmol) in ethyl acetate (50 mL) was stirred at 25° C. for 5 hours. After completion, the resulting solution was filtrated, and the filtrate was concentrated under reduced pressure to afford ethyl 4-[6-[bis[(4-methoxyphenyl)methyl]amino]-4-methyl-3-(trifluoromethyl)-2-pyridyl]-2-oxo-cyclohexanecarboxylate (2.7 g, 4.61 mmol, 91.1% yield) as white oil. LCMS (ESI, m/z): 585.2 [M+H]+.

Step 4: 7-[6-[bis[(4-methoxyphenyl)methyl]amino]-4-methyl-3-(trifluoromethyl)-2-pyridyl]-5,6,7,8-tetrahydro-3H-quinazolin-4-one

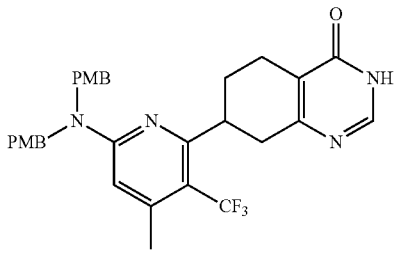

A solution of ethyl 4-[6-[bis[(4-methoxyphenyl)methyl] amino]-4-methyl-3-(trifluoromethyl)-2-pyridyl]-2-oxo-cyclohexanecarboxylate (2.95 g, 5.04 mmol), formamidinium acetate (3.15 g, 30.26 mmol) and sodium methanolate (2.72 g, 50.43 mmol) in methanol (50 mL) was stirred at 25° C. for 5 hours. After completion, the resulting solution was concentrated under vacuum. The residue was purified by flash chromatography on silica gel eluting with dichloromethane/methanol (93/7) to afford 7-[6-[bis[(4-methoxyphenyl)methyl]amino]-4-methyl-3-(trifluoromethyl)-2-pyridyl]-5,6,7,8-tetrahydro-3H-quinazolin-4-one (1.51 g, 2.68 mmol, 53.1% yield) as a white oil. LCMS (ESI, m/z): 565.2 [M+H]+.

Step 5: N,N-bis[(4-methoxyphenyl)methyl]-4-methyl-6-(4-piperazin-1-yl-5,6,7,8-tetrahydroquinazolin-7-yl)-5-(trifluoromethyl)pyridin-2-amine

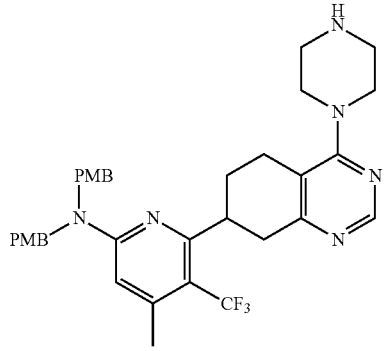

A solution of 7-[6-[bis[(4-methoxyphenyl)methyl] amino]-4-methyl-3-(trifluoromethyl)-2-pyridyl]-5,6,7,8-tetrahydro-3H-quinazolin-4-one (0.99 g, 1.74 mmol), piperazine (3.01 g, 34.89 mmol) and BOP (1.54 g, 3.49 mmol) in chloroform (30 mL) was stirred at 70° C. for 12 hours. After completion, the resulting solution was concentrated under vacuum. The residue was purified by reverse-phase column eluting with water/acetonitrile (65/35) to afford N,N-bis[(4-methoxyphenyl)methyl]-4-methyl-6-(4-piperazin-1-yl-5,6,7,8-tetrahydroquinazolin-7-yl)-5-(trifluoromethyl)pyridin-2-amine (0.46 g, 0.72 mmol, 41.3% yield) as a yellow solid. LCMS (ESI, m/z): 633.3 [M+H]+.

Step 6: 4-methyl-6-(4-piperazin-1-yl-5,6,7,8-tetrahydroquinazolin-7-yl)-5-(trifluoromethyl)pyridin-2-amine

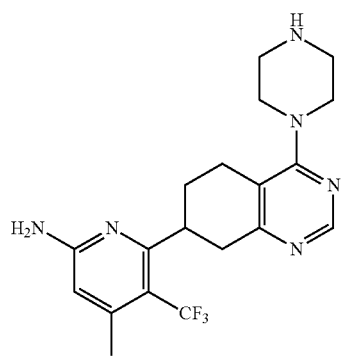 [SMILES: Cc1cc(N)nc(C2CCc3c(ncnc3N3CCNCC3)C2)c1C(F)(F)F]

A solution of N,N-bis[(4-methoxyphenyl)methyl]-4-methyl-6-(4-piperazin-1-yl-5,6,7,8-tetrahydroquinazolin-7-yl)-5-(trifluoromethyl)pyridin-2-amine (651 mg, 1.03 mmol) in trifluoroacetic acid (10 mL, 134.65 mmol) was stirred at 50° C. for 12 hours. After completion, the resulting solution was concentrated under vacuum. The residue was diluted with dichloromethane and adjusted to pH 9 with N,N-diisopropylethylamine. The resulting solution was concentrated under vacuum. The residue was purified by reverse-phase column with eluting with water/acetonitrile (62/38) to afford 4-methyl-6-(4-piperazin-1-yl-5,6,7,8-tetrahydroquinazolin-7-yl)-5-(trifluoromethyl)pyridin-2-amine (191 mg, 0.49 mmol, 47.5% yield) as a yellow solid. LCMS (ESI, m/z): 393 [M+H]$^+$.

Step 7: 1-[4-[7-[6-amino-4-methyl-3-(trifluoromethyl)-2-pyridyl]-5,6,7,8-tetrahydroquinazolin-4-yl]piperazin-1-yl]prop-2-en-1-one

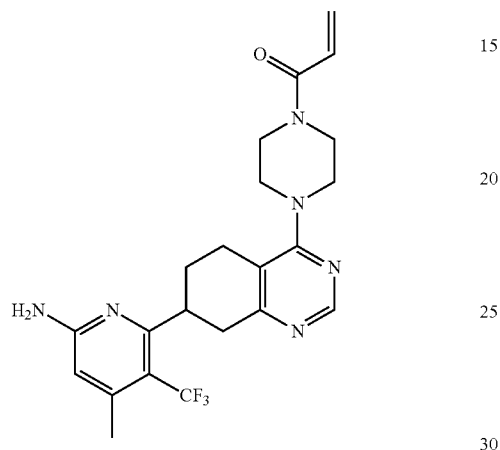

A solution of acrylic acid (0.19 g, 2.57 mmol), HATU (0.98 g, 2.57 mmol) and N,N-diisopropylethylamine (0.13 g, 1.03 mmol) in dichloromethane (5 mL) was stirred at 25° C. for 30 minutes. Then the solution was added to the solution of 4-methyl-6-(4-piperazin-1-yl-5,6,7,8-tetrahydroquinazolin-7-yl)-5-(trifluoromethyl)pyridin-2-amine (0.19 g, 0.49 mmol) in dichloromethane (5 mL) and N,N-dimethylformamide (5 mL) at 25° C., and the resulting solution was stirred at 25° C. for 1 hour. After completion, the resulting solution was quenched with water and extracted with dichloromethane. The organic layer was concentrated under vacuum. The residue was purified by flash chromatography on silica gel eluting with dichloromethane/methanol (93/7) to afford 120 mg crude. Then the crude was further purified by Prep-HPLC with the following condition to afford 1-[4-[7-[6-amino-4-methyl-3-(trifluoromethyl)-2-pyridyl]-5,6,7,8-tetrahydroquinazolin-4-yl]piperazin-1-yl]prop-2-en-1-one (68.8 mg, 0.15 mmol, 30.6% yield) as a white solid. Prep-HPLC condition: Column: XBridge Prep OBD C18 Column 30×150 mm 5 um; Mobile Phase A: Water (10 mmoL/L NH$_4$HCO$_3$), Mobile Phase B: ACN; Flow rate: 25 mL/min; Gradient: 28% B to 52% B in 7 min; 254220 nm; Rt: 5.85 min.

Example 26: $^1$H NMR (400 MHz, DMSO-d$_6$, ppm) 8.47 (s, 1H), 6.83 (dd, J=16.7, 10.5 Hz, 1H), 6.49 (s, 2H), 6.22 (s, 1H), 6.15 (dd, J=16.7, 2.4 Hz, 1H), 5.72 (dd, J=10.4, 2.4 Hz, 1H), 3.82-3.68 (m, 2H), 3.67-3.54 (m, 2H), 3.49-3.40 (m, 3H), 3.32-3.16 (m, 3H), 2.85-2.75 (m, 2H), 2.65-2.56 (m, 1H), 2.29 (s, 3H), 1.92 (d, J=12.7 Hz, 1H), 1.80-1.65 (m, 1H). LCMS (ESI, m/z): 447.2 [M+H]$^+$.

Examples 27a and 27b

Example 27a

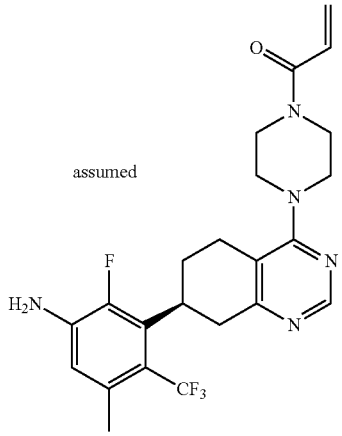

assumed

Example 27b

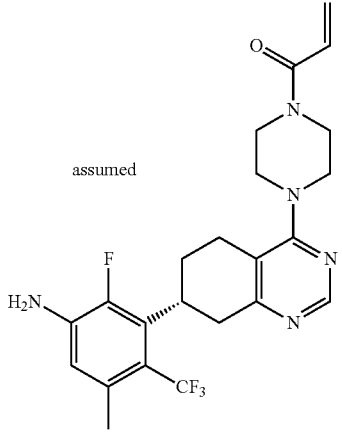

assumed

1-[4-[(7S)-7-[3-amino-2-fluoro-5-methyl-6-(trifluoromethyl)phenyl]-5,6,7,8-tetrahydroquinazolin-4-yl]piperazin-1-yl]prop-2-en-1-one (Example 27a); and 1-[4-[(7R)-7-[3-amino-2-fluoro-5-methyl-6-(trifluoromethyl)phenyl]-5,6,7,8-tetrahydroquinazolin-4-yl]piperazin-1-yl]prop-2-en-1-one (Example 27b)

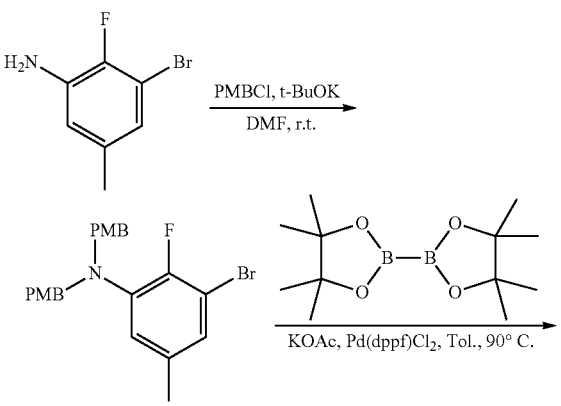

447
-continued
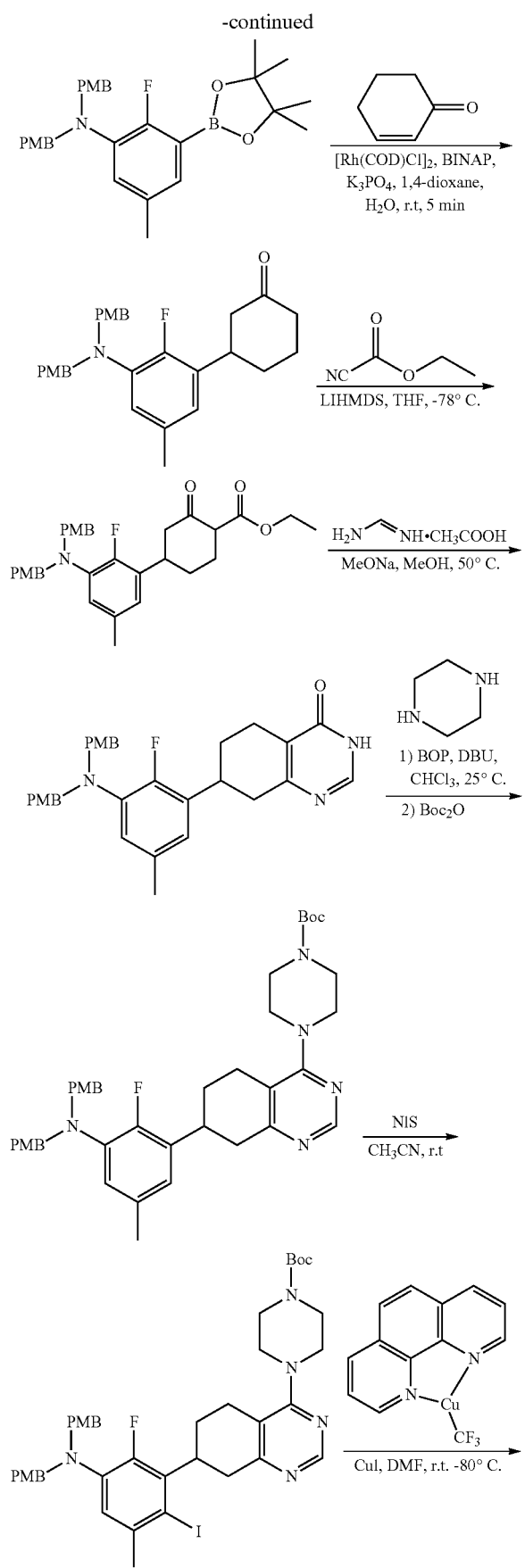
448
-continued
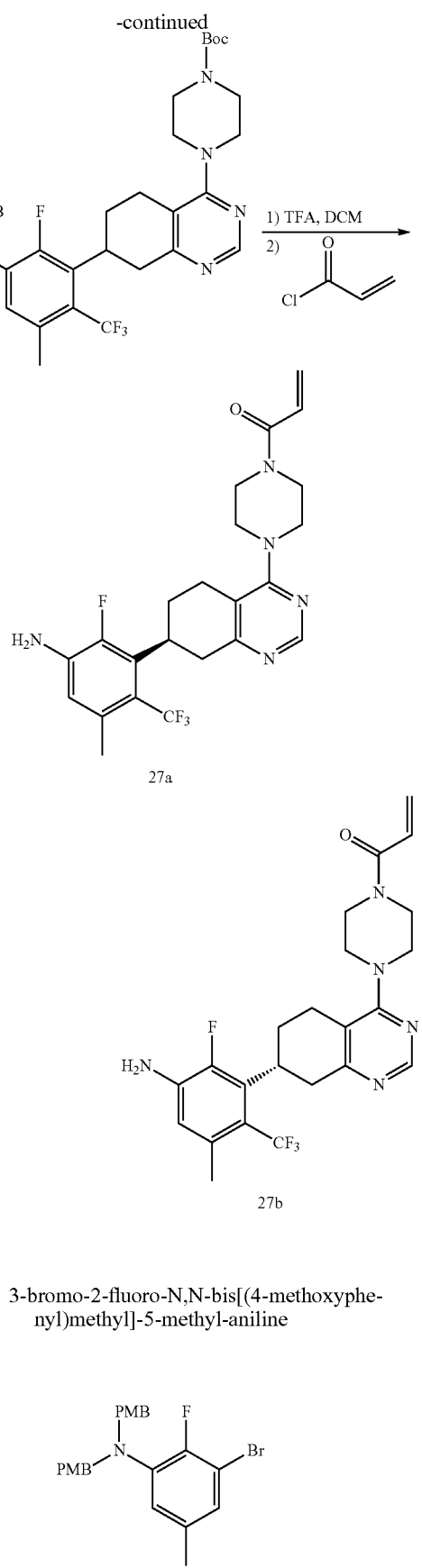
Step 1: 3-bromo-2-fluoro-N,N-bis[(4-methoxyphenyl)methyl]-5-methyl-aniline
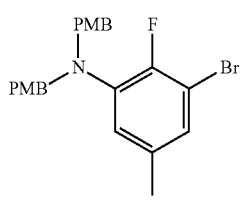

A solution of 3-bromo-2-fluoro-5-methyl-aniline (6.5 g, 31.8 mmol), and potassium tert-butoxide (10.7 g, 95.5 mmol) in N,N-dimethylformamide (65 mL) was stirred at 25° C. for 5 minutes. Then 4-methoxybenzylchloride (17.2 mL, 127.4 mmol) was added and stirred at 25° C. for 16 hours. After completion, the resulting solution was diluted with water and extracted with ethyl acetate. Then the organic layers were combined, washed with brine, dried over anhydrous sodium sulfate and concentrated under vacuum. The residue was triturated in methanol and vacuum filtered to afford 3-bromo-2-fluoro-N,N-bis[(4-methoxyphenyl)methyl]-5-methyl-aniline (9 g, 20.25 mmol, 63.6% yield) as a white solid. LCMS (ESI, m/z): 444.1 [M+H]$^+$.

Step 2: 2-fluoro-N,N-bis[(4-methoxyphenyl)methyl]-5-methyl-3-(4,4,5,5-tetramethyl-1,3,2-dioxaborolan-2-yl)aniline

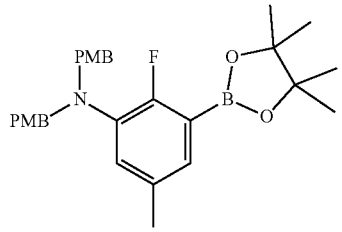

Under nitrogen, a solution of bis(pinacolato)diboron (15.4 g, 60.7 mmol), 3-bromo-2-fluoro-N,N-bis[(4-methoxyphenyl)methyl]-5-methyl-aniline (9.0 g, 20.2 mmol), [1,1'-bis(diphenylphosphino)ferrocene]dichloropalladium(II) (1.48 g, 2.0 mmol) and potassium acetate (3.9 g, 40.5 mmol) in toluene (90 mL) was stirred for 2 hours at 90° C. After completion, the resulting solution was concentrated under vacuum. The residue was dissolved with dichloromethane and washed with brine. The organic layer was dried over anhydrous sodium sulfate and concentrated under vacuum. The residue was purified by flash chromatography on silica gel eluting with petroleum ether/ethyl acetate (5/1) to afford 2-fluoro-N,N-bis[(4-methoxyphenyl)methyl]-5-methyl-3-(4,4,5,5-tetramethyl-1,3,2-dioxaborolan-2-yl)aniline (9 g, 14.6 mmol, 72.3% yield) as a white solid. LCMS (ESI, m/z): 492.3 [M+H]$^+$.

Step 3: 3-[3-[bis[(4-methoxyphenyl)methyl]amino]-2-fluoro-5-methyl-phenyl]cyclohexanone

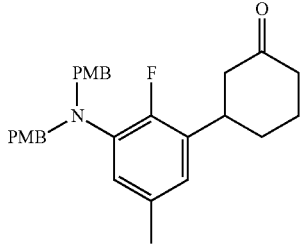

Under nitrogen, a solution of 2-cyclohexen-1-one (8.8 g, 91.58 mmol), 2-fluoro-N,N-bis[(4-methoxyphenyl)methyl]-5-methyl-3-(4,4,5,5-tetramethyl-1,3,2-dioxaborolan-2-yl)aniline (9.0 g, 18.3 mmol), chloro(1,5-cyclooctadiene)rhodium(I) dimer (902.9 mg, 1.8 mmol), BINAP (2.28 g, 3.6 mmol) and potassium phosphate (11.64 g, 54.9 mmol) in 1,4-dioxane (180 mL) and water (36 mL) was stirred at 30° C. for 5 minutes. After completion, the resulting solution was concentrated under vacuum. The residue was dissolved with dichloromethane and washed with brine. The organic layer was dried over anhydrous sodium sulfate and concentrated under vacuum. The residue was purified by flash chromatography on silica gel eluting with petroleum ether/ethyl acetate (5/1) to afford 3-[3-[bis[(4-methoxyphenyl)methyl]amino]-2-fluoro-5-methyl-phenyl]cyclohexanone (5.5 g, 11.9 mmol, 65.1% yield) as a yellow oil. LCMS (ESI, m/z): 462.3 [M+H]$^+$.

Step 4: ethyl 4-[3-[bis[(4-methoxyphenyl)methyl]amino]-2-fluoro-5-methyl-phenyl]-2-oxo-cyclohexanecarboxylate

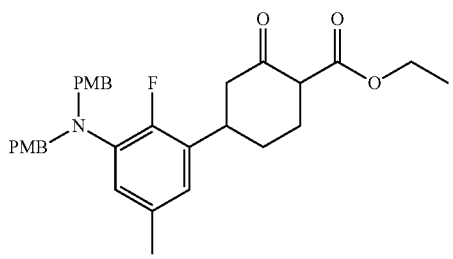

Under nitrogen, a solution of 3-[3-[bis[(4-methoxyphenyl)methyl]amino]-2-fluoro-5-methyl-phenyl]cyclohexanone (4.5 g, 9.7 mmol) in tetrahydrofuran (45 mL) and lithium bis(trimethylsilyl)amide (1 M in THF) (29.0 mL, 29.2 mmol) was added at −78° C. The resulting solution was stirred for 20 minutes at −78° C. Then ethyl cyanoformate (2.8 g, 28.6 mmol) was added and stirred at −78° C. for 30 minutes. After completion, the reaction was quenched with water and extracted with dichloromethane. Then the organic layers were combined, dried over anhydrous sodium sulfate and concentrated under vacuum. The crude product would be directly used in the next step without purification. LCMS (ESI, m/z): 534.3 [M+H]$^+$ Step 5: 7-[3-[bis[(4-methoxyphenyl)methyl]amino]-2-fluoro-5-methyl-phenyl]-5,6,7,8-tetrahydro-3H-quinazolin-4-one

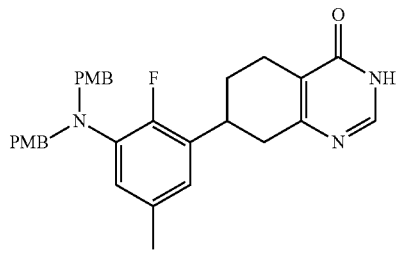

A solution of ethyl 4-[3-[bis[(4-methoxyphenyl)methyl]amino]-2-fluoro-5-methyl-phenyl]-2-oxo-cyclohexanecarboxylate (10.0 g, 18.7 mmol), formamidine acetate (11.6 g, 112.44 mmol) and sodium methanolate (10.8 g, 187.4 mmol) in methanol (100 mL) was stirred at 50° C. for 1 hour. After completion, the resulting solution was adjusted to pH 8 with saturated ammonium chloride solution and extracted with dichloromethane. Then the organic layers were combined, dried over anhydrous sodium sulfate and concentrated under vacuum. The residue was purified by flash chromatography on silica gel eluting with dichloromethane/methanol (10/1) to afford 7-[3-[bis[(4-methoxyphenyl)methyl]amino]-2-fluoro-5-methyl-phenyl]-5,6,7,8-tetrahydro-3H-quinazolin-4-one (5 g, 9.7 mmol, 51.9% yield) as a yellow oil. LCMS (ESI, m/z): 514.2 [M+H]⁺.

Step 6: tert-butyl 4-[7-[3-[bis[(4-methoxyphenyl)methyl]amino]-2-fluoro-5-methyl-phenyl]-5,6,7,8-tetrahydroquinazolin-4-yl]piperazine-1-carboxylate

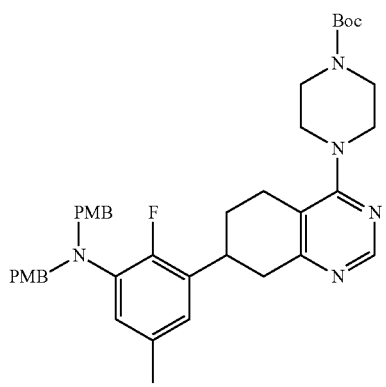

A solution of 7-[3-[bis[(4-methoxyphenyl)methyl]amino]-2-fluoro-5-methyl-phenyl]-5,6,7,8-tetrahydro-3H-quinazolin-4-one (5.0 g, 9.7 mmol), piperazine (8.3 g, 97.3 mmol), (Benzotriazol-1-yloxy)tris(dimethylamino)phosphonium hexafluorophosphate (8 g, 18.8 mmol) and DBU (4.4 g, 29.2 mmol) in chloroform (150 mL) was stirred at 25° C. for 30 minutes. Then di-tert-butyldicarbonate (53.1 g, 243.3 mmol) was added and stirred for 30 minutes. After completion, the solvent was diluted with dichloromethane and washed with brine. Then the organic layer was dried over anhydrous sodium sulfate and concentrated under vacuum. The residue was purified by flash chromatography on silica gel eluting with petroleum ether/ethyl acetate (4/6) to afford tert-butyl 4-[7-[3-[bis[(4-methoxyphenyl)methyl]amino]-2-fluoro-5-methyl-phenyl]-5,6,7,8-tetrahydroquinazolin-4-yl]piperazine-1-carboxylate (4 g, 5.8 mmol, 60.3% yield) as a yellow oil. LCMS (ESI, m/z): 682.4 [M+H]⁺

Step 7: tert-butyl 4-[7-[3-[bis[(4-methoxyphenyl)methyl]amino]-2-fluoro-6-iodo-5-methyl-phenyl]-5,6,7,8-tetrahydroquinazolin-4-yl]piperazine-1-carboxylate

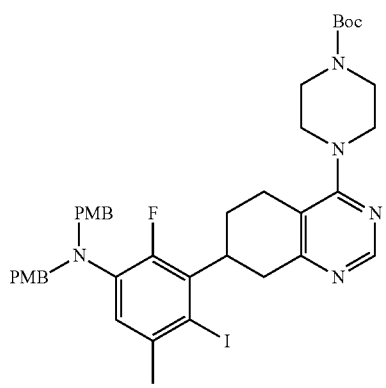

A solution of N-iodosuccinimide (0.49 g, 2.2 mmol) and tert-butyl 4-[7-[3-[bis[(4-methoxyphenyl)methyl]amino]-2-fluoro-5-methyl-phenyl]-5,6,7,8-tetrahydroquinazolin-4-yl]piperazine-1-carboxylate (1.0 g, 1.4 mmol) in acetonitrile (10 mL) was stirred at 25° C. for 1 hour. After completion, the reaction was concentrated under vacuum. The residue was purified by flash chromatography on silica gel eluting with acetonitrile/water (9/1) to afford tert-butyl 4-[7-[3-[bis[(4-methoxyphenyl)methyl]amino]-2-fluoro-6-iodo-5-methyl-phenyl]-5,6,7,8-tetrahydroquinazolin-4-yl]piperazine-1-carboxylate (500 mg, 0.6 mmol, 42.2% yield) as a yellow solid. LCMS (ESI, m/z): 808.3 [M+H]⁺

Step 8: tert-butyl 4-[7-[3-[bis[(4-methoxyphenyl)methyl]amino]-2-fluoro-5-methyl-6-(trifluoromethyl)phenyl]-5,6,7,8-tetrahydroquinazolin-4-yl]piperazine-1-carboxylate

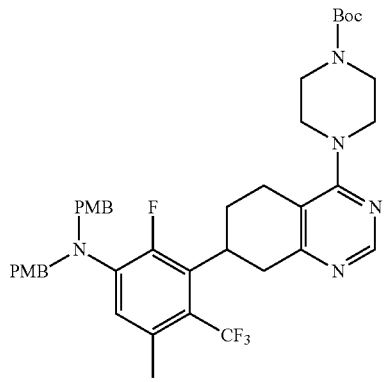

Under nitrogen, a solution of tert-butyl 4-[7-[3-[bis[(4-methoxyphenyl)methyl]amino]-2-fluoro-6-iodo-5-methyl-phenyl]-5,6,7,8-tetrahydroquinazolin-4-yl]piperazine-1-carboxylate (500 mg, 0.62 mmol), (1,10-phenanthroline)(trifluoromethyl)copper(I) (1.93 g, 6.2 mmol), cuprous iodide (2.34 g, 12.3 mmol) and in N,N-dimethylformamide (10 mL) at 80° C. for 16 hours. After completion, the filtrate was collected by filtration and diluted with water, extracted with ethyl acetate. Then the organic layers were combined, dried over anhydrous sodium sulfate and concentrated under vacuum. The residue was purified by flash chromatography on silica gel eluting with dichloromethane/ethyl acetate (7/3) to afford tert-butyl 4-[7-[3-[bis[(4-methoxyphenyl)methyl] amino]-2-fluoro-5-methyl-6-(trifluoromethyl)phenyl]-5,6,7, 8-tetrahydroquinazolin-4-yl]piperazine-1-carboxylate (280 mg, 0.26 mmol, 42.2% yield) as a yellow solid. LCMS (ESI, m/z): 750.3 [M+H]⁺

Step 9a: 2-fluoro-5-methyl-3-(4-piperazin-1-yl-5,6, 7,8-tetrahydroquinazolin-7-yl)-4-(trifluoromethyl) aniline

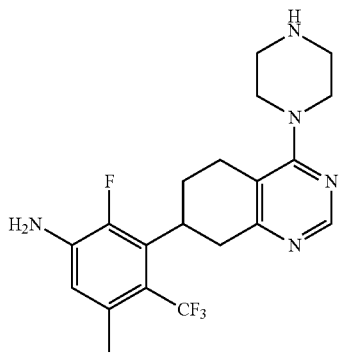 [SMILES: Cc1cc(N)c(F)c(C2CCc3c(ncnc3N3CCNCC3)C2)c1C(F)(F)F]

A solution of tert-butyl 4-[7-[3-[bis[(4-methoxyphenyl) methyl]amino]-2-fluoro-5-methyl-6-(trifluoromethyl)phenyl]-5,6,7,8-tetrahydroquinazolin-4-yl]piperazine-1-carboxylate (260.0 mg, 0.35 mmol) and trifluoroacetic acid (0.5 mL, 6.73 mmol) in dichloromethane (3 mL) was stirred at 25° C. for 2 hours. After completion, the resulting solution was concentrated under vacuum to afford a crude product (150 mg, 90% purity) which was used directly for next step without purification. LCMS (ESI, m/z): 410.2 [M+H]⁺

Step 9b: 1-[4-[(7S)-7-[3-amino-2-fluoro-5-methyl-6-(trifluoromethyl)phenyl]-5,6,7,8-tetrahydroquinazolin-4-yl]piperazin-1-yl]prop-2-en-1-one (Example 27a) and 1-[4-[(7R)-7-[3-amino-2-fluoro-5-methyl-6-(trifluoromethyl)phenyl]-5,6,7,8-tetrahydroquinazolin-4-yl]piperazin-1-yl]prop-2-en-1-one (Example 27b)

27a
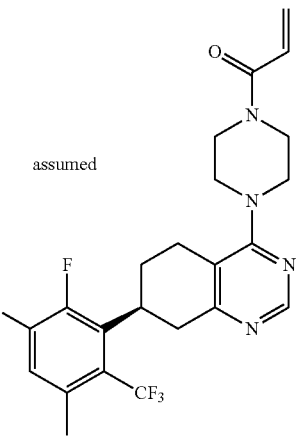

27b
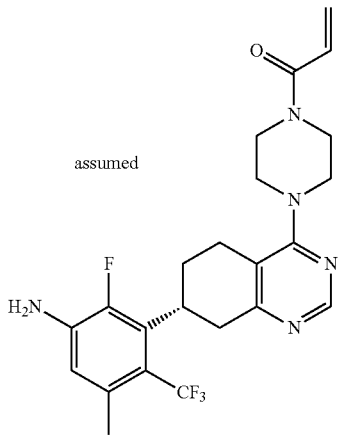

A solution of 2-fluoro-5-methyl-3-(4-piperazin-1-yl-5,6, 7,8-tetrahydroquinazolin-7-yl)-4-(trifluoromethyl)aniline (150.0 mg, 90% purity) and N,N-diisopropylethylamine (141.7 mg, 1.1 mmol) in dichloromethane (5 mL) was stirred at −78° C. for 3 minutes. Then acryloyl chloride (33.1 mg, 0.3 mmol) was added and stirred at −78° C. for 1 hour. After completion, the resulting solution was concentrated under vacuum. The residue was purified by flash chromatography on silica gel eluting with dichloromethane/methanol (20/1) to afford 70 mg crude product. The crude product was purified by Prep-HPLC to get 26 mg white solid. The product was further purified by Chiral-Prep-HPLC with following condition (Column: (CHIRALPAK IA, 2*25 cm, 5 um; Mobile Phase A: MTBE (10 mM NH3-MEOH)—HPLC—Mobile Phase B: EtOH—HPLC; Flow rate: 15 m/min; Gradient: 10 B to 10 B in 15 min; 254/220 nm) to afford the title compounds. The stereo chemistry of title compounds was arbitrarily assigned.

Example 27a: 1-[4-[(7S)-7-[3-amino-2-fluoro-5-methyl-6-(trifluoromethyl)phenyl]-5,6,7,8-tetrahydroquinazolin-4-yl]piperazin-1-yl]prop-2-en-1-one (9 mg, 0.019 mmol, 5.3% yield, white solid). ¹H NMR (400 MHz, DMSO-d₆, ppm) δ 8.48 (s, 1H), 6.83 (dd, J=16.7, 10.4 Hz, 1H), 6.56 (d, J=8.8 Hz, 1H), 6.14 (dd, J=16.7, 2.4 Hz, 1H), 5.79 (s, 2H), 5.72 (dd, J=10.4, 2.0 Hz, 1H), 3.85-3.68 (m, 2H), 3.61 (s, 2H), 3.53-3.43 (m, 2H), 3.40-3.35 (m, 1H), 3.31-3.21 (m, 2H), 3.1-2.98 (m, 1H), 2.96-2.89 (m, 1H), 2.80-2.70 (m, 1H), 2.64 (d, J=16.1 Hz, 1H), 2.29 (s, 3H), 2.09-1.90 (m, 2H). LCMS (ESI, m/z): 464.2 [M+H]⁺. Chiral HPLC: Column: CHIRALPAK IA-3, 4.6*50 mm, 3 um; detected at 254 nm; MtBE(0.1% DEA): EtOH=90:10; Flow rate: 1 mL/min; Retention time: 1.296 min; (faster peak).

Example 27b: 1-[4-[(7R)-7-[3-amino-2-fluoro-5-methyl-6-(trifluoromethyl)phenyl]-5,6,7,8-tetrahydroquinazolin-4-yl]piperazin-1-yl]prop-2-en-1-one (6.8 mg, 0.014 mmol, 4% yield, white solid). ¹H NMR (400 MHz, DMSO-d₆, ppm) δ 8.49 (s, 1H), 6.83 (dd, J=16.7, 10.5 Hz, 1H), 6.56 (d, J=8.8 Hz, 1H), 6.14 (dd, J=16.7, 2.4 Hz, 1H), 5.79 (s, 2H), 5.72 (dd, J=9.6, 2.4 Hz, 1H), 3.85-3.75 (m, 2H), 3.61-3.45 (m, 4H), 3.40-3.35 (m, 1H), 3.30-3.20 (m, 2H), 3.11-2.98 (m, 1H), 2.95-2.85 (m, 1H), 2.82-2.70 (m, 1H), 2.69-2.59 (m, 1H), 2.30 (m, 3H), 2.10-1.90 (m, 2H). LCMS (ESI, m/z): 464.2 [M+H]⁺. Chiral HPLC: Column: CHIRALPAK IA-3, 4.6*50 mm, 3 um; detected at 254 nm; MtBE(0.1% DEA): EtOH=90:10; Flow rate: 1 mL/min; Retention time: 1.825 min; (slower peak).

Examples 28a and 28b
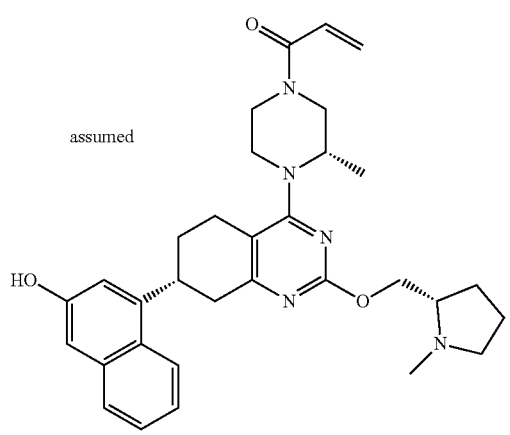
Example 28a
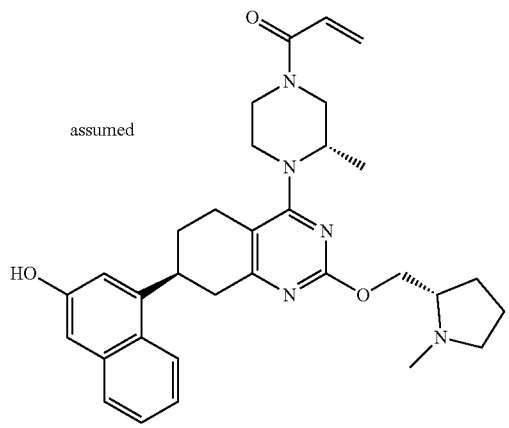
Example 28b
1-[(3S)-4-[(7R)-7-(3-hydroxy-1-naphthyl)-2-[[(2S)-1-methylpyrrolidin-2-yl]methoxy]-5,6,7,8-tetrahydroquinazolin-4-yl]-3-methyl-piperazin-1-yl]prop-2-en-1-one (Example 28a); and
1-[(3S)-4-[(7S)-7-(3-hydroxy-1-naphthyl)-2-[[(2S)-1-methylpyrrolidin-2-yl]methoxy]-5,6,7,8-tetrahydroquinazolin-4-yl]-3-methyl-piperazin-1-yl]prop-2-en-1-one (Example 28b)
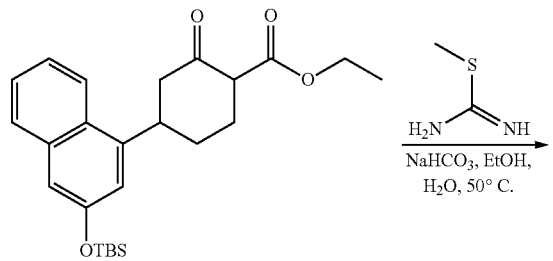
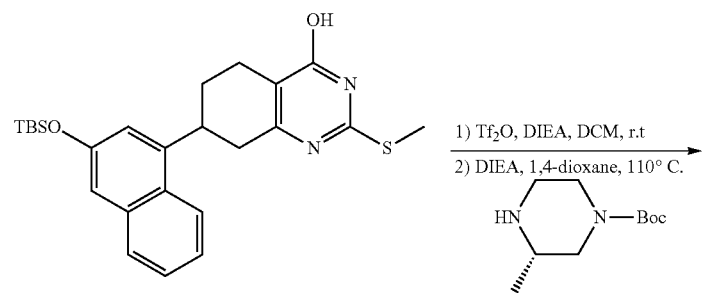

-continued
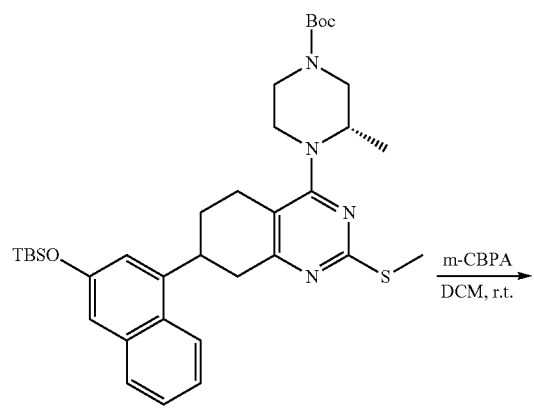
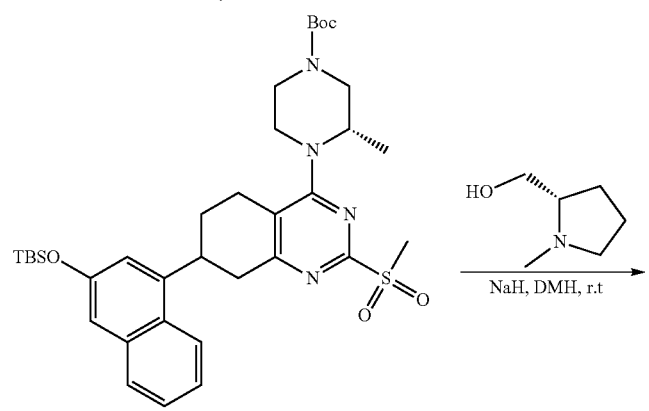
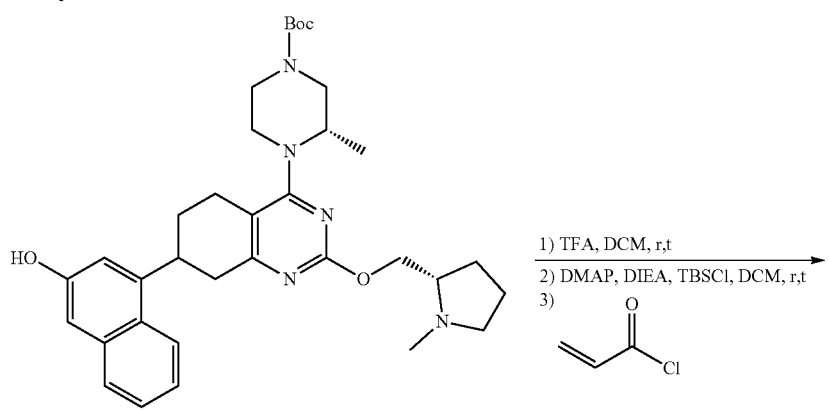
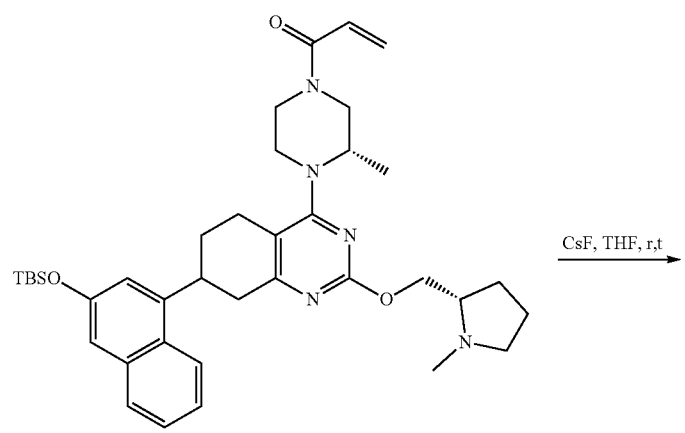

-continued

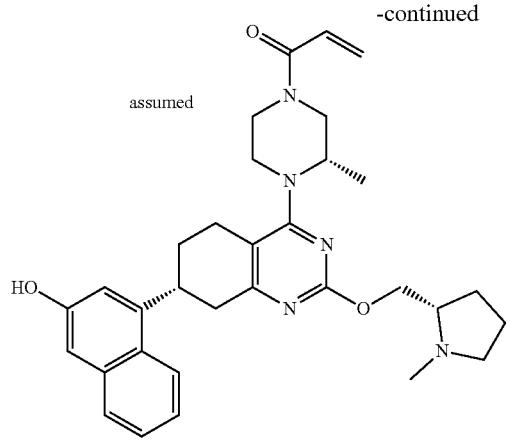

28a

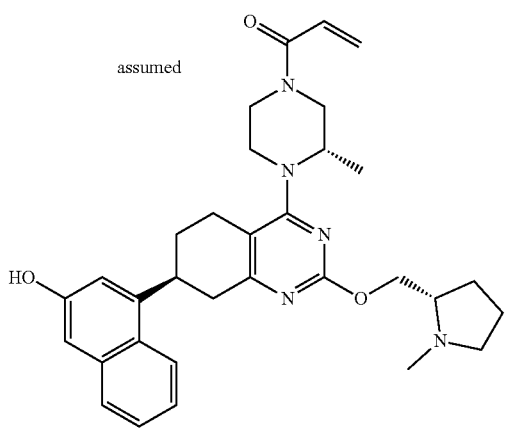

28b

Step 1: 7-[3-[tert-butyl(dimethyl)silyl]oxy-1-naphthyl]-2-methylsulfanyl-5,6,7,8-tetrahydroquinazolin-4-ol Step 2: tert-butyl (3S)-4-[7-[3-[tert-butyl(dimethyl)silyl]oxy-1-naphthyl]-2-methylsulfanyl-5,6,7,8-tetrahydroquinazolin-4-yl]-3-methyl-piperazine-1-carboxylate

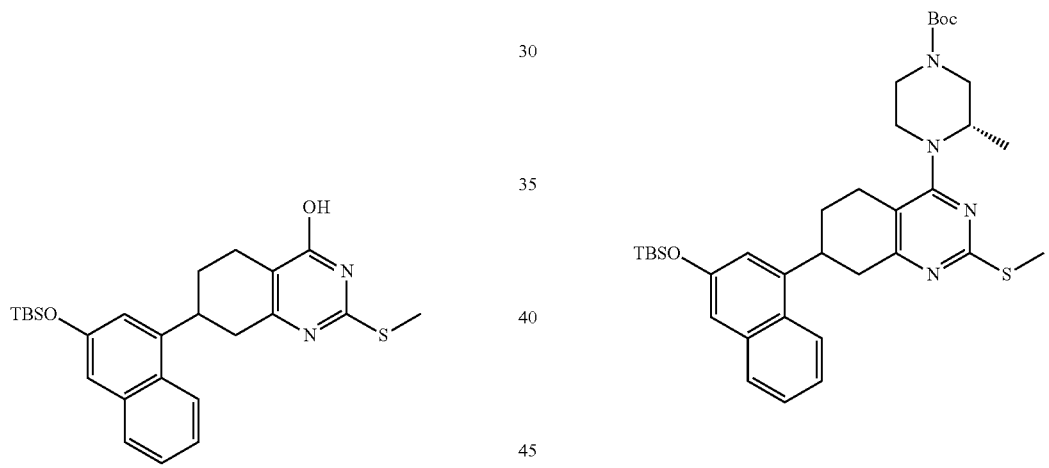

A solution of ethyl 4-[3-[tert-butyl(dimethyl)silyl]oxy-1-naphthyl]-2-oxo-cyclohexanecarboxylate (10.0 g, 23.4 mmol), 2-methyl-2-thiopseudourea sulfate (65.25 g, 234.4 mmol) and sodium bicarbonate (39.38 g, 468.8 mmol) in ethanol (120 mL) and water (25 mL) was stirred at 50° C. for 3 hours. After completion, the reaction was diluted with water and extracted with dichloromethane. Then the organic layers were combined, dried over anhydrous sodium sulfate and concentrated under vacuum. The residue was purified by flash chromatography on silica gel eluting with dichloromethane/methanol (97/3) to afford 7-[3-[tert-butyl(dimethyl)silyl]oxy-1-naphthyl]-2-methylsulfanyl-5,6,7,8-tetrahydroquinazolin-4-ol (5 g, 11.0 mmol, 47.1% yield) as a white solid. LCMS (ESI, m/z): 453.2 [M+H]+.

A solution of 7-[3-[tert-butyl(dimethyl)silyl]oxy-1-naphthyl]-2-methylsulfanyl-5,6,7,8-tetrahydroquinazolin-4-ol (2.0 g, 4.4 mmol) and N,N-diisopropylethylamine (2.84 g, 22.0 mmol) in dichloromethane (20 mL) was stirred at 25° C. for 3 minutes. Then trifluoromethanesulfonic anhydride (2.49 g, 8.8 mmol) was added and stirred at 25° C. for 1 hour. After completion, the resulting solution was concentrated under reduced pressure and dissolved in 1,4-dioxane (30 mL). Then N,N-diisopropylethylamine (4.41 g, 34.2 mmol) and tert-butyl (3S)-3-methyl-1-piperazinecarboxylate (1.37 g, 6.8 mmol) in was added and the mixture were stirred at 110° C. for 16 hours. After completion, resulting solution was concentrated under vacuum. The residue was purified by flash chromatography on silica gel eluting with hexane/ethyl acetate (7/1) to afford tert-butyl (3S)-4-[7-[3-[tert-butyl(dimethyl)silyl]oxy-1-naphthyl]-2-methylsulfanyl-5,6,7,8-tetrahydroquinazolin-4-yl]-3-methyl-piperazine-1-carboxylate (1.8 g, 2.8 mmol, 63.6% yield) as a yellow solid. LCMS (ESI, m/z): 635.3 [M+H]+.

Step 3: tert-butyl (3S)-4-[7-[3-[tert-butyl(dimethyl)silyl]oxy-1-naphthyl]-2-methylsulfonyl-5,6,7,8-tetrahydroquinazolin-4-yl]-3-methyl-piperazine-1-carboxylate

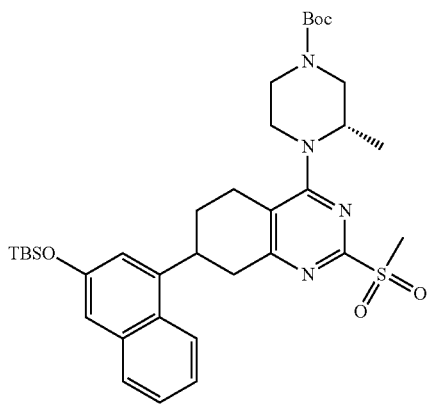 [SMILES: C[C@H]1CN(C(=O)OC(C)(C)C)CCN1c1nc(S(C)(=O)=O)nc2c1CCC(c1cc(O[Si](C)(C)C(C)(C)C)cc3ccccc13)C2]

A solution of tert-butyl (3S)-4-[7-[3-[tert-butyl(dimethyl)silyl]oxy-1-naphthyl]-2-methylsulfanyl-5,6,7,8-tetrahydroquinazolin-4-yl]-3-methyl-piperazine-1-carboxylate (2.0 g, 3.1 mmol) and 3-chloroperoxybenzoic acid (1.6 g, 9.4 mmol) in dichloromethane (20 mL) was stirred at 25° C. for 2 hours. After completion, the resulting solution was quenched with saturated sodium sulfite solution. The resulting solution was extracted with ethyl acetate, dried over anhydrous sodium sulfate and concentrated under vacuum to afford tert-butyl (3S)-4-[7-[3-[tert-butyl(dimethyl)silyl]oxy-1-naphthyl]-2-methylsulfonyl-5,6,7,8-tetrahydroquinazolin-4-yl]-3-methyl-piperazine-1-carboxylate (1.5 g, 2.2 mmol, 71% yield) as a yellow solid. LCMS (ESI, m/z): 667.3 $[M+H]^+$.

Step 4: tert-butyl (3S)-4-[7-(3-hydroxy-1-naphthyl)-2-[[(2S)-1-methylpyrrolidin-2-yl]methoxy]-5,6,7,8-tetrahydroquinazolin-4-yl]-3-methyl-piperazine-1-carboxylate

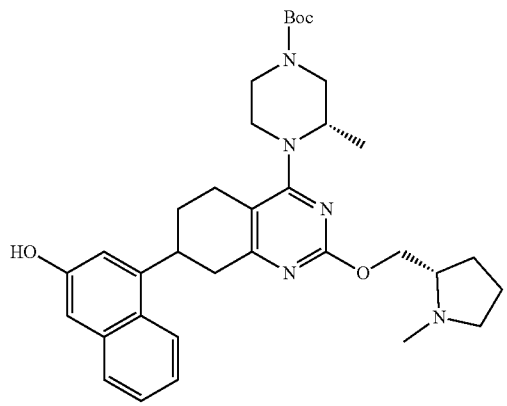 [SMILES: C[C@H]1CN(C(=O)OC(C)(C)C)CCN1c1nc(OC[C@@H]2CCCN2C)nc2c1CCC(c1cc(O)cc3ccccc13)C2]

A solution of N-methyl-1-prolinol (1.72 g, 14.9 mmol) in N,N-dimethylformamide (20 mL) was stirred at 25° C. for 5 minutes. Then sodium hydride (479.8 mg, 11.99 mmol, 60% dispersion in mineral oil) was added and stirred at 0° C. for 30 minutes. Then tert-butyl (3S)-4-[7-[3-[tert-butyl(dim-ethyl)silyl]oxy-1-naphthyl]-2-methylsulfonyl-5,6,7,8-tetrahydroquinazolin-4-yl]-3-methyl-piperazine-1-carboxylate (2.0 g, 3 mmol) was added and stirred at 25° C. for 1 hour. the resulting solution was adjusted to pH 8 with saturated ammonium chloride solution, extracted with ethyl acetate and washed with water. The organic layer was dried over anhydrous sodium sulfate and concentrated under vacuum. The residue was purified by flash chromatography on silica gel eluting with dichloromethane/methanol (10/1) to afford tert-butyl (3S)-4-[7-(3-hydroxy-1-naphthyl)-2-[[(2S)-1-methylpyrrolidin-2-yl]methoxy]-5,6,7,8-tetrahydroquinazolin-4-yl]-3-methyl-piperazine-1-carboxylate (1 g, 1.7 mmol, 56.7% yield) as a yellow solid. LCMS (ESI, m/z): 588.3 $[M+H]^+$.

Step 5: 1-[(3S)-4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]-3-methyl-piperazin-1-yl]prop-2-en-1-one

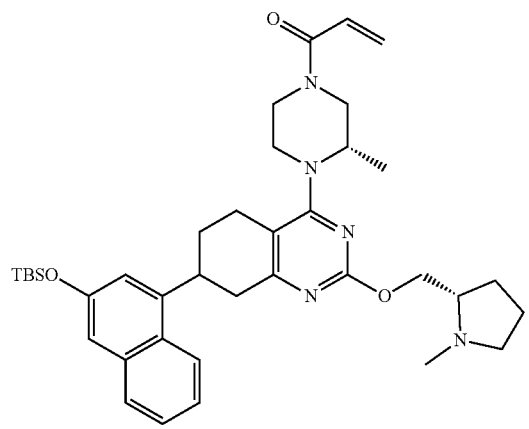 [SMILES: C=CC(=O)N1CCN(c2nc(OC[C@@H]3CCCN3C)nc3c2CCC(c2cc(O[Si](C)(C)C(C)(C)C)cc4ccccc24)C3)[C@@H](C)C1]

A solution of tert-butyl (3S)-4-[7-(3-hydroxy-1-naphthyl)-2-[[(2S)-1-methylpyrrolidin-2-yl]methoxy]-5,6,7,8-tetrahydroquinazolin-4-yl]-3-methyl-piperazine-1-carboxylate (1.3 g, 2.2 mmol) and trifluoroacetic acid (3 mL, 39.4 mmol) in dichloromethane (15 mL) was stirred at 25° C. for 30 minutes. After completion, the resulting solution was concentrated under reduced pressure and dissolved in dichloromethane (20 mL). Then N,N-diisopropylethylamine (1.4 g, 11 mmol) and 4-dimethylaminopyridine (268 mg, 2.2 mmol) were added and the system was stirred at 25° C. for 5 minutes. Then tert-butyldimethylsilyl chloride (663.0 mg, 4.4 mmol) was added and stirred at 25° C. for 1 hour. Then acryloyl chloride (198 mg, 2.2 mmol) was added and stirred at 25° C. for 30 minutes. After completion, the resulting solution was concentrated under vacuum. The residue was purified by flash chromatography on silica gel eluting with dichloromethane/methanol (20/1) to afford 1-[(3S)-4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]-3-methyl-piperazin-1-yl]prop-2-en-1-one (300 mg, 0.4 mmol, 18.2% yield) as a yellow solid. LCMS (ESI, m/z): 656.4 $[M+H]^+$.

Step 6: 1-[(3S)-4-[(7R)-7-(3-hydroxy-1-naphthyl)-2-[[(2S)-1-methylpyrrolidin-2-yl]methoxy]-5,6,7,8-tetrahydroquinazolin-4-yl]-3-methyl-piperazin-1-yl]prop-2-en-1-one (Example 28a) and 1-[(3S)-4-[(7S)-7-(3-hydroxy-1-naphthyl)-2-[[(2S)-1-methylpyrrolidin-2-yl]methoxy]-5,6,7,8-tetrahydroquinazolin-4-yl]-3-methyl-piperazin-1-yl]prop-2-en-1-one (Example 28b)

28a

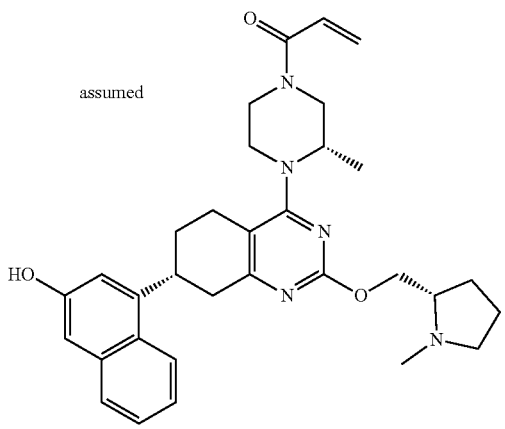

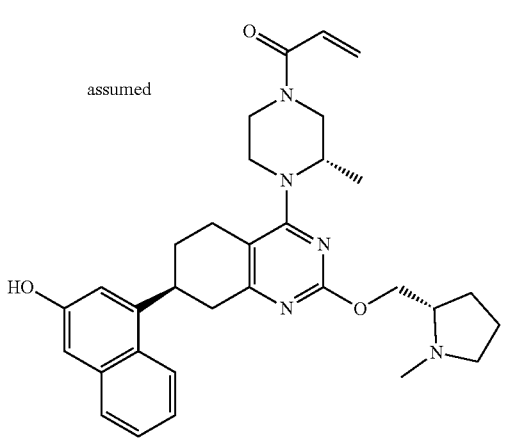

28b

A solution of 1-[(3S)-4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]-3-methyl-piperazin-1-yl]prop-2-en-1-one (700.0 mg, 1.07 mmol) and caesium fluoride (648.8 mg, 4.2 mmol) in tetrahydrofuran (10 mL) was stirred at 25° C. for 1 hour. After completion, the resulting solution was diluted with water and extracted with dichloromethane. Then the organic layers were collected, dried over anhydrous sodium sulfate and concentrated under vacuum. The residue was purified by flash chromatography on silica gel eluting with dichloromethane/methanol (10/1) to afford crude solid. The crude product was purified by Prep-HPLC to afford 150 mg white solid with the following conditions: Column: XBridge Prep C18 OBD Column 19×150 mm 5 um; Mobile Phase A: Water (10 MMOL/L NH4HCO3), Mobile Phase B: ACN; Flow rate: 60 mL/min; Gradient: 30% B to 48% B in 7 min; 254 nm; Rt: 6.5 min. The product was further purified by Chiral-Prep-HPLC with following condition: (Column, CHIRALPAK IA-3, 0.46*5 cm; 3 um; mobile phase: (Hex:DCM=3:1)(0.1% DEA): EtOH=50:50; Detector, UV 254 nm.) to afford the title compounds. The absolute configuration of the title compounds was inferred from potency data and a protein X-ray structure of compound 21b.

Example 28a: 1-[(3S)-4-[(7R)-7-(3-hydroxy-1-naphthyl)-2-[[(2S)-1-methylpyrrolidin-2-yl]methoxy]-5,6,7,8-tetrahydroquinazolin-4-yl]-3-methyl-piperazin-1-yl]prop-2-en-1-one (42.9 mg, 0.079 mmol, 7.4% yield, white solid). $^1$H NMR (400 MHz, DMSO-$d_6$, ppm) δ 9.68 (s, 1H), 8.08 (d, J=8.5 Hz, 1H), 7.77-7.63 (m, 1H), 7.40 (t, J=7.4 Hz, 1H), 7.30 (t, J=7.2, Hz, 1H), 7.01 (s, 2H), 6.94-6.76 (m, 1H), 6.21-6.12 (m, 1H), 5.72 (dd, J=10.3, 2.4 Hz, 1H), 4.38-4.00 (m, 5H), 3.94-3.81 (m, 2H), 3.65-3.42 (m, 2H), 3.31-3.18 (m, 1H), 3.08 (dd, J=18.1, 5.3 Hz, 1H), 2.98-2.84 (m, 3H), 2.83-2.72 (m, 1H), 2.63-2.53 (m, 1H), 2.33 (s, 3H), 2.20-2.07 (m, 2H), 1.96-1.77 (m, 2H), 1.72-1.55 (m, 3H), 1.02-0.98 (m, 3H). LCMS (ESI, m/z): 542.3 [M+H]$^+$. Chiral HPLC: Column: CHIRALPAK IA-3, 4.6*50 mm, 3 um; detected at 254 nm; MtBE(0.1% DEA): EtOH=90:10; Flow rate: 1 mL/min; Retention time: 1.350 min (slower peak).

Example 28b: 1-[(3S)-4-[(7S)-7-(3-hydroxy-1-naphthyl)-2-[[(2S)-1-methylpyrrolidin-2-yl]methoxy]-5,6,7,8-tetrahydroquinazolin-4-yl]-3-methyl-piperazin-1-yl]prop-2-en-1-one (42.3 mg, 0.078 mmol, 7.3% yield, white solid). $^1$H NMR (400 MHz, DMSO-$d_6$, ppm) δ 9.67 (s, 1H), 8.07 (d, J=8.5 Hz, 1H), 7.71 (d, J=8.1 Hz, 1H), 7.40 (t, J=7.5 Hz, 1H), 7.30 (t, J=7.2, Hz, 1H), 7.04-6.97 (m, 2H), 6.93-6.75 (m, 1H), 6.23-6.12 (m, 1H), 5.73 (dd, J=10.4, 2.4 Hz, 1H), 4.42-3.99 (m, 5H), 3.93-3.79 (m, 3H), 3.52-3.36 (m, 1H), 3.25-3.00 (m, 3H), 2.99-2.83 (m, 3H), 2.83-2.71 (m, 1H), 2.34 (s, 3H), 2.20-2.07 (m, 2H), 1.99-1.78 (m, 2H), 1.73-1.53 (m, 3H), 1.28-1.18 (m, 3H). LCMS (ESI, m/z): 542.3 [M+H]$^+$. LCMS (ESI, m/z): 542.3 [M+H]$^+$. Chiral HPLC: Column: CHIRALPAK IA-3, 4.6*50 mm, 3 m; detected at 254 nm; (Hex:DCM=3:1) (0.1% DEA): EtOH=50:50, Flow rate: 1 mL/min; Retention time: 0.983 min; (faster peak).

Examples 29a and 29b

Example 29a

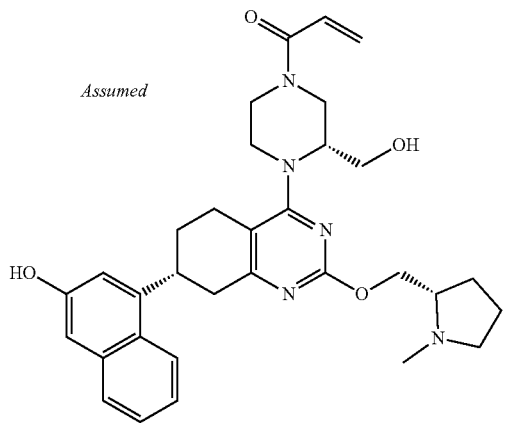

465
-continued
Example 29b
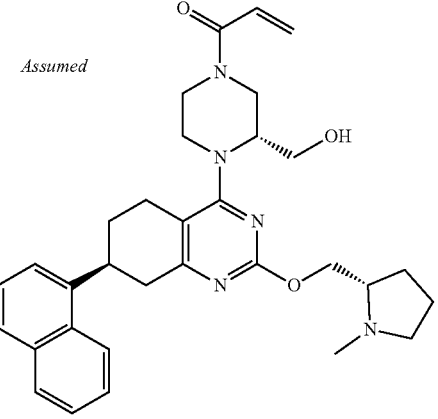
Assumed
466
1-[(3R)-3-(hydroxymethyl)-4-[(7R)-7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one (Example 29a); and
1-[(3R)-3-(hydroxymethyl)-4-[(7S)-7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one (Example 29b)
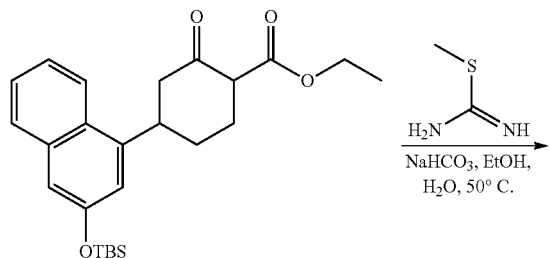
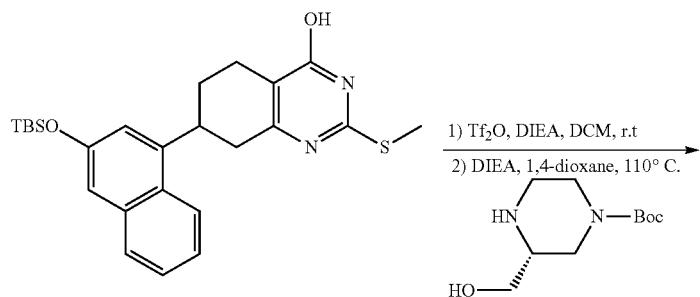
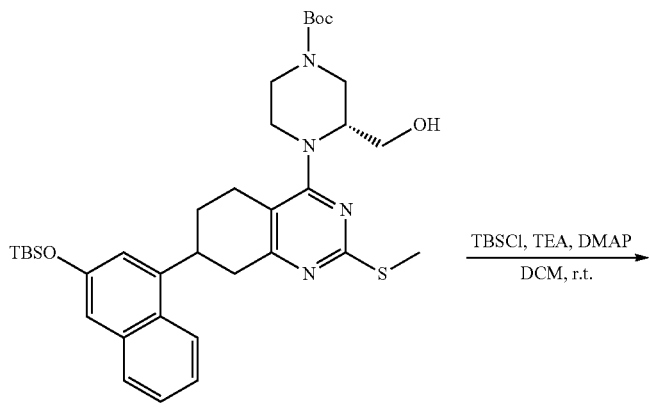

-continued
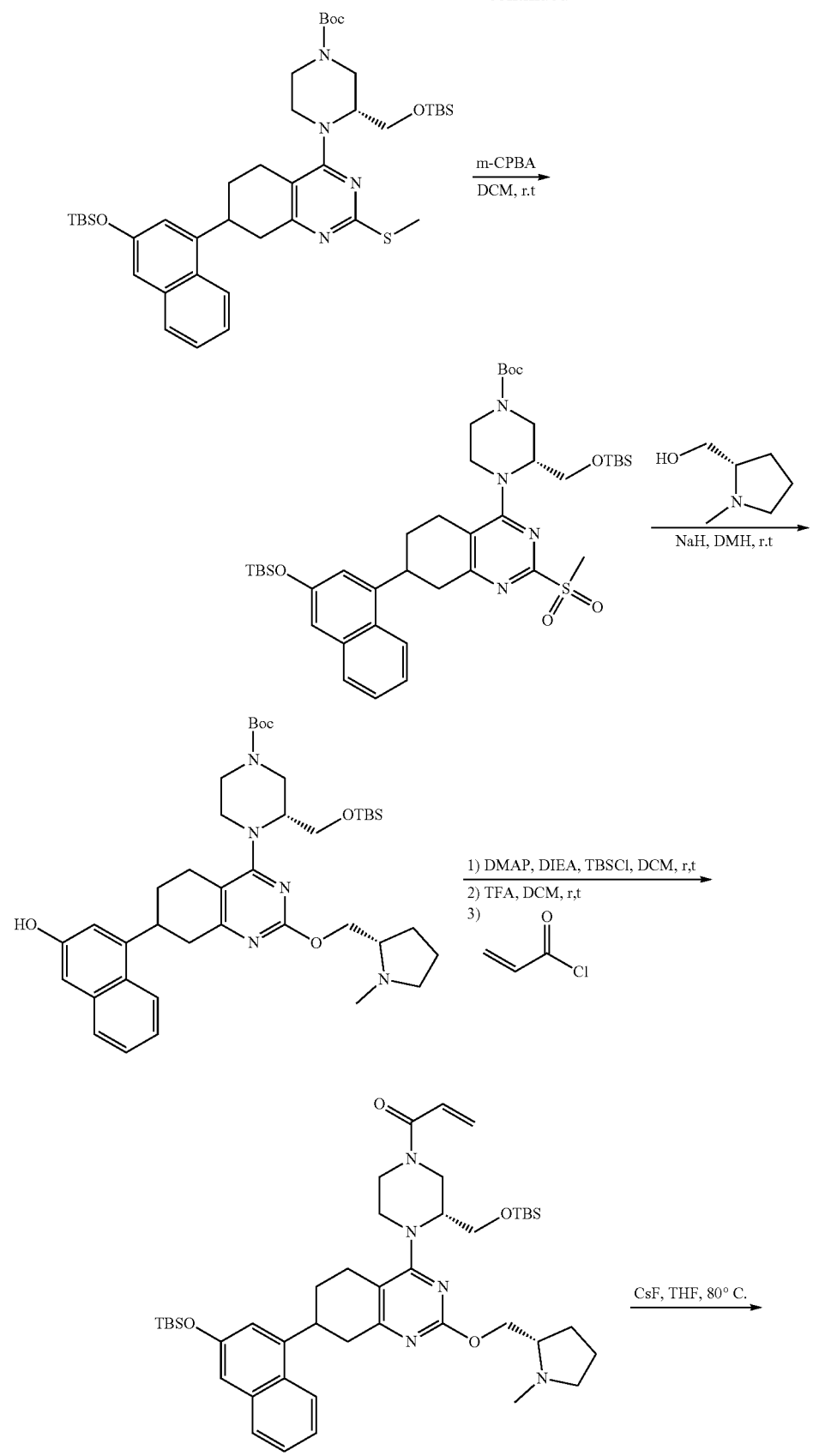

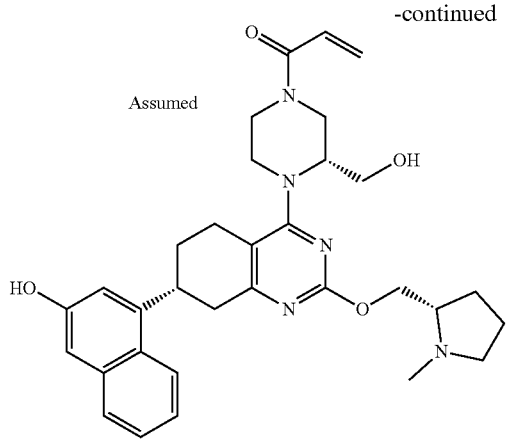

29a

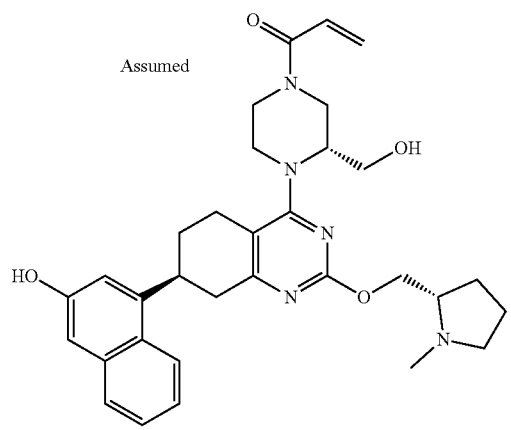

29b

Step 1: 7-[3-[tert-butyl(dimethyl)silyl]oxy-1-naphthyl]-2-methylsulfanyl-5,6,7,8-tetrahydroquinazolin-4-ol Step 2: tert-butyl (3R)-4-[7-[3-[tert-butyl(dimethyl)silyl]oxy-1-naphthyl]-2-methylsulfanyl-5,6,7,8-tetrahydroquinazolin-4-yl]-3-(hydroxymethyl)piperazine-1-carboxylate

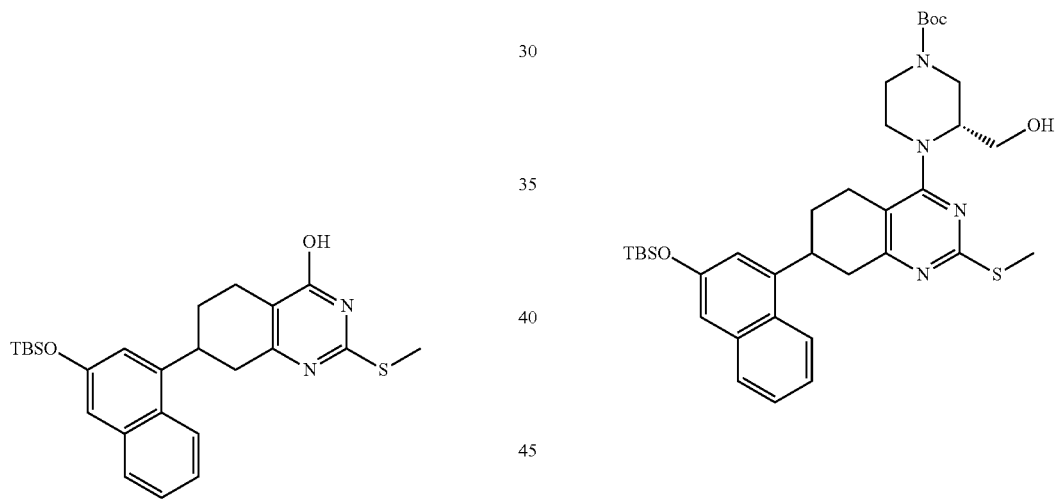

A solution of ethyl 4-[3-[tert-butyl(dimethyl)silyl]oxy-1-naphthyl]-2-oxo-cyclohexanecarboxylate (10.0 g, 23.4 mmol), 2-methyl-2-thiopseudourea sulfate (65.25 g, 234.4 mmol) and sodium bicarbonate (39.38 g, 468.8 mmol) in ethanol (120 mL) and water (25 mL) was stirred at 50° C. for 3 hours. After completion, the reaction was diluted with water and extracted with dichloromethane. Then the organic layers were combined, dried over anhydrous sodium sulfate and concentrated under vacuum. The residue was purified by flash chromatography on silica gel eluting with dichloromethane/methanol (97/3) to afford 7-[3-[tert-butyl(dimethyl)silyl]oxy-1-naphthyl]-2-methylsulfanyl-5,6,7,8-tetrahydroquinazolin-4-ol (5 g, 11.0 mmol, 47.1% yield) as a white solid. LCMS (ESI, m/z): 453.2 [1M+H]$^+$.

A solution of 7-[3-[tert-butyl(dimethyl)silyl]oxy-1-naphthyl]-2-methylsulfanyl-5,6,7,8-tetrahydroquinazolin-4-ol (5.0 g, 11.05 mmol) and N,N-diisopropylethylamine (7.17 g, 55.2 mmol) in dichloromethane (50 mL) was stirred at 25° C. for 3 minutes. Then trifluoromethanesulfonic anhydride (6.2 g, 22.1 mmol) was added and stirred at 25° C. for 1 hour. After completion, the resulting solution was concentrated under reduced pressure and dissolved in 1,4-dioxane (75 mL). Then N,N-diisopropylethylamine (11.0 g, 85.5 mmol) and (R)-4-n-boc-2-hydroxymethyl-piperazine (3.7 g, 17.1 mmol) were added and stirred at 110° C. for 16 hours. After completion, the resulting solution was concentrated under vacuum. The residue was purified by flash chromatography on silica gel eluting with hexane/ethyl acetate (10/1) to afford tert-butyl (3R)-4-[7-[3-[tert-butyl(dimethyl)silyl]oxy-1-naphthyl]-2-methylsulfanyl-5,6,7,8-tetrahydroquinazolin-4-yl]-3-(hydroxymethyl)piperazine-1-carboxylate (4 g, 6.1 mmol, 71.9% yield) as a yellow solid. LCMS (ESI, m/z): 651.3 [M+H]$^+$.

Step 3: tert-butyl (3R)-3-[[tert-butyl(dimethyl)silyl]oxymethyl]-4-[7-[3-[tert-butyl(dimethyl)silyl]oxy-1-naphthyl]-2-methylsulfanyl-5,6,7,8-tetrahydroquinazolin-4-yl]piperazine-1-carboxylate

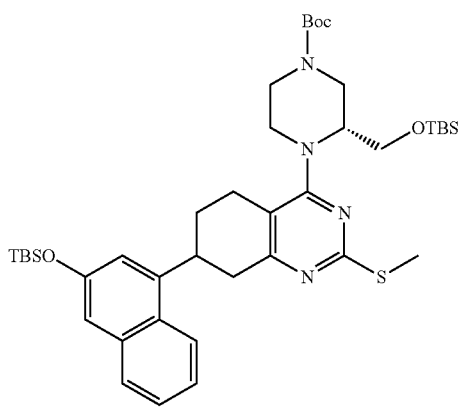 [SMILES: CSc1nc2c(c(N3CCN(C(=O)OC(C)(C)C)C[C@@H]3CO[Si](C)(C)C(C)(C)C)n1)CCC(c1cc(O[Si](C)(C)C(C)(C)C)cc3ccccc13)C2]

A solution of tert-butyl (3R)-4-[7-[3-[tert-butyl(dimethyl)silyl]oxy-1-naphthyl]-2-methylsulfanyl-5,6,7,8-tetrahydroquinazolin-4-yl]-3-(hydroxymethyl)piperazine-1-carboxylate (4.0 g, 6.14 mmol), 4-dimethylaminopyridine (749.6 mg, 6.14 mmol) and triethylamine (1.8 g, 18.43 mmol) in dichloromethane (40 mL) was stirred at 25° C. for 5 minutes. Then tert-butyldimethylsilyl chloride (1.8 g, 12.29 mmol) was added and stirred at 25° C. for 1 hour. After completion, the resulting solution was washed with water, dried over anhydrous sodium sulfate and concentrated under vacuum to afford tert-butyl (3R)-3-[[tert-butyl(dimethyl)silyl]oxymethyl]-4-[7-[3-[tert-butyl(dimethyl)silyl]oxy-1-naphthyl]-2-methylsulfanyl-5,6,7,8-tetrahydroquinazolin-4-yl]piperazine-1-carboxylate (4.2 g, 5.5 mmol, 89.3% yield) LCMS (ESI, m/z): 765.4 [M+H]$^+$.

Step 4: tert-butyl (3R)-3-[[tert-butyl(dimethyl)silyl]oxymethyl]-4-[7-[3-[tert-butyl(dimethyl)silyl]oxy-1-naphthyl]-2-methylsulfonyl-5,6,7,8-tetrahydroquinazolin-4-yl]piperazine-1-carboxylate

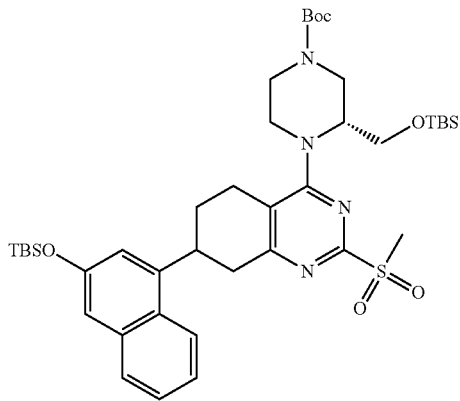 [SMILES: CC(C)(C)OC(=O)N1CCN(c2nc(S(C)(=O)=O)nc3c2CCC(c2cc(O[Si](C)(C)C(C)(C)C)cc4ccccc24)C3)[C@@H](CO[Si](C)(C)C(C)(C)C)C1]

A solution of tert-butyl (3R)-3-[[tert-butyl(dimethyl)silyl]oxymethyl]-4-[7-[3-[tert-butyl(dimethyl)silyl]oxy-1-naphthyl]-2-methylsulfanyl-5,6,7,8-tetrahydroquinazolin-4-yl]piperazine-1-carboxylate (4.0 g, 5.2 mmol) and 3-Chloroperoxybenzoic acid (2.7 g, 15.6 mmol) in dichloromethane (40 mL) was stirred at 25° C. for 2 hours. After completion, the resulting solution was concentrated under vacuum. The residue was purified by flash chromatography on silica gel eluting with hexane/ethyl acetate (5/1) to afford tert-butyl (3R)-3-[[tert-butyl(dimethyl)silyl]oxymethyl]-4-[7-[3-[tert-butyl(dimethyl)silyl]oxy-1-naphthyl]-2-methylsulfonyl-5,6,7,8-tetrahydroquinazolin-4-yl]piperazine-1-carboxylate (2.3 g, 2.8 mmol, 55.2% yield) as a white solid. LCMS (ESI, m/z): 797.4 [M+H]$^+$.

Step 5: tert-butyl (3R)-3-[[tert-butyl(dimethyl)silyl]oxymethyl]-4-[7-(3-hydroxy-1-naphthyl)-2-[[(2S)-1-methylpyrrolidin-2-yl]methoxy]-5,6,7,8-tetrahydroquinazolin-4-yl]piperazine-1-carboxylate

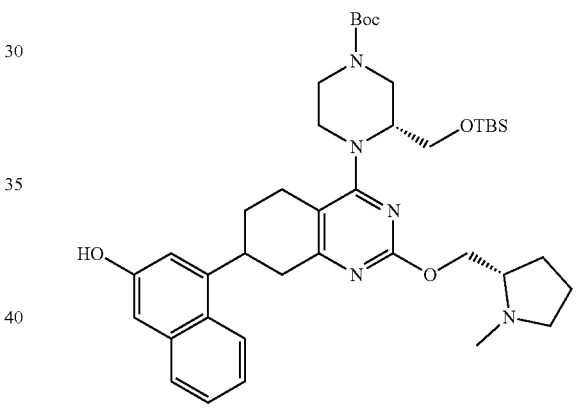

A solution of N-methyl-1-prolinol (1.44 g, 12.5 mmol) in N,N-dimethylformamide (20 mL) was stirred at 25° C. for 5 minutes. Then sodium hydride (401.4 mg, 10.0 mmol, 60% dispersion in mineral oil) was added and stirred at 0° C. for 30 minutes. Then tert-butyl (3R)-3-[[tert-butyl(dimethyl)silyl]oxymethyl]-4-[7-[3-[tert-butyl(dimethyl)silyl]oxy-1-naphthyl]-2-methylsulfonyl-5,6,7,8-tetrahydroquinazolin-4-yl]piperazine-1-carboxylate (2.0 g, 2.5 mmol) was added and stirred at 25° C. for 1 hour. After completion, the resulting solution was adjusted to pH 8 with saturated ammonium chloride solution and extracted with ethyl acetate, washed with water. The organic layer was dried over anhydrous sodium sulfate and concentrated under vacuum. The residue was purified by flash chromatography on silica gel eluting with dichloromethane/methanol (10/1) to afford tert-butyl (3R)-3-[[tert-butyl(dimethyl)silyl]oxymethyl]-4-[7-(3-hydroxy-1-naphthyl)-2-[[(2S)-1-methylpyrrolidin-2-yl]methoxy]-5,6,7,8-tetrahydroquinazolin-4-yl]piperazine-1-carboxylate (1.3 g, 1.8 mmol, 72.2% yield) as a yellow solid. LCMS (ESI, m/z): 718.4 [M+H]$^+$.

Step 6a: tert-butyl (3R)-3-[[tert-butyl(dimethyl)silyl]oxymethyl]-4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]piperazine-1-carboxylate

Step 6b: 1-[(3R)-3-[[tert-butyl(dimethyl)silyl]oxymethyl]-4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]piperazin-1-yl]prop-2-en-1-one

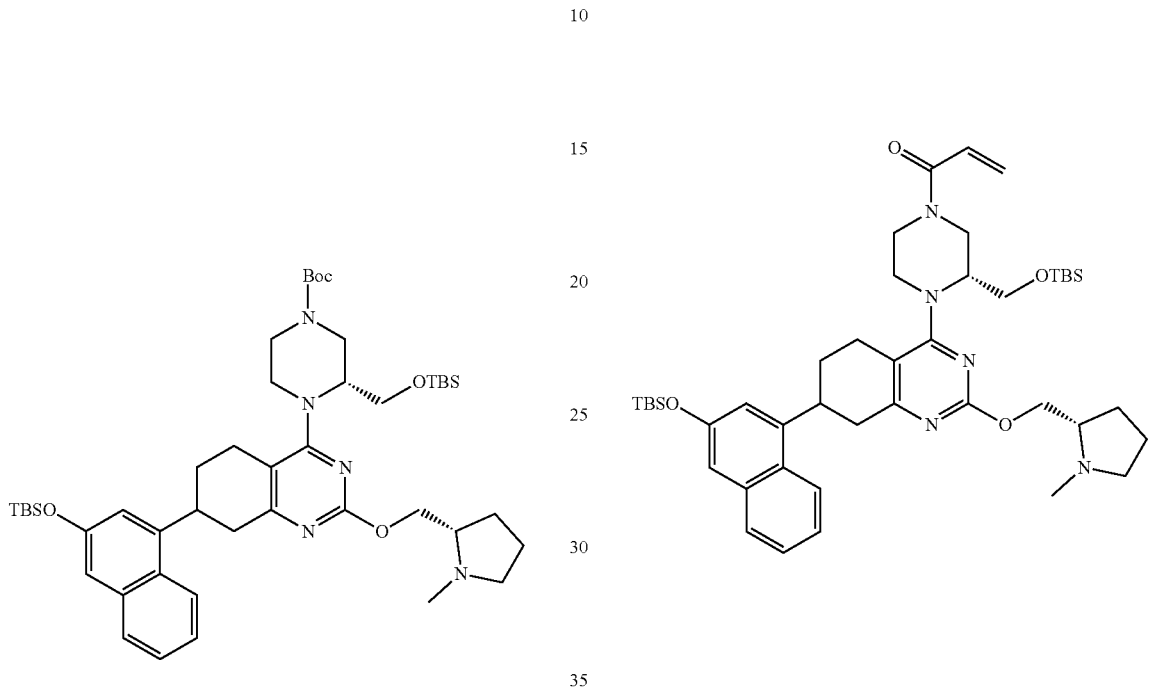

A solution of tert-butyl (3R)-3-[[tert-butyl(dimethyl)silyl]oxymethyl]-4-[7-(3-hydroxy-1-naphthyl]-2-[[(2S)-1-methylpyrrolidin-2-yl]methoxy]-5,6,7,8-tetrahydroquinazolin-4-yl]piperazine-1-carboxylate (400.0 mg, 0.5 mmol), N,N-diisopropylethylamine (215.6 mg, 1.67 mmol) and 4-dimethylaminopyridine (67.9 mg, 0.5 mmol) in dichloromethane (4 mL) was stirred at 25° C. for 3 minutes. Then tert-Butyldimethylsilyl chloride (167.1 mg, 1.1 mmol) was added and stirred at 25° C. for 2 hours. After completion, the reaction was diluted with dichloromethane, washed with water and dried over anhydrous sodium sulfate. The resulting solution was concentrated under vacuum. The residue was purified by flash chromatography on silica gel eluting with dichloromethane/methanol (20:1) to afford tert-butyl (3R)-3-[[tert-butyl(dimethyl)silyl]oxymethyl]-4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]piperazine-1-carboxylate (400 mg, 0.5 mmol, 86.3% yield) as a yellow solid. LCMS (ESI, m/z): 832.5 [M+H]$^+$.

A solution of tert-butyl (3R)-3-[[tert-butyl(dimethyl)silyl]oxymethyl]-4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]piperazine-1-carboxylate (400.0 mg, 0.4 mmol) and trifluoroacetic acid (164.3 mg, 1.4 mmol) in dichloromethane (8 mL) was stirred at 25° C. for 4 hours. After completion, the resulting solution was concentrated under reduced pressure and dissolved in dichloromethane (5 mL). Then N,N-diisopropylethylamine (264.2 mg, 2.0 mmol) was added and stirred at 25° C. for 3 minutes. Then acryloyl chloride (37.0 mg, 0.4 mmol) was added and stirred at 25° C. for 1 hour. After completion, the resulting solution was concentrated under vacuum. The residue was purified by flash chromatography on silica gel eluting with dichloromethane/methanol (10/1) to afford 1-[(3R)-3-[[tert-butyl(dimethyl)silyl]oxymethyl]-4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]piperazin-1-yl]prop-2-en-1-one (200 mg, 0.25 mmol, 62.1% yield) as a yellow solid. LCMS (ESI, m/z): 786.5 [M+H]$^+$.

Step 7: 1-[(3R)-3-(hydroxymethyl)-4-[(7R)-7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one (Example 29a) and 1-[(3R)-3-(hydroxymethyl)-4-[(7S)-7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one (Example 29b)

29a

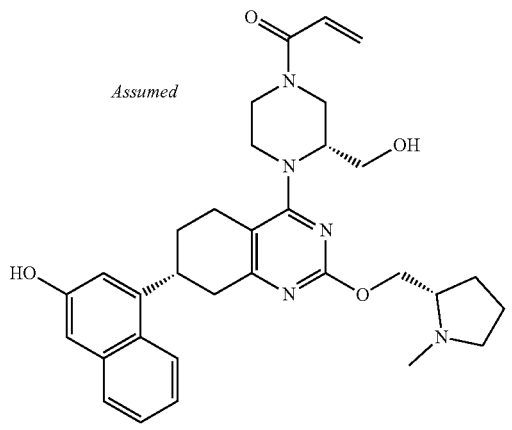

29b

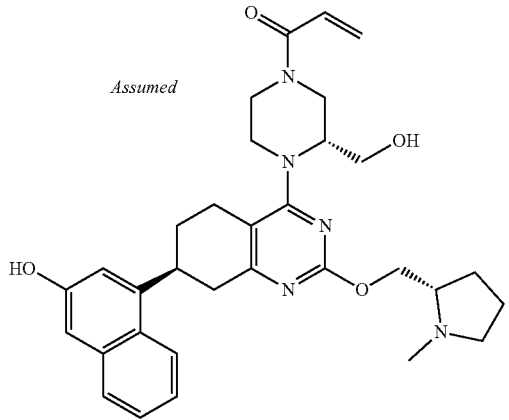

A solution of 1-[(3R)-3-[[tert-butyl(dimethyl)silyl]oxymethyl]-4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]piperazin-1-yl]prop-2-en-1-one (200.0 mg, 0.2 mmol) and Caesium fluoride (199.1 mg, 0.76 mmol) in tetrahydrofuran (10 mL) was stirred at 80° C. for 24 hours. After completion, after filtration, the filtrate was concentrated under reduced pressure to afford 120 mg crude solid. The product was further purified by Prep-HPLC with following condition (Column: XBridge Prep Phenyl OBD Column, 5 um, 19*250 mm; Mobile Phase A:Water (10 MMOL/L NH4HCO3+0.1% NH3·H2O), Mobile Phase B: ACN; Flow rate: 25 mL/min; Gradient: 31 B to 49 B in 10 min; 254 220 nm) to afford the title compounds. The absolute configuration of the title compounds was inferred from potency data and a protein X-ray structure of compound 21b.

Example 29a: 1-[(3R)-3-(hydroxymethyl)-4-[(7R)-7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one (1.7 mg, 0.003 mmol, 1.2% yield, white solid). $^1$H NMR (300 MHz, DMSO-$d_6$, ppm) δ 9.67 (s, 1H), 8.06 (d, J=8.6 Hz, 1H), 7.71 (d, J=8.1 Hz, 1H), 7.50-7.20 (m, 2H), 7.02 (s, 2H), 6.95-6.70 (m, 1H), 6.15 (d, J=16.5 Hz, 1H), 5.72 (d, J=11.4 Hz, 1H), 4.92-4.51 (m, 1H), 4.50-4.31 (m, 1H), 4.29-4.18 (m, 2H), 4.17-3.92 (m, 2H), 3.91-3.73 (m, 2H), 3.66 (d, J=13.0 Hz, 1H), 3.15-3.00 (m, 2H), 2.99-2.88 (m, 3H), 2.85-2.77 (m, 2H), 2.63-2.60 (m, 1H), 2.41-2.31 (m, 4H), 2.25-2.07 (m, 3H), 2.02-1.90 (m, 1H), 1.89-1.75 (m, 1H), 1.73-1.55 (m, 3H). LCMS (ESI, m/z): 558.3 [M+H]$^+$.

Example 29b: 1-[(3R)-3-(hydroxymethyl)-4-[(7S)-7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one (4 mg, 0.007 mmol, 2.8% yield, white solid). $^1$H NMR (400 MHz, DMSO-$d_6$, ppm) δ 9.66 (s, 1H), 8.06 (d, J=8.7 Hz, 1H), 7.70 (dd, J=8.2, 1.4 Hz, 1H), 7.44-7.35 (m, 1H), 7.34-7.26 (m, 1H), 7.04-6.96 (m, 2H), 6.89-6.72 (m, 1H), 6.14 (dd, J=17.0, 2.4 Hz, 1H), 5.71 (dd, J=10.4, 2.4 Hz, 1H), 5.07-4.76 (m, 1H), 4.47-4.22 (m, 3H), 4.19-4.02 (m, 2H), 4.00-3.76 (m, 3H), 3.75-3.54 (m, 2H), 3.20-2.72 (m, 7H), 2.35 (s, 3H), 2.25-2.06 (m, 2H), 2.00-1.88 (m, 2H), 1.86-1.76 (m, 1H), 1.74-1.53 (m, 3H). LCMS (ESI, m/z): 558.3 [M+H]$^+$.

Examples 30a and 30b

Example 30a

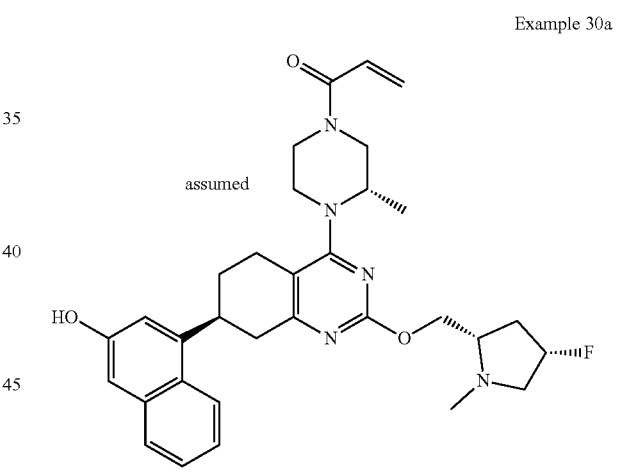

Example 30b

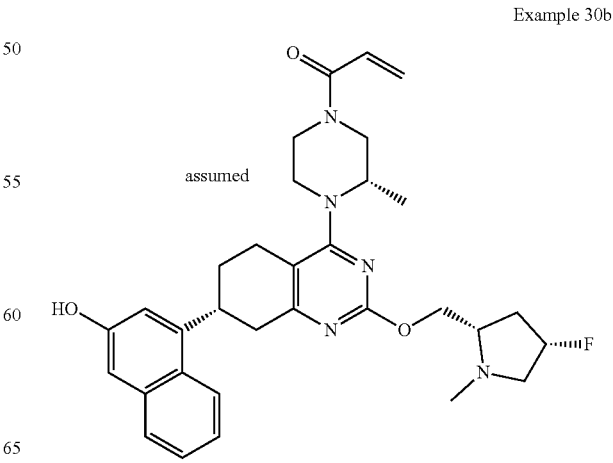

1-[(3S)-4-[(7S)-2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one (Example 30a); and
1-[(3S)-4-[(7R)-2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one (Example 30b)
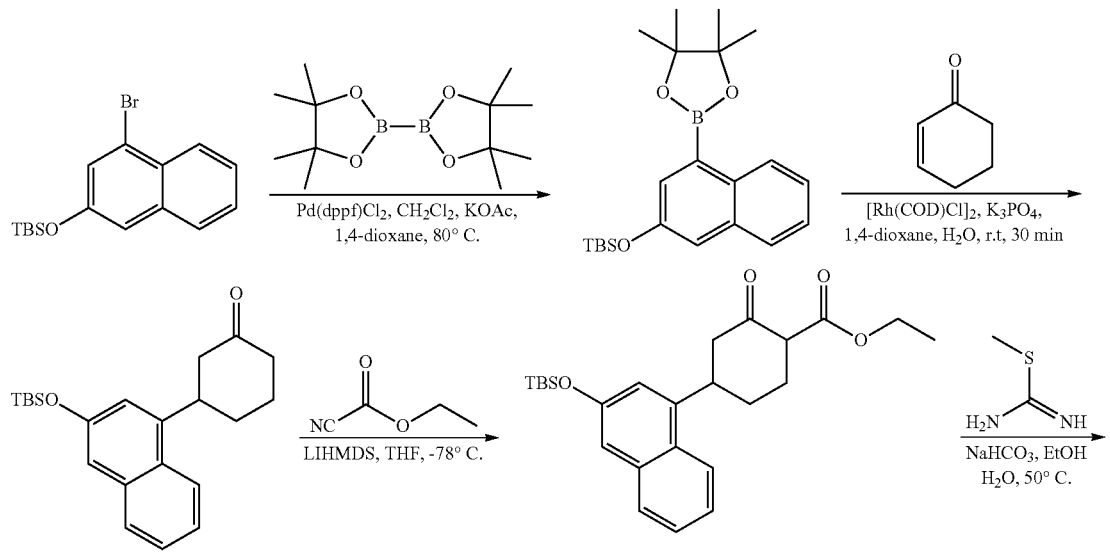
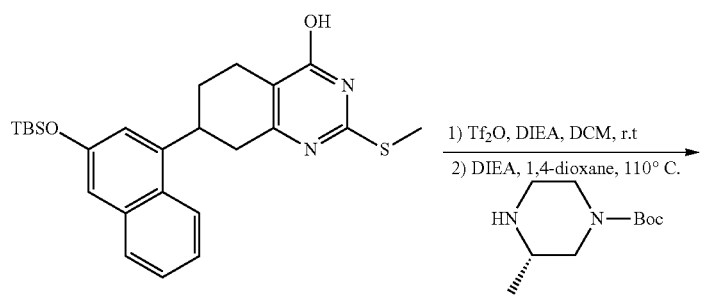
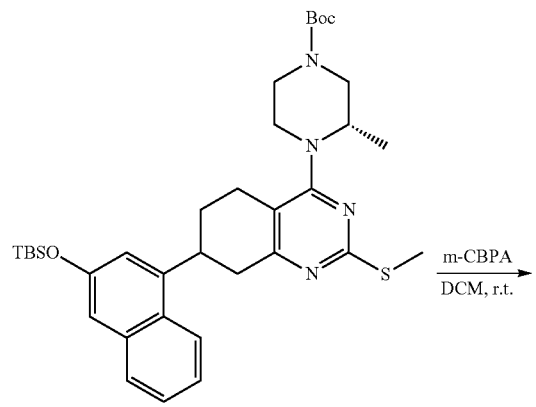

-continued
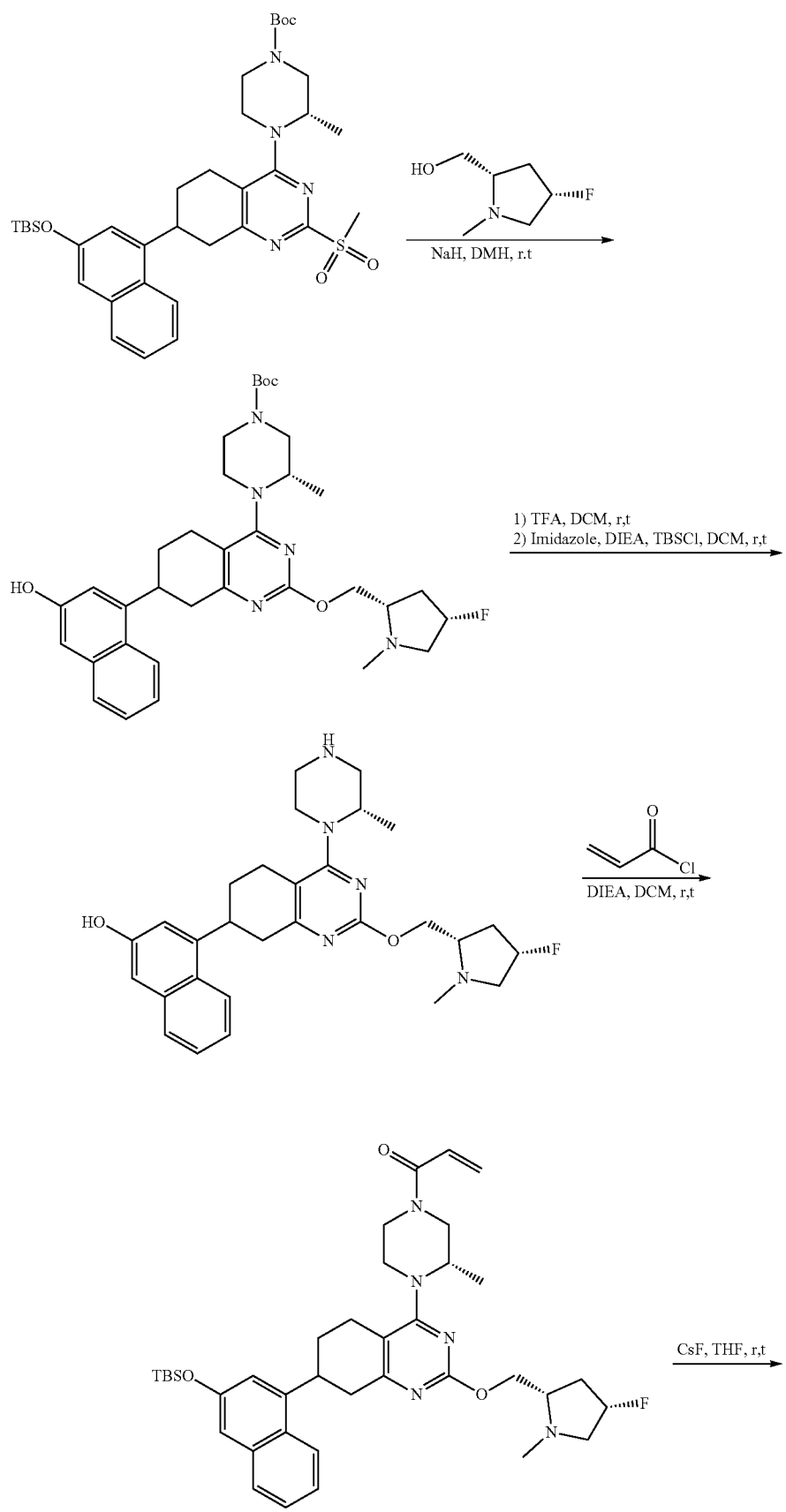

481

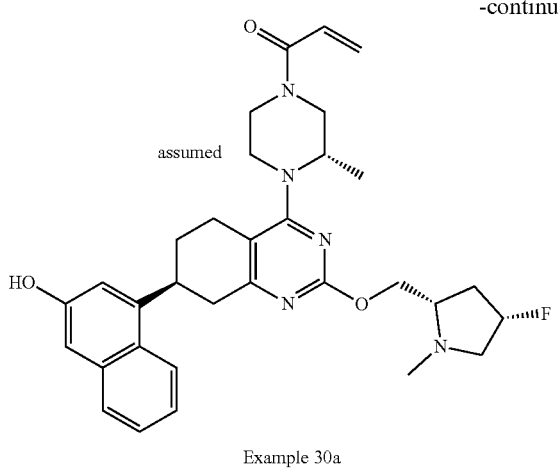

Example 30a

482

-continued

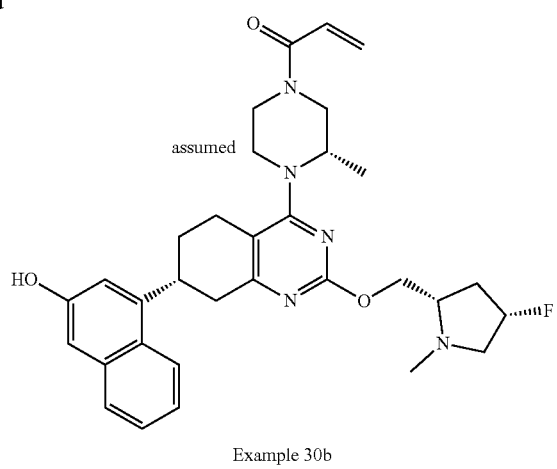

Example 30b

Step 1: tert-butyl-dimethyl-[[4-(4,4,5,5-tetramethyl-1,3,2-dioxaborolan-2-yl)-2-naphthyl]oxy]silane Step 2: 3-[3-[tert-butyl(dimethyl)silyl]oxy-1-naphthyl]cyclohexanone

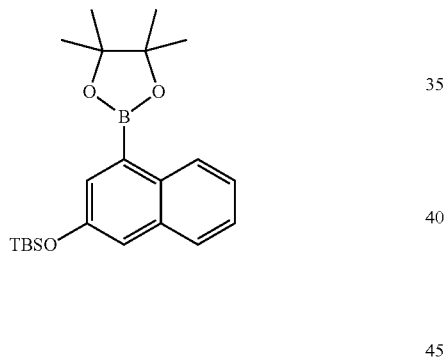

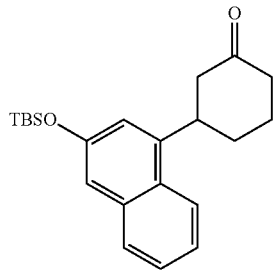 [SMILES: CC(C)(C)[Si](C)(C)Oc1cc(C2CCCC(=O)C2)c2ccccc2c1]

Under nitrogen, a solution of (4-bromo-2-naphthyl)oxy-tert-butyl-dimethyl-silane (20.0 g, 59.2 mmol), bis(pinacolato)diboron (45 g, 177.8 mmol), 1,1'-bis(diphenylphosphino)ferrocene-palladium(II)dichloride dichloromethane complex (4.9 g, 5.9 mmol) and potassium acetate (17.4 g, 177.8 mmol) in 1,4-dioxane (200 mL) was stirred at 80° C. for 2 hours. After completion, the resulting solution was diluted with was water and extracted with dichloromethane. Then the organic layers were collected and washed with brine. Then the organic layer was dried over anhydrous sodium sulfate and concentrated under vacuum. The residue was purified by flash chromatography on silica gel eluting with hexane/ethyl acetate (10/1) to afford tert-butyl-dimethyl-[[4-(4,4,5,5-tetramethyl-1,3,2-dioxaborolan-2-yl)-2-naphthyl]oxy]silane (18 g, 46.8 mmol, 79% yield) as a yellow solid. LCMS (ESI, m/z): 385.2 [M+H]⁺.

Under nitrogen, a solution of 2-cyclohexen-1-one (12.5 g, 130.08 mmol), tert-butyl-dimethyl-[[4-(4,4,5,5-tetramethyl-1,3,2-dioxaborolan-2-yl)-2-naphthyl]oxy]silane (10.0 g, 26.0 mmol), potassium phosphate (16.55 g, 78.0 mmol) and chloro(1,5-cyclooctadiene)rhodium(I) dimer (1.28 g, 2.6 mmol) in 1,4-dioxane (100 mL) and water (20 mL) was stirred at 25° C. for 30 minutes. After completion, the reaction was diluted with dichloromethane, washed by water and dried over anhydrous sodium sulfate. The organic layer was concentrated under vacuum. The residue was purified by flash chromatography on silica gel eluting with hexane/ethyl acetate (10/1) to afford 3-[3-[tert-butyl(dimethyl)silyl]oxy-1-naphthyl]cyclohexanone (8 g, 22.5 mmol, 86.7% yield) as a white solid. LCMS (ESI, m/z): 355.2 [M+H]⁺.

Step 3: ethyl 4-[3-[tert-butyl(dimethyl)silyl]oxy-1-naphthyl]-2-oxo-cyclohexanecarboxylate

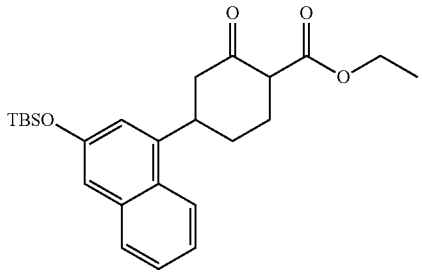 [SMILES: CCOC(=O)C1CCC(c2cc(O[Si](C)(C)C(C)(C)C)cc3ccccc23)CC1=O]

Under nitrogen, a solution of 3-[3-[tert-butyl(dimethyl)silyl]oxy-1-naphthyl]cyclohexanone (10.0 g, 28.2 mmol) in tetrahydrofuran (100 mL) was stirred at −78° C. for 2 minutes. Then Lithium bis(trimethylsilyl)amide (1 M in THF) (84 mL, 84.6 mmol) was added and stirred at −78° C. for 1 hour. Then ethyl cyanoformate (4.19 g, 42.3 mmol) was added and stirred at −78° C. for 30 minutes. The reaction was quenched with water, extracted with Ethyl acetate, dried over anhydrous sodium sulfate and concentrated under vacuum. The residue was purified by flash chromatography on silica gel eluting with hexane/ethyl acetate (20/1) to afford ethyl 4-[3-[tert-butyl(dimethyl)silyl] oxy-1-naphthyl]-2-oxo-cyclohexanecarboxylate (7 g, 16.4 mmol, 58.2% yield) as a yellow oil. LCMS (ESI, m/z): 427.2 [M+H]$^+$.

Step 4: 7-[3-[tert-butyl(dimethyl)silyl]oxy-1-naphthyl]-2-methylsulfanyl-5,6,7,8-tetrahydroquinazolin-4-ol

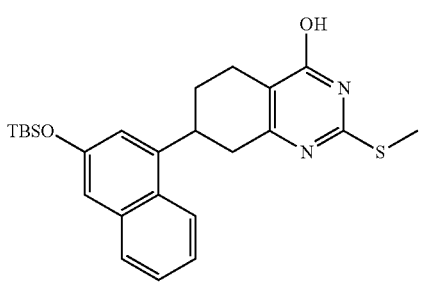 [SMILES: CSc1nc(O)c2c(n1)CC(c1cc(O[Si](C)(C)C(C)(C)C)cc3ccccc13)CC2]

A solution of ethyl 4-[3-[tert-butyl(dimethyl)silyl]oxy-1-naphthyl]-2-oxo-cyclohexanecarboxylate (10.0 g, 23.4 mmol), 2-methyl-2-thiopseudourea sulfate (65.25 g, 234.4 mmol) and Sodium bicarbonate (39.3 g, 468.8 mmol) in Ethanol (120 mL) and Water (25 mL) was stirred at 50° C. for 3 hours. After completion, the reaction was diluted with water and extracted with dichloromethane. Then the organic layers were combined, dried over anhydrous sodium sulfate and concentrated under vacuum. The residue was purified by flash chromatography on silica gel eluting with dichloromethane/methanol (97/3) to afford 7-[3-[tert-butyl(dimethyl)silyl]oxy-1-naphthyl]-2-methylsulfanyl-5,6,7,8-tetrahydroquinazolin-4-ol (5 g, 11.0 mmol, 47.1% yield) as a white solid. LCMS (ESI, m/z): 453.2 [M+H]$^+$.

Step 5: tert-butyl (3S)-4-[7-[3-[tert-butyl(dimethyl) silyl]oxy-1-naphthyl]-2-methylsulfanyl-5,6,7,8-tetrahydroquinazolin-4-yl]-3-methyl-piperazine-1-carboxylate

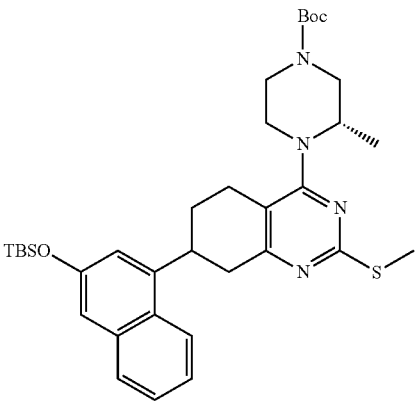

A solution of 7-[3-[tert-butyl(dimethyl)silyl]oxy-1-naphthyl]-2-methylsulfanyl-5,6,7,8-tetrahydroquinazolin-4-ol (2.0 g, 4.4 mmol) and N,N-diisopropylethylamine (2.8 g, 22.0 mmol) in dichloromethane (20 mL) was stirred at 25° C. for 3 minutes. Then Trifluoromethanesulfonic anhydride (2.49 g, 8.8 mmol) was added and stirred at 25° C. for 1 hour. After completion, the reaction was concentrated under reduced pressure. Then the residue, N,N-diisopropylethylamine (4.41 g, 34.2 mmol) and tert-butyl (3S)-3-methyl-1-piperazinecarboxylate (1.3 g, 6.8 mmol) in 1,4-dioxane (30 mL) was stirred at 110° C. for 16 hours. After completion, the resulting solution was concentrated under vacuum. The residue was purified by flash chromatography on silica gel eluting with hexane/ethyl acetate (7/1) to afford tert-butyl (3S)-4-[7-[3-[tert-butyl(dimethyl)silyl]oxy-1-naphthyl]-2-methylsulfanyl-5,6,7,8-tetrahydroquinazolin-4-yl]-3-methyl-piperazine-1-carboxylate (1.8 g, 2.8 mmol, 63.6% yield) as a yellow solid. LCMS (ESI, m/z): 635.3 [M+H]$^+$.

Step 6: tert-butyl (3S)-4-[7-[3-[tert-butyl(dimethyl) silyl]oxy-1-naphthyl]-2-methylsulfonyl-5,6,7,8-tetrahydroquinazolin-4-yl]-3-methyl-piperazine-1-carboxylate

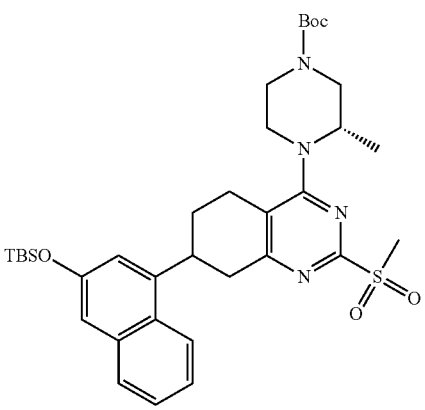 [SMILES: C[C@H]1CN(C(=O)OC(C)(C)C)CCN1c1nc(S(C)(=O)=O)nc2c1CCC(c1cc(O[Si](C)(C)C(C)(C)C)cc3ccccc13)C2]

A solution of tert-butyl (3S)-4-[7-[3-[tert-butyl(dimethyl)silyl]oxy-1-naphthyl]-2-methylsulfanyl-5,6,7,8-tetrahydroquinazolin-4-yl]-3-methyl-piperazine-1-carboxylate (2.0 g, 3.1 mmol) and 3-Chloroperoxybenzoic acid (1.63 g, 9.4 mmol) in dichloromethane (20 mL) was stirred at 25° C. for 2 hours. After completion, the resulting solution was quenched with saturated sodium sulfite solution. The resulting solution was extracted with Ethyl acetate, dried over anhydrous sodium sulfate and concentrated under vacuum to afford tert-butyl (3S)-4-[7-[3-[tert-butyl(dimethyl)silyl]oxy-1-naphthyl]-2-methylsulfonyl-5,6,7,8-tetrahydroquinazolin-4-yl]-3-methyl-piperazine-1-carboxylate (1.5 g, 2.2 mmol, 71% yield) as a yellow solid. LCMS (ESI, m/z): 667.3 [M+H]$^+$.

Step 7: tert-butyl (3S)-4-[2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazine-1-carboxylate

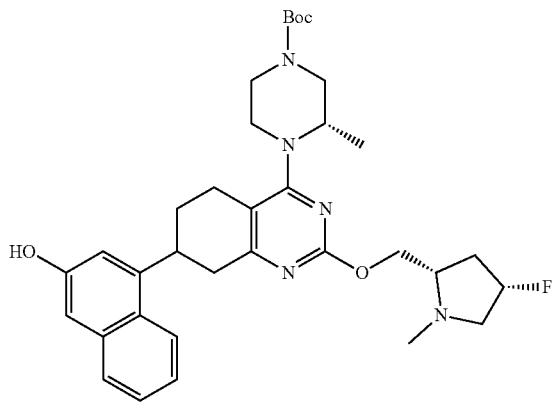 [SMILES: C[C@H]1CN(C(=O)OC(C)(C)C)CCN1c1nc(OC[C@@H]2C[C@H](F)CN2C)nc2c1CCC(c1cc(O)cc3ccccc13)C2]

A solution of [(2S,4S)-4-fluoro-1-methyl-pyrrolidin-2-yl]methanol (2.0 g, 14.99 mmol) in N,N-Dimethylformamide (20 mL) was stirred at 25° C. for 5 minutes. Then sodium hydride (479.8 mg, 11.9 mmol, 60% dispersion in mineral oil) was added and stirred at 0° C. for 30 minutes. Then tert-butyl (3S)-4-[7-[3-[tert-butyl(dimethyl)silyl]oxy-1-naphthyl]-2-methylsulfonyl-5,6,7,8-tetrahydroquinazolin-4-yl]-3-methyl-piperazine-1-carboxylate (2.0 g, 3 mmol) was added and stirred at 25° C. for 1 hour. After completion, the resulting solution was adjusted to pH 8 with saturated ammonium chloride solution. The solvent was extracted with ethyl acetate, washed with water. The organic layer was dried over anhydrous sodium sulfate and concentrated under vacuum. The residue was purified by flash chromatography on silica gel eluting with dichloromethane/methanol (10/1) to afford tert-butyl (3S)-4-[2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazine-1-carboxylate (500 mg, 0.82 mmol, 27.5% yield) as a yellow solid. LCMS (ESI, m/z): 606.3 [M+H]$^+$ Step 8: tert-butyl-[[4-[2-[[(2S,4S)-4-fluoro-1-methyl-pyrrolidin-2-yl]methoxy]-4-[(2S)-2-methylpiperazin-1-yl]-5,6,7,8-tetrahydroquinazolin-7-yl]-2-naphthyl]oxy]-dimethyl-silane

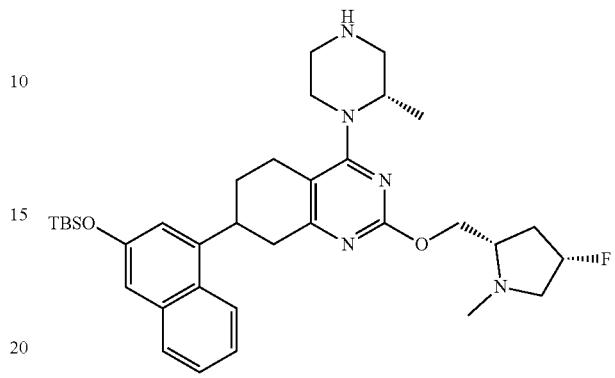

A solution of tert-butyl (3S)-4-[2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazine-1-carboxylate (500.0 mg, 0.83 mmol) and trifluoroacetic acid (1882.0 mg, 16.5 mmol) in dichloromethane (25 mL) was stirred at 25° C. for 1 hour. After completion, the resulting solution was concentrated under vacuum and dissolved in dichloromethane (20 mL) Then imidazole (168.58 mg, 2.48 mmol) and N,N-Diisopropylethylamine (2.1 g, 16.51 mmol) in dichloromethane (25 mL) was stirred at 25° C. for 3 minutes. Then tert-Butyldimethylsilyl chloride (249.2 mg, 1.65 mmol) was added and stirred at 25° C. for 2 hours. After completion, the resulting solution was concentrated under vacuum. The residue was purified by flash chromatography on silica gel eluting with methanol/water (30:20) to afford tert-butyl-[[4-[2-[[(2S,4S)-4-fluoro-1-methyl-pyrrolidin-2-yl]methoxy]-4-[(2S)-2-methylpiperazin-1-yl]-5,6,7,8-tetrahydroquinazolin-7-yl]-2-naphthyl]oxy]-dimethyl-silane (360 mg, 0.58 mmol, 70% yield) as a white solid. LCMS (ESI, m/z): 620.3 [M+H]$^+$ Step 9: 1-[(3S)-4-[7-[3-[tert-butyl(dimethyl)silyl]oxy-1-naphthyl]-2-[[(2S,4S)-4-fluoro-1-methyl-pyrrolidin-2-yl]methoxy]-5,6,7,8-tetrahydroquinazolin-4-yl]-3-methyl-piperazin-1-yl]prop-2-en-1-one

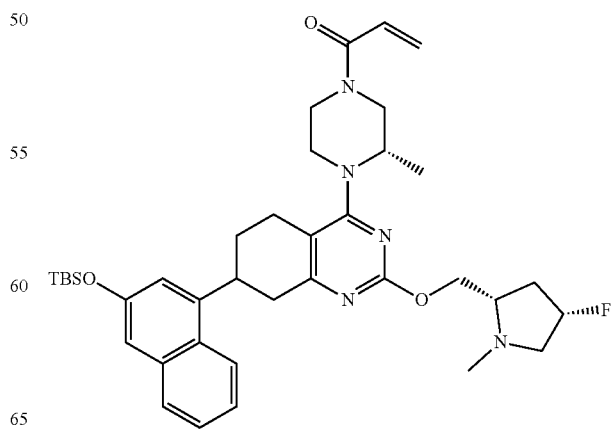

A solution of tert-butyl-[[4-[2-[[(2S,4S)-4-fluoro-1-methyl-pyrrolidin-2-yl]methoxy]-4-[(2S)-2-methylpiperazin-1-yl]-5,6,7,8-tetrahydroquinazolin-7-yl]-2-naphthyl]oxy]-dimethyl-silane (360.0 mg, 0.58 mmol) and N,N-diisopropylethylamine (224.7 mg, 1.74 mmol) in dichloromethane (9 mL) was stirred at 25° C. for 3 minutes. Then acryloyl chloride (63.0 mg, 0.70 mmol) was added and stirred at 25° C. for 30 minutes. After completion, the resulting solution was concentrated under vacuum. The residue was purified by flash chromatography on silica gel eluting with dichloromethane/methanol (20/1) to afford 1-[(3S)-4-[7-[3-[tert-butyl(dimethyl)silyl]oxy-1-naphthyl]-2-[[(2S,4S)-4-fluoro-1-methyl-pyrrolidin-2-yl]methoxy]-5,6,7,8-tetrahydroquinazolin-4-yl]-3-methyl-piperazin-1-yl]prop-2-en-1-one (320 mg, 0.47 mmol, 81.8% yield) as a yellow solid. LCMS (ESI, m/z): 674.3 [M+H]$^+$ Step 10: one 1-[(3S)-4-[(7S)-2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one (Example 30a) and 1-[(3S)-4-[(7R)-2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1- (Example 30b)

Example 30a

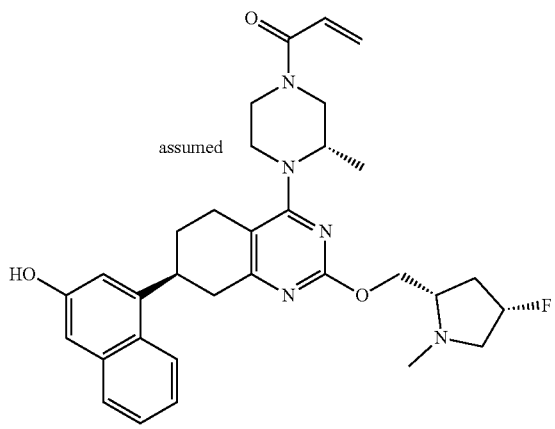

Example 30b

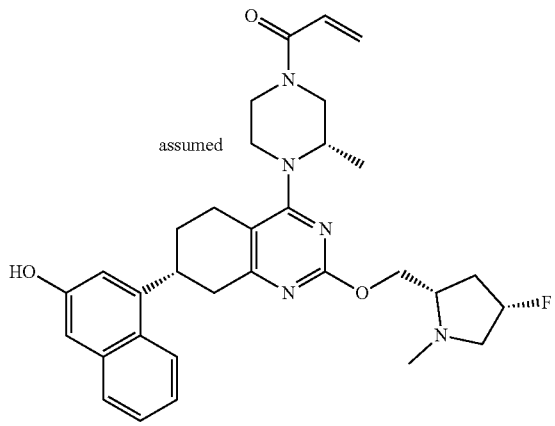

A solution of 1-[(3S)-4-[7-[3-[tert-butyl(dimethyl)silyl]oxy-1-naphthyl]-2-[[(2S,4S)-4-fluoro-1-methyl-pyrrolidin-2-yl]methoxy]-5,6,7,8-tetrahydroquinazolin-4-yl]-3-methyl-piperazin-1-yl]prop-2-en-1-one (360.0 mg, 0.53 mmol) and Caesium fluoride (324.7 mg, 2.14 mmol) in tetrahydrofuran (5 mL) was stirred at 25° C. for 1 hour. After completion, the resulting solution was diluted with water and extracted with dichloromethane. Then the organic layers were collected, dried over anhydrous sodium sulfate and concentrated under vacuum. The residue was purified by flash chromatography on silica gel eluting with dichloromethane/methanol (10/1) to afford crude solid. The crude product was purified by Prep-HPLC to afford 150 mg white solid with the following conditions: Column: XBridge Shield RP18 OBD Column, 30*150 mm, 5 um; Mobile Phase A:Water (10 MMOL/L NH4HCO3), Mobile Phase B: ACN; Flow rate: 60 mL/min; Gradient: 28 B to 42 B in 10 min; 254 nm; RT: 8.52. The product was further purified by Chiral-Prep-HPLC with following condition (Column, CHIRALPAK IA-3, 0.46*5 cm; 3 um; mobile phase: (Hex: DCM=3:1)(0.1% DEA): EtOH=50:50; Detector, UV 254 nm) to afford the title compounds. The absolute configuration of the title compounds was inferred from potency data and a protein X-ray structure of compound 21b.

Example 30a: 1-[(3S)-4-[(7S)-2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one (49.8 mg, 0.089 mmol, 16.7% yield). $^1$H NMR (400 MHz, DMSO-d$_6$, ppm) δ 9.66 (s, 1H), 8.08 (d, J=8.6 Hz, 1H), 7.70 (dd, J=8.3, 1.3 Hz, 1H), 7.40 (t, J=7.2 Hz, 1H), 7.31 (t, J=7.2 Hz, 1H), 7.02 (s, 2H), 6.93-6.75 (m, 1H), 6.16 (dd, J=16.8, 6.8 Hz, 1H), 5.72 (dd, J=10.4, 2.4 Hz, 1H), 5.23-5.03 (m, 1H), 4.38-4.22 (m, 2H), 4.19-4.04 (m, 2H), 3.98-3.75 (s, 2H), 3.66-3.43 (m, 2H), 3.35-3.20 (m, 1H), 3.19-3.03 (m, 2H), 3.00-2.85 (m, 2H), 2.83-2.72 (m, 1H), 2.65-2.55 (m, 2H), 2.48-2.37 (m, 1H), 2.39-2.27 (m, 4H), 2.13 (d, J=12.4 Hz, 1H), 1.90-1.69 (m, 2H), 1.02-0.98 (m, 3H). LCMS (ESI, m/z): 560.3 [M+H]$^+$. Chiral HPLC: Column: CHIRALPAK IC-3, 4.6*50 mm 3 um; detected at 254 nm; (Hex:DCM=3:1)(0.1% DEA): EtOH=50:50, Flow rate: 1 mL/min; Retention time: 2.482 min; (slower peak).

Example 30b: 1-[(3S)-4-[(7R)-2-[[(2S,4S)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one (43.8 mg, 0.078 mmol, 14.7% yield). $^1$H NMR (400 MHz, DMSO-d$_6$, ppm) δ 9.66 (s, 1H), 8.08 (d, J=8.6 Hz, 1H), 7.70 (dd, J=8.3, 1.3 Hz, 1H), 7.40 (t, J=7.2 Hz, 1H), 7.31 (t, J=7.2 Hz, 1H), 7.02 (s, 2H), 6.93-6.75 (m, 1H), 6.16 (dd, J=16.8, 6.8 Hz, 1H), 5.72 (dd, J=10.4, 2.4 Hz, 1H), 5.23-5.03 (m, 1H), 4.38-4.22 (m, 2H), 4.19-4.04 (m, 2H), 3.98-3.75 (s, 2H), 3.66-3.43 (m, 2H), 3.35-3.20 (m, 1H), 3.19-3.03 (m, 2H), 3.00-2.85 (m, 2H), 2.83-2.72 (m, 1H), 2.65-2.55 (m, 2H), 2.48-2.37 (m, 1H), 2.39-2.27 (m, 4H), 2.13 (d, J=12.4 Hz, 1H), 1.90-1.69 (m, 2H), 1.02-0.98 (m, 3H). LCMS (ESI, m/z): 560.3 [M+H]$^+$. Chiral HPLC: Column: CHIRALPAK IC-3, 4.6*50 mm 3 um; detected at 254 nm; (Hex:DCM=3:1)(0.1% DEA): EtOH=50:50, Flow rate: 1 mL/min; Retention time: 1.306 min; (faster peak).

Examples 31a and 31b
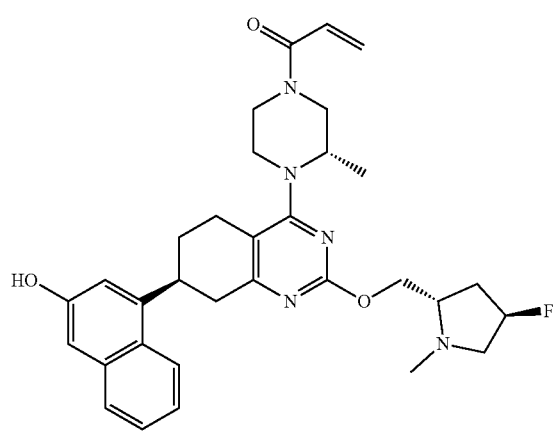
Example 31a
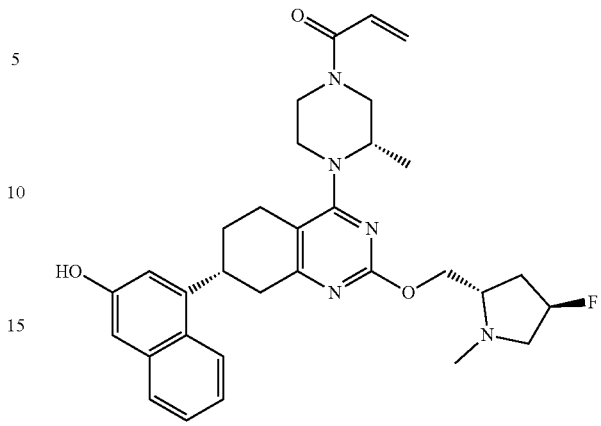
Example 31b
1-[(3S)-4-[(7S)-2-[[(2S,4R)-4-fluoro-1-methyl-pyrrolidin-2-yl]methoxy]-7-(3-hydroxy-1l-naphthyl)-5,6,7,8-tetrahydroquinazolin-4-yl]-3-methyl-piperazin-1-yl]prop-2-en-1-one (Example 31a); and
1-[(3S)-4-[(7R)-2-[[(2S,4R)-4-fluoro-1l-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one (Example 31b)
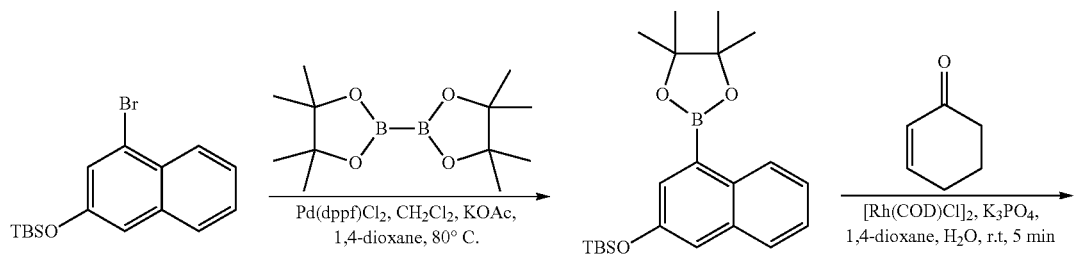
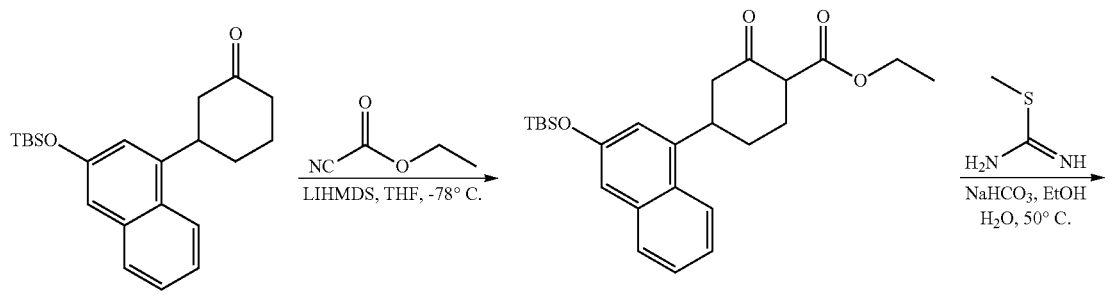

-continued
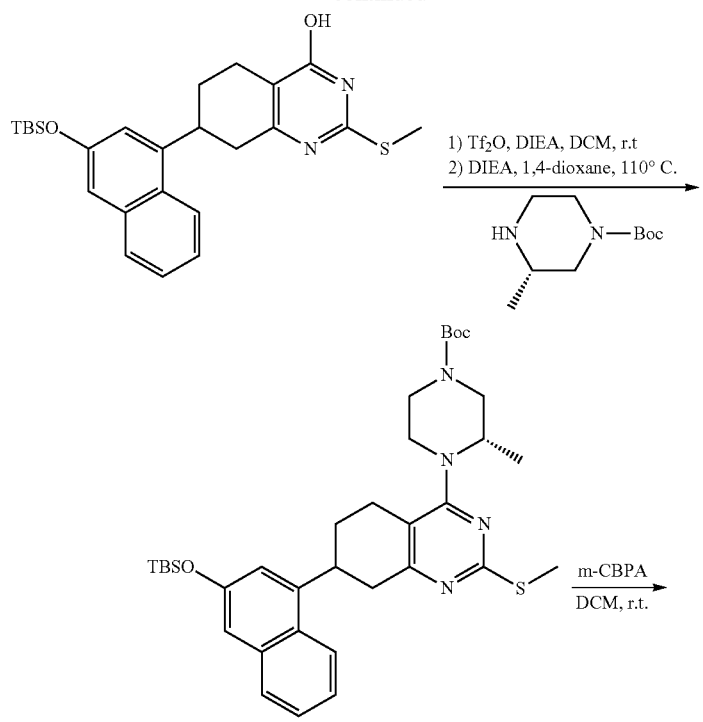
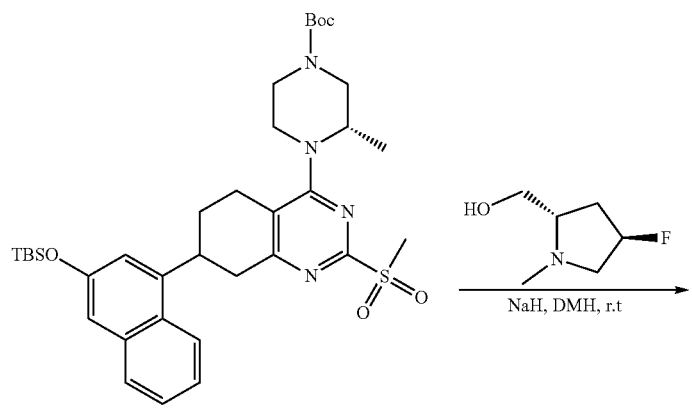
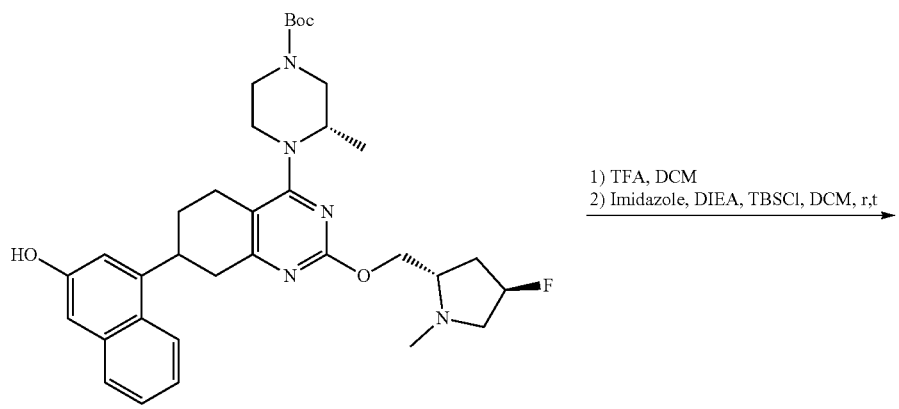

493
494
-continued
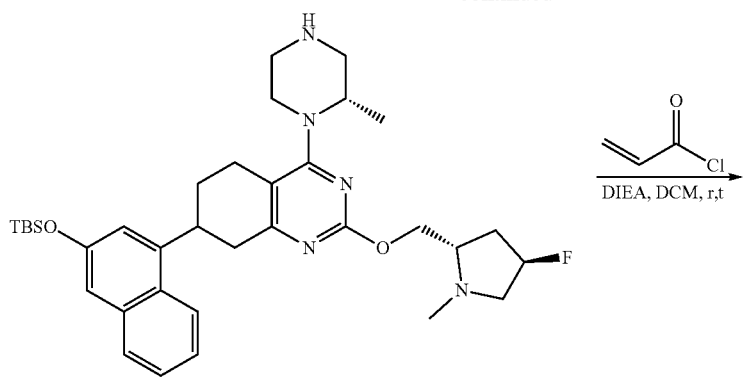
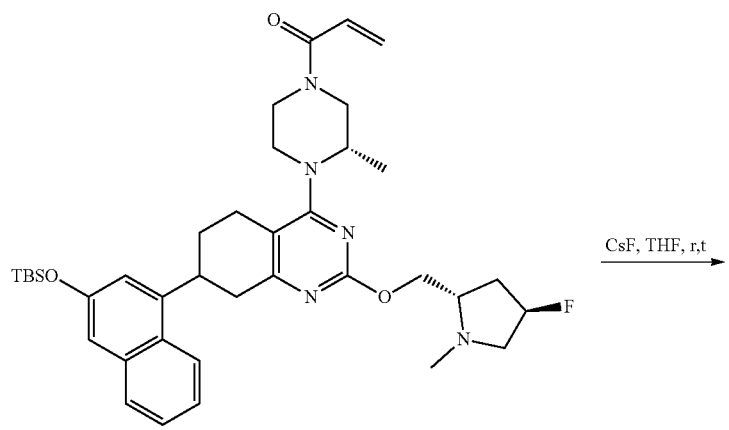
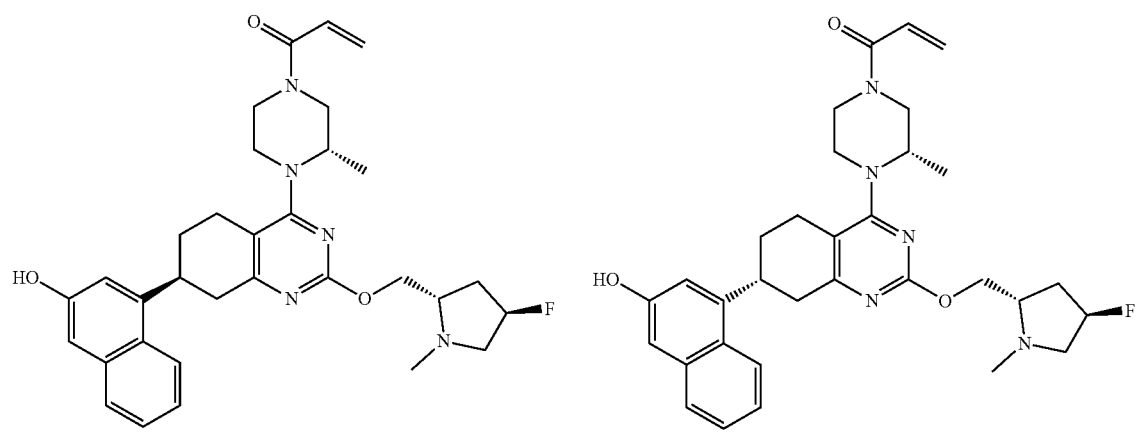
Example 31a
Example 31b

Step 1: tert-butyl-dimethyl-[[14-(4,4,5,5-tetramethyl-1,3,2-dioxaborolan-2-yl)-2-naphthyl]oxy]silane

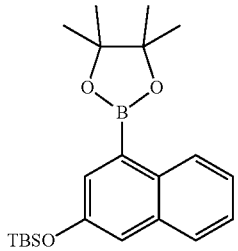 [SMILES: CC1(C)OB(c2cc(O[Si](C)(C)C(C)(C)C)cc3ccccc23)OC1(C)C]

Under nitrogen, a solution of (4-bromo-2-naphthyl)oxy-tert-butyl-dimethyl-silane (20.0 g, 59.2 mmol), bis(pinacolato)diboron (45 g, 177.8 mmol), 1,1'-bis(diphenylphosphino)ferrocene-palladium(II)dichloride dichloromethane complex (4.9 g, 5.9 mmol) and potassium acetate (17.4 g, 177.8 mmol) in 1,4-dioxane (200 mL) was stirred at 80° C. for 2 hours. After completion, the resulting solution was concentrated under vacuum. the resulting solution was diluted with dichloromethane and washed with brine. Then the organic layer was dried over anhydrous sodium sulfate and concentrated under vacuum. The residue was purified by flash chromatography on silica gel eluting with hexane/ethyl acetate (10/1) to afford tert-butyl-dimethyl-[[4-(4,4,5,5-tetramethyl-1,3,2-dioxaborolan-2-yl)-2-naphthyl]oxy]silane (18 g, 46.8 mmol, 79% yield) as a yellow solid. LCMS (ESI, m/z): 385.2 [M+H]$^+$.

Step 2: 3-[3-[tert-butyl(dimethyl)silyl]oxy-1-naphthyl]cyclohexanone

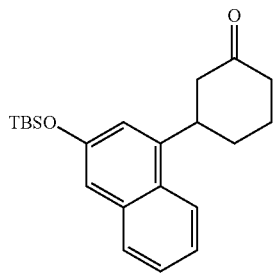 [SMILES: CC(C)(C)[Si](C)(C)Oc1cc(C2CCCC(=O)C2)c2ccccc2c1]

Under nitrogen, a solution of 2-cyclohexen-1-one (12.5 g, 130.08 mmol), tert-butyl-dimethyl-[[4-(4,4,5,5-tetramethyl-1,3,2-dioxaborolan-2-yl)-2-naphthyl]oxy]silane (10.0 g, 26.0 mmol), potassium phosphate (16.55 g, 78.0 mmol) and chloro(1,5-cyclooctadiene)rhodium(I) dimer (1.28 g, 2.6 mmol) in 1,4-dioxane (100 mL) and water (20 mL) was stirred at 25° C. for 30 minutes. After completion, the reaction was diluted with dichloromethane, washed by water and dried over anhydrous sodium sulfate. The organic layer was concentrated under vacuum. The residue was purified by flash chromatography on silica gel eluting with hexane/ethyl acetate (10/1) to afford 3-[3-[tert-butyl(dimethyl)silyl]oxy-1-naphthyl]cyclohexanone (8 g, 22.5 mmol, 86.7% yield) as a white solid. LCMS (ESI, m/z): 355.2 [M+H]$^+$.

Step 3: ethyl 4-[3-[tert-butyl(dimethyl)silyl]oxy-1-naphthyl]-2-oxo-cyclohexanecarboxylate

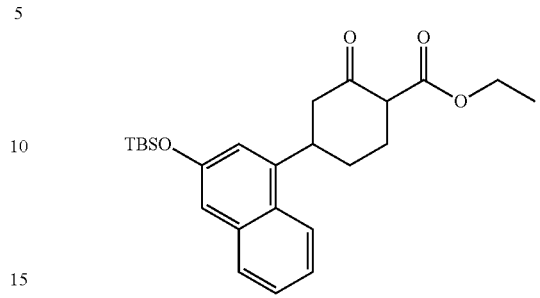

Under nitrogen, a solution of 3-[3-[tert-butyl(dimethyl)silyl]oxy-1-naphthyl]cyclohexanone (10.0 g, 28.2 mmol) in tetrahydrofuran (100 mL) was stirred at −78° C. for 2 minutes. Then lithium bis(trimethylsilyl)amide (1 M in THF) (84 mL, 84.6 mmol) was added and stirred at −78° C. for 1 hour. Then ethyl cyanoformate (4.19 g, 42.3 mmol) was added and stirred at −78° C. for 30 minutes. After completion the reaction was quenched with water, extracted with ethyl acetate, dried over anhydrous sodium sulfate and concentrated under vacuum. The residue was purified by flash chromatography on silica gel eluting with hexane/ethyl acetate (20/1) to afford ethyl 4-[3-[tert-butyl(dimethyl)silyl]oxy-1-naphthyl]-2-oxo-cyclohexanecarboxylate (7 g, 16.4 mmol, 58.2% yield) as a yellow oil. LCMS (ESI, m/z): 427.2 [M+H]$^+$.

Step 4: 7-[3-[tert-butyl(dimethyl)silyl]oxy-1-naphthyl]-2-methylsulfanyl-5,6,7,8-tetrahydroquinazolin-4-ol

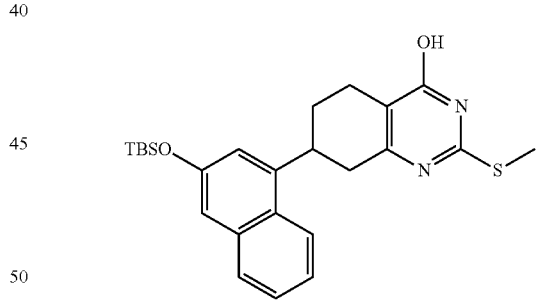

A solution of ethyl 4-[3-[tert-butyl(dimethyl)silyl]oxy-1-naphthyl]-2-oxo-cyclohexanecarboxylate (10.0 g, 23.4 mmol), 2-methyl-2-thiopseudourea sulfate (65.2 g, 234.4 mmol) and sodium bicarbonate (39.3 g, 468.8 mmol) in ethanol (120 mL) and water (25 mL) was stirred at 50° C. for 3 hours. After completion, the reaction was diluted with water and extracted with dichloromethane. Then the organic layers were combined, dried over anhydrous sodium sulfate and concentrated under vacuum. The residue was purified by flash chromatography on silica gel eluting with dichloromethane/methanol (97/3) to afford 7-[3-[tert-butyl(dimethyl)silyl]oxy-1-naphthyl]-2-methylsulfanyl-5,6,7,8-tetrahydroquinazolin-4-ol (5 g, 11.0 mmol, 47.1% yield) as a white solid. LCMS (ESI, m/z): 453.2 [M+H]$^+$.

Step 5: tert-butyl (3S)-4-[7-[3-[tert-butyl(dimethyl)silyl]oxy-1-naphthyl]-2-methylsulfanyl-5,6,7,8-tetrahydroquinazolin-4-yl]-3-methyl-piperazine-1-carboxylate

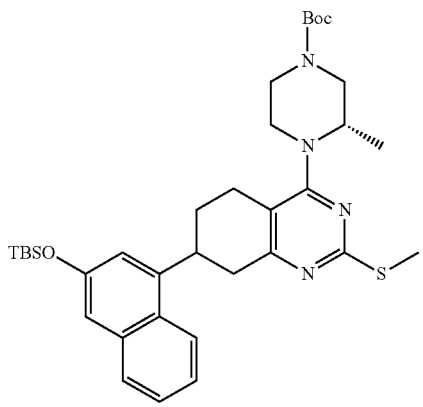 [SMILES: CSc1nc2c(c(N3CCN(C(=O)OC(C)(C)C)C[C@@H]3C)n1)CCC(c1cc(O[Si](C)(C)C(C)(C)C)cc3ccccc13)C2]

A solution of 7-[3-[tert-butyl(dimethyl)silyl]oxy-1-naphthyl]-2-methylsulfanyl-5,6,7,8-tetrahydroquinazolin-4-ol (2.0 g, 4.4 mmol) and N,N-diisopropylethylamine (2.8 g, 22.0 mmol) in dichloromethane (20 mL) was stirred at 25° C. for 3 minutes. Then trifluoromethanesulfonic anhydride (2.49 g, 8.8 mmol) was added and stirred at 25° C. for 1 hour. After completion, the reaction was concentrated under reduced pressure. Then the residue, N,N-diisopropylethylamine (4.41 g, 34.2 mmol) and tert-butyl (3S)-3-methyl-1-piperazinecarboxylate (1.37 g, 6.8 mmol) in 1,4-dioxane (30 mL) was stirred at 110° C. for 16 hours. After completion, the resulting solution was concentrated under vacuum. The residue was purified by flash chromatography on silica gel eluting with hexane/ethyl acetate (7/1) to afford tert-butyl (3S)-4-[7-[3-[tert-butyl(dimethyl)silyl]oxy-1-naphthyl]-2-methylsulfanyl-5,6,7,8-tetrahydroquinazolin-4-yl]-3-methyl-piperazine-1-carboxylate (1.8 g, 2.8 mmol, 63.6% yield) as a yellow solid. LCMS (ESI, m/z): 635.3 [M+H]$^+$.

Step 6: tert-butyl (3S)-4-[7-[3-[tert-butyl(dimethyl)silyl]oxy-1-naphthyl]-2-methylsulfonyl-5,6,7,8-tetrahydroquinazolin-4-yl]-3-methyl-piperazine-1-carboxylate

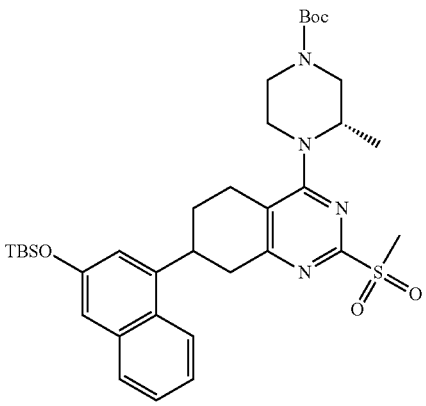

A solution of tert-butyl (3S)-4-[7-[3-[tert-butyl(dimethyl)silyl]oxy-1-naphthyl]-2-methylsulfanyl-5,6,7,8-tetrahydroquinazolin-4-yl]-3-methyl-piperazine-1-carboxylate (2.0 g, 3.1 mmol) and 3-chloroperoxybenzoic acid (1.63 g, 9.4 mmol) in dichloromethane (20 mL) was stirred at 25° C. for 2 hours. After completion, the resulting solution was quenched with saturated sodium sulfite solution. The resulting solution was extracted with ethyl acetate, dried over anhydrous sodium sulfate and concentrated under vacuum to afford tert-butyl (3S)-4-[7-[3-[tert-butyl(dimethyl)silyl]oxy-1-naphthyl]-2-methylsulfonyl-5,6,7,8-tetrahydroquinazolin-4-yl]-3-methyl-piperazine-1-carboxylate (1.5 g, 2.2 mmol, 71% yield) as a yellow solid. LCMS (ESI, m/z): 667.3 [M+H]$^+$.

Step 7: tert-butyl (3S)-4-[2-[[(2S,4R)-4-fluoro-1-methyl-pyrrolidin-2-yl]methoxy]-7-(3-hydroxy-1-naphthyl)-5,6,7,8-tetrahydroquinazolin-4-yl]-3-methyl-piperazine-1-carboxylate

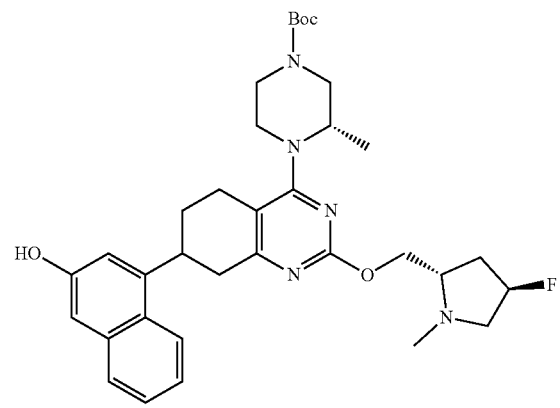 [SMILES: C[C@H]1CN(C(=O)OC(C)(C)C)CCN1c1nc(OC[C@@H]2C[C@@H](F)CN2C)nc2c1CCC(c1cc(O)cc3ccccc13)C2]

A solution of [(2S,4R)-4-fluoro-1-methyl-pyrrolidin-2-yl]methanol (2.0 g, 14.99 mmol) in N,N-dimethylformamide (20 mL) was stirred at 25° C. for 5 minutes. Then sodium hydride (479.8 mg, 11.9 mmol, 60% dispersion in mineral oil) was added and stirred at 0° C. for 30 minutes. Then tert-butyl (3S)-4-[7-[3-[tert-butyl(dimethyl)silyl]oxy-1-naphthyl]-2-methylsulfonyl-5,6,7,8-tetrahydroquinazolin-4-yl]-3-methyl-piperazine-1-carboxylate (2.0 g, 3 mmol) was added and stirred at 25° C. for 1 hour. After completion, the resulting solution was adjusted to pH 8 with saturated ammonium chloride solution. The solvent was extracted with ethyl acetate, washed with water. The organic layer was dried over anhydrous sodium sulfate and concentrated under vacuum. The residue was purified by flash chromatography on silica gel eluting with dichloromethane/methanol (10/1) to afford tert-butyl (3S)-4-[2-[[(2S,4R)-4-fluoro-1-methyl-pyrrolidin-2-yl]methoxy]-7-(3-hydroxy-1-naphthyl)-5,6,7,8-tetrahydroquinazolin-4-yl]-3-methyl-piperazine-1-carboxylate (500 mg, 0.82 mmol, 27.5% yield) as a yellow solid. LCMS (ESI, m/z): 606.3 [M+H]$^+$.

Step 8: tert-butyl-[[4-[2-[[(2S,4R)-4-fluoro-1-methyl-pyrrolidin-2-yl]methoxy]-4-[(2S)-2-methylpiperazin-1-yl]-5,6,7,8-tetrahydroquinazolin-7-yl]-2-naphthyl]oxy]-dimethyl-silane

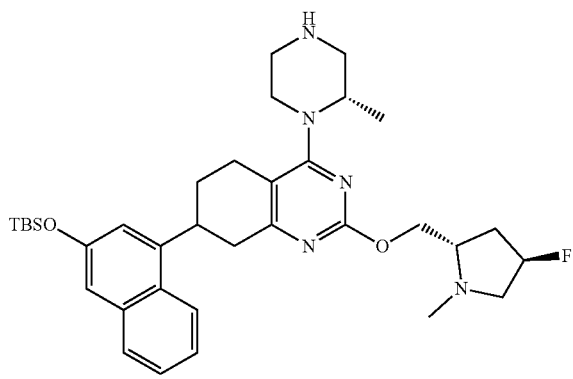 [SMILES: C[C@H]1CNCCN1c1nc(OC[C@@H]2C[C@@H](F)CN2C)nc2c1CCC(c1cc(O[Si](C)(C)C(C)(C)C)cc3ccccc13)C2]

A solution of tert-butyl (3S)-4-[2-[[(2S,4R)-4-fluoro-1-methyl-pyrrolidin-2-yl]methoxy]-7-(3-hydroxy-1-naphthyl)-5,6,7,8-tetrahydroquinazolin-4-yl]-3-methyl-piperazine-1-carboxylate (500.0 mg, 0.83 mmol) and trifluoroacetic acid (1.8 g, 16.5 mmol) in dichloromethane (25 mL) was stirred at 25° C. for 1 hour. the resulting solution was concentrated under vacuum. The residue, imidazole (168.5 mg, 2.48 mmol) and N,N-diisopropylethylamine (2.1 g, 16.51 mmol) in dichloromethane (25 mL) was stirred at 25° C. for 3 minutes. Then tert-Butyldimethylsilyl chloride (249.2 mg, 1.65 mmol) was added and stirred at 25° C. for 2 hours. After completion, the resulting solution was concentrated under vacuum. The residue was purified by flash chromatography on silica gel eluting with methanol/water (30/20) to afford tert-butyl-[[4-[2-[[(2S,4R)-4-fluoro-1-methyl-pyrrolidin-2-yl]methoxy]-4-[(2S)-2-methylpiperazin-1-yl]-5,6,7,8-tetrahydroquinazolin-7-yl]-2-naphthyl]oxy]-dimethyl-silane (360 mg, 0.58 mmol, 70% yield) as a white solid. LCMS (ESI, m/z): 620.3 [M+H]$^+$.

Step 9: 1-[(3S)-4-[7-[3-[tert-butyl(dimethyl)silyl]oxy-1-naphthyl]-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one

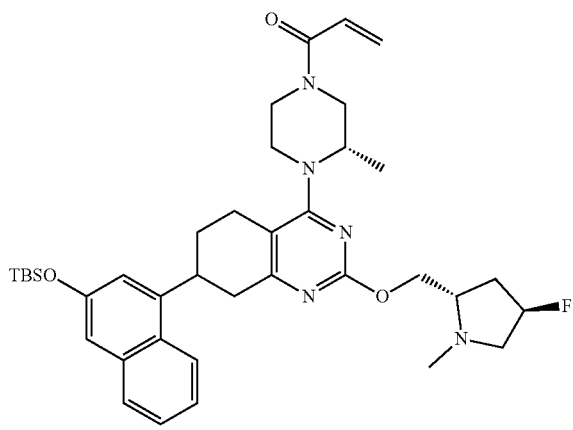 [SMILES: C=CC(=O)N1CCN(c2nc(OC[C@@H]3C[C@@H](F)CN3C)nc3c2CCC(c2cc(O[Si](C)(C)C(C)(C)C)cc4ccccc24)C3)[C@@H](C)C1]

A solution of tert-butyl-[[4-[2-[[(2S,4R)-4-fluoro-1-methyl-pyrrolidin-2-yl]methoxy]-4-[(2S)-2-methylpiperazin-1-yl]-5,6,7,8-tetrahydroquinazolin-7-yl]-2-naphthyl]oxy]-dimethyl-silane (360.0 mg, 0.58 mmol) and N,N-diisopropylethylamine (224.7 mg, 1.74 mmol) in dichloromethane (9 mL) was stirred at 25° C. for 3 minutes. Then acryloyl chloride (63.0 mg, 0.70 mmol) was added and stirred at 25° C. for 30 minutes. After completion, the resulting solution was concentrated under vacuum. The residue was purified by flash chromatography on silica gel eluting with dichloromethane/methanol (20/1) to afford 1-[(3S)-4-[7-[3-[tert-butyl(dimethyl)silyl]oxy-1-naphthyl]-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one (320 mg, 0.47 mmol, 81.8% yield) as a yellow solid. LCMS (ESI, m/z): 674.3 [M+H]$^+$.

Step 10: 1-[(3S)-4-[(7S)-2-[[(2S,4R)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one (Example 31a) and 1-[(3S)-4-[(7R)-2-[[(2S,4R)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one (Example 31b)

Example 31a

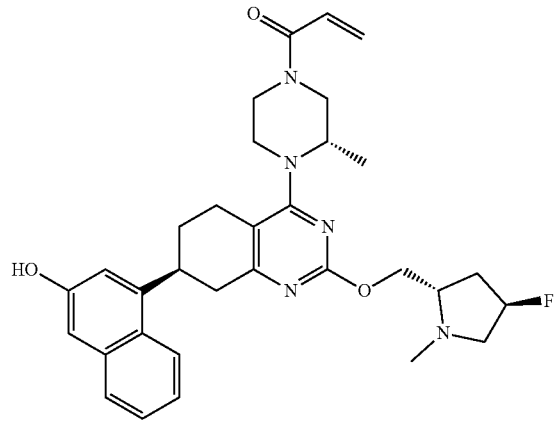

Example 31b

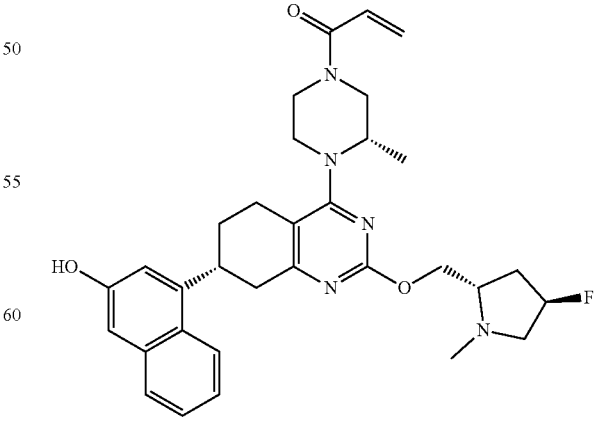

A solution of 1-[(3S)-4-[7-[3-[tert-butyl(dimethyl)silyl]oxy-1-naphthyl]-2-[[(2S,4R)-4-fluoro-1-methyl-pyrrolidin- 2-yl]methoxy]-5,6,7,8-tetrahydroquinazolin-4-yl]-3-methyl-piperazin-1-yl]prop-2-en-1-one (320.0 mg, 0.47 mmol) and Caesium fluoride (288.6 mg, 1.9 mmol) in tetrahydrofuran (5 mL) was stirred at 25° C. for 1 hour. After completion, the resulting solution was diluted with water and extracted with dichloromethane. Then the organic layers were collected, dried over anhydrous sodium sulfate and concentrated under vacuum. The residue was purified by flash chromatography on silica gel eluting with dichloromethane/methanol (10/1) to afford crude solid. The crude product was purified by Prep-HPLC to afford 150 mg white solid with the following conditions: Column: Column: Xselect CSH F-Phenyl OBD column, 19*250, 5 um; Mobile Phase A: Water (10 MMOL/L NH4HCO3), Mobile Phase B: EtOH; Flow rate: 25 mL/min; Gradient: 73 B to 78 B in 8 min; 254 nm; RT1:7.3. The product was further purified by Chiral-Prep-HPLC with following condition (Column, CHIRALPAK IC-3, 0.46*5 cm; 3 um; mobile phase: (Hex: DCM=3:1)(0.1% DEA): EtOH=50:50; Detector, UV 254 nm.) to afford the title compounds. The absolute configuration of the title compounds was inferred from potency data and a protein X-ray structure of compound 21b.

Example 31a: 1-[(3S)-4-[(7S)-2-[[(2S,4R)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one (43 mg, 0.076 mmol, 16.2% yield, white solid). $^1$H NMR (400 MHz, DMSO-d$_6$, ppm) δ 9.70 (s, 1H), 8.06 (d, J=8.6 Hz, 1H), 7.71 (dd, J=8.3, 1.4 Hz, 1H), 7.40 (t, J=7.2 Hz, 1H), 7.31 (t, J=7.2 Hz, 1H), 7.05-6.95 (m, 2H), 6.94-6.76 (m, 1H), 6.23-6.10 (m, 1H), 5.73 (dd, J=10.4, 2.4 Hz, 1H), 5.29-5.07 (m, 1H), 4.43-4.27 (m, 2H), 4.22-4.03 (m, 3H), 3.92-3.82 (m, 2H), 3.52-3.38 (m, 2H), 3.37-3.40 (m, 1H), 3.26-3.14 (m, 1H), 3.08 (dd, J=18.2, 5.6 Hz, 2H), 2.99-2.85 (m, 2H), 2.78 (dd, J=18.2, 10.4 Hz, 1H), 2.47-2.40 (m, 1H), 2.38 (s, 3H), 2.19-2.05 (m, 2H), 1.96-1.78 (m, 2H), 1.24 (s, 3H). LCMS (ESI, m/z): 560.3 [M+H]$^+$. Chiral HPLC: Column: CHIRALPAK IC-3, 4.6*50 mm, 3 um; detected at 254 nm; (Hex:DCM=3:1) (0.1% DEA): EtOH=50:50, Flow rate: 1 mL/min; Retention time: 2.852 min; (slower peak).

Example 31b: 1-[(3S)-4-[(7R)-2-[[(2S,4R)-4-fluoro-1-methyl-pyrrolidin-2-yl]methoxy]-7-(3-hydroxy-1-naphthyl)-5,6,7,8-tetrahydroquinazolin-4-yl]-3-methyl-piperazin-1-yl]prop-2-en-1-one (42 mg, 0.075 mmol, 15.8% yield, white solid). $^1$H NMR (400 MHz, DMSO-d$_6$, ppm) δ 9.74 (s, 1H), 8.08 (d, J=8.5 Hz, 1H), 7.70 (dd, J=8.2, 1.4 Hz, 1H), 7.40 (t, J=7.2 Hz, 1H), 7.29 (t, J=8.3, 6.8, 1.4 Hz, 1H), 7.01 (s, 2H), 6.93-6.75 (m, 1H), 6.16 (dd, J=16.6, 6.8 Hz, 1H), 5.72 (dd, J=10.4, 2.4 Hz, 1H), 5.23-5.10 (m, 1H), 4.38-4.24 (m, 2H), 4.20-4.02 (m, 2H), 3.95-3.80 (m, 2H), 3.64-3.43 (m, 2H), 3.42-3.21 (m, 3H), 3.09 (dd, J=18.1, 5.2 Hz, 1H), 2.97-2.72 (m, 3H), 2.63-2.53 (m, 1H), 2.48-2.41 (m, 1H), 2.37 (s, 3H), 2.18-2.02 (m, 2H), 1.97-1.75 (m, 2H), 1.02-0.98 (m, 3H). LCMS (ESI, m/z): 560.3 [M+H]$^+$. Chiral HPLC: Column: CHIRALPAK IC-3, 4.6*50 mm, 3 um, 3 um; detected at 254 nm; (Hex:DCM=3:1) (0.1% DEA): EtOH=50:50, Flow rate: 1 mL/min; Retention time: 1.317 min; (faster peak).

Examples 32a and 32b

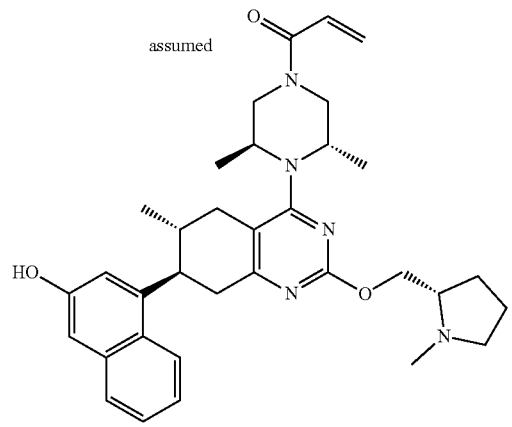

Example 32a

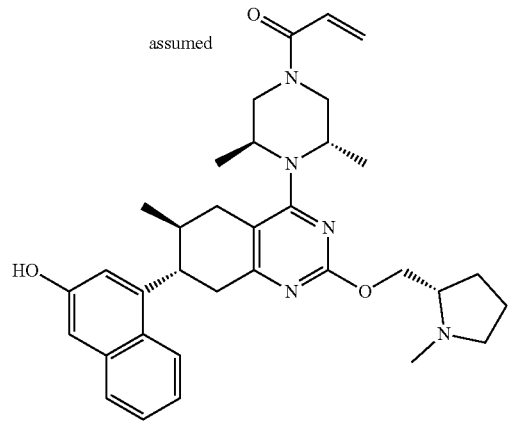

Example 32b

1-[(3S,5S)-4-[(6R,7R)-7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one (Example 32a); and
1-[(3S,5S)-4-[(6S,7S)-7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one (Example 32b)
5
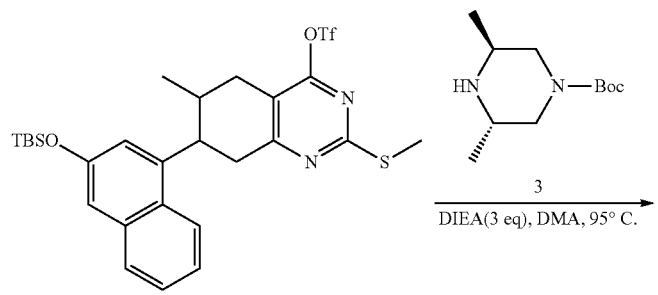
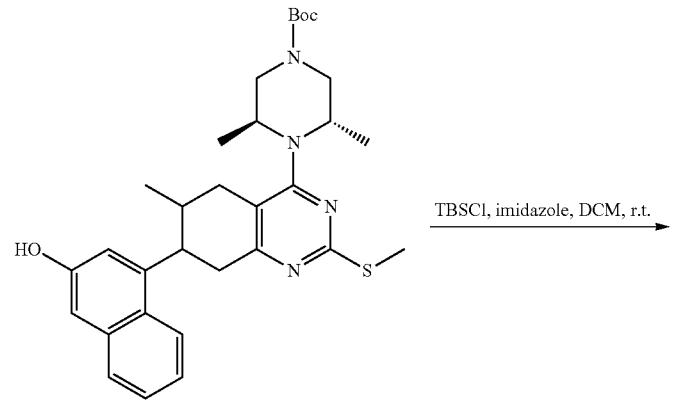
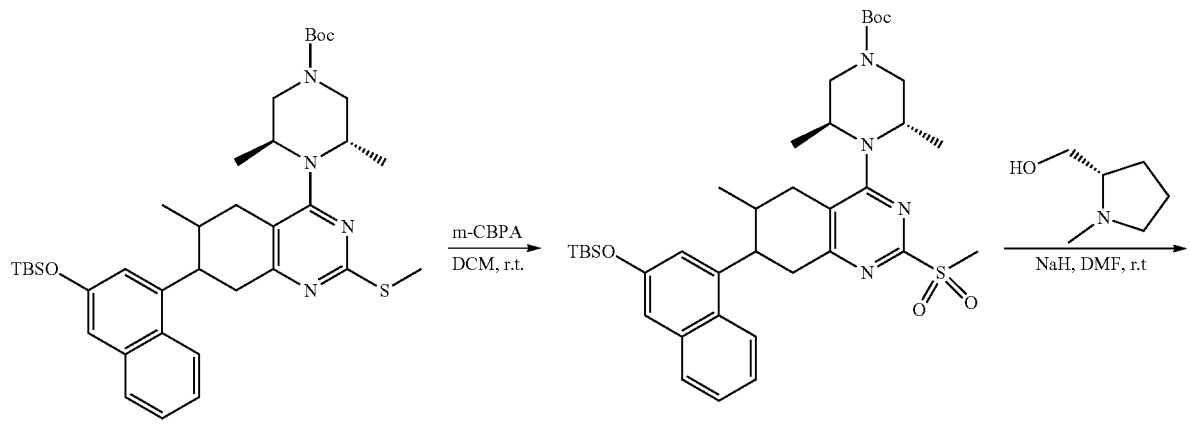

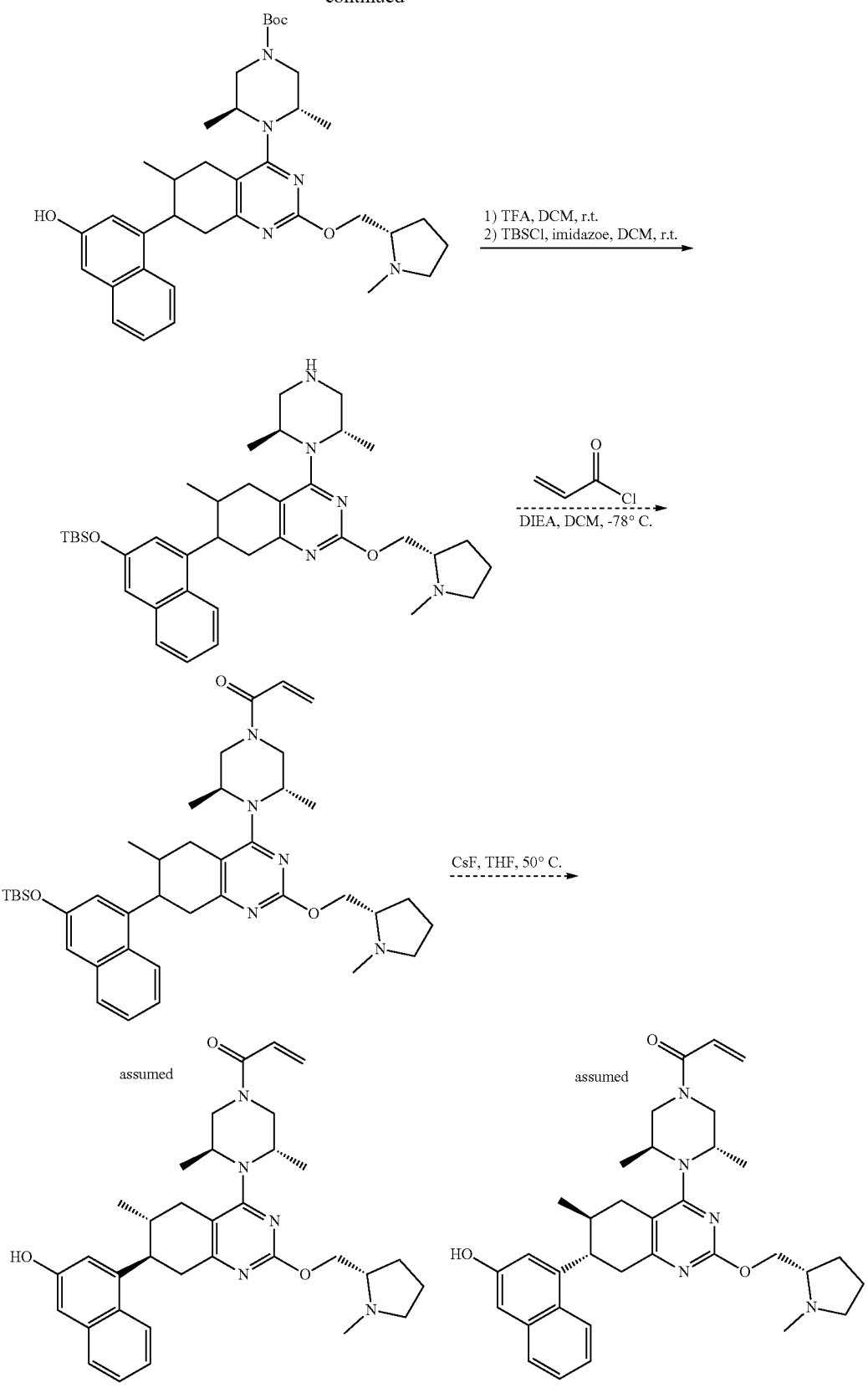

Step 1: tert-butyl (3S,5S)-4-[7-(3-hydroxy-1-naph-thyl)-6-methyl-2-methylsulfanyl-5,6,7,8-tetrahydro-quinazolin-4-yl]-3,5-dimethyl-piperazine-1l-car-boxylate

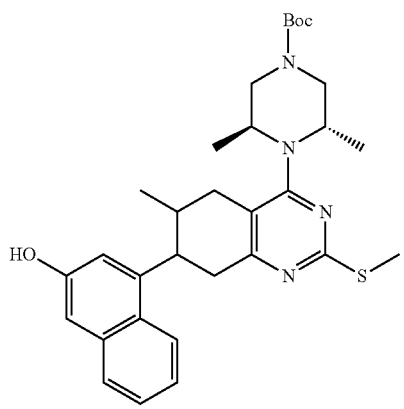 [SMILES: CSc1nc2c(c(N3[C@@H](C)CN(C(=O)OC(C)(C)C)C[C@@H]3C)n1)CC(C)C(c1cc(O)cc3ccccc13)C2]

A solution of [7-[3-[tert-butyl(dimethyl)silyl]oxy-1-naph-thyl]-6-methyl-2-methylsulfanyl-5,6,7,8-tetrahydroqui-nazolin-4-yl] trifluoromethanesulfonate (2.0 g, 3.3 mmol), tert-butyl (3S,5S)-3,5-dimethylpiperazine-1-carboxylate (1.43 g, 6.6 mmol) and N,N-diisopropylethylamine (1.29 g, 10.0 mmol) in N,N-dimethylacetamide (20 mL) was stirred at 95° C. for 48 hours. After completion, the resulting solution was diluted with water, extracted with ethyl acetate, dried over anhydrous sodium sulfate and concentrated under vacuum. The residue was purified by flash chromatography on silica gel eluting with petroleum ether/ethyl acetate (7:3) to afford tert-butyl (3S,5S)-4-[7-(3-hydroxy-1-naphthyl)-6-methyl-2-methylsulfanyl-5,6,7,8-tetrahydroquinazolin-4-yl]-3,5-dimethyl-piperazine-1-carboxylate (600 mg, 1.1 mmol, 32.7% yield) as a yellow solid. LCMS (ESI, m/z): 549.3 [M+H]$^+$.

Step 2: tert-butyl (3S,5S)-4-[7-[3-[tert-butyl(dim-ethyl)silyl]oxy-1-naphthyl]-6-methyl-2-methylsulfa-nyl-5,6,7,8-tetrahydroquinazolin-4-yl]-3,5-dimethyl-piperazine-1-carboxylate

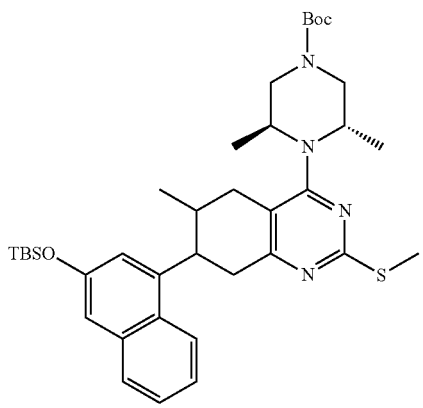 [SMILES: CSc1nc2c(c(N3[C@@H](C)CN(C(=O)OC(C)(C)C)C[C@@H]3C)n1)CC(C)C(c1cc(O[Si](C)(C)C(C)(C)C)cc3ccccc13)C2]

A solution of tert-butyl (3S,5S)-4-[7-(3-hydroxy-1-naph-thyl)-6-methyl-2-methylsulfanyl-5,6,7,8-tetrahydroqui-nazolin-4-yl]-3,5-dimethyl-piperazine-1-carboxylate (600.0 mg, 1.1 mmol), tert-butyldimethylsilyl chloride (494.3 mg, 3.2 mmol), N,N-diisopropylethylamine (705.2 mg, 5.4 mmol) and imidazole (223.3 mg, 3.2 mmol) in dichloromethane (6 mL) was stirred at 25° C. for 1 hour. After completion, the resulting solution was concentrated under vacuum. The residue was purified by flash chromatography on silica gel eluting with petroleum ether/ethyl acetate (10/1) to afford tert-butyl (3S,5S)-4-[7-[3-[tert-butyl(dim-ethyl)silyl]oxy-1-naphthyl]-6-methyl-2-methylsulfanyl-5,6, 7,8-tetrahydroquinazolin-4-yl]-3,5-dimethyl-piperazine-1-carboxylate (580 mg, 0.8 mmol, 80% yield) as a yellow solid. LCMS (ESI, m/z): 663.4 [M+H]$^+$.

Step 3: tert-butyl (3S,5S)-4-[7-[3-[tert-butyl(dim-ethyl)silyl]oxy-1-naphthyl]-6-methyl-2-methylsulfo-nyl-5,6,7,8-tetrahydroquinazolin-4-yl]-3,5-dimethyl-piperazine-1-carboxylate

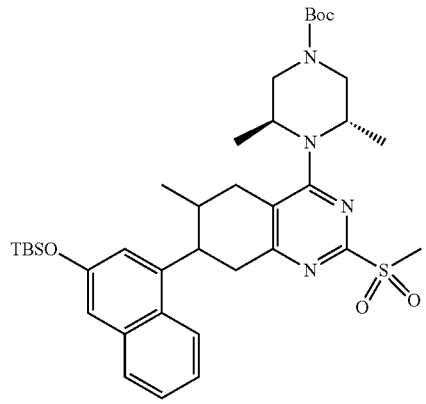 [SMILES: CC1Cc2c(nc(S(C)(=O)=O)nc2N2[C@@H](C)CN(C(=O)OC(C)(C)C)C[C@@H]2C)CC1c1cc(O[Si](C)(C)C(C)(C)C)cc2ccccc12]

A solution of tert-butyl (3S,5S)-4-[7-[3-[tert-butyl(dim-ethyl)silyl]oxy-1-naphthyl]-6-methyl-2-methylsulfanyl-5,6, 7,8-tetrahydroquinazolin-4-yl]-3,5-dimethyl-piperazine-1-carboxylate (580 mg, 0.87 mmol) and 3-chloroperoxybenzoic acid (299 mg, 1.74 mmol) in dichloromethane (6 mL) was stirred at 25° C. for 30 minutes. After completion, the resulting solution was quenched by saturated, extracted with dichloromethane and dried over anhydrous sodium sulfate. The solvent was concentrated under vacuum to afford crude solid. LCMS (ESI, m/z): 695.4 [M+H]$^+$.

Step 4: tert-butyl (3S,5S)-4-[7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazine-1-carboxylate

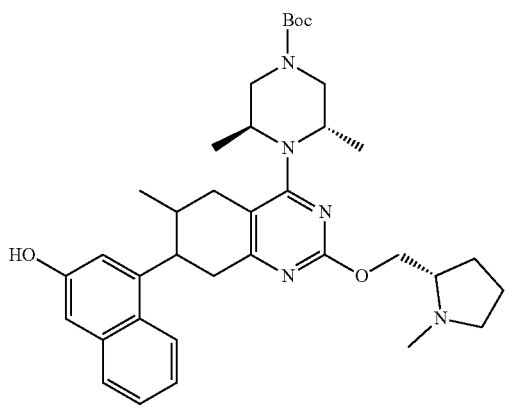 [SMILES: CC1Cc2c(nc(OC[C@@H]3CCCN3C)nc2N2[C@@H](C)CN(C(=O)OC(C)(C)C)C[C@@H]2C)CC1c1cc(O)cc2ccccc12]

A solution of N-methyl-1-prolinol (0.48 g, 4.1 mmol) in DMF (6 mL) was stirred at 25° C. for 5 minutes. Then sodium hydride (0.13 g, 3.34 mmol, 60% dispersion in mineral oil) was added and stirred at 0° C. for 10 minutes. Then tert-butyl (3S,5S)-4-[7-[3-[tert-butyl(dimethyl)silyl]oxy-1-naphthyl]-6-methyl-2-methylsulfonyl-5,6,7,8-tetrahydroquinazolin-4-yl]-3,5-dimethyl-piperazine-1-carboxylate (0.58 g, 0.8 mmol) was added and stirred at 25° C. for 20 minutes. the resulting solution was adjusted to pH 8 with saturated ammonium chloride solution. The solvent was extracted with ethyl acetate, washed with water. The organic layer was dried over anhydrous sodium sulfate and concentrated under vacuum. The residue was purified by flash chromatography on silica gel eluting with dichloromethane/methanol (10/1) to afford tert-butyl (3S,5S)-4-[7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazine-1-carboxylate (400 mg, 0.6 mmol, 77.8% yield) as a yellow solid. LCMS (ESI, m/z): 616.4 [M+H]$^+$.

Step 5: tert-butyl-[[4-[4-[(2S,6S)-2,6-dimethylpiperazin-1-yl]-6-methyl-2-[[(2S)-1-methylpyrrolidin-2-yl]methoxy]-5,6,7,8-tetrahydroquinazolin-7-yl]-2-naphthyl]oxy]-dimethyl-silane

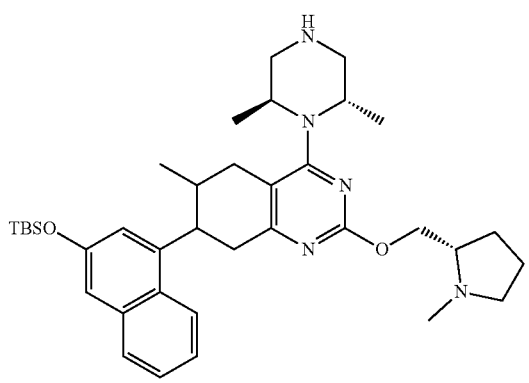 [SMILES: CC1Cc2c(nc(OC[C@@H]3CCCN3C)nc2N2[C@@H](C)CNC[C@@H]2C)CC1c1cc(O[Si](C)(C)C(C)(C)C)cc2ccccc12]

A solution of tert-butyl (3S,5S)-4-[7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazine-1-carboxylate (400.0 mg, 0.6 mmol) and trifluoroacetic acid (1.48 g, 12.9 mmol) in dichloromethane (6 mL) was stirred at 25° C. for 1 hour. the resulting solution was concentrated under vacuum. The residue, imidazole (132.66 mg, 1.95 mmol) and N,N-Diisopropylethylamine (1.6 g, 12.9 mmol) in dichloromethane (6 mL) was stirred at 25° C. for 3 minutes. Then tert-Butyldimethylsilyl chloride (196.1 mg, 1.3 mmol) was added and stirred at 25° C. for 2 hours. After completion, the resulting solution was concentrated under vacuum. The residue was purified by flash chromatography on silica gel eluting with methanol/water (4:6) to afford tert-butyl-[[4-[4-[(2S,6S)-2,6-dimethylpiperazin-1-yl]-6-methyl-2-[[(2S)-1-methylpyrrolidin-2-yl]methoxy]-5,6,7,8-tetrahydroquinazolin-7-yl]-2-naphthyl]oxy]-dimethyl-silane (280 mg, 0.4 mmol, 68.4% yield) as a yellow solid. LCMS (ESI, m/z): 630.4 [M+H]$^+$.

Step 6: 1-[(3S,5S)-4-[7-[3-[tert-butyl(dimethyl)silyl]oxy-1-naphthyl]-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one

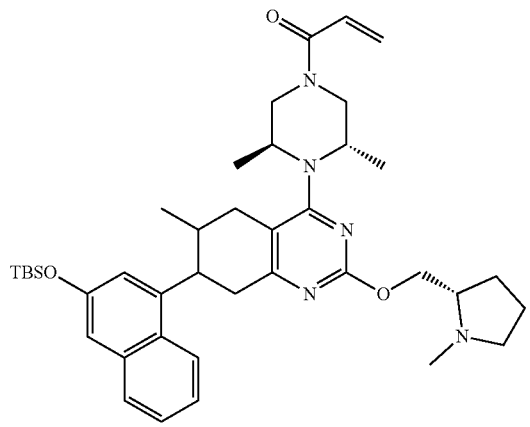 [SMILES: C=CC(=O)N1C[C@H](C)N(c2nc(OC[C@@H]3CCCN3C)nc3c2CC(C)C(c2cc(O[Si](C)(C)C(C)(C)C)cc4ccccc24)C3)[C@@H](C)C1]

A solution of tert-butyl-[[4-[4-[(2S,6S)-2,6-dimethylpiperazin-1-yl]-6-methyl-2-[[(2S)-1-methylpyrrolidin-2-yl]methoxy]-5,6,7,8-tetrahydroquinazolin-7-yl]-2-naphthyl]oxy]-dimethyl-silane (380.0 mg, 0.6 mmol) and N,N-diisopropylethylamine (233.4 mg, 1.8 mmol) in dichloromethane (4 mL) was stirred at 25° C. for 3 minutes. Then acryloyl chloride (65.5 mg, 0.7 mmol) was added and stirred at −78° C. for 30 minutes. the resulting solution was concentrated under vacuum. The residue was purified by flash chromatography on silica gel eluting with dichloromethane/methanol (20:1) to afford 1-[(3S,5S)-4-[7-[3-[tert-butyl(dimethyl)silyl]oxy-1-naphthyl]-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one (280 mg, 0.4 mmol, 67.9% yield) as a yellow solid. LCMS (ESI, m/z): 684.4 [M+H]$^+$.

Step 7: 1-[(3S,5S)-4-[(6R,7R)-7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one (Example 32a) and 1-[(3S,5S)-4-[(6S,7S)-7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one (Example 32b)

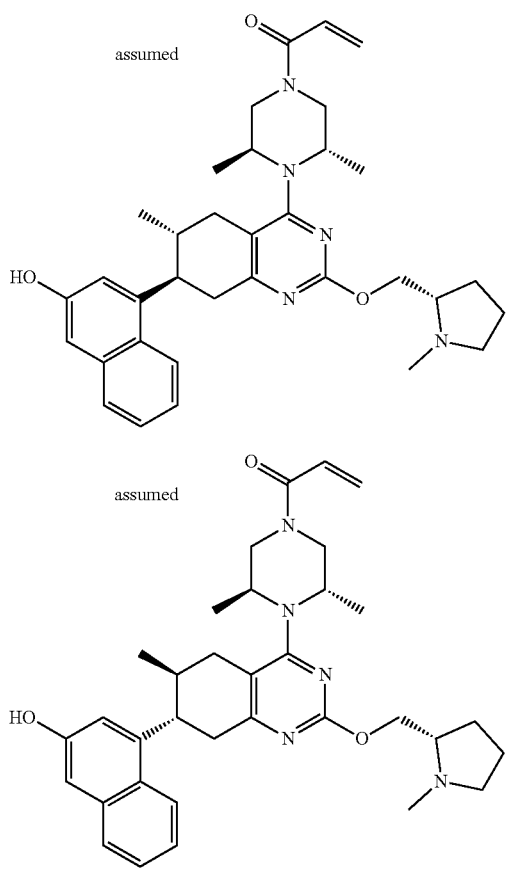

A solution of 1-[(3S,5S)-4-[7-[3-[tert-butyl(dimethyl)silyl]oxy-1-naphthyl]-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one (268.0 mg, 0.4 mmol) and caesium fluoride (242.5 mg, 1.6 mmol) in tetrahydrofuran (3 mL) was stirred at 50° C. for 1 hour. The reaction was diluted with water, extracted with dichloromethane and dried over anhydrous sodium sulfate. the resulting solution was concentrated under vacuum. The residue was purified by flash chromatography on silica gel eluting with dichloromethane/methanol (10/1) to afford crude solid. The crude product was purified by Prep-HPLC to afford 150 mg white solid with the following conditions: Column: Xselect CSH F-Phenyl OBD column, 19*250, 5 um; Mobile Phase A: Water (10 MMOL/L NH4HCO3), Mobile Phase B: EtOH; Flow rate: 25 mL/min; Gradient: 73 B to 78 B in 8 min; 254 nm; RT1:7.3. The product was further purified by Chiral-Prep-HPLC with following condition (Column, CHIRAL-PAK IC-3, 0.46*5 cm; 3 um; mobile phase: (Hex:DCM=3:1)(0.1% DEA): EtOH=80:20; Detector, UV 254 nm) to afford the title compounds. The stereo chemistry of title compounds was arbitrarily assigned.

Example 32a: 1-[(3S,5S)-4-[(6R,7R)-7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one (40.8 mg, 0.071 mmol, 18% yield, white solid). $^1$H NMR (400 MHz, DMSO-$d_6$, ppm) δ 9.63 (s, 1H), 8.08 (d, J=8.6 Hz, 1H), 7.69 (dd, J=8.3, 1.3 Hz, 1H), 7.38 (t, J=7.4 Hz, 1H), 7.27 (t, J=7.4 Hz, 1H), 7.01 (s, 1H), 6.93 (s, 1H), 6.84 (dd, J=16.6, 10.5 Hz, 1H), 6.15 (dd, J=16.6, 2.5 Hz, 1H), 5.70 (dd, J=10.4, 2.4 Hz, 1H), 4.26 (dd, J=10.7, 5.0 Hz, 1H), 4.05 (dd, J=10.7, 6.4 Hz, 1H), 3.91-3.37 (m, 7H), 3.07-2.87 (m, 3H), 2.69-2.58 (m, 1H), 2.58-2.52 (m, 1H), 2.48-2.38 (m, 1H), 2.33 (s, 3H), 2.26 (s, 1H), 2.21-2.09 (m, 1H), 1.99-1.86 (m, 1H), 1.74-1.50 (m, 3H), 1.01 (d, J=6.0 Hz, 6H), 0.87 (d, J=6.5 Hz, 3H). LCMS (ESI, m/z): 570.3 [M+H]$^+$. Chiral HPLC: Column: CHIRALPAK IC-3, 4.6*50 mm, 3 um; detected at 254 nm; (Hex:DCM=3:1) (0.1% DEA): EtOH=80:20, Flow rate: 1 mL/min; Retention time: 1.326 min; (faster peak).

Example 32b: 1-[(3S,5S)-4-[(6S,7S)-7-(3-hydroxy-1-naphthyl)-6-methyl-2-[[(2S)-1-methylpyrrolidin-2-yl]methoxy]-5,6,7,8-tetrahydroquinazolin-4-yl]-3,5-dimethyl-piperazin-1-yl]prop-2-en-1-one (35.1 mg, 0.061 mmol, 15.4% yield, white solid). $^1$H NMR (400 MHz, DMSO-$d_6$, ppm) δ 9.67 (s, 1H), 8.17 (d, J=8.6 Hz, 1H), 7.70 (d, J=8.2 Hz, 1H), 7.38 (t, J=7.5 Hz, 1H), 7.26 (t, J=7.6 Hz, 1H), 7.05 (s, 1H), 7.02 (s, 1H), 6.97-6.77 (m, 1H), 6.18 (dd, J=16.6, 2.4 Hz, 1H), 5.73 (dd, J=10.4, 2.4 Hz, 1H), 4.23 (dd, J=10.8, 5.0 Hz, 1H), 4.08 (dd, J=10.8, 6.4 Hz, 1H), 3.72 (s, 3H), 3.32 (s, 5H), 3.06-2.77 (m, 4H), 2.59-2.52 (m, 1H), 2.31 (s, 3H), 2.19-2.05 (m, 2H), 1.95-1.84 (m, 1H), 1.72-1.49 (m, 3H), 0.93 (s, 6H), 0.79 (d, J=6.3 Hz, 3H). LCMS (ESI, m/z): 570.3 [M+H]$^+$. Chiral HPLC: Column: CHIRALPAK IC-3, 4.6*50 mm, 3 um; detected at 254 nm; (Hex:DCM=3:1) (0.1% DEA): EtOH=80:20, Flow rate: 1 mL/min; Retention time: 1.933 min; (slower peak).

Examples 33a and 33b

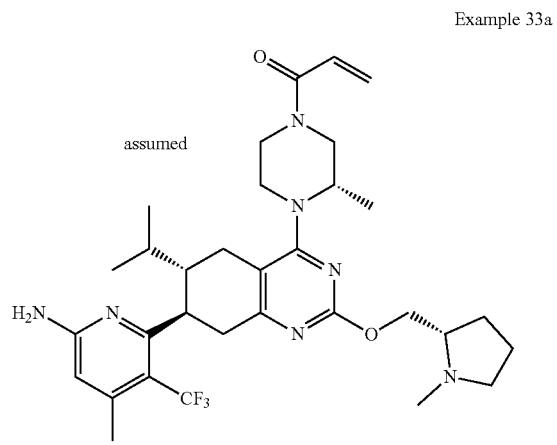

Example 33a

Example 33b
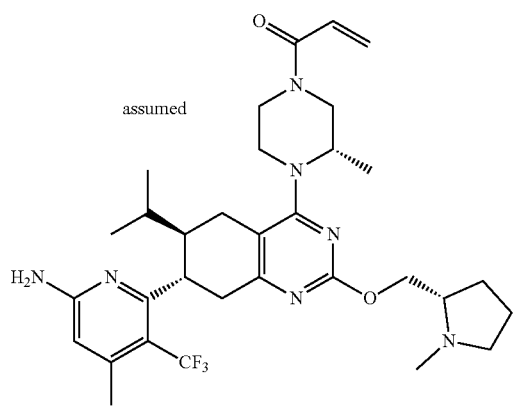
1-((S)-4-(((6S,7R)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one (Example 33a); and
1-((S)-4-(((6R,7S)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one (Example 33b)
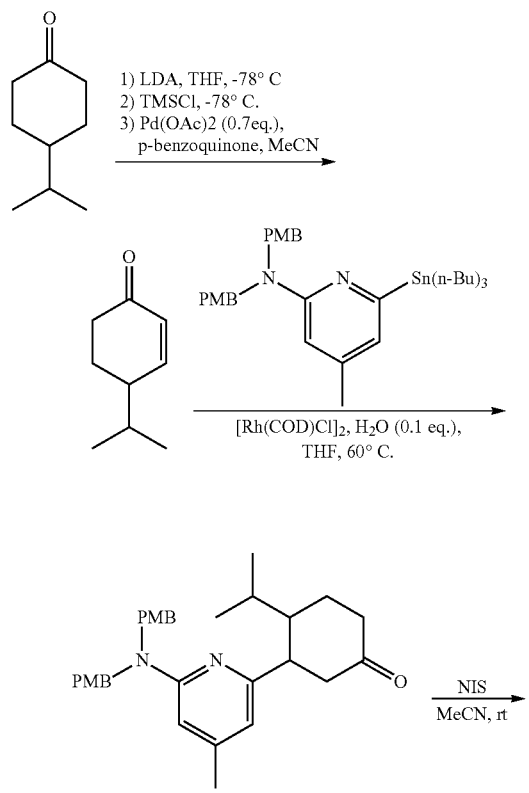
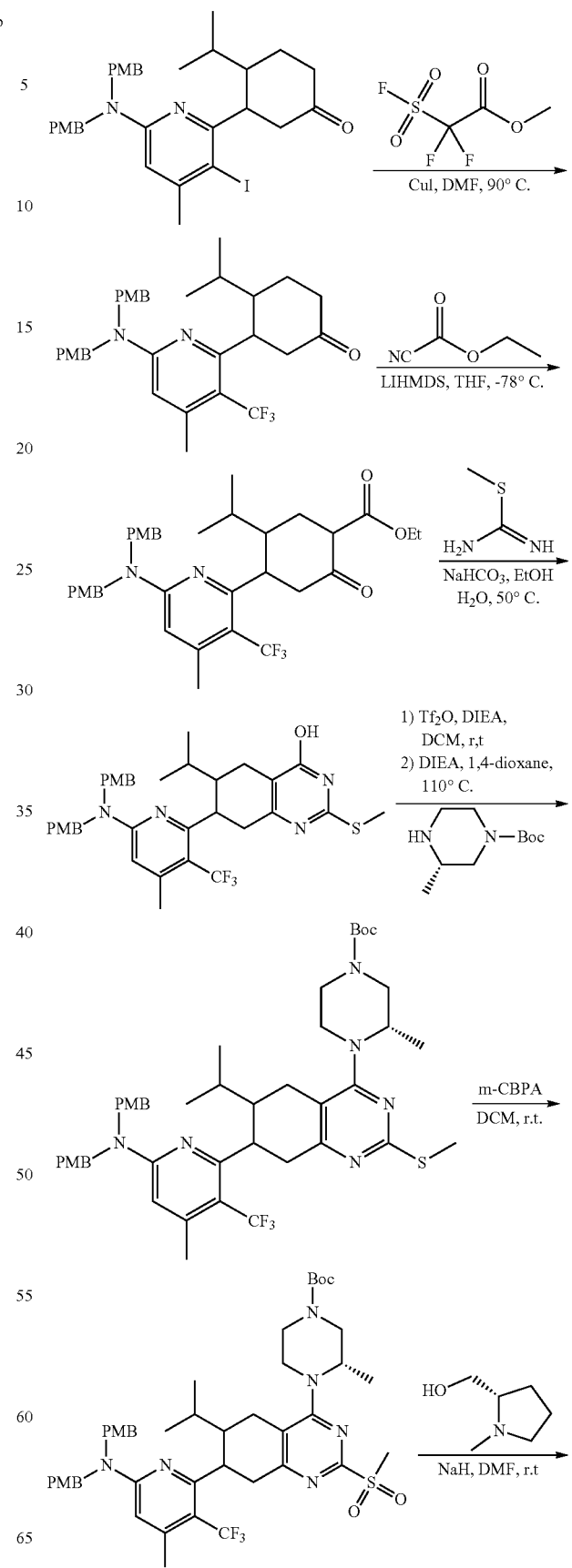

515

-continued

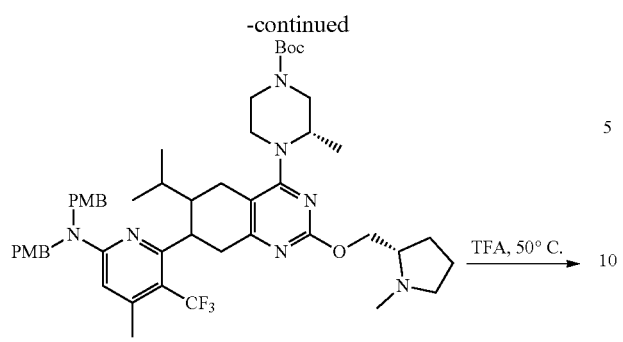

TFA, 50° C.

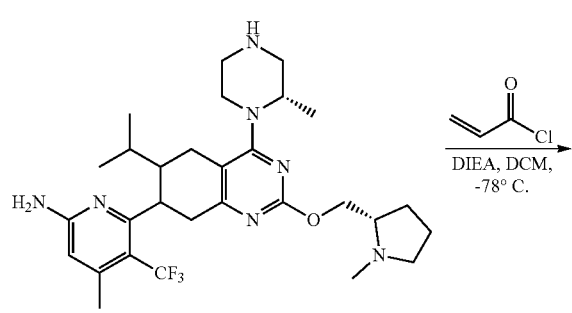

DIEA, DCM, -78° C.

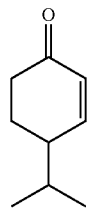

assumed

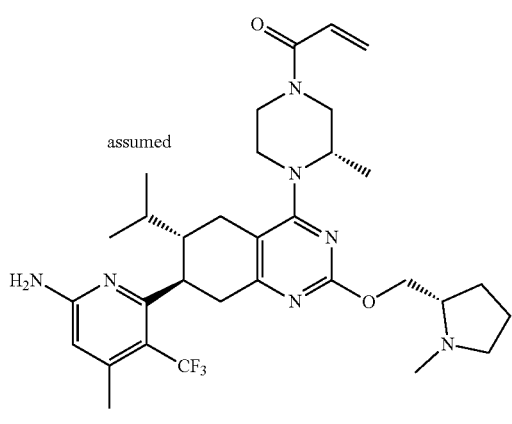

33a assumed

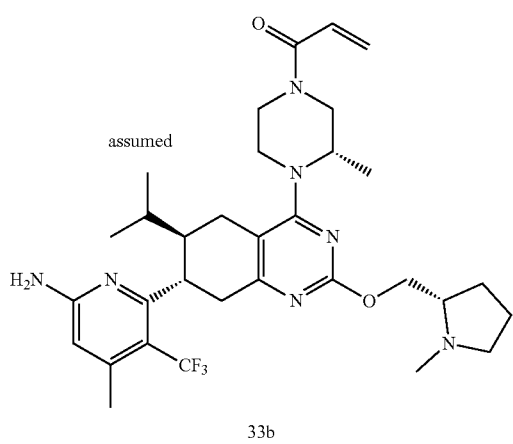

33b

516

Step 1: 4-isopropylcyclohex-2-en-1-one

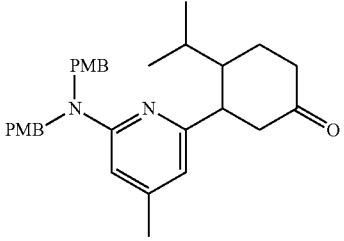

Under nitrogen, a solution of 4-isopropylcyclohexanone (40.0 g, 285.2 mmol) in tetrahydrofuran (400 mL) was stirred for 5 minutes at −78° C. and lithium diisopropylamide (2 M in THF) (240 mL, 427.9 mmol) was added and stirred at −78° C. for 1 hour. Then chlorotrimethylsilane (36.7 mL, 427.9 mmol) was added and stirred at −78° C. for 1 hour. After completion, the reaction was diluted with dichloromethane and washed with brine. Then the organic layer was dried over anhydrous sodium sulfate and concentrated under vacuum. A solution of p-benzoquinone (20.64 g, 191.15 mmol) and palladium (II) acetate (42.8 g, 191.1 mmol) in acetonitrile (400 mL) was stirred at 25° C. for 10 minutes. Then (4-isopropylcyclohexen-1-yl)oxy-trimethylsilane (58.0 g, 273.1 mmol) was added and stirred at 25° C. for 16 hours. After completion, after filtration, the filtrate was concentrated under reduced pressure. The residue was purified by flash chromatography on silica gel eluting with petroleum ether/diethyl ether (88/12) to afford 4-isopropylcyclohex-2-en-1-one (16 g, 115.7 mmol, 42.4% yield) as yellow oil. LCMS (ESI, m/z): 139.1 [M+H]⁺.

Step 2: 3-[6-[bis[(4-methoxyphenyl)methyl]amino]-4-methyl-2-pyridyl]-4-isopropyl-cyclohexanone Under nitrogen, a solution of 4-isopropylcyclohex-2-en-1-one (9.76 g, 70.5 mmol) and chloro(1,5-cyclooctadiene) rhodium(I) dimer (2.32 g, 4.7 mmol) in tetrahydrofuran (300 mL) was stirred at 60° C. for 5 minutes. Then N,N-bis[(4-methoxyphenyl)methyl]-4-methyl-6-tributylstannyl-pyridin-2-amine (30.0 g, 47.0 mmol) was added and stirred at 60° C. for 20 hours. After completion, the organic layer was dried over anhydrous sodium sulfate and concentrated under vacuum. The residue was purified by flash chromatography on silica gel eluting with petroleum ether/ethyl acetate (85/15) to afford 3-[6-[bis[(4-methoxyphenyl)methyl] amino]-4-methyl-2-pyridyl]-4-isopropyl-cyclohexanone (4 g, 8.2 mmol, 17.5% yield) as a yellow oil. LCMS (ESI, m/z): 487.3 [M+H]⁺.

Step 3: 3-[6-[bis[(4-methoxyphenyl)methyl]amino]-3-iodo-4-methyl-2-pyridyl]-4-isopropyl-cyclohexanone

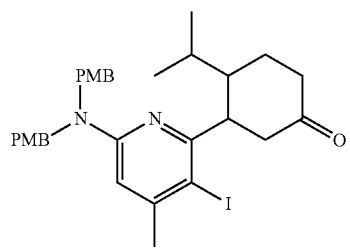

A solution of 3-[6-[bis[(4-methoxyphenyl)methyl]amino]-4-methyl-2-pyridyl]-4-isopropyl-cyclohexanone (6.0 g, 12.33 mmol) and N-iodosuccinimide (4.16 g, 18.4 mmol) in acetonitrile (60 mL) was stirred at 25° C. for 1 hour. After completion, the resulting solution was concentrated under vacuum. The residue was purified by flash chromatography on silica gel eluting with petroleum ether/ethyl acetate (85/15) to afford 3-[6-[bis[(4-methoxyphenyl)methyl]amino]-3-iodo-4-methyl-2-pyridyl]-4-isopropyl-cyclohexanone (6.6 g, 10.7 mmol, 87.4% yield) as a red oil. LCMS (ESI, m/z): 612.2 [M+H]+.

Step 4: 3-[6-[bis[(4-methoxyphenyl)methyl]amino]-4-methyl-3-(trifluoromethyl)-2-pyridyl]-4-isopropyl-cyclohexanone

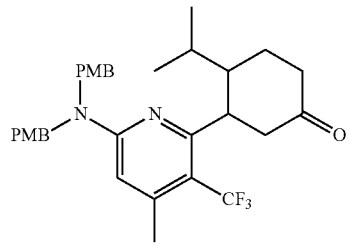

Under nitrogen, a solution of 3-[6-[bis[(4-methoxyphenyl)methyl]amino]-3-iodo-4-methyl-2-pyridyl]-4-isopropyl-cyclohexanone (6.6 g, 10.7 mmol), methyl 2,2-difluoro-2-(fluorosulfonyl)acetate (10.3 g, 53.8 mmol) and copper iodide (4.0 g, 21.5 mmol) in N,N-dimethylformamide (70 mL) was stirred at 90° C. for 1 hour. After completion, after filtration, the filtrate was diluted with water. The resulting solution was extracted with dichloromethane. The organic layers were combined, washed with water, dried over anhydrous sodium sulfate and concentrated under vacuum. The residue was purified by flash chromatography on silica gel eluting with petroleum ether/ethyl acetate (85/15) to afford 3-[6-[bis[(4-methoxyphenyl)methyl]amino]-4-methyl-3-(trifluoromethyl)-2-pyridyl]-4-isopropyl-cyclohexanone (4.7 g, 8.4 mmol, 78.6% yield) as a yellow oil. LCMS (ESI, m/z): 555.3 [M+H]+.

Step 5: ethyl 4-[6-[bis[(4-methoxyphenyl)methyl]amino]-4-methyl-3-(trifluoromethyl)-2-pyridyl]-5-isopropyl-2-oxo-cyclohexanecarboxylate

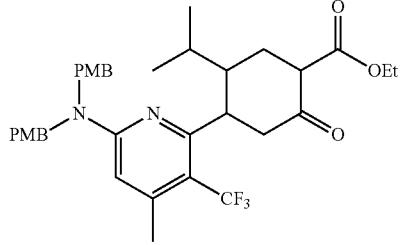

Under nitrogen, a solution of 3-[6-[bis[(4-methoxyphenyl)methyl]amino]-4-methyl-3-(trifluoromethyl)-2-pyridyl]-4-isopropyl-cyclohexanone (4.6 g, 8.29 mmol) in tetrahydrofuran (50 mL) was stirred at −78° C. for 2 minutes. Then lithium bis(trimethylsilyl)amide (1 M in THF) (16. mL, 16.59 mmol) was added and stirred at −78° C. for 20 minutes. Then ethyl cyanoformate (1.89 g, 19.08 mmol) was added and stirred at −78° C. for 30 minutes. After completion, the reaction was quenched with water, extracted with dichloromethane, dried over anhydrous sodium sulfate and concentrated under vacuum. The residue was purified by flash chromatography on silica gel eluting with petroleum ether/ethyl acetate (9:1) to afford ethyl 4-[6-[bis[(4-methoxyphenyl)methyl]amino]-4-methyl-3-(trifluoromethyl)-2-pyridyl]-5-isopropyl-2-oxo-cyclohexanecarboxylate (4 g, 6.3 mmol, 77% yield) as a yellow oil. LCMS (ESI, m/z): 627.3 [M+H]+.

Step 6: 7-[6-[bis[(4-methoxyphenyl)methyl]amino]-4-methyl-3-(trifluoromethyl)-2-pyridyl]-6-isopropyl-2-methylsulfanyl-5,6,7,8-tetrahydroquinazolin-4-ol

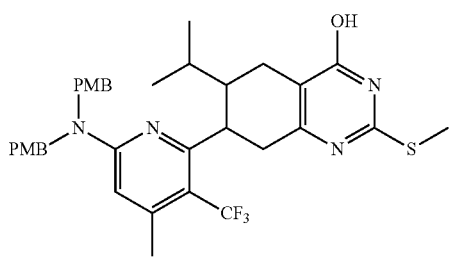

A solution of ethyl 4-[6-[bis[(4-methoxyphenyl)methyl]amino]-4-methyl-3-(trifluoromethyl)-2-pyridyl]-5-isopropyl-2-oxo-cyclohexanecarboxylate (4.0 g, 6.3 mmol), methyl carbamimidothioate (1:2) (17.77 g, 63.83 mmol) and sodium bicarbonate (10.72 g, 127.6 mmol) in ethanol (40 mL) and water (8 mL) was stirred at 50° C. for 3 hours. After completion, the reaction was diluted with water and extracted with dichloromethane. Then the organic layers were combined, dried over anhydrous sodium sulfate and concentrated under vacuum. The residue was purified by flash chromatography on silica gel eluting with petroleum ether/ethyl acetate (85/15) to afford 7-[6-[bis[(4-methoxyphenyl)methyl]amino]-4-methyl-3-(trifluoromethyl)-2-pyridyl]-6-isopropyl-2-methylsulfanyl-5,6,7,8-tetrahydroquinazolin-4-ol (2 g, 3.0 mmol, 48% yield) as a white solid. LCMS (ESI, m/z): 653.3 [M+H]⁺.

Step 7: tert-butyl (3S)-4-[7-[6-[bis[(4-methoxyphenyl)methyl]amino]-4-methyl-3-(trifluoromethyl)-2-pyridyl]-6-isopropyl-2-methylsulfanyl-5,6,7,8-tetrahydroquinazolin-4-yl]-3-methyl-piperazine-1-carboxylate

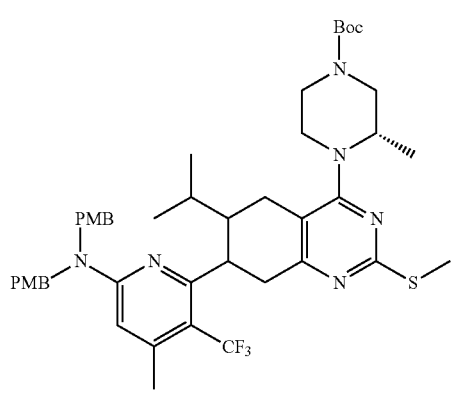

A solution of 7-[6-[bis[(4-methoxyphenyl)methyl]amino]-4-methyl-3-(trifluoromethyl)-2-pyridyl]-6-isopropyl-2-methylsulfanyl-5,6,7,8-tetrahydroquinazolin-4-ol (2.0 g, 3.06 mmol), N,N-diisopropylethylamine (1.98 g, 15.3 mmol) and trifluoromethanesulfonic anhydride (1.56 g, 5.5 mmol) in dichloromethane (20 mL) was stirred at 25° C. for 1 hour. After completion, the reaction was concentrated under reduced pressure. Then the residue, N,N-diisopropylethylamine (1.98 g, 15.3 mmol) and tert-butyl (3S)-3-methyl-1-piperazinecarboxylate (1.23 g, 6.1 mmol) in 1,4-dioxane (20 mL) was stirred at 110° C. for 16 hours. After completion, the resulting solution was concentrated under vacuum. The residue was purified by flash chromatography on silica gel eluting with petroleum ether/ethyl acetate (85/15) to afford tert-butyl (3S)-4-[7-[6-[bis[(4-methoxyphenyl)methyl]amino]-4-methyl-3-(trifluoromethyl)-2-pyridyl]-6-isopropyl-2-methylsulfanyl-5,6,7,8-tetrahydroquinazolin-4-yl]-3-methyl-piperazine-1-carboxylate (1.4 g, 1.6 mmol, 54.7% yield) as a white solid. LCMS (ESI, m/z): 835.4 [M+H]⁺

Step 8: tert-butyl (3S)-4-[7-[6-[bis[(4-methoxyphenyl)methyl]amino]-4-methyl-3-(trifluoromethyl)-2-pyridyl]-6-isopropyl-2-methylsulfonyl-5,6,7,8-tetrahydroquinazolin-4-yl]-3-methyl-piperazine-1-carboxylate

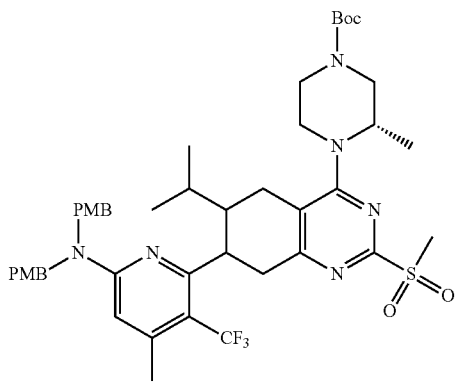

A solution of tert-butyl (3S)-4-[7-[6-[bis[(4-methoxyphenyl)methyl]amino]-4-methyl-3-(trifluoromethyl)-2-pyridyl]-6-isopropyl-2-methylsulfanyl-5,6,7,8-tetrahydroquinazolin-4-yl]-3-methyl-piperazine-1-carboxylate (1.6 g, 1.9 mmol) and 3-chloroperoxybenzoic acid (0.33 g, 1.9 mmol) in dichloromethane (16 mL) was stirred at 25° C. for 30 minutes. The resulting solution was quenched by saturated sodium sulfite solution, extracted with dichloromethane. Then the organic layers were collected, dried over anhydrous sodium sulfate and concentrated under vacuum. The residue was purified by flash chromatography on silica gel eluting with petroleum ether/ethyl acetate (5/1) to afford tert-butyl (3S)-4-[7-[6-[bis[(4-methoxyphenyl)methyl]amino]-4-methyl-3-(trifluoromethyl)-2-pyridyl]-6-isopropyl-2-methylsulfonyl-5,6,7,8-tetrahydroquinazolin-4-yl]-3-methyl-piperazine-1-carboxylate (1 g, 1.1 mmol, 60.2% yield) as a white solid. LCMS (ESI, m/z): 867.4 [M+H]⁺

Step 9: tert-butyl (3S)-4-[7-[6-[bis[(4-methoxyphenyl)methyl]amino]-4-methyl-3-(trifluoromethyl)-2-pyridyl]-6-isopropyl-2-[[(2S)-1-methylpyrrolidin-2-yl]methoxy]-5,6,7,8-tetrahydroquinazolin-4-yl]-3-methyl-piperazine-1-carboxylate

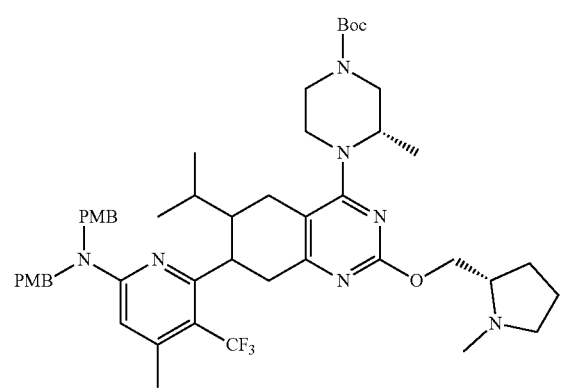

A solution of [(2S)-1-methylpyrrolidin-2-yl]methanol (0.27 g, 2.3 mmol) in N,N-dimethylformamide (10 mL) was stirred at 25° C. for 5 minutes. Then sodium hydride (0.18 g, 4.6 mmol, 60% dispersion in mineral oil) was added and stirred at 0° C. for 10 minutes. Then tert-butyl (3S)-4-[7-[6-[bis[(4-methoxyphenyl)methyl]amino]-4-methyl-3-(trifluoromethyl)-2-pyridyl]-6-isopropyl-2-methylsulfonyl-5,6,7,8-tetrahydroquinazolin-4-yl]-3-methyl-piperazine-1-carboxylate (1.0 g, 1.15 mmol) was added and stirred at 25° C. for 30 minutes. The resulting solution was adjusted to pH 8 with ammonium chloride. The solvent was diluted with water, extracted with EA, washed with water. The organic layer was dried over anhydrous sodium sulfate and concentrated under vacuum. The residue was purified by flash chromatography on silica gel eluting with dichloromethane/methanol (10/1) to afford tert-butyl (3S)-4-[7-[6-[bis[(4-methoxyphenyl)methyl]amino]-4-methyl-3-(trifluoromethyl)-2-pyridyl]-6-isopropyl-2-[[(2S)-1-methylpyrrolidin-2-yl]methoxy]-5,6,7,8-tetrahydroquinazolin-4-yl]-3-methyl-piperazine-1-carboxylate (500 mg, 0.5 mmol, 48.1% yield) as a white solid. LCMS (ESI, m/z): 902.5 [M+H]$^+$ Step 10: 6-[6-isopropyl-4-[(2S)-2-methylpiperazin-1-yl]-2-[[(2S)-1-methylpyrrolidin-2-yl]methoxy]-5,6,7,8-tetrahydroquinazolin-7-yl]-4-methyl-5-(trifluoromethyl)pyridin-2-amine

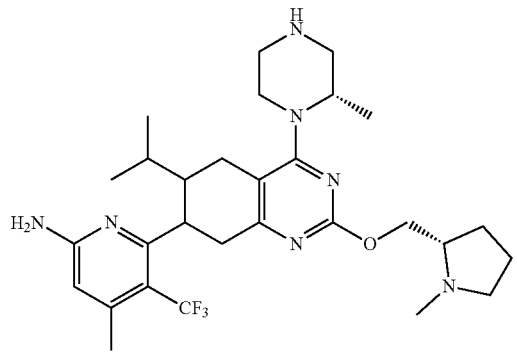 [SMILES: Cc1cc(N)nc(C2Cc3nc(OC[C@@H]4CCCN4C)nc(N4CCNC[C@@H]4C)c3CC2C(C)C)c1C(F)(F)F]

A solution of tert-butyl (3S)-4-[7-[6-[bis[(4-methoxyphenyl)methyl]amino]-4-methyl-3-(trifluoromethyl)-2-pyridyl]-6-isopropyl-2-[[(2S)-1-methylpyrrolidin-2-yl]methoxy]-5,6,7,8-tetrahydroquinazolin-4-yl]-3-methyl-piperazine-1-carboxylate (500.0 mg, 0.5 mmol) in trifluoroacetic acid (5 mL, 67.3 mmol) was stirred at 50° C. for 8 hours. The resulting solution was concentrated under vacuum. The residue was purified by flash chromatography on silica gel eluting with Acetonitrile/water (1:1) to afford 6-[6-isopropyl-4-[(2S)-2-methylpiperazin-1-yl]-2-[[(2S)-1-methylpyrrolidin-2-yl]methoxy]-5,6,7,8-tetrahydroquinazolin-7-yl]-4-methyl-5-(trifluoromethyl)pyridin-2-amine (200 mg, 0.3 mmol, 64.2% yield) as a white solid. LCMS (ESI, m/z): 562.3 [M+H]$^+$ Step 11: 1-((S)-4-((6S,7R)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one (Example 33a) and 1-((S)-4-((6R,7S)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one (Example 33b)

33a

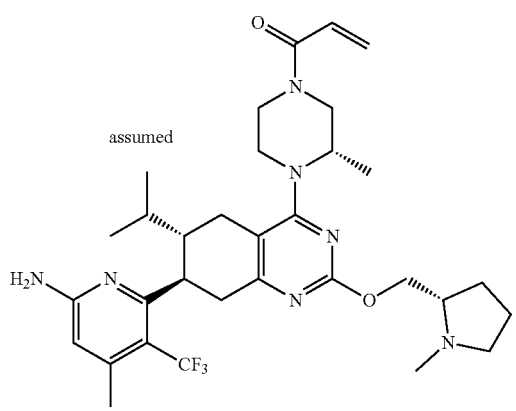

33b

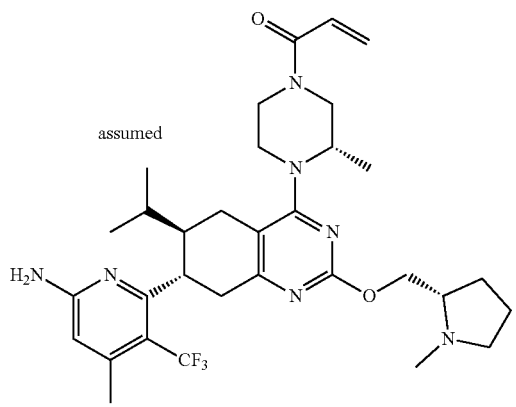

A solution of 6-[6-isopropyl-4-[(2S)-2-methylpiperazin-1-yl]-2-[[(2S)-1-methylpyrrolidin-2-yl]methoxy]-5,6,7,8-tetrahydroquinazolin-7-yl]-4-methyl-5-(trifluoromethyl)pyridin-2-amine (200.0 mg, 0.3600 mmol) and N,N-diisopropylethylamine (137.8 mg, 1.07 mmol) in dichloromethane (2 mL) was stirred at −78° C. for 5 minutes. Then acryloyl chloride (32.05 mg, 0.3600 mmol) was added and stirred at −78° C. for 30 minutes. the resulting solution was concentrated under vacuum. The residue was purified by flash chromatography on silica gel eluting with dichloromethane/methanol (10/1) to afford 110 mg solid. The crude product was purified by Prep-HPLC to afford 50 mg white solid with the following conditions: Column: XBridge Shield RP18 OBD Column, 30*150 mm, 5 um; Mobile Phase A: Water (10 MMOL/L NH4HCO3), Mobile Phase B: ACN; Flow rate: 60 mL/min; Gradient: 44 B to 65 B in 7 min; 254 nm; RT1:5.87. The product was further purified by Chiral-Prep-HPLC with following condition (Column: CHIRAL ART Cellulose-SB, 2*25 cm, 5 um; Mobile Phase A: Hex (8 mmol/L NH3·MeOH)—HPLC, Mobile Phase B: EtOH—HPLC; Flow rate: 20 mL/min; Gradient: 20 B to 20 B in 12 min; 220/254 nm) to afford the title compounds. The stereo chemistry of title compounds was arbitrarily assigned.

Example 33a: 1-((S)-4-((6S,7R)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one (20 mg, 0.0325 mmol, 9.1% yield, white solid). $^1$H NMR (300 MHz, DMSO-$d_6$, ppm) δ 6.95-6.70 (m, 1H), 6.44 (s, 2H), 6.26-6.07 (m, 2H), 5.71 (dd, J=10.4, 2.5 Hz, 1H), 4.43-3.75 (m, 6H), 3.58-3.36 (m, 1H), 3.21-2.90 (m, 4H), 2.87-2.69 (m, 2H), 2.65-2.55 (m, 1H), 2.44-2.39 (m, 1H), 2.36-2.11 (m, 8H), 2.08-1.81 (m, 2H), 1.73-1.43 (m, 4H), 1.31-1.18 (m, 3H), 0.85 (d, J=6.8 Hz, 3H), 0.72 (d, J=6.8 Hz, 3H). LCMS (ESI, m/z): 616.4 [M+H]$^+$. Chiral HPLC: Column: CHIRAL ART Cellulose-SB, 4.6*100 mm, 3 um; detected at 254 nm; Hex (0.1% DEA): EtOH=80:20, Flow rate: 1 mL/min; Retention time: 2.435 min; (faster peak).

Example 33b: 1-((S)-4-((6R,7S)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one (18.2 mg, 0.0296 mmol, 8.3% yield, white solid). $^1$H NMR (300 MHz, DMSO-$d_6$, ppm) δ 6.89-6.71 (m, 1H), 6.43 (s, 2H), 6.26-6.09 (m, 2H), 5.71 (dd, J=10.4, 2.4 Hz, 1H), 4.41-4.11 (m, 3H), 4.08-3.83 (m, 2H), 3.66-3.41 (m, 2H), 3.29-3.11 (m, 2H), 2.99-2.69 (m, 4H), 2.45-2.23 (m, 8H), 2.23-1.99 (m, 2H), 1.97-1.80 (m, 1H), 1.76-1.39 (m, 4H), 1.24 (d, J=4.5 Hz, 1H), 1.01 (d, J=5.9 Hz, 3H), 0.85 (d, J=6.9 Hz, 3H), 0.73 (d, J=6.9 Hz, 3H). LCMS (ESI, m/z): 616.4 [M+H]$^+$. Chiral HPLC: Column: CHIRAL ART Cellulose-SB, 4.6*100 mm, 3 um; detected at 254 nm; Hex (0.1% DEA): EtOH=80:20, Flow rate: 1 mL/min; Retention time: 2.945 min; (slower peak).

Examples 34a, 34b, 34c, and 34d

Example 34a

Example 34b

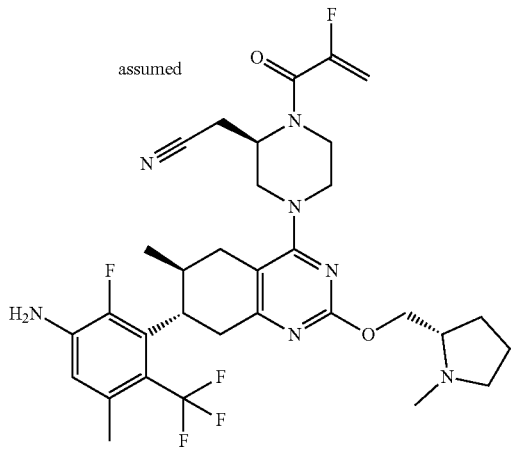

Example 34c

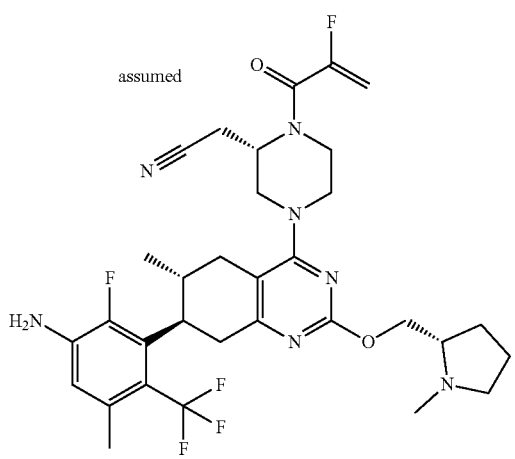

Example 34d

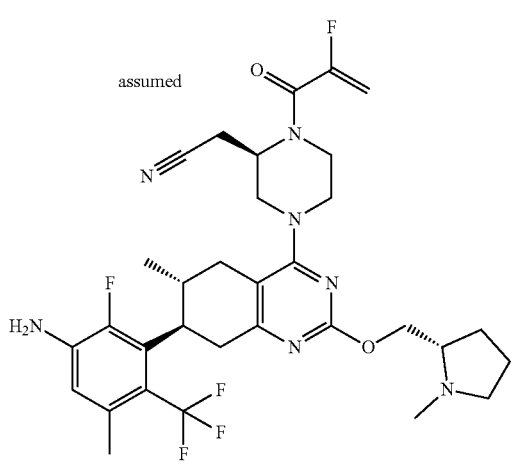

2-((R)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Example 34a); and 2-((R)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Example 34b); and 2-((S)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Example 34c); and 2-((S)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Example 34d)

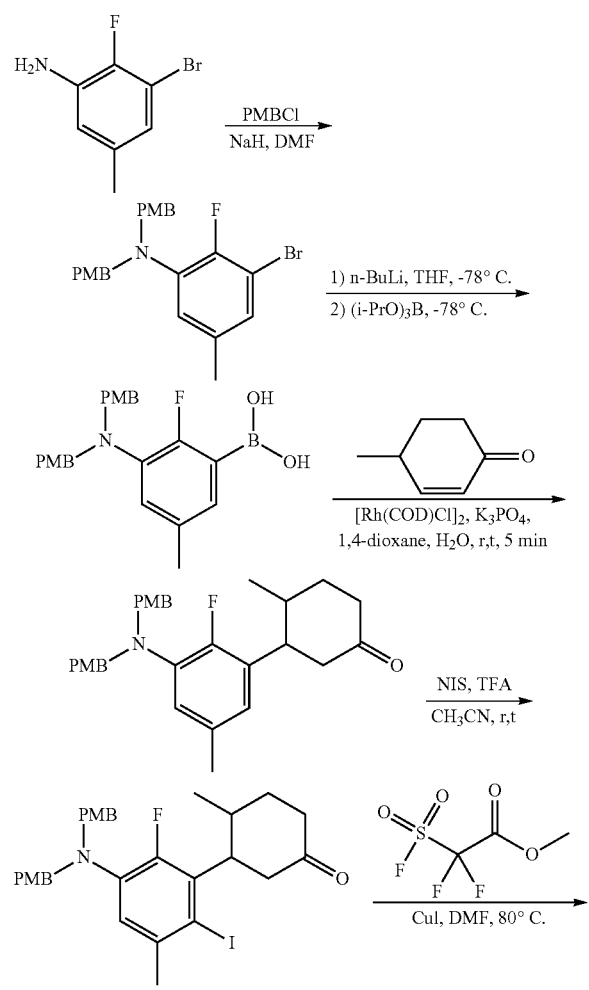

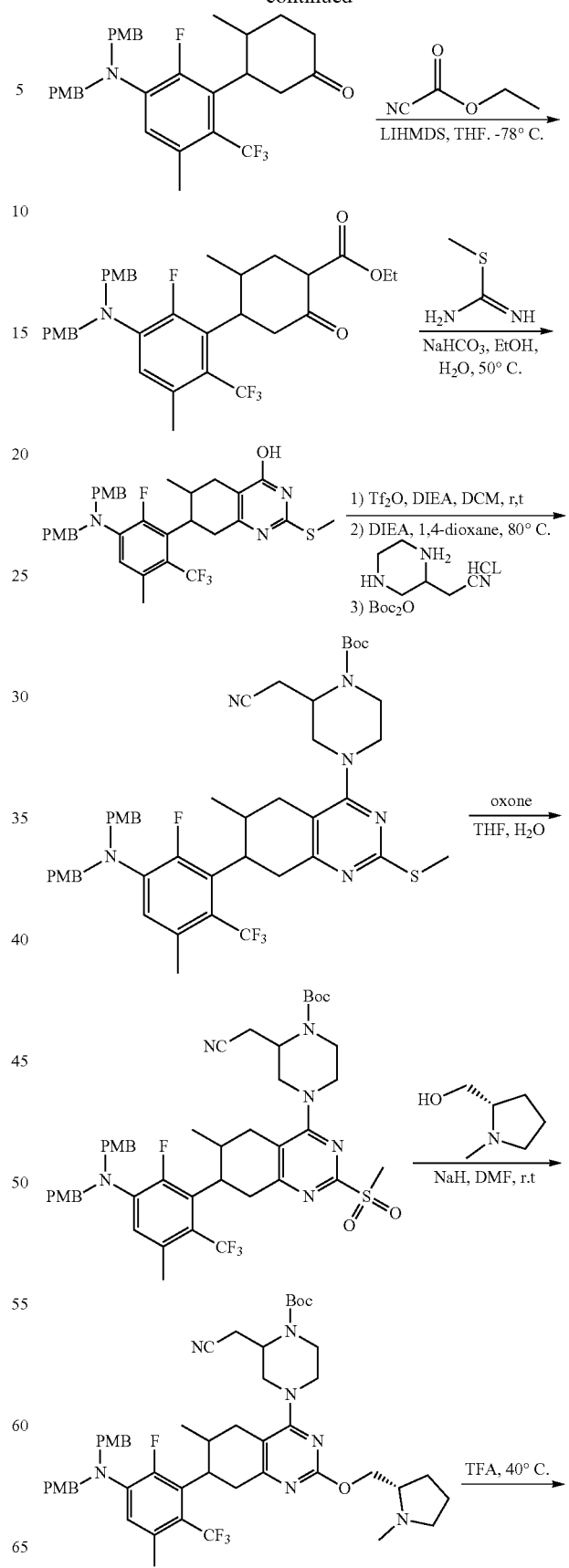

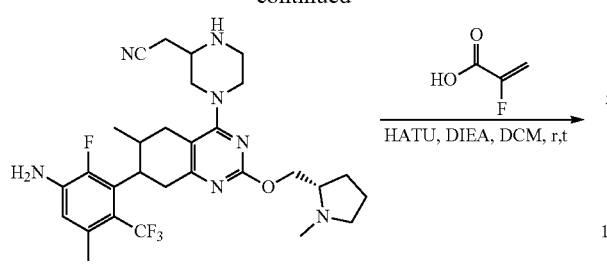

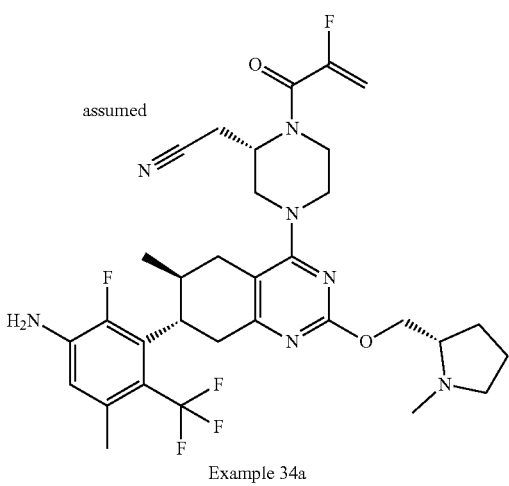

Example 34a

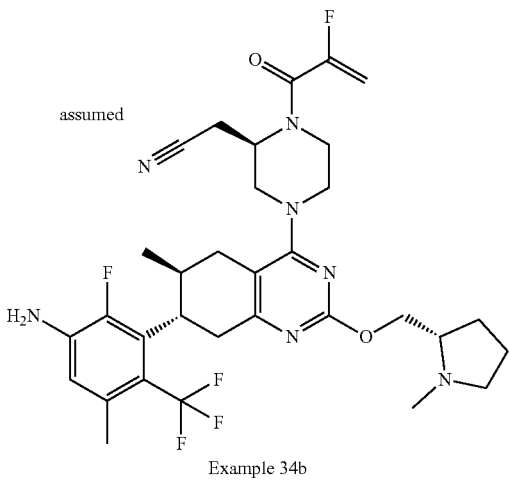

Example 34b

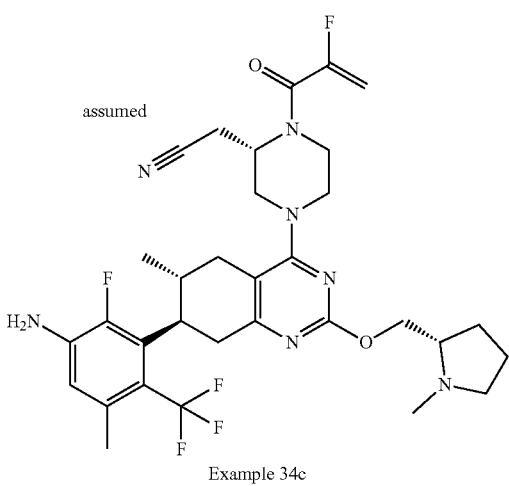

Example 34c

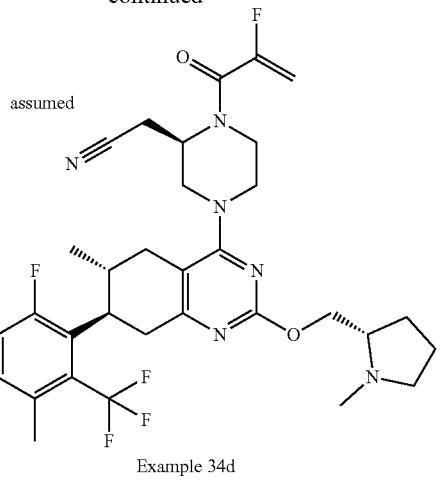

Example 34d

Step 1: 3-bromo-2-fluoro-N,N-bis[(4-methoxyphenyl)methyl]-5-methyl-aniline

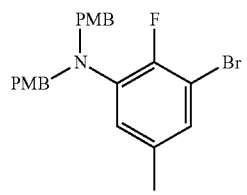

A solution of 3-bromo-2-fluoro-5-methyl-aniline (20.0 g, 98.02 mmol) and sodium hydride (19.6 g, 490.1 mmol, 60% dispersion in mineral oil) in N,N-dimethylformamide (150 mL) was stirred at 0° C. for 0.5 hours. Then 4-methoxybenzylchloride (79.6 mL, 588.12 mmol) was added and stirred at room temperature for 6 hours. After completion, the reaction was quenched by saturated ammonium chloride solution. The resulting solution was extracted with ethyl acetate, dried over anhydrous sodium sulfate and concentrated under vacuum. The residue was diluted with methanol. After filtration, the solids were collected and washed by methanol to afford 3-bromo-2-fluoro-N,N-bis[(4-methoxyphenyl)methyl]-5-methyl-aniline (40 g, 90.0 mmol, 91.8% yield) as a yellow solid. LC-MS: (ESI, m/z): 444.1 [M+H]$^+$.

Step 2: (3-(bis(4-methoxybenzyl)amino)-2-fluoro-5-methylphenyl)boronic acid

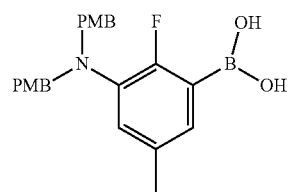

Under nitrogen, a solution of triisopropyl borate (44.01 g, 234.01 mmol) in tetrahydrofuran (200 mL) was stirred at −78° C. for 5 minutes. Then 3-bromo-2-fluoro-N,N-bis[(4-methoxyphenyl)methyl]-5-methyl-aniline (20.0 g, 46.8 mmol) was added dropwise and stirred at −78° C. for 30 minutes. Then n-butyllithium (2.5 M in hexane) (28 mL, 70.2 mmol) was added and stirred at −78° C. for 20 minutes. After completion, the resulting solution was concentrated under vacuum.

Step 3: 3-(3-(bis(4-methoxybenzyl)amino)-2-fluoro-5-methylphenyl)-4-methylcyclohexan-1-one

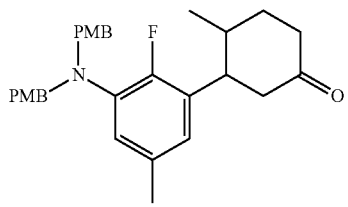

Under nitrogen, the residue from the previous step, 4-methylcyclohex-2-en-1-one (5.1 g, 46.8 mmol) and chloro(1,5-cyclooctadiene)rhodium(I) dimer (2.3 g, 4.68 mmol) in 1,4-dioxane (200 mL) was stirred at 25° C. for 5 minutes. Then saturated potassium phosphate solution (40 mL) was added and stirred at 25° C. for 1 hour. After completion, the reaction was diluted with water, extracted with ethyl acetate, dried over anhydrous sodium sulfate and concentrated under vacuum. The residue was purified by flash chromatography on silica gel eluting with petroleum ether/ethyl acetate (10/1) to afford 3-(3-(bis(4-methoxybenzyl)amino)-2-fluoro-5-methylphenyl)-4-methylcyclohexan-1-one (11 g, 23.9 mmol, 51.3% yield) as a yellow solid. LC-MS: (ESI, m/z): 476.3 [M+H]$^+$.

Step 4: 3-[3-[bis[(4-methoxyphenyl)methyl]amino]-2-fluoro-6-iodo-5-methyl-phenyl]-4-methyl-cyclohexanone

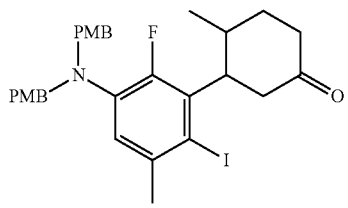

A solution of 3-(3-(bis(4-methoxybenzyl)amino)-2-fluoro-5-methylphenyl)-4-methylcyclohexan-1-one (25.0 g, 52.5 mmol) and N-iodosuccinimide (14.1 g, 63.0 mmol) in acetonitrile (250 mL) was stirred at room temperature for 2 minutes. Then trifluoroacetic acid (0.6 g, 5.2 mmol) was added and stirred at 25° C. for 20 minutes. After completion, the resulting solution was concentrated under vacuum. The solution was diluted with water. The resulting solution was extracted with ethyl acetate and the organic layers were combined. The organic layer was dried over anhydrous sodium sulfate and concentrated under vacuum. The residue was purified by flash chromatography on silica gel eluting with petroleum ether/ethyl acetate (3/1) to afford 3-[3-[bis[(4-methoxyphenyl)methyl]amino]-2-fluoro-6-iodo-5-methyl-phenyl]-4-methyl-cyclohexanone (30 g, 49.8 mmol, 94.9% yield) as a yellow oil. LC-MS: (ESI, m/z): 602.1 [M+H]$^+$.

Step 5: 3-[3-[bis[(4-methoxyphenyl)methyl]amino]-2-fluoro-5-methyl-6-(trifluoromethyl)phenyl]-4-methyl-cyclohexanone

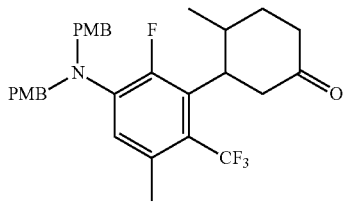

Under nitrogen, a solution of 3-[3-[bis[(4-methoxyphenyl)methyl]amino]-2-fluoro-6-iodo-5-methyl-phenyl]-4-methyl-cyclohexanone (20.0 g, 33.2 mmol), methyl 2,2-difluoro-2-(fluorosulfonyl)acetate (31.9 g, 166.2 mmol) and cuprous iodide (12.6 g, 66.5 mmol) in N,N-dimethylformamide (200 mL) was stirred at 80° C. for 2 hours. After completion, the reaction was quenched with water. The resulting solution was extracted with ethyl acetate and the organic layers were combined. The organic layer was dried over anhydrous sodium sulfate and concentrated under vacuum. The residue was purified by flash chromatography on silica gel eluting with petroleum ether/ethyl acetate (5/1) to afford 3-[3-[bis[(4-methoxyphenyl)methyl]amino]-2-fluoro-5-methyl-6-(trifluoromethyl)phenyl]-4-methyl-cyclohexanone (12 g, 22.0 mmol, 66.4% yield) as a yellow oil. LC-MS: (ESI, m/z): 544.2 [M+H]$^+$.

Step 6: ethyl 4-[3-[bis[(4-methoxyphenyl)methyl]amino]-2-fluoro-5-methyl-6-(trifluoromethyl)phenyl]-5-methyl-2-oxo-cyclohexanecarboxylate

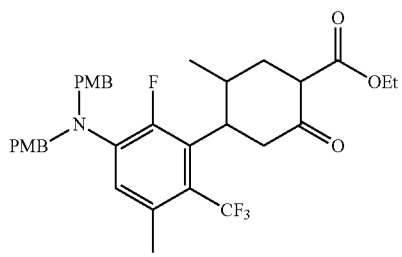

Under nitrogen, a solution of 3-[3-[bis[(4-methoxyphenyl)methyl]amino]-2-fluoro-5-methyl-6-(trifluoromethyl)phenyl]-4-methyl-cyclohexanone (10.0 g, 18.4 mmol) in tetrahydrofuran (100 mL) was stirred at −78° C. for 3 minutes. Lithium bis(trimethylsilyl)amide (1.0 M in THF) (33 mL, 33 mmol) was added dropwised and stirred at −78° C. for 10 minutes. Then ethyl cyanoformate (4.1 g, 42.3 mmol) was added and stirred at −78° C. for 20 minutes. After completion, the reaction was quenched with water, extracted with ethyl acetate, dried over anhydrous sodium sulfate and concentrated under vacuum to afford crude product. The crude product was used for next step directly without purification. LC-MS: (ESI, m/z): 616.3 [M+H]$^+$.

Step 7: 7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-ol

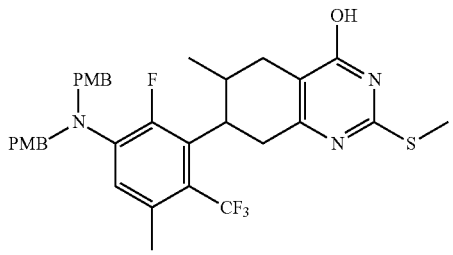

A solution of ethyl 4-[3-[bis[(4-methoxyphenyl)methyl]amino]-2-fluoro-5-methyl-6-(trifluoromethyl)phenyl]-5-methyl-2-oxo-cyclohexanecarboxylate (20.0 g, 32.4 mmol), 2-methyl-2-thiopseudourea sulfate (90.3 g, 324.8 mmol) and sodium bicarbonate (54.5 g, 649.7 mmol) in ethanol (200 mL) and water (40 mL) was stirred at 50° C. for 4 hours. After completion, the resulting solution was diluted with water and extracted with ethyl acetate. Then the organic layers were collected, washed with brine, dried over anhydrous sodium sulfate and concentrated under vacuum. The residue was purified by flash chromatography on silica gel eluting with dichloromethane/ethyl acetate (4/1) to afford 7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-ol (7 g, 10.9 mmol, 33.6% yield) as a yellow solid. LC-MS: (ESI, m/z): 642.2 [M+H]+.

Step 8: tert-butyl 4-[7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-yl]-2-(cyanomethyl)piperazine-1-carboxylate

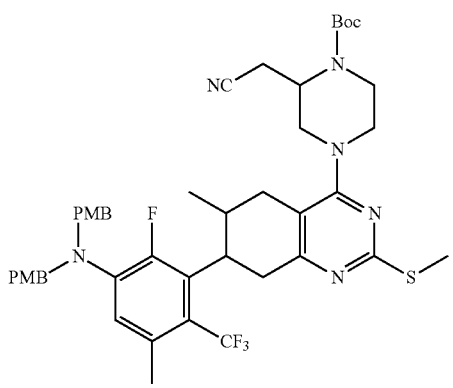

A solution of 7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-ol (7.2 g, 11.2 mmol), trifluoromethanesulfonic anhydride (5.7 g, 20.2 mmol) and N,N-diisopropylethylamine (8.68 g, 67.3 mmol) in dichloromethane (72 mL) was stirred at 25° C. for 1 hour. After completion, the reaction was concentrated under reduced pressure. Then the residue, N,N-Diisopropylethylamine (8.68 g, 67.3 mmol) and 2-piperazin-2-2-piperazin-2-ylacetonitrile (2.8 g, 22.44 mmol) in 1,4-dioxane (72 mL) was stirred at 80° C. for 2 hours. Then di-tert-butyldicarbonate (12.24 g, 56.1 mmol) was added and stirred at 25° C. for 1 hour. After completion, the resulting solution was concentrated under vacuum. The residue was purified by flash chromatography on silica gel eluting with petroleum ether/ethyl acetate (10/1) to afford tert-butyl 4-[7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-yl]-2-(cyanomethyl)piperazine-1-carboxylate (8 g, 9.4 mmol, 84% yield) as a white solid. LC-MS: (ESI, m/z): 849.4 [M+H]+.

Step 9: tert-butyl 4-[7-[3-[bis[(4-methoxyphenyl)methyl]amino]-2-fluoro-5-methyl-6-(trifluoromethyl)phenyl]-6-methyl-2-methylsulfonyl-5,6,7,8-tetrahydroquinazolin-4-yl]-2-(cyanomethyl)piperazine-1-carboxylate

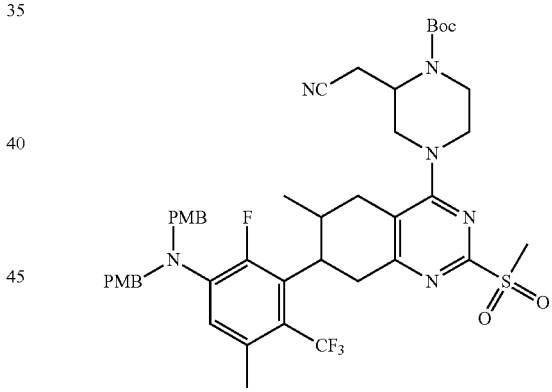

A solution of tert-butyl 4-[7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-yl]-2-(cyanomethyl)piperazine-1-carboxylate (8.0 g, 9.42 mmol) and potassium peroxymonosulfate (17.3 g, 28.2 mmol) in tetrahydrofuran (80 mL) and water (40 mL) was stirred at room temperature for 3 hours. After completion, the solvent was concentrated under vacuum, the reaction was quenched by sodium sulfite, extracted with ethyl acetate, dried over anhydrous sodium sulfate and concentrated under vacuum to afford white crude product. The crude product was used for next step directly without purification. LC-MS: (ESI, m/z): 881.4 [M+H]+.

Step 10: tert-butyl 4-[7-[3-[bis[(4-methoxyphenyl)methyl]amino]-2-fluoro-5-methyl-6-(trifluoromethyl)phenyl]-6-methyl-2-[[(2S)-1-methylpyrrolidin-2-yl]methoxy]-5,6,7,8-tetrahydroquinazolin-4-yl]-2-(cyanomethyl)piperazine-1-carboxylate

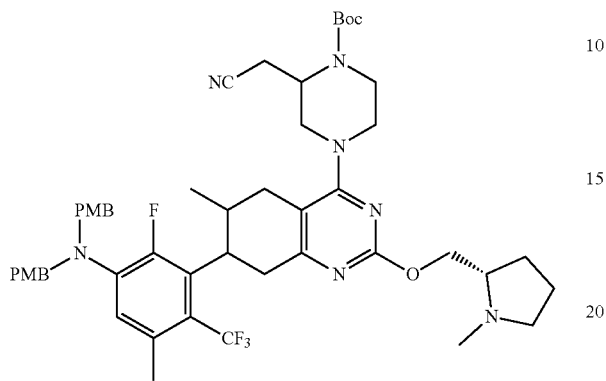

A solution of sodium hydride (1.82 g, 45.4 mmol, 60% dispersion in mineral oil) and N-methyl-1-prolinol (2.09 g, 18.1 mmol) in DMF (80 mL) was stirred at 0° C. for 10 minutes. Then tert-butyl 4-[7-[3-[bis[(4-methoxyphenyl)methyl]amino]-2-fluoro-5-methyl-6-(trifluoromethyl)phenyl]-6-methyl-2-methylsulfonyl-5,6,7,8-tetrahydroquinazolin-4-yl]-2-(cyanomethyl)piperazine-1-carboxylate (8.0 g, 9.0 mmol) was added and stirred at room temperature for 30 minutes. After completion, the reaction was quenched with saturated ammonium chloride solution and extracted with dichloromethane. Then the organic layers were collected, dried over anhydrous sodium sulfate and concentrated under vacuum. The residue was purified by flash chromatography on silica gel eluting with dichloromethane/methanol (7/1) to afford tert-butyl 4-[7-[3-[bis[(4-methoxyphenyl)methyl]amino]-2-fluoro-5-methyl-6-(trifluoromethyl)phenyl]-6-methyl-2-[[(2S)-1-methylpyrrolidin-2-yl]methoxy]-5,6,7,8-tetrahydroquinazolin-4-yl]-2-(cyanomethyl)piperazine-1-carboxylate (5 g, 5.4 mmol, 60.1% yield) as a yellow solid. LC-MS: (ESI, m/z): 916.5 [M+H]$^+$.

Step 11: 2-[4-[7-[3-amino-2-fluoro-5-methyl-6-(trifluoromethyl)phenyl]-6-methyl-2-[[(2S)-1-methylpyrrolidin-2-yl]methoxy]-5,6,7,8-tetrahydroquinazolin-4-yl]piperazin-2-yl]acetonitrile

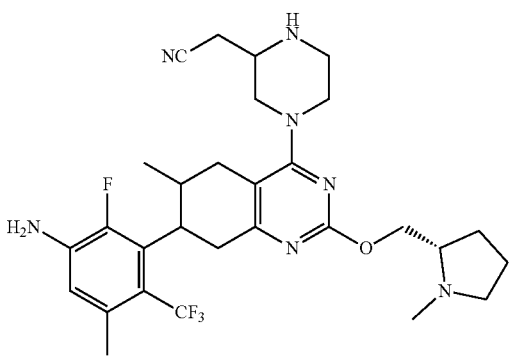 [SMILES: Cc1cc(N)c(F)c(C2Cc3nc(OC[C@@H]4CCCN4C)nc(N4CCNC(CC#N)C4)c3CC2C)c1C(F)(F)F]

A solution of tert-butyl 4-[7-[3-[bis[(4-methoxyphenyl)methyl]amino]-2-fluoro-5-methyl-6-(trifluoromethyl)phenyl]-6-methyl-2-[[(2S)-1-methylpyrrolidin-2-yl]methoxy]-5,6,7,8-tetrahydroquinazolin-4-yl]-2-(cyanomethyl)piperazine-1-carboxylate (2.0 g, 2.1 mmol) in trifluoroacetic acid (24.89 g, 218.3 mmol) was stirred at 40° C. for 7 minutes. the resulting solution was concentrated under vacuum. The residue was purified by flash chromatography on silica gel eluting with acetonitrile/water (2:3) to afford 2-[4-[7-[3-amino-2-fluoro-5-methyl-6-(trifluoromethyl)phenyl]-6-methyl-2-[[(2S)-1-methylpyrrolidin-2-yl]methoxy]-5,6,7,8-tetrahydroquinazolin-4-yl]piperazin-2-yl]acetonitrile (1 g, 1.7 mmol, 79.6% yield) as a yellow solid. LC-MS: (ESI, m/z): 576.3 [M+H]$^+$.

Step 12: 2-((R)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Example 34a); 2-((R)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Example 34b); 2-((S)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Example 34c); and 2-((S)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Example 34d)

Example 34a

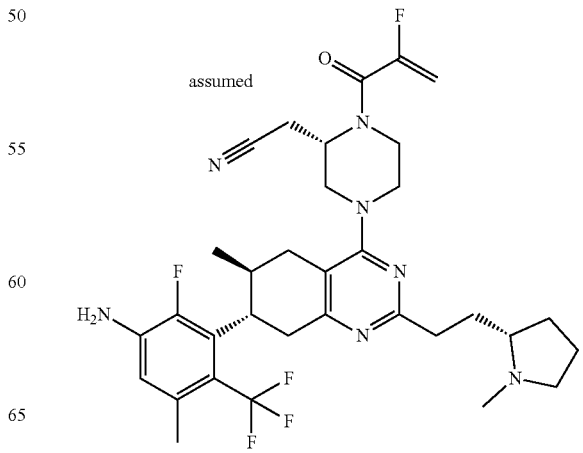

Example 34b

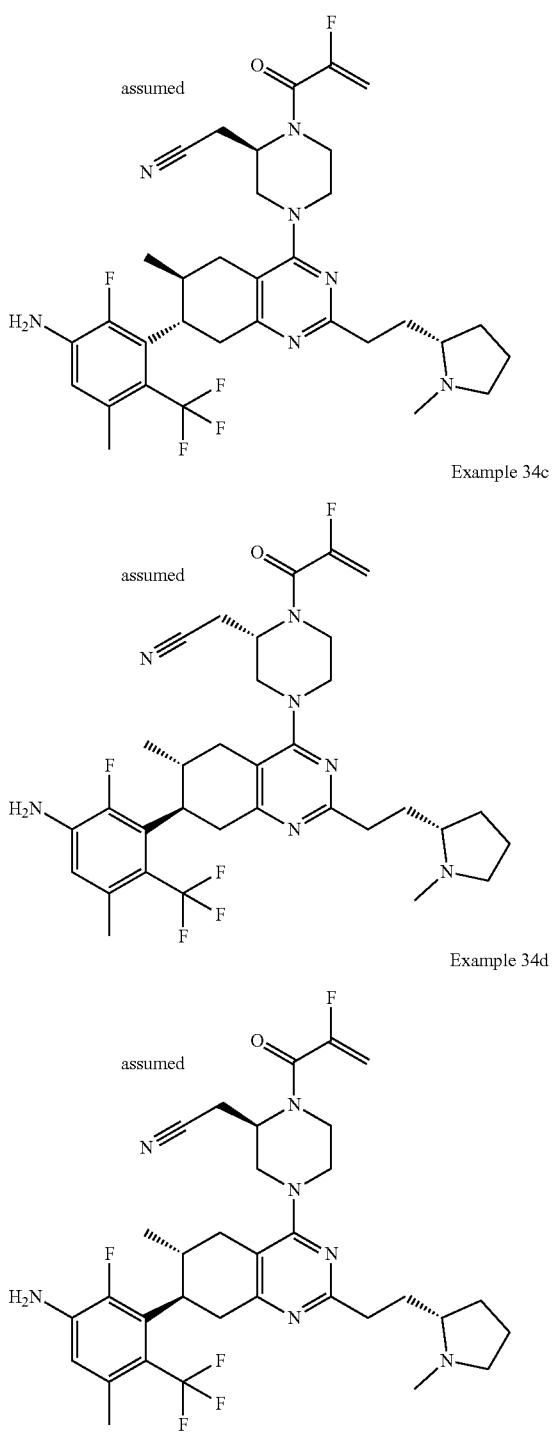

Example 34c

Example 34d

A solution of 2-[4-[7-[3-amino-2-fluoro-5-methyl-6-(trifluoromethyl)phenyl]-6-methyl-2-[[(2S)-1-methylpyrrolidin-2-yl]methoxy]-5,6,7,8-tetrahydroquinazolin-4-yl]piperazin-2-yl]acetonitrile (1.9 g, 3.3 mmol), 2-fluoroacrylic acid (297.2 mg, 3.3 mmol) and N,N-diisopropylethylamine (1.28 g, 9.9 mmol) in dichloromethane (38 mL) was stirred at 25° C. Then HATU (1.38 g, 3.6 mmol) was added and stirred at 25° C. for 1 hour. After completion, the resulting solution was concentrated under vacuum. The residue was purified by flash chromatography on silica gel eluting with dichloromethane/methanol (10/1) to afford 1.1 g crude solid. The crude product was purified by Prep-HPLC with the following conditions: Column: Xselect CSH OBD Column 30*150 mm 5 um; Mobile Phase A:Water (0.1% FA), Mobile Phase B: ACN; Flow rate: 60 mL/min; Gradient: 18 B to 42 B in 8 min; 254/220 nm; RT1:6.67; to afford 600 mg product. The product was further purified by Chiral-Prep-HPLC to afford the title compounds. The absolute configuration of the title compounds was inferred from potency data and a protein X-ray structure of compound 21b.

Example 34a: 2-((R)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (61 mg, 0.09 mmol, 2.9% yield, white solid). $^1$H NMR (300 MHz, DMSO-$d_6$, ppm) δ 6.58 (d, J=8.8 Hz, 1H), 5.76 (s, 2H), 5.45-5.13 (m, 2H), 4.80 (brs, 1H), 4.21 (dd, J=10.8, 4.8 Hz, 1H), 4.04 (dd, J=10.8, 6.4 Hz, 1H), 3.95-3.81 (m, 2H), 3.40-3.30 (m, 2H), 3.27-3.17 (m, 2H), 3.16-3.02 (m, 2H), 2.97-2.84 (m, 4H), 2.84-2.72 (m, 2H), 2.53 (s, 1H), 2.37-2.25 (m, 7H), 2.19-2.10 (m, 1H), 1.96-1.83 (m, 1H), 1.72-1.50 (m, 3H), 0.83 (d, J=6.0 Hz, 3H). LC-MS: (ESI, m/z): 648.3 [M+H]$^+$. Chiral HPLC: Column: CHIRALPAK IE-3, 4.6*50 mm 3 um; detected at 254 nm; (Hex:DCM=3:1) (0.1% DEA): EtOH=80:20, Flow rate: 1 mL/min; Retention time: 1.884 min; (faster peak).

Example 34b: 2-((R)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (54.6 mg, 0.08 mmol, 2.6% yield, white solid). $^1$H NMR (300 MHz, DMSO-$d_6$, ppm) δ 6.57 (d, J=8.8 Hz, 1H), 5.77 (s, 2H), 5.43-5.19 (m, 2H), 4.76 (brs, 1H), 4.22 (dd, J=10.8, 5.0 Hz, 1H), 4.10-3.92 (m, 3H), 3.81 (d, J=12.6 Hz, 1H), 3.40-3.35 (m, 1H), 3.19 (d, J=6.3 Hz, 1H), 3.13 (d, J=6.4 Hz, 1H), 3.09-2.75 (m, 6H), 2.69-2.60 (m, 1H), 2.60-2.55 (m, 1H), 2.45-2.10 (m, 9H), 2.00-1.82 (m, 1H), 1.73-1.48 (m, 3H), 0.83 (d, J=6.2 Hz, 3H). LC-MS: (ESI, m/z): 648.3 [M+H]$^+$. Chiral HPLC: Column: CHIRALPAK IE-3, 4.6*50 mm 3 um; detected at 254 nm; (Hex:DCM=3:1)(0.1% DEA): EtOH=80:20, Flow rate: 1 mL/min; Retention time: 2.272 min; (slower peak).

Example 34c: 2-((S)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (76.3 mg, 0.1 mmol, 3.6% yield, white solid). $^1$H NMR (300 MHz, DMSO-$d_6$, ppm) δ 6.58 (d, J=8.9 Hz, 1H), 5.75 (s, 2H), 5.46-5.13 (m, 2H), 4.76 (s, 1H), 4.23 (dd, J=10.8, 5.0 Hz, 1H), 4.13-3.93 (m, 3H), 3.81 (d, J=12.8 Hz, 1H), 3.45-3.40 (m, 1H), 3.31-3.257 (m, 1H), 3.21-2.77 (m, 7H), 2.68-2.53 (m, 2H), 2.43-2.12 (m, 9H), 1.98-1.84 (m, 1H), 1.73-1.51 (m, 3H), 0.82 (d, J=6.2 Hz, 3H). LC-MS: (ESI, m/z): 648.3 [M+H]$^+$. Chiral HPLC: Column: CHIRALPAK IC-3, 4.6*50 mm, 3 um; detected at 254 nm; Hex (0.1% DEA): EtOH=60:40, Flow rate: 1 mL/min; Retention time: 2.489 min; (faster peak).

Example 34d: 2-((S)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (85.2 mg, 0.1 mmol, 4% yield, white solid). $^1$H NMR (300 MHz, DMSO-$d_6$, ppm) δ 6.57 (d, J=8.9 Hz, 1H), 5.76 (s, 2H), 5.45-5.13 (m, 2H), 4.80 (brs, 1H), 4.24 (dd, J=10.7, 4.8 Hz, 1H), 4.04-3.78 (m, 4H), 3.41-3.03 (m, 5H), 2.97-2.69 (m, 6H), 2.36-2.09 (m, 9H), 1.97-1.81 (m, 1H), 1.73-1.50 (m, 3H), 0.83 (d, J=6.0 Hz, 3H). LC-MS: (ESI, m/z): 648.3

[M+H]+. Chiral HPLC: Column: CHIRALPAK IC-3, 4.6*50 mm, 3 um; detected at 254 nm; Hex (0.1% DEA): EtOH=60:40, Flow rate: 1 mL/min; Retention time: 3.293 min; (slower peak).

Examples 35a, 35b, 35c, and 35d

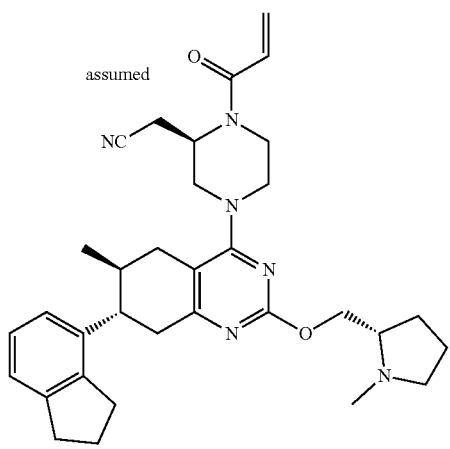

Example 35a

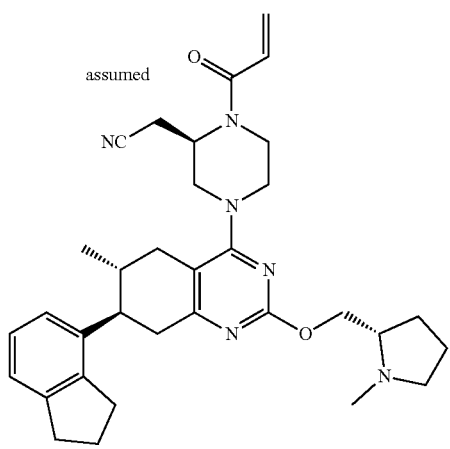

Example 35b

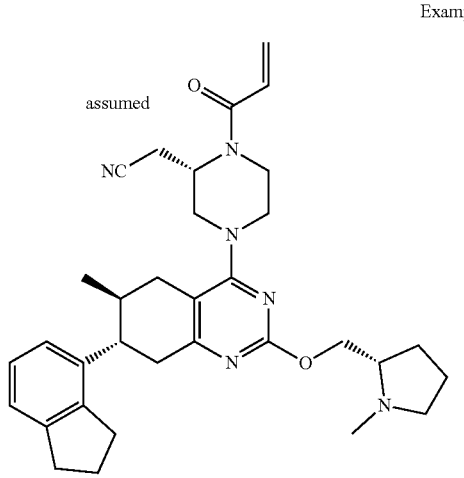

Example 35c

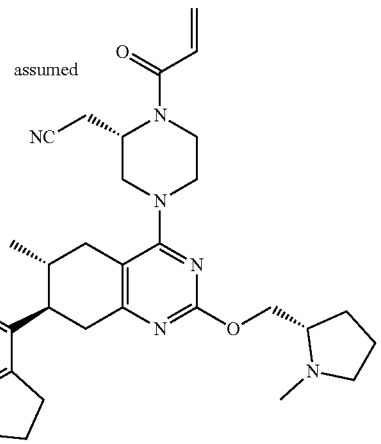

Example 35d 2-((R)-1-acryloyl-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (Example 35a); and 2-((R)-1-acryloyl-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (Example 35b); and 2-((S)-1-acryloyl-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (Example 35c); and 2-((S)-1-acryloyl-4-((6R,7R)-7-(2,3-dihydro-H-inden-4-yl)-6-methyl-2-(((S)-1-methylpyrrolidin-2-yl)methoxy)-5,6,7,8-tetrahydroquinazolin-4-yl)piperazin-2-yl)acetonitrile (Example 35d)

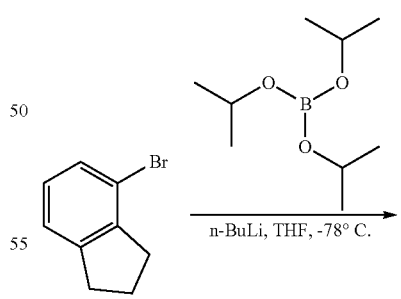

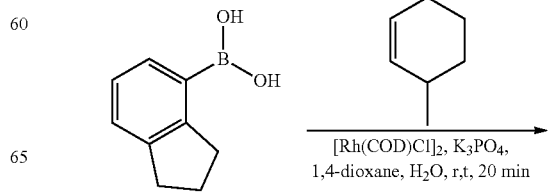

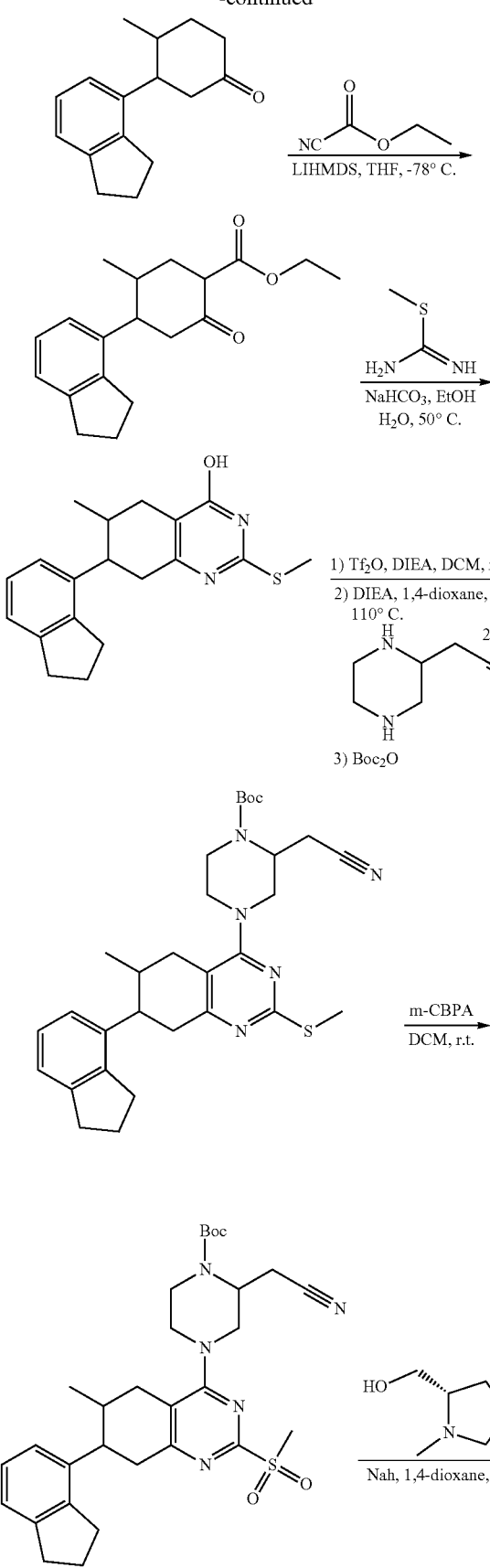
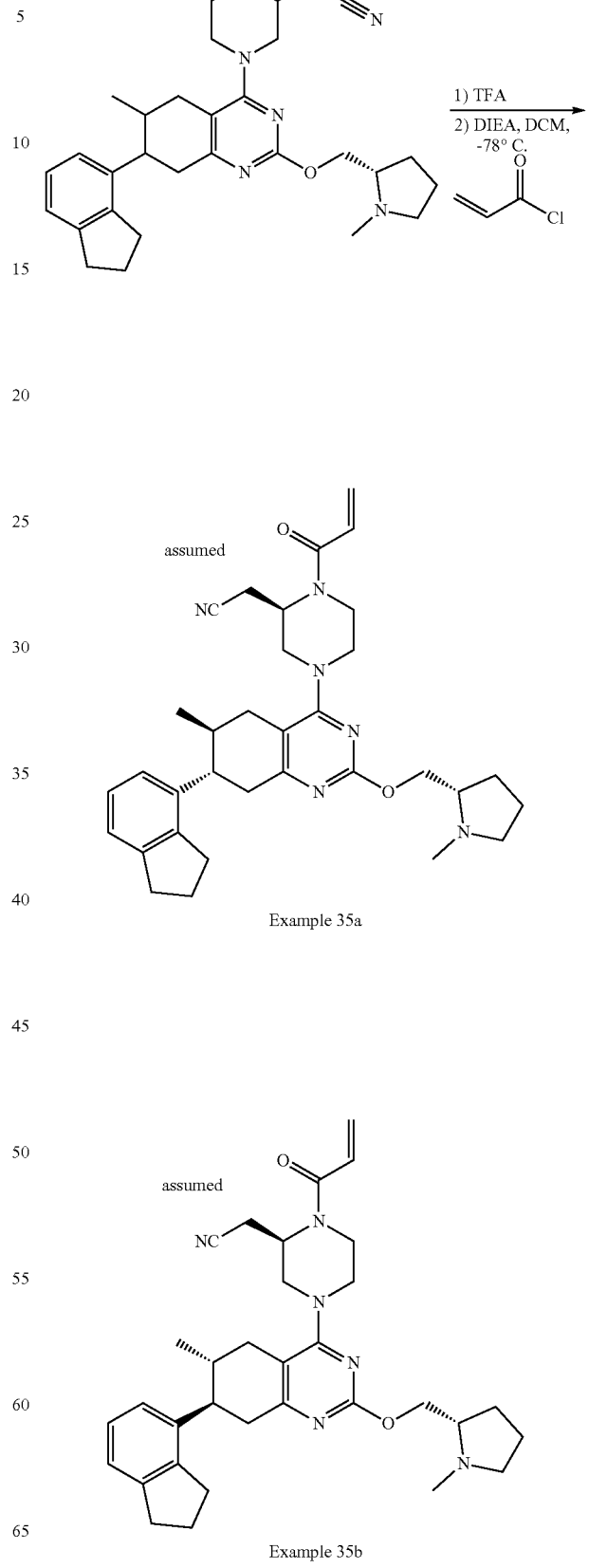
Example 35a
Example 35b

-continued

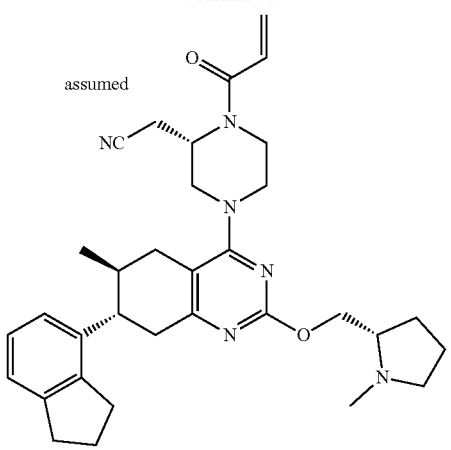

Example 35c

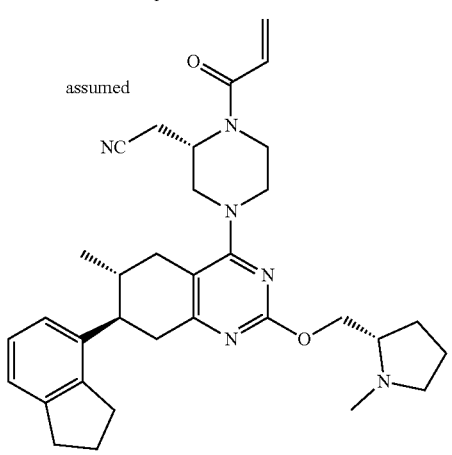

Example 35d

Step 1: indan-4-ylboronic acid

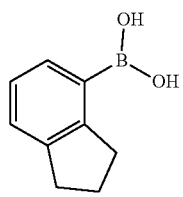 [SMILES: OB(O)c1cccc2c1CCC2]

Under nitrogen, a solution of 4-bromoindane (5.0 g, 25.3 mmol) in tetrahydrofuran (50 mL) was stirred at −78° C. for 5 minutes. Then triisopropyl borate (23.86 g, 126.8 mmol) was added dropwised and stirred at −78° C. for 30 minutes. Then n-butyllithium (2.5 M in hexane) (15 mL, 38.0 mmol) was added and stirred at −78° C. for 20 minutes. After completion, the reaction was quenched with water, extracted with dichloromethane, dried over anhydrous sodium sulfate and concentrated under vacuum. The residue was purified by flash chromatography on silica gel eluting with dichloromethane/ethyl acetate (9/1) to afford indan-4-ylboronic acid (2.7 g, 16.6 mmol, 65.7% yield) as a white solid. LCMS (ESI, m/z): 161.1 [M−H]⁻.

Step 2: 3-indan-4-yl-4-methyl-cyclohexanone

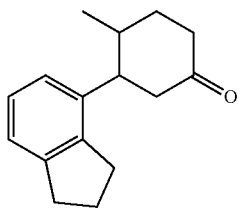 [SMILES: CC1CCC(=O)CC1c1cccc2c1CCC2]

Under nitrogen, a solution of indan-4-ylboronic acid (5.0 g, 30.8 mmol), 4-methylcyclohex-2-en-1-one (6.8 g, 61.7 mmol), chloro(1,5-cyclooctadiene)rhodium(I) dimer (1.52 g, 3.0 mmol) and potassium phosphate (19.6 g, 92.6 mmol) in 1,4-dioxane (50 mL) and water (10 mL) was stirred at 25° C. for 20 minutes. After completion, the resulting solution was diluted with water, extracted with dichloromethane, dried over anhydrous sodium sulfate and concentrated under vacuum. The residue was purified by flash chromatography on silica gel eluting with petroleum ether/ethyl acetate (5/1) to afford 3-indan-4-yl-4-methyl-cyclohexanone (4 g, 17.5 mmol, 56.8% yield) as yellow oil. LCMS (ESI, m/z): 229.2 [M+H]⁺.

Step 3: ethyl 4-indan-4-yl-5-methyl-2-oxo-cyclohexanecarboxylate

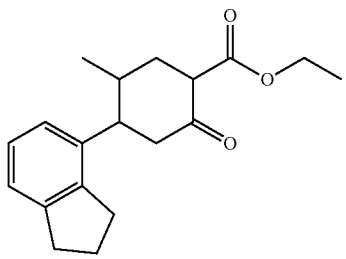 [SMILES: CCOC(=O)C1CC(C)C(c2cccc3c2CCC3)CC1=O]

Under nitrogen, a solution of 3-indan-4-yl-4-methyl-cyclohexanone (3.6 g, 15.7 mmol) in tetrahydrofuran (40 mL) was stirred at −78° C. for 2 minutes. Then lithium bis(trimethylsilyl)amide (1 M in THF) (31 mL, 31 mmol) was added and stirred at −78° C. for 20 minutes. Then ethyl cyanoformate (3.5 g, 36.26 mmol) was added and stirred at −78° C. for 30 minutes. After completion, the reaction was quenched with water, extracted with dichloromethane. Then the organic layers were collected, dried over anhydrous sodium sulfate and concentrated under vacuum. The residue was purified by flash chromatography on silica gel eluting with petroleum ether/ethyl acetate (9/1) to afford ethyl 4-indan-4-yl-5-methyl-2-oxo-cyclohexanecarboxylate (4 g, 13.3 mmol, 84.5% yield) as yellow oil. LCMS (ESI, m/z): 301.2 [M+H]⁺.

Step 4: 7-indan-4-yl-6-methyl-2-methylsulfanyl-5,6,7,8-tetrahydroquinazolin-4-ol

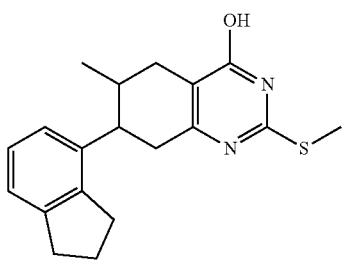 [SMILES: CSc1nc(O)c2c(n1)CC(c1cccc3c1CCC3)C(C)C2]

A solution of ethyl 4-indan-4-yl-5-methyl-2-oxo-cyclohexanecarboxylate (4.0 g, 13.3 mmol), 2-methyl-2-thiopseudourea sulfate (37.1 g, 133.1 mmol) and sodium bicarbonate (22.3 g, 266.3 mmol) in ethanol (40 mL) and water (8 mL) was stirred at 50° C. for 3 hours. After completion, the reaction was diluted with water and extracted with dichloromethane. Then the organic layers were combined, dried over anhydrous sodium sulfate and concentrated under vacuum. The residue was purified by flash chromatography on silica gel eluting with dichloromethane/ethyl acetate (7/3) to afford 7-indan-4-yl-6-methyl-2-methylsulfanyl-5,6,7,8-tetrahydroquinazolin-4-ol (2 g, 6.12 mmol, 46% yield) as a white solid. LCMS (ESI, m/z): 327.1 [M+H]$^+$.

Step 5: tert-butyl 2-(cyanomethyl)-4-(7-indan-4-yl-6-methyl-2-methylsulfanyl-5,6,7,8-tetrahydroquinazolin-4-yl)piperazine-1-carboxylate

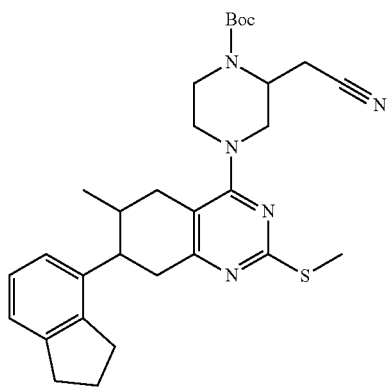 [SMILES: CSc1nc2c(c(N3CCN(C(=O)OC(C)(C)C)C(CC#N)C3)n1)CC(C)C(c1cccc3c1CCC3)C2]

A solution of 7-indan-4-yl-6-methyl-2-methylsulfanyl-5,6,7,8-tetrahydroquinazolin-4-ol (2.0 g, 6.1 mmol), trifluoromethanesulfonic anhydride (3.11 g, 11.0 mmol) and N,N-diisopropylethylamine (3.95 g, 30.6 mmol) in dichloromethane (20 mL) was stirred at 25° C. for 1 hour. After completion, reaction was concentrated under reduced pressure. Then the residue, N,N-diisopropylethylamine (3.9 g, 30.6 mmol) and 2-piperazin-2-ylacetonitrile (1.5 g, 12.2 mmol) in 1,4-dioxane (20 mL) was stirred at 110° C. for 2 hours. Then di-tert-butyldicarbonate (5.3 g, 24.5 mmol) was added and stirred at 25° C. for 1 hour. After completion, the resulting solution was concentrated under vacuum. The residue was purified by flash chromatography on silica gel eluting with petroleum ether/ethyl acetate (10/1) to afford tert-butyl 2-(cyanomethyl)-4-(7-indan-4-yl-6-methyl-2-methylsulfanyl-5,6,7,8-tetrahydroquinazolin-4-yl)piperazine-1-carboxylate (2.5 g, 4.6 mmol, 76.5% yield) as a white solid. LCMS (ESI, m/z): 534.3 [M+H]$^+$.

Step 6: tert-butyl 2-(cyanomethyl)-4-(7-indan-4-yl-6-methyl-2-methylsulfonyl-5,6,7,8-tetrahydroquinazolin-4-yl)piperazine-1-carboxylate

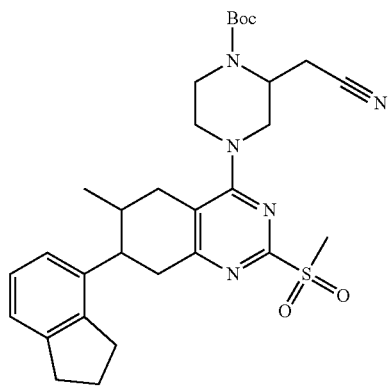 [SMILES: CC1Cc2c(nc(S(C)(=O)=O)nc2N2CCN(C(=O)OC(C)(C)C)C(CC#N)C2)CC1c1cccc2c1CCC2]

A solution of tert-butyl 2-(cyanomethyl)-4-(7-indan-4-yl-6-methyl-2-methylsulfanyl-5,6,7,8-tetrahydroquinazolin-4-yl)piperazine-1-carboxylate (2.5 g, 4.6 mmol) and 3-chloroperoxybenzoic acid (1.61 g, 9.3 mmol) in dichloromethane (25 mL) was stirred at 25° C. for 30 minutes. After completion, the resulting solution was quenched by saturated sodium sulfite solution, extracted with dichloromethane. Then the organic layers were collected, dried over anhydrous sodium sulfate and concentrated under vacuum. The residue was purified by flash chromatography on silica gel eluting with petroleum ether/ethyl acetate (5/1) to afford tert-butyl 2-(cyanomethyl)-4-(7-indan-4-yl-6-methyl-2-methylsulfonyl-5,6,7,8-tetrahydroquinazolin-4-yl)piperazine-1-carboxylate (1.6 g, 2.8 mmol, 60.4% yield) as a white solid. LCMS (ESI, m/z): 566.3 [M+H]$^+$.

Step 7: tert-butyl 2-(cyanomethyl)-4-[7-indan-4-yl-6-methyl-2-[[(2S)-1-methylpyrrolidin-2-yl]methoxy]-5,6,7,8-tetrahydroquinazolin-4-yl]piperazine-1-carboxylate

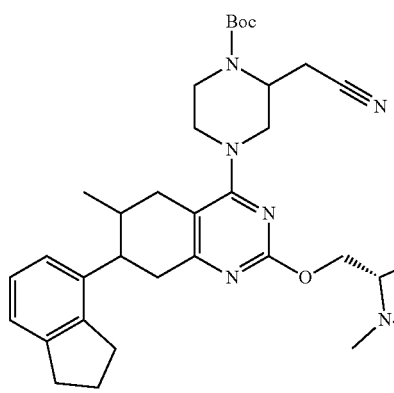

A solution of N-methyl-1-prolinol (0.65 g, 5.6 mmol) in 1,4-dioxane (80 mL) was stirred at 25° C. for 5 minutes.

Then sodium hydride (0.4 g, 11.3 mmol, 60% dispersion in mineral oil) was added and stirred at 0° C. for 10 minutes. Then tert-butyl 2-(cyanomethyl)-4-(7-indan-4-yl-6-methyl-2-methylsulfonyl-5,6,7,8-tetrahydroquinazolin-4-yl)piperazine-1-carboxylate (1.6 g, 2.8 mmol) was added and stirred at 25° C. for 30 minutes. After completion, the resulting solution was adjusted to pH 8 with saturated ammonium chloride solution. The solvent was diluted with water, extracted with ethyl acetate, washed with water. The organic layer was dried over anhydrous sodium sulfate and concentrated under vacuum. The residue was purified by flash chromatography on silica gel eluting with dichloromethane/methanol (10/1) to afford tert-butyl 2-(cyanomethyl)-4-[7-indan-4-yl-6-methyl-2-[[(2S)-1-methylpyrrolidin-2-yl]methoxy]-5,6,7,8-tetrahydroquinazolin-4-yl]piperazine-1-carboxylate (1.1 g, 1.8 mmol, 64.7% yield) as a white solid. LCMS (ESI, m/z): 601.4 [M+H]+

Step 8: 2-((R)-1-acryloyl-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (Example 35a); 2-((R)-1-acryloyl-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (Example 35b); 2-((S)-1-acryloyl-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (Example 35c); and 2-((S)-1-acryloyl-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (Example 35d)

Example 35a

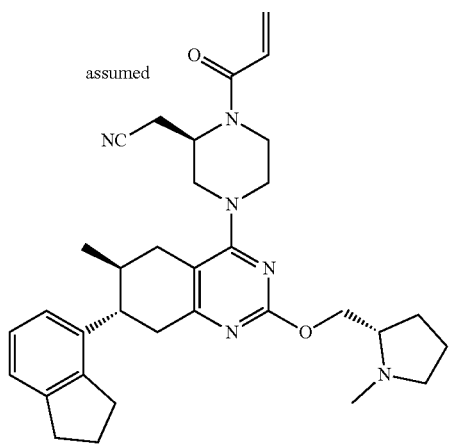

Example 35b

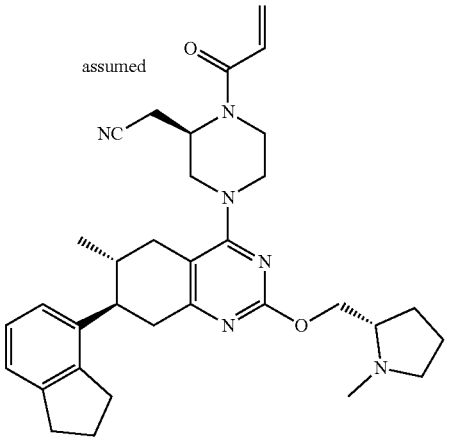

Example 35c

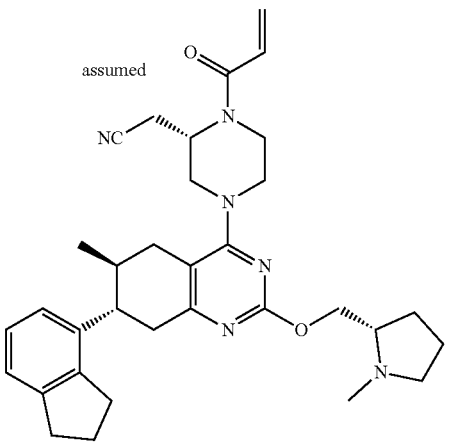

Example 35d

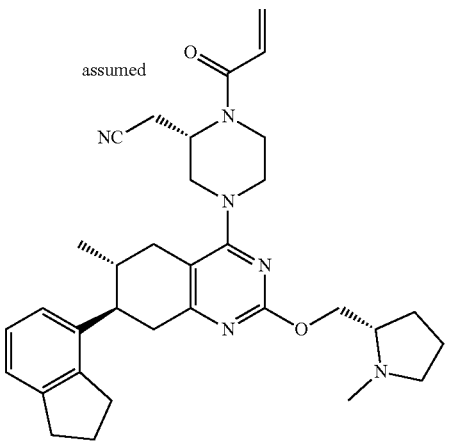

A solution of tert-butyl 2-(cyanomethyl)-4-[7-indan-4-yl-6-methyl-2-[[(2S)-1-methylpyrrolidin-2-yl]methoxy]-5,6,7,8-tetrahydroquinazolin-4-yl]piperazine-1-carboxylate (1.0 g, 1.6 mmol) and trifluoroacetic acid (3.8 g, 33.2 mmol) in dichloromethane (10 mL) was stirred at 25° C. for 30 minutes. After completion, the resulting solution was concentrated under reduced pressure and dissolved in dichloromethane (10 mL). Then N,N-diisopropylethylamine (2.1 g, 16.6 mmol) was added and stirred at −78° C. for 20 minutes. After completion, the resulting solution was concentrated under vacuum. The residue was purified by flash chromatography on silica gel eluting with dichloromethane/methanol (10/1) to afford 1 g crude solid. The crude product was purified by Prep-HPLC with the following conditions: (Column: XBridge Prep OBD C18 Column, 30×150 mm 5 um; Mobile Phase A: Water (10 MMOL/L NH4HCO3), Mobile Phase B: ACN; Flow rate: 60 mL/min; Gradient: 41 B to 71 B in 7 min; 254 nm; RT1:6.11) to afford 250 mg white solid as a mixture of four isomer. The product was further purified by Chiral-Prep-HPLC with following condition (Column, CHIRALPAK IC-3 mobile phase: (Hex: DCM=3:1)(0.1% DEA): EtOH=50:50; Detector, UV 254 nm) and (Column, CHIRAL Cellulose-SB mobile phase: MtBE(0.1% DEA):IPA=80:20; Detector, UV 254 nm.) to afford the title compounds. The absolute configuration of the title compounds was inferred from potency data and a protein X-ray structure of compound 21b.

Example 35a: 2-((R)-1-acryloyl-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (23.7 mg, 0.042 mmol, 2.6% yield, white solid). $^1$H NMR (300 MHz, DMSO-$d_6$, ppm) δ 7.20-6.99 (m, 3H), 6.98-6.74 (m, 1H), 6.18 (dd, J=16.6, 2.3 Hz, 1H), 5.76 (dd, J=10.4, 2.3 Hz, 1H), 5.00-4.80 (m, 1H), 4.45-4.31 (m, 1H), 4.28-4.17 (m, 1H), 4.09-3.96 (m, 2H), 3.93-3.74 (m, 2H), 3.70-3.55 (m, 1H), 3.30-3.10 (m, 2H), 2.99-2.63 (m, 12H), 2.32 (s, 3H), 2.20-2.09 (m, 1H), 2.07-1.83 (m, 4H), 1.73-1.48 (m, 3H), 0.79 (d, J=6.4 Hz, 3H). LCMS (ESI, m/z): 555.3 [M+H]$^+$.

Chiral HPLC: Column: CHIRALPAK IC-3, 4.6*50 mm 3 um; detected at 254 nm; (Hex:DCM=3:1) (0.1% DEA): EtOH=50:50, Flow rate: 1 mL/min; Retention time: 1.967 min; (faster peak).

Example 35b: 2-((R)-1-acryloyl-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (20.6 mg, 0.036 mmol, 2.2% yield). $^1$H NMR (300 MHz, DMSO-$d_6$, ppm) δ 7.20-6.95 (m, 3H), 6.94-6.76 (m, 1H), 6.18 (dd, J=16.6, 2.3 Hz, 1H), 5.77 (dd, J=10.4, 2.4 Hz, 1H), 4.95-4.78 (m, 1H), 4.53-3.86 (m, 4H), 3.81-3.61 (m, 1H), 3.52-3.38 (m, 1H), 3.19-2.58 (m, 14H), 2.44-2.37 (m, 1H), 2.32 (s, 3H), 2.21-1.81 (m, 5H), 1.72-1.47 (m, 3H), 0.80 (d, J=6.2 Hz, 3H). LCMS (ESI, m/z): 555.3 [M+H]$^+$. Chiral HPLC: Column: CHIRAL ART Cellulose-SB, 4.6*100 mm, 3 m; detected at 254 nm; MtBE (0.1% DEA):IPA=80:20, Flow rate: 1 mL/min; Retention time: 2.972 min; (slower peak).

Example 35c: 2-((S)-1-acryloyl-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (20.3 mg, 0.036 mmol, 2.2% yield). $^1$H NMR (300 MHz, DMSO-$d_6$, ppm) δ 7.18-6.97 (m, 3H), 6.93-6.76 (m, 1H), 6.18 (dd, J=16.7, 2.4 Hz, 1H), 5.77 (dd, J=10.4, 2.3 Hz, 1H), 4.95-4.78 (m, 1H), 4.48-3.63 (m, 5H), 3.51-3.35 (m, 1H), 3.25-2.58 (m, 14H), 2.41 (s, 1H), 2.32 (s, 3H), 2.20-1.79 (m, 5H), 1.72-1.45 (m, 3H), 0.80 (d, J=6.3 Hz, 3H). LCMS (ESI, m/z): 555.3 [M+H]$^+$. Chiral HPLC: Column: CHIRAL ART Cellulose-SB, 4.6*100 mm, 3 m; detected at 254 nm; MtBE(0.1% DEA):IPA=80:20, Flow rate: 1 mL/min; Retention time: 2.480 min; (faster peak).

Example 35d: 2-((S)-1-acryloyl-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (23.1 mg, 0.041 mmol, 2.5% yield). $^1$H NMR (300 MHz, DMSO-$d_6$, ppm) δ 7.20-7.01 (m, 3H), 6.97-6.77 (m, 1H), 6.18 (dd, J=16.6, 2.3 Hz, 1H), 5.77 (dd, J=10.4, 2.3 Hz, 1H), 4.98-4.78 (m, 1H), 4.47-4.31 (m, 1H), 4.23 (dd, J=10.7, 4.8 Hz, 1H), 4.08-3.93 (m, 2H), 3.92-3.72 (m, 2H), 3.70-3.51 (m, 1H), 3.29-3.10 (m, 2H), 3.01-2.63 (m, 12H), 2.31 (s, 3H), 2.16-2.13 (m, 1H), 2.04-1.82 (m, 4H), 1.70-1.47 (m, 3H), 0.79 (d, J=6.3 Hz, 3H). LCMS (ESI, m/z): 555.3 [M+H]$^+$. Chiral HPLC: Column: CHIRALPAK IC-3, 4.6*50 mm 3 um; detected at 254 nm; (Hex:DCM=3:1) (0.1% DEA): EtOH=50:50, Flow rate: 1 mL/min; Retention time: 3.610 min; (slower peak).

Examples 36a and 36b

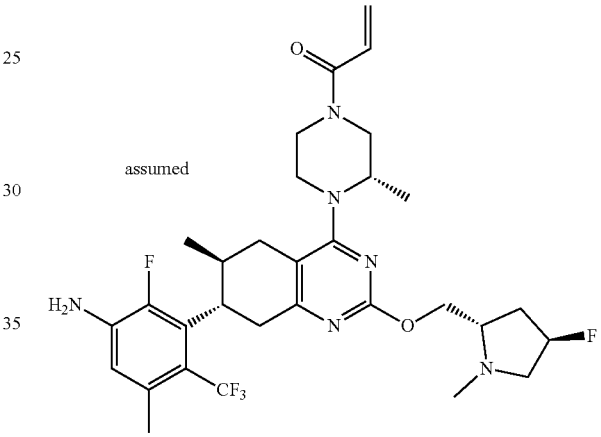

Example 36a

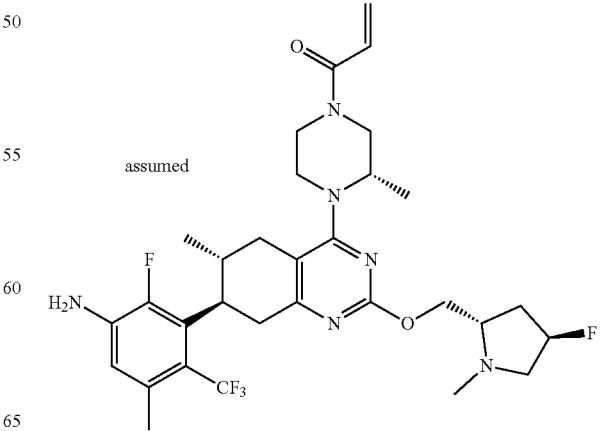

Example 36b

549
1-[(3S)-4-[(6S,7S)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one (Example 36a); and
1-[(3S)-4-[(6R,7R)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one (Example 36b)
550
-continued
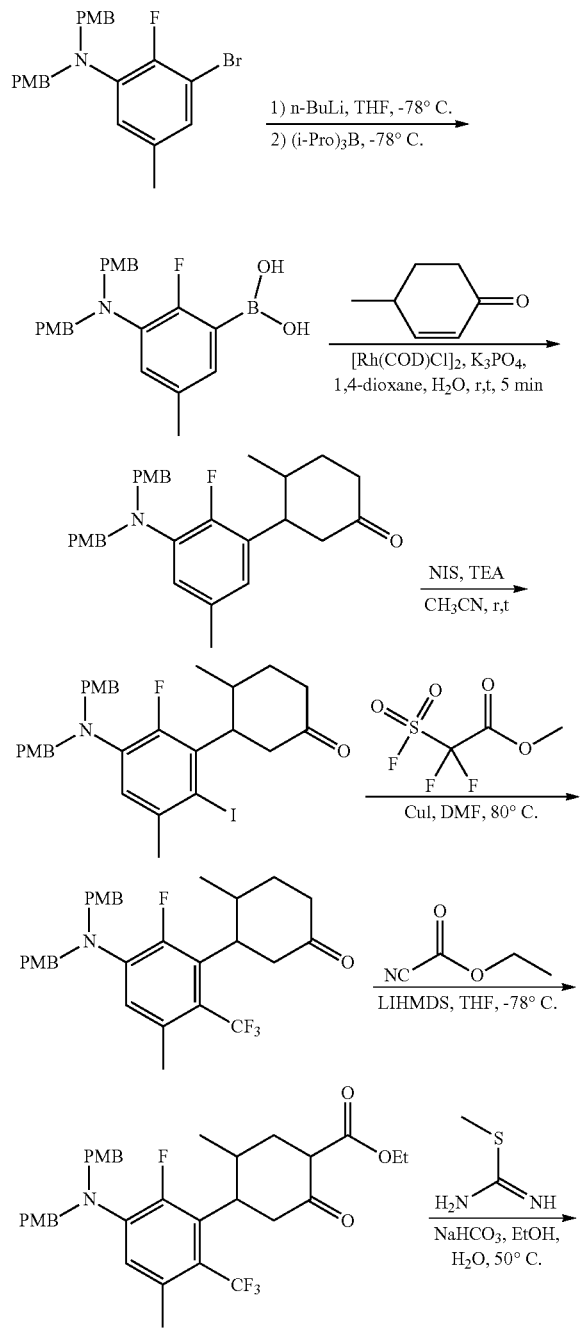
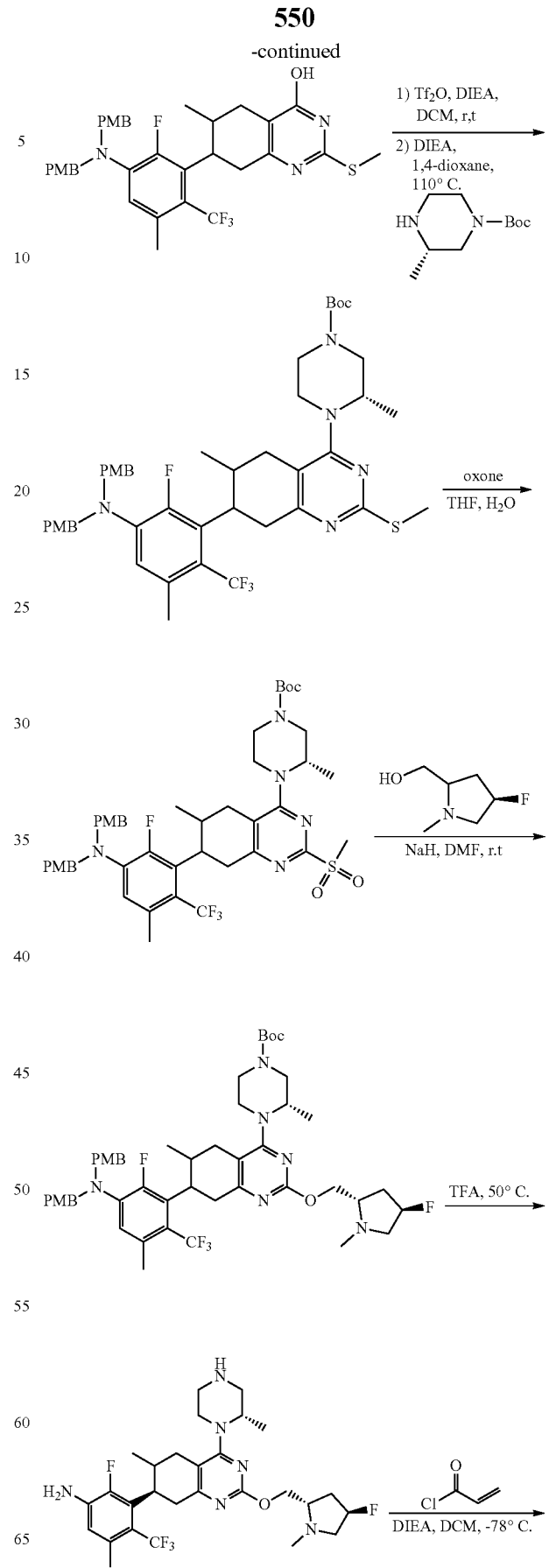

-continued assumed

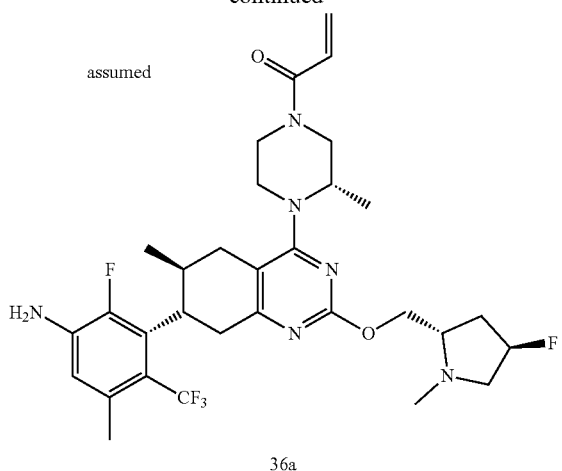

36a assumed

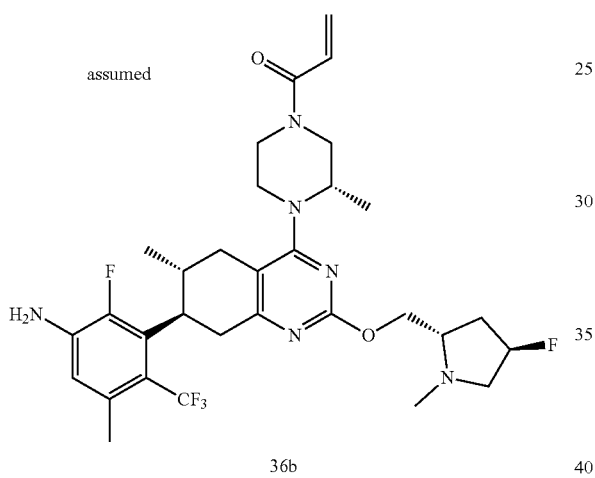

36b

Step 1: (3-(bis(4-methoxybenzyl)amino)-2-fluoro-5-methylphenyl)boronic acid

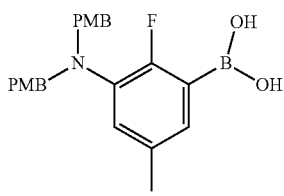

Under nitrogen, a solution of 3-bromo-2-fluoro-N,N-bis(4-methoxybenzyl)-5-methylaniline (20.0 g, 46.8 mmol) in tetrahydrofuran (200 mL) was stirred at −78° C. for 5 minutes. Then n-butyllithium (2.5 M in hexane) (28 mL, 70.2 mmol) was added dropwised and stirred at −78° C. for 30 minutes. Then triisopropyl borate (44.0 g, 234.0 mmol) was added and stirred at −78° C. for 20 minutes. After completion, the resulting solution was concentrated under vacuum.

Step 2: 3-(3-(bis(4-methoxybenzyl)amino)-2-fluoro-5-methylphenyl)-4-methylcyclohexan-1-one

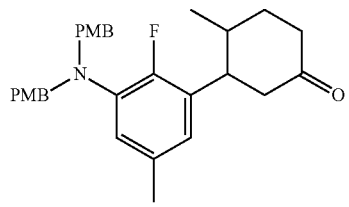

Under nitrogen, the residue from the previous step, 4-methylcyclohex-2-en-1-one (5.1 g, 46.8 mmol) and chloro(1,5-cyclooctadiene)rhodium(I) dimer (2.3 g, 4.68 mmol) in 1,4-dioxane (200 mL) was stirred at 25° C. for 5 minutes. Then saturated potassium phosphate solution (40 mL) was added and stirred at 25° C. for 1 hour. After completion, the reaction was diluted with water, extracted with ethyl acetate, dried over anhydrous sodium sulfate and concentrated under vacuum. The residue was purified by flash chromatography on silica gel eluting with petroleum ether/ethyl acetate (10/1) to afford 3-(3-(bis(4-methoxybenzyl)amino)-2-fluoro-5-methylphenyl)-4-methylcyclohexan-1-one (11 g, 23.9 mmol, 51.3% yield) as a yellow solid. LC-MS: (ESI, m/z): 476.3 [M+H]$^+$.

Step 3: 3-[3-[bis[(4-methoxyphenyl)methyl]amino]-2-fluoro-6-iodo-5-methyl-phenyl]-4-methyl-cyclohexanone

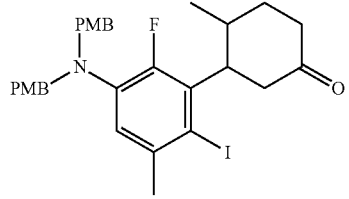

A solution of 3-(3-(bis(4-methoxybenzyl)amino)-2-fluoro-5-methylphenyl)-4-methylcyclohexan-1-one (25.0 g, 52.5 mmol) and N-iodosuccinimide (14.1 g, 63.0 mmol) in acetonitrile (250 mL) was stirred at room temperature for 2 minutes. Then trifluoroacetic acid (0.6 g, 5.2 mmol) was added and stirred at 25° C. for 20 minutes. After completion, the resulting solution was concentrated under vacuum. The solution was diluted with water. The resulting solution was extracted with ethyl acetate and the organic layers were combined. The organic layer was dried over anhydrous sodium sulfate and concentrated under vacuum. The residue was purified by flash chromatography on silica gel eluting with petroleum ether/ethyl acetate (3/1) to afford 3-[3-[bis[(4-methoxyphenyl)methyl]amino]-2-fluoro-6-iodo-5-methyl-phenyl]-4-methyl-cyclohexanone (30 g, 49.8 mmol, 94.9% yield) as a yellow oil. LC-MS: (ESI, m/z): 602.1 [M+H]$^+$.

Step 4: 3-[3-[bis[(4-methoxyphenyl)methyl]amino]-2-fluoro-5-methyl-6-(trifluoromethyl)phenyl]-4-methyl-cyclohexanone

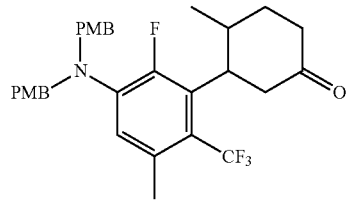

Under nitrogen, a solution of 3-[3-[bis[(4-methoxyphenyl)methyl]amino]-2-fluoro-6-iodo-5-methyl-phenyl]-4-methyl-cyclohexanone (20.0 g, 33.2 mmol), methyl 2,2-difluoro-2-(fluorosulfonyl)acetate (31.9 g, 166.2 mmol) and cuprous iodide (12.6 g, 66.5 mmol) in N,N-dimethylformamide (200 mL) was stirred at 80° C. for 2 hours. After completion, the reaction was quenched with water. The resulting solution was extracted with ethyl acetate and the organic layers were combined. The organic layer was dried over anhydrous sodium sulfate and concentrated under vacuum. The residue was purified by flash chromatography on silica gel eluting with petroleum ether/ethyl acetate (5/1) to afford 3-[3-[bis[(4-methoxyphenyl)methyl]amino]-2-fluoro-5-methyl-6-(trifluoromethyl)phenyl]-4-methyl-cyclohexanone (12 g, 22.0 mmol, 66.4% yield) as a yellow oil. LC-MS: (ESI, m/z): 544.2 [M+H]$^+$.

Step 5: ethyl 4-[3-[bis[(4-methoxyphenyl)methyl]amino]-2-fluoro-5-methyl-6-(trifluoromethyl)phenyl]-5-methyl-2-oxo-cyclohexanecarboxylate

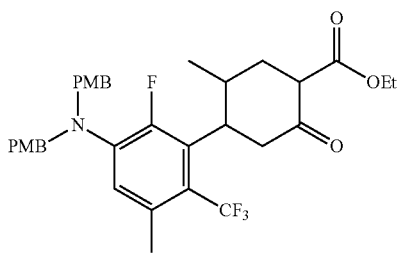

Under nitrogen, a solution of 3-[3-[bis[(4-methoxyphenyl)methyl]amino]-2-fluoro-5-methyl-6-(trifluoromethyl)phenyl]-4-methyl-cyclohexanone (10.0 g, 18.4 mmol) in tetrahydrofuran (100 mL) was stirred at −78° C. for 3 minutes. Lithium bis(trimethylsilyl)amide (1.0 M in THF) (33 mL, 33 mmol) was added dropwised and stirred at −78° C. for 10 minutes. Then ethyl cyanoformate (4.1 g, 42.3 mmol) was added and stirred at −78° C. for 20 minutes. After completion, the reaction was quenched with water, extracted with ethyl acetate, dried over anhydrous sodium sulfate and concentrated under vacuum to afford crude product. The crude product was used for next step directly without purification. LC-MS: (ESI, m/z): 616.3 [M+H]$^+$.

Step 6: 7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-ol

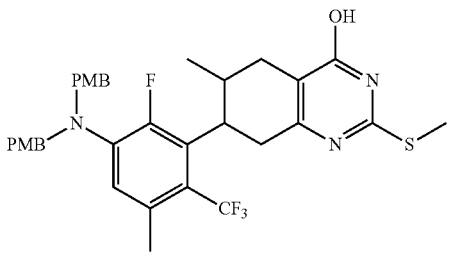

A solution of ethyl 4-[3-[bis[(4-methoxyphenyl)methyl]amino]-2-fluoro-5-methyl-6-(trifluoromethyl)phenyl]-5-methyl-2-oxo-cyclohexanecarboxylate (20.0 g, 32.4 mmol), 2-methyl-2-thiopseudourea sulfate (90.3 g, 324.8 mmol) and sodium bicarbonate (54.5 g, 649.7 mmol) in ethanol (200 mL) and water (40 mL) was stirred at 50° C. for 4 hours. After completion, the resulting solution was diluted with water and extracted with ethyl acetate. Then the organic layers were collected, washed with brine, dried over anhydrous sodium sulfate and concentrated under vacuum. The residue was purified by flash chromatography on silica gel eluting with dichloromethane/ethyl acetate (4/1) to afford 7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-ol (7 g, 10.9 mmol, 33.6% yield) as a yellow solid. LC-MS: (ESI, m/z): 642.2 [M+H]$^+$.

Step 7: tert-butyl (3S)-4-[7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-yl]-3-methyl-piperazine-1-carboxylate

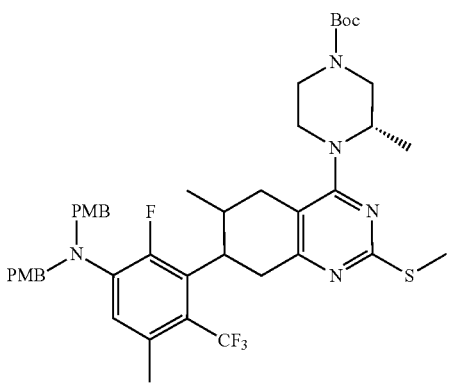

A solution of 7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-ol (4.4 g, 6.8 mmol), N,N-diisopropylethylamine (4.4 g, 34.2 mmol) and trifluoromethanesulfonic anhydride (3.4 g, 12.3 mmol) in dichloromethane (50 mL) was stirred at 25° C. for 1 hour. After completion, reaction was concentrated under reduced pressure. Then the residue, N,N-diisopropylethylamine (4.42 g, 34.2 mmol) and tert-butyl (3S)-3-methyl-1-piperazinecarboxylate (2.7 g, 13.7 mmol) in 1,4-dioxane (50 mL) was stirred at 110° C. for 16 hours. After completion, the resulting solution was concentrated under vacuum. The residue was purified by flash chromatography on silica gel eluting with petroleum ether/ethyl acetate (85/15) to afford tert-butyl (3S)-4-[7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-yl]-3-methyl-piperazine-1-carboxylate (3.5 g, 4.2 mmol, 62% yield) as a white solid. LC-MS: (ESI, m/z): 824.4 [M+H]+.

Step 8: tert-butyl (3S)-4-[7-[3-[bis[(4-methoxyphenyl)methyl]amino]-2-fluoro-5-methyl-6-(trifluoromethyl)phenyl]-6-methyl-2-methylsulfonyl-5,6,7,8-tetrahydroquinazolin-4-yl]-3-methyl-piperazine-1-carboxylate

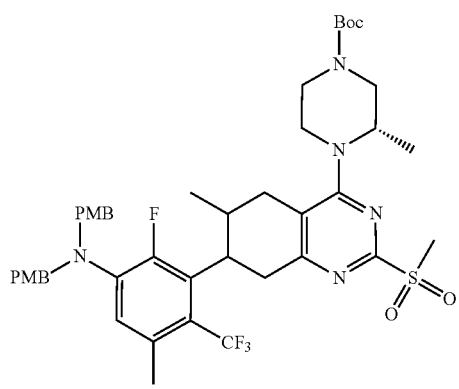

A solution of tert-butyl (3S)-4-[7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-yl]-3-methyl-piperazine-1-carboxylate (3.5 g, 4.2 mmol) and potassium peroxymonosulfate (7.8 g, 12.7 mmol) in tetrahydrofuran (35 mL) and water (17.5 mL) was stirred at room temperature for 3 hours. After completion, the reaction was quenched by saturated sodium sulfite solution, extracted with ethyl acetate. Then the organic layers were collected, dried over anhydrous sodium sulfate and concentrated under vacuum to afford crude product. The crude product was used for next step directly without purification. LC-MS: (ESI, m/z): 856.4 [M+H]+.

Step 9: tert-butyl (3S)-4-[7-[3-[bis[(4-methoxyphenyl)methyl]amino]-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazine-1-carboxylate

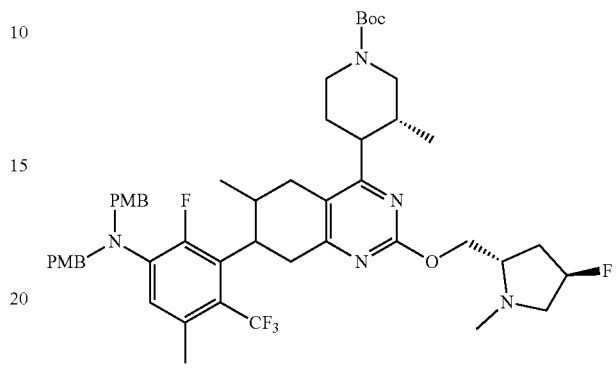

A solution of sodium hydride (0.5 g, 13.6 mmol, 60% dispersion in mineral oil) and [(2S,4R)-4-fluoro-1-methyl-pyrrolidin-2-yl]methanol (0.7 g, 5.4 mmol) in DMF (26 mL) was stirred at 0° C. for 10 minutes. Then tert-butyl (3S)-4-[7-[3-[bis[(4-methoxyphenyl)methyl]amino]-2-fluoro-5-methyl-6-(trifluoromethyl)phenyl]-6-methyl-2-methylsulfonyl-5,6,7,8-tetrahydroquinazolin-4-yl]-3-methyl-piperazine-1-carboxylate (2.6 g, 2.7 mmol) was added and stirred at room temperature for 30 minutes. After completion, the reaction was quenched with saturated ammonium chloride solution and extracted with dichloromethane. Then the organic layers were collected, dried over anhydrous sodium sulfate and concentrated under vacuum. The residue was purified by flash chromatography on silica gel eluting with dichloromethane/ethyl acetate (3/1) to afford tert-butyl (3S)-4-[7-[3-[bis[(4-methoxyphenyl)methyl]amino]-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazine-1-carboxylate (1.2 g, 1.3 mmol, 48.3% yield) as a yellow solid. LC-MS: (ESI, m/z): 908.5 [M+H]+.

Step 10: 2-fluoro-3-[2-[[(2S,4R)-4-fluoro-1-methyl-pyrrolidin-2-yl]methoxy]-6-methyl-4-[(2S)-2-methylpiperazin-1-yl]-5,6,7,8-tetrahydroquinazolin-7-yl]-5-methyl-4-(trifluoromethyl)aniline

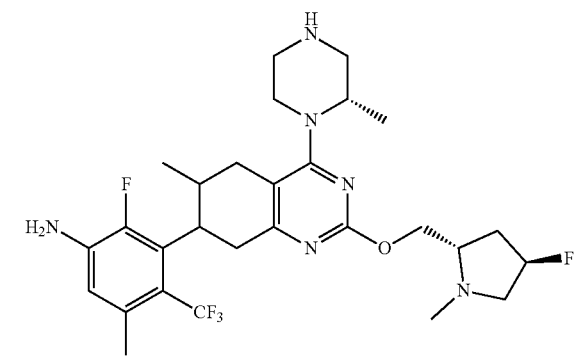 [SMILES: Cc1cc(N)c(F)c(C2Cc3nc(OC[C@@H]4C[C@@H](F)CN4C)nc(N4CCNC[C@@H]4C)c3CC2C)c1C(F)(F)F]

A solution of tert-butyl (3S)-4-[7-[3-[bis[(4-methoxyphenyl)methyl]amino]-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazine-1-carboxylate (1.2 g, 1.3 mmol) in trifluoroacetic acid (3.0 g, 26.4 mmol) was stirred at 50° C. for 2 hours. the resulting solution was concentrated under vacuum. The residue was purified by flash chromatography on silica gel eluting with Acetonitrile/water (2:3) to afford 2-fluoro-3-[2-[[(2S,4R)-4-fluoro-1-methyl-pyrrolidin-2-yl]methoxy]-6-methyl-4-[(2S)-2-methylpiperazin-1-yl]-5,6,7,8-tetrahydroquinazolin-7-yl]-5-methyl-4-(trifluoromethyl)aniline (0.6 g, 1.1 mmol, 89.3% yield) as a yellow solid. LC-MS: (ESI, m/z): 569.3 [M+H]⁺.

Step 11: 1-[(3S)-4-[(6S,7S)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one (Example 36a); and 1-[(3S)-4-[(6R,7R)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one (Example 36b)

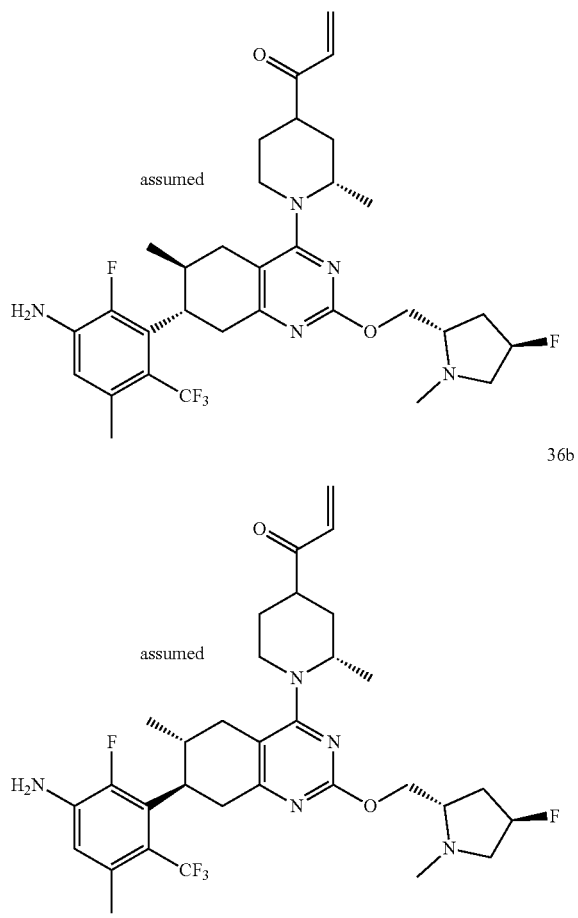

A solution of 2-fluoro-3-[2-[[(2S,4R)-4-fluoro-1-methyl-pyrrolidin-2-yl]methoxy]-6-methyl-4-[(2S)-2-methylpiperazin-1-yl]-5,6,7,8-tetrahydroquinazolin-7-yl]-5-methyl-4-(trifluoromethyl)aniline (0.65 g, 1.1 mmol), acrylic acid (0.08 g, 1.1 mmol) and N,N-diisopropylethylamine (0.44 g, 3.43 mmol) in dichloromethane (6 mL) was stirred at −78° C. for 5 minutes. Then HATU (434.6 mg, 1.1 mmol) was added and stirred at 25° C. for 10 minutes. After completion, the solvent was diluted with dichloromethane and washed with brine. Then the organic layer was dried over anhydrous sodium sulfate and concentrated under vacuum. The residue was purified by flash chromatography on silica gel eluting with dichloromethane/methanol (10/1) to afford 350 mg crude solid. The crude product was purified by Prep-HPLC with the following conditions: (Column: XBridge Prep OBD C18 Column, 30×150 mm 5 um; Mobile Phase A: Water (10 MMOL/L NH4HCO3), Mobile Phase B: ACN; Flow rate: 60 mL/min; Gradient: 40 B to 70 B in 7 min; 254 nm; RT1:5.77) to get 120 mg crude product as a mixture of two isomers. The product was further purified by Chiral-Prep-HPLC with following condition (Column: CHIRALPAK IE-3 4.6*50 mm 3 um; Mobile Phase Hex (0.1% DEA): EtOH=50:50; Flow rate: 1 mL/min; Gradient: maintaining 20% B for 13 min; 220/254 nm) to afford the title compounds. The absolute configuration of the title compounds was inferred from potency data and a protein X-ray structure of compound 21b.

Example 36a: 1-[(3S)-4-[(6S,7S)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one (41.9 mg, 0.06 mmol, 5.9% yield, white solid). ¹H NMR (300 MHz, DMSO-d₆, ppm) δ 6.95-6.73 (m, 1H), 6.57 (d, J=8.8 Hz, 1H), 6.16 (d, J=16.4 Hz, 1H), 5.85-5.66 (m, 3H), 5.16 (d, J=56.0 Hz, 1H), 4.37-3.98 (m, 4H), 3.74 (dd, J=74.8, 13.6 Hz, 1H), 3.53-3.34 (m, 3H), 3.31-3.29 (m, 1H), 3.28-3.03 (m, 2H), 2.95-2.78 (m, 3H), 2.59 (d, J=14.9 Hz, 1H), 2.48-2.00 (m, 10H), 1.97-1.74 (m, 1H), 0.97 (t, J=7.9 Hz, 3H), 0.81 (d, J=6.2 Hz, 3H). LC-MS: (ESI, m/z): 623.4 [M+H]⁺. Chiral HPLC: Column: CHIRALPAK IE-3, 4.6*50 mm 3 um; detected at 254 nm; Hex (0.1% DEA): EtOH=50:50; Flow rate: 1 mL/min; Retention time: 2.058 min; (slower peak).

Example 36b: 1-[(3S)-4-[(6R,7R)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one (50.1 mg, 0.08 mmol, 7% yield, white solid). ¹H NMR (300 MHz, DMSO-d₆, ppm) δ 6.93-6.73 (m, 1H), 6.58 (d, J=8.8 Hz, 1H), 6.22-6.10 (m, 1H), 5.87-5.67 (m, 3H), 5.17 (d, J=56.1 Hz, 1H), 4.44-4.02 (m, 5H), 3.99-3.76 (m, 2H), 3.54-3.36 (m, 2H), 3.32-3.28 (m, 1H), 3.21-3.04 (m, 2H), 2.96-2.80 (m, 3H), 2.45-2.26 (m, 8H), 2.25-2.01 (m, 2H), 1.98-1.74 (m, 1H), 1.34-1.21 (m, 3H), 0.81 (d, J=6.3 Hz, 3H). LC-MS: (ESI, m/z): 623.4 [M+H]⁺. Chiral HPLC: Column: CHIRALPAK IE-3, 4.6*50 mm 3 um; detected at 254 nm; Hex (0.1% DEA): EtOH=50:50; Flow rate: 1 mL/min; Retention time: 1.606 min; (faster peak).

Examples 37a and 37b
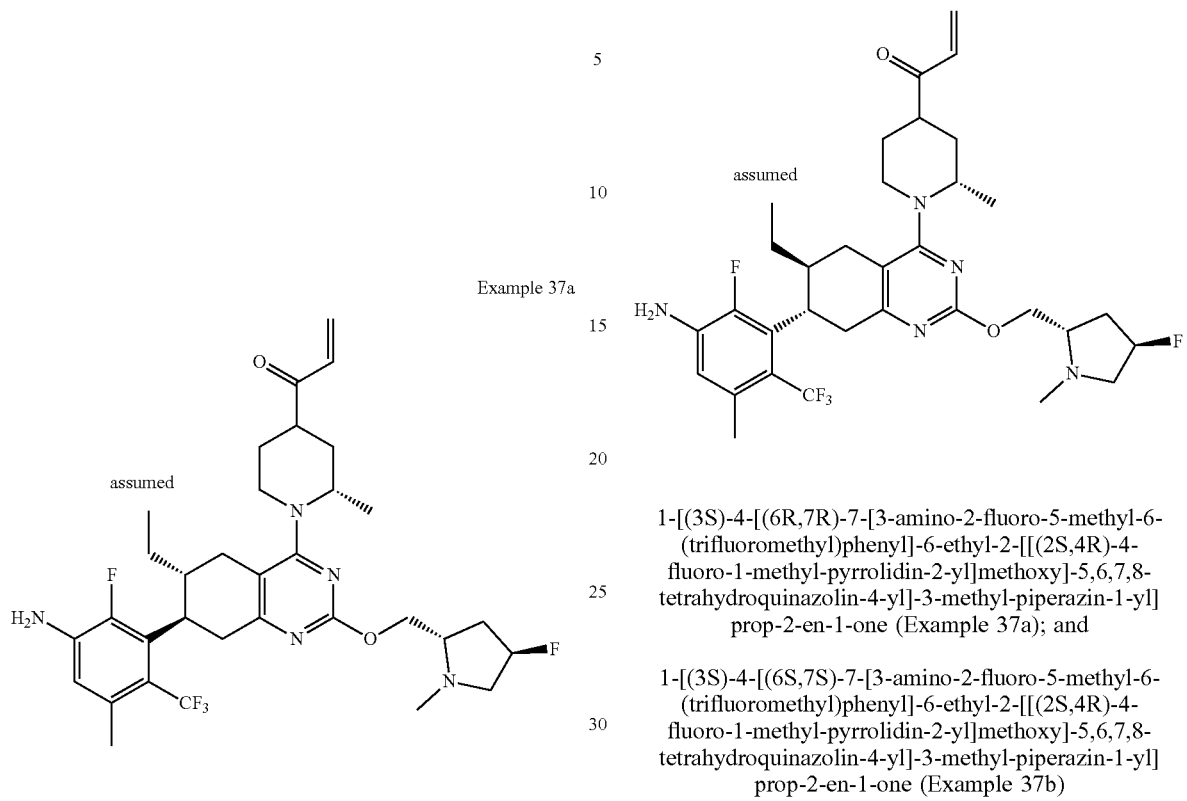
Example 37a
1-[(3S)-4-[(6R,7R)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl] prop-2-en-1-one (Example 37a); and
1-[(3S)-4-[(6S,7S)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl] prop-2-en-1-one (Example 37b)
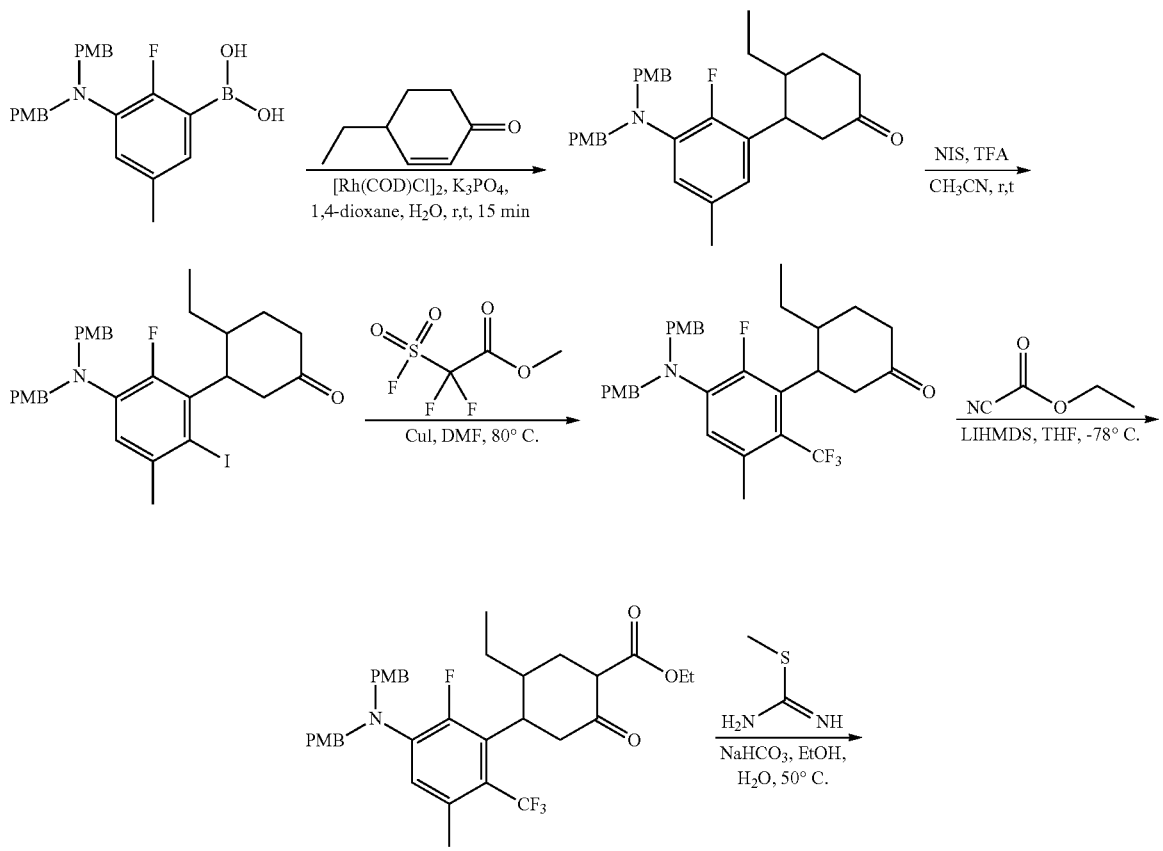

-continued
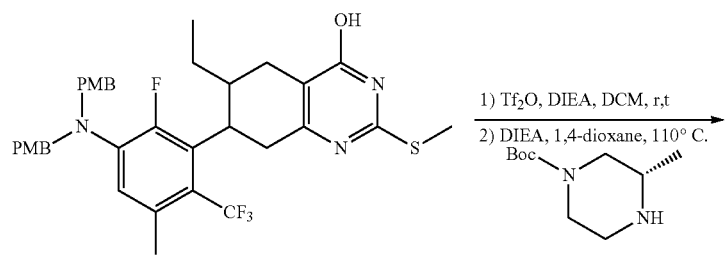
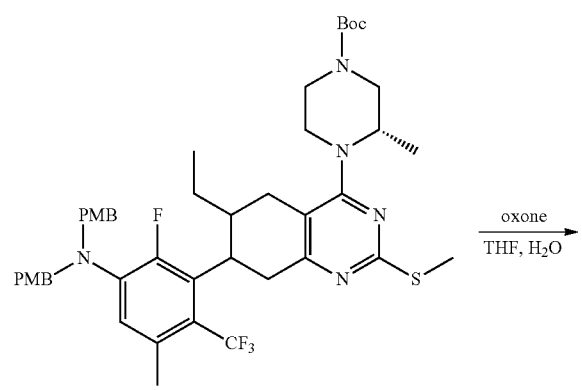
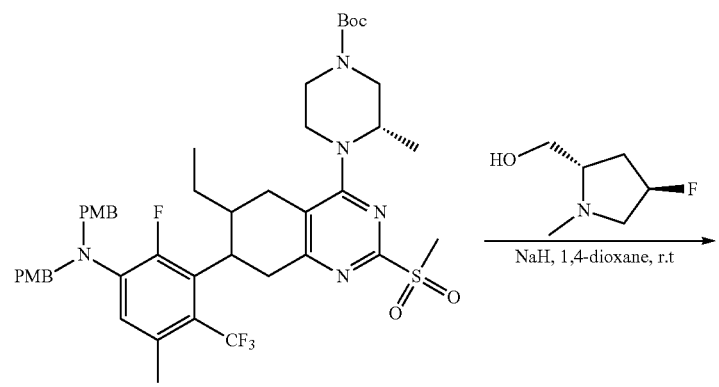
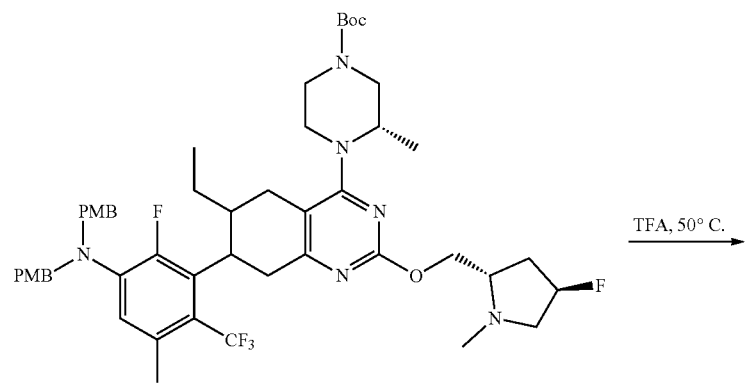

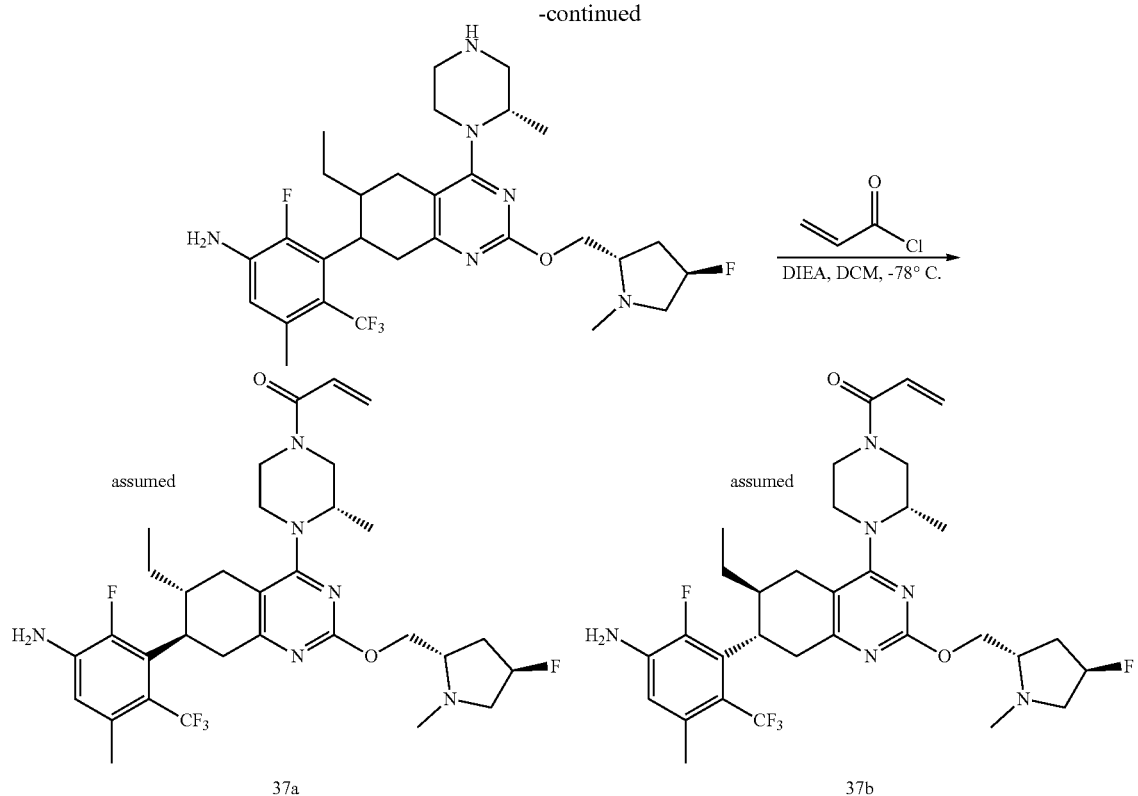

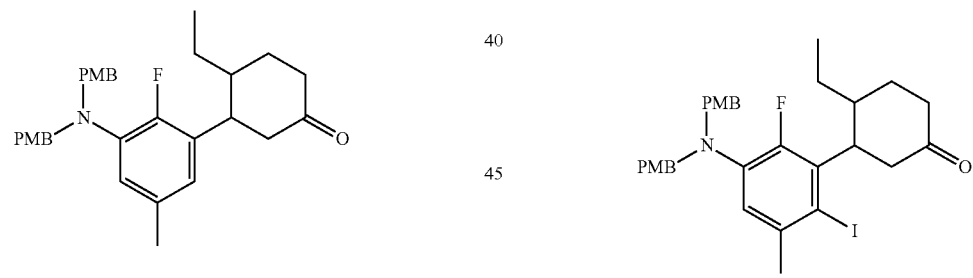

Step 1: 3-[3-[bis[(4-methoxyphenyl)methyl]amino]-2-fluoro-5-methyl-phenyl]-4-ethyl-cyclohexanone Step 2: 3-[3-[bis[(4-methoxyphenyl)methyl]amino]-2-fluoro-6-iodo-5-methyl-phenyl]-4-ethyl-cyclohexanone Under nitrogen, a solution of [3-[bis[(4-methoxyphenyl)methyl]amino]-2-fluoro-5-methyl-phenyl]boronic acid (20.0 g, 48.87 mmol), 4-ethylcyclohex-2-en-1-one (6.07 g, 48.87 mmol), chloro(1,5-cyclooctadiene)rhodium(I) dimer (1.2 g, 2.44 mmol) and potassium phosphate (31.1 g, 146.61 mmol) in 1,4-dioxane (200 mL) and water (40 mL) was stirred at room temperature for 15 minutes. After completion, the resulting solution was concentrated under vacuum. The residue was diluted with water, extracted with dichloromethane and the organic layers were combined. The organic layer was dried over anhydrous sodium sulfate and concentrated under vacuum. The residue was purified by flash chromatography on silica gel eluting with petroleum ether/ethyl acetate (3/1) to afford 3-[3-[bis[(4-methoxyphenyl)methyl]amino]-2-fluoro-5-methyl-phenyl]-4-ethyl-cyclohexanone (10 g, 20.4 mmol, 41.8% yield) as a colorless oil. LC-MS: (ESI, m/z): 490.3 [M+H]$^+$.

A solution of 3-[3-[bis[(4-methoxyphenyl)methyl]amino]-2-fluoro-5-methyl-phenyl]-4-ethyl-cyclohexanone (10.0 g, 20.42 mmol) and N-iodosuccinimide (5.5 g, 24.51 mmol) in acetonitrile (200 mL) was stirred at room temperature for 2 minutes. Then trifluoroacetic acid (0.2 g, 2.04 mmol) was added and stirred at 25° C. for 20 minutes. After completion, the reaction was quenched with saturated sodium sulfite, extracted with ethyl acetate and the organic layers were combined. The organic layer was dried over anhydrous sodium sulfate and concentrated under vacuum. The residue was purified by flash chromatography on silica gel eluting with petroleum ether/ethyl acetate (3/1) to afford 3-[3-[bis[(4-methoxyphenyl)methyl]amino]-2-fluoro-6-iodo-5-methyl-phenyl]-4-ethyl-cyclohexanone (9 g, 14.62 mmol, 71.6% yield) as a yellow oil. LC-MS: (ESI, m/z): 616.1 [M+H]$^+$.

Step 3: 3-[3-[bis[(4-methoxyphenyl)methyl]amino]-2-fluoro-5-methyl-6-(trifluoromethyl)phenyl]-4-ethyl-cyclohexanone

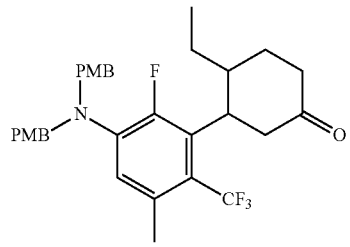

Under nitrogen, a solution of 3-[3-[bis[(4-methoxyphenyl)methyl]amino]-2-fluoro-6-iodo-5-methyl-phenyl]-4-ethyl-cyclohexanone (9.0 g, 14.62 mmol), methyl 2,2-difluoro-2-(fluorosulfonyl)acetate (14.04 g, 73.11 mmol) and cuprous iodide (5.5 g, 29.24 mmol) in N,N-dimethylformamide (90 mL) was stirred at 80° C. for 2 hours. After completion, the reaction was diluted with water. The resulting solution was extracted with ethyl acetate and the organic layers were combined. The organic layer was dried over anhydrous sodium sulfate and concentrated under vacuum. The residue was purified by flash chromatography on silica gel eluting with petroleum ether/ethyl acetate (5/1) to afford 3-[3-[bis[(4-methoxyphenyl)methyl]amino]-2-fluoro-5-methyl-6-(trifluoromethyl)phenyl]-4-ethyl-cyclohexanone (5 g, 8.96 mmol, 61.3% yield) as a yellow oil. LC-MS: (ESI, m/z): 558.2 [M+H]$^+$.

Step 4: ethyl 4-[3-[bis[(4-methoxyphenyl)methyl]amino]-2-fluoro-5-methyl-6-(trifluoromethyl)phenyl]-5-ethyl-2-oxo-cyclohexanecarboxylate

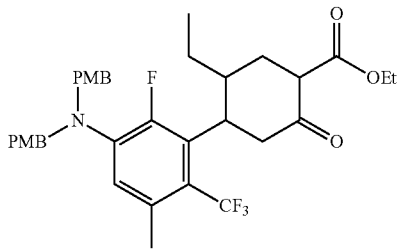

Under nitrogen, a solution of 3-[3-[bis[(4-methoxyphenyl)methyl]amino]-2-fluoro-5-methyl-6-(trifluoromethyl)phenyl]-4-ethyl-cyclohexanone (5.0 g, 8.97 mmol) in tetrahydrofuran (2 mL) was added lithium bis(trimethylsilyl)amide (1 M in THF) (13.4 mL, 13.45 mmol) at −78° C. The resulting solution was stirred for 0.5 hour at −78° C. Then ethyl cyanoformate (1.5 g, 15.24 mmol) was added and stirred at −78° C. for 2 hours. Reaction was quenched by addition of water, extracted with ethyl acetate, dried over anhydrous sodium sulfate and concentrated under vacuum to afford crude product. The crude product was used for next step directly without purification. LC-MS: (ESI, m/z): 630.3 [M+H]$^+$.

Step 5: 7-[3-[bis[(4-methoxyphenyl)methyl]amino]-2-fluoro-5-methyl-6-(trifluoromethyl)phenyl]-6-ethyl-2-methylsulfanyl-5,6,7,8-tetrahydroquinazolin-4-ol

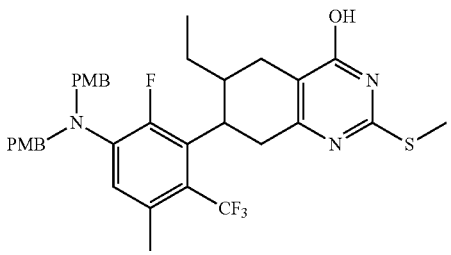

A solution of ethyl 4-[3-[bis[(4-methoxyphenyl)methyl]amino]-2-fluoro-5-methyl-6-(trifluoromethyl)phenyl]-5-ethyl-2-oxo-cyclohexanecarboxylate (5.0 g, 7.94 mmol), 2-methyl-2-thiopseudourea sulfate (22.0 g, 79.41 mmol) and sodium bicarbonate (13.3 g, 158.81 mmol) in ethanol (50 mL) and water (10 mL) was stirred at 50° C. for 4 hours. After completion, the resulting solution was concentrated under vacuum. The residue was dissolved with dichloromethane and washed with brine. The organic layer was dried over anhydrous sodium sulfate and concentrated under vacuum. The residue was purified by flash chromatography on silica gel eluting with dichloromethane/ethyl acetate (4/1) to afford 7-[3-[bis[(4-methoxyphenyl)methyl]amino]-2-fluoro-5-methyl-6-(trifluoromethyl)phenyl]-6-ethyl-2-methylsulfanyl-5,6,7,8-tetrahydroquinazolin-4-ol (1.5 g, 2.28 mmol, 28.8% yield) as a yellow solid. LC-MS: (ESI, m/z): 656.2 [M+H]$^+$.

Step 6: tert-butyl (3S)-4-[7-[3-[bis[(4-methoxyphenyl)methyl]amino]-2-fluoro-5-methyl-6-(trifluoromethyl)phenyl]-6-ethyl-2-methylsulfanyl-5,6,7,8-tetrahydroquinazolin-4-yl]-3-methyl-piperazine-1-carboxylate

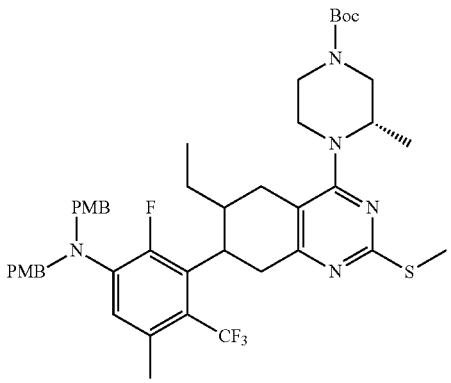

A solution of 7-[3-[bis[(4-methoxyphenyl)methyl]amino]-2-fluoro-5-methyl-6-(trifluoromethyl)phenyl]-6-ethyl-2-methylsulfanyl-5,6,7,8-tetrahydroquinazolin-4-ol (1.5 g, 2.29 mmol), N,N-Diisopropylethylamine (1.4 g, 11.44 mmol) and trifluoromethanesulfonic anhydride (1.1 g, 4.12 mmol) in dichloromethane (15 mL) was stirred at 25° C. for 1 hour. After completion, reaction was concentrated under reduced pressure. Then the residue, N,N-Diisopropylethylamine (1.4 g, 11.44 mmol) and tert-butyl (3S)-3-methyl-1-piperazinecarboxylate (0.9 g, 4.57 mmol) in 1,4-dioxane (15 mL) was stirred at 110° C. for 16 hours. After completion, the resulting solution was concentrated under vacuum. The residue was purified by flash chromatography on silica gel eluting with petroleum ether/ethyl acetate (85/15) to afford tert-butyl (3S)-4-[7-[3-[bis[(4-methoxyphenyl)methyl]amino]-2-fluoro-5-methyl-6-(trifluoromethyl)phenyl]-6-ethyl-2-methylsulfanyl-5,6,7,8-tetrahydroquinazolin-4-yl]-3-methyl-piperazine-1-carboxylate (1.3 g, 1.55 mmol, 67.8% yield) as a white solid. LC-MS: (ESI, m/z): 838.4 [M+H]$^+$.

Step 7: tert-butyl (3S)-4-(7-(3-(bis(4-methoxybenzyl)amino)-2-fluoro-5-methyl-6-(trifluoromethyl)phenyl)-6-ethyl-2-(methylsulfonyl)-5,6,7,8-tetrahydroquinazolin-4-yl)-3-methylpiperazine-1-carboxylate

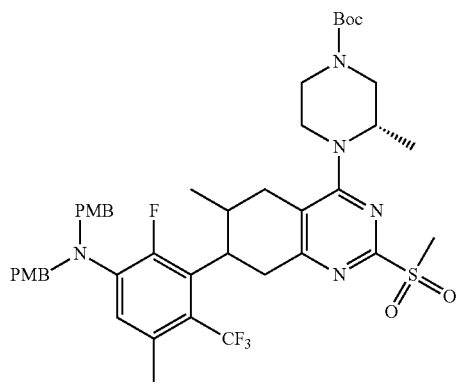

A solution of tert-butyl (3S)-4-[7-[3-[bis[(4-methoxyphenyl)methyl]amino]-2-fluoro-5-methyl-6-(trifluoromethyl)phenyl]-6-ethyl-2-methylsulfanyl-5,6,7,8-tetrahydroquinazolin-4-yl]-3-methyl-piperazine-1-carboxylate (3.5 g, 4.2 mmol) and potassium peroxymonosulfate (7.8 g, 12.7 mmol) in tetrahydrofuran (35 mL) and water (17.5 mL) was stirred at room temperature for 3 hours. After completion, the reaction was quenched by saturated sodium sulfite solution, extracted with ethyl acetate, dried over anhydrous sodium sulfate and concentrated under vacuum to afford crude product. The crude product was used for next step directly without purification. LC-MS: (ESI, m/z): 870.4 [M+H]$^+$.

Step 8: tert-butyl (3S)-4-[7-[3-[bis[(4-methoxyphenyl)methyl]amino]-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazine-1-carboxylate

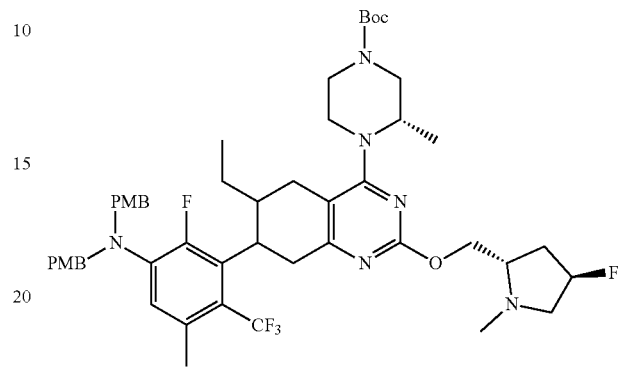

A solution of sodium hydride (0.3 g, 7.47 mmol, 60% dispersion in mineral oil) and [(2S,4R)-4-fluoro-1-methyl-pyrrolidin-2-yl]methanol (0.4 g, 2.99 mmol) in 1,4-dioxane (12.79 mL) was stirred at 0° C. for 10 minutes. Then tert-butyl (3S)-4-[7-[3-[bis[(4-methoxyphenyl)methyl]amino]-2-fluoro-5-methyl-6-(trifluoromethyl)phenyl]-6-ethyl-2-methylsulfonyl-5,6,7,8-tetrahydroquinazolin-4-yl]-3-methyl-piperazine-1-carboxylate (1.3 g, 1.49 mmol) was added and stirred at room temperature for 30 minutes. After completion, the reaction was quenched with saturated ammonium chloride solution. The resulting solution was extracted with ethyl acetate, dried over anhydrous sodium sulfate and concentrated under vacuum. The residue was purified by flash chromatography on silica gel eluting with dichloromethane/ethyl acetate (3/1) to afford tert-butyl (3S)-4-[7-[3-[bis[(4-methoxyphenyl)methyl]amino]-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazine-1-carboxylate (0.8 g, 0.86 mmol, 58% yield) as a yellow solid. LC-MS: (ESI, m/z): 923.5 [M+H]$^+$.

Step 9: 3-[6-ethyl-2-[[(2S,4R)-4-fluoro-1-methyl-pyrrolidin-2-yl]methoxy]-4-[(2S)-2-methylpiperazin-1-yl]-5,6,7,8-tetrahydroquinazolin-7-yl]-2-fluoro-5-methyl-4-(trifluoromethyl)aniline

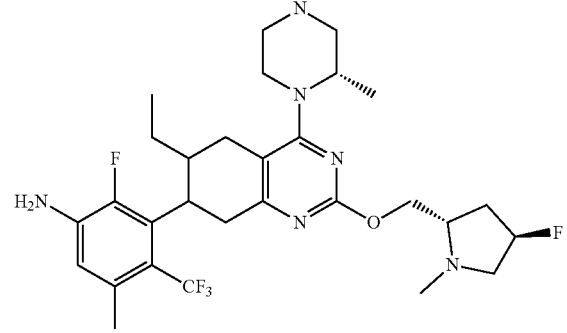

A solution of tert-butyl (3S)-4-[7-[3-[bis[(4-methoxyphenyl)methyl]amino]-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazine-1-carboxylate (0.8 g, 0.87 mmol) in trifluoroacetic acid (1.9 g, 17.33 mmol) was stirred at 50° C. for 2 hours. The resulting solution was concentrated under vacuum. The residue was purified by flash chromatography on silica gel eluting with Acetonitrile/water (1:1) to afford 3-[6-ethyl-2-[[(2S,4R)-4-fluoro-1-methyl-pyrrolidin-2-yl]methoxy]-4-[(2S)-2-methylpiperazin-1-yl]-5,6,7,8-tetrahydroquinazolin-7-yl]-2-fluoro-5-methyl-4-(trifluoromethyl)aniline (0.3 g, 0.51 mmol, 59.4% yield) as a yellow solid. LC-MS: (ESI, m/z): 583.3 [M+H]$^+$ Step 10: 1-[(3S)-4-[(6R,7R)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one (Example 37a) and 1-[(3S)-4-[(6S,7S)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one (Example 37b)

A solution of 3-[6-ethyl-2-[[(2S,4R)-4-fluoro-1-methyl-pyrrolidin-2-yl]methoxy]-4-[(2S)-2-methylpiperazin-1-yl]-5,6,7,8-tetrahydroquinazolin-7-yl]-2-fluoro-5-methyl-4-(trifluoromethyl)aniline (0.3 g, 0.48 mmol), acrylic acid (0.03 g, 0.48 mmol) and N,N-diisopropylethylamine (0.19 g, 1.44 mmol) in dichloromethane (2.8 mL) was stirred at −78° C. for 5 minutes. Then HATU (182.7 mg, 0.48 mmol) was added and stirred at 25° C. for 10 minutes. After completion, the solvent was diluted with dichloromethane and washed with brine. Then the organic layer was dried over anhydrous sodium sulfate and concentrated under vacuum. The residue was purified by flash chromatography on silica gel eluting with dichloromethane/methanol (10/1) to afford 110 mg crude product. The product was further purified by Chiral-Prep-HPLC with following condition (Column: CHIRAL-PAK Cellulose-SB4.6*100 mm 3 um; Mobile Phase Hex (0.1% DEA):IPA=70:30; Flow rate: 1 m/min; RT1:3.785; RT2:5.481) to afford the title compounds. The stereo chemistry of title compounds was arbitrarily assigned.

37a

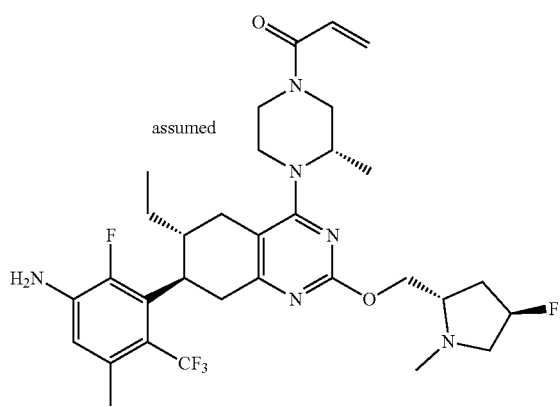

Example 37a: 1-[(3S)-4-[(6R,7R)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one (31.6 mg, 0.049 mmol, 10.3% yield, white solid). $^1$H NMR (300 MHz, DMSO-d$_6$, ppm) δ 6.92-6.75 (m, 1H), 6.58 (d, J=9.0 Hz, 1H), 6.1-6.12 (m, 1H), 5.78-5.70 (m, 3H), 5.17 (d, J=56.2 Hz, 1H), 4.41-3.82 (m, 6H), 3.50-3.36 (m, 2H), 3.20-3.04 (m, 3H), 2.91-2.82 (m, 3H), 2.64-2.57 (m, 1H), 2.41-2.23 (m, 8H), 2.17-1.77 (m, 3H), 1.29-1.18 (m, 4H), 1.07-0.94 (m, 1H), 0.87-0.82 (m, 3H). LC-MS: (ESI, m/z): 637.3 [M+H]$^+$. Chiral HPLC: Column: CHIRAL ART Cellulose-SB, 4.6*100 mm, 3.0 um; detected at 254 nm; Hex (0.1% DEA):IPA=70:30; Flow rate: 1 mL/min; Retention time: 3.785 min; (faster peak).

37b

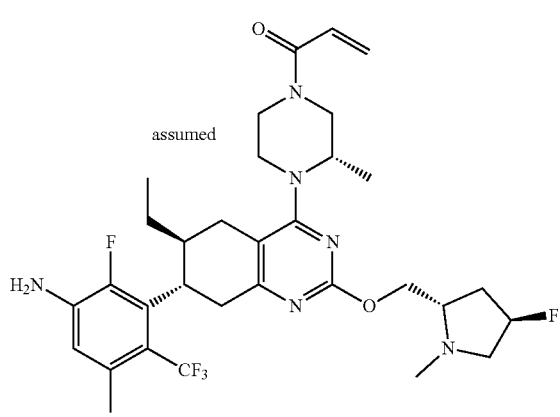

Example 37b: 1-[(3S)-4-[(6S,7S)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one (31.3 mg, 0.049 mmol, 10.2% yield, white solid). $^1$H NMR (300 MHz, DMSO-d$_6$, ppm) δ 6.87-6.75 (m, 1H), 6.59 (d, J=9.0 Hz, 1H), 6.19-6.14 (m, 1H), 5.79-5.71 (m, 3H), 5.26-5.08 (m, 1H), 4.28-4.12 (m, 4H), 4.08-3.82 (m, 1H), 3.49-3.37 (m, 2H), 3.27-3.08 (m, 2H), 2.97-2.84 (m, 3H), 2.73-2.64 (m, 1H), 2.47 (s, 1H), 2.36 (s, 4H), 2.32-2.27 (m, 4H), 2.17-1.75 (m, 4H), 1.29-1.13 (m, 1H), 1.05-0.95 (m, 4H), 0.84-0.82 (m, 3H). LC-MS: (ESI, m/z): 637.3 [M+H]$^+$. Chiral HPLC: Column: CHIRAL ART Cellulose-SB, 4.6*100 mm, 3.0 um; detected at 254 nm; Hex (0.1% DEA):IPA=70:30; Flow rate: 1 mL/min; Retention time: 5.481 min; (slower peak).

Examples 38a, 38b, 38c, and 38d 2-((S)-4-(((6R,7R)-7-(3-amino-2-fluoro-5-methyl-6-
(trifluoromethyl)phenyl)-2-(((2S,4R)-4-fluoro-1-
methylpyrrolidin-2-yl)methoxy)-6-methyl-5,6,7,8-
tetrahydroquinazolin-4-yl)-1-(2-fluoroacryloyl)
piperazin-2-yl)acetonitrile (Example 38b); and

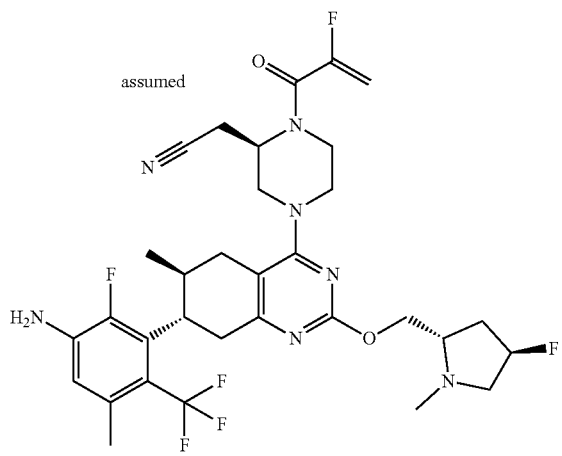

Example 38a

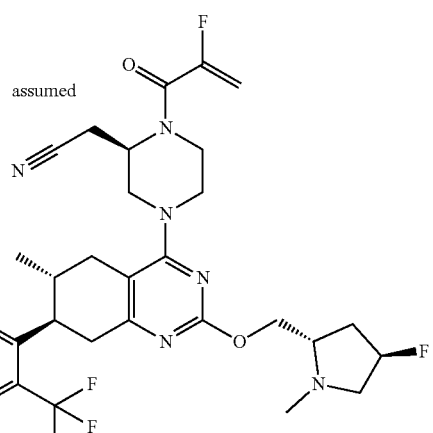

Example 38c 2-((R)-4-(((6S,7S)-7-(3-amino-2-fluoro-5-methyl-6-
(trifluoromethyl)phenyl)-2-(((2S,4R)-4-fluoro-1-
methylpyrrolidin-2-yl)methoxy)-6-methyl-5,6,7,8-
tetrahydroquinazolin-4-yl)-1-(2-fluoroacryloyl)
piperazin-2-yl)acetonitrile (Example 38a); and 2-((R)-4-(((6R,7R)-7-(3-amino-2-fluoro-5-methyl-6-
(trifluoromethyl)phenyl)-2-(((2S,4R)-4-fluoro-1-
methylpyrrolidin-2-yl)methoxy)-6-methyl-5,6,7,8-
tetrahydroquinazolin-4-yl)-1-(2-fluoroacryloyl)
piperazin-2-yl)acetonitrile (Example 38c); and

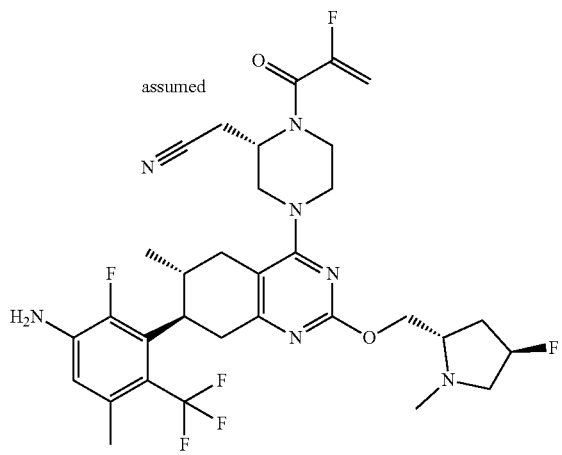

Example 38b

Example 38d 2-((S)-4-((6S,7S)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile (Example 38d)
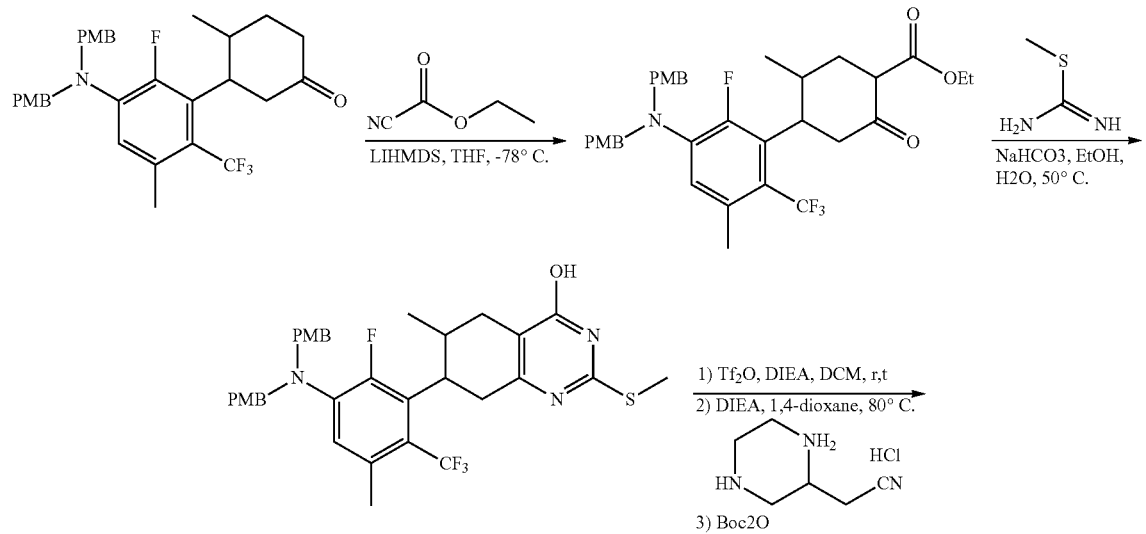
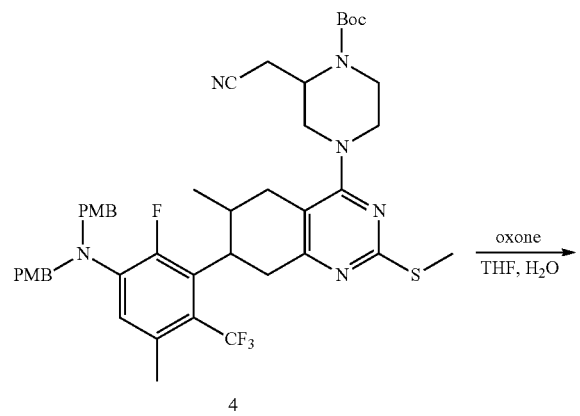
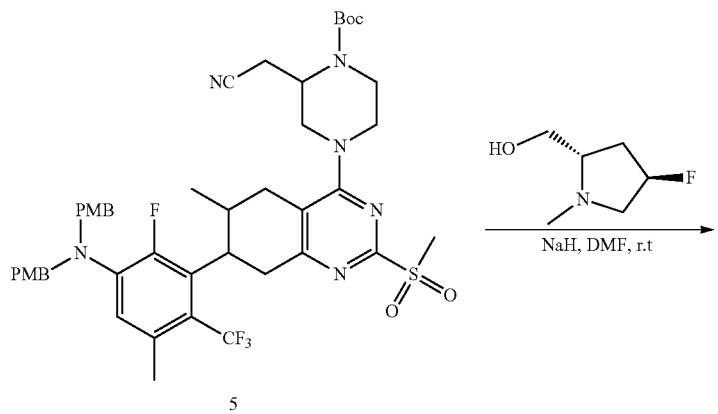

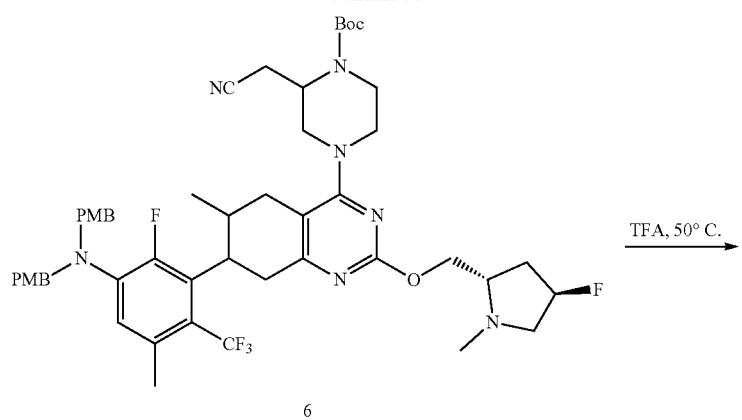
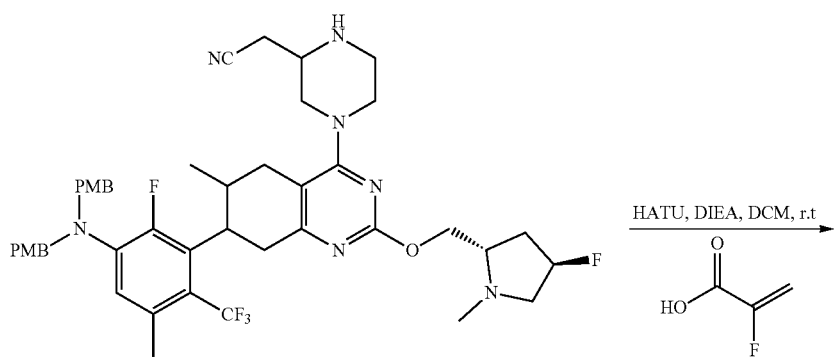
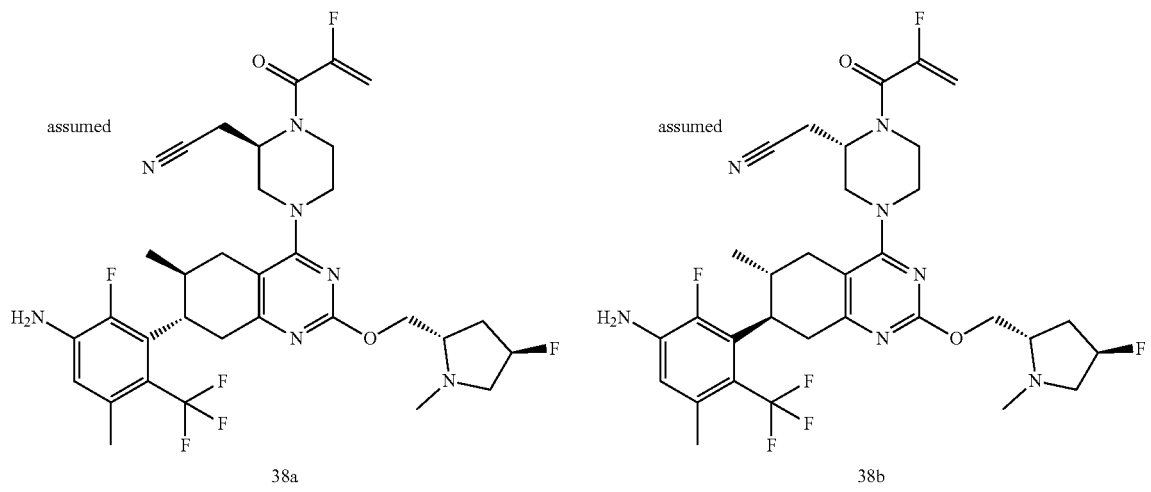 [SMILES: C=C(F)C(=O)N1CCN(c2nc(OC[C@@H]3C[C@@H](F)CN3C)nc3c2C[C@@H](C)[C@H](c2c(F)c(N)cc(C)c2C(F)(F)F)C3)C[C@H]1CC#N ; C=C(F)C(=O)N1CCN(c2nc(OC[C@@H]3C[C@@H](F)CN3C)nc3c2C[C@H](C)[C@@H](c2c(F)c(N)cc(C)c2C(F)(F)F)C3)C[C@@H]1CC#N]

577 578

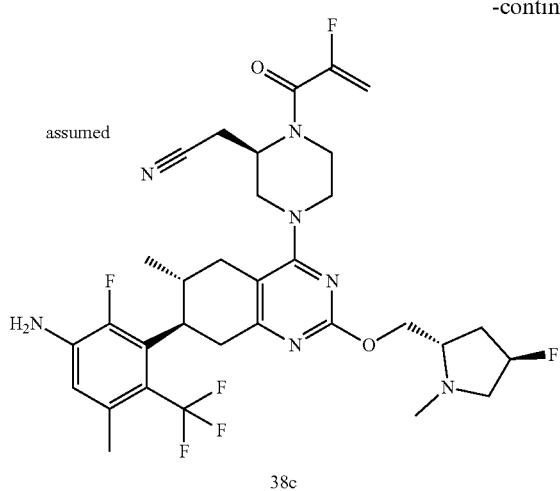

38c

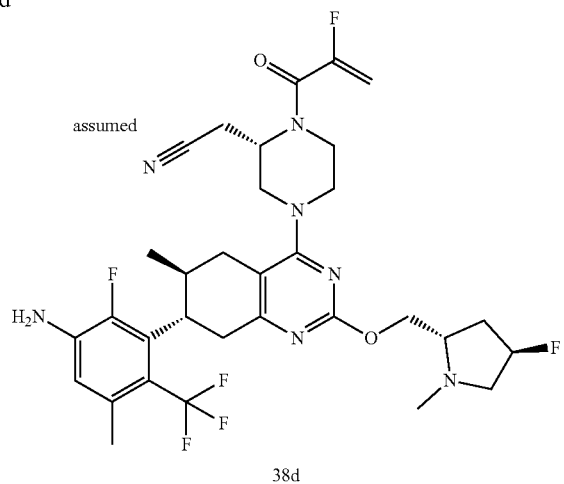

38d

Step 1: ethyl 4-[3-[bis[(4-methoxyphenyl)methyl]amino]-2-fluoro-5-methyl-6-(trifluoromethyl)phenyl]-5-methyl-2-oxo-cyclohexanecarboxylate Step 2: 7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-ol

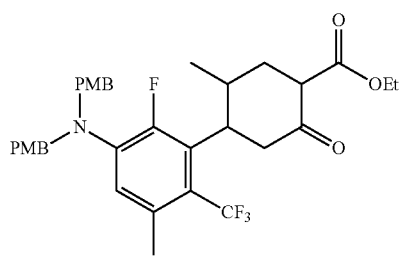

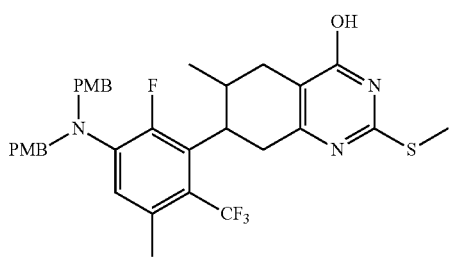

Under nitrogen, a solution of 3-[3-[bis[(4-methoxyphenyl)methyl]amino]-2-fluoro-5-methyl-6-(trifluoromethyl)phenyl]-4-methyl-cyclohexanone (10.0 g, 18.4 mmol) in tetrahydrofuran (100 mL) was stirred at −78° C. for 3 minutes. Lithium bis(trimethylsilyl)amide (1.0 M in THF) (33 mL, 33 mmol) was added dropwised and stirred at −78° C. for 10 minutes. Then ethyl cyanoformate (4.1 g, 42.3 mmol) was added and stirred at −78° C. for 20 minutes. After completion, the reaction was quenched with water, extracted with Ethyl acetate, dried over anhydrous sodium sulfate and concentrated under vacuum to afford crude product. The crude product was used for next step directly without purification. LC-MS: (ESI, m/z): 616.3 [M+H]+.

A solution of ethyl 4-[3-[bis[(4-methoxyphenyl)methyl]amino]-2-fluoro-5-methyl-6-(trifluoromethyl)phenyl]-5-methyl-2-oxo-cyclohexanecarboxylate (20.0 g, 32.4 mmol), 2-methyl-2-thiopseudourea sulfate (90.3 g, 324.8 mmol) and sodium bicarbonate (54.5 g, 649.7 mmol) in ethanol (200 mL) and water (40 mL) was stirred at 50° C. for 4 hours. After completion, the resulting solution was concentrated under vacuum. The residue was dissolved with dichloromethane and washed with brine. The organic layer was dried over anhydrous sodium sulfate and concentrated under vacuum. The residue was purified by flash chromatography on silica gel eluting with dichloromethane/ethyl acetate (4/1) to afford 7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-ol (7 g, 10.9 mmol, 33.6% yield) as a yellow solid. LC-MS: (ESI, m/z): 642.2 [M+H]+.

Step 3: tert-butyl 4-[7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-yl]-2-(cyanomethyl)piperazine-1-carboxylate

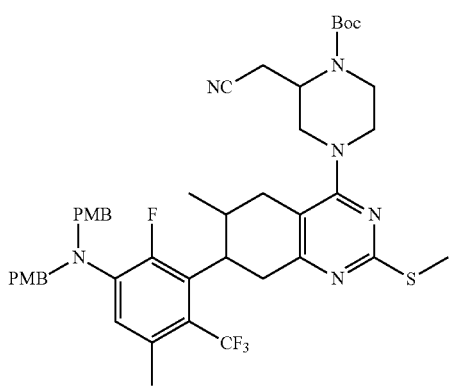

A solution of 7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-ol (7.2 g, 11.2 mmol), trifluoromethanesulfonic anhydride (5.7 g, 20.2 mmol) and N,N-diisopropylethylamine (8.6 g, 67.3 mmol) in dichloromethane (72 mL) was stirred at 25° C. for 1 hour. After completion, the reaction was concentrated under reduced pressure. Then the residue, N,N-diisopropylethylamine (8.6 g, 67.3 mmol) and 2-piperazin-2-2-piperazin-2-ylacetonitrile (2.8 g, 22.44 mmol) in 1,4-dioxane (72 mL) was stirred at 80° C. for 2 hours. Then di-tert-butyldicarbonate (12.2 g, 56.1 mmol) was added and stirred at 25° C. for 1 hour. After completion, the resulting solution was concentrated under vacuum. The residue was purified by flash chromatography on silica gel eluting with petroleum ether/ethyl acetate (10/1) to afford tert-butyl 4-[7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-yl]-2-(cyanomethyl)piperazine-1-carboxylate (8 g, 9.4 mmol, 84% yield) as a white solid. LC-MS: (ESI, m/z): 849.4 [M+H]$^+$.

Step 4: tert-butyl 4-[7-[3-[bis[(4-methoxyphenyl)methyl]amino]-2-fluoro-5-methyl-6-(trifluoromethyl)phenyl]-6-methyl-2-methylsulfonyl-5,6,7,8-tetrahydroquinazolin-4-yl]-2-(cyanomethyl)piperazine-1-carboxylate

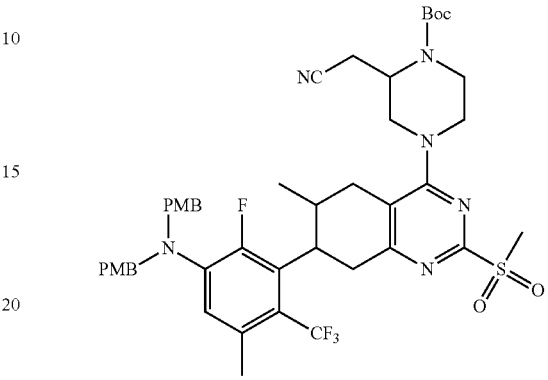

A solution of tert-butyl 4-[7-[3-[bis[(4-methoxyphenyl)methyl]amino]-2-fluoro-5-methyl-6-(trifluoromethyl)phenyl]-6-methyl-2-methylsulfanyl-5,6,7,8-tetrahydroquinazolin-4-yl]-2-(cyanomethyl)piperazine-1-carboxylate (8.0 g, 9.42 mmol) and potassium peroxymonosulfate (17.3 g, 28.2 mmol) in tetrahydrofuran (80 mL) and water (40 mL) was stirred at room temperature for 3 hours. After completion, the solvent was concentrated under vacuum, the reaction was quenched by sodium sulfite, extracted with ethyl acetate, dried over anhydrous sodium sulfate and concentrated under vacuum to afford white crude product. The crude product was used for next step directly without purification. LC-MS: (ESI, m/z): 881.4 [M+H]$^+$.

Step 5: tert-butyl 4-[7-[3-[bis[(4-methoxyphenyl)methyl]amino]-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-2-(cyanomethyl)piperazine-1-carboxylate

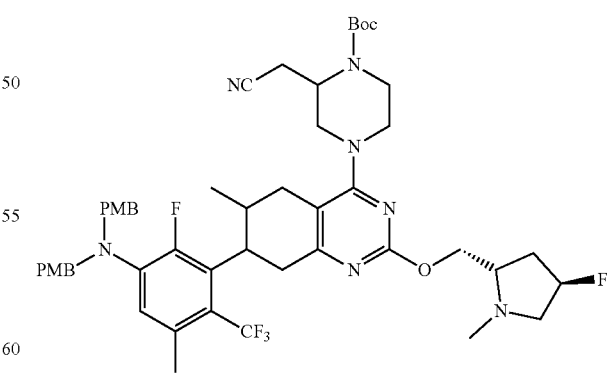

A solution of sodium hydride (1.1 g, 28.38 mmol, 60% dispersion in mineral oil) and [(2S,4R)-4-fluoro-1-methyl-pyrrolidin-2-yl]methanol (1.5 g, 11.35 mmol) in DMF (50 mL) was stirred at 0° C. for 10 minutes. Then tert-butyl 4-[7-[3-[bis[(4-methoxyphenyl)methyl]amino]-2-fluoro-5- methyl-6-(trifluoromethyl)phenyl]-6-methyl-2-methylsulfonyl-5,6,7,8-tetrahydroquinazolin-4-yl]-2-(cyanomethyl)piperazine-1-carboxylate (5.0 g, 5.68 mmol) was added and stirred at room temperature for 30 minutes. After completion, the reaction was quenched with saturated ammonium chloride solution. The resulting solution was extracted with ethyl acetate, dried over anhydrous sodium sulfate and concentrated under vacuum. The residue was purified by flash chromatography on silica gel eluting with dichloromethane/methanol (7/1) to afford tert-butyl 4-[7-[3-[bis[(4-methoxyphenyl)methyl]amino]-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-2-(cyanomethyl)piperazine-1-carboxylate (2.8 g, 2.99 mmol, 52.8% yield) as a yellow solid. LC-MS: (ESI, m/z): 934.5 [M+H]$^+$.

Step 6: 2-(4-(7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)piperazin-2-yl)acetonitrile

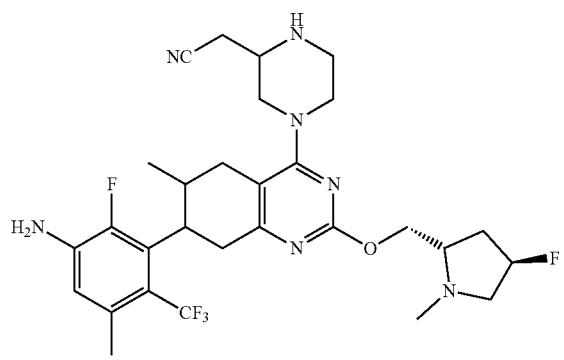

A solution of tert-butyl 4-[7-[3-[bis[(4-methoxyphenyl)methyl]amino]-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-2-(cyanomethyl)piperazine-1-carboxylate (2.8 g, 3 mmol) in trifluoroacetic acid (34.17 g, 299.77 mmol) was stirred at 50° C. for 7 minutes. the resulting solution was concentrated under vacuum. The residue was purified by flash chromatography on silica gel eluting with Acetonitrile/water (2:3) to afford 2-[4-[7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]piperazin-2-yl]acetonitrile (1.2 g, 2.0 mmol, 67.4% yield) as a yellow solid. LC-MS: (ESI, m/z): 594.3 [M+H]$^+$.

Step 7: 2-((R)-4-((6S,7S)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile (Example 38a); and 2-((S)-4-((6R,7R)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile (Example 38b); and 2-((R)-4-((6R,7R)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile (Example 38c); and 2-((S)-4-((6S,7S)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile (Example 38d)

38a

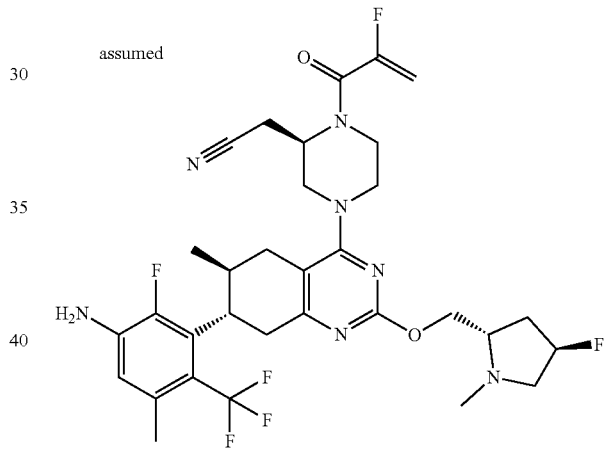

38b

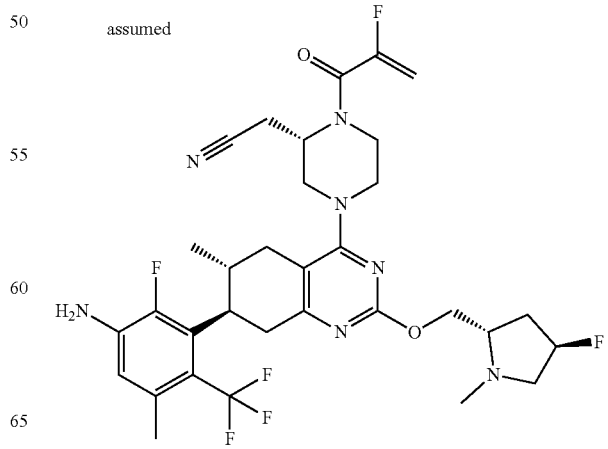

-continued

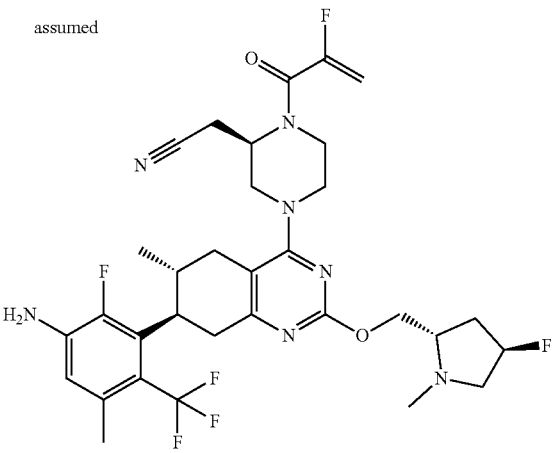

38c

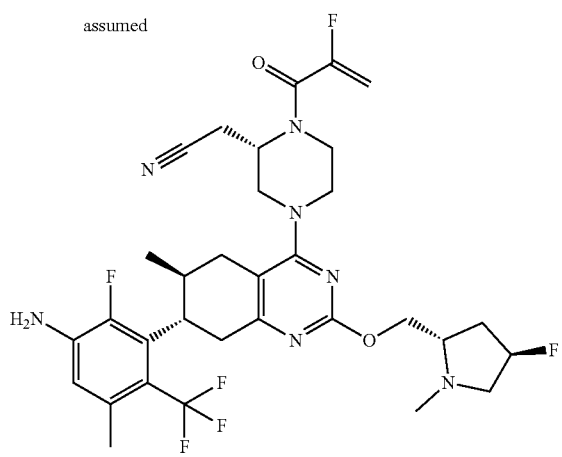

38d

A solution of 2-[4-[7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]piperazin-2-yl]acetonitrile (1.2 g, 2.02 mmol), 2-fluoroacrylic acid (182.0 mg, 2.02 mmol) and N,N-diisopropylethylamine (0.7 g, 6.06 mmol) in dichloromethane (12 mL) was stirred at 25° C. Then HATU (0.8 g, 2.22 mmol) was added and stirred at 25° C. for 1 hour. After completion, the solvent was diluted with dichloromethane and washed with brine. Then the organic layer was dried over anhydrous sodium sulfate and concentrated under vacuum. The residue was purified by flash chromatography on silica gel eluting with dichloromethane/methanol (10/1) to afford 500 mg solid. The product was further purified by Chiral-Prep-HPLC to afford the title compounds. The absolute configuration of the title compounds was inferred from potency data and a protein X-ray structure of compound 21b.

Example 38a: 2-((R)-4-((6S,7S)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile (49.6 mg, 0.074 mmol, 3.7% yield, white solid). $^1$H NMR (300 MHz, DMSO-$d_6$, ppm) δ 6.57 (d, J=8.8 Hz, 1H), 5.77 (s, 2H), 5.40-5.35 (m, 3H), 4.84 (brs, 1H), 4.33-4.10 (m, 2H), 3.94-3.82 (m, 3H), 3.49-3.41 (m, 3H), 3.25-3.05 (m, 3H), 3.01-2.66 (m, 6H), 2.44-2.17 (m, 8H), 2.15-2.00 (m, 1H), 1.95-1.73 (m, 1H), 0.84 (d, J=6.0 Hz, 3H). LC-MS: (ESI, m/z): 666.3 [M+H]$^+$. Chiral HPLC: Column: CHIRALPAK IE-3, 4.6*50 mm, 3 um; detected at 254 nm; (Hex:DCM=3:1)(0.1% IPAmine): EtOH=90:10 Flow rate: 1 mL/min; Retention time: 3.658 min; (Faster peak).

Example 38b: 2-((S)-4-((6R,7R)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile (43.4 mg, 0.065 mmol, 3.2% yield, white solid). $^1$H NMR (300 MHz, DMSO-$d_6$, ppm) δ 6.57 (d, J=8.8 Hz, 1H), 5.78 (s, 2H), 5.46-5.06 (m, 3H), 4.79 (brs, 1H), 4.27-4.26 (m, 1H), 4.13 (dd, J=11.0, 5.4 Hz, 1H), 3.98-3.75 (m, 3H), 3.61-3.36 (m, 3H), 3.30-3.23 (m, 1H), 3.22-3.15 (m, 1H), 3.14-2.90 (m, 4H), 2.89-2.77 (m, 2H), 2.68-2.57 (m, 1H), 2.46-2.19 (m, 8H), 2.17-2.00 (m, 1H), 1.97-1.73 (m, 1H), 0.82 (d, J=6.2 Hz, 3H). LC-MS: (ESI, m/z): 666.3 [M+H]$^+$. Chiral HPLC: Column: CHIRALPAK IE-3, 4.6*50 mm, 3 um; detected at 254 nm; (Hex:DCM=3:1)(0.1% IPAmine): EtOH=90:10 Flow rate: 1 mL/min; Retention time: 3.185 min; (slower peak).

Example 38c: 2-((R)-4-((6R,7R)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile (39.2 mg, 0.058 mmol, 2.9% yield, white solid). $^1$H NMR (300 MHz, DMSO-$d_6$, ppm) δ 6.58 (d, J=8.8 Hz, 1H), 5.78 (s, 2H), 5.47-5.06 (m, 3H), 4.72 (brs, 1H), 4.30 (dd, J=11.1, 4.7 Hz, 1H), 4.13 (dd, J=10.9, 5.4 Hz, 1H), 3.89 (dd, J=22.7, 13.3 Hz, 3H), 3.59-3.40 (m, 3H), 3.29-3.04 (m, 3H), 2.98-2.72 (m, 6H), 2.46-2.27 (m, 8H), 2.24-2.05 (m, 1H), 1.98-1.76 (m, 1H), 0.84 (d, J=6.1 Hz, 3H). LC-MS: (ESI, m/z): 666.3 [M+H]$^+$. Chiral HPLC: Column: CHIRALPAK IE-3, 4.6*50 mm 3 um; detected at 254 nm; (Hex:DCM=3:1)(0.1% DEA): EtOH=90:10, Flow rate: 1 mL/min; Retention time: 3.421 min; (Faster peak).

Example 38d: 2-((S)-4-((6S,7S)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile (49.2 mg, 0.073 mmol, 3.7% yield, white solid). $^1$H NMR (300 MHz, DMSO-$d_6$, ppm) δ 6.58 (d, J=8.8 Hz, 1H), 5.79 (s, 2H), 5.48-5.03 (m, 3H), 4.78 (brs, 1H), 4.26 (dd, J=11.0, 4.8 Hz, 1H), 4.16 (dd, J=11.0, 5.4 Hz, 1H), 4.01 (d, J=13.5 Hz, 1H), 3.82 (d, J=12.7 Hz, 1H), 3.52-3.25 (m, 5H), 3.22-2.79 (m, 7H), 2.69-2.57 (m, 1H), 2.44-2.25 (m, 8H), 2.20-1.99 (m, 1H), 1.97-1.72 (m, 1H), 0.83 (d, J=6.2 Hz, 3H). LC-MS: (ESI, m/z): 666.3 [M+H]$^+$. Chiral HPLC: Column: CHIRALPAK IE-3, 4.6*50 mm, 3 um; detected at 254 nm; (Hex:DCM=3:1)(0.1% IPAmine): EtOH=90:10 Flow rate: 1 mL/min; Retention time: 4.292; (slower peak).

585
Example 39
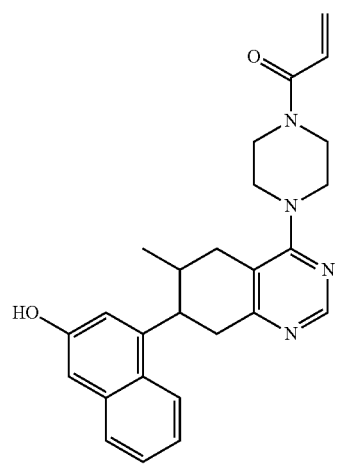 [SMILES: C=CC(=O)N1CCN(c2ncnc3c2CC(C)C(c2cc(O)cc4ccccc24)C3)CC1]
1-(4-(7-(3-hydroxynaphthalen-1-yl)-6-methyl-5,6,7,8-tetrahydroquinazolin-4-yl)piperazin-1-yl)prop-2-en-1-one
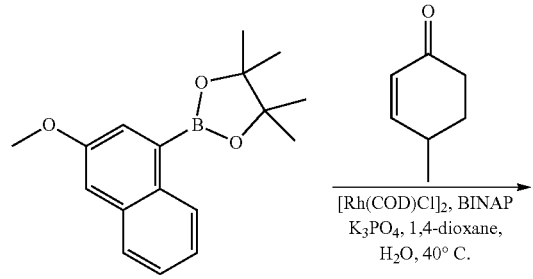
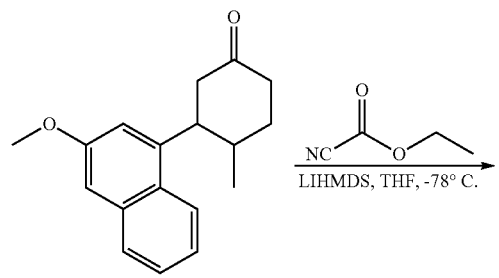
586
-continued
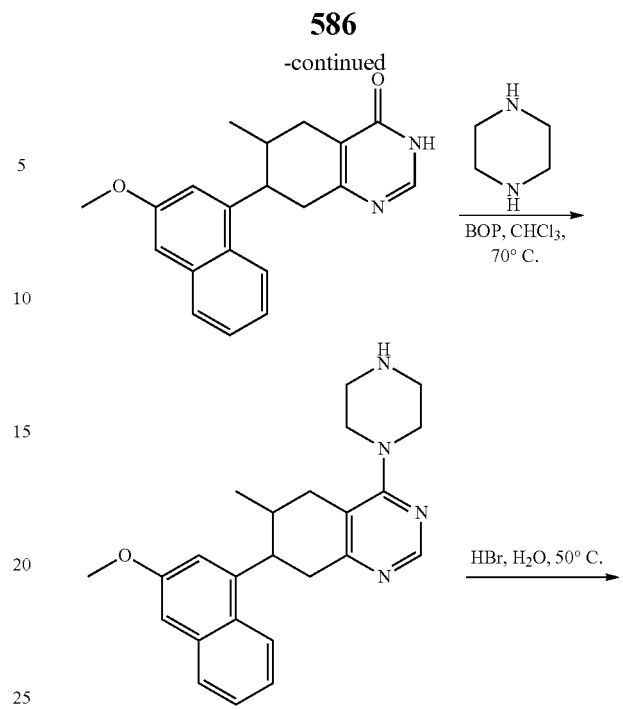
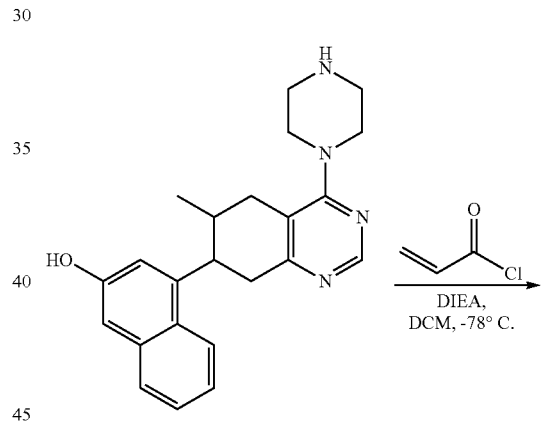
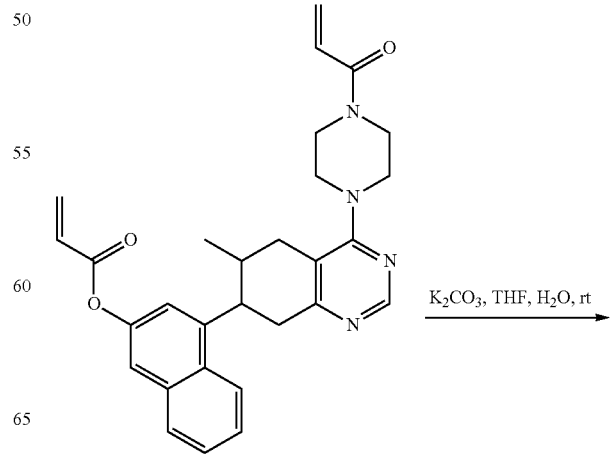
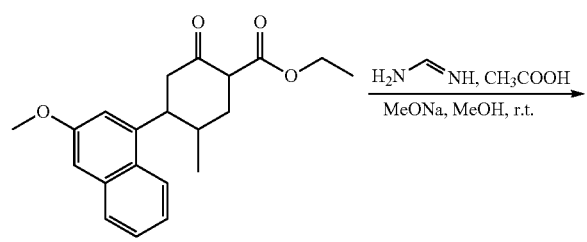

-continued

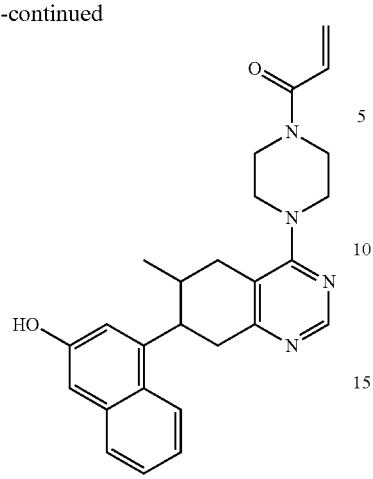

Step 1:
3-(3-methoxy-1-naphthyl)-4-methyl-cyclohexanone

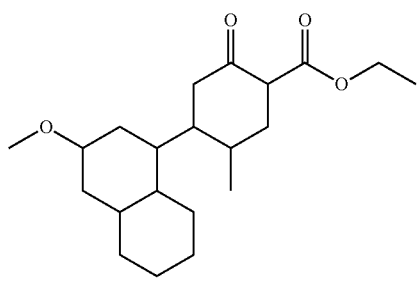 [SMILES: CCOC(=O)C1CC(C)C(C2CC(OC)CC3CCCCC32)CC1=O]

Under nitrogen, a solution of 2-(3-methoxy-1-naphthyl)-4,4,5,5-tetramethyl-1,3,2-dioxaborolane (1.0 g, 3.52 mmol) and 1,1'-binaphthyl-2,2'-diphemyl phosphine (0.44 g, 0.70 mmol) in 1,4-dioxane (10 mL), water (10 mL) was added 4-methylcyclohex-2-en-1-one (0.78 g, 7.04 mmol). Then [Rh(COD)Cl]₂ (0.17 g, 0.35 mmol), potassium phosphate (1.49 g, 7.04 mmol) was added and stirred at 40° C. for 0.5 hours. After completion, the solution was diluted with water and extracted with ethyl acetate. Then the organic layers were combined, dried over anhydrous sodium sulfate and concentrated under vacuum. The residue was purified by flash chromatography on silica gel eluting with ethyl acetate/petroleum ether (1/6) to afford 3-(3-methoxy-1-naphthyl)-4-methyl-cyclohexanone (500 mg, 1.86 mmol, 52.9% yield) as a yellow oil. LCMS (ESI, m/z): 269.4 [M+H]⁺.

Step 2: ethyl 4-(3-methoxy-1-naphthyl)-5-methyl-2-oxo-cyclohexanecarboxylate

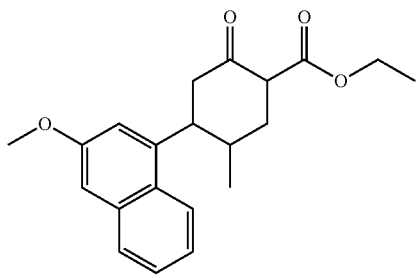 [SMILES: CCOC(=O)C1CC(C)C(c2cc(OC)cc3ccccc23)CC1=O]

Under nitrogen, a solution of 3-(3-methoxy-1-naphthyl)-4-methyl-cyclohexanone (0.6 g, 2.24 mmol) in tetrahydrofuran (15 mL) was added LiHMDS (1.3 mL, 2M in THF) at −78° C. The resulting solution was stirred for 0.5 h at −78° C. Then ethyl cyanoformate (0.33 g, 3.35 mmol) was added and stirred at −78° C. for 3 hours. After completion, the solution was diluted with water and extracted with ethyl acetate. Then the organic layers were combined, dried over anhydrous sodium sulfate and concentrated under vacuum. The residue was purified by flash chromatography on silica gel eluting with ethyl acetate/petroleum ether (1/8) to afford ethyl 4-(3-methoxy-1-naphthyl)-5-methyl-2-oxo-cyclohexanecarboxylate (200 mg, 0.58 mmol, 26.3% yield) as a yellow oil. LCMS (ESI, m/z): 341.2 [M+H]⁺.

Step 3: 7-(3-methoxy-1-naphthyl)-6-methyl-5,6,7,8-tetrahydro-3H-quinazolin-4-one

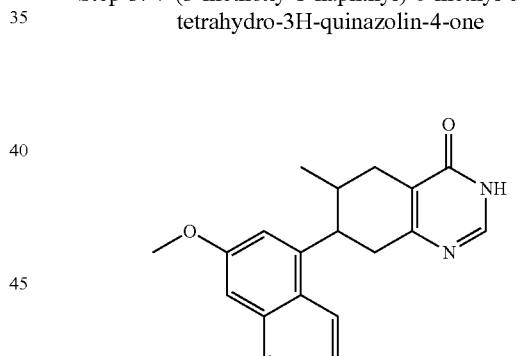

A solution of ethyl 4-(3-methoxy-1-naphthyl)-5-methyl-2-oxo-cyclohexanecarboxylate (200.0 mg, 0.59 mmol) and formamidine acetate (367.0 mg, 3.53 mmol) in methanol (6 mL) was stirred at 25° C. for 0.5 h. Then sodium methanolate (317.26 mg, 5.88 mmol) was added and stirred at 25° C. for 9 hours. After completion, the solution was diluted with water and extracted with ethyl acetate. Then the organic layers were combined, dried over anhydrous sodium sulfate and concentrated under vacuum. The residue was purified by flash chromatography on silica gel eluting with methanol/dichloromethane (1/10) to afford 7-(3-methoxy-1-naphthyl)-6-methyl-5,6,7,8-tetrahydro-3H-quinazolin-4-one (110 mg, 0.34 mmol, 58.4% yield) as a yellow oil. LCMS (ESI, m/z): 321.2 [M+H]⁺.

Step 4: 7-(3-methoxy-1-naphthyl)-6-methyl-4-piperazin-1-yl-5,6,7,8-tetrahydroquinazoline

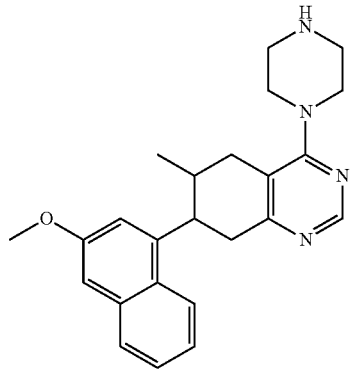 [SMILES: COc1cc(C2Cc3ncnc(N4CCNCC4)c3CC2C)c2ccccc2c1]

A solution of 7-(3-methoxy-1-naphthyl)-6-methyl-5,6,7,8-tetrahydro-3H-quinazolin-4-one (2.00 g, 6.2 mmol) and benzotriazol-1-yloxytris(dimethylamino)-phosphonium hexafluorophosphate (5.5 g, 12.5 mmol) was dissolved in DCM (20 mL). Then piperazine (17.5 g, 124.8 mmol) was added and stirred at 70° C. for 10 hours. After completion, the solution was diluted with water and extracted with ethyl acetate. Then the organic layers were combined, dried over anhydrous sodium sulfate and concentrated under vacuum. The residue was purified by flash chromatography on silica gel eluting with methanol/dichloromethane (1/10) to afford 7-(3-methoxy-1-naphthyl)-6-methyl-4-piperazin-1-yl-5,6,7,8-tetrahydroquinazoline (1.5 g, 0.38 mmol, 62.5% yield) as a yellow oil. LCMS (ESI, m/z): 389.2 [M+H]$^+$.

Step 5: 4-(6-methyl-4-piperazin-1-yl-5,6,7,8-tetrahydroquinazolin-7-yl)naphthalen-2-ol

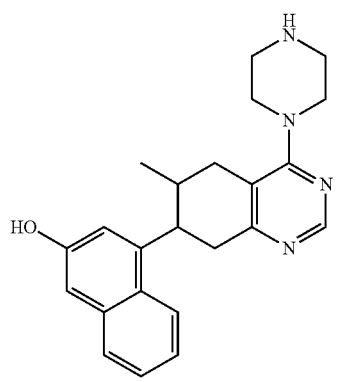 [SMILES: CC1Cc2c(ncnc2N2CCNCC2)CC1c1cc(O)cc2ccccc12]

A solution of 7-(3-methoxy-1-naphthyl)-6-methyl-4-piperazin-1-yl-5,6,7,8-tetrahydroquinazoline (180.0 mg, 0.46 mmol) in HBr (1 mL) (40% in H$_2$O) was stirred at 50° C. for 4 hours. After completion, the resulting solution was concentrated under vacuum. The residue was purified by flash chromatography on silica gel eluting with dichloromethane/methanol (1/10) to afford 4-(6-methyl-4-piperazin-1-yl-5,6,7,8-tetrahydroquinazolin-7-yl)naphthalen-2-ol (120 mg, 0.32 mmol, 69.2% yield) as a white solid. LCMS (ESI, m/z): 375.5 [M+H]$^+$.

Step 6: [4-[6-methyl-4-(4-prop-2-enoylpiperazin-1-yl)-5,6,7,8-tetrahydroquinazolin-7-yl]-2-naphthyl] prop-2-enoate

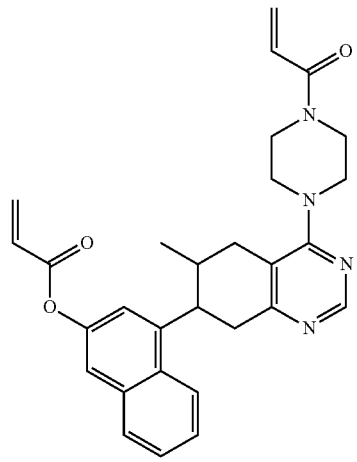 [SMILES: C=CC(=O)Oc1cc(C2Cc3ncnc(N4CCN(C(=O)C=C)CC4)c3CC2C)c2ccccc2c1]

A solution of 4-(6-methyl-4-piperazin-1-yl-5,6,7,8-tetrahydroquinazolin-7-yl)naphthalen-2-ol (100.0 mg, 0.27 mmol) and N,N-diisopropylethylamine (103.34 mg, 0.80 mmol) in dichloromethane (6 mL) was stirred at −78° C. for 0.5 hours. Then acryloyl chloride (24.17 mg, 0.27 mmol) was added and stirred at 25° C. for 0.5 hours. After completion, the solution was diluted with water and extracted with ethyl acetate. Then the organic layers were combined, dried over anhydrous sodium sulfate and concentrated under vacuum. The residue was purified by flash chromatography on silica gel eluting with methanol/dichloromethane (1/10) to afford [4-[6-methyl-4-(4-prop-2-enoylpiperazin-1-yl)-5,6,7,8-tetrahydroquinazolin-7-yl]-2-naphthyl] prop-2-enoate (90 mg, 0.18 mmol, 69.2% yield). LCMS (ESI, m/z): 483.6 [M+H]$^+$

Step 7: 1-(4-(7-(3-hydroxynaphthalen-1-yl)-6-methyl-5,6,7,8-tetrahydroquinazolin-4-yl)piperazin-1-yl)prop-2-en-1-one

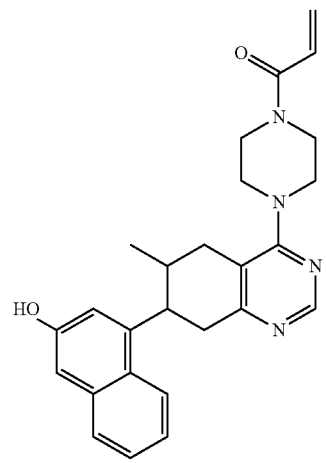 [SMILES: C=CC(=O)N1CCN(c2ncnc3c2CC(C)C(c2cc(O)cc4ccccc24)C3)CC1]

A solution of [4-[6-methyl-4-(4-prop-2-enoylpiperazin-1-yl)-5,6,7,8-tetrahydroquinazolin-7-yl]-2-naphthyl] prop-2- enoate (100.0 mg, 0.21 mmol) and $K_2CO_3$ (28.64 mg, 0.21 mmol) in tetrahydrofuran (2 mL) was stirred at 25° C. for 2 hours. After completion, the resulting solution was concentrated under vacuum. The residue was purified by Prep-HPLC with following conditions: (Column: XBridge Prep OBD C18 Column, 30×150 mm 5 um; Mobile Phase A:Water (10 mmol/L $NH_4HCO_3$), Mobile Phase B: ACN; Flow rate: 60 mL/min; Gradient: 32 B to 54 B in 7 min; 254/220 nm) to afford 1-[4-[7-(3-hydroxy-1-naphthyl)-6-methyl-5,6,7,8-tetrahydroquinazolin-4-yl]piperazin-1-yl]prop-2-en-1-one (3.3 mg, 0.0077 mmol, 3.7% yield) as a white solid. LCMS (ESI, m/z): 429.2 $[M+H]^+$.

Example 39: $^1$H NMR (400 MHz, Methanol-$d_4$, ppm) δ 8.47 (s, 1H), 8.11 (d, J=8.0 Hz, 1H), 7.68 (d, J=8.0 Hz, 1H), 7.39-7.35 (m, 1H), 7.31-7.27 (m, 1H), 7.03-7.01 (m, 2H), 6.84-6.77 (m, 1H), 6.27-6.22 (m, 1H), 5.80-5.77 (m, 1H), 3.89-3.85 (m, 2H), 3.77 (s, 3H), 3.67-3.62 (m, 2H), 3.48-3.42 (m, 2H), 3.27-3.22 (m, 1H), 2.98 (s, 1H), 2.85-2.80 (m, 1H), 2.71-2.65 (m, 1H), 2.22 (s, 1H), 0.95 (d, J=8.0 Hz, 3H).

Examples 40a, 40b, 40c, and 40d

Example 40a

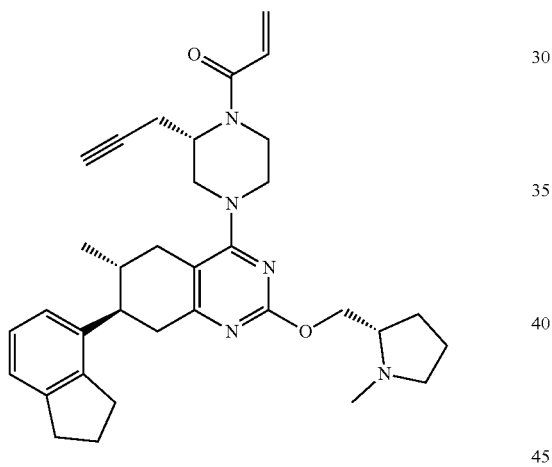

Example 40b

Example 40c

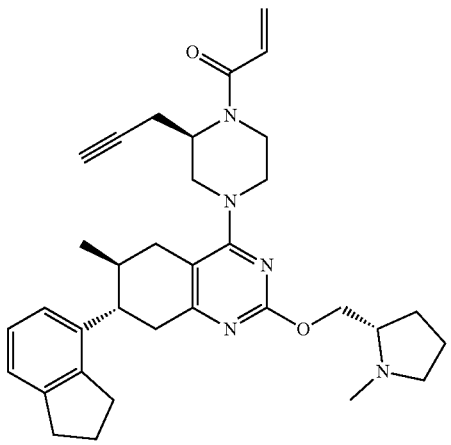

Example 40d

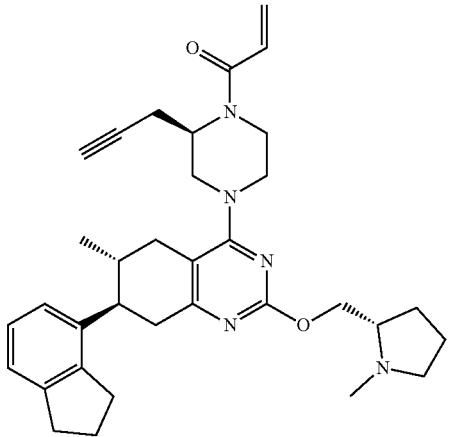

1-((S)-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (Example 40a); and 1-((S)-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (Example 40b); and 1-((R)-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (Example 40c); and 1-((R)-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (Example 40d)

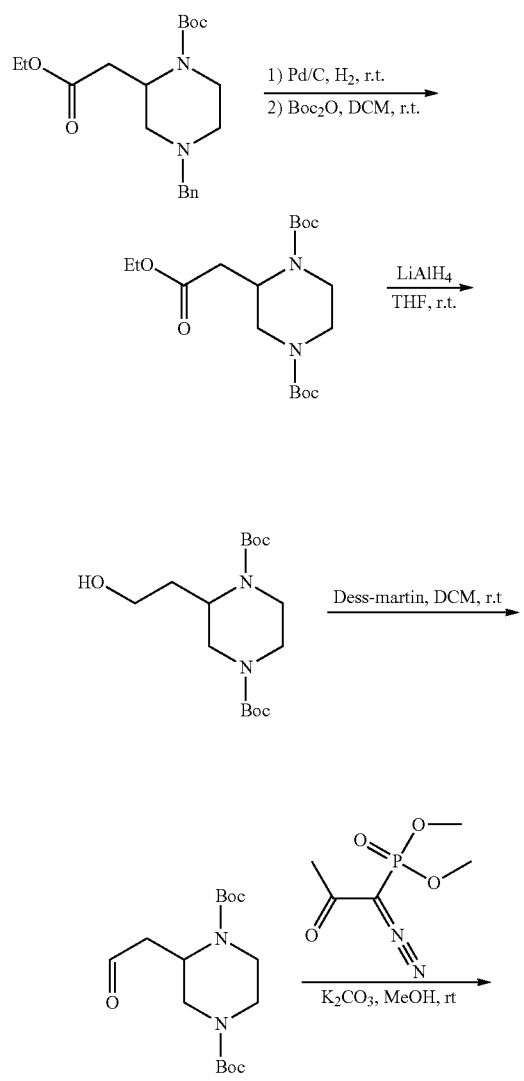

-continued

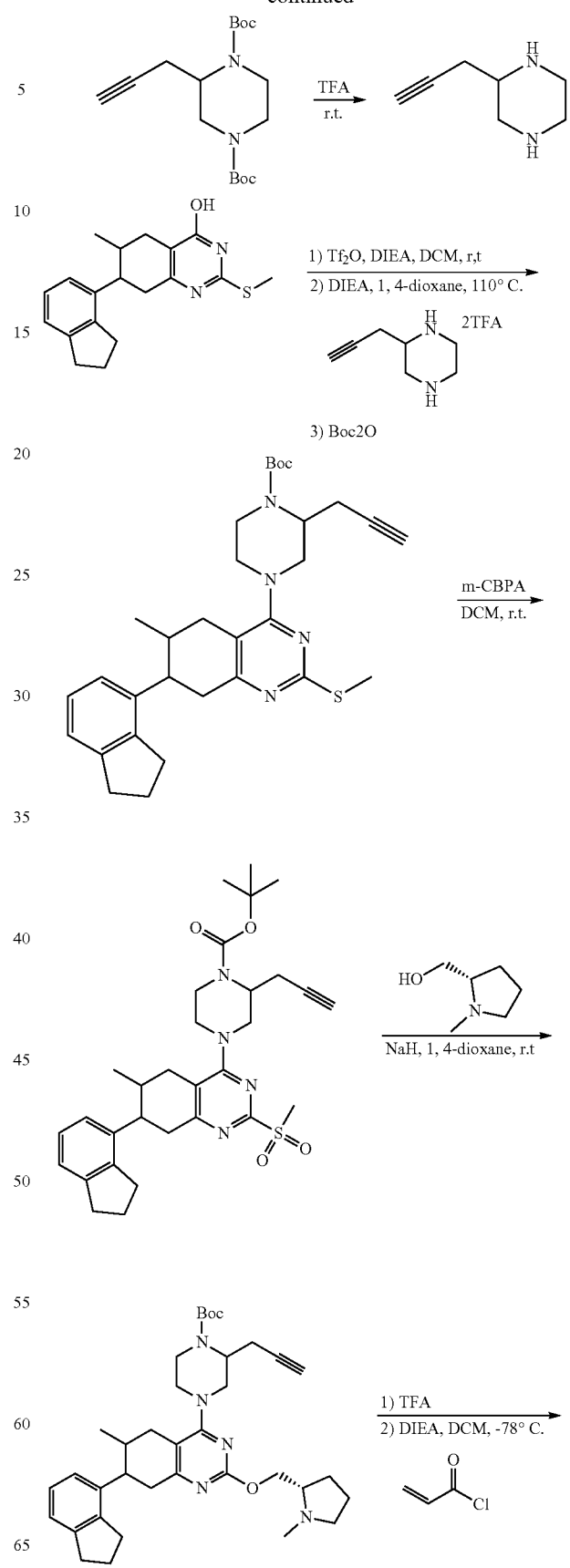

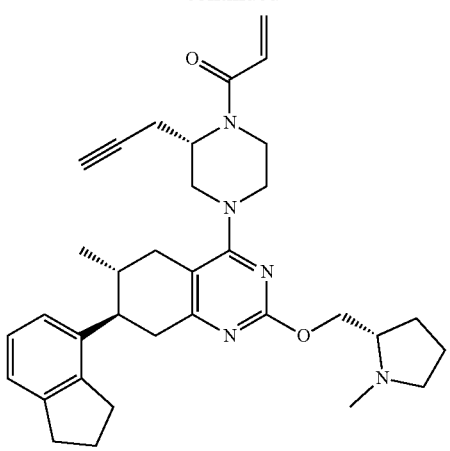

Example 40a

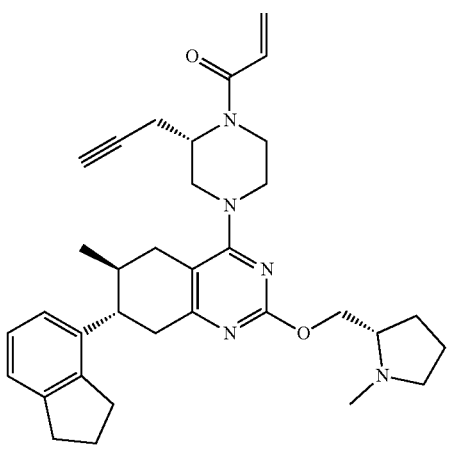

Example 40b

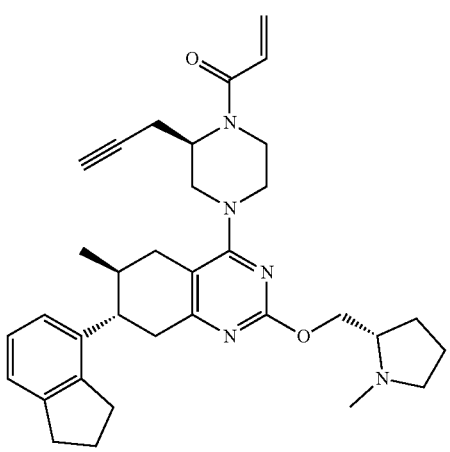

Example 40c

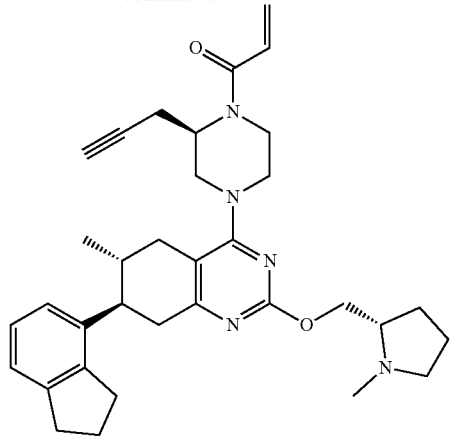

Example 40d

Step 1: di-tert-butyl 2-(2-ethoxy-2-oxo-ethyl) piperazine-1,4-dicarboxylate

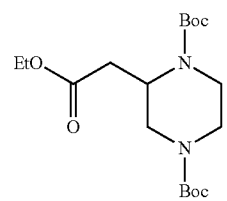 [SMILES: CCOC(=O)CC1CN(C(=O)OC(C)(C)C)CCN1C(=O)OC(C)(C)C]

Under hydrogen, a solution of tert-butyl 4-benzyl-2-(2-ethoxy-2-oxo-ethyl) piperazine-1-carboxylate (10.0 g, 27.59 mmol) and Pd/C (0.50 g, 27.59 mmol) in methanol (100 mL) was stirred at 25° C. for 4 hours. After completion, the resulting solution was concentrated under vacuum. The residue was dissolved in dichloromethane (200 mL) and di-tert-butyl dicarbonate (12.04 g, 55.18 mmol) N,N-diisopropylethylamine (10.68 g, 82.77 mmol) was added and stirred at 25° C. for 5 hours. After completion, the solvent was diluted with dichloromethane and washed with brine. Then the organic layer was dried over anhydrous sodium sulfate and concentrated under vacuum to afford di-tert-butyl 2-(2-ethoxy-2-oxo-ethyl) piperazine-1,4-dicarboxylate (12.2 g, 0.19 mmol, 0.70% yield, 60% purity) as a yellow oil. The crude product would be directly used in the next step without purification. LCMS (ESI, m/z): 373.5 [M+H]$^+$.

Step 2: di-tert-butyl 2-(2-hydroxyethyl)piperazine-1,4-dicarboxylate

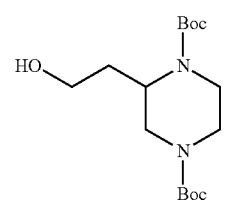 [SMILES: CC(C)(C)OC(=O)N1CCN(C(=O)OC(C)(C)C)C(CCO)C1]

A solution of di-tert-butyl 2-(2-ethoxy-2-oxo-ethyl) piperazine-1, 4-dicarboxylate (5.00 g, 13.42 mmol) in tetrahydrofuran (100 mL) was stirred at 25° C. for 0.5 hours. Then lithium aluminium hydride (1.02 g, 26.85 mmol) was added and stirred at 25° C. for 3 hours. After completion, the reaction was quenched by water. After filtration, the filtrate was concentrated under reduced pressure to afford di-tert-butyl 2-(2-hydroxyethyl) piperazine-1,4-dicarboxylate (3.2 g crude, 70% purity) which was used directly for next step without purification. LCMS (ESI, m/z): 331.4 [M+H]$^+$.

Step 3: di-tert-butyl 2-(2-oxoethyl) piperazine-1,4-dicarboxylate

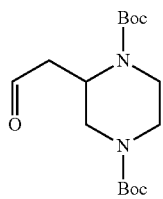 [SMILES: CC(C)(C)OC(=O)N1CCN(C(=O)OC(C)(C)C)C(CC=O)C1]

A solution of di-tert-butyl 2-(2-hydroxyethyl) piperazine-1, 4-dicarboxylate (5.00 g, 15.13 mmol) and Dess-Martin reagent (12.84 g, 30.26 mmol) in dichloromethane (100 mL) was stirred at 25° C. for 5 hours. After completion, the resulting solution was diluted with ethyl acetate and washed with water. The organic layer was dried over anhydrous sodium sulfate and concentrated under vacuum to afford di-tert-butyl 2-(2-oxoethyl) piperazine-1, 4-dicarboxylate (3.5 g, 0.07 mmol, 0.50% yield, 68% purity) as yellow oil. The crude product would be directly used in the next step without purification. LCMS (ESI, m/z): 329.4 [M+H]$^+$.

Step 4: di-tert-butyl 2-(prop-2-yn-1-yl) piperazine-1,4-dicarboxylate

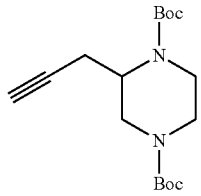 [SMILES: C#CCC1CN(C(=O)OC(C)(C)C)CCN1C(=O)OC(C)(C)C]

A solution of di-tert-butyl 2-(2-oxoethyl) piperazine-1, 4-dicarboxylate (1.00 g, 3.05 mmol) and potassium carbonate (0.84 g, 6.09 mmol) in methanol (30 mL) was stirred at 25° C. for 0.5 hours. Then 1-diazo-1-dimethoxyphosphoryl-propan-2-one (0.58 g, 3.05 mmol) was added and stirred at 25° C. for 6 hours. After completion, the solution was diluted with water and extracted with ethyl acetate. Then the organic layers were combined, dried over anhydrous sodium sulfate and concentrated under vacuum to afford di-tert-butyl 2-prop-2-ynylpiperazine-1,4-dicarboxylate (500 mg, 0.01 mmol, 0.40% yield, 70% purity) as a yellow oil. The crude product would be directly used in the next step without purification. LCMS (ESI, m/z): 325.4 [M+H]$^+$.

Step 5: 2-(prop-2-yn-1-yl)piperazine

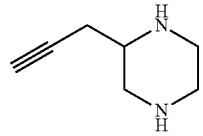

A solution of di-tert-butyl 2-prop-2-ynylpiperazine-1,4-dicarboxylate (0.70 g, 2.16 mmol) and trifluoroacetic acid (5.00 mL) in dichloromethane (5.00 mL) was stirred at 25° C. for 3 hours. After completion, the resulting solution was concentrated under vacuum to afford 2-prop-2-ynylpiperazine (300 mg, 0.01 mmol, 0.70% yield, 60% purity) as yellow oil. The crude product would be directly used in the next step without purification. LCMS (ESI, m/z): 125.2 [M+H]$^+$.

Step 6: tert-butyl 4-(7-(2, 3-dihydro-1H-inden-4-yl)-6-methyl-2-(methylthio)-5, 6, 7, 8-tetrahydroquinazolin-4-yl)-2-(prop-2-yn-1-yl)piperazine-1-carboxylate

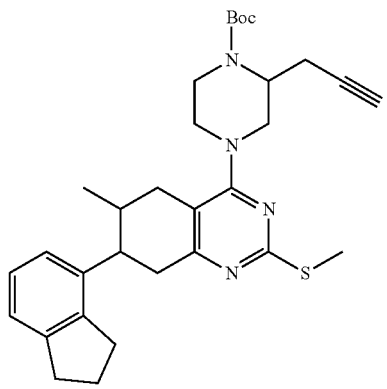 [SMILES: C#CCC1CN(c2nc(SC)nc3c2CC(C)C(c2cccc4c2CCC4)C3)CCN1C(=O)OC(C)(C)C]

A solution of 7-(2,3-dihydro-1H-inden-4-yl)-6-methyl-2-(methylthio)-5,6,7,8-tetrahydroquinazolin-4-ol (600.0 mg, 1.84 mmol) and N,N-diisopropylethylamine (474 mg, 3.68 mmol) in dichloromethane (10 mL) was stirred at 25° C. for 0.2 hours. Then trifluoromethanesulfonic anhydride (777 mg, 2.76 mmol) was added and stirred at 25° C. for 2 hours. After completion, the resulting solution was concentrated under reduced pressure and dissolved in 1,4-dioxane (10 mL). Then N,N-diisopropylethylamine (474.18 mg, 3.68 mmol) and 2-prop-2-ynylpiperazine (456.46 mg, 3.68 mmol) were added and stirred at 110° C. for 3 hours. Then di-tert-butyl dicarbonate (802 mg, 3.68 mmol) was added and stirred at 110° C. for 1 hour. After completion, the resulting solution was diluted with ethyl acetate and washed with water. The organic layer was dried over anhydrous sodium sulfate and concentrated under vacuum. The residue was purified by flash chromatography on silica gel eluting with ethyl acetate/petroleum ether (1/6) to afford tert-butyl 4-(7-(2, 3-dihydro-1H-inden-4-yl)-6-methyl-2-(methylthio)-5, 6, 7, 8-tetrahydroquinazolin-4-yl)-2-(prop-2-yn-1-yl)piperazine-1-carboxylate (500 mg, 0.94 mmol, 51.1% yield) as a yellow solid. LCMS (ESI, m/z): 533.7 [M+H]$^+$.

Step 7: tert-butyl 4-(7-(2, 3-dihydro-1H-inden-4-yl)-6-methyl-2-(methylsulfonyl)-5, 6, 7, 8-tetrahydroquinazolin-4-yl)-2-(prop-2-yn-1-yl) piperazine-1-carboxylate

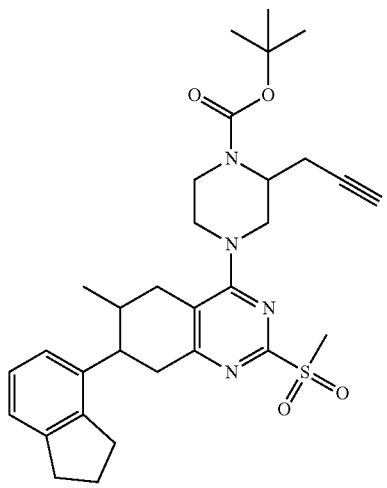 [SMILES: C#CCC1CN(c2nc(S(C)(=O)=O)nc3c2CC(C)C(c2cccc4c2CCC4)C3)CCN1C(=O)OC(C)(C)C]

A solution of tert-butyl 4-(7-(2, 3-dihydro-1H-inden-4-yl)-6-methyl-2-(methylthio)-5, 6, 7, 8-tetrahydroquinazolin-4-yl)-2-(prop-2-yn-1-yl)piperazine-1-carboxylate (700.0 mg, 1.31 mmol) and 3-chloroperoxybenzoic acid (453.5 mg, 2.63 mmol) in dichloromethane (10 mL) was stirred at 25° C. for 3 hours. After completion, the resulting solution was diluted with dichloromethane and washed with water. The organic layer was dried over anhydrous sodium sulfate and concentrated under vacuum. The residue was purified by flash chromatography on silica gel eluting with ethyl acetate/petroleum ether (1/5) to afford tert-butyl 4-(7-indan-4-yl-6-methyl-2-methylsulfonyl-5,6,7,8-tetrahydroquinazolin-4-yl)-2-prop-2-ynyl-piperazine-1-carboxylate (560 mg, 0.99 mmol, 75.5% yield) as a yellow solid. LCMS (ESI, m/z): 565.7 [M+H]⁺.

Step 8: tert-butyl 4-(7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazine-1-carboxylate

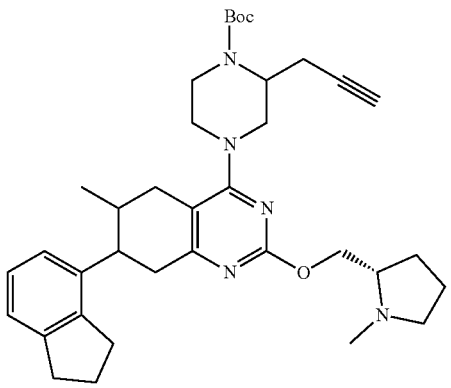

A solution of N-methyl-1-prolinol (214.13 mg, 1.86 mmol), sodium hydride (59.5 mg, 2.48 mmol, 60% dispersion in mineral oil) in 1,4-dioxane (6 mL) was stirred at 25° C. for 0.5 hours. Then tert-butyl 4-(7-indan-4-yl-6-methyl-2-methylsulfonyl-5,6,7,8-tetrahydroquinazolin-4-yl)-2-prop-2-ynyl-piperazine-1-carboxylate (700.0 mg, 1.24 mmol) was added and stirred at 25° C. for 2 hours. After completion, the resulting solution was diluted with dichloromethane and washed with water. The organic layer was dried over anhydrous sodium sulfate and concentrated under vacuum. The residue was purified by flash chromatography on silica gel eluting with ethyl acetate/petroleum ether (1/4) to afford tert-butyl 4-(7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazine-1-carboxylate (300 mg, 0.50 mmol, 40.4% yield) as a yellow solid. LCMS (ESI, m/z): 600.8 [M+H]⁺.

Step 9: 1-((S)-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (Example 40a); 1-((S)-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (Example 40b); and 1-((R)-4-((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (Example 40c); 1-((R)-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one and (Example 40d)

Example 40a

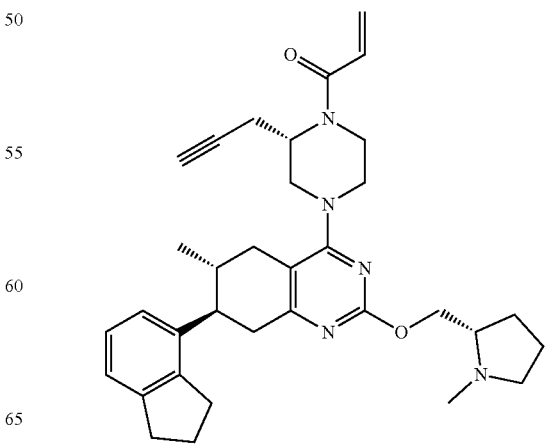

Example 40b

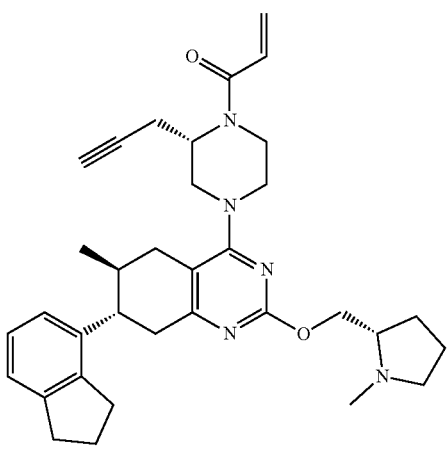

Example 40c

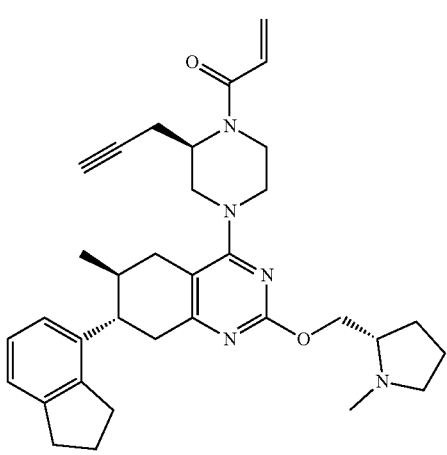

Example 40d

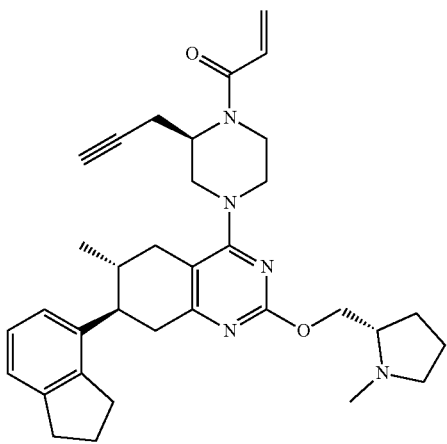

Example 40b

A solution of tert-butyl 4-(7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazine-1-carboxylate (300.0 mg, 0.50 mmol) and trifluoroacetic acid (2 mL) in dichloromethane (6 mL) was stirred at 25° C. for 2 hours. The resulting solution was concentrated under vacuum. Then reaction mixture was diluted with dichloromethane (30 mL). Then N,N-diisopropylethylamine (129.04 mg, 1 mmol) and acryloyl chloride (45.27 mg, 0.50 mmol) was added and stirred at −78° C. for 1 hour. After completion, the solution was quenched with water, diluted with EA and washed with brine. The organic layer was concentrated under vacuum. The crude product was further isolated by Prep-HPLC with the following conditions: (Column: Column: XBridge Shield RP18 OBD Column, 19*250 mm, 10 um; Mobile Phase A: Water (10 mmol/l NH$_4$HCO$_3$+ 0.1% NH$_3$·H$_2$O), Mobile Phase B: ACN; Flow rate: 25 mL/min; Gradient: 55 B to 68 B in 10 min; 254 nm). The product was further purified by Chiral-Prep-HPLC with following condition: (Column, CHIRAL Cellulose-SB4.6*100 mm 3 um, mobile phase, Hex (0.1% DEA): EtOH=80:20; Detector, UV 220/254 nm) and (Column: CHIRALPAK AD-H, 2.0 cm I.D.*25 cm L; Mobile Phase A: Hex (8 mmol/L NH3·MeOH)—HPLC, Mobile Phase B: IPA—HPLC; Flow rate: 20 mL/min; Gradient: 20 B to 20 B in 16 min; 220/254 nm) to afford the title compounds. The absolute configuration of the title compounds was inferred from potency data and a protein X-ray structure of compound 21b.

Example 40a: 1-((S)-4-(((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (10.4 mg, 0.019 mmol, 3.8% yield, white solid) (10 mg, 0.018 mmol, 3.6% yield, white solid). $^1$H NMR (400 MHz, Methanol-d$_4$) δ 7.14-7.08 (m, 2H), 7.01 (d, J=7.4 Hz, 1H), 6.83 (s, 1H), 6.26 (d, J=16.0 Hz, 1H), 5.80 (d, J=10.6, 1H), 4.51 (s, 1H), 4.38-4.35 (m, 1H), 4.33-4.31 (m, 1H), 4.18 (d, J=13.7 Hz, 1H), 4.04-4.01 (m, 1H), 3.71 (s, 1H), 3.50-3.40 (m, 1H), 3.15-3.09 (m, 2H), 3.00-2.92 (m, 7H), 2.81-2.74 (m, 3H), 2.62-2.52 (m, 6H), 2.42 (s, 2H), 2.13-2.02 (m, 4H), 1.86-1.81 (m, 2H), 1.76-1.68 (m, 1H), 0.89 (s, 3H). LCMS (ESI, m/z): 554.4 [M+H]$^+$. Chiral HPLC: Reg AD 0.46*10 cm; 5 um; detected at 254 nm; Hex (0.1% DEA): EtOH=80/20; flow=1.0 mL/min; Retention time: 2.857 min (faster peak).

Example 40b: 1-((S)-4-(((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (10.3 mg, 0.019 mmol, 3.7% yield, white solid). $^1$H NMR (400 MHz, Methanol-d$_4$) δ 7.14-7.08 (m, 2H), 7.01 (d, J=7.4 Hz, 1H), 6.81 (s, 1H), 6.25 (d, J=16.0 Hz, 1H), 5.81 (d, J=10.6, 1H), 4.52 (s, 1H), 4.38-4.36 (m, 1H), 4.33-4.30 (m, 1H), 4.17 (d, J=13.7 Hz, 1H), 4.04-4.01 (m, 1H), 3.71 (s, 1H), 3.50-3.40 (m, 1H), 3.15-3.09 (m, 2H), 3.00-2.92 (m, 7H), 2.81-2.74 (m, 3H), 2.62-2.52 (m, 6H), 2.42 (s, 2H), 2.13-2.02 (m, 4H), 1.86-1.81 (m, 2H), 1.76-1.68 (m, 1H), 0.89 (s, 3H). LCMS (ESI, m/z): 554.4 [M+H]$^+$. Chiral HPLC: Reg AD 0.46*10 cm; 5 um; detected at 254 nm; Hex (0.1% DEA): EtOH=80/20; flow=1.0 mL/min; Retention time: 5.192 min (slower peak).

Example 40c: 1-((R)-4-(((6S,7S)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (10.1 mg, 0.018 mmol, 3.6% yield, white solid). $^1$H NMR (400 MHz, Methanol-d$_4$) δ 7.13-7.07 (m, 2H), 7.00 (d, J=7.4 Hz, 1H), 6.82 (s, 1H), 6.24 (d, J=16.0 Hz, 1H), 5.80 (d, J=10.6, 1H), 4.51 (s, 1H), 4.38-4.36 (m, 1H), 4.33-4.30 (m, 1H), 4.17 (d, J=13.7 Hz, 1H), 4.04-4.01 (m, 1H), 3.71 (s, 1H), 3.50-3.40 (m, 1H), 3.15-3.09 (m, 2H), 3.00-2.92 (m, 7H), 2.81-2.74 (m, 3H), 2.62-2.52 (m, 6H), 2.42 (s, 2H), 2.13-2.02 (m, 4H), 1.86-1.81 (m, 2H), 1.76-1.68 (m, 1H), 0.89 (s, 3H). LCMS (ESI, m/z): 554.4 [M+H]$^+$. Chiral HPLC: Cellulose-SB4.6*100 mm 3 um; detected at 254 nm; Hex (0.1% DEA): EtOH=80/20; flow=1.0 mL/min; Retention time: 2.908 min (slower peak).

Example 40d: 1-((R)-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)-2-(prop-2-yn-1-yl)piperazin-1-yl)prop-2-en-1-one (10 mg, 0.018 mmol, 3.6% yield, white solid). ¹H NMR (400 MHz, Methanol-d₄) δ 7.14-7.08 (m, 2H), 7.01 (d, J=7.4 Hz, 1H), 6.81 (s, 1H), 6.25 (d, J=16.0 Hz, 1H), 5.81 (d, J=10.6 Hz, 1H), 4.52 (s, 1H), 4.38-4.36 (m, 1H), 4.33-4.30 (m, 1H), 4.17 (d, J=13.7 Hz, 1H), 4.04-4.01 (m, 1H), 3.71 (s, 1H), 3.50-3.40 (m, 1H), 3.15-3.09 (m, 2H), 3.00-2.92 (m, 7H), 2.81-2.74 (m, 3H), 2.62-2.52 (m, 6H), 2.42 (s, 2H), 2.13-2.02 (m, 4H), 1.86-1.81 (m, 2H), 1.76-1.68 (m, 1H), 0.89 (s, 3H). LCMS (ESI, m/z): 554.4 [M+H]⁺. Chiral HPLC: Cellulose-SB4.6*100 mm 3 um; detected at 254 nm; Hex (0.1% DEA): EtOH=80:20; flow=1.0 mL/min; Retention time: 2.505 min (faster peak).

Examples 41a and 41b

Example 41a

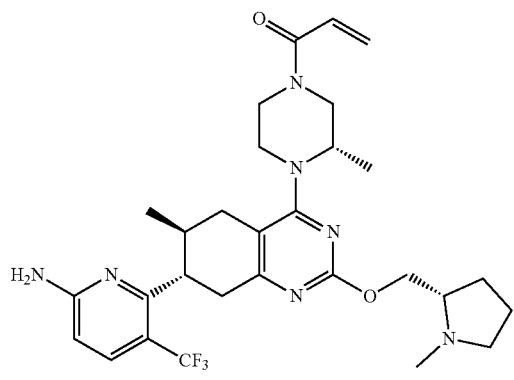

Example 41b

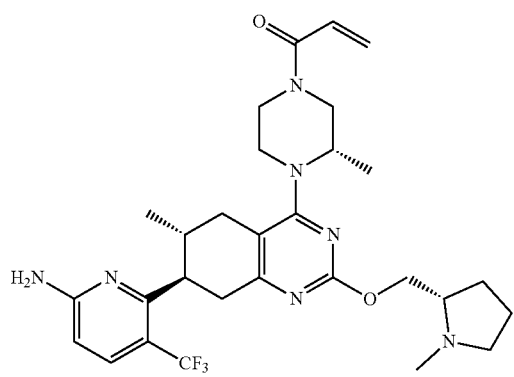

1-((S)-4-((6S,7S)-7-(6-amino-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 41a); and 1-((S)-4-((6R,7R)-7-(6-amino-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 41b)

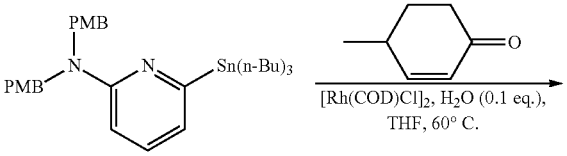

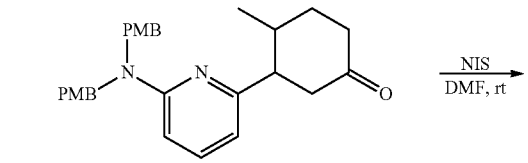

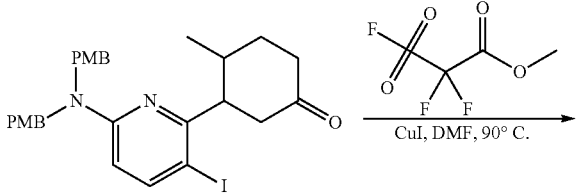

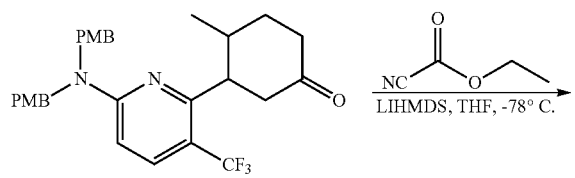

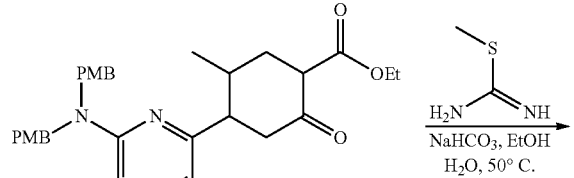

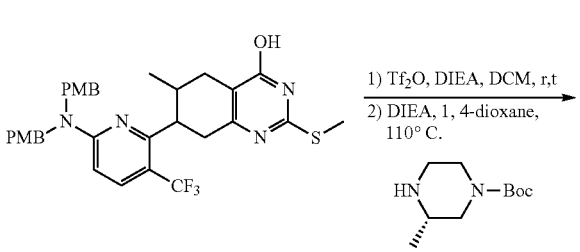

-continued

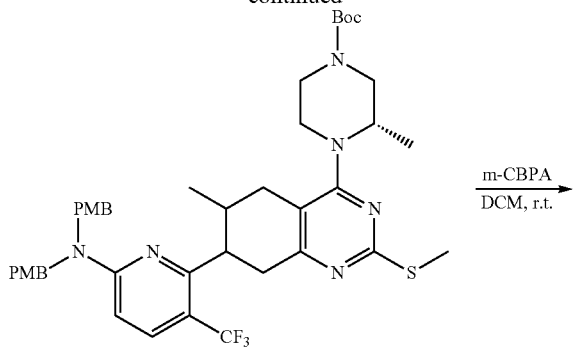

m-CBPA
DCM, r.t.

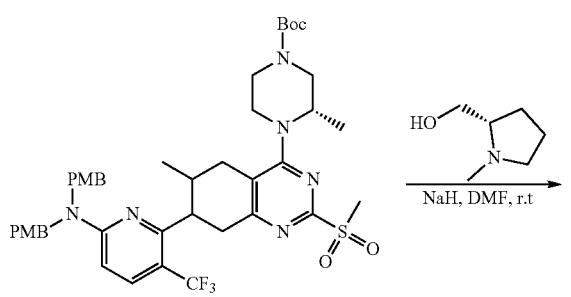

NaH, DMF, r.t

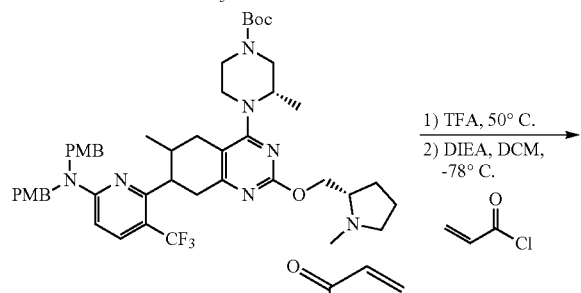

1) TFA, 50° C.
2) DIEA, DCM, −78° C.

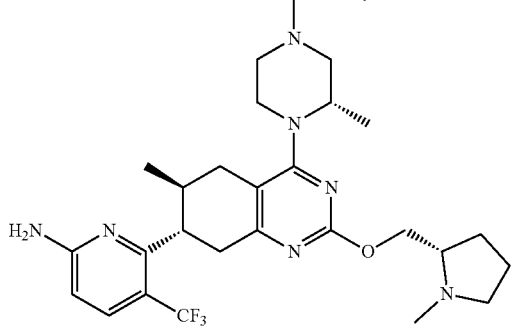

41a

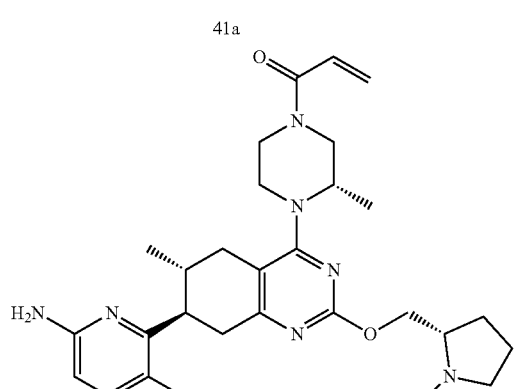

41b

Step 1: 3-[6-[bis[(4-methoxyphenyl)methyl]amino]-2-pyridyl]-4-methyl-cyclohexanone

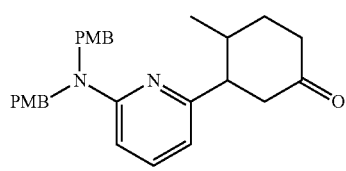

Under nitrogen, a solution of 4-methylcyclohex-2-en-1-one (4.24 g, 38.49 mmol) and [Rh(COD)Cl]$_2$ (1.58 g, 3.21 mmol) in tetrahydrofuran (400 mL) and water (40 ml) was added N,N-bis[(4-methoxyphenyl)methyl]-6-tributylstannyl-pyridin-2-amine (20.0 g, 32.08 mmol). The resulting solution was stirred at 60° C. for 2 hours. After completion, the solution was diluted with water and extracted with ethyl acetate. Then the organic layers were combined, dried over anhydrous sodium sulfate and concentrated under vacuum. The residue was purified by flash chromatography on silica gel eluting with ethyl acetate/petroleum ether (1/6) to afford 3-[6-[bis[(4-methoxyphenyl)methyl]amino]-2-pyridyl]-4-methyl-cyclohexanone (5.00 g, 11.25 mmol, 35.1% yield) as a yellow solid. LCMS (ESI, m/z): 445.6 [M+H]$^+$.

Step 2: 3-[6-[bis[(4-methoxyphenyl)methyl]amino]-3-iodo-2-pyridyl]-4-methyl-cyclohexanone

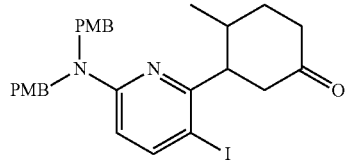

A solution of 3-[6-[bis[(4-methoxyphenyl)methyl]amino]-2-pyridyl]-4-methyl-cyclohexanone (6.00 g, 13.5 mmol) and N-iodosuccinimide (3.48 g, 16.2 mmol) in N,N-dimethylformamide (50 mL) was stirred at 25° C. for 2 hours. After completion, the resulting solution was diluted with ethyl acetate and washed with brine. The organic layer was dried over anhydrous sodium sulfate and concentrated under vacuum. The residue was purified by flash chromatography on silica gel eluting with ethyl acetate/petroleum ether (1/7) to afford 3-[6-[bis[(4-methoxyphenyl)methyl]amino]-3-iodo-2-pyridyl]-4-methyl-cyclohexanone (5.2 g, 9.12 mmol, 67.5% yield) as a yellow solid. LCMS (ESI, m/z): 571.1 [M+H]$^+$.

Step 3: 3-[6-[bis[(4-methoxyphenyl)methyl]amino]-3-(trifluoromethyl)-2-pyridyl]-4-methyl-cyclohexanone

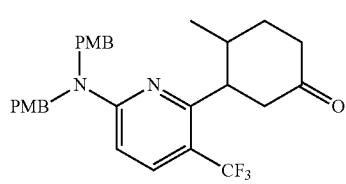

Under nitrogen, a solution of 3-[6-[bis[(4-methoxyphenyl)methyl]amino]-3-iodo-2-pyridyl]-4-methyl-cyclohexanone (5.6 g, 9.82 mmol) and cuprous iodide (1.87 g, 9.82 mmol) in N,N-dimethylformamide (10 mL) was added methyl methyl 2,2-difluoro-2-(fluorosulfonyl)acetate (9.33 g, 49.08 mmol). The resulting solution was stirred at 90° C. for 5 hours. After completion, the resulting solution was diluted with ethyl acetate and washed with brine. The organic layer was dried over anhydrous sodium sulfate and concentrated under vacuum. The residue was purified by flash chromatography on silica gel eluting with ethyl acetate/petroleum ether (1/6) to afford 3-[6-[bis[(4-methoxyphenyl)methyl]amino]-3-(trifluoromethyl)-2-pyridyl]-4-methyl-cyclohexanone (4.2 g, 8.19 mmol, 83.5% yield) as a yellow oil. LCMS (ESI, m/z): 513.6 [M+H]+.

Step 4: ethyl 4-[6-[bis[(4-methoxyphenyl)methyl]amino]-3-(trifluoromethyl)-2-pyridyl]-5-methyl-2-oxo-cyclohexanecarboxylate

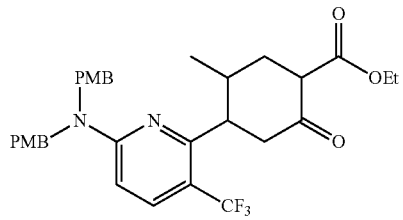

Under nitrogen, a solution of 3-[6-[bis[(4-methoxyphenyl)methyl]amino]-3-(trifluoromethyl)-2-pyridyl]-4-methyl-cyclohexanone (1.80 g, 3.51 mmol) in tetrahydrofuran (20 mL) was added LiHMDS (2.11 mL, 4.21 mmol) (1M in THF) at −78° C. The resulting solution was stirred for 0.5h at −78° C. Then ethyl cyanoformate (0.52 g, 5.27 mmol) was added and stirred at −78° C. for 2 hours. The reaction was quenched with water. After completion, the resulting solution was diluted with ethyl acetate and washed with brine. The organic layer was dried over anhydrous sodium sulfate and concentrated under vacuum. The residue was purified by flash chromatography on silica gel eluting with ethyl acetate/petroleum ether (1/5) to afford ethyl 4-[6-[bis[(4-methoxyphenyl)methyl]amino]-3-(trifluoromethyl)-2-pyridyl]-5-methyl-2-oxo-cyclohexanecarboxylate (600 mg, 1.03 mmol, 29.2% yield) as a yellow oil. LCMS (ESI, m/z): 585.6 [M+H]+.

Step 5: 7-[6-[bis[(4-methoxyphenyl)methyl]amino]-3-(trifluoromethyl)-2-pyridyl]-6-methyl-2-methylsulfanyl-5,6,7,8-tetrahydroquinazolin-4-ol

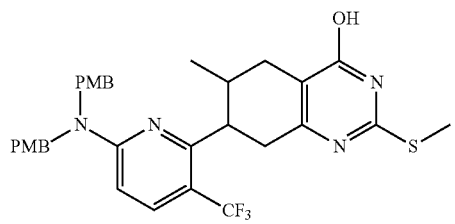

A solution of ethyl 4-[6-[bis[(4-methoxyphenyl)methyl]amino]-3-(trifluoromethyl)-2-pyridyl]-5-methyl-2-oxo-cyclohexanecarboxylate (1.5 g, 2.57 mmol) and 2-methylisothiourea (2.31 g, 25.66 mmol), sodium bicarbonate (4.31 g, 51.31 mmol) in water (10 mL) and ethanol (50 mL) was stirred at 50° C. for 9 hours. After completion, the resulting solution was diluted with ethyl acetate and washed with brine. The organic layer was dried over anhydrous sodium sulfate and concentrated under vacuum. The residue was purified by flash chromatography on silica gel eluting with dichloromethane/methanol (10/1) to afford 7-[6-[bis[(4-methoxyphenyl)methyl]amino]-3-(trifluoromethyl)-2-pyridyl]-6-methyl-2-methylsulfanyl-5,6,7,8-tetrahydroquinazolin-4-ol (0.65 g, 1.06 mmol, 41.5% yield) as a yellow solid. LCMS (ESI, m/z): 611.7 [M+H]+.

Step 6: tert-butyl (3S)-4-[7-[6-[bis[(4-methoxyphenyl)methyl]amino]-3-(trifluoromethyl)-2-pyridyl]-6-methyl-2-methylsulfanyl-5,6,7,8-tetrahydroquinazolin-4-yl]-3-methyl-piperazine-1-carboxylate

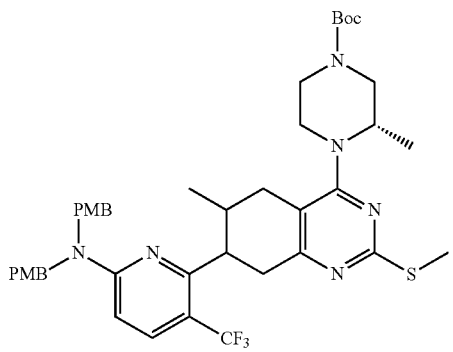

A solution of 7-[6-[bis[(4-methoxyphenyl)methyl]amino]-3-(trifluoromethyl)-2-pyridyl]-6-methyl-2-methylsulfanyl-5,6,7,8-tetrahydroquinazolin-4-ol (500.0 mg, 0.82 mmol) and trifluoromethanesulfonic anhydride (346.5 mg, 1.23 mmol) in DCM (50 mL) was stirred at 25° C. for 3 hours. Then the residue was concentrated under vacuum. The tert-butyl (3S)-3-methyl-1-piperazinecarboxylate (983.87 mg, 4.91 mmol) and N,N-diisopropylethylamine (316.85 mg, 2.46 mmol) in 1,4-dioxane (50 mL) was added and stirred at 110° C. for 3 hours. After completion, the resulting solution was diluted with ethyl acetate and washed with brine. The organic layer was dried over anhydrous sodium sulfate and concentrated under vacuum. The residue was purified by flash chromatography on silica gel eluting with methanol/dichloromethane (1/10) to afford tert-butyl (3S)-4-[7-[6-[bis[(4-methoxyphenyl)methyl]amino]-3-(trifluoromethyl)-2-pyridyl]-6-methyl-2-methylsulfanyl-5,6,7,8-tetrahydroquinazolin-4-yl]-3-methyl-piperazine-1-carboxylate (300 mg, 0.38 mmol, 46.2% yield) as a yellow solid. LC-MS: (ESI, m/z): 794.0 [M+H]+.

Step 7: tert-butyl (3S)-4-[7-[6-[bis[(4-methoxyphenyl)methyl]amino]-3-(trifluoromethyl)-2-pyridyl]-6-methyl-2-methylsulfonyl-5,6,7,8-tetrahydroquinazolin-4-yl]-3-methyl-piperazine-1-carboxylate

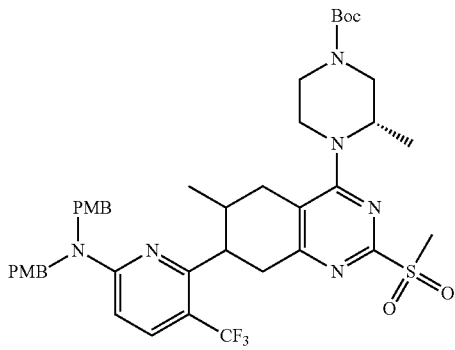

A solution of tert-butyl (3S)-4-[7-[6-[bis[(4-methoxyphenyl)methyl]amino]-3-(trifluoromethyl)-2-pyridyl]-6-methyl-2-methylsulfanyl-5,6,7,8-tetrahydroquinazolin-4-yl]-3-methyl-piperazine-1-carboxylate (300.0 mg, 0.38 mmol) and 3-chloroperoxybenzoic acid (130.58 mg, 0.76 mmol) in dichloromethane (10 mL) was stirred at 25° C. for 3 hours. After completion, the resulting solution was diluted with ethyl acetate and washed with brine. The organic layer was dried over anhydrous sodium sulfate and concentrated under vacuum. The residue was purified by flash chromatography on silica gel eluting with methanol/dichloromethane (1/10) to afford tert-butyl (3S)-4-[7-[6-[bis[(4-methoxyphenyl)methyl]amino]-3-(trifluoromethyl)-2-pyridyl]-6-methyl-2-methylsulfonyl-5,6,7,8-tetrahydroquinazolin-4-yl]-3-methyl-piperazine-1-carboxylate (200 mg, 0.24 mmol, 64.1% yield) as a yellow solid. LC-MS: (ESI, m/z): 825.0 [M+H]$^+$.

Step 8: tert-butyl (3S)-4-[7-[6-[bis[(4-methoxyphenyl)methyl]amino]-3-(trifluoromethyl)-2-pyridyl]-6-methyl-2-[[(2S)-1-methylpyrrolidin-2-yl]methoxy]-5,6,7,8-tetrahydroquinazolin-4-yl]-3-methyl-piperazine-1-carboxylate

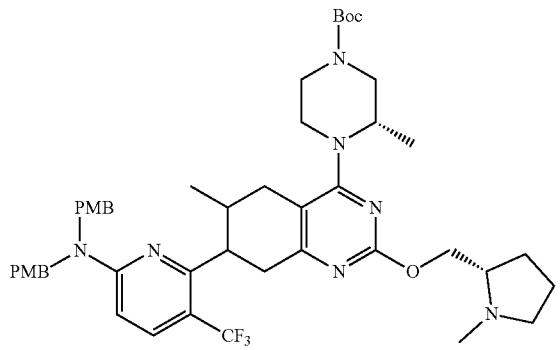

A solution of n-methyl-1-prolinol (55.84 mg, 0.48 mmol) and sodium hydride (12.8 mg, 0.53 mmol, 60% dispersion in mineral oil) in DMF (3 mL) was stirred at 25° C. for 2 hours. Then tert-butyl (3S)-4-[7-[6-[bis[(4-methoxyphenyl)methyl]amino]-3-(trifluoromethyl)-2-pyridyl]-6-methyl-2-methylsulfonyl-5,6,7,8-tetrahydroquinazolin-4-yl]-3-methyl-piperazine-1-carboxylate (200.0 mg, 0.24 mmol) was added and stirred at 25° C. for 3 hours. After completion, the resulting solution was diluted with ethyl acetate and washed with brine. The organic layer was dried over anhydrous sodium sulfate and concentrated under vacuum. The residue was purified by flash chromatography on silica gel eluting with ethyl acetate/petroleum ether (1/4) to afford tert-butyl (3S)-4-[7-[6-[bis[(4-methoxyphenyl)methyl]amino]-3-(trifluoromethyl)-2-pyridyl]-6-methyl-2-[[(2S)-1-methylpyrrolidin-2-yl]methoxy]-5,6,7,8-tetrahydroquinazolin-4-yl]-3-methyl-piperazine-1-carboxylate (120 mg, 0.14 mmol, 57.6% yield) as a yellow solid. LC-MS: (ESI, m/z): 860.0 [M+H]$^+$.

Step 9: 1-((S)-4-((6S,7S)-7-(6-amino-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 41a); and 1-((S)-4-((6R,7R)-7-(6-amino-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Example 41b)

41a

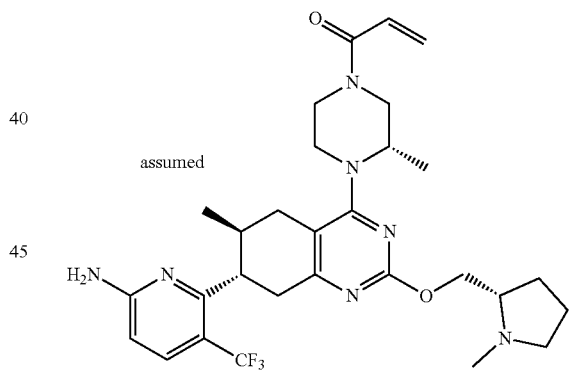

41b

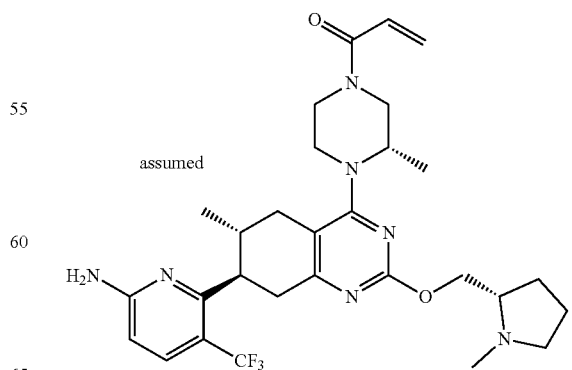

A solution of tert-butyl (3S)-4-[7-[6-[bis[(4-methoxyphenyl)methyl]amino]-3-(trifluoromethyl)-2-pyridyl]-6-methyl-2-[[(2S)-1-methylpyrrolidin-2-yl]methoxy]-5,6,7,8-tetrahydroquinazolin-4-yl]-3-methyl-piperazine-1-carboxylate (200.0 mg, 0.23 mmol) and trifluoroacetic acid (6 ml) was stirred at 50° C. for 3 hours. After completion, the resulting solution was concentrated under vacuum. The residue was dissolved in dichloromethane (5 mL), then acryloyl chloride (21.05 mg, 0.23 mmol) and N,N-diisopropylethylamine (89 mg, 0.69 mmol) were added and stirred at −78° C. for 2 hours. After completion, the solution was quenched with water, diluted with ethyl acetate and washed with brine. The organic layer was concentrated under vacuum. The crude product was further isolated by Prep-HPLC with the following conditions Column: CHIRALPAK IE, 2*25 cm, 5 um; Mobile Phase A: MTBE (10 mM NH$_3$-MeOH)—HPLC, Mobile Phase B: MeOH—HPLC; Flow rate: 20 mL/min; Gradient: 15 B to 15 B in 27 min; 220/254 nm; RT1:17.672; RT2:23.294. The product was further purified by Chiral-Prep-HPLC with following condition (Column, CHIRAL ART Cellulose-SB, 2*25 cm, 5 um; mobile phase, Hex—HPLC and ethanol-HPLC (hold 40% ethanol—HPLC in 10 min); Detector, UV 220/254 nm) to afford the title compounds. The absolute configuration of the title compounds was inferred from potency data and a protein X-ray structure of compound 21b.

Example 41a: 1-((S)-4-((6S,7S)-7-(6-amino-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (12.5 mg, 0.022 mmol, 9.4% yield, white solid). $^1$H NMR (400 MHz, Methanol-d$_4$) δ 7.63 (d, J=8.0 Hz, 1H), 6.89-6.76 (m, 1H), 6.44 (d, J=8.0 Hz, 1H), 6.30-6.25 (m, 1H), 5.82-5.79 (m, 1H), 4.49-4.44 (m, 1H), 4.37-4.28 (m, 2H), 4.13-4.08 (m, 1H), 4.97-4.93 (m, 1H), 3.79-3.74 (m, 1H), 3.62-3.39 (m, 3H), 3.15-3.03 (m, 3H), 2.94-2.86 (m, 1H), 2.79 (s, 1H), 2.71-2.65 (m, 1H), 2.52 (s, 3H), 2.49-2.36 (m, 2H), 2.20 (s, 1H), 2.14-2.05 (m, 1H), 1.87-1.80 (m, 2H), 1.75-1.68 (m, 1H), 1.13 (d, J=8 Hz, 3H), 0.87 (d, J=8 Hz, 3H). LC-MS: (ESI, m/z): 574.3 [M+H]$^+$. Chiral HPLC: CHIRALPAK IE-3 4.6*50 mm 3 um; detected at 254 nm; Hex (0.1% DEA): EtOH=60:40; flow=1.0 mL/min; Retention time: 2.711 min (Slower peak).

Example 41b: 1-((S)-4-((6R,7R)-7-(6-amino-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (10 mg, 0.017 mmol, 7.5% yield, white solid). $^1$H NMR (400 MHz, Methanol-d$_4$) δ 7.63 (d, J=8.0 Hz, 1H), 6.89-6.75 (m, 1H), 6.44 (d, J=8.0 Hz, 1H), 6.30-6.24 (m, 1H), 5.82-5.79 (m, 1H), 4.53-4.49 (m, 1H), 4.39-4.22 (m, 3H), 4.12-4.07 (m, 1H), 3.96-3.93 (m, 1H), 3.69-3.61 (m, 1H), 3.49-3.43 (m, 1H), 3.28-3.22 (m, 1H), 3.15-3.02 (m, 3H), 2.90-2.84 (m, 1H), 2.78 (s, 1H), 2.64-2.59 (m, 1H), 2.53 (s, 3H), 2.50-2.46 (m, 1H), 2.43-2.35 (m, 1H), 2.20 (s, 1H), 2.17-2.07 (m, 1H), 1.88-1.81 (m, 2H), 1.76-1.67 (m, 1H), 1.42-1.39 (m, 3H), 0.87 (d, J=8 Hz, 3H). LC-MS: (ESI, m/z): 574.3 [M+H]$^+$. Chiral HPLC: CHIRALPAK IE-3 4.6*50 mm 3 um; detected at 254 nm; Hex (0.1% DEA): EtOH=60:40; flow=1.0 mL/min; Retention time: 2.194 min (First peak).

Examples 42a and 42b

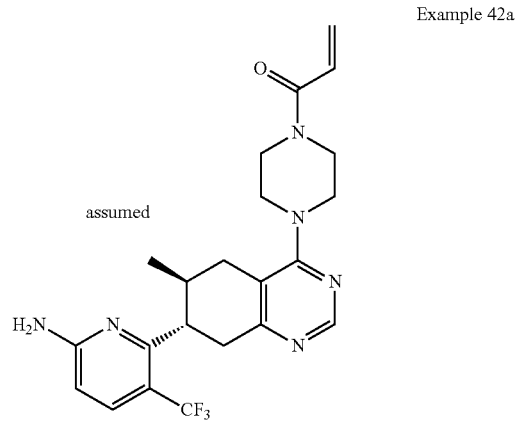

Example 42a
assumed

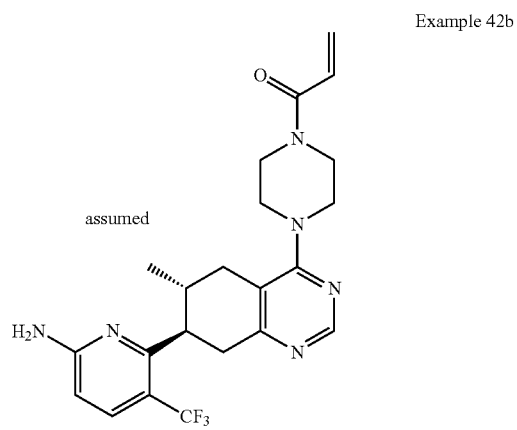

Example 42b
assumed 1-(4-((6S,7S)-7-(6-amino-3-(trifluoromethyl)pyridin-2-yl)-6-methyl-5,6,7,8-tetrahydroquinazolin-4-yl)piperazin-1-yl)prop-2-en-1-one (Example 42a); and 1-(4-((6R,7R)-7-(6-amino-3-(trifluoromethyl)pyridin-2-yl)-6-methyl-5,6,7,8-tetrahydroquinazolin-4-yl)piperazin-1-yl)prop-2-en-1-one (Example 42b)

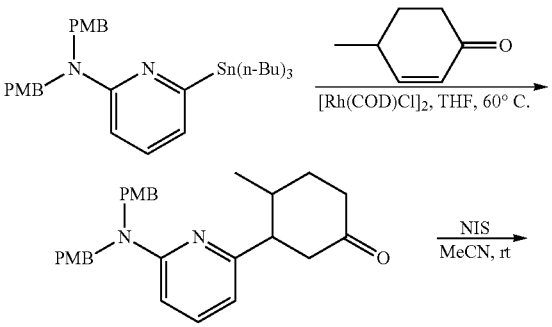

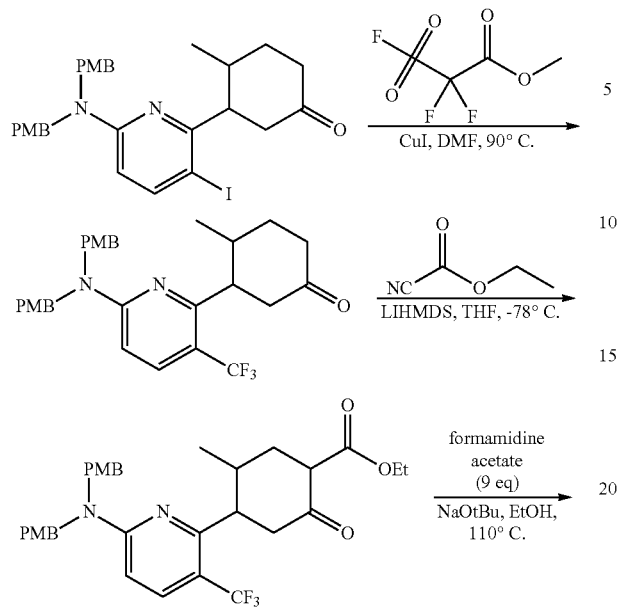

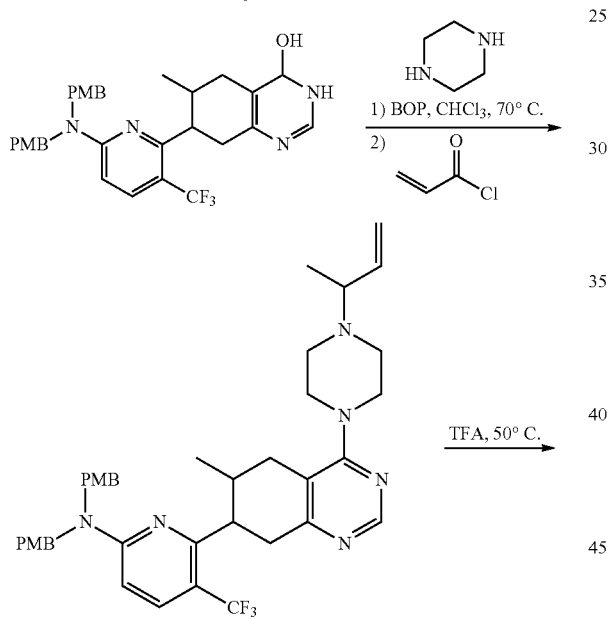

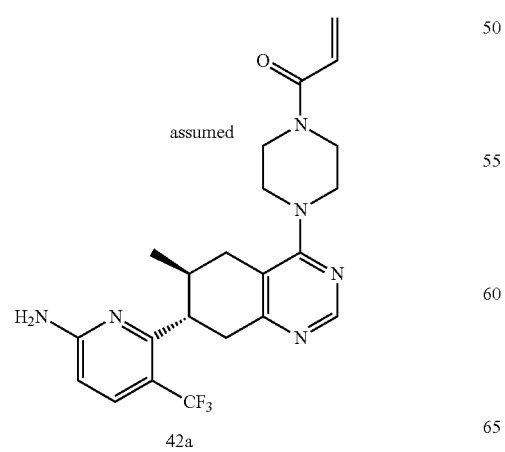

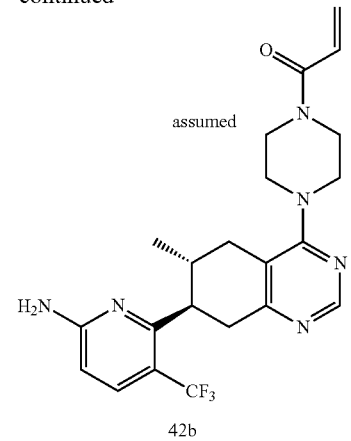

Step 1: 3-[6-[bis[(4-methoxyphenyl)methyl]amino]-2-pyridyl]-4-methyl-cyclohexanone Under nitrogen, a solution of N,N-bis[(4-methoxyphenyl)methyl]-6-tributylstannyl-pyridin-2-amine (20.0 g, 32.08 mmol) and 4-methylcyclohex-2-en-1-one (4.24 g, 38.49 mmol) in tetrahydrofuran (100 mL) was added [Rh(COD)Cl]$_2$ (1.58 g, 3.21 mmol). The resulting solution was stirred at 60° C. for 3 hours. After completion, the resulting solution was diluted with ethyl acetate and washed with water. The organic layer was dried over anhydrous sodium sulfate and concentrated under vacuum. The residue was purified by flash chromatography on silica gel eluting with ethyl acetate/petroleum ether (1/3) to afford 3-[6-[bis[(4-methoxyphenyl)methyl]amino]-2-pyridyl]-4-methyl-cyclohexanone (8 g, 17.9 mmol, 56.1% yield) as a yellow oil. LCMS (ESI, m/z): 445.6 [M+H]$^+$.

Step 2: 3-[6-[bis[(4-methoxyphenyl)methyl]amino]-3-iodo-2-pyridyl]-4-methyl-cyclohexanone A solution of 3-[6-[bis[(4-methoxyphenyl)methyl]amino]-2-pyridyl]-4-methyl-cyclohexanone (5.00 g, 11.25 mmol) and N-iodosuccinimide (2.53 g, 11.25 mmol) in acetonitrile (100 mL) was stirred at 25° C. for 4 hours. After completion, the resulting solution was diluted with ethyl acetate and washed with water. The organic layer was dried over anhydrous sodium sulfate and concentrated under vacuum. The residue was purified by flash chromatography on silica gel eluting with ethyl acetate/petroleum ether (1/4) to afford 3-[6-[bis[(4-methoxyphenyl)methyl]amino]-3-iodo-2-pyridyl]-4-methyl-cyclohexanone (5.00 g, 8.76 mmol, 77.9% yield) as a yellow oil. LCMS (ESI, m/z): 571.5 [M+H]⁺.

Step 3: 3-[6-[bis[(4-methoxyphenyl)methyl]amino]-3-(trifluoromethyl)-2-pyridyl]-4-methyl-cyclohexanone

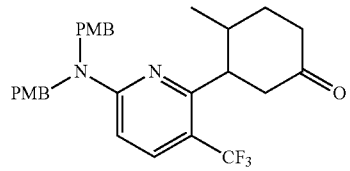

Under nitrogen, a solution of 3-[6-[bis[(4-methoxyphenyl)methyl]amino]-3-iodo-2-pyridyl]-4-methyl-cyclohexanone (5.00 g, 8.76 mmol) and methyl 2,2-difluoro-2-(fluorosulfonyl)acetate (10.10 g, 52.59 mmol) in N,N-dimethylformamide (30 mL) was added cuprous iodide (1.67 g, 8.76 mmol). The resulting solution was stirred at 90° C. for 5 hours. After completion, the resulting solution was diluted with water and extracted with ethyl acetate. Then the organic layers were combined, dried over anhydrous sodium sulfate and concentrated under vacuum. The residue was purified by flash chromatography on silica gel eluting with ethyl acetate/petroleum ether (1/4) to afford 3-[6-[bis[(4-methoxyphenyl)methyl]amino]-3-(trifluoromethyl)-2-pyridyl]-4-methyl-cyclohexanone (3.50 g, 6.83 mmol, 77.9% yield) as a yellow oil. LCMS (ESI, m/z): 513.6 [M+H]⁺.

Step 4: ethyl 4-[6-[bis[(4-methoxyphenyl)methyl]amino]-3-(trifluoromethyl)-2-pyridyl]-5-methyl-2-oxo-cyclohexanecarboxylate

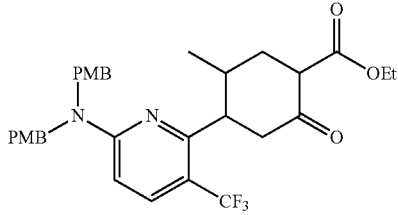

Under nitrogen, a solution of 3-[6-[bis[(4-methoxyphenyl)methyl]amino]-3-(trifluoromethyl)-2-pyridyl]-4-methyl-cyclohexanone (2.00 g, 3.90 mmol) in tetrahydrofuran (20 mL) was added LiHMDS (2.34 mL, 4.68 mmol) (2 M in THF) at −78° C. The resulting solution was stirred 0.5 h at −78° C. Then ethyl cyanoformate (0.58 g, 5.85 mmol) was added and stirred at −78° C. for 3 hours. After completion, the resulting solution was diluted with ethyl acetate and washed with water. The organic layer was dried over anhydrous sodium sulfate and concentrated under vacuum. The residue was purified by flash chromatography on silica gel eluting with ethyl acetate/petroleum ether (1/5) to afford ethyl 4-[6-[bis[(4-methoxyphenyl)methyl]amino]-3-(trifluoromethyl)-2-pyridyl]-5-methyl-2-oxo-cyclohexanecarboxylate (1.20 g, 2.05 mmol, 52.6% yield) as a yellow oil. LCMS (ESI, m/z): 585.6 [M+H]⁺.

Step 5: 7-[6-[bis[(4-methoxyphenyl)methyl]amino]-3-(trifluoromethyl)-2-pyridyl]-6-methyl-5,6,7,8-tetrahydro-3H-quinazolin-4-one

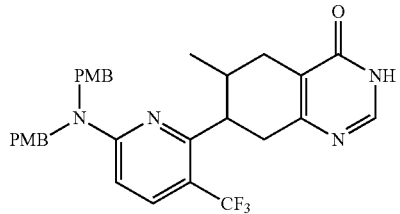

A solution of ethyl 4-[6-[bis[(4-methoxyphenyl)methyl]amino]-3-(trifluoromethyl)-2-pyridyl]-5-methyl-2-oxo-cyclohexanecarboxylate (1.50 g, 2.57 mmol) and formamidine acetate (0.82 g, 15.39 mmol) in ethanol (20 mL). Then sodium tert-butoxide (3.45 g, 30.79 mmol) was added and stirred at 110° C. for 3 hours. After completion, the resulting solution was diluted with ethyl acetate and washed with water. The organic layer was dried over anhydrous sodium sulfate and concentrated under vacuum. The residue was purified by flash chromatography on silica gel eluting with methanol/dichloromethane (1/9) to afford 7-[6-[bis[(4-methoxyphenyl)methyl]amino]-3-(trifluoromethyl)-2-pyridyl]-6-methyl-5,6,7,8-tetrahydro-3H-quinazolin-4-one (1.10 g, 1.95 mmol, 75.9% yield) as a yellow oil. LCMS (ESI, m/z): 565.6 [M+H]⁺.

Step 6a: N, N-bis[(4-methoxyphenyl)methyl]-6-(6-methyl-4-piperazin-1-yl-5,6,7,8-tetrahydroquinazolin-7-yl)-5-(trifluoromethyl)pyridin-2-amine

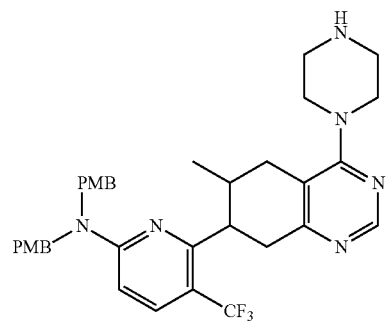

A solution of 7-[6-[bis[(4-methoxyphenyl)methyl]amino]-3-(trifluoromethyl)-2-pyridyl]-6-methyl-5,6,7,8-tetrahydro-3H-quinazolin-4-one (750.0 mg, 1.33 mmol) and 1H-benzotriazol-1-yloxytris(dimethylamino)phosphoniumhexafluorophosphate (1.17 g, 2.66 mmol) in chloroform (30 mL) was stirred at 25° C. for 0.5 hours. Then piperazine (1.14 g, 13.28 mmol) was added and stirred at 70° C. for 9 hours. After completion, the resulting solution was diluted with ethyl acetate and washed with water. The organic layer was dried over anhydrous sodium sulfate and concentrated under vacuum. The residue was purified by flash chromatography on silica gel eluting with dichloromethane/methanol (9/1) to afford N, N-bis[(4-methoxyphenyl)methyl]-6-(6-methyl-4-piperazin-1-yl-5,6,7,8-tetrahydroquinazolin-7-yl)-5-(trifluoromethyl)pyridin-2-amine (600 mg, 0.95 mmol, 71.4% yield) as a yellow oil. LC-MS: (ESI, m/z): 633.7 [M+H]$^+$.

Step 6b: 1-[4-[7-[6-[bis[(4-methoxyphenyl)methyl]amino]-3-(trifluoromethyl)-2-pyridyl]-6-methyl-5,6,7,8-tetrahydroquinazolin-4-yl]piperazin-1-yl]prop-2-en-1-one Step 7: 1-(4-((6S,7S)-7-(6-amino-3-(trifluoromethyl)pyridin-2-yl)-6-methyl-5,6,7,8-tetrahydroquinazolin-4-yl)piperazin-1-yl)prop-2-en-1-one (Example 42a); and 1-(4-((6R,7R)-7-(6-amino-3-(trifluoromethyl)pyridin-2-yl)-6-methyl-5,6,7,8-tetrahydroquinazolin-4-yl)piperazin-1-yl)prop-2-en-1-one (Example 42b)

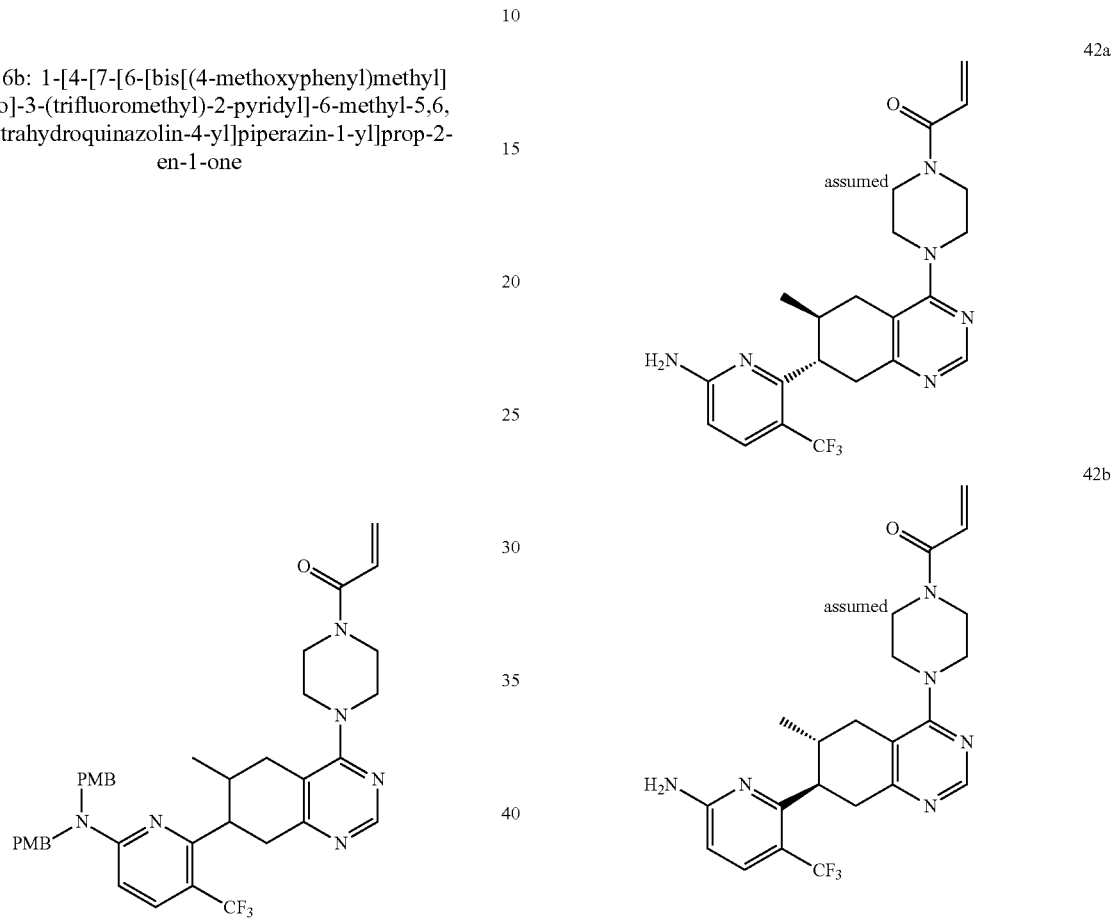

A solution of N,N-bis[(4-methoxyphenyl)methyl]-6-(6-methyl-4-piperazin-1-yl-5,6,7,8-tetrahydroquinazolin-7-yl)-5-(trifluoromethyl)pyridin-2-amine (300.0 mg, 0.47 mmol) and N,N-diisopropylethylamine (122.33 mg, 0.95 mmol) in dichloromethane (6 mL) was stirred at 25° C. for 0.5 hour. Then acryloyl chloride (42.91 mg, 0.47 mmol) was added and stirred at 25° C. for 1 hour. After completion, the resulting solution was diluted with ethyl acetate and washed with water. The organic layer was dried over anhydrous sodium sulfate and concentrated under vacuum. The residue was purified by flash chromatography on silica gel eluting with dichloromethane/methanol (10/1) to afford 1-[4-[7-[6-[bis[(4-methoxyphenyl)methyl]amino]-3-(trifluoromethyl)-2-pyridyl]-6-methyl-5,6,7,8-tetrahydroquinazolin-4-yl]piperazin-1-yl]prop-2-en-1-one (150 mg, 0.22 mmol, 46.1% yield) as a yellow oil. LC-MS: (ESI, m/z): 687.8 [M+H]$^+$ A solution of 1-[4-[7-[6-[bis[(4-methoxyphenyl)methyl]amino]-3-(trifluoromethyl)-2-pyridyl]-6-methyl-5,6,7,8-tetrahydroquinazolin-4-yl]piperazin-1-yl]prop-2-en-1-one (150.0 mg, 0.22 mmol) and trifluoroacetic acid (10 mL) was stirred at 50° C. for 3 hours. After completion, the solution was quenched with water, diluted with ethyl acetate and washed with brine. The organic layer was concentrated under vacuum. The crude product was further isolated by Prep-HPLC with the following conditions Column: CHIRALPAK IE, 2*25 cm, 5 um; Mobile Phase A: MTBE (10 mM NH$_3$-MeOH)—HPLC, Mobile Phase B: MeOH—HPLC; Flow rate: 20 mL/min; Gradient: 15 B to 15 B in 27 min; 220/254 nm; RT1: 17.672; RT2: 23.294. The product was purified by Chiral-Prep-HPLC with the following conditions: (Column, CHIRAL ART Cellulose-SB, 2*25 cm, 5 um; mobile phase, Hex—HPLC and ethanol-HPLC (hold 40% ethanol—HPLC in 10 min); Detector, UV 220/254 nm) to afford the title compounds. The absolute configuration of the title compounds was inferred from potency data and a protein X-ray structure of compound 21b.

Example 42a: 1-(4-((6S,7S)-7-(6-amino-3-(trifluoromethyl)pyridin-2-yl)-6-methyl-5,6,7,8-tetrahydroquinazolin-4-yl)piperazin-1-yl)prop-2-en-1-one (13 mg, 0.029 mmol, 13.3% yield) as a white solid. $^1$H NMR (400 MHz, Methanol-$d_4$) δ 8.48 (s, 1H), 7.65 (d, J=8.0 Hz, 1H), 6.83 (dd, J=16.0, 12.0 Hz, 1H), 6.46 (d, J=8.0 Hz, 1H), 6.30-6.25 (m, 1H), 5.82-5.79 (m, 1H), 3.93-3.88 (m, 2H), 3.82-3.73 (m, 4H), 3.58-3.54 (m, 2H), 3.22-3.14 (m, 2H), 3.04-2.95 (m, 1H), 2.80-2.75 (m, 1H), 2.65-2.58 (m, 1H), 2.25 (s, 1H), 0.89 (d, J=8.0 Hz, 3H). LC-MS: (ESI, m/z): 447.2 [M+H]$^+$. Chiral HPLC: CHIRALPAK IE-30.46*5 cm; 3 um; detected at 254 nm; (Hex:DCM=3:1)(0.1% DEA): EtOH=90:10; flow=1.0 mL/min; Retention time: 4.577 min (slower peak).

Example 42b: 1-(4-((6R,7R)-7-(6-amino-3-(trifluoromethyl)pyridin-2-yl)-6-methyl-5,6,7,8-tetrahydroquinazolin-4-yl)piperazin-1-yl)prop-2-en-1-one (15 mg, 0.034 mmol, 15.4% yield) as a white solid. $^1$H NMR (400 MHz, Methanol-$d_4$) δ 8.46 (s, 1H), 7.65 (d, J=8.0 Hz, 1H), 6.87 (dd, J=16.0, 12.0 Hz, 1H), 6.46 (d, J=8.0 Hz, 1H), 6.30-6.25 (m, 1H), 5.82-5.79 (m, 1H), 3.93-3.88 (m, 2H), 3.78-3.73 (m, 4H), 3.49-3.41 (m, 2H), 3.21-3.12 (m, 2H), 3.04-2.95 (m, 1H), 2.80-2.75 (m, 1H), 2.65-2.58 (m, 1H), 2.26 (s, 1H), 0.90 (d, J=8.0 Hz, 3H). LC-MS: (ESI, m/z): 447.2 [M+H]$^+$. Chiral HPLC: CHIRALPAK IE-30.46*5 cm; 3 um; detected at 254 nm; (Hex:DCM=3:1)(0.1% DEA): EtOH=90:10; flow=1.0 mL/min; Retention time: 3.815 min (Faster peak).

Example 43

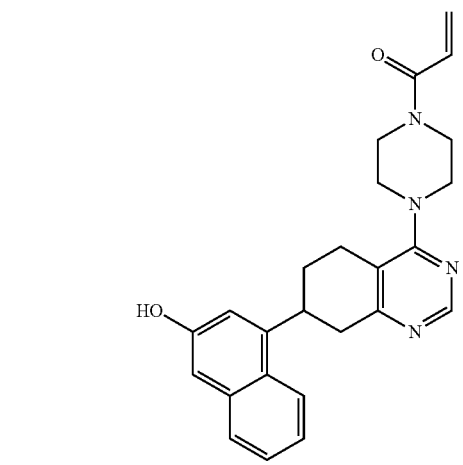

1-[4-[7-(3-hydroxy-1-naphthyl)-5,6,7,8-tetrahydroquinazolin-4-yl]piperazin-1-yl]prop-2-en-1-one

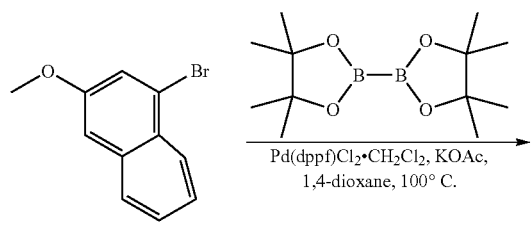

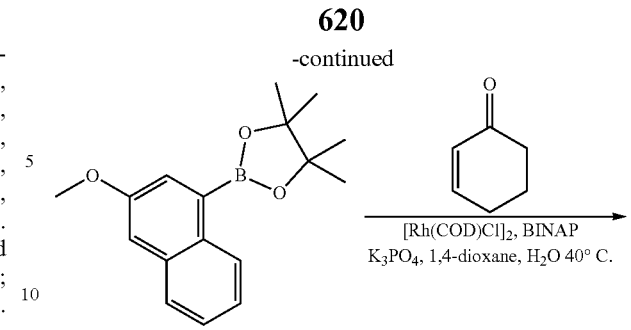

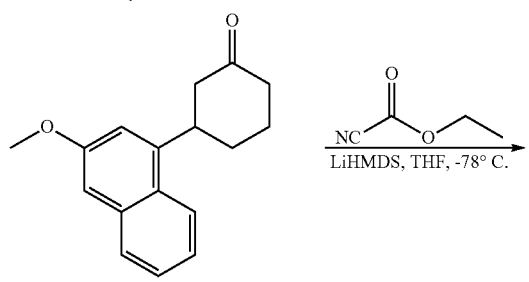

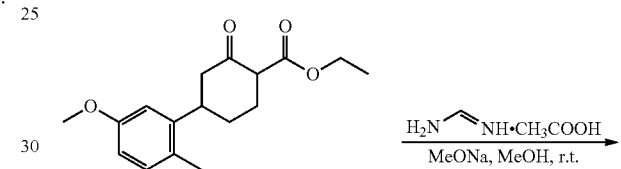

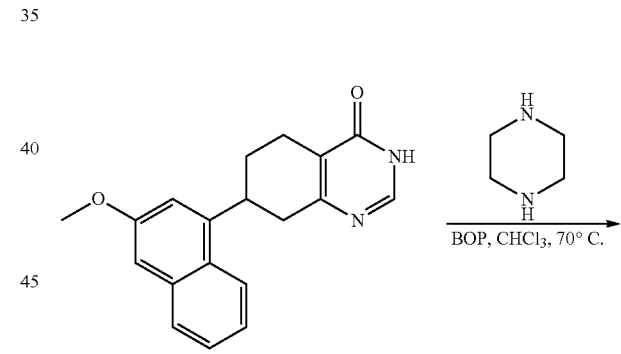

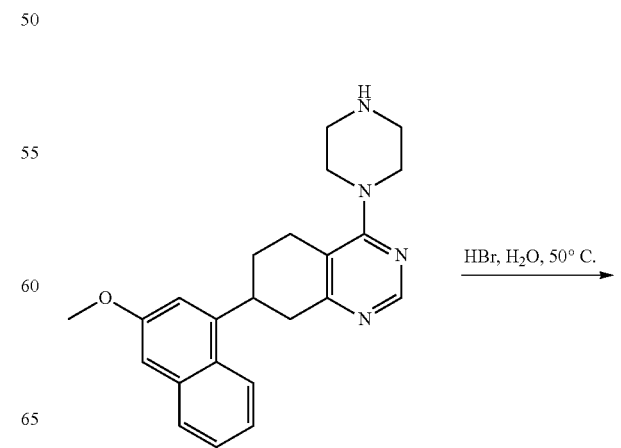

622

Step 2: 3-(3-methoxy-1-naphthyl)cyclohexanone

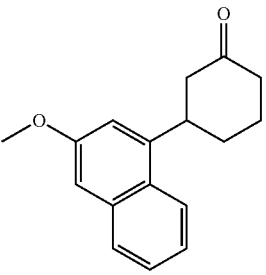

Under nitrogen, a solution of 2-(3-methoxy-1-naphthyl)-4,4,5,5-tetramethyl-1,3,2-dioxaborolane (0.2 g, 0.70 mmol) and 2-cyclohexen-1-one (0.14 g, 1.41 mmol), [Rh(CODCl)]$_2$ (0.03 g, 0.07 mmol), 1,1'-binaphthyl-2,2'-diphemyl phosphine (0.09 g, 0.14 mmol) in 1,4-dioxane (4 mL), water (1 mL) was added potassium phosphate (0.3 g, 1.41 mmol). The resulting solution was stirred at 40° C. for 0.5 hours. After completion, the solution was diluted with water and extracted with ethyl acetate. Then the organic layers were combined, dried over anhydrous sodium sulfate and concentrated under vacuum. The residue was purified by flash chromatography on silica gel eluting with ethyl acetate/petroleum ether (1/7) to afford 3-(3-methoxy-1-naphthyl)cyclohexanone (130 mg, 0.51 mmol, 72.6% yield) as a yellow solid. LCMS (ESI, m/z): 255.3 [M+H]$^+$.

Step 3: ethyl 4-(3-methoxy-1-naphthyl)-2-oxo-cyclohexanecarboxylate

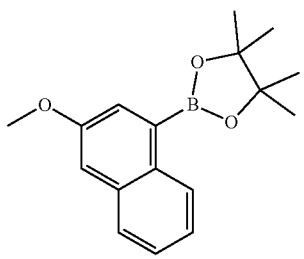

Under nitrogen, a solution of 3-(3-methoxy-1-naphthyl)cyclohexanone (0.80 g, 3.15 mmol) in tetrahydrofuran (20 mL) was added LiHMDS (3.77 mL, 3.77 mmol) (1M in THF) at −78° C. The resulting solution was stirred for 0.5h at −78° C. Then ethyl cyanoformate (0.47 g, 4.72 mmol) was added and stirred at −78° C. for 3 hours. After completion, the solution was diluted with water and extracted with ethyl acetate. Then the organic layers were combined, dried over anhydrous sodium sulfate and concentrated under vacuum. The residue was purified by flash chromatography on silica gel eluting with ethyl acetate/petroleum ether (1/5) to afford ethyl 4-(3-methoxy-1-naphthyl)-2-oxo-cyclohexanecarboxylate (0.60 g, 1.84 mmol, 58.4% yield) as a yellow solid. LCMS (ESI, m/z): 327.4 [M+H]$^+$.

621

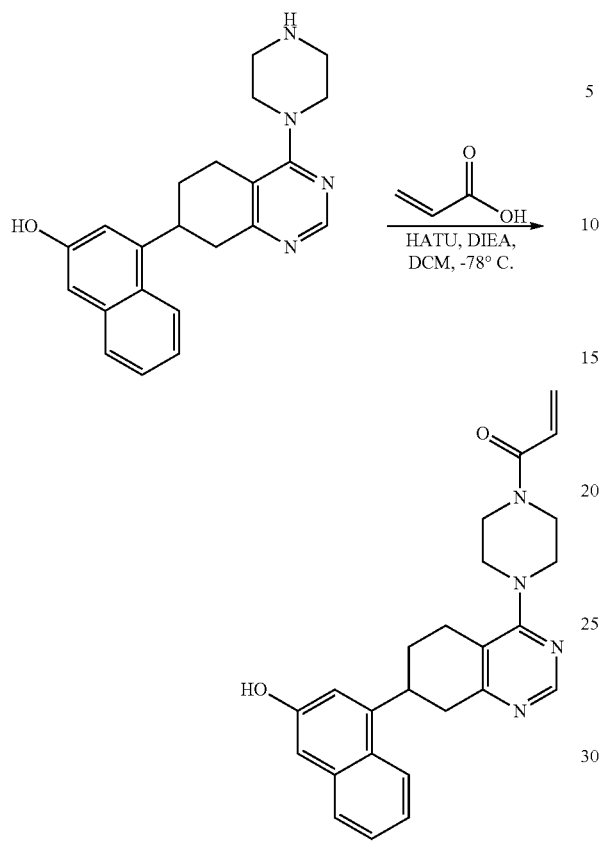

Step 1: 2-(3-methoxy-1-naphthyl)-4,4,5,5-tetramethyl-1,3,2-dioxaborolane

Under nitrogen, a solution of 1-bromo-3-methoxy-naphthalene (2.0 g, 8.44 mmol), Pd(dppf)Cl$_2$ (0.62 g, 0.84 mmol), bis(pinacolato)diboron (6.43 g, 25.31 mmol), potassium acetate (1.65 g, 16.87 mmol) in 1,4-dioxane (20 mL) was formed. The resulting solution was stirred at 100° C. for 3 hours. After completion, the solution was diluted with water and extracted with ethyl acetate. Then the organic layers were combined, dried over anhydrous sodium sulfate and concentrated under vacuum. The residue was purified by flash chromatogtaphy on silica gel eluting with petroleum ether/ethyl acetate (10/1) to afford 2-(3-methoxy-1-naphthyl)-4,4,5,5-tetramethyl-1,3,2-dioxaborolane (1.2 g, 4.2 mmol, 50.1% yield) as a yellow solid. LCMS (ESI, m/z): 285.2 [M+H]$^+$.

Step 4: 7-(3-methoxy-1-naphthyl)-5,6,7,8-tetrahydro-3H-quinazolin-4-one

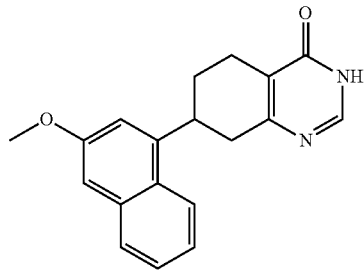 [SMILES: COc1cc(C2CCc3c(nc[nH]c3=O)C2)c2ccccc2c1]

A solution of ethyl 4-(3-methoxy-1-naphthyl)-2-oxo-cyclohexanecarboxylate (0.60 g, 1.84 mmol) and formamidine acetate (1.15 g, 11.03 mmol) in methanol (20 mL) was stirred at 25° C. Then sodium methanolate (0.99 g, 18.38 mmol) was added and stirred at 25° C. for 12 hours. After completion, the solution was diluted with water and extracted with ethyl acetate. Then the organic layers were combined, dried over anhydrous sodium sulfate and concentrated under vacuum. The residue was purified by flash chromatography on silica gel eluting with dichloromethane/methanol (8/1) to afford 7-(3-methoxy-1-naphthyl)-5,6,7,8-tetrahydro-3H-quinazolin-4-one (400 mg, 1.31 mmol, 71% yield) as a yellow solid. LCMS (ESI, m/z): 307.4 [M+H]$^+$.

Step 5: 7-(3-methoxy-1-naphthyl)-4-piperazin-1-yl-5,6,7,8-tetrahydroquinazoline

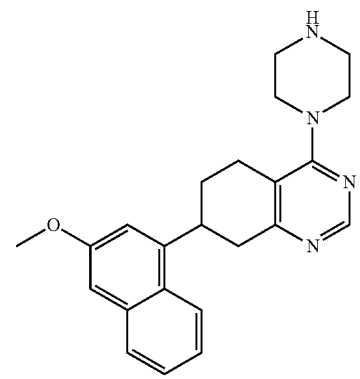 [SMILES: COc1cc(C2CCc3c(ncnc3N3CCNCC3)C2)c2ccccc2c1]

A solution of 7-(3-methoxy-1-naphthyl)-5,6,7,8-tetrahydro-3H-quinazolin-4-one (0.40 g, 1.31 mmol) and piperazine (1.12 g, 13.06 mmol) in chloroform (20 mL). Then 1H-benzotriazol-1-yloxytris (dimethylamino)phosphonium hexafluorophosphate (1.15 g, 2.61 mmol) was added and stirred at 70° C. for 9 hours. After completion, the resulting solution was concentrated under vacuum. The residue was purified by flash chromatography on silica gel eluting with dichloromethane/methanol (8/1) to afford 7-(3-methoxy-1-naphthyl)-4-piperazin-1-yl-5,6,7,8-tetrahydroquinazoline (200 mg, 0.53 mmol, 40.9% yield) as a yellow solid. LCMS (ESI, m/z): 375.5 [M+H]$^+$.

Step 6: 4-(4-piperazin-1-yl-5,6,7,8-tetrahydroquinazolin-7-yl)naphthalen-2-ol

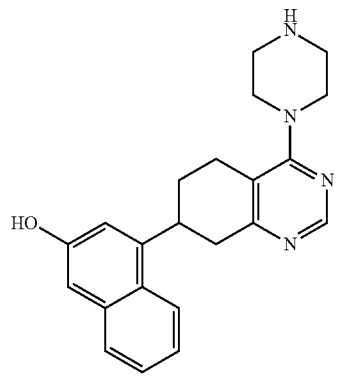

A solution of 7-(3-methoxy-1-naphthyl)-4-piperazin-1-yl-5,6,7,8-tetrahydroquinazoline (0.5 g, 1.34 mmol) and HBr—H$_2$O (10 mL) (40% in H$_2$O) in water (10 mL) was stirred at 50° C. for 1 hours. After completion, the solution was diluted with water and extracted with ethyl acetate. Then the organic layers were combined, dried over anhydrous sodium sulfate and concentrated under vacuum. The residue was purified by flash chromatography on silica gel eluting with dichloromethane/methanol (10/1) to afford 4-(4-piperazin-1-yl-5,6,7,8-tetrahydroquinazolin-7-yl)naphthalen-2-ol (0.20 g, 0.56 mmol, 41.6% yield) as a yellow oil. LCMS (ESI, m/z): 361.5 [M+H]$^+$.

Step 7: 1-[4-[7-(3-hydroxy-1-naphthyl)-5,6,7,8-tetrahydroquinazolin-4-yl]piperazin-1-yl]prop-2-en-1-one

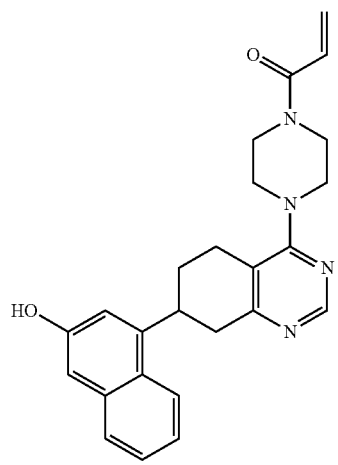

A solution of 4-(4-piperazin-1-yl-5,6,7,8-tetrahydroquinazolin-7-yl)naphthalen-2-ol (0.10 g, 0.28 mmol) and HATU (0.21 g, 0.55 mmol), N,N-diisopropylethylamine (0.14 g, 1.11 mmol) in dichloromethane (5 mL) was stirred at −78° C. for 0.5 hour. Then acrylic acid (0.03 g, 0.42 mmol) was added and stirred at −78° C. for 4 hours. After completion, the solution was diluted with water and extracted with ethyl acetate. Then the organic layers were combined, dried over anhydrous sodium sulfate and concentrated under vacuum. The crude product was further isolated by Prep-HPLC with the following conditions (Column: Xbridge Shield RP18 OBD Column 30*150 mm, 5 um; Mobile Phase A: Water (10 mmol/L NH$_4$HCO$_3$), Mobile Phase B: CAN; Flow rate: 60 mL/min; Gradient: 26% B to 50% B in 7 min; 220/254 nm; Rt: 6.53 min) to afford 1-[4-[7-(3-hydroxy-1-naphthyl)-5,6,7,8-tetrahydroquinazolin-4-yl]425iperazine-1-yl]prop-2-en-1-one (3.2 mg, 0.0068 mmol, 2.4% yield) as a white solid. LCMS (ESI, m/z): 415.2[M+H]$^+$.

Example 43: $^1$H NMR (400 MHz, Methanol-d$_4$) δ 8.50 (s, 1H), 8.08 (d, J=8.0 Hz, 1H), 7.70 (d, J=8.0 Hz, 1H), 7.43-7.39 (m, 1H), 7.36-7.32 (m, 1H), 7.04-7.02 (m, 2H), 6.86-6.80 (m, 1H), 6.27-6.24 (m, 1H), 5.80-5.75 (m, 1H), 4.06-3.99 (m, 1H), 3.92-3.86 (m, 2H), 3.80-3.75 (m, 2H), 3.68-3.63 (m, 2H), 3.53-3.46 (m, 2H), 3.38-3.36 (m, 1H), 3.05-2.90 (m, 2H), 2.80-2.74 (m, 1H), 2.32-2.28 (m, 1H), 2.07-1.97 (m, 1H).

Examples 44a and 44b

1-[4-[(7R)-7-(4-isoquinolyl)-5,6,7,8-tetrahydroquinazolin-4-yl]piperazin-1-yl]prop-2-en-1-one (Example 44a); and 1-[4-[(7S)-7-(4-isoquinolyl)-5,6,7,8-tetrahydroquinazolin-4-yl]piperazin-1-yl]prop-2-en-1-one (Example 44b)

Example 44a

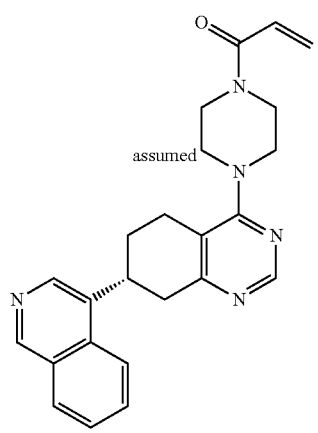

Example 44b

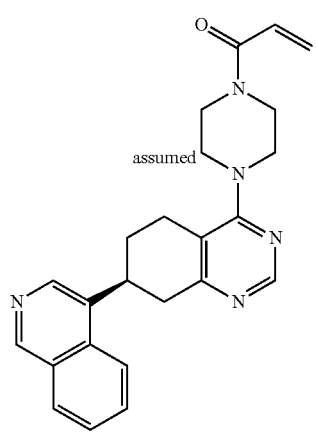

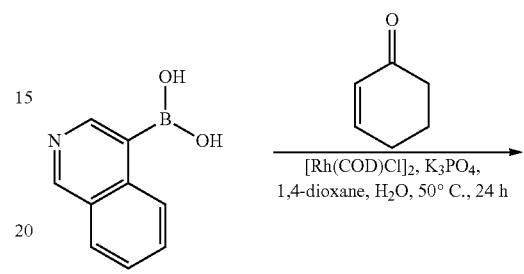

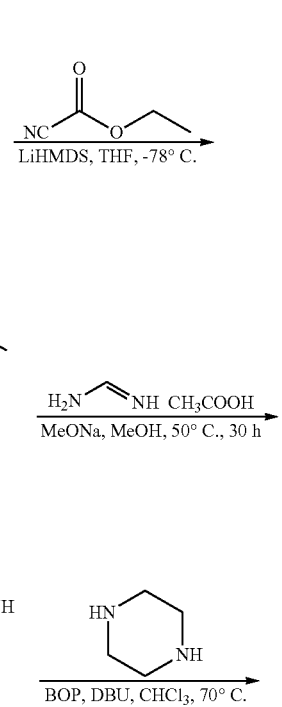

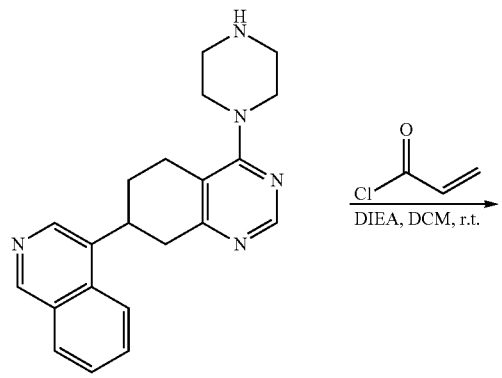

627

-continued

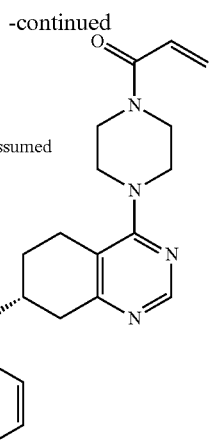

44a

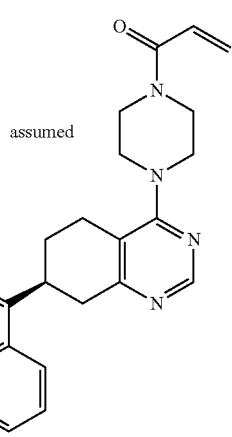

44b

Step 1: 3-(4-isoquinolyl)cyclohexanone

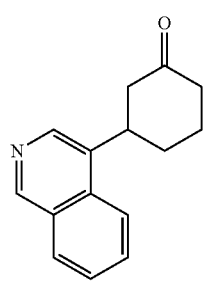 [SMILES: O=C1CCCC(c2cncc3ccccc23)C1]

Under nitrogen, a solution of isoquinoline-4-boronicacid (6.8 g, 39.3 mmol), chloro(1,5-cyclooctadiene)rhodium(I) dimer (0.97 g, 1.96 mmol) and 2-cyclohexen-1-one (7.56 g, 78.6 mmol) in 1,4-dioxane (62 mL) was stirred at 25° C. for 10 minutes. Then saturated potassium phosphate solution (5 mL, 39.3 mmol) was added and stirred at 50° C. for 24 hours. After completion, the resulting solution was concentrated under vacuum. The residue was purified by flash chromatography on silica gel eluting with dichloromethane/methanol (10/1) to afford 3-(4-isoquinolyl) cyclohexanone (6.07 g, 26.94 mmol, 68.6% yield) as brown oil. LC-MS: (ESI, m/z): 226.0 [M+H]$^+$.

628

Step 2: ethyl 4-(4-isoquinolyl)-2-oxo-cyclohexanecarboxylate

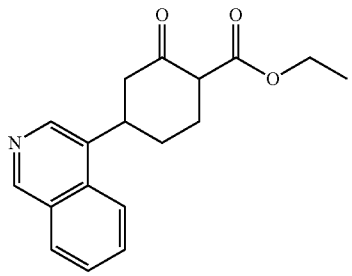 [SMILES: CCOC(=O)C1CCC(c2cncc3ccccc23)CC1=O]

Under nitrogen, a solution of 3-(4-isoquinolyl)cyclohexanone (6.0 g, 26.6 mmol) in tetrahydrofuran (40 mL) was stirred at −78° C. for 5 minutes. Lithium bis(trimethylsilyl)amide (1.0 M in THF) (40.4 mL, 40.4 mmol) was added dropwised and stirred at −78° C. for 10 minutes. Then ethyl cyanoformate (6.07 g, 61.25 mmol) was added and stirred at −78° C. for 20 minutes. After completion, the reaction was quenched with water, extracted with Ethyl acetate, dried over anhydrous sodium sulfate and concentrated under vacuum to afford crude product. The crude product was used for next step directly without purification. LC-MS: (ESI, m/z): 298.1 [M+H]$^+$.

Step 3: 7-(4-isoquinolyl)-5,6,7,8-tetrahydro-3H-quinazolin-4-one

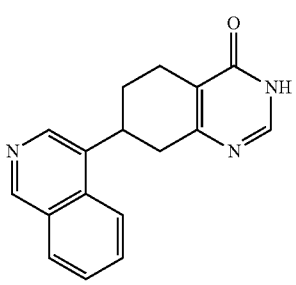 [SMILES: O=c1[nH]cnc2c1CCC(c1cncc3ccccc13)C2]

A solution of ethyl 4-(4-isoquinolyl)-2-oxo-cyclohexanecarboxylate (6.7 g, 22.53 mmol) in methanol (67 mL) was stirred at 50° C. for 10 minutes. Then sodium methanolate (12.17 g, 225.32 mmol) and formamidine acetate (14.08 g, 135.19 mmol) were added and stirred at 50° C. for 30 hours. After completion, the resulting solution was concentrated under vacuum. The residue was dissolved with ethyl acetate and washed with brine. The organic layer was dried over anhydrous sodium sulfate and concentrated under vacuum. The residue was purified by flash chromatography on silica gel eluting with dichloromethane/methanol (5/1) to afford 7-(4-isoquinolyl)-5,6,7,8-tetrahydro-3H-quinazolin-4-one (1.8 g, 6.49 mmol, 28.8% yield) as a brown oil. LC-MS: (ESI, m/z): 278.1 [M+H]$^+$.

Step 4: 7-(4-isoquinolyl)-4-piperazin-1-yl-5,6,7,8-tetrahydroquinazoline

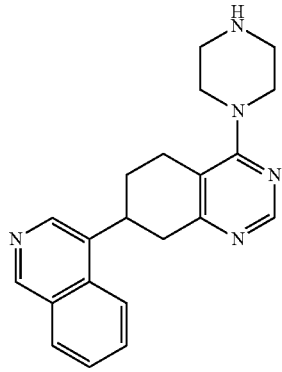 [SMILES: c1ccc2c(C3CCc4c(ncnc4N4CCNCC4)C3)cncc2c1]

A solution of 7-(4-isoquinolyl)-5,6,7,8-tetrahydro-3H-quinazolin-4-one (1.0 g, 3.61 mmol), piperazine (3.11 g, 36.06 mmol) and DBU (1.65 g, 10.82 mmol) in chloroform (100 mL) was stirred at 25° C. for 5 minutes. Then BOP (1.59 g, 3.61 mmol) was added and stirred at 70° C. for 2 hours. After completion, the resulting solution was concentrated under vacuum. The residue was purified by flash chromatography on silica gel eluting with water/acetonitrile (4:1) to afford 7-(4-isoquinolyl)-4-piperazin-1-yl-5,6,7,8-tetrahydroquinazoline (250 mg, 0.72 mmol, 20.1% yield) as a brown oil. LC-MS: (ESI, m/z): 346.2 [M+H]$^+$.

Step 5: 1-[4-[(7R)-7-(4-isoquinolyl)-5,6,7,8-tetrahydroquinazolin-4-yl]piperazin-1-yl]prop-2-en-1-one (Example 44a); and 1-[4-[(7S)-7-(4-isoquinolyl)-5,6,7,8-tetrahydroquinazolin-4-yl]piperazin-1-yl]prop-2-en-1-one (Example 44b)

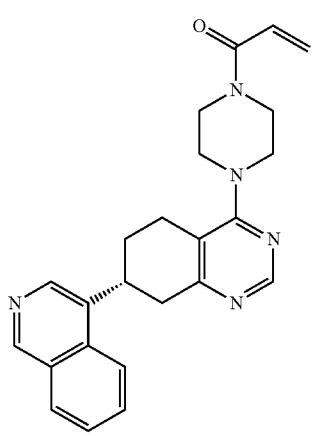

44a

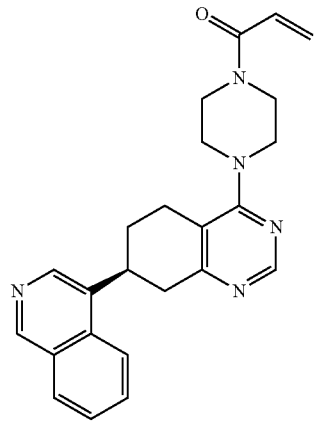

44b

A solution of 7-(4-isoquinolyl)-4-piperazin-1-yl-5,6,7,8-tetrahydroquinazoline (145.0 mg, 0.42 mmol) and N,N-diisopropylethylamine (271.2 mg, 2.1 mmol) in dichloromethane (5 mL) was stirred at 25° C. for 10 minutes. Then acryloyl chloride (37.9 mg, 0.42 mmol) was added and stirred at 25° C. for 30 minutes. The resulting solution was concentrated under vacuum. The residue was purified by flash chromatography on silica gel eluting with water/acetonitrile (3:1) to afford 35 mg crude solid. The product was further purified by Chiral-Prep-HPLC with following condition (Column, CHIRAL ART Cellulose-SB, 4.6*100 mm, 3 um; mobile phase: Mobile Phase A: (Hex:DCM=1:1)(0.1% DEA): EtOH=50:50, Mobile Phase B: Flow rate: 1 m/min; Detector, UV 254 nm) to afford the title compounds. The stereochemistry or absolute configuration of the title compounds was assigned based on potency.

Example 44a: 1-[4-[(7R)-7-(4-isoquinolyl)-5,6,7,8-tetrahydroquinazolin-4-yl]piperazin-1-yl]prop-2-en-1-one (10.4 mg, 0.02 mmol, 6.2% yield, white solid). $^1$H NMR (300 MHz, DMSO-d$_6$, ppm) δ 9.22 (s, 1H), 8.54 (s, 1H), 8.48 (s, 1H), 8.31 (d, J=9 Hz, 1H), 8.19 (d, J=9 Hz, 1H), 7.88-7.83 (m, 1H), 7.75-7.70 (m, 1H), 6.90-6.80 (m, 1H), 6.16 (dd, J=16.2, 2.4 Hz, 1H), 5.73 (dd, J=10.5, 2.4 Hz, 1H), 3.95-3.90 (m, 1H), 3.78-3.55 (m, 4H), 3.54-3.49 (m, 3H), 3.34-3.18 (m, 2H), 3.05-2.95 (m, 2H), 2.70-2.52 (m, 1H), 2.19 (m, 1H), 2.10-1.90 (m, 1H). LC-MS: (ESI, m/z): 400.3 [M+H]$^+$. Chiral HPLC: Column: CHIRAL ART Cellulose-SB, 4.6*100 mm, 3 um; detected at 254 nm; (Hex:DCM=1:1)(0.1% DEA): EtOH=50:50; Flow rate: 1 mL/min; Retention time: 1.596 min; (faster peak).

Example 44b: 1-[4-[(7S)-7-(4-isoquinolyl)-5,6,7,8-tetrahydroquinazolin-4-yl]piperazin-1-yl]prop-2-en-1-one (10 mg, 0.02 mmol, 6% yield, white solid). $^1$H NMR (300 MHz, DMSO-d$_6$, ppm) δ 9.56 (s, 1H), 8.78 (s, 1H), 8.55 (s, 1H), 8.47-8.39 (m, 2H), 8.11-8.06 (m, 1H), 7.94-7.89 (m, 1H), 6.89-6.80 (m, 1H), 6.18 (dd, J=16.8, 2.1 Hz, 1H), 5.76 (dd, J=10.2, 2.1 Hz, 1H), 4.09-3.91 (m, 3H), 3.82-3.79 (m, 2H), 3.69-3.62 (m, 2H), 3.57-3.22 (m, 2H), 3.18-3.08 (m, 3H), 2.78-2.73 (d, J=15 Hz, 1H), 2.25-2.21 (m, 1H), 2.07-2.03 (m, 1H). LC-MS: (ESI, m/z): 400.3 [M+H]$^+$. Chiral HPLC: Column: CHIRAL ART Cellulose-SB, 4.6*100 mm, 3 um; detected at 254 nm; (Hex:DCM=1:1)(0.1% DEA): EtOH=50:50; Flow rate: 1 mL/min; Retention time: 2.431 min (slower peak).

Example 45a

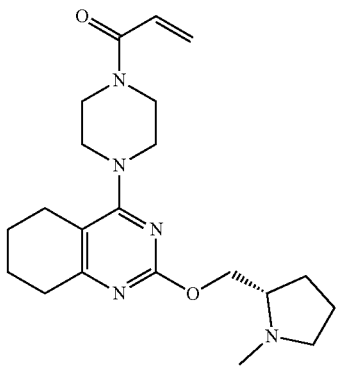 [SMILES: C=CC(=O)N1CCN(c2nc(OC[C@@H]3CCCN3C)nc3c2CCCC3)CC1]

1-[4-[2-[[(2S)-1-methylpyrrolidin-2-yl]methoxy]-5,6,7,8-tetrahydroquinazolin-4-yl]piperazin-1-yl]prop-2-en-1-one

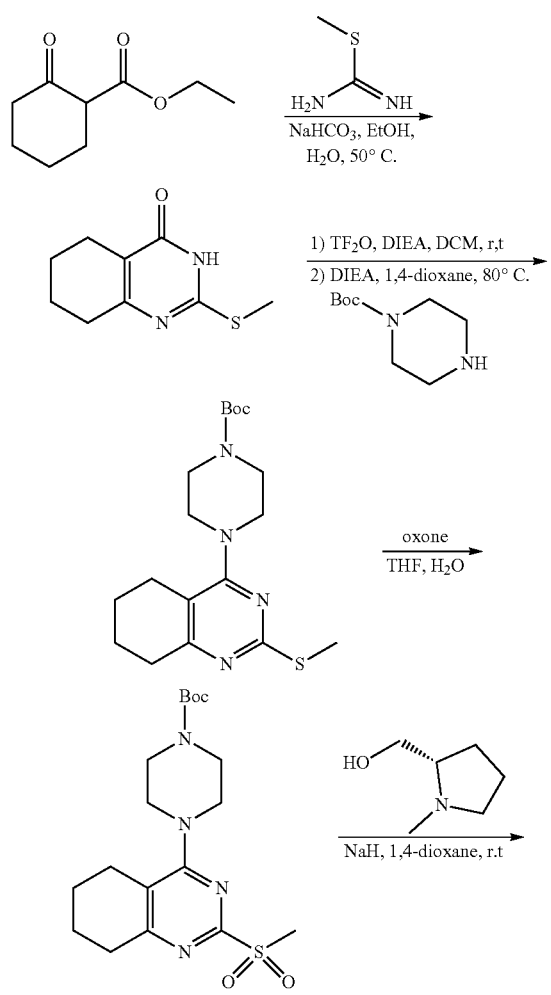

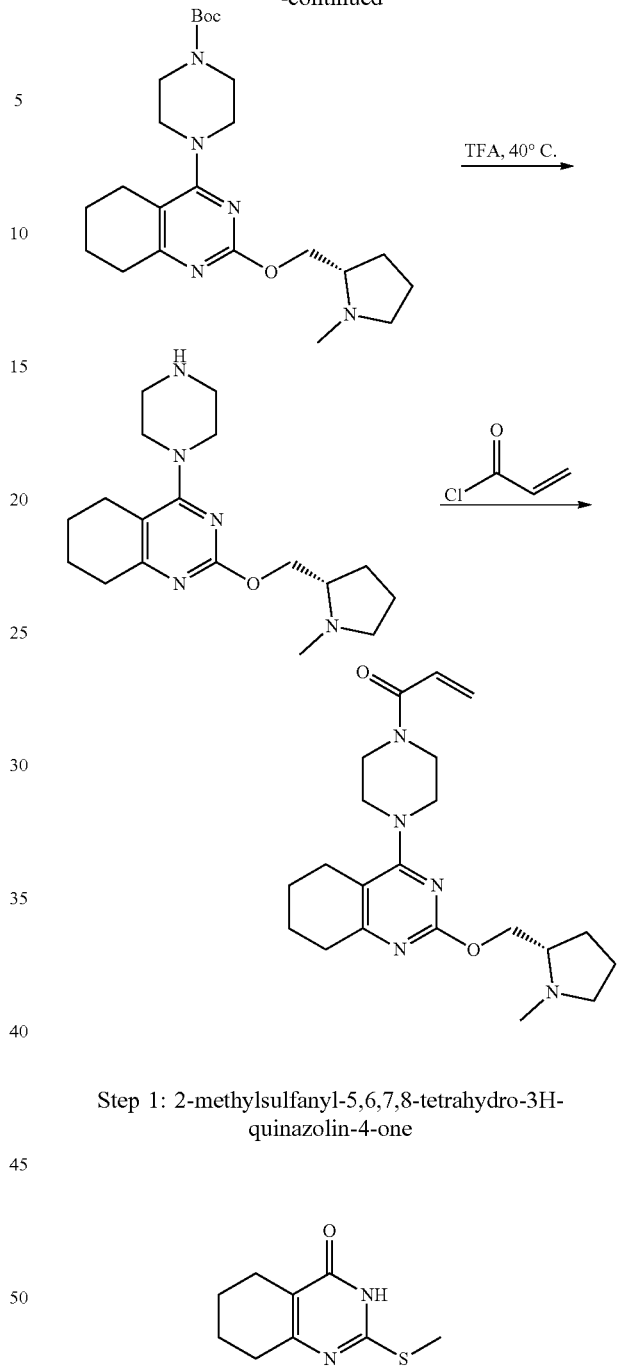

Step 1: 2-methylsulfanyl-5,6,7,8-tetrahydro-3H-quinazolin-4-one

A solution of ethyl 2-cyclohexanonecarboxylate (5.0 g, 29.3 mmol), methyl-2-thiopseudourea sulfate (55.3 g, 293.7 mmol) and sodium bicarbonate (49.4 g, 587.5 mmol) in water (10 mL) and ethanol (50 mL) was stirred for 2 hours at 50° C. After completion, the resulting solution was concentrated under vacuum. The residue was dissolved with ethyl acetate and washed with brine. The organic layer was dried over anhydrous sodium sulfate and concentrated under vacuum. The residue was purified by flash chromatography on silica gel eluting with dichloromethane/methanol (10/1) to afford 2-methylsulfanyl-5,6,7,8-tetrahydro-3H-quinazolin-4-one (5.1 g, 88.5%) as an orange solid. LC-MS: (ESI, m/z): 197.1 [M+H]$^+$

Step 2: tert-butyl 4-(2-methylsulfanyl-5,6,7,8-tetrahydroquinazolin-4-yl)piperazine-1-carboxylate

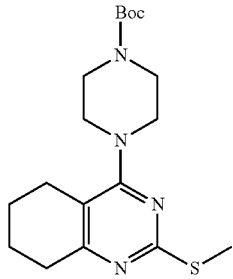 [SMILES: CSc1nc2c(c(N3CCN(C(=O)OC(C)(C)C)CC3)n1)CCCC2]

A solution of 2-methylsulfanyl-5,6,7,8-tetrahydro-3H-quinazolin-4-one (2.6 g, 13.25 mmol) in dichloromethane (26 mL) was stirred at 25° C. for 5 minutes. Then N,N-diisopropylethylamine (5.14 g, 39.74 mmol) and trifluoromethanesulfonic anhydride (6.73 g, 23.84 mmol) were added and stirred at 25° C. for 2 hours. After completion, the reaction was concentrated under reduced pressure. Then the residue, tert-butyl 1-piperazinecarboxylate (12.2 g, 65.48 mmol) and N,N-diisopropylethylamine (5.08 g, 39.29 mmol) in 1, 4-dioxane (695 mL) was stirred at 80° C. for 2 hours. After completion, the resulting solution was concentrated under vacuum. The residue was purified by flash chromatography on silica gel eluting with dichloromethane/methanol (10/1) to afford tert-butyl 4-(2-methylsulfanyl-5, 6,7,8-tetrahydroquinazolin-4-yl)piperazine-1-carboxylate (2.5 g, 6.85 mmol, 52.4% yield) as a white solid. LC-MS: (ESI, m/z): 365.4 [M+H]$^+$

Step 3: tert-butyl 4-(2-methylsulfonyl-5,6,7,8-tetrahydroquinazolin-4-yl)piperazine-1-carboxylate

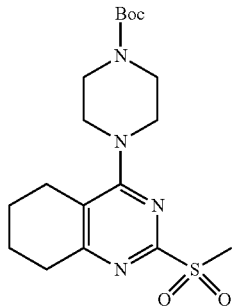 [SMILES: CC(C)(C)OC(=O)N1CCN(c2nc(S(C)(=O)=O)nc3c2CCCC3)CC1]

A solution of tert-butyl 4-(2-methylsulfanyl-5,6,7,8-tetrahydroquinazolin-4-yl)piperazine-1-carboxylate (2.0 g, 5.49 mmol) and potassium peroxymonosulfate (10.12 g, 16.46 mmol) in tetrahydrofuran (20 mL) and water (10 mL) was stirred at room temperature for 3 hours. After completion, the reaction was quenched by saturated sodium sulfite solution, extracted with ethyl acetate, dried over anhydrous sodium sulfate and concentrated under vacuum to afford crude product. The crude product was used for next step directly without purification. LC-MS: (ESI, m/z): 397.4 [M+H]$^+$

Step 4: tert-butyl 4-[2-[[(2S)-1-methylpyrrolidin-2-yl]methoxy]-5,6,7,8-tetrahydroquinazolin-4-yl]piperazine-1-carboxylate

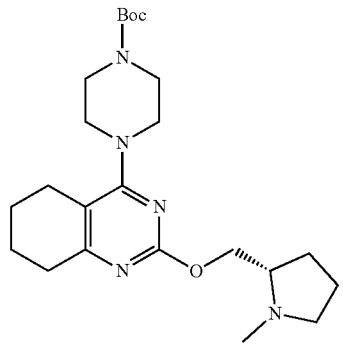 [SMILES: CN1CCC[C@H]1COc1nc2c(c(N3CCN(C(=O)OC(C)(C)C)CC3)n1)CCCC2]

A solution of sodium hydride (0.68 g, 28.25 mmol, 60% dispersion in mineral oil) and N-methyl-1-prolinol (1.86 g, 16.14 mmol) in 1,4-dioxane (16 mL) was stirred at 0° C. for 10 minutes. Then tert-butyl 4-(2-methylsulfonyl-5,6,7,8-tetrahydroquinazolin-4-yl)piperazine-1-carboxylate (1.6 g, 4.04 mmol) was added and stirred at room temperature for 30 minutes. After completion, the reaction was quenched with saturated ammonium chloride solution and extracted with dichloromethane. Then the organic layers were collected, dried over anhydrous sodium sulfate and concentrated under vacuum. The residue was purified by flash chromatography on silica gel eluting with acetonitrile/water (1/5) to afford tert-butyl 4-[2-[[(2S)-1-methylpyrrolidin-2-yl]methoxy]-5,6,7,8-tetrahydroquinazolin-4-yl]piperazine-1-carboxylate (1.4 g, 3.24 mmol, 80.4% yield) as a yellow solid. LC-MS: (ESI, m/z): 432.3 [M+H]$^+$

Step 5: (S)-2-((1-methylpyrrolidin-2-yl)methoxy)-4-(piperazin-1-yl)-5,6,7,8-tetrahydroquinazoline

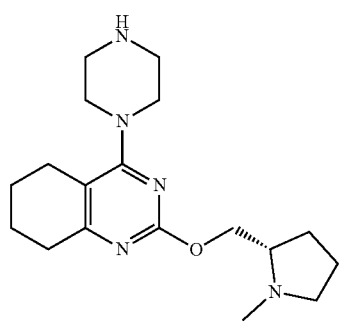 [SMILES: CN1CCC[C@H]1COc1nc2c(c(N3CCNCC3)n1)CCCC2]

A solution of tert-butyl 4-[2-[[(2S)-1-methylpyrrolidin-2-yl]methoxy]-5,6,7,8-tetrahydroquinazolin-4-yl]piperazine-1-carboxylate (1.4 g, 3.244 mmol) in trifluoroacetic acid (6.4 g, 56.11 mmol) was stirred at 40° C. for 2 hours. The resulting solution was concentrated under vacuum. The residue was purified by flash chromatography on silica gel eluting with Acetonitrile/water (1:4) to afford (S)-2-((1-methylpyrrolidin-2-yl)methoxy)-4-(piperazin-1-yl)-5,6,7,8-tetrahydroquinazoline (0.6 g, 1.81 mmol, 56.1% yield) as a yellow solid. LC-MS: (ESI, m/z): 332.2 [M+H]$^+$

Step 6: 1-[4-[2-[[(2S)-1-methylpyrrolidin-2-yl]methoxy]-5,6,7,8-tetrahydroquinazolin-4-yl]piperazin-1-yl]prop-2-en-1-one

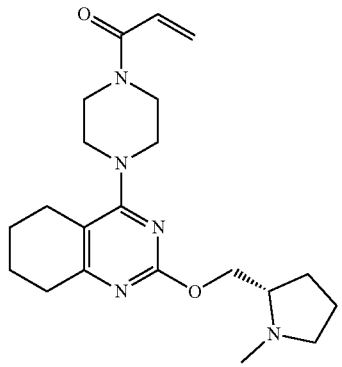 [SMILES: C=CC(=O)N1CCN(c2nc(OC[C@@H]3CCCN3C)nc3c2CCCC3)CC1]

A solution of (S)-2-((1-methylpyrrolidin-2-yl)methoxy)-4-(piperazin-1-yl)-5,6,7,8-tetrahydroquinazoline (0.6 g, 1.81 mmol) in dichloromethane (10 mL) was stirred at −78° C. for 5 min. Then acryloyl chloride (0.2 g, 2.2 mmol) was added and stirred at −78° C. for 10 minutes. After completion, the resulting solution was concentrated under vacuum. The residue was purified by flash chromatography on silica gel eluting with dichloromethane/methanol (10/1) to afford 1-[4-[2-[[(2S)-1-methylpyrrolidin-2-yl]methoxy]-5,6,7,8-tetrahydroquinazolin-4-yl]piperazin-1-yl]prop-2-en-1-one (60 mg, 0.16 mmol, 8.8% yield) as a while solid.

Example 45a: $^1$H NMR (300 MHz, DMSO-$d_6$, ppm) δ 6.83 (dd, J=16.7, 10.4 Hz, 1H), 6.14 (dd, J=16.7, 2.4 Hz, 1H), 5.80-5.63 (m, 1H), 4.51-4.33 (m, 2H), 3.77-3.54 (m, 5H), 3.35 (s, 7H), 2.96-2.81 (m, 1H), 2.75 (s, 3H), 2.65 (m, 2H), 2.22-2.07 (m, 1H), 2.01-1.84 (m, 2H), 1.82-1.69 (m, 3H), 1.67-1.55 (m, 2H). LC-MS: (ESI, m/z): 386.3 [M+H]$^+$.

Examples 46a and 46b

Example 46a

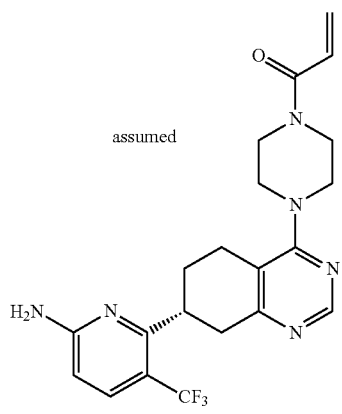

Example 46b

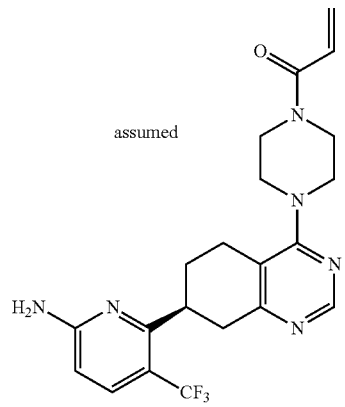

(R)-1-(4-(7-(6-amino-3-(trifluoromethyl)pyridin-2-yl)-5,6,7,8-tetrahydroquinazolin-4-yl)piperazin-1-yl)prop-2-en-1-one (Example 46a); and (S)-1-(4-(7-(6-amino-3-(trifluoromethyl)pyridin-2-yl)-5,6,7,8-tetrahydroquinazolin-4-yl)piperazin-1-yl)prop-2-en-1-one (Example 46b)

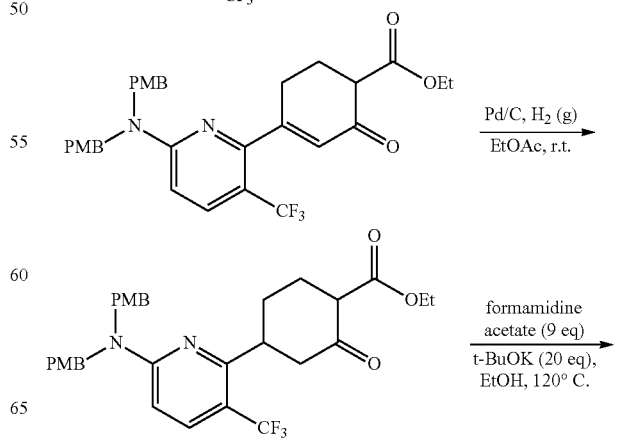

637
-continued

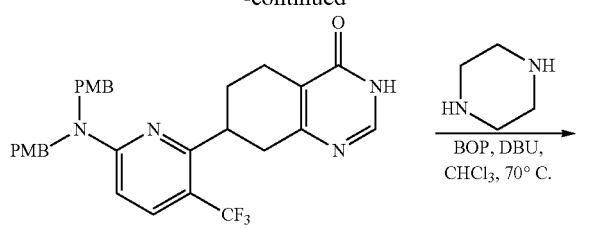

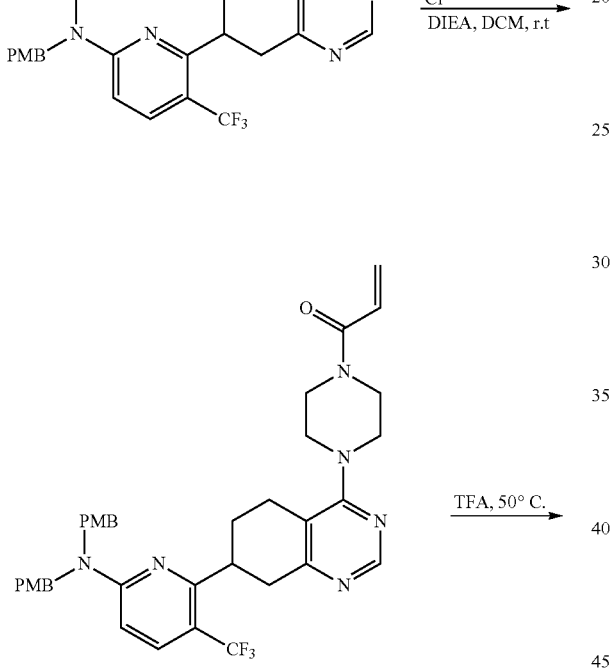

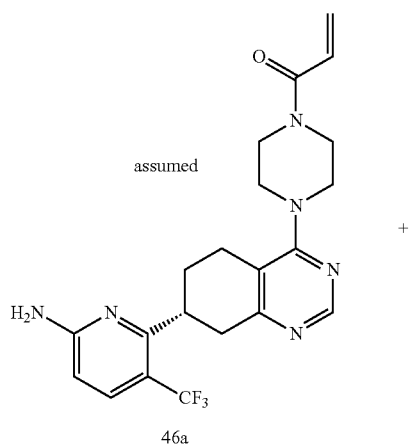

638
-continued

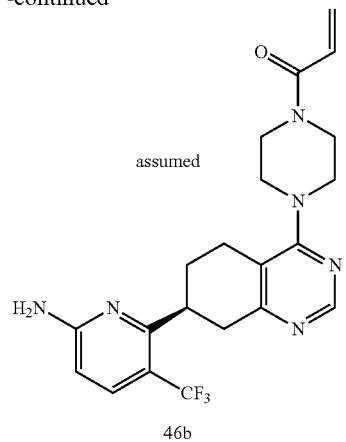

46b

Step 1: 6-chloro-N,N-bis[(4-methoxyphenyl)methyl]-5-(trifluoromethyl)pyridin-2-amine

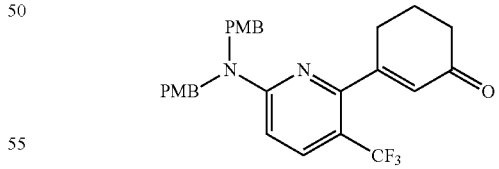

To a solution of 6-chloro-5-(trifluoromethyl)pyridin-2-amine (18.0 g, 91.58 mmol) and t-BuOK (30.77 g, 274.73 mmol) in DMF (200 mL) was added 4-methoxybenzylchloride (71.43 g, 457.88 mmol) at 25° C. and stirred at 25° C. for 1 hour. After completion, the reaction mixture was diluted with water and extracted with ethyl acetate. The organic layers were combined and concentrated under vacuum. The residue was purified by flash chromatography on silica gel eluting with petroleum ether/ethyl acetate (17%) to afford 22 g (55%) of 6-chloro-N,N-bis[(4-methoxyphenyl)methyl]-5-(trifluoromethyl)pyridin-2-amine as a yellow solid. LC-MS: (ESI, m/z): 437.1 [M+H]⁺.

Step 2: 3-[6-[bis[(4-methoxyphenyl)methyl]amino]-3-(trifluoromethyl)-2-pyridyl]cyclohex-2-en-1-one Under nitrogen, a solution of 6-chloro-N,N-bis[(4-methoxyphenyl)methyl]-5-(trifluoromethyl)pyridin-2-amine (8.07 g, 18.47 mmol), 3-(4,4,5,5-tetramethyl-1,3,2-dioxaborolan-2-yl)cyclohex-2-en-1-one (6.15 g, 27.71 mmol), bis(triphenylphosphine)palladium(II) chloride (1.3 g, 1.85 mmol), potassium fluoride (2.14 g, 36.95 mmol) and water (54 mL) in acetonitrile (270 mL) was stirred at 110° C. for 12 hours. After completion, the resulting solution was concentrated under vacuum. The residue was purified by flash chromatography on silica gel eluting with petroleum Step 3: ethyl 4-[6-[bis[(4-methoxyphenyl)methyl]
amino]-3-(trifluoromethyl)-2-pyridyl]-2-oxo-cyclo-
hex-3-ene-1-carboxylate

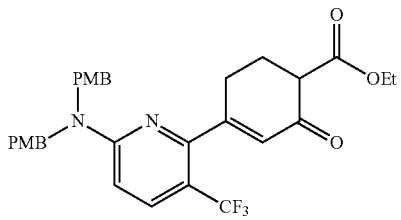

A solution of 3-[6-[bis[(4-methoxyphenyl)methyl]
amino]-3-(trifluoromethyl)-2-pyridyl]cyclohex-2-en-1-one
(8.1 g, 16.31 mmol) and lithium bis(trimethylsilyl)amide
(32.63 mL, 32.63 mmol) in tetrahydrofuran (80 mL) was
stirred at −78° C. for 1 hour. Then ethyl cyanoformate (4.04
g, 40.78 mmol) was added and stirred at −78° C. for 2 hours.
After completion, the resulting solution was concentrated
under vacuum. The residue was purified by flash chroma-
tography on silica gel eluting with petroleum ether/ethyl
acetate (20%) to afford 7.2 g (77.6%) of ethyl 4-[6-[bis[(4-
methoxyphenyl)methyl]amino]-3-(trifluoromethyl)-2-
pyridyl]-2-oxo-cyclohex-3-ene-1-carboxylate as a yellow
oil. LC-MS: (ESI, m/z): 569.2 [M+H]$^+$.

Step 4: ethyl 4-[6-[bis[(4-methoxyphenyl)methyl]
amino]-3-(trifluoromethyl)-2-pyridyl]-2-oxo-cyclo-
hexanecarboxylate

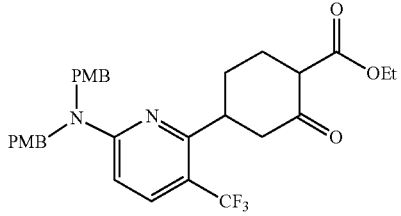

Under hydrogen, a solution of ethyl 4-[6-[bis[(4-
methoxyphenyl)methyl]amino]-3-(trifluoromethyl)-2-
pyridyl]-2-oxo-cyclohex-3-ene-1-carboxylate (7.2 g, 12.66
mmol) and Pd/C (12.663 mmol) in ethyl acetate (23 mL)
was stirred for 12 hours at 25° C. After completion, the
solution was filtered and the filtrate was concentrated under
reduced pressure. The residue was purified by flash chro-
matography on silica gel eluting with petroleum ether/ethyl
acetate (20%) to afford 6.29 g (87.1%) of ethyl 4-[6-[bis
[(4-methoxyphenyl)methyl]amino]-3-(trifluoromethyl)-2-
pyridyl]-2-oxo-cyclohexanecarboxylate as a yellow oil. LC-
MS: (ESI, m/z): 571.3 [M+H]$^+$.

Step 5: 7-[6-[bis[(4-methoxyphenyl)methyl]amino]-
3-(trifluoromethyl)-2-pyridyl]-5,6,7,8-tetrahydro-
3H-quinazolin-4-one

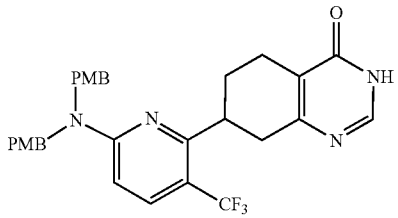

A solution of ethyl 4-[6-[bis[(4-methoxyphenyl)methyl]
amino]-3-(trifluoromethyl)-2-pyridyl]-2-oxo-cyclohexan-
ecarboxylate (6.29 g, 11.4 mmol), formamidine acetate
(11.37 g, 109.32 mmol) and potassium tert-butoxide (15.92
g, 142.12 mmol) in ethanol (100 mL) was stirred at 120° C.
for 2 hours. After completion, the resulting solution was
concentrated under vacuum. The residue was purified by
flash chromatography on silica gel eluting with dichlo-
romethane/methanol (5%) to afford 2.9 g (48.2%) of 7-[6-
[bis[(4-methoxyphenyl)methyl]amino]-3-(trifluoromethyl)-
2-pyridyl]-5,6,7,8-tetrahydro-3H-quinazolin-4-one as a
black solid. LC-MS: (ESI, m/z): 551.2 [M+H]$^+$.

Step 6: N,N-bis[(4-methoxyphenyl)methyl]-6-(4-
piperazin-1-yl-5,6,7,8-tetrahydroquinazolin-7-yl)-5-
(trifluoromethyl)pyridin-2-amine

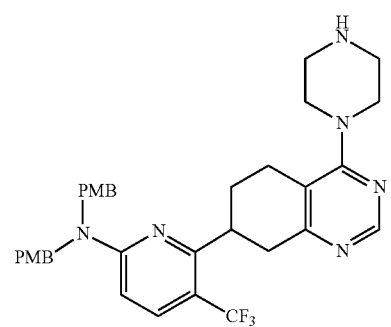

A solution of 7-[6-[bis[(4-methoxyphenyl)methyl]
amino]-3-(trifluoromethyl)-2-pyridyl]-5,6,7,8-tetrahydro-
3H-quinazolin-4-one (1.5 g, 2.72 mmol), piperazine (0.7 g,
8.17 mmol), benzotriazol-1-yloxytris(dimethylamino)-
phosphonium hexafluorophosphate (1.57 g, 3.54 mmol), and
1,8-Diazabicyclo[5.4.0]undec-7-ene (1.24 g, 8.17 mmol) in
chloroform (25 mL) was stirred at 70° C. for 24 hours. After
completion, the solvent was diluted with water and extracted
with dichloromethane. The organic layers were combined
and concentrated under vacuum. The crude product would
be directly used in the next step without purification. LC-
MS: (ESI, m/z): 619.3 [M+H]$^+$.

Step 7: 1-[4-[7-[6-[bis[(4-methoxyphenyl)methyl]amino]-3-(trifluoromethyl)-2-pyridyl]-5,6,7,8-tetrahydroquinazolin-4-yl]piperazin-1-yl]prop-2-en-1-one

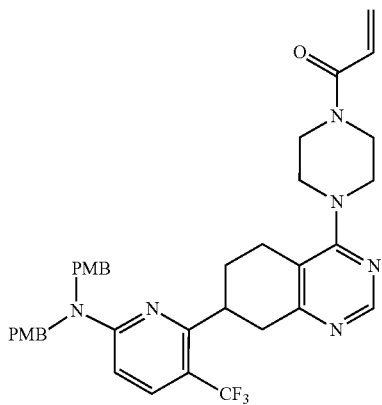

A solution of N,N-bis[(4-methoxyphenyl)methyl]-6-(4-piperazin-1-yl-5,6,7,8-tetrahydroquinazolin-7-yl)-5-(trifluoromethyl)pyridin-2-amine (1.75 g, 2.83 mmol) and N,N-diisopropylethylamine (1.82 g, 14.14 mmol) in dichloromethane (30 mL) was stirred at 0° C. for 5 minutes. Then acryloyl chloride (0.23 g, 2.55 mmol) was added at 0° C. and stirred at 25° C. for 2 hours. After completion, the resulting solution was concentrated under vacuum. The residue was purified by a reversed-phase chromatography to afford 0.97 g (51%) of 1-[4-[7-[6-[bis[(4-methoxyphenyl)methyl]amino]-3-(trifluoromethyl)-2-pyridyl]-5,6,7,8-tetrahydroquinazolin-4-yl]piperazin-1-yl]prop-2-en-1-one as a light yellow solid. LC-MS: (ESI, m/z): 673.3 [M+H]$^+$.

Step 8: (R)-1-(4-(7-(6-amino-3-(trifluoromethyl)pyridin-2-yl)-5,6,7,8-tetrahydroquinazolin-4-yl)piperazin-1-yl)prop-2-en-1-one (Example 46a) and (S)-1-(4-(7-(6-amino-3-(trifluoromethyl)pyridin-2-yl)-5,6,7,8-tetrahydroquinazolin-4-yl)piperazin-1-yl)prop-2-en-1-one (Example 46b)

46a

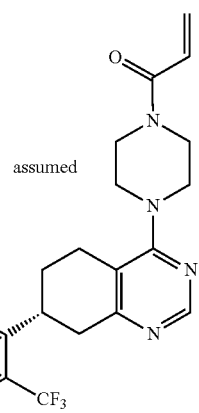

assumed

46b

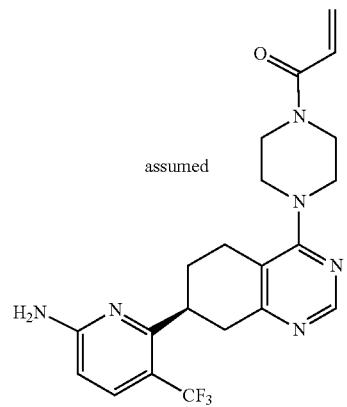

assumed

A solution of 1-[4-[7-[6-[bis[(4-methoxyphenyl)methyl]amino]-3-(trifluoromethyl)-2-pyridyl]-5,6,7,8-tetrahydroquinazolin-4-yl]piperazin-1-yl]prop-2-en-1-one (950.0 mg, 1.41 mmol) in trifluoroacetic acid (70 mL, 1.41 mmol) was stirred at 50° C. for 8 hours. After completion, the resulting solution was concentrated under vacuum. The residue was purified by a reversed-phase chromatography directly with the following conditions: Column, C18 silica gel; mobile phase, A: water, B: MeCN, B % (5%-70% in 30 min); Detector, UV 254 nm to afford 380 mg of crude product as a white solid. The product was further purified by Chiral-Prep-HPLC with following condition (Column, CHIRALPAK ID-3 4.6*50 mm 3 um; mobile phase, Hex (0.1% DEA):IPA=50:50; Detector, 254 nm; Flow, 1.0 m/min; Temperature: 25° C., 220/254 nm) to afford the title compounds. The stereochemistry or absolute configuration of the title compounds was assigned based on potency.

Example 46a: (R)-1-(4-(7-(6-amino-3-(trifluoromethyl)pyridin-2-yl)-5,6,7,8-tetrahydroquinazolin-4-yl)piperazin-1-yl)prop-2-en-1-one (115.6 mg, 18.9% yield, white solid). $^1$H NMR (400 MHz, DMSO-d$_6$, ppm) δ 8.47 (s, 1H), 7.61 (d, J=8.0 Hz, 1H), 6.85-6.79 (m, 1H), 6.63 (s, 2H), 6.38 (d, J=8.0 Hz, 1H), 6.14 (dd, J=16.8, 2.4 Hz, 1H), 5.71 (dd, J=8.0, 2.4 Hz, 1H), 3.73-3.70 (m, 2H), 3.61-3.60 (m, 2H), 3.52-3.47 (m, 2H), 3.27-3.17 (m, 4H), 2.85-2.79 (m, 2H), 2.77-2.60 (m, 1H), 1.96-1.93 (m, 1H), 1.79-1.68 (m, 1H). LC-MS: (ESI, m/z): 433.2 [M+H]$^+$. Chiral HPLC: Column: CHIRALPAK ID-3 4.6*50 mm 3 um; detected at 254 nm; Hex (0.1% DEA):IPA=50:50, Flow rate: 1 mL/min; Retention time: 1.597 min; (Faster peak).

Example 46b: (S)-1-(4-(7-(6-amino-3-(trifluoromethyl)pyridin-2-yl)-5,6,7,8-tetrahydroquinazolin-4-yl)piperazin-1-yl)prop-2-en-1-one (131.7 mg, 21.6% yield, white solid). $^1$H NMR (400 MHz, DMSO-d$_6$, ppm) δ 8.47 (s, 1H), 7.61 (d, J=8.0 Hz, 1H), 6.86-6.79 (m, 1H), 6.63 (s, 2H), 6.38 (d, J=8.0 Hz, 1H), 6.14 (dd, J=16.8, 2.4 Hz, 1H), 5.71 (dd, J=8.0, 2.4 Hz, 1H), 3.74-3.70 (m, 2H), 3.61-3.60 (m, 2H), 3.52-3.47 (m, 2H), 3.27-3.20 (m, 4H), 2.85-2.79 (m, 2H), 2.64-2.60 (m, 1H), 1.96-1.91 (m, 1H), 1.79-1.68 (m, 1H). LC-MS: (ESI, m/z): 433.2 [M+H]$^+$. Chiral HPLC: Column: CHIRALPAK ID-3 4.6*50 mm 3 um; detected at 254 nm; Hex (0.1% DEA):IPA=50:50, Flow rate: 1 mL/min; Retention time: 2.452 min; (Slower peak).

Examples 47a, 47b, 47c, and 47d
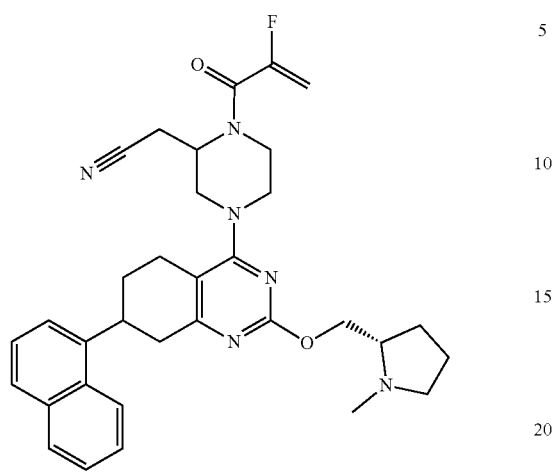
2-[1-(2-Fluoroprop-2-enoyl)-4-[2-[[(2S)-1-methylpyrrolidin-2-yl]methoxy]-7-(1-naphthyl)-5,6,7,8-tetrahydroquinazolin-4-yl]piperazin-2-yl]acetonitrile (Mixture of four compounds separated by cSFC)
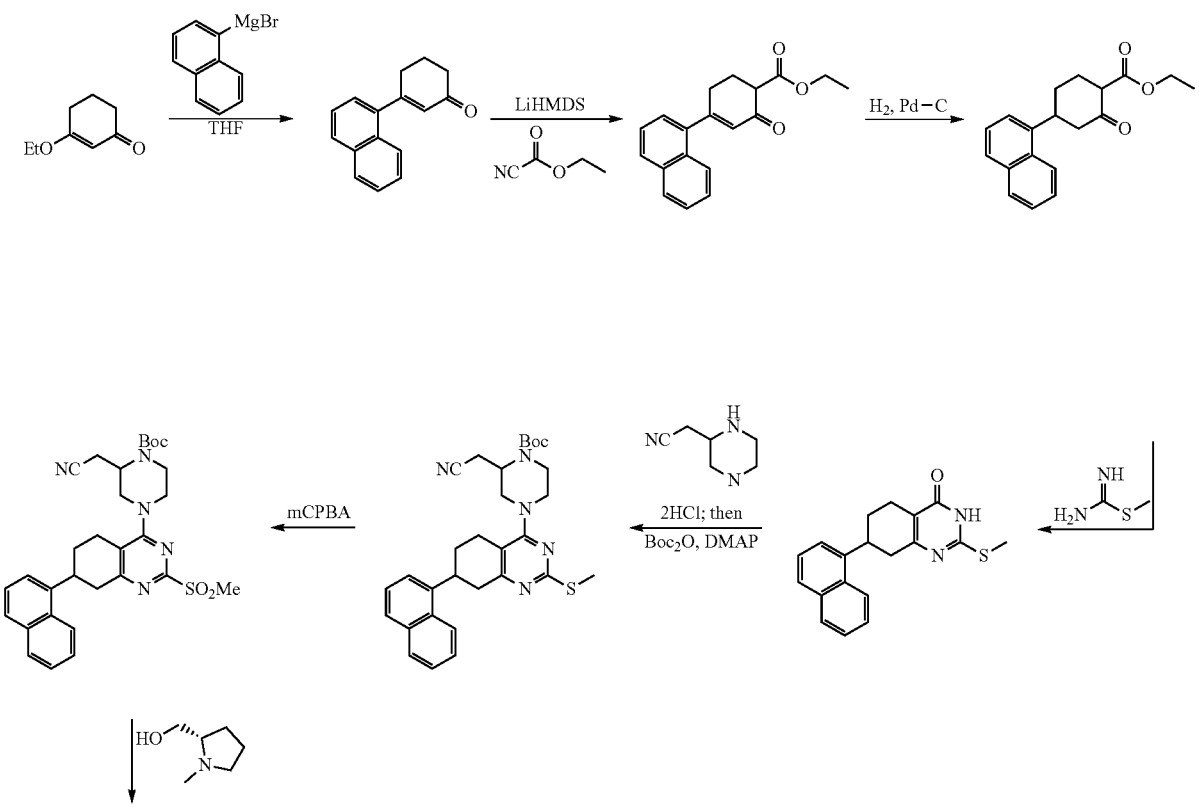

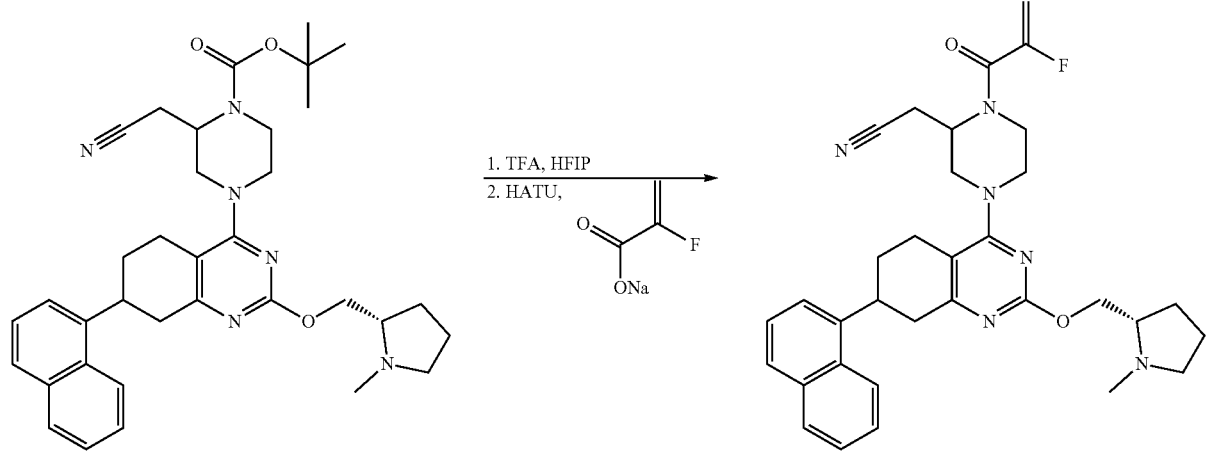

Step 1: 3-(1-Naphthyl)cyclohex-2-en-1-one

Step 2: Ethyl 4-(1-naphthyl)-2-oxo-cyclohex-3-ene-1-carboxylate

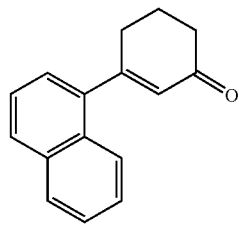 [SMILES: O=C1C=C(c2cccc3ccccc23)CCC1]

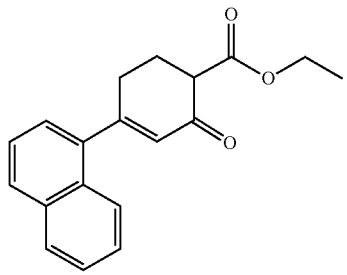 [SMILES: CCOC(=O)C1CCC(c2cccc3ccccc23)=CC1=O]

To a 200 mL RBF was added 1-Naphthylmagnesium bromide (50.00 mL, 25.0 mmol, 50.00 mL). The mixture was cooled to −78° C. and 3-ethoxy-2-cyclohexen-1-one (1 equiv., 25.0 mmol, 3500 mg, 3.51 mL) was added. The reaction was stirred for 45 minutes at −78° C. and warmed to room temperature. The reaction was quenched with 1N HCl (60 mL) and the mixture was poured into a separatory funnel and the layers were separated. The aqueous layer was extracted with isopropyl acetate (10 mL). The organic layers were combined and concentrated and chromatographed with silica gel using isopropyl acetate/heptane mixtures to afford 3.5 g of the desired product as a clear oil. 1H NMR matched literature reported values (Tetrahedron, 65, 2009, 489). $^1$H NMR (400 MHz, Chloroform-d) δ 7.95-7.76 (m, 3H), 7.55-7.44 (m, 3H), 7.32 (dd, J=7.1, 1.2 Hz, 1H), 6.21 (d, J=1.6 Hz, 1H), 2.77 (td, J=6.0, 1.6 Hz, 2H), 2.60 (t, J=6.7 Hz, 2H), 2.26 (p, J=6.3 Hz, 2H).

To a solution of 3-(1-naphthyl)cyclohex-2-en-1-one (5.1 g, 22.9 mmol) in dry THF (100 mL) cooled in dry-ice acetone bath was added lithium hexamethyldisilazide (45.9 mL, 1 M) and the resulting mixture stirred for 1 hour. To this was added ethyl cyanofomate (3.40 mL, 34.4 mmol) neat and the mixture was stirred for 0.5 hours. The dry-ice bath was removed and the reaction mixture was quenched with saturated ammonium chloride solution and was allowed to warm to room temperature. The reaction mixture was diluted with iso-propylacetate (IPAC) and the organic layer separated. The organic layer was washed with brine, dried over sodium sulfate, concentrated and the residue was purified by flash chromatography (silica gel, 0-30% IPAC/heptane) to obtain ethyl 4-(1-naphthyl)-2-oxo-cyclohex-3-ene-1-carboxylate (6.50 g, 96%): $^1$H NMR (400 MHz, Chloroform-d) δ 7.96-7.78 (m, 3H), 7.59-7.41 (m, 3H), 7.37-7.30 (m, 1H), 6.31-6.18 (m, 1H), 4.41-4.16 (m, 2H), 3.57 (dd, J=9.4, 5.0 Hz, 1H), 3.00-2.75 (m, 2H), 2.67-2.58 (m, 1H), 2.49-2.39 (m, 1H), 1.34 (t, J=7.1 Hz, 3H); LC/MS (ESI): m+H=295.0.

Step 3: Ethyl 4-(1-naphthyl)-2-oxo-cyclohexanecarboxylate

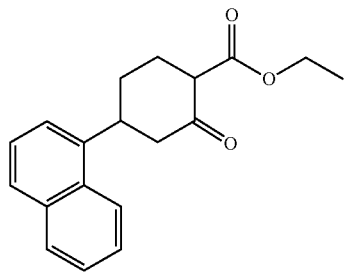 [SMILES: CCOC(=O)C1CCC(c2cccc3ccccc23)CC1=O]

A mixture of ethyl 4-(1-naphthyl)-2-oxo-cyclohex-3-ene-1-carboxylate (6.50 g, 22.1 mmol) in ethanol (100 mL) and 10% Pd—C(0.65 g) was deoxygenated with hydrogen purge and evacuation three times and then allowed to stir under a hydrogen balloon overnight. The reaction mixture was filtered through celite and was washed with DCM. The combined filtrate was concentrated and purified by flash chromatography (silica gel, 0-20% IPAC/heptane) to obtain ethyl 4-(1-naphthyl)-2-oxo-cyclohexanecarboxylate (1.85 g 28%) as an oil: $^1$H NMR (400 MHz, Chloroform-d) δ 12.30 (d, J=1.1 Hz, 1H), 8.08 (d, J=8.3 Hz, 1H), 7.87 (d, J=8.0 Hz, 1H), 7.75 (d, J=8.1 Hz, 1H), 7.55-7.35 (m, 4H), 4.39-4.07 (m, 2H), 4.00-3.52 (m, 1H), 2.94-1.74 (m, 6H), 1.33 (t, J=7.1, 3H).); LC/MS (ESI): m+H=297.0.

Step 4: 2-Methylsulfanyl-7-(1-naphthyl)-5,6,7,8-tetrahydro-3H-quinazolin-4-one

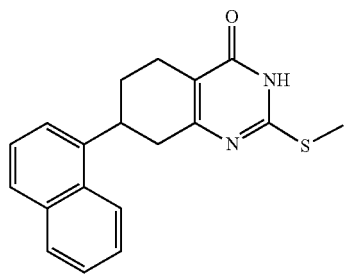 [SMILES: CSc1nc2c(c(=O)[nH]1)CCC(c1cccc3ccccc13)C2]

To a mixture of ethyl 4-(1-naphthyl)-2-oxo-cyclohexanecarboxylate (1.50 g, 5.1 mmol) and 2-methyl-2-thiopseudourea sulfate (4.31 g, 15.2 mmol) in ethanol (25 mL) was added saturated sodium bicarbonate (25 mL) and the mixture was heated at 50° C. for 4 hours. The reaction mixture was cooled and the solid was removed by filtration. The filtrate was treated with saturated ammonium chloride and extracted with IPAC. The organic layer was washed with brine, dried over sodium sulfate and concentrated. The residue was combined with the above solid and purified by flash chromatography (silica gel, 0-5% MeOH/DCM) to obtain 2-methylsulfanyl-7-(1-naphthyl)-5,6,7,8-tetrahydro-3H-quinazolin-4-one (0.35 g, 21.5% yield): $^1$H NMR (400 MHz, DMSO-d$_6$) δ 12.28 (s, 1H), 8.20 (d, J=8.1 Hz, 1H), 7.94 (dd, J=7.6, 1.9 Hz, 1H), 7.81 (d, J=7.9 Hz, 1H), 7.61-7.42 (m, 4H), 3.83 (d, J=12.9 Hz, 1H), 2.83 (qd, J=18.0, 7.7 Hz, 2H), 2.52 (s, 2H), 2.45 (s, 3H), 2.09 (d, J=12.8 Hz, 1H), 1.97-1.82 (m, 1H); LC/MS (ESI): m+H=323.0.

Step 5: tert-Butyl 2-(cyanomethyl)-4-[2-methylsulfanyl-7-(1-naphthyl)-5,6,7,8-tetrahydroquinazolin-4-yl]piperazine-1-carboxylate

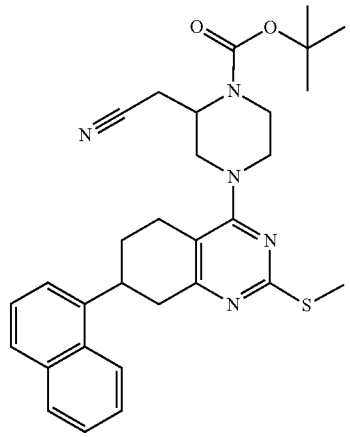 [SMILES: CSc1nc2c(c(N3CCN(C(=O)OC(C)(C)C)C(CC#N)C3)n1)CCC(c1cccc3ccccc13)C2]

2-Methylsulfanyl-7-(1-naphthyl)-5,6,7,8-tetrahydro-3H-quinazolin-4-one (0.35 g, 1.1 mmol) was dissolved in dichloromethane (5 mL) and DIPEA (0.70 mL 4.0 mmol) was added. To this mixture was added trifluoromethanesulfonic anhydride (0.28 mL; 1.63 mmol) and the mixture was stirred for 0.5 hours. The reaction mixture was concentrated and purified by flash to obtain the triflate (0.45 g, 91%):); LC/MS (ESI): m+H=455.0.

To the above triflate in dimethylacetamide (3 mL) were added (±)2-piperazin-2-ylacetonitrile dihydrochloride (0.29 g, 1.48 mmol) and DIPEA (0.7 mL, 4.0 mmol) and the mixture was heated at 85° C. for 1 hour and then cooled to room temperature and di-tert-butyl dicarbonate (0.65 g, 3.0 mmol) and N,N-dimethylaminopyridine (12 mg, 10%) were added and stirred at room temperature for 2 hours. The reaction mixture was diluted with IPAC, washed with water, brine, dried over sodium sulfate and concentrated. The residue was purified by flash chromatography (silica gel, 0-100% IAPC/heptane) to obtain tert-butyl 2-(cyanomethyl)-4-[2-methylsulfanyl-7-(1-naphthyl)-5,6,7,8-tetrahydroquinazolin-4-yl]piperazine-1-carboxylate (0.35 g, 66%): LC/MS (ESI): m+H=530.3.

Step 6: tert-Butyl 2-(cyanomethyl)-4-[2-methyl-sulfonyl-7-(1-naphthyl)-5,6,7,8-tetrahydroquinazolin-4-yl]piperazine-1-carboxylate

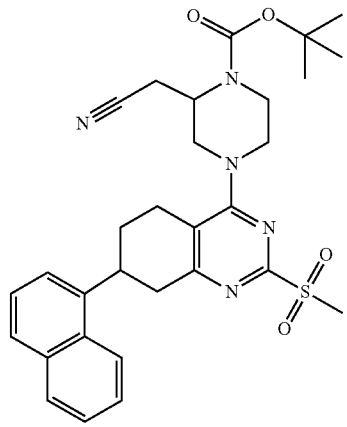 [SMILES: CC(C)(C)OC(=O)N1CCN(c2nc(S(C)(=O)=O)nc3c2CCC(c2cccc4ccccc24)C3)CC1CC#N]

m-Chloroperoxybenzoic acid (0.46 g, 2.1 mmol) was added to an ice-cold solution of tert-butyl 2-(cyanomethyl)-4-[2-methylsulfanyl-7-(1-naphthyl)-5,6,7,8-tetrahydroquinazolin-4-yl]piperazine-1-carboxylate (0.50 g, 0.94 mmol) in THF (30 mL) and stirred for 2 hours. The reaction mixture was then quenched with sodium bisulfite solution and extracted with IPAC. The organic layer was washed with brine, dried over sodium sulfate and concentrated. The residue was purified by flash chromatography (silica gel, 20-100% IPAC/heptane) to obtain tert-Butyl 2-(cyanomethyl)-4-[2-methylsulfonyl-7-(1-naphthyl)-5,6,7,8-tetrahydroquinazolin-4-yl]piperazine-1-carboxylate (0.50 g, 94%): LC/MS (ESI): m+H=562.3.

Step 7: tert-butyl 2-(cyanomethyl)-4-[2-[[(2S)-1-methylpyrrolidin-2-yl]methoxy]-7-(1-naphthyl)-5,6,7,8-tetrahydroquinazolin-4-yl]piperazine-1-carboxylate

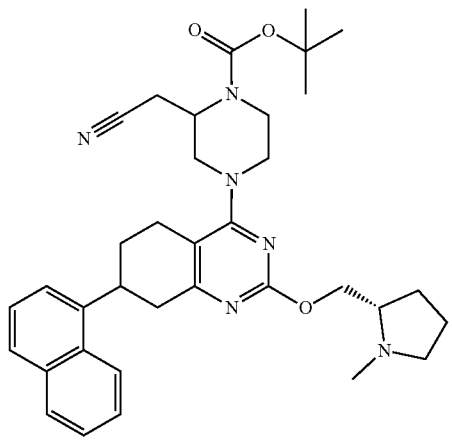 [SMILES: CN1CCC[C@H]1COc1nc2c(c(N3CCN(C(=O)OC(C)(C)C)C(CC#N)C3)n1)CCC(c1cccc3ccccc13)C2]

To a solution of [(2S)-1-methylpyrrolidin-2-yl]methanol (0.21 g, 1.78 mmol) in THF (5 mL) was added potassium hexamethyldisilazide (2.2 mL 1 M solution) and the mixture stirred for 10 minutes and then cooled in ice-bath. To this was added a solution of the above tert-butyl 2-(cyanomethyl)-4-[2-methylsulfonyl-7-(1-naphthyl)-5,6,7,8-tetrahydroquinazolin-4-yl]piperazine-1-carboxylate in THF (5 mL) and the resulting mixture stirred for 3 hours, quenched with water and extracted with IPAC. The organic layer was washed with brine, dried over sodium sulfate and concentrated. The residue was purified by column chromatography (silica gel, 0-10% MeOH-DCM) to obtain tert-butyl 2-(cyanomethyl)-4-[2-[[(2S)-1-methylpyrrolidin-2-yl]methoxy]-7-(1-naphthyl)-5,6,7,8-tetrahydroquinazolin-4-yl]piperazine-1-carboxylate (0.34 g, 64%): LC/MS (ESI): m+H=597.4.

Step 8: 2-[1-(2-Fluoroprop-2-enoyl)-4-[2-[[(2S)-1-methylpyrrolidin-2-yl]methoxy]-7-(1-naphthyl)-5,6,7,8-tetrahydroquinazolin-4-yl]piperazin-2-yl]acetonitrile

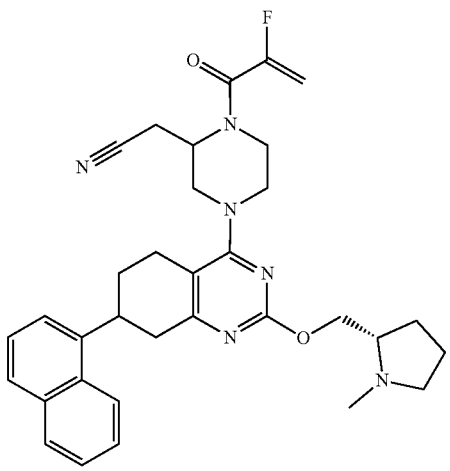 [SMILES: C=C(F)C(=O)N1CCN(c2nc(OC[C@@H]3CCCN3C)nc3c2CCC(c2cccc4ccccc24)C3)CC1CC#N]

tert-Butyl 2-(cyanomethyl)-4-[2-[[(2S)-1-methylpyrrolidin-2-yl]methoxy]-7-(1-naphthyl)-5,6,7,8-tetrahydroquinazolin-4-yl]piperazine-1-carboxylate (0.35 mg, 0.57 mmol) was dissolved in 10% TFA/HFIP and stirred for 2 hours. To this an additional TFA (0.5 ml) was added and stirred for 0.5 hours and then concentrated with toluene. The residue was co-evaporated with toluene two more times. The residue was dissolved in IPAC and stirred over a small amount of sodium bicarbonate and organic layer separated, dried over sodium sulfate and concentrated. Purified by flash: 0-10% ammonical methanol-DCM to obtain 2-(4-(2-(((S)-1-methylpyrrolidin-2-yl)methoxy)-7-(naphthalen-1-yl)-5,6,7,8-tetrahydroquinazolin-4-yl)piperazin-2-yl)acetonitrile (0.16 g); LC/MS (ESI): m+H=497.4.

To an ice-cold solution of the above compound in DMF (3 mL) were added sodium 2-fluoroacrylate (0.08 g, 0.7 mmol); HATU (0.27 g, 1.42 mmol) and DIPEA (0.25 mL, 1.4 mmol) and the mixture was stirred for 10 minutes and was allowed warm to room temperature and stirred for 1 hour. The reaction mixture was diluted with DCM and water. The organic layer separated, washed with brine and dried over sodium sulfate and concentrated. The residue was purified by rHPLC and the diastereomers were separated by cSFC (column: Chiralpak-ID; mobile phase: EtOH w/0.1% NH$_4$OH) to obtain a mixture of four compounds (47a, 47b 47c, 4d). Data for the most potent isomer (47d): $^1$H NMR (400 MHz, DMSO-d$_6$) δ 8.24 (d, J=8.0 Hz, 1H), 7.96 (dd, J=7.5, 2.1 Hz, 1H), 7.86-7.75 (m, 1H), 7.60-7.52 (m, 2H), 7.48 (dd, J=7.2, 5.7 Hz, 2H), 5.39 (dd, J=18.0, 4.1 Hz, 1H), 5.28 (dd, J=49.8, 4.1 Hz, 1H), 4.27 (dd, J=10.9, 4.9 Hz, 1H), 4.07 (s, 1H), 3.96 (d, J=13.5 Hz, 3H), 3.85 (d, J=13.7 Hz, 1H), 3.42-3.35 (m, 1H), 3.21 (dd, J=13.3, 3.6 Hz, 2H), 3.10 (dd, J=18.3, 5.2 Hz, 2H), 3.01-2.63 (m, 7H), 2.35 (d, J=13.4 Hz, 3H), 2.16 (d, J=12.9 Hz, 2H), 1.90 (td, J=11.9, 4.4 Hz, 2H), 1.78-1.53 (m, 3H); LC/MS (ESI): m+H=569.3.

Example 48a

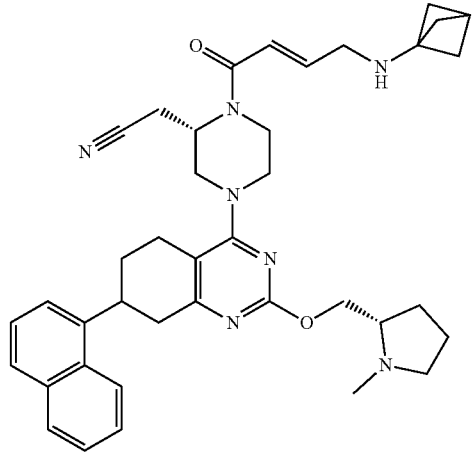 [SMILES: CN1CCC[C@H]1COc1nc2c(c(N3CCN(C(=O)/C=C/CNC45CC(C4)C5)[C@@H](CC#N)C3)n1)CCC(c1cccc3ccccc13)C2]

2-((2S)-1-((E)-4-(bicyclo[1.1.1]pentan-1-ylamino)but-2-enoyl)-4-(2-(((S)-1-methylpyrrolidin-2-yl)methoxy)-7-(naphthalen-1-yl)-5,6,7,8-tetrahydroquinazolin-4-yl)piperazin-2-yl)acetonitrile

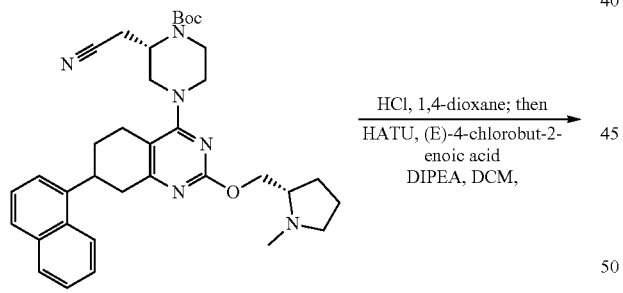

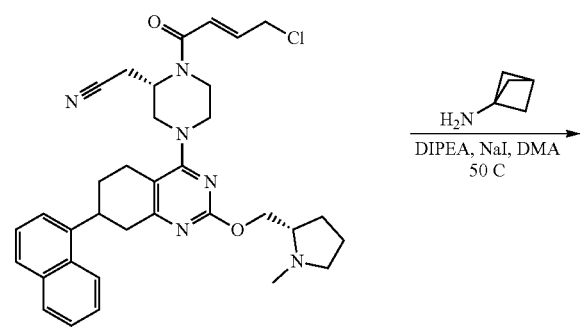

-continued

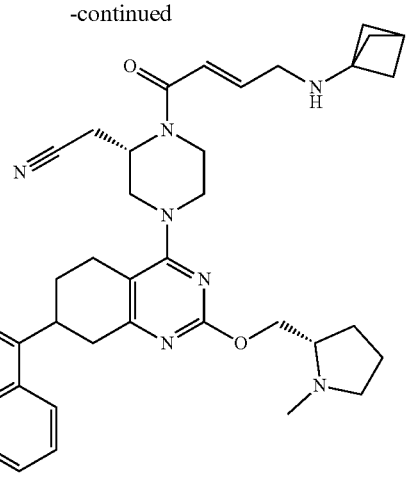

Step 1: 2-((2S)-1-((E)-4-Chlorobut-2-enoyl)-4-(2-(((S)-1-methylpyrrolidin-2-yl)methoxy)-7-(naphthalen-1-yl)-5,6,7,8-tetrahydroquinazolin-4-yl)piperazin-2-yl)acetonitrile

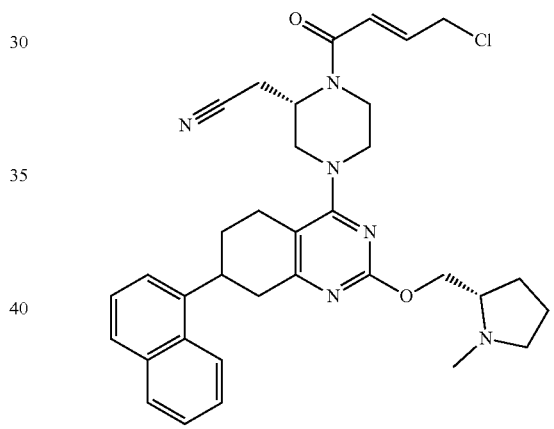

tert-Butyl 2-(cyanomethyl)-4-(2-(((S)-1-methylpyrrolidin-2-yl)methoxy)-7-(naphthalen-1-yl)-5,6,7,8-tetrahydroquinazolin-4-yl)piperazine-1-carboxylate (40 mg) as a single isomer (example 47) was dissolved in DCM treated with HCl-dioxane (1 mL, 4M) and the mixture stirred for 2 hours and then concentrated. The resulting residue was treated with (E)-4-chlorobut-2-enoic acid (18 mg, 0.13 mmol), HATU (52 mg, 0.13 mmol) and DIPEA (0.05 mL) in DCM in ice-bath for 1 hour. The reaction mixture was diluted with water and DCM and the organic layer separated, washed with brine, dried over sod sulfate and concentrated and the residue was purified by flash chromatography (silica gel, 0-5% MeOH/DCM) to obtain 2-((2S)-1-((E)-4-chlorobut-2-enoyl)-4-(2-(((S)-1-methylpyrrolidin-2-yl)methoxy)-7-(naphthalen-1-yl)-5,6,7,8-tetrahydroquinazolin-4-yl)piperazin-2-yl)acetonitrile (20 mg): LC/MS (ESI): m+H=599.3.

Step 2: 2-((2S)-1-((E)-4-(bicyclo[1.1.1]pentan-1-ylamino)but-2-enoyl)-4-(2-(((S)-1-methylpyrrolidin-2-yl)methoxy)-7-(naphthalen-1-yl)-5,6,7,8-tetrahydroquinazolin-4-yl)piperazin-2-yl)acetonitrile
(Example 48a)

The above compound (10 mg) was dissolved in DMA (0.5 ml) and bicyclo[1.1.1]pentan-1-amine: HCl, DIPEA (4.2 mg, 0.03 mmol), sodium iodide (4.7 mg, 0.03 mmol) and DIPEA (4.0 mg, 0.03 mmol) were added and the mixture was heated at 50° C. overnight. The reaction mixture was cooled, diluted with IPAC, washed with water, brine, dried over sodium sulfate and concentrated. The residue was purified by flash chromatography (silica gel, 0-10% MeOH/DCM) to obtain the title compound (3.2 mg, 30%): $^1$H NMR (400 MHz, DMSO-$d_6$) δ 8.24 (d, J=8.3 Hz, 1H), 8.02-7.87 (m, 1H), 7.82 (d, J=7.8 Hz, 1H), 7.62-7.43 (m, 4H), 6.76 (dt, J=15.1, 4.9 Hz, 1H), 6.71-6.54 (m, 1H), 4.86 (d, J=91.1 Hz, 1H), 4.25 (dd, J=10.8, 4.8 Hz, 1H), 4.14-3.71 (m, 5H), 3.26-3.04 (m, 4H), 3.04-2.80 (m, 6H), 2.83-2.62 (m, 2H), 2.33 (d, J=3.2 Hz, 5H), 2.16 (q, J=8.5 Hz, 2H), 1.99-1.83 (m, 2H), 1.77 (s, 1H), 1.75-1.52 (m, 9H). LC/MS (ESI): m+H=646.4.

Example 49a

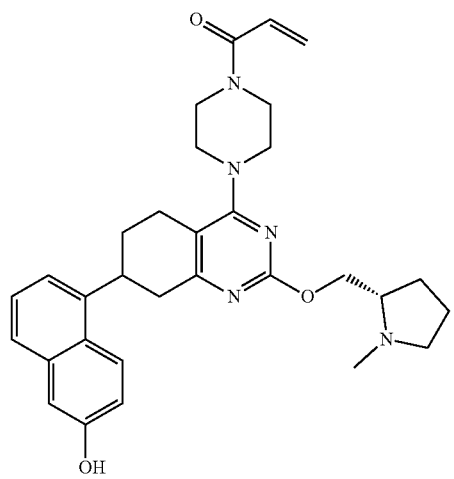 [SMILES: C=CC(=O)N1CCN(c2nc(OC[C@@H]3CCCN3C)nc3c2CCC(c2cccc4cc(O)ccc24)C3)CC1]

1-[4-[7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one

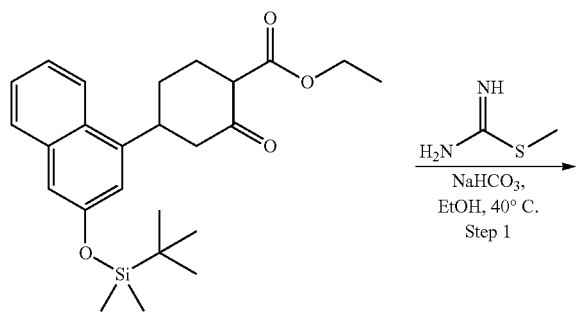

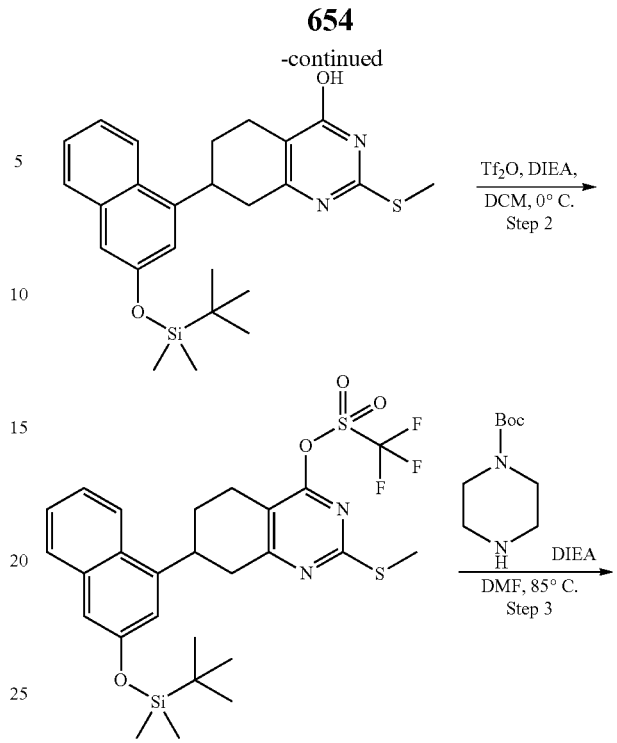

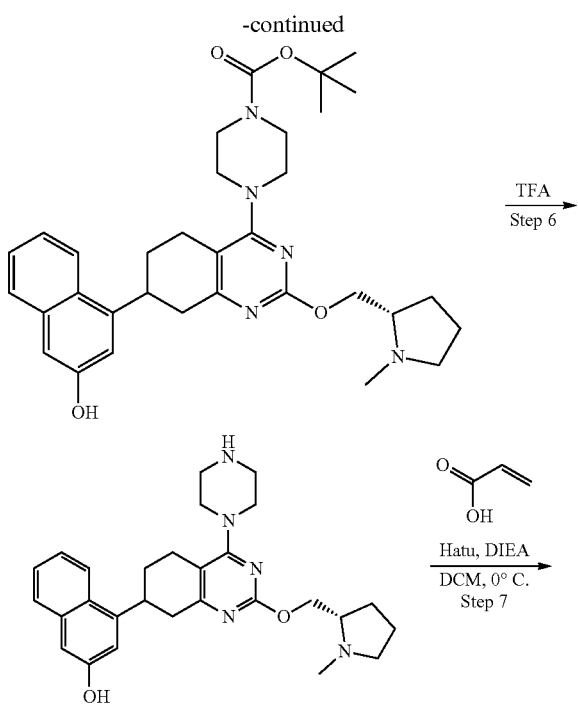

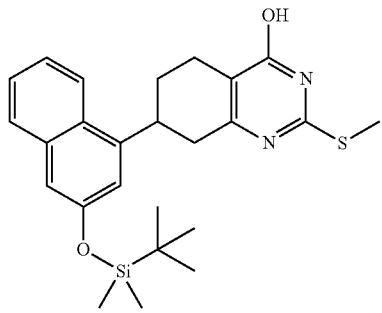 [SMILES: CSc1nc(O)c2c(n1)CC(c1cc(O[Si](C)(C)C(C)(C)C)cc3ccccc13)CC2]

Step 1: 7-(3-((tert-butyldimethylsilyl)oxy)naphthalen-1-yl)-2-(methylthio)-5,6,7,8-tetrahydroquinazolin-4-ol Ethyl 4-[3-[tert-butyl(dimethyl)silyl]oxy-1-naphthyl]-2-oxo-cyclohexanecarboxylate was initially prepared using a procedure analogous to step 3 of Example 43, wherein the methyl ether therein was replaced with a tert-butyl(dimethyl)silylether. Then, to a solution of ethyl 4-[3-[tert-butyl(dimethyl)silyl]oxy-1-naphthyl]-2-oxo-cyclohexanecarboxylate (530 mg, 1.24 mmol) and 2-methyl-2-thiopseudourea sulfate (1.06 g, 3.73 mmol) in ethanol (24.00 mL) was added saturated solution of saturated sodium bicarbonate (12.00 mL). The reaction mixture was stirred at 40° C. for 12 hours. The reaction was quenched with sat·NH$_4$Cl then extracted with EtOAc. The organic layers was dried with sodium sulfate, filtered, and concentrated via rotovap. The crude product was purified by flash chromatography on silica (eluting with iPrOAc/Hep) to afford 7-(3-(((tert-butyldimethylsilyl)oxy)naphthalen-1-yl)-2-(methylthio)-5,6,7,8-tetrahydroquinazolin-4-ol (355 mg, 63%). LCMS (ESI, m/z): 453.1 [M+H]$^+$.

Step 2: 7-(3-(((tert-butyldimethylsilyl)oxy)naphthalen-1-yl)-2-(methylthio)-5,6,7,8-tetrahydroquinazolin-4-yl trifluoromethanesulfonate

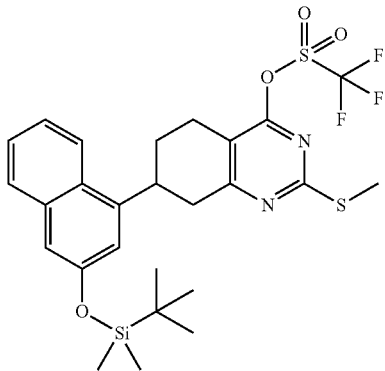 [SMILES: CSc1nc2c(c(OS(=O)(=O)C(F)(F)F)n1)CCC(c1cc(O[Si](C)(C)C(C)(C)C)cc3ccccc13)C2]

To a solution of 7-[3-[tert-butyl(dimethyl)silyl]oxy-1-naphthyl]-2-methylsulfanyl-5,6,7,8-tetrahydroquinazolin-4-ol (450 mg, 1.00 mmol) in dichloromethane (50 mL) at 0° C. was added N,N-diisopropylethylamine (0.520 mL, 3.00 mmol) and trifluoromethanesulfonic anhydride (1M) in methylene chloride (1.20 mL, 1.20 mmol). The reaction mixture was stirred at 0° C. for 20 minutes. The reaction was concentrated and the crude product was used without purification. LCMS (ESI, m/z): 558.0 [M+H]$^+$.

Step 3: tert-butyl 4-(7-(3-((tert-butyldimethylsilyl)oxy)naphthalen-1-yl)-2-(methylthio)-5,6,7,8-tetrahydroquinazolin-4-yl)piperazine-1-carboxylate

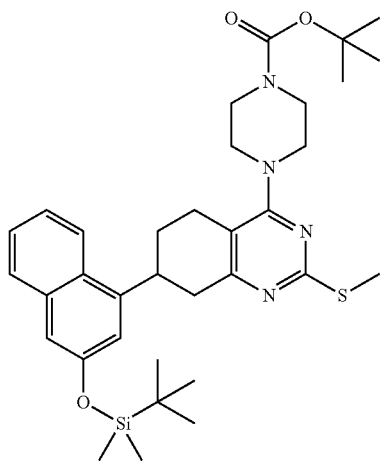 [SMILES: CSc1nc2c(c(N3CCN(C(=O)OC(C)(C)C)CC3)n1)CCC(c1cc(O[Si](C)(C)C(C)(C)C)cc3ccccc13)C2]

To a solution of 7-(3-((tert-butyldimethylsilyl)oxy)naphthalen-1-yl)-2-(methylthio)-5,6,7,8-tetrahydroquinazolin-4-yl trifluoromethanesulfonate (90 mg, 0.15 mmol) in N,N-dimethylformamide (1.5 mL) was added N,N-diisopropylethylamine (0.100 mL, 0.60 mmol) and 1-boc-piperazine (64.0 mg, 0.34 mmol). The reaction mixture was stirred at 85° C. for 2 hours. The reaction was quenched with water and extracted with EtOAc. The organic layers was dried with sodium sulfate, filtered, and concentrated via rotovap. The crude product was purified by flash chromatography on silica (eluting with iPrOAc/Hep) to afford tert-butyl 4-(7-(3-((tert-butyldimethylsilyl)oxy)naphthalen-1-yl)-2-(methylthio)-5,6,7,8-tetrahydroquinazolin-4-yl)piperazine-1-carboxylate (62 mg, 65%). LCMS (ESI, m/z): 621.3 [M+H]$^+$.

Step 4: tert-butyl 4-(7-(3-((tert-butyldimethylsilyl)oxy)naphthalen-1-yl)-2-(methylsulfonyl)-5,6,7,8-tetrahydroquinazolin-4-yl)piperazine-1-carboxylate

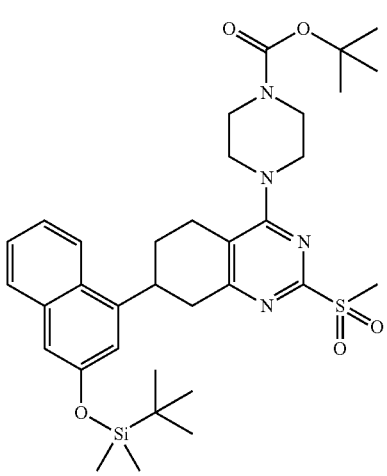 [SMILES: CC(C)(C)OC(=O)N1CCN(c2nc(S(C)(=O)=O)nc3c2CCC(c2cc(O[Si](C)(C)C(C)(C)C)cc4ccccc24)C3)CC1]

To a solution of tert-butyl 4-[7-[3-[tert-butyl(dimethyl)silyl]oxy-1-naphthyl]-2-methylsulfanyl-5,6,7,8-tetrahydroquinazolin-4-yl]piperazine-1-carboxylate (125 mg, 0.201 mmol) in dichloromethane (4.00 mL) was added 3-chloroperoxybenzoic acid (113 mg, 0.503 mmol). The reaction was stirred at r.t. for 2 hours then quenched by NaHSO$_3$ solution (5 mL). The reaction mixture was diluted with DCM (10 mL) and washed with water (10 mL). The organic layers was dried with sodium sulfate, filtered, and concentrated via rotovap. The crude product was purified by flash chromatography on silica (eluting with iPrOAc/Hep) to give tert-butyl 4-(7-(3-((tert-butyldimethylsilyl)oxy)naphthalen-1-yl)-2-(methylsulfonyl)-5,6,7,8-tetrahydroquinazolin-4-yl)piperazine-1-carboxylate (85 mg, 65%). LCMS (ESI, m/z): 653.2 [M+H]$^+$.

Step 5: tert-butyl 4-(7-(3-hydroxynaphthalen-1-yl)-2-(((S)-1-methylpyrrolidin-2-yl)methoxy)-5,6,7,8-tetrahydroquinazolin-4-yl)piperazine-1-carboxylate

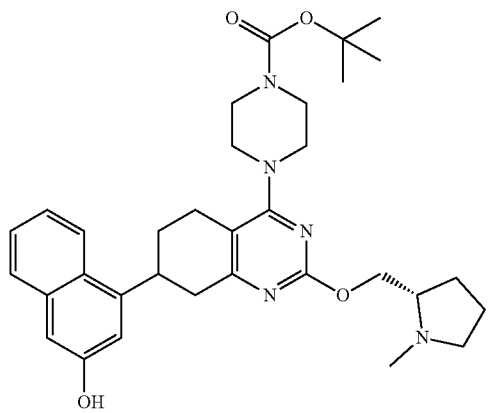 [SMILES: CN1CCC[C@H]1COc1nc2c(c(N3CCN(C(=O)OC(C)(C)C)CC3)n1)CCC(c1cc(O)cc3ccccc13)C2]

To a solution of [(2S)-1-methylpyrrolidin-2-yl]methanol (37 mg, 0.31 mmol) in tetrahydrofuran (1.5 mL) was added potassium bis(trimethylsilyl)amide (0.9 M) in tetrahydrofuran (0.34 mL, 0.34 mmol) at room temperature. The reaction was cooled to 0° C. then solution of tert-butyl 4-(7-(3-((tert-butyldimethylsilyl)oxy)naphthalen-1-yl)-2-(methylsulfonyl)-5,6,7,8-tetrahydroquinazolin-4-yl)piperazine-1-carboxylate (100 mg, 0.15 mmol) in THF (2 mL) was added. The reaction was left to gently warm to room temperature for 18 hours. The reaction mixture was quenched with water and extracted with EtOAc. The organic layers was dried with sodium sulfate, filtered, and concentrated via rotovap. The crude product was purified by flash chromatography on silica (eluting with MeOH/DCM) to give tert-butyl 4-(7-(3-hydroxynaphthalen-1-yl)-2-(((S)-1-methylpyrrolidin-2-yl)methoxy)-5,6,7,8-tetrahydroquinazolin-4-yl)piperazine-1-carboxylate (44 mg, 50%). LCMS (ESI, m/z): 574.3 [M+H]$^+$.

Step 6: 4-(2-(((S)-1-methylpyrrolidin-2-yl)methoxy)-4-(piperazin-1-yl)-5,6,7,8-tetrahydroquinazolin-7-yl)naphthalen-2-ol

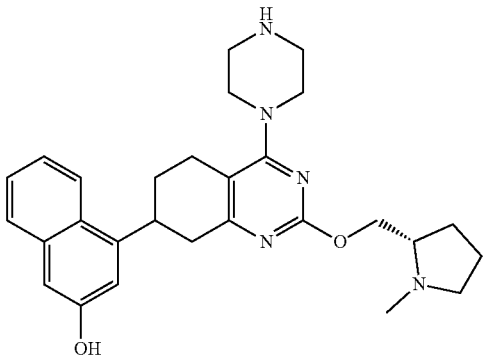 [SMILES: CN1CCC[C@H]1COc1nc2c(c(N3CCNCC3)n1)CCC(c1cc(O)cc3ccccc13)C2]

A solution of tert-butyl 4-(7-(3-hydroxynaphthalen-1-yl)-2-(((S)-1-methylpyrrolidin-2-yl)methoxy)-5,6,7,8-tetrahydroquinazolin-4-yl)piperazine-1-carboxylate (132 mg, 0.230 mmol) in 5% trifluoroacetic acid in hexafluoro-2-propanol (3.5 mL, 2.30 mmol) was stirred at r.t. for 60 minutes. The reaction was concentrated and the crude product was purified by flash chromatography on silica (eluting with MeOH/DCM) to give 4-(2-(((S)-1-methylpyrrolidin-2-yl)methoxy)-4-(piperazin-1-yl)-5,6,7,8-tetrahydroquinazolin-7-yl)naphthalen-2-ol (70 mg, 64%). LCMS (ESI, m/z): 474.2 [M+H]$^+$.

Step 7: 1-[4-[7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one

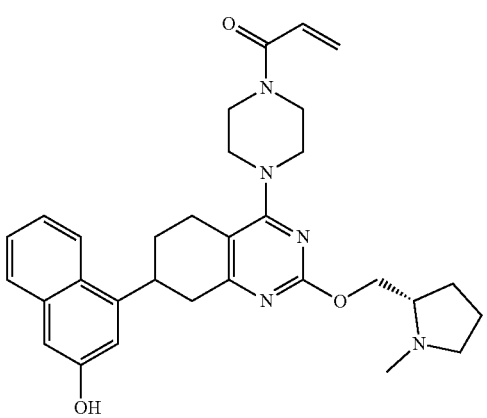

To a solution of 4-(2-(((S)-1-methylpyrrolidin-2-yl)methoxy)-4-(piperazin-1-yl)-5,6,7,8-tetrahydroquinazolin-7-yl)naphthalen-2-ol (A, 70 mg, 0.15 mmol) and N,N-diisopropylethylamine (0.13 ml, 0.74 mmol) in dichloromethane (1.5 mL) was added acrylic acid (0.012 mL, 0.161 mmol) and HATU (86.0 mg, 0.222 mmol) at −78° C. then the reaction mixture was warmed and stirred at 0° C. for 15 minutes. The reaction was quenched with water and extracted with EtOAc. The organic layers was dried with sodium sulfate, filtered, and concentrated via rotovap. The crude product was submitted for reverse-phase HPLC to give 1-[4-[7-(3-hydroxy-1-naphthyl)-2-[[(2S)-1-methylpyrrolidin-2-yl]methoxy]-5,6,7,8-tetrahydroquinazolin-4-yl]piperazin-1-yl]prop-2-en-1-one as white solid.

Example 49a: $^1$H NMR (400 MHz, DMSO-d6) δ 9.67 (s, 1H), 8.06 (d, J=8.5 Hz, 1H), 7.71 (dd, J=8.2, 1.4 Hz, 1H), 7.41 (ddd, J=7.9, 6.7, 1.1 Hz, 1H), 7.31 (ddd, J=8.3, 6.8, 1.3 Hz, 1H), 7.01 (dd, J=13.9, 2.1 Hz, 2H), 6.83 (dd, J=16.7, 10.5 Hz, 1H), 6.16 (dd, J=16.7, 2.4 Hz, 1H), 5.73 (dd, J=10.4, 2.4 Hz, 1H), 4.57 (d, J=12.5 Hz, 1H), 4.44 (ddd, J=12.5, 6.7, 4.2 Hz, 1H), 3.89 (s, 1H), 3.83-3.49 (m, 8H), 3.11 (d, J=16.8 Hz, 2H), 2.92 (s, 4H), 2.80 (ddd, J=17.0, 10.5, 5.0 Hz, 1H), 2.58 (d, J=15.8 Hz, 1H), 2.29-2.10 (m, 2H), 1.96 (d, J=87.1 Hz, 4H), 1.25 (d, J=12.8 Hz, 1H). LCMS (ESI, m/z): 528.3 [M+H]$^+$.

Example 50a

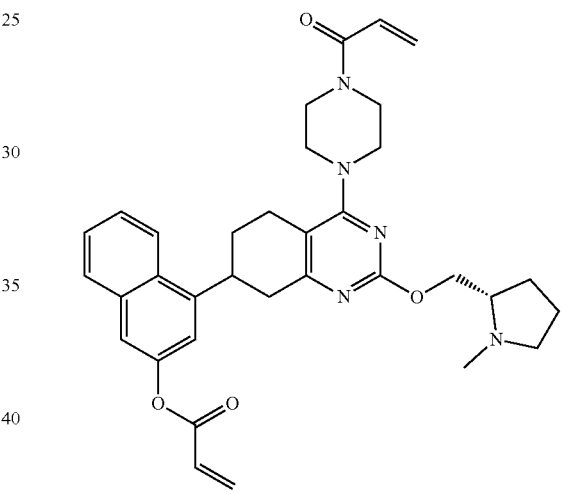

4-(4-(4-acryloylpiperazin-1-yl)-2-(((S)-1-methylpyrrolidin-2-yl)methoxy)-5,6,7,8-tetrahydroquinazolin-7-yl)naphthalen-2-yl acrylate 4-(4-(4-acryloylpiperazin-1-yl)-2-(((S)-1-methylpyrrolidin-2-yl)methoxy)-5,6,7,8-tetrahydroquinazolin-7-yl)naphthalen-2-yl acrylate was obtained as a side product from the reaction described in step 7 of Example 49a.

Example 50a: $^1$H NMR (400 MHz, DMSO-d6) δ 8.27 (d, J=13.9 Hz, 1H), 7.96 (dt, J=6.8, 3.5 Hz, 1H), 7.66 (d, J=2.2 Hz, 1H), 7.58 (dt, J=6.7, 3.3 Hz, 2H), 7.27 (d, J=2.3 Hz, 1H), 6.84 (dd, J=16.7, 10.5 Hz, 2H), 6.58 (dd, J=17.2, 1.6 Hz, 1H), 6.46 (dd, J=17.3, 10.1 Hz, 1H), 6.21-6.10 (m, 2H), 5.72 (dd, J=10.4, 2.4 Hz, 1H), 4.25 (dd, J=10.7, 4.9 Hz, 1H), 4.09-3.92 (m, 3H), 3.64 (s, 4H), 3.13-2.75 (m, 4H), 2.61-2.54 (m, 1H), 2.23-2.04 (m, 4H), 1.97-1.79 (m, 4H), 1.72-1.51 (m, 5H), 1.24 (s, 2H). LCMS (ESI, m/z): 582.3 [M+H]$^+$.

Example 51

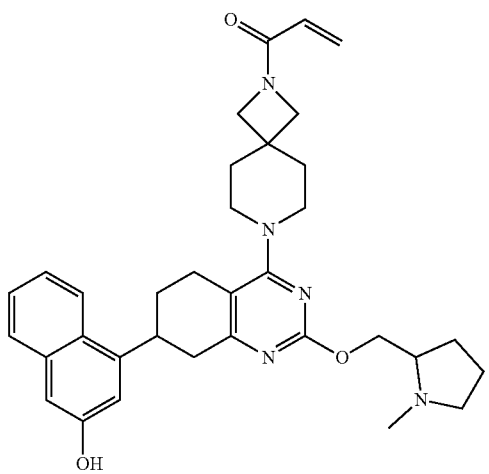 [SMILES: C=CC(=O)N1CC2(CCN(c3nc(OCC4CCCN4C)nc4c3CCC(c3cc(O)cc5ccccc35)C4)CC2)C1]

1-[7-[7-(3-hydroxy-1-naphthyl)-2-[(1-methylpyrrolidin-2-yl)methoxy]-5,6,7,8-tetrahydroquinazolin-4-yl]-2,7-diazaspiro[3.5]nonan-2-yl]prop-2-en-1-one Example 51 was prepared according to the procedure set forth in Example 49a, except that in Step 3 of Example 51, commercially available tert-butyl 2,7-diazaspiro[3.5]nonane-2-carboxylate was used instead of tert-butyl piperazine-1-carboxylate as the alternative reagent.

Example 51: $^1$H NMR (400 MHz, DMSO-d6) δ 9.66 (s, 1H), 8.07 (d, J=8.5 Hz, 1H), 7.70 (dd, J=8.3, 1.3 Hz, 1H), 7.39 (ddd, J=8.1, 6.7, 1.1 Hz, 1H), 7.30 (ddd, J=8.3, 6.8, 1.4 Hz, 1H), 7.03-6.96 (m, 2H), 6.33 (dd, J=17.0, 10.3 Hz, 1H), 6.11 (dd, J=17.0, 2.3 Hz, 1H), 5.67 (dd, J=10.3, 2.3 Hz, 1H), 4.24 (dd, J=10.7, 4.8 Hz, 1H), 4.06-3.94 (m, 3H), 3.91-3.82 (m, 1H), 3.75-3.65 (m, 2H), 3.06 (dd, J=18.2, 5.3 Hz, 1H), 2.98-2.83 (m, 2H), 2.75 (dd, J=18.1, 10.6 Hz, 1H), 2.33 (s, 3H), 2.14 (td, J=15.1, 13.2, 9.4 Hz, 2H), 1.98-1.71 (m, 6H), 1.71-1.48 (m, 4H). LCMS (ESI, m/z): 568.3 [M+H]$^+$.

Example 52a

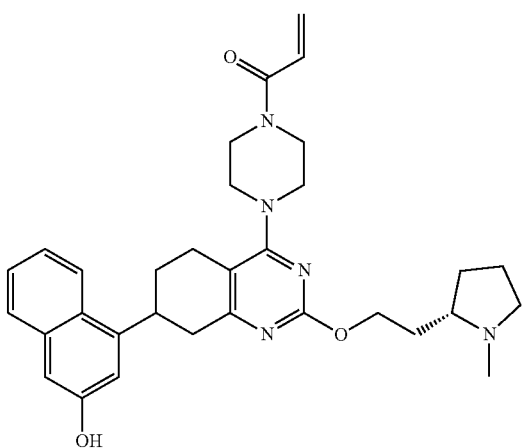 [SMILES: C=CC(=O)N1CCN(c2nc(OCC[C@@H]3CCCN3C)nc3c2CCC(c2cc(O)cc4ccccc24)C3)CC1]

1-(4-(7-(3-hydroxynaphthalen-1-yl)-2-(2-((S)-1-methylpyrrolidin-2-yl)ethoxy)-5,6,7,8-tetrahydroquinazolin-4-yl)piperazin-1-yl)prop-2-en-1-one Example 52a was prepared according to the procedure set forth in Example 49a except that in Step 5 of Example 52a, commercially available (S)-2-(1-methylpyrrolidin-2-yl)ethan-1-ol was used instead of (S)-(1-methylpyrrolidin-2-yl)methanol as the alternative reagent.

Example 52a: $^1$H NMR (400 MHz, DMSO-d6) δ 9.66 (s, 1H), 8.06 (d, J=8.5 Hz, 1H), 7.71 (dd, J=8.3, 1.4 Hz, 1H), 7.40 (ddd, J=8.0, 6.6, 1.0 Hz, 1H), 7.31 (ddd, J=8.2, 6.6, 1.3 Hz, 1H), 7.01 (dd, J=13.1, 2.4 Hz, 2H), 6.88-6.78 (m, 1H), 6.15 (dd, J=16.6, 2.4 Hz, 1H), 5.73 (dd, J=10.4, 2.4 Hz, 1H), 4.40-4.20 (m, 2H), 3.87 (s, 1H), 3.82-3.57 (m, 5H), 3.51 (td, J=9.2, 6.9, 3.1 Hz, 3H), 3.16-3.03 (m, 2H), 2.99-2.70 (m, 6H), 2.63-2.53 (m, 1H), 2.41-2.10 (m, 3H), 2.05-1.78 (m, 4H), 1.69 (s, 1H). LCMS (ESI, m/z): 542.4 [M+H]$^+$.

Example 53a

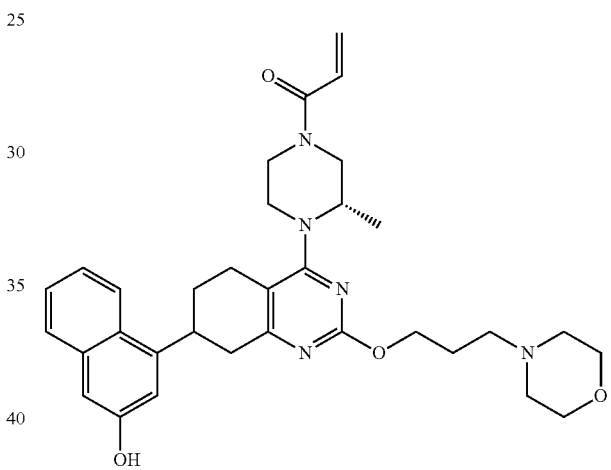

1-((3S)-4-(7-(3-hydroxynaphthalen-1-yl)-2-(3-morpholinopropoxy)-5,6,7,8-tetrahydroquinazolin-4-yl)-3-methylpiperazin-1-yl)prop-2-en-1-one Example 53a was prepared according to the procedure set forth in Example 49a except that in Step 5 of Example 53a, commercially available 3-morpholinopropan-1-ol was used instead of (S)-(1-methylpyrrolidin-2-yl)methanol as the alternative reagent.

Example 53a: $^1$H NMR (400 MHz, DMSO-d6) δ 9.64 (d, J=3.6 Hz, 1H), 8.07 (t, J=8.9 Hz, 1H), 7.70 (dd, J=8.3, 1.3 Hz, 1H), 7.40 (ddd, J=8.0, 6.7, 1.1 Hz, 1H), 7.30 (ddt, J=8.0, 6.7, 1.3 Hz, 1H), 7.00 (dd, J=12.1, 2.4 Hz, 2H), 6.95-6.73 (m, 1H), 6.17 (d, J=16.8 Hz, 1H), 5.72 (dt, J=10.4, 2.3 Hz, 1H), 4.44-3.97 (m, 5H), 3.85 (t, J=12.6 Hz, 2H), 3.56 (s, 4H), 3.44 (s, 1H), 3.21-3.01 (m, 2H), 3.00-2.64 (m, 3H), 2.37 (s, 5H), 2.12 (d, J=12.3 Hz, 1H), 1.94-1.75 (m, 3H), 1.23 (d, J=6.6 Hz, 2H), 1.08-0.95 (m, 1H). LCMS (ESI, m/z): 572.3 [M+H]$^+$.

Example 54a

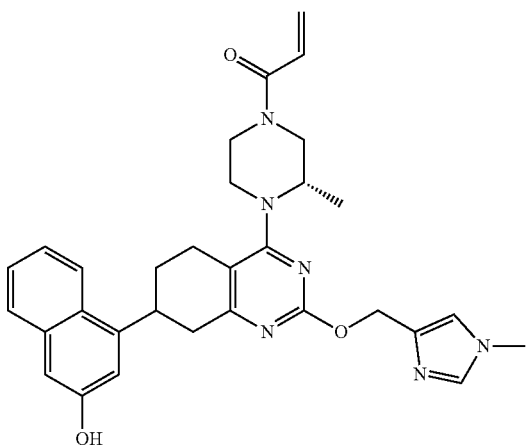

1-((3S)-4-(7-(3-hydroxynaphthalen-1-yl)-2-((1-methyl-1H-imidazol-4-yl)methoxy)-5,6,7,8-tetrahydroquinazolin-4-yl)-3-methylpiperazin-1-yl)prop-2-en-1-one Example 54a was prepared according to the procedure set forth in Example 49a except that in Step 5 of Example 54a, commercially available (1-methyl-1H-imidazol-4-yl)methanol was used instead of (S)-(1-methylpyrrolidin-2-yl)methanol as the alternative reagent.

Example 54a: $^1$H NMR (400 MHz, DMSO-d6) δ 9.65 (d, J=3.6 Hz, 1H), 8.06 (dt, J=17.2, 8.7 Hz, 1H), 7.71 (dd, J=8.3, 1.4 Hz, 1H), 7.62 (s, 1H), 7.45-7.24 (m, 2H), 7.19 (d, J=1.3 Hz, 1H), 7.05-6.95 (m, 3H), 6.83 (s, 1H), 6.17 (d, J=16.3 Hz, 1H), 5.72 (dt, J=10.5, 2.3 Hz, 1H), 5.12 (d, J=2.3 Hz, 2H), 4.36 (s, 1H), 4.26 (s, 1H), 4.16 (d, J=13.3 Hz, 1H), 4.04 (d, J=11.8 Hz, OH), 3.87 (d, J=10.0 Hz, 2H), 3.73-3.56 (m, 4H), 3.46 (s, 1H), 3.11 (dt, J=18.4, 5.8 Hz, 1H), 2.91 (s, 2H), 2.88-2.70 (m, 1H), 2.46 (s, 1H), 2.13 (d, J=12.5 Hz, 1H), 1.83 (d, J=11.7 Hz, 2H), 1.23 (d, J=6.3 Hz, 2H), 1.02 (dd, J=13.0, 6.5 Hz, 2H). LCMS (ESI, m/z): 539.3 [M+H]$^+$.

Example 55a

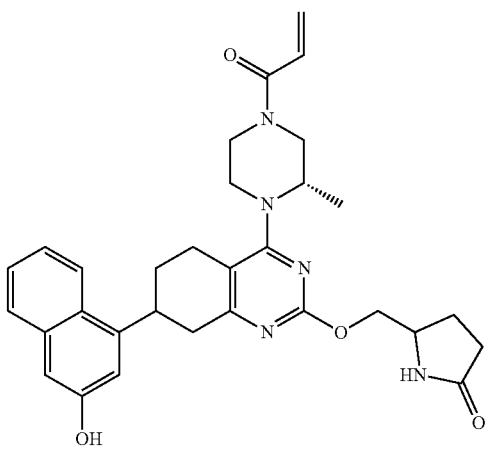 [SMILES: C=CC(=O)N1CCN(c2nc(OCC3CCC(=O)N3)nc3c2CCC(c2cc(O)cc4ccccc24)C3)[C@@H](C)C1]

5-(((4-((S)-4-acryloyl-2-methylpiperazin-1-yl)-7-(3-hydroxynaphthalen-1-yl)-5,6,7,8-tetrahydroquinazolin-2-yl)oxy)methyl)pyrrolidin-2-one Example 55a was prepared according to the procedure set forth in Example 49a except that in Step 5 of Example 55a, commercially available 5-(hydroxymethyl)pyrrolidin-2-one was used instead of (S)-(1-methylpyrrolidin-2-yl)methanol as the alternative reagent.

Example 55a: LCMS (ESI, m/z): 542.2 [M+H]$^+$.

Example 56a

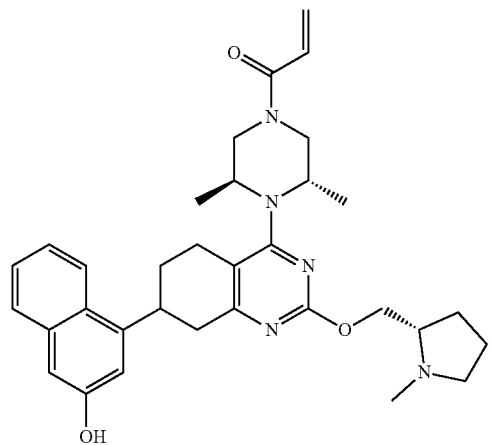 [SMILES: C=CC(=O)N1C[C@H](C)N(c2nc(OC[C@@H]3CCCN3C)nc3c2CCC(c2cc(O)cc4ccccc24)C3)[C@@H](C)C1]

1-((3S,5S)-4-(7-(3-hydroxynaphthalen-1-yl)-2-(((S)-1-methylpyrrolidin-2-yl)methoxy)-5,6,7,8-tetrahydroquinazolin-4-yl)-3,5-dimethylpiperazin-1-yl)prop-2-en-1-one Example 56a was prepared according to the procedure set forth in Example 49a except that in Step 3 of Example 56a, commercially available tert-butyl (3S,5S)-3,5-dimethylpiperazine-1-carboxylate was used instead of tert-butyl piperazine-1-carboxylate as the alternative reagent.

Example 56a: LCMS (ESI, m/z): 556.4 [M+H]$^+$.

Examples 57a, 57b, 57c, and 57d

Examples 57a, 57b, 57c, and 57d were prepared according to the procedure set forth in Example 49a except that in Step 5 of Examples 57a, 57b, 57c, and 57d, commercially available 4-(hydroxymethyl)-3-methyloxazolidin-2-one was used instead of (S)-(1-methylpyrrolidin-2-yl)methanol as the alternative reagent.

Example 57a: Peak 1 from cSFC (column: Chiralpak-IA; mobile phase: MeOH with 0.1% NH$_4$OH; RT=0.875 min):

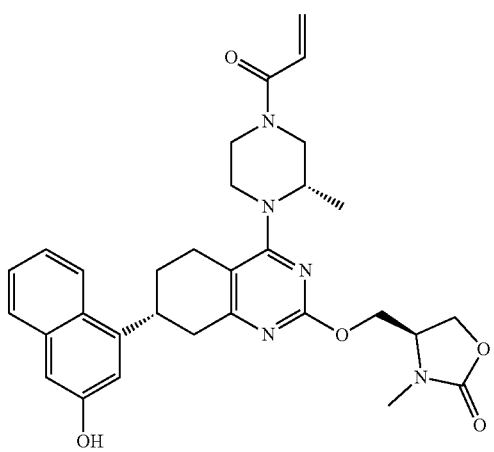 [SMILES: C=CC(=O)N1CCN(c2nc(OC[C@H]3COC(=O)N3C)nc3c2CC[C@@H](c2cc(O)cc4ccccc24)C3)[C@@H](C)C1]

(S)-4-((((R)-4-((S)-4-acryloyl-2-methylpiperazin-1-yl)-7-(3-hydroxynaphthalen-1-yl)-5,6,7,8-tetrahydro-quinazolin-2-yl)oxy)methyl)-3-methyloxazolidin-2-one Example 57a: $^1$H NMR (400 MHz, DMSO-d6) δ 9.66 (s, 1H), 8.08 (d, J=8.5 Hz, 1H), 7.70 (dd, J=8.3, 1.3 Hz, 1H), 7.40 (ddd, J=8.0, 6.7, 1.1 Hz, 1H), 7.30 (ddd, J=8.3, 6.8, 1.4 Hz, 1H), 7.01 (q, J=2.3 Hz, 2H), 6.94-6.73 (m, 1H), 6.16 (dd, J=16.7, 6.7 Hz, 1H), 5.73 (dd, J=10.5, 2.4 Hz, 1H), 4.49 (dd, J=11.8, 3.6 Hz, 1H), 4.44-4.24 (m, 3H), 4.23-4.01 (m, 3H), 3.88 (d, J=8.8 Hz, 1H), 3.65-3.44 (m, 1H), 3.10 (dd, J=18.3, 5.2 Hz, 1H), 2.89 (d, J=12.7 Hz, 2H), 2.78 (s, 4H), 2.59 (t, J=10.6 Hz, 1H), 2.13 (d, J=12.4 Hz, 1H), 1.92-1.74 (m, 1H), 1.00 (ddd, J=20.1, 13.9, 6.6 Hz, 4H). LCMS (ESI, m/z): 558.3 [M+H]$^+$.

Example 57b: Peak 2 from cSFC (column: Chiralpak-IA; mobile phase: MeOH with 0.1% NH$_4$OH; RT=0.952 min):

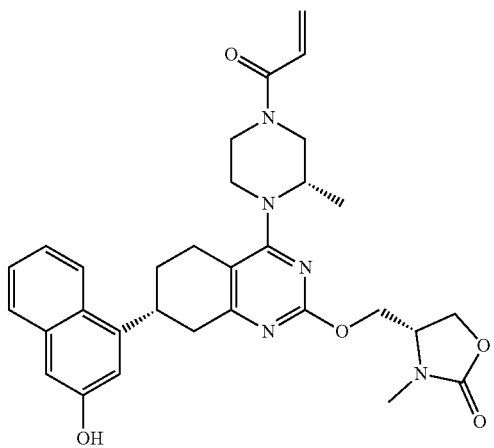 [SMILES: C=CC(=O)N1CCN(c2nc(OC[C@@H]3COC(=O)N3C)nc3c2CC[C@@H](c2cc(O)cc4ccccc24)C3)[C@@H](C)C1]

(R)-4-((((R)-4-((S)-4-acryloyl-2-methylpiperazin-1-yl)-7-(3-hydroxynaphthalen-1-yl)-5,6,7,8-tetrahydro-quinazolin-2-yl)oxy)methyl)-3-methyloxazolidin-2-one Example 57b: $^1$H NMR (400 MHz, DMSO-d6) δ 9.66 (s, 1H), 8.08 (d, J=8.5 Hz, 1H), 7.70 (dd, J=8.2, 1.3 Hz, 1H), 7.40 (ddd, J=8.1, 6.7, 1.1 Hz, 1H), 7.30 (ddd, J=8.3, 6.8, 1.4 Hz, 1H), 7.01 (q, J=2.4 Hz, 2H), 6.83 (dd, J=22.1, 12.6 Hz, 1H), 6.16 (dd, J=16.6, 6.7 Hz, 1H), 5.73 (dd, J=10.4, 2.4 Hz, 1H), 4.50-4.26 (m, 4H), 4.22-4.02 (m, 3H), 3.87 (s, 1H), 3.61 (d, J=12.9 Hz, OH), 3.51 (s, 2H), 3.10 (dd, J=18.3, 5.2 Hz, 1H), 2.91 (s, 2H), 2.87-2.73 (m, 1H), 2.79 (s, 3H), 2.57 (d, J=14.0 Hz, 1H), 2.13 (d, J=12.4 Hz, 1H), 1.00 (ddd, J=21.3, 14.4, 6.4 Hz, 4H). LCMS (ESI, m/z): 558.3 [M+H]$^+$.

Example 57c: Peak 3 from cSFC (column: Chiralpak-IA; mobile phase: MeOH with 0.1% NH$_4$OH; RT=1.27 min):

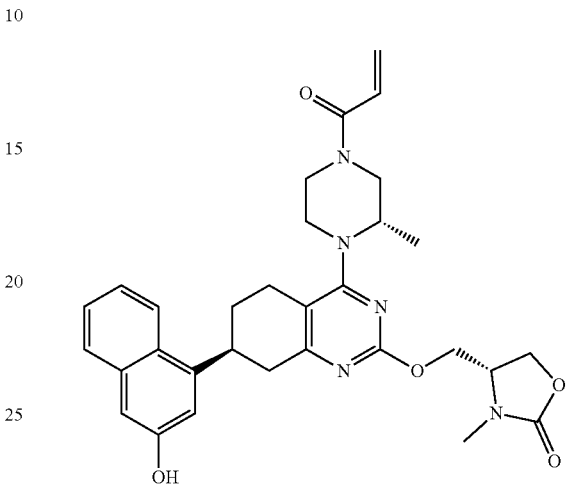

(R)-4-((((S)-4-((S)-4-acryloyl-2-methylpiperazin-1-yl)-7-(3-hydroxynaphthalen-1-yl)-5,6,7,8-tetrahydro-quinazolin-2-yl)oxy)methyl)-3-methyloxazolidin-2-one Example 57c: $^1$H NMR (400 MHz, DMSO-d6) δ 9.65 (s, 1H), 8.06 (d, J=8.5 Hz, 1H), 7.70 (dd, J=8.3, 1.3 Hz, 1H), 7.40 (ddd, J=8.0, 6.7, 1.1 Hz, 1H), 7.30 (ddd, J=8.3, 6.8, 1.4 Hz, 1H), 7.05-6.95 (m, 2H), 6.83 (ddd, J=26.1, 16.4, 10.3 Hz, 1H), 6.22-6.11 (m, 1H), 5.72 (dd, J=10.4, 2.4 Hz, 1H), 4.50-4.28 (m, 3H), 4.24-4.04 (m, 4H), 3.88 (d, J=13.4 Hz, 3H), 3.35 (s, 1H), 3.15-3.02 (m, 1H), 2.93 (s, 1H), 2.79 (s, 4H), 2.59-2.49 (m, 2H), 2.12 (d, J=12.3 Hz, 1H), 1.23 (s, 3H), 0.96 (t, J=6.5 Hz, 1H). LCMS (ESI, m/z): 558.3 [M+H]$^+$.

Example 57d: Peak 4 from cSFC (column: Chiralpak-IA; mobile phase: MeOH with 0.1% NH$_4$OH; RT=1.63 min):

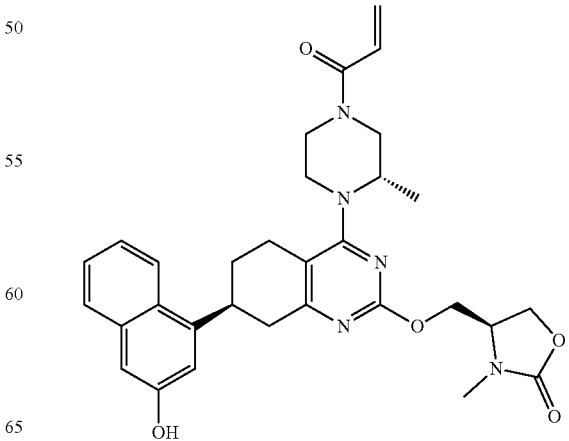

667

(S)-4-((((S)-4-((S)-4-acryloyl-2-methylpiperazin-1-yl)-7-(3-hydroxynaphthalen-1-yl)-5,6,7,8-tetrahydroquinazolin-2-yl)oxy)methyl)-3-methyloxazolidin-2-one Example 57d: ¹H NMR (400 MHz, DMSO-d6) δ 9.65 (s, 1H), 8.06 (d, J=8.4 Hz, 1H), 7.70 (dd, J=8.2, 1.3 Hz, 1H), 7.40 (ddd, J=8.0, 6.8, 1.1 Hz, 1H), 7.30 (ddd, J=8.3, 6.8, 1.4 Hz, 1H), 7.05-6.94 (m, 2H), 6.93-6.73 (m, 1H), 6.16 (dd, J=16.6, 7.8 Hz, 1H), 5.72 (dd, J=10.4, 2.4 Hz, 1H), 4.48-4.26 (m, 4H), 4.17 (s, 2H), 4.17-4.00 (m, 2H), 3.88 (d, J=13.4 Hz, 3H), 3.19-3.02 (m, 2H), 2.79 (s, 3H), 2.86-2.67 (m, 1H), 2.47 (s, 1H), 2.12 (d, J=12.5 Hz, 1H), 1.32-1.19 (m, 4H), 1.07-0.92 (m, 1H). LCMS (ESI, m/z): 558.3 [M+H]⁺.

Example 58a

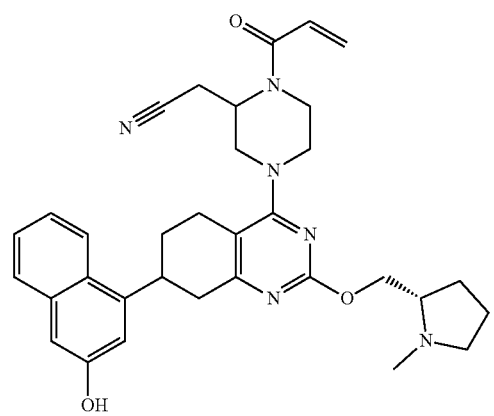 [SMILES: C=CC(=O)N1CCN(c2nc(OC[C@@H]3CCCN3C)nc3c2CCC(c2cc(O)cc4ccccc24)C3)CC1CC#N]

2-(1-acryloyl-4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile

668

-continued

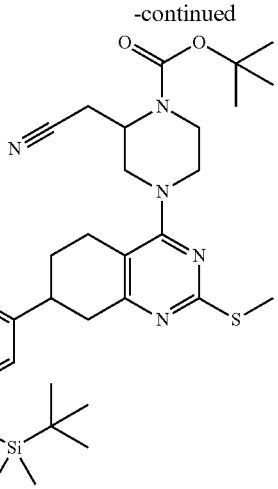

mCPBA,
DCM, 25° C.
Step 2

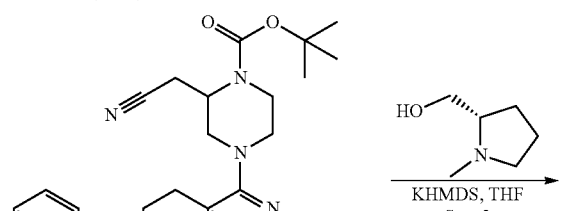

HO
KHMDS, THF
Step 3

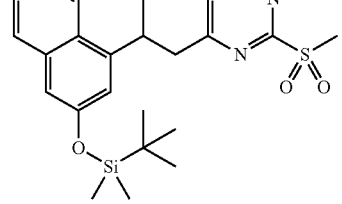

TFA
Step 4

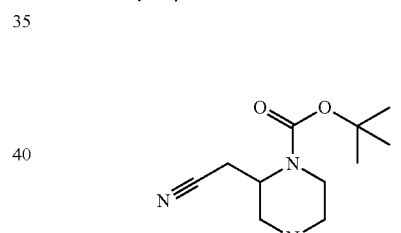

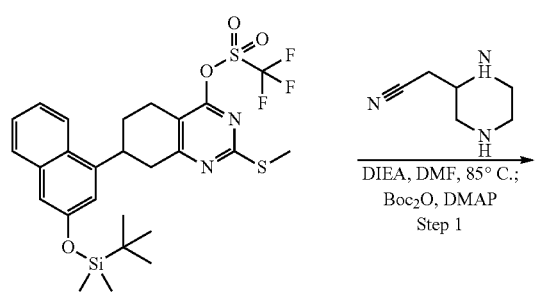

DIEA, DMF, 85° C.;
Boc₂O, DMAP
Step 1

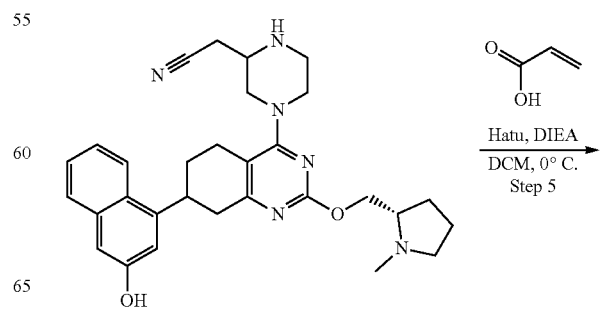

Hatu, DIEA
DCM, 0° C.
Step 5

Step 1: tert-butyl 4-(7-(3-((tert-butyldimethylsilyl)oxy)naphthalen-1-yl)-2-(methylthio)-5,6,7,8-tetrahydroquinazolin-4-yl)-2-(cyanomethyl)piperazine-1-carboxylate

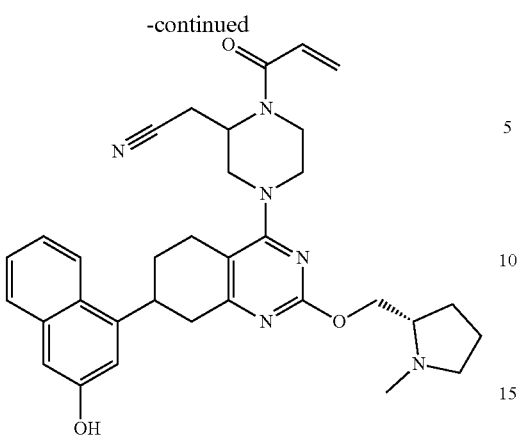

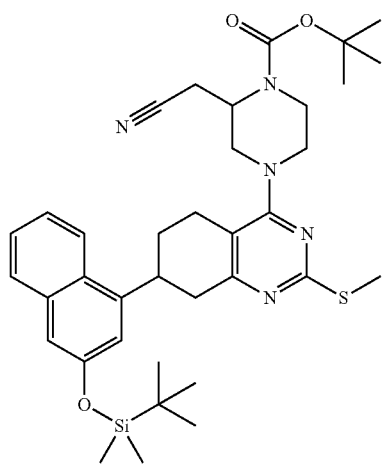 [SMILES: CSc1nc2c(c(N3CCN(C(=O)OC(C)(C)C)C(CC#N)C3)n1)CCC(c1cc(O[Si](C)(C)C(C)(C)C)cc3ccccc13)C2]

To a solution of [7-[3-[tert-butyl(dimethyl)silyl]oxy-1-naphthyl]-2-methylsulfanyl-5,6,7,8-tetrahydroquinazolin-4-yl] trifluoromethanesulfonate (500 mg, 0.855 mmol) in N,N-dimethylformamide (9.0 mL) was added N,N-diisopropylethylamine (0.60 mL, 3.4 mmol) and 2-(piperazin-2-yl)acetonitrile (245.0 mg, 1.88 mmol). The reaction mixture was stirred at 85° C. for 1 hour. The reaction mixture was cooled to r.t. then 4-dimethylaminopyridine (10.00 mg, 0.085 mmol) and di-tert-butyl dicarbonate (577 mg, 2.57 mmol) was added then stirred at r.t. for 18 hours. The reaction mixture was quenched with water and extracted with EtOAc. The organic layers was dried with sodium sulfate, filtered, and concentrated via rotovap. The crude product was purified by flash chromatography on silica (eluting with MeOH/DCM) to give tert-butyl 4-(7-(3-((tert-butyldimethylsilyl)oxy)naphthalen-1-yl)-2-(methylthio)-5,6,7,8-tetrahydroquinazolin-4-yl)-2-(cyanomethyl)piperazine-1-carboxylate (392 mg, 69%). LCMS (ESI, m/z): 660.4 [M+H]+.

Step 2: tert-butyl 4-(7-(3-((tert-butyldimethylsilyl)oxy)naphthalen-1-yl)-2-(methylsulfonyl)-5,6,7,8-tetrahydroquinazolin-4-yl)-2-(cyanomethyl)piperazine-1-carboxylate

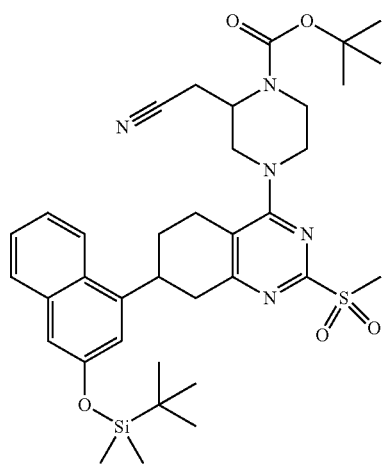 [SMILES: CC(C)(C)OC(=O)N1CCN(c2nc(S(C)(=O)=O)nc3c2CCC(c2cc(O[Si](C)(C)C(C)(C)C)cc4ccccc24)C3)CC1CC#N]

To a solution of tert-butyl 4-(7-(3-((tert-butyldimethylsilyl)oxy)naphthalen-1-yl)-2-(methylthio)-5,6,7,8-tetrahydroquinazolin-4-yl)-2-(cyanomethyl)piperazine-1-carboxylate (392 mg, 0.590 mmol) in tetrahydrofuran (12.0 mL) was added 3-chloroperoxybenzoic acid (333 mg, 1.49 mmol). The reaction was stirred at 25° C. for 2 hours then quenched by NaHSO₃ solution (10 ml). The reaction mixture was diluted with DCM (20 mL), washed with water (15 mL). The organic layers was dried with sodium sulfate, filtered, and concentrated via rotovap. The crude product was purified by flash chromatography on silica (eluting with iPrOAc/Hep) to give tert-butyl 4-(7-(3-((tert-butyldimethylsilyl)oxy)naphthalen-1-yl)-2-(methylsulfonyl)-5,6,7,8-tetrahydroquinazolin-4-yl)-2-(cyanomethyl)piperazine-1-carboxylate (200 mg, 49%). LCMS (ESI, m/z): 692.3 [M+H]+.

Step 3: tert-butyl 2-(cyanomethyl)-4-(7-(3-hydroxynaphthalen-1-yl)-2-(((S)-1-methylpyrrolidin-2-yl)methoxy)-5,6,7,8-tetrahydroquinazolin-4-yl)piperazine-1-carboxylate

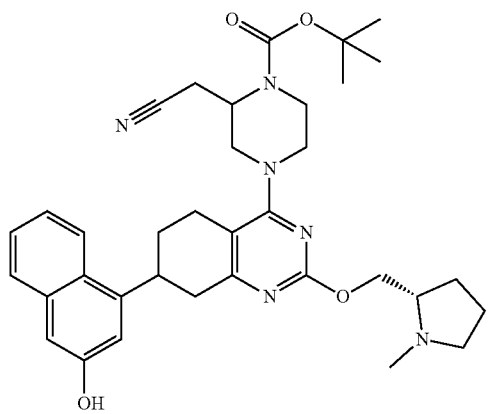 [SMILES: CN1CCC[C@H]1COc1nc2c(c(N3CCN(C(=O)OC(C)(C)C)C(CC#N)C3)n1)CCC(c1cc(O)cc3ccccc13)C2]

To a solution of [(2S)-1-methylpyrrolidin-2-yl]methanol (0.14 mL, 139 mg, 1.2 mmol,) in tetrahydrofuran (6.0 mL)

was added potassium bis(trimethylsilyl)amide (0.91 M) in tetrahydrofuran (1.3 mL, 1.3 mmol) at room temperature. The reaction was cooled to 0° C. then a solution of tert-butyl 4-[7-[3-[tert-butyl(dimethyl)silyl]oxy-1-naphthyl]-2-methylsulfonyl-5,6,7,8-tetrahydroquinazolin-4-yl]-2-(cyanomethyl)piperazine-1-carboxylate (400 mg, 0.58 mmol) in THF (3 mL) was added. The reaction was left to gently warm to room temperature for 12 hours. The reaction mixture was quenched with water and extracted with EtOAc. The organic layers was dried with sodium sulfate, filtered, and concentrated via rotovap. The crude product was used without purification. LCMS (ESI, m/z): 613.3 [M+H]$^+$.

Step 4: 2-(4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile

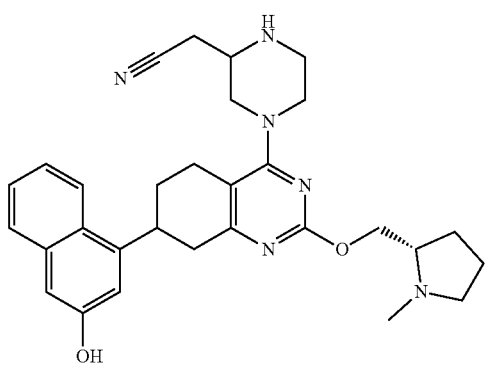 [SMILES: CN1CCC[C@H]1COc1nc2c(c(N3CCNC(CC#N)C3)n1)CCC(c1cc(O)cc3ccccc13)C2]

A solution of tert-butyl 2-(cyanomethyl)-4-(7-(3-hydroxynaphthalen-1-yl)-2-(((S)-1-methylpyrrolidin-2-yl)methoxy)-5,6,7,8-tetrahydroquinazolin-4-yl)piperazine-1-carboxylate (280 mg, 0.38 mmol) in 5% trifluoroacetic acid in hexafluoro-2-propanol (5.8 mL, 3.8 mmol) was stirred at r.t. for 24 hours. The reaction was concentrated and the crude product was purified by flash chromatography on silica (eluting with MeOH/DCM) to give 2-(4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile (84 mg, 43%). LCMS (ESI, m/z): 513.2 [M+H]$^+$.

Step 5: 2-(1-acryloyl-4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile

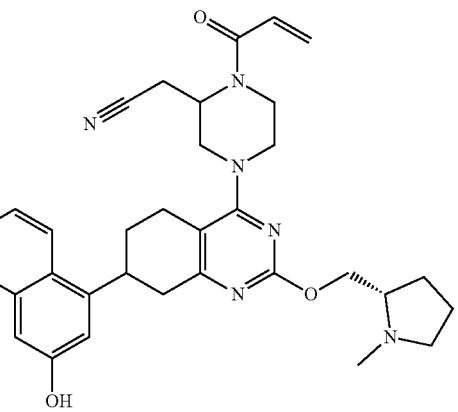

To a solution of 2-(4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile (A, 200 mg, 0.3902 mmol) and N,N-diisopropylethylamine (252.1 mg, 0.340 mL, 1.951 mmol) in dichloromethane (5170 mg, 3.902 mL, 60.7 mmol) was added acryloyl chloride (38.84 mg, 0.03493 mL, 0.4292 mmol) and HATU at −78° C. The reaction mixture was stirred at 0° C. for 15 minutes. The reaction was quenched with water and extracted with EtOAc. The organic layers was dried with sodium sulfate, filtered, and concentrated via rotovap. The crude product was submitted for reverse-phase HPLC to give 2-(1-acryloyl-4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile as white solid. Then compound was submitted for chiral SFC to give four isomers.

Example 58a: $^1$H NMR (400 MHz, DMSO-d6) δ 9.65 (d, J=10.9 Hz, 1H), 8.10-8.00 (m, 1H), 7.77-7.66 (m, 1H), 7.44-7.35 (m, 1H), 7.31 (ddd, J=8.3, 6.7, 1.4 Hz, 1H), 7.05-6.77 (m, 4H), 6.18 (dt, J=16.6, 2.4 Hz, 1H), 5.77 (dd, J=10.5, 2.3 Hz, 1H), 5.07-4.32 (m, 2H), 4.31-4.17 (m, 1H), 4.17-3.99 (m, 2H), 3.86 (t, J=16.4 Hz, 4H), 3.14-2.62 (m, 11H), 2.34 (d, J=3.0 Hz, 4H), 2.16 (qd, J=8.8, 2.8 Hz, 3H), 1.98-1.77 (m, 3H), 1.74-1.49 (m, 4H), 1.23 (s, 2H), 0.91 (ddd, J=39.9, 10.0, 5.1 Hz, 1H). LCMS (ESI, m/z): 567.3 [M+H]$^+$.

Examples 58b, 58c, 58d, and 58e

Example 58a was subjected to cSFC (column: Chiralpak-IA; mobile phase: MeOH with 0.1% NH$_4$OH) to produce Examples 58b, 58c, 58d, and 58e. 58b, 58c, 58d, and 58e: LCMS (ESI, m/z): 567.3 [M+H]$^+$. The absolute stereochemistry of these compounds was inferred from potency data and a protein X-ray structure of compound 21b.

673

Example 58b: Peak 1 from cSFC:

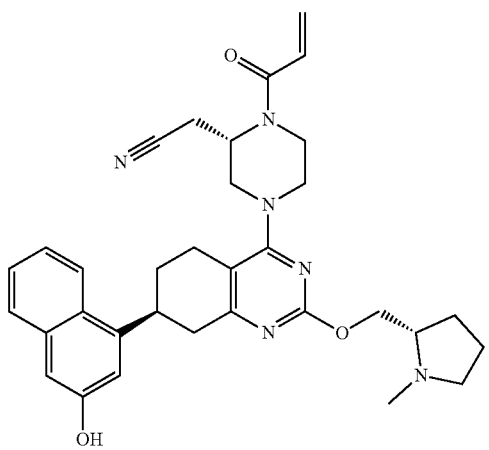 [SMILES: C=CC(=O)N1CCN(c2nc(OC[C@@H]3CCCN3C)nc3c2CC[C@H](c2cc(O)cc4ccccc24)C3)C[C@@H]1CC#N]

2-((S)-1-acryloyl-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 58c: Peak 2 from cSFC:

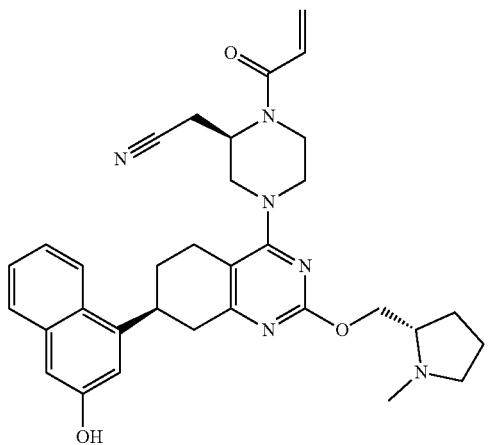 [SMILES: C=CC(=O)N1CCN(c2nc(OC[C@@H]3CCCN3C)nc3c2CC[C@H](c2cc(O)cc4ccccc24)C3)C[C@H]1CC#N]

674

2-((R)-1-acryloyl-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 58d: Peak 3 from cSFC:

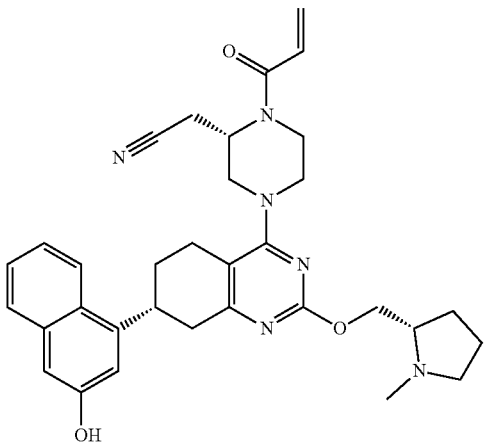 [SMILES: C=CC(=O)N1CCN(c2nc(OC[C@@H]3CCCN3C)nc3c2CC[C@@H](c2cc(O)cc4ccccc24)C3)C[C@@H]1CC#N]

2-((S)-1-acryloyl-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 58e: Peak 4 from cSFC:

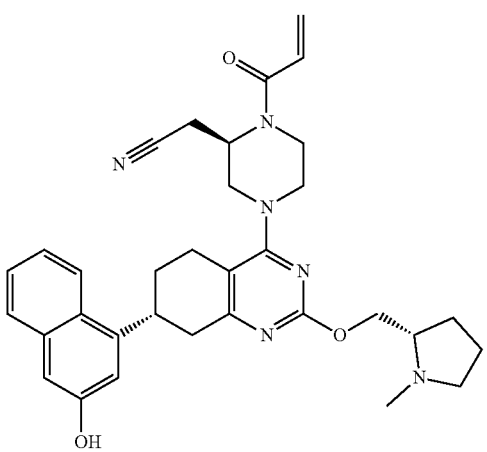 [SMILES: C=CC(=O)N1CCN(c2nc(OC[C@@H]3CCCN3C)nc3c2CC[C@@H](c2cc(O)cc4ccccc24)C3)C[C@H]1CC#N]

2-((R)-1-acryloyl-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 59a

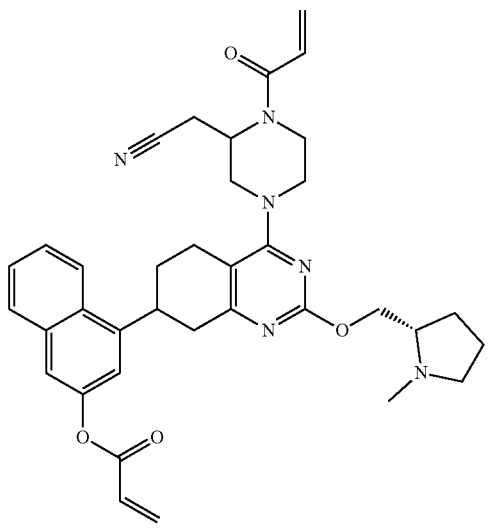 [SMILES: C=CC(=O)Oc1cc(C2CCc3c(nc(OC[C@@H]4CCCN4C)nc3N3CCN(C(=O)C=C)C(CC#N)C3)C2)c2ccccc2c1]

4-(4-(4-acryloyl-3-(cyanomethyl)piperazin-1-yl)-2-(((S)-1-methylpyrrolidin-2-yl)methoxy)-5,6,7,8-tetrahydroquinazolin-7-yl)naphthalen-2-yl acrylate Example 59a was preprepared as a side product according to the procedure set forth in Example 58a.
Example 59a: LCMS (ESI, m/z): 621.3 [M+H]⁺.

Example 60

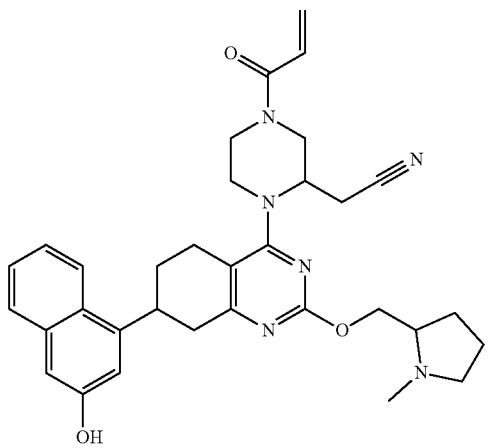 [SMILES: C=CC(=O)N1CCN(c2nc(OCC3CCCN3C)nc3c2CCC(c2cc(O)cc4ccccc24)C3)C(CC#N)C1]

2-(4-acryloyl-1-(7-(3-hydroxynaphthalen-1-yl)-2-((1-methylpyrrolidin-2-yl)methoxy)-5,6,7,8-tetrahydroquinazolin-4-yl)piperazin-2-yl)acetonitrile Example 60 was preprepared according to the procedure set forth in Example 58a except that in Step 1 of Example 60, tert-butyl 3-(cyanomethyl)piperazine-1-carboxylate was used instead of 2-(piperazin-2-yl)acetonitrile as the alternative reagent.
Example 60: LCMS (ESI, m/z): 621.3 [M+H]⁺.

Example 61a

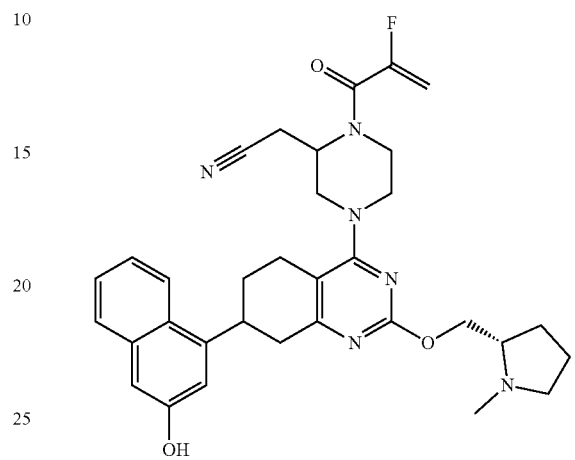

2-(1-(2-fluoroacryloyl)-4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile

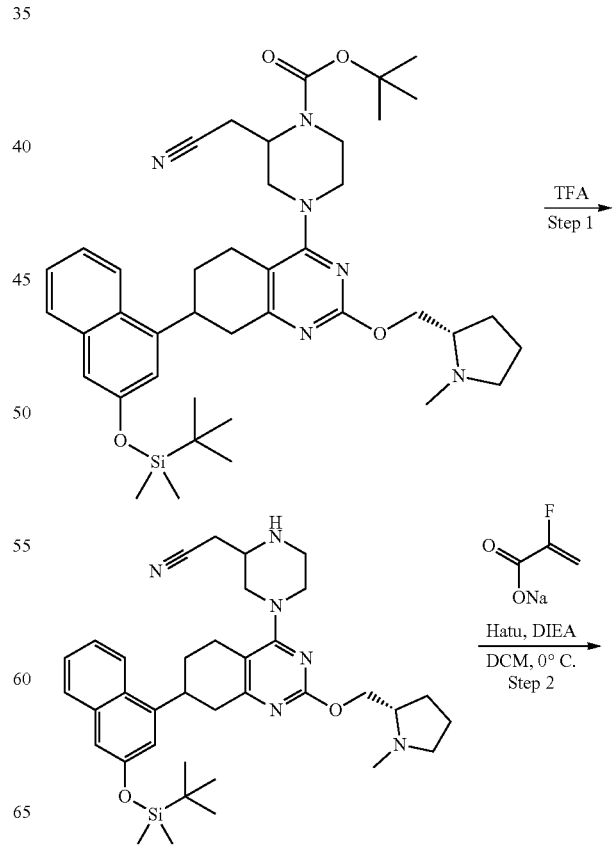

677

-continued

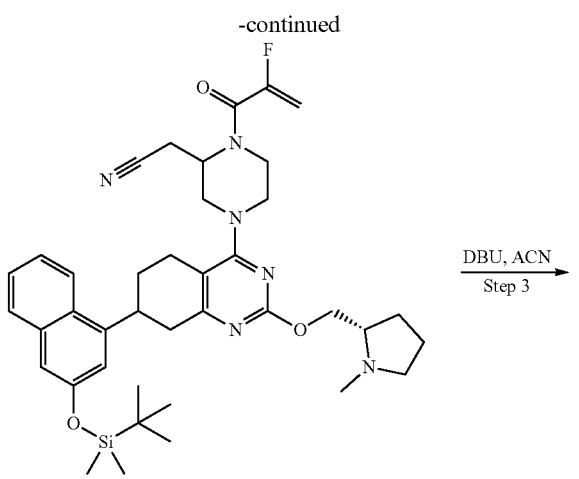

→ DBU, ACN
Step 3

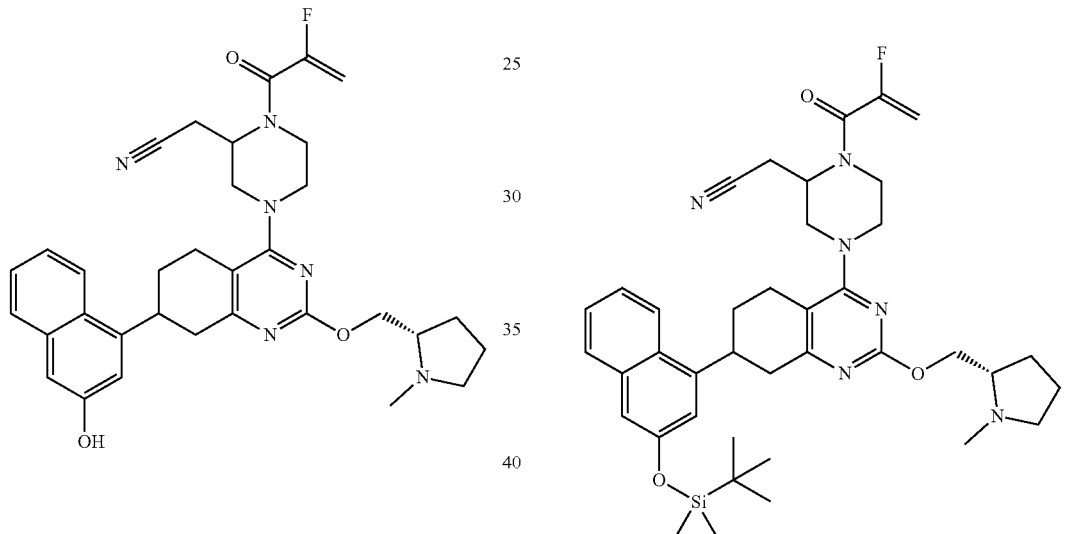

Step 1: 2-(4-(7-(3-((tert-butyldimethylsilyl)oxy)
naphthalen-1-yl)-2-(((S)-1-methylpyrrolidin-2-yl)
methoxy)-5,6,7,8-tetrahydroquinazolin-4-yl)piper-
azin-2-yl) acetonitrile

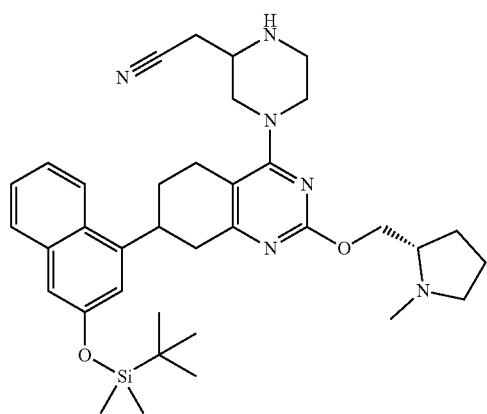 [SMILES: CN1CCC[C@H]1COc1nc2c(c(N3CCNC(CC#N)C3)n1)CCC(c1cc(O[Si](C)(C)C(C)(C)C)cc3ccccc13)C2]

678

A solution of tert-butyl 4-[7-[3-[tert-butyl(dimethyl)silyl] oxy-1-naphthyl]-2-[[(2S)-1-methylpyrrolidin-2-yl] methoxy]-5,6,7,8-tetrahydroquinazolin-4-yl]-2-(cyanomethyl)piperazine-1-carboxylate (700 mg, 0.963 mmol) in 5% trifluoroacetic acid in hexafluoro-2-propanol (14.5 mL, 9.63 mmol) was stirred at r.t. for 4 hours. The reaction was diluted with EtOAc and washed sat·NaHCO₃. The organic layers was dried with sodium sulfate, filtered, and concentrated via rotovap. The reaction was concentrated and the crude product was purified by flash chromatography on silica (eluting with MeOH/DCM) to give 2-(4-(7-(3-((tert-butyldimethylsilyl)oxy)naphthalen-1-yl)-2-(((S)-1-methylpyrrolidin-2-yl)methoxy)-5,6,7,8-tetrahydroquinazolin-4-yl)piperazin-2-yl) acetonitrile (511 mg, 85%). LCMS (ESI, m/z): 627.3 [M+H]⁺.

Step 2: 2-(4-(7-(3-(((tert-butyldimethylsilyl)oxy)
naphthalen-1-yl)-2-(((S)-1-methylpyrrolidin-2-yl)
methoxy)-5,6,7,8-tetrahydroquinazolin-4-yl)-1-(2-
fluoroacryloyl)piperazin-2-yl)acetonitrile To a solution of 2-[4-[7-[3-[tert-butyl(dimethyl)silyl]oxy-1-naphthyl]-2-[[(2S)-1-methylpyrrolidin-2-yl]methoxy]-5,6,7,8-tetrahydroquinazolin-4-yl]piperazin-2-yl]acetonitrile (258 mg, 0.41 mmol), 2-fluoroprop-2-enoyloxysodium (101.4 mg, 0.91 mmol) and N,N-diisopropylethylamine (0.36 mL, 2.1 mmol) in DCM (8.0 mL) was added HATU (412 mg, 1.0 mmol) at 0° C. and warmed to R.T. for 2 hours. The reaction was quenched with water and extracted with EtOAc. The organic layers was dried with sodium sulfate, filtered, and concentrated via rotovap. The crude product was purified by flash chromatography on silica (eluting with MeOH/DCM) to give 2-(4-(7-(3-((tert-butyldimethylsilyl)oxy)naphthalen-1-yl)-2-(((S)-1-methylpyrrolidin-2-yl)methoxy)-5,6,7,8-tetrahydroquinazolin-4-yl)-1-(2-fluoroacryloyl)piperazin-2-yl)acetonitrile (254 mg, 88%). LCMS (ESI, m/z): 699.3 [M+H]⁺.

Step 3: 2-(1-(2-fluoroacryloyl)-4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile

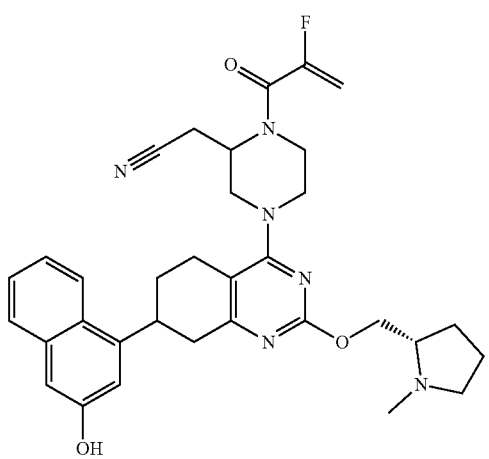

To a solution of 2-(4-(7-(3-((tert-butyldimethylsilyl)oxy)naphthalen-1-yl)-2-(((S)-1-methylpyrrolidin-2-yl)methoxy)-5,6,7,8-tetrahydroquinazolin-4-yl)-1-(2-fluoroacryloyl)piperazin-2-yl)acetonitrile (254 mg, 0.363 mmol) in acetonitrile (18.0 mL) and WATER (1.8 mL) was added 1,8-diazabicyclo[5.4.0]undec-7-ene (0.11 mL, 0.76 mmol). The reaction mixture was stirred at r.t. for 1 hour. The reaction was quenched with sat·NH$_4$Cl and extracted with EtOAc. The organic layers was dried with sodium sulfate, filtered, and concentrated via rotovap. The crude product was submitted for reverse-phase HPLC to give 2-(1-(2-fluoroacryloyl)-4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile as white solid. Then compound was submitted for chiral SFC to give four isomers.

Example 61a: LCMS (ESI, m/z): 585.3 [M+H]$^+$.

Examples 61b. 61c. 61d. and 61e

Example 61a was subjected to cSFC (column: Chiralpak-IA; mobile phase: MeOH with 0.1% NH40H) to produce Examples 61b, 61c, 61d, and 61e. 61b, 61c, 61d, and 61e: LCMS (ESI, m/z): 585.3 [M+H]+. The absolute stereochemistry of these compounds was inferred from potency data and a protein X-ray structure of compound 21b.

Examples 61b, 61c, 61d, and 61e: $^1$H NMR (400 MHz, DMSO-d6) δ 9.67 (d, J=8.8 Hz, 2H), 8.04 (t, J=7.6 Hz, 1H), 7.71 (d, J=8.2 Hz, 1H), 7.41 (ddd, J=8.2, 6.7, 1.2 Hz, 1H), 7.31 (ddd, J=8.3, 6.8, 1.4 Hz, 1H), 7.05-6.93 (m, 2H), 5.40 (ddd, J=18.0, 4.1, 2.3 Hz, 1H), 5.28 (d, J=50.0 Hz, 1H), 4.83 (s, 1H), 4.55 (s, 1H), 4.44 (t, J=9.5 Hz, 1H), 4.01 (t, J=12.5 Hz, 2H), 3.87 (d, J=11.8 Hz, 4H), 3.67-3.51 (m, 1H), 3.09 (td, J=12.8, 12.3, 6.9 Hz, 3H), 3.01-2.72 (m, 8H), 2.28-1.95 (m, 3H), 1.88 (d, J=21.5 Hz, 3H). LCMS (ESI, m/z): 585.3 [M+H]$^+$.

Example 61b: Peak 1 from cSFC:

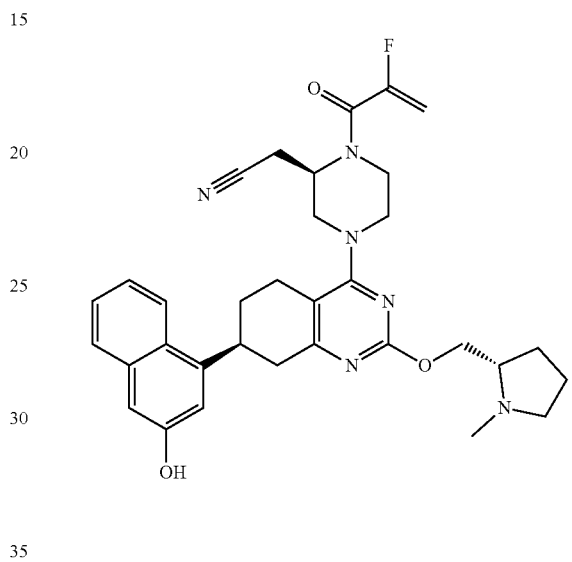

2-((R)-1-(2-fluoroacryloyl)-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 61c: Peak 2 from cSFC:

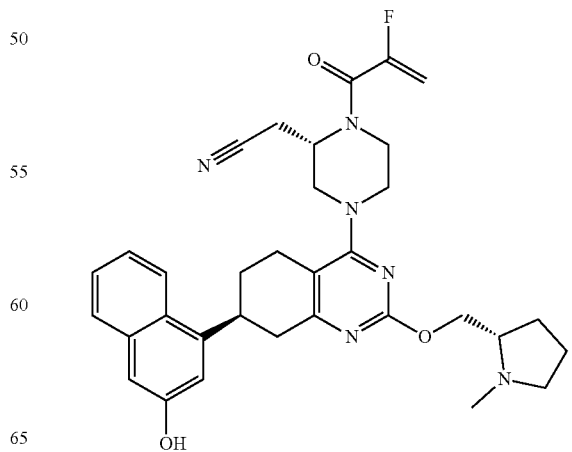

681

2-((S)-1-(2-fluoroacryloyl)-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 61d: Peak 3 from cSFC:

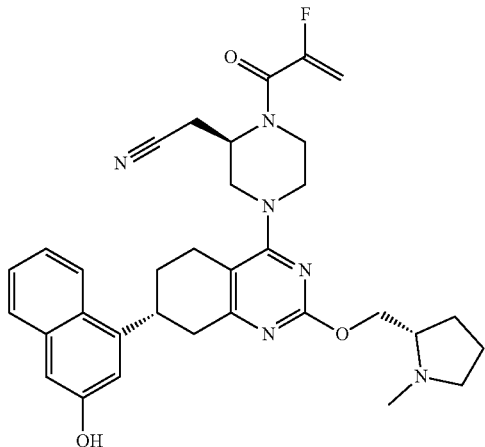 [SMILES: C=C(F)C(=O)N1CCN(c2nc(OC[C@@H]3CCCN3C)nc3c2CC[C@@H](c2cc(O)cc4ccccc24)C3)C[C@H]1CC#N]

2-((R)-1-(2-fluoroacryloyl)-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 61e: Peak 4 from cSFC:

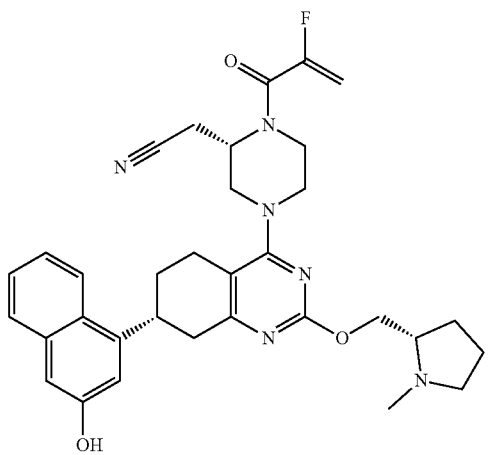 [SMILES: C=C(F)C(=O)N1CCN(c2nc(OC[C@@H]3CCCN3C)nc3c2CC[C@@H](c2cc(O)cc4ccccc24)C3)C[C@@H]1CC#N]

682

2-((S)-1-(2-fluoroacryloyl)-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 62a

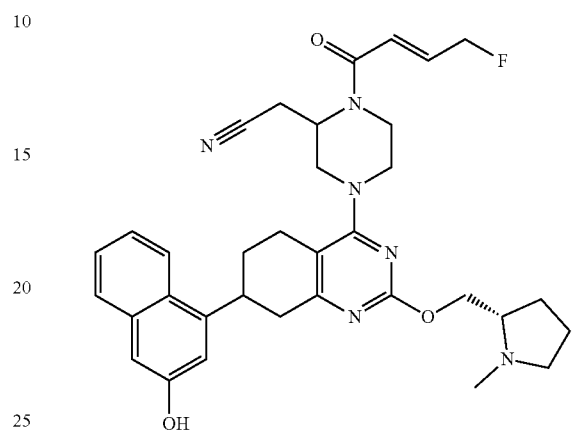

2-(1-((E)-4-fluorobut-2-enoyl)-4-(7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 62a was preprepared according to the procedure set forth in Example 61a except that in Step 2 of Example 62a, commercially available (E)-4-fluorobut-2-enoic acid was used instead of 2-fluoroprop-2-enoyloxysodium as the alternative reagent.

Example 62a: $^1$H NMR (400 MHz, DMSO-d6) δ 9.68 (d, J=9.8 Hz, 1H), 8.09-8.00 (m, 1H), 7.71 (d, J=8.1 Hz, 1H), 7.40 (ddd, J=7.9, 6.7, 1.1 Hz, 1H), 7.31 (ddd, J=8.3, 6.8, 1.4 Hz, 1H), 7.05-6.69 (m, 4H), 5.10 (t, J=42.4 Hz, 3H), 4.52 (d, J=69.0 Hz, 3H), 3.91 (d, J=40.6 Hz, 4H), 3.16-2.69 (m, 11H), 2.15 (s, 2H), 1.88 (d, J=24.6 Hz, 4H). LCMS (ESI, m/z): 599.3 [M+H]$^+$.

Examples 62b, 62c, 62d, and 62e

Example 62a was subjected to cSFC (column: Chiralpak-IA; mobile phase: MeOH with 0.1% NH$_4$OH) to produce Examples 62b, 62c, 62d, and 62e. 62b, 62c, 62d, and 62e: LCMS (ESI, m/z): 599.3 [M+H]$^+$. The absolute stereochemistry of these compounds was inferred from potency data and a protein X-ray structure of compound 21b.

Example 62b: Peak 1 from cSFC:

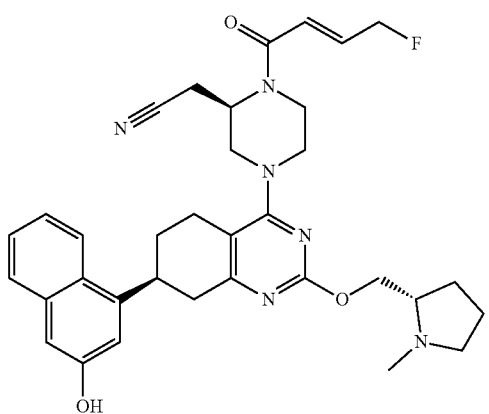 [SMILES: CN1CCC[C@H]1COc1nc2c(c(N3CCN(C(=O)/C=C/CF)[C@H](CC#N)C3)n1)CC[C@H](c1cc(O)cc3ccccc13)C2]

2-((R)-1-((E)-4-fluorobut-2-enoyl)-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 62c: Peak 2 from cSFC:

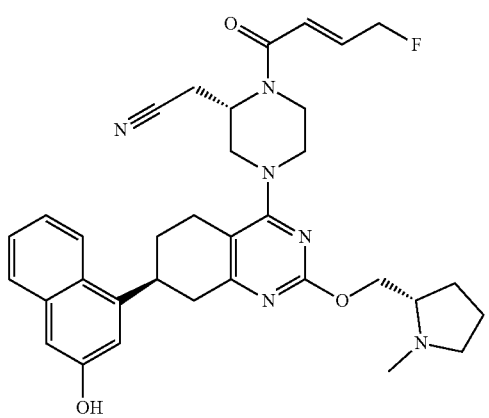 [SMILES: CN1CCC[C@H]1COc1nc2c(c(N3CCN(C(=O)/C=C/CF)[C@@H](CC#N)C3)n1)CC[C@H](c1cc(O)cc3ccccc13)C2]

2-((S)-1-((E)-4-fluorobut-2-enoyl)-4-((S)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 62d: Peak 3 from cSFC:

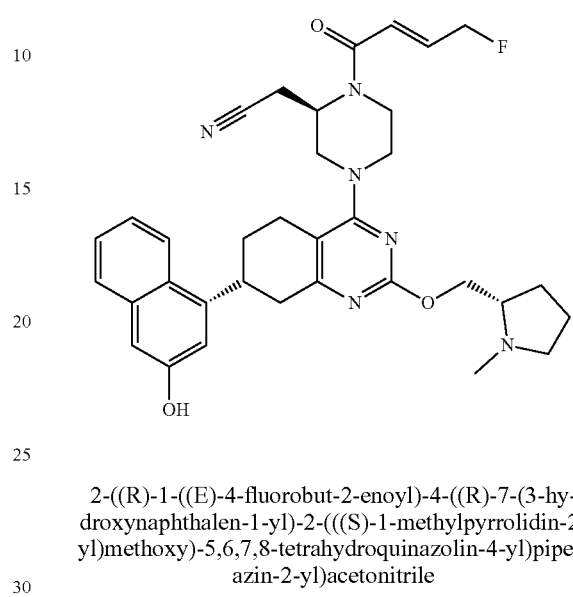

2-((R)-1-((E)-4-fluorobut-2-enoyl)-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile Example 62e: Peak 4 from cSFC:

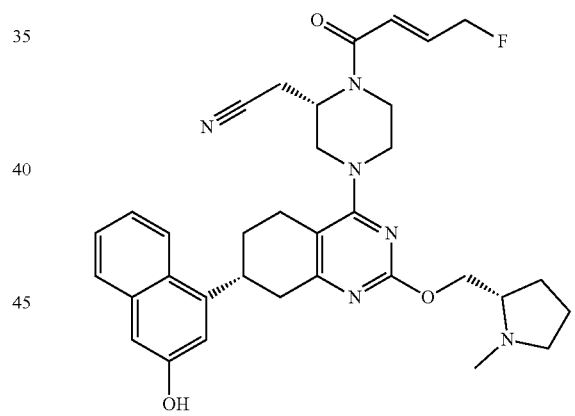

2-((S)-1-((E)-4-fluorobut-2-enoyl)-4-((R)-7-(3-hydroxynaphthalen-1-yl)-2-(((S)-1-methylpyrrolidin-2-yl)methoxy)-5,6,7,8-tetrahydroquinazolin-4-yl)piperazin-2-yl)acetonitrile The data from Examples 1-62e is summarized in Table 1.

BIOLOGICAL EXAMPLES

K-Ras G12C, SOS1, Raf RBD Homogeneous Time Resolved Fluorescence (HTRF) Assay for Inhibition of GTP Exchange To determine the potency of compounds for inhibiting nucleotide exchange, various concentrations were incubated with K-Ras G12C (25 nM in reaction, 12.5 nM final). After 18 hours at room temperature, the SOS1 GTP exchange factor (1.67 nM during exchange, 1.25 nM final) was added to initiate nucleotide exchange to GTP (200 μM during exchange, 150 μM final). The level of GTP exchange was assessed by addition of a Ras binding domain derived from C-Raf and the HTRF detection antibodies Tb-anti-FLAG and D2-anti-his (Cis-Bio) at 50 nM, 1 nM and 12.5 nM, respectively. After 2 hours, the ratio of 665 nm to 615 nM emission with 320 nM excitation was measured on an Envision plate reader (Perkin Elmer).

The final reaction volume was 20 μl in a ProxiPlate-384F Plus (Perkin Elmer), in buffer containing 20 mM HEPES, 150 mM NaCl, 1 mM MgCl2, 0.1% BSA, 0.03% Tween-20 and 1 mM DTT. K-Ras G12C (residues 2-188) and SOS1 (residues 564-1049) had N-terminal 6-His and the Raf-RBD construct (residues 51-186 of RAF1) had an N-terminal Flag-tag. All constructs were expressed in E. coli and had a Tev cleavage site between the tag and protein of interest that was not used during purification. HTRF data are presented below in Table 2.

Western Blot Assay for in Cell Alkylation of K-Ras G12C

HCC1171 cells were maintained in RPMI1640 supplemented with 10% FBS. Cells were plated in a 96-well plate at 20,000 cells/well and the following day compounds were added to the cells. After 18 hours at 37° C., cells were lysed in RIPA buffer (Sigma R0278) with 0.5% SDS and protease/phosphatase inhibitor cocktail. After through mixing to enable complete lysis, the lysates were cleared by centrifugation before 20 μl was transferred from each well and combined with loading buffer and reducing agent. After heating for 10 minutes at 95° C., 15 μl of each sample was loaded onto a 4-20% Tris-Glycine gel and electrophoresed at 110V for 165 minutes in SDS-PAGE running buffer. Gels were transferred to a nitrocellulose membrane, blocked for 1 hour and stained overnight at 4° C. with primary antibody against K-Ras (polyclonal Proteintech 12063-1-AP). The membrane was then washed thoroughly and counterstained with anti-rabbit IRDye 800CW (LI-COR 926-32211) for one hour at room temperature. After final washes, the membrane was imaged on a LI-COR Odyssey CLx at medium resolution. Alkylated K-Ras was visible by an electrophoretic shift from unmodified K-Ras. To quantify this affect, the LICOR software was used to draw a rectangle over alkylated and unalkylated bands for each well and measured the total fluorescent intensity (FI) in each of these bands. The following formula was then used to calculate % alkylation: $FI_{(alkylated)}/(FI_{(alkylated)}+FI_{(unalkylated)})*100$ for each well.

A 7 point dose response curve was used to determine the $IC_{50}$ for each compound. Cell alkylation data are presented below in Table 2.

Table 3 provides the results of the HTRF and Western Blot Assays as previously described above.

TABLE 2

| Example # | K-Ras G12C HTRF IC50 (μM) | K-Ras G12C-alkylation HCC1171 Western EC50 (μM) |
|---|---|---|
| 1a | >50 | 10 |
| 1b | >50 | 10 |
| 2 | 0.84 | 6.1 |
| 3a | >50 | 30 |
| 3b | 0.71 | 5.5 |
| 4a | >50 | — |
| 4b | 0.39 | 1.3 |
| 5a | >20 | 3 |
| 5b | 0.045 | 0.18 |
| 6a | 2.3 | 3 |
| 6b | >50 | 3 |
| 7a | 0.087 | 2.5 |
| 8a | 3.5 | 3 |
| 8b | 0.045 | 0.089 |
| 9a | 4.2 | — |
| 9b | >50 | — |
| 10a | 19 | — |
| 10b | 0.27 | 1 |
| 11a | 1.3 | 3 |
| 11b | <0.01 | 0.047 |
| 12a | 0.61 | 1.1 |
| 12b | <0.01 | 0.0033 |
| 13a | 2 | — |
| 13b | 0.084 | 0.69 |
| 14a | >50 | 1 |
| 14b | >50 | 1 |
| 15a | 0.068 | 0.43 |
| 15b | 8.6 | 30 |
| 16 | 0.12 | 1.2 |
| 17 | 0.7 | 6.7 |
| 18a | 0.024 | 0.28 |
| 19a | 0.93 | 12 |
| 19b | >30 | — |
| 20a | <0.01 | 0.014 |
| 20b | 1.4 | 2.1 |
| 21a | 1.1 | 2.3 |
| 21b | <0.01 | 0.006 |
| 22a | 0.02 | 0.1 |
| 22b | <0.01 | 0.0061 |
| 23a | 0.72 | 1 |
| 23b | <0.01 | 0.0066 |
| 24a | >50 | 3 |
| 24b | 0.021 | 0.49 |
| 25a | 5.4 | 1 |
| 26 | 0.27 | 2.2 |
| 26a | 0.18 | 1.2 |
| 26b | 4.8 | 17 |
| 27a | 0.089 | 0.34 |
| 27b | 3 | 3 |
| 28a | 0.13 | 1 |
| 28b | <0.01 | 0.023 |
| 29a | 0.53 | 9.3 |
| 29b | <0.01 | 0.33 |
| 30a | 0.011 | 0.04 |
| 30b | 1.2 | 3 |
| 31a | <0.01 | 0.013 |
| 31b | 0.25 | 2 |
| 32a | <0.01 | 0.12 |
| 32b | 0.056 | 0.92 |
| 33a | <0.01 | 0.051 |
| 33b | 0.3 | 2.2 |
| 34a | 8.9 | >3 |
| 34b | 0.68 | 1.2 |
| 34c | <0.01 | 0.014 |
| 34d | <0.01 | 0.0067 |
| 35a | 0.19 | 0.55 |
| 35b | 0.011 | 0.017 |
| 35c | 0.022 | 0.046 |
| 35d | <0.01 | 0.00098 |
| 36a | 0.36 | 0.27 |
| 36b | <0.01 | 0.006 |
| 37a | <0.01 | 0.0045 |
| 37b | 2.2 | 1 |
| 38a | 3.6 | 1 |
| 38b | <0.01 | 0.0032 |
| 38c | 0.015 | 0.024 |
| 38d | 1.7 | 1 |
| 39 | 0.18 | 0.72 |
| 40a | <0.01 | 0.1 |
| 40b | 0.56 | 1 |
| 40c | 1.2 | 1 |
| 40d | 0.029 | 1 |
| 41a | 0.5 | 0.88 |
| 41b | <0.01 | 0.0081 |
| 42a | 2.7 | 3 |
| 42b | 0.067 | 0.36 |
| 43 | 0.2 | 3 |
| 44a | >50 | 1 |
| 44b | 8.7 | 1 |

TABLE 2-continued

| Example # | K-Ras G12C HTRF IC50 (µM) | K-Ras G12C-alkylation HCC1171 Western EC50 (µM) |
|---|---|---|
| 45a | >50 | — |
| 46a | 2 | 3 |
| 46b | 0.23 | 0.97 |
| 47a | 0.15 | 0.53 |
| 47b | 1.5 | 3 |
| 47c | 0.13 | 0.45 |
| 47d | <0.01 | 0.03 |
| 48a | 0.011 | 0.15 |
| 49a | 0.023 | 0.17 |
| 50a | 0.16 | 0.17 |
| 51 | 0.046 | 0.33 |
| 52a | 0.051 | 0.99 |
| 53a | 0.022 | 0.23 |
| 54a | 0.47 | 3 |
| 55a | 1.4 | 6.7 |
| 56a | 0.073 | 0.62 |
| 57a | 20 | 3 |
| 57b | 14 | 3 |
| 57c | 0.053 | 0.83 |
| 57d | 0.045 | 0.88 |
| 58a | 0.028 | 0.01 |
| 58b | 0.13 | 1.9 |
| 58c | 0.029 | 0.34 |
| 58d | 0.024 | 0.0063 |
| 58e | 0.029 | 0.11 |
| 59a | 0.25 | 0.029 |
| 60 | 0.026 | 1.3 |
| 61a | 0.038 | 0.016 |
| 61b | 0.64 | 2.8 |
| 61c | 0.083 | 1.8 |
| 61d | 0.028 | 0.011 |
| 61e | 0.09 | 1.5 |
| 62a | 0.018 | 0.014 |
| 62b | 0.18 | 2.9 |
| 62c | 0.073 | 1 |
| 62d | <0.01 | 0.0064 |
| 62e | 0.66 | 0.45 |

Whole Blood Stability Assay

A whole blood stability assay was performed using fresh blood with a drug final concentration of 1 µM. The drug-blood mixtures were incubated at 37° C. for 180 minutes. The half-life of Afatinib and other test compounds are set forth in Table 3.

TABLE 3

| Example # | Half-life (min) |
|---|---|
| 12b | >540 |
| 20a | 230 |
| 21b | >540 |
| 22b | >540 |
| 23b | 280 |
| 28b | 420 |
| 31a | 410 |
| 34c | >540 |
| 34d | >540 |
| 35b | 91 |
| 35d | 87 |
| 36b | >540 |
| 37a | >540 |
| 38b | >540 |
| 38c | 140 |
| 41b | 200 |
| Afatinib | 75 |

K-Ras G12C Viability and Selectivity 3D Culture CTG Assay

A proliferation assessment may assess the effect of compounds on viability and the specificity for K-Ras G12C driven cancer cell lines. A proliferation assessment is carried out using 3 G12C-driven (H358, HCC1171 and HCC1792) and 2 non-G12C-driven (PC-9 and A427) lines in ultra-low attachment plates to encourage growth of 3D spheroids. On day 1, 1000 cells per well are seeded into 384-well black clear round bottom ultra-low attachment plates (Corning 3830) in 50 µl of RPMI1640 media supplemented with 10% FBS and 2 mM L-Glutamine. On the following day, various concentrations of compounds are added, using a dose response titration starting at 20 uM and keeping the final DMSO amount constant at 0.3%. Seven days after addition of compounds, the amount of viable cells are determined by adding 40 µl of CTG 3D reagent (Promega G9683) which lyses the cells and generates a luciferase signal in proportion to the amount of ATP released. Plates are shaken vigorously for 25 minutes. Plates are then incubated for an additional 10 minutes. Plates are then centrifuged briefly prior to reading luminescence on an Envision plate reader (Perkin Elmer). Luminescence from wells treated with DMSO only is used to determine total proliferation and 1 uM Staurosporine use to determine 100% inhibition.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually.

What is claimed is:
1. A compound of Formula (II):

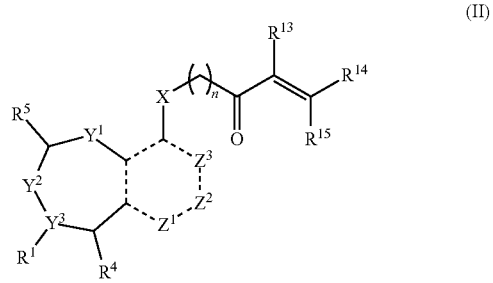

or a pharmaceutically acceptable salt thereof;
wherein,
$R^1$ is

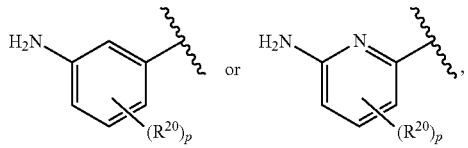

wherein each $R^{20}$ is independently selected from the group consisting of $C_{1-6}$ alkyl, —$NH_2$, —$NH(CH_3)$, —$N(CH_3)_2$, halo, $C_{1-6}$ haloalkyl, $C_{3-6}$ cycloalkyl, $C_{1-6}$ hydroxyalkyl, —OC(=O)CH=$CH_2$, and hydroxy, and p is 0, 1, 2, 3, or 4;

$Y^1$ is absent;

$Y^2$ is C(H)($R^8$);

$Y^3$ is CH;

$Z^1$ is N;

$Z^2$ is C(-L-$R^{10a}$);

$Z^3$ is N;

$R^4$ and $R^5$ are each hydrogen;

$R^8$ is selected from the group consisting of H and $C_1$-$C_6$ alkyl;

-L-$R^{10a}$ is selected from the group consisting of

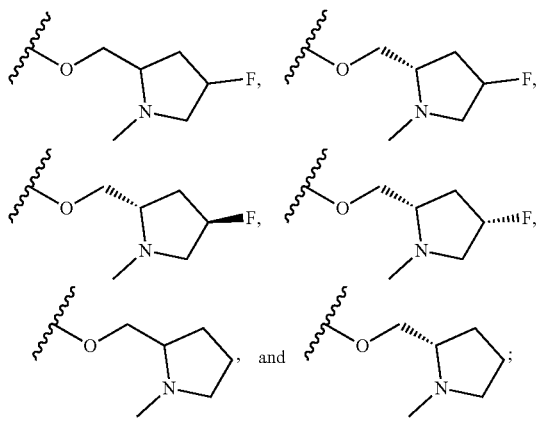

$R^{13}$, $R^{14}$, and $R^{15}$ are each H, or $R^{13}$ is F and $R^{14}$ and $R^{15}$ are each H;

X is substituted or unsubstituted piperazine, wherein the substituted piperazine is substituted with one or more groups selected from the group consisting of $CH_3$, $CH_2CN$, $CH_2OH$, CN, $CF_3$, $CH_2CF_3$, and $CHF_2$;

n is 0; and

------ represents a single bond or a double bond.

2. The compound of claim 1, or a pharmaceutically acceptable salt thereof, wherein each $R^{20}$ is independently selected from the group consisting of $C_{1-6}$ alkyl, —$NH_2$, —$NH(CH_3)$, —$N(CH_3)_2$, halo, $C_{1-6}$ haloalkyl, and $C_{3-6}$ cycloalkyl.

3. The compound of claim 1, or a pharmaceutically acceptable salt thereof, wherein $R^1$ is

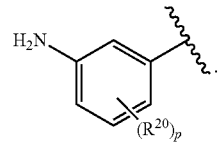

4. The compound of claim 1, or a pharmaceutically acceptable salt thereof, wherein $R^1$ is

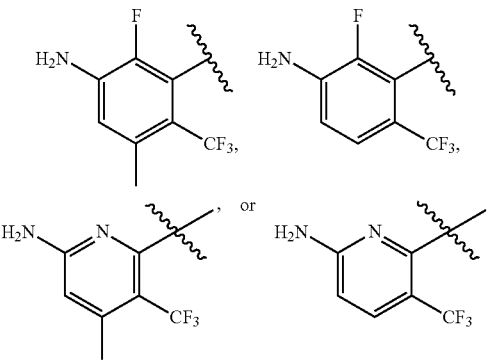

5. The compound of claim 4, or a pharmaceutically acceptable salt thereof, wherein $R^1$ is

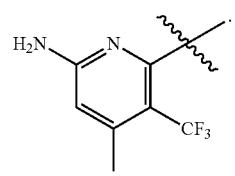 [SMILES: *c1nc(N)cc(C)c1C(F)(F)F]

6. The compound of claim 1, or a pharmaceutically acceptable salt thereof, wherein X is selected from the group consisting of:

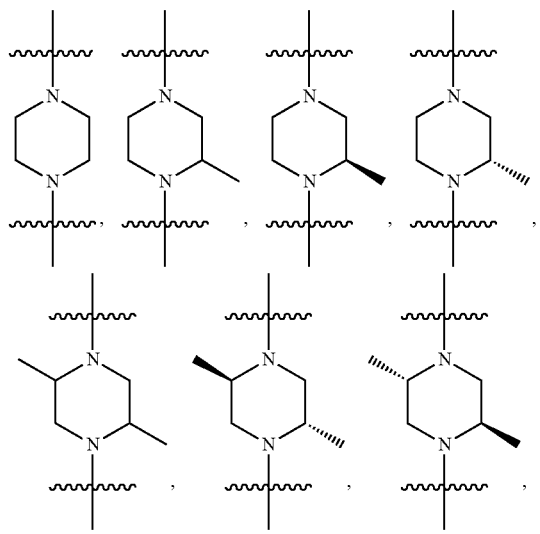

-continued
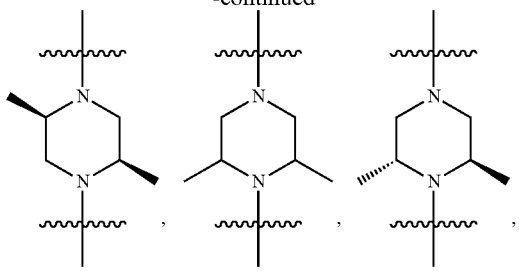
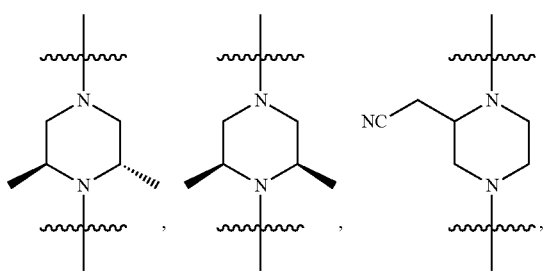
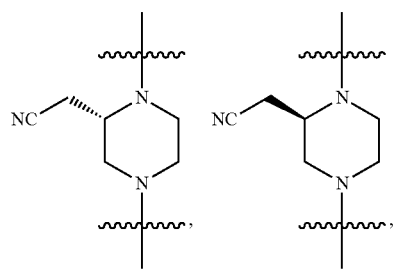
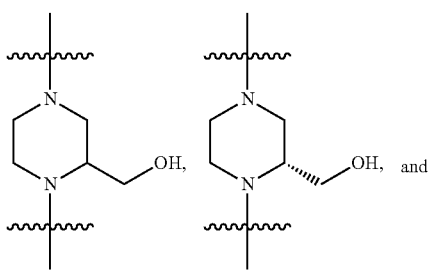
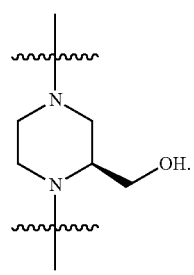 [SMILES: *N1CCN(*)[C@H](CO)C1]
7. The compound of claim 1, having a formula selected from the group consisting of:
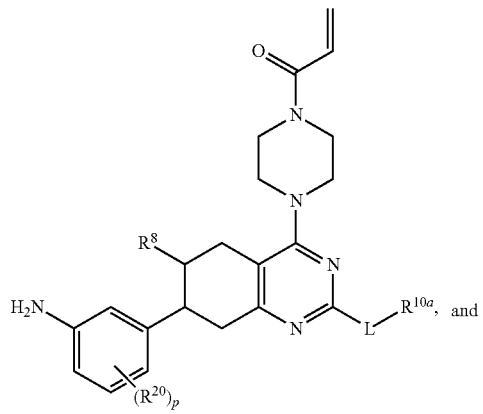
(IIn-1)
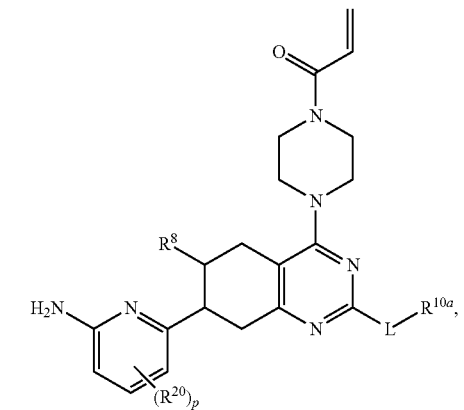
(IIn-3)
or a pharmaceutically acceptable salt thereof.
8. The compound of claim 1 having a formula selected from the group consisting of:
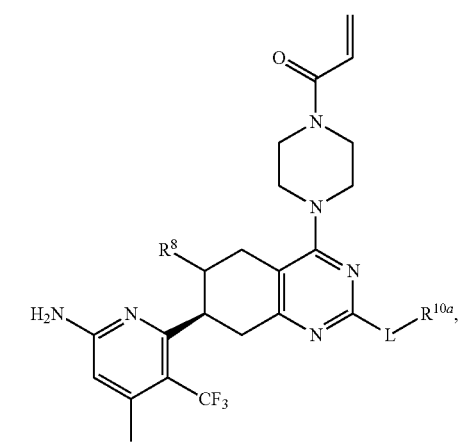
(IIn-6)

-continued (IIn-7)

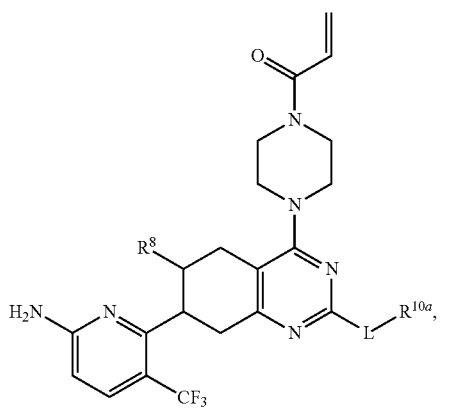

(IIn-8)

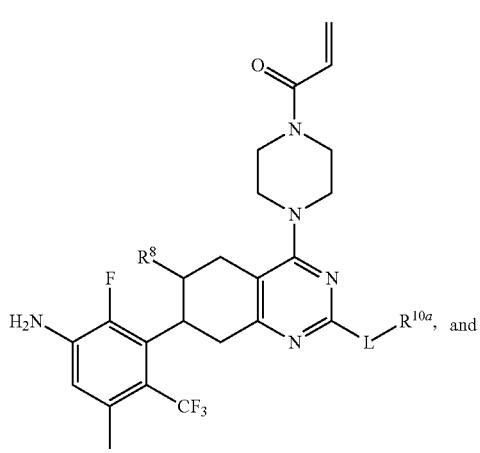

(IIn-9)

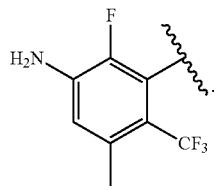 [SMILES: *c1c(F)c(N)cc(C)c1C(F)(F)F]

or a pharmaceutically acceptable salt thereof.

9. A pharmaceutical composition comprising the compound of claim 1, or a pharmaceutically acceptable salt thereof, and a pharmaceutically acceptable excipient.

10. A method of treating cancer mediated by a K-Ras G12C mutation, the method comprising administering to an individual in need thereof a therapeutically effective amount of the compound of claim 1, or a pharmaceutically acceptable salt thereof, wherein the cancer is a hematological cancer, pancreatic cancer, MYH associated polyposis, colorectal cancer, lung cancer, or is agnostic.

11. A method for treating cancer mediated by a K-Ras G12C mutation in an individual having such cancer, the method comprising:
determining if the individual has the mutation; and
if the individual is determined to have the mutation, then administering to the individual a therapeutically effective amount of the compound of claim 1, or a pharmaceutically acceptable salt thereof;
wherein the cancer is a hematological cancer, pancreatic cancer, MYH associated polyposis, colorectal cancer, lung cancer, or is agnostic.

12. The compound of claim 4, or a pharmaceutically acceptable salt thereof, wherein $R^1$ is

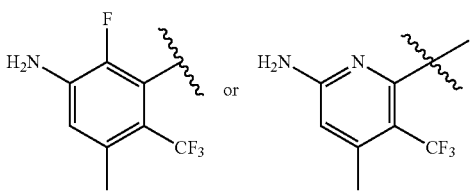

13. The compound of claim 12, or a pharmaceutically acceptable salt thereof, wherein $R^1$ is:

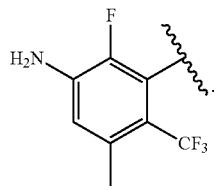 [SMILES: *c1c(F)c(N)cc(C)c1C(F)(F)F]

14. The compound of claim 1, or a pharmaceutically acceptable salt thereof, wherein $R^8$ is selected from the group consisting of H, methyl, ethyl, and isopropyl.

15. The compound of claim 14, or a pharmaceutically acceptable salt thereof, wherein $R^8$ is selected from the group consisting of H and methyl.

16. The compound of claim 1, selected from the group consisting of:
1-(4-(7-(3-amino-2-fluoro-5,6-dimethylphenyl)-6-methyl-2-((1-methylpyrrolidin-2-yl)methoxy)-5,6,7,8-tetrahydroquinazolin-4-yl)-3-methylpiperazin-1-yl)prop-2-en-1-one (Compound 11);
1-[(3S)-4-[(6S,7S)-7-(3-amino-2-fluoro-5,6-dimethylphenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one (Compound 11a);
1-[(3S)-4-[(6R,7R)-7-(3-amino-2-fluoro-5,6-dimethylphenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one (Compound 11b);
1-(4-(7-(3-amino-2-fluoro-5-methyl-6-(trifluoromethyl)phenyl)-6-methyl-2-((1-methylpyrrolidin-2-yl)methoxy)-5,6,7,8-tetrahydroquinazolin-4-yl)-3-methylpiperazin-1-yl)prop-2-en-1-one (Compound 12);
1-((S)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Compound 12a);

1-((S)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Compound 12b);

1-(4-(7-(6-amino-4-methyl-3-(trifluoromethyl)pyridin-2-yl)-6-methyl-2-((1-methylpyrrolidin-2-yl)methoxy)-5,6,7,8-tetrahydroquinazolin-4-yl)piperazin-1-yl)prop-2-en-1-one (Compound 20);

1-(4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one (Compound 20a);

1-(4-((6S,7S)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one (Compound 20b);

1-(4-(7-(6-amino-4-methyl-3-(trifluoromethyl)pyridin-2-yl)-6-methyl-2-((1-methylpyrrolidin-2-yl)methoxy)-5,6,7,8-tetrahydroquinazolin-4-yl)-3-methylpiperazin-1-yl)prop-2-en-1-one (Compound 21);

1-((S)-4-((6S,7S)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Compound 21a);

1-((S)-4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Compound 21b);

1-(4-(7-(3-amino-2-fluoro-6-(trifluoromethyl)phenyl)-6-methyl-2-((1-methylpyrrolidin-2-yl)methoxy)-5,6,7,8-tetrahydroquinazolin-4-yl)-3-methylpiperazin-1-yl)prop-2-en-1-one (Compound 23);

1-((S)-4-((6S,7S)-7-(3-amino-2-fluoro-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Compound 23a);

1-((S)-4-((6R,7R)-7-(3-amino-2-fluoro-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Compound 23b);

1-(4-(7-(6-amino-3-cyclopropyl-4-methylpyridin-2-yl)-2-((4-fluoro-1-methylpyrrolidin-2-yl)methoxy)-6-methyl-5,6,7,8-tetrahydroquinazolin-4-yl)-3-methylpiperazin-1-yl)prop-2-en-1-one (Compound 24);

1-((S)-4-((6S,7S)-7-(6-amino-3-cyclopropyl-4-methylpyridin-2-yl)-2-(((2S,4R)-4-fluoro-1-methylpyrrolidin-2-yl)methoxy)-6-methyl-5,6,7,8-tetrahydroquinazolin-4-yl)-3-methylpiperazin-1-yl)prop-2-en-1-one (Compound 24a);

1-((S)-4-((6R,7R)-7-(6-amino-3-cyclopropyl-4-methylpyridin-2-yl)-2-(((2S,4R)-4-fluoro-1-methylpyrrolidin-2-yl)methoxy)-6-methyl-5,6,7,8-tetrahydroquinazolin-4-yl)-3-methylpiperazin-1-yl)prop-2-en-1-one (Compound 24b);

1-(4-(7-(6-amino-4-methyl-3-(trifluoromethyl)pyridin-2-yl)-6-isopropyl-2-((1-methylpyrrolidin-2-yl)methoxy)-5,6,7,8-tetrahydroquinazolin-4-yl)-3-methylpiperazin-1-yl)prop-2-en-1-one (Compound 33);

1-((S)-4-((6S,7R)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one (Compound 33a);

1-((S)-4-((6R,7S)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one (Compound 33b);

2-(4-(7-(3-amino-2-fluoro-5-methyl-6-(trifluoromethyl)phenyl)-6-methyl-2-((1-methylpyrrolidin-2-yl)methoxy)-5,6,7,8-tetrahydroquinazolin-4-yl)-1-(2-fluoroacryloyl)piperazin-2-yl)acetonitrile (Compound 34);

2-((R)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Compound 34a);

2-((R)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Compound 34b);

2-((S)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Compound 34c);

2-((S)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Compound 34d);

1-(4-(7-(3-amino-2-fluoro-5-methyl-6-(trifluoromethyl)phenyl)-2-((4-fluoro-1-methylpyrrolidin-2-yl)methoxy)-6-methyl-5,6,7,8-tetrahydroquinazolin-4-yl)-3-methylpiperazin-1-yl)prop-2-en-1-one (Compound 36);

1-[(3S)-4-[(6S,7S)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one (Compound 36a);

1-[(3S)-4-[(6R,7R)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one (Compound 36b);

1-(4-(7-(3-amino-2-fluoro-5-methyl-6-(trifluoromethyl)phenyl)-6-ethyl-2-((4-fluoro-1-methylpyrrolidin-2-yl)methoxy)-5,6,7,8-tetrahydroquinazolin-4-yl)-3-methylpiperazin-1-yl)prop-2-en-1-one (Compound 37);

1-[(3S)-4-[(6R,7R)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one (Compound 37a);

1-[(3S)-4-[(6S,7S)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one (Compound 37b);

2-(4-(7-(3-amino-2-fluoro-5-methyl-6-(trifluoromethyl)
phenyl)-2-((4-fluoro-1-methylpyrrolidin-2-yl)
methoxy)-6-methyl-5,6,7,8-tetrahydroquinazolin-4-
yl)-1-(2-fluoroacryloyl)piperazin-2-yl)acetonitrile
(Compound 38);

2-((R)-4-((6S,7S)-7-(3-amino-2-fluoro-5-methyl-6-(trif-
luoromethyl)phenyl)-2-(((2S,4R)-4-fluoro-1-meth-
ylpyrrolidin-2-yl)methoxy)-6-methyl-5,6,7,8-tetrahyd-
roquinazolin-4-yl)-1-(2-fluoroacryloyl)piperazin-2-yl)
acetonitrile (Compound 38a);

2-((S)-4-((6R,7R)-7-(3-amino-2-fluoro-5-methyl-6-(trif-
luoromethyl)phenyl)-2-(((2S,4R)-4-fluoro-1-meth-
ylpyrrolidin-2-yl)methoxy)-6-methyl-5,6,7,8-tetrahyd-
roquinazolin-4-yl)-1-(2-fluoroacryloyl)piperazin-2-yl)
acetonitrile (Compound 38b);

2-((R)-4-((6R,7R)-7-(3-amino-2-fluoro-5-methyl-6-(trif-
luoromethyl)phenyl)-2-(((2S,4R)-4-fluoro-1-meth-
ylpyrrolidin-2-yl)methoxy)-6-methyl-5,6,7,8-tetrahyd-
roquinazolin-4-yl)-1-(2-fluoroacryloyl)piperazin-2-yl)
acetonitrile (Compound 38c);

2-((S)-4-((6S,7S)-7-(3-amino-2-fluoro-5-methyl-6-(trif-
luoromethyl)phenyl)-2-(((2S,4R)-4-fluoro-1-meth-
ylpyrrolidin-2-yl)methoxy)-6-methyl-5,6,7,8-tetrahyd-
roquinazolin-4-yl)-1-(2-fluoroacryloyl)piperazin-2-yl)
acetonitrile (Compound 38d);

1-(4-(7-(6-amino-3-(trifluoromethyl)pyridin-2-yl)-6-
methyl-2-((1-methylpyrrolidin-2-yl)methoxy)-5,6,7,8-
tetrahydroquinazolin-4-yl)-3-methylpiperazin-1-yl)
prop-2-en-1-one (Compound 41);

1-((S)-4-((6S,7S)-7-(6-amino-3-(trifluoromethyl)pyridin-
2-yl)-6-methyl-2-(((S)-1-methylpyrrolidin-2-yl)
methoxy)-5,6,7,8-tetrahydroquinazolin-4-yl)-3-meth-
ylpiperazin-1-yl)prop-2-en-1-one (Compound 41a); or 1-((S)-4-((6R,7R)-7-(6-amino-3-(trifluoromethyl)pyri-
din-2-yl)-6-methyl-2-(((S)-1-methylpyrrolidin-2-yl)
methoxy)-5,6,7,8-tetrahydroquinazolin-4-yl)-3-meth-
ylpiperazin-1-yl)prop-2-en-1-one (Compound 41b);

or a pharmaceutically acceptable salt thereof.

17. The compound of claim 1 having formula:

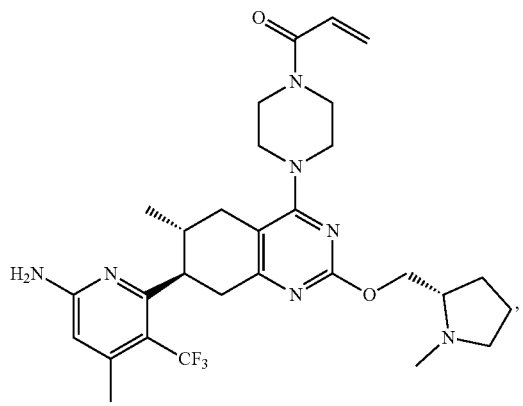

20a

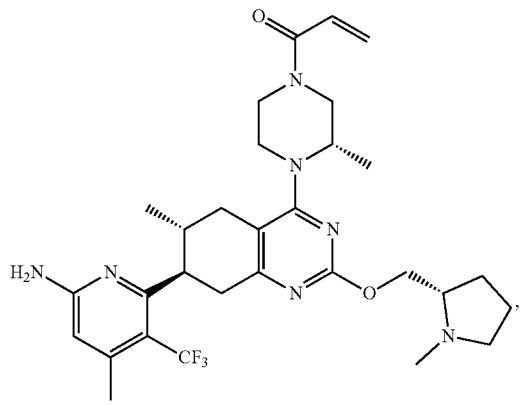

21b

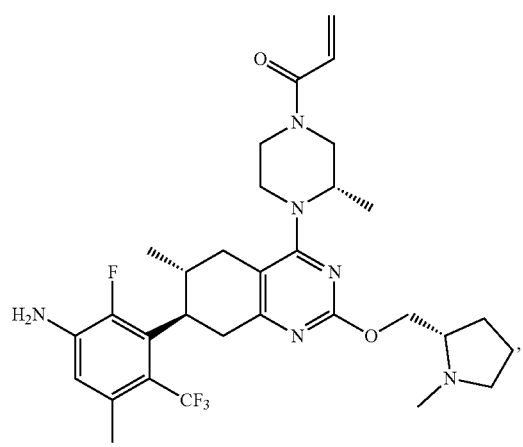

12b

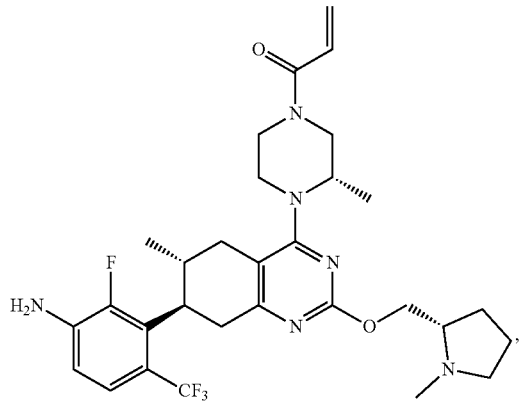

23b or a pharmaceutically acceptable salt thereof.

18. The compound of claim 1 having formula:

21b
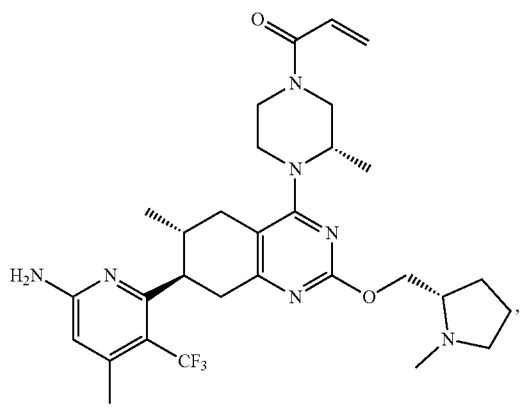
37a
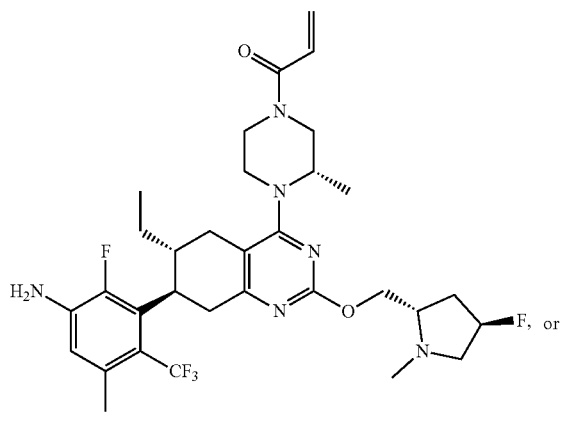
38b
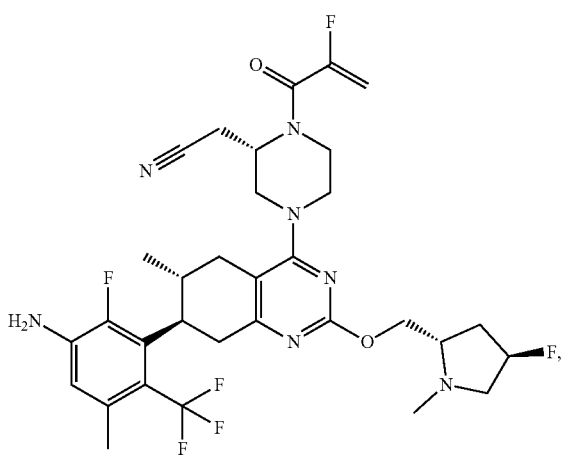 [SMILES: C=C(F)C(=O)N1CCN(c2nc(OC[C@@H]3C[C@@H](F)CN3C)nc3c2C[C@@H](C)[C@H](c2c(F)c(N)cc(C)c2C(F)(F)F)C3)C[C@@H]1CC#N]
or a pharmaceutically acceptable salt thereof.
19. The compound of claim 1 having formula:
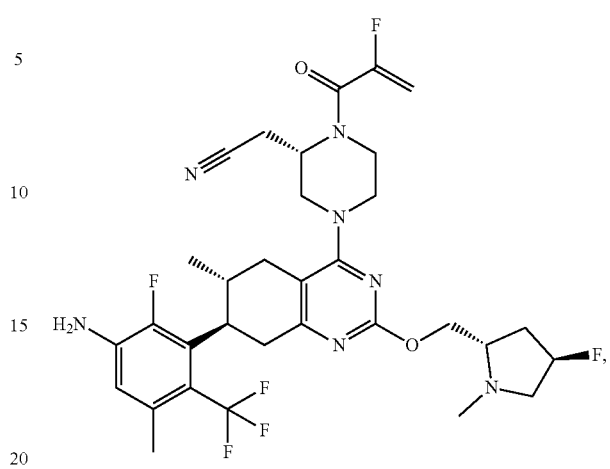
or a pharmaceutically acceptable salt thereof.
20. The compound of claim 1 having formula:
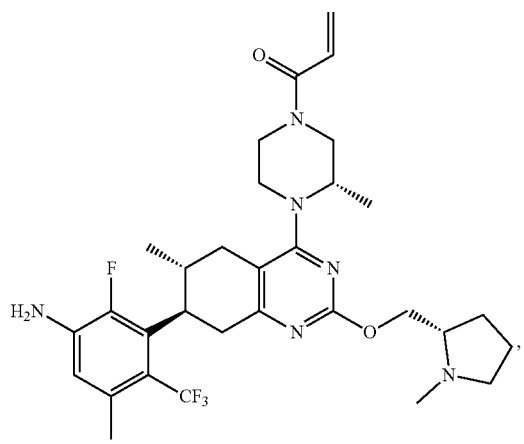 [SMILES: C=CC(=O)N1CCN(c2nc(OC[C@@H]3CCCN3C)nc3c2C[C@@H](C)[C@H](c2c(F)c(N)cc(C)c2C(F)(F)F)C3)[C@@H](C)C1]
or a pharmaceutically acceptable salt thereof.
21. The compound of claim 1 having formula:
or a pharmaceutically acceptable salt thereof.

22. The compound of claim 1 having formula:

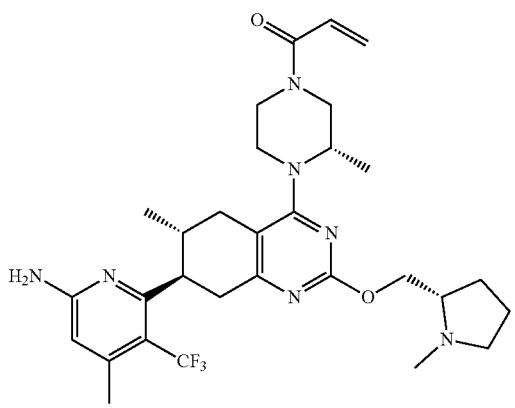 [SMILES: C=CC(=O)N1CCN(c2nc(OC[C@@H]3CCCN3C)nc3c2C[C@@H](C)[C@H](c2nc(N)cc(C)c2C(F)(F)F)C3)[C@@H](C)C1]

or a pharmaceutically acceptable salt thereof.

23. The compound of claim 1 having formula:

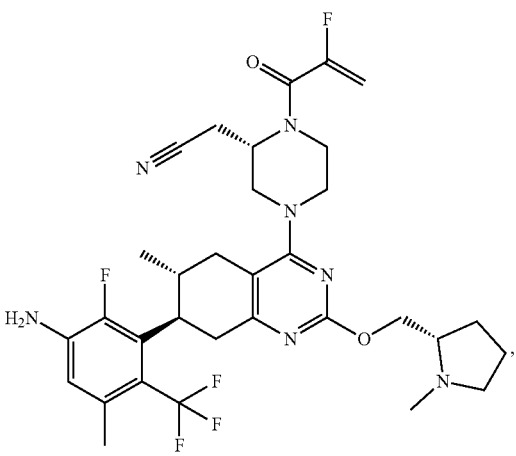 [SMILES: C=C(F)C(=O)N1CCN(c2nc(OC[C@@H]3CCCN3C)nc3c2C[C@@H](C)[C@H](c2c(F)c(N)cc(C)c2C(F)(F)F)C3)C[C@@H]1CC#N]

or a pharmaceutically acceptable salt thereof.

24. The compound of claim 1 having formula:

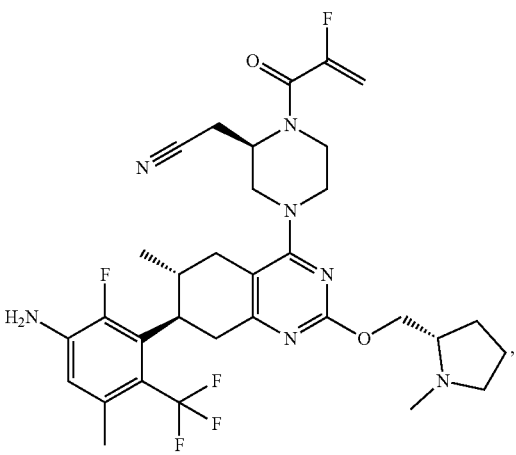 [SMILES: C=C(F)C(=O)N1CCN(c2nc(OC[C@@H]3CCCN3C)nc3c2C[C@@H](C)[C@H](c2c(F)c(N)cc(C)c2C(F)(F)F)C3)C[C@H]1CC#N]

or a pharmaceutically acceptable salt thereof.

25. The compound of claim 1 having formula:

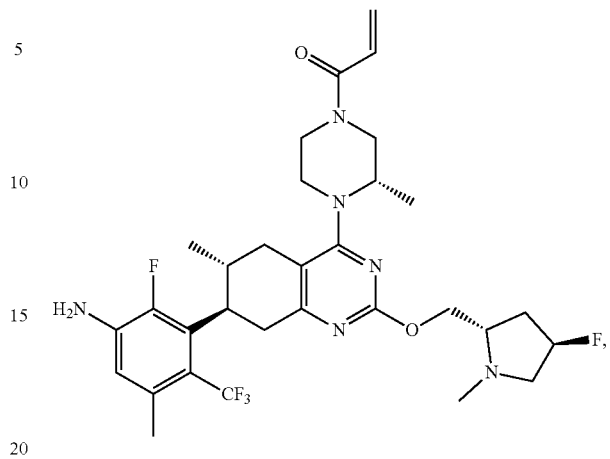

or a pharmaceutically acceptable salt thereof.

26. A compound of formula:
- 1-[(3S)-4-[(6R,7R)-7-(3-amino-2-fluoro-5,6-dimethyl-phenyl)-6-methyl-2-[[(2S)-1-methylpyrrolidin-2-yl]methoxy]-5,6,7,8-tetrahydroquinazolin-4-yl]-3-methyl-piperazin-1-yl]prop-2-en-1-one (Compound 11b);
- 1-((S)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Compound 12b);
- 1-(4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)piperazin-1-yl)prop-2-en-1-one (Compound 20a);
- 1-((S)-4-((6R,7R)-7-(6-amino-4-methyl-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Compound 21b);
- 1-((S)-4-((6R,7R)-7-(3-amino-2-fluoro-6-(trifluoromethyl)phenyl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Compound 23b);
- 1-((S)-4-((6S,7R)-7-(6-amino-4-methyl-3-(trifluoromethyl)pyridin-2-yl)-6-isopropyl-2-(((S)-1-methylpyrrolidin-2-yl)methoxy)-5,6,7,8-tetrahydroquinazolin-4-yl)-3-methylpiperazin-1-yl)prop-2-en-1-one (Compound 33a);
- 2-((S)-4-((6R,7R)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Compound 34c);
- 2-((S)-4-((6S,7S)-7-(3-amino-2-fluoro-5-methyl-6-(trifluoromethyl)phenyl)-6-methyl-2-(((S)-1-methylpyrrolidin-2-yl)methoxy)-5,6,7,8-tetrahydroquinazolin-4-yl)-1-(2-fluoroacryloyl)piperazin-2-yl)acetonitrile (Compound 34d);
- 2-((R)-1-acryloyl-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (Compound 35b);

2-((S)-1-acryloyl-4-((6R,7R)-7-(2,3-dihydro-1H-inden-4-yl)-6-methyl-2-(((S)-1-methylpyrrolidin-2-yl)methoxy)-5,6,7,8-tetrahydroquinazolin-4-yl)piperazin-2-yl)acetonitrile (Compound 35d);

1-[(3S)-4-[(6R,7R)-7-[3-amino-2-fluoro-5-methyl-6-(trifluoromethyl)phenyl]-2-[[(2S,4R)-4-fluoro-1-methyl-pyrrolidin-2-yl]methoxy]-6-methyl-5,6,7,8-tetrahydroquinazolin-4-yl]-3-methyl-piperazin-1-yl]prop-2-en-1-one (Compound 36b);

1-[(3S)-4-[(6R,7R)-7-[3-amino-2-fluoro-5-methyl-6-(trifluoromethyl)phenyl]-6-ethyl-2-[[(2S,4R)-4-fluoro-1-methyl-pyrrolidin-2-yl]methoxy]-5,6,7,8-tetrahydroquinazolin-4-yl]-3-methyl-piperazin-1-yl]prop-2-en-1-one (Compound 37a);

2-((S)-4-((6R,7R)-7-(3-amino-2-fluoro-5-methyl-6-(trifluoromethyl)phenyl)-2-(((2S,4R)-4-fluoro-1-methylpyrrolidin-2-yl)methoxy)-6-methyl-5,6,7,8-tetrahydroquinazolin-4-yl)-1-(2-fluoroacryloyl)piperazin-2-yl)acetonitrile (Compound 38b); or 1-((S)-4-((6R,7R)-7-(6-amino-3-(trifluoromethyl)pyridin-2-yl)-6-methyl-2-(((S)-1-methylpyrrolidin-2-yl)methoxy)-5,6,7,8-tetrahydroquinazolin-4-yl)-3-methylpiperazin-1-yl)prop-2-en-1-one (Compound 41b);

or a pharmaceutically acceptable salt thereof.

27. The method of claim 10, wherein the cancer is lung cancer.

28. The method of claim 11, wherein the cancer is lung cancer.

\* \* \* \* \*